US012686677B2

(12) United States Patent
Hudson et al.

(10) Patent No.: US 12,686,677 B2
(45) Date of Patent: Jul. 21, 2026

(54) COMPOUNDS AND METHODS FOR MODULATING INTERLEUKIN-2-INDUCIBLE T-CELL KINASE

(71) Applicant: Corvus Pharmaceuticals, Inc., South San Francisco, CA (US)

(72) Inventors: Ryan Hudson, San Jose, CA (US); Anne-Marie Beausoleil, San Mateo, CA (US)

(73) Assignee: Corvus Pharmaceuticals, Inc., South San Francisco, CA (US)

( * ) Notice: Subject to any disclaimer, the term of this patent is extended or adjusted under 35 U.S.C. 154(b) by 4 days.

(21) Appl. No.: 18/439,695

(22) Filed: Feb. 12, 2024

(65) Prior Publication Data

US 2024/0383884 A1 Nov. 21, 2024

Related U.S. Application Data

(62) Division of application No. 17/224,410, filed on Apr. 7, 2021, now Pat. No. 11,897,874, which is a division of application No. 16/346,360, filed as application No. PCT/US2017/059871 on Nov. 3, 2017, now Pat. No. 11,008,314.

(60) Provisional application No. 62/417,083, filed on Nov. 3, 2016.

(51) Int. Cl.

| | |
|---|---|
| ***C07D 417/06*** | (2006.01) |
| ***A61K 31/4436*** | (2006.01) |
| ***A61K 31/496*** | (2006.01) |
| ***A61K 31/53*** | (2006.01) |
| ***A61K 31/5513*** | (2006.01) |
| ***A61P 35/00*** | (2006.01) |
| ***A61P 43/00*** | (2006.01) |
| ***C07D 417/10*** | (2006.01) |
| ***C07D 417/12*** | (2006.01) |
| ***C07D 417/14*** | (2006.01) |
| ***C07D 471/08*** | (2006.01) |
| ***C07D 487/04*** | (2006.01) |
| ***C07D 487/08*** | (2006.01) |
| ***C07D 487/10*** | (2006.01) |
| ***C07D 495/04*** | (2006.01) |

(52) U.S. Cl.

CPC ......... *C07D 417/12* (2013.01); *C07D 417/14* (2013.01); *C07D 471/08* (2013.01); *C07D 487/08* (2013.01); *C07D 487/10* (2013.01); *C07D 495/04* (2013.01)

(58) Field of Classification Search

CPC .. C07D 417/06; C07D 417/10; C07D 417/12; C07D 417/14; C07D 471/08; C07D 487/04; C07D 487/08; C07D 487/10; C07D 495/04; A61K 31/4436; A61K 31/496; A61K 31/53; A61K 31/5513; A61K 31/5545; A61P 35/00; A61P 43/00

See application file for complete search history.

(56) References Cited

U.S. PATENT DOCUMENTS

| | | | |
|---|---|---|---|
| 6,706,717 | B2 | 3/2004 | Barrish et al. |
| 9,879,028 | B2 | 1/2018 | Gray et al. |
| 11,008,314 | B2 | 5/2021 | Hudson et al. |
| 2003/0069290 | A1 | 4/2003 | Wishka et al. |
| 2005/0176789 | A1 | 8/2005 | Hadida Ruah et al. |
| 2010/0113520 | A1 | 5/2010 | Miller |
| 2010/0179121 | A1 | 7/2010 | Chen et al. |
| 2016/0000788 | A1 | 1/2016 | Thomas et al. |

FOREIGN PATENT DOCUMENTS

| | | | |
|---|---|---|---|
| CN | 105884711 | A | 8/2016 |
| WO | WO-2014/117292 | A1 | 8/2014 |
| WO | WO-2016/065138 | A1 | 4/2016 |
| WO | WO-2017/044858 | A2 | 3/2017 |

OTHER PUBLICATIONS

Supplementary European Search Report issued in European Patent Application No. EP 17868729.9, mailed Apr. 1, 2020. 8 pages.

*Primary Examiner* — Brenda L Coleman

(74) *Attorney, Agent, or Firm* — Mintz, Levin, Cohn, Ferris, Glovsky and Popeo, P.C.

(57) ABSTRACT

Provided herein, inter alia, are methods and compounds for modulating Interleukin-2-inducible T-cell kinase.

20 Claims, No Drawings

COMPOUNDS AND METHODS FOR MODULATING INTERLEUKIN-2-INDUCIBLE T-CELL KINASE

CROSS-REFERENCES TO RELATED APPLICATIONS

This application is a divisional of U.S. application Ser. No. 17/224,410 filed Apr. 7, 2021, issued as U.S. Pat. No. 11,897,874, which is a divisional of U.S. application Ser. No. 16/346,360 filed Apr. 30, 2019, issued as U.S. Pat. No. 11,008,314, which is a § 371 US national phase of International Application No. PCT/US2017/59871 filed Nov. 3, 2017, which claims priority to U.S. Application No. 62/417,083 filed Nov. 3, 2016, which is incorporated herein by reference in its entirety and for all purposes.

BACKGROUND OF THE INVENTION

Interleukin-2-inducible T-cell kinase (ITK) plays an important role in T-cell development, differentiation, signalling and the production of pro-inflammatory cytokines such as IL-2, IL-4, IL-5, IL-10, IL-13 and IL-17. The modulation of Interleukin-2-inducible T-cell kinase (ITK) activity has been a target for the treatment of inflammation (e.g., inflammatory skin conditions), autoimmune, allergic disease conditions, and cancers (e.g., T-cell cancers such as T-cell lymphoma and lymphoblastic T-cell leukemia). For example, ITK inhibition has been studied for the treatment of diseases such as allergic asthma, atopic dermatitis, allergic dermatitis, and psoriasis. Thus, there is a need in the art for ITK modulators. Provided herein are solutions to these and other problems in the art.

BRIEF SUMMARY OF THE INVENTION

Herein are provided, inter alia, compounds capable of modulating the level of activity of Interleukin-2-inducible T-cell kinase (ITK, TSK) and methods of using the same.

In an aspect is provided a compound, or a pharmaceutically acceptable salt thereof, having the formula:

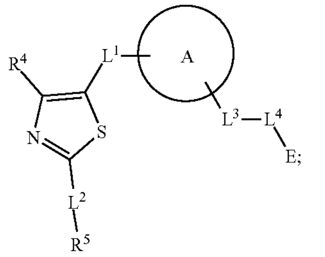

wherein Ring A is

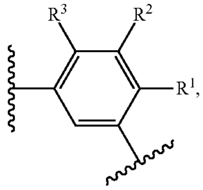

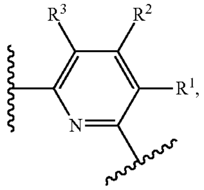

-continued

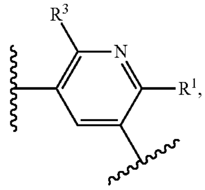

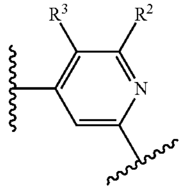
,

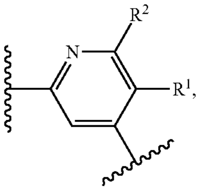

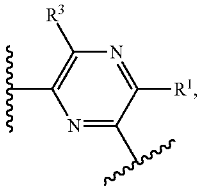

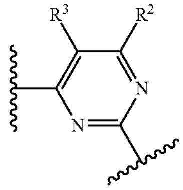
,

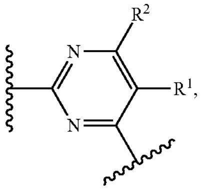

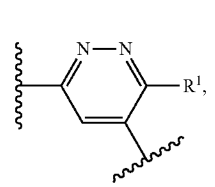

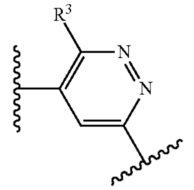

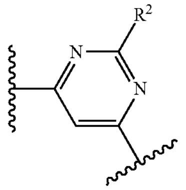
or

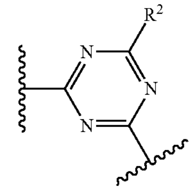
;

$R^1$ is independently hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is —O—, —S—, or substituted or unsubstituted $C_1$-$C_2$ alkylene, or substituted or unsubstituted 2 membered heteroalkylene; $L^2$ is a bond, —NH—, or —NHC(O)—; $L^3$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^6$ is independently hydrogen, —$CX^6_3$, —$CHX^6_2$, —$CH_2X^6$, —CN, —$C(O)R^{6C}$, —$C(O)OR^{6C}$, —$C(O)NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^4$ is a bond, —$S(O)_2$—, —$N(R^7)$—, —O—, —S—, —C(O)—, —$C(O)N(R^7)$—, —$N(R^7)C(O)$—, —$N(R^7)C(O)NH$—, —$NHC(O)N(R^7)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, —$CX^7_3$, —$CHX^7_2$, —$CH_2X^7$, —CN, —$C(O)R^{7C}$, —$C(O)OR^{7C}$, —$C(O)NR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; E is an electrophilic moiety; each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$, $R^{7A}$, $R^{7B}$, and $R^{7C}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; each X, $X^1$, $X^2$, $X^3$, $X^4$, $X^6$, and $X^7$ is independently —F, —Cl, —Br, or —I; n1, n2, n3, and n4 are independently an integer from 0 to 4; m1, m2, m3, m4, v1, v2, v3, and v4 are independently 1 or 2.

In an aspect is provided a pharmaceutical composition including a compound described herein, or pharmaceutically acceptable salt thereof, and a pharmaceutically acceptable excipient.

In an aspect is provided a method of treating cancer including administering to a subject in need thereof an effective amount of a compound described herein.

In an aspect is provided a method of treating an inflammatory disease including administering to a subject in need thereof an effective amount of a compound described herein.

In an aspect is provided a method of treating an autoimmune disease including administering to a subject in need thereof an effective amount of a compound described herein.

In an aspect is provided a method of treating an infectious disease including administering to a subject in need thereof an effective amount of a compound described herein.

In an aspect is provided a method of treating a disease associated with Interleukin-2-inducible T-cell kinase activity including administering to a subject in need thereof an effective amount of a compound described herein.

In an aspect is provided a method of inhibiting Interleukin-2-inducible T-cell kinase activity including contacting the Interleukin-2-inducible T-cell kinase with a compound described herein.

In an aspect is provided a method of inhibiting a TEC kinase activity, the method including: contacting the TEC kinase with a compound described herein.

In an aspect is provided an Interleukin-2-inducible T-cell kinase protein covalently bonded to a compound described herein.

In an aspect is provided an Interleukin-2-inducible T-cell kinase protein covalently bonded to a portion of a compound described herein.

DETAILED DESCRIPTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbon atoms (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S, and wherein the nitrogen and sulfur atoms may optionally be oxidized, and the nitrogen heteroatom may optionally be quaternized). The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. In embodiments, a cycloalkyl is a spirocyclic cycloalkyl, wherein the spirocyclic rings are cycloalkyl rings. In embodiments, a cycloalkyl is a fused ring cycloalkyl, wherein the fused rings are cycloalkyl rings. In embodiments, a cycloalkyl is a bridged ring cycloalkyl, wherein the bridged rings are cycloalkyl rings. For example, a bridged ring cycloalkyl may refer to

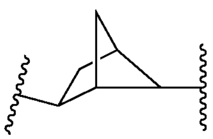,
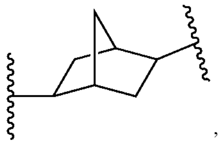,
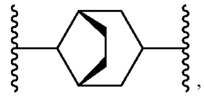,
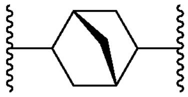 or
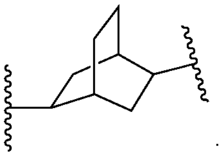.

Non-limiting examples of a bridged ring heterocycloalkyl include

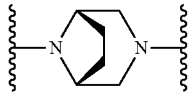,
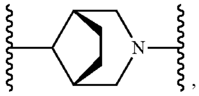,
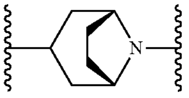, or
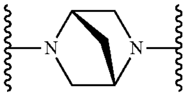.

In embodiments, a cycloalkyl is monocyclic. In embodiments, a cycloalkyl is two rings. In embodiments, a cycloalkyl is three rings. In embodiments, a cycloalkyl is four rings. In embodiments, a cycloalkyl is five rings. In embodiments, a cycloalkyl is polycyclic. In embodiments, a heterocycloalkyl is a spirocyclic heterocycloalkyl, wherein the spirocyclic rings are one or more heterocycloalkyl rings and optionally one or more cycloalkyl rings. For example, spirocyclic heterocycloalkyl may refer to

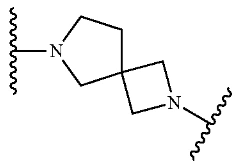
,
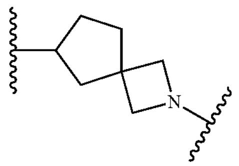
,
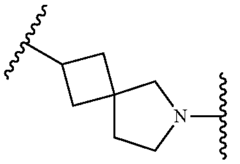
or
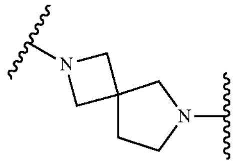
.

In embodiments, a heterocycloalkyl is a fused ring heterocycloalkyl, wherein the fused rings are one or more heterocycloalkyl rings and optionally one or more cycloalkyl rings. For example, a fused ring heterocycloalkyl may refer to

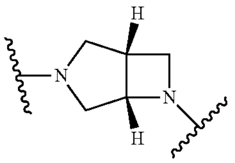
.

In embodiments, a heterocycloalkyl is a bridged ring heterocycloalkyl, wherein the bridged rings are one or more heterocycloalkyl rings and optionally one or more cycloalkyl rings. In embodiments, the rings of a spirocyclic, fused ring, or bridged ring heterocycloalkyl are heterocyclic rings. In embodiments, a heterocycloalkyl is monocyclic. In embodiments, a heterocycloalkyl is two rings. In embodiments, a heterocycloalkyl is three rings. In embodiments, a heterocycloalkyl is four rings. In embodiments, a heterocycloalkyl is five rings. In embodiments, a heterocycloalkyl is polycyclic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. In embodiments, an aryl is a fused ring aryl, wherein the fused rings are one or more aryl rings and optionally one or more cycloalkyl and/or heterocycloalkyl rings. In embodiments, an aryl is a bridged ring aryl, wherein the bridged rings are one or more aryl rings and optionally one or more cycloalkyl and/or heterocycloalkyl rings. In embodiments, the rings of a fused ring aryl or bridged ring aryl are aryl rings. In embodiments, an aryl is monocyclic. In embodiments, an aryl is two rings. In embodiments, an aryl is three rings. In embodiments, an aryl is four rings. In embodiments, an aryl is five rings. In embodiments, an aryl is polycyclic. In embodiments, a heteroaryl is a fused ring heteroaryl, wherein the fused rings are one or more heteroaryl rings and optionally one or more cycloalkyl, heterocycloalkyl, and/or aryl rings. In embodiments, a heteroaryl is a bridged ring heteroaryl, wherein the bridged rings are one or more heteroaryl rings and optionally one or more cycloalkyl, heterocycloalkyl, and/or aryl rings. In embodiments, the rings of a fused ring heteroaryl or bridged ring heteroaryl are heteroaryl rings. In embodiments, a heteroaryl is monocyclic. In embodiments, a heteroaryl is two rings. In embodiments, a heteroaryl is three rings. In embodiments, a heteroaryl is four rings. In embodiments, a heteroaryl is five rings. In embodiments, a heteroaryl is polycyclic. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzooxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〰" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

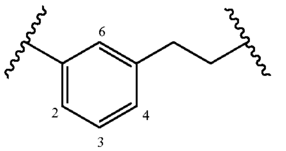

or

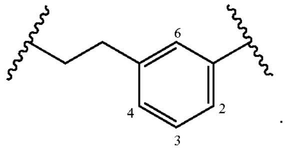

.

An alkylarylene moiety may be substituted (e.g. with a substituent group) on the alkylene moiety or the arylene linker (e.g. at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, —NR—C(NR'R"R"')=NR"", —NR—C(NR'R")=NR"', —S(O)R', $—S(O)_2R'$, $—S(O)_2NR'R"$, $—NRSO_2R'$, —NR'NR"R"', —ONR'R", —NR'C(O)NR"NR"'R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, —NR—C(NR'R"R"')=NR"", —NR—C(NR'R")=NR"', —S(O)R', $—S(O)_2R'$, $—S(O)_2NR'R"$, $—NRSO_2R'$, —NR'NR"R"', —ONR'R", —NR'C(O)NR"NR"'R"", —CN, $—NO_2$, —R', $—N_3$, $—CH(Ph)_2$, fluoro($C_1$-$C_4$)alkoxy, and fluoro($C_1$-$C_4$)alkyl, $—NR'SO_2R"$, —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings, bridged rings, or spirocyclic rings, a substituent depicted as associated with one member of the fused rings, bridged rings, or spirocyclic rings (a floating substituent on a single ring), may be a substituent on any of the fused rings, bridged rings, or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different bridged rings, or different spirocyclic rings, and each substituent may optionally be different. Where a point of attachment of a ring to the remainder of a molecule is not limited to a single atom (a floating substituent), the attachment point may be any atom of the ring and in the case of fused rings, bridged rings, or spirocyclic rings, any atom of any of the fused rings, bridged rings, or spirocyclic rings while obeying the rules of chemical valency. Where a ring, fused rings, bridged rings, or spirocyclic rings contain one or more ring heteroatoms and the ring, fused rings, bridged rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure and form a bridged ring structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'-$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'-$, $-O-$, $-NR-$, $-S-$, $-S(O)-$, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X' is $-O-$, $-NR'-$, $-S-$, $-S(O)-$, $-S(O)_2-$, or $-S(O)_2NR'-$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHN_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, $—CCl_3$, $—CBr_3$, $—CF_3$, $—CI_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, FIGURES, or tables below.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "covalent cysteine modifier moiety" as used herein refers to a substituent that is capable of reacting with the sulfhydryl functional group of a cysteine amino acid (e.g. cysteine 442 of the Interleukin-2-inducible T-cell kinase (ITK, TSK) (e.g., human Interleukin-2-inducible T-cell kinase (ITK, TSK)), or amino acid corresponding to cysteine 442 of the Interleukin-2-inducible T-cell kinase) to form a covalent bond. Thus, the covalent cysteine modifier moiety is typically electrophilic.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dyes, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "Interleukin-2-inducible T-cell kinase inhibitor" or "ITK compound" or "ITK inhibitor" refers to a compound (e.g. a compound described herein) that reduces the activity of Interleukin-2-inducible T-cell kinase when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An amino acid residue in a protein "corresponds" to a given residue when it occupies the same essential structural position within the protein as the given residue. For example, a selected residue in a selected protein corresponds to Cys442 of human Interleukin-2-inducible T-cell kinase protein when the selected residue occupies the same essential spatial or other structural relationship as Cys442 in human Interleukin-2-inducible T-cell kinase protein. In some embodiments, where a selected protein is aligned for maximum homology with the human Interleukin-2-inducible T-cell kinase protein, the position in the aligned selected protein aligning with Cys442 is said to correspond to Cys442. Instead of a primary sequence alignment, a three dimensional structural alignment can also be used, e.g., where the structure of the selected protein is aligned for maximum correspondence with the human Interleukin-2-inducible T-cell kinase protein and the overall structures compared. In this case, an amino acid that occupies the same essential position as Cys442 in the structural model is said to correspond to the Cys442 residue.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "Interleukin-2-inducible T-cell kinase inhibitor" and "ITK inhibitor" is a compound that negatively affects (e.g. decreases) the activity or function of Interleukin-2-inducible T-cell kinase relative to the activity or function of Interleukin-2-inducible T-cell kinase in the absence of the inhibitor (e.g., wherein the ITK inhibitor binds ITK).

The terms "Interleukin-2-inducible T-cell kinase" and "ITK" refer to a protein (including homologs, isoforms, and functional fragments thereof) with Interleukin-2-inducible T-cell kinase activity. The term includes any recombinant or naturally-occurring form of Interleukin-2-inducible T-cell kinase or variants thereof that maintain Interleukin-2-inducible T-cell kinase activity (e.g. within at least 30%, 40%, 50%, 60%, 70%, 80%, 90%, 95%, or 100% activity compared to wildtype Interleukin-2-inducible T-cell kinase). In embodiments, the Interleukin-2-inducible T-cell kinase protein encoded by the ITK gene has the amino acid sequence set forth in or corresponding to Entrez 3702, UniProt Q08881, or RefSeq (protein) NP_005537. In embodiments, the Interleukin-2-inducible T-cell kinase ITK gene has the nucleic acid sequence set forth in RefSeq (mRNA) NM_005546. In embodiments, the amino acid sequence or nucleic acid sequence is the sequence known at the time of filing of the present application. In embodiments, the sequence corresponds to GI: 15718680. In embodiments, the sequence corresponds to NP_005537.3. In embodiments, the sequence corresponds to NM_005546.3. In embodiments, the sequence corresponds to GI: 21614549. In embodiments, the Interleukin-2-inducible T-cell kinase is a human Interleukin-2-inducible T-cell kinase, such as a human cancer causing Interleukin-2-inducible T-cell kinase.

The terms "Tec kinase" and "Tec kinase family" refer to a protein family (including homologs, isoforms, and functional fragments thereof) of non-receptor protein tyrosine kinases including the proteins TEC, BTK (Bruton's Tyrosine Kinase), ITK/EMT/TSK, BMX, and TXK/RLK. The term includes any recombinant or naturally-occurring form of a Tec family kinase or variant thereof that maintains Tec family kinase activity (e.g. within at least 30%, 40%, 50%, 60%, 70%, 80%, 90%, 95%, or 100% activity compared to wildtype Tec family kinase).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemia, lymphoma, melanoma, carcinomas, and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "lymphoma" refers to a neoplasm of the hematopoietic and lymphoid tissues (e.g., blood, bone marrow, lymph, or lymph tissues). Non-limiting examples of lymphoma include B-acute lymphoblastic lymphoma, non-Hodgkin's lymphomas (e.g., Burkitt's, Small Cell, and Large Cell lymphomas), or Hodgkin's lymphoma.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient", "subject", or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, such as treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (e.g., a compound described herein) required to decrease the activity of an enzyme relative to the absence of the antagonist. A "function disrupting amount," as used herein, refers to the amount of antagonist (e.g., a compound described herein) required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, an Interleukin-2-inducible T-cell kinase associated disease modulator is a compound that reduces the severity of one or more symptoms of a disease associated with Interleukin-2-inducible T-cell kinase (e.g. cancer, inflammatory disease, autoimmune disease, or infectious disease). An Interleukin-2-inducible T-cell kinase modulator is a compound that increases or decreases the activity or function or level of activity or level of function of Interleukin-2-inducible T-cell kinase.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with Interleukin-2-inducible T-cell kinase activity, Interleukin-2-inducible T-cell kinase associated cancer, Interleukin-2-inducible T-cell kinase associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. For example, a cancer associated with Interleukin-2-inducible T-cell kinase activity or function may be a cancer that results (entirely or partially) from aberrant Interleukin-2-inducible T-cell kinase function (e.g. enzyme activity, protein-protein interaction, signaling pathway) or a cancer wherein a particular symptom of the disease is caused (entirely or partially) by aberrant Interleukin-2-inducible T-cell kinase activity or function. As used herein, what is described as being associated with a disease, if a causative agent, could be a target for treatment of the disease. For example, a cancer associated with Interleukin-2-inducible T-cell kinase activity or function or a Interleukin-2-inducible T-cell kinase associated disease (e.g., cancer, inflammatory disease, autoimmune disease, or infectious disease), may be treated with a Interleukin-2-inducible T-cell kinase modulator or Interleukin-2-inducible T-cell kinase inhibitor, in the instance where increased Interleukin-2-inducible T-cell kinase activity or function (e.g. signaling pathway activity) causes the disease (e.g., cancer, inflammatory disease, autoimmune disease, or infectious disease). For example, an inflammatory disease associated with Interleukin-2-inducible T-cell kinase activity or function or an Interleukin-2-inducible T-cell kinase associated inflammatory disease, may be treated with an Interleukin-2-inducible T-cell kinase modulator or Interleukin-2-inducible T-cell kinase inhibitor, in the instance where increased Interleukin-2-inducible T-cell kinase activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components. For example, binding of a Interleukin-2-inducible T-cell kinase with a compound as described herein may reduce the level of a product of the Interleukin-2-inducible T-cell kinase catalyzed reaction or the level of a downstream derivative of the product or binding may reduce the interactions between the Interleukin-2-inducible T-cell kinase enzyme or an Interleukin-2-inducible T-cell kinase reaction product and downstream effectors or signaling pathway components, resulting in changes in cell growth, proliferation, or survival.

The term "electrophilic chemical moiety" is used in accordance with its plain ordinary chemical meaning and refers to a monovalent chemical group that is electrophilic.

Compounds

In an aspect is provided a compound having the formula:

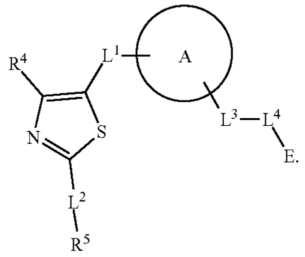

Ring A is

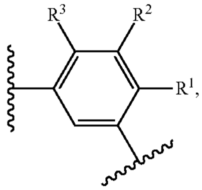
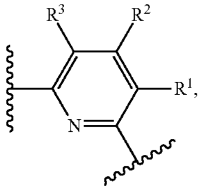
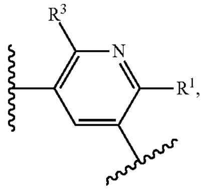
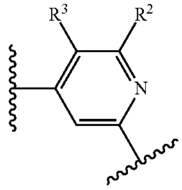
,
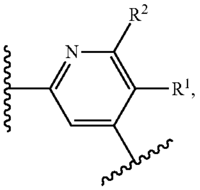
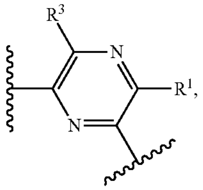
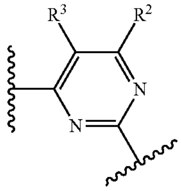
,
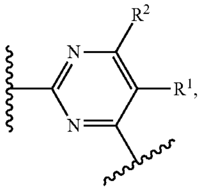
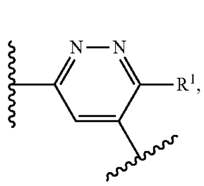
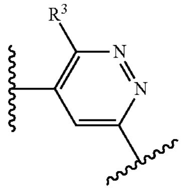
,
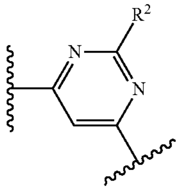
or
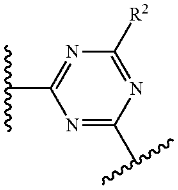
.

$R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—N(O)_{m1}$, $—NR^{1A}R^{1B}$, $—C(O)\ R^{1C}$, $—C(O)—OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_2R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ is $-O-$, $-S-$, or substituted or unsubstituted $C_1$-$C_2$ alkylene, or substituted or unsubstituted 2 membered heteroalkylene.

$L^2$ is a bond, $-NH-$, $-C(O)NH-$, or $-NHC(O)-$.

$L^3$ is a bond, $-S(O)_2-$, $-N(R^6)-$, $-O-$, $-S-$, $-C(O)-$, $-C(O)N(R^6)-$, $-N(R^6)C(O)-$, $-N(R^6)C(O)NH-$, $-NHC(O)N(R^6)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^6$ is independently hydrogen, $-CX^6_3$, $-CHX^6_2$, $-CH_2X^6$, $-CN$, $-C(O)R^{6C}$, $-C(O)OR^{6C}$, $-C(O)NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^4$ is a bond, $-S(O)_2-$, $-N(R^7)-$, $-O-$, $-S-$, $-C(O)-$, $-C(O)N(R^7)-$, $-N(R^7)C(O)-$, $-N(R^7)C(O)NH-$, $-NHC(O)N(R^7)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^7$ is independently hydrogen, $-CX^7_3$, $-CHX^7_2$, $-CH_2X^7$, $-CN$, $-C(O)R^{7C}$, $-C(O)OR^{7C}$, $-C(O)NR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

E is an electrophilic moiety.

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$, $R^{7A}$, $R^{7B}$, and $R^{7C}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl.

Each X, $X^1$, $X^2$, $X^3$, $X^4$, $X^6$, and $X^7$ is independently $-F$, $-Cl$, $-Br$, or $-I$.

The symbols n1, n2, n3, and n4 are each independently an integer from 0 to 4.

The symbols m1, m2, m3, m4, v1, v2, v3, and v4 are each independently 1 or 2.

In embodiments, the compound has the formula:

(I)

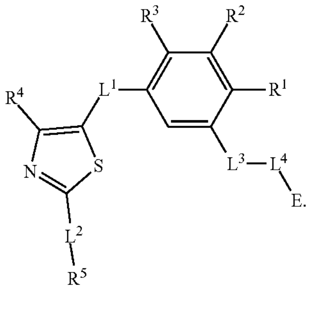

$R^1$, $R^2$, $R^3$, $R^4$, $R^5$, $L^1$, $L^2$, $L^3$, $L^4$, and E are as described herein.

In embodiments, the compound has the formula:

(II)

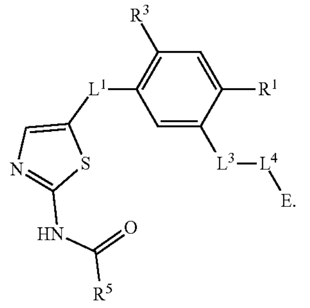

$R^1$, $R^3$, $R^5$, $L^1$, $L^3$, $L^4$, and E are as described herein.

In embodiments, the compound has the formula:

(IIA)

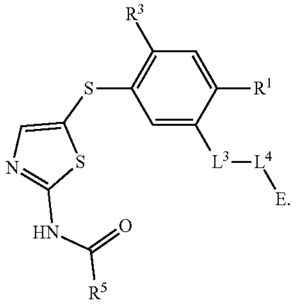

$R^1$, $R^3$, $R^5$, $L^3$, $L^4$, and E are as described herein.

In embodiments, the compound has the formula:

(IIB)

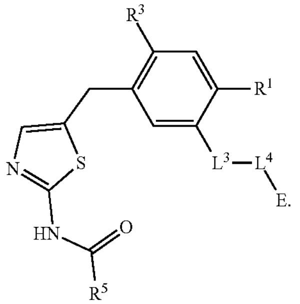

$R^1$, $R^3$, $R^5$, $L^3$, $L^4$, and E are as described herein.

In embodiments, the compound has the formula:

(IIC)

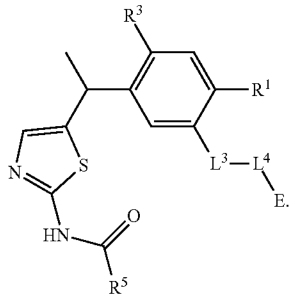

$R^1$, $R^3$, $R^5$, $L^3$, $L^4$, and E are as described herein.

In embodiments, the compound has the formula:

(III)

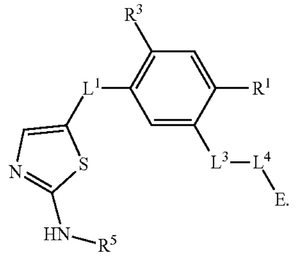

$R^1$, $R^3$, $R^5$, $L^3$, $L^4$, and E are as described herein.

In embodiments, the compound has the formula:

(IIIA)

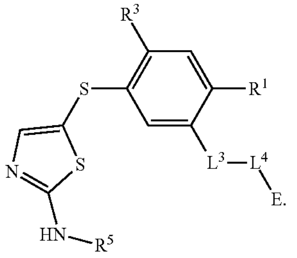

$R^1$, $R^3$, $R^5$, $L^3$, $L^4$, and E are as described herein.

In embodiments, the compound has the formula:

(IIIB)

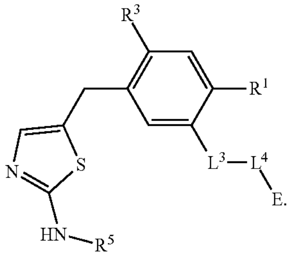

$R^1$, $R^3$, $R^5$, $L^3$, $L^4$, and E are as described herein.

In embodiments, the compound has the formula:

(IIIC)

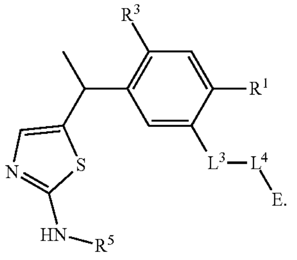

$R^1$, $R^3$, $R^5$, $L^3$, $L^4$, and E are as described herein.

In embodiments, Ring A is
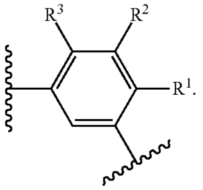
In embodiments, Ring A is
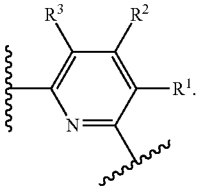
In embodiments, Ring A is
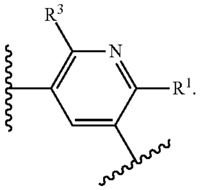
In embodiments, Ring A is
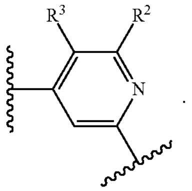
In embodiments, Ring A is
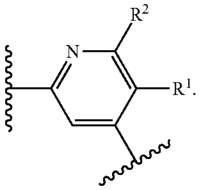
In embodiments, Ring A is
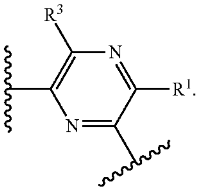
In embodiments, Ring A is
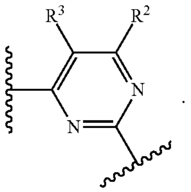
In embodiments, Ring A is
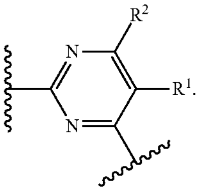
In embodiments, Ring A is
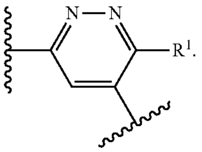
In embodiments, Ring A is
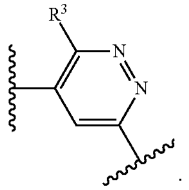
In embodiments, Ring A is
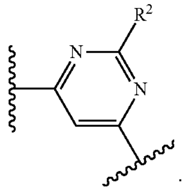

In embodiments, Ring A is

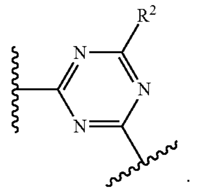

In embodiments, $R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^1$ is independently hydrogen, halogen, $—CX^1_3$, $—CHX^1_2$, $—CH_2X^1$, $—OCX^1_3$, $—OCH_2X^1$, $—OCHX^1_2$, substituted or unsubstituted alkyl, or substituted or unsubstituted heteroalkyl. In embodiments, $R^1$ is independently hydrogen, halogen, $—CX^1_3$, $—CHX^1_2$, $—CH_2X^1$, $—OCX^1_3$, $—OCH_2X^1$, $—OCHX^1_2$, substituted or unsubstituted ($C_1$-$C_4$) alkyl, or substituted or unsubstituted 2 to 4 membered heteroalkyl. In embodiments, $R^1$ is hydrogen, halogen, $—CH_3$, $—CH_2CH_3$, $—CX^1_3$, $—CHX^1_2$, $—CH_2X^1$, $—OCH_3$, $—OCX^1_3$, $—OCH_2X^1$, $—OCHX^1_2$, $—SCH_3$, $—SCX^1_3$, $—SCH_2X^1$, or $—SCHX^1_2$. In embodiments, $R^1$ is hydrogen, halogen, $—CH_3$, $—CH_2CH_3$, $—CF_3$, or $—OCH_3$. In embodiments, $R^1$ is $—CH_3$, $—CH_2CH_3$, or $—OCH_3$. In embodiments, $R^1$ is $—OCH_3$. In embodiments, $R^1$ is independently hydrogen, halogen, $—CX^1_3$, $—CHX^1_2$, $—CH_2X^1$, $—OCX^1_3$, $—OCH_2X^1$, $—OCHX^1_2$, —CN, substituted or unsubstituted alkyl, or substituted or unsubstituted heteroalkyl. In embodiments, $R^1$ is independently hydrogen, halogen, $—CX^1_3$, $—CHX^1_2$, $—CH_2X^1$, $—OCX^1_3$, $—OCH_2X^1$, $—OCHX^1_2$, —CN, substituted or unsubstituted ($C_1$-$C_4$) alkyl, or substituted or unsubstituted 2 to 4 membered heteroalkyl. In embodiments, $R^1$ is hydrogen, halogen, $—CH_3$, $—CH_2CH_3$, $—CX^1_3$, $—CHX^1_2$, $—CH_2X^1$, $—OCH_3$, $—OCX^1_3$, $—OCH_2X^1$, $—OCHX^1_2$, —CN, $—SCH_3$, $—SCX^1_3$, $—SCH_2X^1$, or $—SCHX^1_2$. In embodiments, $R^1$ is hydrogen, halogen, —CN, $—CH_3$, $—CF_3$, or $—OCH_3$. In embodiments, $R^1$ is halogen or $—CH_3$. In embodiments, $R^1$ is —Cl or $—CH_3$. In embodiments, $R^1$ is $—CH_3$. In embodiments, $R^1$ is hydrogen. In embodiments, $R^1$ is $—CH_3$ or $—CH_2CH_3$.

In embodiments, $R^1$ is independently hydrogen, halogen, $—CX^1_3$, —CN, —OH, $—NH_2$, —SH, $—OCX^1_3$, $—OCHX^1_2$, $—OCH_2X^1$, $—CHX^1_2$, $—CH_2X^1$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^1$ is independently hydrogen, halogen, $—CX^1_3$, —CN, —OH, $—NH_2$, —SH, $—OCX^1_3$, $—OCHX^1_2$, $—OCH_2X^1$, $—CHX^1_2$, $—CH_2X^1$, unsubstituted $C_1$-$C_4$ alkyl, or unsubstituted 2 to 4 membered heteroalkyl.

In embodiments, $R^1$ is independently hydrogen. In embodiments, $R^1$ is independently halogen. In embodiments, $R^1$ is independently $—CX^1_3$. In embodiments, $R^1$ is independently $—CHX^1_2$. In embodiments, $R^1$ is independently $—CH_2X^1$. In embodiments, $R^1$ is independently $—OCX^1_3$. In embodiments, $R^1$ is independently $—OCH_2X^1$. In embodiments, $R^1$ is independently $—OCHX^1_2$. In embodiments, $R^1$ is independently —CN. In embodiments, $R^1$ is independently $—SO_{n1}R^{1D}$. In embodiments, $R^1$ is independently $—SO_{v1}NR^{1A}R^{1B}$. In embodiments, $R^1$ is independently $—NHC(O)NR^{1A}R^{1B}$. In embodiments, $R^1$ is independently $—N(O)_{m1}$. In embodiments, $R^1$ is independently $—NR^{1A}R^{1B}$. In embodiments, $R^1$ is independently $—C(O)R^{1C}$. In embodiments, $R^1$ is independently $—C(O)—OR^{1C}$. In embodiments, $R^1$ is independently $—C(O)NR^{1A}R^{1B}$. In embodiments, $R^1$ is independently $—OR^{1D}$. In embodiments, $R^1$ is independently $—NR^{1A}SO_2R^{1D}$. In embodiments, $R^1$ is independently $—NR^{1A}C(O)R^{1C}$. In embodiments, $R^1$ is independently $—NR^{1A}C(O)OR^{1C}$. In embodiments, $R^1$ is independently $—NR^{1A}OR^{1C}$. In embodiments, $R^1$ is independently —OH. In embodiments, $R^1$ is independently $—NH_2$. In embodiments, $R^1$ is independently —COOH. In embodiments, $R^1$ is independently $—CONH_2$. In embodiments, $R^1$ is independently $—NO_2$. In embodiments, $R^1$ is independently —SH. In embodiments, $R^1$ is independently $—CF_3$. In embodiments, $R^1$ is independently $—CHF_2$. In embodiments, $R^1$ is independently $—CH_2F$. In embodiments, $R^1$ is independently $—OCF_3$. In embodiments, $R^1$ is independently $—OCH_2F$. In embodiments, $R^1$ is independently $—OCHF_2$. In embodiments, $R^1$ is independently $—OCH_3$. In embodiments, $R^1$ is independently $—OCH_2CH_3$. In embodiments, $R^1$ is independently $—OCH_2CH_2CH_3$. In embodiments, $R^1$ is independently $—OCH(CH_3)_2$. In embodiments, $R^1$ is independently $—OC(CH_3)_3$. In embodiments, $R^1$ is independently $—SCH_3$. In embodiments, $R^1$ is independently $—SCH_2CH_3$. In embodiments, $R^1$ is independently $—SCH_2CH_2CH_3$. In embodiments, $R^1$ is independently $—SCH(CH_3)_2$. In embodiments, $R^1$ is independently $—SC(CH_3)_3$. In embodiments, $R^1$ is independently $—CH_3$. In embodiments, $R^1$ is independently $—CH_2CH_3$. In embodiments, $R^1$ is independently $—CH_2CH_2CH_3$. In embodiments, $R^1$ is independently $—CH(CH_3)_2$. In embodiments, $R^1$ is independently $—C(CH_3)_3$. In embodiments, $R^1$ is independently —F. In embodiments, $R^1$ is independently —Cl. In embodiments, $R^1$ is independently —Br. In embodiments, $R^1$ is independently —I.

In embodiments, $R^1$ is independently substituted or unsubstituted alkyl (e.g., $C_1$-$C_8$, $C_1$-$C_6$, $C_1$-$C_4$, or $C_1$-$C_2$). In embodiments, $R^1$ is independently substituted alkyl (e.g., $C_1$-$C_8$, $C_1$-$C_6$, $C_1$-$C_4$, or $C_1$-$C_2$). In embodiments, $R^1$ is independently unsubstituted alkyl (e.g., $C_1$-$C_8$, $C_1$-$C_6$, $C_1$-$C_4$, or $C_1$-$C_2$). In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted isopropyl. In embodiments, $R^1$ is independently unsubstituted tert-butyl. In embodiments, $R^1$ is independently substituted or unsubstituted heteroalkyl (e.g., 2 to 8 membered, 2 to 6 membered, 4 to 6 membered, 2 to 3 membered, or 4 to 5 membered). In embodiments, $R^1$ is independently substituted heteroalkyl (e.g., 2 to 8 membered, 2 to 6 membered, 4 to 6 membered, 2 to 3 membered, or 4 to 5 membered). In embodiments, $R^1$ is independently unsubstituted heteroalkyl (e.g., 2 to 8 membered, 2 to 6 membered, 4 to 6 membered, 2 to 3 membered, or 4 to 5 membered). In embodiments, $R^1$ is independently substituted or unsubstituted cycloalkyl (e.g., $C_3$-$C_8$, $C_3$-$C_6$, $C_4$-$C_6$, or $C_5$-$C_6$). In embodiments, $R^1$ is independently substituted cycloalkyl (e.g., $C_3$-$C_8$, $C_3$-$C_6$, $C_4$-$C_6$, or $C_5$-$C_6$). In embodiments, $R^1$ is independently unsubstituted cycloalkyl (e.g., $C_3$-$C_8$, $C_3$-$C_6$, $C_4$-$C_6$, or $C_5$-$C_6$). In embodiments, $R^1$ is independently substituted or unsubstituted heterocycloalkyl (e.g., 3 to 8 membered, 3 to 6 membered, 4 to 6 membered, 4 to 5 membered, or 5 to 6 membered). In embodiments, $R^1$ is independently substituted heterocycloalkyl (e.g., 3 to 8 membered, 3 to 6 membered, 4 to 6 membered, 4 to 5 membered, or 5 to 6 membered). In embodiments, $R^1$ is independently unsubstituted heterocycloalkyl (e.g., 3 to 8 membered, 3 to 6 membered, 4 to 6 membered, 4 to 5 membered, or 5 to 6 membered). In embodiments, $R^1$ is independently substituted or unsubstituted aryl (e.g., $C_6$-$C_{10}$ or phenyl). In embodiments, $R^1$ is independently substituted aryl (e.g., $C_6$-$C_{10}$ or phenyl). In embodiments, $R^1$ is independently unsubstituted aryl (e.g., $C_6$-$C_{10}$ or phenyl). In embodiments, $R^1$ is independently substituted or unsubstituted heteroaryl (e.g., 5 to 10 membered, 5 to 9 membered, or 5 to 6 membered). In embodiments, $R^1$ is independently substituted heteroaryl (e.g., 5 to 10 membered, 5 to 9 membered, or 5 to 6 membered). In embodiments, $R^1$ is independently unsubstituted heteroaryl (e.g., 5 to 10 membered, 5 to 9 membered, or 5 to 6 membered).

In embodiments, $R^{1A}$ is independently hydrogen. In embodiments, $R^{1A}$ is independently —$CX^{1A}_3$. In embodiments, $R^{1A}$ is independently —$CHX^{1A}_2$. In embodiments, $R^{1A}$ is independently —$CH_2X^{1A}$. In embodiments, $R^{1A}$ is independently —CN. In embodiments, $R^{1A}$ is independently —COOH. In embodiments, $R^{1A}$ is independently —$CONH_2$. In embodiments, $X^{1A}$ is independently —F, —Cl, —Br, or —I.

In embodiments, $R^{1A}$ is independently substituted or unsubstituted alkyl (e.g., $C_1$-$C_8$, $C_1$-$C_6$, $C_1$-$C_4$, or $C_1$-$C_2$). In embodiments, $R^{1A}$ is independently substituted alkyl (e.g., $C_1$-$C_8$, $C_1$-$C_6$, $C_1$-$C_4$, or $C_1$-$C_2$). In embodiments, $R^{1A}$ is independently unsubstituted alkyl (e.g., $C_1$-$C_8$, $C_1$-$C_6$, $C_1$-$C_4$, or $C_1$-$C_2$). In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl. In embodiments, $R^{1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted heteroalkyl (e.g., 2 to 8 membered, 2 to 6 membered, 4 to 6 membered, 2 to 3 membered, or 4 to 5 membered). In embodiments, $R^{1A}$ is independently unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted or unsubstituted cycloalkyl (e.g., $C_3$-$C_8$, $C_3$-$C_6$, $C_4$-$C_6$, or $C_5$-$C_6$). In embodiments, $R^{1A}$ is independently substituted cycloalkyl (e.g., $C_3$-$C_8$, $C_3$-$C_6$, $C_4$-$C_6$, or $C_5$-$C_6$). In embodiments, $R^{1A}$ is independently unsubstituted cycloalkyl (e.g., $C_3$-$C_8$, $C_3$-$C_6$, $C_4$-$C_6$, or $C_5$-$C_6$). In embodiments, $R^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted heterocycloalkyl (e.g., 3 to 8 membered, 3 to 6 membered, 4 to 6 membered, 4 to 5 membered, or 5 to 6 membered). In embodiments, $R^{1A}$ is independently unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted or unsubstituted aryl (e.g., $C_6$-$C_{10}$ or phenyl). In embodiments, $R^{1A}$ is independently substituted aryl (e.g., $C_6$-$C_{10}$ or phenyl). In embodiments, $R^{1A}$ is independently unsubstituted aryl (e.g., $C_6$-$C_{10}$ or phenyl). In embodiments, $R^{1A}$ is independently substituted or unsubstituted heteroaryl (e.g., 5 to 10 membered, 5 to 9 membered, or 5 to 6 membered). In embodiments, $R^{1A}$ is independently substituted heteroaryl (e.g., 5 to 10 membered, 5 to 9 membered, or 5 to 6 membered). In embodiments, $R^{1A}$ is independently unsubstituted heteroaryl (e.g., 5 to 10 membered, 5 to 9 membered, or 5 to 6 membered).

In embodiments, $R^{1B}$ is independently hydrogen. In embodiments, $R^{1B}$ is independently —$CX^{1B}_3$. In embodiments, $R^{1B}$ is independently —$CHX^{1B}_2$. In embodiments, $R^{1B}$ is independently —$CH_2X^{1B}$. In embodiments, $R^{1B}$ is independently —CN. In embodiments, $R^{1B}$ is independently —COOH. In embodiments, $R^{1B}$ is independently —$CONH_2$. In embodiments, $X^{1B}$ is independently —F, —Cl, —Br, or —I.

In embodiments, $R^{1B}$ is independently substituted or unsubstituted alkyl (e.g., $C_1$-$C_8$, $C_1$-$C_6$, $C_1$-$C_4$, or $C_1$-$C_2$). In embodiments, $R^{1B}$ is independently substituted alkyl (e.g., $C_1$-$C_8$, $C_1$-$C_6$, $C_1$-$C_4$, or $C_1$-$C_2$). In embodiments, $R^{1B}$ is independently unsubstituted alkyl (e.g., $C_1$-$C_8$, $C_1$-$C_6$, $C_1$-$C_4$, or $C_1$-$C_2$). In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl. In embodiments, $R^{1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted heteroalkyl (e.g., 2 to 8 membered, 2 to 6 membered, 4 to 6 membered, 2 to 3 membered, or 4 to 5 membered). In embodiments, $R^{1B}$ is independently unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted or unsubstituted cycloalkyl (e.g., $C_3$-$C_8$, $C_3$-$C_6$, $C_4$-$C_6$, or $C_5$-$C_6$). In embodiments, $R^{1B}$ is independently substituted cycloalkyl (e.g., $C_3$-$C_8$, $C_3$-$C_6$, $C_4$-$C_6$, or $C_5$-$C_6$). In embodiments, $R^{1B}$ is independently unsubstituted cycloalkyl (e.g., $C_3$-$C_8$, $C_3$-$C_6$, $C_4$-$C_6$, or $C_5$-$C_6$). In embodiments, $R^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted heterocycloalkyl (e.g., 3 to 8 membered, 3 to 6 membered, 4 to 6 membered, 4 to 5 membered, or 5 to 6 membered). In embodiments, $R^{1B}$ is independently unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted or unsubstituted aryl (e.g., $C_6$-$C_{10}$ or phenyl). In embodiments, $R^{1B}$ is independently substituted aryl (e.g., $C_6$-$C_{10}$ or phenyl). In embodiments, $R^{1B}$ is independently unsubstituted aryl (e.g., $C_6$-$C_{10}$ or phenyl). In embodiments, $R^{1B}$ is independently substituted or unsubstituted heteroaryl (e.g., 5 to 10 membered, 5 to 9 membered, or 5 to 6 membered). In embodiments, $R^{1B}$ is independently substituted heteroaryl (e.g., 5 to 10 membered, 5 to 9 membered, or 5 to 6 membered). In embodiments, $R^{1B}$ is independently unsubstituted heteroaryl (e.g., 5 to 10 membered, 5 to 9 membered, or 5 to 6 membered).

In embodiments, $R^{1A}$ and $R^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{1A}$ and $R^{1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form a substituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form an unsubstituted heteroaryl (e.g., 5 to 10 membered, 5 to 9 membered, or 5 to 6 membered).

In embodiments, $R^{1C}$ is independently hydrogen. In embodiments, $R^{1C}$ is independently $-CX^{1C}_3$. In embodiments, $R^{1C}$ is independently $-CHX^{1C}_2$. In embodiments, $R^{1C}$ is independently $-CH_2X^{1C}$. In embodiments, $R^{1C}$ is independently —CN. In embodiments, $R^{1C}$ is independently —COOH. In embodiments, $R^{1C}$ is independently $-CONH_2$. In embodiments, $X^{1C}$ is independently —F, —Cl, —Br, or —I.

In embodiments, $R^{1C}$ is independently substituted or unsubstituted alkyl (e.g., $C_1$-$C_8$, $C_1$-$C_6$, $C_1$-$C_4$, or $C_1$-$C_2$). In embodiments, $R^{1C}$ is independently substituted alkyl (e.g., $C_1$-$C_8$, $C_1$-$C_6$, $C_1$-$C_4$, or $C_1$-$C_2$). In embodiments, $R^{1C}$ is independently unsubstituted alkyl (e.g., $C_1$-$C_8$, $C_1$-$C_6$, $C_1$-$C_4$, or $C_1$-$C_2$). In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl. In embodiments, $R^{1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted heteroalkyl (e.g., 2 to 8 membered, 2 to 6 membered, 4 to 6 membered, 2 to 3 membered, or 4 to 5 membered). In embodiments, $R^{1C}$ is independently unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted or unsubstituted cycloalkyl (e.g., $C_3$-$C_8$, $C_3$-$C_6$, $C_4$-$C_6$, or $C_5$-$C_6$). In embodiments, $R^{1C}$ is independently substituted cycloalkyl (e.g., $C_3$-$C_8$, $C_3$-$C_6$, $C_4$-$C_6$, or $C_5$-$C_6$). In embodiments, $R^{1C}$ is independently unsubstituted cycloalkyl (e.g., $C_3$-$C_8$, $C_3$-$C_6$, $C_4$-$C_6$, or $C_5$-$C_6$). In embodiments, $R^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted heterocycloalkyl (e.g., 3 to 8 membered, 3 to 6 membered, 4 to 6 membered, 4 to 5 membered, or 5 to 6 membered). In embodiments, $R^{1C}$ is independently unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted or unsubstituted aryl (e.g., $C_6$-$C_{10}$ or phenyl). In embodiments, $R^{1C}$ is independently substituted aryl (e.g., $C_6$-$C_{10}$ or phenyl). In embodiments, $R^{1C}$ is independently unsubstituted aryl (e.g., $C_6$-$C_{10}$ or phenyl). In embodiments, $R^{1C}$ is independently substituted or unsubstituted heteroaryl (e.g., 5 to 10 membered, 5 to 9 membered, or 5 to 6 membered). In embodiments, $R^{1C}$ is independently substituted heteroaryl (e.g., 5 to 10 membered, 5 to 9 membered, or 5 to 6 membered). In embodiments, $R^{1C}$ is independently unsubstituted heteroaryl (e.g., 5 to 10 membered, 5 to 9 membered, or 5 to 6 membered).

In embodiments, $R^{1D}$ is independently hydrogen. In embodiments, $R^{1D}$ is independently $-CX^{1D}_3$. In embodiments, $R^{1D}$ is independently $-CHX^{1D}_2$. In embodiments, $R^{1D}$ is independently $-CH_2X^{1D}$. In embodiments, $R^{1D}$ is independently —CN. In embodiments, $R^{1D}$ is independently —COOH. In embodiments, $R^{1D}$ is independently $-CONH_2$. In embodiments, $X^{1D}$ is independently —F, —Cl, —Br, or —I.

In embodiments, $R^{1D}$ is independently substituted or unsubstituted alkyl (e.g., $C_1$-$C_8$, $C_1$-$C_6$, $C_1$-$C_4$, or $C_1$-$C_2$). In embodiments, $R^{1D}$ is independently substituted alkyl (e.g., $C_1$-$C_8$, $C_1$-$C_6$, $C_1$-$C_4$, or $C_1$-$C_2$). In embodiments, $R^{1D}$ is independently unsubstituted alkyl (e.g., $C_1$-$C_8$, $C_1$-$C_6$, $C_1$-$C_4$, or $C_1$-$C_2$). In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl. In embodiments, $R^{1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted heteroalkyl (e.g., 2 to 8 membered, 2 to 6 membered, 4 to 6 membered, 2 to 3 membered, or 4 to 5 membered). In embodiments, $R^{1D}$ is independently unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted or unsubstituted cycloalkyl (e.g., $C_3$-$C_8$, $C_3$-$C_6$, $C_4$-$C_6$, or $C_5$-$C_6$). In embodiments, $R^{1D}$ is independently substituted cycloalkyl (e.g., $C_3$-$C_8$, $C_3$-$C_6$, $C_4$-$C_6$, or $C_5$-$C_6$). In embodiments, $R^{1D}$ is independently unsubstituted cycloalkyl (e.g., $C_3$-$C_8$, $C_3$-$C_6$, $C_4$-$C_6$, or $C_5$-$C_6$). In embodiments, $R^{1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted heterocycloalkyl (e.g., 3 to 8 membered, 3 to 6 membered, 4 to 6 membered, 4 to 5 membered, or 5 to 6 membered). In embodiments, $R^{1D}$ is independently unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted or unsubstituted aryl (e.g., $C_6$-$C_{10}$ or phenyl). In embodiments, $R^{1D}$ is independently substituted aryl (e.g., $C_6$-$C_{10}$ or phenyl). In embodiments, $R^{1D}$ is independently unsubstituted aryl (e.g., $C_6$-$C_{10}$ or phenyl). In embodiments, $R^{1D}$ is independently substituted or unsubstituted heteroaryl (e.g., 5 to 10 membered, 5 to 9 membered, or 5 to 6 membered). In embodiments, $R^{1D}$ is independently substituted heteroaryl (e.g., 5 to 10 membered, 5 to 9 membered, or 5 to 6 membered). In embodiments, RD is independently unsubstituted heteroaryl (e.g., 5 to 10 membered, 5 to 9 membered, or 5 to 6 membered).

In embodiments, $R^1$ is independently hydrogen, halogen, $-CX^1_3$, $-CHX^1_2$, $-CH_2X^1$, $-OCX^1_3$, $-OCH_2X^1$, $-OCHX^1_2$, —CN, —OH, $-NH_2$, —COOH, $-CONH_2$, $-NO_2$, —SH, $-SO_3H$, $-SO_4H$, $-SO_2NH_2$, $-NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^1$ is independently —F, —Cl, —Br, or —I. In embodiments, $R^1$ is independently hydrogen. In embodiments, $R^1$ is independently unsubstituted methyl. In embodiments, $R^1$ is independently unsubstituted ethyl.

$R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), or $R^{21}$-substituted or unsubstituted heteroaryl (e.g., 5 to 10 membered, 5 to 9 membered, or 5 to 6 membered). In embodiments, $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20}$ is independently —F, —Cl, —Br, or —I. In embodiments, $R^{20}$ is independently unsubstituted methyl. In embodiments, $R^{20}$ is independently unsubstituted ethyl.

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered). In embodiments, $R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21}$ is independently —F, —Cl, —Br, or —I. In embodiments, $R^{21}$ is independently unsubstituted methyl. In embodiments, $R^{21}$ is independently unsubstituted ethyl.

$R^{22}$ is independently oxo, halogen, —$CX^{22}_3$, —$CHX^{22}_2$, —$CH_2X^{22}$, —$OCX^{22}_3$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22}$ is independently —F, —Cl, —Br, or —I. In embodiments, $R^{22}$ is independently unsubstituted methyl. In embodiments, $R^{22}$ is independently unsubstituted ethyl.

In embodiments, $R^{1A}$ is independently hydrogen, —$CX^{1A}_3$, —$CHX^{1A}_2$, —$CH_2X^{1A}$, —CN, —COOH, —$CONH_2$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 to 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 8 membered, 3 to 6 membered, 4 to 6 membered, 4 to 5 membered, or 5 to 6 membered), $R^{20A}$-substituted or unsubstituted aryl (e.g., $C_6$-$C_{10}$ or phenyl), or $R^{20A}$-substituted or unsubstituted heteroaryl (e.g., 5 to 10 membered, 5 to 9 membered, or 5 to 6 membered). In embodiments, $R^{1A}$ is independently hydrogen, —$CX^{1A}_3$, —$CHX^{1A}_2$, —$CH_2X^{1A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1A}$ is independently —F, —Cl, —Br, or —I. In embodiments, $R^{1A}$ is independently hydrogen. In embodiments, $R^{1A}$ is independently unsubstituted methyl. In embodiments, $R^{1A}$ is independently unsubstituted ethyl.

In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered) or $R^{20A}$-substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 8 membered, 3 to 6 membered, 4 to 6 membered, 4 to 5 membered, or 5 to 6 membered), $R^{21A}$-substituted or unsubstituted aryl (e.g., $C_6$-$C_{10}$ or phenyl), or $R^{21A}$-substituted or unsubstituted heteroaryl (e.g., 5 to 10 membered, 5 to 9 membered, or 5 to 6 membered). In embodiments, $R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20A}$ is independently —F, —Cl, —Br, or —I. In embodiments, $R^{20A}$ is independently unsubstituted methyl. In embodiments, $R^{20A}$ is independently unsubstituted ethyl.

$R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{22A}$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 to 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_{10}$ or phenyl), or $R^{22A}$-substituted or unsubstituted heteroaryl (e.g., 5 to 10 membered, 5 to 9 membered, or 5 to 6 membered). In embodiments, $R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21A}$ is independently —F, —Cl, —Br, or —I. In embodiments, $R^{21A}$ is independently unsubstituted methyl. In embodiments, $R^{21A}$ is independently unsubstituted ethyl.

$R^{22A}$ is independently oxo, halogen, —$CX^{22A}_3$, —$CHX^{22A}_2$, —$CH_2X^{22A}$, —$OCX^{22A}_3$, —$OCH_2X^{22A}$, —$OCHX^{22A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22A}$ is independently —F, —Cl, —Br, or —I. In embodiments, $R^{22A}$ is independently unsubstituted methyl. In embodiments, $R^{22A}$ is independently unsubstituted ethyl.

In embodiments, $R^{1B}$ is independently hydrogen, —$CX^{1B}_3$, —$CHX^{1B}_2$, —$CH_2X^{1B}$, —CN, —COOH, —$CONH_2$, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 to 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$-substituted or unsubstituted heterocycloalkyl (e.g., 3 to 8 membered, 3 to 6 membered, 4 to 6 membered, 4 to 5 membered, or 5 to 6 membered), $R^{20B}$-substituted or unsubstituted aryl (e.g., $C_6$-$C_{10}$ or phenyl), or $R^{20B}$-substituted or unsubstituted heteroaryl (e.g., 5 to 10 membered, 5 to 9 membered, or 5 to 6 membered). In embodiments, $R^{1B}$ is independently hydrogen, —$CX^{1B}_3$, —$CHX^{1B}_2$, —$CH_2X^{1B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1B}$ is independently —F, —Cl, —Br, or —I. In embodiments, $R^{1B}$ is independently hydrogen. In embodiments, $R^{1B}$ is independently unsubstituted methyl. In embodiments, $R^{1B}$ is independently unsubstituted ethyl.

In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered) or $R^{20B}$-substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{21B}$-substituted or unsubstituted alkyl (e.g., $C_1$-$C_8$, $C_1$-$C_6$, $C_1$-$C_4$, or $C_1$-$C_2$), $R^{21B}$-substituted or unsubstituted heteroalkyl (e.g., 2 to 8 membered, 2 to 6 membered, 4 to 6 membered, 2 to 3 membered, or 4 to 5 membered), $R^{21B}$-substituted or unsubstituted cycloalkyl (e.g., $C_3$-$C_8$, $C_3$-$C_6$, $C_4$-$C_6$, or $C_5$-$C_6$), $R^{21B}$-substituted or unsubstituted heterocycloalkyl (e.g., 3 to 8 membered, 3 to 6 membered, 4 to 6 membered, 4 to 5 membered, or 5 to 6 membered), $R^{21B}$-substituted or unsubstituted aryl (e.g., $C_6$-$C_{10}$ or phenyl), or $R^{21B}$-substituted or unsubstituted heteroaryl (e.g., 5 to 10 membered, 5 to 9 membered, or 5 to 6 membered). In embodiments, $R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20B}$ is independently —F, —Cl, —Br, or —I. In embodiments, $R^{20B}$ is independently unsubstituted methyl. In embodiments, $R^{20B}$ is independently unsubstituted ethyl.

$R^{21B}$ is independently oxo, halogen, —$CX^{21B}_3$, —$CHX^{21B}_2$, —$CH_2X^{21B}$, —$OCX^{21B}_3$, —$OCH_2X^{21B}$, —$OCHX^{21B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{22B}$-substituted or unsubstituted alkyl (e.g., $C_1$-$C_8$, $C_1$-$C_6$, $C_1$-$C_4$, or $C_1$-$C_2$), $R^{22B}$-substituted or unsubstituted heteroalkyl (e.g., 2 to 8 membered, 2 to 6 membered, 4 to 6 membered, 2 to 3 membered, or 4 to 5 membered), $R^{22B}$-substituted or unsubstituted cycloalkyl (e.g., $C_3$-$C_8$, $C_3$-$C_6$, $C_4$-$C_6$, or $C_5$-$C_6$), $R^{22B}$-substituted or unsubstituted heterocycloalkyl (e.g., 3 to 8 membered, 3 to 6 membered, 4 to 6 membered, 4 to 5 membered, or 5 to 6 membered), $R^{22B}$-substituted or unsubstituted aryl (e.g., $C_6$-$C_{10}$ or phenyl), or $R^{22B}$-substituted or unsubstituted heteroaryl (e.g., 5 to 10 membered, 5 to 9 membered, or 5 to 6 membered). In embodiments, $R^{21B}$ is independently oxo, halogen, —$CX^{21B}_3$, —$CHX^{21B}_2$, —$CH_2X^{21B}$, —$OCX^{21B}_3$, —$OCH_2X^{21B}$, —$OCHX^{21B}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21B}$ is independently —F, —Cl, —Br, or —I. In embodiments, $R^{21B}$ is independently unsubstituted methyl. In embodiments, $R^{21B}$ is independently unsubstituted ethyl.

$R^{22B}$ is independently oxo, halogen, —$CX^{22B}_3$, —$CHX^{22B}_2$, —$CH_2X^{22B}$, —$OCX^{22B}_3$, —$OCH_2X^{22B}$, —$OCHX^{22B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22B}$ is independently —F, —Cl, —Br, or —I. In embodiments, $R^{22B}$ is independently unsubstituted methyl. In embodiments, $R^{22B}$ is independently unsubstituted ethyl.

In embodiments, $R^{1C}$ is independently hydrogen, —$CX^{1C}_3$, —$CHX^{1C}_2$, —$CH_2X^{1C}$, —CN, —COOH, —$CONH_2$, $R^{20C}$-substituted or unsubstituted alkyl (e.g., $C_1$-$C_8$, $C_1$-$C_6$, $C_1$-$C_4$, or $C_1$-$C_2$), $R^{20C}$-substituted or unsubstituted heteroalkyl (e.g., 2 to 8 membered, 2 to 6 membered, 4 to 6 membered, 2 to 3 membered, or 4 to 5 membered), $R^{20C}$-substituted or unsubstituted cycloalkyl (e.g., $C_3$-$C_8$, $C_3$-$C_6$, $C_4$-$C_6$, or $C_5$-$C_6$), $R^{20C}$-substituted or unsubstituted heterocycloalkyl (e.g., 3 to 8 membered, 3 to 6 membered, 4 to 6 membered, 4 to 5 membered, or 5 to 6 membered), $R^{20C}$-substituted or unsubstituted aryl (e.g., $C_6$-$C_{10}$ or phenyl), or $R^{20C}$-substituted or unsubstituted heteroaryl (e.g., 5 to 10 membered, 5 to 9 membered, or 5 to 6 membered). In embodiments, $R^{1C}$ is independently hydrogen, —$CX^{1C}_3$, —$CHX^{1C}_2$, —$CH_2X^{1C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1C}$ is independently —F, —Cl, —Br, or —I. In embodiments, $R^{1C}$ is independently hydrogen. In embodiments, $R^{1C}$ is independently unsubstituted methyl. In embodiments, $R^{1C}$ is independently unsubstituted ethyl.

$R^{20C}$ is independently oxo, halogen, —$CX^{20C}_3$, —$CHX^{20C}_2$, —$CH_2X^{20C}$, —$OCX^{20C}$, —$OCH_2X^{20C}$, —$OCHX^{20C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{21C}$-substituted or unsubstituted alkyl (e.g., $C_1$-$C_8$, $C_1$-$C_6$, $C_1$-$C_4$, or $C_1$-$C_2$), $R^{21C}$-substituted or unsubstituted heteroalkyl (e.g., 2 to 8 membered, 2 to 6 membered, 4 to 6 membered, 2 to 3 membered, or 4 to 5 membered), $R^{21C}$-substituted or unsubstituted cycloalkyl (e.g., $C_3$-$C_8$, $C_3$-$C_6$, $C_4$-$C_6$, or $C_5$-$C_6$), $R^{21C}$-substituted or unsubstituted heterocycloalkyl (e.g., 3 to 8 membered, 3 to 6 membered, 4 to 6 membered, 4 to 5 membered, or 5 to 6 membered), $R^{21C}$-substituted or unsubstituted aryl (e.g., $C_6$-$C_{10}$ or phenyl), or $R^{21C}$-substituted or unsubstituted heteroaryl (e.g., 5 to 10 membered, 5 to 9 membered, or 5 to 6 membered). In embodiments, $R^{20C}$ is independently oxo, halogen, —$CX^{20C}_3$, —$CHX^{20C}_2$, —$CH_2X^{20C}$, —$OCX^{20C}$, —$OCH_2X^{20C}$, —$OCHX^{20C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20C}$ is independently —F, —Cl, —Br, or —I. In embodiments, $R^{20C}$ is independently unsubstituted methyl. In embodiments, $R^{20C}$ is independently unsubstituted ethyl.

$R^{21C}$ is independently oxo, halogen, —$CX^{21C}_3$, —$CHX^{21C}_2$, —$CH_2X^{21C}$, —$OCX^{21C}$, —$OCH_2X^{21C}$, —$OCHX^{21C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{22C}$-substituted or unsubstituted alkyl (e.g., $C_1$-$C_8$, $C_1$-$C_6$, $C_1$-$C_4$, or $C_1$-$C_2$), $R^{22C}$-substituted or unsubstituted heteroalkyl (e.g., 2 to 8 membered, 2 to 6 membered, 4 to 6 membered, 2 to 3 membered, or 4 to 5 membered), $R^{22C}$-substituted or unsubstituted cycloalkyl (e.g., $C_3$-$C_8$, $C_3$-$C_6$, $C_4$-$C_6$, or $C_5$-$C_6$), $R^{22C}$-substituted or unsubstituted heterocycloalkyl (e.g., 3 to 8 membered, 3 to 6 membered, 4 to 6 membered, 4 to 5 membered, or 5 to 6 membered), $R^{22C}$-substituted or unsubstituted aryl (e.g., $C_6$-$C_{10}$ or phenyl), or $R^{22C}$-substituted or unsubstituted heteroaryl (e.g., 5 to 10 membered, 5 to 9 membered, or 5 to 6 membered). In embodiments, $R^{21C}$ is independently oxo, halogen, —$CX^{21C}_3$, —$CHX^{21C}_2$, —$CH_2X^{21C}$, —$OCX^{21C}_3$, —$OCH_2X^{21C}$, —$OCHX^{21C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21C}$ is independently —F, —Cl, —Br, or —I. In embodiments, $R^{21C}$ is independently unsubstituted methyl. In embodiments, $R^{21C}$ is independently unsubstituted ethyl.

$R^{22C}$ is independently oxo, halogen, —$CX^{22C}_3$, —$CHX^{22C}_2$, —$CH_2X^{22C}$, —$OCX^{22C}$, —$OCH_2X^{22C}$, —$OCHX^{22C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22C}$ is independently —F, —Cl, —Br, or —I. In embodiments, $R^{22C}$ is independently unsubstituted methyl. In embodiments, $R^{22C}$ is independently unsubstituted ethyl.

In embodiments, $R^{1D}$ is independently hydrogen, —$CX^{1D}_3$, —$CHX^{1D}_2$, —$CH_2X^{1D}$, —CN, —COOH, —$CONH_2$, $R^{20D}$-substituted or unsubstituted alkyl (e.g., $C_1$-$C_8$, $C_1$-$C_6$, $C_1$-$C_4$, or $C_1$-$C_2$), $R^{20D}$-substituted or unsubstituted heteroalkyl (e.g., 2 to 8 membered, 2 to 6 membered, 4 to 6 membered, 2 to 3 membered, or 4 to 5 membered), $R^{20D}$-substituted or unsubstituted cycloalkyl (e.g., $C_3$-$C_8$, $C_3$-$C_6$, $C_4$-$C_6$, or $C_5$-$C_6$), $R^{20D}$-substituted or unsubstituted heterocycloalkyl (e.g., 3 to 8 membered, 3 to 6 membered, 4 to 6 membered, 4 to 5 membered, or 5 to 6 membered), $R^{20D}$-substituted or unsubstituted aryl (e.g., $C_6$-$C_{10}$ or phenyl), or $R^{20D}$-substituted or unsubstituted heteroaryl (e.g., 5 to 10 membered, 5 to 9 membered, or 5 to 6 membered). In embodiments, $R^{1D}$ is independently hydrogen, —$CX^{1D}_3$, —$CHX^{1D}_2$, —$CH_2X^{1D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1D}$ is independently —F, —Cl, —Br, or —I. In embodiments, $R^{1D}$ is independently hydrogen. In embodiments, $R^{1D}$ is independently unsubstituted methyl. In embodiments, RD is independently unsubstituted ethyl.

$R^{20D}$ is independently oxo, halogen, $—CX^{20D}_3$, $—CHX^{20D}_2$, $—CH_2X^{20D}$, $—OCX^{20D}_3$, $—OCH_2X^{20D}$, $—OCHX^{20D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{21D}$-substituted or unsubstituted alkyl (e.g., $C_1$-$C_8$, $C_1$-$C_6$, $C_1$-$C_4$, or $C_1$-$C_2$), $R^{21D}$-substituted or unsubstituted heteroalkyl (e.g., 2 to 8 membered, 2 to 6 membered, 4 to 6 membered, 2 to 3 membered, or 4 to 5 membered), $R^{21D}$-substituted or unsubstituted cycloalkyl (e.g., $C_3$-$C_8$, $C_3$-$C_6$, $C_4$-$C_6$, or $C_5$-$C_6$), $R^{21D}$-substituted or unsubstituted heterocycloalkyl (e.g., 3 to 8 membered, 3 to 6 membered, 4 to 6 membered, 4 to 5 membered, or 5 to 6 membered), $R^{21D}$-substituted or unsubstituted aryl (e.g., $C_6$-$C_{10}$ or phenyl), or $R^{21D}$-substituted or unsubstituted heteroaryl (e.g., 5 to 10 membered, 5 to 9 membered, or 5 to 6 membered). In embodiments, $R^{20D}$ is independently oxo, halogen, $—CX^{20D}_3$, $—CHX^{20D}_2$, $—CH_2X^{20D}$, $—OCX^{20D}_3$, $—OCH_2X^{20D}$, $—OCHX^{20D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20D}$ is independently —F, —Cl, —Br, or —I. In embodiments, $R^{20D}$ is independently unsubstituted methyl. In embodiments, $R^{20D}$ is independently unsubstituted ethyl.

$R^{21D}$ is independently oxo, halogen, $—CX^{21D}_3$, $—CHX^{21D}_2$, $—CH_2X^{21D}$, $—OCX^{21D}_3$, $—OCH_2X^{21D}$, $—OCHX^{21D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{22D}$-substituted or unsubstituted alkyl (e.g., $C_1$-$C_8$, $C_1$-$C_6$, $C_1$-$C_4$, or $C_1$-$C_2$), $R^{22D}$-substituted or unsubstituted heteroalkyl (e.g., 2 to 8 membered, 2 to 6 membered, 4 to 6 membered, 2 to 3 membered, or 4 to 5 membered), $R^{22D}$-substituted or unsubstituted cycloalkyl (e.g., $C_3$-$C_8$, $C_3$-$C_6$, $C_4$-$C_6$, or $C_5$-$C_6$), $R^{22D}$-substituted or unsubstituted heterocycloalkyl (e.g., 3 to 8 membered, 3 to 6 membered, 4 to 6 membered, 4 to 5 membered, or 5 to 6 membered), $R^{22D}$-substituted or unsubstituted aryl (e.g., $C_6$-$C_{10}$ or phenyl), or $R^{22D}$-substituted or unsubstituted heteroaryl (e.g., 5 to 10 membered, 5 to 9 membered, or 5 to 6 membered). In embodiments, $R^{21D}$ is independently oxo, halogen, $—CX^{21D}_3$, $—CHX^{21D}_2$, $—CH_2X^{21D}$, $—OCX^{21D}_3$, $—OCH_2X^{21D}$, $—OCHX^{21D}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21D}$ is independently —F, —Cl, —Br, or —I. In embodiments, $R^{21D}$ is independently unsubstituted methyl. In embodiments, $R^{21D}$ is independently unsubstituted ethyl.

$R^{22D}$ is independently oxo, halogen, $—CX^{22D}_3$, $—CHX^{22D}_2$, $—CH_2X^{22D}$, $—OCX^{22D}_3$, $—OCH_2X^{22D}$, $—OCHX^{22D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22D}$ is independently —F, —Cl, —Br, or —I. In embodiments, $R^{22D}$ is independently unsubstituted methyl. In embodiments, $R^{22D}$ is independently unsubstituted ethyl.

In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, substituted or unsubstituted alkyl, or substituted or unsubstituted heteroalkyl. In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, substituted or unsubstituted ($C_1$-$C_4$) alkyl, or substituted or unsubstituted 2 to 4 membered heteroalkyl. In embodiments, $R^2$ is hydrogen, halogen, $—CH_3$, $—CH_2CH_3$, $—CX^2_3$, $—CHX^2_2$, $—CH_2X^2$, $—OCH_3$, $—OCX^2_3$, $—OCH_2X^2$, $—OCHX^2_2$, $—SCH_3$, $—SCX^2_3$, $—SCH_2X^2$, or $—SCHX^2_2$. In embodiments, $R^2$ is hydrogen, halogen, $—CH_3$, $—CH_2CH_3$, $—CF_3$, or $—OCH_3$. In embodiments, $R^2$ is $—CH_3$, $—CH_2CH_3$, or $—OCH_3$. In embodiments, $R^2$ is $—OCH_3$. In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, —CN, substituted or unsubstituted alkyl, or substituted or unsubstituted heteroalkyl. In embodiments, $R^2$ is independently hydrogen, halogen, —$CX^2_3$, —$CHX^2_2$, —$CH_2X^2$, —$OCX^2_3$, —$OCH_2X^2$, —$OCHX^2_2$, —CN, substituted or unsubstituted ($C_1$-$C_4$) alkyl, or substituted or unsubstituted 2 to 4 membered heteroalkyl. In embodiments, $R^2$ is hydrogen, halogen, —$CH_3$, —$CH_2CH_3$, —$CX^2_3$, —$CHX^2_2$, —$CH_2X^2$, —$OCH_3$, —$OCX^2_3$, —$OCH_2X^2$, —$OCHX^2_2$, —CN, —$SCH_3$, —$SCX^2_3$, —$SCH_2X^2$, or —$SCHX^2_2$. In embodiments, $R^2$ is hydrogen, halogen, —CN, —$CH_3$, —$CF_3$, or —$OCH_3$. In embodiments, $R^2$ is halogen or —$CH_3$. In embodiments, $R^2$ is —Cl or —$CH_3$. In embodiments, $R^2$ is —$CH_3$. In embodiments, $R^2$ is hydrogen. In embodiments, $R^2$ is —$CH_3$ or —$CH_2CH_3$.

In embodiments, $R^2$ is independently hydrogen, halogen, —$CX^2_3$, —CN, —OH, —$NH_2$, —SH, —$OCX^2_3$, —$OCHX^2_2$, —$OCH_2X^2$, —$CHX^2_2$, —$CH_2X^2$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently hydrogen, halogen, —$CX^2_3$, —CN, —OH, —$NH_2$, —SH, —$OCX^2_3$, —$OCHX^2_2$, —$OCH_2X^2$, —$CHX^2_2$, —$CH_2X^2$, unsubstituted $C_1$-$C_4$ alkyl, or unsubstituted 2 to 4 membered heteroalkyl.

In embodiments, $R^2$ is independently hydrogen. In embodiments, $R^2$ is independently halogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^2_2$. In embodiments, $R^2$ is independently —CN. In embodiments, $R^2$ is independently —$SO_{n2}R^{2D}$. In embodiments, $R^2$ is independently —$SO_{v2}NR^{2A}R^{2B}$. In embodiments, $R^2$ is independently —$NHC(O)NR^{2A}R^{2B}$. In embodiments, $R^2$ is independently —$N(O)_{m2}$. In embodiments, $R^2$ is independently —$NR^{2A}R^{2B}$. In embodiments, $R^2$ is independently —$C(O)R^{2C}$. In embodiments, $R^2$ is independently —C(O)—$OR^{2C}$. In embodiments, $R^2$ is independently —$C(O)NR^{2A}R^{2B}$. In embodiments, $R^2$ is independently —$OR^{2D}$. In embodiments, $R^2$ is independently —$NR^{2A}SO_2R^{2D}$. In embodiments, $R^2$ is independently —$NR^{2A}C(O)R^{2C}$. In embodiments, $R^2$ is independently —$NR^{2A}C(O)OR^{2C}$. In embodiments, $R^2$ is independently —$NR^{2A}OR^{2C}$. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$NO_2$. In embodiments, $R^2$ is independently —SH. In embodiments, $R^2$ is independently —$CF_3$. In embodiments, $R^2$ is independently —$CHF_2$. In embodiments, $R^2$ is independently —$CH_2F$. In embodiments, $R^2$ is independently —$OCF_3$. In embodiments, $R^2$ is independently —$OCH_2F$. In embodiments, $R^2$ is independently —$OCHF_2$. In embodiments, $R^2$ is independently —$OCH_3$. In embodiments, $R^2$ is independently —$OCH_2CH_3$. In embodiments, $R^2$ is independently —$OCH_2CH_2CH_3$. In embodiments, $R^2$ is independently —$OCH(CH_3)_2$. In embodiments, $R^2$ is independently —$OC(CH_3)_3$. In embodiments, $R^2$ is independently —$SCH_3$. In embodiments, $R^2$ is independently —$SCH_2CH_3$. In embodiments, $R^2$ is independently —$SCH_2CH_2CH_3$. In embodiments, $R^2$ is independently —$SCH(CH_3)_2$. In embodiments, $R^2$ is independently —$SC(CH_3)_3$. In embodiments, $R^2$ is independently —$CH_3$. In embodiments, $R^2$ is independently —$CH_2CH_3$. In embodiments, $R^2$ is independently —$CH_2CH_2CH_3$. In embodiments, $R^2$ is independently —$CH(CH_3)_2$. In embodiments, $R^2$ is independently —$C(CH_3)_3$. In embodiments, $R^2$ is independently —F. In embodiments, $R^2$ is independently —Cl. In embodiments, $R^2$ is independently —Br. In embodiments, $R^2$ is independently —I.

In embodiments, $R^2$ is independently substituted or unsubstituted alkyl (e.g., $C_1$-$C_8$, $C_1$-$C_6$, $C_1$-$C_4$, or $C_1$-$C_2$). In embodiments, $R^2$ is independently substituted alkyl (e.g., $C_1$-$C_8$, $C_1$-$C_6$, $C_1$-$C_4$, or $C_1$-$C_2$). In embodiments, $R^2$ is independently unsubstituted alkyl (e.g., $C_1$-$C_8$, $C_1$-$C_6$, $C_1$-$C_4$, or $C_1$-$C_2$). In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted isopropyl. In embodiments, $R^2$ is independently unsubstituted tert-butyl. In embodiments, $R^2$ is independently substituted or unsubstituted heteroalkyl (e.g., 2 to 8 membered, 2 to 6 membered, 4 to 6 membered, 2 to 3 membered, or 4 to 5 membered). In embodiments, $R^2$ is independently substituted heteroalkyl (e.g., 2 to 8 membered, 2 to 6 membered, 4 to 6 membered, 2 to 3 membered, or 4 to 5 membered). In embodiments, $R^2$ is independently unsubstituted heteroalkyl (e.g., 2 to 8 membered, 2 to 6 membered, 4 to 6 membered, 2 to 3 membered, or 4 to 5 membered). In embodiments, $R^2$ is independently substituted or unsubstituted cycloalkyl (e.g., $C_3$-$C_8$, $C_3$-$C_6$, $C_4$-$C_6$, or $C_5$-$C_6$). In embodiments, $R^2$ is independently substituted cycloalkyl (e.g., $C_3$-$C_8$, $C_3$-$C_6$, $C_4$-$C_6$, or $C_5$-$C_6$). In embodiments, $R^2$ is independently unsubstituted cycloalkyl (e.g., $C_3$-$C_8$, $C_3$-$C_6$, $C_4$-$C_6$, or $C_5$-$C_6$). In embodiments, $R^2$ is independently substituted or unsubstituted heterocycloalkyl (e.g., 3 to 8 membered, 3 to 6 membered, 4 to 6 membered, 4 to 5 membered, or 5 to 6 membered). In embodiments, $R^2$ is independently substituted heterocycloalkyl (e.g., 3 to 8 membered, 3 to 6 membered, 4 to 6 membered, 4 to 5 membered, or 5 to 6 membered). In embodiments, $R^2$ is independently unsubstituted heterocycloalkyl (e.g., 3 to 8 membered, 3 to 6 membered, 4 to 6 membered, 4 to 5 membered, or 5 to 6 membered). In embodiments, $R^2$ is independently substituted or unsubstituted aryl (e.g., $C_6$-$C_{10}$ or phenyl). In embodiments, $R^2$ is independently substituted aryl (e.g., $C_6$-$C_{10}$ or phenyl). In embodiments, $R^2$ is independently unsubstituted aryl (e.g., $C_6$-$C_{10}$ or phenyl). In embodiments, $R^2$ is independently substituted or unsubstituted heteroaryl (e.g., 5 to 10 membered, 5 to 9 membered, or 5 to 6 membered). In embodiments, $R^2$ is independently substituted heteroaryl (e.g., 5 to 10 membered, 5 to 9 membered, or 5 to 6 membered). In embodiments, $R^2$ is independently unsubstituted heteroaryl (e.g., 5 to 10 membered, 5 to 9 membered, or 5 to 6 membered).

In embodiments, $R^{2A}$ is independently hydrogen. In embodiments, $R^{2A}$ is independently —$CX^{2A}_3$. In embodiments, $R^{2A}$ is independently —$CHX^{2A}_2$. In embodiments, $R^{2A}$ is independently —$CH_2X^{2A}$. In embodiments, $R^{2A}$ is independently —CN. In embodiments, $R^{2A}$ is independently —COOH. In embodiments, $R^{2A}$ is independently —$CONH_2$. In embodiments, $X^{2A}$ is independently —F, —Cl, —Br, or —I.

In embodiments, $R^{2A}$ is independently substituted or unsubstituted alkyl (e.g., $C_1$-$C_8$, $C_1$-$C_6$, $C_1$-$C_4$, or $C_1$-$C_2$). In embodiments, $R^{2A}$ is independently substituted alkyl (e.g., $C_1$-$C_8$, $C_1$-$C_6$, $C_1$-$C_4$, or $C_1$-$C_2$). In embodiments, $R^{2A}$ is independently unsubstituted alkyl (e.g., $C_1$-$C_8$, $C_1$-$C_6$, $C_1$-$C_4$, or $C_1$-$C_2$). In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted tert-butyl. In embodiments, $R^{2A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted heteroalkyl (e.g., 2 to 8 membered, 2 to 6 membered, 4 to 6 membered, 2 to 3 membered, or 4 to 5 membered). In embodiments, $R^{2A}$ is independently unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted or unsubstituted cycloalkyl (e.g., $C_3$-$C_8$, $C_3$-$C_6$, $C_4$-$C_6$, or $C_5$-$C_6$). In embodiments, $R^{2A}$ is independently substituted cycloalkyl (e.g., $C_3$-$C_8$, $C_3$-$C_6$, $C_4$-$C_6$, or $C_5$-$C_6$). In embodiments, $R^{2A}$ is independently unsubstituted cycloalkyl (e.g., $C_3$-$C_8$, $C_3$-$C_6$, $C_4$-$C_6$, or $C_5$-$C_6$). In embodiments, $R^{2A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted heterocycloalkyl (e.g., 3 to 8 membered, 3 to 6 membered, 4 to 6 membered, 4 to 5 membered, or 5 to 6 membered). In embodiments, $R^{2A}$ is independently unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted or unsubstituted aryl (e.g., $C_6$-$C_{10}$ or phenyl). In embodiments, $R^{2A}$ is independently substituted aryl (e.g., $C_6$-$C_{10}$ or phenyl). In embodiments, $R^{2A}$ is independently unsubstituted aryl (e.g., $C_6$-$C_{10}$ or phenyl). In embodiments, $R^{2A}$ is independently substituted or unsubstituted heteroaryl (e.g., 5 to 10 membered, 5 to 9 membered, or 5 to 6 membered). In embodiments, $R^{2A}$ is independently substituted heteroaryl (e.g., 5 to 10 membered, 5 to 9 membered, or 5 to 6 membered). In embodiments, $R^{2A}$ is independently unsubstituted heteroaryl (e.g., 5 to 10 membered, 5 to 9 membered, or 5 to 6 membered).

In embodiments, $R^{2B}$ is independently hydrogen. In embodiments, $R^{2B}$ is independently —$CX^{2B}_3$. In embodiments, $R^{2B}$ is independently —$CHX^{2B}_2$. In embodiments, $R^{2B}$ is independently —$CH_2X^{2B}$. In embodiments, $R^{2B}$ is independently —CN. In embodiments, $R^{2B}$ is independently —COOH. In embodiments, $R^{2B}$ is independently —$CONH_2$. In embodiments, $X^{2B}$ is independently —F, —Cl, —Br, or —I.

In embodiments, $R^{2B}$ is independently substituted or unsubstituted alkyl (e.g., $C_1$-$C_8$, $C_1$-$C_6$, $C_1$-$C_4$, or $C_1$-$C_2$). In embodiments, $R^{2B}$ is independently substituted alkyl (e.g., $C_1$-$C_8$, $C_1$-$C_6$, $C_1$-$C_4$, or $C_1$-$C_2$). In embodiments, $R^{2B}$ is independently unsubstituted alkyl (e.g., $C_1$-$C_8$, $C_1$-$C_6$, $C_1$-$C_4$, or $C_1$-$C_2$). In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl. In embodiments, $R^{2B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted heteroalkyl (e.g., 2 to 8 membered, 2 to 6 membered, 4 to 6 membered, 2 to 3 membered, or 4 to 5 membered). In embodiments, $R^{2B}$ is independently unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted or unsubstituted cycloalkyl (e.g., $C_3$-$C_8$, $C_3$-$C_6$, $C_4$-$C_6$, or $C_5$-$C_6$). In embodiments, $R^{2B}$ is independently substituted cycloalkyl (e.g., $C_3$-$C_8$, $C_3$-$C_6$, $C_4$-$C_6$, or $C_5$-$C_6$). In embodiments, $R^{2B}$ is independently unsubstituted cycloalkyl (e.g., $C_3$-$C_8$, $C_3$-$C_6$, $C_4$-$C_6$, or $C_5$-$C_6$). In embodiments, $R^{2B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted heterocycloalkyl (e.g., 3 to 8 membered, 3 to 6 membered, 4 to 6 membered, 4 to 5 membered, or 5 to 6 membered). In embodiments, $R^{2B}$ is independently unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted or unsubstituted aryl (e.g., $C_6$-$C_{10}$ or phenyl). In embodiments, $R^{2B}$ is independently substituted aryl (e.g., $C_6$-$C_{10}$ or phenyl). In embodiments, $R^{2B}$ is independently unsubstituted aryl (e.g., $C_6$-$C_{10}$ or phenyl). In embodiments, $R^{2B}$ is independently substituted or unsubstituted heteroaryl (e.g., 5 to 10 membered, 5 to 9 membered, or 5 to 6 membered). In embodiments, $R^{2B}$ is independently substituted heteroaryl (e.g., 5 to 10 membered, 5 to 9 membered, or 5 to 6 membered). In embodiments, $R^{2B}$ is independently unsubstituted heteroaryl (e.g., 5 to 10 membered, 5 to 9 membered, or 5 to 6 membered).

In embodiments, $R^{2A}$ and $R^{2B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{2A}$ and $R^{2B}$ substituents bonded to the same nitrogen atom may be joined to form a substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may be joined to form a substituted heteroaryl (e.g., 5 to 10 membered, 5 to 9 membered, or 5 to 6 membered). In embodiments, $R^{2A}$ and $R^{2B}$ substituents bonded to the same nitrogen atom may be joined to form an unsubstituted heteroaryl (e.g., 5 to 10 membered, 5 to 9 membered, or 5 to 6 membered).

In embodiments, $R^{2C}$ is independently hydrogen. In embodiments, $R^{2C}$ is independently —$CX^{2C}_3$. In embodiments, $R^{2C}$ is independently —$CHX^{2C}_2$. In embodiments, $R^{2C}$ is independently —$CH_2X^{2C}$. In embodiments, $R^{2C}$ is independently —CN. In embodiments, $R^{2C}$ is independently —COOH. In embodiments, $R^{2C}$ is independently —$CONH_2$. In embodiments, $X^{2C}$ is independently —F, —Cl, —Br, or —I.

In embodiments, $R^{2C}$ is independently substituted or unsubstituted alkyl (e.g., $C_1$-$C_8$, $C_1$-$C_6$, $C_1$-$C_4$, or $C_1$-$C_2$). In embodiments, $R^{2C}$ is independently substituted alkyl (e.g., $C_1$-$C_8$, $C_1$-$C_6$, $C_1$-$C_4$, or $C_1$-$C_2$). In embodiments, $R^{2C}$ is independently unsubstituted alkyl (e.g., $C_1$-$C_8$, $C_1$-$C_6$, $C_1$-$C_4$, or $C_1$-$C_2$). In embodiments, $R^{2C}$ is independently unsubstituted methyl. In embodiments, $R^{2C}$ is independently unsubstituted ethyl. In embodiments, $R^{2C}$ is independently unsubstituted propyl. In embodiments, $R^{2C}$ is independently unsubstituted isopropyl. In embodiments, $R^{2C}$ is independently unsubstituted tert-butyl. In embodiments, $R^{2C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted heteroalkyl (e.g., 2 to 8 membered, 2 to 6 membered, 4 to 6 membered, 2 to 3 membered, or 4 to 5 membered). In embodiments, $R^{2C}$ is independently unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted or unsubstituted cycloalkyl (e.g., $C_3$-$C_8$, $C_3$-$C_6$, $C_4$-$C_6$, or $C_5$-$C_6$). In embodiments, $R^{2C}$ is independently substituted cycloalkyl (e.g., $C_3$-$C_8$, $C_3$-$C_6$, $C_4$-$C_6$, or $C_5$-$C_6$). In embodiments, $R^{2C}$ is independently unsubstituted cycloalkyl (e.g., $C_3$-$C_8$, $C_3$-$C_6$, $C_4$-$C_6$, or $C_5$-$C_6$). In embodiments, $R^{2C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted heterocycloalkyl (e.g., 3 to 8 membered, 3 to 6 membered, 4 to 6 membered, 4 to 5 membered, or 5 to 6 membered). In embodiments, $R^{2C}$ is independently unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted or unsubstituted aryl (e.g., $C_6$-$C_{10}$ or phenyl). In embodiments, $R^{2C}$ is independently substituted aryl (e.g., $C_6$-$C_{10}$ or phenyl). In embodiments, $R^{2C}$ is independently unsubstituted aryl (e.g., $C_6$-$C_{10}$ or phenyl). In embodiments, $R^{2C}$ is independently substituted or unsubstituted heteroaryl (e.g., 5 to 10 membered, 5 to 9 membered, or 5 to 6 membered). In embodiments, $R^{2C}$ is independently substituted heteroaryl (e.g., 5 to 10 membered, 5 to 9 membered, or 5 to 6 membered). In embodiments, $R^{2C}$ is independently unsubstituted heteroaryl (e.g., 5 to 10 membered, 5 to 9 membered, or 5 to 6 membered).

In embodiments, $R^{2D}$ is independently hydrogen. In embodiments, $R^{2D}$ is independently $—CX^{2D}_3$. In embodiments, $R^{2D}$ is independently $—CHX^{2D}_2$. In embodiments, $R^{2D}$ is independently $—CH_2X^{2D}$. In embodiments, $R^{2D}$ is independently —CN. In embodiments, $R^{2D}$ is independently —COOH. In embodiments, $R^{2D}$ is independently $—CONH_2$. In embodiments, $X^{2D}$ is independently —F, —Cl, —Br, or —I.

In embodiments, $R^{2D}$ is independently substituted or unsubstituted alkyl (e.g., $C_1$-$C_8$, $C_1$-$C_6$, $C_1$-$C_4$, or $C_1$-$C_2$). In embodiments, $R^{2D}$ is independently substituted alkyl (e.g., $C_1$-$C_8$, $C_1$-$C_6$, $C_1$-$C_4$, or $C_1$-$C_2$). In embodiments, $R^{2D}$ is independently unsubstituted alkyl (e.g., $C_1$-$C_8$, $C_1$-$C_6$, $C_1$-$C_4$, or $C_1$-$C_2$). In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted isopropyl. In embodiments, $R^{2D}$ is independently unsubstituted tert-butyl. In embodiments, $R^{2D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted heteroalkyl (e.g., 2 to 8 membered, 2 to 6 membered, 4 to 6 membered, 2 to 3 membered, or 4 to 5 membered). In embodiments, $R^{2D}$ is independently unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted or unsubstituted cycloalkyl (e.g., $C_3$-$C_8$, $C_3$-$C_6$, $C_4$-$C_6$, or $C_5$-$C_6$). In embodiments, $R^{2D}$ is independently substituted cycloalkyl (e.g., $C_3$-$C_8$, $C_3$-$C_6$, $C_4$-$C_6$, or $C_5$-$C_6$). In embodiments, $R^{2D}$ is independently unsubstituted cycloalkyl (e.g., $C_3$-$C_8$, $C_3$-$C_6$, $C_4$-$C_6$, or $C_5$-$C_6$). In embodiments, $R^{2D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted heterocycloalkyl (e.g., 3 to 8 membered, 3 to 6 membered, 4 to 6 membered, 4 to 5 membered, or 5 to 6 membered). In embodiments, $R^{2D}$ is independently unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted or unsubstituted aryl (e.g., $C_6$-$C_{10}$ or phenyl). In embodiments, $R^{2D}$ is independently substituted aryl (e.g., $C_6$-$C_{10}$ or phenyl). In embodiments, $R^{2D}$ is independently unsubstituted aryl (e.g., $C_6$-$C_{10}$ or phenyl). In embodiments, $R^{2D}$ is independently substituted or unsubstituted heteroaryl (e.g., 5 to 10 membered, 5 to 9 membered, or 5 to 6 membered). In embodiments, $R^{2D}$ is independently substituted heteroaryl (e.g., 5 to 10 membered, 5 to 9 membered, or 5 to 6 membered). In embodiments, $R^{2D}$ is independently unsubstituted heteroaryl (e.g., 5 to 10 membered, 5 to 9 membered, or 5 to 6 membered).

In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{23}$-substituted or unsubstituted alkyl (e.g., $C_1$-$C_8$, $C_1$-$C_6$, $C_1$-$C_4$, or $C_1$-$C_2$), $R^{23}$-substituted or unsubstituted heteroalkyl (e.g., 2 to 8 membered, 2 to 6 membered, 4 to 6 membered, 2 to 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 8 membered, 3 to 6 membered, 4 to 6 membered, 4 to 5 membered, or 5 to 6 membered), $R^{23}$-substituted or unsubstituted aryl (e.g., $C_6$-$C_{10}$ or phenyl), or $R^{23}$-substituted or unsubstituted heteroaryl (e.g., 5 to 10 membered, 5 to 9 membered, or 5 to 6 membered). In embodiments, $R^2$ is independently hydrogen, halogen, $—CX^2_3$, $—CHX^2_2$, $—CH_2X^2$, $—OCX^2_3$, $—OCH_2X^2$, $—OCHX^2_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^2$ is independently —F, —Cl, —Br, or —I. In embodiments, $R^2$ is independently hydrogen. In embodiments, $R^2$ is independently unsubstituted methyl. In embodiments, $R^2$ is independently unsubstituted ethyl.

$R^{23}$ is independently oxo, halogen, $—CX^{23}_3$, $—CHX^{23}_2$, $—CH_2X^{23}$, $—OCX^{23}_3$, $—OCH_2X^{23}$, $—OCHX^{23}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered). In embodiments, $R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23}$ is independently —F, —Cl, —Br, or —I. In embodiments, $R^{23}$ is independently unsubstituted methyl. In embodiments, $R^{23}$ is independently unsubstituted ethyl.

$R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered). In embodiments, $R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24}$ is independently —F, —Cl, —Br, or —I. In embodiments, $R^{24}$ is independently unsubstituted methyl. In embodiments, $R^{24}$ is independently unsubstituted ethyl.

$R^{25}$ is independently oxo, halogen, —$CX^{25}_3$, —$CHX^{25}_2$, —$CH_2X^{25}$, —$OCX^{25}_3$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25}$ is independently —F, —Cl, —Br, or —I. In embodiments, $R^{25}$ is independently unsubstituted methyl. In embodiments, $R^{25}$ is independently unsubstituted ethyl.

In embodiments, $R^{2A}$ is independently hydrogen, —$CX^{2A}_3$, —$CHX^{2A}_2$, —$CH_2X^{2A}$, —CN, —COOH, —$CONH_2$, $R^{23A}$-substituted or unsubstituted alkyl (e.g., $C_1$-$C_8$, $C_1$-$C_6$, $C_1$-$C_4$, or $C_1$-$C_2$), $R^{23A}$-substituted or unsubstituted heteroalkyl (e.g., 2 to 8 membered, 2 to 6 membered, 4 to 6 membered, 2 to 3 membered, or 4 to 5 membered), $R^{23A}$-substituted or unsubstituted cycloalkyl (e.g., $C_3$-$C_8$, $C_3$-$C_6$, $C_4$-$C_6$, or $C_5$-$C_6$), $R^{23A}$-substituted or unsubstituted heterocycloalkyl (e.g., 3 to 8 membered, 3 to 6 membered, 4 to 6 membered, 4 to 5 membered, or 5 to 6 membered), $R^{23A}$-substituted or unsubstituted aryl (e.g., $C_6$-$C_{10}$ or phenyl), or $R^{23A}$-substituted or unsubstituted heteroaryl (e.g., 5 to 10 membered, 5 to 9 membered, or 5 to 6 membered). In embodiments, $R^{2A}$ is independently hydrogen, —$CX^{2A}_3$, —$CHX^{2A}_2$, —$CH_2X^{2A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2A}$ is independently —F, —Cl, —Br, or —I. In embodiments, $R^{2A}$ is independently hydrogen. In embodiments, $R^{2A}$ is independently unsubstituted methyl. In embodiments, $R^{2A}$ is independently unsubstituted ethyl.

In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered) or $R^{23A}$-substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23A}$ is independently oxo, halogen, —$CX^{2}_{3A_3}$, —$CHX^{23A}_2$, —$CH_2X^{23A}$, —$OCX^{2}_{3A_3}$, —$OCH_2X^{23A}$, —$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{24A}$-substituted or unsubstituted alkyl (e.g., $C_1$-$C_8$, $C_1$-$C_6$, $C_1$-$C_4$, or $C_1$-$C_2$), $R^{24A}$-substituted or unsubstituted heteroalkyl (e.g., 2 to 8 membered, 2 to 6 membered, 4 to 6 membered, 2 to 3 membered, or 4 to 5 membered), $R^{24A}$-substituted or unsubstituted cycloalkyl (e.g., $C_3$-$C_8$, $C_3$-$C_6$, $C_4$-$C_6$, or $C_5$-$C_6$), $R^{24A}$-substituted or unsubstituted heterocycloalkyl (e.g., 3 to 8 membered, 3 to 6 membered, 4 to 6 membered, 4 to 5 membered, or 5 to 6 membered), $R^{24A}$-substituted or unsubstituted aryl (e.g., $C_6$-$C_{10}$ or phenyl), or $R^{24A}$-substituted or unsubstituted heteroaryl (e.g., 5 to 10 membered, 5 to 9 membered, or 5 to 6 membered). In embodiments, $R^{23A}$ is independently oxo, halogen, —$CX^{2}{}_{3A_3}$, —$CHX^{23A}_2$, —$CH_2X^{23A}$, —$OCX^{2}{}_{3A_3}$, —$OCH_2X^{23A}$, —$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23A}$ is independently —F, —Cl, —Br, or —I. In embodiments, $R^{23A}$ is independently unsubstituted methyl. In embodiments, $R^{23A}$ is independently unsubstituted ethyl.

$R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{25A}$-substituted or unsubstituted alkyl (e.g., $C_1$-$C_8$, $C_1$-$C_6$, $C_1$-$C_4$, or $C_1$-$C_2$), $R^{25A}$-substituted or unsubstituted heteroalkyl (e.g., 2 to 8 membered, 2 to 6 membered, 4 to 6 membered, 2 to 3 membered, or 4 to 5 membered), $R^{25A}$-substituted or unsubstituted cycloalkyl (e.g., $C_3$-$C_8$, $C_3$-$C_6$, $C_4$-$C_6$, or $C_5$-$C_6$), $R^{25A}$-substituted or unsubstituted heterocycloalkyl (e.g., 3 to 8 membered, 3 to 6 membered, 4 to 6 membered, 4 to 5 membered, or 5 to 6 membered), $R^{25A}$-substituted or unsubstituted aryl (e.g., $C_6$-$C_{10}$ or phenyl), or $R^{25A}$-substituted or unsubstituted heteroaryl (e.g., 5 to 10 membered, 5 to 9 membered, or 5 to 6 membered). In embodiments, $R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24A}$ is independently —F, —Cl, —Br, or —I. In embodiments, $R^{24A}$ is independently unsubstituted methyl. In embodiments, $R^{24A}$ is independently unsubstituted ethyl.

$R^{25A}$ is independently oxo, halogen, —$CX^{25A}_3$, —$CHX^{25A}_2$, —$CH_2X^{25A}$, —$OCX^{25A}_3$, —$OCH_2X^{25A}$, —$OCHX^{25A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25A}$ is independently —F, —Cl, —Br, or —I. In embodiments, $R^{25A}$ is independently unsubstituted methyl. In embodiments, $R^{25A}$ is independently unsubstituted ethyl.

In embodiments, $R^{2B}$ is independently hydrogen, —$CX^{2B}_3$, —$CHX^{2B}_2$, —$CH_2X^{2B}$, —CN, —COOH, —$CONH_2$, $R^{23B}$-substituted or unsubstituted alkyl (e.g., $C_1$-$C_8$, $C_1$-$C_6$, $C_1$-$C_4$, or $C_1$-$C_2$), $R^{23B}$-substituted or unsubstituted heteroalkyl (e.g., 2 to 8 membered, 2 to 6 membered, 4 to 6 membered, 2 to 3 membered, or 4 to 5 membered), $R^{23B}$-substituted or unsubstituted cycloalkyl (e.g., $C_3$-$C_8$, $C_3$-$C_6$, $C_4$-$C_6$, or $C_5$-$C_6$), $R^{23B}$-substituted or unsubstituted heterocycloalkyl (e.g., 3 to 8 membered, 3 to 6 membered, 4 to 6 membered, 4 to 5 membered, or 5 to 6 membered), $R^{23B}$-substituted or unsubstituted aryl (e.g., $C_6$-$C_{10}$ or phenyl), or $R^{23B}$-substituted or unsubstituted heteroaryl (e.g., 5 to 10 membered, 5 to 9 membered, or 5 to 6 membered). In embodiments, $R^{2B}$ is independently hydrogen, —$CX^{2B}_3$, —$CHX^{2B}_2$, —$CH_2X^{2B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2B}$ is independently —F, —Cl, —Br, or —I. In embodiments, $R^{2B}$ is independently hydrogen. In embodiments, $R^{2B}$ is independently unsubstituted methyl. In embodiments, $R^{2B}$ is independently unsubstituted ethyl.

In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered) or $R^{23B}$-substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23B}$ is independently oxo, halogen, —$CX^{23B}_3$, —$CHX^{23B}_2$, —$CH_2X^{23B}$, —$OCX^{2}{}_{3B_3}$, —$OCH_2X^{23B}$, —$OCHX^{23B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{24B}$-substituted or unsubstituted alkyl (e.g., $C_1$-$C_8$, $C_1$-$C_6$, $C_1$-$C_4$, or $C_1$-$C_2$), $R^{24B}$-substituted or unsubstituted heteroalkyl (e.g., 2 to 8 membered, 2 to 6 membered, 4 to 6 membered, 2 to 3 membered, or 4 to 5 membered), $R^{24B}$-substituted or unsubstituted cycloalkyl (e.g., $C_3$-$C_8$, $C_3$-$C_6$, $C_4$-$C_6$, or $C_5$-$C_6$), $R^{24B}$-substituted or unsubstituted heterocycloalkyl (e.g., 3 to 8 membered, 3 to 6 membered, 4 to 6 membered, 4 to 5 membered, or 5 to 6 membered), $R^{24B}$-substituted or unsubstituted aryl (e.g., $C_6$-$C_{10}$ or phenyl), or $R^{24B}$-substituted or unsubstituted heteroaryl (e.g., 5 to 10 membered, 5 to 9 membered, or 5 to 6 membered). In embodiments, $R^{23B}$ is independently oxo, halogen, —$CX^{23B}_3$, —$CHX^{23B}_2$, —$CH_2X^{23B}$, —$OCX^{23B}_3$, —$OCH_2X^{23B}$, —$OCHX^{23B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23B}$ is independently —F, —Cl, —Br, or —I. In embodiments, $R^{23B}$ is independently unsubstituted methyl. In embodiments, $R^{23B}$ is independently unsubstituted ethyl.

$R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{25B}$-substituted or unsubstituted alkyl (e.g., $C_1$-$C_8$, $C_1$-$C_6$, $C_1$-$C_4$, or $C_1$-$C_2$), $R^{25B}$-substituted or unsubstituted heteroalkyl (e.g., 2 to 8 membered, 2 to 6 membered, 4 to 6 membered, 2 to 3 membered, or 4 to 5 membered), $R^{25B}$-substituted or unsubstituted cycloalkyl (e.g., $C_3$-$C_8$, $C_3$-$C_6$, $C_4$-$C_6$, or $C_5$-$C_6$), $R^{25B}$-substituted or unsubstituted heterocycloalkyl (e.g., 3 to 8 membered, 3 to 6 membered, 4 to 6 membered, 4 to 5 membered, or 5 to 6 membered), $R^{25B}$-substituted or unsubstituted aryl (e.g., $C_6$-$C_{10}$ or phenyl), or $R^{25B}$-substituted or unsubstituted heteroaryl (e.g., 5 to 10 membered, 5 to 9 membered, or 5 to 6 membered). In embodiments, $R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24B}$ is independently —F, —Cl, —Br, or —I. In embodiments, $R^{24B}$ is independently unsubstituted methyl. In embodiments, $R^{24B}$ is independently unsubstituted ethyl.

$R^{25B}$ is independently oxo, halogen, —$CX^{25B}_3$, —$CHX^{25B}_2$, —$CH_2X^{25B}$, —$OCX^{25B}_3$, —$OCH_2X^{25B}$, —$OCHX^{25B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25B}$ is independently —F, —Cl, —Br, or —I. In embodiments, $R^{25B}$ is independently unsubstituted methyl. In embodiments, $R^{25B}$ is independently unsubstituted ethyl.

In embodiments, $R^{2C}$ is independently hydrogen, —$CX^{2C}_3$, —$CHX^{2C}_2$, —$CH_2X^{2C}$, —CN, —COOH, —$CONH_2$, $R^{23C}$-substituted or unsubstituted alkyl (e.g., $C_1$-$C_8$, $C_1$-$C_6$, $C_1$-$C_4$, or $C_1$-$C_2$), $R^{23C}$-substituted or unsubstituted heteroalkyl (e.g., 2 to 8 membered, 2 to 6 membered, 4 to 6 membered, 2 to 3 membered, or 4 to 5 membered), $R^{23C}$-substituted or unsubstituted cycloalkyl (e.g., $C_3$-$C_8$, $C_3$-$C_6$, $C_4$-$C_6$, or $C_5$-$C_6$), $R^{23C}$-substituted or unsubstituted heterocycloalkyl (e.g., 3 to 8 membered, 3 to 6 membered, 4 to 6 membered, 4 to 5 membered, or 5 to 6 membered), $R^{23C}$-substituted or unsubstituted aryl (e.g., $C_6$-$C_{10}$ or phenyl), or $R^{23C}$-substituted or unsubstituted heteroaryl (e.g., 5 to 10 membered, 5 to 9 membered, or 5 to 6 membered). In embodiments, $R^{2C}$ is independently hydrogen, —$CX^{2C}_3$, —$CHX^{2C}_2$, —$CH_2X^{2C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2C}$ is independently —F, —Cl, —Br, or —I. In embodiments, $R^{2C}$ is independently hydrogen. In embodiments, $R^{2C}$ is independently unsubstituted methyl. In embodiments, $R^{2C}$ is independently unsubstituted ethyl.

$R^{23C}$ is independently oxo, halogen, —$CX^{23C}_3$, —$CHX^{23C}_2$, —$CH_2X^{23C}$, —$OCX^{23}{}_{C}$, —$OCH_2X^{23C}$, —$OCHX^{23C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{24C}$-substituted or unsubstituted alkyl (e.g., $C_1$-$C_8$, $C_1$-$C_6$, $C_1$-$C_4$, or $C_1$-$C_2$), $R^{24C}$-substituted or unsubstituted heteroalkyl (e.g., 2 to 8 membered, 2 to 6 membered, 4 to 6 membered, 2 to 3 membered, or 4 to 5 membered), $R^{24C}$-substituted or unsubstituted cycloalkyl (e.g., $C_3$-$C_8$, $C_3$-$C_6$, $C_4$-$C_6$, or $C_5$-$C_6$), $R^{24C}$-substituted or unsubstituted heterocycloalkyl (e.g., 3 to 8 membered, 3 to 6 membered, 4 to 6 membered, 4 to 5 membered, or 5 to 6 membered), $R^{24C}$-substituted or unsubstituted aryl (e.g., $C_6$-$C_{10}$ or phenyl), or $R^{24C}$-substituted or unsubstituted heteroaryl (e.g., 5 to 10 membered, 5 to 9 membered, or 5 to 6 membered). In embodiments, $R^{23C}$ is independently oxo, halogen, $-CX^{23C}{}_3$, $-CHX^{23C}{}_2$, $-CH_2X^{23C}$, $-OCX^{23}{}_C$, $-OCH_2X^{23C}$, $-OCHX^{23C}{}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23C}$ is independently —F, —Cl, —Br, or —I. In embodiments, $R^{23C}$ is independently unsubstituted methyl. In embodiments, $R^{23C}$ is independently unsubstituted ethyl.

$R^{24C}$ is independently oxo, halogen, $-CX^{24C}{}_3$, $-CHX^{24C}{}_2$, $-CH_2X^{24C}$, $-OCX^{24C}$, $-OCH_2X^{24C}$, $-OCHX^{24C}{}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{25C}$-substituted or unsubstituted alkyl (e.g., $C_1$-$C_8$, $C_1$-$C_6$, $C_1$-$C_4$, or $C_1$-$C_2$), $R^{25C}$-substituted or unsubstituted heteroalkyl (e.g., 2 to 8 membered, 2 to 6 membered, 4 to 6 membered, 2 to 3 membered, or 4 to 5 membered), $R^{25C}$-substituted or unsubstituted cycloalkyl (e.g., $C_3$-$C_8$, $C_3$-$C_6$, $C_4$-$C_6$, or $C_5$-$C_6$), $R^{25C}$-substituted or unsubstituted heterocycloalkyl (e.g., 3 to 8 membered, 3 to 6 membered, 4 to 6 membered, 4 to 5 membered, or 5 to 6 membered), $R^{25C}$-substituted or unsubstituted aryl (e.g., $C_6$-$C_{10}$ or phenyl), or $R^{25C}$-substituted or unsubstituted heteroaryl (e.g., 5 to 10 membered, 5 to 9 membered, or 5 to 6 membered). In embodiments, $R^{24C}$ is independently oxo, halogen, $-CX^{24C}{}_3$, $-CHX^{24C}{}_2$, $-CH_2X^{24C}$, $-OCX^{24C}{}_3$, $-OCH_2X^{24C}$, $-OCHX^{24C}{}_2$, —CN, —OH, $-NH_2$, —CO OH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24C}$ is independently —F, —Cl, —Br, or —I. In embodiments, $R^{24C}$ is independently unsubstituted methyl. In embodiments, $R^{24C}$ is independently unsubstituted ethyl.

$R^{25C}$ is independently oxo, halogen, $-CX^{25C}{}_3$, $-CHX^{25C}{}_2$, $-CH_2X^{25C}$, $-OCX^{25C}$, $-OCH_2X^{25C}$, $-OCHX^{25C}{}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25C}$ is independently —F, —Cl, —Br, or —I. In embodiments, $R^{25C}$ is independently unsubstituted methyl. In embodiments, $R^{25C}$ is independently unsubstituted ethyl.

In embodiments, $R^{2D}$ is independently hydrogen, $-CX^{2D}{}_3$, $-CHX^{2D}{}_2$, $-CH_2X^{2D}$, —CN, —COOH, $-CONH_2$, $R^{23D}$-substituted or unsubstituted alkyl (e.g., $C_1$-$C_8$, $C_1$-$C_6$, $C_1$-$C_4$, or $C_1$-$C_2$), $R^{23D}$-substituted or unsubstituted heteroalkyl (e.g., 2 to 8 membered, 2 to 6 membered, 4 to 6 membered, 2 to 3 membered, or 4 to 5 membered), $R^{23D}$-substituted or unsubstituted cycloalkyl (e.g., $C_3$-$C_8$, $C_3$-$C_6$, $C_4$-$C_6$, or $C_5$-$C_6$), $R^{23D}$-substituted or unsubstituted heterocycloalkyl (e.g., 3 to 8 membered, 3 to 6 membered, 4 to 6 membered, 4 to 5 membered, or 5 to 6 membered), $R^{23D}$-substituted or unsubstituted aryl (e.g., $C_6$-$C_{10}$ or phenyl), or $R^{23D}$-substituted or unsubstituted heteroaryl (e.g., 5 to 10 membered, 5 to 9 membered, or 5 to 6 membered). In embodiments, $R^{2D}$ is independently hydrogen, $-CX^{2D}{}_3$, $-CHX^{2D}{}_2$, $-CH_2X^{2D}$, —CN, —COOH, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2D}$ is independently —F, —Cl, —Br, or —I. In embodiments, $R^{2D}$ is independently hydrogen. In embodiments, $R^{2D}$ is independently unsubstituted methyl. In embodiments, $R^{2D}$ is independently unsubstituted ethyl.

$R^{23D}$ is independently oxo, halogen, $-CX^{2}{}_{3D_3}$, $-CHX^{23D}{}_2$, $-CH_2X^{23D}$, $-OCX^{2}{}_{3D_3}$, $-OCH_2X^{23D}$, $-OCHX^{23D}{}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{24D}$-substituted or unsubstituted alkyl (e.g., $C_1$-$C_8$, $C_1$-$C_6$, $C_1$-$C_4$, or $C_1$-$C_2$), $R^{24D}$-substituted or unsubstituted heteroalkyl (e.g., 2 to 8 membered, 2 to 6 membered, 4 to 6 membered, 2 to 3 membered, or 4 to 5 membered), $R^{24D}$-substituted or unsubstituted cycloalkyl (e.g., $C_3$-$C_8$, $C_3$-$C_6$, $C_4$-$C_6$, or $C_5$-$C_6$), $R^{24D}$-substituted or unsubstituted heterocycloalkyl (e.g., 3 to 8 membered, 3 to 6 membered, 4 to 6 membered, 4 to 5 membered, or 5 to 6 membered), $R^{24D}$-substituted or unsubstituted aryl (e.g., $C_6$-$C_{10}$ or phenyl), or $R^{24D}$-substituted or unsubstituted heteroaryl (e.g., 5 to 10 membered, 5 to 9 membered, or 5 to 6 membered). In embodiments, $R^{23D}$ is independently oxo, halogen, $-CX^{23D}{}_3$, $-CHX^{23D}{}_2$, $-CH_2X^{23D}$, $-OCX^{23D}{}_3$, $-OCH_2X^{23D}$, $-OCHX^{23D}{}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23D}$ is independently —F, —Cl, —Br, or —I.

In embodiments, $R^{23D}$ is independently unsubstituted methyl. In embodiments, $R^{23D}$ is independently unsubstituted ethyl.

$R^{24D}$ is independently oxo, halogen, $—CX^{24D}_3$, $—CHX^{24D}_2$, $—CH_2X^{24D}$, $—OCX^{24D}_3$, $—OCH_2X^{24D}$, $—OCHX^{24D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{25D}$-substituted or unsubstituted alkyl (e.g., $C_1$-$C_8$, $C_1$-$C_6$, $C_1$-$C_4$, or $C_1$-$C_2$), $R^{25D}$-substituted or unsubstituted heteroalkyl (e.g., 2 to 8 membered, 2 to 6 membered, 4 to 6 membered, 2 to 3 membered, or 4 to 5 membered), $R^{25D}$-substituted or unsubstituted cycloalkyl (e.g., $C_3$-$C_8$, $C_3$-$C_6$, $C_4$-$C_6$, or $C_5$-$C_6$), $R^{25D}$-substituted or unsubstituted heterocycloalkyl (e.g., 3 to 8 membered, 3 to 6 membered, 4 to 6 membered, 4 to 5 membered, or 5 to 6 membered), $R^{25D}$-substituted or unsubstituted aryl (e.g., $C_6$-$C_{10}$ or phenyl), or $R^{25D}$-substituted or unsubstituted heteroaryl (e.g., 5 to 10 membered, 5 to 9 membered, or 5 to 6 membered). In embodiments, $R^{24D}$ is independently oxo, halogen, $—CX^{24D}_3$, $—CHX^{24D}_2$, $—CH_2X^{24D}$, $—OCX^{24D}_3$, $—OCH_2X^{24D}$, $—OCHX^{24D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24D}$ is independently —F, —Cl, —Br, or —I. In embodiments, $R^{24D}$ is independently unsubstituted methyl. In embodiments, $R^{24D}$ is independently unsubstituted ethyl.

$R^{25D}$ is independently oxo, halogen, $—CX^{25D}_3$, $—CHX^{25D}_2$, $—CH_2X^{25D}$, $—OCX^{25D}_3$, $—OCH_2X^{25D}$, $—OCHX^{25D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25D}$ is independently —F, —Cl, —Br, or —I. In embodiments, $R^{25D}$ is independently unsubstituted methyl. In embodiments, $R^{25D}$ is independently unsubstituted ethyl.

In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, substituted or unsubstituted alkyl, or substituted or unsubstituted heteroalkyl. In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, substituted or unsubstituted ($C_1$-$C_4$) alkyl, or substituted or unsubstituted 2 to 4 membered heteroalkyl. In embodiments, $R^3$ is hydrogen, halogen, $—CH_3$, $—CH_2CH_3$, $—CX^3_3$, $—CHX^3_2$, $—CH_2X^3$, $—OCH_3$, $—OCX^3_3$, $—OCH_2X^3$, $—OCHX^3_2$, $—SCH_3$, $—SCX^3_3$, $—SCH_2X^3$, or $—SCHX^3_2$. In embodiments, $R^3$ is hydrogen, halogen, $—CH_3$, $—CH_2CH_3$, $—CF_3$, or $—OCH_3$. In embodiments, $R^3$ is $—CH_3$, $—CH_2CH_3$, or $—OCH_3$. In embodiments, $R^3$ is $—OCH_3$. In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, substituted or unsubstituted alkyl, or substituted or unsubstituted heteroalkyl. In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, substituted or unsubstituted ($C_1$-$C_4$) alkyl, or substituted or unsubstituted 2 to 4 membered heteroalkyl. In embodiments, $R^3$ is hydrogen, halogen, $—CH_3$, $—CH_2CH_3$, $—CX^3_3$, $—CHX^3_2$, $—CH_2X^3$, $—OCH_3$, $—OCX^3_3$, $—OCH_2X^3$, $—OCHX^3_2$, —CN, $—SCH_3$, $—SCX^3_3$, $—SCH_2X^3$, or $—SCHX^3_2$. In embodiments, $R^3$ is hydrogen, halogen, —CN, $—CH_3$, $—CF_3$, or $—OCH_3$. In embodiments, $R^3$ is halogen or $—CH_3$. In embodiments, $R^3$ is —Cl or $—CH_3$. In embodiments, $R^3$ is $—CH_3$. In embodiments, $R^3$ is hydrogen. In embodiments, $R^3$ is $—CH_3$ or $—CH_2CH_3$. In embodiments, $R^3$ is —Cl.

In embodiments, $R^3$ is independently hydrogen, halogen, $—CX^3_3$, —CN, —OH, $—NH_2$, —SH, $—OCX^3_3$, $—OCHX^3_2$, $—OCH_2X^3$, $—CHX^3_2$, $—CH_2X^3$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently hydrogen, halogen, $—CX^3_3$, —CN, —OH, $—NH_2$, —SH, $—OCX^3_3$, $—OCHX^3_2$, $—OCH_2X^3$, $—CHX^3_2$, $—CH_2X^3$, unsubstituted $C_1$-$C_4$ alkyl, or unsubstituted 2 to 4 membered heteroalkyl.

In embodiments, $R^3$ is independently hydrogen. In embodiments, $R^3$ is independently halogen. In embodiments, $R^3$ is independently $—CX^3_3$. In embodiments, $R^3$ is independently $—CHX^3_2$. In embodiments, $R^3$ is independently $—CH_2X^3$. In embodiments, $R^3$ is independently $—OCX^3_3$. In embodiments, $R^3$ is independently $—OCH_2X^3$. In embodiments, $R^3$ is independently $—OCHX^3_2$. In embodiments, $R^3$ is independently —CN. In embodiments, $R^3$ is independently $—SO_{n3}R^{3D}$. In embodiments, $R^3$ is independently $—SO_{v3}NR^{3A}R^{3B}$. In embodiments, $R^3$ is independently $—NHC(O)NR^{3A}R^{3B}$. In embodiments, $R^3$ is independently $—N(O)_{m3}$. In embodiments, $R^3$ is independently $—NR^{3A}R^{3B}$. In embodiments, $R^3$ is independently $—C(O)R^{3C}$. In embodiments, $R^3$ is independently $—C(O)—OR^{3C}$. In embodiments, $R^3$ is independently $—C(O)NR^{3A}R^{3B}$. In embodiments, $R^3$ is independently —$OR^{3D}$. In embodiments, $R^3$ is independently —$NR^{3A}SO_2R^{3D}$. In embodiments, $R^3$ is independently —$NR^{3A}C(O)R^{3C}$ In embodiments, $R^3$ is independently —$NR^{3A}C(O)OR^{3C}$. In embodiments, $R^3$ is independently —$NR^{3A}OR^{3C}$. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —$NO_2$. In embodiments, $R^3$ is independently —SH. In embodiments, $R^3$ is independently —$CF_3$. In embodiments, $R^3$ is independently —$CHF_2$. In embodiments, $R^3$ is independently —$CH_2F$. In embodiments, $R^3$ is independently —$OCF_3$. In embodiments, $R^3$ is independently —$OCH_2F$. In embodiments, $R^3$ is independently —$OCHF_2$. In embodiments, $R^3$ is independently —$OCH_3$. In embodiments, $R^3$ is independently —$OCH_2CH_3$. In embodiments, $R^3$ is independently —$OCH_2CH_2CH_3$. In embodiments, $R^3$ is independently —$OCH(CH_3)_2$. In embodiments, $R^3$ is independently —$OC(CH_3)_3$. In embodiments, $R^3$ is independently —$SCH_3$. In embodiments, $R^3$ is independently —$SCH_2CH_3$. In embodiments, $R^3$ is independently —$SCH_2CH_2CH_3$. In embodiments, $R^3$ is independently —$SCH(CH_3)_2$. In embodiments, $R^3$ is independently —$SC(CH_3)_3$. In embodiments, $R^3$ is independently —$CH_3$. In embodiments, $R^3$ is independently —$CH_2CH_3$. In embodiments, $R^3$ is independently —$CH_2CH_2CH_3$. In embodiments, $R^3$ is independently —$CH(CH_3)_2$. In embodiments, $R^3$ is independently —$C(CH_3)_3$. In embodiments, $R^3$ is independently —F. In embodiments, $R^3$ is independently —Cl. In embodiments, $R^3$ is independently —Br. In embodiments, $R^3$ is independently —I.

In embodiments, $R^3$ is independently substituted or unsubstituted alkyl (e.g., $C_1$-$C_8$, $C_1$-$C_6$, $C_1$-$C_4$, or $C_1$-$C_2$). In embodiments, $R^3$ is independently substituted alkyl (e.g., $C_1$-$C_8$, $C_1$-$C_6$, $C_1$-$C_4$, or $C_1$-$C_2$). In embodiments, $R^3$ is independently unsubstituted alkyl (e.g., $C_1$-$C_8$, $C_1$-$C_6$, $C_1$-$C_4$, or $C_1$-$C_2$). In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted isopropyl. In embodiments, $R^3$ is independently unsubstituted tert-butyl. In embodiments, $R^3$ is independently substituted or unsubstituted heteroalkyl (e.g., 2 to 8 membered, 2 to 6 membered, 4 to 6 membered, 2 to 3 membered, or 4 to 5 membered). In embodiments, $R^3$ is independently substituted heteroalkyl (e.g., 2 to 8 membered, 2 to 6 membered, 4 to 6 membered, 2 to 3 membered, or 4 to 5 membered). In embodiments, $R^3$ is independently unsubstituted heteroalkyl (e.g., 2 to 8 membered, 2 to 6 membered, 4 to 6 membered, 2 to 3 membered, or 4 to 5 membered). In embodiments, $R^3$ is independently substituted or unsubstituted cycloalkyl (e.g., $C_3$-$C_8$, $C_3$-$C_6$, $C_4$-$C_6$, or $C_5$-$C_6$). In embodiments, $R^3$ is independently substituted cycloalkyl (e.g., $C_3$-$C_8$, $C_3$-$C_6$, $C_4$-$C_6$, or $C_5$-$C_6$). In embodiments, $R^3$ is independently unsubstituted cycloalkyl (e.g., $C_3$-$C_8$, $C_3$-$C_6$, $C_4$-$C_6$, or $C_5$-$C_6$). In embodiments, $R^3$ is independently substituted or unsubstituted heterocycloalkyl (e.g., 3 to 8 membered, 3 to 6 membered, 4 to 6 membered, 4 to 5 membered, or 5 to 6 membered). In embodiments, $R^3$ is independently substituted heterocycloalkyl (e.g., 3 to 8 membered, 3 to 6 membered, 4 to 6 membered, 4 to 5 membered, or 5 to 6 membered). In embodiments, $R^3$ is independently unsubstituted heterocycloalkyl (e.g., 3 to 8 membered, 3 to 6 membered, 4 to 6 membered, 4 to 5 membered, or 5 to 6 membered). In embodiments, $R^3$ is independently substituted or unsubstituted aryl (e.g., $C_6$-$C_{10}$ or phenyl). In embodiments, $R^3$ is independently substituted aryl (e.g., $C_6$-$C_{10}$ or phenyl). In embodiments, $R^3$ is independently unsubstituted aryl (e.g., $C_6$-$C_{10}$ or phenyl). In embodiments, $R^3$ is independently substituted or unsubstituted heteroaryl (e.g., 5 to 10 membered, 5 to 9 membered, or 5 to 6 membered). In embodiments, $R^3$ is independently substituted heteroaryl (e.g., 5 to 10 membered, 5 to 9 membered, or 5 to 6 membered). In embodiments, $R^3$ is independently unsubstituted heteroaryl (e.g., 5 to 10 membered, 5 to 9 membered, or 5 to 6 membered).

In embodiments, $R^{3A}$ is independently hydrogen. In embodiments, $R^{3A}$ is independently —$CX^{3A}_3$. In embodiments, $R^{3A}$ is independently —$CHX^{3A}_2$. In embodiments, $R^{3A}$ is independently —$CH_2X^{3A}$. In embodiments, $R^{3A}$ is independently —CN. In embodiments, $R^{3A}$ is independently —COOH. In embodiments, $R^{3A}$ is independently —$CONH_2$. In embodiments, $X^{3A}$ is independently —F, —Cl, —Br, or —I.

In embodiments, $R^{3A}$ is independently substituted or unsubstituted alkyl (e.g., $C_1$-$C_8$, $C_1$-$C_6$, $C_1$-$C_4$, or $C_1$-$C_2$). In embodiments, $R^{3A}$ is independently substituted alkyl (e.g., $C_1$-$C_8$, $C_1$-$C_6$, $C_1$-$C_4$, or $C_1$-$C_2$). In embodiments, $R^{3A}$ is independently unsubstituted alkyl (e.g., $C_1$-$C_8$, $C_1$-$C_6$, $C_1$-$C_4$, or $C_1$-$C_2$). In embodiments, $R^{3A}$ is independently unsubstituted methyl. In embodiments, $R^{3A}$ is independently unsubstituted ethyl. In embodiments, $R^{3A}$ is independently unsubstituted propyl. In embodiments, $R^{3A}$ is independently unsubstituted isopropyl. In embodiments, $R^{3A}$ is independently unsubstituted tert-butyl. In embodiments, $R^{3A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted heteroalkyl (e.g., 2 to 8 membered, 2 to 6 membered, 4 to 6 membered, 2 to 3 membered, or 4 to 5 membered). In embodiments, $R^{3A}$ is independently unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted or unsubstituted cycloalkyl (e.g., $C_3$-$C_8$, $C_3$-$C_6$, $C_4$-$C_6$, or $C_5$-$C_6$). In embodiments, $R^{3A}$ is independently substituted cycloalkyl (e.g., $C_3$-$C_8$, $C_3$-$C_6$, $C_4$-$C_6$, or $C_5$-$C_6$). In embodiments, $R^{3A}$ is independently unsubstituted cycloalkyl (e.g., $C_3$-$C_8$, $C_3$-$C_6$, $C_4$-$C_6$, or $C_5$-$C_6$). In embodiments, $R^{3A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted heterocycloalkyl (e.g., 3 to 8 membered, 3 to 6 membered, 4 to 6 membered, 4 to 5 membered, or 5 to 6 membered). In embodiments, $R^{3A}$ is independently unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted or unsubstituted aryl (e.g., $C_6$-$C_{10}$ or phenyl). In embodiments, $R^{3A}$ is independently substituted aryl (e.g., $C_6$-$C_{10}$ or phenyl). In embodiments, $R^{3A}$ is independently unsubstituted aryl (e.g., $C_6$-$C_{10}$ or phenyl). In embodiments, $R^{3A}$ is independently substituted or unsubstituted heteroaryl (e.g., 5 to 10 membered, 5 to 9 membered, or 5 to 6 membered). In embodiments, $R^{3A}$ is independently substituted heteroaryl (e.g., 5 to 10 membered, 5 to 9 membered, or 5 to 6 membered). In embodiments, $R^{3A}$ is independently unsubstituted heteroaryl (e.g., 5 to 10 membered, 5 to 9 membered, or 5 to 6 membered).

In embodiments, $R^{3B}$ is independently hydrogen. In embodiments, $R^{3B}$ is independently —$CX^{3B}_3$. In embodiments, $R^{3B}$ is independently —$CHX^{3B}_2$. In embodiments, $R^{3B}$ is independently —$CH_2X^{3B}$. In embodiments, $R^{3B}$ is independently —CN. In embodiments, $R^{3B}$ is independently —COOH. In embodiments, $R^{3B}$ is independently —$CONH_2$. In embodiments, $X^{3B}$ is independently —F, —Cl, —Br, or —I.

In embodiments, $R^{3B}$ is independently substituted or unsubstituted alkyl (e.g., $C_1$-$C_8$, $C_1$-$C_6$, $C_1$-$C_4$, or $C_1$-$C_2$). In embodiments, $R^{3B}$ is independently substituted alkyl (e.g., $C_1$-$C_8$, $C_1$-$C_6$, $C_1$-$C_4$, or $C_1$-$C_2$). In embodiments, $R^{3B}$ is independently unsubstituted alkyl (e.g., $C_1$-$C_8$, $C_1$-$C_6$, $C_1$-$C_4$, or $C_1$-$C_2$). In embodiments, $R^{3B}$ is independently unsubstituted methyl. In embodiments, $R^{3B}$ is independently unsubstituted ethyl. In embodiments, $R^{3B}$ is independently unsubstituted propyl. In embodiments, $R^{3B}$ is independently unsubstituted isopropyl. In embodiments, $R^{3B}$ is independently unsubstituted tert-butyl. In embodiments, $R^{3B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted heteroalkyl (e.g., 2 to 8 membered, 2 to 6 membered, 4 to 6 membered, 2 to 3 membered, or 4 to 5 membered). In embodiments, $R^{3B}$ is independently unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted or unsubstituted cycloalkyl (e.g., $C_3$-$C_8$, $C_3$-$C_6$, $C_4$-$C_6$, or $C_5$-$C_6$). In embodiments, $R^{3B}$ is independently substituted cycloalkyl (e.g., $C_3$-$C_8$, $C_3$-$C_6$, $C_4$-$C_6$, or $C_5$-$C_6$). In embodiments, $R^{3B}$ is independently unsubstituted cycloalkyl (e.g., $C_3$-$C_8$, $C_3$-$C_6$, $C_4$-$C_6$, or $C_5$-$C_6$). In embodiments, $R^{3B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted heterocycloalkyl (e.g., 3 to 8 membered, 3 to 6 membered, 4 to 6 membered, 4 to 5 membered, or 5 to 6 membered). In embodiments, $R^{3B}$ is independently unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted or unsubstituted aryl (e.g., $C_6$-$C_{10}$ or phenyl). In embodiments, $R^{3B}$ is independently substituted aryl (e.g., $C_6$-$C_{10}$ or phenyl). In embodiments, $R^{3B}$ is independently unsubstituted aryl (e.g., $C_6$-$C_{10}$ or phenyl). In embodiments, $R^{3B}$ is independently substituted or unsubstituted heteroaryl (e.g., 5 to 10 membered, 5 to 9 membered, or 5 to 6 membered). In embodiments, $R^{3B}$ is independently substituted heteroaryl (e.g., 5 to 10 membered, 5 to 9 membered, or 5 to 6 membered). In embodiments, $R^{3B}$ is independently unsubstituted heteroaryl (e.g., 5 to 10 membered, 5 to 9 membered, or 5 to 6 membered).

In embodiments, $R^{3A}$ and $R^{3B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{3A}$ and $R^{3B}$ substituents bonded to the same nitrogen atom may be joined to form a substituted or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may be joined to form a substituted heteroaryl (e.g., 5 to 10 membered, 5 to 9 membered, or 5 to 6 membered). In embodiments, $R^{3A}$ and $R^{3B}$ substituents bonded to the same nitrogen atom may be joined to form an unsubstituted heteroaryl (e.g., 5 to 10 membered, 5 to 9 membered, or 5 to 6 membered).

In embodiments, $R^{3C}$ is independently hydrogen. In embodiments, $R^{3C}$ is independently —$CX^{3C}_3$. In embodiments, $R^{3C}$ is independently —$CHX^{3C}_2$. In embodiments, $R^{3C}$ is independently —$CH_2X^{3C}$. In embodiments, $R^{3C}$ is independently —CN. In embodiments, $R^{3C}$ is independently —COOH. In embodiments, $R^{3C}$ is independently —$CONH_2$. In embodiments, $X^{3C}$ is independently —F, —Cl, —Br, or —I.

In embodiments, $R^{3C}$ is independently substituted or unsubstituted alkyl (e.g., $C_1$-$C_8$, $C_1$-$C_6$, $C_1$-$C_4$, or $C_1$-$C_2$). In embodiments, $R^{3C}$ is independently substituted alkyl (e.g., $C_1$-$C_8$, $C_1$-$C_6$, $C_1$-$C_4$, or $C_1$-$C_2$). In embodiments, $R^{3C}$ is independently unsubstituted alkyl (e.g., $C_1$-$C_8$, $C_1$-$C_6$, $C_1$-$C_4$, or $C_1$-$C_2$). In embodiments, $R^{3C}$ is independently unsubstituted methyl. In embodiments, $R^{3C}$ is independently unsubstituted ethyl. In embodiments, $R^{3C}$ is independently unsubstituted propyl. In embodiments, $R^{3C}$ is independently unsubstituted isopropyl. In embodiments, $R^{3C}$ is independently unsubstituted tert-butyl. In embodiments, $R^{3C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3C}$ is independently substituted heteroalkyl (e.g., 2 to 8 membered, 2 to 6 membered, 4 to 6 membered, 2 to 3 membered, or 4 to 5 membered). In embodiments, $R^{3C}$ is independently unsubstituted heteroalkyl (e.g., 2 to 8 membered, 2 to 6 membered, 4 to 6 membered, 2 to 3 membered, or 4 to 5 membered). In embodiments, $R^{3C}$ is independently substituted or unsubstituted cycloalkyl (e.g., $C_3$-$C_8$, $C_3$-$C_6$, $C_4$-$C_6$, or $C_5$-$C_6$). In embodiments, $R^{3C}$ is independently substituted cycloalkyl (e.g., $C_3$-$C_8$, $C_3$-$C_6$, $C_4$-$C_6$, or $C_5$-$C_6$). In embodiments, $R^{3C}$ is independently unsubstituted cycloalkyl (e.g., $C_3$-$C_8$, $C_3$-$C_6$, $C_4$-$C_6$, or $C_5$-$C_6$). In embodiments, $R^{3C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3C}$ is independently substituted heterocycloalkyl (e.g., 3 to 8 membered, 3 to 6 membered, 4 to 6 membered, 4 to 5 membered, or 5 to 6 membered). In embodiments, $R^{3C}$ is independently unsubstituted heterocycloalkyl (e.g., 3 to 8 membered, 3 to 6 membered, 4 to 6 membered, 4 to 5 membered, or 5 to 6 membered). In embodiments, $R^{3C}$ is independently substituted or unsubstituted aryl (e.g., $C_6$-$C_{10}$ or phenyl). In embodiments, $R^{3C}$ is independently substituted aryl (e.g., $C_6$-$C_{10}$ or phenyl). In embodiments, $R^{3C}$ is independently unsubstituted aryl (e.g., $C_6$-$C_{10}$ or phenyl). In embodiments, $R^{3C}$ is independently substituted or unsubstituted heteroaryl (e.g., 5 to 10 membered, 5 to 9 membered, or 5 to 6 membered). In embodiments, $R^{3C}$ is independently substituted heteroaryl (e.g., 5 to 10 membered, 5 to 9 membered, or 5 to 6 membered). In embodiments, $R^{3C}$ is independently unsubstituted heteroaryl (e.g., 5 to 10 membered, 5 to 9 membered, or 5 to 6 membered).

In embodiments, $R^{3D}$ is independently hydrogen. In embodiments, $R^{3D}$ is independently —$CX^{3D}_3$. In embodiments, $R^{3D}$ is independently —$CHX^{3D}_2$. In embodiments, $R^{3D}$ is independently —$CH_2X^{3D}$. In embodiments, $R^{3D}$ is independently —CN. In embodiments, $R^{3D}$ is independently —COOH. In embodiments, $R^{3D}$ is independently —$CONH_2$. In embodiments, $X^{3D}$ is independently —F, —Cl, —Br, or —I.

In embodiments, $R^{3D}$ is independently substituted or unsubstituted alkyl (e.g., $C_1$-$C_8$, $C_1$-$C_6$, $C_1$-$C_4$, or $C_1$-$C_2$). In embodiments, $R^{3D}$ is independently substituted alkyl (e.g., $C_1$-$C_8$, $C_1$-$C_6$, $C_1$-$C_4$, or $C_1$-$C_2$). In embodiments, $R^{3D}$ is independently unsubstituted alkyl (e.g., $C_1$-$C_8$, $C_1$-$C_6$, $C_1$-$C_4$, or $C_1$-$C_2$). In embodiments, $R^{3D}$ is independently unsubstituted methyl. In embodiments, $R^{3D}$ is independently unsubstituted ethyl. In embodiments, $R^{3D}$ is independently unsubstituted propyl. In embodiments, $R^{3D}$ is independently unsubstituted isopropyl. In embodiments, $R^{3D}$ is independently unsubstituted tert-butyl. In embodiments, $R^{3D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3D}$ is independently substituted heteroalkyl (e.g., 2 to 8 membered, 2 to 6 membered, 4 to 6 membered, 2 to 3 membered, or 4 to 5 membered). In embodiments, $R^{3D}$ is independently unsubstituted heteroalkyl (e.g., 2 to 8 membered, 2 to 6 membered, 4 to 6 membered, 2 to 3 membered, or 4 to 5 membered). In embodiments, $R^{3D}$ is independently substituted or unsubstituted cycloalkyl (e.g., $C_3$-$C_8$, $C_3$-$C_6$, $C_4$-$C_6$, or $C_5$-$C_6$). In embodiments, $R^{3D}$ is independently substituted cycloalkyl (e.g., $C_3$-$C_8$, $C_3$-$C_6$, $C_4$-$C_6$, or $C_5$-$C_6$). In embodiments, $R^{3D}$ is independently unsubstituted cycloalkyl (e.g., $C_3$-$C_8$, $C_3$-$C_6$, $C_4$-$C_6$, or $C_5$-$C_6$). In embodiments, $R^{3D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3D}$ is independently substituted heterocycloalkyl (e.g., 3 to 8 membered, 3 to 6 membered, 4 to 6 membered, 4 to 5 membered, or 5 to 6 membered). In embodiments, $R^{3D}$ is independently unsubstituted heterocycloalkyl (e.g., 3 to 8 membered, 3 to 6 membered, 4 to 6 membered, 4 to 5 membered, or 5 to 6 membered). In embodiments, $R^{3D}$ is independently substituted or unsubstituted aryl (e.g., $C_6$-$C_{10}$ or phenyl). In embodiments, $R^{3D}$ is independently substituted aryl (e.g., $C_6$-$C_{10}$ or phenyl). In embodiments, $R^{3D}$ is independently unsubstituted aryl (e.g., $C_6$-$C_{10}$ or phenyl). In embodiments, $R^{3D}$ is independently substituted or unsubstituted heteroaryl (e.g., 5 to 10 membered, 5 to 9 membered, or 5 to 6 membered). In embodiments, $R^{3D}$ is independently substituted heteroaryl (e.g., 5 to 10 membered, 5 to 9 membered, or 5 to 6 membered). In embodiments, $R^{3D}$ is independently unsubstituted heteroaryl (e.g., 5 to 10 membered, 5 to 9 membered, or 5 to 6 membered).

In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{26}$-substituted or unsubstituted alkyl (e.g., $C_1$-$C_8$, $C_1$-$C_6$, $C_1$-$C_4$, or $C_1$-$C_2$), $R^{26}$-substituted or unsubstituted heteroalkyl (e.g., 2 to 8 membered, 2 to 6 membered, 4 to 6 membered, 2 to 3 membered, or 4 to 5 membered), $R^{26}$-substituted or unsubstituted cycloalkyl (e.g., $C_3$-$C_8$, $C_3$-$C_6$, $C_4$-$C_6$, or $C_5$-$C_6$), $R^{26}$-substituted or unsubstituted heterocycloalkyl (e.g., 3 to 8 membered, 3 to 6 membered, 4 to 6 membered, 4 to 5 membered, or 5 to 6 membered), $R^{26}$-substituted or unsubstituted aryl (e.g., $C_6$-$C_{10}$ or phenyl), or $R^{26}$-substituted or unsubstituted heteroaryl (e.g., 5 to 10 membered, 5 to 9 membered, or 5 to 6 membered). In embodiments, $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^3$ is independently —F, —Cl, —Br, or —I. In embodiments, $R^3$ is independently hydrogen. In embodiments, $R^3$ is independently unsubstituted methyl. In embodiments, $R^3$ is independently unsubstituted ethyl.

$R^{26}$ is independently oxo, halogen, $—CX^{26}_3$, $—CHX^{26}_2$, $—CH_2X^{26}$, $—OCX^{26}_3$, $—OCH_2X^{26}$, $—OCHX^{26}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 to 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 8 membered, 3 to 6 membered, 4 to 6 membered, 4 to 5 membered, or 5 to 6 membered), $R^{27}$-substituted or unsubstituted aryl (e.g., $C_6$-$C_{10}$ or phenyl), or $R^{27}$-substituted or unsubstituted heteroaryl (e.g., 5 to 10 membered, 5 to 9 membered, or 5 to 6 membered). In embodiments, $R^{26}$ is independently oxo, halogen, $—CX^{26}_3$, $—CHX^{26}_2$, $—CH_2X^{26}$, $—OCX^{26}_3$, $—OCH_2X^{26}$, $—OCHX^{26}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O) NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{26}$ is independently —F, —Cl, —Br, or —I. In embodiments, $R^{26}$ is independently unsubstituted methyl. In embodiments, $R^{26}$ is independently unsubstituted ethyl.

$R^{27}$ is independently oxo, halogen, $—CX^{27}_3$, $—CHX^{27}_2$, $—CH_2X^{27}$, $—OCX^{27}_3$, $—OCH_2X^{27}$, $—OCHX^{27}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 to 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 8 membered, 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered). In embodiments, $R^{27}$ is independently oxo, halogen, $—CX^{27}_3$, $—CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27}$ is independently —F, —Cl, —Br, or —I. In embodiments, $R^{27}$ is independently unsubstituted methyl. In embodiments, $R^{27}$ is independently unsubstituted ethyl.

$R^{28}$ is independently oxo, halogen, —$CX^{28}_3$, —$CHX^{28}_2$, —$CH_2X^{28}$, —$OCX^{28}_3$, —$OCH_2X^{28}$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21}$ is independently —F, —Cl, —Br, or —I. In embodiments, $R^{28}$ is independently unsubstituted methyl. In embodiments, $R^{28}$ is independently unsubstituted ethyl.

In embodiments, $R^{3A}$ is independently hydrogen, —$CX^{3A}_3$, —$CHX^{3A}_2$, —$CH_2X^{3A}$, —CN, —COOH, —$CONH_2$, $R^{26A}$-substituted or unsubstituted alkyl (e.g., $C_1$-$C_8$, $C_1$-$C_6$, $C_1$-$C_4$, or $C_1$-$C_2$), $R^{26A}$-substituted or unsubstituted heteroalkyl (e.g., 2 to 8 membered, 2 to 6 membered, 4 to 6 membered, 2 to 3 membered, or 4 to 5 membered), $R^{26A}$-substituted or unsubstituted cycloalkyl (e.g., $C_3$-$C_8$, $C_3$-$C_6$, $C_4$-$C_6$, or $C_5$-$C_6$), $R^{26A}$-substituted or unsubstituted heterocycloalkyl (e.g., 3 to 8 membered, 3 to 6 membered, 4 to 6 membered, 4 to 5 membered, or 5 to 6 membered), $R^{26A}$-substituted or unsubstituted aryl (e.g., $C_6$-$C_{10}$ or phenyl), or $R^{26A}$-substituted or unsubstituted heteroaryl (e.g., 5 to 10 membered, 5 to 9 membered, or 5 to 6 membered). In embodiments, $R^{3A}$ is independently hydrogen, —$CX^{3A}_3$, —$CHX^{3A}_2$, —$CH_2X^{3A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3A}$ is independently —F, —Cl, —Br, or —I. In embodiments, $R^{3A}$ is independently hydrogen. In embodiments, $R^{3A}$ is independently unsubstituted methyl. In embodiments, $R^{3A}$ is independently unsubstituted ethyl.

In embodiments, $R^{3A}$ and $R^{3B}$ substituents bonded to the same nitrogen atom may optionally be joined to form a $R^{26A}$-substituted or unsubstituted heterocycloalkyl (e.g., 3 to 8 membered, 3 to 6 membered, 4 to 6 membered, 4 to 5 membered, or 5 to 6 membered) or $R^{26A}$-substituted or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form a $R^{26A}$-substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{26A}$ is independently oxo, halogen, —$CX^{26A}_3$, —$CHX^{26A}_2$, —$CH_2X^{26A}$, —$OCX^{26A}_3$, —$OCH_2X^{26A}$, —$OCHX^{26A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{27A}$-substituted or unsubstituted alkyl (e.g., $C_1$-$C_8$, $C_1$-$C_6$, $C_1$-$C_4$, or $C_1$-$C_2$), $R^{27A}$-substituted or unsubstituted heteroalkyl (e.g., 2 to 8 membered, 2 to 6 membered, 4 to 6 membered, 2 to 3 membered, or 4 to 5 membered), $R^{27A}$-substituted or unsubstituted cycloalkyl (e.g., $C_3$-$C_8$, $C_3$-$C_6$, $C_4$-$C_6$, or $C_5$-$C_6$), $R^{27A}$-substituted or unsubstituted heterocycloalkyl (e.g., 3 to 8 membered, 3 to 6 membered, 4 to 6 membered, 4 to 5 membered, or 5 to 6 membered), $R^{27A}$-substituted or unsubstituted aryl (e.g., $C_6$-$C_{10}$ or phenyl), or $R^{27A}$-substituted or unsubstituted heteroaryl (e.g., 5 to 10 membered, 5 to 9 membered, or 5 to 6 membered). In embodiments, $R^{26A}$ is independently oxo, halogen, —$CX^{26A}_3$, —$CHX^{26A}_2$, —$CH_2X^{26A}$, —$OCX^{26A}_3$, —$OCH_2X^{26A}$, —$OCHX^{26A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{26A}$ is independently —F, —Cl, —Br, or —I. In embodiments, $R^{26A}$ is independently unsubstituted methyl. In embodiments, $R^{26A}$ is independently unsubstituted ethyl.

$R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{28A}$-substituted or unsubstituted alkyl (e.g., $C_1$-$C_8$, $C_1$-$C_6$, $C_1$-$C_4$, or $C_1$-$C_2$), $R^{28A}$-substituted or unsubstituted heteroalkyl (e.g., 2 to 8 membered, 2 to 6 membered, 4 to 6 membered, 2 to 3 membered, or 4 to 5 membered), $R^{28A}$-substituted or unsubstituted cycloalkyl (e.g., $C_3$-$C_8$, $C_3$-$C_6$, $C_4$-$C_6$, or $C_5$-$C_6$), $R^{28A}$-substituted or unsubstituted heterocycloalkyl (e.g., 3 to 8 membered, 3 to 6 membered, 4 to 6 membered, 4 to 5 membered, or 5 to 6 membered), $R^{28A}$-substituted or unsubstituted aryl (e.g., $C_6$-$C_{10}$ or phenyl), or $R^{28A}$-substituted or unsubstituted heteroaryl (e.g., 5 to 10 membered, 5 to 9 membered, or 5 to 6 membered). In embodiments, $R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27A}$ is independently —F, —Cl, —Br, or —I. In embodiments, $R^{27A}$ is independently unsubstituted methyl. In embodiments, $R^{27A}$ is independently unsubstituted ethyl.

$R^{28A}$ is independently oxo, halogen, —$CX^{28A}_3$, —$CHX^{28A}_2$, —$CH_2X^{28A}$, —$OCX^{28A}_3$, —$OCH_2X^{28A}$, —$OCHX^{28A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28A}$ is independently —F, —Cl, —Br, or —I. In embodiments, $R^{28A}$ is independently unsubstituted methyl. In embodiments, $R^{28A}$ is independently unsubstituted ethyl.

In embodiments, $R^{3B}$ is independently hydrogen, —$CX^{3B}_3$, —$CHX^{3B}_2$, —$CH_2X^{3B}$—CN, —COOH, —$CONH_2$, $R^{26B}$-substituted or unsubstituted alkyl (e.g., $C_1$-$C_8$, $C_1$-$C_6$, $C_1$-$C_4$, or $C_1$-$C_2$), $R^{26B}$-substituted or unsubstituted heteroalkyl (e.g., 2 to 8 membered, 2 to 6 membered, 4 to 6 membered, 2 to 3 membered, or 4 to 5 membered), $R^{26B}$-substituted or unsubstituted cycloalkyl (e.g., $C_3$-$C_8$, $C_3$-$C_6$, $C_4$-$C_6$, or $C_5$-$C_6$), $R^{26B}$-substituted or unsubstituted heterocycloalkyl (e.g., 3 to 8 membered, 3 to 6 membered, 4 to 6 membered, 4 to 5 membered, or 5 to 6 membered), $R^{26B}$-substituted or unsubstituted aryl (e.g., $C_6$-$C_{10}$ or phenyl), or $R^{26B}$-substituted or unsubstituted heteroaryl (e.g., 5 to 10 membered, 5 to 9 membered, or 5 to 6 membered). In embodiments, $R^{3B}$ is independently hydrogen, —$CX^{3B}_3$, —$CHX^{3B}_2$, —$CH_2X^{3B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3B}$ is independently —F, —Cl, —Br, or —I. In embodiments, $R^{3B}$ is independently hydrogen. In embodiments, $R^{3B}$ is independently unsubstituted methyl. In embodiments, $R^{3B}$ is independently unsubstituted ethyl.

In embodiments, $R^{3A}$ and $R^{3B}$ substituents bonded to the same nitrogen atom may optionally be joined to form a $R^{26B}$-substituted or unsubstituted heterocycloalkyl (e.g., 3 to 8 membered, 3 to 6 membered, 4 to 6 membered, 4 to 5 membered, or 5 to 6 membered) or $R^{26B}$-substituted or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form a $R^{26B}$-substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{26B}$ is independently oxo, halogen, —$CX^{26B}_3$, —$CHX^{26B}_2$, —$CH_2X^{26B}$, —$OCX^{26B}_3$, —$OCH_2X^{26B}$, —$OCHX^{26B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{27B}$-substituted or unsubstituted alkyl (e.g., $C_1$-$C_8$, $C_1$-$C_6$, $C_1$-$C_4$, or $C_1$-$C_2$), $R^{27B}$-substituted or unsubstituted heteroalkyl (e.g., 2 to 8 membered, 2 to 6 membered, 4 to 6 membered, 2 to 3 membered, or 4 to 5 membered), $R^{27B}$-substituted or unsubstituted cycloalkyl (e.g., $C_3$-$C_8$, $C_3$-$C_6$, $C_4$-$C_6$, or $C_5$-$C_6$), $R^{27B}$-substituted or unsubstituted heterocycloalkyl (e.g., 3 to 8 membered, 3 to 6 membered, 4 to 6 membered, 4 to 5 membered, or 5 to 6 membered), $R^{27B}$-substituted or unsubstituted aryl (e.g., $C_6$-$C_{10}$ or phenyl), or $R^{27B}$-substituted or unsubstituted heteroaryl (e.g., 5 to 10 membered, 5 to 9 membered, or 5 to 6 membered). In embodiments, $R^{26B}$ is independently oxo, halogen, —$CX^{26B}_3$, —$CHX^{26B}_2$, —$CH_2X^{26B}$, —$OCX^{26B}_3$, —$OCH_2X^{26B}$, —$OCHX^{26B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{26B}$ is independently —F, —Cl, —Br, or —I. In embodiments, $R^{26B}$ is independently unsubstituted methyl. In embodiments, $R^{26B}$ is independently unsubstituted ethyl.

$R^{27B}$ is independently oxo, halogen, —$CX^{27B}_3$, —$CHX^{27B}_2$, —$CH_2X^{27B}$, —$OCX^{27B}_3$, —$OCH_2X^{27B}$, —$OCHX^{27B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{28B}$-substituted or unsubstituted alkyl (e.g., $C_1$-$C_8$, $C_1$-$C_6$, $C_1$-$C_4$, or $C_1$-$C_2$), $R^{28B}$-substituted or unsubstituted heteroalkyl (e.g., 2 to 8 membered, 2 to 6 membered, 4 to 6 membered, 2 to 3 membered, or 4 to 5 membered), $R^{28B}$-substituted or unsubstituted cycloalkyl (e.g., $C_3$-$C_8$, $C_3$-$C_6$, $C_4$-$C_6$, or $C_5$-$C_6$), $R^{28B}$-substituted or unsubstituted heterocycloalkyl (e.g., 3 to 8 membered, 3 to 6 membered, 4 to 6 membered, 4 to 5 membered, or 5 to 6 membered), $R^{28B}$-substituted or unsubstituted aryl (e.g., $C_6$-$C_{10}$ or phenyl), or $R^{28B}$-substituted or unsubstituted heteroaryl (e.g., 5 to 10 membered, 5 to 9 membered, or 5 to 6 membered). In embodiments, $R^{27B}$ is independently oxo, halogen, $-CX^{27B}_3$, $-CHX^{27B}_2$, $-CH_2X^{27B}$, $-OCX^{27B}_3$, $-OCH_2X^{27B}$, $-OCHX^{27B}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC═(O)$NHNH_2$, —NHC═(O)$NH_2$, $-NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27B}$ is independently —F, —Cl, —Br, or —I. In embodiments, $R^{27B}$ is independently unsubstituted methyl. In embodiments, $R^{27B}$ is independently unsubstituted ethyl.

$R^{28B}$ is independently oxo, halogen, $-CX^{28B}_3$, $-CHX^{28B}_2$, $-CH_2X^{28B}$, $-OCX^{28B}_3$, $-OCH_2X^{28B}$, $-OCHX^{28B}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC═(O)$NHNH_2$, —NHC═(O)$NH_2$, $-NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28B}$ is independently —F, —Cl, —Br, or —I. In embodiments, $R^{28B}$ is independently unsubstituted methyl. In embodiments, $R^{28B}$ is independently unsubstituted ethyl.

In embodiments, $R^{3C}$ is independently hydrogen, $-CX^{3C}_3$, $-CHX^{3C}_2$, $-CH_2X^{3C}$, —CN, —COOH, $-CONH_2$, $R^{26C}$-substituted or unsubstituted alkyl (e.g., $C_1$-$C_8$, $C_1$-$C_6$, $C_1$-$C_4$, or $C_1$-$C_2$), $R^{26C}$-substituted or unsubstituted heteroalkyl (e.g., 2 to 8 membered, 2 to 6 membered, 4 to 6 membered, 2 to 3 membered, or 4 to 5 membered), $R^{26C}$-substituted or unsubstituted cycloalkyl (e.g., $C_3$-$C_8$, $C_3$-$C_6$, $C_4$-$C_6$, or $C_5$-$C_6$), $R^{26C}$-substituted or unsubstituted heterocycloalkyl (e.g., 3 to 8 membered, 3 to 6 membered, 4 to 6 membered, 4 to 5 membered, or 5 to 6 membered), $R^{26C}$-substituted or unsubstituted aryl (e.g., $C_6$-$C_{10}$ or phenyl), or $R^{26C}$-substituted or unsubstituted heteroaryl (e.g., 5 to 10 membered, 5 to 9 membered, or 5 to 6 membered). In embodiments, $R^{3C}$ is independently hydrogen, $-CX^{3C}_3$, $-CHX^{3C}_2$, $-CH_2X^{3C}$, —CN, —COOH, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3C}$ is independently —F, —Cl, —Br, or —I. In embodiments, $R^{3C}$ is independently hydrogen. In embodiments, $R^{3C}$ is independently unsubstituted methyl. In embodiments, $R^{3C}$ is independently unsubstituted ethyl.

$R^{26C}$ is independently oxo, halogen, $-CX^{26C}_3$, $-CHX^{26C}_2$, $-CH_2X^{26C}$, $-OCX^{26C}$, $-OCH_2X^{26C}$, $-OCHX^{26C}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC═(O)$NHNH_2$, —NHC═(O)$NH_2$, $-NHSO_2H$, —NHC═(O)H, —NHC(O)—OH, —NHOH, $R^{27C}$-substituted or unsubstituted alkyl (e.g., $C_1$-$C_8$, $C_1$-$C_6$, $C_1$-$C_4$, or $C_1$-$C_2$), $R^{27C}$-substituted or unsubstituted heteroalkyl (e.g., 2 to 8 membered, 2 to 6 membered, 4 to 6 membered, 2 to 3 membered, or 4 to 5 membered), $R^{27C}$-substituted or unsubstituted cycloalkyl (e.g., $C_3$-$C_8$, $C_3$-$C_6$, $C_4$-$C_6$, or $C_5$-$C_6$), $R^{27C}$-substituted or unsubstituted heterocycloalkyl (e.g., 3 to 8 membered, 3 to 6 membered, 4 to 6 membered, 4 to 5 membered, or 5 to 6 membered), $R^{27C}$-substituted or unsubstituted aryl (e.g., $C_6$-$C_{10}$ or phenyl), or $R^{27C}$-substituted or unsubstituted heteroaryl (e.g., 5 to 10 membered, 5 to 9 membered, or 5 to 6 membered). In embodiments, $R^{26C}$ is independently oxo, halogen, $-CX^{26C}_3$, $-CHX^{26C}_2$, $-CH_2X^{26C}$, $-OCX^{26C}$, $-OCH_2X^{26C}$, $-OCHX^{26C}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC═(O)$NHNH_2$, —NHC═(O)$NH_2$, $-NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{26C}$ is independently —F, —Cl, —Br, or —I. In embodiments, $R^{26C}$ is independently unsubstituted methyl. In embodiments, $R^{26C}$ is independently unsubstituted ethyl.

$R^{27C}$ is independently oxo, halogen, $-CX^{27C}_3$, $-CHX^{27C}_2$, $-CH_2X^{27C}$, $-OCX^{27C}$, $-OCH_2X^{27C}$, $-OCHX^{27C}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC═(O)$NHNH_2$, —NHC═(O)$NH_2$, $-NHSO_2H$, —NHC═(O)H, —NHC(O)—OH, —NHOH, $R^{28C}$-substituted or unsubstituted alkyl (e.g., $C_1$-$C_8$, $C_1$-$C_6$, $C_1$-$C_4$, or $C_1$-$C_2$), $R^{28C}$-substituted or unsubstituted heteroalkyl (e.g., 2 to 8 membered, 2 to 6 membered, 4 to 6 membered, 2 to 3 membered, or 4 to 5 membered), $R^{28C}$-substituted or unsubstituted cycloalkyl (e.g., $C_3$-$C_8$, $C_3$-$C_6$, $C_4$-$C_6$, or $C_5$-$C_6$), $R^{28C}$-substituted or unsubstituted heterocycloalkyl (e.g., 3 to 8 membered, 3 to 6 membered, 4 to 6 membered, 4 to 5 membered, or 5 to 6 membered), $R^{28C}$-substituted or unsubstituted aryl (e.g., $C_6$-$C_{10}$ or phenyl), or $R^{28C}$-substituted or unsubstituted heteroaryl (e.g., 5 to 10 membered, 5 to 9 membered, or 5 to 6 membered). In embodiments, $R^{27C}$ is independently oxo, halogen, $-CX^{27C}_3$, $-CHX^{27C}_2$, $-CH_2X^{27C}$, $-OCX^{27C}_3$, $-OCH_2X^{27C}$, $-OCHX^{27C}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, —NHC═(O)$NHNH_2$, —NHC═(O)$NH_2$, $-NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27C}$ is independently —F, —Cl, —Br, or —I. In embodiments, $R^{27C}$ is independently unsubstituted methyl. In embodiments, $R^{27C}$ is independently unsubstituted ethyl.

$R^{28C}$ is independently oxo, halogen, $—CX^{28C}_3$, $—CHX^{28C}_2$, $—CH_2X^{28C}$, $—OCX^{28C}$, $—OCH_2X^{28C}$, $—OCHX^{28C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28C}$ is independently —F, —Cl, —Br, or —I. In embodiments, $R^{28C}$ is independently unsubstituted methyl. In embodiments, $R^{28C}$ is independently unsubstituted ethyl.

In embodiments, $R^{3D}$ is independently hydrogen, $—CX^{3D}_3$, $—CHX^{3D}_2$, $—CH_2X^{3D}$—CN, —COOH, $—CONH_2$, $R^{26D}$-substituted or unsubstituted alkyl (e.g., $C_1$-$C_8$, $C_1$-$C_6$, $C_1$-$C_4$, or $C_1$-$C_2$), $R^{26D}$-substituted or unsubstituted heteroalkyl (e.g., 2 to 8 membered, 2 to 6 membered, 4 to 6 membered, 2 to 3 membered, or 4 to 5 membered), $R^{26D}$-substituted or unsubstituted cycloalkyl (e.g., $C_3$-$C_8$, $C_3$-$C_6$, $C_4$-$C_6$, or $C_5$-$C_6$), $R^{26D}$-substituted or unsubstituted heterocycloalkyl (e.g., 3 to 8 membered, 3 to 6 membered, 4 to 6 membered, 4 to 5 membered, or 5 to 6 membered), $R^{26D}$-substituted or unsubstituted aryl (e.g., $C_6$-$C_{10}$ or phenyl), or $R^{26D}$-substituted or unsubstituted heteroaryl (e.g., 5 to 10 membered, 5 to 9 membered, or 5 to 6 membered). In embodiments, $R^{3D}$ is independently hydrogen, $—CX^{3D}_3$, $—CHX^{3D}_2$, $—CH_2X^{3D}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3D}$ is independently —F, —Cl, —Br, or —I. In embodiments, $R^{3D}$ is independently hydrogen. In embodiments, $R^{3D}$ is independently unsubstituted methyl. In embodiments, $R^{3D}$ is independently unsubstituted ethyl.

$R^{26D}$ is independently oxo, halogen, $—CX^{26D}_3$, $—CHX^{26D}_2$, $—CH_2X^{26D}$, $—OCX^{26D}_3$, $—OCH_2X^{26D}$, $—OCHX^{26D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{27D}$-substituted or unsubstituted alkyl (e.g., $C_1$-$C_8$, $C_1$-$C_6$, $C_1$-$C_4$, or $C_1$-$C_2$), $R^{27D}$-substituted or unsubstituted heteroalkyl (e.g., 2 to 8 membered, 2 to 6 membered, 4 to 6 membered, 2 to 3 membered, or 4 to 5 membered), $R^{27D}$-substituted or unsubstituted cycloalkyl (e.g., $C_3$-$C_8$, $C_3$-$C_6$, $C_4$-$C_6$, or $C_5$-$C_6$), $R^{27D}$-substituted or unsubstituted heterocycloalkyl (e.g., 3 to 8 membered, 3 to 6 membered, 4 to 6 membered, 4 to 5 membered, or 5 to 6 membered), $R^{27D}$-substituted or unsubstituted aryl (e.g., $C_6$-$C_{10}$ or phenyl), or $R^{27D}$-substituted or unsubstituted heteroaryl (e.g., 5 to 10 membered, 5 to 9 membered, or 5 to 6 membered). In embodiments, $R^{26D}$ is independently oxo, halogen, $—CX^{26D}_3$, $—CHX^{26D}_2$, $—CH_2X^{26D}$, $—OCX^{26D}_3$, $—OCH_2X^{26D}$, $—OCHX^{26D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{26D}$ is independently —F, —Cl, —Br, or —I. In embodiments, $R^{26D}$ is independently unsubstituted methyl. In embodiments, $R^{26D}$ is independently unsubstituted ethyl.

$R^{27D}$ is independently oxo, halogen, $—CX^{27D}_3$, $—CHX^{27D}_2$, $—CH_2X^{27D}$, $—OCX^{27D}_3$, $—OCH_2X^{27D}$, $—OCHX^{27D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{28D}$-substituted or unsubstituted alkyl (e.g., $C_1$-$C_8$, $C_1$-$C_6$, $C_1$-$C_4$, or $C_1$-$C_2$), $R^{28D}$-substituted or unsubstituted heteroalkyl (e.g., 2 to 8 membered, 2 to 6 membered, 4 to 6 membered, 2 to 3 membered, or 4 to 5 membered), $R^{28D}$-substituted or unsubstituted cycloalkyl (e.g., $C_3$-$C_8$, $C_3$-$C_6$, $C_4$-$C_6$, or $C_5$-$C_6$), $R^{28D}$-substituted or unsubstituted heterocycloalkyl (e.g., 3 to 8 membered, 3 to 6 membered, 4 to 6 membered, 4 to 5 membered, or 5 to 6 membered), $R^{28D}$-substituted or unsubstituted aryl (e.g., $C_6$-$C_{10}$ or phenyl), or $R^{28D}$-substituted or unsubstituted heteroaryl (e.g., 5 to 10 membered, 5 to 9 membered, or 5 to 6 membered). In embodiments, $R^{27D}$ is independently oxo, halogen, $—CX^{27D}_3$, $—CHX^{27D}_2$, $—CH_2X^{27D}$, $—OCX^{27D}_3$, $—OCH_2X^{27D}$, $—OCHX^{27D}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27D}$ is independently —F, —Cl, —Br, or —I. In embodiments, $R^{27D}$ is independently unsubstituted methyl. In embodiments, $R^{27D}$ is independently unsubstituted ethyl.

$R^{28D}$ is independently oxo, halogen, $—CX^{28D}_3$, $—CHX^{28D}_2$, $—CH_2X^{28D}$, $—OCX^{28D}_3$, $—OCH_2X^{28D}$, $—OCHX^{28D}_2$, —CN, —OH, $—NH_2$, —COOH, $—CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28D}$ is independently —F, —Cl, —Br, or —I. In embodiments, $R^{28D}$ is independently unsubstituted methyl. In embodiments, $R^{28D}$ is independently unsubstituted ethyl.

In embodiments, $R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —$N(O)_{m4}$, —$NR^{4A}R^{4B}$, —C(O)$R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^4$ is independently —F, —Cl, —Br, or —I.

In embodiments, $R^4$ is independently hydrogen, halogen, —$CX^4_3$, —$CHX^4_2$, —$CH_2X^4$, —$OCX^4_3$, —$OCH_2X^4$, —$OCHX^4_2$, substituted or unsubstituted alkyl, or substituted or unsubstituted heteroalkyl. In embodiments, $R^4$ is independently hydrogen, halogen, —$CX^4_3$, —$CHX^4_2$, —$CH_2X^4$, —$OCX^4_3$, —$OCH_2X^4$, —$OCHX^4_2$, substituted or unsubstituted ($C_1$-$C_4$) alkyl, or substituted or unsubstituted 2 to 4 membered heteroalkyl. In embodiments, $R^4$ is hydrogen, halogen, —$CH_3$, —$CH_2CH_3$, —$CX^4_3$, —$CHX^4_2$, —$CH_2X^4$, —$OCH_3$, —$OCX^4_3$, —$OCH_2X^4$, —$OCHX^4_2$, —$SCH_3$, —$SCX^4_3$, —$SCH_2X^4$, or —$SCHX^4_2$. In embodiments, $R^4$ is hydrogen, halogen, —$CH_3$, —$CH_2CH_3$, —$CF_3$, or —$OCH_3$. In embodiments, $R^4$ is —$CH_3$, —$CH_2CH_3$, or —$OCH_3$. In embodiments, $R^4$ is —$OCH_3$.

In embodiments, $R^4$ is independently hydrogen. In embodiments, $R^4$ is independently halogen. In embodiments, $R^4$ is independently —$CX^4_3$. In embodiments, $R^4$ is independently —$CHX^{42}$. In embodiments, $R^4$ is independently —$CH_2X^4$. In embodiments, $R^4$ is independently —$OCX^4_3$. In embodiments, $R^4$ is independently —$OCH_2X^4$. In embodiments, $R^4$ is independently —$OCHX^4_2$. In embodiments, $R^4$ is independently —CN. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$NO_2$. In embodiments, $R^4$ is independently —SH. In embodiments, $R^4$ is independently —$CF_3$. In embodiments, $R^4$ is independently —$CHF_2$. In embodiments, $R^4$ is independently —$CH_2F$. In embodiments, $R^4$ is independently —$OCF_3$. In embodiments, $R^4$ is independently —$OCH_2F$. In embodiments, $R^4$ is independently —$OCHF_2$. In embodiments, $R^4$ is independently —$OCH_3$. In embodiments, $R^4$ is independently —$OCH_2CH_3$. In embodiments, $R^4$ is independently —$OCH_2CH_2CH_3$. In embodiments, $R^4$ is independently —$OCH(CH_3)_2$. In embodiments, $R^4$ is independently —$OC(CH_3)_3$. In embodiments, $R^4$ is independently —$SCH_3$. In embodiments, $R^4$ is independently —$SCH_2CH_3$. In embodiments, $R^4$ is independently —$SCH_2CH_2CH_3$. In embodiments, $R^4$ is independently —$SCH(CH_3)_2$. In embodiments, $R^4$ is independently —$SC(CH_3)_3$. In embodiments, $R^4$ is independently —$CH_3$. In embodiments, $R^4$ is independently —$CH_2CH_3$. In embodiments, $R^4$ is independently —$CH_2CH_2CH_3$. In embodiments, $R^4$ is independently —$CH(CH_3)_2$. In embodiments, $R^4$ is independently —$C(CH_3)_3$. In embodiments, $R^4$ is independently —F. In embodiments, $R^4$ is independently —Cl. In embodiments, $R^4$ is independently —Br. In embodiments, $R^4$ is independently —I.

In embodiments, $R^4$ is independently substituted or unsubstituted alkyl (e.g., $C_1$-$C_8$, $C_1$-$C_6$, $C_1$-$C_4$, or $C_1$-$C_2$). In embodiments, $R^4$ is independently substituted alkyl (e.g., $C_1$-$C_8$, $C_1$-$C_6$, $C_1$-$C_4$, or $C_1$-$C_2$). In embodiments, $R^4$ is independently unsubstituted alkyl (e.g., $C_1$-$C_8$, $C_1$-$C_6$, $C_1$-$C_4$, or $C_1$-$C_2$). In embodiments, $R^4$ is independently unsubstituted methyl. In embodiments, $R^4$ is independently unsubstituted ethyl. In embodiments, $R^4$ is independently unsubstituted propyl. In embodiments, $R^4$ is independently unsubstituted isopropyl. In embodiments, $R^4$ is independently unsubstituted tert-butyl. In embodiments, $R^4$ is independently substituted or unsubstituted heteroalkyl (e.g., 2 to 8 membered, 2 to 6 membered, 4 to 6 membered, 2 to 3 membered, or 4 to 5 membered). In embodiments, $R^4$ is independently substituted heteroalkyl (e.g., 2 to 8 membered, 2 to 6 membered, 4 to 6 membered, 2 to 3 membered, or 4 to 5 membered). In embodiments, $R^4$ is independently unsubstituted heteroalkyl (e.g., 2 to 8 membered, 2 to 6 membered, 4 to 6 membered, 2 to 3 membered, or 4 to 5 membered). In embodiments, $R^4$ is independently substituted or unsubstituted cycloalkyl (e.g., $C_3$-$C_8$, $C_3$-$C_6$, $C_4$-$C_6$, or $C_5$-$C_6$). In embodiments, $R^4$ is independently substituted cycloalkyl (e.g., $C_3$-$C_8$, $C_3$-$C_6$, $C_4$-$C_6$, or $C_5$-$C_6$). In embodiments, $R^4$ is independently unsubstituted cycloalkyl (e.g., $C_3$-$C_8$, $C_3$-$C_6$, $C_4$-$C_6$, or $C_5$-$C_6$). In embodiments, $R^4$ is independently substituted or unsubstituted heterocycloalkyl (e.g., 3 to 8 membered, 3 to 6 membered, 4 to 6 membered, 4 to 5 membered, or 5 to 6 membered). In embodiments, $R^4$ is independently substituted heterocycloalkyl (e.g., 3 to 8 membered, 3 to 6 membered, 4 to 6 membered, 4 to 5 membered, or 5 to 6 membered). In embodiments, $R^4$ is independently unsubstituted heterocycloalkyl (e.g., 3 to 8 membered, 3 to 6 membered, 4 to 6 membered, 4 to 5 membered, or 5 to 6 membered). In embodiments, $R^4$ is independently substituted or unsubstituted aryl (e.g., $C_6$-$C_{10}$ or phenyl). In embodiments, $R^4$ is independently substituted aryl (e.g., $C_6$-$C_{10}$ or phenyl). In embodiments, $R^4$ is independently unsubstituted aryl (e.g., $C_6$-$C_{10}$ or phenyl). In embodiments, $R^4$ is independently substituted or unsubstituted heteroaryl (e.g., 5 to 10 membered, 5 to 9 membered, or 5 to 6 membered). In embodiments, $R^4$ is independently substituted heteroaryl (e.g., 5 to 10 membered, 5 to 9 membered, or 5 to 6 membered). In embodiments, $R^4$ is independently unsubstituted heteroaryl (e.g., 5 to 10 membered, 5 to 9 membered, or 5 to 6 membered).

In embodiments, $R^{4A}$ is independently hydrogen. In embodiments, $R^{4A}$ is independently —$CX^{4A}_3$. In embodiments, $R^{4A}$ is independently —$CHX^{4A}_2$. In embodiments, $R^{4A}$ is independently —$CH_2X^{4A}$. In embodiments, $R^{4A}$ is independently —CN. In embodiments, $R^{4A}$ is independently —COOH. In embodiments, $R^{4A}$ is independently —$CONH_2$. In embodiments, $X^{4A}$ is independently —F, —Cl, —Br, or —I.

In embodiments, $R^{4A}$ is independently substituted or unsubstituted alkyl (e.g., $C_1$-$C_8$, $C_1$-$C_6$, $C_1$-$C_4$, or $C_1$-$C_2$). In embodiments, $R^{4A}$ is independently substituted alkyl (e.g., $C_1$-$C_8$, $C_1$-$C_6$, $C_1$-$C_4$, or $C_1$-$C_2$). In embodiments, $R^{4A}$ is independently unsubstituted alkyl (e.g., $C_1$-$C_8$, $C_1$-$C_6$, $C_1$-$C_4$, or $C_1$-$C_2$). In embodiments, $R^{4A}$ is independently unsubstituted methyl. In embodiments, $R^{4A}$ is independently unsubstituted ethyl. In embodiments, $R^{4A}$ is independently unsubstituted propyl. In embodiments, $R^{4A}$ is independently unsubstituted isopropyl. In embodiments, $R^{4A}$ is independently unsubstituted tert-butyl. In embodiments, $R^{4A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4A}$ is independently substituted heteroalkyl (e.g., 2 to 8 membered, 2 to 6 membered, 4 to 6 membered, 2 to 3 membered, or 4 to 5 membered). In embodiments, $R^{4A}$ is independently unsubstituted heteroalkyl (e.g., 2 to 8 membered, 2 to 6 membered, 4 to 6 membered, 2 to 3 membered, or 4 to 5 membered). In embodiments, $R^{4A}$ is independently substituted or unsubstituted cycloalkyl (e.g., $C_3$-$C_8$, $C_3$-$C_6$, $C_4$-$C_6$, or $C_5$-$C_6$). In embodiments, $R^{4A}$ is independently substituted cycloalkyl (e.g., $C_3$-$C_8$, $C_3$-$C_6$, $C_4$-$C_6$, or $C_5$-$C_6$). In embodiments, $R^{4A}$ is independently unsubstituted cycloalkyl (e.g., $C_3$-$C_8$, $C_3$-$C_6$, $C_4$-$C_6$, or $C_5$-$C_6$). In embodiments, $R^{4A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ is independently substituted heterocycloalkyl (e.g., 3 to 8 membered, 3 to 6 membered, 4 to 6 membered, 4 to 5 membered, or 5 to 6 membered). In embodiments, $R^{4A}$ is independently unsubstituted heterocycloalkyl (e.g., 3 to 8 membered, 3 to 6 membered, 4 to 6 membered, 4 to 5 membered, or 5 to 6 membered). In embodiments, $R^{4A}$ is independently substituted or unsubstituted aryl (e.g., $C_6$-$C_{10}$ or phenyl). In embodiments, $R^{4A}$ is independently substituted aryl (e.g., $C_6$-$C_{10}$ or phenyl). In embodiments, $R^{4A}$ is independently unsubstituted aryl (e.g., $C_6$-$C_{10}$ or phenyl). In embodiments, $R^{4A}$ is independently substituted or unsubstituted heteroaryl (e.g., 5 to 10 membered, 5 to 9 membered, or 5 to 6 membered). In embodiments, $R^{4A}$ is independently substituted heteroaryl (e.g., 5 to 10 membered, 5 to 9 membered, or 5 to 6 membered). In embodiments, $R^{4A}$ is independently unsubstituted heteroaryl (e.g., 5 to 10 membered, 5 to 9 membered, or 5 to 6 membered).

In embodiments, $R^{4B}$ is independently hydrogen. In embodiments, $R^{4B}$ is independently —$CX^{4B}_3$. In embodiments, $R^{4B}$ is independently —$CHX^{4B}_2$. In embodiments, $R^{4B}$ is independently —$CH_2X^{4B}$. In embodiments, $R^{4B}$ is independently —CN. In embodiments, $R^{4B}$ is independently —COOH. In embodiments, $R^{4B}$ is independently —$CONH_2$. In embodiments, $X^{4B}$ is independently —F, —Cl, —Br, or —I.

In embodiments, $R^{4B}$ is independently substituted or unsubstituted alkyl (e.g., $C_1$-$C_8$, $C_1$-$C_6$, $C_1$-$C_4$, or $C_1$-$C_2$). In embodiments, $R^{4B}$ is independently substituted alkyl (e.g., $C_1$-$C_8$, $C_1$-$C_6$, $C_1$-$C_4$, or $C_1$-$C_2$). In embodiments, $R^{4B}$ is independently unsubstituted alkyl (e.g., $C_1$-$C_8$, $C_1$-$C_6$, $C_1$-$C_4$, or $C_1$-$C_2$). In embodiments, $R^{4B}$ is independently unsubstituted methyl. In embodiments, $R^{4B}$ is independently unsubstituted ethyl. In embodiments, $R^{4B}$ is independently unsubstituted propyl. In embodiments, $R^{4B}$ is independently unsubstituted isopropyl. In embodiments, $R^{4B}$ is independently unsubstituted tert-butyl. In embodiments, $R^{4B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4B}$ is independently substituted heteroalkyl (e.g., 2 to 8 membered, 2 to 6 membered, 4 to 6 membered, 2 to 3 membered, or 4 to 5 membered). In embodiments, $R^{4B}$ is independently unsubstituted heteroalkyl (e.g., 2 to 8 membered, 2 to 6 membered, 4 to 6 membered, 2 to 3 membered, or 4 to 5 membered). In embodiments, $R^{4B}$ is independently substituted or unsubstituted cycloalkyl (e.g., $C_3$-$C_8$, $C_3$-$C_6$, $C_4$-$C_6$, or $C_5$-$C_6$). In embodiments, $R^{4B}$ is independently substituted cycloalkyl (e.g., $C_3$-$C_8$, $C_3$-$C_6$, $C_4$-$C_6$, or $C_5$-$C_6$). In embodiments, $R^{4B}$ is independently unsubstituted cycloalkyl (e.g., $C_3$-$C_8$, $C_3$-$C_6$, $C_4$-$C_6$, or $C_5$-$C_6$). In embodiments, $R^{4B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4B}$ is independently substituted heterocycloalkyl (e.g., 3 to 8 membered, 3 to 6 membered, 4 to 6 membered, 4 to 5 membered, or 5 to 6 membered). In embodiments, $R^{4B}$ is independently unsubstituted heterocycloalkyl (e.g., 3 to 8 membered, 3 to 6 membered, 4 to 6 membered, 4 to 5 membered, or 5 to 6 membered). In embodiments, $R^{4B}$ is independently substituted or unsubstituted aryl (e.g., $C_6$-$C_{10}$ or phenyl). In embodiments, $R^{4B}$ is independently substituted aryl (e.g., $C_6$-$C_{10}$ or phenyl). In embodiments, $R^{4B}$ is independently unsubstituted aryl (e.g., $C_6$-$C_{10}$ or phenyl). In embodiments, $R^{4B}$ is independently substituted or unsubstituted heteroaryl (e.g., 5 to 10 membered, 5 to 9 membered, or 5 to 6 membered). In embodiments, $R^{4B}$ is independently substituted heteroaryl (e.g., 5 to 10 membered, 5 to 9 membered, or 5 to 6 membered). In embodiments, $R^{4B}$ is independently unsubstituted heteroaryl (e.g., 5 to 10 membered, 5 to 9 membered, or 5 to 6 membered).

In embodiments, $R^{4A}$ and $R^{4B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{4A}$ and $R^{4B}$ substituents bonded to the same nitrogen atom may be joined to form a substituted or unsubstituted heteroaryl (e.g., 5 to 10 membered, 5 to 9 membered, or 5 to 6 membered). In embodiments, $R^{4A}$ and $R^{4B}$ substituents bonded to the same nitrogen atom may be joined to form a substituted heteroaryl (e.g., 5 to 10 membered, 5 to 9 membered, or 5 to 6 membered). In embodiments, $R^{4A}$ and $R^{4B}$ substituents bonded to the same nitrogen atom may be joined to form an unsubstituted heteroaryl (e.g., 5 to 10 membered, 5 to 9 membered, or 5 to 6 membered).

In embodiments, $R^{4C}$ is independently hydrogen. In embodiments, $R^{4C}$ is independently —$CX^{4C}_3$. In embodiments, $R^{4C}$ is independently —$CHX^{4C}_2$. In embodiments, $R^{4C}$ is independently —$CH_2X^{4C}$. In embodiments, $R^{4C}$ is independently —CN. In embodiments, $R^{4C}$ is independently —COOH. In embodiments, $R^{4C}$ is independently —$CONH_2$. In embodiments, $X^{4C}$ is independently —F, —Cl, —Br, or —I.

In embodiments, $R^{4C}$ is independently substituted or unsubstituted alkyl (e.g., $C_1$-$C_8$, $C_1$-$C_6$, $C_1$-$C_4$, or $C_1$-$C_2$). In embodiments, $R^{4C}$ is independently substituted alkyl (e.g., $C_1$-$C_8$, $C_1$-$C_6$, $C_1$-$C_4$, or $C_1$-$C_2$). In embodiments, $R^{4C}$ is independently unsubstituted alkyl (e.g., $C_1$-$C_8$, $C_1$-$C_6$, $C_1$-$C_4$, or $C_1$-$C_2$). In embodiments, $R^{4C}$ is independently unsubstituted methyl. In embodiments, $R^{4C}$ is independently unsubstituted ethyl. In embodiments, $R^{4C}$ is independently unsubstituted propyl. In embodiments, $R^{4C}$ is independently unsubstituted isopropyl. In embodiments, $R^{4C}$ is independently unsubstituted tert-butyl. In embodiments, $R^{4C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4C}$ is independently substituted heteroalkyl (e.g., 2 to 8 membered, 2 to 6 membered, 4 to 6 membered, 2 to 3 membered, or 4 to 5 membered). In embodiments, $R^{4C}$ is independently unsubstituted heteroalkyl (e.g., 2 to 8 membered, 2 to 6 membered, 4 to 6 membered, 2 to 3 membered, or 4 to 5 membered). In embodiments, $R^{4C}$ is independently substituted or unsubstituted cycloalkyl (e.g., $C_3$-$C_8$, $C_3$-$C_6$, $C_4$-$C_6$, or $C_5$-$C_6$). In embodiments, $R^{4C}$ is independently substituted cycloalkyl (e.g., $C_3$-$C_8$, $C_3$-$C_6$, $C_4$-$C_6$, or $C_5$-$C_6$). In embodiments, $R^{4C}$ is independently unsubstituted cycloalkyl (e.g., $C_3$-$C_8$, $C_3$-$C_6$, $C_4$-$C_6$, or $C_5$-$C_6$). In embodiments, $R^{4C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4C}$ is independently substituted heterocycloalkyl (e.g., 3 to 8 membered, 3 to 6 membered, 4 to 6 membered, 4 to 5 membered, or 5 to 6 membered). In embodiments, $R^{4C}$ is independently unsubstituted heterocycloalkyl (e.g., 3 to 8 membered, 3 to 6 membered, 4 to 6 membered, 4 to 5 membered, or 5 to 6 membered). In embodiments, $R^{4C}$ is independently substituted or unsubstituted aryl (e.g., $C_6$-$C_{10}$ or phenyl). In embodiments, $R^{4C}$ is independently substituted aryl (e.g., $C_6$-$C_{10}$ or phenyl). In embodiments, $R^{4C}$ is independently unsubstituted aryl (e.g., $C_6$-$C_{10}$ or phenyl). In embodiments, $R^{4C}$ is independently substituted or unsubstituted heteroaryl (e.g., 5 to 10 membered, 5 to 9 membered, or 5 to 6 membered). In embodiments, $R^{4C}$ is independently substituted heteroaryl (e.g., 5 to 10 membered, 5 to 9 membered, or 5 to 6 membered). In embodiments, $R^{4C}$ is independently unsubstituted heteroaryl (e.g., 5 to 10 membered, 5 to 9 membered, or 5 to 6 membered).

In embodiments, $R^{4D}$ is independently hydrogen. In embodiments, $R^{4D}$ is independently —$CX^{4D}_3$. In embodiments, $R^{4D}$ is independently —$CHX^{4D}_2$. In embodiments, $R^{4D}$ is independently —$CH_2X^{4D}$. In embodiments, $R^{4D}$ is independently —CN. In embodiments, $R^{4D}$ is independently —COOH. In embodiments, $R^{4D}$ is independently —$CONH_2$. In embodiments, $X^{4D}$ is independently —F, —Cl, —Br, or —I.

In embodiments, $R^{4D}$ is independently substituted or unsubstituted alkyl (e.g., $C_1$-$C_8$, $C_1$-$C_6$, $C_1$-$C_4$, or $C_1$-$C_2$). In embodiments, $R^{4D}$ is independently substituted alkyl (e.g., $C_1$-$C_8$, $C_1$-$C_6$, $C_1$-$C_4$, or $C_1$-$C_2$). In embodiments, $R^{4D}$ is independently unsubstituted alkyl (e.g., $C_1$-$C_8$, $C_1$-$C_6$, $C_1$-$C_4$, or $C_1$-$C_2$). In embodiments, $R^{4D}$ is independently unsubstituted methyl. In embodiments, $R^{4D}$ is independently unsubstituted ethyl. In embodiments, $R^{4D}$ is independently unsubstituted propyl. In embodiments, $R^{4D}$ is independently unsubstituted isopropyl. In embodiments, $R^{4D}$ is independently unsubstituted tert-butyl. In embodiments, $R^{4D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4D}$ is independently substituted heteroalkyl (e.g., 2 to 8 membered, 2 to 6 membered, 4 to 6 membered, 2 to 3 membered, or 4 to 5 membered). In embodiments, $R^{4D}$ is independently unsubstituted heteroalkyl (e.g., 2 to 8 membered, 2 to 6 membered, 4 to 6 membered, 2 to 3 membered, or 4 to 5 membered). In embodiments, $R^{4D}$ is independently substituted or unsubstituted cycloalkyl (e.g., $C_3$-$C_8$, $C_3$-$C_6$, $C_4$-$C_6$, or $C_5$-$C_6$). In embodiments, $R^{4D}$ is independently substituted cycloalkyl (e.g., $C_3$-$C_8$, $C_3$-$C_6$, $C_4$-$C_6$, or $C_5$-$C_6$). In embodiments, $R^{4D}$ is independently unsubstituted cycloalkyl (e.g., $C_3$-$C_8$, $C_3$-$C_6$, $C_4$-$C_6$, or $C_5$-$C_6$). In embodiments, $R^{4D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4D}$ is independently substituted heterocycloalkyl (e.g., 3 to 8 membered, 3 to 6 membered, 4 to 6 membered, 4 to 5 membered, or 5 to 6 membered). In embodiments, $R^{4D}$ is independently unsubstituted heterocycloalkyl (e.g., 3 to 8 membered, 3 to 6 membered, 4 to 6 membered, 4 to 5 membered, or 5 to 6 membered). In embodiments, $R^{4D}$ is independently substituted or unsubstituted aryl (e.g., $C_6$-$C_{10}$ or phenyl). In embodiments, $R^{4D}$ is independently substituted aryl (e.g., $C_6$-$C_{10}$ or phenyl). In embodiments, $R^{4D}$ is independently unsubstituted aryl (e.g., $C_6$-$C_{10}$ or phenyl). In embodiments, $R^{4D}$ is independently substituted or unsubstituted heteroaryl (e.g., 5 to 10 membered, 5 to 9 membered, or 5 to 6 membered). In embodiments, $R^{4D}$ is independently substituted heteroaryl (e.g., 5 to 10 membered, 5 to 9 membered, or 5 to 6 membered). In embodiments, $R^{4D}$ is independently unsubstituted heteroaryl (e.g., 5 to 10 membered, 5 to 9 membered, or 5 to 6 membered).

In embodiments, $R^5$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^5$ is independently substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is independently substituted or unsubstituted ($C_1$-$C_4$) alkyl. In embodiments, $R^5$ is independently unsubstituted ($C_1$-$C_4$) alkyl. In embodiments, $R^5$ is independently unsubstituted methyl, unsubstituted ethyl, unsubstituted isopropyl, or unsubstituted tert-butyl. In embodiments, $R^5$ is independently unsubstituted methyl or unsubstituted ethyl. In embodiments, $R^5$ is independently unsubstituted methyl. In embodiments, $R^5$ is independently unsubstituted ethyl. In embodiments, $R^5$ is independently substituted or unsubstituted 2 to 8 membered heteroalkyl. In embodiments, $R^5$ is independently substituted or unsubstituted 2 to 4 membered heteroalkyl. In embodiments, $R^5$ is independently unsubstituted 2 to 4 membered heteroalkyl. In embodiments, $R^5$ is independently —$CH_2N(CH_3)_2$. In embodiments, $R^5$ is independently substituted or unsubstituted ($C_3$-$C_6$) cycloalkyl. In embodiments, $R^5$ is independently unsubstituted ($C_3$-$C_6$) cycloalkyl. In embodiments, $R^5$ is independently unsubstituted cyclopropyl, unsubstituted cyclobutyl, or unsubstituted cyclopentyl. In embodiments, $R^5$ is independently unsubstituted cyclopropyl or unsubstituted cyclobutyl. In embodiments, $R^5$ is independently unsubstituted cyclopropyl. In embodiments, $R^5$ is independently substituted or unsubstituted 3 to 6 membered heterocycloalkyl. In embodiments, $R^5$ is independently substituted or unsubstituted 5 to 6 membered heterocycloalkyl. In embodiments, $R^5$ is independently substituted or unsubstituted 6 membered heterocycloalkyl. In embodiments, $R^5$ is independently substituted or unsubstituted piperidinyl. In embodiments, $R^5$ is independently

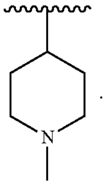

.

In embodiments, $R^5$ is independently substituted or unsubstituted phenyl. In embodiments, $R^5$ is independently unsubstituted phenyl. In embodiments, $R^5$ is independently 2-substituted phenyl. In embodiments, $R^5$ is independently 3-substituted phenyl. In embodiments, $R^5$ is independently 4-substituted phenyl. In embodiments, $R^5$ is independently phenyl substituted with halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently phenyl substituted with halogen, substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is independently phenyl substituted with —F,

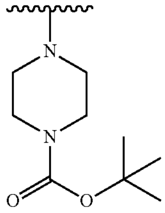

,

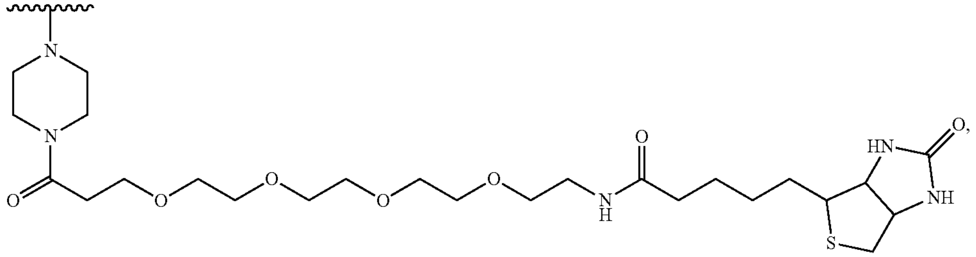

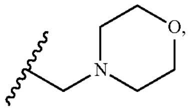

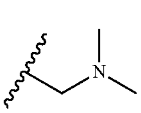

, or

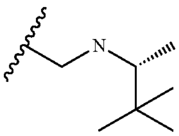

.

In embodiments, $R^5$ is independently

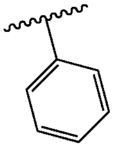

,

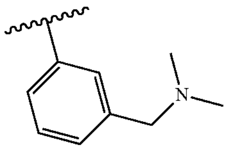

,

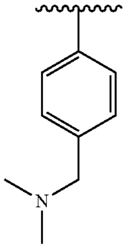

,

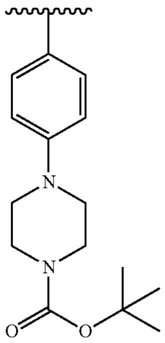

,

-continued

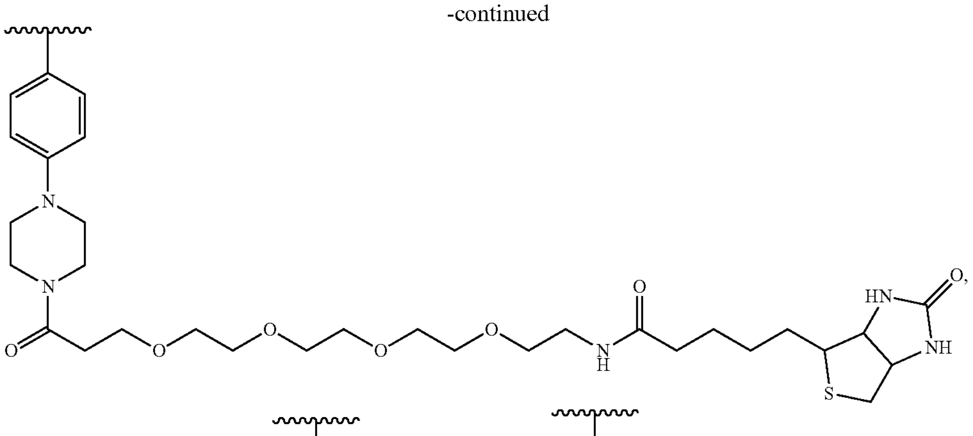

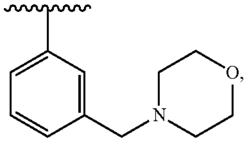
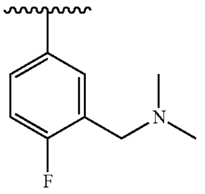
, or
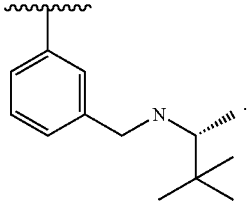

In embodiments, $R^5$ is independently —$N(CH_3)_2$. In embodiments, $R^5$ is independently —$NH(CH_3)$. In embodiments, $R^5$ is independently —$N(CH_2CH_3)_2$. In embodiments, $R^5$ is independently —$NH(CH_2CH_3)$. In embodiments, $R^5$ is independently —$N(CH_3)(CH_2CH_3)$. In embodiments, $R^5$ is independently —$CH_3$. In embodiments, $R^5$ is independently —$CH_2CH_3$. In embodiments, $R^5$ is independently unsubstituted isopropyl. In embodiments, $R^5$ is independently unsubstituted tert-butyl.

In embodiments, $R^5$ is independently

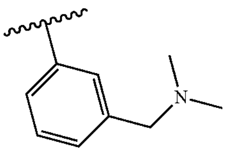
or
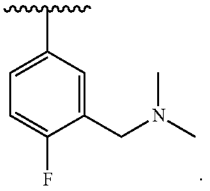
.

In embodiments, $R^5$ is independently substituted or unsubstituted heteroaryl. In embodiments, $R^5$ is independently substituted or unsubstituted 5 to 6 membered heteroaryl. In embodiments, $R^5$ is independently substituted or unsubstituted pyridyl, substituted or unsubstituted thienyl, substituted or unsubstituted furanyl, substituted or unsubstituted pyrrolyl, substituted or unsubstituted imidazolyl, substituted or unsubstituted pyrazolyl, substituted or unsubstituted thiazolyl, substituted or unsubstituted isothiazolyl, substituted or unsubstituted oxazolyl, or substituted or unsubstituted isoxazolyl.

In embodiments, $R^5$ is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is substituted or unsubstituted $C_3$-$C_8$ cycloalkyl. In embodiments, $R^5$ is substituted or unsubstituted $C_3$-$C_6$ cycloalkyl. In embodiments, $R^5$ is substituted or unsubstituted $C_5$-$C_6$ cycloalkyl. In embodiments, $R^5$ is substituted or unsubstituted $C_6$ cycloalkyl. In embodiments, $R^5$ is substituted or unsubstituted $C_5$ cycloalkyl. In embodiments, $R^5$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is $R^{32}$-substituted $C_3$-$C_8$ cycloalkyl. In embodiments, $R^5$ is $R^{32}$-substituted $C_3$-$C_6$ cycloalkyl. In embodiments, $R^5$ is $R^{32}$-substituted $C_5$-$C_6$ cycloalkyl. In embodiments, $R^5$ is $R^{32}$-substituted $C_6$ cycloalkyl. In embodiments, $R^5$ is $R^{32}$-substituted $C_5$ cycloalkyl. In embodiments, $R^5$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is an unsubstituted $C_3$-$C_8$ cycloalkyl. In embodiments, $R^5$ is an unsubstituted $C_3$-$C_6$ cycloalkyl. In embodiments, $R^5$ is an unsubstituted $C_5$-$C_6$ cycloalkyl. In embodiments, $R^5$ is an unsubstituted $C_6$ cycloalkyl. In embodiments, $R^5$ is an unsubstituted $C_5$ cycloalkyl.

In embodiments, $R^5$ is substituted or unsubstituted aziridinyl, substituted or unsubstituted oziranyl, substituted or unsubstituted thiiranyl, substituted or unsubstituted azetidinyl, substituted or unsubstituted 1,2-dihydroazotyl, substituted or unsubstituted oxetanyl, substituted or unsubstituted 2H-oxetyl, substituted or unsubstituted thietanyl, substituted or unsubstituted 2H-thietyl, substituted or unsubstituted pyrrolidinyl, substituted or unsubstituted 2,5-dihydro-1H-pyrrolyl, substituted or unsubstituted 4,5-dihydro-1H-imidazolyl, substituted or unsubstituted imidazolinyl, substituted or unsubstituted pyrazolinyl, substituted or unsubstituted tetrahydrofuranyl, substituted or unsubstituted thiolanyl, substituted or unsubstituted piperidinyl, substituted or unsubstituted piperazinyl, substituted or unsubstituted 2H-pyranyl, substituted or unsubstituted morpholinyl, substituted or unsubstituted 1,4-dioxanyl, tetrahydro-2H-pyranyl, substituted or unsubstituted thianyl, or substituted or unsubstituted dithianyl. In embodiments, $R^5$ is $R^{32}$-substituted aziridinyl, $R^{32}$-substituted oziranyl, $R^{32}$-substituted thiiranyl, $R^{32}$-substituted azetidinyl, $R^{32}$-substituted 1,2-dihydroazotyl, $R^{32}$-substituted oxetanyl, $R^{32}$-substituted 2H-oxetyl, $R^{32}$-substituted thietanyl, $R^{32}$-substituted 2H-thietyl, $R^{32}$-substituted pyrrolidinyl, $R^{32}$-substituted 2,5-dihydro-1H-pyrrolyl, $R^{32}$-substituted 4,5-dihydro-1H-imidazolyl, $R^{32}$-substituted imidazolinyl, $R^{32}$-substituted pyrazolinyl, $R^{32}$-substituted tetrahydrofuranyl, $R^{32}$-substituted thiolanyl, $R^{32}$-substituted piperidinyl, $R^{32}$-substituted piperazinyl, $R^{32}$-substituted 2H-pyranyl, $R^{32}$-substituted morpholinyl, $R^{32}$-substituted 1,4-dioxanyl, tetrahydro-2H-pyranyl, $R^{32}$-substituted thianyl, or $R^{32}$-substituted dithianyl. In embodiments, $R^5$ is an unsubstituted aziridinyl, an unsubstituted oziranyl, an unsubstituted thiiranyl, an unsubstituted azetidinyl, an unsubstituted 1,2-dihydroazotyl, an unsubstituted oxetanyl, an unsubstituted 2H-oxetyl, an unsubstituted thietanyl, an unsubstituted 2H-thietyl, an unsubstituted pyrrolidinyl, an unsubstituted 2,5-dihydro-1H-pyrrolyl, an unsubstituted 4,5-dihydro-1H-imidazolyl, an unsubstituted imidazolinyl, an unsubstituted pyrazolinyl, an unsubstituted tetrahydrofuranyl, an unsubstituted thiolanyl, an unsubstituted piperidinyl, an unsubstituted piperazinyl, an unsubstituted 2H-pyranyl, an unsubstituted morpholinyl, an unsubstituted 1,4-dioxanyl, tetrahydro-2H-pyranyl, an unsubstituted thianyl, or an unsubstituted dithianyl.

In embodiments, $R^5$ is substituted or unsubstituted ($C_6$-$C_{10}$) aryl. In embodiments, $R^5$ is substituted or unsubstituted phenyl. In embodiments, $R^5$ is substituted or unsubstituted naphthyl. In embodiments, $R^5$ is $R^{32}$-substituted ($C_6$-$C_{10}$) aryl. In embodiments, $R^5$ is $R^{32}$-substituted phenyl. In embodiments, $R^5$ is $R^{32}$-substituted naphthyl. In embodiments, $R^5$ is an unsubstituted ($C_6$-$C_{10}$) aryl. In embodiments, $R^5$ is an unsubstituted phenyl. In embodiments, $R^5$ is an unsubstituted naphthyl.

In embodiments, $R^5$ is imidazolyl, substituted or unsubstituted pyrrolyl, substituted or unsubstituted pyrazolyl, substituted or unsubstituted triazolyl, substituted or unsubstituted tetrazolyl, substituted or unsubstituted furanyl, substituted or unsubstituted oxazolyl, substituted or unsubstituted isooxazolyl, substituted or unsubstituted oxadiazolyl, substituted or unsubstituted oxatriazolyl, substituted or unsubstituted thienyl, substituted or unsubstituted thiazolyl, substituted or unsubstituted isothiazolyl, substituted or unsubstituted pyridinyl, substituted or unsubstituted pyrazinyl, substituted or unsubstituted pyrimidinyl, substituted or unsubstituted pyridazinyl, or substituted or unsubstituted triazinyl (e.g., 1,3,5-triazinyl, 1,2,3-triazinyl, or 1,2,4-triazinyl). In embodiments, $R^5$ is imidazolyl, $R^{32}$-substituted pyrrolyl, $R^{32}$-substituted pyrazolyl, $R^{32}$-substituted triazolyl, $R^{32}$-substituted tetrazolyl, $R^{32}$-substituted furanyl, $R^{32}$-substituted oxazolyl, $R^{32}$-substituted isooxazolyl, $R^{32}$-substituted oxadiazolyl, $R^{32}$-substituted oxatriazolyl, $R^{32}$-substituted thienyl, $R^{32}$-substituted thiazolyl, $R^{32}$-substituted isothiazolyl, $R^{32}$-substituted pyridinyl, $R^{32}$-substituted pyrazinyl, $R^{32}$-substituted pyrimidinyl, $R^{32}$-substituted pyridazinyl, or $R^{32}$-substituted triazinyl (e.g., 1,3,5-triazinyl, 1,2,3-triazinyl, or 1,2,4-triazinyl). In embodiments, $R^5$ is imidazolyl, an unsubstituted pyrrolyl, an unsubstituted pyrazolyl, an unsubstituted triazolyl, an unsubstituted tetrazolyl, an unsubstituted furanyl, an unsubstituted oxazolyl, an unsubstituted isooxazolyl, an unsubstituted oxadiazolyl, an unsubstituted oxatriazolyl, an unsubstituted thienyl, an unsubstituted thiazolyl, an unsubstituted isothiazolyl, an unsubstituted pyridinyl, an unsubstituted pyrazinyl, an unsubstituted pyrimidinyl, an unsubstituted pyridazinyl, or an unsubstituted triazinyl (e.g., 1,3,5-triazinyl, 1,2,3-triazinyl, or 1,2,4-triazinyl).

In embodiments, $R^5$ is independently

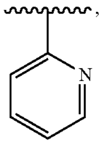, 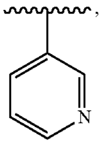, 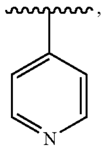, 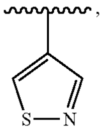, 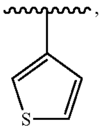,

-continued

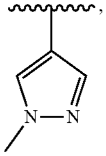, 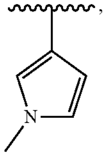, 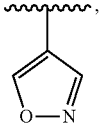, 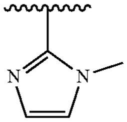, 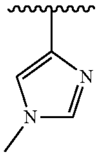, 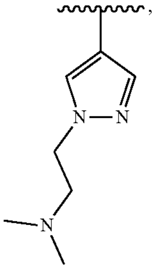, 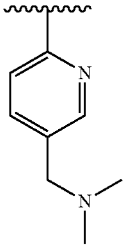, 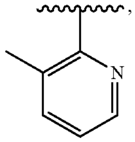, 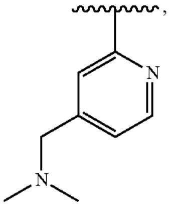, 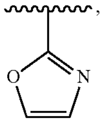, 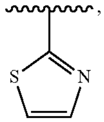, 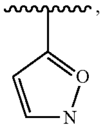, or 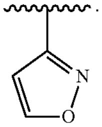.

In embodiments, $R^5$ is independently

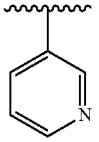, 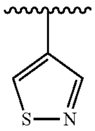, 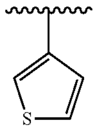, 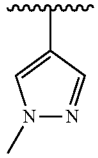, or 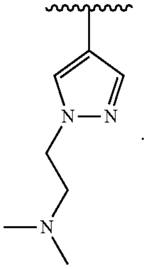.

In embodiments, $R^5$ is

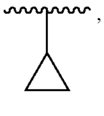, 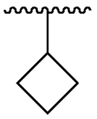, 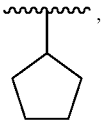, 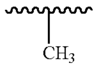, 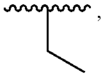, 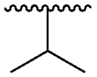, 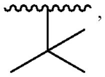, 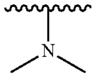, -continued
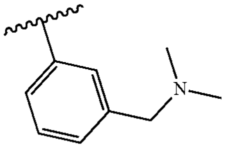, 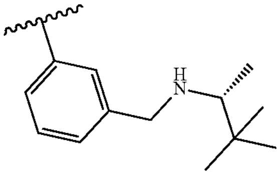,
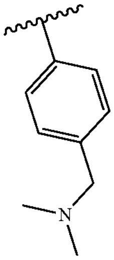, 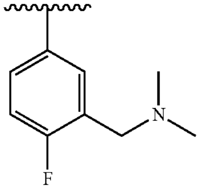, 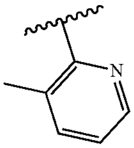,
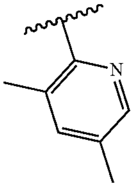, 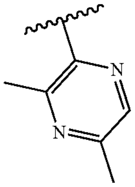, 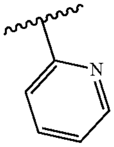, 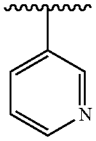,
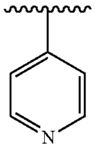, 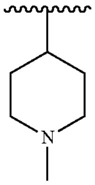, 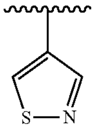, 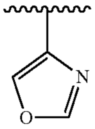,
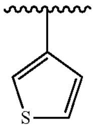, 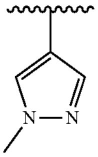, 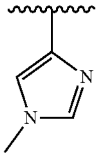, 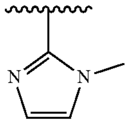, or
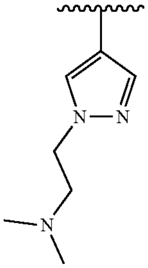.
In embodiments, $R^5$ is
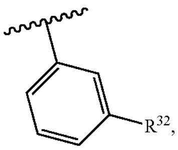, 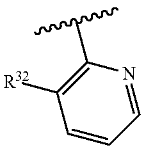, or 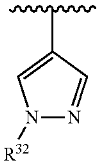.
In embodiments, $R^5$ is independently
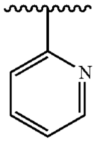.
In embodiments, $R^5$ is independently
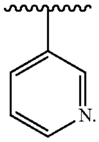.
In embodiments, $R^5$ is independently
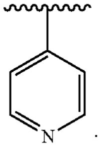.
In embodiments, $R^5$ is independently
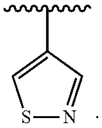.
In embodiments, $R^5$ is independently
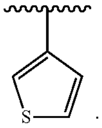.
In embodiments, $R^5$ is independently
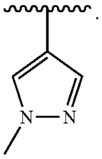.
In embodiments, $R^5$ is independently
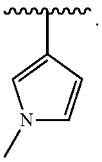.

In embodiments, $R^5$ is independently

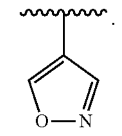

In embodiments, $R^5$ is independently

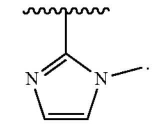 [SMILES: *c1nccn1C]

In embodiments, $R^5$ is independently

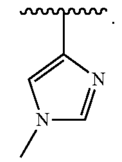

In embodiments, $R^5$ is independently

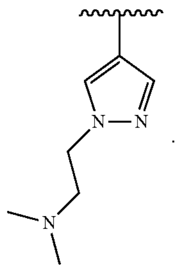 [SMILES: *c1cnn(CCN(C)C)c1]

In embodiments, $R^5$ is independently

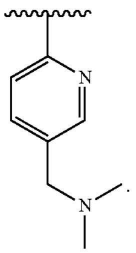 [SMILES: *c1ccc(CN(C)C)cn1]

In embodiments, $R^5$ is independently

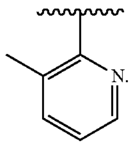 [SMILES: *c1ncccc1C]

In embodiments, $R^5$ is independently

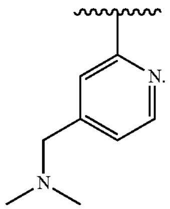 [SMILES: *c1cc(CN(C)C)ccn1]

In embodiments, $R^5$ is independently

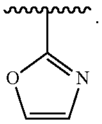 [SMILES: *c1ncco1]

In embodiments, $R^5$ is independently

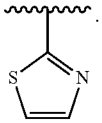

In embodiments, $R^5$ is independently

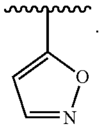

In embodiments, $R^5$ is independently

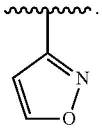

In embodiments, $R^5$ is independently

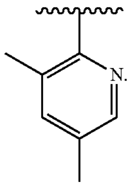 [SMILES: *c1ncc(C)cc1C]

In embodiments, $R^5$ is independently

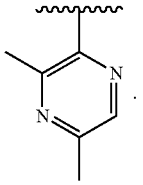 [SMILES: *c1ncc(C)nc1C]

In embodiments, $R^5$ is independently

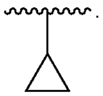 [SMILES: *C1CC1]

In embodiments, $R^5$ is independently

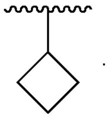 [SMILES: *C1CCC1]

In embodiments, $R^5$ is independently

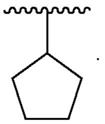 [SMILES: *C1CCCC1]

In embodiments, $R^5$ is independently

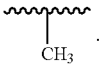

In embodiments, $R^5$ is independently

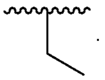 [SMILES: *CC]

In embodiments, $R^5$ is independently

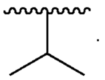

In embodiments, $R^5$ is independently

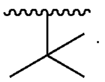

In embodiments, $R^5$ is independently

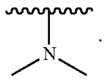

In embodiments, $R^5$ is independently

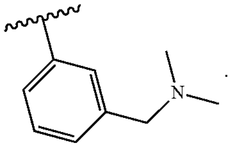 [SMILES: *c1cccc(CN(C)C)c1]

In embodiments, $R^5$ is independently

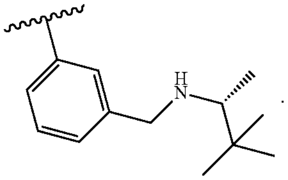 [SMILES: *c1cccc(CN[C@H](C)C(C)(C)C)c1]

In embodiments, $R^5$ is independently

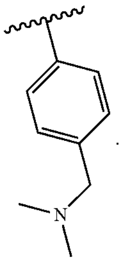 [SMILES: *c1ccc(CN(C)C)cc1]

In embodiments, $R^5$ is independently

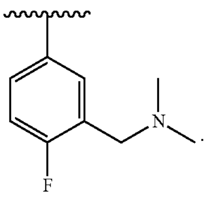 [SMILES: *c1ccc(F)c(CN(C)C)c1]

In embodiments, $R^5$ is independently

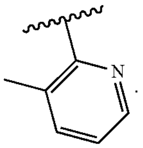 [SMILES: *c1ncccc1C]

In embodiments, $R^5$ is independently

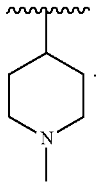 [SMILES: *C1CCN(C)CC1]

In embodiments, $R^5$ is independently

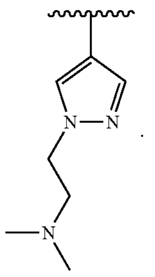 [SMILES: *c1cnn(CCN(C)C)c1]

In embodiments, $R^5$ is independently

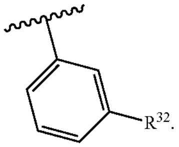

In embodiments, $R^5$ is independently

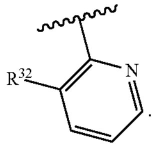

In embodiments, $R^5$ is independently

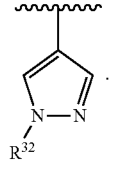

In embodiments, $R^5$ is independently substituted or unsubstituted alkyl (e.g., $C_1$-$C_8$, $C_1$-$C_6$, $C_1$-$C_4$, or $C_1$-$C_2$). In embodiments, $R^5$ is independently substituted alkyl (e.g., $C_1$-$C_8$, $C_1$-$C_6$, $C_1$-$C_4$, or $C_1$-$C_2$). In embodiments, $R^5$ is independently unsubstituted alkyl (e.g., $C_1$-$C_8$, $C_1$-$C_6$, $C_1$-$C_4$, or $C_1$-$C_2$). In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently unsubstituted isopropyl. In embodiments, $R^5$ is independently unsubstituted tert-butyl. In embodiments, $R^5$ is independently substituted or unsubstituted heteroalkyl (e.g., 2 to 8 membered, 2 to 6 membered, 4 to 6 membered, 2 to 3 membered, or 4 to 5 membered). In embodiments, $R^5$ is independently substituted heteroalkyl (e.g., 2 to 8 membered, 2 to 6 membered, 4 to 6 membered, 2 to 3 membered, or 4 to 5 membered). In embodiments, $R^5$ is independently unsubstituted heteroalkyl (e.g., 2 to 8 membered, 2 to 6 membered, 4 to 6 membered, 2 to 3 membered, or 4 to 5 membered). In embodiments, $R^5$ is independently substituted or unsubstituted cycloalkyl (e.g., $C_3$-$C_8$, $C_3$-$C_6$, $C_4$-$C_6$, or $C_5$-$C_6$). In embodiments, $R^5$ is independently substituted cycloalkyl (e.g., $C_3$-$C_8$, $C_3$-$C_6$, $C_4$-$C_6$, or $C_5$-$C_6$). In embodiments, $R^5$ is independently unsubstituted cycloalkyl (e.g., $C_3$-$C_8$, $C_3$-$C_6$, $C_4$-$C_6$, or $C_5$-$C_6$). In embodiments, $R^5$ is independently substituted or unsubstituted heterocycloalkyl (e.g., 3 to 8 membered, 3 to 6 membered, 4 to 6 membered, 4 to 5 membered, or 5 to 6 membered). In embodiments, $R^5$ is independently substituted heterocycloalkyl (e.g., 3 to 8 membered, 3 to 6 membered, 4 to 6 membered, 4 to 5 membered, or 5 to 6 membered). In embodiments, $R^5$ is independently unsubstituted heterocycloalkyl (e.g., 3 to 8 membered, 3 to 6 membered, 4 to 6 membered, 4 to 5 membered, or 5 to 6 membered). In embodiments, $R^5$ is independently substituted or unsubstituted aryl (e.g., $C_6$-$C_{10}$ or phenyl). In embodiments, $R^5$ is independently substituted aryl (e.g., $C_6$-$C_{10}$ or phenyl). In embodiments, $R^5$ is independently unsubstituted aryl (e.g., $C_6$-$C_{10}$ or phenyl). In embodiments, $R^5$ is independently substituted or unsubstituted heteroaryl (e.g., 5 to 10 membered, 5 to 9 membered, or 5 to 6 membered). In embodiments, $R^5$ is independently substituted heteroaryl (e.g., 5 to 10 membered, 5 to 9 membered, or 5 to 6 membered). In embodiments, $R^5$ is independently unsubstituted heteroaryl (e.g., 5 to 10 membered, 5 to 9 membered, or 5 to 6 membered).

In embodiments, $R^5$ is substituted or unsubstituted pyrrolidinyl. In embodiments, $R^5$ is substituted or unsubstituted tetrahydrofuranyl. In embodiments, $R^5$ is substituted or unsubstituted imidazolidinyl. In embodiments, $R^5$ is substituted or unsubstituted pyrazolidinyl. In embodiments, $R^5$ is substituted or unsubstituted oxazolidinyl. In embodiments, $R^5$ is substituted or unsubstituted isoxazolidinyl. In embodiments, $R^5$ is substituted or unsubstituted thiazolidinyl. In embodiments, $R^5$ is substituted or unsubstituted isothiazolidinyl. In embodiments, $R^5$ is substituted or unsubstituted dioxolanyl. In embodiments, $R^5$ is substituted or unsubstituted dithiolanyl. In embodiments, $R^5$ is substituted or unsubstituted piperidinyl. In embodiments, $R^5$ is substituted or unsubstituted oxanyl. In embodiments, $R^5$ is substituted or unsubstituted piperazinyl. In embodiments, $R^5$ is substituted or unsubstituted morpholinyl. In embodiments, $R^5$ is substituted or unsubstituted pyridinyl. In embodiments, $R^5$ is substituted or unsubstituted triazolyl. In embodiments, $R^5$ is substituted or unsubstituted tetrazolyl. In embodiments, $R^5$ is substituted or unsubstituted benzo[d][1,3]dioxolyl. In embodiments, $R^5$ is substituted or unsubstituted phenyl. In embodiments, $R^5$ is substituted or unsubstituted pyridyl. In embodiments, $R^5$ is substituted or unsubstituted pyridazinyl. In embodiments, $R^5$ is substituted or unsubstituted pyrimidinyl. In embodiments, $R^5$ is substituted or unsubstituted pyrazinyl. In embodiments, $R^5$ is substituted or unsubstituted piperidinyl. In embodiments, $R^5$ is substituted or unsubstituted tetrahydropyranyl. In embodiments, $R^5$ is substituted or unsubstituted tetrahydrothiopyranyl. In embodiments, $R^5$ is substituted or unsubstituted cyclohexyl. In embodiments, $R^5$ is substituted or unsubstituted cyclopentyl. In embodiments, $R^5$ is substituted or unsubstituted cycloheptyl. In embodiments, $R^5$ is substituted or unsubstituted cyclobutyl. In embodiments, $R^5$ is substituted or unsubstituted cyclopropyl. In embodiments, $R^5$ is substituted or unsubstituted pyrrolyl. In embodiments, $R^5$ is substituted or unsubstituted furanyl. In embodiments, $R^5$ is substituted or unsubstituted thienyl. In embodiments, $R^5$ is substituted or unsubstituted pyrazolyl. In embodiments, $R^5$ is substituted or unsubstituted imidazolyl. In embodiments, $R^5$ is substituted or unsubstituted isoxazolyl. In embodiments, $R^5$ is substituted or unsubstituted oxazolyl. In embodiments, $R^5$ is substituted or unsubstituted isothiazolyl. In embodiments, $R^5$ is substituted or unsubstituted thiazolyl. In embodiments, $R^5$ is substituted or unsubstituted naphthyl. In embodiments, $R^5$ is substituted or unsubstituted quinolinyl. In embodiments, $R^5$ is substituted or unsubstituted isoquinolinyl. In embodiments, $R^5$ is substituted or unsubstituted indolyl. In embodiments, $R^5$ is substituted or unsubstituted benzimidazolyl. In embodiments, $R^5$ is substituted or unsubstituted indazolyl. In embodiments, $R^5$ is substituted or unsubstituted isoindolyl. In embodiments, $R^5$ is substituted or unsubstituted benzofuranyl. In embodiments, $R^5$ is substituted or unsubstituted benzo[c]thienyl. In embodiments, $R^5$ is substituted or unsubstituted 2,3-dihydro-1H-indenyl. In embodiments, $R^5$ is substituted or unsubstituted 1,2,3,4-tetrahydronaphthyl. In embodiments, $R^5$ is substituted or unsubstituted triazolyl. In embodiments, $R^5$ is substituted or unsubstituted quinoxalinyl. In embodiments, $R^5$ is substituted or unsubstituted quinazolinyl. In embodiments, $R^5$ is substituted or unsubstituted triazinyl. In embodiments, $R^5$ is substituted or unsubstituted cinnolinyl. In embodiments, $R^5$ is substituted or unsubstituted phthalazinyl. In embodiments, $R^5$ is substituted or unsubstituted benzoxazolyl. In embodiments, $R^5$ is substituted or unsubstituted benzisoxazolyl. In embodiments, $R^5$ is substituted or unsubstituted benzothiazolyl. In embodiments, $R^5$ is substituted or unsubstituted benzisothiazolyl. In embodiments, $R^5$ is substituted or unsubstituted benzo[d][1,2,3]triazolyl. In embodiments, $R^5$ is substituted or unsubstituted adamantyl.

In embodiments, $R^5$ is substituted pyrrolidinyl. In embodiments, $R^5$ is substituted tetrahydrofuranyl. In embodiments, $R^5$ is substituted imidazolidinyl. In embodiments, $R^5$ is substituted pyrazolidinyl. In embodiments, $R^5$ is substituted oxazolidinyl. In embodiments, $R^5$ is substituted isoxazolidinyl. In embodiments, $R^5$ is substituted thiazolidinyl. In embodiments, $R^5$ is substituted isothiazolidinyl. In embodiments, $R^5$ is substituted dioxolanyl. In embodiments, $R^5$ is substituted dithiolanyl. In embodiments, $R^5$ is substituted piperidinyl. In embodiments, $R^5$ is substituted oxanyl. In embodiments, $R^5$ is substituted piperazinyl. In embodiments, $R^5$ is substituted morpholinyl. In embodiments, $R^5$ is substituted pyridinyl. In embodiments, $R^5$ is substituted triazolyl. In embodiments, $R^5$ is substituted tetrazolyl. In embodiments, $R^5$ is substituted benzo[d][1,3]dioxolyl. In embodiments, $R^5$ is substituted phenyl. In embodiments, $R^5$ is substituted pyridyl. In embodiments, $R^5$ is substituted pyridazinyl. In embodiments, $R^5$ is substituted pyrimidinyl. In embodiments, $R^5$ is substituted pyrazinyl. In embodiments, $R^5$ is substituted piperidinyl. In embodiments, $R^5$ is substituted tetrahydropyranyl. In embodiments, $R^5$ is substituted tetrahydrothiopyranyl. In embodiments, $R^5$ is substituted cyclohexyl. In embodiments, $R^5$ is substituted cyclopentyl. In embodiments, $R^5$ is substituted cycloheptyl. In embodiments, $R^5$ is substituted cyclobutyl. In embodiments, $R^5$ is substituted cyclopropyl. In embodiments, $R^5$ is substituted pyrrolyl. In embodiments, $R^5$ is substituted furanyl. In embodiments, $R^5$ is substituted thienyl. In embodiments, $R^5$ is substituted pyrazolyl. In embodiments, $R^5$ is substituted imidazolyl. In embodiments, $R^5$ is substituted isoxazolyl. In embodiments, $R^5$ is substituted oxazolyl. In embodiments, $R^5$ is substituted isothiazolyl. In embodiments, $R^5$ is substituted thiazolyl. In embodiments, $R^5$ is substituted naphthyl. In embodiments, $R^5$ is substituted quinolinyl. In embodiments, $R^5$ is substituted isoquinolinyl. In embodiments, $R^5$ is substituted indolyl. In embodiments, $R^5$ is substituted benzimidazolyl. In embodiments, $R^5$ is substituted indazolyl. In embodiments, $R^5$ is substituted isoindolyl. In embodiments, $R^5$ is substituted benzofuranyl. In embodiments, $R^5$ is substituted benzo[c]thienyl. In embodiments, $R^5$ is substituted 2,3-dihydro-1H-indenyl. In embodiments, $R^5$ is substituted 1,2,3,4-tetrahydronaphthyl. In embodiments, $R^5$ is substituted triazolyl. In embodiments, $R^5$ is substituted quinoxalinyl. In embodiments, $R^5$ is substituted quinazolinyl. In embodiments, $R^5$ is substituted triazinyl. In embodiments, $R^5$ is substituted cinnolinyl. In embodiments, $R^5$ is substituted phthalazinyl. In embodiments, $R^5$ is substituted benzoxazolyl. In embodiments, $R^5$ is substituted benzisoxazolyl. In embodiments, $R^5$ is substituted benzothiazolyl. In embodiments, $R^5$ is substituted benzisothiazolyl. In embodiments, $R^5$ is substituted benzo[d][1,2,3]triazolyl. In embodiments, $R^5$ is substituted adamantyl.

In embodiments, $R^5$ is $R^{32}$-substituted pyrrolidinyl. In embodiments, $R^5$ is $R^{32}$-substituted tetrahydrofuranyl. In embodiments, $R^5$ is $R^{32}$-substituted imidazolidinyl. In embodiments, $R^5$ is $R^{32}$-substituted pyrazolidinyl. In embodiments, $R^5$ is $R^{32}$-substituted oxazolidinyl. In embodiments, $R^5$ is $R^{32}$-substituted isoxazolidinyl. In embodiments, $R^5$ is $R^{32}$-substituted thiazolidinyl. In embodiments, $R^5$ is $R^{32}$-substituted isothiazolidinyl. In embodiments, $R^5$ is $R^{32}$-substituted dioxolanyl. In embodiments, $R^5$ is $R^{32}$-substituted dithiolanyl. In embodiments, $R^5$ is $R^{32}$-substituted piperidinyl. In embodiments, $R^5$ is $R^{32}$-substituted oxanyl. In embodiments, $R^5$ is $R^{32}$-substituted piperazinyl. In embodiments, $R^5$ is $R^{32}$-substituted morpholinyl. In embodiments, $R^5$ is $R^{32}$-substituted pyridinyl. In embodiments, $R^5$ is $R^{32}$-substituted triazolyl. In embodiments, $R^5$ is $R^{32}$-substituted tetrazolyl. In embodiments, $R^5$ is $R^{32}$-substituted benzo[d][1,3]dioxolyl. In embodiments, $R^5$ is $R^{32}$-substituted phenyl. In embodiments, $R^5$ is $R^{32}$-substituted pyridyl. In embodiments, $R^5$ is $R^{32}$-substituted pyridazinyl. In embodiments, $R^5$ is $R^{32}$-substituted pyrimidinyl. In embodiments, $R^5$ is $R^{32}$-substituted pyrazinyl. In embodiments, $R^5$ is $R^{32}$-substituted piperidinyl. In embodiments, $R^5$ is $R^{32}$-substituted tetrahydropyranyl. In embodiments, $R^5$ is $R^{32}$-substituted tetrahydrothiopyranyl. In embodiments, $R^5$ is $R^{32}$-substituted cyclohexyl. In embodiments, $R^5$ is $R^{32}$-substituted cyclopentyl. In embodiments, $R^5$ is $R^{32}$-substituted cycloheptyl. In embodiments, $R^5$ is $R^{32}$-substituted cyclobutyl. In embodiments, $R^5$ is $R^{32}$-substituted cyclopropyl. In embodiments, $R^5$ is $R^{32}$-substituted pyrrolyl. In embodiments, $R^5$ is $R^{32}$-substituted furanyl. In embodiments, $R^5$ is $R^{32}$-substituted thienyl. In embodiments, $R^5$ is $R^{32}$-substituted pyrazolyl. In embodiments, $R^5$ is $R^{32}$-substituted imidazolyl. In embodiments, $R^5$ is $R^{32}$-substituted isoxazolyl. In embodiments, $R^5$ is $R^{32}$-substituted oxazolyl. In embodiments, $R^5$ is $R^{32}$-substituted isothiazolyl. In embodiments, $R^5$ is $R^{32}$-substituted thiazolyl. In embodiments, $R^5$ is $R^{32}$-substituted naphthyl. In embodiments, $R^5$ is $R^{32}$-substituted quinolinyl. In embodiments, $R^5$ is $R^{32}$-substituted isoquinolinyl. In embodiments, $R^5$ is $R^{32}$-substituted indolyl. In embodiments, $R^5$ is $R^{32}$-substituted benzimidazolyl. In embodiments, $R^5$ is $R^{32}$-substituted indazolyl. In embodiments, $R^5$ is $R^{32}$-substituted isoindolyl. In embodiments, $R^5$ is $R^{32}$-substituted benzofuranyl. In embodiments, $R^5$ is $R^{32}$-substituted benzo[c]thienyl. In embodiments, $R^5$ is $R^{32}$-substituted 2,3-dihydro-1H-indenyl. In embodiments, $R^5$ is $R^{32}$-substituted 1,2,3,4- tetrahydronaphthyl. In embodiments, $R^5$ is $R^{32}$-substituted triazolyl. In embodiments, $R^5$ is $R^{32}$-substituted quinoxalinyl. In embodiments, $R^5$ is $R^{32}$-substituted quinazolinyl. In embodiments, $R^5$ is $R^{32}$-substituted triazinyl. In embodiments, $R^5$ is $R^{32}$-substituted cinnolinyl. In embodiments, $R^5$ is $R^{32}$-substituted phthalazinyl. In embodiments, $R^5$ is $R^{32}$-substituted benzoxazolyl. In embodiments, $R^5$ is $R^{32}$-substituted benzisoxazolyl. In embodiments, $R^5$ is $R^{32}$-substituted benzothiazolyl. In embodiments, $R^5$ is $R^{32}$-substituted benzisothiazolyl. In embodiments, $R^5$ is $R^{32}$-substituted benzo[d][1,2,3]triazolyl. In embodiments, $R^5$ is $R^{32}$-substituted adamantyl.

In embodiments, $R^5$ is unsubstituted pyrrolidinyl. In embodiments, $R^5$ is unsubstituted tetrahydrofuranyl. In embodiments, $R^5$ is unsubstituted imidazolidinyl. In embodiments, $R^5$ is unsubstituted pyrazolidinyl. In embodiments, $R^5$ is unsubstituted oxazolidinyl. In embodiments, $R^5$ is unsubstituted isoxazolidinyl. In embodiments, $R^5$ is unsubstituted thiazolidinyl. In embodiments, $R^5$ is unsubstituted isothiazolidinyl. In embodiments, $R^5$ is unsubstituted dioxolanyl. In embodiments, $R^5$ is unsubstituted dithiolanyl. In embodiments, $R^5$ is unsubstituted piperidinyl. In embodiments, $R^5$ is unsubstituted oxanyl. In embodiments, $R^5$ is unsubstituted piperazinyl. In embodiments, $R^5$ is unsubstituted morpholinyl. In embodiments, $R^5$ is unsubstituted pyridinyl. In embodiments, $R^5$ is unsubstituted triazolyl. In embodiments, $R^5$ is unsubstituted tetrazolyl. In embodiments, $R^5$ is unsubstituted benzo[d][1,3]dioxolyl. In embodiments, $R^5$ is unsubstituted phenyl. In embodiments, $R^5$ is unsubstituted pyridyl. In embodiments, $R^5$ is unsubstituted pyridazinyl. In embodiments, $R^5$ is unsubstituted pyrimidinyl. In embodiments, $R^5$ is unsubstituted pyrazinyl. In embodiments, $R^5$ is unsubstituted piperidinyl. In embodiments, $R^5$ is unsubstituted tetrahydropyranyl. In embodiments, $R^5$ is unsubstituted tetrahydrothiopyranyl. In embodiments, $R^5$ is unsubstituted cyclohexyl. In embodiments, $R^5$ is unsubstituted cyclopentyl. In embodiments, $R^5$ is unsubstituted cycloheptyl. In embodiments, $R^5$ is unsubstituted cyclobutyl. In embodiments, $R^5$ is unsubstituted cyclopropyl. In embodiments, $R^5$ is unsubstituted pyrrolyl. In embodiments, $R^5$ is unsubstituted furanyl. In embodiments, $R^5$ is unsubstituted thienyl. In embodiments, $R^5$ is unsubstituted pyrazolyl. In embodiments, $R^5$ is unsubstituted imidazolyl. In embodiments, $R^5$ is unsubstituted isoxazolyl. In embodiments, $R^5$ is unsubstituted oxazolyl. In embodiments, $R^5$ is unsubstituted isothiazolyl. In embodiments, $R^5$ is unsubstituted thiazolyl. In embodiments, $R^5$ is unsubstituted naphthyl. In embodiments, $R^5$ is unsubstituted quinolinyl. In embodiments, $R^5$ is unsubstituted isoquinolinyl. In embodiments, $R^5$ is unsubstituted indolyl. In embodiments, $R^5$ is unsubstituted benzimidazolyl. In embodiments, $R^5$ is unsubstituted indazolyl. In embodiments, $R^5$ is unsubstituted isoindolyl. In embodiments, $R^5$ is unsubstituted benzofuranyl. In embodiments, $R^5$ is unsubstituted benzo[c]thienyl. In embodiments, $R^5$ is unsubstituted 2,3-dihydro-1H-indenyl. In embodiments, $R^5$ is unsubstituted 1,2,3,4-tetrahydronaphthyl. In embodiments, $R^5$ is unsubstituted triazolyl. In embodiments, $R^5$ is unsubstituted quinoxalinyl. In embodiments, $R^5$ is unsubstituted quinazolinyl. In embodiments, $R^5$ is unsubstituted triazinyl. In embodiments, $R^5$ is unsubstituted cinnolinyl. In embodiments, $R^5$ is unsubstituted phthalazinyl. In embodiments, $R^5$ is unsubstituted benzoxazolyl. In embodiments, $R^5$ is unsubstituted benzisoxazolyl. In embodiments, $R^5$ is unsubstituted benzothiazolyl. In embodiments, $R^5$ is unsubstituted benzisothiazolyl. In embodiments, $R^5$ is unsubstituted benzo[d][1,2,3]triazolyl. In embodiments, $R^5$ is unsubstituted adamantyl.

In embodiments, $R^5$ is independently $R^{32}$-substituted or unsubstituted alkyl (e.g., $C_1$-$C_8$, $C_1$-$C_6$, $C_1$-$C_4$, or $C_1$-$C_2$), $R^{32}$-substituted or unsubstituted heteroalkyl (e.g., 2 to 8 membered, 2 to 6 membered, 4 to 6 membered, 2 to 3 membered, or 4 to 5 membered), $R^{32}$-substituted or unsubstituted cycloalkyl (e.g., $C_3$-$C_8$, $C_3$-$C_6$, $C_4$-$C_6$, or $C_5$-$C_6$), $R^{32}$-substituted or unsubstituted heterocycloalkyl (e.g., 3 to 8 membered, 3 to 6 membered, 4 to 6 membered, 4 to 5 membered, or 5 to 6 membered), $R^{32}$-substituted or unsubstituted aryl (e.g., $C_6$-$C_{10}$ or phenyl), or $R^{32}$-substituted or unsubstituted heteroaryl (e.g., 5 to 10 membered, 5 to 9 membered, or 5 to 6 membered). In embodiments, $R^5$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^5$ is independently hydrogen. In embodiments, $R^5$ is independently unsubstituted methyl. In embodiments, $R^5$ is independently unsubstituted ethyl.

$R^{32}$ is independently oxo, halogen, $-CX^{32}_3$, $-CHX^{32}_2$, $-CH_2X^{32}$, $-OCX^{32}_3$, $-OCH_2X^{32}$, $-OCHX^{32}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 8 membered, 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered). In embodiments, $R^{32}$ is independently oxo, halogen, $-CX^{32}_3$, $-CHX^{32}_2$, $-CH_2X^{32}$, $-OCX^{32}_3$, $-OCH_2X^{32}$, $-OCHX^{32}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)\ NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{32}$ is independently —F, —Cl, —Br, or —I. In embodiments, $R^{32}$ is independently unsubstituted methyl. In embodiments, $R^{32}$ is independently unsubstituted ethyl. In embodiments, $R^{32}$ is independently $-CH_3$, $-CH_2N(CH_3)_2$, or

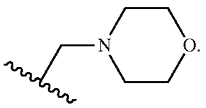 [SMILES: *CN1CCOCC1]

In embodiments, $R^{32}$ is independently —$CH_3$. In embodiments, $R^{32}$ is independently —$CH_2N(CH_3)_2$. In embodiments, $R^{32}$ is independently —$CH_2CH_2N(CH_3)_2$. In embodiments, $R^{32}$ is independently

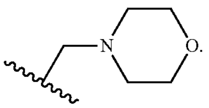

In embodiments, $R^{32}$ is independently halogen. In embodiments, $R^{32}$ is independently —F. In embodiments, $R^{32}$ is independently

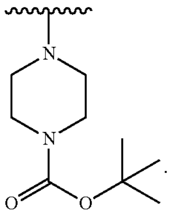 [SMILES: *N1CCN(C(=O)OC(C)(C)C)CC1]

In embodiments, $R^{32}$ is independently

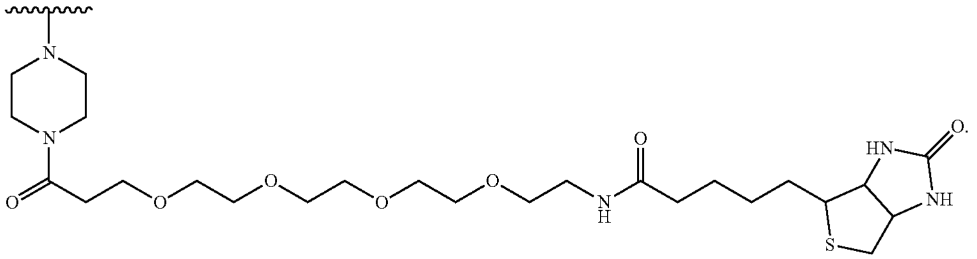 [SMILES: *N1CCN(C(=O)CCOCCOCCOCCOCCNC(=O)CCCCC2SCC3NC(=O)NC32)CC1]

In embodiments, $R^{32}$ is independently

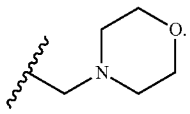 [SMILES: *CN1CCOCC1]

In embodiments, $R^{32}$ is independently

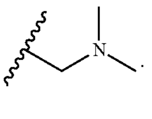 [SMILES: *CN(C)C]

In embodiments, $R^{32}$ is independently

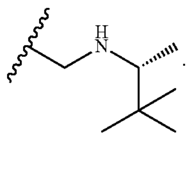 [SMILES: *CN[C@H](C)C(C)(C)C]

In embodiments, $R^{32}$ is $R^{33}$-substituted or unsubstituted alkyl (e.g., $C_1$-$C_8$ alkyl, $C_1$-$C_6$ alkyl, or $C_1$-$C_4$ alkyl). In embodiments, $R^{32}$ is $R^{33}$-substituted alkyl (e.g., $C_1$-$C_8$ alkyl, $C_1$-$C_6$ alkyl, or $C_1$-$C_4$ alkyl). In embodiments, $R^{32}$ is an unsubstituted alkyl (e.g., $C_1$-$C_8$ alkyl, $C_1$-$C_6$ alkyl, or $C_1$-$C_4$ alkyl).

In embodiments, $R^{32}$ is $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{32}$ is $R^{33}$-substituted heteroalkyl (e.g., 2 to 8 membered heteroalkyl, 2 to 6 membered heteroalkyl, or 2 to 4 membered heteroalkyl). In embodiments, $R^{32}$ is an unsubstituted heteroalkyl (e.g., 2 to 8 membered heteroalkyl, 2 to 6 membered heteroalkyl, or 2 to 4 membered heteroalkyl).

In embodiments, $R^{32}$ is $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{32}$ is $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{32}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{32}$ is $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32}$ is $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{32}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32}$ is $R^{33}$-substituted or unsubstituted aryl (e.g., $C_6$-$C_{10}$ aryl, $C_{10}$ aryl, or phenyl). In embodiments, $R^{32}$ is $R^{33}$-substituted aryl (e.g., $C_6$-$C_{10}$ aryl, $C_{10}$ aryl, or phenyl). In embodiments, $R^{32}$ is an unsubstituted aryl (e.g., $C_6$-$C_{10}$ aryl, $C_{10}$ aryl, or phenyl).

In embodiments, $R^{32}$ is $R^{33}$-substituted or unsubstituted heteroaryl (e.g., 5 to 10 membered heteroaryl, 5 to 9 membered heteroaryl, or 5 to 6 membered heteroaryl). In embodiments, $R^{32}$ is $R^{33}$-substituted heteroaryl (e.g., 5 to 10 membered heteroaryl, 5 to 9 membered heteroaryl, or 5 to 6 membered heteroaryl). In embodiments, $R^{32}$ is an unsubstituted heteroaryl (e.g., 5 to 10 membered heteroaryl, 5 to 9 membered heteroaryl, or 5 to 6 membered heteroaryl).

$R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, 2 to 3 membered, or 4 to 5 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 8 membered, 3 to 6 membered, 4 to 6 membered, 4 to 5 membered, or 5 to 6 membered), $R^{34}$-substituted or unsubstituted aryl (e.g., $C_6$-$C_{10}$ or phenyl), or $R^{34}$-substituted or unsubstituted heteroaryl (e.g., 5 to 10 membered, 5 to 9 membered, or 5 to 6 membered). In embodiments, $R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{33}$ is independently —F, —Cl, —Br, or —I. In embodiments, $R^{33}$ is independently unsubstituted methyl. In embodiments, $R^{33}$ is independently unsubstituted ethyl.

$R^{34}$ is independently oxo, halogen, —$CX^{34}_3$, —$CHX^{34}_2$, —$CH_2X^{34}$, —$OCX^{34}_3$, —$OCH_2X^{34}$, —$OCHX^{34}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{34}$ is independently —F, —Cl, —Br, or —I. In embodiments, $R^{34}$ is independently unsubstituted methyl. In embodiments, $R^{34}$ is independently unsubstituted ethyl.

In embodiments, $R^6$ is independently hydrogen, —$CX^6_3$, —$CHX^6_2$, —$CH_2X^6$, —CN, —C(O)$R^{6C}$, —C(O)—$OR^{6C}$, —C(O)$NR^{6A}R^{6B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^6$ is independently hydrogen. In embodiments, $R^6$ is independently —$CX^6_3$. In embodiments, $R^6$ is independently —$CHX^6_2$. In embodiments, $R^6$ is independently —$CH_2X^6$. In embodiments, $R^6$ is independently —CN. In embodiments, $R^6$ is independently —C(O)$R^{6C}$. In embodiments, $R^6$ is independently —C(O)—$OR^{6C}$. In embodiments, $R^6$ is independently —C(O)$NR^{6A}R^{6B}$. In embodiments, $R^6$ is independently —COOH. In embodiments, $R^6$ is independently —$CONH_2$. In embodiments, $R^6$ is independently —$CF_3$. In embodiments, $R^6$ is independently —$CHF_2$. In embodiments, $R^6$ is independently —$CH_2F$. In embodiments, $R^6$ is independently —$CH_3$. In embodiments, $R^6$ is independently —$CH_2CH_3$. In embodiments, $R^6$ is independently —$CH_2CH_2CH_3$. In embodiments, $R^6$ is independently —$CH(CH_3)_2$. In embodiments, $R^6$ is independently —$C(CH_3)_3$.

In embodiments, $R^6$ is independently substituted or unsubstituted alkyl (e.g., $C_1$-$C_8$, $C_1$-$C_6$, $C_1$-$C_4$, or $C_1$-$C_2$). In embodiments, $R^6$ is independently substituted alkyl (e.g., $C_1$-$C_8$, $C_1$-$C_6$, $C_1$-$C_4$, or $C_1$-$C_2$). In embodiments, $R^6$ is independently unsubstituted alkyl (e.g., $C_1$-$C_8$, $C_1$-$C_6$, $C_1$-$C_4$, or $C_1$-$C_2$). In embodiments, $R^6$ is independently unsubstituted methyl. In embodiments, $R^6$ is independently unsubstituted ethyl. In embodiments, $R^6$ is independently unsubstituted propyl. In embodiments, $R^6$ is independently unsubstituted isopropyl. In embodiments, $R^6$ is independently unsubstituted tert-butyl. In embodiments, $R^6$ is independently substituted or unsubstituted heteroalkyl (e.g., 2 to 8 membered, 2 to 6 membered, 4 to 6 membered, 2 to 3 membered, or 4 to 5 membered). In embodiments, $R^6$ is independently substituted heteroalkyl (e.g., 2 to 8 membered, 2 to 6 membered, 4 to 6 membered, 2 to 3 membered, or 4 to 5 membered). In embodiments, $R^6$ is independently unsubstituted heteroalkyl (e.g., 2 to 8 membered, 2 to 6 membered, 4 to 6 membered, 2 to 3 membered, or 4 to 5 membered). In embodiments, $R^6$ is independently substituted or unsubstituted cycloalkyl (e.g., $C_3$-$C_8$, $C_3$-$C_6$, $C_4$-$C_6$, or $C_5$-$C_6$). In embodiments, $R^6$ is independently substituted cycloalkyl (e.g., $C_3$-$C_8$, $C_3$-$C_6$, $C_4$-$C_6$, or $C_5$-$C_6$). In embodiments, $R^6$ is independently unsubstituted cycloalkyl (e.g., $C_3$-$C_8$, $C_3$-$C_6$, $C_4$-$C_6$, or $C_5$-$C_6$). In embodiments, $R^6$ is independently substituted or unsubstituted heterocycloalkyl (e.g., 3 to 8 membered, 3 to 6 membered, 4 to 6 membered, 4 to 5 membered, or 5 to 6 membered). In embodiments, $R^6$ is independently substituted heterocycloalkyl (e.g., 3 to 8 membered, 3 to 6 membered, 4 to 6 membered, 4 to 5 membered, or 5 to 6 membered). In embodiments, $R^6$ is independently unsubstituted heterocycloalkyl (e.g., 3 to 8 membered, 3 to 6 membered, 4 to 6 membered, 4 to 5 membered, or 5 to 6 membered). In embodiments, $R^6$ is independently substituted or unsubstituted aryl (e.g., $C_6$-$C_{10}$ or phenyl). In embodiments, $R^6$ is independently substituted aryl (e.g., $C_6$-$C_{10}$ or phenyl). In embodiments, $R^6$ is independently unsubstituted aryl (e.g., $C_6$-$C_{10}$ or phenyl). In embodiments, $R^6$ is independently substituted or unsubstituted heteroaryl (e.g., 5 to 10 membered, 5 to 9 membered, or 5 to 6 membered). In embodiments, $R^6$ is independently substituted heteroaryl (e.g., 5 to 10 membered, 5 to 9 membered, or 5 to 6 membered). In embodiments, $R^6$ is independently unsubstituted heteroaryl (e.g., 5 to 10 membered, 5 to 9 membered, or 5 to 6 membered).

In embodiments, $R^{6A}$ is independently hydrogen. In embodiments, $R^{6A}$ is independently —$CX^{6A}_3$. In embodiments, $R^{6A}$ is independently —$CHX^{6A}_2$. In embodiments, $R^{6A}$ is independently —$CH_2X^{6A}$. In embodiments, $R^{6A}$ is independently —CN. In embodiments, $R^{6A}$ is independently —COOH. In embodiments, $R^{6A}$ is independently —$CONH_2$. In embodiments, $X^{6A}$ is independently —F, —Cl, —Br, or —I.

In embodiments, $R^{6A}$ is independently substituted or unsubstituted alkyl (e.g., $C_1$-$C_8$, $C_1$-$C_6$, $C_1$-$C_4$, or $C_1$-$C_2$). In embodiments, $R^{6A}$ is independently substituted alkyl (e.g., $C_1$-$C_8$, $C_1$-$C_6$, $C_1$-$C_4$, or $C_1$-$C_2$). In embodiments, $R^{6A}$ is independently unsubstituted alkyl (e.g., $C_1$-$C_8$, $C_1$-$C_6$, $C_1$-$C_4$, or $C_1$-$C_2$). In embodiments, $R^{6A}$ is independently unsubstituted methyl. In embodiments, $R^{6A}$ is independently unsubstituted ethyl. In embodiments, $R^{6A}$ is independently unsubstituted propyl. In embodiments, $R^{6A}$ is independently unsubstituted isopropyl. In embodiments, $R^{6A}$ is independently unsubstituted tert-butyl. In embodiments, $R^{6A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{6A}$ is independently substituted heteroalkyl (e.g., 2 to 8 membered, 2 to 6 membered, 4 to 6 membered, 2 to 3 membered, or 4 to 5 membered). In embodiments, $R^{6A}$ is independently unsubstituted heteroalkyl (e.g., 2 to 8 membered, 2 to 6 membered, 4 to 6 membered, 2 to 3 membered, or 4 to 5 membered). In embodiments, $R^{6A}$ is independently substituted or unsubstituted cycloalkyl (e.g., $C_3$-$C_8$, $C_3$-$C_6$, $C_4$-$C_6$, or $C_5$-$C_6$). In embodiments, $R^{6A}$ is independently substituted cycloalkyl (e.g., $C_3$-$C_8$, $C_3$-$C_6$, $C_4$-$C_6$, or $C_5$-$C_6$). In embodiments, $R^{6A}$ is independently unsubstituted cycloalkyl (e.g., $C_3$-$C_8$, $C_3$-$C_6$, $C_4$-$C_6$, or $C_5$-$C_6$). In embodiments, $R^{6A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{6A}$ is independently substituted heterocycloalkyl (e.g., 3 to 8 membered, 3 to 6 membered, 4 to 6 membered, 4 to 5 membered, or 5 to 6 membered). In embodiments, $R^{6A}$ is independently unsubstituted heterocycloalkyl (e.g., 3 to 8 membered, 3 to 6 membered, 4 to 6 membered, 4 to 5 membered, or 5 to 6 membered). In embodiments, $R^{6A}$ is independently substituted or unsubstituted aryl (e.g., $C_6$-$C_{10}$ or phenyl). In embodiments, $R^{6A}$ is independently substituted aryl (e.g., $C_6$-$C_{10}$ or phenyl). In embodiments, $R^{6A}$ is independently unsubstituted aryl (e.g., $C_6$-$C_{10}$ or phenyl). In embodiments, $R^{6A}$ is independently substituted or unsubstituted heteroaryl (e.g., 5 to 10 membered, 5 to 9 membered, or 5 to 6 membered). In embodiments, $R^{6A}$ is independently substituted heteroaryl (e.g., 5 to 10 membered, 5 to 9 membered, or 5 to 6 membered). In embodiments, $R^{6A}$ is independently unsubstituted heteroaryl (e.g., 5 to 10 membered, 5 to 9 membered, or 5 to 6 membered).

In embodiments, $R^{6B}$ is independently hydrogen. In embodiments, $R^{6B}$ is independently $-CX^{6B}_3$. In embodiments, $R^{6B}$ is independently $-CHX^{6B}_2$. In embodiments, $R^{6B}$ is independently $-CH_2X^{6B}$. In embodiments, $R^{6B}$ is independently —CN. In embodiments, $R^{6B}$ is independently —COOH. In embodiments, $R^{6B}$ is independently $-CONH_2$. In embodiments, $X^{6B}$ is independently —F, —Cl, —Br, or —I.

In embodiments, $R^{6B}$ is independently substituted or unsubstituted alkyl (e.g., $C_1$-$C_8$, $C_1$-$C_6$, $C_1$-$C_4$, or $C_1$-$C_2$). In embodiments, $R^{6B}$ is independently substituted alkyl (e.g., $C_1$-$C_8$, $C_1$-$C_6$, $C_1$-$C_4$, or $C_1$-$C_2$). In embodiments, $R^{6B}$ is independently unsubstituted alkyl (e.g., $C_1$-$C_8$, $C_1$-$C_6$, $C_1$-$C_4$, or $C_1$-$C_2$). In embodiments, $R^{6B}$ is independently unsubstituted methyl. In embodiments, $R^{6B}$ is independently unsubstituted ethyl. In embodiments, $R^{6B}$ is independently unsubstituted propyl. In embodiments, $R^{6B}$ is independently unsubstituted isopropyl. In embodiments, $R^{6B}$ is independently unsubstituted tert-butyl. In embodiments, $R^{6B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{6B}$ is independently substituted heteroalkyl (e.g., 2 to 8 membered, 2 to 6 membered, 4 to 6 membered, 2 to 3 membered, or 4 to 5 membered). In embodiments, $R^{6B}$ is independently unsubstituted heteroalkyl (e.g., 2 to 8 membered, 2 to 6 membered, 4 to 6 membered, 2 to 3 membered, or 4 to 5 membered). In embodiments, $R^{6B}$ is independently substituted or unsubstituted cycloalkyl (e.g., $C_3$-$C_8$, $C_3$-$C_6$, $C_4$-$C_6$, or $C_5$-$C_6$). In embodiments, $R^{6B}$ is independently substituted cycloalkyl (e.g., $C_3$-$C_8$, $C_3$-$C_6$, $C_4$-$C_6$, or $C_5$-$C_6$). In embodiments, $R^{6B}$ is independently unsubstituted cycloalkyl (e.g., $C_3$-$C_8$, $C_3$-$C_6$, $C_4$-$C_6$, or $C_5$-$C_6$). In embodiments, $R^{6B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{6B}$ is independently substituted heterocycloalkyl (e.g., 3 to 8 membered, 3 to 6 membered, 4 to 6 membered, 4 to 5 membered, or 5 to 6 membered). In embodiments, $R^{6B}$ is independently unsubstituted heterocycloalkyl (e.g., 3 to 8 membered, 3 to 6 membered, 4 to 6 membered, 4 to 5 membered, or 5 to 6 membered). In embodiments, $R^{6B}$ is independently substituted or unsubstituted aryl (e.g., $C_6$-$C_{10}$ or phenyl). In embodiments, $R^{6B}$ is independently substituted aryl (e.g., $C_6$-$C_{10}$ or phenyl). In embodiments, $R^{6B}$ is independently unsubstituted aryl (e.g., $C_6$-$C_{10}$ or phenyl). In embodiments, $R^{6B}$ is independently substituted or unsubstituted heteroaryl (e.g., 5 to 10 membered, 5 to 9 membered, or 5 to 6 membered). In embodiments, $R^{6B}$ is independently substituted heteroaryl (e.g., 5 to 10 membered, 5 to 9 membered, or 5 to 6 membered). In embodiments, $R^{6B}$ is independently unsubstituted heteroaryl (e.g., 5 to 10 membered, 5 to 9 membered, or 5 to 6 membered).

In embodiments, $R^{6A}$ and $R^{6B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{6A}$ and $R^{6B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{6A}$ and $R^{6B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{6A}$ and $R^{6B}$ substituents bonded to the same nitrogen atom may be joined to form a substituted or unsubstituted heteroaryl (e.g., 5 to 10 membered, 5 to 9 membered, or 5 to 6 membered). In embodiments, $R^{6A}$ and $R^{6B}$ substituents bonded to the same nitrogen atom may be joined to form a substituted heteroaryl (e.g., 5 to 10 membered, 5 to 9 membered, or 5 to 6 membered). In embodiments, $R^{6A}$ and $R^{6B}$ substituents bonded to the same nitrogen atom may be joined to form an unsubstituted heteroaryl (e.g., 5 to 10 membered, 5 to 9 membered, or 5 to 6 membered).

In embodiments, $R^{6C}$ is independently hydrogen. In embodiments, $R^{6C}$ is independently $-CX^{6C}_3$. In embodiments, $R^{6C}$ is independently $-CHX^{6C}_2$. In embodiments, $R^{6C}$ is independently $-CH_2X^{6C}$. In embodiments, $R^{6C}$ is independently —CN. In embodiments, $R^{6C}$ is independently —COOH. In embodiments, $R^{6C}$ is independently $-CONH_2$. In embodiments, $X^{6C}$ is independently —F, —Cl, —Br, or —I.

In embodiments, $R^{6C}$ is independently substituted or unsubstituted alkyl (e.g., $C_1$-$C_8$, $C_1$-$C_6$, $C_1$-$C_4$, or $C_1$-$C_2$). In embodiments, $R^{6C}$ is independently substituted alkyl (e.g., $C_1$-$C_8$, $C_1$-$C_6$, $C_1$-$C_4$, or $C_1$-$C_2$). In embodiments, $R^{6C}$ is independently unsubstituted alkyl (e.g., $C_1$-$C_8$, $C_1$-$C_6$, $C_1$-$C_4$, or $C_1$-$C_2$). In embodiments, $R^{6C}$ is independently unsubstituted methyl. In embodiments, $R^{6C}$ is independently unsubstituted ethyl. In embodiments, $R^{6C}$ is independently unsubstituted propyl. In embodiments, $R^{6C}$ is independently unsubstituted isopropyl. In embodiments, $R^{6C}$ is independently unsubstituted tert-butyl. In embodiments, $R^{6C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{6C}$ is independently substituted heteroalkyl (e.g., 2 to 8 membered, 2 to 6 membered, 4 to 6 membered, 2 to 3 membered, or 4 to 5 membered). In embodiments, $R^{6C}$ is independently unsubstituted heteroalkyl (e.g., 2 to 8 membered, 2 to 6 membered, 4 to 6 membered, 2 to 3 membered, or 4 to 5 membered). In embodiments, $R^{6C}$ is independently substituted or unsubstituted cycloalkyl (e.g., $C_3$-$C_8$, $C_3$-$C_6$, $C_4$-$C_6$, or $C_5$-$C_6$). In embodiments, $R^{6C}$ is independently substituted cycloalkyl (e.g., $C_3$-$C_8$, $C_3$-$C_6$, $C_4$-$C_6$, or $C_5$-$C_6$). In embodiments, $R^{6C}$ is independently unsubstituted cycloalkyl (e.g., $C_3$-$C_8$, $C_3$-$C_6$, $C_4$-$C_6$, or $C_5$-$C_6$). In embodiments, $R^{6C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{6C}$ is independently substituted heterocycloalkyl (e.g., 3 to 8 membered, 3 to 6 membered, 4 to 6 membered, 4 to 5 membered, or 5 to 6 membered). In embodiments, $R^{6C}$ is independently unsubstituted heterocycloalkyl (e.g., 3 to 8 membered, 3 to 6 membered, 4 to 6 membered, 4 to 5 membered, or 5 to 6 membered). In embodiments, $R^{6C}$ is independently substituted or unsubstituted aryl (e.g., $C_6$-$C_{10}$ or phenyl). In embodiments, $R^{6C}$ is independently substituted aryl (e.g., $C_6$-$C_{10}$ or phenyl). In embodiments, $R^{6C}$ is independently unsubstituted aryl (e.g., $C_6$-$C_{10}$ or phenyl). In embodiments, $R^{6C}$ is independently substituted or unsubstituted heteroaryl (e.g., 5 to 10 membered, 5 to 9 membered, or 5 to 6 membered). In embodiments, $R^{6C}$ is independently substituted heteroaryl (e.g., 5 to 10 membered, 5 to 9 membered, or 5 to 6 membered). In embodiments, $R^{6C}$ is independently unsubstituted heteroaryl (e.g., 5 to 10 membered, 5 to 9 membered, or 5 to 6 membered).

In embodiments, $R^6$ is independently hydrogen, —$CX^6_3$, —$CHX^6_2$, —$CH_2X^6$, —CN, —COOH, —$CONH_2$, $R^{35}$-substituted or unsubstituted alkyl (e.g., $C_1$-$C_8$, $C_1$-$C_6$, $C_1$-$C_4$, or $C_1$-$C_2$), $R^{35}$-substituted or unsubstituted heteroalkyl (e.g., 2 to 8 membered, 2 to 6 membered, 4 to 6 membered, 2 to 3 membered, or 4 to 5 membered), $R^{35}$-substituted or unsubstituted cycloalkyl (e.g., $C_3$-$C_8$, $C_3$-$C_6$, $C_4$-$C_6$, or $C_5$-$C_6$), $R^{35}$-substituted or unsubstituted heterocycloalkyl (e.g., 3 to 8 membered, 3 to 6 membered, 4 to 6 membered, 4 to 5 membered, or 5 to 6 membered), $R^{35}$-substituted or unsubstituted aryl (e.g., $C_6$-$C_{10}$ or phenyl), or $R^{35}$-substituted or unsubstituted heteroaryl (e.g., 5 to 10 membered, 5 to 9 membered, or 5 to 6 membered). In embodiments, $R^6$ is independently hydrogen, —$CX^6_3$, —$CHX^6_2$, —$CH_2X^6$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^6$ is independently —F, —Cl, —Br, or —I. In embodiments, $R^6$ is independently hydrogen. In embodiments, $R^6$ is independently unsubstituted methyl. In embodiments, $R^6$ is independently unsubstituted ethyl.

$R^{35}$ is independently oxo, halogen, —$CX^{35}_3$, —$CHX^{35}_2$, —$CH_2X^{35}$, —$OCX^{35}_3$, —$OCH_2X^{35}$, —$OCHX^{35}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 8 membered, 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered). In embodiments, $R^{35}$ is independently oxo, halogen, —$CX^{35}_3$, —$CHX^{35}_2$, —$CH_2X^{35}$, —$OCX^{35}_3$, —$OCH_2X^{35}$, —$OCHX^{35}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{35}$ is independently —F, —Cl, —Br, or —I. In embodiments, $R^{35}$ is independently unsubstituted methyl. In embodiments, $R^{35}$ is independently unsubstituted ethyl.

$R^{36}$ is independently oxo, halogen, —$CX^{36}_3$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, 2 to 3 membered, or 4 to 5 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 8 membered, 3 to 6 membered, 4 to 6 membered, 4 to 5 membered, or 5 to 6 membered), $R^{37}$-substituted or unsubstituted aryl (e.g., $C_6$-$C_{10}$ or phenyl), or $R^{37}$-substituted or unsubstituted heteroaryl (e.g., 5 to 10 membered, 5 to 9 membered, or 5 to 6 membered). In embodiments, $R^{36}$ is independently oxo, halogen, —$CX^{36}_3$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{36}$ is independently —F, —Cl, —Br, or —I. In embodiments, $R^{36}$ is independently unsubstituted methyl. In embodiments, $R^{36}$ is independently unsubstituted ethyl.

$R^{37}$ is independently oxo, halogen, —$CX^{37}_3$, —$CHX^{37}_2$, —$CH_2X^{37}$, —$OCX^{37}_3$, —$OCH_2X^{37}$, —$OCHX^{37}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{37}$ is independently —F, —Cl, —Br, or —I. In embodiments, $R^{37}$ is independently unsubstituted methyl. In embodiments, $R^{37}$ is independently unsubstituted ethyl.

In embodiments, $R^{6A}$ is independently hydrogen, —$CX^{6A}_3$, —$CHX^{6A}_2$, —$CH_2X^{6A}$, —CN, —COOH, —$CONH_2$, $R^{35A}$-substituted or unsubstituted alkyl (e.g., $C_1$-$C_8$, $C_1$-$C_6$, $C_1$-$C_4$, or $C_1$-$C_2$), $R^{35A}$-substituted or unsubstituted heteroalkyl (e.g., 2 to 8 membered, 2 to 6 membered, 4 to 6 membered, 2 to 3 membered, or 4 to 5 membered), $R^{35A}$-substituted or unsubstituted cycloalkyl (e.g., $C_3$-$C_8$, $C_3$-$C_6$, $C_4$-$C_6$, or $C_5$-$C_6$), $R^{35A}$-substituted or unsubstituted heterocycloalkyl (e.g., 3 to 8 membered, 3 to 6 membered, 4 to 6 membered, 4 to 5 membered, or 5 to 6 membered), $R^{35A}$-substituted or unsubstituted aryl (e.g., $C_6$-$C_{10}$ or phenyl), or $R^{35A}$-substituted or unsubstituted heteroaryl (e.g., 5 to 10 membered, 5 to 9 membered, or 5 to 6 membered). In embodiments, $R^{6A}$ is independently hydrogen, —$CX^{6A}_3$, —$CHX^{6A}_2$, —$CH_2X^{6A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{6A}$ is independently —F, —Cl, —Br, or —I. In embodiments, $R^{6A}$ is independently hydrogen. In embodiments, $R^{6A}$ is independently unsubstituted methyl. In embodiments, $R^{6A}$ is independently unsubstituted ethyl.

In embodiments, $R^{6A}$ and $R^{6B}$ substituents bonded to the same nitrogen atom may optionally be joined to form a $R^{35A}$-substituted or unsubstituted heterocycloalkyl (e.g., 3 to 8 membered, 3 to 6 membered, 4 to 6 membered, 4 to 5 membered, or 5 to 6 membered) or $R^{35A}$-substituted or unsubstituted heteroaryl (e.g., 5 to 10 membered, 5 to 9 membered, or 5 to 6 membered). In embodiments, $R^{6A}$ and $R^{6B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{6A}$ and $R^{6B}$ substituents bonded to the same nitrogen atom may optionally be joined to form a $R^{35A}$-substituted or unsubstituted heterocycloalkyl (e.g., 3 to 8 membered, 3 to 6 membered, 4 to 6 membered, 4 to 5 membered, or 5 to 6 membered). In embodiments, $R^{6A}$ and $R^{6B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{35A}$ is independently oxo, halogen, —$CX^{35A}_3$, —$CHX^{35A}_2$, —$CH_2X^{35A}$, —$OCX^{35A}_3$, —$OCH_2X^{35A}$, —$OCHX^{35A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{36A}$-substituted or unsubstituted alkyl (e.g., $C_1$-$C_8$, $C_1$-$C_6$, $C_1$-$C_4$, or $C_1$-$C_2$), $R^{36A}$-substituted or unsubstituted heteroalkyl (e.g., 2 to 8 membered, 2 to 6 membered, 4 to 6 membered, 2 to 3 membered, or 4 to 5 membered), $R^{36A}$-substituted or unsubstituted cycloalkyl (e.g., $C_3$-$C_8$, $C_3$-$C_6$, $C_4$-$C_6$, or $C_5$-$C_6$), $R^{36A}$-substituted or unsubstituted heterocycloalkyl (e.g., 3 to 8 membered, 3 to 6 membered, 4 to 6 membered, 4 to 5 membered, or 5 to 6 membered), $R^{36A}$-substituted or unsubstituted aryl (e.g., $C_6$-$C_{10}$ or phenyl), or $R^{36A}$-substituted or unsubstituted heteroaryl (e.g., 5 to 10 membered, 5 to 9 membered, or 5 to 6 membered). In embodiments, $R^{35A}$ is independently oxo, halogen, —$CX^{35A}_3$, —$CHX^{35A}_2$, —$CH_2X^{35A}$, —$OCX^{35A}_3$, —$OCH_2X^{35}{}_A$, —$OCHX^{35A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{35A}$ is independently —F, —Cl, —Br, or —I. In embodiments, $R^{35A}$ is independently unsubstituted methyl. In embodiments, $R^{35A}$ is independently unsubstituted ethyl.

$R^{36A}$ is independently oxo, halogen, —$CX^{36A}_3$, —$CHX^{36A}_2$, —$CH_2X^{36A}$, —$OCX^{36A}_3$, |—$OCH_2X^{36A}$, —$OCHX^{36A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{37A}$-substituted or unsubstituted alkyl (e.g., $C_1$-$C_8$, $C_1$-$C_6$, $C_1$-$C_4$, or $C_1$-$C_2$), $R^{37A}$-substituted or unsubstituted heteroalkyl (e.g., 2 to 8 membered, 2 to 6 membered, 4 to 6 membered, 2 to 3 membered, or 4 to 5 membered), $R^{37A}$-substituted or unsubstituted cycloalkyl (e.g., $C_3$-$C_8$, $C_3$-$C_6$, $C_4$-$C_6$, or $C_5$-$C_6$), $R^{37A}$-substituted or unsubstituted heterocycloalkyl (e.g., 3 to 8 membered, 3 to 6 membered, 4 to 6 membered, 4 to 5 membered, or 5 to 6 membered), $R^{37A}$-substituted or unsubstituted aryl (e.g., $C_6$-$C_{10}$ or phenyl), or $R^{37A}$-substituted or unsubstituted heteroaryl (e.g., 5 to 10 membered, 5 to 9 membered, or 5 to 6 membered). In embodiments, $R^{36A}$ is independently oxo, halogen, —$CX^{36A}_3$, —$CHX^{36A}_2$, —$CH_2X^{36A}$, —$OCX^{36A}_3$, —$OCH_2X^{36A}$, —$OCHX^{36A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{36A}$ is independently —F, —Cl, —Br, or —I. In embodiments, $R^{36A}$ is independently unsubstituted methyl. In embodiments, $R^{36A}$ is independently unsubstituted ethyl.

$R^{37A}$ is independently oxo, halogen, $—CX^{37A}_3$, $—CHX^{37A}_2$, $—CH_2X^{37A}$, $—OCX^{37A}_3$, $—OCH_2X^{37A}$, $—OCHX^{37A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{37A}$ is independently —F, —Cl, —Br, or —I. In embodiments, $R^{37A}$ is independently unsubstituted methyl. In embodiments, $R^{37A}$ is independently unsubstituted ethyl.

In embodiments, $R^{6B}$ is independently hydrogen, $—CX^{6B}_3$, $—CHX^{6B}_2$, $—CH_2X^{6B}$, —CN, —COOH, $—CONH_2$, $R^{35B}$-substituted or unsubstituted alkyl (e.g., $C_1$-$C_8$, $C_1$-$C_6$, $C_1$-$C_4$, or $C_1$-$C_2$), $R^{35B}$-substituted or unsubstituted heteroalkyl (e.g., 2 to 8 membered, 2 to 6 membered, 4 to 6 membered, 2 to 3 membered, or 4 to 5 membered), $R^{35B}$-substituted or unsubstituted cycloalkyl (e.g., $C_3$-$C_8$, $C_3$-$C_6$, $C_4$-$C_6$, or $C_5$-$C_6$), $R^{35B}$-substituted or unsubstituted heterocycloalkyl (e.g., 3 to 8 membered, 3 to 6 membered, 4 to 6 membered, 4 to 5 membered, or 5 to 6 membered), $R^{35B}$-substituted or unsubstituted aryl (e.g., $C_6$-$C_{10}$ or phenyl), or $R^{35B}$-substituted or unsubstituted heteroaryl (e.g., 5 to 10 membered, 5 to 9 membered, or 5 to 6 membered). In embodiments, $R^{6B}$ is independently hydrogen, $—CX^{6B}_3$, $—CHX^{6B}_2$, $—CH_2X^{6B}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{6B}$ is independently —F, —Cl, —Br, or —I. In embodiments, $R^{6B}$ is independently hydrogen. In embodiments, $R^{6B}$ is independently unsubstituted methyl. In embodiments, $R^{6B}$ is independently unsubstituted ethyl.

In embodiments, $R^{6A}$ and $R^{6B}$ substituents bonded to the same nitrogen atom may optionally be joined to form a $R^{35B}$-substituted or unsubstituted heterocycloalkyl (e.g., 3 to 8 membered, 3 to 6 membered, 4 to 6 membered, 4 to 5 membered, or 5 to 6 membered) or $R^{35B}$-substituted or unsubstituted heteroaryl (e.g., 5 to 10 membered, 5 to 9 membered, or 5 to 6 membered). In embodiments, $R^{6A}$ and $R^{6B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{6A}$ and $R^{6B}$ substituents bonded to the same nitrogen atom may optionally be joined to form a $R^{35B}$-substituted or unsubstituted heterocycloalkyl (e.g., 3 to 8 membered, 3 to 6 membered, 4 to 6 membered, 4 to 5 membered, or 5 to 6 membered). In embodiments, $R^{6A}$ and $R^{6B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{35B}$ is independently oxo, halogen, $—CX^{35B}_3$, $—CHX^{35B}_2$, $—CH_2X^{35B}$, $—OCX^{35B}_3$, $—OCH_2X^{35B}$, $—OCHX^{35B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, $R^{36B}$-substituted or unsubstituted alkyl (e.g., $C_1$-$C_8$, $C_1$-$C_6$, $C_1$-$C_4$, or $C_1$-$C_2$), $R^{36B}$-substituted or unsubstituted heteroalkyl (e.g., 2 to 8 membered, 2 to 6 membered, 4 to 6 membered, 2 to 3 membered, or 4 to 5 membered), $R^{36B}$-substituted or unsubstituted cycloalkyl (e.g., $C_3$-$C_8$, $C_3$-$C_6$, $C_4$-$C_6$, or $C_5$-$C_6$), $R^{36B}$-substituted or unsubstituted heterocycloalkyl (e.g., 3 to 8 membered, 3 to 6 membered, 4 to 6 membered, 4 to 5 membered, or 5 to 6 membered), $R^{36B}$-substituted or unsubstituted aryl (e.g., $C_6$-$C_{10}$ or phenyl), or $R^{36B}$-substituted or unsubstituted heteroaryl (e.g., 5 to 10 membered, 5 to 9 membered, or 5 to 6 membered). In embodiments, $R^{35B}$ is independently oxo, halogen, $—CX^{35B}_3$, $—CHX^{35B}_2$, $—CH_2X^{35B}$, $—OCX^{35B}_3$, $—OCH_2X^{35B}$, $—OCHX^{35B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{35B}$ is independently —F, —Cl, —Br, or —I. In embodiments, $R^{35B}$ is independently unsubstituted methyl. In embodiments, $R^{35B}$ is independently unsubstituted ethyl.

$R^{36B}$ is independently oxo, halogen, $—CX^{36B}_3$, $—CHX^{36B}_2$, $—CH_2X^{36B}$, $—OCX^{36B}_3$, $—OCH_2X^{36B}$, $—OCHX^{36B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, $R^{37B}$-substituted or unsubstituted alkyl (e.g., $C_1$-$C_8$, $C_1$-$C_6$, $C_1$-$C_4$, or $C_1$-$C_2$), $R^{37B}$-substituted or unsubstituted heteroalkyl (e.g., 2 to 8 membered, 2 to 6 membered, 4 to 6 membered, 2 to 3 membered, or 4 to 5 membered), $R^{37B}$-substituted or unsubstituted cycloalkyl (e.g., $C_3$-$C_8$, $C_3$-$C_6$, $C_4$-$C_6$, or $C_5$-$C_6$), $R^{37B}$-substituted or unsubstituted heterocycloalkyl (e.g., 3 to 8 membered, 3 to 6 membered, 4 to 6 membered, 4 to 5 membered, or 5 to 6 membered), $R^{37B}$-substituted or unsubstituted aryl (e.g., $C_6$-$C_{10}$ or phenyl), or $R^{37B}$-substituted or unsubstituted heteroaryl (e.g., 5 to 10 membered, 5 to 9 membered, or 5 to 6 membered). In embodiments, $R^{36B}$ is independently oxo, halogen, $—CX^{36B}_3$, $—CHX^{36B}_2$, $—CH_2X^{36B}$, $OCX^{36B}_3$— $OCH_2X^{36B}$, $—OCHX^{36B}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{36B}$ is independently —F, —Cl, —Br, or —I. In embodiments, $R^{36B}$ is independently unsubstituted methyl. In embodiments, $R^{36B}$ is independently unsubstituted ethyl.

$R^{37B}$ is independently oxo, halogen, $—CX^{37B}_3$, $—CHX^{37B}_2$, $—CH_2X^{37B}$, $—OCX^{37B}_3$, $—OCH_2X^{37B}$, $—OCHX^{37B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{37B}$ is independently —F, —Cl, —Br, or —I. In embodiments, $R^{37B}$ is independently unsubstituted methyl. In embodiments, $R^{37B}$ is independently unsubstituted ethyl.

In embodiments, $R^{6C}$ is independently hydrogen, $—CX^{6C}_3$, $—CHX^{6C}_2$, $—CH_2X^{6C}$, —CN, —COOH, $—CONH_2$, $R^{35C}$-substituted or unsubstituted alkyl (e.g., $C_1$-$C_8$, $C_1$-$C_6$, $C_1$-$C_4$, or $C_1$-$C_2$), $R^{35C}$-substituted or unsubstituted heteroalkyl (e.g., 2 to 8 membered, 2 to 6 membered, 4 to 6 membered, 2 to 3 membered, or 4 to 5 membered), $R^{35C}$-substituted or unsubstituted cycloalkyl (e.g., $C_3$-$C_8$, $C_3$-$C_6$, $C_4$-$C_6$, or $C_5$-$C_6$), $R^{35C}$-substituted or unsubstituted heterocycloalkyl (e.g., 3 to 8 membered, 3 to 6 membered, 4 to 6 membered, 4 to 5 membered, or 5 to 6 membered), $R^{35C}$-substituted or unsubstituted aryl (e.g., $C_6$-$C_{10}$ or phenyl), or $R^{35C}$-substituted or unsubstituted heteroaryl (e.g., 5 to 10 membered, 5 to 9 membered, or 5 to 6 membered). In embodiments, $R^{6C}$ is independently hydrogen, $—CX^{6C}_3$, $—CHX^{6C}_2$, $—CH_2X^{6C}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{6C}$ is independently —F, —Cl, —Br, or —I. In embodiments, $R^{6C}$ is independently hydrogen. In embodiments, $R^{6C}$ is independently unsubstituted methyl. In embodiments, $R^{6C}$ is independently unsubstituted ethyl.

$R^{35C}$ is independently oxo, halogen, $—CX^{35C}_3$, $—CHX^{35C}_2$, $—CH_2X^{35C}$, $—OCX^{35C}_3$, $—OCH_2X^{35C}$, $—OCHX^{35C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, $R^{36C}$-substituted or unsubstituted alkyl (e.g., $C_1$-$C_8$, $C_1$-$C_6$, $C_1$-$C_4$, or $C_1$-$C_2$), $R^{36C}$-substituted or unsubstituted heteroalkyl (e.g., 2 to 8 membered, 2 to 6 membered, 4 to 6 membered, 2 to 3 membered, or 4 to 5 membered), $R^{36C}$-substituted or unsubstituted cycloalkyl (e.g., $C_3$-$C_8$, $C_3$-$C_6$, $C_4$-$C_6$, or $C_5$-$C_6$), $R^{36C}$-substituted or unsubstituted heterocycloalkyl (e.g., 3 to 8 membered, 3 to 6 membered, 4 to 6 membered, 4 to 5 membered, or 5 to 6 membered), $R^{36C}$-substituted or unsubstituted aryl (e.g., $C_6$-$C_{10}$ or phenyl), or $R^{36C}$-substituted or unsubstituted heteroaryl (e.g., 5 to 10 membered, 5 to 9 membered, or 5 to 6 membered). In embodiments, $R^{35C}$ is independently oxo, halogen, $—CX^{35C}_3$, $—CHX^{35C}_2$, $—CH_2X^{35C}$, $—OCX^{35C}_3$, $—OCH_2X^{35C}$, $—OCHX^{35C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{35C}$ is independently —F, —Cl, —Br, or —I. In embodiments, $R^{35C}$ is independently unsubstituted methyl. In embodiments, $R^{35C}$ is independently unsubstituted ethyl.

$R^{36C}$ is independently oxo, halogen, $—CX^{36C}_3$, $—CHX^{36C}_2$, $—CH_2X^{36C}$, $—OCX^{36C}_3$, $—OCH_2X^{36C}$, $—OCHX^{36C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, $R^{37C}$-substituted or unsubstituted alkyl (e.g., $C_1$-$C_8$, $C_1$-$C_6$, $C_1$-$C_4$, or $C_1$-$C_2$), $R^{37C}$-substituted or unsubstituted heteroalkyl (e.g., 2 to 8 membered, 2 to 6 membered, 4 to 6 membered, 2 to 3 membered, or 4 to 5 membered), $R^{37C}$-substituted or unsubstituted cycloalkyl (e.g., $C_3$-$C_8$, $C_3$-$C_6$, $C_4$-$C_6$, or $C_5$-$C_6$), $R^{37C}$-substituted or unsubstituted heterocycloalkyl (e.g., 3 to 8 membered, 3 to 6 membered, 4 to 6 membered, 4 to 5 membered, or 5 to 6 membered), $R^{37C}$-substituted or unsubstituted aryl (e.g., $C_6$-$C_{10}$ or phenyl), or $R^{37C}$-substituted or unsubstituted heteroaryl (e.g., 5 to 10 membered, 5 to 9 membered, or 5 to 6 membered). In embodiments, $R^{36C}$ is independently oxo, halogen, $—CX^{36C}_3$, $—CHX^{36C}_2$, $—CH_2X^{36C}$, $—OCX^{36C}_3$, $—OCH_2X^{36C}$, $—OCHX^{36C}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{36C}$ is independently —F, —Cl, —Br, or —I. In embodiments, $R^{36C}$ is independently unsubstituted methyl. In embodiments, $R^{36C}$ is independently unsubstituted ethyl.

$R^{37C}$ is independently oxo, halogen, $—CX^{37C}_3$, $—CHX^{37C}_2$, $—CH_2X^{37C}$, $—OCX^{37C}$, $—OCH_2X^{37C}$, $—OCHX^{37C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{37C}$ is independently —F, —Cl, —Br, or —I. In embodiments, $R^{37C}$ is independently unsubstituted methyl. In embodiments, $R^{37C}$ is independently unsubstituted ethyl.

In embodiments, $R^7$ is independently hydrogen, —$CX^{7}_3$, —$CHX^{7}_2$, —$CH_2X^7$, —CN, —C(O)$R^{7C}$, —C(O)—O$R^{7C}$, —C(O)N$R^{7A}R^{7B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is independently hydrogen. In embodiments, $R^7$ is independently —$CX^7_3$. In embodiments, $R^7$ is independently —$CHX^7_2$. In embodiments, $R^7$ is independently —$CH_2X^7$. In embodiments, $R^7$ is independently —CN. In embodiments, $R^7$ is independently —C(O)$R^{7C}$. In embodiments, $R^7$ is independently —C(O)—O$R^{7C}$. In embodiments, $R^7$ is independently —C(O)N$R^{7A}R^{7B}$. In embodiments, $R^7$ is independently —COOH. In embodiments, $R^7$ is independently —$CONH_2$. In embodiments, $R^7$ is independently —$CF_3$. In embodiments, $R^7$ is independently —$CHF_2$. In embodiments, $R^7$ is independently —$CH_2F$. In embodiments, $R^7$ is independently —$CH_3$. In embodiments, $R^7$ is independently —$CH_2CH_3$. In embodiments, $R^7$ is independently —$CH_2CH_2CH_3$. In embodiments, $R^7$ is independently —$CH(CH_3)_2$. In embodiments, $R^7$ is independently —$C(CH_3)_3$.

In embodiments, $R^7$ is independently substituted or unsubstituted alkyl (e.g., $C_1$-$C_8$, $C_1$-$C_6$, $C_1$-$C_4$, or $C_1$-$C_2$). In embodiments, $R^7$ is independently substituted alkyl (e.g., $C_1$-$C_8$, $C_1$-$C_6$, $C_1$-$C_4$, or $C_1$-$C_2$). In embodiments, $R^7$ is independently unsubstituted alkyl (e.g., $C_1$-$C_8$, $C_1$-$C_6$, $C_1$-$C_4$, or $C_1$-$C_2$). In embodiments, $R^7$ is independently unsubstituted methyl. In embodiments, $R^7$ is independently unsubstituted ethyl. In embodiments, $R^7$ is independently unsubstituted propyl. In embodiments, $R^7$ is independently unsubstituted isopropyl. In embodiments, $R^7$ is independently unsubstituted tert-butyl. In embodiments, $R^7$ is independently substituted or unsubstituted heteroalkyl (e.g., 2 to 8 membered, 2 to 6 membered, 4 to 6 membered, 2 to 3 membered, or 4 to 5 membered). In embodiments, $R^7$ is independently substituted heteroalkyl (e.g., 2 to 8 membered, 2 to 6 membered, 4 to 6 membered, 2 to 3 membered, or 4 to 5 membered). In embodiments, $R^7$ is independently unsubstituted heteroalkyl (e.g., 2 to 8 membered, 2 to 6 membered, 4 to 6 membered, 2 to 3 membered, or 4 to 5 membered). In embodiments, $R^7$ is independently substituted or unsubstituted cycloalkyl (e.g., $C_3$-$C_8$, $C_3$-$C_6$, $C_4$-$C_6$, or $C_5$-$C_6$). In embodiments, $R^7$ is independently substituted cycloalkyl (e.g., $C_3$-$C_8$, $C_3$-$C_6$, $C_4$-$C_6$, or $C_5$-$C_6$). In embodiments, $R^7$ is independently unsubstituted cycloalkyl (e.g., $C_3$-$C_8$, $C_3$-$C_6$, $C_4$-$C_6$, or $C_5$-$C_6$). In embodiments, $R^7$ is independently substituted or unsubstituted heterocycloalkyl (e.g., 3 to 8 membered, 3 to 6 membered, 4 to 6 membered, 4 to 5 membered, or 5 to 6 membered). In embodiments, $R^7$ is independently substituted heterocycloalkyl (e.g., 3 to 8 membered, 3 to 6 membered, 4 to 6 membered, 4 to 5 membered, or 5 to 6 membered). In embodiments, $R^7$ is independently unsubstituted heterocycloalkyl (e.g., 3 to 8 membered, 3 to 6 membered, 4 to 6 membered, 4 to 5 membered, or 5 to 6 membered). In embodiments, $R^7$ is independently substituted or unsubstituted aryl (e.g., $C_6$-$C_{10}$ or phenyl). In embodiments, $R^7$ is independently substituted aryl (e.g., $C_6$-$C_{10}$ or phenyl). In embodiments, $R^7$ is independently unsubstituted aryl (e.g., $C_6$-$C_{10}$ or phenyl). In embodiments, $R^7$ is independently substituted or unsubstituted heteroaryl (e.g., 5 to 10 membered, 5 to 9 membered, or 5 to 6 membered). In embodiments, $R^7$ is independently substituted heteroaryl (e.g., 5 to 10 membered, 5 to 9 membered, or 5 to 6 membered). In embodiments, $R^7$ is independently unsubstituted heteroaryl (e.g., 5 to 10 membered, 5 to 9 membered, or 5 to 6 membered).

In embodiments, $R^{7A}$ is independently hydrogen. In embodiments, $R^{7A}$ is independently —$CX^{7A}_3$. In embodiments, $R^{7A}$ is independently —$CHX^{7A}_2$. In embodiments, $R^{7A}$ is independently —$CH_2X^{7A}$. In embodiments, $R^{7A}$ is independently —CN. In embodiments, $R^{7A}$ is independently —COOH. In embodiments, $R^{7A}$ is independently —$CONH_2$. In embodiments, $X^{7A}$ is independently —F, —Cl, —Br, or —I.

In embodiments, $R^{7A}$ is independently substituted or unsubstituted alkyl (e.g., $C_1$-$C_8$, $C_1$-$C_6$, $C_1$-$C_4$, or $C_1$-$C_2$). In embodiments, $R^{7A}$ is independently substituted alkyl (e.g., $C_1$-$C_8$, $C_1$-$C_6$, $C_1$-$C_4$, or $C_1$-$C_2$). In embodiments, $R^{7A}$ is independently unsubstituted alkyl (e.g., $C_1$-$C_8$, $C_1$-$C_6$, $C_1$-$C_4$, or $C_1$-$C_2$). In embodiments, $R^{7A}$ is independently unsubstituted methyl. In embodiments, $R^{7A}$ is independently unsubstituted ethyl. In embodiments, $R^{7A}$ is independently unsubstituted propyl. In embodiments, $R^{7A}$ is independently unsubstituted isopropyl. In embodiments, $R^{7A}$ is independently unsubstituted tert-butyl. In embodiments, $R^{7A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7A}$ is independently substituted heteroalkyl (e.g., 2 to 8 membered, 2 to 6 membered, 4 to 6 membered, 2 to 3 membered, or 4 to 5 membered). In embodiments, $R^{7A}$ is independently unsubstituted heteroalkyl (e.g., 2 to 8 membered, 2 to 6 membered, 4 to 6 membered, 2 to 3 membered, or 4 to 5 membered). In embodiments, $R^{7A}$ is independently substituted or unsubstituted cycloalkyl (e.g., $C_3$-$C_8$, $C_3$-$C_6$, $C_4$-$C_6$, or $C_5$-$C_6$). In embodiments, $R^{7A}$ is independently substituted cycloalkyl (e.g., $C_3$-$C_8$, $C_3$-$C_6$, $C_4$-$C_6$, or $C_5$-$C_6$). In embodiments, $R^{7A}$ is independently unsubstituted cycloalkyl (e.g., $C_3$-$C_8$, $C_3$-$C_6$, $C_4$-$C_6$, or $C_5$-$C_6$). In embodiments, $R^{7A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ is independently substituted heterocycloalkyl (e.g., 3 to 8 membered, 3 to 6 membered, 4 to 6 membered, 4 to 5 membered, or 5 to 6 membered). In embodiments, $R^{7A}$ is independently unsubstituted heterocycloalkyl (e.g., 3 to 8 membered, 3 to 6 membered, 4 to 6 membered, 4 to 5 membered, or 5 to 6 membered). In embodiments, $R^{7A}$ is independently substituted or unsubstituted aryl (e.g., $C_6$-$C_{10}$ or phenyl). In embodiments, $R^{7A}$ is independently substituted aryl (e.g., $C_6$-$C_{10}$ or phenyl). In embodiments, $R^{7A}$ is independently unsubstituted aryl (e.g., $C_6$-$C_{10}$ or phenyl). In embodiments, $R^{7A}$ is independently substituted or unsubstituted heteroaryl (e.g., 5 to 10 membered, 5 to 9 membered, or 5 to 6 membered). In embodiments, $R^{7A}$ is independently substituted heteroaryl (e.g., 5 to 10 membered, 5 to 9 membered, or 5 to 6 membered). In embodiments, $R^{7A}$ is independently unsubstituted heteroaryl (e.g., 5 to 10 membered, 5 to 9 membered, or 5 to 6 membered).

In embodiments, $R^{7B}$ is independently hydrogen. In embodiments, $R^{7B}$ is independently $—CX^{7B}_3$. In embodiments, $R^{7B}$ is independently $—CHX^{7B}_2$. In embodiments, $R^{7B}$ is independently $—CH_2X^{7B}$. In embodiments, $R^{7B}$ is independently —CN. In embodiments, $R^{7B}$ is independently —COOH. In embodiments, $R^{7B}$ is independently $—CONH_2$. In embodiments, $X^7B$ is independently —F, —Cl, —Br, or —I.

In embodiments, $R^{7B}$ is independently substituted or unsubstituted alkyl (e.g., $C_1$-$C_8$, $C_1$-$C_6$, $C_1$-$C_4$, or $C_1$-$C_2$). In embodiments, $R^{7B}$ is independently substituted alkyl (e.g., $C_1$-$C_8$, $C_1$-$C_6$, $C_1$-$C_4$, or $C_1$-$C_2$). In embodiments, $R^{7B}$ is independently unsubstituted alkyl (e.g., $C_1$-$C_8$, $C_1$-$C_6$, $C_1$-$C_4$, or $C_1$-$C_2$). In embodiments, $R^{7B}$ is independently unsubstituted methyl. In embodiments, $R^{7B}$ is independently unsubstituted ethyl. In embodiments, $R^{7B}$ is independently unsubstituted propyl. In embodiments, $R^{7B}$ is independently unsubstituted isopropyl. In embodiments, $R^{7B}$ is independently unsubstituted tert-butyl. In embodiments, $R^{7B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7B}$ is independently substituted heteroalkyl (e.g., 2 to 8 membered, 2 to 6 membered, 4 to 6 membered, 2 to 3 membered, or 4 to 5 membered). In embodiments, $R^{7B}$ is independently unsubstituted heteroalkyl (e.g., 2 to 8 membered, 2 to 6 membered, 4 to 6 membered, 2 to 3 membered, or 4 to 5 membered). In embodiments, $R^{7B}$ is independently substituted or unsubstituted cycloalkyl (e.g., $C_3$-$C_8$, $C_3$-$C_6$, $C_4$-$C_6$, or $C_5$-$C_6$). In embodiments, $R^{7B}$ is independently substituted cycloalkyl (e.g., $C_3$-$C_8$, $C_3$-$C_6$, $C_4$-$C_6$, or $C_5$-$C_6$). In embodiments, $R^{7B}$ is independently unsubstituted cycloalkyl (e.g., $C_3$-$C_8$, $C_3$-$C_6$, $C_4$-$C_6$, or $C_5$-$C_6$). In embodiments, $R^{7B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7B}$ is independently substituted heterocycloalkyl (e.g., 3 to 8 membered, 3 to 6 membered, 4 to 6 membered, 4 to 5 membered, or 5 to 6 membered). In embodiments, $R^{7B}$ is independently unsubstituted heterocycloalkyl (e.g., 3 to 8 membered, 3 to 6 membered, 4 to 6 membered, 4 to 5 membered, or 5 to 6 membered). In embodiments, $R^{7B}$ is independently substituted or unsubstituted aryl (e.g., $C_6$-$C_{10}$ or phenyl). In embodiments, $R^{7B}$ is independently substituted aryl (e.g., $C_6$-$C_{10}$ or phenyl). In embodiments, $R^{7B}$ is independently unsubstituted aryl (e.g., $C_6$-$C_{10}$ or phenyl). In embodiments, $R^{7B}$ is independently substituted or unsubstituted heteroaryl (e.g., 5 to 10 membered, 5 to 9 membered, or 5 to 6 membered). In embodiments, $R^{7B}$ is independently substituted heteroaryl (e.g., 5 to 10 membered, 5 to 9 membered, or 5 to 6 membered). In embodiments, $R^{7B}$ is independently unsubstituted heteroaryl (e.g., 5 to 10 membered, 5 to 9 membered, or 5 to 6 membered).

In embodiments, $R^{7A}$ and $R^{7B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{7A}$ and $R^{7B}$ substituents bonded to the same nitrogen atom may be joined to form a substituted or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may be joined to form a substituted heteroaryl (e.g., 5 to 10 membered, 5 to 9 membered, or 5 to 6 membered). In embodiments, $R^{7A}$ and $R^{7B}$ substituents bonded to the same nitrogen atom may be joined to form an unsubstituted heteroaryl (e.g., 5 to 10 membered, 5 to 9 membered, or 5 to 6 membered).

In embodiments, $R^{7C}$ is independently hydrogen. In embodiments, $R^{7C}$ is independently $—CX^{7'}3$. In embodiments, $R^{7C}$ is independently $—CHX^{7C}_2$. In embodiments, $R^{7C}$ is independently $—CH_2X^{7C}$. In embodiments, $R^{7C}$ is independently —CN. In embodiments, $R^{7C}$ is independently —COOH. In embodiments, $R^{7C}$ is independently $—CONH_2$. In embodiments, $X^{7C}$ is independently —F, —Cl, —Br, or —I.

In embodiments, $R^{7C}$ is independently substituted or unsubstituted alkyl (e.g., $C_1$-$C_8$, $C_1$-$C_6$, $C_1$-$C_4$, or $C_1$-$C_2$). In embodiments, $R^{7C}$ is independently substituted alkyl (e.g., $C_1$-$C_8$, $C_1$-$C_6$, $C_1$-$C_4$, or $C_1$-$C_2$). In embodiments, $R^{7C}$ is independently unsubstituted alkyl (e.g., $C_1$-$C_8$, $C_1$-$C_6$, $C_1$-$C_4$, or $C_1$-$C_2$). In embodiments, $R^{7C}$ is independently unsubstituted methyl. In embodiments, $R^{7C}$ is independently unsubstituted ethyl. In embodiments, $R^{7C}$ is independently unsubstituted propyl. In embodiments, $R^{7C}$ is independently unsubstituted isopropyl. In embodiments, $R^{7C}$ is independently unsubstituted tert-butyl. In embodiments, $R^{7C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7C}$ is independently substituted heteroalkyl (e.g., 2 to 8 membered, 2 to 6 membered, 4 to 6 membered, 2 to 3 membered, or 4 to 5 membered). In embodiments, $R^{7C}$ is independently unsubstituted heteroalkyl (e.g., 2 to 8 membered, 2 to 6 membered, 4 to 6 membered, 2 to 3 membered, or 4 to 5 membered). In embodiments, $R^{7C}$ is independently substituted or unsubstituted cycloalkyl (e.g., $C_3$-$C_8$, $C_3$-$C_6$, $C_4$-$C_6$, or $C_5$-$C_6$). In embodiments, $R^{7C}$ is independently substituted cycloalkyl (e.g., $C_3$-$C_8$, $C_3$-$C_6$, $C_4$-$C_6$, or $C_5$-$C_6$). In embodiments, $R^{7C}$ is independently unsubstituted cycloalkyl (e.g., $C_3$-$C_8$, $C_3$-$C_6$, $C_4$-$C_6$, or $C_5$-$C_6$). In embodiments, $R^{7C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7C}$ is independently substituted heterocycloalkyl (e.g., 3 to 8 membered, 3 to 6 membered, 4 to 6 membered, 4 to 5 membered, or 5 to 6 membered). In embodiments, $R^{7C}$ is independently unsubstituted heterocycloalkyl (e.g., 3 to 8 membered, 3 to 6 membered, 4 to 6 membered, 4 to 5 membered, or 5 to 6 membered). In embodiments, $R^{7C}$ is independently substituted or unsubstituted aryl (e.g., $C_6$-$C_{10}$ or phenyl). In embodiments, $R^{7C}$ is independently substituted aryl (e.g., $C_6$-$C_{10}$ or phenyl). In embodiments, $R^{7C}$ is independently unsubstituted aryl (e.g., $C_6$-$C_{10}$ or phenyl). In embodiments, $R^{7C}$ is independently substituted or unsubstituted heteroaryl (e.g., 5 to 10 membered, 5 to 9 membered, or 5 to 6 membered). In embodiments, $R^{7C}$ is independently substituted heteroaryl (e.g., 5 to 10 membered, 5 to 9 membered, or 5 to 6 membered). In embodiments, $R^{7C}$ is independently unsubstituted heteroaryl (e.g., 5 to 10 membered, 5 to 9 membered, or 5 to 6 membered).

In embodiments, $R^7$ is independently hydrogen, $-CX^7_3$, $-CHX^7_2$, $-CH_2X^7$, —CN, —COOH, $-CONH_2$, $R^{38}$-substituted or unsubstituted alkyl (e.g., $C_1$-$C_8$, $C_1$-$C_6$, $C_1$-$C_4$, or $C_1$-$C_2$), $R^{38}$-substituted or unsubstituted heteroalkyl (e.g., 2 to 8 membered, 2 to 6 membered, 4 to 6 membered, 2 to 3 membered, or 4 to 5 membered), $R^{38}$-substituted or unsubstituted cycloalkyl (e.g., $C_3$-$C_8$, $C_3$-$C_6$, $C_4$-$C_6$, or $C_5$-$C_6$), $R^{38}$-substituted or unsubstituted heterocycloalkyl (e.g., 3 to 8 membered, 3 to 6 membered, 4 to 6 membered, 4 to 5 membered, or 5 to 6 membered), $R^{38}$-substituted or unsubstituted aryl (e.g., $C_6$-$C_{10}$ or phenyl), or $R^{38}$-substituted or unsubstituted heteroaryl (e.g., 5 to 10 membered, 5 to 9 membered, or 5 to 6 membered). In embodiments, $R^7$ is independently hydrogen, $-CX^7_3$, $-CHX^7_2$, $-CH_2X^7$, —CN, —COOH, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^7$ is independently —F, —Cl, —Br, or —I. In embodiments, $R^7$ is independently hydrogen. In embodiments, $R^7$ is independently unsubstituted methyl. In embodiments, $R^7$ is independently unsubstituted ethyl.

$R^{38}$ is independently oxo, halogen, $-CX^{38}_3$, $-CHX^{38}_2$, $-CH_2X^{38}$, $-OCX^{38}_3$, $-OCH_2X^{38}$, $-OCHX^{38}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 8 membered, 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). In embodiments, $R^{38}$ is independently oxo, halogen, $-CX^{38}_3$, $-CHX^{38}_2$, $-CH_2X^{38}$, $-OCX^{38}_3$, $-OCH_2X^{38}$, $-OCHX^{38}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)$ $NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38}$ is independently —F, —Cl, —Br, or —I. In embodiments, $R^{38}$ is independently unsubstituted methyl. In embodiments, $R^{38}$ is independently unsubstituted ethyl.

$R^{39}$ is independently oxo, halogen, $-CX^{39}_3$, $-CHX^{39}_2$, $-CH_2X^{39}$, $-OCX^{39}_3$, $-OCH_2X^{39}$, $-OCHX^{39}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered). In embodiments, $R^{39}$ is independently oxo, halogen, $-CX^{39}_3$, $-CHX^{39}_2$, $-CH_2X^{39}$, $-OCX^{39}_3$, $-OCH_2X^{39}$, $-OCHX^{39}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)$ $NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{39}$ is independently —F, —Cl, —Br, or —I. In embodiments, $R^{39}$ is independently unsubstituted methyl. In embodiments, $R^{39}$ is independently unsubstituted ethyl.

$R^{40}$ is independently oxo, halogen, $-CX^{40}_3$, $-CHX^{40}_2$, $-CH_2X^{40}$, $-OCX^{40}_3$, $-OCH_2X^{40}$, $-OCHX^{40}_2$, —CN, —OH, $-NH_2$, —COOH, $-CONH_2$, $-NO_2$, —SH, $-SO_3H$, $-SO_4H$, $-SO_2NH_2$, $-NHN_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40}$ is independently —F, —Cl, —Br, or —I. In embodiments, $R^{40}$ is independently unsubstituted methyl. In embodiments, $R^{40}$ is independently unsubstituted ethyl.

In embodiments, $R^{7A}$ is independently hydrogen, $-CX^{7A}_3$, $-CHX^{7A}_2$, $-CH_2X^{7A}$, —CN, —COOH, $-CONH_2$, $R^{38A}$-substituted or unsubstituted alkyl (e.g., $C_1$-$C_8$, $C_1$-$C_6$, $C_1$-$C_4$, or $C_1$-$C_2$), $R^{38A}$-substituted or unsubstituted heteroalkyl (e.g., 2 to 8 membered, 2 to 6 membered, 4 to 6 membered, 2 to 3 membered, or 4 to 5 membered), $R^{38A}$-substituted or unsubstituted cycloalkyl (e.g., $C_3$-$C_8$, $C_3$-$C_6$, $C_4$-$C_6$, or $C_5$-$C_6$), $R^{38A}$-substituted or unsubstituted heterocycloalkyl (e.g., 3 to 8 membered, 3 to 6 membered, 4 to 6 membered, 4 to 5 membered, or 5 to 6 membered), $R^{38A}$-substituted or unsubstituted aryl (e.g., $C_6$-$C_{10}$ or phenyl), or $R^{38A}$-substituted or unsubstituted heteroaryl (e.g., 5 to 10 membered, 5 to 9 membered, or 5 to 6 membered). In embodiments, $R^{7A}$ is independently hydrogen, $-CX^{7A}_3$, $-CHX^{7A}_2$, $-CH_2X^{7A}$, —CN, —COOH, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7A}$ is independently —F, —Cl, —Br, or —I. In embodiments, $R^{7A}$ is independently hydrogen. In embodiments, $R^{7A}$ is independently unsubstituted methyl. In embodiments, $R^{7A}$ is independently unsubstituted ethyl.

In embodiments, $R^{7A}$ and $R^{7B}$ substituents bonded to the same nitrogen atom may optionally be joined to form a $R^{38A}$-substituted or unsubstituted heterocycloalkyl (e.g., 3 to 8 membered, 3 to 6 membered, 4 to 6 membered, 4 to 5 membered, or 5 to 6 membered) or $R^{38A}$-substituted or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form a $R^{38A}$-substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{38A}$ is independently oxo, halogen, $—CX^{38A}_3$, $—CHX^{38A}_2$, $—CH_2X^{38A}$, $—OCX^{38A}_3$, $—OCH_2X^{38A}$, $—OCHX^{38A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{39A}$-substituted or unsubstituted alkyl (e.g., $C_1$-$C_8$, $C_1$-$C_6$, $C_1$-$C_4$, or $C_1$-$C_2$), $R^{39A}$-substituted or unsubstituted heteroalkyl (e.g., 2 to 8 membered, 2 to 6 membered, 4 to 6 membered, 2 to 3 membered, or 4 to 5 membered), $R^{39A}$-substituted or unsubstituted cycloalkyl (e.g., $C_3$-$C_8$, $C_3$-$C_6$, $C_4$-$C_6$, or $C_5$-$C_6$), $R^{39A}$-substituted or unsubstituted heterocycloalkyl (e.g., 3 to 8 membered, 3 to 6 membered, 4 to 6 membered, 4 to 5 membered, or 5 to 6 membered), $R^{39A}$-substituted or unsubstituted aryl (e.g., $C_6$-$C_{10}$ or phenyl), or $R^{39A}$-substituted or unsubstituted heteroaryl (e.g., 5 to 10 membered, 5 to 9 membered, or 5 to 6 membered). In embodiments, $R^{38A}$ is independently oxo, halogen, $—CX^{38A}_3$, $—CHX^{38A}_2$, $—CH_2X^{38A}$, $—OCX^{38A}_3$, $—OCH_2X^{38A}$, $—OCHX^{38A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38A}$ is independently —F, —Cl, —Br, or —I. In embodiments, $R^{38A}$ is independently unsubstituted methyl. In embodiments, $R^{38A}$ is independently unsubstituted ethyl.

$R^{39A}$ is independently oxo, halogen, $—CX^{39A}_3$, $—CHX^{39A}_2$, $—CH_2X^{39A}$, $—OCX^{39A}_3$, $—OCH_2X^{39A}$, $—OCHX^{39A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{40A}$-substituted or unsubstituted alkyl (e.g., $C_1$-$C_8$, $C_1$-$C_6$, $C_1$-$C_4$, or $C_1$-$C_2$), $R^{40A}$-substituted or unsubstituted heteroalkyl (e.g., 2 to 8 membered, 2 to 6 membered, 4 to 6 membered, 2 to 3 membered, or 4 to 5 membered), $R^{40A}$-substituted or unsubstituted cycloalkyl (e.g., $C_3$-$C_8$, $C_3$-$C_6$, $C_4$-$C_6$, or $C_5$-$C_6$), $R^{40A}$-substituted or unsubstituted heterocycloalkyl (e.g., 3 to 8 membered, 3 to 6 membered, 4 to 6 membered, 4 to 5 membered, or 5 to 6 membered), $R^{40A}$-substituted or unsubstituted aryl (e.g., $C_6$-$C_{10}$ or phenyl), or $R^{40A}$-substituted or unsubstituted heteroaryl (e.g., 5 to 10 membered, 5 to 9 membered, or 5 to 6 membered). In embodiments, $R^{39A}$ is independently oxo, halogen, $—CX^{39A}_3$, $—CHX^{39A}_2$, $—CH_2X^{39A}$, $—OCX^{39A}_3$, $—OCH_2X^{39A}$, $—OCHX^{39A}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{39A}$ is independently —F, —Cl, —Br, or —I. In embodiments, $R^{39A}$ is independently unsubstituted methyl. In embodiments, $R^{39A}$ is independently unsubstituted ethyl.

$R^{40A}$ is independently oxo, halogen, $—CX^{40A}_3$, $—CHX^{40A}_2$, $—CH_2X^{40A}$, $—OCX^{40A}_3$, $—OCH_2X^{40A}$, $—OCHX^{40A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40A}$ is independently —F, —Cl, —Br, or —I. In embodiments, $R^{40A}$ is independently unsubstituted methyl. In embodiments, $R^{40A}$ is independently unsubstituted ethyl.

In embodiments, $R^{7B}$ is independently hydrogen, $—CX^{7B}_3$, $—CHX^{7B}_2$, $—CH_2X^{7B}$, —CN, —COOH, $—CONH_2$, $R^{38B}$-substituted or unsubstituted alkyl (e.g., $C_1$-$C_8$, $C_1$-$C_6$, $C_1$-$C_4$, or $C_1$-$C_2$), $R^{38B}$-substituted or unsubstituted heteroalkyl (e.g., 2 to 8 membered, 2 to 6 membered, 4 to 6 membered, 2 to 3 membered, or 4 to 5 membered), $R^{38B}$-substituted or unsubstituted cycloalkyl (e.g., $C_3$-$C_8$, $C_3$-$C_6$, $C_4$-$C_6$, or $C_5$-$C_6$), $R^{38B}$-substituted or unsubstituted heterocycloalkyl (e.g., 3 to 8 membered, 3 to 6 membered, 4 to 6 membered, 4 to 5 membered, or 5 to 6 membered), $R^{38B}$-substituted or unsubstituted aryl (e.g., $C_6$-$C_{10}$ or phenyl), or $R^{38B}$-substituted or unsubstituted heteroaryl (e.g., 5 to 10 membered, 5 to 9 membered, or 5 to 6 membered). In embodiments, $R^{7B}$ is independently hydrogen, —$CX^{7B}_3$, —$CHX^{7B}_2$, —$CH_2X^{7B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7B}$ is independently —F, —Cl, —Br, or —I. In embodiments, $R^{7B}$ is independently hydrogen. In embodiments, $R^{7B}$ is independently unsubstituted methyl. In embodiments, $R^{7B}$ is independently unsubstituted ethyl.

In embodiments, $R^{7A}$ and $R^{7B}$ substituents bonded to the same nitrogen atom may optionally be joined to form a $R^{38B}$-substituted or unsubstituted heterocycloalkyl (e.g., 3 to 8 membered, 3 to 6 membered, 4 to 6 membered, 4 to 5 membered, or 5 to 6 membered) or $R^{38B}$-substituted or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form a $R^{38B}$-substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{38B}$ is independently oxo, halogen, —$CX^{38B}_3$, —$CHX^{38B}_2$, —$CH_2X^{38B}$, —$OCX^{38B}_3$, —$OCH_2X^{38B}$, —$OCHX^{38B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{39B}$-substituted or unsubstituted alkyl (e.g., $C_1$-$C_8$, $C_1$-$C_6$, $C_1$-$C_4$, or $C_1$-$C_2$), $R^{39B}$-substituted or unsubstituted heteroalkyl (e.g., 2 to 8 membered, 2 to 6 membered, 4 to 6 membered, 2 to 3 membered, or 4 to 5 membered), $R^{39B}$-substituted or unsubstituted cycloalkyl (e.g., $C_3$-$C_8$, $C_3$-$C_6$, $C_4$-$C_6$, or $C_5$-$C_6$), $R^{39B}$-substituted or unsubstituted heterocycloalkyl (e.g., 3 to 8 membered, 3 to 6 membered, 4 to 6 membered, 4 to 5 membered, or 5 to 6 membered), $R^{39B}$-substituted or unsubstituted aryl (e.g., $C_6$-$C_{10}$ or phenyl), or $R^{39B}$-substituted or unsubstituted heteroaryl (e.g., 5 to 10 membered, 5 to 9 membered, or 5 to 6 membered). In embodiments, $R^{38B}$ is independently oxo, halogen, —$CX^{38B}_3$, —$CHX^{38B}_2$, —$CH_2X^{38B}$, —$OCX^{38B}_3$, —$OCH_2X^{38B}$, —$OCHX^{38B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38B}$ is independently —F, —Cl, —Br, or —I. In embodiments, $R^{38B}$ is independently unsubstituted methyl. In embodiments, $R^{38B}$ is independently unsubstituted ethyl.

$R^{39B}$ is independently oxo, halogen, —$CX^{39B}_3$, —$CHX^{39B}_2$, —$CH_2X^{39B}$, —$OCX^{39B}_3$, —$OCH_2X^{39B}$, —$OCHX^{39B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{40B}$-substituted or unsubstituted alkyl (e.g., $C_1$-$C_8$, $C_1$-$C_6$, $C_1$-$C_4$, or $C_1$-$C_2$), $R^{40B}$-substituted or unsubstituted heteroalkyl (e.g., 2 to 8 membered, 2 to 6 membered, 4 to 6 membered, 2 to 3 membered, or 4 to 5 membered), $R^{40B}$-substituted or unsubstituted cycloalkyl (e.g., $C_3$-$C_8$, $C_3$-$C_6$, $C_4$-$C_6$, or $C_5$-$C_6$), $R^{40B}$-substituted or unsubstituted heterocycloalkyl (e.g., 3 to 8 membered, 3 to 6 membered, 4 to 6 membered, 4 to 5 membered, or 5 to 6 membered), $R^{40B}$-substituted or unsubstituted aryl (e.g., $C_6$-$C_{10}$ or phenyl), or $R^{40B}$-substituted or unsubstituted heteroaryl (e.g., 5 to 10 membered, 5 to 9 membered, or 5 to 6 membered). In embodiments, $R^{39B}$ is independently oxo, halogen, —$CX^{39B}_3$, —$CHX^{39B}_2$, —$CH_2X^{39B}$, —$OCX^{39B}_3$—$OCH_2X^{39B}$, —$OCHX^{39B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{39B}$ is independently —F, —Cl, —Br, or —I. In embodiments, $R^{39B}$ is independently unsubstituted methyl. In embodiments, $R^{39B}$ is independently unsubstituted ethyl.

$R^{40B}$ is independently oxo, halogen, —$CX^{40B}_3$, —$CHX^{40B}_2$, —$CH_2X^{40B}$, —$OCX^{40B}_3$, —$OCH_2X^{40B}$, —$OCHX^{40B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40B}$ is independently —F, —Cl, —Br, or —I. In embodiments, $R^{40B}$ is independently unsubstituted methyl. In embodiments, $R^{40B}$ is independently unsubstituted ethyl.

In embodiments, $R^{7C}$ is independently hydrogen, —$CX^{7C}_3$, —$CHX^{7C}_2$, —$CH_2X^{7C}$, —CN, —COOH, —$CONH_2$, $R^{31C}$-substituted or unsubstituted alkyl (e.g., $C_1$-$C_8$, $C_1$-$C_6$, $C_1$-$C_4$, or $C_1$-$C_2$), $R^{38C}$-substituted or unsubstituted heteroalkyl (e.g., 2 to 8 membered, 2 to 6 membered, 4 to 6 membered, 2 to 3 membered, or 4 to 5 membered), $R^{38C}$-substituted or unsubstituted cycloalkyl (e.g., $C_3$-$C_8$, $C_3$-$C_6$, $C_4$-$C_6$, or $C_5$-$C_6$), $R^{38C}$-substituted or unsubstituted heterocycloalkyl (e.g., 3 to 8 membered, 3 to 6 membered, 4 to 6 membered, 4 to 5 membered, or 5 to 6 membered), $R^{38C}$-substituted or unsubstituted aryl (e.g., $C_6$-$C_{10}$ or phenyl), or $R^{38C}$-substituted or unsubstituted heteroaryl (e.g., 5 to 10 membered, 5 to 9 membered, or 5 to 6 membered). In embodiments, $R^{7C}$ is independently hydrogen, —$CX^{7C}_3$, —$CHX^{7C}_2$, —$CH_2X^{7C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7C}$ is independently —F, —Cl, —Br, or —I. In embodiments, $R^{7C}$ is independently hydrogen. In embodiments, $R^{7C}$ is independently unsubstituted methyl. In embodiments, $R^{7C}$ is independently unsubstituted ethyl.

$R^{38C}$ is independently oxo, halogen, —$CX^{38C}_3$, —$CHX^{38C}_2$, —$CH_2X^{38C}$, —$OCX^{38C}_3$, —$OCH_2X^{38C}$, —$OCHX^{38C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{39C}$-substituted or unsubstituted alkyl (e.g., $C_1$-$C_8$, $C_1$-$C_6$, $C_1$-$C_4$, or $C_1$-$C_2$), $R^{39C}$-substituted or unsubstituted heteroalkyl (e.g., 2 to 8 membered, 2 to 6 membered, 4 to 6 membered, 2 to 3 membered, or 4 to 5 membered), $R^{39C}$-substituted or unsubstituted cycloalkyl (e.g., $C_3$-$C_8$, $C_3$-$C_6$, $C_4$-$C_6$, or $C_5$-$C_6$), $R^{39C}$-substituted or unsubstituted heterocycloalkyl (e.g., 3 to 8 membered, 3 to 6 membered, 4 to 6 membered, 4 to 5 membered, or 5 to 6 membered), $R^{39C}$-substituted or unsubstituted aryl (e.g., $C_6$-$C_{10}$ or phenyl), or $R^{39C}$-substituted or unsubstituted heteroaryl (e.g., 5 to 10 membered, 5 to 9 membered, or 5 to 6 membered). In embodiments, $R^{38C}$ is independently oxo, halogen, —$CX^{38C}_3$, —$CHX^{38C}_2$, —$CH_2X^{38C}$, —$OCX^{38C}_3$, —$OCH_2X^{38C}$, —$OCHX^{38C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38C}$ is independently —F, —Cl, —Br, or —I. In embodiments, $R^{38C}$ is independently unsubstituted methyl. In embodiments, $R^{38C}$ is independently unsubstituted ethyl.

$R^{39C}$ is independently oxo, halogen, —$CX^{39C}_3$, —$CHX^{39C}_2$, —$CH_2X^{39C}$, —$OCX^{39C}_3$, —$OCH_2X^{39C}$, —$OCHX^{39C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{40C}$-substituted or unsubstituted alkyl (e.g., $C_1$-$C_8$, $C_1$-$C_6$, $C_1$-$C_4$, or $C_1$-$C_2$), $R^{40C}$-substituted or unsubstituted heteroalkyl (e.g., 2 to 8 membered, 2 to 6 membered, 4 to 6 membered, 2 to 3 membered, or 4 to 5 membered), $R^{40C}$-substituted or unsubstituted cycloalkyl (e.g., $C_3$-$C_8$, $C_3$-$C_6$, $C_4$-$C_6$, or $C_5$-$C_6$), $R^{40C}$-substituted or unsubstituted heterocycloalkyl (e.g., 3 to 8 membered, 3 to 6 membered, 4 to 6 membered, 4 to 5 membered, or 5 to 6 membered), $R^{40C}$-substituted or unsubstituted aryl (e.g., $C_6$-$C_{10}$ or phenyl), or $R^{40C}$-substituted or unsubstituted heteroaryl (e.g., 5 to 10 membered, 5 to 9 membered, or 5 to 6 membered). In embodiments, $R^{39C}$ is independently oxo, halogen, —$CX^{39C}_3$, —$CHX^{39C}_2$, —$CH_2X^{39C}$, —$OCX^{39C}_3$, —$OCH_2X^{39C}$, —$OCHX^{39C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{39C}$ is independently —F, —Cl, —Br, or —I. In embodiments, $R^{39C}$ is independently unsubstituted methyl. In embodiments, $R^{39C}$ is independently unsubstituted ethyl.

$R^{40C}$ is independently oxo, halogen, —$CX^{40C}_3$, $CHX^{40C}_2$, —$CH_2X^{40C}$, —$OCX^{40C}_3$, —$OCH_2X^{40C}$, —$OCHX^{40C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40C}$ is independently —F, —Cl, —Br, or —I. In embodiments, $R^{40C}$ is independently unsubstituted methyl. In embodiments, $R^{40C}$ is independently unsubstituted ethyl.

$L^1$ is —O—, —S—, substituted or unsubstituted $C_1$-$C_2$ alkylene (e.g., —$CH_2$—, —$CH_2CH_2$—, —$C(CH_3)H$—, or —$CH(CH_3)CH_2$—), or substituted or unsubstituted 2 membered heteroalkylene (e.g., —$CH_2O$—, —$OCH_2$—, —$CH_2S$—, —$SCH_2$—, —$CH_2NH$—, —$NHCH_2$—, —CH $(CH_3)O$—, —$OCH(CH_3)$—, —$CH(CH_3)S$—, —SCH $(CH_3)$—, —$CH(CH_3)NH$—, —$NHCH(CH_3)$—, —$CH_2N$ $(CH_3)$—, or —$N(CH_3)CH_2$—). In embodiments, $L^1$ is —O—, —S—, or substituted or unsubstituted methylene. In embodiments, $L^1$ is —$SCH_2$—. In embodiments, $L^1$ is —O—. In embodiments, $L^1$ is —S—. In embodiments, $L^1$ is —$CH(CH_3)$—.

In embodiments, $L^1$ is independently —O—, —S—, $R^{41}$-substituted or unsubstituted $C_1$-$C_2$ alkylene (e.g., $C_1$ or $C_2$) or $R^{41}$-substituted or unsubstituted 2 membered heteroalkylene. In embodiments, $L^1$ is independently —O—, —S—, unsubstituted $C_1$-$C_2$ alkylene (e.g., $C_1$ or $C_2$) or unsubstituted 2 membered heteroalkylene. In embodiments, $L^1$ is independently unsubstituted methylene. In embodiments, $L^1$ is independently unsubstituted ethylene.

$R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{42}$-substituted or unsubstituted alkyl (e.g., $C_1$-$C_8$, $C_1$-$C_6$, $C_1$-$C_4$, or $C_1$-$C_2$), $R^{42}$-substituted or unsubstituted heteroalkyl (e.g., 2 to 8 membered, 2 to 6 membered, 4 to 6 membered, 2 to 3 membered, or 4 to 5 membered), $R^{42}$-substituted or unsubstituted cycloalkyl (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 8 membered, 3 to 6 membered, 4 to 6 membered, 4 to 5 membered, or 5 to 6 membered), $R^{42}$-substituted or unsubstituted aryl (e.g., $C_6$-$C_{10}$ or phenyl), or $R^{42}$-substituted or unsubstituted heteroaryl (e.g., 5 to 10 membered, 5 to 9 membered, or 5 to 6 membered). In embodiments, $R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41}$ is independently —F, —Cl, —Br, or —I. In embodiments, $R^{41}$ is independently unsubstituted methyl. In embodiments, $R^{41}$ is independently unsubstituted ethyl.

$R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{43}$-substituted or unsubstituted alkyl (e.g., $C_1$-$C_8$, $C_1$-$C_6$, $C_1$-$C_4$, or $C_1$-$C_2$), $R^{43}$-substituted or unsubstituted heteroalkyl (e.g., 2 to 8 membered, 2 to 6 membered, 4 to 6 membered, 2 to 3 membered, or 4 to 5 membered), $R^{43}$-substituted or unsubstituted cycloalkyl (e.g., $C_3$-$C_8$, $C_3$-$C_6$, $C_4$-$C_6$, or $C_5$-$C_6$), $R^{43}$-substituted or unsubstituted heterocycloalkyl (e.g., 3 to 8 membered, 3 to 6 membered, 4 to 6 membered, 4 to 5 membered, or 5 to 6 membered), $R^{43}$-substituted or unsubstituted aryl (e.g., $C_6$-$C_{10}$ or phenyl), or $R^{43}$-substituted or unsubstituted heteroaryl (e.g., 5 to 10 membered, 5 to 9 membered, or 5 to 6 membered). In embodiments, $R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{42}$ is independently —F, —Cl, —Br, or —I. In embodiments, $R^{42}$ is independently unsubstituted methyl. In embodiments, $R^{42}$ is independently unsubstituted ethyl.

$R^{43}$ is independently oxo, halogen, —$CX^{43}_3$, —$CHX^{43}_2$, —$CH_2X^{43}$, —$OCX^{43}_3$, —$OCH_2X^{43}$, —$OCHX^{43}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{43}$ is independently —F, —Cl, —Br, or —I. In embodiments, $R^{43}$ is independently unsubstituted methyl. In embodiments, $R^{43}$ is independently unsubstituted ethyl.

In embodiments, $L^2$ is a bond. In embodiments, $L^2$ is —NH—. In embodiments, $L^2$ is —NHC(O)—.

In embodiments, $L^3$ is a bond, —N($R^6$)—, —C(O)—, —C(O)N($R^6$)—, —N($R^6$)C(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenyl), or substituted or unsubstituted heteroarylene (e.g., 5 to 10 membered, 5 to 9 membered, or 5 to 6 membered).

In embodiments, $L^3$ is a bond, —N($R^6$)—, —C(O)—, or —C(O)N($R^6$)—; and $R^6$ is independently hydrogen, —$CX^6_3$, —$CHX^6_2$, —$CH_2X^6$, or unsubstituted ($C_1$-$C_4$) alkyl. In embodiments, $L^3$ is a bond, —N($R^6$)—, —C(O)—, or —C(O)N($R^6$)—; and $R^6$ is independently hydrogen or unsubstituted methyl. In embodiments, $L^3$ is a bond, —C(O)—, —C(O)N($CH_3$)—, —N($CH_3$)—, or —NH—. In embodiments, $L^3$ is a bond. In embodiments, $L^3$ is —C(O)—. In embodiments, $L^3$ is a bond. In embodiments, $L^3$ is —N($R^6$)—. In embodiments, $L^3$ is —C(O)—. In embodiments, $L^3$ is —C(O)N($R^6$)—. In embodiments, $L^3$ is —NH—. In embodiments, $L^3$ is —C(O)—. In embodiments, $L^3$ is —C(O)NH—. In embodiments, $L^3$ is —N($CH_3$)—. In embodiments, $L^3$ is —C(O)N($CH_3$)—. In embodiments, $L^3$ is —N($CH_2CH_3$)—. In embodiments, $L^3$ is —C(O)N($CH_2CH_3$)—.

In embodiments, $L^3$ is independently substituted or unsubstituted alkylene (e.g., $C_1$-$C_8$, $C_1$-$C_6$, $C_1$-$C_4$, or $C_1$-$C_2$). In embodiments, $L^3$ is independently substituted alkylene (e.g., $C_1$-$C_8$, $C_1$-$C_6$, $C_1$-$C_4$, or $C_1$-$C_2$). In embodiments, $L^3$ is independently unsubstituted alkylene (e.g., $C_1$-$C_8$, $C_1$-$C_6$, $C_1$-$C_4$, or $C_1$-$C_2$). In embodiments, $L^3$ is independently unsubstituted methylene. In embodiments, $L^3$ is independently unsubstituted ethylene. In embodiments, $L^3$ is independently unsubstituted propylene. In embodiments, $L^3$ is independently unsubstituted isopropylene. In embodiments, $L^3$ is independently unsubstituted tert-butylene. In embodiments, $L^3$ is independently substituted or unsubstituted heteroalkylene (e.g., 2 to 8 membered, 2 to 6 membered, 4 to 6 membered, 2 to 3 membered, or 4 to 5 membered). In embodiments, $L^3$ is independently substituted heteroalkylene (e.g., 2 to 8 membered, 2 to 6 membered, 4 to 6 membered, 2 to 3 membered, or 4 to 5 membered). In embodiments, $L^3$ is independently unsubstituted heteroalkylene (e.g., 2 to 8 membered, 2 to 6 membered, 4 to 6 membered, 2 to 3 membered, or 4 to 5 membered). In embodiments, $L^3$ is independently substituted or unsubstituted cycloalkylene (e.g., $C_3$-$C_8$, $C_3$-$C_6$, $C_4$-$C_6$, or $C_5$-$C_6$). In embodiments, $L^3$ is independently substituted cycloalkylene (e.g., $C_3$-$C_8$, $C_3$-$C_6$, $C_4$-$C_6$, or $C_5$-$C_6$). In embodiments, $L^3$ is independently unsubstituted cycloalkylene (e.g., $C_3$-$C_8$, $C_3$-$C_6$, $C_4$-$C_6$, or $C_5$-$C_6$). In embodiments, $L^3$ is independently substituted or unsubstituted heterocycloalkylene (e.g., 3 to 8 membered, 3 to 6 membered, 4 to 6 membered, 4 to 5 membered, or 5 to 6 membered). In embodiments, $L^3$ is independently substituted heterocycloalkylene (e.g., 3 to 8 membered, 3 to 6 membered, 4 to 6 membered, 4 to 5 membered, or 5 to 6 membered). In embodiments, $L^3$ is independently unsubstituted heterocycloalkylene (e.g., 3 to 8 membered, 3 to 6 membered, 4 to 6 membered, 4 to 5 membered, or 5 to 6 membered). In embodiments, $L^3$ is independently substituted or unsubstituted arylene (e.g., $C_6$-$C_{10}$ or phenylene). In embodiments, $L^3$ is independently substituted arylene (e.g., $C_6$-$C_{10}$ or phenylene). In embodiments, $L^3$ is independently unsubstituted arylene (e.g., $C_6$-$C_{10}$ or phenylene). In embodiments, $L^3$ is independently substituted or unsubstituted heteroarylene (e.g., 5 to 10 membered, 5 to 9 membered, or 5 to 6 membered). In embodiments, $L^3$ is independently substituted heteroarylene (e.g., 5 to 10 membered, 5 to 9 membered, or 5 to 6 membered). In embodiments, $L^3$ is independently unsubstituted heteroarylene (e.g., 5 to 10 membered, 5 to 9 membered, or 5 to 6 membered).

In embodiments, $L^3$ is independently bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, $R^{44}$-substituted or unsubstituted alkylene (e.g., $C_1$-$C_8$, $C_1$-$C_6$, $C_1$-$C_4$, or $C_1$-$C_2$), $R^{44}$-substituted or unsubstituted heteroalkylene (e.g., 2 to 8 membered, 2 to 6 membered, 4 to 6 membered, 2 to 3 membered, or 4 to 5 membered), $R^{44}$-substituted or unsubstituted cycloalkylene (e.g., $C_3$-$C_8$, $C_3$-$C_6$, $C_4$-$C_6$, or $C_5$-$C_6$), $R^{44}$-substituted or unsubstituted heterocycloalkylene (e.g., 3 to 8 membered, 3 to 6 membered, 4 to 6 membered, 4 to 5 membered, or 5 to 6 membered), $R^{44}$-substituted or unsubstituted arylene (e.g., $C_6$-$C_{10}$ or phenylene), or $R^{44}$-substituted or unsubstituted heteroarylene (e.g., 5 to 10 membered, 5 to 9 membered, or 5 to 6 membered). In embodiments, $L^3$ is independently bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 8 membered, 3 to 6 membered, 4 to 6 membered, 4 to 5 membered, or 5 to 6 membered), unsubstituted arylene (e.g., $C_6$-$C_{10}$ or phenylene), or unsubstituted heteroarylene (e.g., 5 to 10 membered, 5 to 9 membered, or 5 to 6 membered). In embodiments, $L^3$ is independently unsubstituted methylene. In embodiments, $L^3$ is independently unsubstituted ethylene. In embodiments, $L^3$ is independently methyl-substituted methylene.

$R^{44}$ is independently oxo, halogen, —$CX^{44}_3$, —$CHX^{44}_2$, —$CH_2X^{44}$, —$OCX^{44}_3$, —$OCH_2X^{44}$, —$OCHX^{44}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{45}$-substituted or unsubstituted alkyl (e.g., $C_1$-$C_8$, $C_1$-$C_6$, $C_1$-$C_4$, or $C_1$-$C_2$), $R^{45}$-substituted or unsubstituted heteroalkyl (e.g., 2 to 8 membered, 2 to 6 membered, 4 to 6 membered, 2 to 3 membered, or 4 to 5 membered), $R^{45}$-substituted or unsubstituted cycloalkyl (e.g., $C_3$-$C_8$, $C_3$-$C_6$, $C_4$-$C_6$, or $C_5$-$C_6$), $R^{45}$-substituted or unsubstituted heterocycloalkyl (e.g., 3 to 8 membered, 3 to 6 membered, 4 to 6 membered, 4 to 5 membered, or 5 to 6 membered), $R^{45}$-substituted or unsubstituted aryl (e.g., $C_6$-$C_{10}$ or phenyl), or $R^{45}$-substituted or unsubstituted heteroaryl (e.g., 5 to 10 membered, 5 to 9 membered, or 5 to 6 membered). In embodiments, $R^{44}$ is independently oxo, halogen, —$CX^{44}_3$, —$CHX^{44}_2$, —$CH_2X^{44}$, —$OCX^{44}_3$, —$OCH_2X^{44}$, —$OCHX^{44}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{44}$ is independently —F, —Cl, —Br, or —I. In embodiments, $R^{44}$ is independently unsubstituted methyl. In embodiments, $R^{44}$ is independently unsubstituted ethyl.

$R^{45}$ is independently oxo, halogen, —$CX^{45}_3$, —$CHX^{45}_2$, —$CH_2X^{45}$, —$OCX^{45}_3$, —$OCH_2X^{45}$, —$OCHX^{45}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{46}$-substituted or unsubstituted alkyl (e.g., $C_1$-$C_8$, $C_1$-$C_6$, $C_1$-$C_4$, or $C_1$-$C_2$), $R^{46}$-substituted or unsubstituted heteroalkyl (e.g., 2 to 8 membered, 2 to 6 membered, 4 to 6 membered, 2 to 3 membered, or 4 to 5 membered), $R^{46}$-substituted or unsubstituted cycloalkyl (e.g., $C_3$-$C_8$, $C_3$-$C_6$, $C_4$-$C_6$, or $C_5$-$C_6$), $R^{46}$-substituted or unsubstituted heterocycloalkyl (e.g., 3 to 8 membered, 3 to 6 membered, 4 to 6 membered, 4 to 5 membered, or 5 to 6 membered), $R^{46}$-substituted or unsubstituted aryl (e.g., $C_6$-$C_{10}$ or phenyl), or $R^{46}$-substituted or unsubstituted heteroaryl (e.g., 5 to 10 membered, 5 to 9 membered, or 5 to 6 membered). In embodiments, $R^{45}$ is independently oxo, halogen, —$CX^{45}_3$, —$CHX^{45}_2$, —$CH_2X^{45}$, —$OCX^{45}_3$, —$OCH_2X^{45}$, —$OCHX^{45}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{45}$ is independently —F, —Cl, —Br, or —I. In embodiments, $R^{45}$ is independently unsubstituted methyl. In embodiments, $R^{45}$ is independently unsubstituted ethyl.

$R^{46}$ is independently oxo, halogen, —$CX^{46}_3$, —$CHX^{46}_2$, —$CH_2X^{46}$, —$OCX^{46}_3$, —$OCH_2X^{46}$, —$OCHX^{46}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{46}$ is independently —F, —Cl, —Br, or —I. In embodiments, $R^{46}$ is independently unsubstituted methyl. In embodiments, $R^{46}$ is independently unsubstituted ethyl.

In embodiments, $L^4$ is a bond, —N($R^7$)—, —C(O)—, —C(O)N($R^7$)—, —N($R^7$)C(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenyl), or substituted or unsubstituted heteroarylene (e.g., 5 to 10 membered, 5 to 9 membered, or 5 to 6 membered).

In embodiments, $L^4$ is a bond. In embodiments, $L^4$ is —N($R^7$)—. In embodiments, $L^4$ is —C(O)N($R^7$)—. In embodiments, $L^4$ is —NH—. In embodiments, $L^4$ is —C(O)—. In embodiments, $L^4$ is —C(O)NH—. In embodiments, $L^4$ is —N($CH_3$)—. In embodiments, $L^4$ is —C(O)N($CH_3$)—. In embodiments, $L^4$ is —N($CH_2CH_3$)—. In embodiments, $L^4$ is —C(O)N($CH_2CH_3$)—. In embodiments, $L^4$ is a bond, —N($R^7$)—, —C(O)—, —C(O)N($R^7$)—, substituted or unsubstituted heterocycloalkylene, substituted or unsubstituted fused ring heterocycloalkylene, substituted or unsubstituted spirocyclic heterocycloalkylene, or substituted or unsubstituted bridged ring heterocycloalkylene; and $R^7$ is independently hydrogen, —$CX^7_3$, —$CHX^7_2$, —$CH_2X^7$, or unsubstituted ($C_1$-$C_4$) alkyl.

In embodiments, $L^4$ is a bond, substituted or unsubstituted monocyclic heterocycloalkylene (e.g., 3 to 10 membered, 3 to 8 membered, 3 to 6 membered, 4 to 6 membered, 4 to 5 membered, or 5 to 6 membered), substituted or unsubstituted fused ring heterocycloalkylene (e.g., 5 to 10 membered, 7 to 10 membered, 6 to 10 membered, or 7 to 8 membered), substituted or unsubstituted spirocyclic heterocycloalkylene (e.g., 7 to 10 membered, 6 to 10 membered, 7 to 8 membered), or substituted or unsubstituted bridged ring heterocycloalkylene (e.g., 5 to 10 membered, 7 to 10 membered, 6 to 10 membered, or 7 to 8 membered). In embodiments, $L^4$ is an unsubstituted 7 to 8 membered bridged ring heterocycloalkylene. In embodiments, $L^4$ is an unsubstituted 7 to 8 membered fused ring heterocycloalkylene. In embodiments, $L^4$ is an unsubstituted 7 to 8 membered spirocyclic heterocycloalkylene. In embodiments, $L^4$ is an unsubstituted 5 to 8 membered monocyclic heterocycloalkylene.

In embodiments, $L^4$ is a methyl-substituted 5 to 8 membered monocyclic heterocycloalkylene. In embodiments, $L^4$ is a methyl-substituted 5 to 7 membered monocyclic heterocycloalkylene. In embodiments, $L^4$ is a methyl-substituted 6 to 8 membered monocyclic heterocycloalkylene. In embodiments, $L^4$ is a methyl-substituted 6 to 7 membered monocyclic heterocycloalkylene.

In embodiments, $L^4$ is an ethyl-substituted 5 to 8 membered monocyclic heterocycloalkylene. In embodiments, $L^4$ is an ethyl-substituted 5 to 7 membered monocyclic heterocycloalkylene. In embodiments, $L^4$ is an ethyl-substituted 6 to 8 membered monocyclic heterocycloalkylene. In embodiments, $L^4$ is an ethyl-substituted 6 to 7 membered monocyclic heterocycloalkylene.

In embodiments, $L^4$ is a cyano-substituted 5 to 8 membered monocyclic heterocycloalkylene. In embodiments, $L^4$ is a cyano-substituted 5 to 7 membered monocyclic heterocycloalkylene. In embodiments, $L^4$ is a cyano-substituted 6 to 8 membered monocyclic heterocycloalkylene. In embodiments, $L^4$ is a cyano-substituted 6 to 7 membered monocyclic heterocycloalkylene.

In embodiments, $L^4$ is a halo-substituted 5 to 8 membered monocyclic heterocycloalkylene. In embodiments, $L^4$ is a halo-substituted 5 to 7 membered monocyclic heterocycloalkylene. In embodiments, $L^4$ is a halo-substituted 6 to 8 membered monocyclic heterocycloalkylene. In embodiments, $L^4$ is a halo-substituted 6 to 7 membered monocyclic heterocycloalkylene.

In embodiments, $L^4$ is an unsubstituted 5 to 8 membered monocyclic heterocycloalkylene. In embodiments, $L^4$ is an unsubstituted 5 to 7 membered monocyclic heterocycloalkylene. In embodiments, $L^4$ is an unsubstituted 6 to 8 membered monocyclic heterocycloalkylene. In embodiments, $L^4$ is an unsubstituted 6 to 7 membered monocyclic heterocycloalkylene.

In embodiments, $L^4$ is an ethyl-substituted 5 to 8 membered monocyclic heterocycloalkylene. In embodiments, $L^4$ is an ethyl-substituted 5 to 7 membered monocyclic heterocycloalkylene. In embodiments, $L^4$ is an ethyl-substituted 6 to 8 membered monocyclic heterocycloalkylene. In embodiments, $L^4$ is an ethyl-substituted 6 to 7 membered monocyclic heterocycloalkylene.

In embodiments, $L^4$ is an isopropyl-substituted 5 to 8 membered monocyclic heterocycloalkylene. In embodiments, $L^4$ is an isopropyl-substituted 5 to 7 membered monocyclic heterocycloalkylene. In embodiments, $L^4$ is an isopropyl-substituted 6 to 8 membered monocyclic heterocycloalkylene. In embodiments, $L^4$ is an isopropyl-substituted 6 to 7 membered monocyclic heterocycloalkylene.

In embodiments, $L^4$ is a tert-butyl-substituted 5 to 8 membered monocyclic heterocycloalkylene. In embodiments, $L^4$ is a tert-butyl-substituted 5 to 7 membered monocyclic heterocycloalkylene. In embodiments, $L^4$ is a tert-butyl-substituted 6 to 8 membered monocyclic heterocycloalkylene. In embodiments, $L^4$ is a tert-butyl-substituted 6 to 7 membered monocyclic heterocycloalkylene.

In embodiments, $L^4$ is a substituted or unsubstituted 4 to 10 membered monocyclic heterocycloalkylene. In embodiments, $L^4$ is a substituted or unsubstituted 5 to 10 membered monocyclic heterocycloalkylene. In embodiments, $L^4$ is a substituted or unsubstituted 5 to 8 membered monocyclic heterocycloalkylene. In embodiments, $L^4$ is a substituted 4 to 10 membered monocyclic heterocycloalkylene. In embodiments, $L^4$ is a substituted 5 to 10 membered monocyclic heterocycloalkylene. In embodiments, $L^4$ is a substituted 5 to 8 membered monocyclic heterocycloalkylene. In embodiments, $L^4$ is a $R^{47}$-substituted 4 to 10 membered monocyclic heterocycloalkylene. In embodiments, $L^4$ is a $R^{47}$-substituted 5 to 10 membered monocyclic heterocycloalkylene. In embodiments, $L^4$ is a $R^{47}$-substituted 5 to 8 membered monocyclic heterocycloalkylene. In embodiments, $L^4$ is an unsubstituted 4 to 10 membered monocyclic heterocycloalkylene. In embodiments, $L^4$ is an unsubstituted 5 to 10 membered monocyclic heterocycloalkylene. In embodiments, $L^4$ is an unsubstituted 5 to 8 membered monocyclic heterocycloalkylene.

In embodiments, $L^4$ is a substituted or unsubstituted 5 to 10 membered fused ring heterocycloalkylene. In embodiments, $L^4$ is a substituted or unsubstituted 6 to 10 membered fused ring heterocycloalkylene. In embodiments, $L^4$ is a substituted or unsubstituted 7 to 8 membered fused ring heterocycloalkylene. In embodiments, $L^4$ is a substituted 5 to 10 membered fused ring heterocycloalkylene. In embodiments, $L^4$ is a substituted 6 to 10 membered fused ring heterocycloalkylene. In embodiments, $L^4$ is a substituted 7 to 8 membered fused ring heterocycloalkylene. In embodiments, $L^4$ is a $R^{47}$-substituted 5 to 10 membered fused ring heterocycloalkylene. In embodiments, $L^4$ is a $R^{47}$-substituted 6 to 10 membered fused ring heterocycloalkylene. In embodiments, $L^4$ is a $R^{47}$-substituted 7 to 8 membered fused ring heterocycloalkylene. In embodiments, $L^4$ is an unsubstituted 5 to 10 membered fused ring heterocycloalkylene. In embodiments, $L^4$ is an unsubstituted 6 to 10 membered fused ring heterocycloalkylene. In embodiments, $L^4$ is an unsubstituted 7 to 8 membered fused ring heterocycloalkylene.

In embodiments, $L^4$ is a substituted or unsubstituted 6 to 10 membered spirocyclic heterocycloalkylene. In embodiments, $L^4$ is a substituted or unsubstituted 7 to 10 membered spirocyclic heterocycloalkylene. In embodiments, $L^4$ is a substituted or unsubstituted 7 to 8 membered spirocyclic heterocycloalkylene. In embodiments, $L^4$ is a substituted 6 to 10 membered spirocyclic heterocycloalkylene. In embodiments, $L^4$ is a substituted 7 to 10 membered spirocyclic heterocycloalkylene. In embodiments, $L^4$ is a substituted 7 to 8 membered spirocyclic heterocycloalkylene. In embodiments, $L^4$ is a $R^{47}$-substituted 6 to 10 membered spirocyclic heterocycloalkylene. In embodiments, $L^4$ is a $R^{47}$-substituted 7 to 10 membered spirocyclic heterocycloalkylene. In embodiments, $L^4$ is a $R^{47}$-substituted 7 to 8 membered spirocyclic heterocycloalkylene. In embodiments, $L^4$ is an unsubstituted 6 to 10 membered spirocyclic heterocycloalkylene. In embodiments, $L^4$ is an unsubstituted 7 to 10 membered spirocyclic heterocycloalkylene. In embodiments, $L^4$ is an unsubstituted 7 to 8 membered spirocyclic heterocycloalkylene.

In embodiments, $L^4$ is a substituted or unsubstituted 5 to 10 membered bridged ring heterocycloalkylene. In embodiments, $L^4$ is a substituted or unsubstituted 7 to 8 membered bridged ring heterocycloalkylene. In embodiments, $L^4$ is a substituted 5 to 10 membered bridged ring heterocycloalkylene. In embodiments, $L^4$ is a substituted 7 to 8 membered bridged ring heterocycloalkylene. In embodiments, $L^4$ is a $R^{47}$-substituted 5 to 10 membered bridged ring heterocycloalkylene. In embodiments, $L^4$ is a $R^{47}$-substituted 7 to 8 membered bridged ring heterocycloalkylene. In embodiments, $L^4$ is an unsubstituted 5 to 10 membered bridged ring heterocycloalkylene. In embodiments, $L^4$ is an unsubstituted 7 to 8 membered bridged ring heterocycloalkylene.

In embodiments, $L^4$ is a $R^{47}$-substituted 5 membered bridged ring heterocycloalkylene. In embodiments, $L^4$ is a $R^{47}$-substituted 6 membered bridged ring heterocycloalkylene. In embodiments, $L^4$ is a $R^{47}$-substituted 7 membered bridged ring heterocycloalkylene. In embodiments, $L^4$ is a $R^{47}$-substituted 8 membered bridged ring heterocycloalkylene. In embodiments, $L^4$ is a $R^{47}$-substituted 9 membered bridged ring heterocycloalkylene. In embodiments, $L^4$ is a $R^{47}$-substituted 10 membered bridged ring heterocycloalkylene. In embodiments, $L^4$ is an unsubstituted 5 membered bridged ring heterocycloalkylene. In embodiments, $L^4$ is an unsubstituted 6 membered bridged ring heterocycloalkylene. In embodiments, $L^4$ is an unsubstituted 7 membered bridged ring heterocycloalkylene. In embodiments, $L^4$ is an unsubstituted 8 membered bridged ring heterocycloalkylene. In embodiments, $L^4$ is an unsubstituted 9 membered bridged ring heterocycloalkylene. In embodiments, $L^4$ is an unsubstituted 10 membered bridged ring heterocycloalkylene.

In embodiments, $L^4$ is a $R^{47}$-substituted 5 membered heterocycloalkylene. In embodiments, $L^4$ is a $R^{47}$-substituted 6 membered heterocycloalkylene. In embodiments, $L^4$ is a $R^{47}$-substituted 7 membered heterocycloalkylene. In embodiments, $L^4$ is a $R^{47}$-substituted 8 membered heterocycloalkylene. In embodiments, $L^4$ is a $R^{47}$-substituted 9 membered heterocycloalkylene. In embodiments, $L^4$ is a $R^{47}$-substituted 10 membered heterocycloalkylene. In embodiments, $L^4$ is an unsubstituted 5 membered heterocycloalkylene. In embodiments, $L^4$ is an unsubstituted 6 membered heterocycloalkylene. In embodiments, $L^4$ is an unsubstituted 7 membered heterocycloalkylene. In embodiments, $L^4$ is an unsubstituted 8 membered heterocycloalkylene. In embodiments, $L^4$ is an unsubstituted 9 membered heterocycloalkylene. In embodiments, $L^4$ is an unsubstituted 10 membered heterocycloalkylene.

In embodiments, $L^4$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is substituted or unsubstituted $C_3$-$C_8$ cycloalkylene. In embodiments, $L^4$ is substituted or unsubstituted $C_3$-$C_6$ cycloalkylene. In embodiments, $L^4$ is substituted or unsubstituted $C_5$-$C_6$ cycloalkylene. In embodiments, $L^4$ is substituted or unsubstituted $C_6$ cycloalkylene. In embodiments, $L^4$ is substituted or unsubstituted $C_5$ cycloalkylene. In embodiments, $L^4$ is substituted cycloalkylene (e.g., $C_3$-$C_8$ cycloalkylene, $C_3$-$C_6$ cycloalkylene, or $C_5$-$C_6$ cycloalkylene). In embodiments, $L^4$ is substituted $C_3$-$C_8$ cycloalkylene. In embodiments, $L^4$ is substituted $C_3$-$C_6$ cycloalkylene. In embodiments, $L^4$ is substituted $C_5$-$C_6$ cycloalkylene. In embodiments, $L^4$ is substituted $C_6$ cycloalkylene. In embodiments, $L^4$ is substituted $C_5$ cycloalkylene. In embodiments, $L^4$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is an unsubstituted $C_3$-$C_8$ cycloalkylene. In embodiments, $L^4$ is an unsubstituted $C_3$-$C_6$ cycloalkylene. In embodiments, $L^4$ is an unsubstituted $C_5$-$C_6$ cycloalkylene. In embodiments, $L^4$ is an unsubstituted $C_6$ cycloalkylene. In embodiments, $L^4$ is an unsubstituted $C_5$ cycloalkylene.

In embodiments, $L^4$ is substituted or unsubstituted aziridinylene, substituted or unsubstituted oziranylene, substituted or unsubstituted thiiranylene, substituted or unsubstituted azetidinylene, substituted or unsubstituted 1,2-dihydroazotylene, substituted or unsubstituted oxetanylene, substituted or unsubstituted 2H-oxetylene, substituted or unsubstituted thietanylene, substituted or unsubstituted 2H-thietylene, substituted or unsubstituted pyrrolidinylene, substituted or unsubstituted 2,5-dihydro-1H-pyrrolylene, substituted or unsubstituted 4,5-dihydro-1H-imidazolylene, substituted or unsubstituted imidazolinylene, substituted or unsubstituted pyrazolinylene, substituted or unsubstituted tetrahydrofuranylene, substituted or unsubstituted thiolanylene, substituted or unsubstituted piperidinylene, substituted or unsubstituted piperazinylene, substituted or unsubstituted 2H-pyranylene, substituted or unsubstituted morpholinylene, substituted or unsubstituted 1,4-dioxanylene, substituted or unsubstituted tetrahydro-2H-pyranylene, substituted or unsubstituted thianylene, or substituted or unsubstituted dithianylene. In embodiments, $L^4$ is substituted aziridinylene, substituted oziranylene, substituted thiiranylene, substituted azetidinylene, substituted 1,2-dihydroazotylene, substituted oxetanylene, substituted 2H-oxetylene, substituted thietanylene, substituted 2H-thietylene, substituted pyrrolidinylene, substituted 2,5-dihydro-1H-pyrrolylene, substituted 4,5-dihydro-1H-imidazolylene, substituted imidazolinylene, substituted pyrazolinylene, substituted tetrahydrofuranylene, substituted thiolanylene, substituted piperidinylene, substituted piperazinylene, substituted 2H-pyranylene, substituted morpholinylene, substituted 1,4-dioxanylene, substituted tetrahydro-2H-pyranylene, substituted thianylene, or substituted dithianylene. In embodiments, $L^4$ is an unsubstituted aziridinylene, an unsubstituted oziranylene, an unsubstituted thiiranylene, an unsubstituted azetidinylene, an unsubstituted 1,2-dihydroazotylene, an unsubstituted oxetanylene, an unsubstituted 2H-oxetylene, an unsubstituted thietanylene, an unsubstituted 2H-thietylene, an unsubstituted pyrrolidinylene, an unsubstituted 2,5-dihydro-1H-pyrrolylene, an unsubstituted 4,5-dihydro-1H-imidazolylene, an unsubstituted imidazolinylene, an unsubstituted pyrazolinylene, an unsubstituted tetrahydrofuranylene, an unsubstituted thiolanylene, an unsubstituted piperidinylene, an unsubstituted piperazinylene, an unsubstituted 2H-pyranylene, an unsubstituted morpholinylene, an unsubstituted 1,4-dioxanylene, an unsubstituted tetrahydro-2H-pyranylene, an unsubstituted thianylene, or an unsubstituted dithianylene.

In embodiments, $L^4$ is substituted or unsubstituted ($C_6$-$C_{10}$) arylene. In embodiments, $L^4$ is substituted or unsubstituted phenylene. In embodiments, $L^4$ is substituted or unsubstituted naphthylene. In embodiments, $L^4$ is substituted ($C_6$-$C_{10}$) arylene. In embodiments, $L^4$ is substituted phenylene. In embodiments, $L^4$ is substituted naphthylene. In embodiments, $L^4$ is an unsubstituted ($C_6$-$C_{10}$) arylene. In embodiments, $L^4$ is an unsubstituted phenylene. In embodiments, $L^4$ is an unsubstituted naphthylene.

In embodiments, $L^4$ is substituted or unsubstituted imidazolylene, substituted or unsubstituted pyrrolylene, substituted or unsubstituted pyrazolylene, substituted or unsubstituted triazolylene, substituted or unsubstituted tetrazolylene, substituted or unsubstituted furanylene, substituted or unsubstituted oxazolylene, substituted or unsubstituted isooxazolylene, substituted or unsubstituted oxadiazolylene, substituted or unsubstituted oxatriazolylene, substituted or unsubstituted thienylene, substituted or unsubstituted thiazolylene, substituted or unsubstituted isothiazolylene, substituted or unsubstituted pyridinylene, substituted or unsubstituted pyrazinylene, substituted or unsubstituted pyrimidinylene, substituted or unsubstituted pyridazinylene, substituted or unsubstituted triazinylene (e.g., 1,3,5-triazinylene, 1,2,3-triazinylene, or 1,2,4-triazinylene). In embodiments, $L^4$ is substituted imidazolylene, substituted pyrrolylene, substituted pyrazolylene, substituted triazolylene, substituted tetrazolylene, substituted furanylene, substituted oxazolylene, substituted isooxazolylene, substituted oxadiazolylene, substituted oxatriazolylene, substituted thienylene, substituted thiazolylene, substituted isothiazolylene, substituted pyridinylene, substituted pyrazinylene, substituted pyrimidinylene, substituted pyridazinylene, or substituted triazinylene (e.g., 1,3,5-triazinylene, 1,2,3-triazinylene, or 1,2,4-triazinylene). In embodiments, $L^4$ is an unsubstituted imidazolylene, an unsubstituted pyrrolylene, an unsubstituted pyrazolylene, an unsubstituted triazolylene, an unsubstituted tetrazolylene, an unsubstituted furanylene, an unsubstituted oxazolylene, an unsubstituted isooxazolylene, an unsubstituted oxadiazolylene, an unsubstituted oxatriazolylene, an unsubstituted thienylene, an unsubstituted thiazolylene, an unsubstituted isothiazolylene, an unsubstituted pyridinylene, an unsubstituted pyrazinylene, an unsubstituted pyrimidinylene, an unsubstituted pyridazinylene, or an unsubstituted triazinylene (e.g., 1,3,5-triazinylene, 1,2,3-triazinylene, or 1,2,4-triazinylene).

In embodiments, $L^4$ is a bond, —NH—,

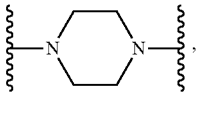, 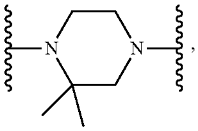,

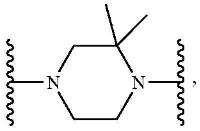, 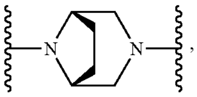,

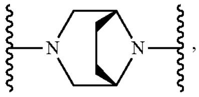, 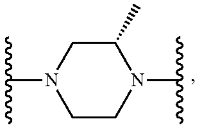,

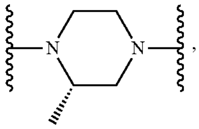, 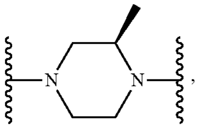,

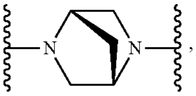, 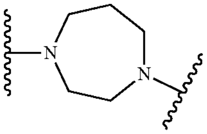,

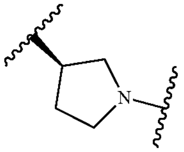, 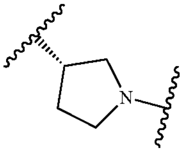,

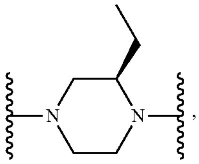, 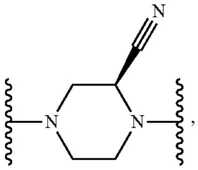,

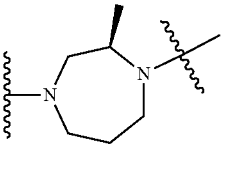, 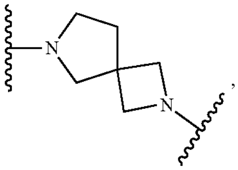,

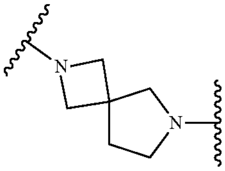, 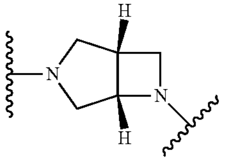,

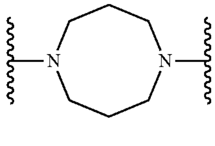, 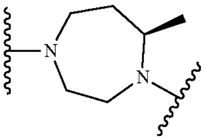,

-continued
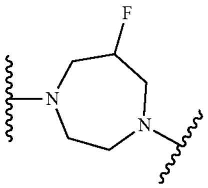, or 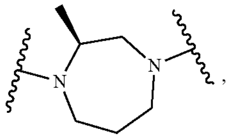,
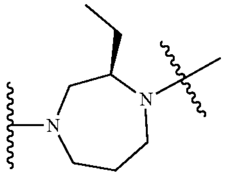,
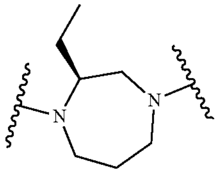, 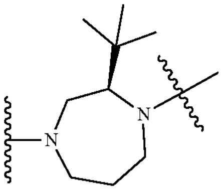,
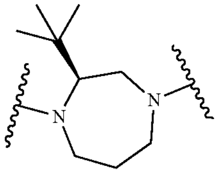, 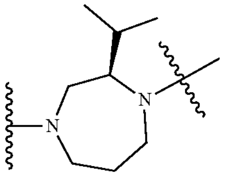,
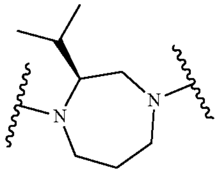, 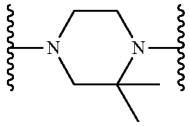,
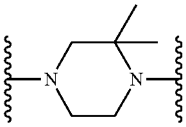, 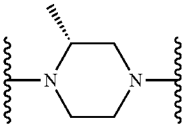,
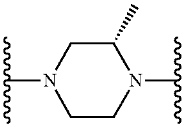, 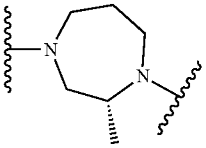, or
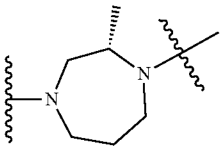.
In embodiments, $L^4$ is a bond, —NH—,
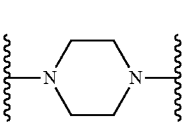, 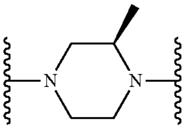,
-continued
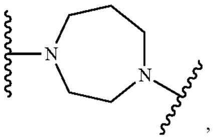, 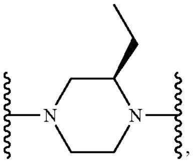,
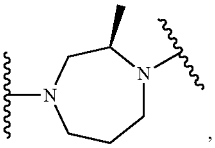, 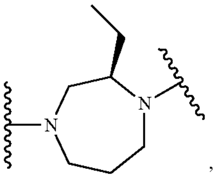,
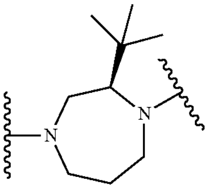, or 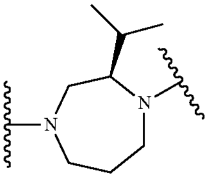.
In embodiments, $L^4$ is a bond. In embodiments, $L^4$ is —NH—. In embodiments, $L^4$ is
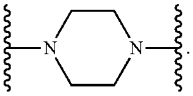.
In embodiments, $L^4$ is
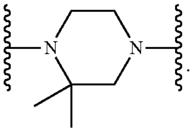 [SMILES: *N1CCN(*)C(C)(C)C1].
In embodiments, $L^4$ is
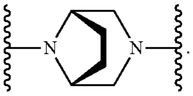.
In embodiments, $L^4$ is
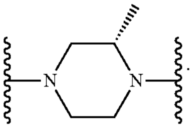 [SMILES: *N1CCN(*)[C@@H](C)C1].
In embodiments, $L^4$ is
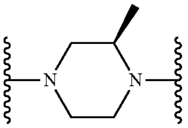.

In embodiments, $L^4$ is
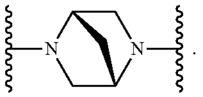 [SMILES: *N1C[C@@H]2C[C@H]1CN2*]
In embodiments, $L^4$ is
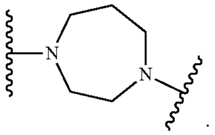 [SMILES: *N1CCCN(*)CC1]
In embodiments, $L^4$ is
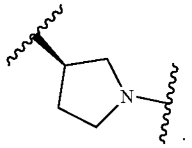 [SMILES: *[C@@H]1CCN(*)C1]
In embodiments, $L^4$ is
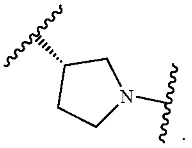 [SMILES: *[C@H]1CCN(*)C1]
In embodiments, $L^4$ is
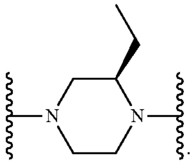 [SMILES: *N1CCN(*)[C@H](CC)C1]
In embodiments $L^4$ is
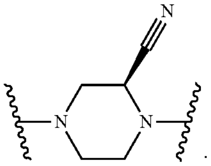 [SMILES: *N1CCN(*)[C@H](C#N)C1]
In embodiments $L^4$ is
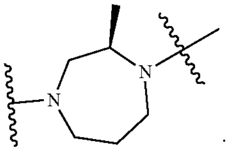 [SMILES: *N1CCCN(*)[C@H](C)C1]
In embodiments, $L^4$ is
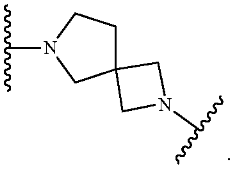 [SMILES: *N1CCC2(C1)CN(*)C2]
In embodiments, $L^4$ is
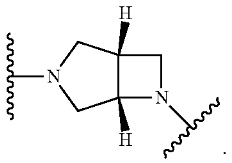 [SMILES: *N1C[C@@H]2CN(*)[C@@H]2C1]
In embodiments, $L^4$ is
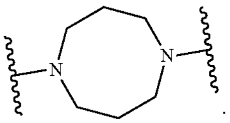 [SMILES: *N1CCCN(*)CCC1]
In embodiments, $L^4$ is
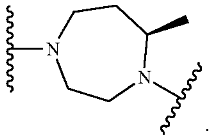 [SMILES: *N1CC[C@@H](C)N(*)CC1]
In embodiments, $L^4$ is
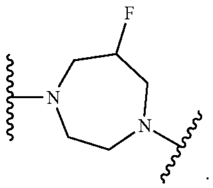 [SMILES: *N1CCN(*)CC(F)C1]

In embodiments, $L^4$ is
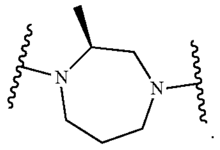 [SMILES: *N1CCCN(*)[C@@H](C)C1]
In embodiments, $L^4$ is
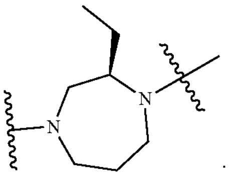 [SMILES: *N1CCCN(*)[C@H](CC)C1]
In embodiments, $L^4$ is
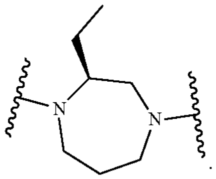 [SMILES: *N1CCCN(*)[C@@H](CC)C1]
In embodiments, $L^4$ is
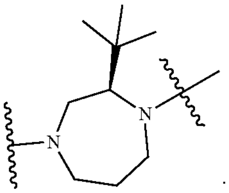 [SMILES: *N1CCCN(*)[C@H](C(C)(C)C)C1]
In embodiments, $L^4$ is.
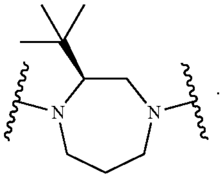 [SMILES: *N1CCCN(*)[C@@H](C(C)(C)C)C1]
In embodiments, $L^4$ is
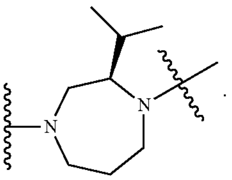 [SMILES: *N1CCCN(*)[C@H](C(C)C)C1]
In embodiments, $L^4$ is
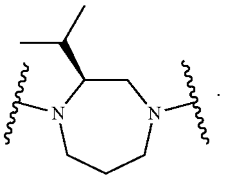 [SMILES: *N1CCCN(*)[C@@H](C(C)C)C1]
In embodiments, $L^4$ is
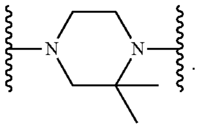
In embodiments, $L^4$ is
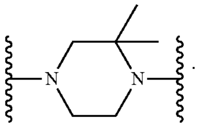 [SMILES: *N1CCN(*)C(C)(C)C1]
In embodiments, $L^4$ is
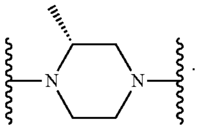 [SMILES: *N1CCN(*)[C@H](C)C1]
In embodiments, $L^4$ is
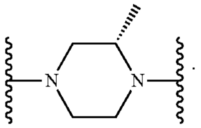 [SMILES: *N1CCN(*)[C@@H](C)C1]
In embodiments, $L^4$ is
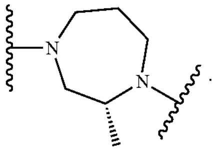 [SMILES: *N1CCCN(*)[C@H](C)C1]
In embodiments, $L^4$ is
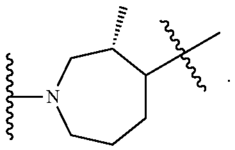 [SMILES: *C1CCCN(*)C[C@@H]1C]

In embodiments, $L^4$ is
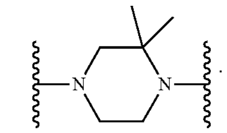 [SMILES: *N1CCN(*)C(C)(C)C1]
In embodiments, $L^4$ is
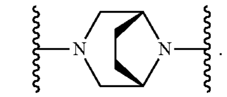 [SMILES: *N1C[C@H]2CC[C@@H](C1)N2*]
In embodiments, $L^4$ is
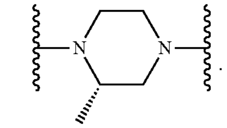 [SMILES: *N1CCN(*)[C@@H](C)C1]
In embodiments, $L^4$ is
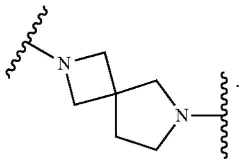 [SMILES: *N1CCC2(C1)CN(*)C2]
In embodiments, $L^4$ is
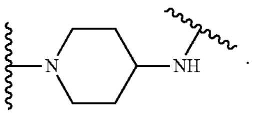 [SMILES: *NC1CCN(*)CC1]
In embodiments, $L^4$ is
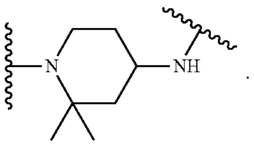 [SMILES: *NC1CCN(*)C(C)(C)C1]
In embodiments, $L^4$ is
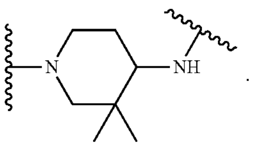 [SMILES: *NC1CCN(*)CC1(C)C]
In embodiments, $L^4$ is
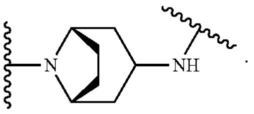 [SMILES: *NC1C[C@H]2CC[C@@H](C1)N2*]
In embodiments, $L^4$ is
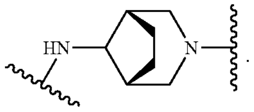 [SMILES: *NC1[C@@H]2CC[C@H]1CN(*)C2]
In embodiments, $L^4$ is
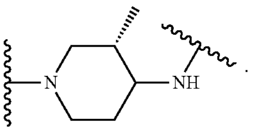 [SMILES: *NC1CCN(*)C[C@@H]1C]
In embodiments, $L^4$ is
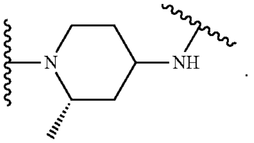 [SMILES: *NC1CCN(*)[C@@H](C)C1]
In embodiments, $L^4$ is
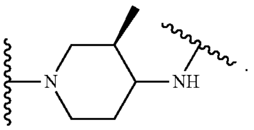 [SMILES: *NC1CCN(*)C[C@H]1C]
In embodiments, $L^4$ is
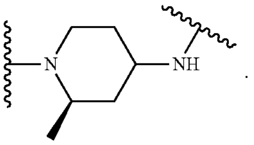 [SMILES: *NC1CCN(*)[C@H](C)C1]
In embodiments, $L^4$ is
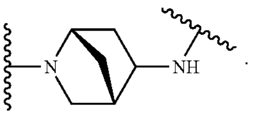 [SMILES: *NC1C[C@@H]2C[C@H]1CN2*]

In embodiments, $L^4$ is
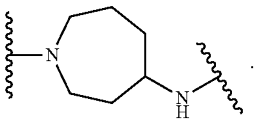 [SMILES: *NC1CCCN(*)CC1]
In embodiments, $L^4$ is
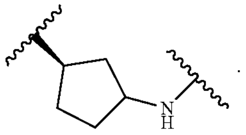 [SMILES: *NC1CC[C@@H](*)C1]
In embodiments, $L^4$ is
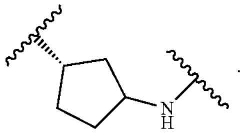 [SMILES: *NC1CC[C@H](*)C1]
In embodiments, $L^4$ is
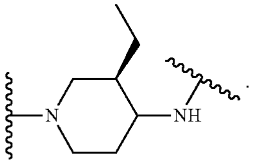 [SMILES: *NC1CCN(*)C[C@H]1CC]
In embodiments, $L^4$ is
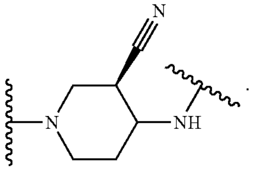 [SMILES: *NC1CCN(*)C[C@H]1C#N]
In embodiments, $L^4$ is
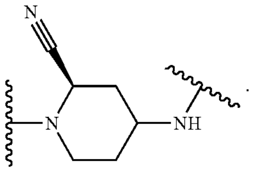 [SMILES: *NC1CCN(*)[C@@H](C#N)C1]
In embodiments, $L^4$ is
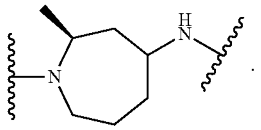 [SMILES: *NC1CCCN(*)[C@@H](C)C1]
In embodiments, $L^4$ is
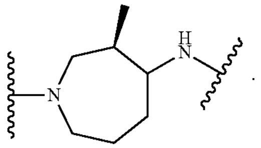 [SMILES: *NC1CCCN(*)C[C@H]1C]
In embodiments, $L^4$ is
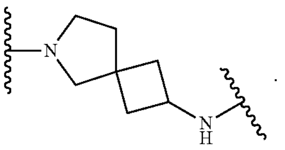 [SMILES: *NC1CC2(CCN(*)C2)C1]
In embodiments, $L^4$ is
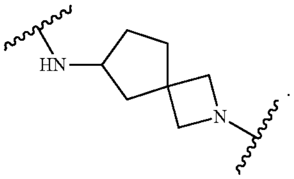 [SMILES: *NC1CCC2(C1)CN(*)C2]
In embodiments, $L^4$ is
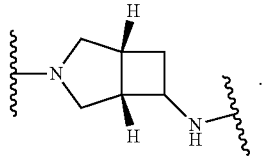 [SMILES: *NC1C[C@H]2CN(*)C[C@@H]12]
In embodiments, $L^4$ is
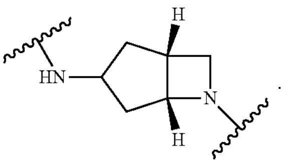 [SMILES: *NC1C[C@@H]2CN(*)[C@@H]2C1]

In embodiments, $L^4$ is
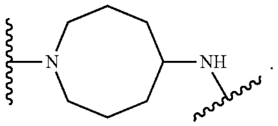 [SMILES: *NC1CCCN(*)CCC1]
In embodiments, $L^4$ is
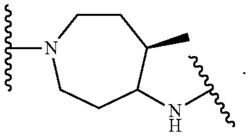 [SMILES: *NC1CCN(*)CC[C@H]1C]
In embodiments, $L^4$ is
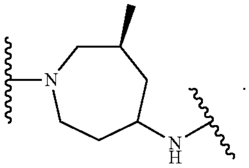 [SMILES: *NC1CCN(*)C[C@@H](C)C1]
In embodiments, $L^4$ is
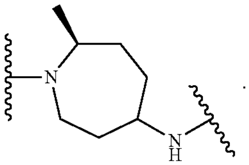 [SMILES: *NC1CC[C@H](C)N(*)CC1]
In embodiments, $L^4$ is
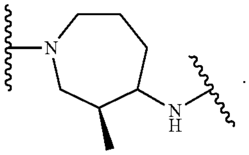 [SMILES: *NC1CCCN(*)C[C@@H]1C]
In embodiments, $L^4$ is
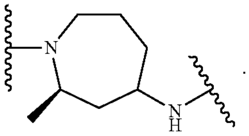 [SMILES: *NC1CCCN(*)[C@H](C)C1]
In embodiments, $L^4$ is
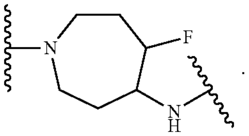 [SMILES: *NC1CCN(*)CCC1F]
In embodiments, $L^4$ is
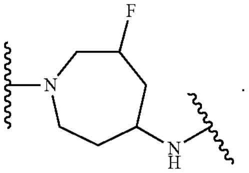 [SMILES: *NC1CCN(*)CC(F)C1]
In embodiments, $L^4$ is
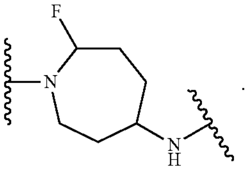 [SMILES: *NC1CCC(F)N(*)CC1]
In embodiments, $L^4$ is
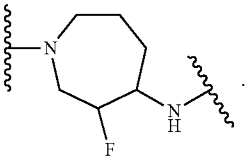 [SMILES: *NC1CCCN(*)CC1F]
In embodiments, $L^4$ is
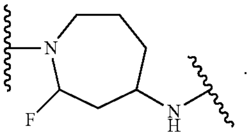 [SMILES: *NC1CCCN(*)C(F)C1]
In embodiments, $L^4$ is
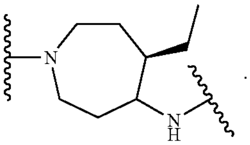 [SMILES: *NC1CCN(*)CC[C@H]1CC]

In embodiments, $L^4$ is
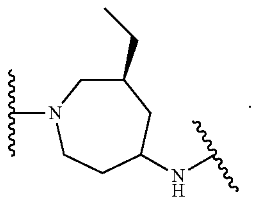 [SMILES: *NC1CCN(*)C[C@@H](CC)C1]
In embodiments, $L^4$ is
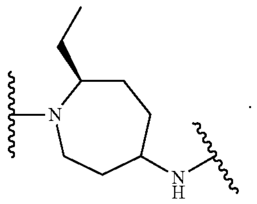 [SMILES: *NC1CC[C@H](CC)N(*)CC1]
In embodiments, $L^4$ is
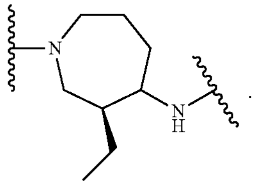 [SMILES: *NC1CCCN(*)C[C@@H]1CC]
In embodiments, $L^4$ is
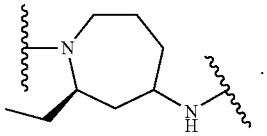 [SMILES: *NC1CCCN(*)[C@H](CC)C1]
In embodiments, $L^4$ is
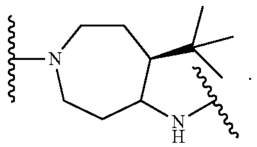 [SMILES: *NC1CCN(*)CC[C@H]1C(C)(C)C]
In embodiments, $L^4$ is
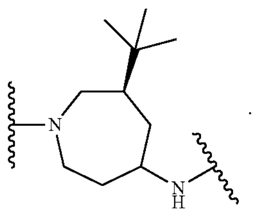 [SMILES: *NC1CCN(*)C[C@@H](C(C)(C)C)C1]
In embodiments, $L^4$ is
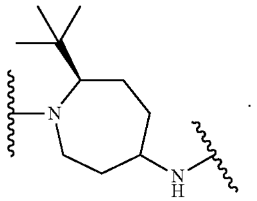 [SMILES: *NC1CC[C@H](C(C)(C)C)N(*)CC1]
In embodiments, $L^4$ is
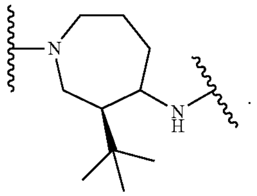 [SMILES: *NC1CCCN(*)C[C@@H]1C(C)(C)C]
In embodiments, $L^4$ is
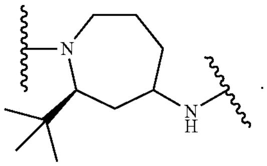 [SMILES: *NC1CCCN(*)[C@H](C(C)(C)C)C1]
In embodiments, $L^4$ is
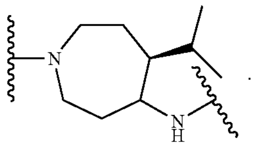 [SMILES: *NC1CCN(*)CC[C@H]1C(C)C]
In embodiments, $L^4$ is
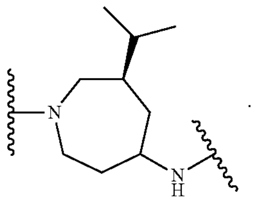 [SMILES: *NC1CCN(*)C[C@@H](C(C)C)C1]
In embodiments, $L^4$ is
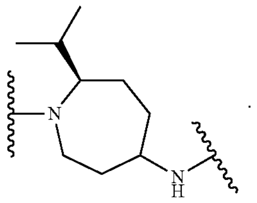 [SMILES: *NC1CC[C@H](C(C)C)N(*)CC1]

In embodiments, $L^4$ is

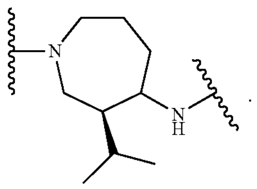 [SMILES: *NC1CCCN(*)C[C@@H]1C(C)C]

In embodiments, $L^4$ is

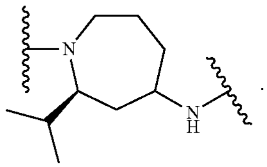 [SMILES: *NC1CCCN(*)[C@H](C(C)C)C1]

In embodiments, $L^4$ is

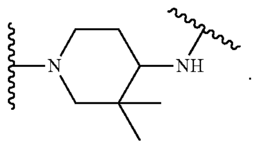 [SMILES: *NC1CCN(*)CC1(C)C]

In embodiments, $L^4$ is

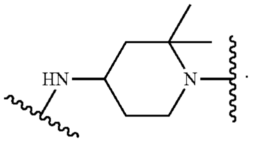 [SMILES: *NC1CCN(*)C(C)(C)C1]

In embodiments, $L^4$ is

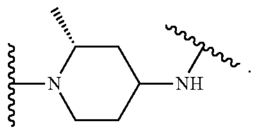

In embodiments, $L^4$ is

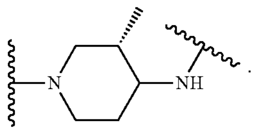

In embodiments, $L^4$ is

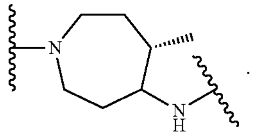 [SMILES: *NC1CCN(*)CC[C@@H]1C]

In embodiments, $L^4$ is H

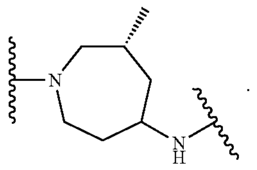 [SMILES: *NC1CCN(*)C[C@H](C)C1]

In embodiments, $L^4$ is

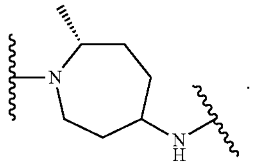 [SMILES: *NC1CC[C@@H](C)N(*)CC1]

In embodiments, $L^4$ is

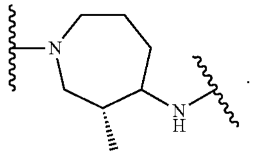 [SMILES: *NC1CCCN(*)C[C@H]1C]

In embodiments, $L^4$ is

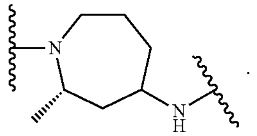

In embodiments, $L^4$ is independently substituted or unsubstituted alkylene (e.g., $C_1$-$C_8$, $C_1$-$C_6$, $C_1$-$C_4$, or $C_1$-$C_2$). In embodiments, $L^4$ is independently substituted alkylene (e.g., $C_1$-$C_8$, $C_1$-$C_6$, $C_1$-$C_4$, or $C_1$-$C_2$). In embodiments, $L^4$ is independently unsubstituted alkylene (e.g., $C_1$-$C_8$, $C_1$-$C_6$, $C_1$-$C_4$, or $C_1$-$C_2$). In embodiments, $L^4$ is independently unsubstituted methylene. In embodiments, $L^4$ is independently unsubstituted ethylene. In embodiments, $L^4$ is independently unsubstituted propylene. In embodiments, $L^4$ is independently unsubstituted isopropylene. In embodiments, $L^4$ is independently unsubstituted tert-butylene. In embodiments, $L^4$ is independently substituted or unsubstituted heteroalkylene (e.g., 2 to 8 membered, 2 to 6 membered, 4 to 6 membered, 2 to 3 membered, or 4 to 5 membered). In embodiments, $L^4$ is independently substituted heteroalkylene (e.g., 2 to 8 membered, 2 to 6 membered, 4 to 6 membered, 2 to 3 membered, or 4 to 5 membered). In embodiments, $L^4$ is independently unsubstituted heteroalkylene (e.g., 2 to 8 membered, 2 to 6 membered, 4 to 6 membered, 2 to 3 membered, or 4 to 5 membered). In embodiments, $L^4$ is independently substituted or unsubstituted cycloalkylene (e.g., $C_3$-$C_8$, $C_3$-$C_6$, $C_4$-$C_6$, or $C_5$-$C_6$). In embodiments, $L^4$ is independently substituted cycloalkylene (e.g., $C_3$-$C_8$, $C_3$-$C_6$, $C_4$-$C_6$, or $C_5$-$C_6$). In embodiments, $L^4$ is independently unsubstituted cycloalkylene (e.g., $C_3$-$C_8$, $C_3$-$C_6$, $C_4$-$C_6$, or $C_5$-$C_6$). In embodiments, $L^4$ is independently substituted or unsubstituted heterocycloalkylene (e.g., 3 to 8 membered, 3 to 6 membered, 4 to 6 membered, 4 to 5 membered, or 5 to 6 membered). In embodiments, $L^4$ is independently substituted heterocycloalkylene (e.g., 3 to 8 membered, 3 to 6 membered, 4 to 6 membered, 4 to 5 membered, or 5 to 6 membered). In embodiments, $L^4$ is independently unsubstituted heterocycloalkylene (e.g., 3 to 8 membered, 3 to 6 membered, 4 to 6 membered, 4 to 5 membered, or 5 to 6 membered). In embodiments, $L^4$ is independently substituted or unsubstituted arylene (e.g., $C_6$-$C_{10}$ or phenylene). In embodiments, $L^4$ is independently substituted arylene (e.g., $C_6$-$C_{10}$ or phenylene). In embodiments, $L^4$ is independently unsubstituted arylene (e.g., $C_6$-$C_{10}$ or phenylene). In embodiments, $L^4$ is independently substituted or unsubstituted heteroarylene (e.g., 5 to 10 membered, 5 to 9 membered, or 5 to 6 membered). In embodiments, $L^4$ is independently substituted heteroarylene (e.g., 5 to 10 membered, 5 to 9 membered, or 5 to 6 membered). In embodiments, $L^4$ is independently unsubstituted heteroarylene (e.g., 5 to 10 membered, 5 to 9 membered, or 5 to 6 membered).

In embodiments, $L^4$ is independently bond, —$S(O)_2$—, —$N(R^7)$—, —O—, —S—, —C(O)—, —$C(O)N(R^7)$—, —$N(R^7)C(O)$—, —$N(R^7)C(O)NH$—, —$NHC(O)N(R^7)$—, —C(O)O—, —OC(O)—, $R^{47}$-substituted or unsubstituted alkylene (e.g., $C_1$-$C_8$, $C_1$-$C_6$, $C_1$-$C_4$, or $C_1$-$C_2$), $R^{47}$-substituted or unsubstituted heteroalkylene (e.g., 2 to 8 membered, 2 to 6 membered, 4 to 6 membered, 2 to 3 membered, or 4 to 5 membered), $R^{47}$-substituted or unsubstituted cycloalkylene (e.g., $C_3$-$C_8$, $C_3$-$C_6$, $C_4$-$C_6$, or $C_5$-$C_6$), $R^{47}$-substituted or unsubstituted heterocycloalkylene (e.g., 3 to 8 membered, 3 to 6 membered, 4 to 6 membered, 4 to 5 membered, or 5 to 6 membered), $R^{47}$-substituted or unsubstituted arylene (e.g., $C_6$-$C_{10}$ or phenylene), or $R^{47}$-substituted or unsubstituted heteroarylene (e.g., 5 to 10 membered, 5 to 9 membered, or 5 to 6 membered). In embodiments, $L^4$ is independently bond, —$S(O)_2$—, —$N(R^7)$—, —O—, —S—, —C(O)—, —$C(O)N(R^7)$—, —$N(R^7)C(O)$—, —$N(R^7)C(O)NH$—, —$NHC(O)N(R^7)$—, —C(O)O—, —OC(O)—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 8 membered, 3 to 6 membered, 4 to 6 membered, 4 to 5 membered, or 5 to 6 membered), unsubstituted arylene (e.g., $C_6$-$C_{10}$ or phenylene), or unsubstituted heteroarylene (e.g., 5 to 10 membered, 5 to 9 membered, or 5 to 6 membered). In embodiments, $L^4$ is independently unsubstituted piperazinyl. In embodiments, $L^4$ is independently unsubstituted 1,4-diazepanyl. In embodiments, $L^4$ is independently methyl-substituted piperazinyl. In embodiments, $L^4$ is independently methyl-substituted 1,4-diazepanyl.

$R^{47}$ is independently oxo, halogen, —$CX^{47}_3$, —$CHX^{47}_2$, —$CH_2X^{47}$, —$OCX^{47}_3$, —$OCH_2X^{47}$, —$OCHX^{47}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{48}$-substituted or unsubstituted alkyl (e.g., $C_1$-$C_8$, $C_1$-$C_6$, $C_1$-$C_4$, or $C_1$-$C_2$), $R^{48}$-substituted or unsubstituted heteroalkyl (e.g., 2 to 8 membered, 2 to 6 membered, 4 to 6 membered, 2 to 3 membered, or 4 to 5 membered), $R^{48}$-substituted or unsubstituted cycloalkyl (e.g., $C_3$-$C_8$, $C_3$-$C_6$, $C_4$-$C_6$, or $C_5$-$C_6$), $R^{48}$-substituted or unsubstituted heterocycloalkyl (e.g., 3 to 8 membered, 3 to 6 membered, 4 to 6 membered, 4 to 5 membered, or 5 to 6 membered), $R^{48}$-substituted or unsubstituted aryl (e.g., $C_6$-$C_{10}$ or phenyl), or $R^{48}$-substituted or unsubstituted heteroaryl (e.g., 5 to 10 membered, 5 to 9 membered, or 5 to 6 membered). In embodiments, $R^{47}$ is independently oxo, halogen, —$CX^{47}_3$, —$CHX^{47}_2$, —$CH_2X^{47}$, —$OCX^{47}_3$, —$OCH_2X^{47}$, —$OCHX^{47}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{47}$ is independently —F, —Cl, —Br, or —I. In embodiments, $R^{47}$ is independently unsubstituted methyl. In embodiments, $R^{47}$ is independently unsubstituted ethyl. In embodiments, $R^{47}$ is $R^{48}$-substituted or unsubstituted methyl. In embodiments, $R^{47}$ is $R^{48}$-substituted or unsubstituted $C_2$ alkyl. In embodiments, $R^{47}$ is $R^{48}$-substituted or unsubstituted $C_3$ alkyl. In embodiments, $R^{47}$ is $R^{48}$-substituted or unsubstituted $C_4$ alkyl. In embodiments, $R^{47}$ is $R^{48}$-substituted or unsubstituted $C_5$ alkyl. In embodiments, $R^{47}$ is $R^{48}$-substituted or unsubstituted $C_6$ alkyl. In embodiments, $R^{47}$ is $R^{48}$-substituted or unsubstituted $C_7$ alkyl. In embodiments, $R^{47}$ is $R^{48}$-substituted or unsubstituted $C_8$ alkyl. In embodiments, $R^{47}$ is $R^{48}$-substituted methyl. In embodiments, $R^{47}$ is $R^{48}$-substituted $C_2$ alkyl. In embodiments, $R^{47}$ is $R^{48}$-substituted $C_3$ alkyl. In embodiments, $R^{47}$ is $R^{48}$-substituted $C_4$ alkyl. In embodiments, $R^{47}$ is $R^{48}$-substituted $C_5$ alkyl. In embodiments, $R^{47}$ is $R^{48}$-substituted $C_6$ alkyl. In embodiments, $R^{47}$ is $R^{48}$-substituted $C_7$ alkyl. In embodiments, $R^{47}$ is $R^{48}$-substituted $C_8$ alkyl. In embodiments, $R^{47}$ is an unsubstituted methyl. In embodiments, $R^{47}$ is an unsubstituted $C_2$ alkyl. In embodiments, $R^{47}$ is an unsubstituted $C_3$ alkyl. In embodiments, $R^{47}$ is an unsubstituted $C_4$ alkyl. In embodiments, $R^{47}$ is an unsubstituted $C_5$ alkyl. In embodiments, $R^{47}$ is an unsubstituted $C_6$ alkyl. In embodiments, $R^{47}$ is an unsubstituted $C_7$ alkyl. In embodiments, $R^{47}$ is an unsubstituted $C_8$ alkyl.

$R^{48}$ is independently oxo, halogen, —$CX^{48}_3$, —$CHX^{48}_2$, —$CH_2X^{48}$, —$OCX^{48}_3$, —$OCH_2X^{48}$, —$OCHX^{48}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{49}$-substituted or unsubstituted alkyl (e.g., $C_1$-$C_8$, $C_1$-$C_6$, $C_1$-$C_4$, or $C_1$-$C_2$), $R^{49}$-substituted or unsubstituted heteroalkyl (e.g., 2 to 8 membered, 2 to 6 membered, 4 to 6 membered, 2 to 3 membered, or 4 to 5 membered), $R^{49}$-substituted or unsubstituted cycloalkyl (e.g., $C_3$-$C_8$, $C_3$-$C_6$, $C_4$-$C_6$, or $C_5$-$C_6$), $R^{49}$-substituted or unsubstituted heterocycloalkyl (e.g., 3 to 8 membered, 3 to 6 membered, 4 to 6 membered, 4 to 5 membered, or 5 to 6 membered), $R^{49}$-substituted or unsubstituted aryl (e.g., $C_6$-$C_{10}$ or phenyl), or $R^{49}$-substituted or unsubstituted heteroaryl (e.g., 5 to 10 membered, 5 to 9 membered, or 5 to 6 membered). In embodiments, $R^{48}$ is independently oxo, halogen, $—CX^{48}_3$, $—CHX^{48}_2$, $—CH_2X^{48}$, $—OCX^{48}_3$, $—OCH_2X^{48}$, $—OCHX^{48}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)\ NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{48}$ is independently —F, —Cl, —Br, or —I. In embodiments, $R^{48}$ is independently unsubstituted methyl. In embodiments, $R^{48}$ is independently unsubstituted ethyl.

$R^{49}$ is independently oxo, halogen, $—CX^{49}_3$, $—CHX^{49}_2$, $—CH_2X^{49}$, $—OCX^{49}_3$, $—OCH_2X^{49}$, $—OCHX^{49}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{49}$ is independently —F, —Cl, —Br, or —I. In embodiments, $R^{49}$ is independently unsubstituted methyl. In embodiments, $R^{49}$ is independently unsubstituted ethyl.

In embodiments, X is —F. In embodiments, X is —Cl. In embodiments, X is —Br. In embodiments, X is —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, $X^4$ is —F. In embodiments, $X^4$ is —Cl. In embodiments, $X^4$ is —Br. In embodiments, $X^4$ is —I. In embodiments, $X^6$ is —F. In embodiments, $X^6$ is —Cl. In embodiments, $X^6$ is —Br. In embodiments, $X^6$ is —I. In embodiments, $X^7$ is —F. In embodiments, $X^7$ is —Cl. In embodiments, $X^7$ is —Br. In embodiments, $X^7$ is —I.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n4 is 0. In embodiments, n4 is 1. In embodiments, n4 is 2. In embodiments, n4 is 3. In embodiments, n4 is 4.

In embodiments, m1 is 1. In embodiments, m1 is 2. In embodiments, m2 is 1. In embodiments, m2 is 2. In embodiments, m3 is 1. In embodiments, m3 is 2. In embodiments, m4 is 1. In embodiments, m4 is 2.

In embodiments, v1 is 1. In embodiments, v1 is 2. In embodiments, v2 is 1. In embodiments, v2 is 2. In embodiments, v3 is 1. In embodiments, v3 is 2. In embodiments, v4 is 1. In embodiments, v4 is 2.

In embodiments, E is a covalent cysteine modifier moiety. In embodiments, E is:

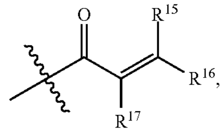,
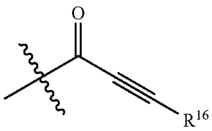,
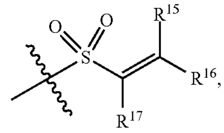,
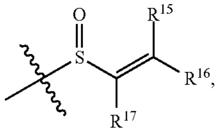,
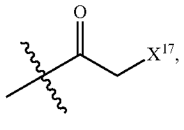, or
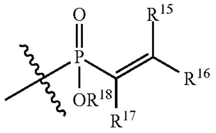.

$R^{15}$ is independently hydrogen, halogen, $—CX^{15}_3$, $—CHX^{15}_2$, $—CH_2X^{15}$, —CN, $—SO_{n15}R^{15D}$, $—SO_{v15}NR^{15A}R^{15B}$, $—NHNR^{15A}R^{15B}$, $—ONR^{15A}R^{15B}$, $—NHC{=}(O)NHNR^{15A}R^{15B}$, $—NHC(O)NR^{15A}R^{15B}$, $—N(O)_{m15}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—OCX^{15}_3$, $—OCHX^{15}_2$, $—OCH_2X^{15}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{16}$ is independently hydrogen, halogen, $—CX^{16}_3$, $—CHX^{16}_2$, $—CH_2X^{16}$, —CN, $—SO_{n16}R^{16D}$, $—SO_{v16}NR^{16A}R^{16B}$, $—NHNR^{16A}R^{16B}$, $—ONR^{16A}R^{16B}$, $—NHC{=}(O)NHNR^{16A}R^{16B}$, $—NHC(O)NR^{16A}R^{16B}$, $—N(O)_{m16}$, $—NR^{16A}R^{16B}$, $C(O)R^{16C}$, $—C(O)—OR^{16C}$, $—C(O)NR^{16A}R^{16B}$, $—OR^{16D}$, $—NR^{16A}SO_2R^{16D}$, $—NR^{16A}C(O)R^{16C}$, $—NR^{16A}C(O)OR^{16C}$, $—NR^{16A}OR^{16C}$, $—OCX^{16}_3$, $—OCHX^{16}_2$, $—OCH_2X^{16}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{17}$ is independently hydrogen, halogen, $—CX^{17}_3$, $—CHX^{17}_2$, $—CH_2X^{17}$, —CN, $—SO_{n17}R^{17D}$, $—SO_{v17}NR^{17A}R^{17B}$, $—NHNR^{17A}R^{17B}$, $—ONR^{17A}R^{17B}$, $—NHC{=}(O)NHNR^{17A}R^{17B}$, $—NHC(O)NR^{17A}R^{17B}$, $—N(O)_{m17}$, $—NR^{17A}R^{17B}$, $—C(O)R^{17C}$, $—C(O)—OR^{17C}$, $—C(O)NR^{17A}R^{17B}$, $—OR^{17D}$, $—NR^{17A}SO_2R^{17D}—$, $—NR^{17A}C(O)R^{17C}$, $—NR^{17A}C(O)OR^{17C}$, $—NR^{17A}OR^{17C}$, $—OCX^{17}_3$, $—OCHX^{17}_2$, $—OCH_2X^{17}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{18}$ is independently hydrogen, —$CX^{18}_3$, —$CHX^{18}_2$, —$CH_2X^{18}$, —C(O)$R^{18C}$, —C(O)O$R^{18C}$, —C(O)N$R^{18A}R^{18B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

Each $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, is independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); $R^{15A}$ and $R^{15B}$ substituents bonded to the same nitrogen atom may optionally be joined to form a substituted or unsubstituted heterocycloalkyl (e.g., 2 to 8 membered, 2 to 6 membered, 4 to 6 membered, 2 to 3 membered, or 4 to 5 membered) or substituted or unsubstituted heteroaryl (e.g., 5 to 10 membered, 5 to 9 membered, or 5 to 6 membered); $R^{16A}$ and $R^{16B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{17A}$ and $R^{17B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{18A}$ and $R^{18B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered). Each X, $X^{15}$, $X^{16}$, $X^{17}$ and $X^{18}$ is independently —F, —Cl, —Br, or —I. The symbols n15, n16, n17, v15, v16, and v17, are each independently an integer from 0 to 4. The symbols m15, m16, and m17 are independently 1 or 2.

In embodiments, E is:

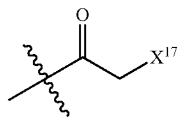

and $X^{17}$ is —Cl. In embodiments, E is:

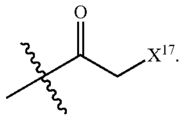

In embodiments, $X^{17}$ is —Cl.

In embodiments, E is:

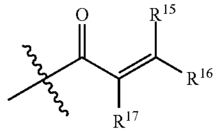

and $R^{15}$, $R^{16}$, and $R^{17}$ are independently hydrogen. In embodiments, E is:

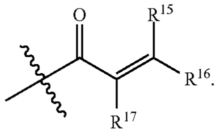

In embodiments, $R^{15}$, $R^{16}$, and $R^{17}$ are independently hydrogen.

In embodiments, E is:

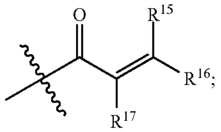

$R^{15}$ is independently hydrogen; $R^{16}$ is independently hydrogen or —$CH_2NR^{16A}R^{16B}$; $R^{17}$ is independently hydrogen; and $R^{16A}$ and $R^{16B}$ are independently hydrogen or unsubstituted alkyl. In embodiments, E is:

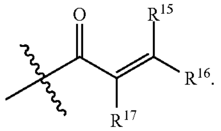

In embodiments, $R^{15}$ is independently hydrogen. In embodiments, $R^{16}$ is independently hydrogen or —$CH_2NR^{16A}R^{16B}$. In embodiments, $R^{17}$ is independently hydrogen. In embodiments, $R^{16A}$ and $R^{16B}$ are independently hydrogen or unsubstituted alkyl. In embodiments, $R^{16A}$ and $R^{16B}$ are independently unsubstituted methyl.

In embodiments, E is:

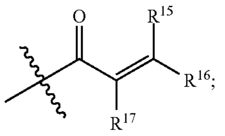

$R^{15}$ is independently hydrogen; $R^{17}$ is independently hydrogen or —$CH_2NR^{17A}R^{17B}$; $R^{16}$ is independently hydrogen; and $R^{17A}$ and $R^{17B}$ are independently hydrogen or unsubstituted alkyl. In embodiments, E is:

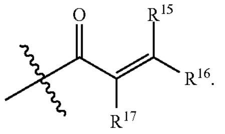

In embodiments, $R^{15}$ is independently hydrogen. In embodiments, $R^{17}$ is independently hydrogen or —$CH_2NR^{17A}R^{17B}$. In embodiments, $R^{16}$ is independently hydrogen. In embodiments, $R^{17A}$ and $R^{17B}$ are independently hydrogen or unsubstituted alkyl. In embodiments, $R^{17A}$ and $R^{17B}$ are independently unsubstituted methyl.

In embodiments, E is:

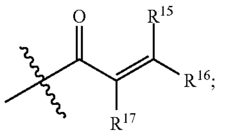

$R^{16}$ is independently hydrogen; $R^{15}$ is independently hydrogen or —$CH_2NR^{15A}R^{15B}$; $R^{17}$ is independently hydrogen; and $R^{15A}$ and $R^{15B}$ are independently hydrogen or unsubstituted alkyl. In embodiments, E is:

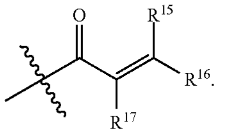

In embodiments, $R^{16}$ is independently hydrogen. In embodiments, $R^{15}$ is independently hydrogen or —$CH_2NR^{15A}R^{15B}$. In embodiments, $R^{17}$ is independently hydrogen. In embodiments, $R^{15A}$ and $R^{15B}$ are independently hydrogen or unsubstituted alkyl. In embodiments, $R^{15A}$ and $R^{15B}$ are independently unsubstituted methyl.

In embodiments, E is:

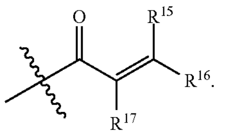

In embodiments, E is:

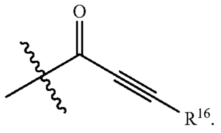

In embodiments, E is:

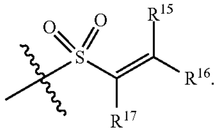

In embodiments, E is:

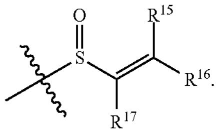

In embodiments, E is:

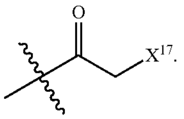

In embodiments, E is:

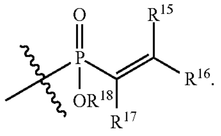

In embodiments, E is:

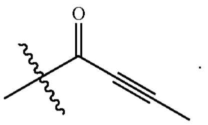 [SMILES: *C(=O)C#CC]

In embodiments, E is:

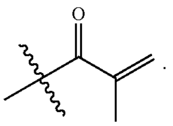 [SMILES: *C(=O)C(=C)C]

In embodiments, E is:

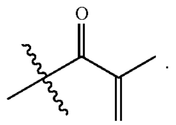 [SMILES: *C(=O)C(=C)C]

In embodiments, E is:

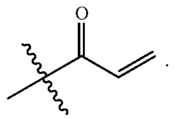 [SMILES: *C(=O)C=C]

In embodiments, E is:

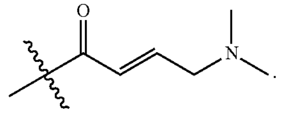 [SMILES: *C(=O)/C=C/CN(C)C]

In embodiments, E is:

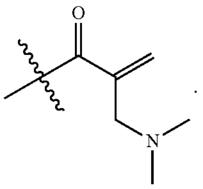 [SMILES: *C(=O)C(=C)CN(C)C]

X may independently be —F. X may independently be —Cl. X may independently be —Br. X may independently be —I. $X^{15}$ may independently be —F. $X^{15}$ may independently be —Cl. $X^{15}$ may independently be —Br. $X^{15}$ may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. n15 may independently be 0. n15 may independently be 1. n15 may independently be 2. n15 may independently be 3. n15 may independently be 4. n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. v15 may independently be 0. v15 may independently be 1. v15 may independently be 2. v15 may independently be 3. v15 may independently be 4. v16 may independently be 0. v16 may independently be 1. v16 may independently be 2. v16 may independently be 3. v16 may independently be 4. v17 may independently be 0. v17 may independently be 1. v17 may independently be 2. v17 may independently be 3. v17 may independently be 4. m15 may independently be 1. m15 may independently be 2. m16 may independently be 1. m16 may independently be 2. m17 may independently be 1. m17 may independently be 2.

In embodiments, $R^{15}$ is hydrogen. In embodiments, $R^{15}$ is halogen. In embodiments, $R^{15}$ is $—CX^{15}_3$. In embodiments, $R^{15}$ is $—CHX^{15}_2$. In embodiments, $R^{15}$ is $—CH_2X^{15}$. In embodiments, $R^{15}$ is —CN. In embodiments, $R^{15}$ is $—SO_{n15}R^{15}$. In embodiments, $R^{15}$ is $—SO_{v15}NR^{15A}R^{15B}$. In embodiments, $R^{15}$ is $—NHNR^{15A}R^{15B}$. In embodiments, $R^{15}$ is $—ONR^{15A}R^{15B}$. In embodiments, $R^{15}$ is $—NHC(O)NHNR^{15A}R^{15B}$. In embodiments, $R^{15}$ is $—NHC(O)NR^{15A}R^{15B}$. In embodiments, $R^{15}$ is $—N(O)_{m15}$. In embodiments, $R^{15}$ is $—NR^{15A}R^{15B}$. In embodiments, $R^{15}$ is $—C(O)R^{15C}$. In embodiments, $R^{15}$ is $—C(O)—OR^{15C}$. In embodiments, $R^{15}$ is $—C(O)NR^{15A}R^{15B}$. In embodiments, $R^{15}$ is $—OR^{15D}$. In embodiments, $R^{15}$ is $—NR^{15A}SO_2R^{15D}$. In embodiments, $R^{15}$ is $—NR^{15A}C(O)R^{15C}$. In embodiments, $R^{15}$ is $—NR^{15A}C(O)OR^{15C}$. In embodiments, $R^{15}$ is $—NR^{15A}OR^{15C}$. In embodiments, $R^{15}$ is $—OCX^{15}_3$. In embodiments, $R^{15}$ is $—OCHX^{15}_2$. In embodiments, $R^{15}$ is $—OCH_2X^{15}$. In embodiments, $R^{15}$ is independently —OH. In embodiments, $R^{15}$ is independently $—NH_2$. In embodiments, $R^{15}$ is independently —COOH. In embodiments, $R^{15}$ is independently $—CONH_2$. In embodiments, $R^{15}$ is independently $—NO_2$. In embodiments, $R^{15}$ is independently —SH. In embodiments, $R^{15}$ is independently $—CF_3$. In embodiments, $R^{15}$ is independently $—CHF_2$. In embodiments, $R^{15}$ is independently $—CH_2F$. In embodiments, $R^{15}$ is independently $—OCF_3$. In embodiments, $R^{15}$ is independently $—OCH_2F$. In embodiments, $R^{15}$ is independently $—OCHF_2$. In embodiments, $R^{15}$ is independently $—OCH_3$. In embodiments, $R^{15}$ is independently $—OCH_2CH_3$. In embodiments, $R^{15}$ is independently $—OCH_2CH_2CH_3$. In embodiments, $R^{15}$ is independently $—OCH(CH_3)_2$. In embodiments, $R^{15}$ is independently $—OC(CH_3)_3$. In embodiments, $R^{15}$ is independently $—SCH_3$. In embodiments, $R^{15}$ is independently $—SCH_2CH_3$. In embodiments, $R^{15}$ is independently $—SCH_2CH_2CH_3$. In embodiments, $R^{15}$ is independently $—SCH(CH_3)_2$. In embodiments, $R^{15}$ is independently $—SC(CH_3)_3$. In embodiments, $R^{15}$ is independently $—CH_3$. In embodiments, $R^{15}$ is independently $—CH_2CH_3$. In embodiments, $R^{15}$ is independently $—CH_2CH_2CH_3$. In embodiments, $R^{15}$ is independently $—CH(CH_3)_2$. In embodiments, $R^{15}$ is independently $—C(CH_3)_3$. In embodiments, $R^{15}$ is independently —F. In embodiments, $R^{15}$ is independently —Cl. In embodiments, $R^{15}$ is independently —Br. In embodiments, $R^{15}$ is independently —I.

In embodiments, $R^{15}$ is independently substituted or unsubstituted alkyl (e.g., $C_1$-$C_8$, $C_1$-$C_6$, $C_1$-$C_4$, or $C_1$-$C_2$). In embodiments, $R^{15}$ is independently substituted alkyl (e.g., $C_1$-$C_8$, $C_1$-$C_6$, $C_1$-$C_4$, or $C_1$-$C_2$). In embodiments, $R^{15}$ is independently unsubstituted alkyl (e.g., $C_1$-$C_8$, $C_1$-$C_6$, $C_1$-$C_4$, or $C_1$-$C_2$). In embodiments, $R^{15}$ is independently unsubstituted methyl. In embodiments, $R^{15}$ is independently unsubstituted ethyl. In embodiments, $R^{15}$ is independently unsubstituted propyl. In embodiments, $R^{15}$ is independently unsubstituted isopropyl. In embodiments, $R^{15}$ is independently unsubstituted tert-butyl. In embodiments, $R^{15}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15}$ is independently substituted heteroalkyl (e.g., 2 to 8 membered, 2 to 6 membered, 4 to 6 membered, 2 to 3 membered, or 4 to 5 membered). In embodiments, $R^{15}$ is independently unsubstituted heteroalkyl (e.g., 2 to 8 membered, 2 to 6 membered, 4 to 6 membered, 2 to 3 membered, or 4 to 5 membered). In embodiments, $R^{15}$ is independently substituted or unsubstituted cycloalkyl (e.g., $C_3$-$C_8$, $C_3$-$C_6$, $C_4$-$C_6$, or $C_5$-$C_6$). In embodiments, $R^{15}$ is independently substituted cycloalkyl (e.g., $C_3$-$C_8$, $C_3$-$C_6$, $C_4$-$C_6$, or $C_5$-$C_6$). In embodiments, $R^{15}$ is independently unsubstituted cycloalkyl (e.g., $C_3$-$C_8$, $C_3$-$C_6$, $C_4$-$C_6$, or $C_5$-$C_6$). In embodiments, $R^{15}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15}$ is independently substituted heterocycloalkyl (e.g., 3 to 8 membered, 3 to 6 membered, 4 to 6 membered, 4 to 5 membered, or 5 to 6 membered). In embodiments, $R^{15}$ is independently unsubstituted heterocycloalkyl (e.g., 3 to 8 membered, 3 to 6 membered, 4 to 6 membered, 4 to 5 membered, or 5 to 6 membered). In embodiments, $R^{15}$ is independently substituted or unsubstituted aryl (e.g., $C_6$-$C_{10}$ or phenyl). In embodiments, $R^{15}$ is independently substituted aryl (e.g., $C_6$-$C_{10}$ or phenyl). In embodiments, $R^{15}$ is independently unsubstituted aryl (e.g., $C_6$-$C_{10}$ or phenyl). In embodiments, $R^{15}$ is independently substituted or unsubstituted heteroaryl (e.g., 5 to 10 membered, 5 to 9 membered, or 5 to 6 membered). In embodiments, $R^{15}$ is independently substituted heteroaryl (e.g., 5 to 10 membered, 5 to 9 membered, or 5 to 6 membered). In embodiments, $R^{15}$ is independently unsubstituted heteroaryl (e.g., 5 to 10 membered, 5 to 9 membered, or 5 to 6 membered).

In embodiments, $R^{15A}$ is independently hydrogen. In embodiments, $R^{15A}$ is independently —$CX^{15A}_3$. In embodiments, $R^{15A}$ is independently —$CHX^{15A}_2$. In embodiments, $R^{15A}$ is independently —$CH_2X^{15A}$. In embodiments, $R^{15A}$ is independently —CN. In embodiments, $R^{15A}$ is independently —COOH. In embodiments, $R^{15A}$ is independently —$CONH_2$. In embodiments, $X^{15A}$ is independently —F, —Cl, —Br, or —I.

In embodiments, $R^{15A}$ is independently substituted or unsubstituted alkyl (e.g., $C_1$-$C_8$, $C_1$-$C_6$, $C_1$-$C_4$, or $C_1$-$C_2$). In embodiments, $R^{15A}$ is independently substituted alkyl (e.g., $C_1$-$C_8$, $C_1$-$C_6$, $C_1$-$C_4$, or $C_1$-$C_2$). In embodiments, $R^{15A}$ is independently unsubstituted alkyl (e.g., $C_1$-$C_8$, $C_1$-$C_6$, $C_1$-$C_4$, or $C_1$-$C_2$). In embodiments, $R^{15A}$ is independently unsubstituted methyl. In embodiments, $R^{15A}$ is independently unsubstituted ethyl. In embodiments, $R^{15A}$ is independently unsubstituted propyl. In embodiments, $R^{15A}$ is independently unsubstituted isopropyl. In embodiments, $R^{15A}$ is independently unsubstituted tert-butyl. In embodiments, $R^{15A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15A}$ is independently substituted heteroalkyl (e.g., 2 to 8 membered, 2 to 6 membered, 4 to 6 membered, 2 to 3 membered, or 4 to 5 membered). In embodiments, $R^{15A}$ is independently unsubstituted heteroalkyl (e.g., 2 to 8 membered, 2 to 6 membered, 4 to 6 membered, 2 to 3 membered, or 4 to 5 membered). In embodiments, $R^{15A}$ is independently substituted or unsubstituted cycloalkyl (e.g., $C_3$-$C_8$, $C_3$-$C_6$, $C_4$-$C_6$, or $C_5$-$C_6$). In embodiments, $R^{15A}$ is independently substituted cycloalkyl (e.g., $C_3$-$C_8$, $C_3$-$C_6$, $C_4$-$C_6$, or $C_5$-$C_6$). In embodiments, $R^{15A}$ is independently unsubstituted cycloalkyl (e.g., $C_3$-$C_8$, $C_3$-$C_6$, $C_4$-$C_6$, or $C_5$-$C_6$). In embodiments, $R^{15A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15A}$ is independently substituted heterocycloalkyl (e.g., 3 to 8 membered, 3 to 6 membered, 4 to 6 membered, 4 to 5 membered, or 5 to 6 membered). In embodiments, $R^{15A}$ is independently unsubstituted heterocycloalkyl (e.g., 3 to 8 membered, 3 to 6 membered, 4 to 6 membered, 4 to 5 membered, or 5 to 6 membered). In embodiments, $R^{15A}$ is independently substituted or unsubstituted aryl (e.g., $C_6$-$C_{10}$ or phenyl). In embodiments, $R^{15A}$ is independently substituted aryl (e.g., $C_6$-$C_{10}$ or phenyl). In embodiments, $R^{15A}$ is independently unsubstituted aryl (e.g., $C_6$-$C_{10}$ or phenyl). In embodiments, $R^{15A}$ is independently substituted or unsubstituted heteroaryl (e.g., 5 to 10 membered, 5 to 9 membered, or 5 to 6 membered). In embodiments, $R^{15A}$ is independently substituted heteroaryl (e.g., 5 to 10 membered, 5 to 9 membered, or 5 to 6 membered). In embodiments, $R^{15A}$ is independently unsubstituted heteroaryl (e.g., 5 to 10 membered, 5 to 9 membered, or 5 to 6 membered).

In embodiments, $R^{15B}$ is independently hydrogen. In embodiments, $R^{15B}$ is independently —$CX^{15B}_3$. In embodiments, $R^{15B}$ is independently —$CHX^{15B}_2$ In embodiments, $R^{15B}$ is independently —$CH_2X^{15B}$. In embodiments, $R^{15B}$ is independently —CN. In embodiments, $R^{15B}$ is independently —COOH. In embodiments, $R^{15B}$ is independently —$CONH_2$. In embodiments, $X^{15B}$ is independently —F, —Cl, —Br, or —I.

In embodiments, $R^{15B}$ is independently substituted or unsubstituted alkyl (e.g., $C_1$-$C_8$, $C_1$-$C_6$, $C_1$-$C_4$, or $C_1$-$C_2$). In embodiments, $R^{15B}$ is independently substituted alkyl (e.g., $C_1$-$C_8$, $C_1$-$C_6$, $C_1$-$C_4$, or $C_1$-$C_2$). In embodiments, $R^{15B}$ is independently unsubstituted alkyl (e.g., $C_1$-$C_8$, $C_1$-$C_6$, $C_1$-$C_4$, or $C_1$-$C_2$). In embodiments, $R^{15B}$ is independently unsubstituted methyl. In embodiments, $R^{15B}$ is independently unsubstituted ethyl. In embodiments, $R^{15B}$ is independently unsubstituted propyl. In embodiments, $R^{15B}$ is independently unsubstituted isopropyl. In embodiments, $R^{15B}$ is independently unsubstituted tert-butyl. In embodiments, $R^{15B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15B}$ is independently substituted heteroalkyl (e.g., 2 to 8 membered, 2 to 6 membered, 4 to 6 membered, 2 to 3 membered, or 4 to 5 membered). In embodiments, $R^{15B}$ is independently unsubstituted heteroalkyl (e.g., 2 to 8 membered, 2 to 6 membered, 4 to 6 membered, 2 to 3 membered, or 4 to 5 membered). In embodiments, $R^{15B}$ is independently substituted or unsubstituted cycloalkyl (e.g., $C_3$-$C_8$, $C_3$-$C_6$, $C_4$-$C_6$, or $C_5$-$C_6$). In embodiments, $R^{15B}$ is independently substituted cycloalkyl (e.g., $C_3$-$C_8$, $C_3$-$C_6$, $C_4$-$C_6$, or $C_5$-$C_6$). In embodiments, $R^{15B}$ is independently unsubstituted cycloalkyl (e.g., $C_3$-$C_8$, $C_3$-$C_6$, $C_4$-$C_6$, or $C_5$-$C_6$). In embodiments, $R^{15B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15B}$ is independently substituted heterocycloalkyl (e.g., 3 to 8 membered, 3 to 6 membered, 4 to 6 membered, 4 to 5 membered, or 5 to 6 membered). In embodiments, $R^{15B}$ is independently unsubstituted heterocycloalkyl (e.g., 3 to 8 membered, 3 to 6 membered, 4 to 6 membered, 4 to 5 membered, or 5 to 6 membered). In embodiments, $R^{15B}$ is independently substituted or unsubstituted aryl (e.g., $C_6$-$C_{10}$ or phenyl). In embodiments, $R^{15B}$ is independently substituted aryl (e.g., $C_6$-$C_{10}$ or phenyl). In embodiments, $R^{15B}$ is independently unsubstituted aryl (e.g., $C_6$-$C_{10}$ or phenyl). In embodiments, $R^{15B}$ is independently substituted or unsubstituted heteroaryl (e.g., 5 to 10 membered, 5 to 9 membered, or 5 to 6 membered). In embodiments, $R^{15B}$ is independently substituted heteroaryl (e.g., 5 to 10 membered, 5 to 9 membered, or 5 to 6 membered). In embodiments, $R^{15B}$ is independently unsubstituted heteroaryl (e.g., 5 to 10 membered, 5 to 9 membered, or 5 to 6 membered).

In embodiments, $R^{15A}$ and $R^{15B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{15A}$ and $R^{15B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{15A}$ and $R^{15B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{15A}$ and $R^{15B}$ substituents bonded to the same nitrogen atom may be joined to form a substituted or unsubstituted heteroaryl (e.g., 5 to 10 membered, 5 to 9 membered, or 5 to 6 membered). In embodiments, $R^{15A}$ and $R^{15B}$ substituents bonded to the same nitrogen atom may be joined to form a substituted heteroaryl (e.g., 5 to 10 membered, 5 to 9 membered, or 5 to 6 membered). In embodiments, $R^{15A}$ and $R^{15B}$ substituents bonded to the same nitrogen atom may be joined to form an unsubstituted heteroaryl (e.g., 5 to 10 membered, 5 to 9 membered, or 5 to 6 membered).

In embodiments, $R^{15C}$ is independently hydrogen. In embodiments, $R^{15C}$ is independently —$CX^{15C}_3$. In embodiments, $R^{15C}$ is independently —$CHX^{15C}_2$. In embodiments, $R^{15C}$ is independently —$CH_2X^{15C}$. In embodiments, $R^{15C}$ is independently —CN. In embodiments, $R^{15C}$ is independently —COOH. In embodiments, $R^{15C}$ is independently —$CONH_2$. In embodiments, $X^{15C}$ is independently —F, —Cl, —Br, or —I.

In embodiments, $R^{15C}$ is independently substituted or unsubstituted alkyl (e.g., $C_1$-$C_8$, $C_1$-$C_6$, $C_1$-$C_4$, or $C_1$-$C_2$). In embodiments, $R^{15C}$ is independently substituted alkyl (e.g., $C_1$-$C_8$, $C_1$-$C_6$, $C_1$-$C_4$, or $C_1$-$C_2$). In embodiments, $R^{15C}$ is independently unsubstituted alkyl (e.g., $C_1$-$C_8$, $C_1$-$C_6$, $C_1$-$C_4$, or $C_1$-$C_2$). In embodiments, $R^{15C}$ is independently unsubstituted methyl. In embodiments, $R^{15C}$ is independently unsubstituted ethyl. In embodiments, $R^{15C}$ is independently unsubstituted propyl. In embodiments, $R^{15C}$ is independently unsubstituted isopropyl. In embodiments, $R^{15C}$ is independently unsubstituted tert-butyl. In embodiments, $R^{15C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15C}$ is independently substituted heteroalkyl (e.g., 2 to 8 membered, 2 to 6 membered, 4 to 6 membered, 2 to 3 membered, or 4 to 5 membered). In embodiments, $R^{15C}$ is independently unsubstituted heteroalkyl (e.g., 2 to 8 membered, 2 to 6 membered, 4 to 6 membered, 2 to 3 membered, or 4 to 5 membered). In embodiments, $R^{15C}$ is independently substituted or unsubstituted cycloalkyl (e.g., $C_3$-$C_8$, $C_3$-$C_6$, $C_4$-$C_6$, or $C_5$-$C_6$). In embodiments, $R^{15C}$ is independently substituted cycloalkyl (e.g., $C_3$-$C_8$, $C_3$-$C_6$, $C_4$-$C_6$, or $C_5$-$C_6$). In embodiments, $R^{15C}$ is independently unsubstituted cycloalkyl (e.g., $C_3$-$C_8$, $C_3$-$C_6$, $C_4$-$C_6$, or $C_5$-$C_6$). In embodiments, $R^{15C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15C}$ is independently substituted heterocycloalkyl (e.g., 3 to 8 membered, 3 to 6 membered, 4 to 6 membered, 4 to 5 membered, or 5 to 6 membered). In embodiments, $R^{15C}$ is independently unsubstituted heterocycloalkyl (e.g., 3 to 8 membered, 3 to 6 membered, 4 to 6 membered, 4 to 5 membered, or 5 to 6 membered). In embodiments, $R^{15C}$ is independently substituted or unsubstituted aryl (e.g., $C_6$-$C_{10}$ or phenyl). In embodiments, $R^{15C}$ is independently substituted aryl (e.g., $C_6$-$C_{10}$ or phenyl). In embodiments, $R^{15C}$ is independently unsubstituted aryl (e.g., $C_6$-$C_{10}$ or phenyl). In embodiments, $R^{15C}$ is independently substituted or unsubstituted heteroaryl (e.g., 5 to 10 membered, 5 to 9 membered, or 5 to 6 membered). In embodiments, $R^{15C}$ is independently substituted heteroaryl (e.g., 5 to 10 membered, 5 to 9 membered, or 5 to 6 membered). In embodiments, $R^{15C}$ is independently unsubstituted heteroaryl (e.g., 5 to 10 membered, 5 to 9 membered, or 5 to 6 membered).

In embodiments, $R^{15D}$ is independently hydrogen. In embodiments, $R^{15D}$ is independently —$CX^{15D}_3$. In embodiments, $R^{15D}$ is independently —$CHX^{15D}_2$. In embodiments, $R^{15D}$ is independently —$CH_2X^{15D}$. In embodiments, $R^{15D}$ is independently —CN. In embodiments, $R^{15D}$ is independently —COOH. In embodiments, $R^{15D}$ is independently —$CONH_2$. In embodiments, $X^{15D}$ independently —F, —Cl, —Br, or —I.

In embodiments, $R^{15D}$ is independently substituted or unsubstituted alkyl (e.g., $C_1$-$C_8$, $C_1$-$C_6$, $C_1$-$C_4$, or $C_1$-$C_2$). In embodiments, $R^{15D}$ is independently substituted alkyl (e.g., $C_1$-$C_8$, $C_1$-$C_6$, $C_1$-$C_4$, or $C_1$-$C_2$). In embodiments, $R^{15D}$ is independently unsubstituted alkyl (e.g., $C_1$-$C_8$, $C_1$-$C_6$, $C_1$-$C_4$, or $C_1$-$C_2$). In embodiments, $R^{15D}$ is independently unsubstituted methyl. In embodiments, $R^{15D}$ is independently unsubstituted ethyl. In embodiments, $R^{15D}$ is independently unsubstituted propyl. In embodiments, $R^{15D}$ is independently unsubstituted isopropyl. In embodiments, $R^{15D}$ is independently unsubstituted tert-butyl. In embodiments, $R^{15D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15D}$ is independently substituted heteroalkyl (e.g., 2 to 8 membered, 2 to 6 membered, 4 to 6 membered, 2 to 3 membered, or 4 to 5 membered). In embodiments, $R^{15D}$ is independently unsubstituted heteroalkyl (e.g., 2 to 8 membered, 2 to 6 membered, 4 to 6 membered, 2 to 3 membered, or 4 to 5 membered). In embodiments, $R^{15D}$ is independently substituted or unsubstituted cycloalkyl (e.g., $C_3$-$C_8$, $C_3$-$C_6$, $C_4$-$C_6$, or $C_5$-$C_6$). In embodiments, $R^{15D}$ is independently substituted cycloalkyl (e.g., $C_3$-$C_8$, $C_3$-$C_6$, $C_4$-$C_6$, or $C_5$-$C_6$). In embodiments, $R^{15D}$ is independently unsubstituted cycloalkyl (e.g., $C_3$-$C_8$, $C_3$-$C_6$, $C_4$-$C_6$, or $C_5$-$C_6$). In embodiments, $R^{15D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15D}$ is independently substituted heterocycloalkyl (e.g., 3 to 8 membered, 3 to 6 membered, 4 to 6 membered, 4 to 5 membered, or 5 to 6 membered). In embodiments, $R^{15D}$ is independently unsubstituted heterocycloalkyl (e.g., 3 to 8 membered, 3 to 6 membered, 4 to 6 membered, 4 to 5 membered, or 5 to 6 membered). In embodiments, $R^{15D}$ is independently substituted or unsubstituted aryl (e.g., $C_6$-$C_{10}$ or phenyl). In embodiments, $R^{15D}$ is independently substituted aryl (e.g., $C_6$-$C_{10}$ or phenyl). In embodiments, $R^{15D}$ is independently unsubstituted aryl (e.g., $C_6$-$C_{10}$ or phenyl). In embodiments, $R^{15D}$ is independently substituted or unsubstituted heteroaryl (e.g., 5 to 10 membered, 5 to 9 membered, or 5 to 6 membered). In embodiments, $R^{15D}$ is independently substituted heteroaryl (e.g., 5 to 10 membered, 5 to 9 membered, or 5 to 6 membered). In embodiments, $R^{15D}$ is independently unsubstituted heteroaryl (e.g., 5 to 10 membered, 5 to 9 membered, or 5 to 6 membered).

In embodiments, $R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)NHNH$_2$, —NHC═(O)NH$_2$, —$NHSO_2H$, —NHC═(O)H, —NHC(O)—OH, —NHOH, $R^{72}$-substituted or unsubstituted alkyl (e.g., $C_1$-$C_8$, $C_1$-$C_6$, $C_1$-$C_4$, or $C_1$-$C_2$), $R^{72}$-substituted or unsubstituted heteroalkyl (e.g., 2 to 8 membered, 2 to 6 membered, 4 to 6 membered, 2 to 3 membered, or 4 to 5 membered), $R^{72}$-substituted or unsubstituted cycloalkyl (e.g., $C_3$-$C_8$, $C_3$-$C_6$, $C_4$-$C_6$, or $C_5$-$C_6$), $R^{72}$-substituted or unsubstituted heterocycloalkyl (e.g., 3 to 8 membered, 3 to 6 membered, 4 to 6 membered, 4 to 5 membered, or 5 to 6 membered), $R^{72}$-substituted or unsubstituted aryl (e.g., $C_6$-$C_{10}$ or phenyl), or $R^{72}$-substituted or unsubstituted heteroaryl (e.g., 5 to 10 membered, 5 to 9 membered, or 5 to 6 membered). In embodiments, $R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15}$ is independently —F, —Cl, —Br, or —I. In embodiments, $R^{15}$ is independently hydrogen. In embodiments, $R^{15}$ is independently unsubstituted methyl. In embodiments, $R^{15}$ is independently unsubstituted ethyl.

$R^{72}$ is independently oxo, halogen, —$CX^{72}_3$, —$CHX^{72}_2$, —$CH_2X^{72}$, —$OCX^{72}_3$, —$OCH_2X^{72}$, —$OCHX^{72}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{73}$-substituted or unsubstituted alkyl (e.g., $C_1$-$C_8$, $C_1$-$C_6$, $C_1$-$C_4$, or $C_1$-$C_2$), $R^{73}$-substituted or unsubstituted heteroalkyl (e.g., 2 to 8 membered, 2 to 6 membered, 4 to 6 membered, 2 to 3 membered, or 4 to 5 membered), $R^{73}$-substituted or unsubstituted cycloalkyl (e.g., $C_3$-$C_8$, $C_3$-$C_6$, $C_4$-$C_6$, or $C_5$-$C_6$), $R^{73}$-substituted or unsubstituted heterocycloalkyl (e.g., 3 to 8 membered, 3 to 6 membered, 4 to 6 membered, 4 to 5 membered, or 5 to 6 membered), $R^{73}$-substituted or unsubstituted aryl (e.g., $C_6$-$C_{10}$ or phenyl), or $R^{73}$-substituted or unsubstituted heteroaryl (e.g., 5 to 10 membered, 5 to 9 membered, or 5 to 6 membered). In embodiments, $R^{72}$ is independently oxo, halogen, —$CX^{72}_3$, —$CHX^{72}_2$, —$CH_2X^{72}$, —$OCX^{72}_3$, —$OCH_2X^{72}$, —$OCHX^{72}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{72}$ is independently —F, —Cl, —Br, or —I. In embodiments, $R^{72}$ is independently unsubstituted methyl. In embodiments, $R^{72}$ is independently unsubstituted ethyl.

$R^{73}$ is independently oxo, halogen, —$CX^{73}_3$, —$CHX^{73}_2$, —$CH_2X^{73}$, —$OCX^{73}_3$, —$OCH_2X^{73}$, —$OCHX^{73}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{74}$-substituted or unsubstituted alkyl (e.g., $C_1$-$C_8$, $C_1$-$C_6$, $C_1$-$C_4$, or $C_1$-$C_2$), $R^{74}$-substituted or unsubstituted heteroalkyl (e.g., 2 to 8 membered, 2 to 6 membered, 4 to 6 membered, 2 to 3 membered, or 4 to 5 membered), $R^{74}$-substituted or unsubstituted cycloalkyl (e.g., $C_3$-$C_8$, $C_3$-$C_6$, $C_4$-$C_6$, or $C_5$-$C_6$), $R^{74}$-substituted or unsubstituted heterocycloalkyl (e.g., 3 to 8 membered, 3 to 6 membered, 4 to 6 membered, 4 to 5 membered, or 5 to 6 membered), $R^{74}$-substituted or unsubstituted aryl (e.g., $C_6$-$C_{10}$ or phenyl), or $R^{74}$-substituted or unsubstituted heteroaryl (e.g., 5 to 10 membered, 5 to 9 membered, or 5 to 6 membered). In embodiments, $R^{73}$ is independently oxo, halogen, —$CX^{73}_3$, —$CHX^{73}_2$, —$CH_2X^{73}$, —$OCX^{73}_3$, —$OCH_2X^{73}$, —$OCHX^{73}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{73}$ is independently —F, —Cl, —Br, or —I. In embodiments, $R^{73}$ is independently unsubstituted methyl. In embodiments, $R^{73}$ is independently unsubstituted ethyl.

$R^{74}$ is independently oxo, halogen, —$CX^{74}_3$, —$CHX^{74}_2$, —$CH_2X^{74}$, —$OCX^{74}_3$, —$OCH_2X^{74}$, —$OCHX^{74}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{74}$ is independently —F, —Cl, —Br, or —I. In embodiments, $R^{74}$ is independently unsubstituted methyl. In embodiments, $R^{74}$ is independently unsubstituted ethyl.

In embodiments, $R^{15A}$ is independently hydrogen, —$CX^{15A}_3$, —$CHX^{15A}_2$, —$CH_2X^{15A}$, —CN, —COOH, —$CONH_2$, $R^{72A}$-substituted or unsubstituted alkyl (e.g., $C_1$-$C_8$, $C_1$-$C_6$, $C_1$-$C_4$, or $C_1$-$C_2$), $R^{72A}$-substituted or unsubstituted heteroalkyl (e.g., 2 to 8 membered, 2 to 6 membered, 4 to 6 membered, 2 to 3 membered, or 4 to 5 membered), $R^{72A}$-substituted or unsubstituted cycloalkyl (e.g., $C_3$-$C_8$, $C_3$-$C_6$, $C_4$-$C_6$, or $C_5$-$C_6$), $R^{72A}$-substituted or unsubstituted heterocycloalkyl (e.g., 3 to 8 membered, 3 to 6 membered, 4 to 6 membered, 4 to 5 membered, or 5 to 6 membered), $R^{72A}$-substituted or unsubstituted aryl (e.g., $C_6$-$C_{10}$ or phenyl), or $R^{72A}$-substituted or unsubstituted heteroaryl (e.g., 5 to 10 membered, 5 to 9 membered, or 5 to 6 membered). In embodiments, $R^{15A}$ is independently hydrogen, —$CX^{15A}_3$, —$CHX^{15A}_2$, —$CH_2X^{15A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15A}$ is independently —F, —Cl, —Br, or —I. In embodiments, $R^{15A}$ is independently hydrogen. In embodiments, $R^{15A}$ is independently unsubstituted methyl. In embodiments, $R^{15A}$ is independently unsubstituted ethyl.

In embodiments, $R^{15A}$ and $R^{15B}$ substituents bonded to the same nitrogen atom may optionally be joined to form a $R^{72A}$-substituted or unsubstituted heterocycloalkyl (e.g., 3 to 8 membered, 3 to 6 membered, 4 to 6 membered, 4 to 5 membered, or 5 to 6 membered) or $R^{72A}$-substituted or unsubstituted heteroaryl (e.g., 5 to 10 membered, 5 to 9 membered, or 5 to 6 membered). In embodiments, $R^{15A}$ and $R^{15B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{15A}$ and $R^{15B}$ substituents bonded to the same nitrogen atom may optionally be joined to form a $R^{72A}$-substituted or unsubstituted heterocycloalkyl (e.g., 3 to 8 membered, 3 to 6 membered, 4 to 6 membered, 4 to 5 membered, or 5 to 6 membered). In embodiments, $R^{15A}$ and $R^{15B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{72A}$ is independently oxo, halogen, —$CX^{72A}_3$, —$CHX^{72A}_2$, —$CH_2X^{72A}$, —$OCX^{72A}_3$, —$OCH_2X^{72A}$, —$OCHX^{72A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{73A}$-substituted or unsubstituted alkyl (e.g., $C_1$-$C_8$, $C_1$-$C_6$, $C_1$-$C_4$, or $C_1$-$C_2$), $R^{73A}$-substituted or unsubstituted heteroalkyl (e.g., 2 to 8 membered, 2 to 6 membered, 4 to 6 membered, 2 to 3 membered, or 4 to 5 membered), $R^{73A}$-substituted or unsubstituted cycloalkyl (e.g., $C_3$-$C_8$, $C_3$-$C_6$, $C_4$-$C_6$, or $C_5$-$C_6$), $R^{73A}$-substituted or unsubstituted heterocycloalkyl (e.g., 3 to 8 membered, 3 to 6 membered, 4 to 6 membered, 4 to 5 membered, or 5 to 6 membered), $R^{73A}$-substituted or unsubstituted aryl (e.g., $C_6$-$C_{10}$ or phenyl), or $R^{73A}$-substituted or unsubstituted heteroaryl (e.g., 5 to 10 membered, 5 to 9 membered, or 5 to 6 membered). In embodiments, $R^{72A}$ is independently oxo, halogen, —$CX^{72A}_3$, —$CHX^{72A}_2$, —$CH_2X^{72A}$, —$OCX^{72A}_3$, —$OCH_2X^{72A}$, —$OCHX^{72A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{72A}$ is independently —F, —Cl, —Br, or —I. In embodiments, $R^{72A}$ is independently unsubstituted methyl. In embodiments, $R^{72A}$ is independently unsubstituted ethyl.

$R^{73A}$ is independently oxo, halogen, —$CX^{73A}_3$, —$CHX^{73A}_2$, —$CH_2X^{73A}$, —$OCX^{73A}_3$, —$OCH_2X^{73A}$, —$OCHX^{73A}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{74A}$-substituted or unsubstituted alkyl (e.g., $C_1$-$C_8$, $C_1$-$C_6$, $C_1$-$C_4$, or $C_1$-$C_2$), $R^{74A}$-substituted or unsubstituted heteroalkyl (e.g., 2 to 8 membered, 2 to 6 membered, 4 to 6 membered, 2 to 3 membered, or 4 to 5 membered), $R^{74A}$-substituted or unsubstituted cycloalkyl (e.g., $C_3$-$C_8$, $C_3$-$C_6$, $C_4$-$C_6$, or $C_5$-$C_6$), $R^{74A}$-substituted or unsubstituted heterocycloalkyl (e.g., 3 to 8 membered, 3 to 6 membered, 4 to 6 membered, 4 to 5 membered, or 5 to 6 membered), $R^{74A}$-substituted or unsubstituted aryl (e.g., $C_6$-$C_{10}$ or phenyl), or $R^{74A}$-substituted or unsubstituted heteroaryl (e.g., 5 to 10 membered, 5 to 9 membered, or 5 to 6 membered). In embodiments, $R^{73A}$ is independently oxo, halogen, —$CX^{73A}_3$, —$CHX^{73A}_2$, —$CH_2X^{73A}$, —$OCX^{73A}_3$, —$OCH_2X^{73A}$, —$OCHX^{73A}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{73A}$ is independently —F, —Cl, —Br, or —I. In embodiments, $R^{73A}$ is independently unsubstituted methyl. In embodiments, $R^{73A}$ is independently unsubstituted ethyl.

$R^{74A}$ is independently oxo, halogen, —$CX^{74A}_3$, —$CHX^{74A}_2$, —$CH_2X^{74A}$, —$OCX^{74A}_3$, —$OCH_2X^{74A}$, —$OCHX^{74A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{74A}$ is independently —F, —Cl, —Br, or —I. In embodiments, $R^{74A}$ is independently unsubstituted methyl. In embodiments, $R^{74A}$ is independently unsubstituted ethyl.

In embodiments, $R^{15B}$ is independently hydrogen, —$CX^{15B}_3$, —$CHX^{15B}_2$, —$CH_2X^{15B}$, —CN, —COOH, —$CONH_2$, $R^{72B}$-substituted or unsubstituted alkyl (e.g., $C_1$-$C_8$, $C_1$-$C_6$, $C_1$-$C_4$, or $C_1$-$C_2$), $R^{72B}$-substituted or unsubstituted heteroalkyl (e.g., 2 to 8 membered, 2 to 6 membered, 4 to 6 membered, 2 to 3 membered, or 4 to 5 membered), $R^{72B}$-substituted or unsubstituted cycloalkyl (e.g., $C_3$-$C_8$, $C_3$-$C_6$, $C_4$-$C_6$, or $C_5$-$C_6$), $R^{72B}$-substituted or unsubstituted heterocycloalkyl (e.g., 3 to 8 membered, 3 to 6 membered, 4 to 6 membered, 4 to 5 membered, or 5 to 6 membered), $R^{72B}$-substituted or unsubstituted aryl (e.g., $C_6$-$C_{10}$ or phenyl), or $R^{72B}$-substituted or unsubstituted heteroaryl (e.g., 5 to 10 membered, 5 to 9 membered, or 5 to 6 membered). In embodiments, $R^{15B}$ is independently hydrogen, —$CX^{15B}_3$, —$CHX^{15B}_2$, —$CH_2X^{15B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15B}$ is independently —F, —Cl, —Br, or —I. In embodiments, $R^{15B}$ is independently hydrogen. In embodiments, $R^{15B}$ is independently unsubstituted methyl. In embodiments, $R^{15B}$ is independently unsubstituted ethyl.

In embodiments, $R^{15A}$ and $R^{15B}$ substituents bonded to the same nitrogen atom may optionally be joined to form a $R^{72B}$-substituted or unsubstituted heterocycloalkyl (e.g., 3 to 8 membered, 3 to 6 membered, 4 to 6 membered, 4 to 5 membered, or 5 to 6 membered) or $R^{72B}$-substituted or unsubstituted heteroaryl (e.g., 5 to 10 membered, 5 to 9 membered, or 5 to 6 membered). In embodiments, $R^{15A}$ and $R^{15B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{15A}$ and $R^{15B}$ substituents bonded to the same nitrogen atom may optionally be joined to form a $R^{72B}$-substituted or unsubstituted heterocycloalkyl (e.g., 3 to 8 membered, 3 to 6 membered, 4 to 6 membered, 4 to 5 membered, or 5 to 6 membered). In embodiments, $R^{15A}$ and $R^{15B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{72B}$ is independently oxo, halogen, —$CX^{72B}_3$, —$CHX^{72B}_2$, —$CH_2X^{72B}$, —$OCX^{72B}_3$, —$OCH_2X^{72B}$, —$OCHX^{72B}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{73B}$-substituted or unsubstituted alkyl (e.g., $C_1$-$C_8$, $C_1$-$C_6$, $C_1$-$C_4$, or $C_1$-$C_2$), $R^{73B}$-substituted or unsubstituted heteroalkyl (e.g., 2 to 8 membered, 2 to 6 membered, 4 to 6 membered, 2 to 3 membered, or 4 to 5 membered), $R^{73B}$-substituted or unsubstituted cycloalkyl (e.g., $C_3$-$C_8$, $C_3$-$C_6$, $C_4$-$C_6$, or $C_5$-$C_6$), $R^{73B}$-substituted or unsubstituted heterocycloalkyl (e.g., 3 to 8 membered, 3 to 6 membered, 4 to 6 membered, 4 to 5 membered, or 5 to 6 membered), $R^{73B}$-substituted or unsubstituted aryl (e.g., $C_6$-$C_{10}$ or phenyl), or $R^{73B}$-substituted or unsubstituted heteroaryl (e.g., 5 to 10 membered, 5 to 9 membered, or 5 to 6 membered). In embodiments, $R^{72B}$ is independently oxo, halogen, —$CX^{72B}_3$, —$CHX^{72B}_2$, —$CH_2X^{72B}$, —$OCX^{72B}_3$, —$OCH_2X^{72B}$, —$OCHX^{72B}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{72B}$ is independently —F, —Cl, —Br, or —I. In embodiments, $R^{72B}$ is independently unsubstituted methyl. In embodiments, $R^{72B}$ is independently unsubstituted ethyl.

$R^{73B}$ is independently oxo, halogen, —$CX^{73B}_3$, —$CHX^{73B}_2$, —$CH_2X^{73B}$, —$OCX^{73B}_3$, —$OCH_2X^{73B}$, —$OCHX^{73B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{74B}$-substituted or unsubstituted alkyl (e.g., $C_1$-$C_8$, $C_1$-$C_6$, $C_1$-$C_4$, or $C_1$-$C_2$), $R^{74B}$-substituted or unsubstituted heteroalkyl (e.g., 2 to 8 membered, 2 to 6 membered, 4 to 6 membered, 2 to 3 membered, or 4 to 5 membered), $R^{74B}$-substituted or unsubstituted cycloalkyl (e.g., $C_3$-$C_8$, $C_3$-$C_6$, $C_4$-$C_6$, or $C_5$-$C_6$), $R^{74B}$-substituted or unsubstituted heterocycloalkyl (e.g., 3 to 8 membered, 3 to 6 membered, 4 to 6 membered, 4 to 5 membered, or 5 to 6 membered), $R^{74B}$-substituted or unsubstituted aryl (e.g., $C_6$-$C_{10}$ or phenyl), or $R^{74B}$-substituted or unsubstituted heteroaryl (e.g., 5 to 10 membered, 5 to 9 membered, or 5 to 6 membered). In embodiments, $R^{73B}$ is independently oxo, halogen, —$CX^{73B}_3$, —$CHX^{73B}_2$, —$CH_2X^{73B}$, —$OCX^{73B}_3$, —$OCH_2X^{73B}$, —$OCHX^{73B}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{73B}$ is independently —F, —Cl, —Br, or —I. In embodiments, $R^{73B}$ is independently unsubstituted methyl. In embodiments, $R^{73B}$ is independently unsubstituted ethyl.

$R^{74B}$ is independently oxo, halogen, —$CX^{74B}_3$, —$CHX^{74B}_2$, —$CH_2X^{74B}$, —$OCX^{74B}_3$, —$OCH_2X^{74B}$, —$OCHX^{74B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{74B}$ is independently —F, —Cl, —Br, or —I. In embodiments, $R^{74B}$ is independently unsubstituted methyl. In embodiments, $R^{74B}$ is independently unsubstituted ethyl.

In embodiments, $R^{15}$ is independently hydrogen, —$CX^{15C}_3$, —$CHX^{15C}_2$, —$CH_2X^{15C}$, —CN, —COOH, —$CONH_2$, $R^{72C}$-substituted or unsubstituted alkyl (e.g., $C_1$-$C_8$, $C_1$-$C_6$, $C_1$-$C_4$, or $C_1$-$C_2$), $R^{72C}$-substituted or unsubstituted heteroalkyl (e.g., 2 to 8 membered, 2 to 6 membered, 4 to 6 membered, 2 to 3 membered, or 4 to 5 membered), $R^{72C}$-substituted or unsubstituted cycloalkyl (e.g., $C_3$-$C_8$, $C_3$-$C_6$, $C_4$-$C_6$, or $C_5$-$C_6$), $R^{72C}$-substituted or unsubstituted heterocycloalkyl (e.g., 3 to 8 membered, 3 to 6 membered, 4 to 6 membered, 4 to 5 membered, or 5 to 6 membered), $R^{72C}$-substituted or unsubstituted aryl (e.g., $C_6$-$C_{10}$ or phenyl), or $R^{72C}$-substituted or unsubstituted heteroaryl (e.g., 5 to 10 membered, 5 to 9 membered, or 5 to 6 membered). In embodiments, $R^{15C}$ is independently hydrogen, —$CX^{15C}_3$, —$CHX^{15C}_2$, —$CH_2X^{15C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15C}$ is independently —F, —Cl, —Br, or —I. In embodiments, $R^{15C}$ is independently hydrogen. In embodiments, $R^{15C}$ is independently unsubstituted methyl. In embodiments, $R^{15C}$ is independently unsubstituted ethyl.

$R^{72C}$ is independently oxo, halogen, —$CX^{72C}_3$, —$CHX^{72C}_2$, —$CH_2X^{72C}$, —$OCX^{72C}$, —$OCH_2X^{72C}$, —$OCHX^{72C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{73C}$-substituted or unsubstituted alkyl (e.g., $C_1$-$C_8$, $C_1$-$C_6$, $C_1$-$C_4$, or $C_1$-$C_2$), $R^{73C}$-substituted or unsubstituted heteroalkyl (e.g., 2 to 8 membered, 2 to 6 membered, 4 to 6 membered, 2 to 3 membered, or 4 to 5 membered), $R^{73C}$-substituted or unsubstituted cycloalkyl (e.g., $C_3$-$C_8$, $C_3$-$C_6$, $C_4$-$C_6$, or $C_5$-$C_6$), $R^{73C}$-substituted or unsubstituted heterocycloalkyl (e.g., 3 to 8 membered, 3 to 6 membered, 4 to 6 membered, 4 to 5 membered, or 5 to 6 membered), $R^{73C}$-substituted or unsubstituted aryl (e.g., $C_6$-$C_{10}$ or phenyl), or $R^{73C}$-substituted or unsubstituted heteroaryl (e.g., 5 to 10 membered, 5 to 9 membered, or 5 to 6 membered). In embodiments, $R^{72C}$ is independently oxo, halogen, —$CX^{72C}_3$, —$CHX^{72C}_2$, —$CH_2X^{72C}$, —$OCX^{72C}_3$, —$OCH_2X^{72C}$, —$OCHX^{72C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{72C}$ is independently —F, —Cl, —Br, or —I. In embodiments, $R^{72C}$ is independently unsubstituted methyl. In embodiments, $R^{72C}$ is independently unsubstituted ethyl.

$R^{73C}$ is independently oxo, halogen, —$CX^{73C}_3$, —$CHX^{73C}_2$, —$CH_2X^{73C}$, —$OCX^{73C}$, —$OCH_2X^{73C}$, —$OCHX^{73C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{74C}$-substituted or unsubstituted alkyl (e.g., $C_1$-$C_8$, $C_1$-$C_6$, $C_1$-$C_4$, or $C_1$-$C_2$), $R^{74C}$-substituted or unsubstituted heteroalkyl (e.g., 2 to 8 membered, 2 to 6 membered, 4 to 6 membered, 2 to 3 membered, or 4 to 5 membered), $R^{74C}$-substituted or unsubstituted cycloalkyl (e.g., $C_3$-$C_8$, $C_3$-$C_6$, $C_4$-$C_6$, or $C_5$-$C_6$), $R^{74C}$-substituted or unsubstituted heterocycloalkyl (e.g., 3 to 8 membered, 3 to 6 membered, 4 to 6 membered, 4 to 5 membered, or 5 to 6 membered), $R^{74C}$-substituted or unsubstituted aryl (e.g., $C_6$-$C_{10}$ or phenyl), or $R^{74C}$-substituted or unsubstituted heteroaryl (e.g., 5 to 10 membered, 5 to 9 membered, or 5 to 6 membered). In embodiments, $R^{73C}$ is independently oxo, halogen, —$CX^{73C}_3$, —$CHX^{73C}_2$, —$CH_2X^{73C}$, —$OCX^{73C}_3$, —$OCH_2X^{73C}$, —$OCHX^{73C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{73C}$ is independently —F, —Cl, —Br, or —I. In embodiments, $R^{73C}$ is independently unsubstituted methyl. In embodiments, $R^{73C}$ is independently unsubstituted ethyl.

$R^{74C}$ is independently oxo, halogen, —$CX^{74C}_3$, —$CHX^{74C}_2$, —$CH_2X^{74C}$, —$OCX^{74C}$, —$OCH_2X^{74C}$, —$OCHX^{74C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{74C}$ is independently —F, —Cl, —Br, or —I. In embodiments, $R^{74C}$ is independently unsubstituted methyl. In embodiments, $R^{74C}$ is independently unsubstituted ethyl.

In embodiments, $R^{15D}$ is independently hydrogen, —$CX^{15D}_3$, —$CHX^{15D}_2$, —$CH_2X^{15D}$, —CN, —COOH, —$CONH_2$, $R^{72D}$-substituted or unsubstituted alkyl (e.g., $C_1$-$C_8$, $C_1$-$C_6$, $C_1$-$C_4$, or $C_1$-$C_2$), $R^{72D}$-substituted or unsubstituted heteroalkyl (e.g., 2 to 8 membered, 2 to 6 membered, 4 to 6 membered, 2 to 3 membered, or 4 to 5 membered), $R^{72D}$-substituted or unsubstituted cycloalkyl (e.g., $C_3$-$C_8$, $C_3$-$C_6$, $C_4$-$C_6$, or $C_5$-$C_6$), $R^{72D}$-substituted or unsubstituted heterocycloalkyl (e.g., 3 to 8 membered, 3 to 6 membered, 4 to 6 membered, 4 to 5 membered, or 5 to 6 membered), $R^{72D}$-substituted or unsubstituted aryl (e.g., $C_6$-$C_{10}$ or phenyl), or $R^{72D}$-substituted or unsubstituted heteroaryl (e.g., 5 to 10 membered, 5 to 9 membered, or 5 to 6 membered). In embodiments, $R^{15D}$ is independently hydrogen, —$CX^{15D}_3$, —$CHX^{15D}_2$, —$CH_2X^{15D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15D}$ is independently —F, —Cl, —Br, or —I. In embodiments, $R^{15D}$ is independently hydrogen. In embodiments, $R^{15D}$ is independently unsubstituted methyl. In embodiments, $R^{15D}$ is independently unsubstituted ethyl.

$R^{72D}$ is independently oxo, halogen, $—CX^{72D}_3$, $—CHX^{72D}_2$, $—CH_2X^{72D}$, $—OCX^{72D}_3$, $—OCH_2X^{72D}$, $—OCHX^{72D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{73D}$-substituted or unsubstituted alkyl (e.g., $C_1$-$C_8$, $C_1$-$C_6$, $C_1$-$C_4$, or $C_1$-$C_2$), $R^{73D}$-substituted or unsubstituted heteroalkyl (e.g., 2 to 8 membered, 2 to 6 membered, 4 to 6 membered, 2 to 3 membered, or 4 to 5 membered), $R^{73D}$-substituted or unsubstituted cycloalkyl (e.g., $C_3$-$C_8$, $C_3$-$C_6$, $C_4$-$C_6$, or $C_5$-$C_6$), $R^{73D}$-substituted or unsubstituted heterocycloalkyl (e.g., 3 to 8 membered, 3 to 6 membered, 4 to 6 membered, 4 to 5 membered, or 5 to 6 membered), $R^{73D}$-substituted or unsubstituted aryl (e.g., $C_6$-$C_{10}$ or phenyl), or $R^{73D}$-substituted or unsubstituted heteroaryl (e.g., 5 to 10 membered, 5 to 9 membered, or 5 to 6 membered). In embodiments, $R^{72D}$ is independently oxo, halogen, $—CX^{72D}_3$, $—CHX^{72D}_2$, $—CH_2X^{72D}$, $—OCX^{72D}_3$, $—OCH_2X^{72D}$, $—OCHX^{72D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{72D}$ is independently —F, —Cl, —Br, or —I. In embodiments, $R^{72D}$ is independently unsubstituted methyl. In embodiments, $R^{72D}$ is independently unsubstituted ethyl.

$R^{73D}$ is independently oxo, halogen, $—CX^{73D}_3$, $—CHX^{73D}_2$, $—CH_2X^{73D}$, $—OCX^{73D}_3$, $—OCH_2X^{73D}$, $—OCHX^{73D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{74D}$-substituted or unsubstituted alkyl (e.g., $C_1$-$C_8$, $C_1$-$C_6$, $C_1$-$C_4$, or $C_1$-$C_2$), $R^{74D}$-substituted or unsubstituted heteroalkyl (e.g., 2 to 8 membered, 2 to 6 membered, 4 to 6 membered, 2 to 3 membered, or 4 to 5 membered), $R^{74D}$-substituted or unsubstituted cycloalkyl (e.g., $C_3$-$C_8$, $C_3$-$C_6$, $C_4$-$C_6$, or $C_5$-$C_6$), $R^{74D}$-substituted or unsubstituted heterocycloalkyl (e.g., 3 to 8 membered, 3 to 6 membered, 4 to 6 membered, 4 to 5 membered, or 5 to 6 membered), $R^{74D}$-substituted or unsubstituted aryl (e.g., $C_6$-$C_{10}$ or phenyl), or $R^{74D}$-substituted or unsubstituted heteroaryl (e.g., 5 to 10 membered, 5 to 9 membered, or 5 to 6 membered). In embodiments, $R^{73D}$ is independently oxo, halogen, $—CX^{73D}_3$, $—CHX^{73D}_2$, $—CH_2X^{73D}$, $—OCX^{73D}_3$, $—OCH_2X^{73D}$, $—OCHX^{73D}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{73D}$ is independently —F, —Cl, —Br, or —I. In embodiments, $R^{73D}$ is independently unsubstituted methyl. In embodiments, $R^{73D}$ is independently unsubstituted ethyl.

$R^{74D}$ is independently oxo, halogen, $—CX^{74D}_3$, $—CHX^{74D}_2$, $—CH_2X^{74D}$, $—OCX^{74D}_3$, $—OCH_2X^{74D}$, $—OCHX^{74D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{74D}$ is independently —F, —Cl, —Br, or —I. In embodiments, $R^{74D}$ is independently unsubstituted methyl. In embodiments, $R^{74D}$ is independently unsubstituted ethyl.

In embodiments, $R^{16}$ is hydrogen. In embodiments, $R^{16}$ is halogen. In embodiments, $R^{16}$ is $—CX^{16}_3$. In embodiments, $R^{16}$ is $—CHX^{16}_2$. In embodiments, $R^{16}$ is $—CH_2X^{16}$. In embodiments, $R^{16}$ is —CN. In embodiments, $R^{16}$ is $—SO_{n16}R^{16D}$. In embodiments, $R^{16}$ is $—SO_{v16}NR^{16A}R^{16B}$. In embodiments, $R^{16}$ is $—NHNR^{16A}R^{16B}$. In embodiments, $R^{16}$ is $—ONR^{16A}R^{16B}$. In embodiments, $R^{16}$ is $—NHC{=}(O)NHNR^{16A}R^{16B}$. In embodiments, $R^{16}$ is $—NHC(O)NR^{16A}R^{16B}$. In embodiments, $R^{16}$ is $—N(O)_{m16}$. In embodiments, $R^{16}$ is $—NR^{16A}R^{16B}$. In embodiments, $R^{16}$ is $—C(O)R^{16C}$. In embodiments, $R^{16}$ is $—C(O)—OR^{16C}$. In embodiments, $R^{16}$ is $—C(O)NR^{16A}R^{16B}$. In embodiments, $R^{16}$ is $—OR^{16D}$. In embodiments, $R^{16}$ is $—NR^{16A}SO_2R^{16D}$. In embodiments, $R^{16}$ is $—NR^{16A}C(O)R^{16C}$. In embodiments, $R^{16}$ is $—NR^{16A}C(O)OR^{16C}$. In embodiments, $R^{16}$ is $—NR^{16A}OR^{16C}$. In embodiments, $R^{16}$ is $—OCX^{16}_3$. In embodiments, $R^{16}$ is $—OCHX^{16}_2$. In embodiments, $R^{16}$ is independently —OH. In embodiments, $R^{16}$ is independently $—NH_2$. In embodiments, $R^{16}$ is independently —COOH. In embodiments, $R^{16}$ is independently $—CONH_2$. In embodiments, $R^{16}$ is independently $—NO_2$. In embodiments, $R^{16}$ is independently —SH. In embodiments, $R^{16}$ is independently $—CF_3$. In embodiments, $R^{16}$ is independently $—CHF_2$. In embodiments, $R^{16}$ is independently $—CH_2F$. In embodiments, $R^{16}$ is independently $—OCF_3$. In embodiments, $R^{16}$ is independently $—OCH_2F$. In embodiments, $R^{16}$ is independently $—OCHF_2$. In embodiments, $R^{16}$ is independently $—OCH_3$. In embodiments, $R^{16}$ is independently $—OCH_2CH_3$. In embodiments, $R^{16}$ is independently $—OCH_2CH_2CH_3$. In embodiments, $R^{16}$ is independently $—OCH(CH_3)_2$. In embodiments, $R^{16}$ is independently $—OC(CH_3)_3$. In embodiments, $R^{16}$ is independently $—SCH_3$. In embodiments, $R^{16}$ is independently $—SCH_2CH_3$. In embodiments, $R^{16}$ is independently $—SCH_2CH_2CH_3$. In embodiments, $R^{16}$ is independently —$SCH(CH_3)_2$. In embodiments, $R^{16}$ is independently —$SC(CH_3)_3$. In embodiments, $R^{16}$ is independently —$CH_3$. In embodiments, $R^{16}$ is independently —$CH_2CH_3$. In embodiments, $R^{16}$ is independently —$CH_2CH_2CH_3$. In embodiments, $R^{16}$ is independently —$CH(CH_3)_2$. In embodiments, $R^{16}$ is independently —$C(CH_3)_3$. In embodiments, $R^{16}$ is independently —F. In embodiments, $R^{16}$ is independently —Cl. In embodiments, $R^{16}$ is independently —Br. In embodiments, $R^{16}$ is independently —I.

In embodiments, $R^{16}$ is independently substituted or unsubstituted alkyl (e.g., $C_1$-$C_8$, $C_1$-$C_6$, $C_1$-$C_4$, or $C_1$-$C_2$). In embodiments, $R^{16}$ is independently substituted alkyl (e.g., $C_1$-$C_8$, $C_1$-$C_6$, $C_1$-$C_4$, or $C_1$-$C_2$). In embodiments, $R^{16}$ is independently unsubstituted alkyl (e.g., $C_1$-$C_8$, $C_1$-$C_6$, $C_1$-$C_4$, or $C_1$-$C_2$). In embodiments, $R^{16}$ is independently unsubstituted methyl. In embodiments, $R^{16}$ is independently unsubstituted ethyl. In embodiments, $R^{16}$ is independently unsubstituted propyl. In embodiments, $R^{16}$ is independently unsubstituted isopropyl. In embodiments, $R^{16}$ is independently unsubstituted tert-butyl. In embodiments, $R^{16}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16}$ is independently substituted heteroalkyl (e.g., 2 to 8 membered, 2 to 6 membered, 4 to 6 membered, 2 to 3 membered, or 4 to 5 membered). In embodiments, $R^{16}$ is independently unsubstituted heteroalkyl (e.g., 2 to 8 membered, 2 to 6 membered, 4 to 6 membered, 2 to 3 membered, or 4 to 5 membered). In embodiments, $R^{16}$ is independently substituted or unsubstituted cycloalkyl (e.g., $C_3$-$C_8$, $C_3$-$C_6$, $C_4$-$C_6$, or $C_5$-$C_6$). In embodiments, $R^{16}$ is independently substituted cycloalkyl (e.g., $C_3$-$C_8$, $C_3$-$C_6$, $C_4$-$C_6$, or $C_5$-$C_6$). In embodiments, $R^{16}$ is independently unsubstituted cycloalkyl (e.g., $C_3$-$C_8$, $C_3$-$C_6$, $C_4$-$C_6$, or $C_5$-$C_6$). In embodiments, $R^{16}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16}$ is independently substituted heterocycloalkyl (e.g., 3 to 8 membered, 3 to 6 membered, 4 to 6 membered, 4 to 5 membered, or 5 to 6 membered). In embodiments, $R^{16}$ is independently unsubstituted heterocycloalkyl (e.g., 3 to 8 membered, 3 to 6 membered, 4 to 6 membered, 4 to 5 membered, or 5 to 6 membered). In embodiments, $R^{16}$ is independently substituted or unsubstituted aryl (e.g., $C_6$-$C_{10}$ or phenyl). In embodiments, $R^{16}$ is independently substituted aryl (e.g., $C_6$-$C_{10}$ or phenyl). In embodiments, $R^{16}$ is independently unsubstituted aryl (e.g., $C_6$-$C_{10}$ or phenyl). In embodiments, $R^{16}$ is independently substituted or unsubstituted heteroaryl (e.g., 5 to 10 membered, 5 to 9 membered, or 5 to 6 membered). In embodiments, $R^{16}$ is independently substituted heteroaryl (e.g., 5 to 10 membered, 5 to 9 membered, or 5 to 6 membered). In embodiments, $R^{16}$ is independently unsubstituted heteroaryl (e.g., 5 to 10 membered, 5 to 9 membered, or 5 to 6 membered).

In embodiments, $R^{16A}$ is independently hydrogen. In embodiments, $R^{16A}$ is independently —$CX^{16A}_3$. In embodiments, $R^{16A}$ is independently —$CHX^{16A}_2$. In embodiments, $R^{16A}$ is independently —$CH_2X^{16A}$. In embodiments, $R^{16A}$ is independently —CN. In embodiments, $R^{16A}$ is independently —COOH. In embodiments, $R^{16A}$ is independently —$CONH_2$. In embodiments, $X^{16A}$ is independently —F, —Cl, —Br, or —I.

In embodiments, $R^{16A}$ is independently substituted or unsubstituted alkyl (e.g., $C_1$-$C_8$, $C_1$-$C_6$, $C_1$-$C_4$, or $C_1$-$C_2$). In embodiments, $R^{16A}$ is independently substituted alkyl (e.g., $C_1$-$C_8$, $C_1$-$C_6$, $C_1$-$C_4$, or $C_1$-$C_2$). In embodiments, $R^{16A}$ is independently unsubstituted alkyl (e.g., $C_1$-$C_8$, $C_1$-$C_6$, $C_1$-$C_4$, or $C_1$-$C_2$). In embodiments, $R^{16A}$ is independently unsubstituted methyl. In embodiments, $R^{16A}$ is independently unsubstituted ethyl. In embodiments, $R^{16A}$ is independently unsubstituted propyl. In embodiments, $R^{16A}$ is independently unsubstituted isopropyl. In embodiments, $R^{16A}$ is independently unsubstituted tert-butyl. In embodiments, $R^{16A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16A}$ is independently substituted heteroalkyl (e.g., 2 to 8 membered, 2 to 6 membered, 4 to 6 membered, 2 to 3 membered, or 4 to 5 membered). In embodiments, $R^{16A}$ is independently unsubstituted heteroalkyl (e.g., 2 to 8 membered, 2 to 6 membered, 4 to 6 membered, 2 to 3 membered, or 4 to 5 membered). In embodiments, $R^{16A}$ is independently substituted or unsubstituted cycloalkyl (e.g., $C_3$-$C_8$, $C_3$-$C_6$, $C_4$-$C_6$, or $C_5$-$C_6$). In embodiments, $R^{16A}$ is independently substituted cycloalkyl (e.g., $C_3$-$C_8$, $C_3$-$C_6$, $C_4$-$C_6$, or $C_5$-$C_6$). In embodiments, $R^{16A}$ is independently unsubstituted cycloalkyl (e.g., $C_3$-$C_8$, $C_3$-$C_6$, $C_4$-$C_6$, or $C_5$-$C_6$). In embodiments, $R^{16A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16A}$ is independently substituted heterocycloalkyl (e.g., 3 to 8 membered, 3 to 6 membered, 4 to 6 membered, 4 to 5 membered, or 5 to 6 membered). In embodiments, $R^{16A}$ is independently unsubstituted heterocycloalkyl (e.g., 3 to 8 membered, 3 to 6 membered, 4 to 6 membered, 4 to 5 membered, or 5 to 6 membered). In embodiments, $R^{16A}$ is independently substituted or unsubstituted aryl (e.g., $C_6$-$C_{10}$ or phenyl). In embodiments, $R^{16A}$ is independently substituted aryl (e.g., $C_6$-$C_{10}$ or phenyl). In embodiments, $R^{16A}$ is independently unsubstituted aryl (e.g., $C_6$-$C_{10}$ or phenyl). In embodiments, $R^{16A}$ is independently substituted or unsubstituted heteroaryl (e.g., 5 to 10 membered, 5 to 9 membered, or 5 to 6 membered). In embodiments, $R^{16A}$ is independently substituted heteroaryl (e.g., 5 to 10 membered, 5 to 9 membered, or 5 to 6 membered). In embodiments, $R^{16A}$ is independently unsubstituted heteroaryl (e.g., 5 to 10 membered, 5 to 9 membered, or 5 to 6 membered).

In embodiments, $R^{16B}$ is independently hydrogen. In embodiments, $R^{16B}$ is independently —$CX^{16B}_3$. In embodiments, $R^{16B}$ is independently —$CHX^{16B}_2$. In embodiments, $R^{16B}$ is independently —$CH_2X^{16B}$. In embodiments, $R^{16B}$ is independently —CN. In embodiments, $R^{16B}$ is independently —COOH. In embodiments, $R^{16B}$ is independently —$CONH_2$. In embodiments, $X^{16B}$ is independently —F, —Cl, —Br, or —I.

In embodiments, $R^{16B}$ is independently substituted or unsubstituted alkyl (e.g., $C_1$-$C_8$, $C_1$-$C_6$, $C_1$-$C_4$, or $C_1$-$C_2$). In embodiments, $R^{16B}$ is independently substituted alkyl (e.g., $C_1$-$C_8$, $C_1$-$C_6$, $C_1$-$C_4$, or $C_1$-$C_2$). In embodiments, $R^{16B}$ is independently unsubstituted alkyl (e.g., $C_1$-$C_8$, $C_1$-$C_6$, $C_1$-$C_4$, or $C_1$-$C_2$). In embodiments, $R^{16B}$ is independently unsubstituted methyl. In embodiments, $R^{16B}$ is independently unsubstituted ethyl. In embodiments, $R^{16B}$ is independently unsubstituted propyl. In embodiments, $R^{16B}$ is independently unsubstituted isopropyl. In embodiments, $R^{16B}$ is independently unsubstituted tert-butyl. In embodiments, $R^{16B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16B}$ is independently substituted heteroalkyl (e.g., 2 to 8 membered, 2 to 6 membered, 4 to 6 membered, 2 to 3 membered, or 4 to 5 membered). In embodiments, $R^{16B}$ is independently unsubstituted heteroalkyl (e.g., 2 to 8 membered, 2 to 6 membered, 4 to 6 membered, 2 to 3 membered, or 4 to 5 membered). In embodiments, $R^{16B}$ is independently substituted or unsubstituted cycloalkyl (e.g., $C_3$-$C_8$, $C_3$-$C_6$, $C_4$-$C_6$, or $C_5$-$C_6$). In embodiments, $R^{16B}$ is independently substituted cycloalkyl (e.g., $C_3$-$C_8$, $C_3$-$C_6$, $C_4$-$C_6$, or $C_5$-$C_6$). In embodiments, $R^{16B}$ is independently unsubstituted cycloalkyl (e.g., $C_3$-$C_8$, $C_3$-$C_6$, $C_4$-$C_6$, or $C_5$-$C_6$). In embodiments, $R^{16B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16B}$ is independently substituted heterocycloalkyl (e.g., 3 to 8 membered, 3 to 6 membered, 4 to 6 membered, 4 to 5 membered, or 5 to 6 membered). In embodiments, $R^{16B}$ is independently unsubstituted heterocycloalkyl (e.g., 3 to 8 membered, 3 to 6 membered, 4 to 6 membered, 4 to 5 membered, or 5 to 6 membered). In embodiments, $R^{16B}$ is independently substituted or unsubstituted aryl (e.g., $C_6$-$C_{10}$ or phenyl). In embodiments, $R^{16B}$ is independently substituted aryl (e.g., $C_6$-$C_{10}$ or phenyl). In embodiments, $R^{16B}$ is independently unsubstituted aryl (e.g., $C_6$-$C_{10}$ or phenyl). In embodiments, $R^{16B}$ is independently substituted or unsubstituted heteroaryl (e.g., 5 to 10 membered, 5 to 9 membered, or 5 to 6 membered). In embodiments, $R^{16B}$ is independently substituted heteroaryl (e.g., 5 to 10 membered, 5 to 9 membered, or 5 to 6 membered). In embodiments, $R^{16B}$ is independently unsubstituted heteroaryl (e.g., 5 to 10 membered, 5 to 9 membered, or 5 to 6 membered).

In embodiments, $R^{16A}$ and $R^{16B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{16A}$ and $R^{16B}$ substituents bonded to the same nitrogen atom may be joined to form a substituted or unsubstituted heteroaryl (e.g., 5 to 10 membered, 5 to 9 membered, or 5 to 6 membered). In embodiments, $R^{16A}$ and $R^{16B}$ substituents bonded to the same nitrogen atom may be joined to form a substituted heteroaryl (e.g., 5 to 10 membered, 5 to 9 membered, or 5 to 6 membered). In embodiments, $R^{16A}$ and $R^{16B}$ substituents bonded to the same nitrogen atom may be joined to form an unsubstituted heteroaryl (e.g., 5 to 10 membered, 5 to 9 membered, or 5 to 6 membered).

In embodiments, $R^{16C}$ is independently hydrogen. In embodiments, $R^{16C}$ is independently —$CX^{16C}_3$. In embodiments, $R^{16C}$ is independently —$CHX^{16C}_2$. In embodiments, $R^{16C}$ is independently —$CH_2X^{16C}$. In embodiments, $R^{16C}$ is independently —CN. In embodiments, $R^{16C}$ is independently —COOH. In embodiments, $R^{16C}$ is independently —$CONH_2$. In embodiments, $X^{16C}$ is independently —F, —Cl, —Br, or —I.

In embodiments, $R^{16C}$ is independently substituted or unsubstituted alkyl (e.g., $C_1$-$C_8$, $C_1$-$C_6$, $C_1$-$C_4$, or $C_1$-$C_2$). In embodiments, $R^{16C}$ is independently substituted alkyl (e.g., $C_1$-$C_8$, $C_1$-$C_6$, $C_1$-$C_4$, or $C_1$-$C_2$). In embodiments, $R^{16C}$ is independently unsubstituted alkyl (e.g., $C_1$-$C_8$, $C_1$-$C_6$, $C_1$-$C_4$, or $C_1$-$C_2$). In embodiments, $R^{16C}$ is independently unsubstituted methyl. In embodiments, $R^{16C}$ is independently unsubstituted ethyl. In embodiments, $R^{16C}$ is independently unsubstituted propyl. In embodiments, $R^{16C}$ is independently unsubstituted isopropyl. In embodiments, $R^{16C}$ is independently unsubstituted tert-butyl. In embodiments, $R^{16C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16C}$ is independently substituted heteroalkyl (e.g., 2 to 8 membered, 2 to 6 membered, 4 to 6 membered, 2 to 3 membered, or 4 to 5 membered). In embodiments, $R^{16C}$ is independently unsubstituted heteroalkyl (e.g., 2 to 8 membered, 2 to 6 membered, 4 to 6 membered, 2 to 3 membered, or 4 to 5 membered). In embodiments, $R^{16C}$ is independently substituted or unsubstituted cycloalkyl (e.g., $C_3$-$C_8$, $C_3$-$C_6$, $C_4$-$C_6$, or $C_5$-$C_6$). In embodiments, $R^{16C}$ is independently substituted cycloalkyl (e.g., $C_3$-$C_8$, $C_3$-$C_6$, $C_4$-$C_6$, or $C_5$-$C_6$). In embodiments, $R^{16C}$ is independently unsubstituted cycloalkyl (e.g., $C_3$-$C_8$, $C_3$-$C_6$, $C_4$-$C_6$, or $C_5$-$C_6$). In embodiments, $R^{16C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16C}$ is independently substituted heterocycloalkyl (e.g., 3 to 8 membered, 3 to 6 membered, 4 to 6 membered, 4 to 5 membered, or 5 to 6 membered). In embodiments, $R^{16C}$ is independently unsubstituted heterocycloalkyl (e.g., 3 to 8 membered, 3 to 6 membered, 4 to 6 membered, 4 to 5 membered, or 5 to 6 membered). In embodiments, $R^{16C}$ is independently substituted or unsubstituted aryl (e.g., $C_6$-$C_{10}$ or phenyl). In embodiments, $R^{16C}$ is independently substituted aryl (e.g., $C_6$-$C_{10}$ or phenyl). In embodiments, $R^{16C}$ is independently unsubstituted aryl (e.g., $C_6$-$C_{10}$ or phenyl). In embodiments, $R^{16C}$ is independently substituted or unsubstituted heteroaryl (e.g., 5 to 10 membered, 5 to 9 membered, or 5 to 6 membered). In embodiments, $R^{16C}$ is independently substituted heteroaryl (e.g., 5 to 10 membered, 5 to 9 membered, or 5 to 6 membered). In embodiments, $R^{16C}$ is independently unsubstituted heteroaryl (e.g., 5 to 10 membered, 5 to 9 membered, or 5 to 6 membered).

In embodiments, $R^{16D}$ is independently hydrogen. In embodiments, $R^{16D}$ is independently —$CX^{16D}_3$. In embodiments, $R^{16D}$ is independently —$CHX^{16D}_2$. In embodiments, $R^{16D}$ is independently —$CH_2X^{16D}$. In embodiments, $R^{16D}$ is independently —CN. In embodiments, $R^{16D}$ is independently —COOH. In embodiments, $R^{16D}$ is independently —$CONH_2$. In embodiments, $X^{16D}$ is independently —F, —Cl, —Br, or —I.

In embodiments, $R^{16D}$ is independently substituted or unsubstituted alkyl (e.g., $C_1$-$C_8$, $C_1$-$C_6$, $C_1$-$C_4$, or $C_1$-$C_2$). In embodiments, $R^{16D}$ is independently substituted alkyl (e.g., $C_1$-$C_8$, $C_1$-$C_6$, $C_1$-$C_4$, or $C_1$-$C_2$). In embodiments, $R^{16D}$ is independently unsubstituted alkyl (e.g., $C_1$-$C_8$, $C_1$-$C_6$, $C_1$-$C_4$, or $C_1$-$C_2$). In embodiments, $R^{16D}$ is independently unsubstituted methyl. In embodiments, $R^{16D}$ is independently unsubstituted ethyl. In embodiments, $R^{16D}$ is independently unsubstituted propyl. In embodiments, $R^{16D}$ is independently unsubstituted isopropyl. In embodiments, $R^{16D}$ is independently unsubstituted tert-butyl. In embodiments, $R^{16D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16D}$ is independently substituted heteroalkyl (e.g., 2 to 8 membered, 2 to 6 membered, 4 to 6 membered, 2 to 3 membered, or 4 to 5 membered). In embodiments, $R^{16D}$ is independently unsubstituted heteroalkyl (e.g., 2 to 8 membered, 2 to 6 membered, 4 to 6 membered, 2 to 3 membered, or 4 to 5 membered). In embodiments, $R^{16D}$ is independently substituted or unsubstituted cycloalkyl (e.g., $C_3$-$C_8$, $C_3$-$C_6$, $C_4$-$C_6$, or $C_5$-$C_6$). In embodiments, $R^{16D}$ is independently substituted cycloalkyl (e.g., $C_3$-$C_8$, $C_3$-$C_6$, $C_4$-$C_6$, or $C_5$-$C_6$). In embodiments, $R^{16D}$ is independently unsubstituted cycloalkyl (e.g., $C_3$-$C_8$, $C_3$-$C_6$, $C_4$-$C_6$, or $C_5$-$C_6$). In embodiments, $R^{16D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16D}$ is independently substituted heterocycloalkyl (e.g., 3 to 8 membered, 3 to 6 membered, 4 to 6 membered, 4 to 5 membered, or 5 to 6 membered). In embodiments, $R^{16D}$ is independently unsubstituted heterocycloalkyl (e.g., 3 to 8 membered, 3 to 6 membered, 4 to 6 membered, 4 to 5 membered, or 5 to 6 membered). In embodiments, $R^{16D}$ is independently substituted or unsubstituted aryl (e.g., $C_6$-$C_{10}$ or phenyl). In embodiments, $R^{16D}$ is independently substituted aryl (e.g., $C_6$-$C_{10}$ or phenyl). In embodiments, $R^{16D}$ is independently unsubstituted aryl (e.g., $C_6$-$C_{10}$ or phenyl). In embodiments, $R^{16D}$ is independently substituted or unsubstituted heteroaryl (e.g., 5 to 10 membered, 5 to 9 membered, or 5 to 6 membered). In embodiments, $R^{16D}$ is independently substituted heteroaryl (e.g., 5 to 10 membered, 5 to 9 membered, or 5 to 6 membered). In embodiments, $R^{16D}$ is independently unsubstituted heteroaryl (e.g., 5 to 10 membered, 5 to 9 membered, or 5 to 6 membered).

In embodiments, $R^{16}$ is independently hydrogen, halogen, $—CX^{16}_3$, $—CHX^{16}_2$, $—CH_2X^{16}$, $—OCX^{16}_3$, $—OCH_2X^{16}$, $—OCHX^{16}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{75}$-substituted or unsubstituted alkyl (e.g., $C_1$-$C_8$, $C_1$-$C_6$, $C_1$-$C_4$, or $C_1$-$C_2$), $R^{75}$-substituted or unsubstituted heteroalkyl (e.g., 2 to 8 membered, 2 to 6 membered, 4 to 6 membered, 2 to 3 membered, or 4 to 5 membered), $R^{75}$-substituted or unsubstituted cycloalkyl (e.g., $C_3$-$C_8$, $C_3$-$C_6$, $C_4$-$C_6$, or $C_5$-$C_6$), $R^{75}$-substituted or unsubstituted heterocycloalkyl (e.g., 3 to 8 membered, 3 to 6 membered, 4 to 6 membered, 4 to 5 membered, or 5 to 6 membered), $R^{75}$-substituted or unsubstituted aryl (e.g., $C_6$-$C_{10}$ or phenyl), or $R^{75}$-substituted or unsubstituted heteroaryl (e.g., 5 to 10 membered, 5 to 9 membered, or 5 to 6 membered). In embodiments, $R^{16}$ is independently hydrogen, halogen, $—CX^{16}_3$, $—CHX^{16}_2$, $—CH_2X^{16}$, $—OCX^{16}_3$, $—OCH_2X^{16}$, $—OCHX^{16}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16}$ is independently —F, —Cl, —Br, or —I. In embodiments, $R^{16}$ is independently hydrogen. In embodiments, $R^{16}$ is independently unsubstituted methyl. In embodiments, $R^{16}$ is independently unsubstituted ethyl.

$R^{75}$ is independently oxo, halogen, $—CX^{75}_3$, $—CHX^{75}_2$, $—CH_2X^{75}$, $—OCX^{75}_3$, $—OCH_2X^{75}$, $—OCHX^{75}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{76}$-substituted or unsubstituted alkyl (e.g., $C_1$-$C_8$, $C_1$-$C_6$, $C_1$-$C_4$, or $C_1$-$C_2$), $R^{76}$-substituted or unsubstituted heteroalkyl (e.g., 2 to 8 membered, 2 to 6 membered, 4 to 6 membered, 2 to 3 membered, or 4 to 5 membered), $R^{76}$-substituted or unsubstituted cycloalkyl (e.g., $C_3$-$C_8$, $C_3$-$C_6$, $C_4$-$C_6$, or $C_5$-$C_6$), $R^{76}$-substituted or unsubstituted heterocycloalkyl (e.g., 3 to 8 membered, 3 to 6 membered, 4 to 6 membered, 4 to 5 membered, or 5 to 6 membered), $R^{76}$-substituted or unsubstituted aryl (e.g., $C_6$-$C_{10}$ or phenyl), or $R^{76}$-substituted or unsubstituted heteroaryl (e.g., 5 to 10 membered, 5 to 9 membered, or 5 to 6 membered). In embodiments, $R^{75}$ is independently oxo, halogen, $—CX^{75}_3$, $—CHX^{75}_2$, $—CH_2X^{75}$, $—OCX^{75}_3$, $—OCH_2X^{75}$, $—OCHX^{75}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)\ NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75}$ is independently —F, —Cl, —Br, or —I. In embodiments, $R^{75}$ is independently unsubstituted methyl. In embodiments, $R^{75}$ is independently unsubstituted ethyl.

$R^{76}$ is independently oxo, halogen, $—CX^{76}_3$, $—CHX^{76}_2$, $—CH_2X^{76}$, $—OCX^{76}_3$, $—OCH_2X^{76}$, $—OCHX^{76}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $R^{77}$-substituted or unsubstituted alkyl (e.g., $C_1$-$C_8$, $C_1$-$C_6$, $C_1$-$C_4$, or $C_1$-$C_2$), $R^{77}$-substituted or unsubstituted heteroalkyl (e.g., 2 to 8 membered, 2 to 6 membered, 4 to 6 membered, 2 to 3 membered, or 4 to 5 membered), $R^{77}$-substituted or unsubstituted cycloalkyl (e.g., $C_3$-$C_8$, $C_3$-$C_6$, $C_4$-$C_6$, or $C_5$-$C_6$), $R^{77}$-substituted or unsubstituted heterocycloalkyl (e.g., 3 to 8 membered, 3 to 6 membered, 4 to 6 membered, 4 to 5 membered, or 5 to 6 membered), $R^{77}$-substituted or unsubstituted aryl (e.g., $C_6$-$C_{10}$ or phenyl), or $R^{77}$-substituted or unsubstituted heteroaryl (e.g., 5 to 10 membered, 5 to 9 membered, or 5 to 6 membered). In embodiments, $R^{76}$ is independently oxo, halogen, $—CX^{76}_3$, $—CHX^{76}_2$, $—CH_2X^{76}$, $—OCX^{76}_3$, $—OCH_2X^{76}$, $—OCHX^{76}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)\ NH_2$, $—NHSO_2H$, $—NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76}$ is independently —F, —Cl, —Br, or —I. In embodiments, $R^{76}$ is independently unsubstituted methyl. In embodiments, $R^{76}$ is independently unsubstituted ethyl.

$R^{77}$ is independently oxo, halogen, —$CX^{77}_3$, —$CHX^{77}_2$, —$CH_2X^{77}$, —$OCX^{77}_3$, —$OCH_2X^{77}$, —$OCHX^{77}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77}$ is independently —F, —Cl, —Br, or —I. In embodiments, $R^{77}$ is independently unsubstituted methyl. In embodiments, $R^{77}$ is independently unsubstituted ethyl.

In embodiments, $R^{16A}$ is independently hydrogen, —$CX^{16A}_3$, —$CHX^{16A}_2$, —$CH_2X^{16A}$, —CN, —COOH, —$CONH_2$, $R^{75A}$-substituted or unsubstituted alkyl (e.g., $C_1$-$C_8$, $C_1$-$C_6$, $C_1$-$C_4$, or $C_1$-$C_2$), $R^{75A}$-substituted or unsubstituted heteroalkyl (e.g., 2 to 8 membered, 2 to 6 membered, 4 to 6 membered, 2 to 3 membered, or 4 to 5 membered), $R^{75A}$-substituted or unsubstituted cycloalkyl (e.g., $C_3$-$C_8$, $C_3$-$C_6$, $C_4$-$C_6$, or $C_5$-$C_6$), $R^{75A}$-substituted or unsubstituted heterocycloalkyl (e.g., 3 to 8 membered, 3 to 6 membered, 4 to 6 membered, 4 to 5 membered, or 5 to 6 membered), $R^{75A}$-substituted or unsubstituted aryl (e.g., $C_6$-$C_{10}$ or phenyl), or $R^{75A}$-substituted or unsubstituted heteroaryl (e.g., 5 to 10 membered, 5 to 9 membered, or 5 to 6 membered). In embodiments, $R^{16A}$ is independently hydrogen, —$CX^{16A}_3$, —$CHX^{16A}_2$, —$CH_2X^{16A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16A}$ is independently —F, —Cl, —Br, or —I. In embodiments, $R^{16A}$ is independently hydrogen. In embodiments, $R^{16A}$ is independently unsubstituted methyl. In embodiments, $R^{16A}$ is independently unsubstituted ethyl.

In embodiments, $R^{16A}$ and $R^{16B}$ substituents bonded to the same nitrogen atom may optionally be joined to form a $R^{75A}$-substituted or unsubstituted heterocycloalkyl (e.g., 3 to 8 membered, 3 to 6 membered, 4 to 6 membered, 4 to 5 membered, or 5 to 6 membered) or $R^{75A}$-substituted or unsubstituted heteroaryl (e.g., 5 to 10 membered, 5 to 9 membered, or 5 to 6 membered). In embodiments, $R^{16A}$ and $R^{16B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{16A}$ and $R^{16B}$ substituents bonded to the same nitrogen atom may optionally be joined to form a $R^{75A}$-substituted or unsubstituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{75A}$ is independently oxo, halogen, —$CX^{75A}_3$, —$CHX^{75A}_2$, —$CH_2X^{75A}$, —$OCX^{75A}_3$, —$OCH_2X^{75A}$, —$OCHX^{75A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{76A}$-substituted or unsubstituted alkyl (e.g., $C_1$-$C_8$, $C_1$-$C_6$, $C_1$-$C_4$, or $C_1$-$C_2$), $R^{76A}$-substituted or unsubstituted heteroalkyl (e.g., 2 to 8 membered, 2 to 6 membered, 4 to 6 membered, 2 to 3 membered, or 4 to 5 membered), $R^{76A}$-substituted or unsubstituted cycloalkyl (e.g., $C_3$-$C_8$, $C_3$-$C_6$, $C_4$-$C_6$, or $C_5$-$C_6$), $R^{76A}$-substituted or unsubstituted heterocycloalkyl (e.g., 3 to 8 membered, 3 to 6 membered, 4 to 6 membered, 4 to 5 membered, or 5 to 6 membered), $R^{76A}$-substituted or unsubstituted aryl (e.g., $C_6$-$C_{10}$ or phenyl), or $R^{76A}$-substituted or unsubstituted heteroaryl (e.g., 5 to 10 membered, 5 to 9 membered, or 5 to 6 membered). In embodiments, $R^{75A}$ is independently oxo, halogen, —$CX^{75A}_3$, —$CHX^{75A}_2$, —$CH_2X^{75A}$, —$OCX^{75A}_3$, —$OCH_2X^{75A}$, —$OCHX^{75A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75A}$ is independently —F, —Cl, —Br, or —I. In embodiments, $R^{75A}$ is independently unsubstituted methyl. In embodiments, $R^{75A}$ is independently unsubstituted ethyl.

$R^{76A}$ is independently oxo, halogen, —$CX^{76A}_3$, —$CHX^{76A}_2$, —$CH_2X^{76A}$, —$OCX^{76A}_3$, —$OCH_2X^{76A}$, —$OCHX^{76A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{77A}$-substituted or unsubstituted alkyl (e.g., $C_1$-$C_8$, $C_1$-$C_6$, $C_1$-$C_4$, or $C_1$-$C_2$), $R^{77A}$-substituted or unsubstituted heteroalkyl (e.g., 2 to 8 membered, 2 to 6 membered, 4 to 6 membered, 2 to 3 membered, or 4 to 5 membered), $R^{77A}$-substituted or unsubstituted cycloalkyl (e.g., $C_3$-$C_8$, $C_3$-$C_6$, $C_4$-$C_6$, or $C_5$-$C_6$), $R^{77A}$-substituted or unsubstituted heterocycloalkyl (e.g., 3 to 8 membered, 3 to 6 membered, 4 to 6 membered, 4 to 5 membered, or 5 to 6 membered), $R^{77A}$-substituted or unsubstituted aryl (e.g., $C_6$-$C_{10}$ or phenyl), or $R^{77A}$-substituted or unsubstituted heteroaryl (e.g., 5 to 10 membered, 5 to 9 membered, or 5 to 6 membered). In embodiments, $R^{76A}$ is independently oxo, halogen, —$CX^{76A}_3$, —$CHX^{76A}_2$, —$CH_2X^{76A}$, —$OCX^{76A}_3$, —$OCH_2X^{76A}$, —$OCHX^{76A}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76A}$ is independently —F, —Cl, —Br, or —I. In embodiments, $R^{76A}$ is independently unsubstituted methyl. In embodiments, $R^{76A}$ is independently unsubstituted ethyl.

$R^{77A}$ is independently oxo, halogen, $—CX^{77A}_3$, $—CHX^{77A}_2$, $—CH_2X^{77A}$, $—OCX^{77A}_3$, $—OCH_2X^{77A}$, $—OCHX^{77A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77A}$ is independently —F, —Cl, —Br, or —I. In embodiments, $R^{77A}$ is independently unsubstituted methyl. In embodiments, $R^{77A}$ is independently unsubstituted ethyl.

In embodiments, $R^{16B}$ is independently hydrogen, $—CX^{16B}_3$, $—CHX^{16B}_2$, $—CH_2X^{16B}$, —CN, —COOH, $—CONH_2$, $R^{75B}$-substituted or unsubstituted alkyl (e.g., $C_1$-$C_8$, $C_1$-$C_6$, $C_1$-$C_4$, or $C_1$-$C_2$), $R^{75B}$-substituted or unsubstituted heteroalkyl (e.g., 2 to 8 membered, 2 to 6 membered, 4 to 6 membered, 2 to 3 membered, or 4 to 5 membered), $R^{75B}$-substituted or unsubstituted cycloalkyl (e.g., $C_3$-$C_8$, $C_3$-$C_6$, $C_4$-$C_6$, or $C_5$-$C_6$), $R^{75B}$-substituted or unsubstituted heterocycloalkyl (e.g., 3 to 8 membered, 3 to 6 membered, 4 to 6 membered, 4 to 5 membered, or 5 to 6 membered), $R^{75B}$-substituted or unsubstituted aryl (e.g., $C_6$-$C_{10}$ or phenyl), or $R^{75B}$-substituted or unsubstituted heteroaryl (e.g., 5 to 10 membered, 5 to 9 membered, or 5 to 6 membered). In embodiments, $R^{16B}$ is independently hydrogen, $—CX^{16B}_3$, $—CHX^{16B}_2$, $—CH_2X^{16B}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16B}$ is independently —F, —Cl, —Br, or —I. In embodiments, $R^{16B}$ is independently hydrogen. In embodiments, $R^{16B}$ is independently unsubstituted methyl. In embodiments, $R^{16B}$ is independently unsubstituted ethyl.

In embodiments, $R^{16A}$ and $R^{16B}$ substituents bonded to the same nitrogen atom may optionally be joined to form a $R^{75B}$-substituted or unsubstituted heterocycloalkyl (e.g., 3 to 8 membered, 3 to 6 membered, 4 to 6 membered, 4 to 5 membered, or 5 to 6 membered) or $R^{75B}$-substituted or unsubstituted heteroaryl (e.g., 5 to 10 membered, 5 to 9 membered, or 5 to 6 membered). In embodiments, $R^{16A}$ and $R^{16B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{16A}$ and $R^{16B}$ substituents bonded to the same nitrogen atom may optionally be joined to form a $R^{75B}$-substituted or unsubstituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{75B}$ is independently oxo, halogen, $—CX^{75B}_3$, $—CHX^{75B}_2$, $—CH_2X^{75B}$, $—OCX^{75B}_3$, $—OCH_2X^{75B}$, $—OCHX^{75B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{76B}$-substituted or unsubstituted alkyl (e.g., $C_1$-$C_8$, $C_1$-$C_6$, $C_1$-$C_4$, or $C_1$-$C_2$), $R^{76B}$-substituted or unsubstituted heteroalkyl (e.g., 2 to 8 membered, 2 to 6 membered, 4 to 6 membered, 2 to 3 membered, or 4 to 5 membered), $R^{76B}$-substituted or unsubstituted cycloalkyl (e.g., $C_3$-$C_8$, $C_3$-$C_6$, $C_4$-$C_6$, or $C_5$-$C_6$), $R^{76B}$-substituted or unsubstituted heterocycloalkyl (e.g., 3 to 8 membered, 3 to 6 membered, 4 to 6 membered, 4 to 5 membered, or 5 to 6 membered), $R^{76B}$-substituted or unsubstituted aryl (e.g., $C_6$-$C_{10}$ or phenyl), or $R^{76B}$-substituted or unsubstituted heteroaryl (e.g., 5 to 10 membered, 5 to 9 membered, or 5 to 6 membered). In embodiments, $R^{75B}$ is independently oxo, halogen, $—CX^{75B}_3$, $—CHX^{75B}_2$, $—CH_2X^{75B}$, $—OCX^{75B}_3$, $—OCH_2X^{75B}$, $—OCHX^{75B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75B}$ is independently —F, —Cl, —Br, or —I. In embodiments, $R^{75B}$ is independently unsubstituted methyl. In embodiments, $R^{75B}$ is independently unsubstituted ethyl.

$R^{76B}$ is independently oxo, halogen, $—CX^{76B}_3$, $—CHX^{76B}_2$, $—CH_2X^{76B}$, $—OCX^{76B}_3$, $—OCH_2X^{76B}$, $—OCHX^{76B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{77B}$-substituted or unsubstituted alkyl (e.g., $C_1$-$C_8$, $C_1$-$C_6$, $C_1$-$C_4$, or $C_1$-$C_2$), $R^{77B}$-substituted or unsubstituted heteroalkyl (e.g., 2 to 8 membered, 2 to 6 membered, 4 to 6 membered, 2 to 3 membered, or 4 to 5 membered), $R^{77B}$-substituted or unsubstituted cycloalkyl (e.g., $C_3$-$C_8$, $C_3$-$C_6$, $C_4$-$C_6$, or $C_5$-$C_6$), $R^{77B}$-substituted or unsubstituted heterocycloalkyl (e.g., 3 to 8 membered, 3 to 6 membered, 4 to 6 membered, 4 to 5 membered, or 5 to 6 membered), $R^{77B}$-substituted or unsubstituted aryl (e.g., $C_6$-$C_{10}$ or phenyl), or $R^{77B}$-substituted or unsubstituted heteroaryl (e.g., 5 to 10 membered, 5 to 9 membered, or 5 to 6 membered). In embodiments, $R^{76B}$ is independently oxo, halogen, $—CX^{76B}_3$, $—CHX^{76B}_2$, $—CH_2X^{76B}$, $—OCX^{76B}_3$, $—OCH_2X^{76B}$, $—OCHX^{76B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76B}$ is independently —F, —Cl, —Br, or —I. In embodiments, $R^{76B}$ is independently unsubstituted methyl. In embodiments, $R^{76B}$ is independently unsubstituted ethyl.

$R^{77B}$ is independently oxo, halogen, $—CX^{77B}_3$, $—CHX^{77B}_2$, $—CH_2X^{77B}$, $—OCX^{77B}_3$, $—OCH_2X^{77B}$, $—OCHX^{77B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77B}$ is independently —F, —Cl, —Br, or —I. In embodiments, $R^{77B}$ is independently unsubstituted methyl. In embodiments, $R^{77B}$ is independently unsubstituted ethyl.

In embodiments, $R^{16C}$ is independently hydrogen, $—CX^{16C}_3$, $—CHX^{16C}_2$, $—CH_2X^{16C}$, —CN, —COOH, $—CONH_2$, $R^{75C}$-substituted or unsubstituted alkyl (e.g., $C_1$-$C_8$, $C_1$-$C_6$, $C_1$-$C_4$, or $C_1$-$C_2$), $R^{75C}$-substituted or unsubstituted heteroalkyl (e.g., 2 to 8 membered, 2 to 6 membered, 4 to 6 membered, 2 to 3 membered, or 4 to 5 membered), $R^{75C}$-substituted or unsubstituted cycloalkyl (e.g., $C_3$-$C_8$, $C_3$-$C_6$, $C_4$-$C_6$, or $C_5$-$C_6$), $R^{75C}$-substituted or unsubstituted heterocycloalkyl (e.g., 3 to 8 membered, 3 to 6 membered, 4 to 6 membered, 4 to 5 membered, or 5 to 6 membered), $R^{75C}$-substituted or unsubstituted aryl (e.g., $C_6$-$C_{10}$ or phenyl), or $R^{75C}$-substituted or unsubstituted heteroaryl (e.g., 5 to 10 membered, 5 to 9 membered, or 5 to 6 membered). In embodiments, $R^{16C}$ is independently hydrogen, $—CX^{16C}_3$, $—CHX^{16C}_2$, $—CH_2X^{16C}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16C}$ is independently —F, —Cl, —Br, or —I. In embodiments, $R^{16C}$ is independently hydrogen. In embodiments, $R^{16C}$ is independently unsubstituted methyl. In embodiments, $R^{16C}$ is independently unsubstituted ethyl.

$R^{75C}$ is independently oxo, halogen, $—CX^{75C}_3$, $—CHX^{75C}_2$, $—CH_2X^{75C}$, $—OCX^{75C}$, $—OCH_2X^{75C}$, $—OCHX^{75C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, $R^{76C}$-substituted or unsubstituted alkyl (e.g., $C_1$-$C_8$, $C_1$-$C_6$, $C_1$-$C_4$, or $C_1$-$C_2$), $R^{76C}$-substituted or unsubstituted heteroalkyl (e.g., 2 to 8 membered, 2 to 6 membered, 4 to 6 membered, 2 to 3 membered, or 4 to 5 membered), $R^{76C}$-substituted or unsubstituted cycloalkyl (e.g., $C_3$-$C_8$, $C_3$-$C_6$, $C_4$-$C_6$, or $C_5$-$C_6$), $R^{76C}$-substituted or unsubstituted heterocycloalkyl (e.g., 3 to 8 membered, 3 to 6 membered, 4 to 6 membered, 4 to 5 membered, or 5 to 6 membered), $R^{76C}$-substituted or unsubstituted aryl (e.g., $C_6$-$C_{10}$ or phenyl), or $R^{76C}$-substituted or unsubstituted heteroaryl (e.g., 5 to 10 membered, 5 to 9 membered, or 5 to 6 membered). In embodiments, $R^{75C}$ is independently oxo, halogen, $—CX^{75C}_3$, $—CHX^{75C}_2$, $—CH_2X^{75C}$, $—OCX^{75C}$, $—OCH_2X^{75C}$, $—OCHX^{75C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75C}$ is independently —F, —Cl, —Br, or —I. In embodiments, $R^{75C}$ is independently unsubstituted methyl. In embodiments, $R^{75C}$ is independently unsubstituted ethyl.

$R^{76C}$ is independently oxo, halogen, $—CX^{76C}_3$, $—CHX^{76C}_2$, $—CH_2X^{76C}$, $—OCX^{76C}$, $—OCH_2X^{76C}$, $—OCHX^{76C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC(O)—OH, —NHOH, $R^{77C}$-substituted or unsubstituted alkyl (e.g., $C_1$-$C_8$, $C_1$-$C_6$, $C_1$-$C_4$, or $C_1$-$C_2$), $R^{77C}$-substituted or unsubstituted heteroalkyl (e.g., 2 to 8 membered, 2 to 6 membered, 4 to 6 membered, 2 to 3 membered, or 4 to 5 membered), $R^{77C}$-substituted or unsubstituted cycloalkyl (e.g., $C_3$-$C_8$, $C_3$-$C_6$, $C_4$-$C_6$, or $C_5$-$C_6$), $R^{77C}$-substituted or unsubstituted heterocycloalkyl (e.g., 3 to 8 membered, 3 to 6 membered, 4 to 6 membered, 4 to 5 membered, or 5 to 6 membered), $R^{77C}$-substituted or unsubstituted aryl (e.g., $C_6$-$C_{10}$ or phenyl), or $R^{77C}$-substituted or unsubstituted heteroaryl (e.g., 5 to 10 membered, 5 to 9 membered, or 5 to 6 membered). In embodiments, $R^{76C}$ is independently oxo, halogen, $—CX^{76C}_3$, $—CHX^{76C}_2$, $—CH_2X^{76C}$, $—OCX^{76C}_3$, $—OCH_2X^{76C}$, $—OCHX^{76C}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76C}$ is independently —F, —Cl, —Br, or —I. In embodiments, $R^{76C}$ is independently unsubstituted methyl. In embodiments, $R^{76C}$ is independently unsubstituted ethyl.

$R^{77C}$ is independently oxo, halogen, $—CX^{77C}_3$, $—CHX^{77C}_2$, $—CH_2X^{77C}$, $—OCX^{77C}$, $—OCH_2X^{77C}$, $—OCHX^{77C}_2$, —CN, —OH, $—NH_2$, —COOH, $—CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77C}$ is independently —F, —Cl, —Br, or —I. In embodiments, $R^{77C}$ is independently unsubstituted methyl. In embodiments, $R^{77C}$ is independently unsubstituted ethyl.

In embodiments, $R^{16D}$ is independently hydrogen, —$CX^{16D}_3$, —$CHX^{16D}_2$, —$CH_2X^{16D}$, —CN, —COOH, —$CONH_2$, $R^{75D}$-substituted or unsubstituted alkyl (e.g., $C_1$-$C_8$, $C_1$-$C_6$, $C_1$-$C_4$, or $C_1$-$C_2$), $R^{75D}$-substituted or unsubstituted heteroalkyl (e.g., 2 to 8 membered, 2 to 6 membered, 4 to 6 membered, 2 to 3 membered, or 4 to 5 membered), $R^{75D}$-substituted or unsubstituted cycloalkyl (e.g., $C_3$-$C_8$, $C_3$-$C_6$, $C_4$-$C_6$, or $C_5$-$C_6$), $R^{75D}$-substituted or unsubstituted heterocycloalkyl (e.g., 3 to 8 membered, 3 to 6 membered, 4 to 6 membered, 4 to 5 membered, or 5 to 6 membered), $R^{75D}$-substituted or unsubstituted aryl (e.g., $C_6$-$C_{10}$ or phenyl), or $R^{75D}$-substituted or unsubstituted heteroaryl (e.g., 5 to 10 membered, 5 to 9 membered, or 5 to 6 membered). In embodiments, $R^{16D}$ is independently hydrogen, —$CX^{16D}_3$, —$CHX^{16D}_2$, —$CH_2X^{16D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16D}$ is independently —F, —Cl, —Br, or —I. In embodiments, $R^{16D}$ is independently hydrogen. In embodiments, $R^{16D}$ is independently unsubstituted methyl. In embodiments, $R^{16D}$ is independently unsubstituted ethyl.

$R^{75D}$ is independently oxo, halogen, —$CX^{75D}_3$, —$CHX^{75D}_2$, —$CH_2X^{75D}$, —$OCX^{75D}_3$, —$OCH_2X^{75D}$, —$OCHX^{75D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{76D}$-substituted or unsubstituted alkyl (e.g., $C_1$-$C_8$, $C_1$-$C_6$, $C_1$-$C_4$, or $C_1$-$C_2$), $R^{76D}$-substituted or unsubstituted heteroalkyl (e.g., 2 to 8 membered, 2 to 6 membered, 4 to 6 membered, 2 to 3 membered, or 4 to 5 membered), $R^{76D}$-substituted or unsubstituted cycloalkyl (e.g., $C_3$-$C_8$, $C_3$-$C_6$, $C_4$-$C_6$, or $C_5$-$C_6$), $R^{76D}$-substituted or unsubstituted heterocycloalkyl (e.g., 3 to 8 membered, 3 to 6 membered, 4 to 6 membered, 4 to 5 membered, or 5 to 6 membered), $R^{76D}$-substituted or unsubstituted aryl (e.g., $C_6$-$C_{10}$ or phenyl), or $R^{76D}$-substituted or unsubstituted heteroaryl (e.g., 5 to 10 membered, 5 to 9 membered, or 5 to 6 membered). In embodiments, $R^{75D}$ is independently oxo, halogen, —$CX^{75D}_3$, —$CHX^{75D}_2$, —$CH_2X^{75D}$, —$OCX^{75D}_3$, —$OCH_2X^{75D}$, —$OCHX^{75D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75D}$ is independently —F, —Cl, —Br, or —I. In embodiments, $R^{75D}$ is independently unsubstituted methyl. In embodiments, $R^{75D}$ is independently unsubstituted ethyl.

$R^{76D}$ is independently oxo, halogen, —$CX^{76D}_3$, —$CHX^{76D}_2$, —$CH_2X^{76D}$, —$OCX^{76D}_3$, —$OCH_2X^{76D}$, —$OCHX^{76D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{77D}$-substituted or unsubstituted alkyl (e.g., $C_1$-$C_8$, $C_1$-$C_6$, $C_1$-$C_4$, or $C_1$-$C_2$), $R^{77D}$-substituted or unsubstituted heteroalkyl (e.g., 2 to 8 membered, 2 to 6 membered, 4 to 6 membered, 2 to 3 membered, or 4 to 5 membered), $R^{77D}$-substituted or unsubstituted cycloalkyl (e.g., $C_3$-$C_8$, $C_3$-$C_6$, $C_4$-$C_6$, or $C_5$-$C_6$), $R^{77D}$-substituted or unsubstituted heterocycloalkyl (e.g., 3 to 8 membered, 3 to 6 membered, 4 to 6 membered, 4 to 5 membered, or 5 to 6 membered), $R^{77D}$-substituted or unsubstituted aryl (e.g., $C_6$-$C_{10}$ or phenyl), or $R^{77D}$-substituted or unsubstituted heteroaryl (e.g., 5 to 10 membered, 5 to 9 membered, or 5 to 6 membered). In embodiments, $R^{76D}$ is independently oxo, halogen, —$CX^{76D}_3$, —$CHX^{76D}_2$, —$CH_2X^{76D}$, —$OCX^{76D}_3$, —$OCH_2X^{76D}$, —$OCHX^{76D}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76D}$ is independently —F, —Cl, —Br, or —I. In embodiments, $R^{76D}$ is independently unsubstituted methyl. In embodiments, $R^{76D}$ is independently unsubstituted ethyl.

$R^{77D}$ is independently oxo, halogen, —$CX^{77D}_3$, —$CHX^{77D}_2$, —$CH_2X^{77D}$, —$OCX^{77D}_3$, —$OCH_2X^{77D}$, —$OCHX^{77D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)—$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77D}$ is independently —F, —Cl, —Br, or —I. In embodiments, $R^{77D}$ is independently unsubstituted methyl. In embodiments, $R^{77D}$ is independently unsubstituted ethyl.

In embodiments, $R^{17}$ is hydrogen. In embodiments, $R^{17}$ is halogen. In embodiments, $R^{17}$ is $-CX^{17}_3$. In embodiments, $R^{17}$ is $-CHX^{17}_2$. In embodiments, $R^{17}$ is $-CH_2X^{17}$. In embodiments, $R^{17}$ is $-CN$. In embodiments, $R^{17}$ is $-SO_{n17}R^{17D}$. In embodiments, $R^{17}$ is $-SO_{v17}NR^{17A}R^{17B}$. In embodiments, $R^{17}$ is $-N-NR^{17A}R^{17B}$. In embodiments, $R^{17}$ is $-ONR^{17A}R^{17B}$. In embodiments, $R^{17}$ is $-NHC=(O)NHNR^{17A}R^{17B}$. In embodiments, $R^{17}$ is $-NHC(O)NR^{17A}R^{17B}$. In embodiments, $R^{17}$ is $-N(O)_{m17}$. In embodiments, $R^{17}$ is $-NR^{17A}R^{17B}$. In embodiments, $R^{17}$ is $-C(O)R^{17C}$. In embodiments, $R^{17}$ is $-C(O)-OR^{17C}$. In embodiments, $R^{17}$ is $-C(O)NR^{17A}R^{17B}$. In embodiments, $R^{17}$ is $-OR^{17D}$. In embodiments, $R^{17}$ is $-NR^{17A}SO_2R^{17D}$. In embodiments, $R^{17}$ is $-NR^{17A}C(O)R^{17C}$. In embodiments, $R^{17}$ is $-NR^{17A}C(O)OR^{17C}$. In embodiments, $R^{17}$ is $-NR^{17A}OR^{17C}$. In embodiments, $R^{17}$ is $-OCX^{17}_3$. In embodiments, $R^{17}$ is $-OCHX^{17}_2$. In embodiments, $R^{17}$ is independently —OH. In embodiments, $R^{17}$ is independently $-NH_2$. In embodiments, $R^{17}$ is independently —COOH. In embodiments, $R^{17}$ is independently $-CONH_2$. In embodiments, $R^{17}$ is independently $-NO_2$. In embodiments, $R^{17}$ is independently —SH. In embodiments, $R^{17}$ is independently $-CF_3$. In embodiments, $R^{17}$ is independently $-CHF_2$. In embodiments, $R^{17}$ is independently $-CH_2F$. In embodiments, $R^{17}$ is independently $-OCF_3$. In embodiments, $R^{17}$ is independently $-OCH_2F$. In embodiments, $R^{17}$ is independently $-OCHF_2$. In embodiments, $R^{17}$ is independently $-OCH_3$. In embodiments, $R^{17}$ is independently $-OCH_2CH_3$. In embodiments, $R^{17}$ is independently $-OCH_2CH_2CH_3$. In embodiments, $R^{17}$ is independently $-OCH(CH_3)_2$. In embodiments, $R^{17}$ is independently $-OC(CH_3)_3$. In embodiments, $R^{17}$ is independently $-SCH_3$. In embodiments, $R^{17}$ is independently $-SCH_2CH_3$. In embodiments, $R^{17}$ is independently $-SCH_2CH_2CH_3$. In embodiments, $R^{17}$ is independently $-SCH(CH_3)_2$. In embodiments, $R^{17}$ is independently $-SC(CH_3)_3$. In embodiments, $R^{17}$ is independently $-CH_3$. In embodiments, $R^{17}$ is independently $-CH_2CH_3$. In embodiments, $R^{17}$ is independently $-CH_2CH_2CH_3$. In embodiments, $R^{17}$ is independently $-CH(CH_3)_2$. In embodiments, $R^{17}$ is independently $-C(CH_3)_3$. In embodiments, $R^{17}$ is independently —F. In embodiments, $R^{17}$ is independently —Cl. In embodiments, $R^{17}$ is independently —Br. In embodiments, $R^{17}$ is independently —I.

In embodiments, $R^{17}$ is independently substituted or unsubstituted alkyl (e.g., $C_1$-$C_8$, $C_1$-$C_6$, $C_1$-$C_4$, or $C_1$-$C_2$). In embodiments, $R^{17}$ is independently substituted alkyl (e.g., $C_1$-$C_8$, $C_1$-$C_6$, $C_1$-$C_4$, or $C_1$-$C_2$). In embodiments, $R^{17}$ is independently unsubstituted alkyl (e.g., $C_1$-$C_8$, $C_1$-$C_6$, $C_1$-$C_4$, or $C_1$-$C_2$). In embodiments, $R^{17}$ is independently unsubstituted methyl. In embodiments, $R^{17}$ is independently unsubstituted ethyl. In embodiments, $R^{17}$ is independently unsubstituted propyl. In embodiments, $R^{17}$ is independently unsubstituted isopropyl. In embodiments, $R^{17}$ is independently unsubstituted tert-butyl. In embodiments, $R^{17}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17}$ is independently substituted heteroalkyl (e.g., 2 to 8 membered, 2 to 6 membered, 4 to 6 membered, 2 to 3 membered, or 4 to 5 membered). In embodiments, $R^{17}$ is independently unsubstituted heteroalkyl (e.g., 2 to 8 membered, 2 to 6 membered, 4 to 6 membered, 2 to 3 membered, or 4 to 5 membered). In embodiments, $R^{17}$ is independently substituted or unsubstituted cycloalkyl (e.g., $C_3$-$C_8$, $C_3$-$C_6$, $C_4$-$C_6$, or $C_5$-$C_6$). In embodiments, $R^{17}$ is independently substituted cycloalkyl (e.g., $C_3$-$C_8$, $C_3$-$C_6$, $C_4$-$C_6$, or $C_5$-$C_6$). In embodiments, $R^{17}$ is independently unsubstituted cycloalkyl (e.g., $C_3$-$C_8$, $C_3$-$C_6$, $C_4$-$C_6$, or $C_5$-$C_6$). In embodiments, $R^{17}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17}$ is independently substituted heterocycloalkyl (e.g., 3 to 8 membered, 3 to 6 membered, 4 to 6 membered, 4 to 5 membered, or 5 to 6 membered). In embodiments, $R^{17}$ is independently unsubstituted heterocycloalkyl (e.g., 3 to 8 membered, 3 to 6 membered, 4 to 6 membered, 4 to 5 membered, or 5 to 6 membered). In embodiments, $R^{17}$ is independently substituted or unsubstituted aryl (e.g., $C_6$-$C_{10}$ or phenyl). In embodiments, $R^{17}$ is independently substituted aryl (e.g., $C_6$-$C_{10}$ or phenyl). In embodiments, $R^{17}$ is independently unsubstituted aryl (e.g., $C_6$-$C_{10}$ or phenyl). In embodiments, $R^{17}$ is independently substituted or unsubstituted heteroaryl (e.g., 5 to 10 membered, 5 to 9 membered, or 5 to 6 membered). In embodiments, $R^{17}$ is independently substituted heteroaryl (e.g., 5 to 10 membered, 5 to 9 membered, or 5 to 6 membered). In embodiments, $R^{17}$ is independently unsubstituted heteroaryl (e.g., 5 to 10 membered, 5 to 9 membered, or 5 to 6 membered).

In embodiments, $R^{17A}$ is independently hydrogen. In embodiments, $R^{17A}$ is independently $-CX^{17A}_3$. In embodiments, $R^{17A}$ is independently $-CHX^{17A}_2$. In embodiments, $R^{17A}$ is independently $-CH_2X^{17A}$. In embodiments, $R^{17A}$ is independently —CN. In embodiments, $R^{17A}$ is independently —COOH. In embodiments, $R^{17A}$ is independently $-CONH_2$. In embodiments, $X^{17A}$ is independently —F, —Cl, —Br, or —I.

In embodiments, $R^{17A}$ is independently substituted or unsubstituted alkyl (e.g., $C_1$-$C_8$, $C_1$-$C_6$, $C_1$-$C_4$, or $C_1$-$C_2$). In embodiments, $R^{17A}$ is independently substituted alkyl (e.g., $C_1$-$C_8$, $C_1$-$C_6$, $C_1$-$C_4$, or $C_1$-$C_2$). In embodiments, $R^{17A}$ is independently unsubstituted alkyl (e.g., $C_1$-$C_8$, $C_1$-$C_6$, $C_1$-$C_4$, or $C_1$-$C_2$). In embodiments, $R^{17A}$ is independently unsubstituted methyl. In embodiments, $R^{17A}$ is independently unsubstituted ethyl. In embodiments, $R^{17A}$ is independently unsubstituted propyl. In embodiments, $R^{17A}$ is independently unsubstituted isopropyl. In embodiments, $R^{17A}$ is independently unsubstituted tert-butyl. In embodiments, $R^{17A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17A}$ is independently substituted heteroalkyl (e.g., 2 to 8 membered, 2 to 6 membered, 4 to 6 membered, 2 to 3 membered, or 4 to 5 membered). In embodiments, $R^{17A}$ is independently unsubstituted heteroalkyl (e.g., 2 to 8 membered, 2 to 6 membered, 4 to 6 membered, 2 to 3 membered, or 4 to 5 membered). In embodiments, $R^{17A}$ is independently substituted or unsubstituted cycloalkyl (e.g., $C_3$-$C_8$, $C_3$-$C_6$, $C_4$-$C_6$, or $C_5$-$C_6$). In embodiments, $R^{17A}$ is independently substituted cycloalkyl (e.g., $C_3$-$C_8$, $C_3$-$C_6$, $C_4$-$C_6$, or $C_5$-$C_6$). In embodiments, $R^{17A}$ is independently unsubstituted cycloalkyl (e.g., $C_3$-$C_8$, $C_3$-$C_6$, $C_4$-$C_6$, or $C_5$-$C_6$). In embodiments, $R^{17A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17A}$ is independently substituted heterocycloalkyl (e.g., 3 to 8 membered, 3 to 6 membered, 4 to 6 membered, 4 to 5 membered, or 5 to 6 membered). In embodiments, $R^{17A}$ is independently unsubstituted heterocycloalkyl (e.g., 3 to 8 membered, 3 to 6 membered, 4 to 6 membered, 4 to 5 membered, or 5 to 6 membered). In embodiments, $R^{17A}$ is independently substituted or unsubstituted aryl (e.g., $C_6$-$C_{10}$ or phenyl). In embodiments, $R^{17A}$ is independently substituted aryl (e.g., $C_6$-$C_{10}$ or phenyl). In embodiments, $R^{17A}$ is independently unsubstituted aryl (e.g., $C_6$-$C_{10}$ or phenyl). In embodiments, $R^{17A}$ is independently substituted or unsubstituted heteroaryl (e.g., 5 to 10 membered, 5 to 9 membered, or 5 to 6 membered). In embodiments, $R^{17A}$ is independently substituted heteroaryl (e.g., 5 to 10 membered, 5 to 9 membered, or 5 to 6 membered). In embodiments, $R^{17A}$ is independently unsubstituted heteroaryl (e.g., 5 to 10 membered, 5 to 9 membered, or 5 to 6 membered).

In embodiments, $R^{17B}$ is independently hydrogen. In embodiments, $R^{17B}$ is independently —$CX^{17B}_3$. In embodiments, $R^{17B}$ is independently —$CHX^{17B}_2$. In embodiments, $R^{17B}$ is independently —$CH_2X^{17B}$. In embodiments, $R^{17B}$ is independently —CN. In embodiments, $R^{17B}$ is independently —COOH. In embodiments, $R^{17B}$ is independently —$CONH_2$. In embodiments, $X^{17B}$ is independently —F, —Cl, —Br, or —I.

In embodiments, $R^{17B}$ is independently substituted or unsubstituted alkyl (e.g., $C_1$-$C_8$, $C_1$-$C_6$, $C_1$-$C_4$, or $C_1$-$C_2$). In embodiments, $R^{17B}$ is independently substituted alkyl (e.g., $C_1$-$C_8$, $C_1$-$C_6$, $C_1$-$C_4$, or $C_1$-$C_2$). In embodiments, $R^{17B}$ is independently unsubstituted alkyl (e.g., $C_1$-$C_8$, $C_1$-$C_6$, $C_1$-$C_4$, or $C_1$-$C_2$). In embodiments, $R^{17B}$ is independently unsubstituted methyl. In embodiments, $R^{17B}$ is independently unsubstituted ethyl. In embodiments, $R^{17B}$ is independently unsubstituted propyl. In embodiments, $R^{17B}$ is independently unsubstituted isopropyl. In embodiments, $R^{17B}$ is independently unsubstituted tert-butyl. In embodiments, $R^{17B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17B}$ is independently substituted heteroalkyl (e.g., 2 to 8 membered, 2 to 6 membered, 4 to 6 membered, 2 to 3 membered, or 4 to 5 membered). In embodiments, $R^{17B}$ is independently unsubstituted heteroalkyl (e.g., 2 to 8 membered, 2 to 6 membered, 4 to 6 membered, 2 to 3 membered, or 4 to 5 membered). In embodiments, $R^{17B}$ is independently substituted or unsubstituted cycloalkyl (e.g., $C_3$-$C_8$, $C_3$-$C_6$, $C_4$-$C_6$, or $C_5$-$C_6$). In embodiments, $R^{17B}$ is independently substituted cycloalkyl (e.g., $C_3$-$C_8$, $C_3$-$C_6$, $C_4$-$C_6$, or $C_5$-$C_6$). In embodiments, $R^{17B}$ is independently unsubstituted cycloalkyl (e.g., $C_3$-$C_8$, $C_3$-$C_6$, $C_4$-$C_6$, or $C_5$-$C_6$). In embodiments, $R^{17B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17B}$ is independently substituted heterocycloalkyl (e.g., 3 to 8 membered, 3 to 6 membered, 4 to 6 membered, 4 to 5 membered, or 5 to 6 membered). In embodiments, $R^{17B}$ is independently unsubstituted heterocycloalkyl (e.g., 3 to 8 membered, 3 to 6 membered, 4 to 6 membered, 4 to 5 membered, or 5 to 6 membered). In embodiments, $R^{17B}$ is independently substituted or unsubstituted aryl (e.g., $C_6$-$C_{10}$ or phenyl). In embodiments, $R^{17B}$ is independently substituted aryl (e.g., $C_6$-$C_{10}$ or phenyl). In embodiments, $R^{17B}$ is independently unsubstituted aryl (e.g., $C_6$-$C_{10}$ or phenyl). In embodiments, $R^{17B}$ is independently substituted or unsubstituted heteroaryl (e.g., 5 to 10 membered, 5 to 9 membered, or 5 to 6 membered). In embodiments, $R^{17B}$ is independently substituted heteroaryl (e.g., 5 to 10 membered, 5 to 9 membered, or 5 to 6 membered). In embodiments, $R^{17B}$ is independently unsubstituted heteroaryl (e.g., 5 to 10 membered, 5 to 9 membered, or 5 to 6 membered).

In embodiments, $R^{17A}$ and $R^{17B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{17A}$ and $R^{17B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{17A}$ and $R^{17B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{17A}$ and $R^{17B}$ substituents bonded to the same nitrogen atom may be joined to form a substituted or unsubstituted heteroaryl (e.g., 5 to 10 membered, 5 to 9 membered, or 5 to 6 membered). In embodiments, $R^{17A}$ and $R^{17B}$ substituents bonded to the same nitrogen atom may be joined to form a substituted heteroaryl (e.g., 5 to 10 membered, 5 to 9 membered, or 5 to 6 membered). In embodiments, $R^{17A}$ and $R^{17B}$ substituents bonded to the same nitrogen atom may be joined to form an unsubstituted heteroaryl (e.g., 5 to 10 membered, 5 to 9 membered, or 5 to 6 membered).

In embodiments, $R^{17C}$ is independently hydrogen. In embodiments, $R^{17C}$ is independently —$CX^{17C}_3$. In embodiments, $R^{17C}$ is independently —$CHX^{17C}_2$. In embodiments, $R^{17C}$ is independently —$CH_2X^{17C}$. In embodiments, $R^{17C}$ is independently —CN. In embodiments, $R^{17C}$ is independently —COOH. In embodiments, $R^{17C}$ is independently —$CONH_2$. In embodiments, $X^{17C}$ is independently —F, —Cl, —Br, or —I.

In embodiments, $R^{17C}$ is independently substituted or unsubstituted alkyl (e.g., $C_1$-$C_8$, $C_1$-$C_6$, $C_1$-$C_4$, or $C_1$-$C_2$). In embodiments, $R^{17C}$ is independently substituted alkyl (e.g., $C_1$-$C_8$, $C_1$-$C_6$, $C_1$-$C_4$, or $C_1$-$C_2$). In embodiments, $R^{17C}$ is independently unsubstituted alkyl (e.g., $C_1$-$C_8$, $C_1$-$C_6$, $C_1$-$C_4$, or $C_1$-$C_2$). In embodiments, $R^{17C}$ is independently unsubstituted methyl. In embodiments, $R^{17C}$ is independently unsubstituted ethyl. In embodiments, $R^{17C}$ is independently unsubstituted propyl. In embodiments, $R^{17C}$ is independently unsubstituted isopropyl. In embodiments, $R^{17C}$ is independently unsubstituted tert-butyl. In embodiments, $R^{17C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17C}$ is independently substituted heteroalkyl (e.g., 2 to 8 membered, 2 to 6 membered, 4 to 6 membered, 2 to 3 membered, or 4 to 5 membered). In embodiments, $R^{17C}$ is independently unsubstituted heteroalkyl (e.g., 2 to 8 membered, 2 to 6 membered, 4 to 6 membered, 2 to 3 membered, or 4 to 5 membered). In embodiments, $R^{17C}$ is independently substituted or unsubstituted cycloalkyl (e.g., $C_3$-$C_8$, $C_3$-$C_6$, $C_4$-$C_6$, or $C_5$-$C_6$). In embodiments, $R^{17C}$ is independently substituted cycloalkyl (e.g., $C_3$-$C_8$, $C_3$-$C_6$, $C_4$-$C_6$, or $C_5$-$C_6$). In embodiments, $R^{17C}$ is independently unsubstituted cycloalkyl (e.g., $C_3$-$C_8$, $C_3$-$C_6$, $C_4$-$C_6$, or $C_5$-$C_6$). In embodiments, $R^{17C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17C}$ is independently substituted heterocycloalkyl (e.g., 3 to 8 membered, 3 to 6 membered, 4 to 6 membered, 4 to 5 membered, or 5 to 6 membered). In embodiments, $R^{17C}$ is independently unsubstituted heterocycloalkyl (e.g., 3 to 8 membered, 3 to 6 membered, 4 to 6 membered, 4 to 5 membered, or 5 to 6 membered). In embodiments, $R^{17C}$ is independently substituted or unsubstituted aryl (e.g., $C_6$-$C_{10}$ or phenyl). In embodiments, $R^{17C}$ is independently substituted aryl (e.g., $C_6$-$C_{10}$ or phenyl). In embodiments, $R^{17C}$ is independently unsubstituted aryl (e.g., $C_6$-$C_{10}$ or phenyl). In embodiments, $R^{17C}$ is independently substituted or unsubstituted heteroaryl (e.g., 5 to 10 membered, 5 to 9 membered, or 5 to 6 membered). In embodiments, $R^{17C}$ is independently substituted heteroaryl (e.g., 5 to 10 membered, 5 to 9 membered, or 5 to 6 membered). In embodiments, $R^{17C}$ is independently unsubstituted heteroaryl (e.g., 5 to 10 membered, 5 to 9 membered, or 5 to 6 membered).

In embodiments, $R^{17D}$ is independently hydrogen. In embodiments, $R^{17D}$ is independently —$CX^{17D}_3$. In embodiments, $R^{17D}$ is independently —$CHX^{17D}_2$. In embodiments, $R^{17D}$ is independently —$CH_2X^{17D}$. In embodiments, $R^{17D}$ is independently —CN. In embodiments, $R^{17D}$ is independently —COOH. In embodiments, $R^{17D}$ is independently —$CONH_2$. In embodiments, $X^{17D}$ independently —F, —Cl, —Br, or —I.

In embodiments, $R^{17D}$ is independently substituted or unsubstituted alkyl (e.g., $C_1$-$C_8$, $C_1$-$C_6$, $C_1$-$C_4$, or $C_1$-$C_2$). In embodiments, $R^{17D}$ is independently substituted alkyl (e.g., $C_1$-$C_8$, $C_1$-$C_6$, $C_1$-$C_4$, or $C_1$-$C_2$). In embodiments, $R^{17D}$ is independently unsubstituted alkyl (e.g., $C_1$-$C_8$, $C_1$-$C_6$, $C_1$-$C_4$, or $C_1$-$C_2$). In embodiments, $R^{17D}$ is independently unsubstituted methyl. In embodiments, $R^{17D}$ is independently unsubstituted ethyl. In embodiments, $R^{17D}$ is independently unsubstituted propyl. In embodiments, $R^{17D}$ is independently unsubstituted isopropyl. In embodiments, $R^{17D}$ is independently unsubstituted tert-butyl. In embodiments, $R^{17D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17D}$ is independently substituted heteroalkyl (e.g., 2 to 8 membered, 2 to 6 membered, 4 to 6 membered, 2 to 3 membered, or 4 to 5 membered). In embodiments, $R^{17D}$ is independently unsubstituted heteroalkyl (e.g., 2 to 8 membered, 2 to 6 membered, 4 to 6 membered, 2 to 3 membered, or 4 to 5 membered). In embodiments, $R^{7D}$ is independently substituted or unsubstituted cycloalkyl (e.g., $C_3$-$C_8$, $C_3$-$C_6$, $C_4$-$C_6$, or $C_5$-$C_6$). In embodiments, $R^{17D}$ is independently substituted cycloalkyl (e.g., $C_3$-$C_8$, $C_3$-$C_6$, $C_4$-$C_6$, or $C_5$-$C_6$). In embodiments, $R^{17D}$ is independently unsubstituted cycloalkyl (e.g., $C_3$-$C_8$, $C_3$-$C_6$, $C_4$-$C_6$, or $C_5$-$C_6$). In embodiments, $R^{17D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17D}$ is independently substituted heterocycloalkyl (e.g., 3 to 8 membered, 3 to 6 membered, 4 to 6 membered, 4 to 5 membered, or 5 to 6 membered). In embodiments, $R^{7D}$ is independently unsubstituted heterocycloalkyl (e.g., 3 to 8 membered, 3 to 6 membered, 4 to 6 membered, 4 to 5 membered, or 5 to 6 membered). In embodiments, $R^{17D}$ is independently substituted or unsubstituted aryl (e.g., $C_6$-$C_{10}$ or phenyl). In embodiments, $R^{17D}$ is independently substituted aryl (e.g., $C_6$-$C_{10}$ or phenyl). In embodiments, $R^{17D}$ is independently unsubstituted aryl (e.g., $C_6$-$C_{10}$ or phenyl). In embodiments, $R^{17D}$ is independently substituted or unsubstituted heteroaryl (e.g., 5 to 10 membered, 5 to 9 membered, or 5 to 6 membered). In embodiments, $R^{7D}$ is independently substituted heteroaryl (e.g., 5 to 10 membered, 5 to 9 membered, or 5 to 6 membered). In embodiments, $R^{17D}$ is independently unsubstituted heteroaryl (e.g., 5 to 10 membered, 5 to 9 membered, or 5 to 6 membered).

In embodiments, $R^{17}$ is independently hydrogen, halogen, —$CX^{173}$, —$CHX^{172}$, —$CH_2X^{17}$, —$OCX^{173}$, —$OCH_2X^{17}$, —$OCHX^{172}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{78}$-substituted or unsubstituted alkyl (e.g., $C_1$-$C_8$, $C_1$-$C_6$, $C_1$-$C_4$, or $C_1$-$C_2$), $R^{78}$-substituted or unsubstituted heteroalkyl (e.g., 2 to 8 membered, 2 to 6 membered, 4 to 6 membered, 2 to 3 membered, or 4 to 5 membered), $R^{78}$-substituted or unsubstituted cycloalkyl (e.g., $C_3$-$C_8$, $C_3$-$C_6$, $C_4$-$C_6$, or $C_5$-$C_6$), $R^{78}$-substituted or unsubstituted heterocycloalkyl (e.g., 3 to 8 membered, 3 to 6 membered, 4 to 6 membered, 4 to 5 membered, or 5 to 6 membered), $R^{78}$-substituted or unsubstituted aryl (e.g., $C_6$-$C_{10}$ or phenyl), or $R^{78}$-substituted or unsubstituted heteroaryl (e.g., 5 to 10 membered, 5 to 9 membered, or 5 to 6 membered). In embodiments, $R^{17}$ is independently hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17}$ is independently —F, —Cl, —Br, or —I. In embodiments, $R^{17}$ is independently hydrogen. In embodiments, $R^{17}$ is independently unsubstituted methyl. In embodiments, $R^{17}$ is independently unsubstituted ethyl.

$R^{78}$ is independently oxo, halogen, —$CX^{78}_3$, —$CHX^{78}_2$, —$CH_2X^{78}$, —$OCX^{78}_3$, —$OCH_2X^{78}$, —$OCHX^{78}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{79}$-substituted or unsubstituted alkyl (e.g., $C_1$-$C_8$, $C_1$-$C_6$, $C_1$-$C_4$, or $C_1$-$C_2$), $R^{79}$-substituted or unsubstituted heteroalkyl (e.g., 2 to 8 membered, 2 to 6 membered, 4 to 6 membered, 2 to 3 membered, or 4 to 5 membered), $R^{79}$-substituted or unsubstituted cycloalkyl (e.g., $C_3$-$C_8$, $C_3$-$C_6$, $C_4$-$C_6$, or $C_5$-$C_6$), $R^{79}$-substituted or unsubstituted heterocycloalkyl (e.g., 3 to 8 membered, 3 to 6 membered, 4 to 6 membered, 4 to 5 membered, or 5 to 6 membered), $R^{79}$-substituted or unsubstituted aryl (e.g., $C_6$-$C_{10}$ or phenyl), or $R^{79}$-substituted or unsubstituted heteroaryl (e.g., 5 to 10 membered, 5 to 9 membered, or 5 to 6 membered). In embodiments, $R^{78}$ is independently oxo, halogen, —$CX^{78}_3$, —$CHX^{78}_2$, —$CH_2X^{78}$, —$OCX^{78}_3$, —$OCH_2X^{78}$, —$OCHX^{78}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78}$ is independently —F, —Cl, —Br, or —I. In embodiments, $R^{78}$ is independently unsubstituted methyl. In embodiments, $R^{78}$ is independently unsubstituted ethyl.

$R^{79}$ is independently oxo, halogen, —$CX^{79}_3$, —$CHX^{79}_2$, —$CH_2X^{79}$, —$OCX^{79}_3$, —$OCH_2X^{79}$, —$OCHX^{79}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{80}$-substituted or unsubstituted alkyl (e.g., $C_1$-$C_8$, $C_1$-$C_6$, $C_1$-$C_4$, or $C_1$-$C_2$), $R^{80}$-substituted or unsubstituted heteroalkyl (e.g., 2 to 8 membered, 2 to 6 membered, 4 to 6 membered, 2 to 3 membered, or 4 to 5 membered), $R^{80}$-substituted or unsubstituted cycloalkyl (e.g., $C_3$-$C_8$, $C_3$-$C_6$, $C_4$-$C_6$, or $C_5$-$C_6$), $R^{80}$-substituted or unsubstituted heterocycloalkyl (e.g., 3 to 8 membered, 3 to 6 membered, 4 to 6 membered, 4 to 5 membered, or 5 to 6 membered), $R^{80}$-substituted or unsubstituted aryl (e.g., $C_6$-$C_{10}$ or phenyl), or $R^{80}$-substituted or unsubstituted heteroaryl (e.g., 5 to 10 membered, 5 to 9 membered, or 5 to 6 membered). In embodiments, $R^{79}$ is independently oxo, halogen, —$CX^{79}_3$, —$CHX^{79}_2$, —$CH_2X^{79}$, —$OCX^{79}_3$, —$OCH_2X^{79}$, —$OCHX^{79}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{79}$ is independently —F, —Cl, —Br, or —I. In embodiments, $R^{79}$ is independently unsubstituted methyl. In embodiments, $R^{79}$ is independently unsubstituted ethyl.

$R^{80}$ is independently oxo, halogen, —$CX^{80}_3$, —$CHX^{80}_2$, —$CH_2X^{80}$, —$OCX^{80}_3$, —$OCH_2X^{80}$, —$OCHX^{80}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{80}$ is independently —F, —Cl, —Br, or —I. In embodiments, $R^{80}$ is independently unsubstituted methyl. In embodiments, $R^{80}$ is independently unsubstituted ethyl.

In embodiments, $R^{17A}$ is independently hydrogen, —$CX^{17A}_3$, —$CHX^{17A}_2$, —$CH_2X^{17A}$, —CN, —COOH, —$CONH_2$, $R^{78A}$-substituted or unsubstituted alkyl (e.g., $C_1$-$C_8$, $C_1$-$C_6$, $C_1$-$C_4$, or $C_1$-$C_2$), $R^{78A}$-substituted or unsubstituted heteroalkyl (e.g., 2 to 8 membered, 2 to 6 membered, 4 to 6 membered, 2 to 3 membered, or 4 to 5 membered), $R^{78A}$-substituted or unsubstituted cycloalkyl (e.g., $C_3$-$C_8$, $C_3$-$C_6$, $C_4$-$C_6$, or $C_5$-$C_6$), $R^{78A}$-substituted or unsubstituted heterocycloalkyl (e.g., 3 to 8 membered, 3 to 6 membered, 4 to 6 membered, 4 to 5 membered, or 5 to 6 membered), $R^{78A}$-substituted or unsubstituted aryl (e.g., $C_6$-$C_{10}$ or phenyl), or $R^{78A}$-substituted or unsubstituted heteroaryl (e.g., 5 to 10 membered, 5 to 9 membered, or 5 to 6 membered). In embodiments, $R^{17A}$ is independently hydrogen, —$CX^{17A}_3$, —$CHX^{17A}_2$, —$CH_2X^{17A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17A}$ is independently —F, —Cl, —Br, or —I. In embodiments, $R^{17A}$ is independently hydrogen. In embodiments, $R^{17A}$ is independently unsubstituted methyl. In embodiments, $R^{17A}$ is independently unsubstituted ethyl.

In embodiments, $R^{17A}$ and $R^{17B}$ substituents bonded to the same nitrogen atom may optionally be joined to form a $R^{78A}$-substituted or unsubstituted heterocycloalkyl (e.g., 3 to 8 membered, 3 to 6 membered, 4 to 6 membered, 4 to 5 membered, or 5 to 6 membered) or $R^{78A}$-substituted or unsubstituted heteroaryl (e.g., 5 to 10 membered, 5 to 9 membered, or 5 to 6 membered). In embodiments, $R^{17A}$ and $R^{17B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{17A}$ and $R^{17B}$ substituents bonded to the same nitrogen atom may optionally be joined to form a $R^{78A}$-substituted or unsubstituted heterocycloalkyl (e.g., 3 to 8 membered, 3 to 6 membered, 4 to 6 membered, 4 to 5 membered, or 5 to 6 membered). In embodiments, $R^{17A}$ and $R^{17B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{78A}$ is independently oxo, halogen, —$CX^{78A}_3$, —$CHX^{78A}_2$, —$CH_2X^{78A}$, —$OCX^{78A}_3$, —$OCH_2X^{78A}$, —$OCHX^{78A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{79A}$-substituted or unsubstituted alkyl (e.g., $C_1$-$C_8$, $C_1$-$C_6$, $C_1$-$C_4$, or $C_1$-$C_2$), $R^{79}$-substituted or unsubstituted heteroalkyl (e.g., 2 to 8 membered, 2 to 6 membered, 4 to 6 membered, 2 to 3 membered, or 4 to 5 membered), $R^{79A}$-substituted or unsubstituted cycloalkyl (e.g., $C_3$-$C_8$, $C_3$-$C_6$, $C_4$-$C_6$, or $C_5$-$C_6$), $R^{79A}$-substituted or unsubstituted heterocycloalkyl (e.g., 3 to 8 membered, 3 to 6 membered, 4 to 6 membered, 4 to 5 membered, or 5 to 6 membered), $R^{79A}$-substituted or unsubstituted aryl (e.g., $C_6$-$C_{10}$ or phenyl), or $R^{79A}$-substituted or unsubstituted heteroaryl (e.g., 5 to 10 membered, 5 to 9 membered, or 5 to 6 membered). In embodiments, $R^{78A}$ is independently oxo, halogen, —$CX^{78A}_3$, —$CHX^{78A}_2$, —$CH_2X^{78A}$, —$OCX^{78A}_3$, —$OCH_2X^{78A}$, —$OCHX^{78A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78A}$ is independently —F, —Cl, —Br, or —I.

In embodiments, $R^{78A}$ is independently unsubstituted methyl. In embodiments, $R^{78A}$ is independently unsubstituted ethyl.

$R^{79A}$ is independently oxo, halogen, $—CX^{79A}_3$, $—CHX^{79A}_2$, $—CH_2X^{79A}$, $—OCX^{79A}_3$, $—OCH_2X^{79A}$, $—OCHX^{79A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{80A}$-substituted or unsubstituted alkyl (e.g., $C_1$-$C_8$, $C_1$-$C_6$, $C_1$-$C_4$, or $C_1$-$C_2$), $R^{80A}$-substituted or unsubstituted heteroalkyl (e.g., 2 to 8 membered, 2 to 6 membered, 4 to 6 membered, 2 to 3 membered, or 4 to 5 membered), $R^{80A}$-substituted or unsubstituted cycloalkyl (e.g., $C_3$-$C_8$, $C_3$-$C_6$, $C_4$-$C_6$, or $C_5$-$C_6$), $R^{80A}$-substituted or unsubstituted heterocycloalkyl (e.g., 3 to 8 membered, 3 to 6 membered, 4 to 6 membered, 4 to 5 membered, or 5 to 6 membered), $R^{80A}$-substituted or unsubstituted aryl (e.g., $C_6$-$C_{10}$ or phenyl), or $R^{80A}$-substituted or unsubstituted heteroaryl (e.g., 5 to 10 membered, 5 to 9 membered, or 5 to 6 membered). In embodiments, $R^{79A}$ is independently oxo, halogen, $—CX^{79A}_3$, $—CHX^{79A}_2$, $—CH_2X^{79A}$, $—OCX^{79A}_3$, $—OCH_2X^{79A}$, $—OCHX^{79A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{79A}$ is independently —F, —Cl, —Br, or —I. In embodiments, $R^{79A}$ is independently unsubstituted methyl. In embodiments, $R^{79A}$ is independently unsubstituted ethyl.

$R^{80A}$ is independently oxo, halogen, $—CX^{80A}_3$, $—CHX^{80A}_2$, $—CH_2X^{80A}$, $—OCX^{80A}_3$, $—OCH_2X^{80A}$, $—OCHX^{80A}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{80A}$ is independently —F, —Cl, —Br, or —I. In embodiments, $R^{80A}$ is independently unsubstituted methyl. In embodiments, $R^{80A}$ is independently unsubstituted ethyl.

In embodiments, $R^{17B}$ is independently hydrogen, $—CX^{17B}_3$, $—CHX^{17B}_2$, $—CH_2X^{17B}$, —CN, —COOH, $—CONH_2$, $R^{78B}$-substituted or unsubstituted alkyl (e.g., $C_1$-$C_8$, $C_1$-$C_6$, $C_1$-$C_4$, or $C_1$-$C_2$), $R^{78B}$-substituted or unsubstituted heteroalkyl (e.g., 2 to 8 membered, 2 to 6 membered, 4 to 6 membered, 2 to 3 membered, or 4 to 5 membered), $R^{78B}$-substituted or unsubstituted cycloalkyl (e.g., $C_3$-$C_8$, $C_3$-$C_6$, $C_4$-$C_6$, or $C_5$-$C_6$), $R^{78B}$-substituted or unsubstituted heterocycloalkyl (e.g., 3 to 8 membered, 3 to 6 membered, 4 to 6 membered, 4 to 5 membered, or 5 to 6 membered), $R^{78B}$-substituted or unsubstituted aryl (e.g., $C_6$-$C_{10}$ or phenyl), or $R^{78B}$-substituted or unsubstituted heteroaryl (e.g., 5 to 10 membered, 5 to 9 membered, or 5 to 6 membered). In embodiments, $R^{17B}$ is independently hydrogen, $—CX^{17B}_3$, $—CHX^{17B}_2$, $—CH_2X^{17B}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17B}$ is independently —F, —Cl, —Br, or —I. In embodiments, $R^{17B}$ is independently hydrogen. In embodiments, $R^{17B}$ is independently unsubstituted methyl. In embodiments, $R^{17B}$ is independently unsubstituted ethyl.

In embodiments, $R^{17A}$ and $R^{17B}$ substituents bonded to the same nitrogen atom may optionally be joined to form a $R^{78B}$-substituted or unsubstituted heterocycloalkyl (e.g., 3 to 8 membered, 3 to 6 membered, 4 to 6 membered, 4 to 5 membered, or 5 to 6 membered) or $R^{78B}$-substituted or unsubstituted heteroaryl (e.g., 5 to 10 membered, 5 to 9 membered, or 5 to 6 membered). In embodiments, $R^{17A}$ and $R^{17B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{17A}$ and $R^{17B}$ substituents bonded to the same nitrogen atom may optionally be joined to form a $R^{78B}$-substituted or unsubstituted heterocycloalkyl (e.g., 3 to 8 membered, 3 to 6 membered, 4 to 6 membered, 4 to 5 membered, or 5 to 6 membered). In embodiments, $R^{17A}$ and $R^{17B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{78B}$ is independently oxo, halogen, $—CX^{78B}_3$, $—CHX^{78B}_2$, $—CH_2X^{78B}$, $—OCX^{78B}_3$, $—OCH_2X^{78B}$, $—OCHX^{78B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{79B}$-substituted or unsubstituted alkyl (e.g., $C_1$-$C_8$, $C_1$-$C_6$, $C_1$-$C_4$, or $C_1$-$C_2$), $R^{79B}$-substituted or unsubstituted heteroalkyl (e.g., 2 to 8 membered, 2 to 6 membered, 4 to 6 membered, 2 to 3 membered, or 4 to 5 membered), $R^{79B}$-substituted or unsubstituted cycloalkyl (e.g., $C_3$-$C_8$, $C_3$-$C_6$, $C_4$-$C_6$, or $C_5$-$C_6$), $R^{79B}$-substituted or unsubstituted heterocycloalkyl (e.g., 3 to 8 membered, 3 to 6 membered, 4 to 6 membered, 4 to 5 membered, or 5 to 6 membered), $R^{79B}$-substituted or unsubstituted aryl (e.g., $C_6$-$C_{10}$ or phenyl), or $R^{79B}$-substituted or unsubstituted heteroaryl (e.g., 5 to 10 membered, 5 to 9 membered, or 5 to 6 membered). In embodiments, $R^{78B}$ is independently oxo, halogen, $—CX^{78B}_3$, $—CHX^{78B}_2$, $—CH_2X^{78B}$, $—OCX^{78B}_3$, $—OCH_2X^{78B}$, $—OCHX^{78B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78B}$ is independently —F, —Cl, —Br, or —I. In embodiments, $R^{78B}$ is independently unsubstituted methyl. In embodiments, $R^{78B}$ is independently unsubstituted ethyl.

$R^{79B}$ is independently oxo, halogen, $—CX^{79B}_3$, $—CHX^{79B}_2$, $—CH_2X^{79B}$, $—OCX^{79B}_3$, $—OCH_2X^{79B}$, $—OCHX^{79B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{80B}$-substituted or unsubstituted alkyl (e.g., $C_1$-$C_8$, $C_1$-$C_6$, $C_1$-$C_4$, or $C_1$-$C_2$), $R^{80B}$-substituted or unsubstituted heteroalkyl (e.g., 2 to 8 membered, 2 to 6 membered, 4 to 6 membered, 2 to 3 membered, or 4 to 5 membered), $R^{80B}$-substituted or unsubstituted cycloalkyl (e.g., $C_3$-$C_8$, $C_3$-$C_6$, $C_4$-$C_6$, or $C_5$-$C_6$), $R^{80B}$-substituted or unsubstituted heterocycloalkyl (e.g., 3 to 8 membered, 3 to 6 membered, 4 to 6 membered, 4 to 5 membered, or 5 to 6 membered), $R^{80B}$-substituted or unsubstituted aryl (e.g., $C_6$-$C_{10}$ or phenyl), or $R^{80B}$-substituted or unsubstituted heteroaryl (e.g., 5 to 10 membered, 5 to 9 membered, or 5 to 6 membered). In embodiments, $R^{79B}$ is independently oxo, halogen, $—CX^{79B}_3$, $—CHX^{79B}_2$, $—CH_2X^{79B}$, $—OCX^{79B}_3$, $—OCH_2X^{79B}$, $—OCHX^{79B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{79B}$ is independently —F, —Cl, —Br, or —I. In embodiments, $R^{79B}$ is independently unsubstituted methyl. In embodiments, $R^{79B}$ is independently unsubstituted ethyl.

$R^{80B}$ is independently oxo, halogen, $—CX^{80B}_3$, $—CHX^{80B}_2$, $—CH_2X^{80B}$, $—OCX^{80B}_3$, $—OCH_2X^{80B}$, $—OCHX^{80B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{80B}$ is independently —F, —Cl, —Br, or —I. In embodiments, $R^{80B}$ is independently unsubstituted methyl. In embodiments, $R^{80B}$ is independently unsubstituted ethyl.

In embodiments, $R^{17C}$ is independently hydrogen, $—CX^{17C}_3$, $—CHX^{17C}_2$, $—CH_2X^{17C}$, —CN, —COOH, $—CONH_2$, $R^{78C}$-substituted or unsubstituted alkyl (e.g., $C_1$-$C_8$, $C_1$-$C_6$, $C_1$-$C_4$, or $C_1$-$C_2$), $R^{78C}$-substituted or unsubstituted heteroalkyl (e.g., 2 to 8 membered, 2 to 6 membered, 4 to 6 membered, 2 to 3 membered, or 4 to 5 membered), $R^{78C}$-substituted or unsubstituted cycloalkyl (e.g., $C_3$-$C_8$, $C_3$-$C_6$, $C_4$-$C_6$, or $C_5$-$C_6$), $R^{78C}$-substituted or unsubstituted heterocycloalkyl (e.g., 3 to 8 membered, 3 to 6 membered, 4 to 6 membered, 4 to 5 membered, or 5 to 6 membered), $R^{78C}$-substituted or unsubstituted aryl (e.g., $C_6$-$C_{10}$ or phenyl), or $R^{78C}$-substituted or unsubstituted heteroaryl (e.g., 5 to 10 membered, 5 to 9 membered, or 5 to 6 membered). In embodiments, $R^{17C}$ is independently hydrogen, $—CX^{17C}3$, $—CHX^{17C}_2$, $—CH_2X^{17C}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17C}$ is independently —F, —Cl, —Br, or —I. In embodiments, $R^{17C}$ is independently hydrogen. In embodiments, $R^{17C}$ is independently unsubstituted methyl. In embodiments, $R^{17C}$ is independently unsubstituted ethyl.

$R^{78C}$ is independently oxo, halogen, $—CX^{78C}_3$, $—CHX^{78C}_2$, $—CH_2X^{78C}$, $—OCX^{78C}$, $—OCH_2X^{78C}$, $—OCHX^{78C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{79C}$-substituted or unsubstituted alkyl (e.g., $C_1$-$C_8$, $C_1$-$C_6$, $C_1$-$C_4$, or $C_1$-$C_2$), $R^{79C}$-substituted or unsubstituted heteroalkyl (e.g., 2 to 8 membered, 2 to 6 membered, 4 to 6 membered, 2 to 3 membered, or 4 to 5 membered), $R^{79C}$-substituted or unsubstituted cycloalkyl (e.g., $C_3$-$C_8$, $C_3$-$C_6$, $C_4$-$C_6$, or $C_5$-$C_6$), $R^{79C}$-substituted or unsubstituted heterocycloalkyl (e.g., 3 to 8 membered, 3 to 6 membered, 4 to 6 membered, 4 to 5 membered, or 5 to 6 membered), $R^{79C}$-substituted or unsubstituted aryl (e.g., $C_6$-$C_{10}$ or phenyl), or $R^{79C}$-substituted or unsubstituted heteroaryl (e.g., 5 to 10 membered, 5 to 9 membered, or 5 to 6 membered). In embodiments, $R^{78C}$ is independently oxo, halogen, $—CX^{78C}_3$, $—CHX^{78C}_2$, $—CH_2X^{78C}$, $—OCX^{78C}_3$, $—OCH_2X^{78C}$, $—OCHX^{78C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78C}$ is independently —F, —Cl, —Br, or —I. In embodiments, $R^{78C}$ is independently unsubstituted methyl. In embodiments, $R^{78C}$ is independently unsubstituted ethyl.

$R^{79C}$ is independently oxo, halogen, $—CX^{79C}_3$, $—CHX^{79C}_2$, $—CH_2X^{79C}$, $—OCX^{79C}$, $—OCH_2X^{79C}$, $—OCHX^{79C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)—OH, —NHOH, $R^{80C}$-substituted or unsubstituted alkyl (e.g., $C_1$-$C_8$, $C_1$-$C_6$, $C_1$-$C_4$, or $C_1$-$C_2$), $R^{80C}$-substituted or unsubstituted heteroalkyl (e.g., 2 to 8 membered, 2 to 6 membered, 4 to 6 membered, 2 to 3 membered, or 4 to 5 membered), $R^{80C}$-substituted or unsubstituted cycloalkyl (e.g., $C_3$-$C_8$, $C_3$-$C_6$, $C_4$-$C_6$, or $C_5$-$C_6$), $R^{80C}$-substituted or unsubstituted heterocycloalkyl (e.g., 3 to 8 membered, 3 to 6 membered, 4 to 6 membered, 4 to 5 membered, or 5 to 6 membered), $R^{80C}$-substituted or unsubstituted aryl (e.g., $C_6$-$C_{10}$ or phenyl), or $R^{80C}$-substituted or unsubstituted heteroaryl (e.g., 5 to 10 membered, 5 to 9 membered, or 5 to 6 membered). In embodiments, $R^{79C}$ is independently oxo, halogen, —$CX^{79C}_3$, —$CHX^{79C}_2$, —$CH_2X^{79C}$, —$OCX^{79C}_3$, —$OCH_2X^{79C}$, —$OCHX^{79C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{79C}$ is independently —F, —Cl, —Br, or —I. In embodiments, $R^{79C}$ is independently unsubstituted methyl. In embodiments, $R^{79C}$ is independently unsubstituted ethyl.

$R^{80C}$ is independently oxo, halogen, —$CX^{80C}_3$, —$CHX^{80C}_2$, —$CH_2X^{80C}$, —$OCX^{80C}_3$, —$OCH_2X^{80C}$, —$OCHX^{80C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{80C}$ is independently —F, —Cl, —Br, or —I. In embodiments, $R^{80C}$ is independently unsubstituted methyl. In embodiments, $R^{80C}$ is independently unsubstituted ethyl.

In embodiments, $R^{17D}$ is independently hydrogen, —$CX^{17D}_3$, —$CHX^{17D}_2$, —$CH_2X^{17D}$—CN, —COOH, —$CONH_2$, $R^{78D}$-substituted or unsubstituted alkyl (e.g., $C_1$-$C_8$, $C_1$-$C_6$, $C_1$-$C_4$, or $C_1$-$C_2$), $R^{78D}$-substituted or unsubstituted heteroalkyl (e.g., 2 to 8 membered, 2 to 6 membered, 4 to 6 membered, 2 to 3 membered, or 4 to 5 membered), $R^{78D}$-substituted or unsubstituted cycloalkyl (e.g., $C_3$-$C_8$, $C_3$-$C_6$, $C_4$-$C_6$, or $C_5$-$C_6$), $R^{78D}$-substituted or unsubstituted heterocycloalkyl (e.g., 3 to 8 membered, 3 to 6 membered, 4 to 6 membered, 4 to 5 membered, or 5 to 6 membered), $R^{78D}$-substituted or unsubstituted aryl (e.g., $C_6$-$C_{10}$ or phenyl), or $R^{78D}$-substituted or unsubstituted heteroaryl (e.g., 5 to 10 membered, 5 to 9 membered, or 5 to 6 membered). In embodiments, $R^{17D}$ is independently hydrogen, —$CX^{17D}_3$, —$CHX^{17D}_2$, —$CH_2X^{17D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17D}$ is independently —F, —Cl, —Br, or —I. In embodiments, $R^{17D}$ is independently hydrogen. In embodiments, $R^{17D}$ is independently unsubstituted methyl. In embodiments, $R^{17D}$ is independently unsubstituted ethyl.

$R^{78D}$ is independently oxo, halogen, —$CX^{78D}_3$, —$CHX^{78D}_2$, —$CH_2X^{78D}$, —$OCX^{78D}_3$, —$OCH_2X^{78D}$, —$OCHX^{78D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{79D}$-substituted or unsubstituted alkyl (e.g., $C_1$-$C_8$, $C_1$-$C_6$, $C_1$-$C_4$, or $C_1$-$C_2$), $R^{79D}$-substituted or unsubstituted heteroalkyl (e.g., 2 to 8 membered, 2 to 6 membered, 4 to 6 membered, 2 to 3 membered, or 4 to 5 membered), $R^{79D}$-substituted or unsubstituted cycloalkyl (e.g., $C_3$-$C_8$, $C_3$-$C_6$, $C_4$-$C_6$, or $C_5$-$C_6$), $R^{79D}$-substituted or unsubstituted heterocycloalkyl (e.g., 3 to 8 membered, 3 to 6 membered, 4 to 6 membered, 4 to 5 membered, or 5 to 6 membered), $R^{79D}$-substituted or unsubstituted aryl (e.g., $C_6$-$C_{10}$ or phenyl), or $R^{79D}$-substituted or unsubstituted heteroaryl (e.g., 5 to 10 membered, 5 to 9 membered, or 5 to 6 membered). In embodiments, $R^{78D}$ is independently oxo, halogen, —$CX^{78D}_3$, —$CHX^{78D}_2$, —$CH_2X^{78D}$, —$OCX^{78D}_3$, —$OCH_2X^{78D}$, —$OCHX^{78D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78D}$ is independently —F, —Cl, —Br, or —I. In embodiments, $R^{78D}$ is independently unsubstituted methyl. In embodiments, $R^{78D}$ is independently unsubstituted ethyl.

$R^{79D}$ is independently oxo, halogen, —$CX^{79D}_3$, —$CHX^{79D}_2$, —$CH_2X^{79D}$, —$OCX^{79D}_3$, —$OCH_2X^{79D}$, —$OCHX^{79D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{80D}$-substituted or unsubstituted alkyl (e.g., $C_1$-$C_8$, $C_1$-$C_6$, $C_1$-$C_4$, or $C_1$-$C_2$), $R^{80D}$-substituted or unsubstituted heteroalkyl (e.g., 2 to 8 membered, 2 to 6 membered, 4 to 6 membered, 2 to 3 membered, or 4 to 5 membered), $R^{80D}$-substituted or unsubstituted cycloalkyl (e.g., $C_3$-$C_8$, $C_3$-$C_6$, $C_4$-$C_6$, or $C_5$-$C_6$), $R^{80D}$-substituted or unsubstituted heterocycloalkyl (e.g., 3 to 8 membered, 3 to 6 membered, 4 to 6 membered, 4 to 5 membered, or 5 to 6 membered), $R^{80D}$-substituted or unsubstituted aryl (e.g., $C_6$-$C_{10}$ or phenyl), or $R^{80D}$-substituted or unsubstituted heteroaryl (e.g., 5 to 10 membered, 5 to 9 membered, or 5 to 6 membered). In embodiments, $R^{79D}$ is independently oxo, halogen, —$CX^{79D}_3$, —$CHX^{79D}_2$, —$CH_2X^{79D}$, —$OCX^{79D}_3$, —$OCH_2X^{79D}$, —$OCHX^{79D}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{79D}$ is independently —F, —Cl, —Br, or —I. In embodiments, $R^{79D}$ is independently unsubstituted methyl. In embodiments, $R^{79D}$ is independently unsubstituted ethyl.

$R^{80D}$ is independently oxo, halogen, $—CX^{80D}_3$, $—CHX^{80D}_2$, $—CH_2X^{80D}$, $—OCX^{80D}_3$, $—OCH_2X^{80D}$, $—OCHX^{80D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{80D}$ is independently —F, —Cl, —Br, or —I. In embodiments, $R^{80D}$ is independently unsubstituted methyl. In embodiments, $R^{80D}$ is independently unsubstituted ethyl.

In embodiments, $R^{18}$ is hydrogen. In embodiments, $R^{18}$ is halogen. In embodiments, $R^{18}$ is $—CX^{18}_3$. In embodiments, $R^{18}$ is $—CHX^{18}_2$. In embodiments, $R^{18}$ is $—CH_2X^{18}$. In embodiments, $R^{18}$ is —CN. In embodiments, $R^{18}$ is $—SO_{n18}R^{18D}$. In embodiments, $R^{18}$ is $—SO_{v18}NR^{18A}R^{18B}$. In embodiments, $R^{18}$ is $—NHNR^{18A}R^{18B}$. In embodiments, $R^{18}$ is $—ONR^{18A}R^{18B}$. In embodiments, $R^{18}$ is $—NHC{=}(O)NHNR^{18A}R^{18B}$. In embodiments, $R^{18}$ is $—NHC(O)NR^{18A}R^{18B}$. In embodiments, $R^{18}$ is $—N(O)_{m18}$. In embodiments, $R^{18}$ is $—NR^{18A}R^{18B}$. In embodiments, $R^{18}$ is $—C(O)R^{18C}$. In embodiments, $R^{18}$ is $—C(O)—OR^{18C}$. In embodiments, $R^{18}$ is $—C(O)NR^{18A}R^{18B}$. In embodiments, $R^{18}$ is $—OR^{18D}$. In embodiments, $R^{18}$ is $—NR^{18A}SO_2R^{18D}$. In embodiments, $R^{18}$ is $—NR^{18A}C(O)R^{18C}$. In embodiments, $R^{18}$ is $—NR^{18A}C(O)OR^{18C}$. In embodiments, $R^{18}$ is $—NR^{18A}OR^{18C}$. In embodiments, $R^{18}$ is $—OCX^{18}_3$. In embodiments, $R^{18}$ is $—OCHX^{18}2$. In embodiments, $R^{18}$ is independently —OH. In embodiments, $R^{18}$ is independently $—NH_2$. In embodiments, $R^{18}$ is independently —COOH. In embodiments, $R^{18}$ is independently $—CONH_2$. In embodiments, $R^{18}$ is independently $—NO_2$. In embodiments, $R^{18}$ is independently —SH. In embodiments, $R^{18}$ is independently $—CF_3$. In embodiments, $R^{18}$ is independently $—CHF_2$. In embodiments, $R^{18}$ is independently $—CH_2F$. In embodiments, $R^{18}$ is independently $—OCF_3$. In embodiments, $R^{18}$ is independently $—OCH_2F$. In embodiments, $R^{18}$ is independently $—OCHF_2$. In embodiments, $R^{18}$ is independently $—OCH_3$. In embodiments, $R^{18}$ is independently $—OCH_2CH_3$. In embodiments, $R^{18}$ is independently $—OCH_2CH_2CH_3$. In embodiments, $R^{18}$ is independently $—OCH(CH_3)_2$. In embodiments, $R^{18}$ is independently $—OC(CH_3)_3$. In embodiments, $R^{18}$ is independently $—SCH_3$. In embodiments, $R^{18}$ is independently $—SCH_2CH_3$. In embodiments, $R^{18}$ is independently $—SCH_2CH_2CH_3$. In embodiments, $R^{18}$ is independently $—SCH(CH_3)_2$. In embodiments, $R^{18}$ is independently $—SC(CH_3)_3$. In embodiments, $R^{18}$ is independently $—CH_3$. In embodiments, $R^{18}$ is independently $—CH_2CH_3$. In embodiments, $R^{18}$ is independently $—CH_2CH_2CH_3$. In embodiments, $R^{18}$ is independently $—CH(CH_3)_2$. In embodiments, $R^{18}$ is independently $—C(CH_3)_3$. In embodiments, $R^{18}$ is independently —F. In embodiments, $R^{18}$ is independently —Cl. In embodiments, $R^{18}$ is independently —Br. In embodiments, $R^{18}$ is independently —I.

In embodiments, $R^{18}$ is independently substituted or unsubstituted alkyl (e.g., $C_1$-$C_8$, $C_1$-$C_6$, $C_1$-$C_4$, or $C_1$-$C_2$). In embodiments, $R^{18}$ is independently substituted alkyl (e.g., $C_1$-$C_8$, $C_1$-$C_6$, $C_1$-$C_4$, or $C_1$-$C_2$). In embodiments, $R^{18}$ is independently unsubstituted alkyl (e.g., $C_1$-$C_8$, $C_1$-$C_6$, $C_1$-$C_4$, or $C_1$-$C_2$). In embodiments, $R^{18}$ is independently unsubstituted methyl. In embodiments, $R^{18}$ is independently unsubstituted ethyl. In embodiments, $R^{18}$ is independently unsubstituted propyl. In embodiments, $R^{18}$ is independently unsubstituted isopropyl. In embodiments, $R^{18}$ is independently unsubstituted tert-butyl. In embodiments, $R^{18}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18}$ is independently substituted heteroalkyl (e.g., 2 to 8 membered, 2 to 6 membered, 4 to 6 membered, 2 to 3 membered, or 4 to 5 membered). In embodiments, $R^{18}$ is independently unsubstituted heteroalkyl (e.g., 2 to 8 membered, 2 to 6 membered, 4 to 6 membered, 2 to 3 membered, or 4 to 5 membered). In embodiments, $R^{18}$ is independently substituted or unsubstituted cycloalkyl (e.g., $C_3$-$C_8$, $C_3$-$C_6$, $C_4$-$C_6$, or $C_5$-$C_6$). In embodiments, $R^{18}$ is independently substituted cycloalkyl (e.g., $C_3$-$C_8$, $C_3$-$C_6$, $C_4$-$C_6$, or $C_5$-$C_6$). In embodiments, $R^{18}$ is independently unsubstituted cycloalkyl (e.g., $C_3$-$C_8$, $C_3$-$C_6$, $C_4$-$C_6$, or $C_5$-$C_6$). In embodiments, $R^{18}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18}$ is independently substituted heterocycloalkyl (e.g., 3 to 8 membered, 3 to 6 membered, 4 to 6 membered, 4 to 5 membered, or 5 to 6 membered). In embodiments, $R^{18}$ is independently unsubstituted heterocycloalkyl (e.g., 3 to 8 membered, 3 to 6 membered, 4 to 6 membered, 4 to 5 membered, or 5 to 6 membered). In embodiments, $R^{18}$ is independently substituted or unsubstituted aryl (e.g., $C_6$-$C_{10}$ or phenyl). In embodiments, $R^{18}$ is independently substituted aryl (e.g., $C_6$-$C_{10}$ or phenyl). In embodiments, $R^{18}$ is independently unsubstituted aryl (e.g., $C_6$-$C_{10}$ or phenyl). In embodiments, $R^{18}$ is independently substituted or unsubstituted heteroaryl (e.g., 5 to 10 membered, 5 to 9 membered, or 5 to 6 membered). In embodiments, $R^{18}$ is independently substituted heteroaryl (e.g., 5 to 10 membered, 5 to 9 membered, or 5 to 6 membered). In embodiments, $R^{18}$ is independently unsubstituted heteroaryl (e.g., 5 to 10 membered, 5 to 9 membered, or 5 to 6 membered).

In embodiments, $R^{18A}$ is independently hydrogen. In embodiments, $R^{18A}$ is independently $—CX^{18A}_3$. In embodiments, $R^{18A}$ is independently $—CHX^{18A}_2$. In embodiments, $R^{18A}$ is independently $—CH_2X^{18A}$. In embodiments, $R^{18A}$ is independently —CN. In embodiments, $R^{18A}$ is independently —COOH. In embodiments, $R^{18A}$ is independently $—CONH_2$. In embodiments, $X^{18A}$ is independently —F, —Cl, —Br, or —I.

In embodiments, $R^{18A}$ is independently substituted or unsubstituted alkyl (e.g., $C_1$-$C_8$, $C_1$-$C_6$, $C_1$-$C_4$, or $C_1$-$C_2$). In embodiments, $R^{18A}$ is independently substituted alkyl (e.g., $C_1$-$C_8$, $C_1$-$C_6$, $C_1$-$C_4$, or $C_1$-$C_2$). In embodiments, $R^{18A}$ is independently unsubstituted alkyl (e.g., $C_1$-$C_8$, $C_1$-$C_6$, $C_1$-$C_4$, or $C_1$-$C_2$). In embodiments, $R^{18A}$ is independently unsubstituted methyl. In embodiments, $R^{18A}$ is independently unsubstituted ethyl. In embodiments, $R^{18A}$ is independently unsubstituted propyl. In embodiments, $R^{18A}$ is independently unsubstituted isopropyl. In embodiments, $R^{18A}$ is independently unsubstituted tert-butyl. In embodiments, $R^{18A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18A}$ is independently substituted heteroalkyl (e.g., 2 to 8 membered, 2 to 6 membered, 4 to 6 membered, 2 to 3 membered, or 4 to 5 membered). In embodiments, $R^{18A}$ is independently unsubstituted heteroalkyl (e.g., 2 to 8 membered, 2 to 6 membered, 4 to 6 membered, 2 to 3 membered, or 4 to 5 membered). In embodiments, $R^{8A}$ is independently substituted or unsubstituted cycloalkyl (e.g., $C_3$-$C_8$, $C_3$-$C_6$, $C_4$-$C_6$, or $C_5$-$C_6$). In embodiments, $R^{18A}$ is independently substituted cycloalkyl (e.g., $C_3$-$C_8$, $C_3$-$C_6$, $C_4$-$C_6$, or $C_5$-$C_6$). In embodiments, $R^{18A}$ is independently unsubstituted cycloalkyl (e.g., $C_3$-$C_8$, $C_3$-$C_6$, $C_4$-$C_6$, or $C_5$-$C_6$). In embodiments, $R^{18A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18A}$ is independently substituted heterocycloalkyl (e.g., 3 to 8 membered, 3 to 6 membered, 4 to 6 membered, 4 to 5 membered, or 5 to 6 membered). In embodiments, $R^{18A}$ is independently unsubstituted heterocycloalkyl (e.g., 3 to 8 membered, 3 to 6 membered, 4 to 6 membered, 4 to 5 membered, or 5 to 6 membered). In embodiments, $R^{18A}$ is independently substituted or unsubstituted aryl (e.g., $C_6$-$C_{10}$ or phenyl). In embodiments, $R^{18A}$ is independently substituted aryl (e.g., $C_6$-$C_{10}$ or phenyl). In embodiments, $R^{18A}$ is independently unsubstituted aryl (e.g., $C_6$-$C_{10}$ or phenyl). In embodiments, $R^{18A}$ is independently substituted or unsubstituted heteroaryl (e.g., 5 to 10 membered, 5 to 9 membered, or 5 to 6 membered). In embodiments, $R^{18A}$ is independently substituted heteroaryl (e.g., 5 to 10 membered, 5 to 9 membered, or 5 to 6 membered). In embodiments, $R^{18A}$ is independently unsubstituted heteroaryl (e.g., 5 to 10 membered, 5 to 9 membered, or 5 to 6 membered).

In embodiments, $R^{18B}$ is independently hydrogen. In embodiments, $R^{18B}$ is independently $—CX^{18B}_3$. In embodiments, $R^{18B}$ is independently $—CHX^{18B}_2$. In embodiments, $R^{18B}$ is independently $—CH_2X^{18B}$. In embodiments, $R^{18B}$ is independently —CN. In embodiments, $R^{18B}$ is independently —COOH. In embodiments, $R^{18B}$ is independently $—CONH_2$. In embodiments, $X^{18B}$ is independently —F, —Cl, —Br, or —I.

In embodiments, $R^{18B}$ is independently substituted or unsubstituted alkyl (e.g., $C_1$-$C_8$, $C_1$-$C_6$, $C_1$-$C_4$, or $C_1$-$C_2$). In embodiments, $R^{18B}$ is independently substituted alkyl (e.g., $C_1$-$C_8$, $C_1$-$C_6$, $C_1$-$C_4$, or $C_1$-$C_2$). In embodiments, $R^{18B}$ is independently unsubstituted alkyl (e.g., $C_1$-$C_8$, $C_1$-$C_6$, $C_1$-$C_4$, or $C_1$-$C_2$). In embodiments, $R^{18B}$ is independently unsubstituted methyl. In embodiments, $R^{18B}$ is independently unsubstituted ethyl. In embodiments, $R^{18B}$ is independently unsubstituted propyl. In embodiments, $R^{18B}$ is independently unsubstituted isopropyl. In embodiments, $R^{18B}$ is independently unsubstituted tert-butyl. In embodiments, $R^{18B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18B}$ is independently substituted heteroalkyl (e.g., 2 to 8 membered, 2 to 6 membered, 4 to 6 membered, 2 to 3 membered, or 4 to 5 membered). In embodiments, $R^{18B}$ is independently unsubstituted heteroalkyl (e.g., 2 to 8 membered, 2 to 6 membered, 4 to 6 membered, 2 to 3 membered, or 4 to 5 membered). In embodiments, $R^{18B}$ is independently substituted or unsubstituted cycloalkyl (e.g., $C_3$-$C_8$, $C_3$-$C_6$, $C_4$-$C_6$, or $C_5$-$C_6$). In embodiments, $R^{18B}$ is independently substituted cycloalkyl (e.g., $C_3$-$C_8$, $C_3$-$C_6$, $C_4$-$C_6$, or $C_5$-$C_6$). In embodiments, $R^{18B}$ is independently unsubstituted cycloalkyl (e.g., $C_3$-$C_8$, $C_3$-$C_6$, $C_4$-$C_6$, or $C_5$-$C_6$). In embodiments, $R^{18B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18B}$ is independently substituted heterocycloalkyl (e.g., 3 to 8 membered, 3 to 6 membered, 4 to 6 membered, 4 to 5 membered, or 5 to 6 membered). In embodiments, $R^{18B}$ is independently unsubstituted heterocycloalkyl (e.g., 3 to 8 membered, 3 to 6 membered, 4 to 6 membered, 4 to 5 membered, or 5 to 6 membered). In embodiments, $R^{18B}$ is independently substituted or unsubstituted aryl (e.g., $C_6$-$C_{10}$ or phenyl). In embodiments, $R^{18B}$ is independently substituted aryl (e.g., $C_6$-$C_{10}$ or phenyl). In embodiments, $R^{18B}$ is independently unsubstituted aryl (e.g., $C_6$-$C_{10}$ or phenyl). In embodiments, $R^{18B}$ is independently substituted or unsubstituted heteroaryl (e.g., 5 to 10 membered, 5 to 9 membered, or 5 to 6 membered). In embodiments, $R^{18B}$ is independently substituted heteroaryl (e.g., 5 to 10 membered, 5 to 9 membered, or 5 to 6 membered). In embodiments, $R^{18B}$ is independently unsubstituted heteroaryl (e.g., 5 to 10 membered, 5 to 9 membered, or 5 to 6 membered).

In embodiments, $R^{18A}$ and $R^{18B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{18A}$ and $R^{18B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{18A}$ and $R^{18B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{18A}$ and $R^{18B}$ substituents bonded to the same nitrogen atom may be joined to form a substituted or unsubstituted heteroaryl (e.g., 5 to 10 membered, 5 to 9 membered, or 5 to 6 membered). In embodiments, $R^{18A}$ and $R^{18B}$ substituents bonded to the same nitrogen atom may be joined to form a substituted heteroaryl (e.g., 5 to 10 membered, 5 to 9 membered, or 5 to 6 membered). In embodiments, $R^{18A}$ and $R^{18B}$ substituents bonded to the same nitrogen atom may be joined to form an unsubstituted heteroaryl (e.g., 5 to 10 membered, 5 to 9 membered, or 5 to 6 membered).

In embodiments, $R^{18C}$ is independently hydrogen. In embodiments, $R^{18C}$ is independently $—CX^{18C}_3$. In embodiments, $R^{18C}$ is independently $—CHX^{18C}_2$. In embodiments, $R^{18C}$ is independently $—CH_2X^{18C}$. In embodiments, $R^{18C}$ is independently —CN. In embodiments, $R^{18C}$ is independently —COOH. In embodiments, $R^{18C}$ is independently $—CONH_2$. In embodiments, $X^{18C}$ is independently —F, —Cl, —Br, or —I.

In embodiments, $R^{18C}$ is independently substituted or unsubstituted alkyl (e.g., $C_1$-$C_8$, $C_1$-$C_6$, $C_1$-$C_4$, or $C_1$-$C_2$). In embodiments, $R^{18C}$ is independently substituted alkyl (e.g., $C_1$-$C_8$, $C_1$-$C_6$, $C_1$-$C_4$, or $C_1$-$C_2$). In embodiments, $R^{18C}$ is independently unsubstituted alkyl (e.g., $C_1$-$C_8$, $C_1$-$C_6$, $C_1$-$C_4$, or $C_1$-$C_2$). In embodiments, $R^{18C}$ is independently unsubstituted methyl. In embodiments, $R^{18C}$ is independently unsubstituted ethyl. In embodiments, $R^{18C}$ is independently unsubstituted propyl. In embodiments, $R^{18C}$ is independently unsubstituted isopropyl. In embodiments, $R^{18C}$ is independently unsubstituted tert-butyl. In embodiments, $R^{18C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18C}$ is independently substituted heteroalkyl (e.g., 2 to 8 membered, 2 to 6 membered, 4 to 6 membered, 2 to 3 membered, or 4 to 5 membered). In embodiments, $R^{18C}$ is independently unsubstituted heteroalkyl (e.g., 2 to 8 membered, 2 to 6 membered, 4 to 6 membered, 2 to 3 membered, or 4 to 5 membered). In embodiments, $R^{18C}$ is independently substituted or unsubstituted cycloalkyl (e.g., $C_3$-$C_8$, $C_3$-$C_6$, $C_4$-$C_6$, or $C_5$-$C_6$). In embodiments, $R^{18C}$ is independently substituted cycloalkyl (e.g., $C_3$-$C_8$, $C_3$-$C_6$, $C_4$-$C_6$, or $C_5$-$C_6$). In embodiments, $R^{18C}$ is independently unsubstituted cycloalkyl (e.g., $C_3$-$C_8$, $C_3$-$C_6$, $C_4$-$C_6$, or $C_5$-$C_6$). In embodiments, $R^{18C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18C}$ is independently substituted heterocycloalkyl (e.g., 3 to 8 membered, 3 to 6 membered, 4 to 6 membered, 4 to 5 membered, or 5 to 6 membered). In embodiments, $R^{18C}$ is independently unsubstituted heterocycloalkyl (e.g., 3 to 8 membered, 3 to 6 membered, 4 to 6 membered, 4 to 5 membered, or 5 to 6 membered). In embodiments, $R^{18C}$ is independently substituted or unsubstituted aryl (e.g., $C_6$-$C_{10}$ or phenyl). In embodiments, $R^{18C}$ is independently substituted aryl (e.g., $C_6$-$C_{10}$ or phenyl). In embodiments, $R^{18C}$ is independently unsubstituted aryl (e.g., $C_6$-$C_{10}$ or phenyl). In embodiments, $R^{18C}$ is independently substituted or unsubstituted heteroaryl (e.g., 5 to 10 membered, 5 to 9 membered, or 5 to 6 membered). In embodiments, $R^{18C}$ is independently substituted heteroaryl (e.g., 5 to 10 membered, 5 to 9 membered, or 5 to 6 membered). In embodiments, $R^{18C}$ is independently unsubstituted heteroaryl (e.g., 5 to 10 membered, 5 to 9 membered, or 5 to 6 membered).

In embodiments, $R^{18D}$ is independently hydrogen. In embodiments, $R^{18D}$ is independently $-CX^{18D}_3$. In embodiments, $R^{18D}$ is independently $-CHX^{18D}_2$. In embodiments, $R^{18D}$ is independently $-CH_2X^{18D}$. In embodiments, $R^{18D}$ is independently —CN. In embodiments, $R^{18D}$ is independently —COOH. In embodiments, $R^{18D}$ is independently $-CONH_2$. In embodiments, $X^{18D}$ independently —F, —Cl, —Br, or —I.

In embodiments, $R^{18D}$ is independently substituted or unsubstituted alkyl (e.g., $C_1$-$C_8$, $C_1$-$C_6$, $C_1$-$C_4$, or $C_1$-$C_2$). In embodiments, $R^{18D}$ is independently substituted alkyl (e.g., $C_1$-$C_8$, $C_1$-$C_6$, $C_1$-$C_4$, or $C_1$-$C_2$). In embodiments, $R^{18D}$ is independently unsubstituted alkyl (e.g., $C_1$-$C_8$, $C_1$-$C_6$, $C_1$-$C_4$, or $C_1$-$C_2$). In embodiments, $R^{18D}$ is independently unsubstituted methyl. In embodiments, $R^{18D}$ is independently unsubstituted ethyl. In embodiments, $R^{18D}$ is independently unsubstituted propyl. In embodiments, $R^{18D}$ is independently unsubstituted isopropyl. In embodiments, $R^{18D}$ is independently unsubstituted tert-butyl. In embodiments, $R^{18D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18D}$ is independently substituted heteroalkyl (e.g., 2 to 8 membered, 2 to 6 membered, 4 to 6 membered, 2 to 3 membered, or 4 to 5 membered). In embodiments, $R^{18D}$ is independently unsubstituted heteroalkyl (e.g., 2 to 8 membered, 2 to 6 membered, 4 to 6 membered, 2 to 3 membered, or 4 to 5 membered). In embodiments, $R^{18D}$ is independently substituted or unsubstituted cycloalkyl (e.g., $C_3$-$C_8$, $C_3$-$C_6$, $C_4$-$C_6$, or $C_5$-$C_6$). In embodiments, $R^{18D}$ is independently substituted cycloalkyl (e.g., $C_3$-$C_8$, $C_3$-$C_6$, $C_4$-$C_6$, or $C_5$-$C_6$). In embodiments, $R^{18D}$ is independently unsubstituted cycloalkyl (e.g., $C_3$-$C_8$, $C_3$-$C_6$, $C_4$-$C_6$, or $C_5$-$C_6$). In embodiments, $R^{18D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18D}$ is independently substituted heterocycloalkyl (e.g., 3 to 8 membered, 3 to 6 membered, 4 to 6 membered, 4 to 5 membered, or 5 to 6 membered). In embodiments, $R^{8D}$ is independently unsubstituted heterocycloalkyl (e.g., 3 to 8 membered, 3 to 6 membered, 4 to 6 membered, 4 to 5 membered, or 5 to 6 membered). In embodiments, $R^{18D}$ is independently substituted or unsubstituted aryl (e.g., $C_6$-$C_{10}$ or phenyl). In embodiments, $R^{18D}$ is independently substituted aryl (e.g., $C_6$-$C_{10}$ or phenyl). In embodiments, $R^{18D}$ is independently unsubstituted aryl (e.g., $C_6$-$C_{10}$ or phenyl). In embodiments, $R^{18D}$ is independently substituted or unsubstituted heteroaryl (e.g., 5 to 10 membered, 5 to 9 membered, or 5 to 6 membered). In embodiments, $R^{18D}$ is independently substituted heteroaryl (e.g., 5 to 10 membered, 5 to 9 membered, or 5 to 6 membered). In embodiments, $R^{18D}$ is independently unsubstituted heteroaryl (e.g., 5 to 10 membered, 5 to 9 membered, or 5 to 6 membered).

In embodiments, $R^{18}$ is independently hydrogen, halogen, $-CX^{18}_3$, $-CHX^{18}_2$, $-CH_2X^{18}$, $-OCX^{18}_3$, $-OCH_2X^{18}$, $-OCHX^{18}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{81}$-substituted or unsubstituted alkyl (e.g., $C_1$-$C_8$, $C_1$-$C_6$, $C_1$-$C_4$, or $C_1$-$C_2$), $R^{81}$-substituted or unsubstituted heteroalkyl (e.g., 2 to 8 membered, 2 to 6 membered, 4 to 6 membered, 2 to 3 membered, or 4 to 5 membered), $R^{81}$-substituted or unsubstituted cycloalkyl (e.g., $C_3$-$C_8$, $C_3$-$C_6$, $C_4$-$C_6$, or $C_5$-$C_6$), $R^{81}$-substituted or unsubstituted heterocycloalkyl (e.g., 3 to 8 membered, 3 to 6 membered, 4 to 6 membered, 4 to 5 membered, or 5 to 6 membered), $R^{81}$-substituted or unsubstituted aryl (e.g., $C_6$-$C_{10}$ or phenyl), or $R^{81}$-substituted or unsubstituted heteroaryl (e.g., 5 to 10 membered, 5 to 9 membered, or 5 to 6 membered). In embodiments, $R^{18}$ is independently hydrogen, halogen, $-CX^{18}_3$, $-CHX^{18}_2$, $-CH_2X^{18}$, $-OCX^{18}_3$, $-OCH_2X^{18}$, $-OCHX^{18}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18}$ is independently —F, —Cl, —Br, or —I. In embodiments, $R^{18}$ is independently hydrogen. In embodiments, $R^{18}$ is independently unsubstituted methyl. In embodiments, $R^{18}$ is independently unsubstituted ethyl.

$R^{81}$ is independently oxo, halogen, $-CX^{81}_3$, $-CHX^{81}_2$, $-CH_2X^{81}$, $-OCX^{81}_3$, $-OCH_2X^{81}$, $-OCHX^{81}_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC{=}(O)NHNH_2$, $-NHC{=}(O)NH_2$, $-NHSO_2H$, $-NHC{=}(O)H$, —NHC(O)—OH, —NHOH, $R^{82}$-substituted or unsubstituted alkyl (e.g., $C_1$-$C_8$, $C_1$-$C_6$, $C_1$-$C_4$, or $C_1$-$C_2$), $R^{82}$-substituted or unsubstituted heteroalkyl (e.g., 2 to 8 membered, 2 to 6 membered, 4 to 6 membered, 2 to 3 membered, or 4 to 5 membered), $R^{82}$-substituted or unsubstituted cycloalkyl (e.g., $C_3$-$C_8$, $C_3$-$C_6$, $C_4$-$C_6$, or $C_5$-$C_6$), $R^{82}$-substituted or unsubstituted heterocycloalkyl (e.g., 3 to 8 membered, 3 to 6 membered, 4 to 6 membered, 4 to 5 membered, or 5 to 6 membered), $R^{82}$-substituted or unsubstituted aryl (e.g., $C_6$-$C_{10}$ or phenyl), or $R^{82}$-substituted or unsubstituted heteroaryl (e.g., 5 to 10 membered, 5 to 9 membered, or 5 to 6 membered). In embodiments, $R^{81}$ is independently oxo, halogen, —$CX^{81}_3$, —$CHX^{81}_2$, —$CH_2X^{81}$, —$OCX^{81}_3$, —$OCH_2X^{81}$, —$OCHX^{81}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{81}$ is independently —F, —Cl, —Br, or —I. In embodiments, $R^{81}$ is independently unsubstituted methyl. In embodiments, $R^{81}$ is independently unsubstituted ethyl.

$R^{82}$ is independently oxo, halogen, —$CX^{82}_3$, —$CHX^{82}_2$, —$CH_2X^{82}$, —$OCX^{82}_3$, —$OCH_2X^{82}$, —$OCHX^{82}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{83}$-substituted or unsubstituted alkyl (e.g., $C_1$-$C_8$, $C_1$-$C_6$, $C_1$-$C_4$, or $C_1$-$C_2$), $R^{83}$-substituted or unsubstituted heteroalkyl (e.g., 2 to 8 membered, 2 to 6 membered, 4 to 6 membered, 2 to 3 membered, or 4 to 5 membered), $R^{83}$-substituted or unsubstituted cycloalkyl (e.g., $C_3$-$C_8$, $C_3$-$C_6$, $C_4$-$C_6$, or $C_5$-$C_6$), $R^{83}$-substituted or unsubstituted heterocycloalkyl (e.g., 3 to 8 membered, 3 to 6 membered, 4 to 6 membered, 4 to 5 membered, or 5 to 6 membered), $R^{83}$-substituted or unsubstituted aryl (e.g., $C_6$-$C_{10}$ or phenyl), or $R^{83}$-substituted or unsubstituted heteroaryl (e.g., 5 to 10 membered, 5 to 9 membered, or 5 to 6 membered). In embodiments, $R^{82}$ is independently oxo, halogen, —$CX^{82}_3$, —$CHX^{82}_2$, —$CH_2X^{82}$, —$OCX^{82}_3$, —$OCH_2X^{82}$, —$OCHX^{82}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{82}$ is independently —F, —Cl, —Br, or —I. In embodiments, $R^{82}$ is independently unsubstituted methyl. In embodiments, $R^{82}$ is independently unsubstituted ethyl.

$R^{83}$ is independently oxo, halogen, —$CX^{83}_3$, —$CHX^{83}_2$, —$CH_2X^{83}$, —$OCX^{83}_3$, —$OCH_2X^{83}$, —$OCHX^{83}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{83}$ is independently —F, —Cl, —Br, or —I. In embodiments, $R^{83}$ is independently unsubstituted methyl. In embodiments, $R^{83}$ is independently unsubstituted ethyl.

In embodiments, $R^{18A}$ is independently hydrogen, —$CX^{18A}_3$, —$CHX^{18A}_2$, —$CH_2X^{18A}$, —CN, —COOH, —$CONH_2$, $R^{81A}$-substituted or unsubstituted alkyl (e.g., $C_1$-$C_8$, $C_1$-$C_6$, $C_1$-$C_4$, or $C_1$-$C_2$), $R^{81A}$-substituted or unsubstituted heteroalkyl (e.g., 2 to 8 membered, 2 to 6 membered, 4 to 6 membered, 2 to 3 membered, or 4 to 5 membered), $R^{81A}$-substituted or unsubstituted cycloalkyl (e.g., $C_3$-$C_8$, $C_3$-$C_6$, $C_4$-$C_6$, or $C_5$-$C_6$), $R^{81A}$-substituted or unsubstituted heterocycloalkyl (e.g., 3 to 8 membered, 3 to 6 membered, 4 to 6 membered, 4 to 5 membered, or 5 to 6 membered), $R^{81A}$-substituted or unsubstituted aryl (e.g., $C_6$-$C_{10}$ or phenyl), or $R^{81A}$-substituted or unsubstituted heteroaryl (e.g., 5 to 10 membered, 5 to 9 membered, or 5 to 6 membered). In embodiments, $R^{18A}$ is independently hydrogen, —$CX^{18A}_3$, —$CHX^{18A}_2$, —$CH_2X^{18A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18A}$ is independently —F, —Cl, —Br, or —I. In embodiments, $R^{18A}$ is independently hydrogen. In embodiments, $R^{18A}$ is independently unsubstituted methyl. In embodiments, $R^{18A}$ is independently unsubstituted ethyl.

In embodiments, $R^{18A}$ and $R^{18B}$ substituents bonded to the same nitrogen atom may optionally be joined to form a $R^{81A}$-substituted or unsubstituted heterocycloalkyl (e.g., 3 to 8 membered, 3 to 6 membered, 4 to 6 membered, 4 to 5 membered, or 5 to 6 membered) or $R^{81A}$ substituted or unsubstituted heteroaryl (e.g., 5 to 10 membered, 5 to 9 membered, or 5 to 6 membered). In embodiments, $R^{18A}$ and $R^{18B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{18A}$ and $R^{18B}$ substituents bonded to the same nitrogen atom may optionally be joined to form a $R^{81A}$-substituted or unsubstituted heterocycloalkyl (e.g., 3 to 8 membered, 3 to 6 membered, 4 to 6 membered, 4 to 5 membered, or 5 to 6 membered). In embodiments, $R^{18A}$ and $R^{18B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{81A}$ is independently oxo, halogen, —$CX^{81A}_3$, —$CHX^{81A}_2$, —$CH_2X^{81A}$, —$OCX^{81A}_3$, —$OCH_2X^{81A}$, —$OCHX^{81A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{82A}$-substituted or unsubstituted alkyl (e.g., $C_1$-$C_8$, $C_1$-$C_6$, $C_1$-$C_4$, or $C_1$-$C_2$), $R^{82A}$-substituted or unsubstituted heteroalkyl (e.g., 2 to 8 membered, 2 to 6 membered, 4 to 6 membered, 2 to 3 membered, or 4 to 5 membered), $R^{82A}$-substituted or unsubstituted cycloalkyl (e.g., $C_3$-$C_8$, $C_3$-$C_6$, $C_4$-$C_6$, or $C_5$-$C_6$), $R^{82A}$-substituted or unsubstituted heterocycloalkyl (e.g., 3 to 8 membered, 3 to 6 membered, 4 to 6 membered, 4 to 5 membered, or 5 to 6 membered), $R^{82A}$-substituted or unsubstituted aryl (e.g., $C_6$-$C_{10}$ or phenyl), or $R^{82A}$-substituted or unsubstituted heteroaryl (e.g., 5 to 10 membered, 5 to 9 membered, or 5 to 6 membered). In embodiments, $R^{81A}$ is independently oxo, halogen, —$CX^{81A}{}_3$, —$CHX^{81A}{}_2$, —$CH_2X^{81A}$, —$OCX^{81A}{}_3$, —$OCH_2X^{81A}$, —$OCHX^{81A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{81A}$ is independently —F, —Cl, —Br, or —I. In embodiments, $R^{81A}$ is independently unsubstituted methyl. In embodiments, $R^{81A}$ is independently unsubstituted ethyl.

$R^{82A}$ is independently oxo, halogen, —$CX^{82A}{}_3$, —$CHX^{82A}{}_2$, —$CH_2X^{82A}$, —$OCX^{82A}{}_3$, —$OCH_2X^{82A}$, —$OCHX^{82A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{83A}$-substituted or unsubstituted alkyl (e.g., $C_1$-$C_8$, $C_1$-$C_6$, $C_1$-$C_4$, or $C_1$-$C_2$), $R^{83A}$-substituted or unsubstituted heteroalkyl (e.g., 2 to 8 membered, 2 to 6 membered, 4 to 6 membered, 2 to 3 membered, or 4 to 5 membered), $R^{83A}$-substituted or unsubstituted cycloalkyl (e.g., $C_3$-$C_8$, $C_3$-$C_6$, $C_4$-$C_6$, or $C_5$-$C_6$), $R^{83A}$-substituted or unsubstituted heterocycloalkyl (e.g., 3 to 8 membered, 3 to 6 membered, 4 to 6 membered, 4 to 5 membered, or 5 to 6 membered), $R^{83A}$-substituted or unsubstituted aryl (e.g., $C_6$-$C_{10}$ or phenyl), or $R^{83A}$-substituted or unsubstituted heteroaryl (e.g., 5 to 10 membered, 5 to 9 membered, or 5 to 6 membered). In embodiments, $R^{82A}$ is independently oxo, halogen, —$CX^{82A}{}_3$, —$CHX^{82A}{}_2$, —$CH_2X^{82A}$, —$OCX^{82A}{}_3$, —$OCH_2X^{82A}$, —$OCHX^{82A}{}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{82A}$ is independently —F, —Cl, —Br, or —I. In embodiments, $R^{82A}$ is independently unsubstituted methyl. In embodiments, $R^{82A}$ is independently unsubstituted ethyl.

$R^{83A}$ is independently oxo, halogen, —$CX^{83A}{}_3$, —$CHX^{83A}{}_2$, —$CH_2X^{83A}$, —$OCX^{83A}{}_3$, —$OCH_2X^{83A}$, —$OCHX^{83A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{83A}$ is independently —F, —Cl, —Br, or —I. In embodiments, $R^{83A}$ is independently unsubstituted methyl. In embodiments, $R^{83A}$ is independently unsubstituted ethyl.

In embodiments, $R^{18B}$ is independently hydrogen, —$CX^{18B}{}_3$, —$CHX^{18B}{}_2$, —$CH_2X^{18B}$, —CN, —COOH, —$CONH_2$, $R^{81B}$-substituted or unsubstituted alkyl (e.g., $C_1$-$C_8$, $C_1$-$C_6$, $C_1$-$C_4$, or $C_1$-$C_2$), $R^{81B}$-substituted or unsubstituted heteroalkyl (e.g., 2 to 8 membered, 2 to 6 membered, 4 to 6 membered, 2 to 3 membered, or 4 to 5 membered), $R^{81B}$-substituted or unsubstituted cycloalkyl (e.g., $C_3$-$C_8$, $C_3$-$C_6$, $C_4$-$C_6$, or $C_5$-$C_6$), $R^{81B}$-substituted or unsubstituted heterocycloalkyl (e.g., 3 to 8 membered, 3 to 6 membered, 4 to 6 membered, 4 to 5 membered, or 5 to 6 membered), $R^{81B}$-substituted or unsubstituted aryl (e.g., $C_6$-$C_{10}$ or phenyl), or $R^{81B}$-substituted or unsubstituted heteroaryl (e.g., 5 to 10 membered, 5 to 9 membered, or 5 to 6 membered). In embodiments, $R^{18B}$ is independently hydrogen, —$CX^{18B}{}_3$, —$CHX^{18B}{}_2$, —$CH_2X^{18B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18B}$ is independently —F, —Cl, —Br, or —I. In embodiments, $R^{18B}$ is independently hydrogen. In embodiments, $R^{18B}$ is independently unsubstituted methyl. In embodiments, $R^{18B}$ is independently unsubstituted ethyl.

In embodiments, $R^{18A}$ and $R^{18B}$ substituents bonded to the same nitrogen atom may optionally be joined to form a $R^{81B}$-substituted or unsubstituted heterocycloalkyl (e.g., 3 to 8 membered, 3 to 6 membered, 4 to 6 membered, 4 to 5 membered, or 5 to 6 membered) or $R^{81B}$-substituted or unsubstituted heteroaryl (e.g., 5 to 10 membered, 5 to 9 membered, or 5 to 6 membered). In embodiments, $R^{18A}$ and $R^{18B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{18A}$ and $R^{18B}$-substituents bonded to the same nitrogen atom may optionally be joined to form a $R^{81B}$-substituted or unsubstituted heterocycloalkyl (e.g., 3 to 8 membered, 3 to 6 membered, 4 to 6 membered, 4 to 5 membered, or 5 to 6 membered). In embodiments, $R^{18A}$ and $R^{18B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{81B}$ is independently oxo, halogen, $—CX^{81B}_3$, $—CHX^{81B}_2$, $—CH_2X^{81B}$, $—OCX^{81B}_3$, $—OCH_2X^{81B}$, $—OCHX^{81B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{82B}$-substituted or unsubstituted alkyl (e.g., $C_1$-$C_8$, $C_1$-$C_6$, $C_1$-$C_4$, or $C_1$-$C_2$), $R^{82B}$-substituted or unsubstituted heteroalkyl (e.g., 2 to 8 membered, 2 to 6 membered, 4 to 6 membered, 2 to 3 membered, or 4 to 5 membered), $R^{82B}$-substituted or unsubstituted cycloalkyl (e.g., $C_3$-$C_8$, $C_3$-$C_6$, $C_4$-$C_6$, or $C_5$-$C_6$), $R^{82B}$-substituted or unsubstituted heterocycloalkyl (e.g., 3 to 8 membered, 3 to 6 membered, 4 to 6 membered, 4 to 5 membered, or 5 to 6 membered), $R^{82B}$-substituted or unsubstituted aryl (e.g., $C_6$-$C_{10}$ or phenyl), or $R^{82B}$-substituted or unsubstituted heteroaryl (e.g., 5 to 10 membered, 5 to 9 membered, or 5 to 6 membered). In embodiments, $R^{81B}$ is independently oxo, halogen, $—CX^{81B}_3$, $—CHX^{81B}_2$, $—CH_2X^{81B}$, $—OCX^{81B}_3$, $—OCH_2X^{81B}$, $—OCHX^{81B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{81B}$ is independently —F, —Cl, —Br, or —I. In embodiments, $R^{81B}$ is independently unsubstituted methyl. In embodiments, $R^{81B}$ is independently unsubstituted ethyl.

$R^{82B}$ is independently oxo, halogen, $—CX^{82B}_3$, $—CHX^{82B}_2$, $—CH_2X^{82B}$, $—OCX^{82B}_3$, $—OCH_2X^{82B}$, $—OCHX^{82B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{83B}$-substituted or unsubstituted alkyl (e.g., $C_1$-$C_8$, $C_1$-$C_6$, $C_1$-$C_4$, or $C_1$-$C_2$), $R^{83B}$-substituted or unsubstituted heteroalkyl (e.g., 2 to 8 membered, 2 to 6 membered, 4 to 6 membered, 2 to 3 membered, or 4 to 5 membered), $R^{83B}$-substituted or unsubstituted cycloalkyl (e.g., $C_3$-$C_8$, $C_3$-$C_6$, $C_4$-$C_6$, or $C_5$-$C_6$), $R^{83B}$-substituted or unsubstituted heterocycloalkyl (e.g., 3 to 8 membered, 3 to 6 membered, 4 to 6 membered, 4 to 5 membered, or 5 to 6 membered), $R^{83B}$-substituted or unsubstituted aryl (e.g., $C_6$-$C_{10}$ or phenyl), or $R^{83B}$-substituted or unsubstituted heteroaryl (e.g., 5 to 10 membered, 5 to 9 membered, or 5 to 6 membered). In embodiments, $R^{82B}$ is independently oxo, halogen, $—CX^{82B}_3$, $—CHX^{82B}_2$, $—CH_2X^{82B}$, $—OCX^{82B}_3$, $—OCH_2X^{82B}$, $—OCHX^{82B}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{82B}$ is independently —F, —Cl, —Br, or —I. In embodiments, $R^{82B}$ is independently unsubstituted methyl. In embodiments, $R^{82B}$ is independently unsubstituted ethyl.

$R^{83B}$ is independently oxo, halogen, $—CX^{83B}_3$, $—CHX^{83B}_2$, $—CH_2X^{83B}$, $—OCX^{83B}_3$, $—OCH_2X^{83B}$, $—OCHX^{83B}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{83B}$ is independently —F, —Cl, —Br, or —I. In embodiments, $R^{83B}$ is independently unsubstituted methyl. In embodiments, $R^{83B}$ is independently unsubstituted ethyl.

In embodiments, $R^{18C}$ is independently hydrogen, $—CX^{18C}_3$, $—CHX^{18C}_2$, $—CH_2X^{18C}$, —CN, —COOH, $—CONH_2$, $R^{81C}$-substituted or unsubstituted alkyl (e.g., $C_1$-$C_8$, $C_1$-$C_6$, $C_1$-$C_4$, or $C_1$-$C_2$), $R^{81C}$-substituted or unsubstituted heteroalkyl (e.g., 2 to 8 membered, 2 to 6 membered, 4 to 6 membered, 2 to 3 membered, or 4 to 5 membered), $R^{81C}$-substituted or unsubstituted cycloalkyl (e.g., $C_3$-$C_8$, $C_3$-$C_6$, $C_4$-$C_6$, or $C_5$-$C_6$), $R^{81C}$-substituted or unsubstituted heterocycloalkyl (e.g., 3 to 8 membered, 3 to 6 membered, 4 to 6 membered, 4 to 5 membered, or 5 to 6 membered), $R^{81C}$-substituted or unsubstituted aryl (e.g., $C_6$-$C_{10}$ or phenyl), or $R^{81C}$-substituted or unsubstituted heteroaryl (e.g., 5 to 10 membered, 5 to 9 membered, or 5 to 6 membered). In embodiments, $R^{18C}$ is independently hydrogen, $—CX^{18C}_3$, $—CHX^{18C}_2$, $—CH_2X^{18C}$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18C}$ is independently —F, —Cl, —Br, or —I. In embodiments, $R^{18C}$ is independently hydrogen. In embodiments, $R^{18C}$ is independently unsubstituted methyl. In embodiments, Rise is independently unsubstituted ethyl.

$R^{81C}$ is independently oxo, halogen, $—CX^{81C}_3$, $—CHX^{81C}_2$, $—CH_2X^{81C}$, $—OCX^{81C}_3$, $—OCH_2X^{81C}$, $—OCHX^{81C}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{82C}$-substituted or unsubstituted alkyl (e.g., $C_1$-$C_8$, $C_1$-$C_6$, $C_1$-$C_4$, or $C_1$-$C_2$), $R^{82C}$-substituted or unsubstituted heteroalkyl (e.g., 2 to 8 membered, 2 to 6 membered, 4 to 6 membered, 2 to 3 membered, or 4 to 5 membered), $R^{82C}$-substituted or unsubstituted cycloalkyl (e.g., $C_3$-$C_8$, $C_3$-$C_6$, $C_4$-$C_6$, or $C_5$-$C_6$), $R^{82C}$-substituted or unsubstituted heterocycloalkyl (e.g., 3 to 8 membered, 3 to 6 membered, 4 to 6 membered, 4 to 5 membered, or 5 to 6 membered), $R^{82C}$-substituted or unsubstituted aryl (e.g., $C_6$-$C_{10}$ or phenyl), or $R^{82C}$-substituted or unsubstituted heteroaryl (e.g., 5 to 10 membered, 5 to 9 membered, or 5 to 6 membered). In embodiments, $R^{81C}$ is independently oxo, halogen, —$CX^{81C}_3$, —$CHX^{81C}_2$, —$CH_2X^{81C}$, —$OCX^{81}$, —$OCH_2X^{81C}$, —$OCHX^{81C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{81C}$ is independently —F, —Cl, —Br, or —I. In embodiments, $R^{81C}$ is independently unsubstituted methyl. In embodiments, $R^{81C}$ is independently unsubstituted ethyl.

$R^{82C}$ is independently oxo, halogen, —$CX^{82C}_3$, —$CHX^{82C}_2$, —$CH_2X^{82C}$, —$OCX^{82C}$, —$OCH_2X^{82C}$, —$OCHX^{82C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{83C}$-substituted or unsubstituted alkyl (e.g., $C_1$-$C_8$, $C_1$-$C_6$, $C_1$-$C_4$, or $C_1$-$C_2$), $R^{83C}$-substituted or unsubstituted heteroalkyl (e.g., 2 to 8 membered, 2 to 6 membered, 4 to 6 membered, 2 to 3 membered, or 4 to 5 membered), $R^{83C}$-substituted or unsubstituted cycloalkyl (e.g., $C_3$-$C_8$, $C_3$-$C_6$, $C_4$-$C_6$, or $C_5$-$C_6$), $R^{83C}$-substituted or unsubstituted heterocycloalkyl (e.g., 3 to 8 membered, 3 to 6 membered, 4 to 6 membered, 4 to 5 membered, or 5 to 6 membered), $R^{83C}$-substituted or unsubstituted aryl (e.g., $C_6$-$C_{10}$ or phenyl), or $R^{83C}$-substituted or unsubstituted heteroaryl (e.g., 5 to 10 membered, 5 to 9 membered, or 5 to 6 membered). In embodiments, $R^{82C}$ is independently oxo, halogen, —$CX^{82C}_3$, —$CHX^{82C}_2$, —$CH_2X^{82C}$, —$OCX^{82C}_3$, —$OCH_2X^{82C}$, —$OCHX^{82C}_2$, —CN, —OH, —$NH_2$, —CO OH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{82C}$ is independently —F, —Cl, —Br, or —I. In embodiments, $R^{82C}$ is independently unsubstituted methyl. In embodiments, $R^{82C}$ is independently unsubstituted ethyl.

$R^{83C}$ is independently oxo, halogen, —$CX^{83C}_3$, —$CHX^{83C}_2$, —$CH_2X^{83C}$, —$OCX^{83C}$, —$OCH_2X^{83C}$, —$OCHX^{83C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{83C}$ is independently —F, —Cl, —Br, or —I. In embodiments, $R^{83C}$ is independently unsubstituted methyl. In embodiments, $R^{83C}$ is independently unsubstituted ethyl.

In embodiments, $R^{18D}$ is independently hydrogen, —$CX^{18D}_3$, —$CHX^{18D}_2$, —$CH_2X^{18D}$—CN, —COOH, —$CONH_2$, $R^{81D}$-substituted or unsubstituted alkyl (e.g., $C_1$-$C_8$, $C_1$-$C_6$, $C_1$-$C_4$, or $C_1$-$C_2$), $R^{81D}$-substituted or unsubstituted heteroalkyl (e.g., 2 to 8 membered, 2 to 6 membered, 4 to 6 membered, 2 to 3 membered, or 4 to 5 membered), $R^{81D}$-substituted or unsubstituted cycloalkyl (e.g., $C_3$-$C_8$, $C_3$-$C_6$, $C_4$-$C_6$, or $C_5$-$C_6$), $R^{81D}$-substituted or unsubstituted heterocycloalkyl (e.g., 3 to 8 membered, 3 to 6 membered, 4 to 6 membered, 4 to 5 membered, or 5 to 6 membered), $R^{81D}$-substituted or unsubstituted aryl (e.g., $C_6$-$C_{10}$ or phenyl), or $R^{81D}$-substituted or unsubstituted heteroaryl (e.g., 5 to 10 membered, 5 to 9 membered, or 5 to 6 membered). In embodiments, $R^{18D}$ is independently hydrogen, —$CX^{18D}_3$, —$CHX^{18D}_2$, —$CH_2X^{18D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18D}$ is independently —F, —Cl, —Br, or —I. In embodiments, $R^{18D}$ is independently hydrogen. In embodiments, $R^{18D}$ is independently unsubstituted methyl. In embodiments, $R^{81D}$ is independently unsubstituted ethyl.

$R^{81D}$ is independently oxo, halogen, —$CX^{81D}_3$, —$CHX^{81D}_2$, —$CH_2X^{81D}$, —$OCX^{81D}_3$, —$OCH_2X^{81D}$, —$OCHX^{81D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{82D}$-substituted or unsubstituted alkyl (e.g., $C_1$-$C_8$, $C_1$-$C_6$, $C_1$-$C_4$, or $C_1$-$C_2$), $R^{82D}$-substituted or unsubstituted heteroalkyl (e.g., 2 to 8 membered, 2 to 6 membered, 4 to 6 membered, 2 to 3 membered, or 4 to 5 membered), $R^{82D}$-substituted or unsubstituted cycloalkyl (e.g., $C_3$-$C_8$, $C_3$-$C_6$, $C_4$-$C_6$, or $C_5$-$C_6$), $R^{82D}$-substituted or unsubstituted heterocycloalkyl (e.g., 3 to 8 membered, 3 to 6 membered, 4 to 6 membered, 4 to 5 membered, or 5 to 6 membered), $R^{82D}$-substituted or unsubstituted aryl (e.g., $C_6$-$C_{10}$ or phenyl), or $R^{82D}$-substituted or unsubstituted heteroaryl (e.g., 5 to 10 membered, 5 to 9 membered, or 5 to 6 membered). In embodiments, $R^{81D}$ is independently oxo, halogen, —$CX^{81D}_3$, —$CHX^{81D}_2$, —$CH_2X^{81D}$, —$OCX^{81D}_3$, —$OCH_2X^{81D}$, —$OCHX^{81D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{81D}$ is independently —F, —Cl, —Br, or —I. In embodiments, $R^{81D}$ is independently unsubstituted methyl. In embodiments, $R^{81D}$ is independently unsubstituted ethyl.

$R^{82D}$ is independently oxo, halogen, $—CX^{82D}_3$, $—CHX^{82D}_2$, $—CH_2X^{82D}$, $—OCX^{82D}_3$, $—OCH_2X^{82D}$, $—OCHX^{82D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{83D}$-substituted or unsubstituted alkyl (e.g., $C_1$-$C_8$, $C_1$-$C_6$, $C_1$-$C_4$, or $C_1$-$C_2$), $R^{83D}$-substituted or unsubstituted heteroalkyl (e.g., 2 to 8 membered, 2 to 6 membered, 4 to 6 membered, 2 to 3 membered, or 4 to 5 membered), $R^{83D}$-substituted or unsubstituted cycloalkyl (e.g., $C_3$-$C_8$, $C_3$-$C_6$, $C_4$-$C_6$, or $C_5$-$C_6$), $R^{83D}$-substituted or unsubstituted heterocycloalkyl (e.g., 3 to 8 membered, 3 to 6 membered, 4 to 6 membered, 4 to 5 membered, or 5 to 6 membered), $R^{83D}$-substituted or unsubstituted aryl (e.g., $C_6$-$C_{10}$ or phenyl), or $R^{83D}$-substituted or unsubstituted heteroaryl (e.g., 5 to 10 membered, 5 to 9 membered, or 5 to 6 membered). In embodiments, $R^{82D}$ is independently oxo, halogen, $—CX^{82D}_3$, $—CHX^{82D}_2$, $—CH_2X^{82D}$, $—OCX^{82D}_3$, $—OCH_2X^{82D}$, $—OCHX^{82D}_2$, —CN, —OH, $—NH_2$, —CO OH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC (O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{82D}$ is independently —F, —Cl, —Br, or —I. In embodiments, $R^{82D}$ is independently unsubstituted methyl. In embodiments, $R^{82D}$ is independently unsubstituted ethyl.

$R^{83D}$ is independently oxo, halogen, $—CX^{83D}_3$, $—CHX^{83D}_2$, $—CH_2X^{83D}$, $—OCX^{83D}_3$, $—OCH_2X^{83D}$, $—OCHX^{83D}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{83D}$ is independently —F, —Cl, —Br, or —I. In embodiments, $R^{83D}$ is independently unsubstituted methyl. In embodiments, $R^{83D}$ is independently unsubstituted ethyl.

In embodiments, $R^{15}$, $R^{16}$, $R^{17}$, and $R^{18}$ are hydrogen.

In embodiments, $R^{15}$ is hydrogen. In embodiments, $R^{16}$ is hydrogen, $—CH_3$, $—CH_2NR^{16A}R^{16B}$, or

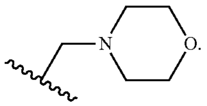 [SMILES: *CN1CCOCC1]

In embodiments, $R^{17}$ is hydrogen. In embodiments, $R^{16A}$ and $R^{16B}$ are independently hydrogen or unsubstituted alkyl. In embodiments, $R^{16A}$ and $R^{16B}$ are independently unsubstituted methyl. In embodiments, $R^{16A}$ is independently hydrogen. In embodiments, $R^{16A}$ is independently unsubstituted alkyl. In embodiments, $R^{16B}$ is independently hydrogen. In embodiments, $R^{16B}$ is independently unsubstituted alkyl. In embodiments, $R^{16A}$ is independently unsubstituted methyl. In embodiments, $R^{16B}$ is independently unsubstituted methyl. In embodiments, $R^{15}$ is hydrogen; $R^{16}$ is hydrogen, $—CH_3$, $—CH_2NR^{16A}R^{16B}$, or

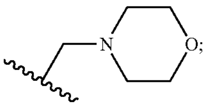 [SMILES: *CN1CCOCC1]

$R^{17}$ is hydrogen; and $R^{16A}$ and $R^{16B}$ are independently hydrogen or unsubstituted alkyl.

In embodiments, $R^{15}$ is hydrogen. In embodiments, $R^{16}$ is hydrogen. In embodiments, $R^{17}$ is hydrogen, $—CH_3$, $—CH_2NR^{17A}R^{17B}$, or

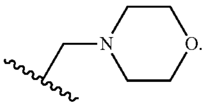

In embodiments, $R^{17A}$ and $R^{17B}$ are independently hydrogen or unsubstituted alkyl. In embodiments, $R^{17A}$ and $R^{17B}$ are independently unsubstituted methyl. In embodiments, $R^{15}$ is hydrogen; $R^{16}$ is hydrogen; $R^{17}$ is hydrogen, $—CH_3$, $—CH_2NR^{17A}R^{17B}$, or

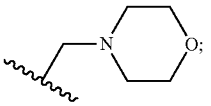 [SMILES: *CN1CCOCC1]

and $R^{17A}$ and $R^{17B}$ are independently hydrogen or unsubstituted alkyl. In embodiments, $R^{17A}$ is independently hydrogen. In embodiments, $R^{17A}$ is independently unsubstituted alkyl. In embodiments, $R^{17B}$ is independently hydrogen. In embodiments, $R^{17B}$ is independently unsubstituted alkyl. In embodiments, $R^{17A}$ is independently unsubstituted methyl. In embodiments, $R^{17B}$ is independently unsubstituted methyl.

In embodiments, $R^{15}$ is hydrogen, $—CH_3$, $—CH_2NR^{15A}R^{15B}$, or

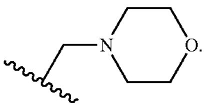 [SMILES: *CN1CCOCC1]

In embodiments, $R^{16}$ is hydrogen. In embodiments, $R^{17}$ is hydrogen. In embodiments, $R^{15A}$ and $R^{15B}$ are independently hydrogen or unsubstituted alkyl. In embodiments, $R^{15A}$ and $R^{15B}$ are independently unsubstituted methyl. In embodiments, $R^{15A}$ is independently hydrogen. In embodiments, $R^{15A}$ is independently unsubstituted alkyl. In embodiments, $R^{15B}$ is independently hydrogen. In embodiments, $R^{15B}$ is independently unsubstituted alkyl. In embodiments, $R^{15A}$ is independently unsubstituted methyl. In embodiments, $R^{15B}$ is independently unsubstituted methyl. In embodiments, $R^{15}$ is hydrogen, $—CH_3$, $—CH_2NR^{15A}R^{15B}$, or

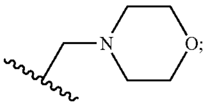 [SMILES: *CN1CCOCC1]

$R^{16}$ is hydrogen; $R^{17}$ is hydrogen; and $R^{15A}$ and $R^{15B}$ are independently hydrogen or unsubstituted alkyl.

In embodiments, E is:

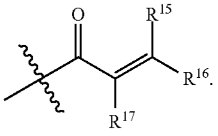

In embodiments, E is:

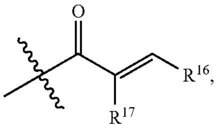

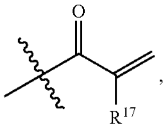 ,

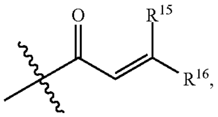

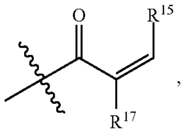 , or

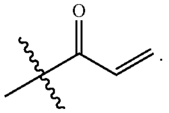

In embodiments, E is:

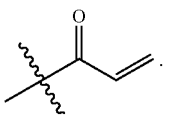 [SMILES: *C(=O)C=C]

In embodiments, E is:

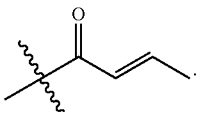 [SMILES: *C(=O)/C=C/C]

In embodiments, E is:

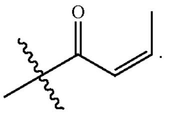

In embodiments, E is:

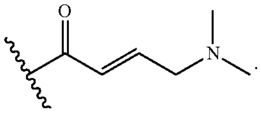 [SMILES: *C(=O)/C=C/CN(C)C]

In embodiments, E is:

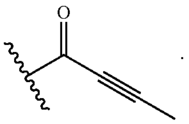 [SMILES: *C(=O)C#CC]

In embodiments, E is $—C(O)CH{=}CH_2$, $—C(O)CH{=}CHCH_2N(CH_3)_2$, $—C(O)C({=}CH_2)CH_2N(CH_3)_2$, $—C(O)C{\equiv}CCH_3$, $—C(O)C({=}CH_2)CH_3$.

In embodiments, the compound has the formula:

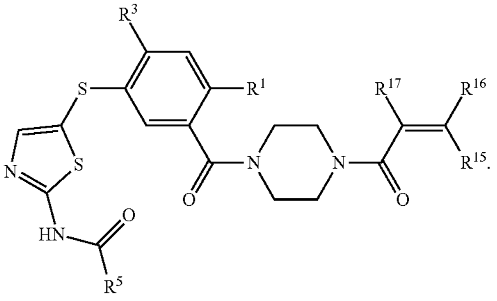

$R^3$, $R^5$, $R^{15}$, $R^{16}$, $R^{17}$ are as described herein. In embodiments, the compound has the formula:

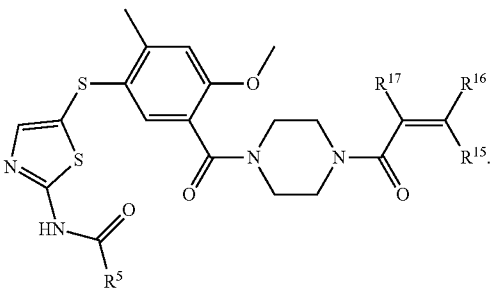

$R^5$, $R^{15}$, $R^{16}$, $R^{17}$ are as described herein. In embodiments, the compound has the formula:

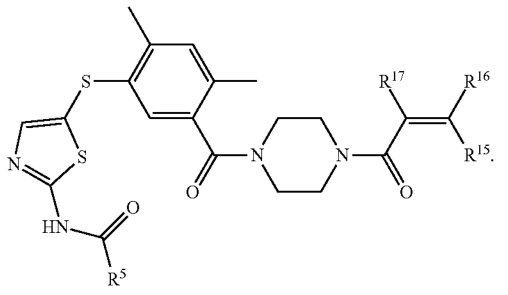

$R^5$, $R^{15}$, $R^{16}$, $R^{17}$ are as described herein. In embodiments, the compound has the formula:

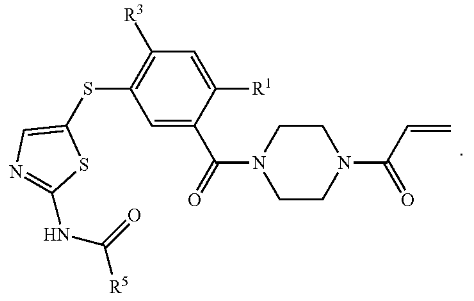

$R^1$, $R^3$, $R^5$ are as described herein. In embodiments, the compound has the formula:

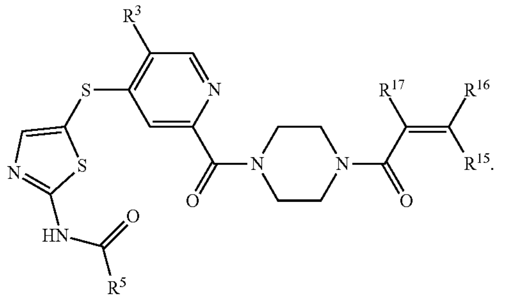

$R^3$, $R^5$, $R^{15}$, $R^{16}$, $R^{17}$ are as described herein. In embodiments, the compound has the formula:

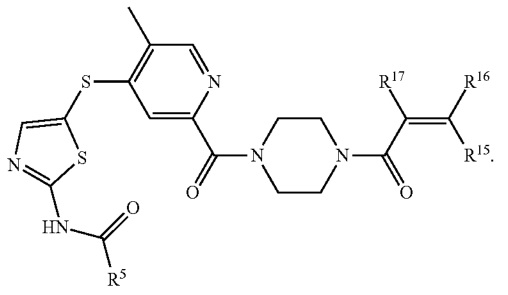

$R^5$, $R^{15}$, $R^{16}$, $R^{17}$ are as described herein. In embodiments, the compound has the formula:

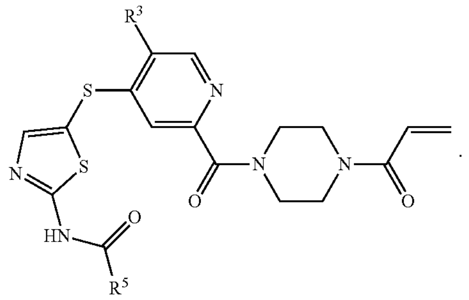

$R^1$, $R^3$, $R^5$ are as described herein. In embodiments, the compound has the formula:

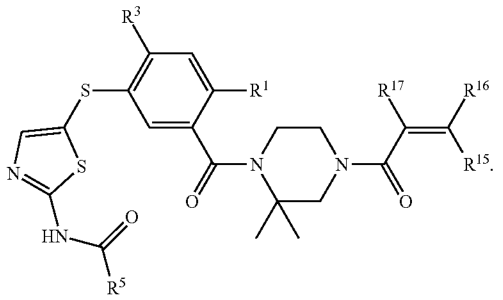

$R^1$, $R^3$, $R^5$, $R^{15}$, $R^{16}$, $R^{17}$ are as described herein. In embodiments, the compound has the formula:

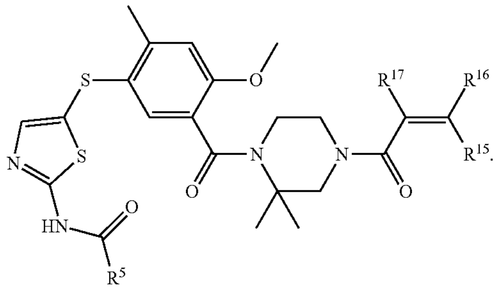

$R^5$, $R^{15}$, $R^{16}$, $R^{17}$ are as described herein. In embodiments, the compound has the formula:

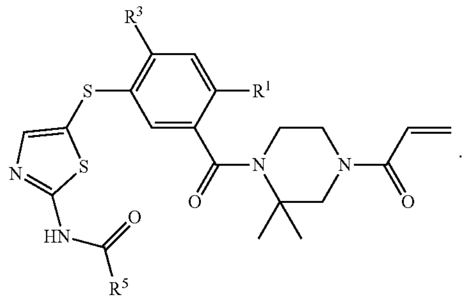

$R^1$, $R^3$, $R^5$ are as described herein. In embodiments, the compound has the formula:

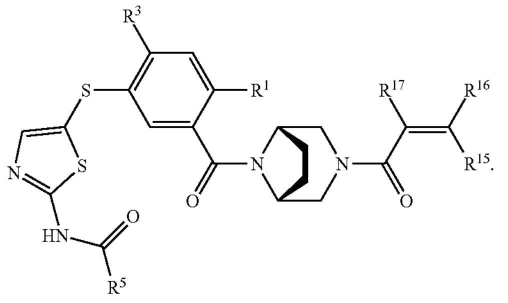

$R^1$, $R^3$, $R^5$, $R^{15}$, $R^{16}$, $R^{17}$ are as described herein. In embodiments, the compound has the formula:

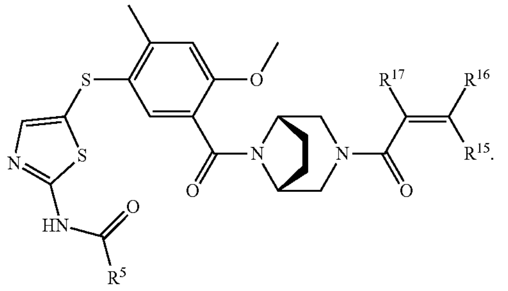

$R^5$, $R^{15}$, $R^{16}$, $R^{17}$ are as described herein. In embodiments, the compound has the formula:

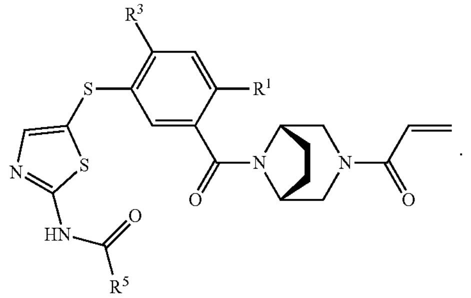

$R^1$, $R^3$, $R^5$ are as described herein. In embodiments, the compound has the formula:

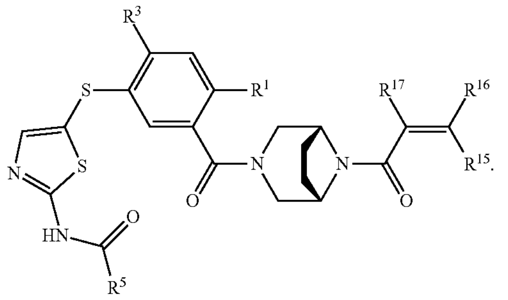

$R^1$, $R^3$, $R^5$, $R^{15}$, $R^{16}$, $R^{17}$ are as described herein. In embodiments, the compound has the formula:

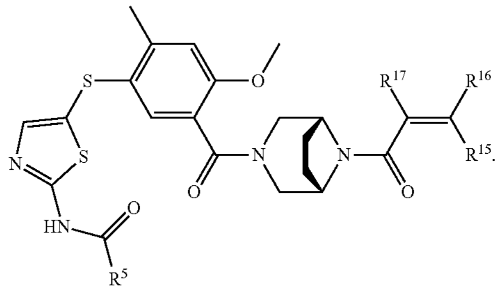

$R^5$, $R^{15}$, $R^{16}$, $R^{17}$ are as described herein. In embodiments, the compound has the formula:

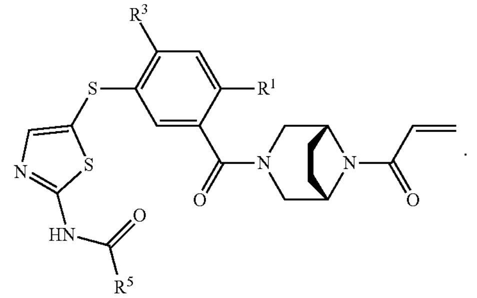

$R^1$, $R^3$, $R^5$ are as described herein. In embodiments, the compound has the formula:

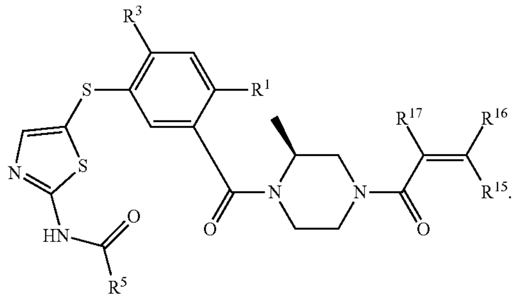

$R^1$, $R^3$, $R^5$, $R^{15}$, $R^{16}$, $R^{17}$ are as described herein. In embodiments, the compound has the formula:

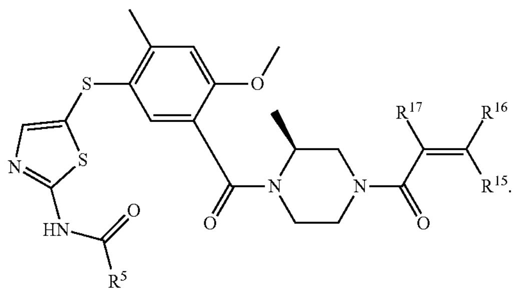

$R^5$, $R^{15}$, $R^{16}$, $R^{17}$ are as described herein. In embodiments, the compound has the formula:

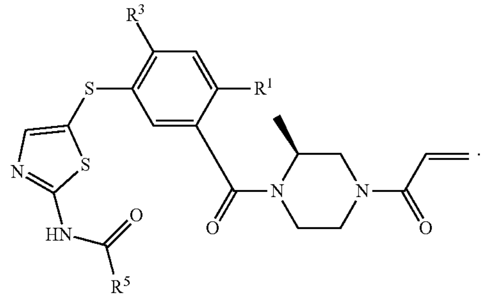

$R^1$, $R^3$, $R^5$ are as described herein. In embodiments, the compound has the formula:

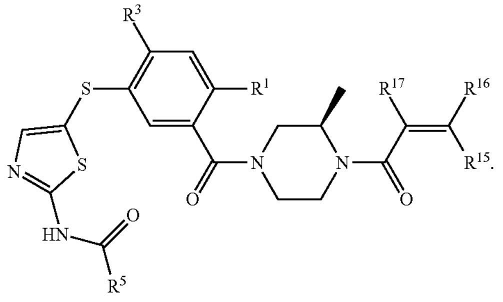

$R^1$, $R^3$, $R^5$, $R^{15}$, $R^{16}$, $R^{17}$ are as described herein. In embodiments, the compound has the formula:

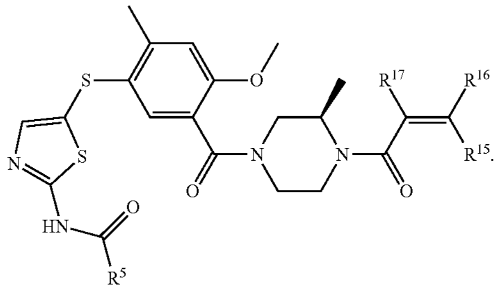

$R^5$, $R^{15}$, $R^{16}$, $R^{17}$ are as described herein. In embodiments, the compound has the formula:

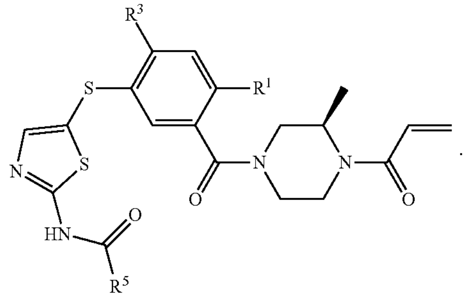

$R^1$, $R^3$, $R^5$ are as described herein. In embodiments, the compound has the formula:

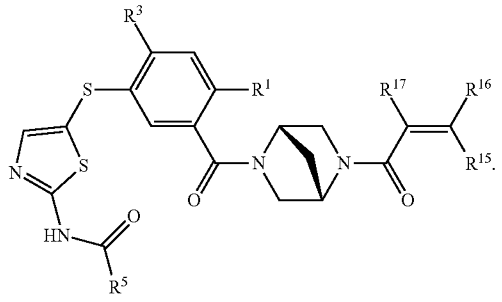

$R^1$, $R^3$, $R^5$, $R^{15}$, $R^{16}$, $R^{17}$ are as described herein. In embodiments, the compound has the formula:

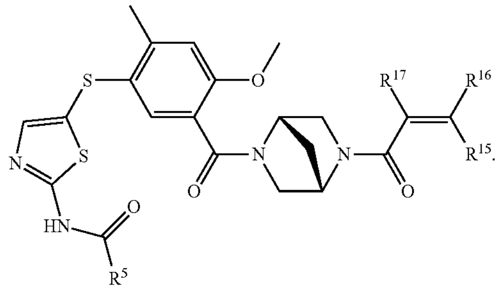

$R^5$, $R^{15}$, $R^{16}$, $R^{17}$ are as described herein. In embodiments, the compound has the formula:

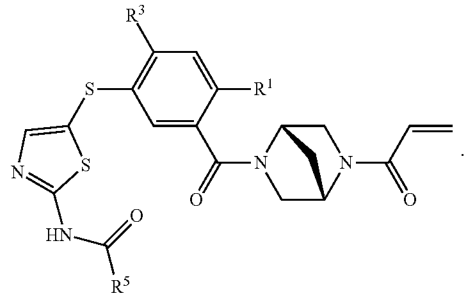

$R^1$, $R^3$, $R^5$ are as described herein. In embodiments, the compound has the formula:

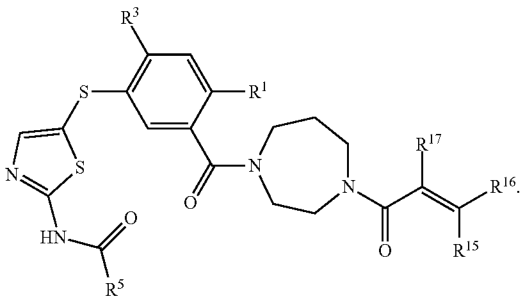

$R^1$, $R^3$, $R^5$, $R^{15}$, $R^{16}$, $R^{17}$ are as described herein. In embodiments, the compound has the formula:

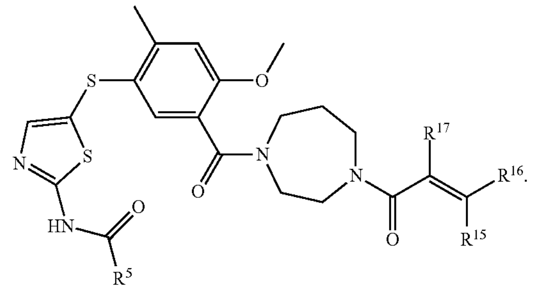

$R^5$, $R^{15}$, $R^{16}$, $R^{17}$ are as described herein. In embodiments, the compound has the formula:

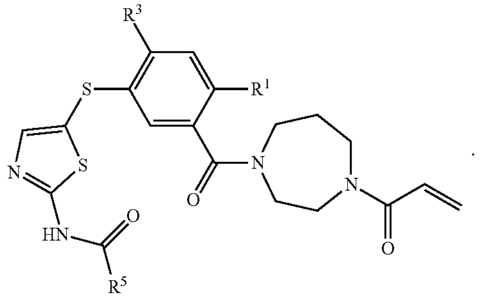

$R^1$, $R^3$, $R^5$ are as described herein. In embodiments, the compound has the formula:

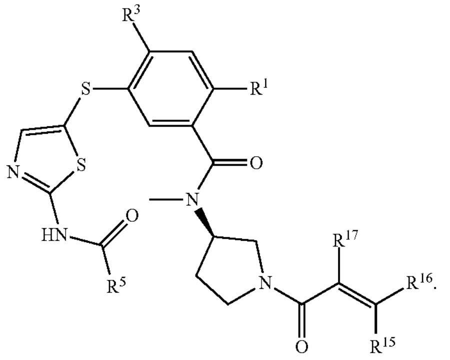

$R^1$, $R^3$, $R^5$, $R^{15}$, $R^{16}$, $R^{17}$ are as described herein. In embodiments, the compound has the formula:

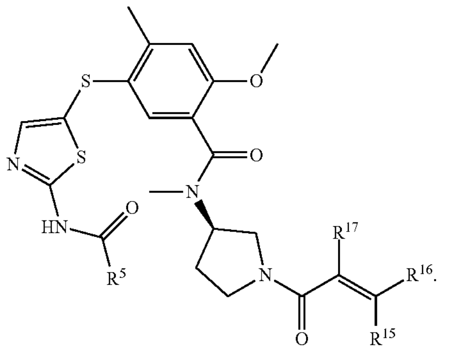

$R^5$, $R^{15}$, $R^{16}$, $R^{17}$ are as described herein. In embodiments, the compound has the formula:

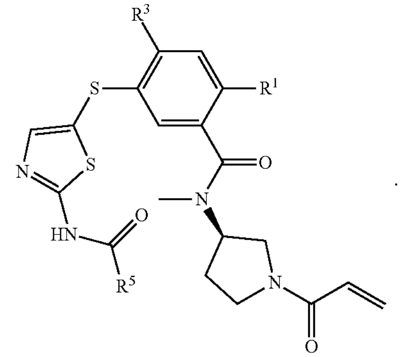

$R^1$, $R^3$, $R^5$ are as described herein. In embodiments, the compound has the formula:

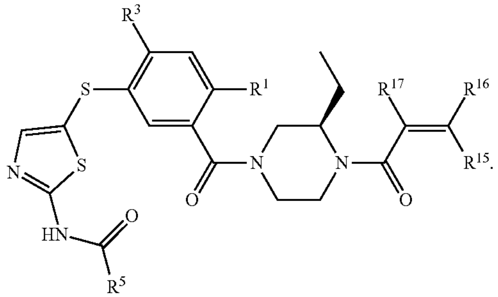

$R^1$, $R^3$, $R^5$, $R^{15}$, $R^{16}$, $R^{17}$ are as described herein. In embodiments, the compound has the formula:

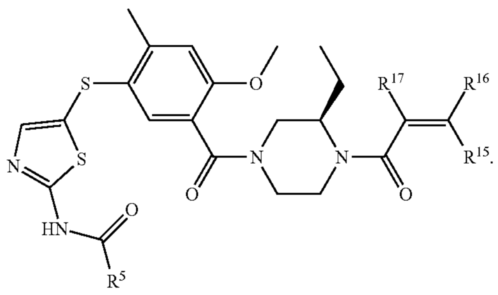

$R^5$, $R^{15}$, $R^{16}$, $R^{17}$ are as described herein. In embodiments, the compound has the formula:

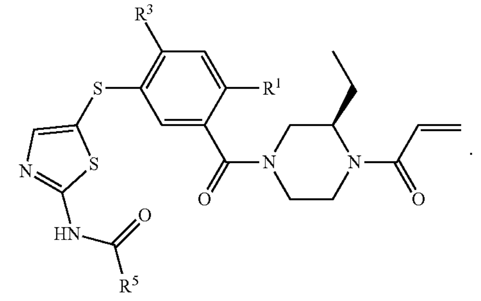

$R^1$, $R^3$, $R^5$ are as described herein. In embodiments, the compound has the formula:

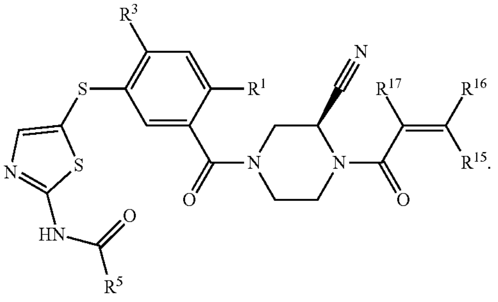

$R^1$, $R^3$, $R^5$, $R^{15}$, $R^{16}$, $R^{17}$ are as described herein. In embodiments, the compound has the formula:

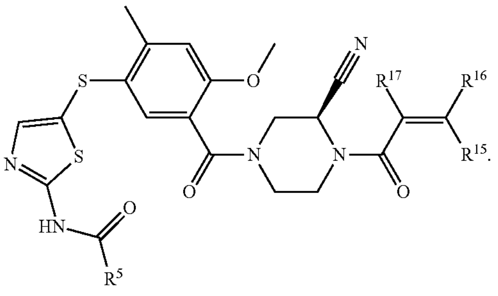

$R^5$, $R^{15}$, $R^{16}$, $R^{17}$ are as described herein. In embodiments, the compound has the formula:

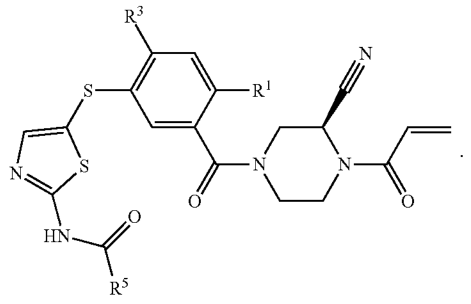

$R^1$, $R^3$, $R^5$ are as described herein. In embodiments, the compound has the formula:

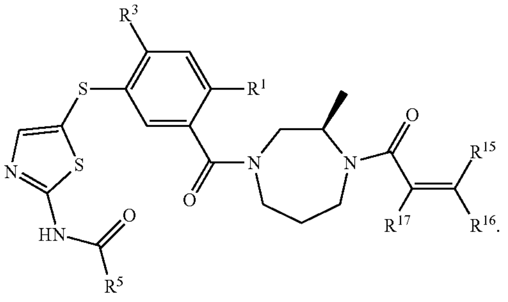

$R^1$, $R^3$, $R^5$, $R^{15}$, $R^{16}$, $R^{17}$ are as described herein. In embodiments, the compound has the formula:

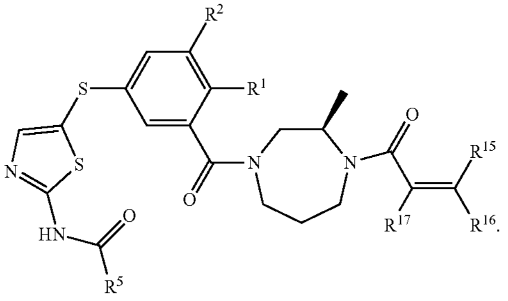

$R^1$, $R^2$, $R^5$, $R^{15}$, $R^{16}$, $R^{17}$ are as described herein. In embodiments, the compound has the formula:

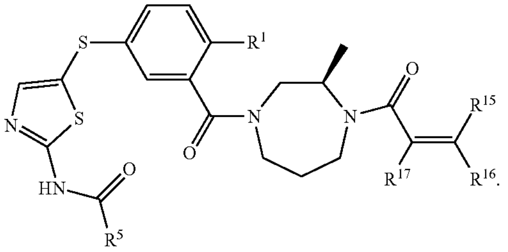

$R^1$, $R^5$, $R^{15}$, $R^{16}$, $R^{17}$ are as described herein. In embodiments, the compound has the formula:

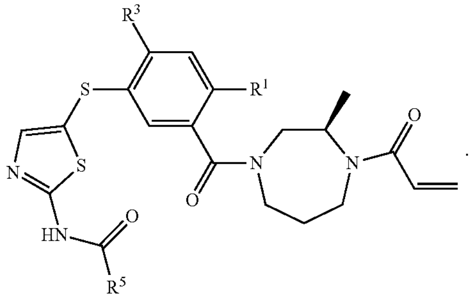

$R^1$, $R^3$, $R^5$ are as described herein. In embodiments, the compound has the formula:

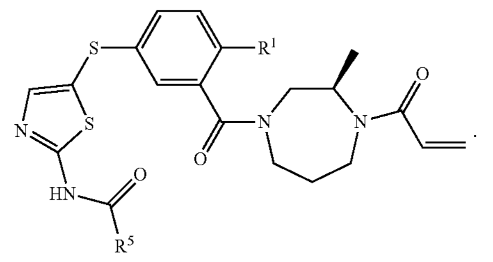

$R^1$ and $R^5$ are as described herein. In embodiments, the compound has the formula:

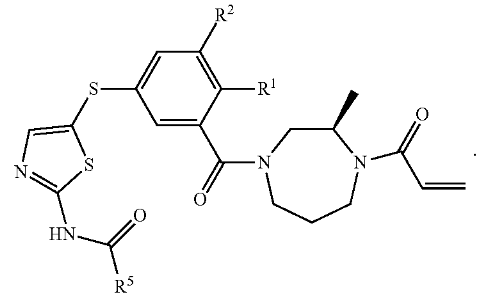

$R^1$, $R^2$, $R^5$ are as described herein. In embodiments, the compound has the formula:

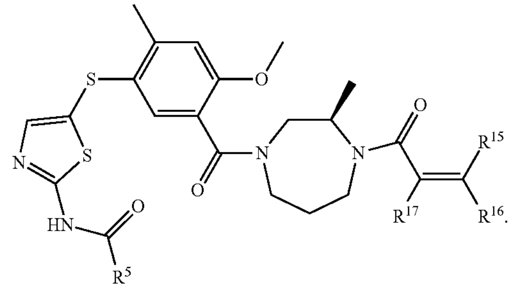

$R^5$, $R^{15}$, $R^{16}$, $R^{17}$ are as described herein. In embodiments, the compound has the formula:

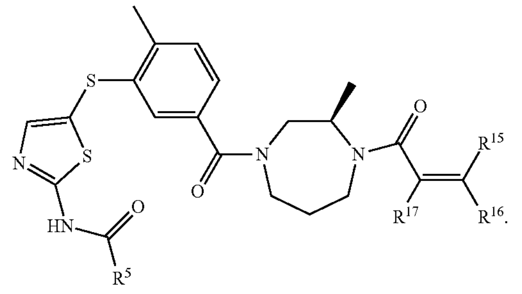

$R^5$, $R^{15}$, $R^{16}$, $R^{17}$ are as described herein. In embodiments, the compound has the formula:

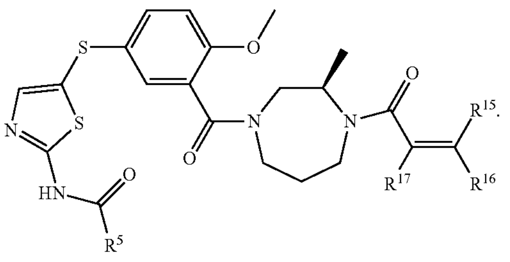

$R^5$, $R^{15}$, $R^{16}$, $R^{17}$ are as described herein. In embodiments, the compound has the formula:

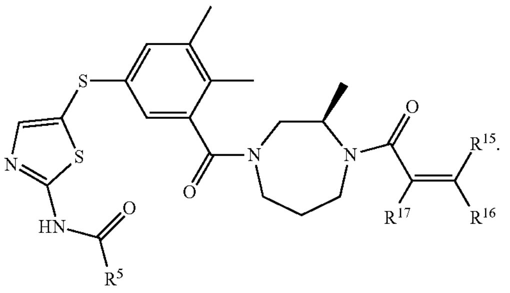

$R^5$, $R^{15}$, $R^{16}$, $R^{17}$ are as described herein. In embodiments, the compound has the formula:

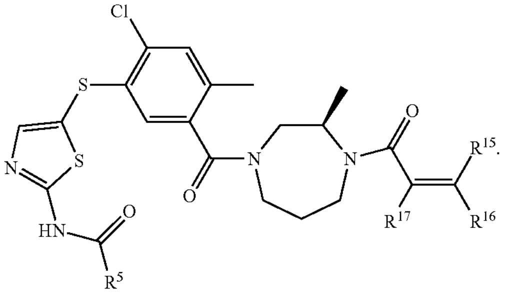

$R^5$, $R^{15}$, $R^{16}$, $R^{17}$ are as described herein. In embodiments, the compound has the formula:

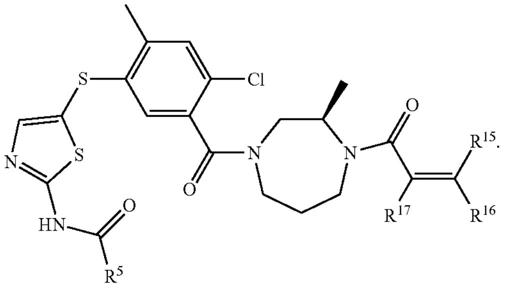

$R^5$, $R^{15}$, $R^{16}$, $R^{17}$ are as described herein. In embodiments, the compound has the formula:

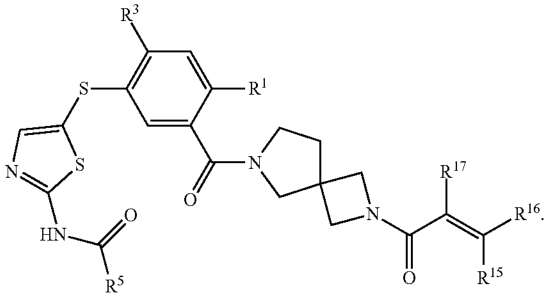

$R^1$, $R^3$, $R^5$, $R^{15}$, $R^{16}$, $R^{17}$ are as described herein. In embodiments, the compound has the formula:

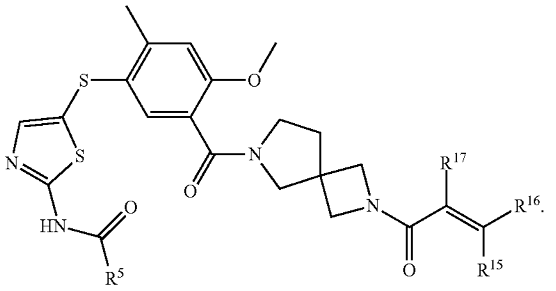

$R^5$, $R^{15}$, $R^{16}$, $R^{17}$ are as described herein. In embodiments, the compound has the formula:

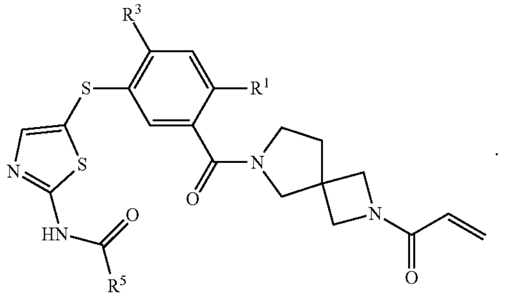

$R^1$, $R^3$, $R^5$ are as described herein. In embodiments, the compound has the formula:

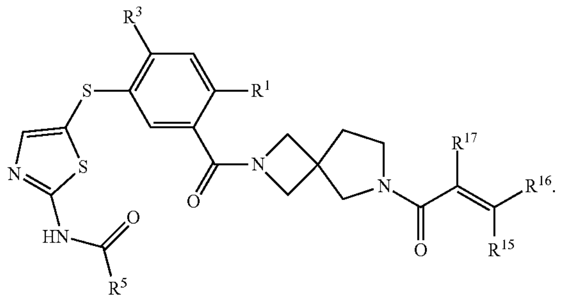

$R^1$, $R^3$, $R^5$, $R^{15}$, $R^{16}$, $R^{17}$ are as described herein. In embodiments, the compound has the formula:

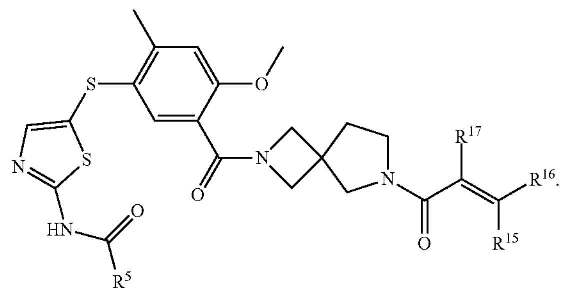

$R^5$, $R^{15}$, $R^{16}$, $R^{17}$ are as described herein. In embodiments, the compound has the formula:

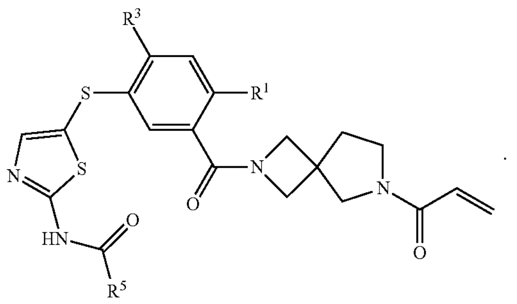

$R^1$, $R^3$, $R^5$ are as described herein. In embodiments, the compound has the formula:

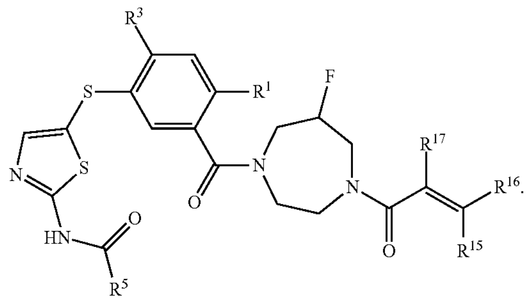

$R^1$, $R^3$, $R^5$, $R^{15}$, $R^{16}$, $R^{17}$ are as described herein. In embodiments, the compound has the formula:

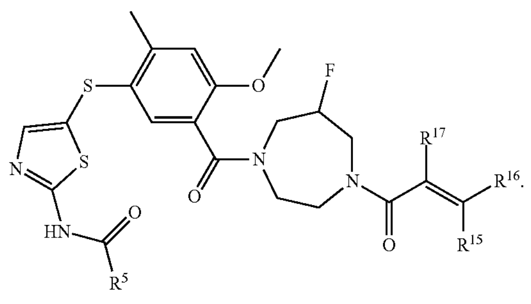

$R^5$, $R^{15}$, $R^{16}$, $R^{17}$ are as described herein. In embodiments, the compound has the formula:

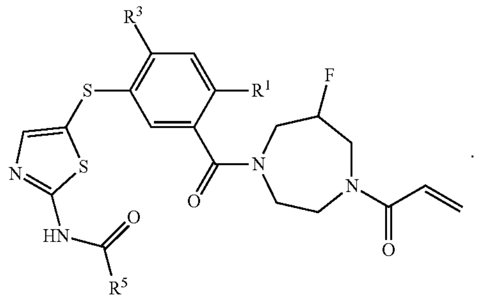

$R^1$, $R^3$, $R^5$ are as described herein. In embodiments, the compound has the formula:

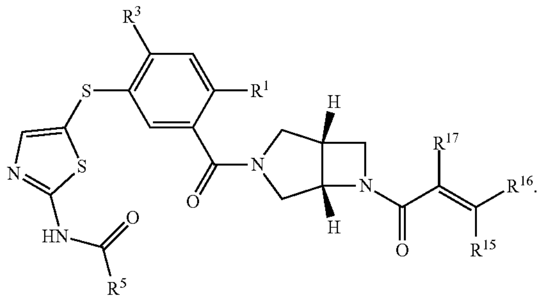

$R^1$, $R^3$, $R^5$, $R^{15}$, $R^{16}$, $R^{17}$ are as described herein. In embodiments, the compound has the formula:

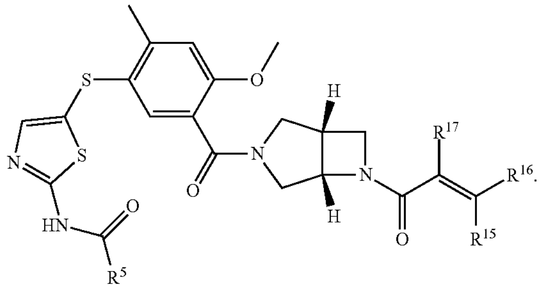

$R^5$, $R^{15}$, $R^{16}$, $R^{17}$ are as described herein. In embodiments, the compound has the formula:

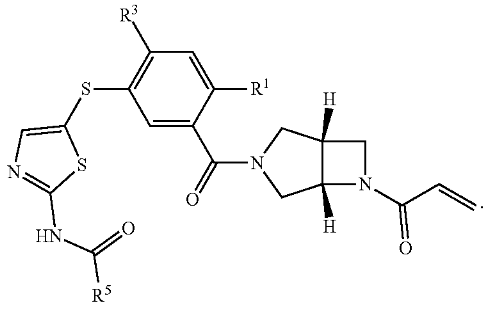

$R^1$, $R^3$, $R^5$ are as described herein. In embodiments, the compound has the formula:

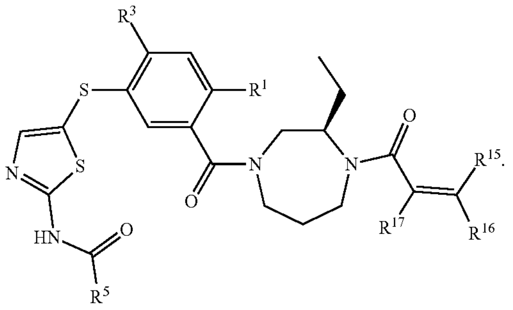

$R^1$, $R^3$, $R^5$, $R^{15}$, $R^{16}$, $R^{17}$ are as described herein. In embodiments, the compound has the formula:

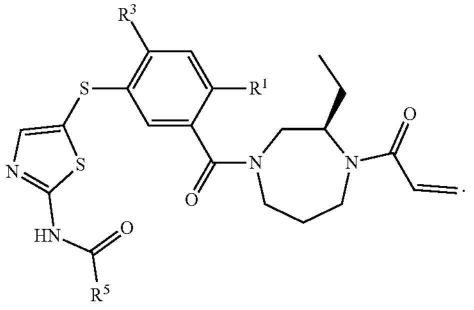

$R^1$, $R^3$, $R^5$ are as described herein. In embodiments, the compound has the formula:

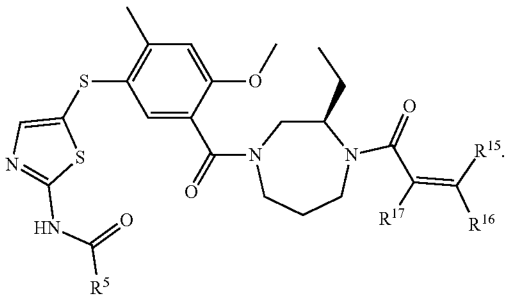

$R^5$, $R^{15}$, $R^{16}$, $R^{17}$ are as described herein. In embodiments, the compound has the formula:

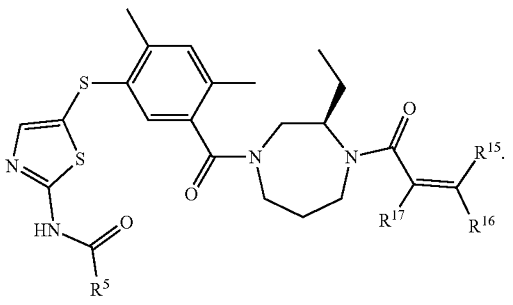

$R^5$, $R^{15}$, $R^{16}$, $R^{17}$ are as described herein. In embodiments, the compound has the formula:

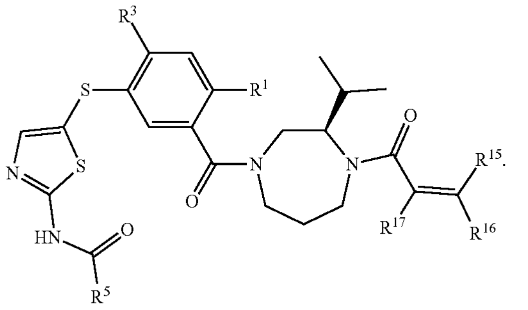

$R^1$, $R^3$, $R^5$, $R^{15}$, $R^{16}$, $R^{17}$ are as described herein. In embodiments, the compound has the formula:

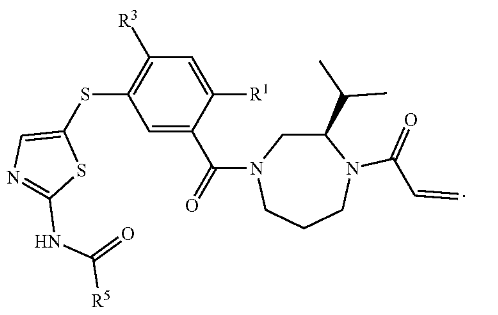

$R^1$, $R^3$, $R^5$ are as described herein. In embodiments, the compound has the formula:

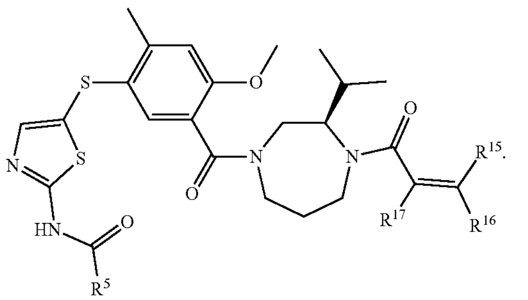

$R^5$, $R^{15}$, $R^{16}$, $R^{17}$ are as described herein. In embodiments, the compound has the formula:

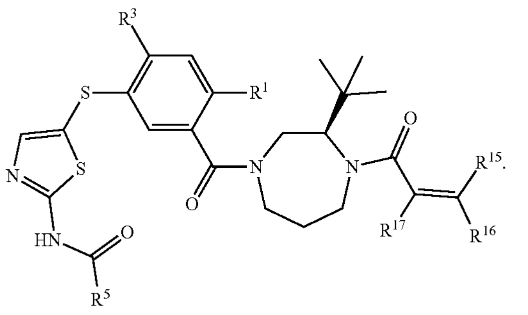

$R^1$, $R^3$, $R^5$, $R^{15}$, $R^{16}$, $R^{17}$ are as described herein. In embodiments, the compound has the formula:

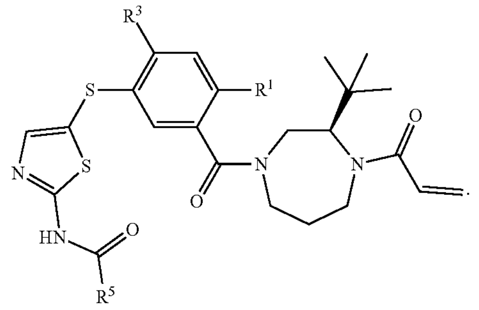

$R^1$, $R^3$, $R^5$ are as described herein. In embodiments, the compound has the formula:

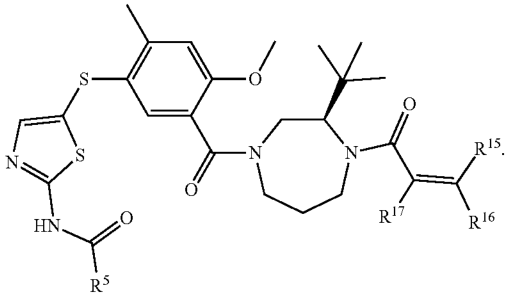

$R^5$, $R^{15}$, $R^{16}$, $R^{17}$ are as described herein. In embodiments, the compound has the formula:

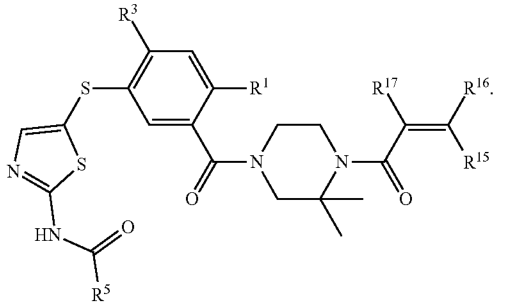

$R^1$, $R^3$, $R^5$, $R^{15}$, $R^{16}$, $R^{17}$ are as described herein. In embodiments, the compound has the formula:

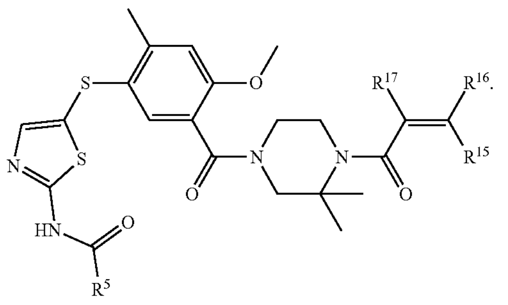

$R^5$, $R^{15}$, $R^{16}$, $R^{17}$ are as described herein. In embodiments, the compound has the formula:

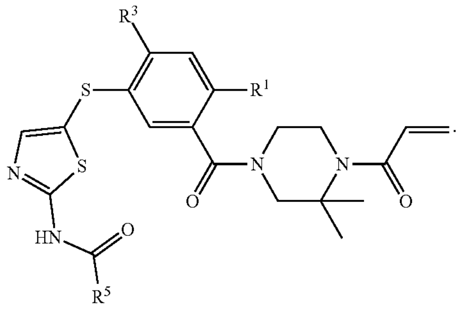

$R^1$, $R^3$, $R^5$ are as described herein. In embodiments, the compound has the formula:

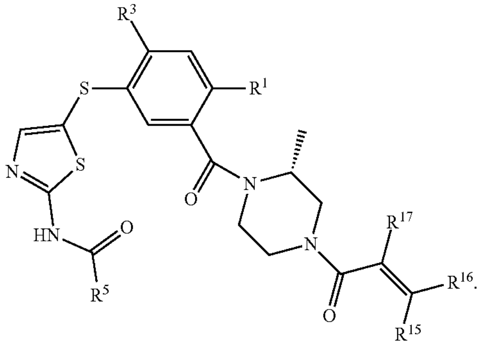

$R^1$, $R^3$, $R^5$, $R^{15}$, $R^{16}$, $R^{17}$ are as described herein. In embodiments, the compound has the formula:

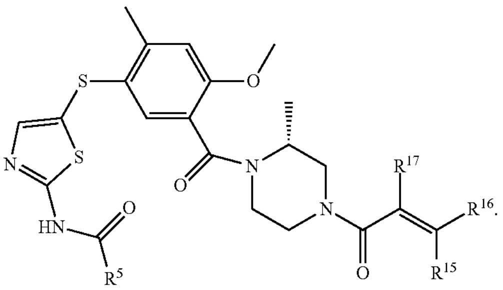

$R^5$, $R^{15}$, $R^{16}$, $R^{17}$ are as described herein. In embodiments, the compound has the formula:

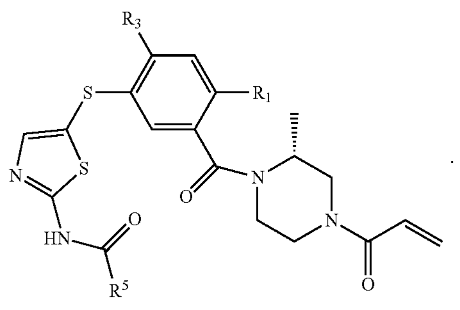

$R^1$, $R^3$, $R^5$ are as described herein. In embodiments, the compound has the formula:

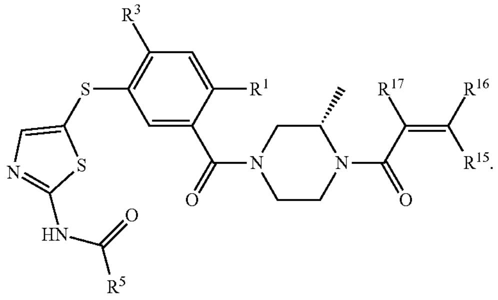

$R^1$, $R^3$, $R^5$, $R^{15}$, $R^{16}$, $R^{17}$ are as described herein. In embodiments, the compound has the formula:

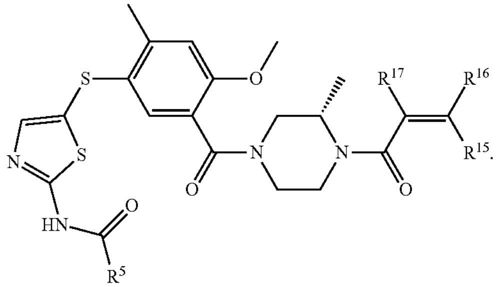

$R^5$, $R^{15}$, $R^{16}$, $R^{17}$ are as described herein. In embodiments, the compound has the formula:

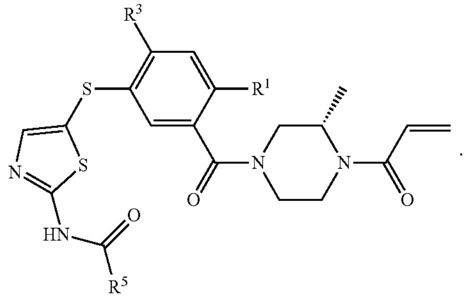

$R^1$, $R^3$, $R^5$ are as described herein. In embodiments, the compound has the formula:

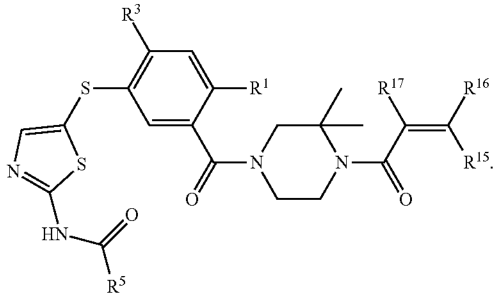

$R^1$, $R^3$, $R^5$, $R^{15}$, $R^{16}$, $R^{17}$ are as described herein. In embodiments, the compound has the formula:

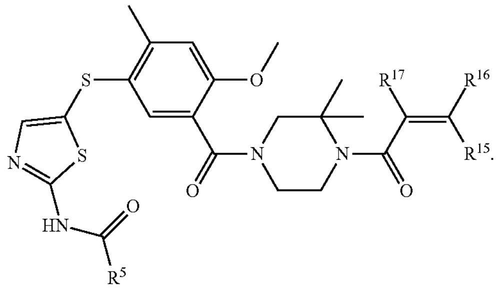

$R^5$, $R^{15}$, $R^{16}$, $R^{17}$ are as described herein. In embodiments, the compound has the formula:

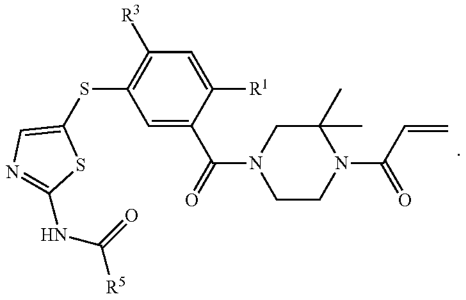

$R^1$, $R^3$, $R^5$ are as described herein. In embodiments, the compound has the formula:

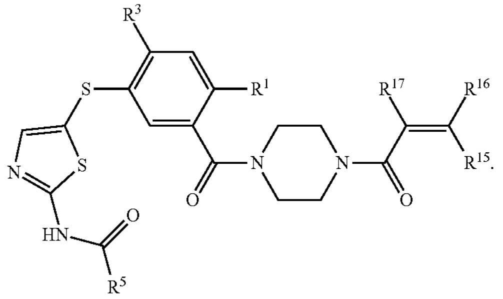

$R^1$, $R^3$, $R^5$, $R^{15}$, $R^{16}$, $R^{17}$ are as described herein. In embodiments, the compound has the formula:

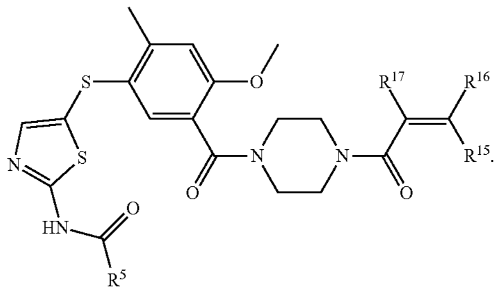

$R^5$, $R^{15}$, $R^{16}$, $R^{17}$ are as described herein. In embodiments, the compound has the formula:

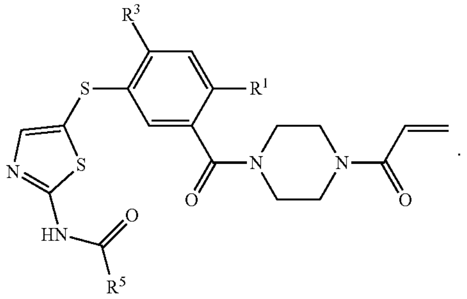

$R^1$, $R^3$, $R^5$ are as described herein. In embodiments, the compound has the formula:

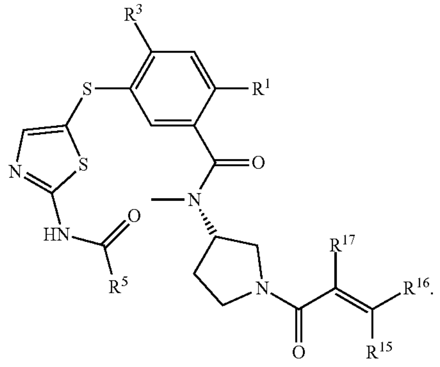

$R^1$, $R^3$, $R^5$, $R^{15}$, $R^{16}$, $R^{17}$ are as described herein. In embodiments, the compound has the formula:

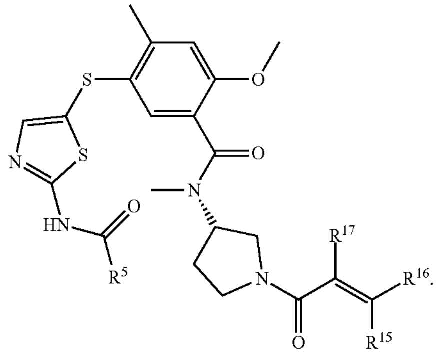

$R^5$, $R^{15}$, $R^{16}$, $R^{17}$ are as described herein. In embodiments, the compound has the formula:

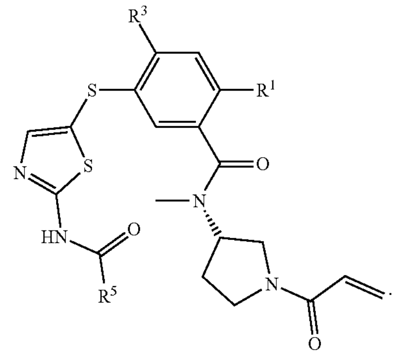

$R^1$, $R^3$, $R^5$ are as described herein. In embodiments, the compound has the formula:

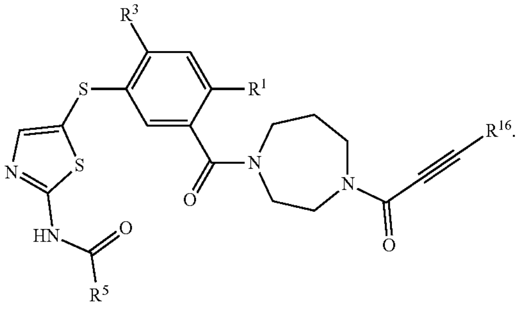

$R^1$, $R^3$, $R^5$, $R^{15}$, $R^{16}$, $R^{17}$ are as described herein. In embodiments, the compound has the formula:

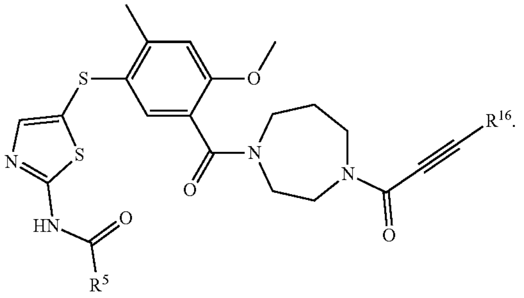

$R^5$, $R^{15}$, $R^{16}$, $R^{17}$ are as described herein. In embodiments, the compound has the formula:

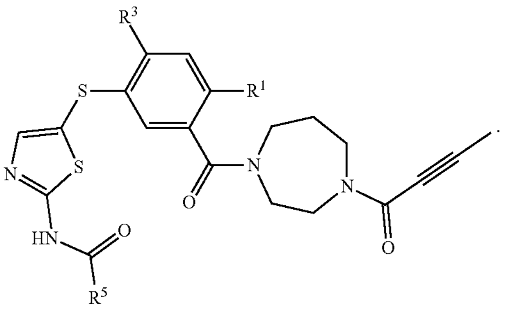

$R^1$, $R^3$, $R^5$ are as described herein. In embodiments, the compound has the formula:

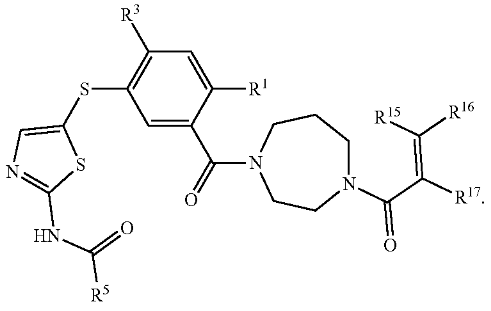

$R^1$, $R^3$, $R^5$, $R^{15}$, $R^{16}$, $R^{17}$ are as described herein. In embodiments, the compound has the formula:

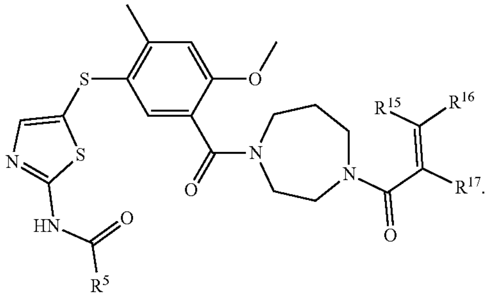

$R^5$, $R^{15}$, $R^{16}$, $R^{17}$ are as described herein. In embodiments, the compound has the formula:

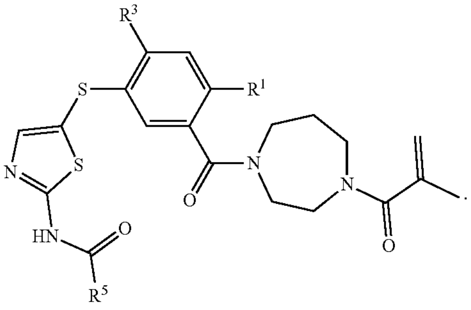

$R^1$, $R^3$, $R^5$ are as described herein. In embodiments, the compound has the formula:

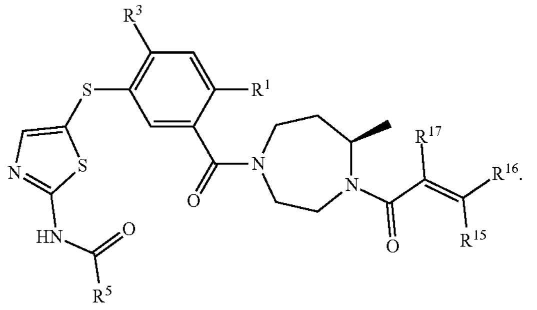

$R^1$, $R^3$, $R^5$, $R^{15}$, $R^{16}$, $R^{17}$ are as described herein. In embodiments, the compound has the formula:

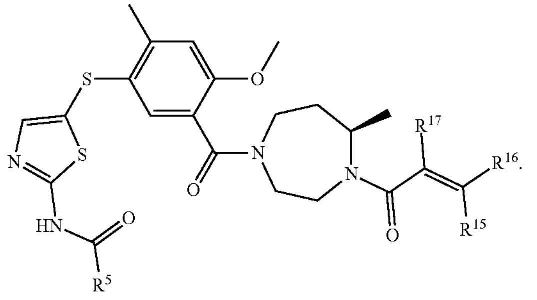

$R^5$, $R^{15}$, $R^{16}$, $R^{17}$ are as described herein. In embodiments, the compound has the formula:

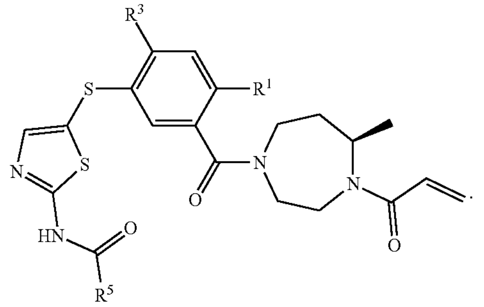

$R^1$, $R^3$, $R^5$ are as described herein. In embodiments, the compound has the formula:

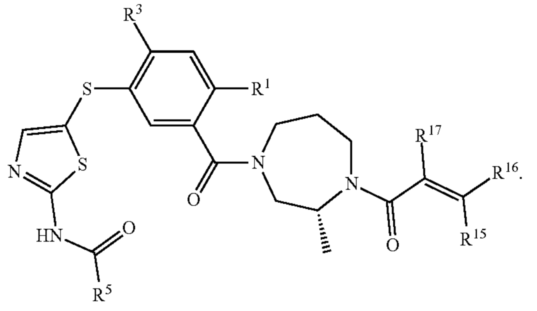

$R^1$, $R^3$, $R^5$, $R^{15}$, $R^{16}$, $R^{17}$ are as described herein. In embodiments, the compound has the formula:

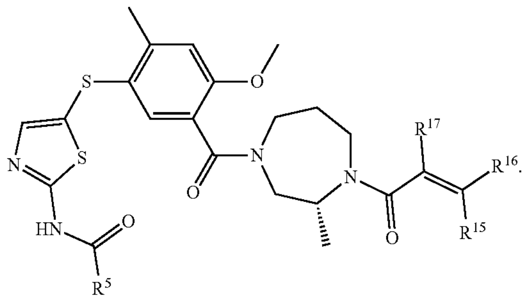

$R^5$, $R^{15}$, $R^{16}$, $R^{17}$ are as described herein. In embodiments, the compound has the formula:

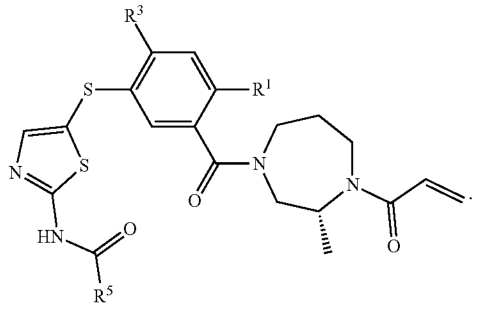

$R^1$, $R^3$, $R^5$ are as described herein. In embodiments, the compound has the formula:

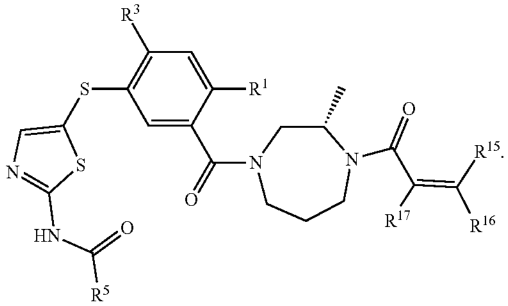

$R^1$, $R^3$, $R^5$, $R^{15}$, $R^{16}$, $R^{17}$ are as described herein. In embodiments, the compound has the formula:

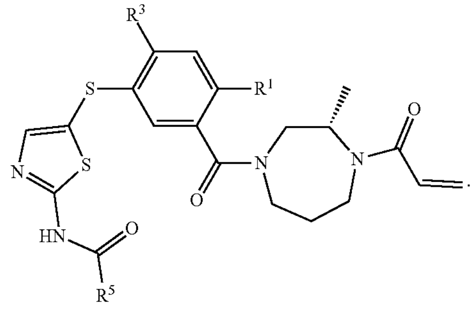

$R^1$, $R^3$, $R^5$ are as described herein. In embodiments, the compound has the formula:

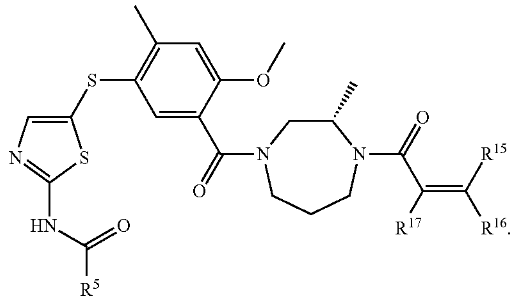

$R^5$, $R^{15}$, $R^{16}$, $R^{17}$ are as described herein. In embodiments, the compound has the formula:

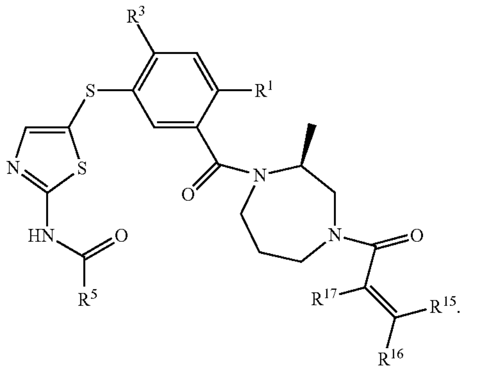

$R^1$, $R^3$, $R^5$, $R^{15}$, $R^{16}$, $R^{17}$ are as described herein. In embodiments, the compound has the formula:

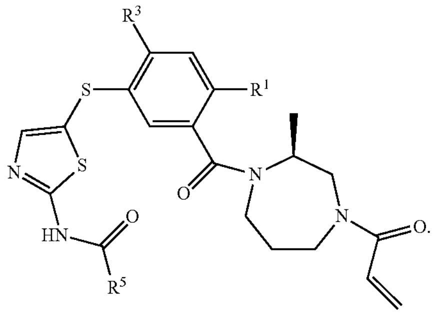

$R^1$, $R^3$, $R^5$ are as described herein. In embodiments, the compound has the formula:

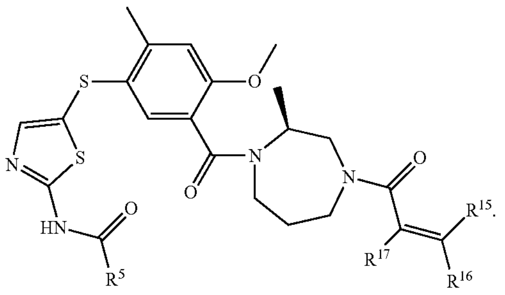

$R^5$, $R^{15}$, $R^{16}$, $R^{17}$ are as described herein. In embodiments, the compound has the formula:

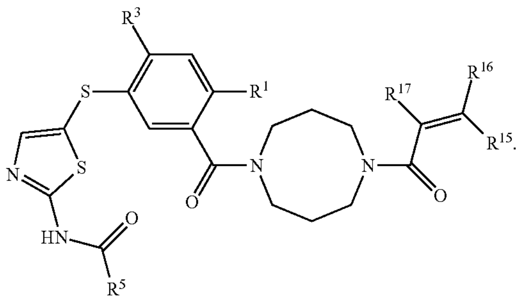

$R^1$, $R^3$, $R^5$, $R^{15}$, $R^{16}$, $R^{17}$ are as described herein. In embodiments, the compound has the formula:

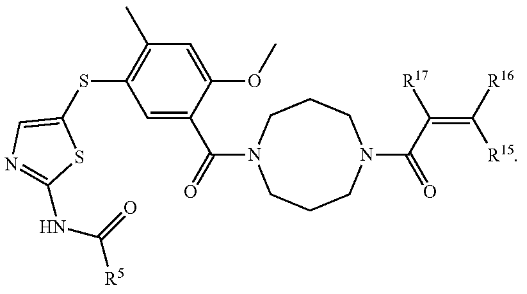

$R^5$, $R^{15}$, $R^{16}$, $R^{17}$ are as described herein. In embodiments, the compound has the formula:

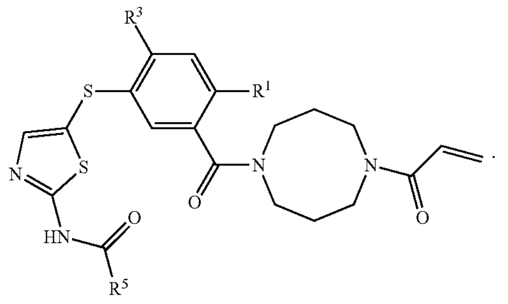

$R^1$, $R^3$, $R^5$ are as described herein. In embodiments, the compound has the formula:

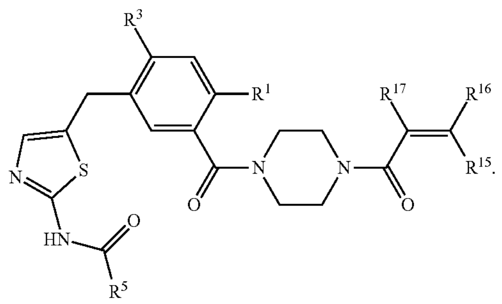

$R^1$, $R^3$, $R^5$, $R^{15}$, $R^{16}$, $R^{17}$ are as described herein. In embodiments, the compound has the formula:

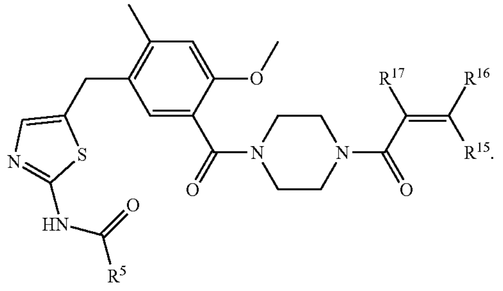

$R^5$, $R^{15}$, $R^{16}$, $R^{17}$ are as described herein. In embodiments, the compound has the formula:

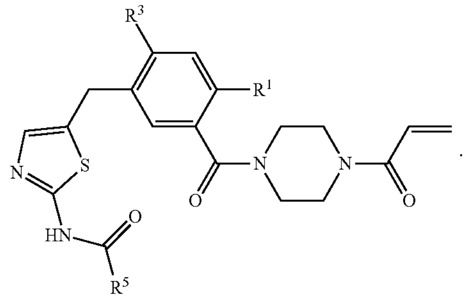

$R^1$, $R^3$, $R^5$ are as described herein. In embodiments, the compound has the formula:

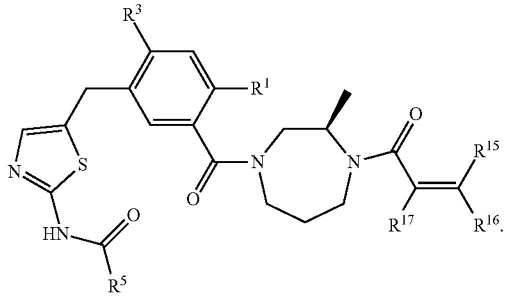

$R^1$, $R^3$, $R^5$, $R^{15}$, $R^{16}$, $R^{17}$ are as described herein. In embodiments, the compound has the formula:

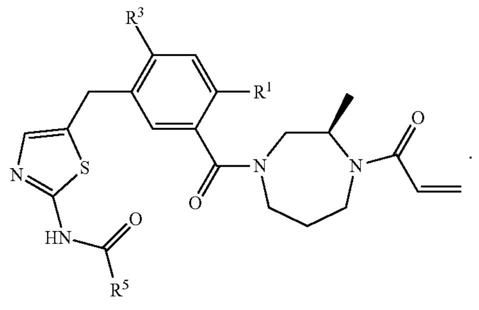

$R^1$, $R^3$, $R^5$ are as described herein. In embodiments, the compound has the formula:

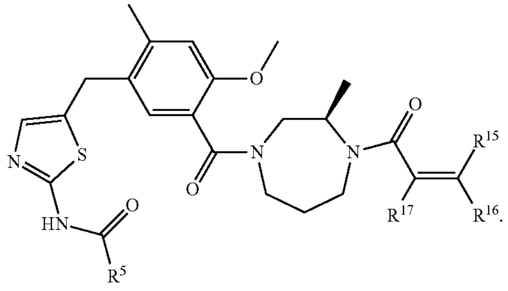

$R^5$, $R^{15}$, $R^{16}$, $R^{17}$ are as described herein. In embodiments, the compound has the formula:

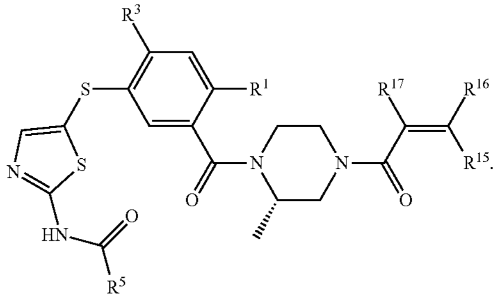

$R^1$, $R^3$, $R^5$, $R^{15}$, $R^{16}$, $R^{17}$ are as described herein. In embodiments, the compound has the formula:

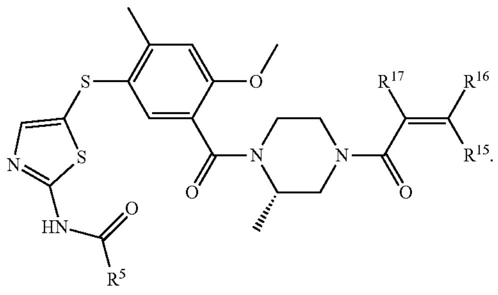

$R^5$, $R^{15}$, $R^{16}$, $R^{17}$ are as described herein. In embodiments, the compound has the formula:

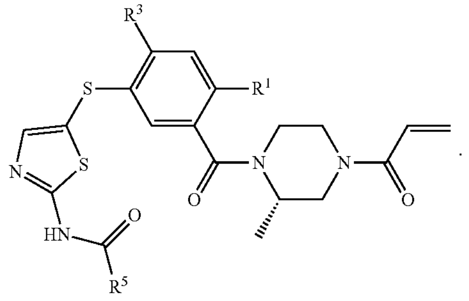

$R^1$, $R^3$, $R^5$ are as described herein. In embodiments, the compound has the formula:

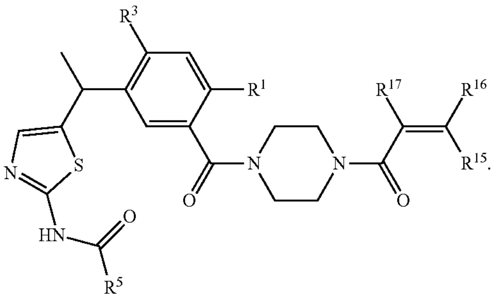

$R^1$, $R^3$, $R^5$, $R^{15}$, $R^{16}$, $R^{17}$ are as described herein. In embodiments, the compound has the formula:

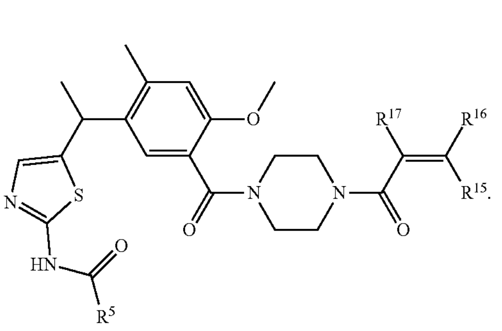

$R^5$, $R^{15}$, $R^{16}$, $R^{17}$ are as described herein. In embodiments, the compound has the formula:

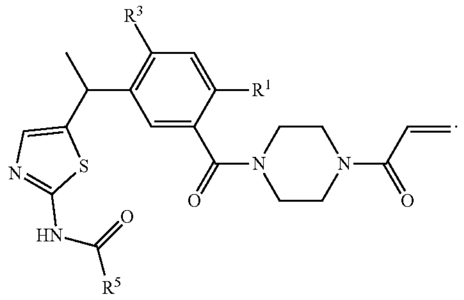

$R^1$, $R^3$, $R^5$ are as described herein.

In embodiments, the compound has the formula:

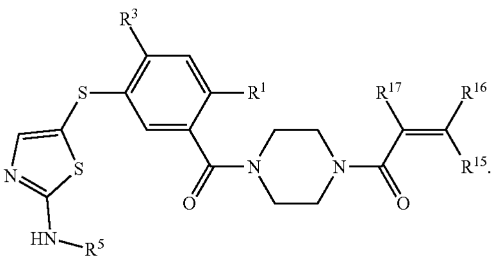

$R^1$, $R^3$, $R^5$, $R^{15}$, $R^{16}$, $R^{17}$ are as described herein. In embodiments, the compound has the formula:

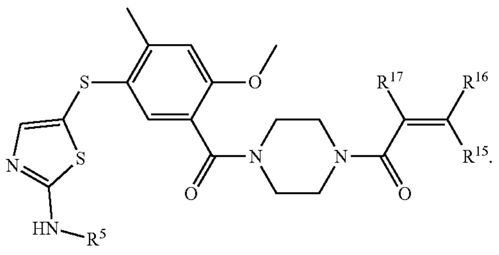

$R^5$, $R^{15}$, $R^{16}$, $R^{17}$ are as described herein. In embodiments, the compound has the formula:

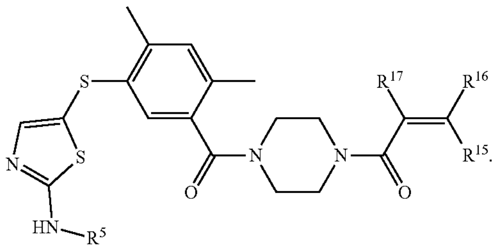

$R^5$, $R^{15}$, $R^{16}$, $R^{17}$ are as described herein. In embodiments, the compound has the formula:

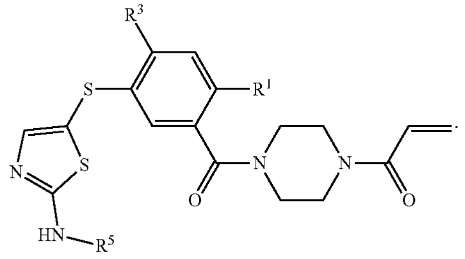

$R^1$, $R^3$, $R^5$ are as described herein. In embodiments, the compound has the formula:

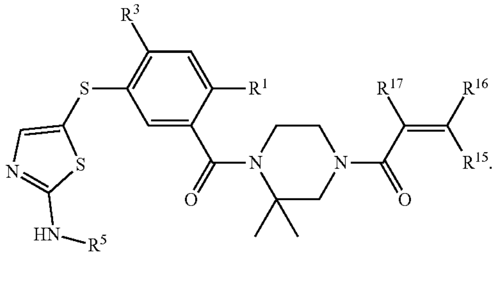

$R^1$, $R^3$, $R^5$, $R^{15}$, $R^{16}$, $R^{17}$ are as described herein. In embodiments, the compound has the formula:

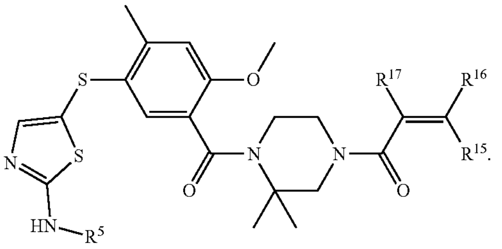

$R^5$, $R^{15}$, $R^{16}$, $R^{17}$ are as described herein. In embodiments, the compound has the formula:

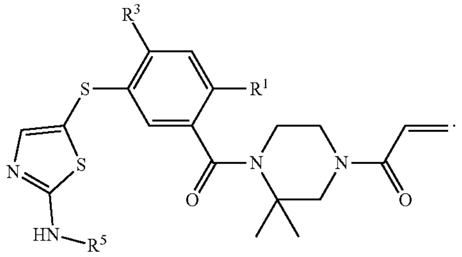

$R^1$, $R^3$, $R^5$ are as described herein. In embodiments, the compound has the formula:

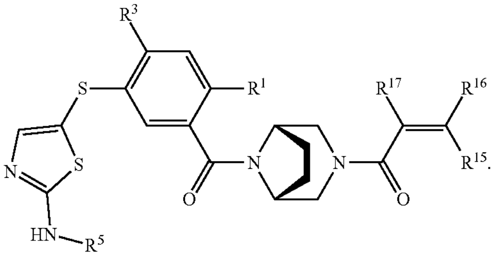

$R^1$, $R^3$, $R^5$, $R^{15}$, $R^{16}$, $R^{17}$ are as described herein. In embodiments, the compound has the formula:

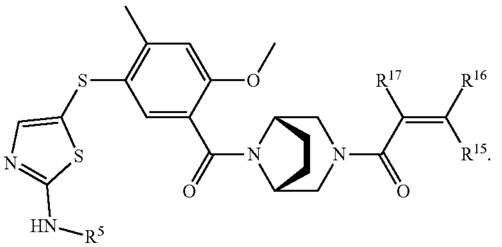

$R^5$, $R^{15}$, $R^{16}$, $R^{17}$ are as described herein. In embodiments, the compound has the formula:

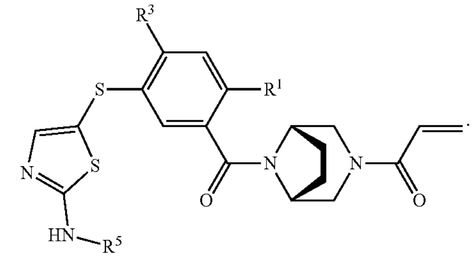

$R^1$, $R^3$, $R^5$ are as described herein. In embodiments, the compound has the formula:

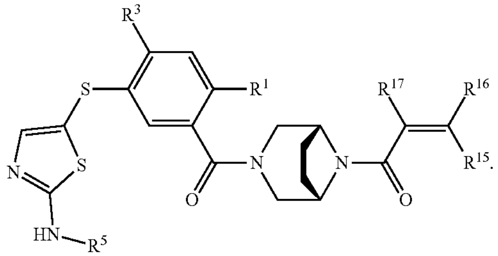

$R^1$, $R^3$, $R^5$, $R^{15}$, $R^{16}$, $R^{17}$ are as described herein. In embodiments, the compound has the formula:

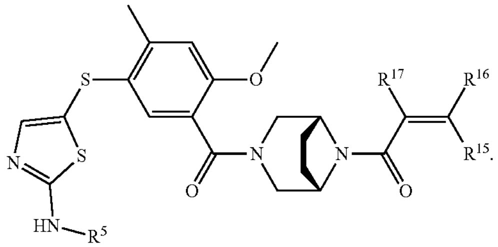

$R^5$, $R^{15}$, $R^{16}$, $R^{17}$ are as described herein. In embodiments, the compound has the formula:

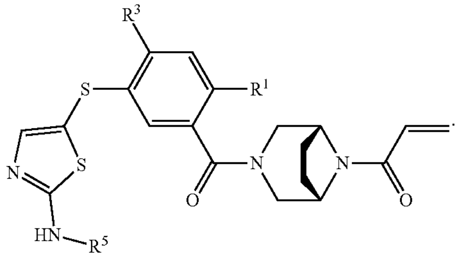

$R^1$, $R^3$, $R^5$ are as described herein. In embodiments, the compound has the formula:

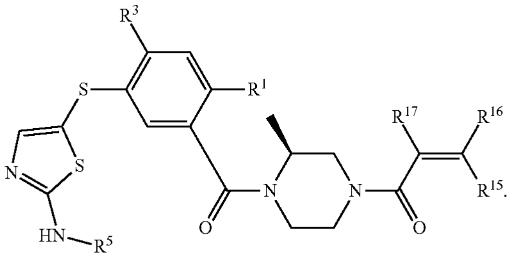

$R^1$, $R^3$, $R^5$, $R^{15}$, $R^{16}$, $R^{17}$ are as described herein. In embodiments, the compound has the formula:

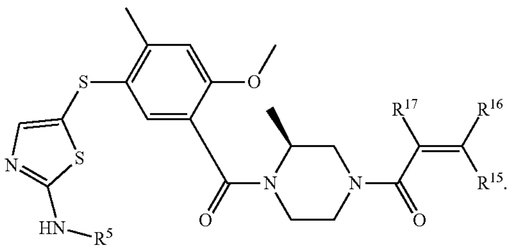

$R^5$, $R^{15}$, $R^{16}$, $R^{17}$ are as described herein. In embodiments, the compound has the formula:

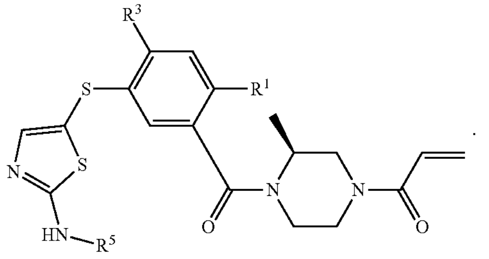

$R^1$, $R^3$, $R^5$ are as described herein. In embodiments, the compound has the formula:

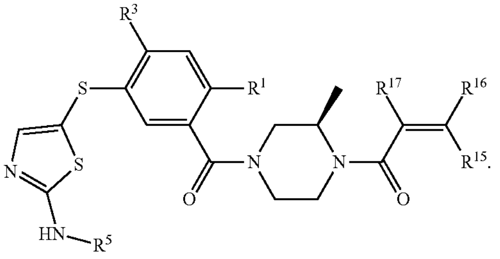

$R^1$, $R^3$, $R^5$, $R^{15}$, $R^{16}$, $R^{17}$ are as described herein. In embodiments, the compound has the formula:

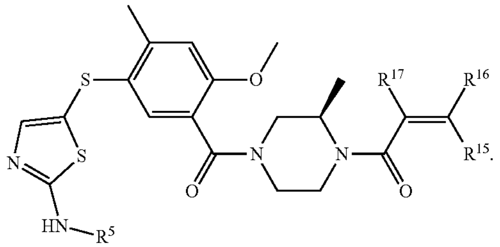

$R^5$, $R^{15}$, $R^{16}$, $R^{17}$ are as described herein. In embodiments, the compound has the formula:

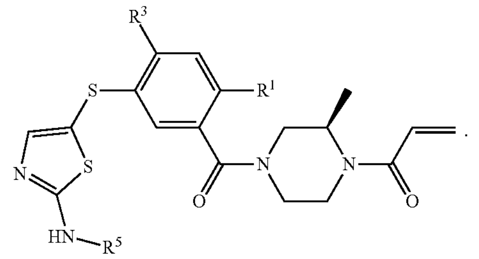

$R^1$, $R^3$, $R^5$ are as described herein. In embodiments, the compound has the formula:

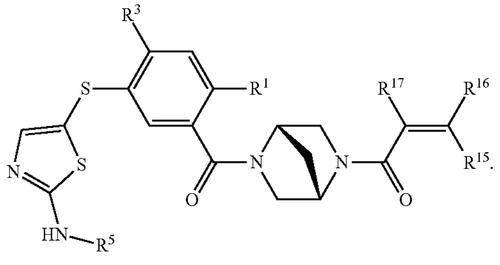

$R^1$, $R^3$, $R^5$, $R^{15}$, $R^{16}$, $R^{17}$ are as described herein. In embodiments, the compound has the formula:

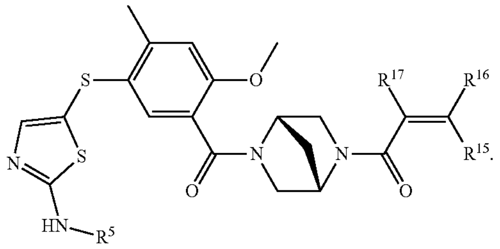

$R^5$, $R^{15}$, $R^{16}$, $R^{17}$ are as described herein. In embodiments, the compound has the formula:

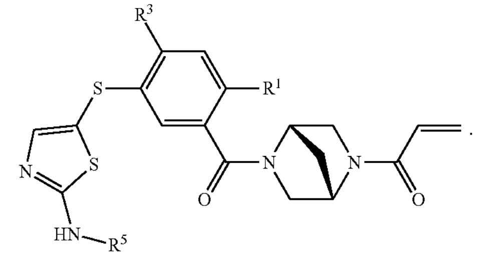

$R^1$, $R^3$, $R^5$ are as described herein. In embodiments, the compound has the formula:

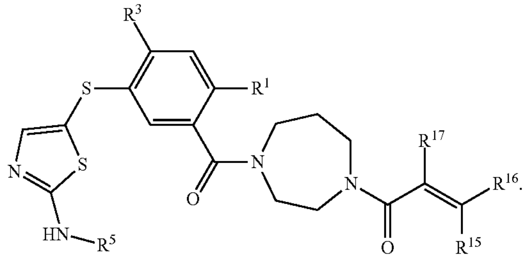

$R^1$, $R^3$, $R^5$, $R^{15}$, $R^{16}$, $R^{17}$ are as described herein. In embodiments, the compound has the formula:

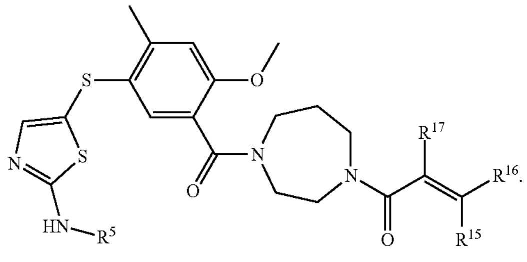

$R^5$, $R^{15}$, $R^{16}$, $R^{17}$ are as described herein. In embodiments, the compound has the formula:

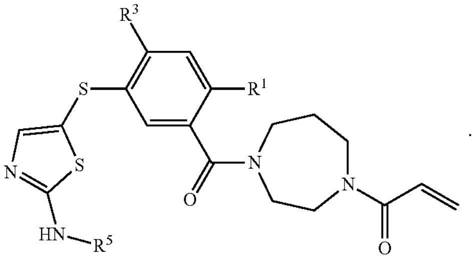

$R^1$, $R^3$, $R^5$ are as described herein. In embodiments, the compound has the formula:

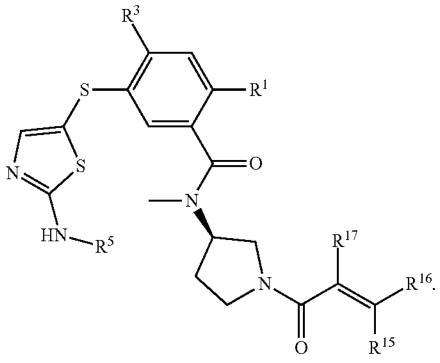

$R^1$, $R^3$, $R^5$, $R^{15}$, $R^{16}$, $R^{17}$ are as described herein. In embodiments, the compound has the formula:

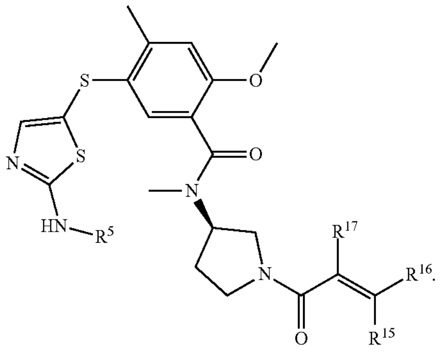

$R^5$, $R^{15}$, $R^{16}$, $R^{17}$ are as described herein. In embodiments, the compound has the formula:

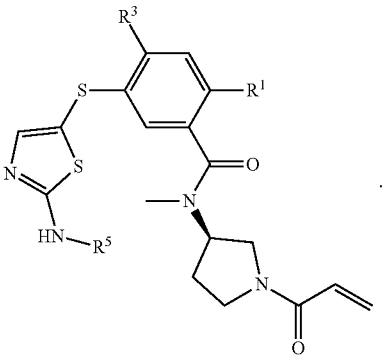

$R^1$, $R^3$, $R^5$ are as described herein. In embodiments, the compound has the formula:

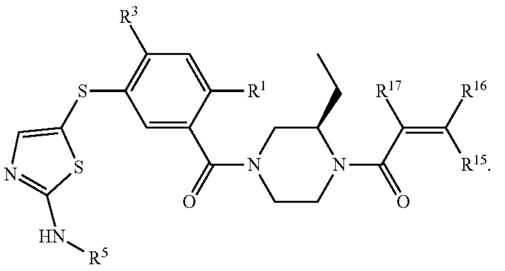

$R^1$, $R^3$, $R^5$, $R^{15}$, $R^{16}$, $R^{17}$ are as described herein. In embodiments, the compound has the formula:

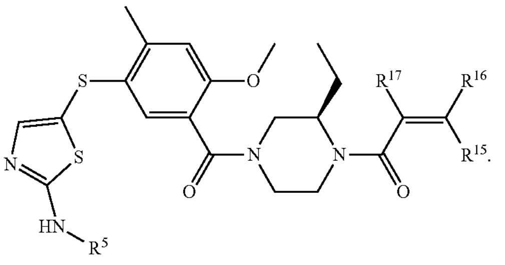

$R^5$, $R^{15}$, $R^{16}$, $R^{17}$ are as described herein. In embodiments, the compound has the formula:

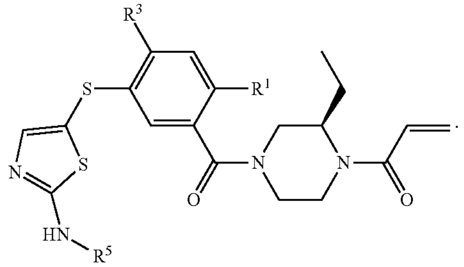

$R^1$, $R^3$, $R^5$ are as described herein. In embodiments, the compound has the formula:

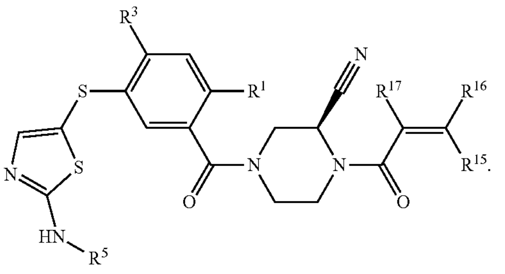

$R^1$, $R^3$, $R^5$, $R^{15}$, $R^{16}$, $R^{17}$ are as described herein. In embodiments, the compound has the formula:

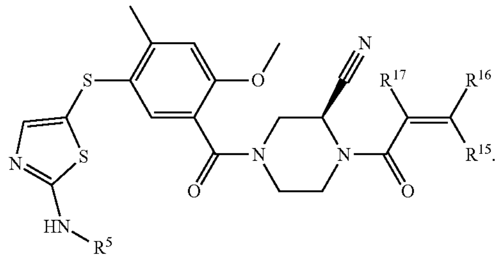

$R^5$, $R^{15}$, $R^{16}$, $R^{17}$ are as described herein. In embodiments, the compound has the formula:

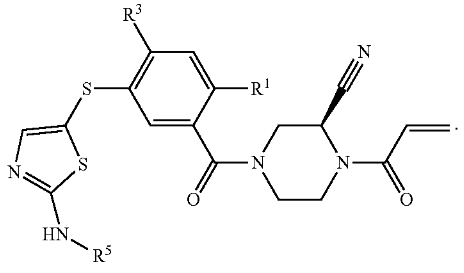

$R^1$, $R^3$, $R^5$ are as described herein. In embodiments, the compound has the formula:

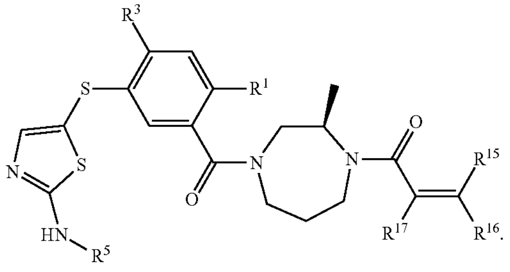

$R^1$, $R^3$, $R^5$, $R^{15}$, $R^{16}$, $R^{17}$ are as described herein. In embodiments, the compound has the formula:

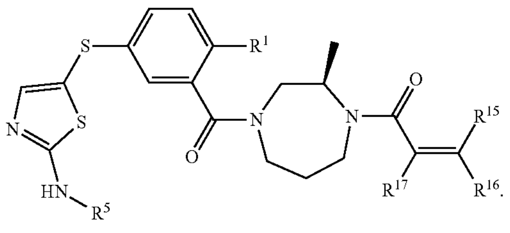

$R^1$, $R^3$, $R^5$, $R^{15}$, $R^{16}$, $R^{17}$ are as described herein. In embodiments, the compound has the formula:

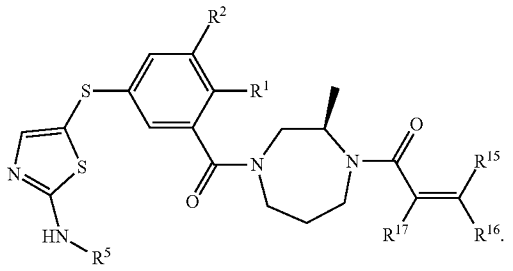

$R^1$, $R^3$, $R^5$, $R^{15}$, $R^{16}$, $R^{17}$ are as described herein. In embodiments, the compound has the formula:

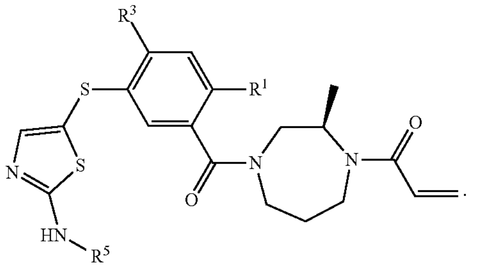

$R^1$, $R^3$, $R^5$ are as described herein. In embodiments, the compound has the formula:

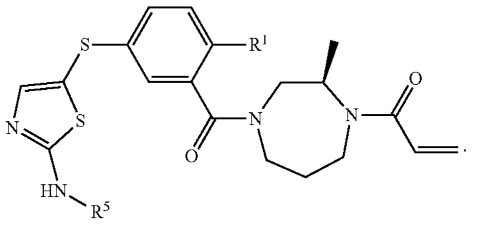

$R^1$ and $R^5$ are as described herein. In embodiments, the compound has the formula:

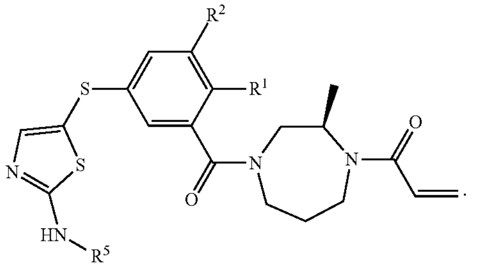

$R^1$, $R^2$, $R^5$ are as described herein. In embodiments, the compound has the formula:

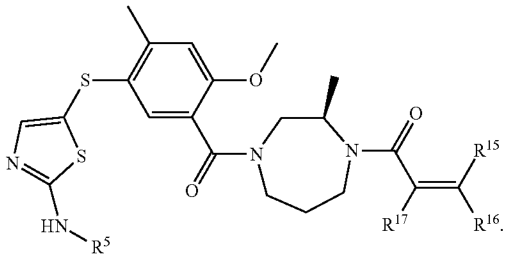

$R^5$, $R^{15}$, $R^{16}$, $R^{17}$ are as described herein. In embodiments, the compound has the formula:

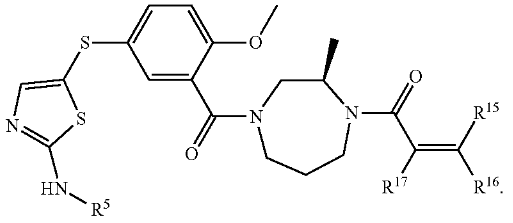

$R^5$, $R^{15}$, $R^{16}$, $R^{17}$ are as described herein. In embodiments, the compound has the formula:

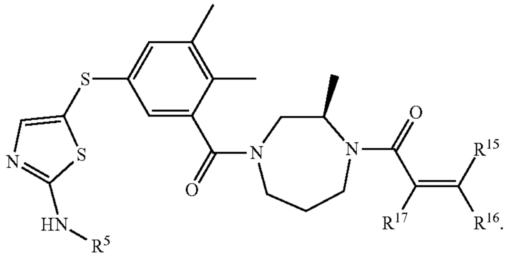

$R^5$, $R^{15}$, $R^{16}$, $R^{17}$ are as described herein. In embodiments, the compound has the formula:

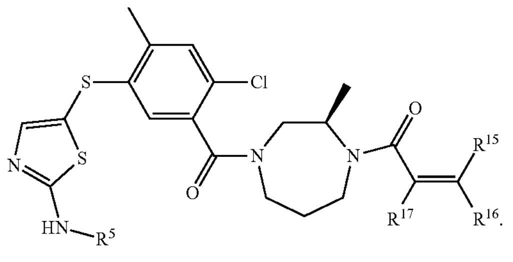

$R^5$, $R^{15}$, $R^{16}$, $R^{17}$ are as described herein. In embodiments, the compound has the formula:

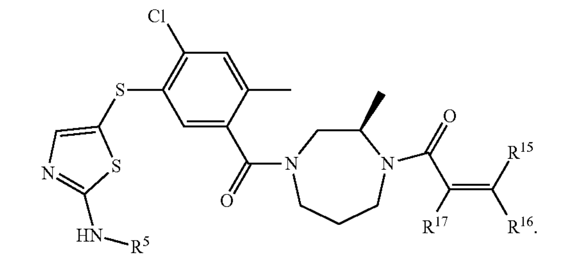

$R^5$, $R^{15}$, $R^{16}$, $R^{17}$ are as described herein. In embodiments, the compound has the formula:

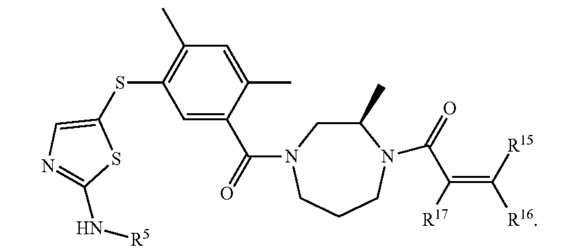

$R^5$, $R^{15}$, $R^{16}$, $R^{17}$ are as described herein. In embodiments, the compound has the formula:

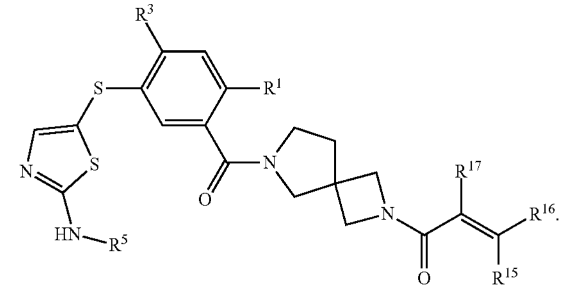

$R^1$, $R^3$, $R^5$, $R^{15}$, $R^{16}$, $R^{17}$ are as described herein. In embodiments, the compound has the formula:

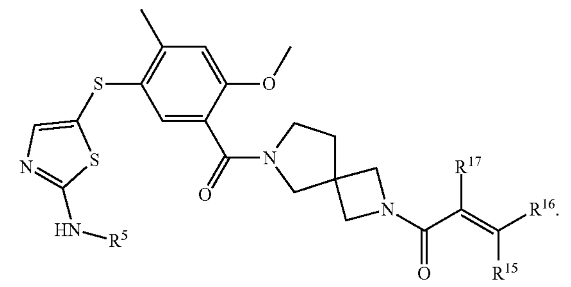

$R^5$, $R^{15}$, $R^{16}$, $R^{17}$ are as described herein. In embodiments, the compound has the formula:

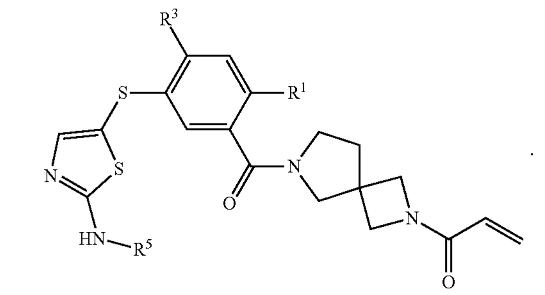

$R^1$, $R^3$, $R^5$ are as described herein. In embodiments, the compound has the formula:

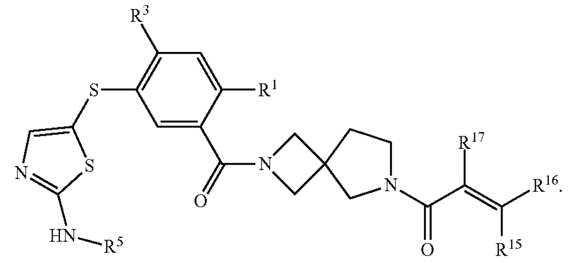

$R^1$, $R^3$, $R^5$, $R^{15}$, $R^{16}$, $R^{17}$ are as described herein. In embodiments, the compound has the formula:

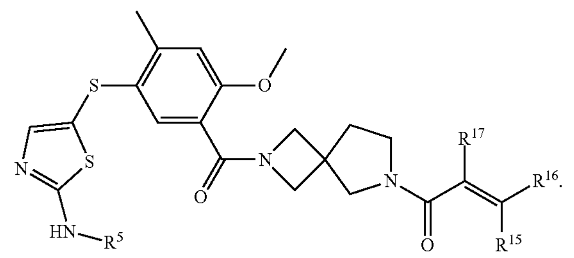

$R^5$, $R^{15}$, $R^{16}$, $R^{17}$ are as described herein. In embodiments, the compound has the formula:

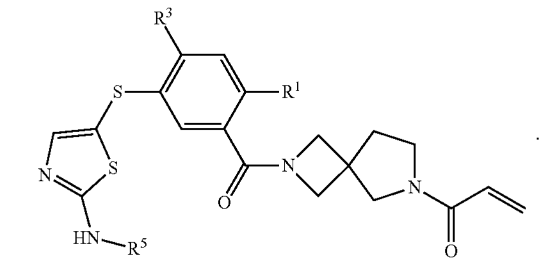

$R^1$, $R^3$, $R^5$ are as described herein. In embodiments, the compound has the formula:

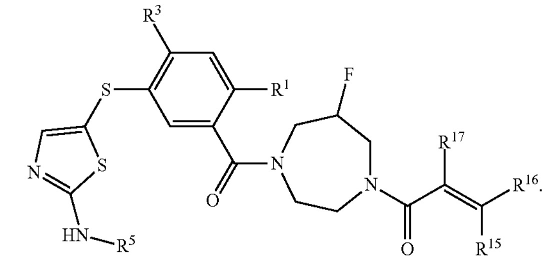

$R^1$, $R^3$, $R^5$, $R^{15}$, $R^{16}$, $R^{17}$ are as described herein. In embodiments, the compound has the formula:

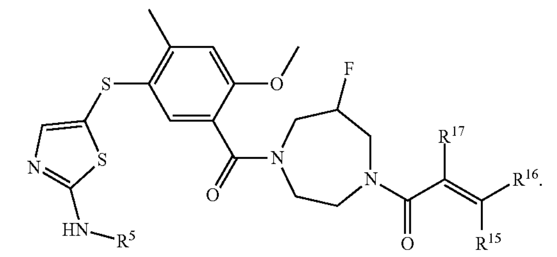

$R^5$, $R^{15}$, $R^{16}$, $R^{17}$ are as described herein. In embodiments, the compound has the formula:

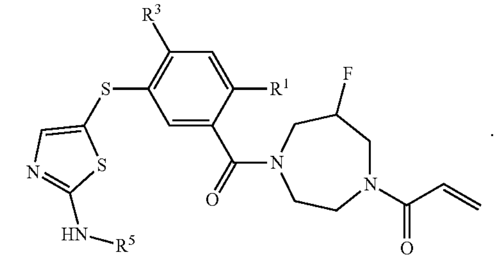

$R^1$, $R^3$, $R^5$ are as described herein. In embodiments, the compound has the formula:

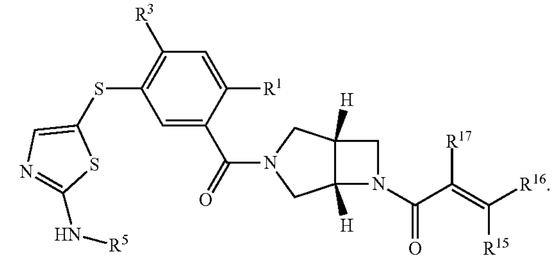

$R^1$, $R^3$, $R^5$, $R^{15}$, $R^{16}$, $R^{17}$ are as described herein. In embodiments, the compound has the formula:

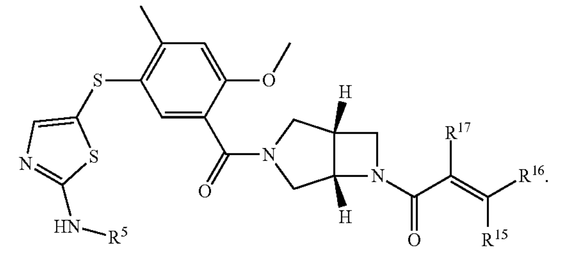

$R^5$, $R^{15}$, $R^{16}$, $R^{17}$ are as described herein. In embodiments, the compound has the formula:

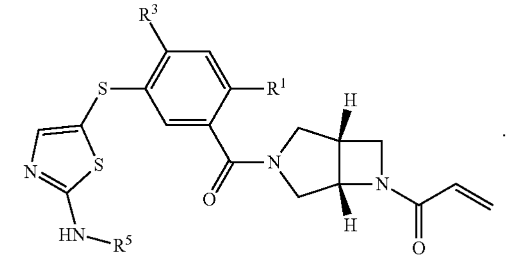

$R^1$, $R^3$, $R^5$ are as described herein. In embodiments, the compound has the formula:

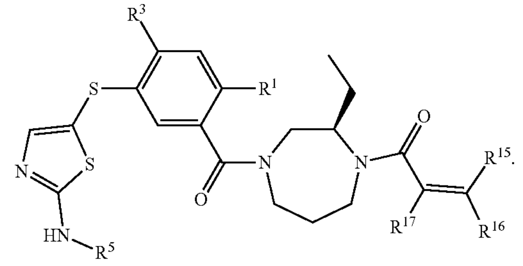

$R^1$, $R^3$, $R^5$, $R^{15}$, $R^{16}$, $R^{17}$ are as described herein. In embodiments, the compound has the formula:

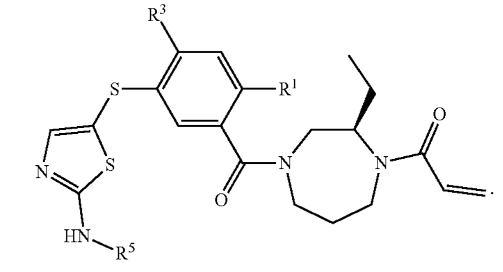

$R^1$, $R^3$, $R^5$ are as described herein. In embodiments, the compound has the formula:

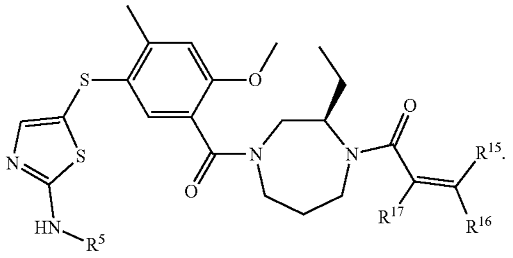

$R^5$, $R^{15}$, $R^{16}$, $R^{17}$ are as described herein. In embodiments, the compound has the formula:

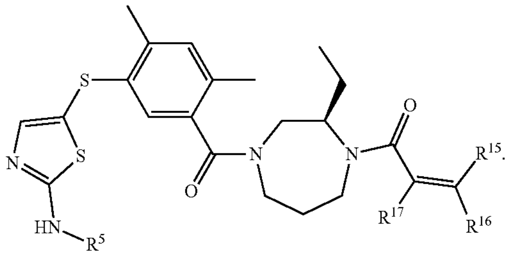

$R^5$, $R^{15}$, $R^{16}$, $R^{17}$ are as described herein. In embodiments, the compound has the formula:

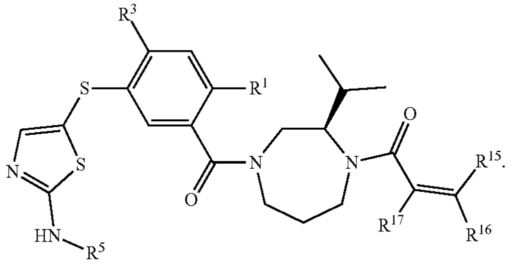

$R^1$, $R^3$, $R^5$, $R^{15}$, $R^{16}$, $R^{17}$ are as described herein. In embodiments, the compound has the formula:

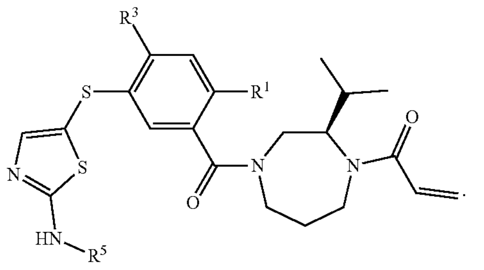

$R^1$, $R^3$, $R^5$ are as described herein. In embodiments, the compound has the formula:

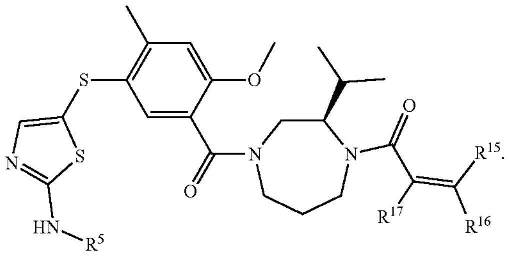

$R^5$, $R^{15}$, $R^{16}$, $R^{17}$ are as described herein. In embodiments, the compound has the formula:

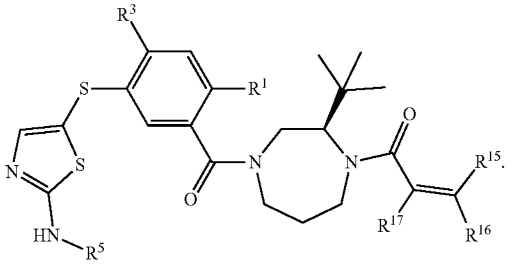

$R^1$, $R^3$, $R^5$, $R^{15}$, $R^{16}$, $R^{17}$ are as described herein. In embodiments, the compound has the formula:

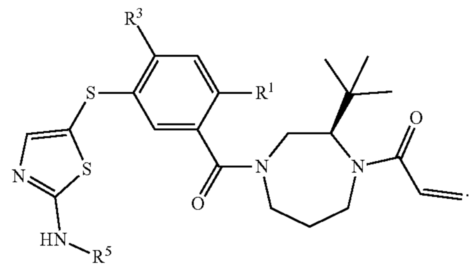

$R^1$, $R^3$, $R^5$ are as described herein. In embodiments, the compound has the formula:

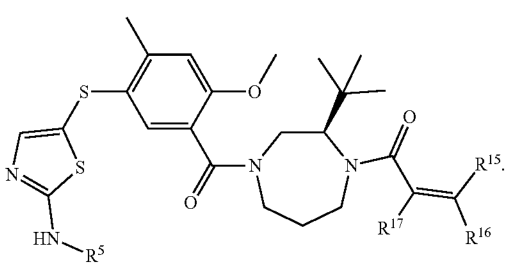

$R^5$, $R^{15}$, $R^{16}$, $R^{17}$ are as described herein. In embodiments, the compound has the formula:

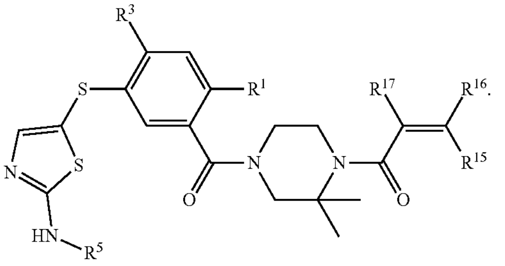

$R^1$, $R^3$, $R^5$, $R^{15}$, $R^{16}$, $R^{17}$ are as described herein. In embodiments, the compound has the formula:

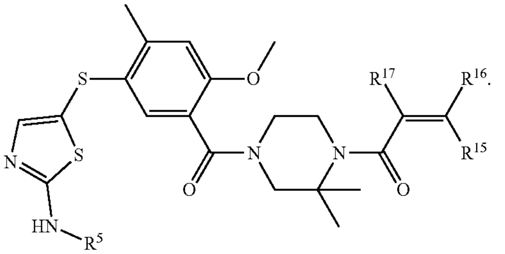

$R^5$, $R^{15}$, $R^{16}$, $R^{17}$ are as described herein. In embodiments, the compound has the formula:

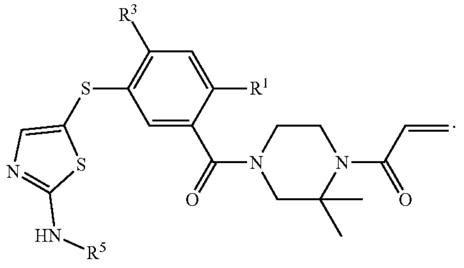

$R^1$, $R^3$, $R^5$ are as described herein. In embodiments, the compound has the formula:

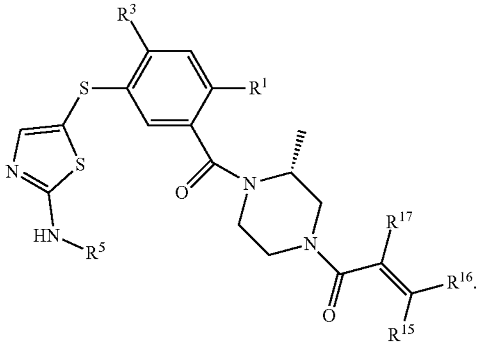

$R^1$, $R^3$, $R^5$, $R^{15}$, $R^{16}$, $R^{17}$ are as described herein. In embodiments, the compound has the formula:

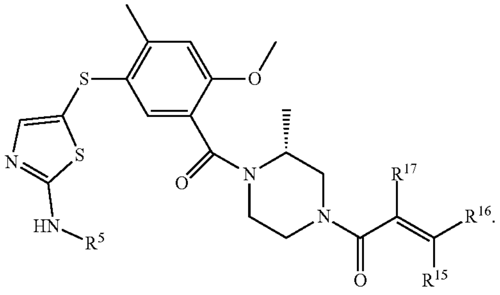

$R^5$, $R^{15}$, $R^{16}$, $R^{17}$ are as described herein. In embodiments, the compound has the formula:

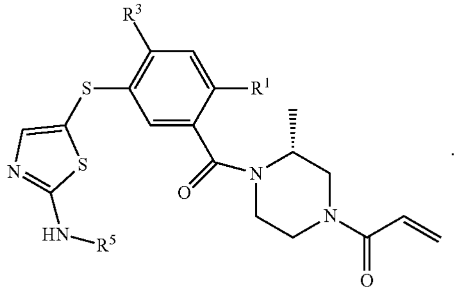

$R^1$, $R^3$, $R^5$ are as described herein. In embodiments, the compound has the formula:

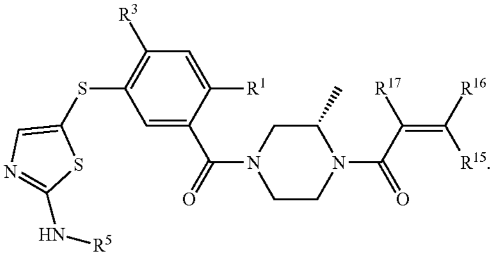

$R^1$, $R^3$, $R^5$, $R^{15}$, $R^{16}$, $R^{17}$ are as described herein. In embodiments, the compound has the formula:

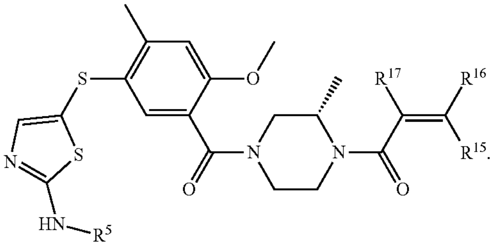

$R^5$, $R^{15}$, $R^{16}$, $R^{17}$ are as described herein. In embodiments, the compound has the formula:

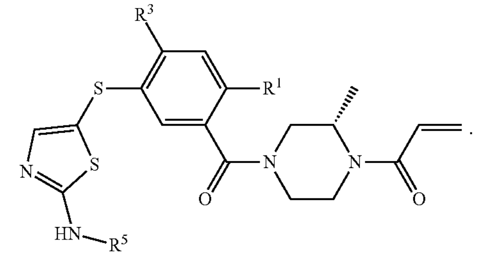

$R^1$, $R^3$, $R^5$ are as described herein. In embodiments, the compound has the formula:

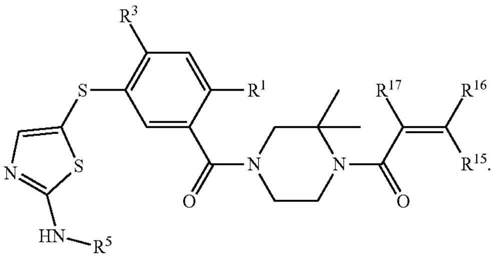

$R^1$, $R^3$, $R^5$, $R^{15}$, $R^{16}$, $R^{17}$ are as described herein. In embodiments, the compound has the formula:

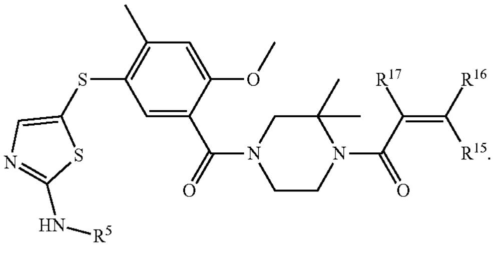

$R^5$, $R^{15}$, $R^{16}$, $R^{17}$ are as described herein. In embodiments, the compound has the formula:

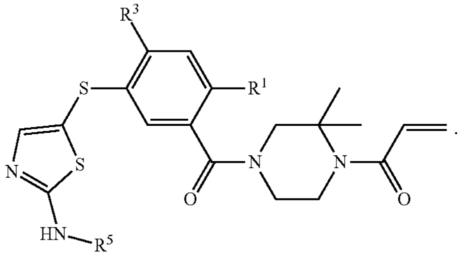

$R^1$, $R^3$, $R^5$ are as described herein. In embodiments, the compound has the formula:

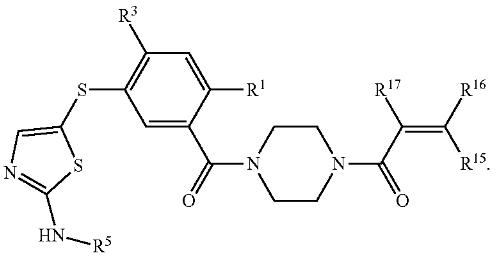

$R^1$, $R^3$, $R^5$, $R^{15}$, $R^{16}$, $R^{17}$ are as described herein. In embodiments, the compound has the formula:

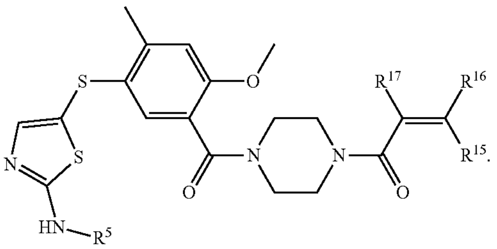

$R^5$, $R^{15}$, $R^{16}$, $R^{17}$ are as described herein. In embodiments, the compound has the formula:

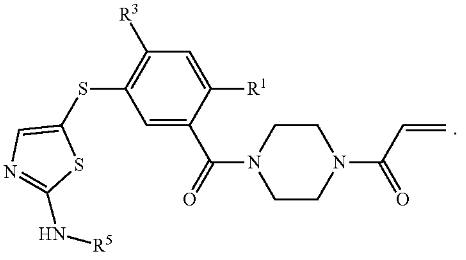

$R^1$, $R^3$, $R^5$ are as described herein. In embodiments, the compound has the formula:

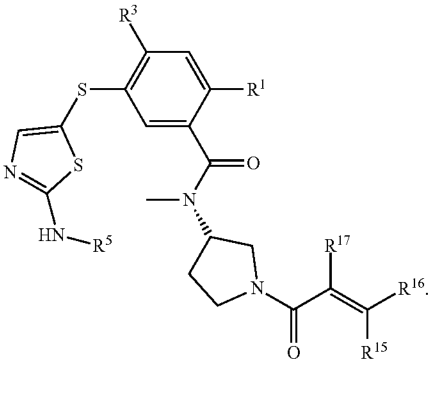

$R^1$, $R^3$, $R^5$, $R^{15}$, $R^{16}$, $R^{17}$ are as described herein. In embodiments, the compound has the formula:

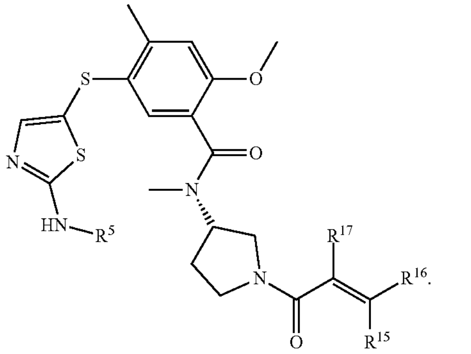

$R^5$, $R^{15}$, $R^{16}$, $R^{17}$ are as described herein. In embodiments, the compound has the formula:

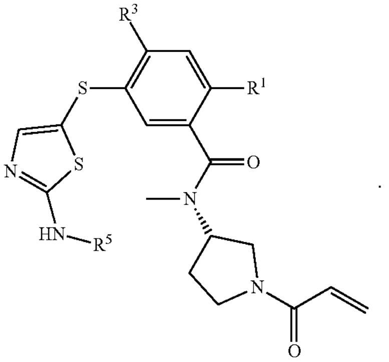

$R^1$, $R^3$, $R^5$ are as described herein. In embodiments, the compound has the formula:

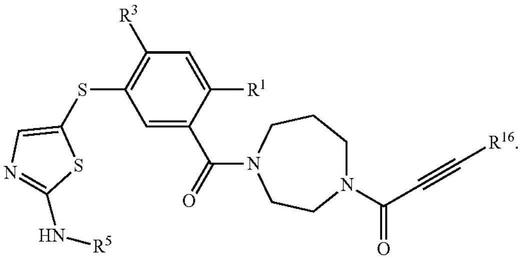

$R^1$, $R^3$, $R^5$, $R^{15}$, $R^{16}$, $R^{17}$ are as described herein. In embodiments, the compound has the formula:

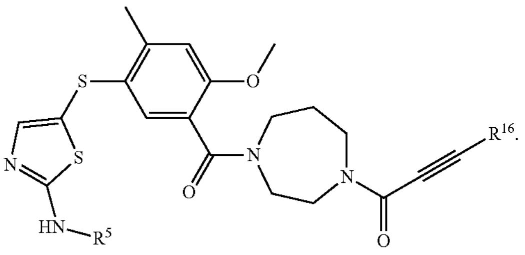

$R^5$, $R^{15}$, $R^{16}$, $R^{17}$ are as described herein. In embodiments, the compound has the formula:

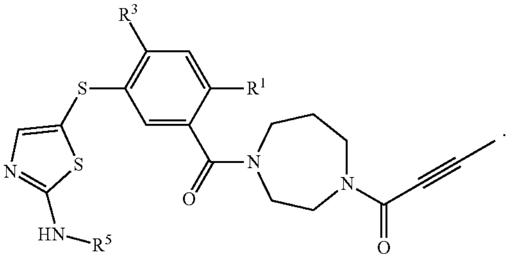

$R^1$, $R^3$, $R^5$ are as described herein. In embodiments, the compound has the formula:

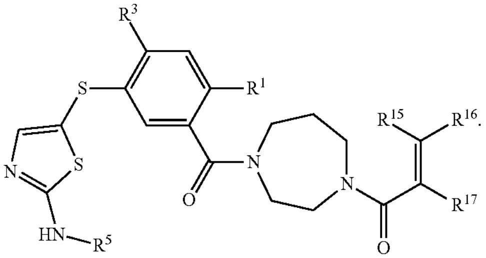

$R^1$, $R^3$, $R^5$, $R^{15}$, $R^{16}$, $R^{17}$ are as described herein. In embodiments, the compound has the formula:

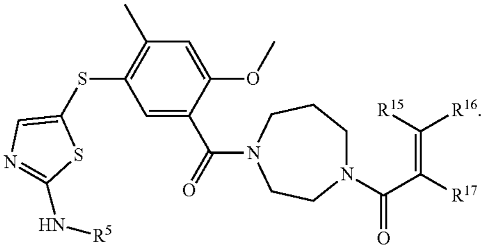

$R^5$, $R^{15}$, $R^{16}$, $R^{17}$ are as described herein. In embodiments, the compound has the formula:

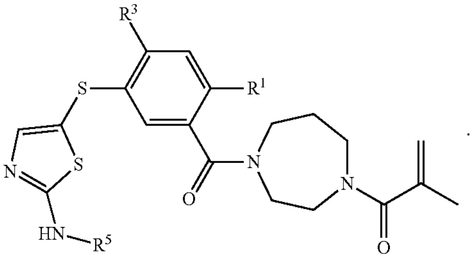

$R^1$, $R^3$, $R^5$ are as described herein. In embodiments, the compound has the formula:

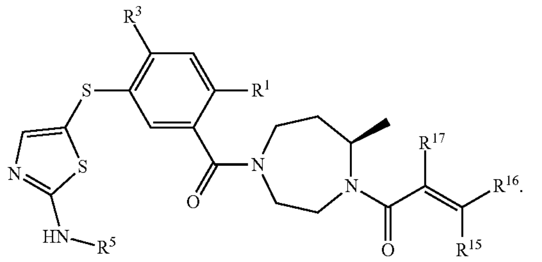

$R^1$, $R^3$, $R^5$, $R^{15}$, $R^{16}$, $R^{17}$ are as described herein. In embodiments, the compound has the formula:

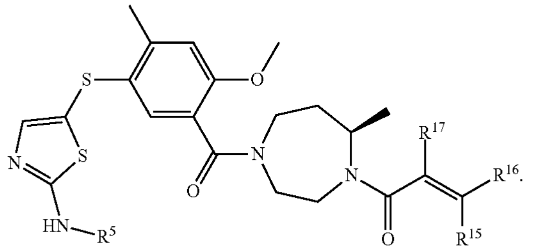

$R^5$, $R^{15}$, $R^{16}$, $R^{17}$ are as described herein. In embodiments, the compound has the formula:

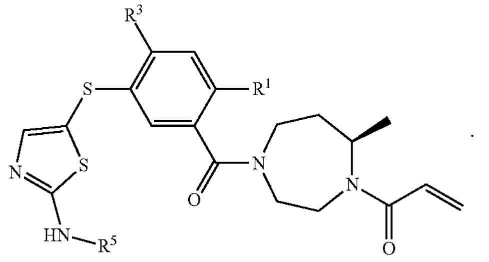

$R^1$, $R^3$, $R^5$ are as described herein. In embodiments, the compound has the formula:

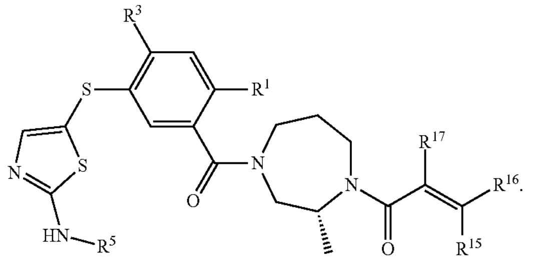

$R^1$, $R^3$, $R^5$, $R^{15}$, $R^{16}$, $R^{17}$ are as described herein. In embodiments, the compound has the formula:

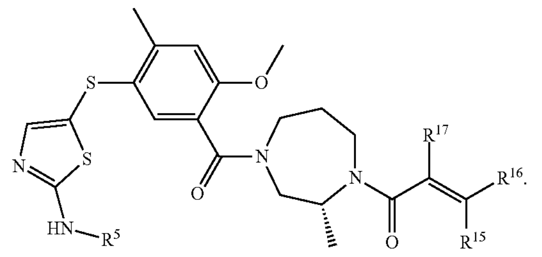

$R^5$, $R^{15}$, $R^{16}$, $R^{17}$ are as described herein. In embodiments, the compound has the formula:

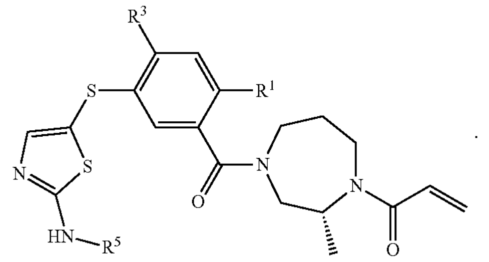

$R^1$, $R^3$, $R^5$ are as described herein.

In embodiments, the compound has the formula:

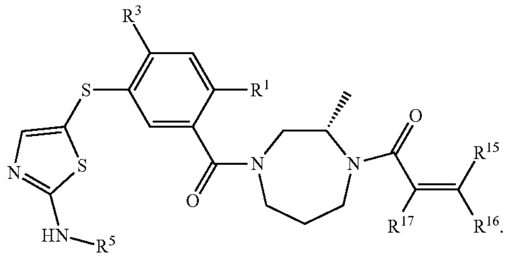

$R^1$, $R^3$, $R^5$, $R^{15}$, $R^{16}$, $R^{17}$ are as described herein. In embodiments, the compound has the formula:

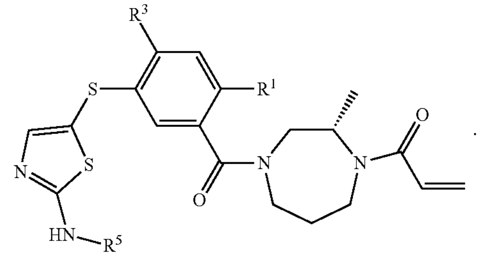

$R^1$, $R^3$, $R^5$ are as described herein. In embodiments, the compound has the formula:

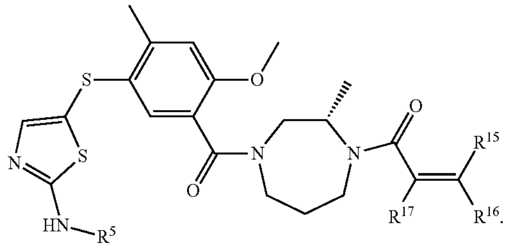

$R^5$, $R^{15}$, $R^{16}$, $R^{17}$ are as described herein. In embodiments, the compound has the formula:

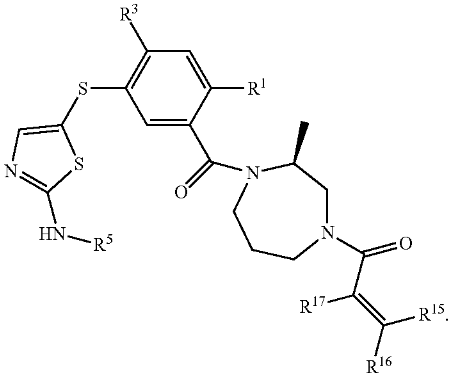

$R^1$, $R^3$, $R^5$, $R^{15}$, $R^{16}$, $R^{17}$ are as described herein. In embodiments, the compound has the formula:

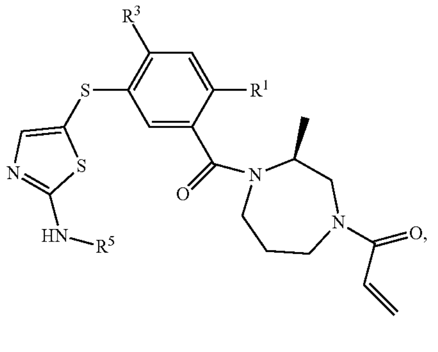

$R^1$, $R^3$, $R^5$ are as described herein. In embodiments, the compound has the formula:

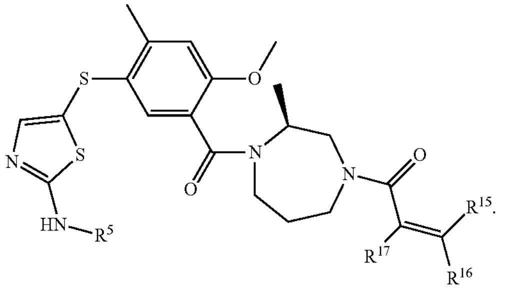

$R^5$, $R^{15}$, $R^{16}$, $R^{17}$ are as described herein. In embodiments, the compound has the formula:

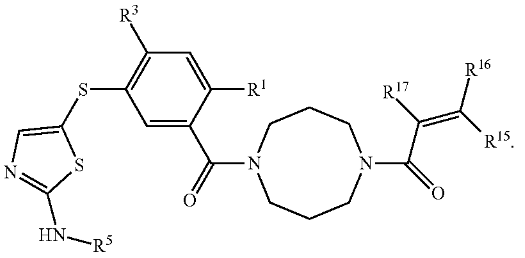

$R^1$, $R^3$, $R^5$, $R^{15}$, $R^{16}$, $R^{17}$ are as described herein. In embodiments, the compound has the formula:

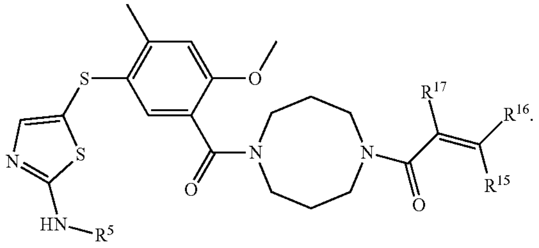

$R^5$, $R^{15}$, $R^{16}$, $R^{17}$ are as described herein. In embodiments, the compound has the formula:

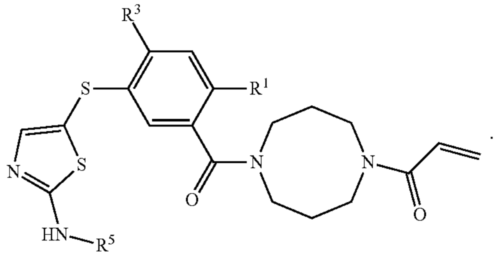

$R^1$, $R^3$, $R^5$ are as described herein. In embodiments, the compound has the formula:

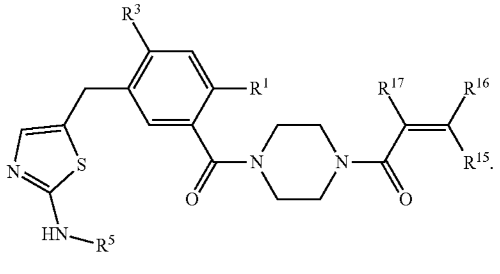

$R^1$, $R^3$, $R^5$, $R^{15}$, $R^{16}$, $R^{17}$ are as described herein. In embodiments, the compound has the formula:

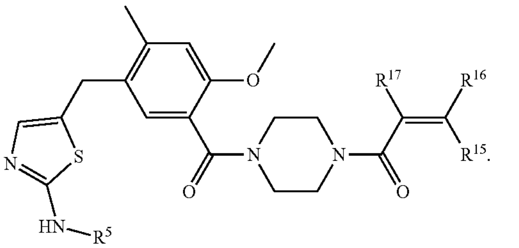

$R^5$, $R^{15}$, $R^{16}$, $R^{17}$ are as described herein. In embodiments, the compound has the formula:

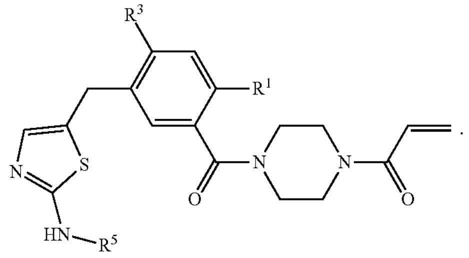

$R^1$, $R^3$, $R^5$ are as described herein. In embodiments, the compound has the formula:

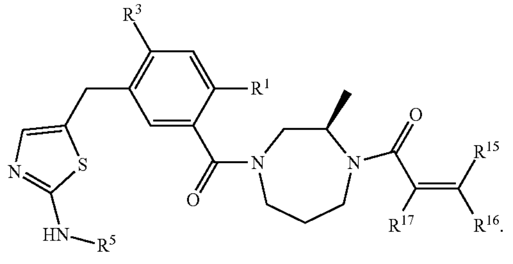

$R^1$, $R^3$, $R^5$, $R^{15}$, $R^{16}$, $R^{17}$ are as described herein. In embodiments, the compound has the formula:

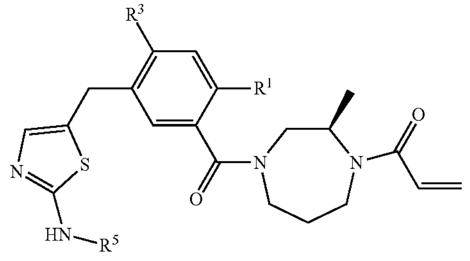

$R^1$, $R^3$, $R^5$ are as described herein. In embodiments, the compound has the formula:

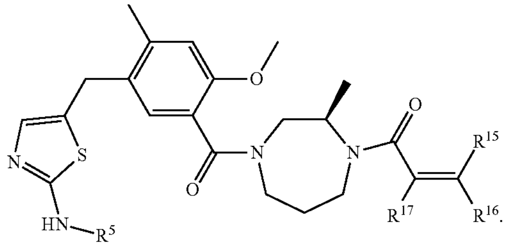

$R^5$, $R^{15}$, $R^{16}$, $R^{17}$ are as described herein.

In embodiments, the compound has the formula:

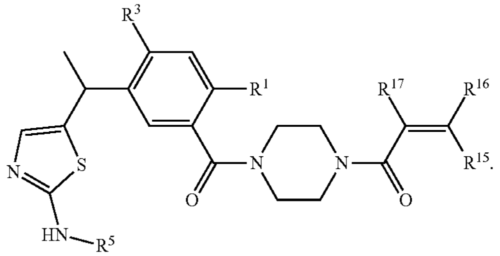

$R^1$, $R^3$, $R^5$, $R^{15}$, $R^{16}$, $R^{17}$ are as described herein. In embodiments, the compound has the formula:

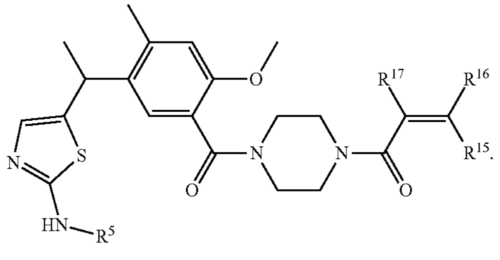

$R^5$, $R^{15}$, $R^{16}$, $R^{17}$ are as described herein. In embodiments, the compound has the formula:

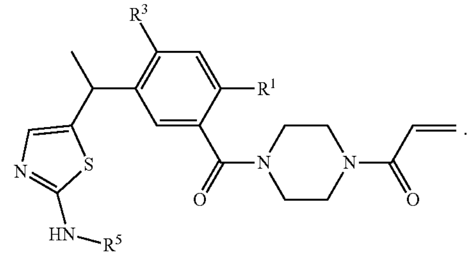

$R^1$, $R^3$, $R^5$ are as described herein. In embodiments, the compound has the formula:

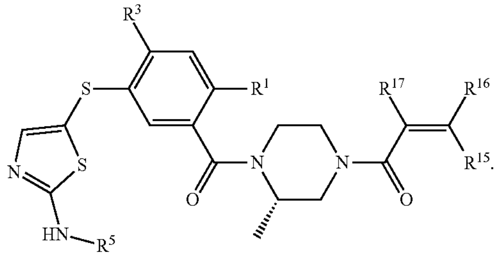

$R^1$, $R^3$, $R^5$, $R^{15}$, $R^{16}$, $R^{17}$ are as described herein. In embodiments, the compound has the formula:

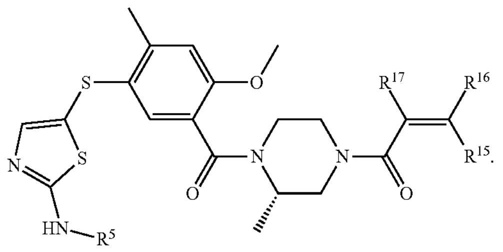

$R^5$, $R^{15}$, $R^{16}$, $R^{17}$ are as described herein. In embodiments, the compound has the formula:

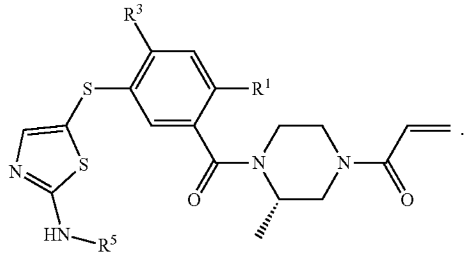

$R^1$, $R^3$, $R^5$ are as described herein.

In embodiments, the compound has the formula:

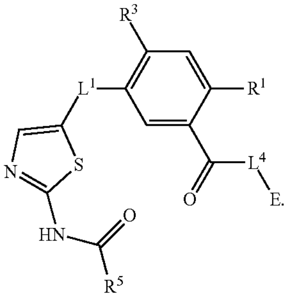

$R^1$, $R^3$, $R^5$, $L^1$, $L^4$, and E are as described herein. In embodiments, $R^1$ is $-OCH_3$, $-CH_3$, or $-CH_2CH_3$. In embodiments, $R^3$ is $-CH_3$ or halogen. In embodiments, $R^3$ is $-CH_3$ or $-Cl$. In embodiments, $L^1$ is $-S-$, $-CH_2-$, or $-CH(CH_3)-$. In embodiments, $-L^4$-E is

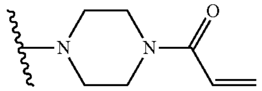 , 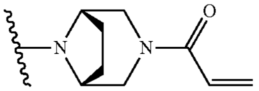 , 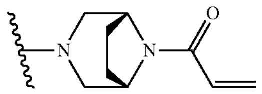 , 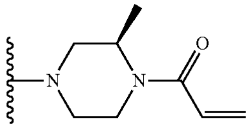 , 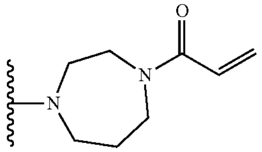 , 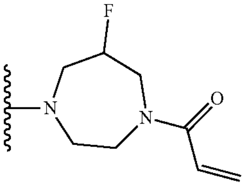 , 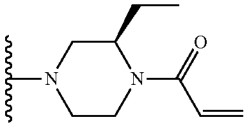 , 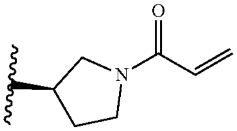 , 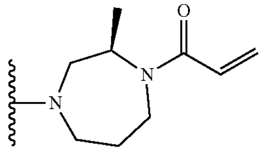 .

In embodiments, $R^5$ is

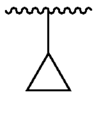 , 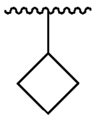 , 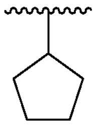 , 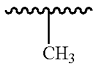 , 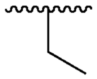 , 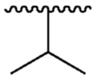 , 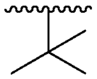 , 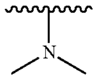 , 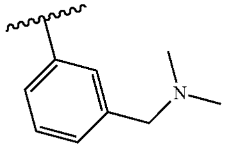 , 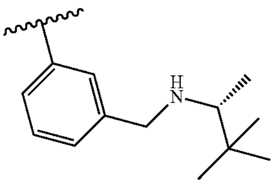 , 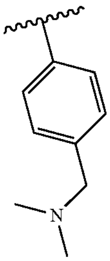 , 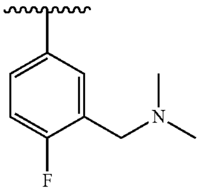 , 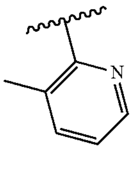 , 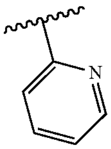 , 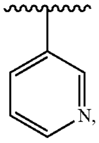 , 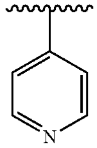 , 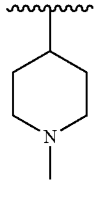 , -continued

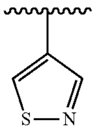, 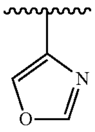, 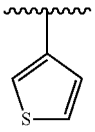, 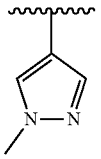,

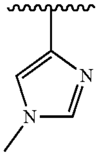, 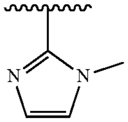, or 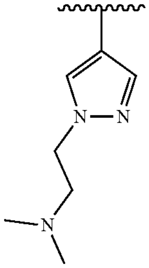.

In embodiments, $R^5$ is

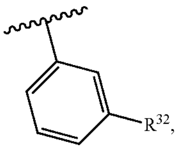, 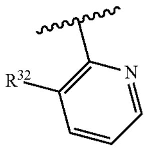, or 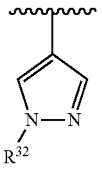.

In embodiments, the compound has the formula:

(I)

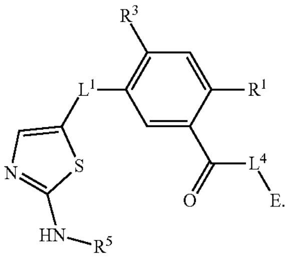

$R^1$, $R^3$, $R^5$, $L^1$, $L^4$, and E are as described herein. In embodiments, $R^1$ is —$OCH_3$, —$CH_3$, or —$CH_2CH_3$. In embodiments, $R^3$ is —$CH_3$ or halogen. In embodiments, $R^3$ is —$CH_3$ or —Cl. In embodiments, $L^1$ is —S—, —$CH_2$—, or —$CH(CH_3)$—. In embodiments, -$L^4$-E is

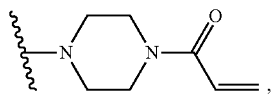, 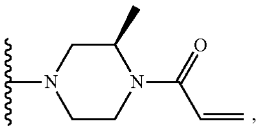,

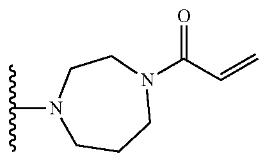, 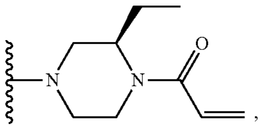, or

-continued

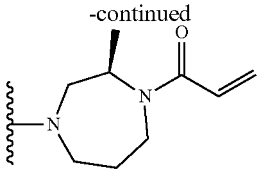.

In embodiments, $R^5$ is substituted pyridyl. In embodiments, $R^5$ is substituted 2-pyridyl. In embodiments, $R^5$ is $R^{32}$-substituted pyridyl. In embodiments, $R^5$ is $R^{32}$-substituted 2-pyridyl. In embodiments, $R^5$ is unsubstituted pyridyl. In embodiments, $R^5$ is

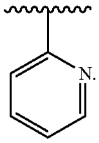 [SMILES: *c1ccccn1]

In embodiments, $R^5$ is substituted heteroaryl. In embodiments, $R^5$ is unsubstituted heteroaryl. In embodiments, $R^5$ is substituted 5 to 6 membered heteroaryl. In embodiments, $R^5$ is unsubstituted 5 to 6 membered heteroaryl. In embodiments, the compound has the formula:

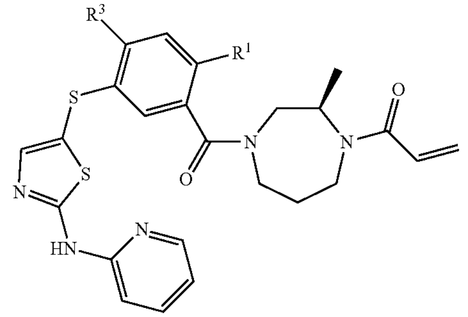,

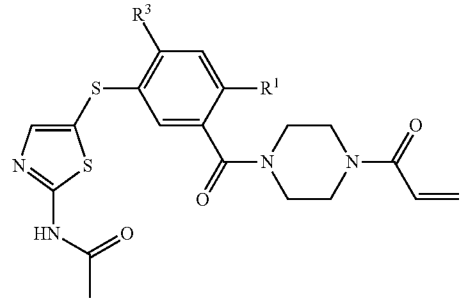,

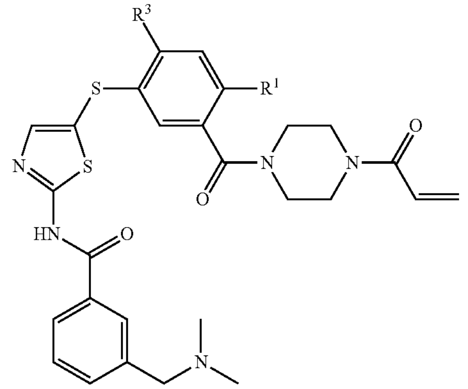,

-continued
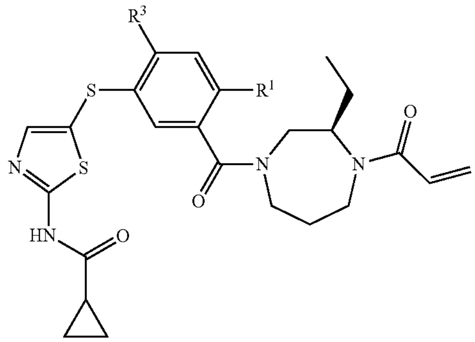
,
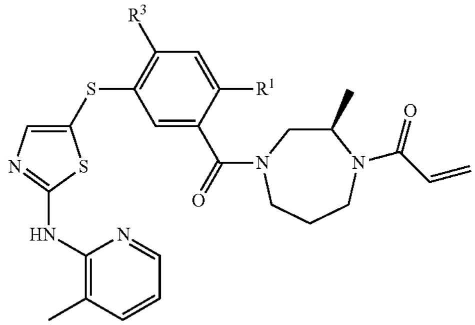
,
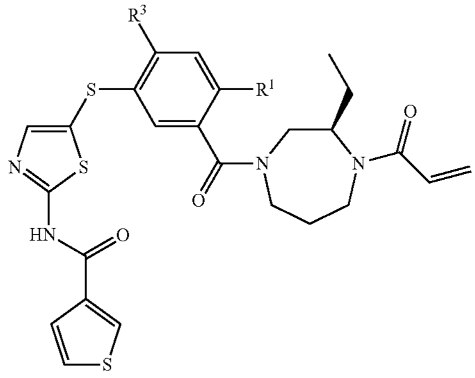
,
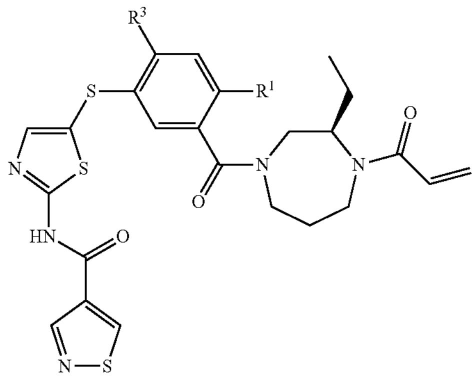
,
-continued
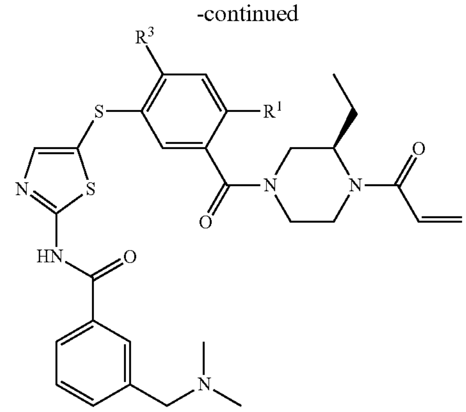
,
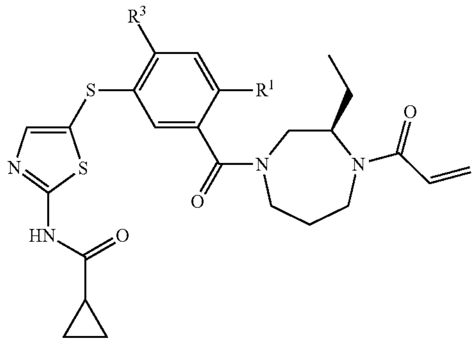
,
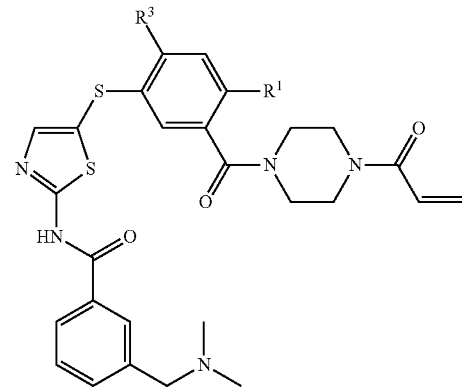
,
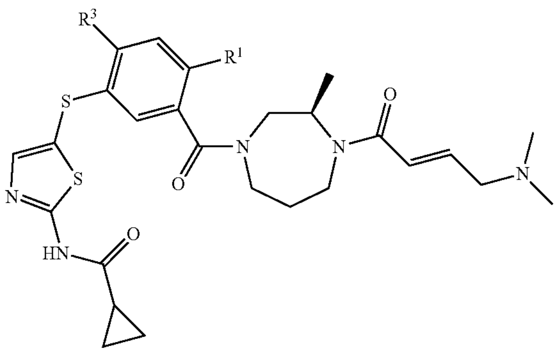
, -continued
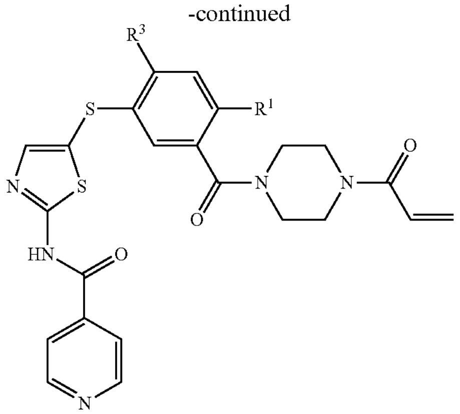
,
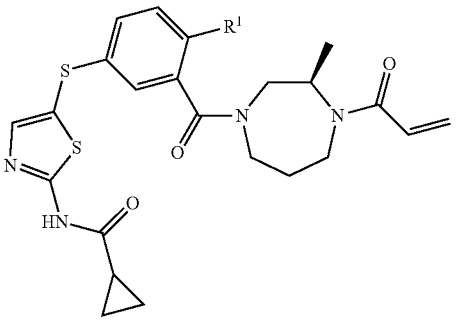
,
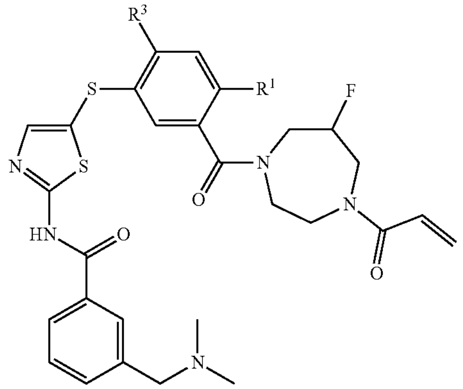
,
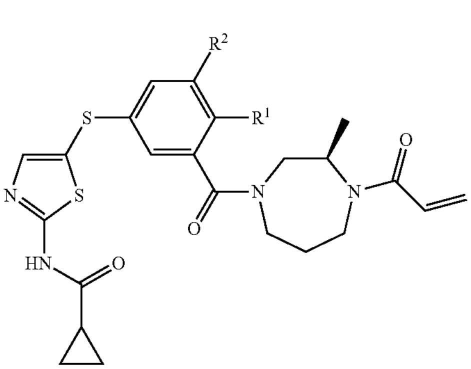
,
-continued
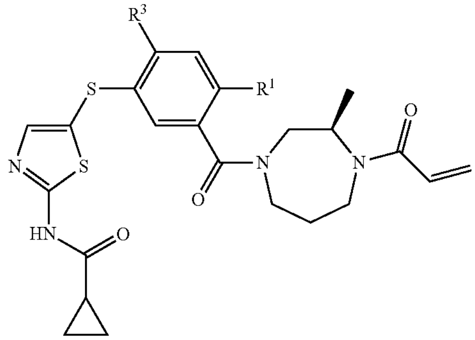
,
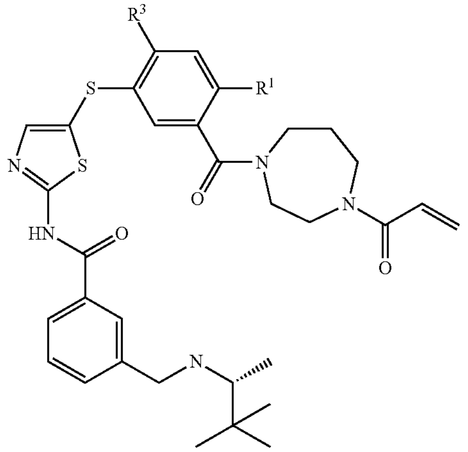
,
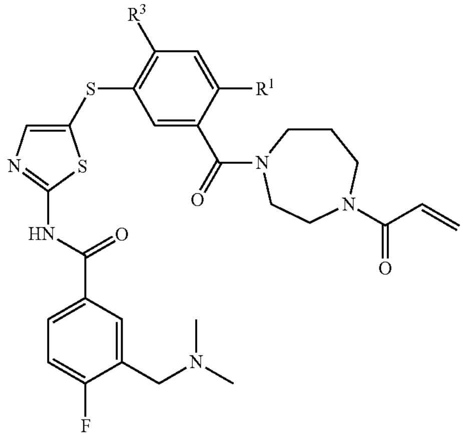
,
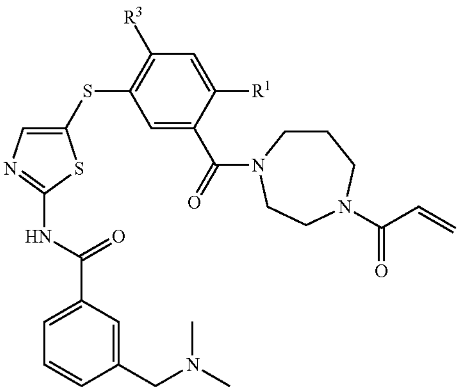
, or -continued

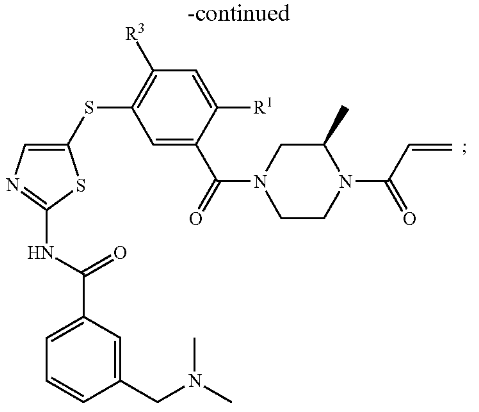

wherein $R^1$, $R^2$, $R^3$ are as described herein. In embodiments, $R^1$ is independently —$CH_3$. In embodiments, $R^1$ is independently —$OCH_3$. In embodiments, $R^1$ is independently —Cl. In embodiments, $R^2$ is independently —$CH_3$. In embodiments, $R^2$ is independently —$OCH_3$. In embodiments, $R^2$ is independently —Cl. In embodiments, $R^3$ is independently —$CH_3$. In embodiments, $R^3$ is independently —$OCH_3$. In embodiments, $R^3$ is independently —Cl.

In embodiments, $R^1$ is independently —$OCH_3$ and $R^3$ is independently —$CH_3$. In embodiments, $R^1$ is independently —$CH_3$ and $R^3$ is independently —$CH_3$. In embodiments, $R^1$ is independently —$CH_3$ and $R^2$ is independently —$CH_3$. In embodiments, $R^1$ is independently —$CH_3$ and $R^3$ is independently —Cl. In embodiments, $R^1$ is independently —Cl and $R^3$ is independently —$CH_3$.

In embodiments, $R^1$ is independently unsubstituted $C_1$-$C_4$ alkyl. In embodiments, $R^1$ is independently unsubstituted $C_1$-$C_4$ alkoxy. In embodiments, $R^1$ is independently halogen. In embodiments, $R^2$ is independently unsubstituted $C_1$-$C_4$ alkyl. In embodiments, $R^2$ is independently unsubstituted $C_1$-$C_4$ alkoxy. In embodiments, $R^2$ is independently halogen. In embodiments, $R^3$ is independently unsubstituted $C_1$-$C_4$ alkyl. In embodiments, $R^3$ is independently unsubstituted $C_1$-$C_4$ alkoxy. In embodiments, $R^3$ is independently halogen.

In embodiments, $R^1$ is independently unsubstituted $C_1$-$C_4$ alkoxy and $R^3$ is independently unsubstituted $C_1$-$C_4$ alkyl. In embodiments, $R^1$ is independently unsubstituted $C_1$-$C_4$ alkyl and $R^3$ is independently unsubstituted $C_1$-$C_4$ alkyl. In embodiments, $R^1$ is independently unsubstituted $C_1$-$C_4$ alkyl and $R^2$ is independently unsubstituted $C_1$-$C_4$ alkyl. In embodiments, $R^1$ is independently unsubstituted $C_1$-$C_4$ alkyl and $R^3$ is independently halogen. In embodiments, $R^1$ is independently halogen and $R^3$ is independently unsubstituted $C_1$-$C_4$ alkyl.

In embodiments, the compound has the formula:

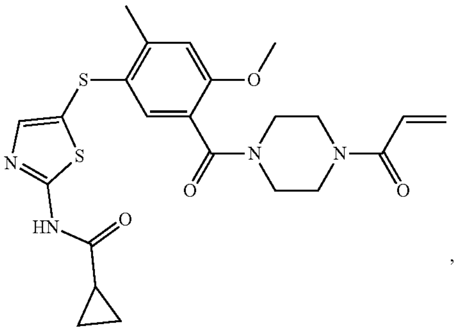
,
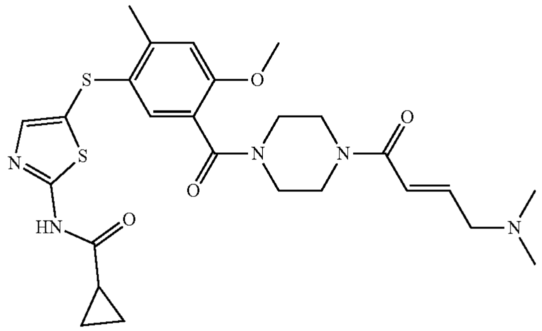
,
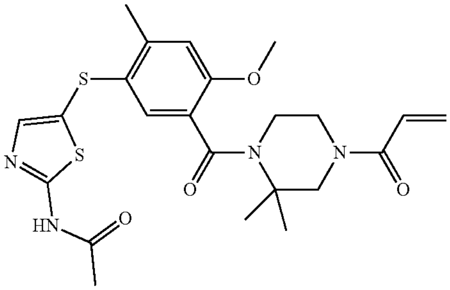
,
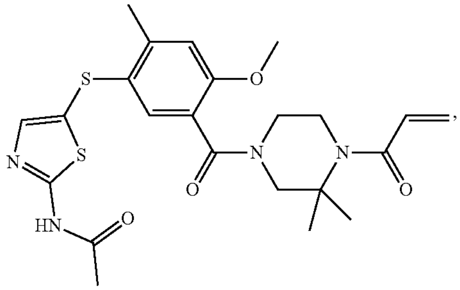
,
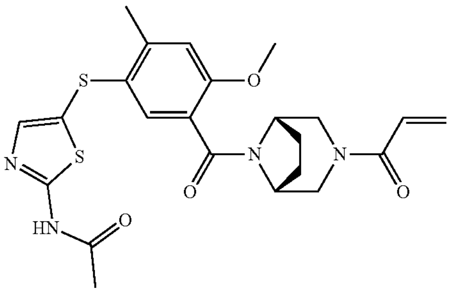
,
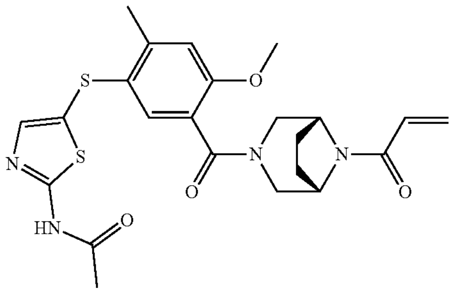
, -continued
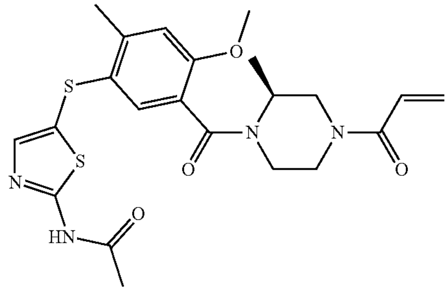
,
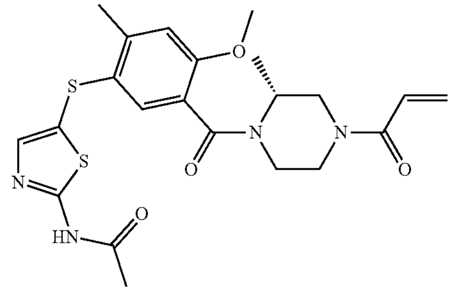
,
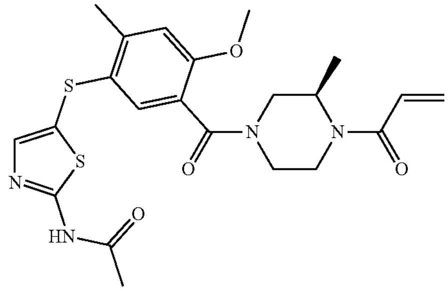
,
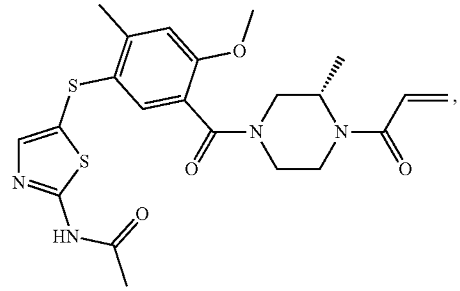
,
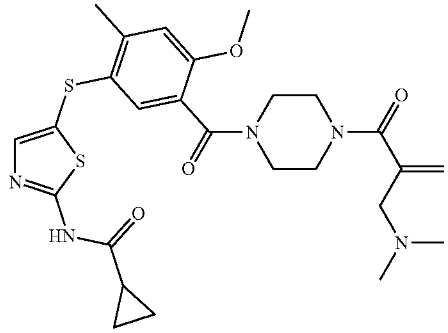
,
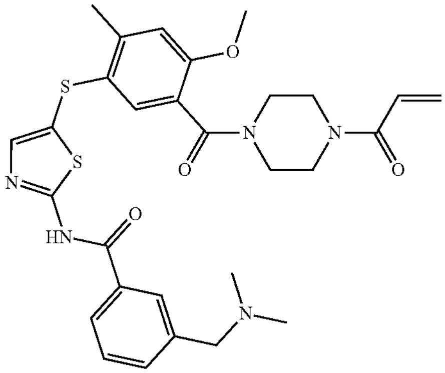
,
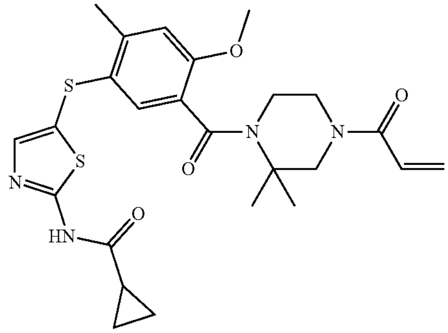
,
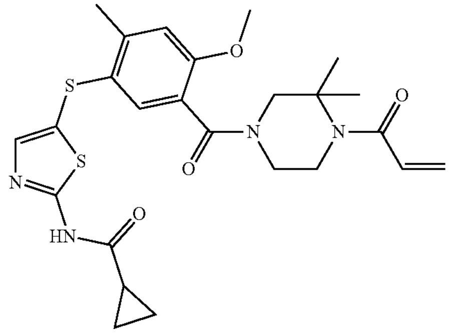
,
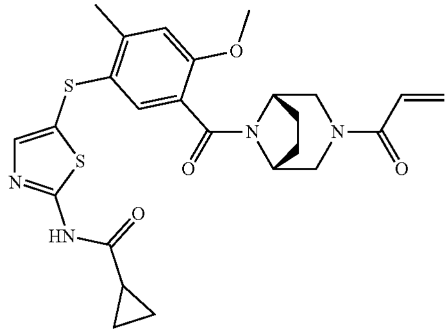
,
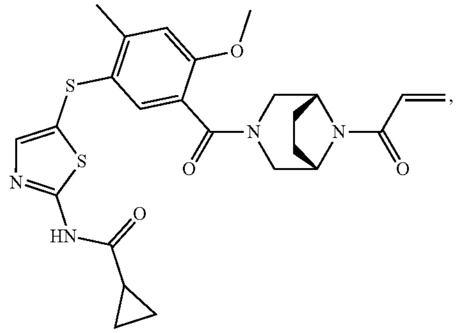
, -continued
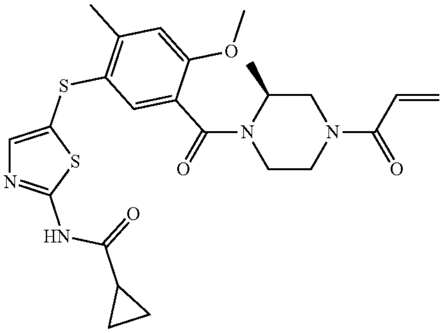,
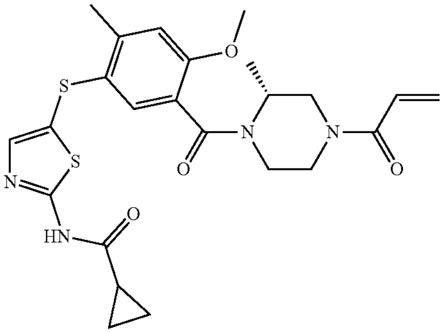,
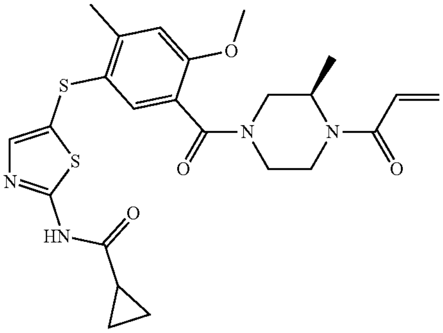,
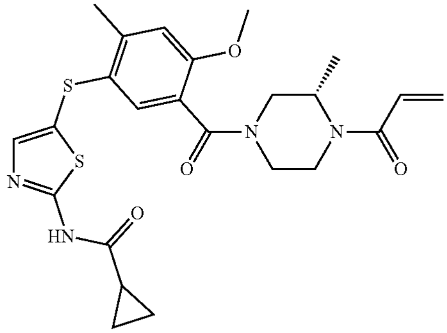,
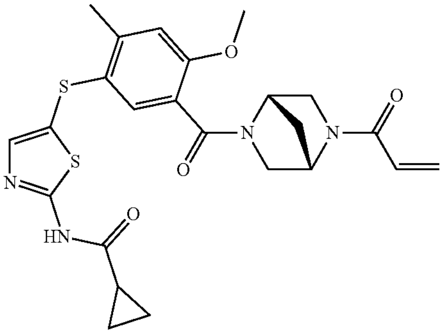,
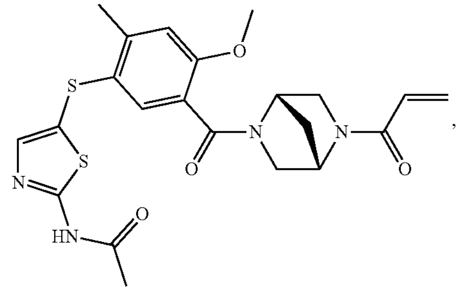,
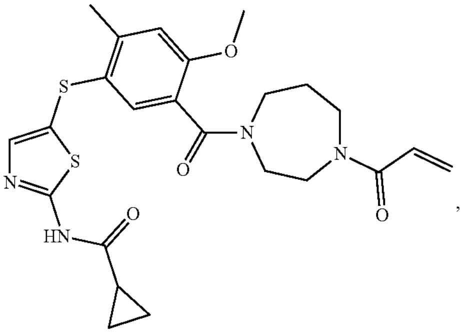,
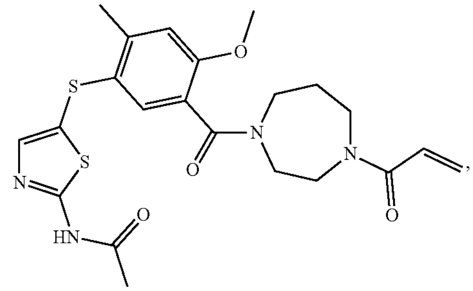,
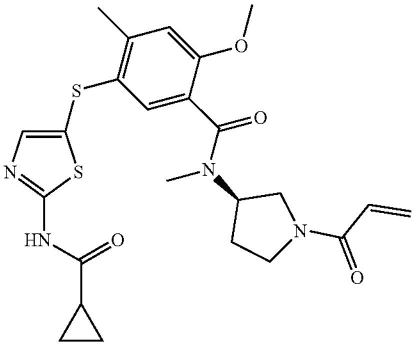,
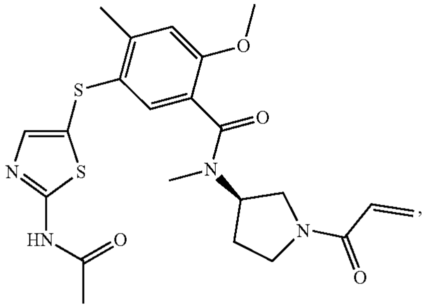, -continued
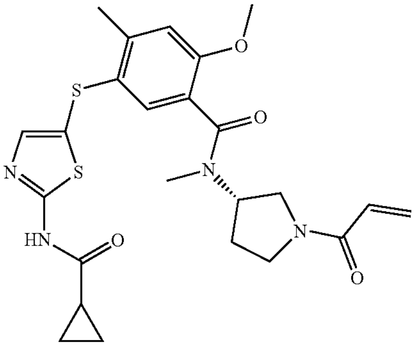
,
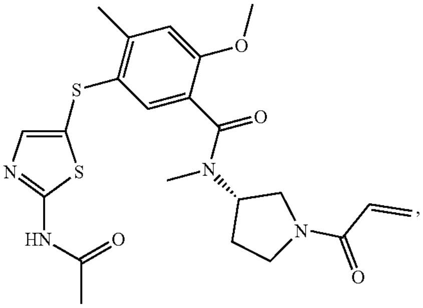
,
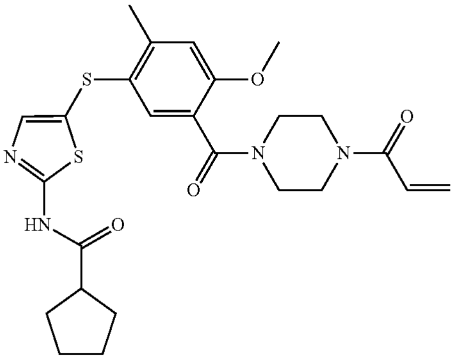
,
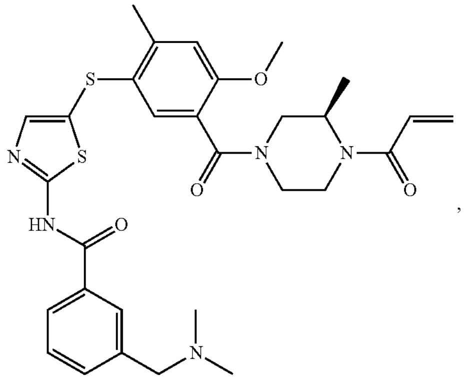
,
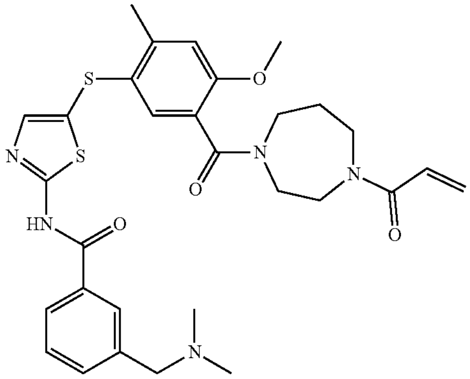
,
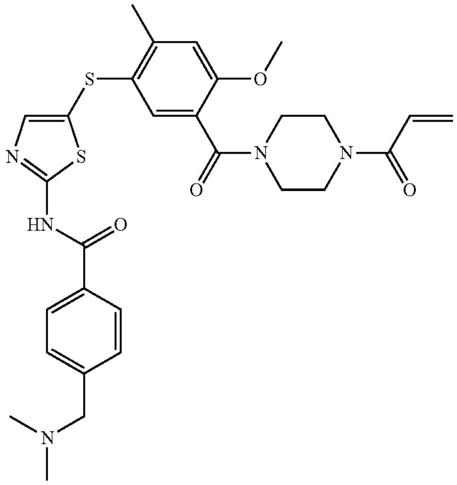
,
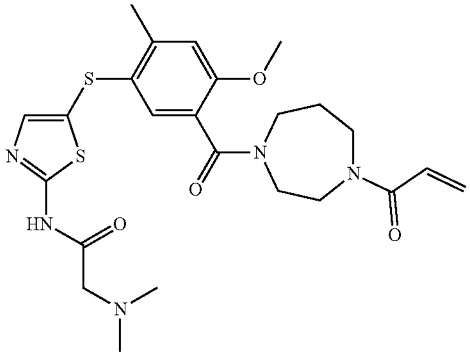
,
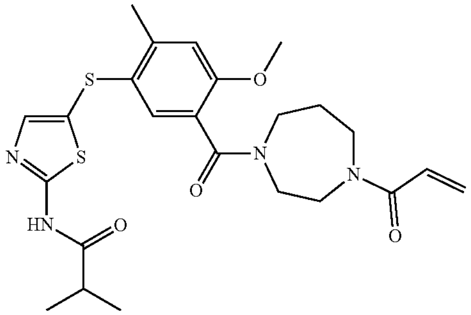
, -continued
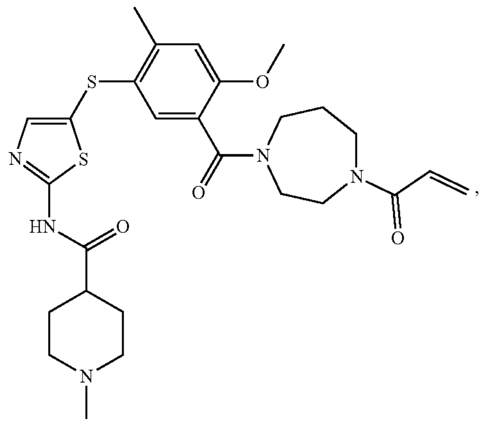
,
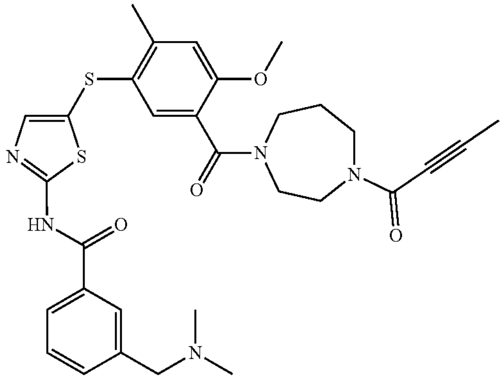
,
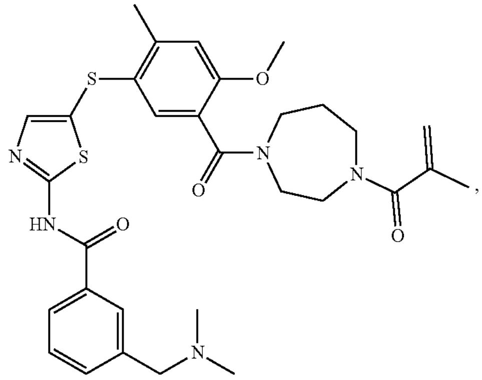
,
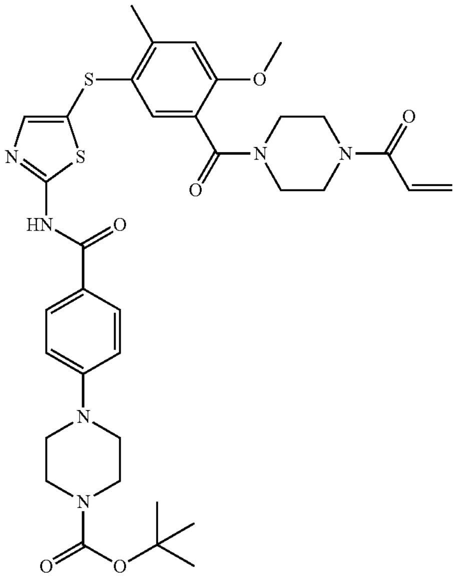
,
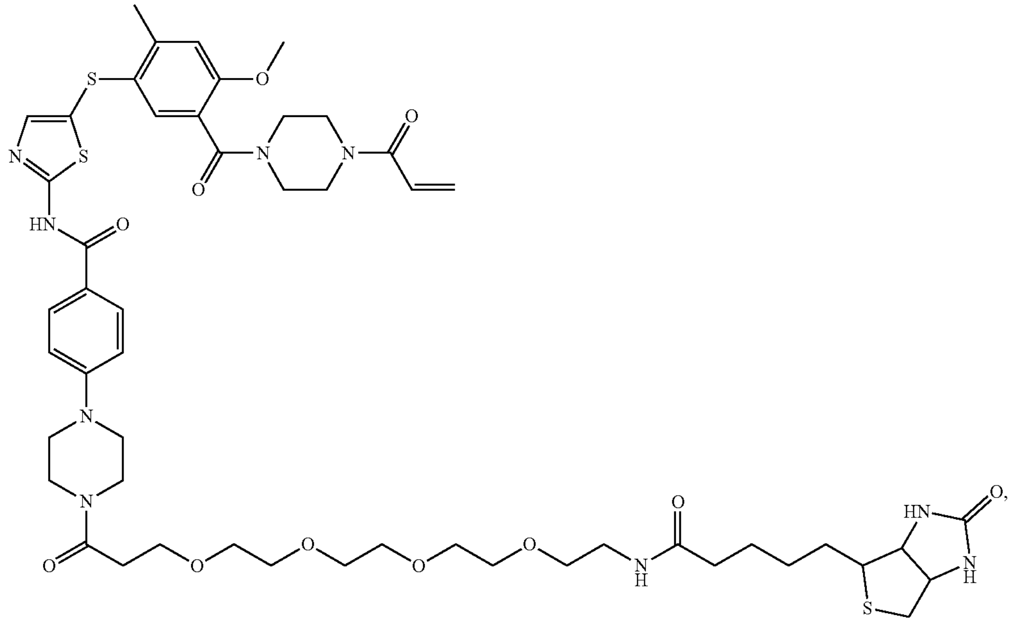
, -continued
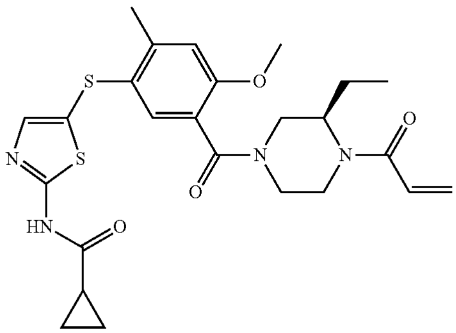
,
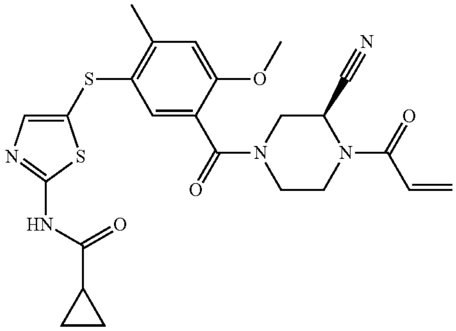
,
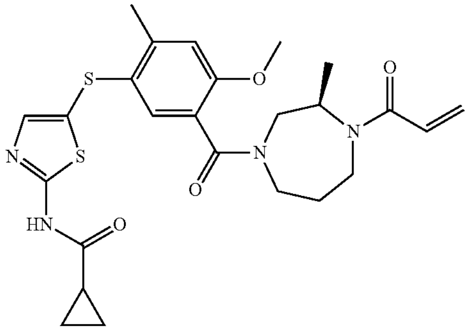
,
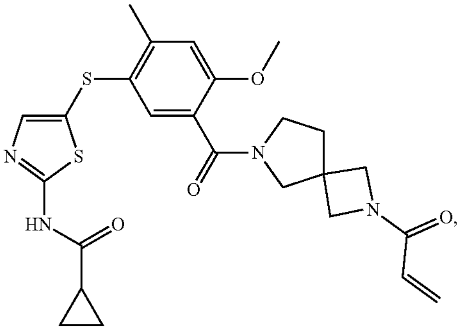
,
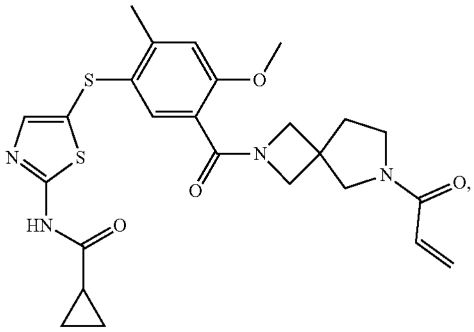
,
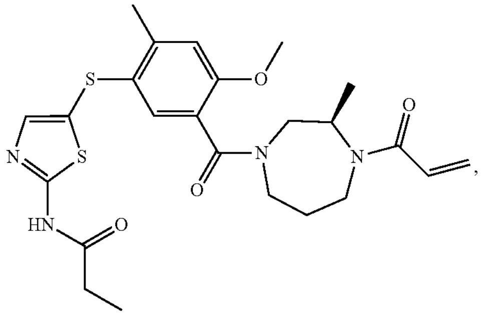
,
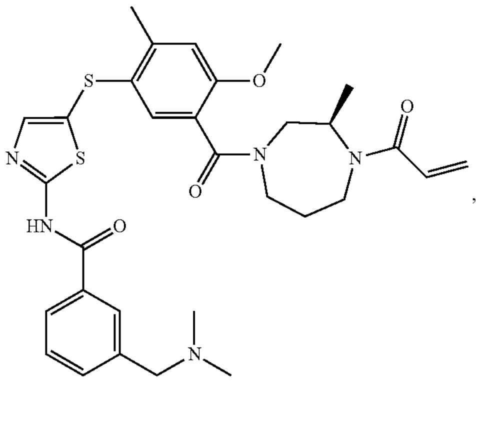
,
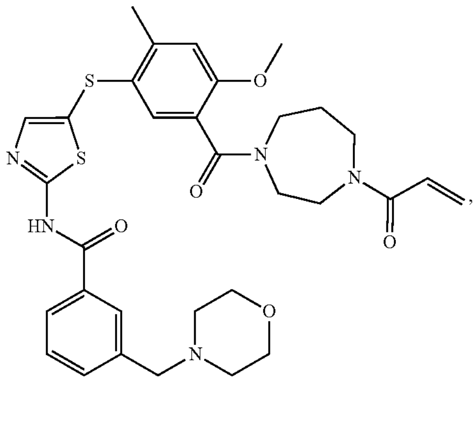
, -continued
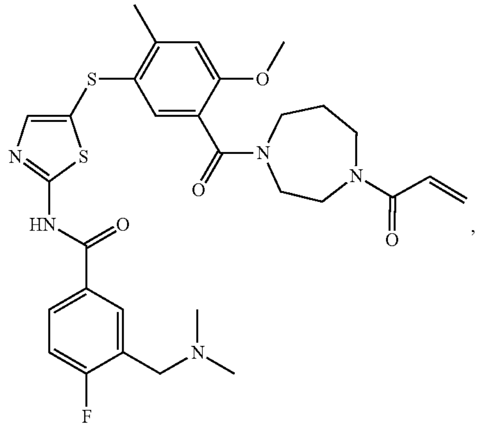
,
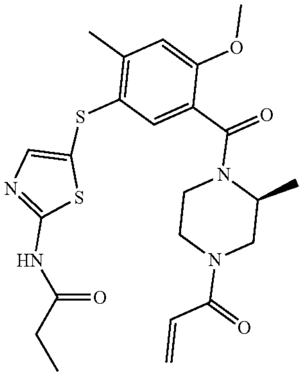
,
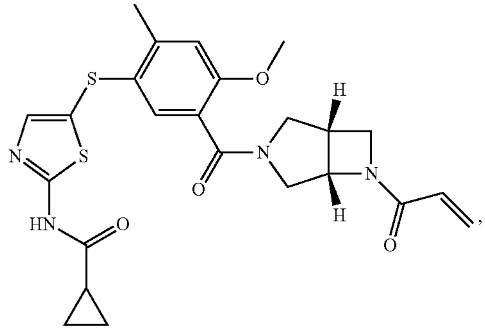
,
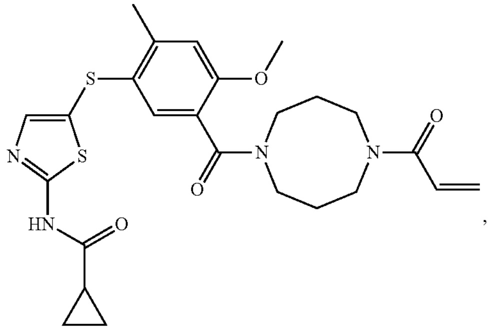
,
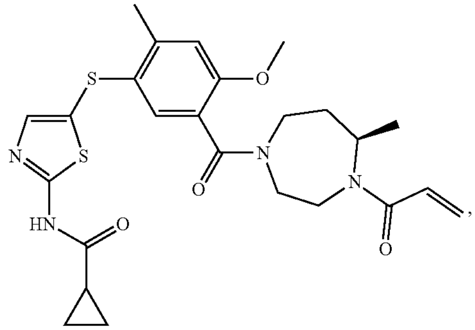
,
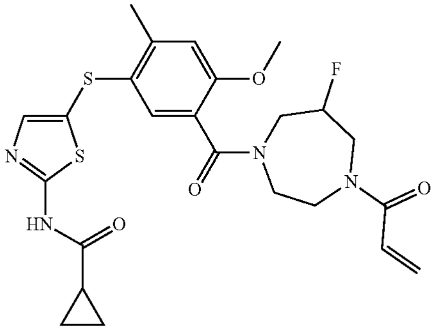
,
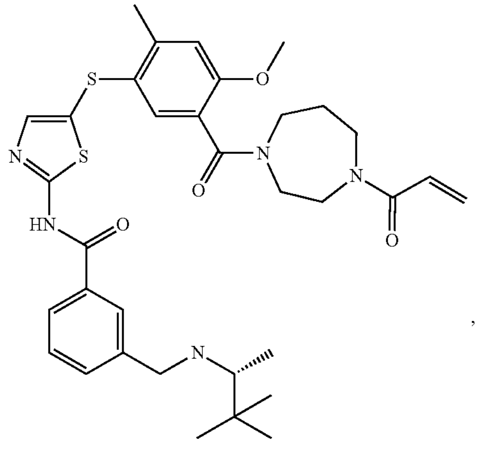
,
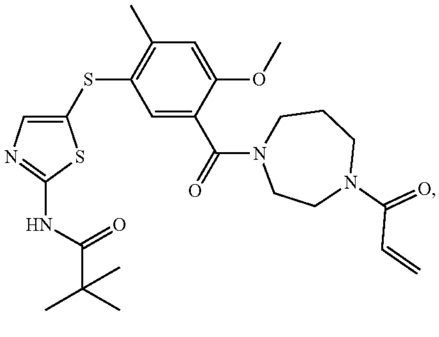
, -continued
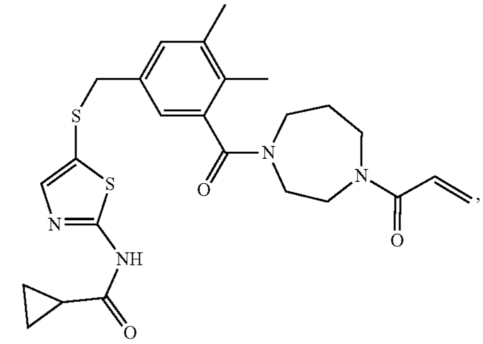
,
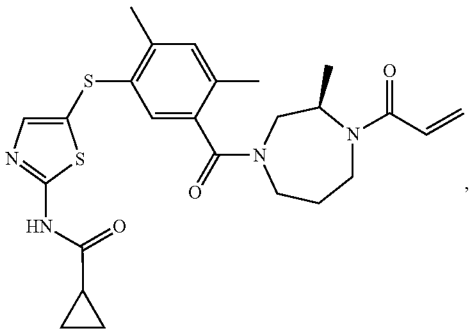
,
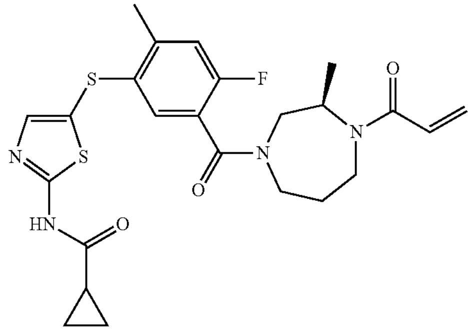
,
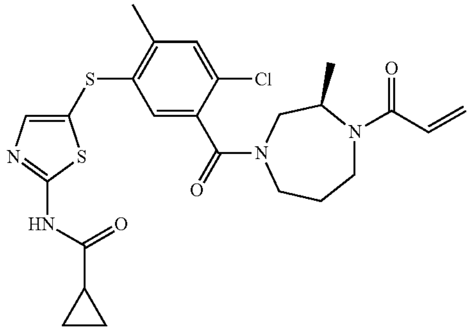
,
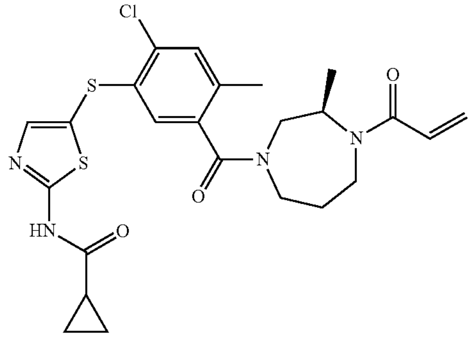
,
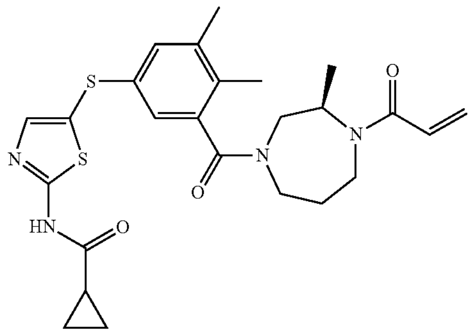
,
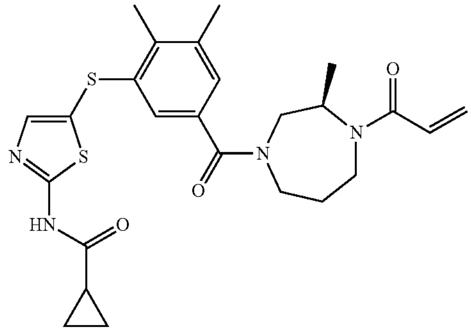
,
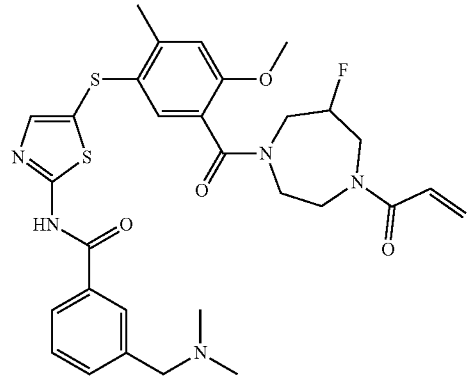
,
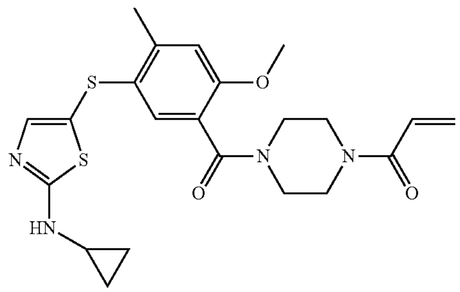
,
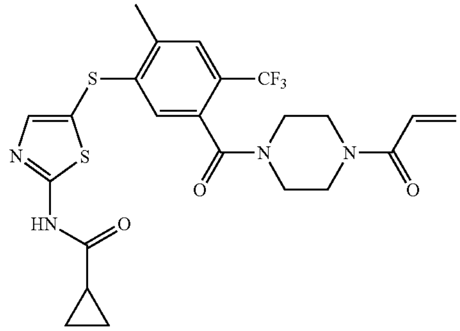
, -continued
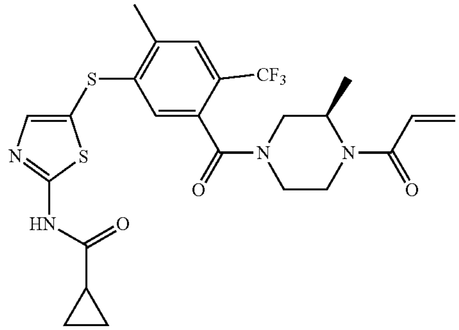
,
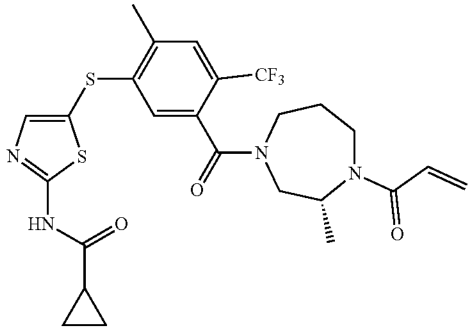
,
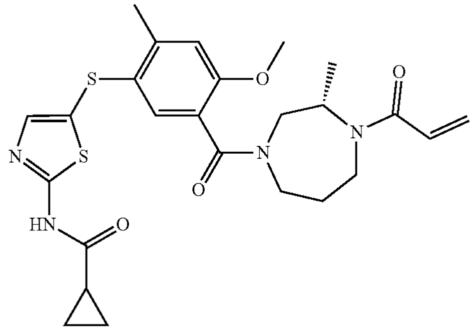
,
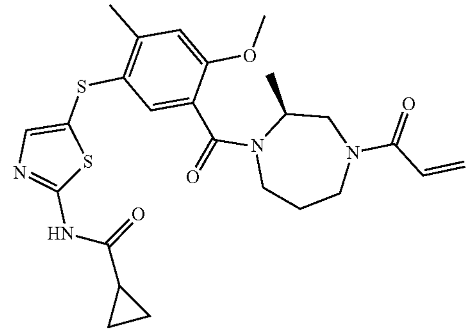
,
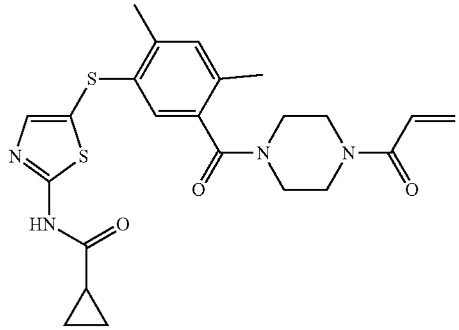
,
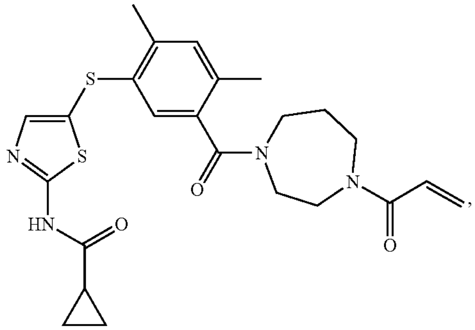
,
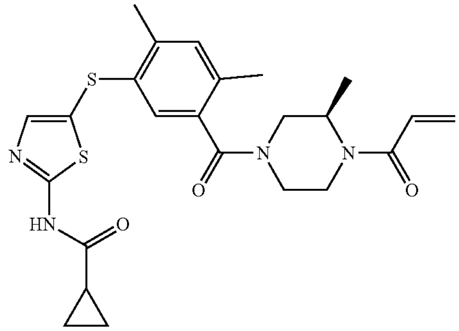
,
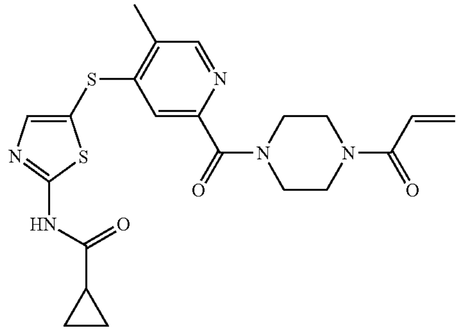
,
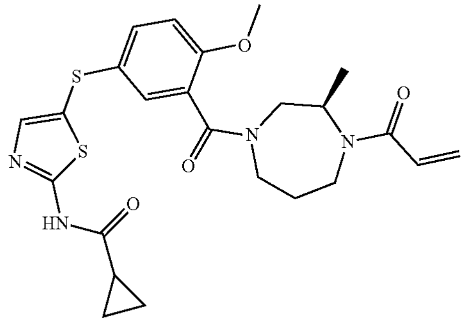
,
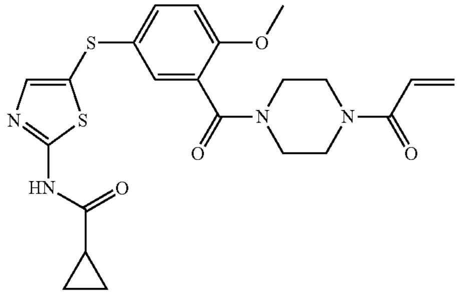
, -continued
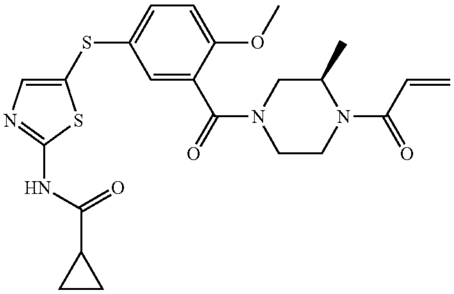,
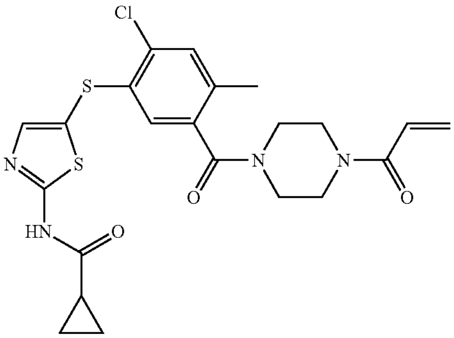,
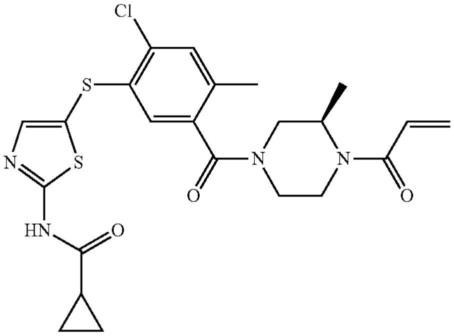,
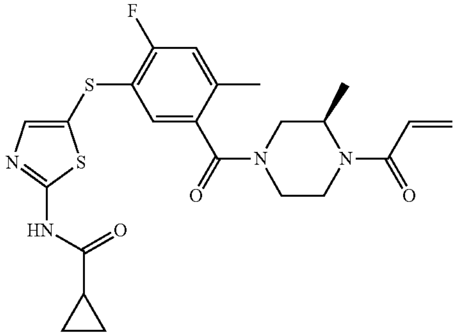,
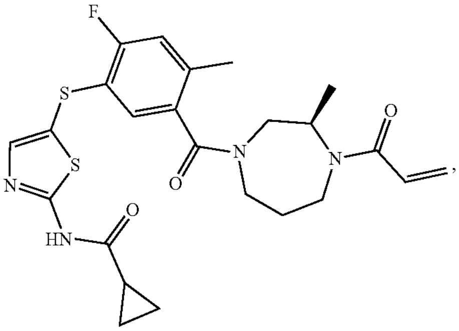,
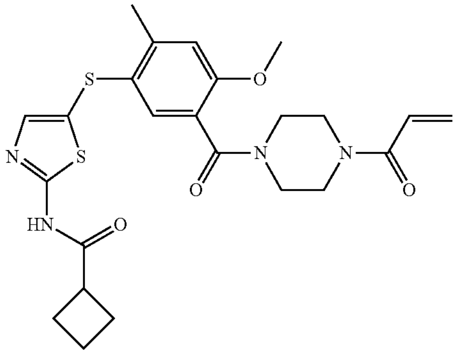,
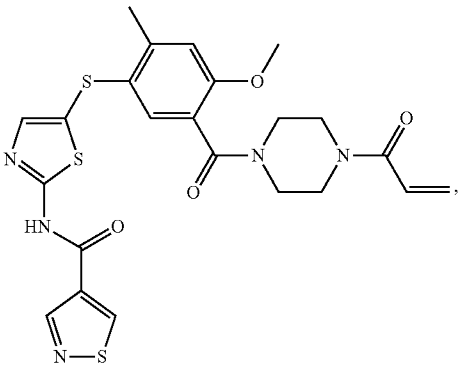,
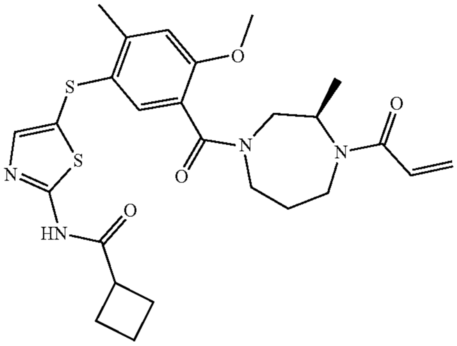, -continued
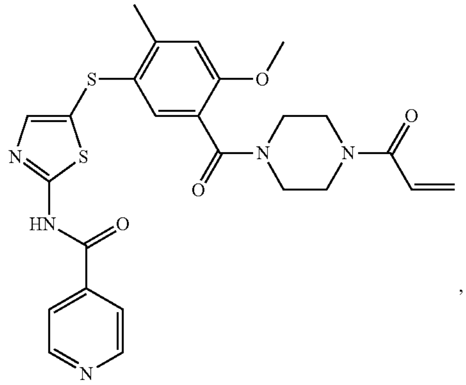
,
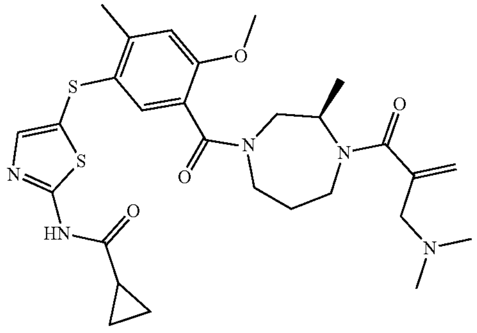
,
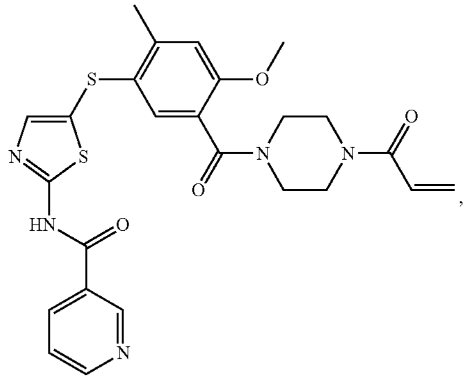
,
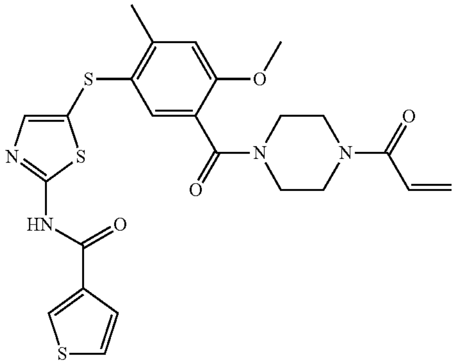
,
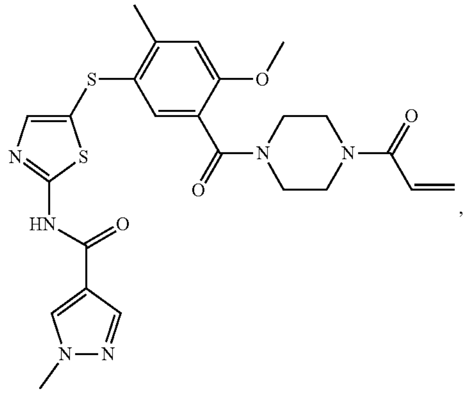
,
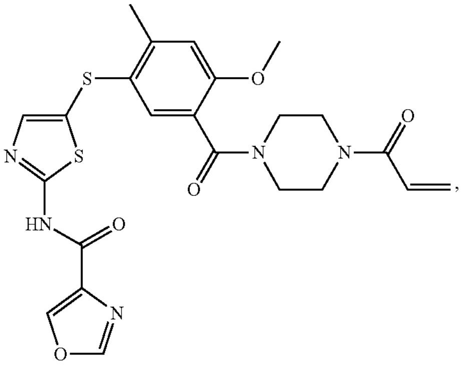
,
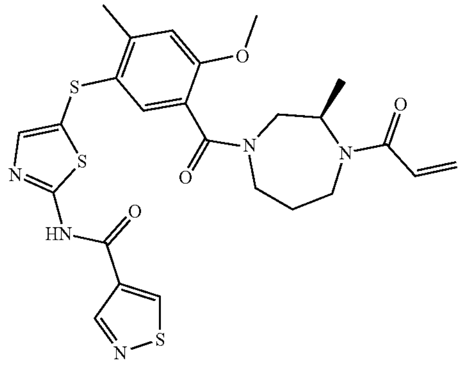
,
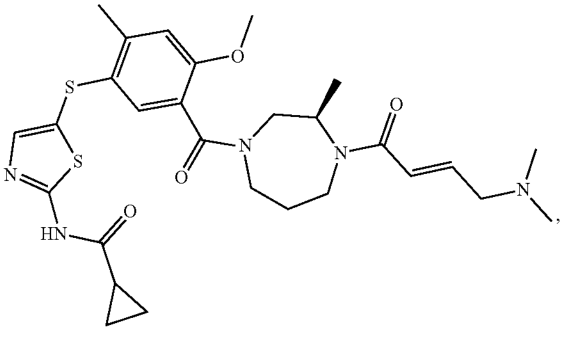
, -continued
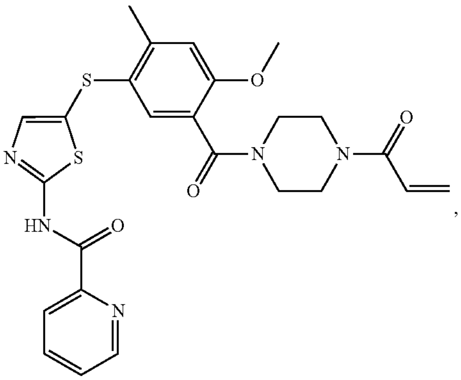
,
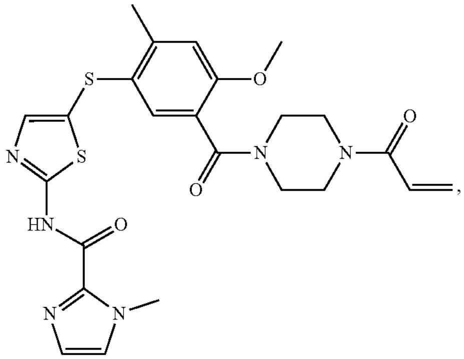
,
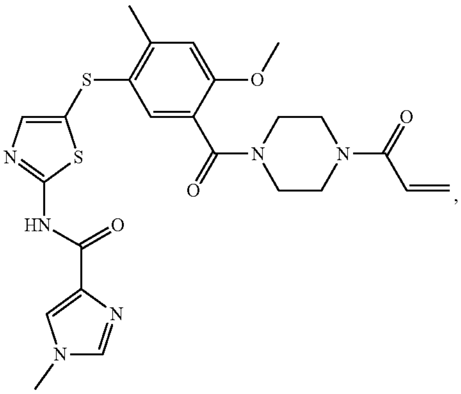
,
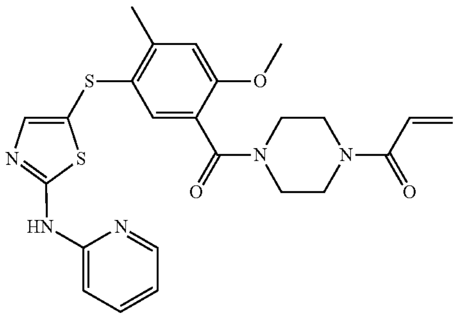
,
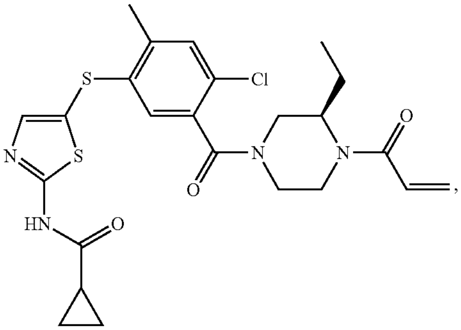
,
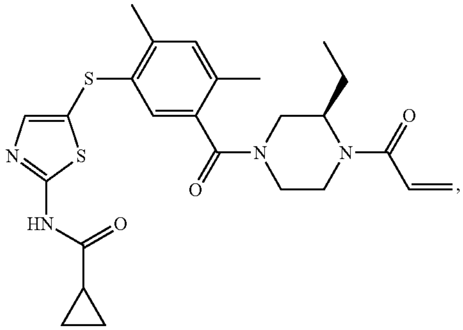
,
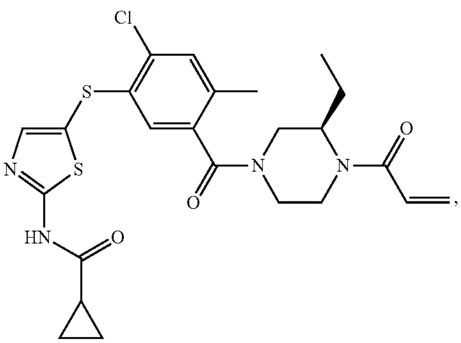
,
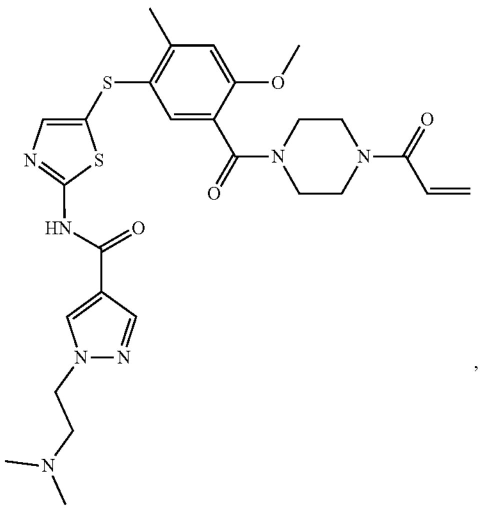
, -continued
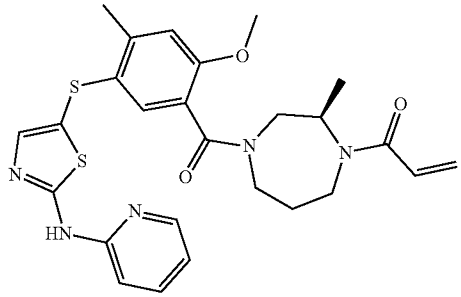
,
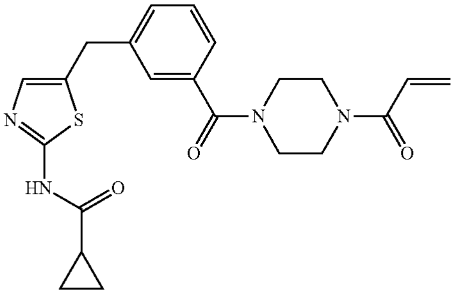
,
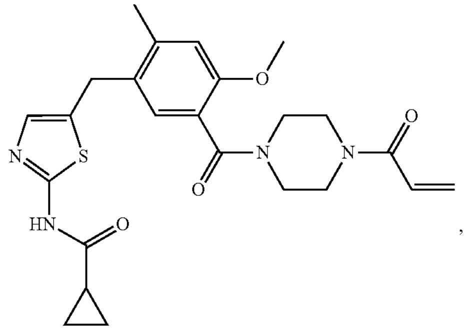
,
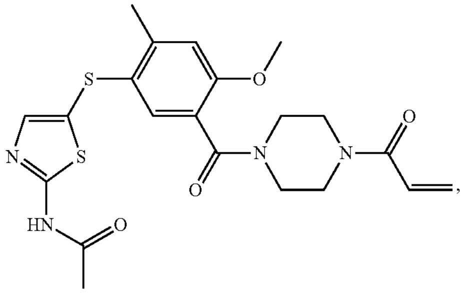
,
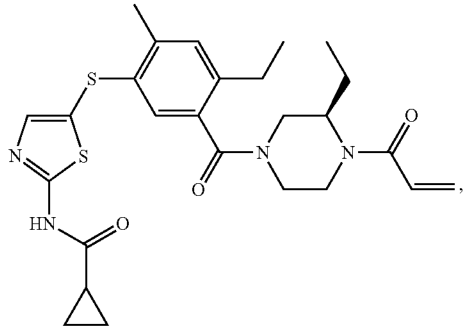
,
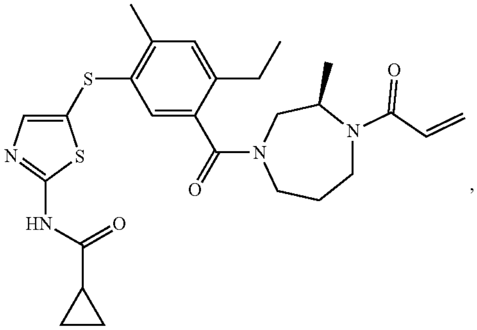
,
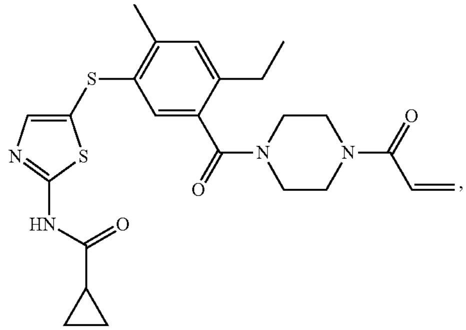
,
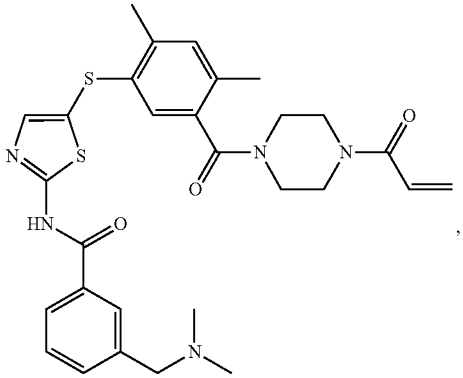
,
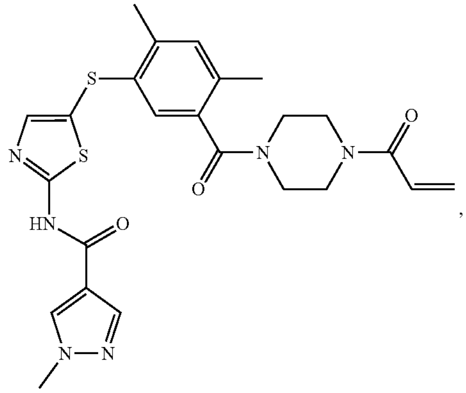
,
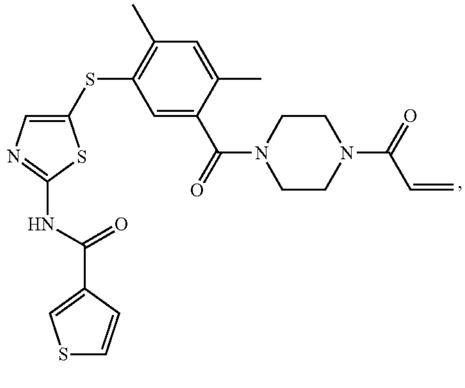
, -continued
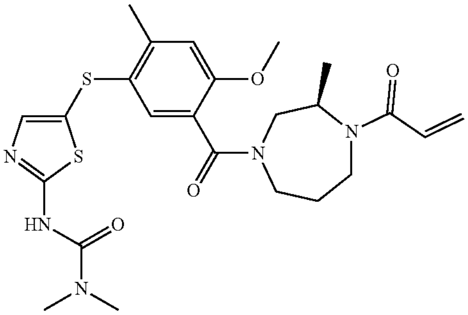,
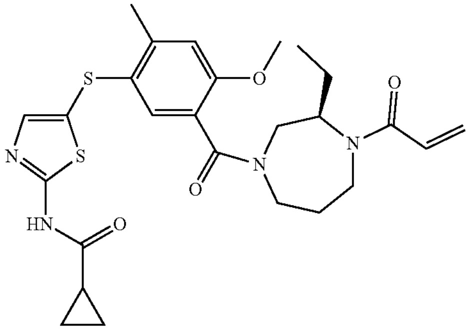,
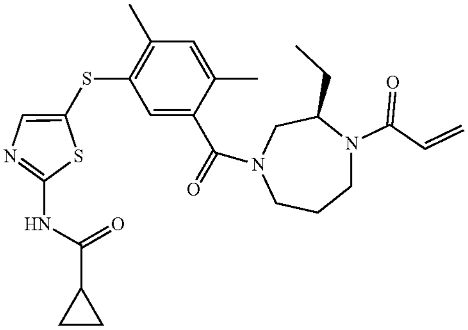,
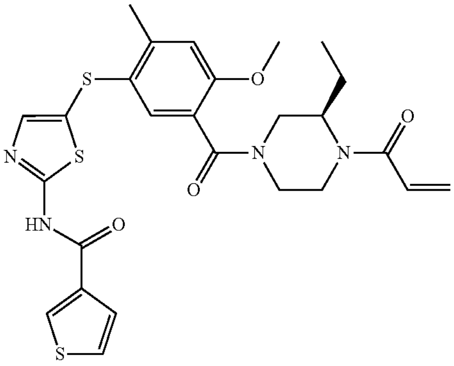,
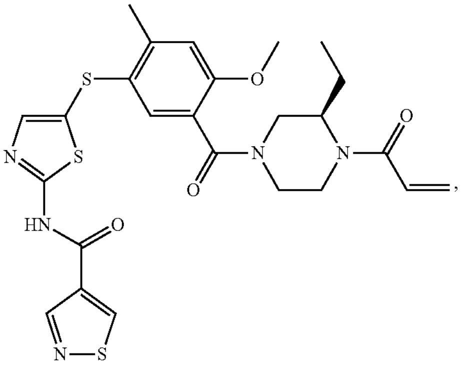,
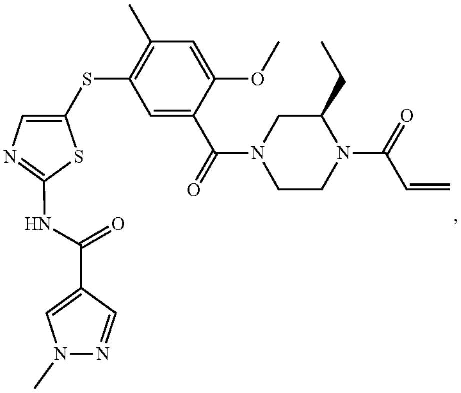,
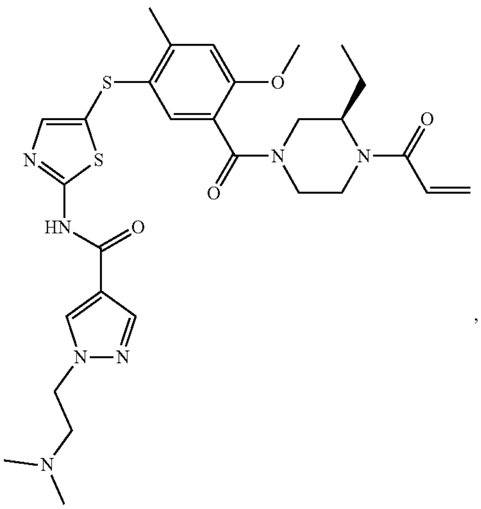,
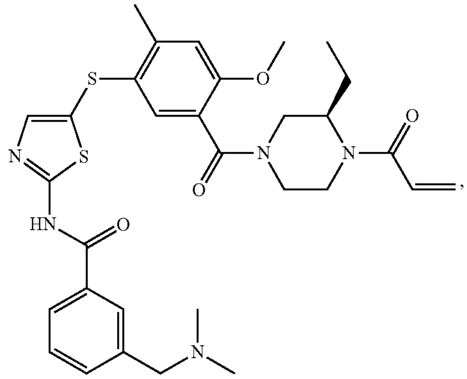, -continued
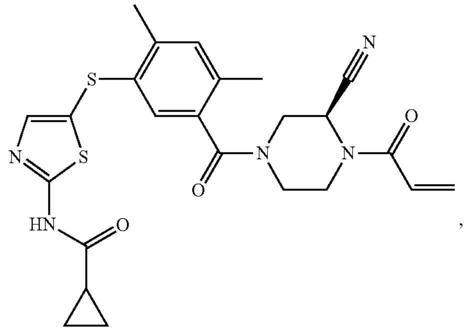
,
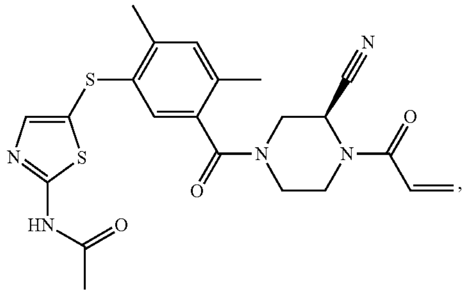
,
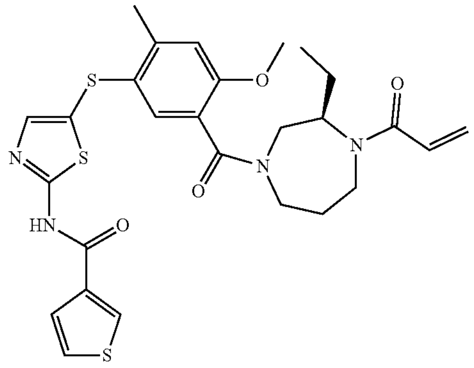
,
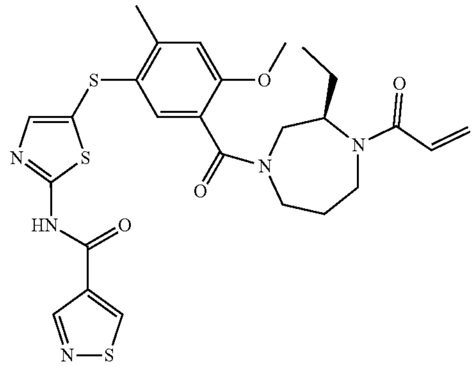
,
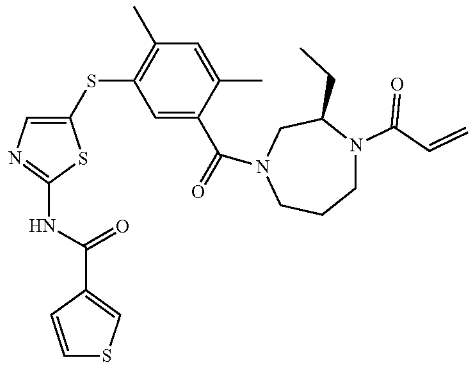
,
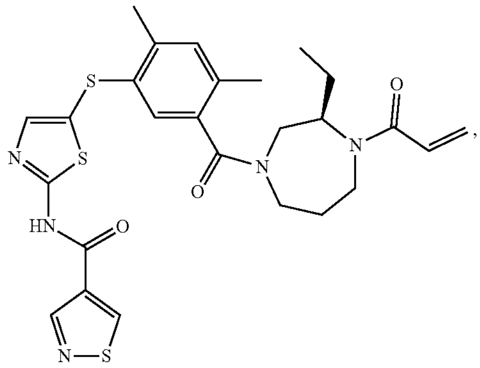
,
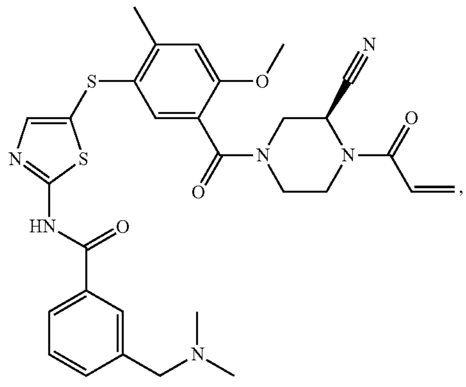
,
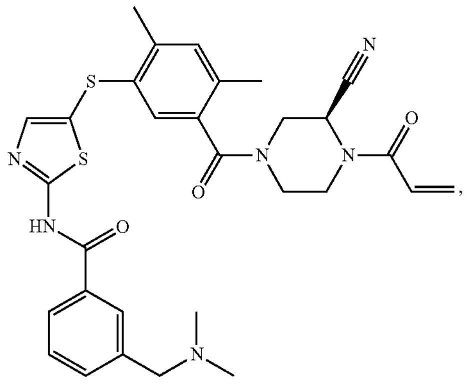
, -continued
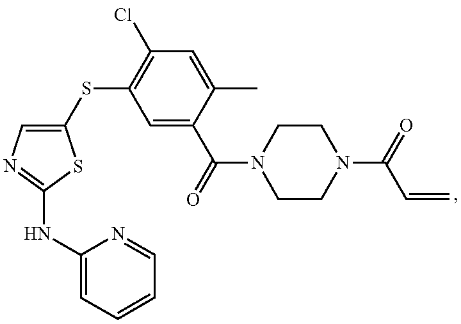,
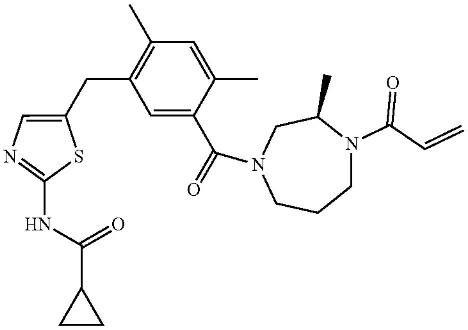,
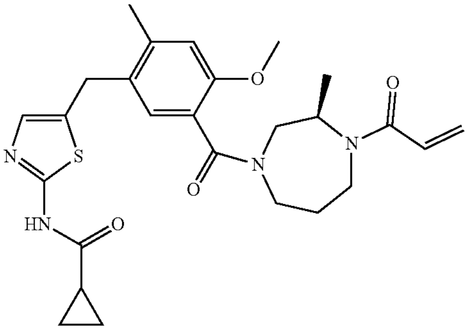,
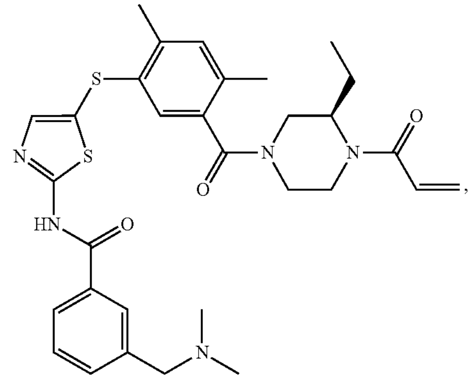,
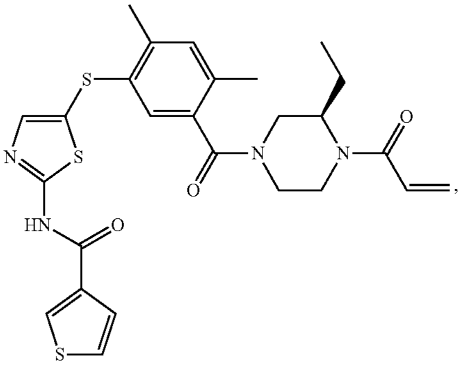,
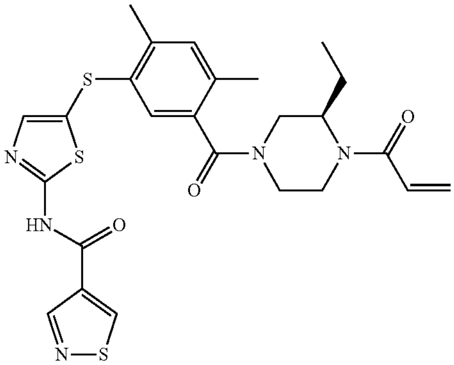,
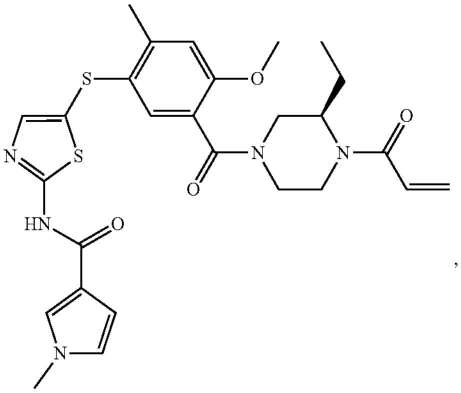,
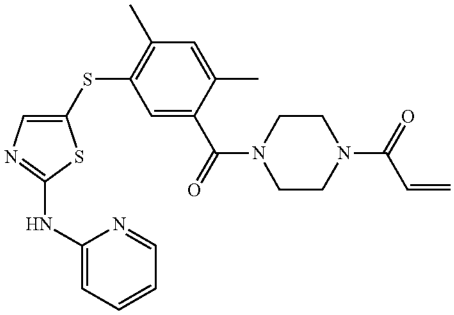, -continued
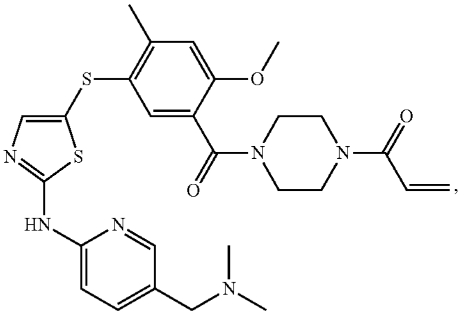
,
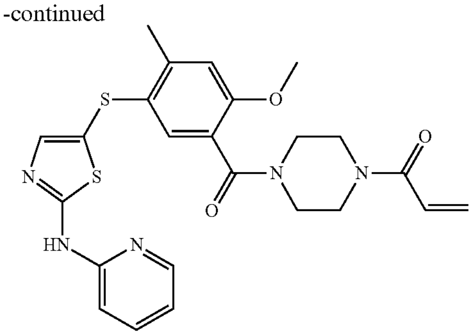
, or
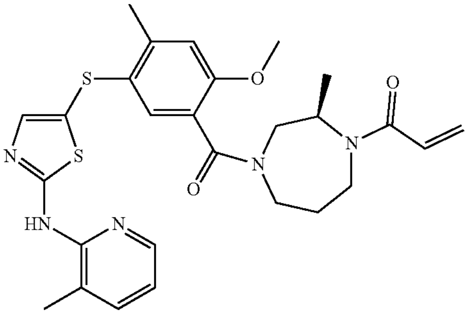
.
In embodiments, the compound has the formula:
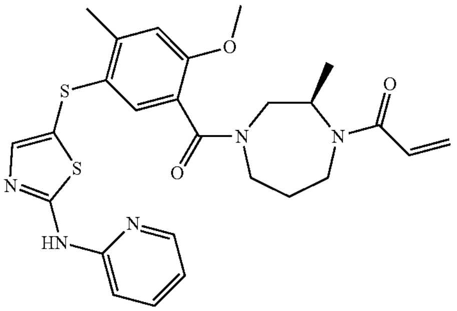
,
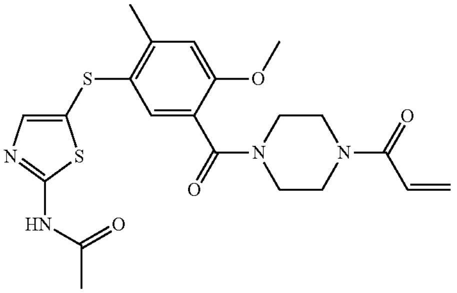
,
-continued
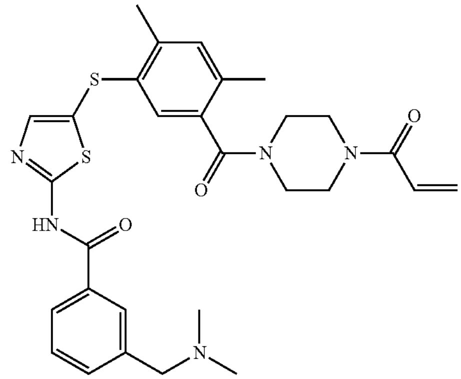
,
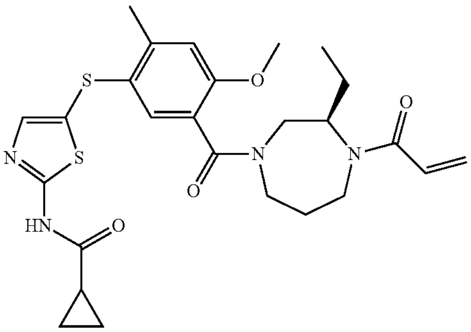
, -continued
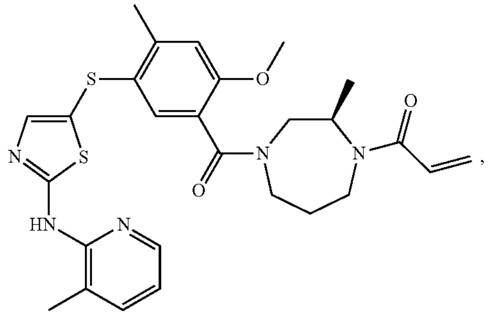
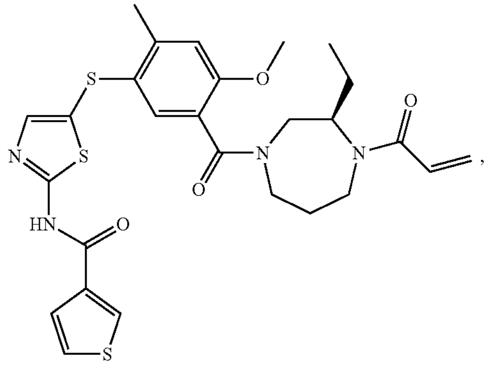
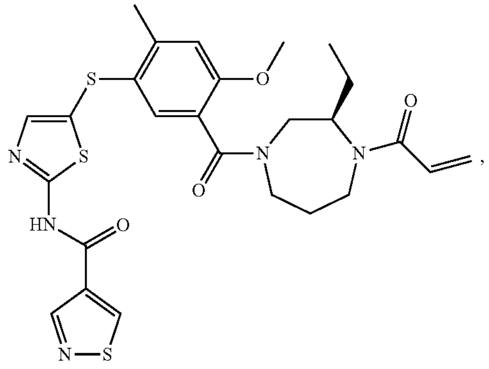 [SMILES: C=CC(=O)N1CCCN(C(=O)c2cc(Sc3cnc(NC(=O)c4cnsc4)s3)c(C)cc2OC)C[C@H]1CC]
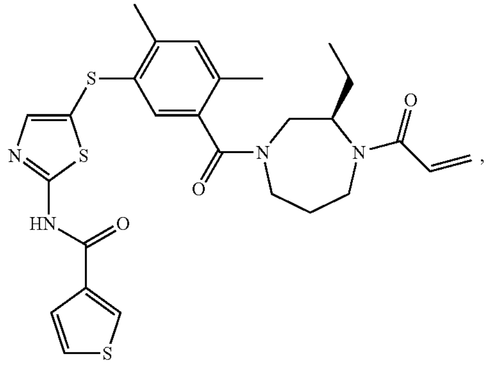
-continued
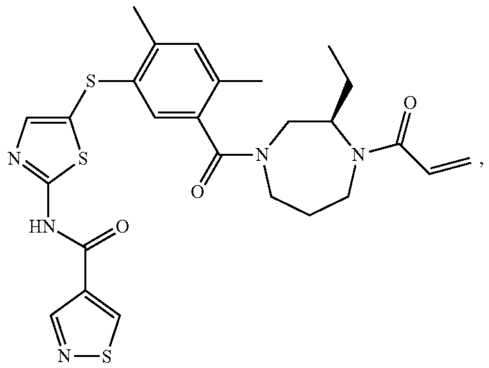
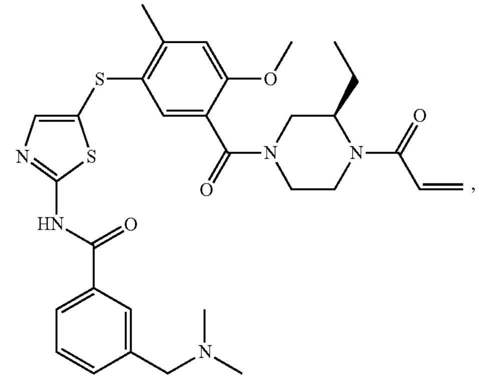
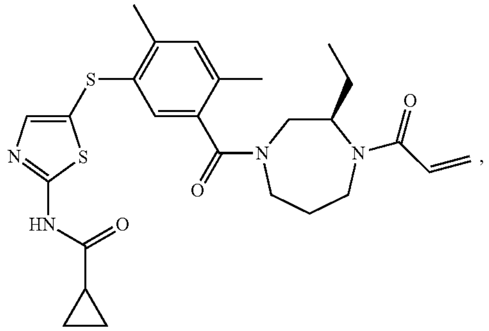
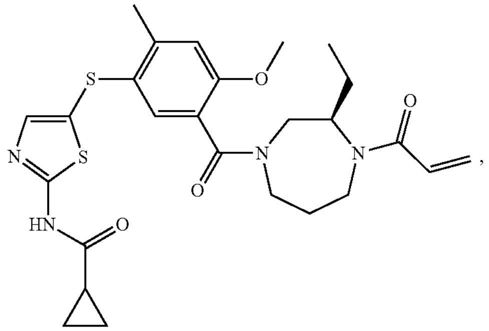

-continued
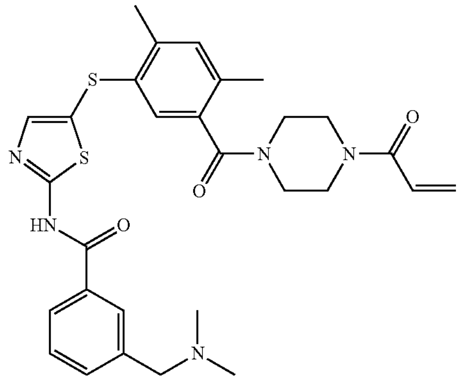
,
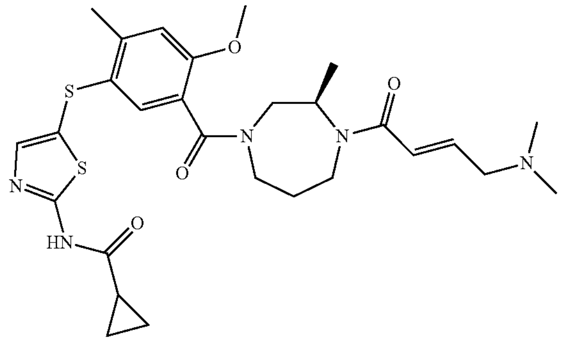
,
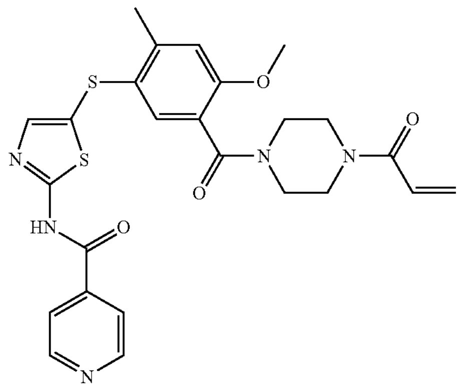
,
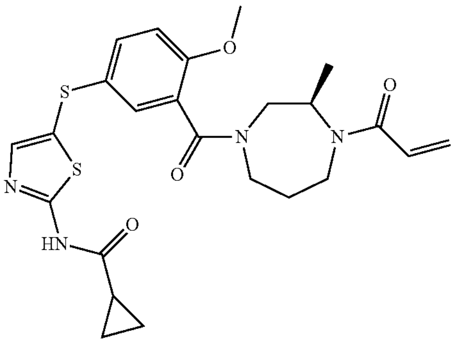
,
-continued
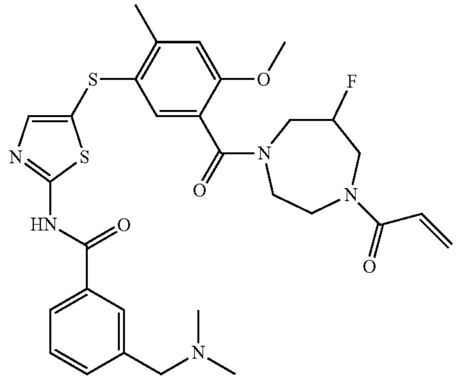
,
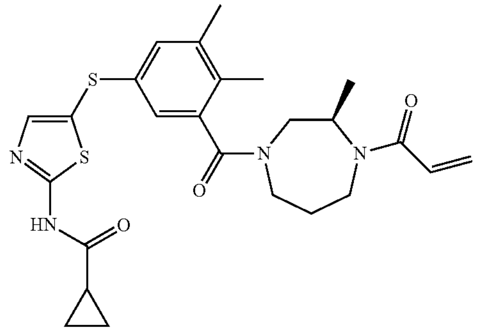
,
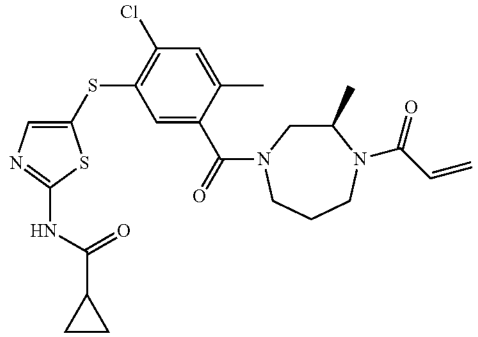
,
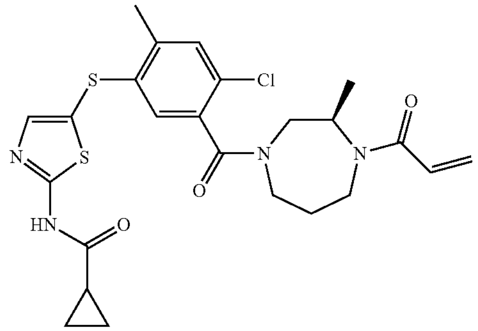
,
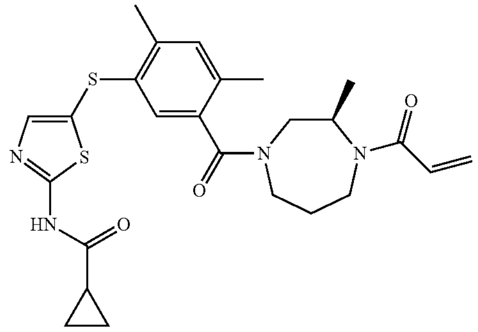
, -continued
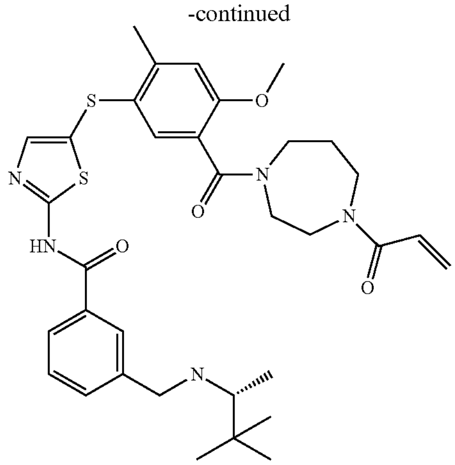
,
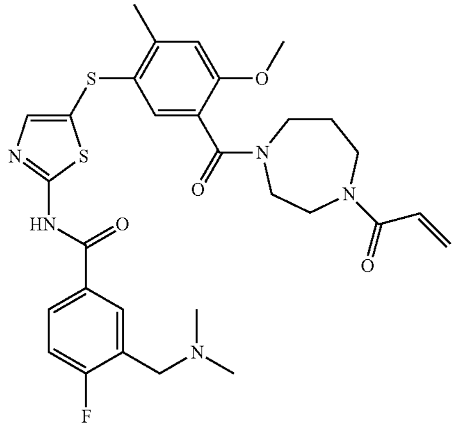
,
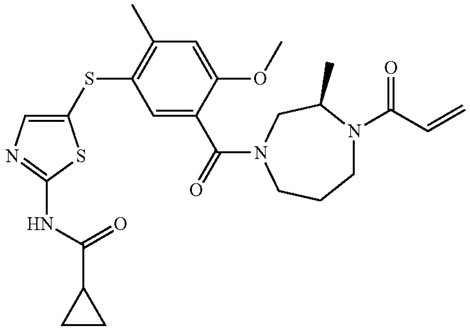
,
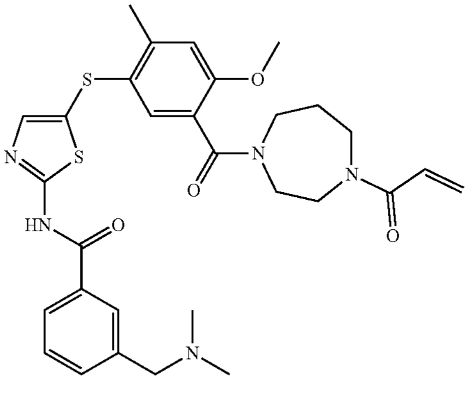
, or
-continued
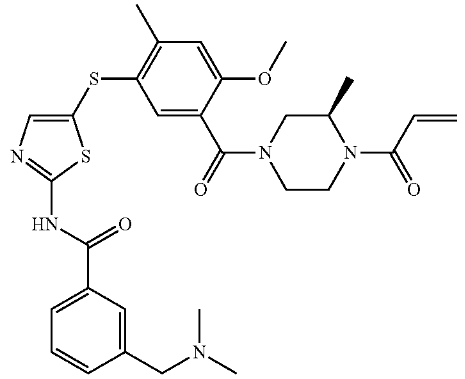
.
In some embodiments, the compound has the formula:
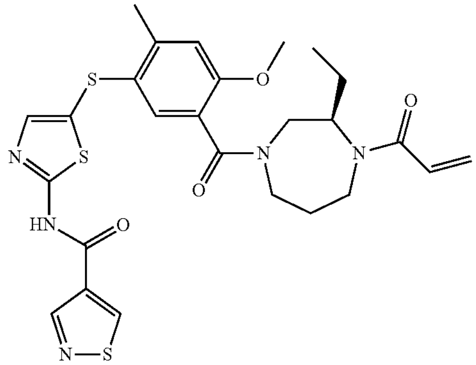
.
In embodiments, the compound has the formula:
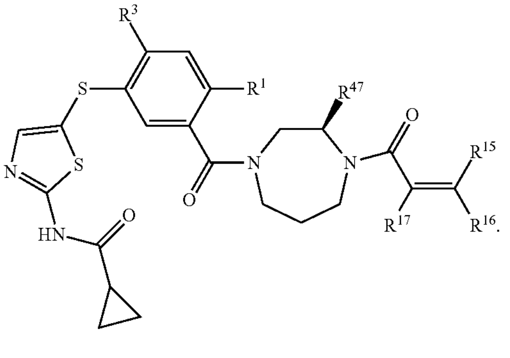
$R^1$, $R^3$, $R^{15}$, $R^{16}$, $R^{17}$, $R^{47}$ are as described herein.

In embodiments, the compound has the formula:

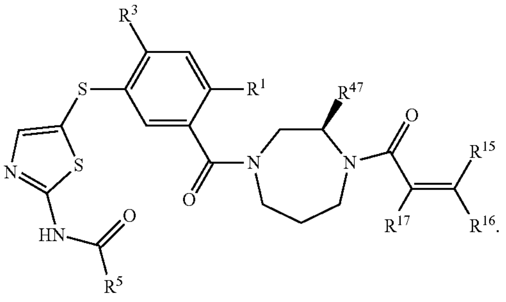

$R^1$, $R^3$, $R^5$, $R^{15}$, $R^{16}$, $R^{17}$, $R^{47}$ are as described herein.

In embodiments, the compound has the formula:

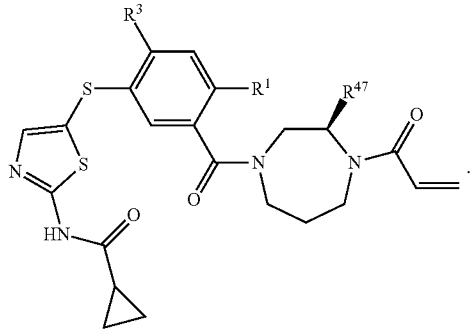

$R^1$, $R^3$, $R^{47}$ are as described herein.

In embodiments, the compound has the formula:

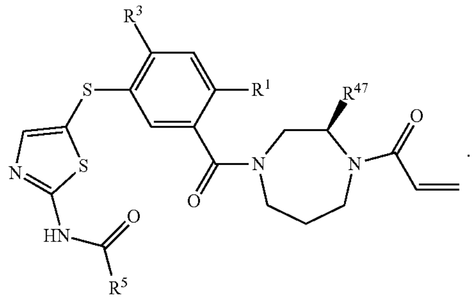

$R^1$, $R^3$, $R^5$, $R^{47}$, are as described herein.

In embodiments, the compound has the formula:

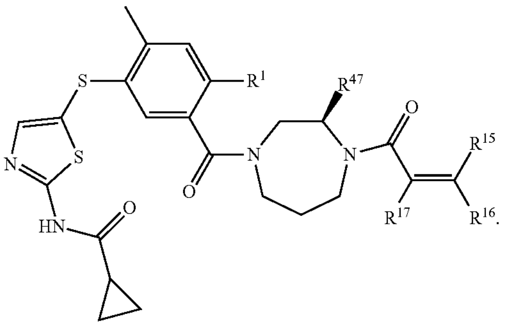

$R^1$, $R^{15}$, $R^{16}$, $R^{17}$, $R^{47}$ are as described herein.

In embodiments, the compound has the formula:

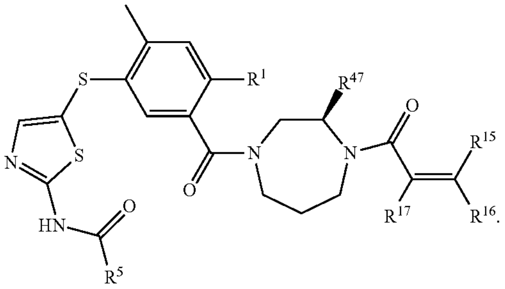

$R^1$, $R^5$, $R^{15}$, $R^{16}$, $R^{17}$, $R^{47}$ are as described herein.

In embodiments, the compound has the formula:

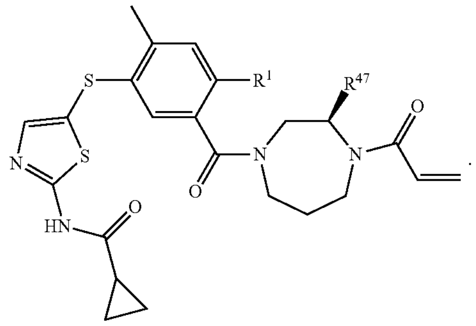

$R^1$ and $R^{47}$ are as described herein.

In embodiments, the compound has the formula:

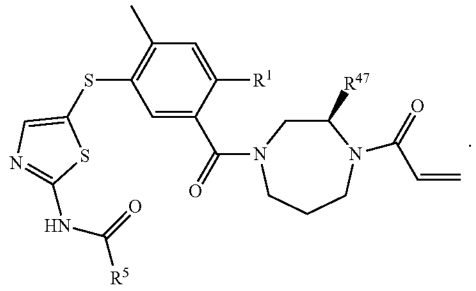

$R^1$, $R^5$, $R^{47}$, are as described herein.

In embodiments, the compound has the formula:

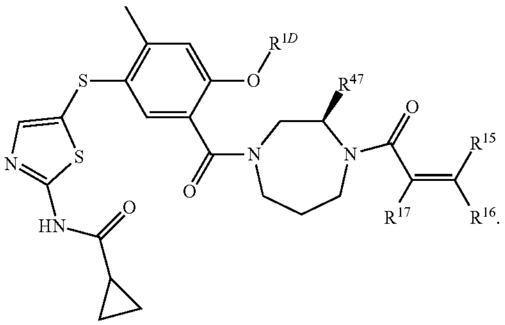

$R^{1D}$, $R^{15}$, $R^{16}$, $R^{17}$, $R^{47}$ are as described herein.

In embodiments, the compound has the formula:

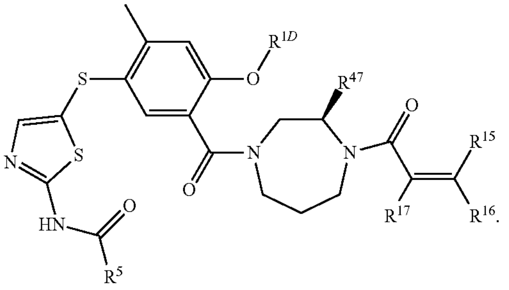

$R^{1D}$, $R^5$, $R^{15}$, $R^{16}$, $R^{17}$, $R^{47}$ are as described herein.

In embodiments, the compound has the formula:

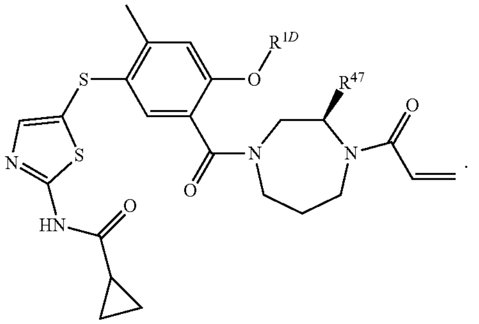

$R^{1D}$ and $R^{47}$ are as described herein.

In embodiments, the compound has the formula:

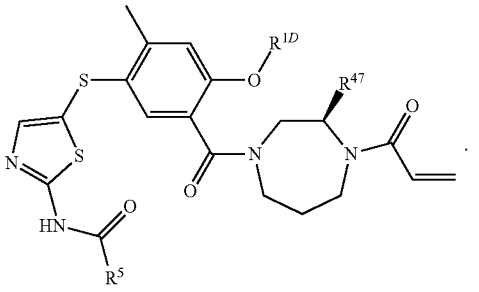

$R^{1D}$, $R^5$, $R^{47}$ are as described herein.

In embodiments, the compound has the formula:

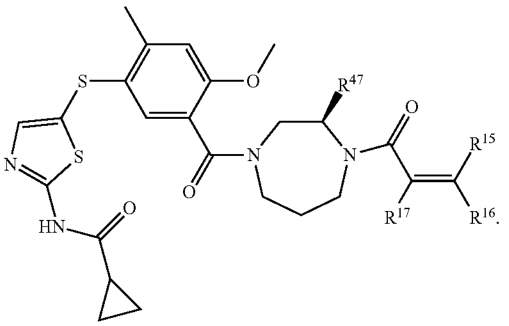

$R^{15}$, $R^{16}$, $R^{17}$, $R^{47}$ are as described herein.

In embodiments, the compound has the formula:

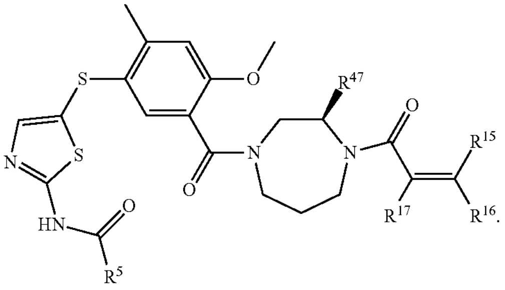

$R^5$, $R^{15}$, $R^{16}$, $R^{17}$, $R^{47}$ are as described herein.

In embodiments, the compound has the formula:

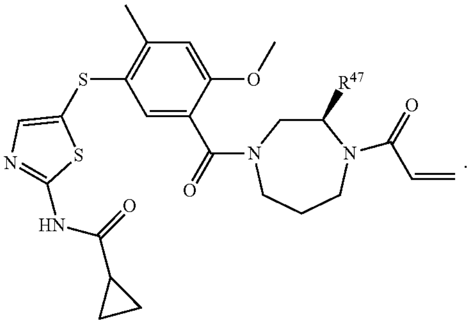

$R^{47}$ is as described herein.

In embodiments, the compound has the formula:

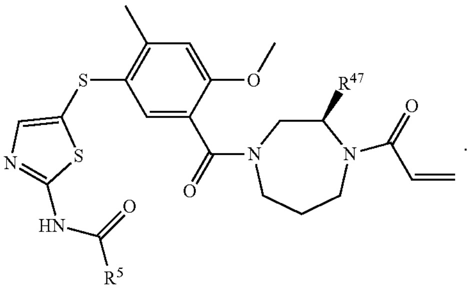

$R^5$ and $R^{47}$ are as described herein.

In embodiments, the compound has the formula:

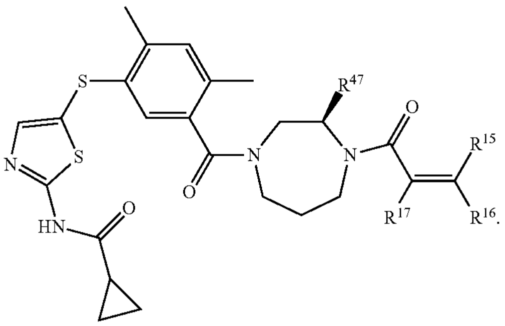

$R^{15}$, $R^{16}$, $R^{17}$, $R^{47}$ are as described herein.

In embodiments, the compound has the formula:

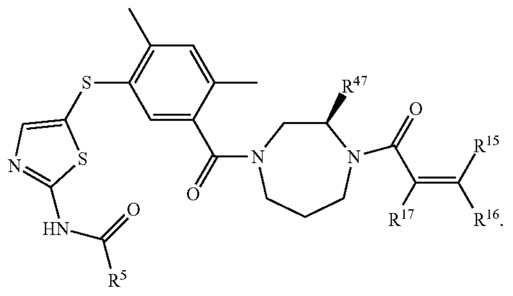

$R^5$, $R^{15}$, $R^{16}$, $R^{17}$, $R^{47}$ are as described herein.

In embodiments, the compound has the formula:

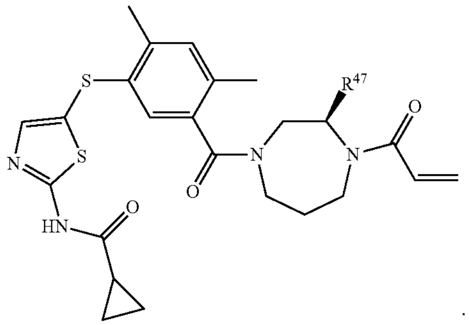

$R^{47}$ is as described herein.

In embodiments, the compound has the formula:

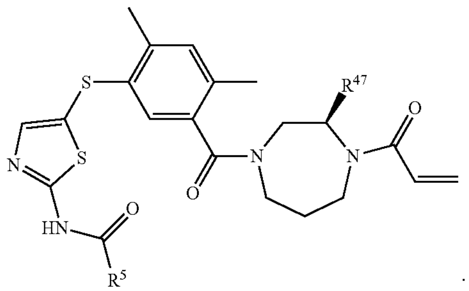

$R^5$ and $R^{47}$ are as described herein.

In embodiments, the compound has the formula:

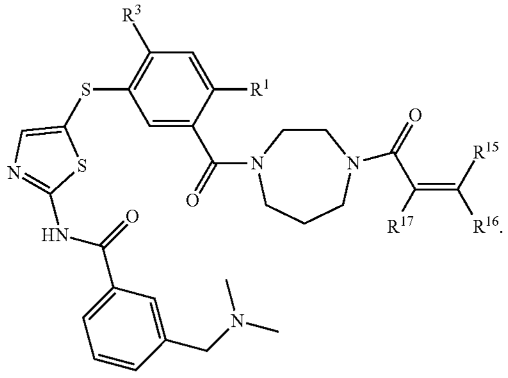

$R^1$, $R^3$, $R^{15}$, $R^{16}$, $R^{17}$ are as described herein.

In embodiments, the compound has the formula:

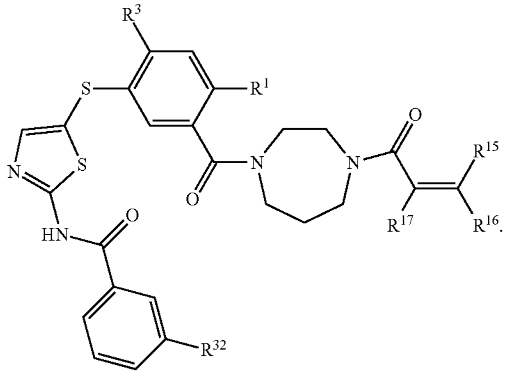

$R^1$, $R^3$, $R^{15}$, $R^{16}$, $R^{17}$, $R^{32}$ are as described herein.

In embodiments, the compound has the formula:

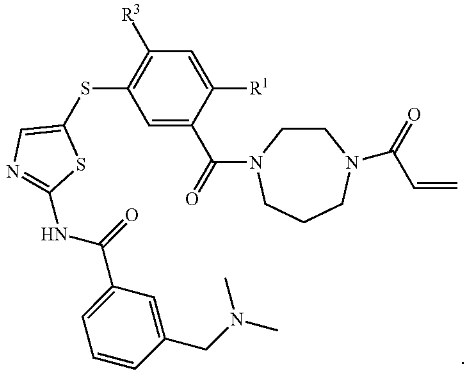

$R^1$ and $R^3$, are as described herein.

In embodiments, the compound has the formula:

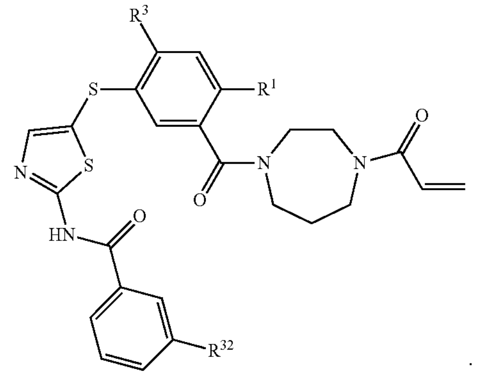

$R^1$, $R^3$, $R^{32}$ are as described herein.

In embodiments, the compound has the formula:

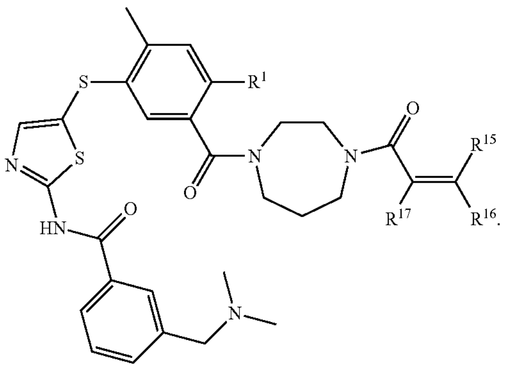

$R^1$, $R^{15}$, $R^{16}$, $R^{17}$ are as described herein.

In embodiments, the compound has the formula:

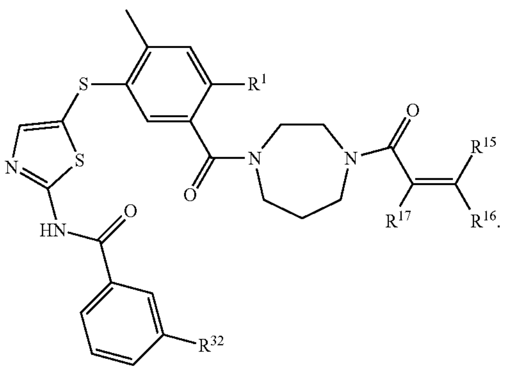

$R^1$, $R^{15}$, $R^{16}$, $R^{17}$, $R^{32}$ are as described herein.

In embodiments, the compound has the formula:

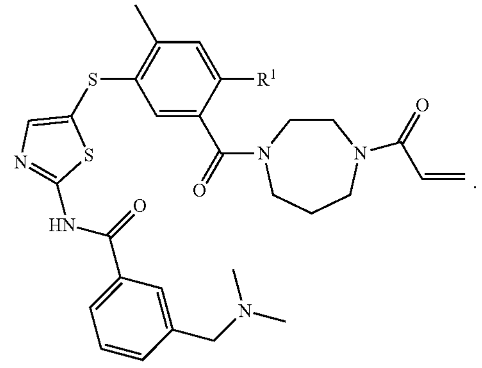

$R^1$ is as described herein.

In embodiments, the compound has the formula:

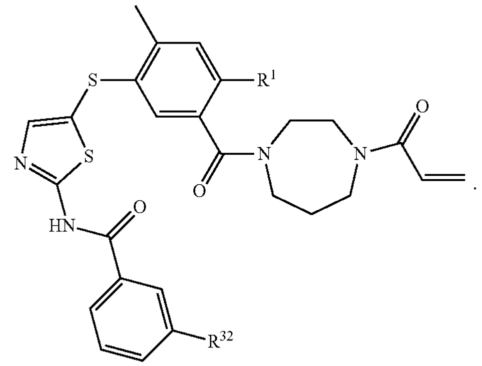

$R^1$ and $R^{32}$ are as described herein.

In embodiments, the compound has the formula:

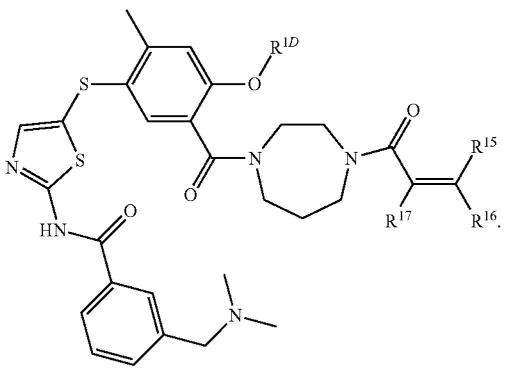

$R^{1D}$, $R^{15}$, $R^{16}$, $R^{17}$ are as described herein.

In embodiments, the compound has the formula:

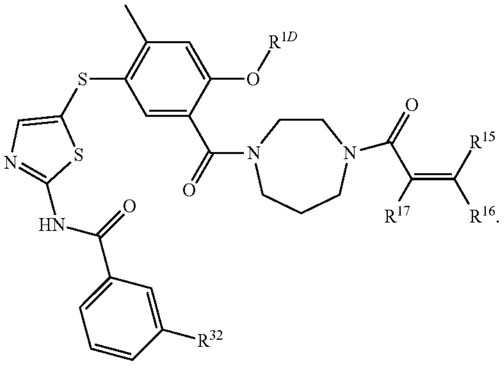

$R^{1D}$, $R^{15}$, $R^{16}$, $R^{17}$, $R^{32}$ are as described herein.

In embodiments, the compound has the formula:

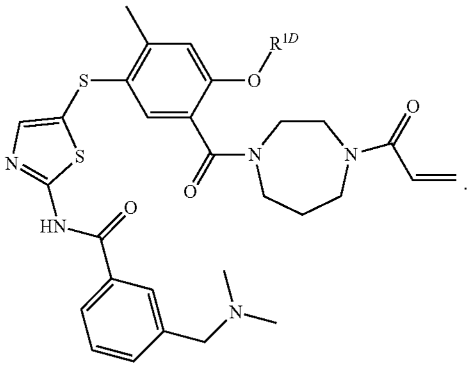

$R^{1D}$ is as described herein.

In embodiments, the compound has the formula:

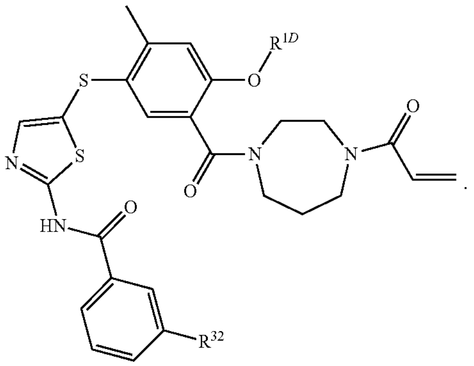

$R^{1D}$ and $R^{32}$ are as described herein.

In embodiments, the compound has the formula:

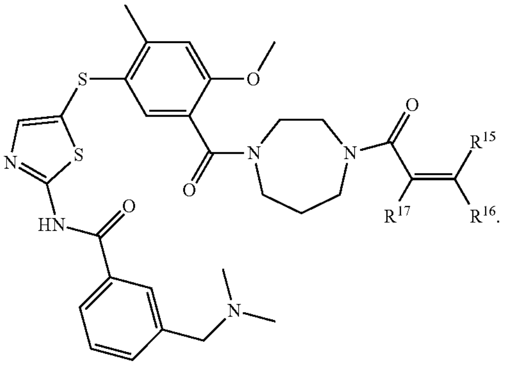

$R^{15}$, $R^{16}$, $R^{17}$ are as described herein.

In embodiments, the compound has the formula:

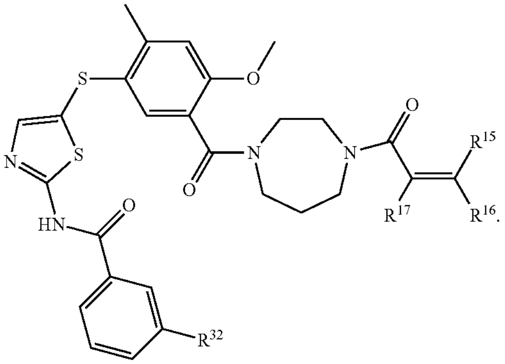

$R^{15}$, $R^{16}$, $R^{17}$, $R^{32}$ are as described herein.

In embodiments, the compound has the formula:

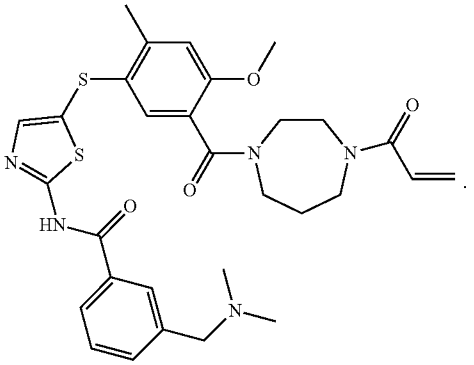 [SMILES: C=CC(=O)N1CCCN(C(=O)c2cc(Sc3cnc(NC(=O)c4cccc(CN(C)C)c4)s3)c(C)cc2OC)CC1]

In embodiments, the compound has the formula:

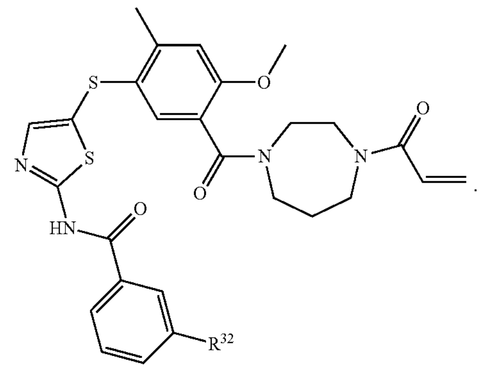

$R^{32}$ is as described herein.

In embodiments, the compound has the formula:

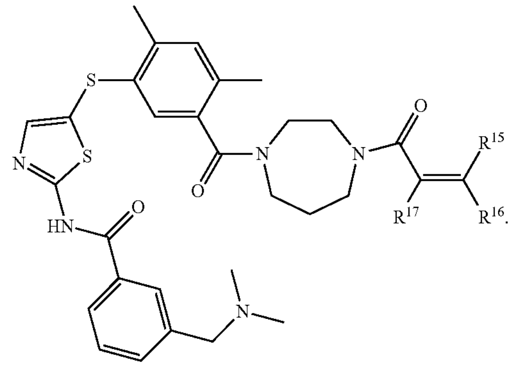

$R^{15}$, $R^{16}$, $R^{17}$ are as described herein.

In embodiments, the compound has the formula:

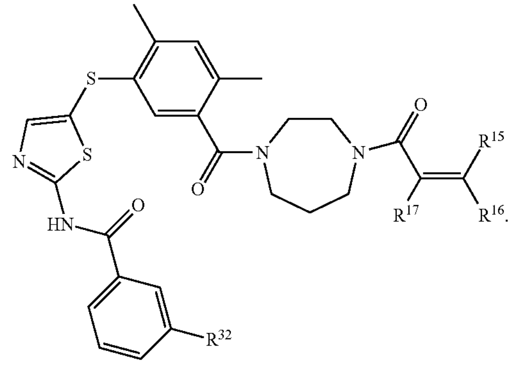

$R^{15}$, $R^{16}$, $R^{17}$, $R^{32}$ are as described herein.

In embodiments, the compound has the formula:

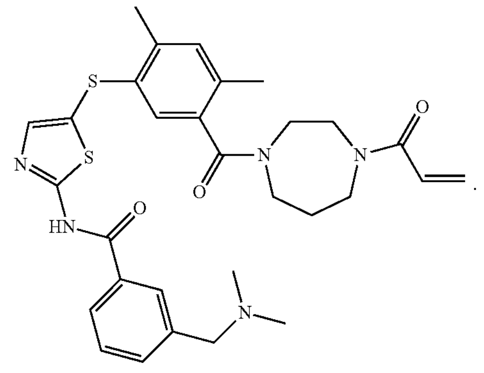 [SMILES: C=CC(=O)N1CCCN(C(=O)c2cc(Sc3cnc(NC(=O)c4cccc(CN(C)C)c4)s3)c(C)cc2C)CC1]

In embodiments, the compound has the formula:

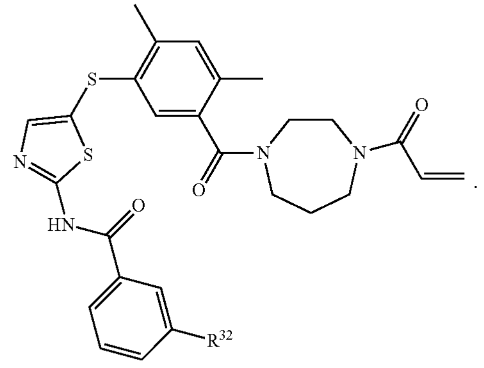

$R^{32}$ is as described herein.

In embodiments, the compound has the formula:

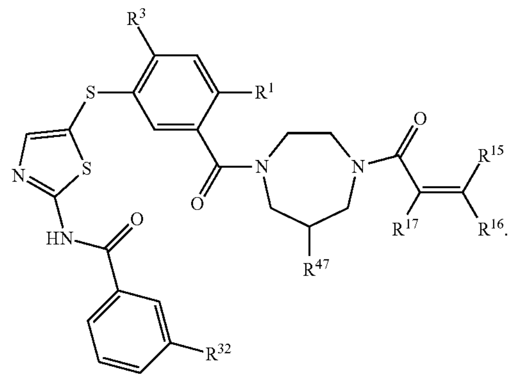

$R^{1}$, $R^{3}$, $R^{15}$, $R^{16}$, $R^{17}$, $R^{32}$, $R^{47}$ are as described herein.

In embodiments, the compound has the formula:

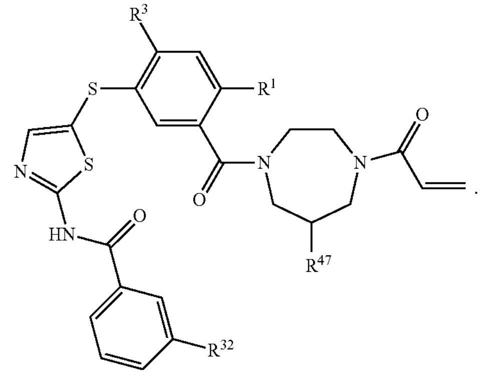

$R^1$, $R^3$, $R^{32}$, $R^{47}$ are as described herein.

In embodiments, the compound has the formula:

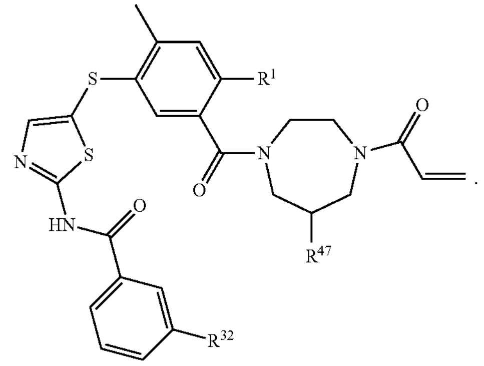

$R^1$, $R^{32}$, $R^{47}$ are as described herein.

In embodiments, the compound has the formula:

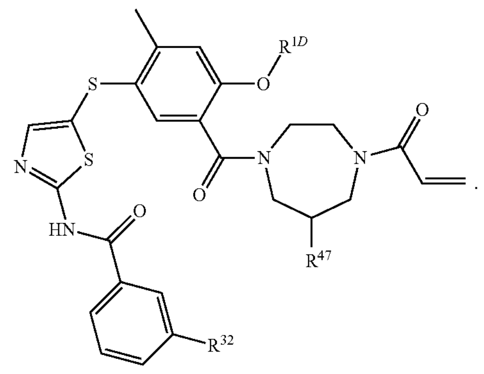

$R^{1D}$, $R^{32}$, $R^{47}$ are as described herein.

In embodiments, the compound has the formula:

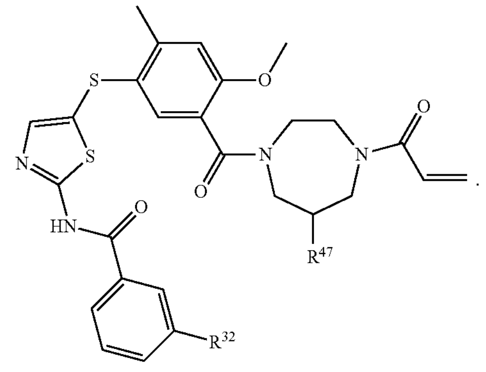

$R^{32}$ and $R^{47}$ is as described herein.

In embodiments, the compound has the formula:

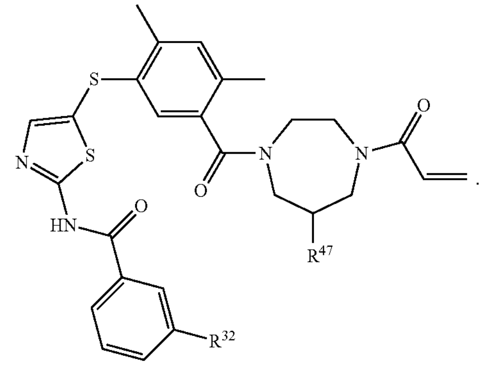

$R^{32}$ and $R^{47}$ is as described herein.

In embodiments, the compound has the formula:

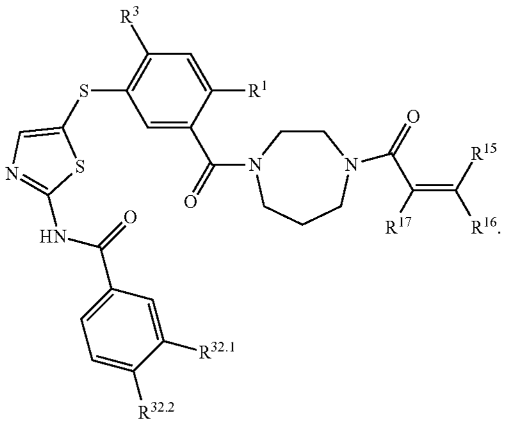

$R^1$, $R^3$, $R^{15}$, $R^{16}$, $R^{17}$, $R^{32.1}$, and $R^{32.2}$ are as described herein.

In embodiments, the compound has the formula:

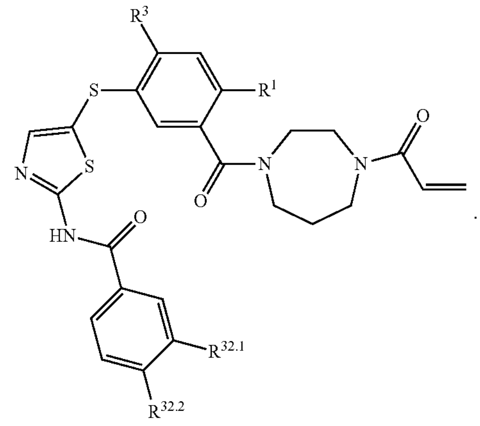

$R^1$, $R^3$, $R^{32.1}$, and $R^{32.2}$ are as described herein.

In embodiments, the compound has the formula:

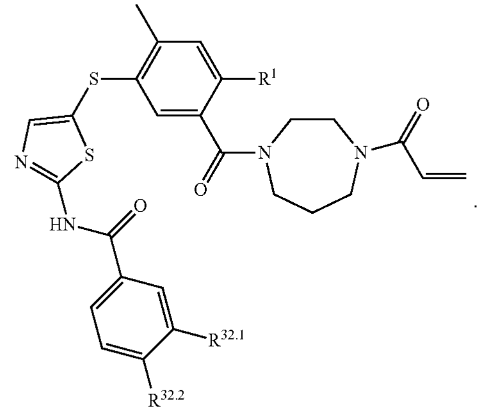

$R^1$, $R^{32.1}$, and $R^{32.2}$ are as described herein.

In embodiments, the compound has the formula:

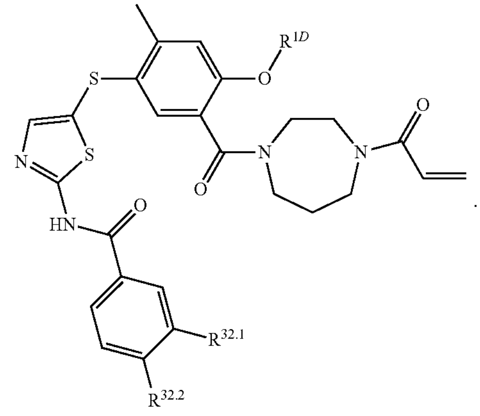

$R^{1D}$, $R^{32.1}$, and $R^{32.2}$ are as described herein.

In embodiments, the compound has the formula:

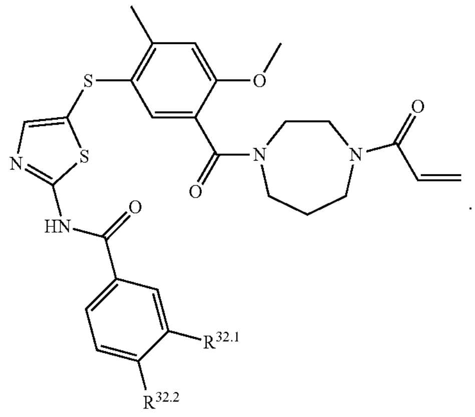

$R^{32.1}$ and $R^{32.2}$ is as described herein.

In embodiments, the compound has the formula:

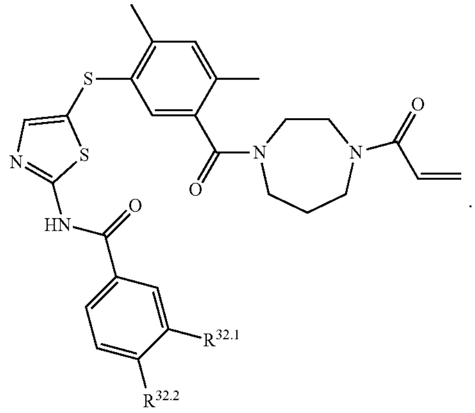

$R^{32.1}$ and $R^{32.2}$ is as described herein.

In embodiments, $R^{47}$ is substituted or unsubstituted $C_1$-$C_6$ alkyl. In embodiments, $R^{47}$ is substituted or unsubstituted 2 to 6 membered heteroalkyl. In embodiments, $R^{47}$ is substituted or unsubstituted $C_3$-$C_8$ cycloalkyl. In embodiments, $R^{47}$ is substituted or unsubstituted 3 to 8 membered heterocycloalkyl. In embodiments, $R^{47}$ is substituted or unsubstituted phenyl. In embodiments, $R^{47}$ is substituted or unsubstituted 5 to 6 membered heteroaryl. In embodiments, $R^{47}$ is independently halogen. In embodiments, $R^{47}$ is independently $—CX^{47}_3$. In embodiments, $R^{47}$ is independently $—CHX^{47}_2$. In embodiments, $R^{47}$ is independently $—CH_2X^{47}$. In embodiments, $R^{47}$ is independently $—CH_3$. In embodiments, $R^{47}$ is independently $—CH_2CH_3$. In embodiments, $R^{47}$ is independently unsubstituted methyl, unsubstituted ethyl, unsubstituted isopropyl, or unsubstituted tert-butyl. In embodiments, $R^{47}$ is independently unsubstituted methyl. In embodiments, $R^{47}$ is independently unsubstituted ethyl. In embodiments, $R^{47}$ is independently unsubstituted propyl. In embodiments, $R^{47}$ is independently unsubstituted n-propyl. In embodiments, $R^{47}$ is independently unsubstituted isopropyl. In embodiments, $R^{47}$ is independently unsubstituted butyl. In embodiments, $R^{47}$ is independently unsubstituted n-butyl. In embodiments, $R^{47}$ is independently unsubstituted isobutyl. In embodiments, $R^{47}$ is independently unsubstituted sec-butyl. In embodiments, $R^{47}$ is independently unsubstituted tert-butyl. In embodiments, $R^{47}$ is independently unsubstituted pentyl. In embodiments, $R^{47}$ is independently unsubstituted hexyl. In embodiments, $R^{47}$ is independently unsubstituted heptyl. In embodiments, $R^{47}$ is independently unsubstituted octyl. In embodiments, $R^{47}$ is independently —$CF_3$. In embodiments, $R^{47}$ is independently —$CCl_3$. In embodiments, $R^{47}$ is independently —$CBr_3$. In embodiments, $R^{47}$ is independently —$CI_3$. In embodiments, $X^{47}$ is independently —F. In embodiments, $X^{47}$ is independently —Cl. In embodiments, $X^{47}$ is independently —Br. In embodiments, $X^{47}$ is independently —I. In embodiments, $R^{47}$ is independently —F. In embodiments, $R^{47}$ is independently —Cl. In embodiments, $R^{47}$ is independently —Br. In embodiments, $R^{47}$ is independently —I.

In embodiments, $R^5$ is independently unsubstituted cyclopropyl. In embodiments, $R^5$ is independently unsubstituted cyclobutyl. In embodiments, $R^5$ is independently unsubstituted cyclopentyl. In embodiments, $R^5$ is independently unsubstituted cyclohexyl. In embodiments, $R^5$ is independently substituted cyclopropyl. In embodiments, $R^5$ is independently substituted cyclobutyl. In embodiments, $R^5$ is independently substituted cyclopentyl. In embodiments, $R^5$ is independently substituted cyclohexyl. In embodiments, $R^5$ is independently $R^{32}$-substituted cyclopropyl. In embodiments, $R^5$ is independently $R^{32}$-substituted cyclobutyl. In embodiments, $R^5$ is independently $R^{32}$-substituted cyclopentyl. In embodiments, $R^5$ is independently $R^{32}$-substituted cyclohexyl. In embodiments, $R^5$ is independently $R^{32}$-substituted phenyl. In embodiments, $R^5$ is independently $R^{32}$-substituted pyridyl. In embodiments, $R^5$ is independently $R^{32}$-substituted 2-pyridyl. In embodiments, $R^5$ is independently $R^{32}$-substituted 3-pyridyl. In embodiments, $R^5$ is independently $R^{32}$-substituted 4-pyridyl. In embodiments, $R^5$ is independently

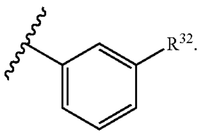

In embodiments, $R^5$ is independently

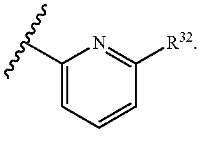

In embodiments, $R^5$ is independently

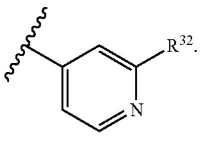

In embodiments, $R^5$ is independently

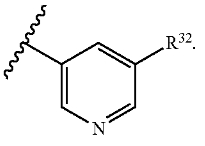

In embodiments, $R^5$ is independently

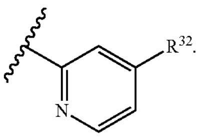

In embodiments, $R^5$ is independently

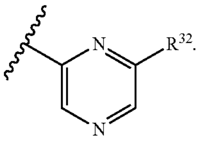

In embodiments, $R^5$ is independently

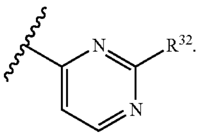

In embodiments, $R^5$ is independently

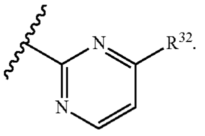

In embodiments, $R^5$ is independently

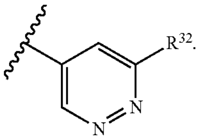

In embodiments, $R^5$ is independently

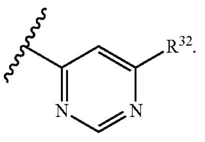

In embodiments, $R^5$ is independently

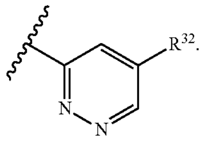

In embodiments, $R^5$ is independently

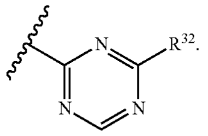

In embodiments, $R^5$ is independently

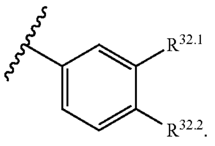

In embodiments, $R^5$ independently

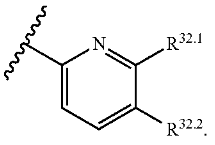

In embodiments, $R^5$ is independently

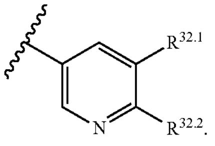

In embodiments, $R^5$ is independently

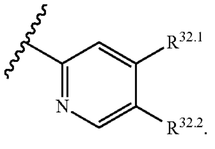

In embodiments, $R^5$ is independently

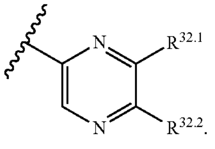

In embodiments, $R^5$ is independently

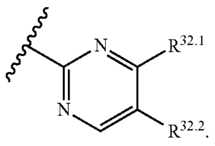

In embodiments, $R^5$ is independently

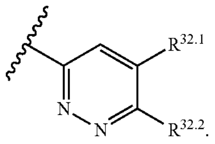

In embodiments, $R^{32}$ is substituted or unsubstituted $C_1$-$C_6$ alkyl. In embodiments, $R^{32}$ is substituted or unsubstituted 2 to 6 membered heteroalkyl. In embodiments, $R^{32}$ is substituted or unsubstituted $C_3$-$C_8$ cycloalkyl. In embodiments, $R^{32}$ is substituted or unsubstituted 3 to 8 membered heterocycloalkyl. In embodiments, $R^{32}$ is substituted or unsubstituted phenyl. In embodiments, $R^{32}$ is substituted or unsubstituted 5 to 6 membered heteroaryl. In embodiments, $R^{32}$ is independently halogen. In embodiments, $R^{32}$ is independently $—CX^{32}_3$. In embodiments, $R^{32}$ is independently $—CHX^{32}_2$. In embodiments, $R^{32}$ is independently $—CH_2X^{32}$. In embodiments, $R^{32}$ is independently $—CH_3$. In embodiments, $R^{32}$ is independently $—CH_2CH_3$. In embodiments, $R^{32}$ is independently unsubstituted methyl, unsubstituted ethyl, unsubstituted isopropyl, or unsubstituted tert-butyl. In embodiments, $R^{32}$ is independently unsubstituted methyl. In embodiments, $R^{32}$ is independently unsubstituted ethyl. In embodiments, $R^{32}$ is independently unsubstituted propyl. In embodiments, $R^{32}$ is independently unsubstituted n-propyl. In embodiments, $R^{32}$ is independently unsubstituted isopropyl. In embodiments, $R^{32}$ is independently unsubstituted butyl. In embodiments, $R^{32}$ is independently unsubstituted n-butyl. In embodiments, $R^{32}$ is independently unsubstituted isobutyl. In embodiments, $R^{32}$ is independently unsubstituted sec-butyl. In embodiments, $R^{32}$ is independently unsubstituted tert-butyl. In embodiments, $R^{32}$ is independently unsubstituted pentyl. In embodiments, $R^{32}$ is independently unsubstituted hexyl. In embodiments, $R^{32}$ is independently unsubstituted heptyl. In embodiments, $R^{32}$ is independently unsubstituted octyl. In embodiments, $R^{32}$ is independently $—CF_3$. In embodiments, $R^{32}$ is independently $—CCl_3$. In embodiments, $R^{32}$ is independently $—CBr_3$. In embodiments, $R^{32}$ is independently $—CI_3$. In embodiments, $X^{32}$ is independently —F. In embodiments, $X^{32}$ is independently —Cl. In embodiments, $X^{32}$ is independently —Br. In embodiments, $X^{32}$ is independently —I. In embodiments, $R^{32}$ is independently $—NH_2$. In embodiments, $R^{32}$ is independently $—NH(CH_3)$. In embodiments, $R^{32}$ is independently $—N(CH_3)_2$. In embodiments, $R^{32}$ is independently $—NH(CH_2CH_3)$. In embodiments, $R^{32}$ is independently $—N(CH_3)(CH_2CH_3)$. In embodiments, $R^{32}$ is independently $—N(CH_2CH_3)_2$. In embodiments, $R^{32}$ is independently —NH(unsubstituted $C_1$-$C_4$ alkyl). In embodiments, $R^{32}$ is independently $—N(CH_3)$(unsubstituted $C_1$-$C_4$ alkyl). In embodiments, $R^{32}$ is independently —N(unsubstituted $C_1$-$C_4$ alkyl$)_2$. In embodiments, $R^{32}$ is independently $—CH_2NH_2$. In embodiments, $R^{32}$ is independently $—CH_2NH(CH_3)$. In embodiments, $R^{32}$ is independently $—CH_2N(CH_3)_2$. In embodiments, $R^{32}$ is independently —$CH_2NH(CH_2CH_3)$. In embodiments, $R^{32}$ is independently —$CH_2N(CH_3)(CH_2CH_3)$. In embodiments, $R^{32}$ is independently —$CH_2N(CH_2CH_3)_2$. In embodiments, $R^{32}$ is independently —$CH_2NH$(unsubstituted $C_1$-$C_4$ alkyl). In embodiments, $R^{32}$ is independently —$CH_2N(CH_3)$(unsubstituted $C_1$-$C_4$ alkyl). In embodiments, $R^{32}$ is independently —$CH_2N$(unsubstituted $C_1$-$C_4$ alkyl)$_2$. In embodiments, $R^{32}$ is independently —$CH_2CH_2NH_2$. In embodiments, $R^{32}$ is independently —$CH_2CH_2NH(CH_3)$. In embodiments, $R^{32}$ is independently —$CH_2CH_2N(CH_3)_2$. In embodiments, $R^{32}$ is independently —$CH_2CH_2NH(CH_2CH_3)$. In embodiments, $R^{32}$ is independently —$CH_2CH_2N(CH_3)(CH_2CH_3)$. In embodiments, $R^{32}$ is independently —$CH_2CH_2N(CH_2CH_3)_2$. In embodiments, $R^{32}$ is independently —$CH_2CH_2NH$(unsubstituted $C_1$-$C_4$ alkyl). In embodiments, $R^{32}$ is independently —$CH_2CH_2N(CH_3)$(unsubstituted $C_1$-$C_4$ alkyl). In embodiments, $R^{32}$ is independently —$CH_2CH_2N$(unsubstituted $C_1$-$C_4$ alkyl)$_2$. In embodiments, $R^{32}$ is independently —NH(unsubstituted $C_1$-$C_8$ alkyl). In embodiments, $R^{32}$ is independently —$N(CH_3)$(unsubstituted $C_1$-$C_8$ alkyl). In embodiments, $R^{32}$ is independently —N(unsubstituted $C_1$-$C_8$ alkyl)$_2$. In embodiments, $R^{32}$ is independently —$CH_2NH$(unsubstituted $C_1$-$C_8$ alkyl). In embodiments, $R^{32}$ is independently —$CH_2N(CH_3)$(unsubstituted $C_1$-$C_8$ alkyl). In embodiments, $R^{32}$ is independently —$CH_2N$(unsubstituted $C_1$-$C_8$ alkyl)$_2$. In embodiments, $R^{32}$ is independently —$CH_2CH_2NH$(unsubstituted $C_1$-$C_8$ alkyl). In embodiments, $R^{32}$ is independently —$CH_2CH_2N(CH_3)$(unsubstituted $C_1$-$C_8$ alkyl). In embodiments, $R^{32}$ is independently —$CH_2CH_2N$(unsubstituted $C_1$-$C_8$ alkyl)$_2$. In embodiments, $R^{32}$ is independently —NH(unsubstituted $C_4$-$C_8$ alkyl). In embodiments, $R^{32}$ is independently —$N(CH_3)$(unsubstituted $C_4$-$C_8$ alkyl). In embodiments, $R^{32}$ is independently —N(unsubstituted $C_4$-$C_8$ alkyl)$_2$. In embodiments, $R^{32}$ is independently —$CH_2NH$(unsubstituted $C_4$-$C_8$ alkyl). In embodiments, $R^{32}$ is independently —$CH_2N(CH_3)$(unsubstituted $C_4$-$C_8$ alkyl). In embodiments, $R^{32}$ is independently —$CH_2N$(unsubstituted $C_4$-$C_8$ alkyl)$_2$. In embodiments, $R^{32}$ is independently —$CH_2CH_2NH$(unsubstituted $C_4$-$C_8$ alkyl). In embodiments, $R^{32}$ is independently —$CH_2CH_2N(CH_3)$(unsubstituted $C_4$-$C_8$ alkyl). In embodiments, $R^{32}$ is independently —$CH_2CH_2N$(unsubstituted $C_4$-$C_8$ alkyl)$_2$. In embodiments, $R^{32}$ is independently —NH(unsubstituted $C_1$-$C_8$ alkyl). In embodiments, $R^{32}$ is independently —$N(CH_3)$(unsubstituted $C_1$-$C_6$ alkyl). In embodiments, $R^{32}$ is independently —N(unsubstituted $C_1$-$C_6$ alkyl)$_2$. In embodiments, $R^{32}$ is independently —$CH_2NH$(unsubstituted $C_1$-$C_6$ alkyl). In embodiments, $R^{32}$ is independently —$CH_2N(CH_3)$(unsubstituted $C_1$-$C_6$ alkyl). In embodiments, $R^{32}$ is independently —$CH_2N$(unsubstituted $C_1$-$C_6$ alkyl)$_2$. In embodiments, $R^{32}$ is independently —$CH_2CH_2NH$(unsubstituted $C_1$-$C_6$ alkyl). In embodiments, $R^{32}$ is independently —$CH_2CH_2N(CH_3)$(unsubstituted $C_1$-$C_6$ alkyl). In embodiments, $R^{32}$ is independently —$CH_2CH_2N$(unsubstituted $C_1$-$C_6$ alkyl)$_2$.

$R^{32.1}$ may be any value (e.g., be equal to) of $R^{32}$, including an aspect or an embodiment. In embodiments, $R^{32.1}$ is substituted or unsubstituted $C_1$-$C_6$ alkyl. In embodiments, $R^{32.1}$ is substituted or unsubstituted 2 to 6 membered heteroalkyl. In embodiments, $R^{32.1}$ is substituted or unsubstituted $C_3$-$C_8$ cycloalkyl. In embodiments, $R^{32.1}$ is substituted or unsubstituted 3 to 8 membered heterocycloalkyl. In embodiments, $R^{32.1}$ is substituted or unsubstituted phenyl. In embodiments, $R^{32.1}$ is substituted or unsubstituted 5 to 6 membered heteroaryl. In embodiments, $R^{32.1}$ is independently halogen. In embodiments, $R^{32.1}$ is independently —$CX^{32.1}_3$. In embodiments, $R^{32.1}$ is independently —$CHX^{32.1}_2$. In embodiments, $R^{32.1}$ is independently —$CH_2X^{32.1}$. In embodiments, $R^{32.1}$ is independently —$CH_3$. In embodiments, $R^{32.1}$ is independently —$CH_2CH_3$. In embodiments, $R^{32.1}$ is independently unsubstituted methyl, unsubstituted ethyl, unsubstituted isopropyl, or unsubstituted tert-butyl. In embodiments, $R^{32.1}$ is independently unsubstituted methyl. In embodiments, $R^{32.1}$ is independently unsubstituted ethyl. In embodiments, $R^{32.1}$ is independently unsubstituted propyl. In embodiments, $R^{32.1}$ is independently unsubstituted n-propyl. In embodiments, $R^{32.1}$ is independently unsubstituted isopropyl. In embodiments, $R^{32.1}$ is independently unsubstituted butyl. In embodiments, $R^{32.1}$ is independently unsubstituted n-butyl. In embodiments, $R^{32.1}$ is independently unsubstituted isobutyl. In embodiments, $R^{32.1}$ is independently unsubstituted sec-butyl. In embodiments, $R^{32.1}$ is independently unsubstituted tert-butyl. In embodiments, $R^{32.1}$ is independently unsubstituted pentyl. In embodiments, $R^{32.1}$ is independently unsubstituted hexyl. In embodiments, $R^{32.1}$ is independently unsubstituted heptyl. In embodiments, $R^{32.1}$ is independently unsubstituted octyl. In embodiments, $R^{32.1}$ is independently —$CF_3$. In embodiments, $R^{32.1}$ is independently —$CCl_3$. In embodiments, $R^{32.1}$ is independently —$CBr_3$. In embodiments, $R^{32.1}$ is independently —$CI_3$. In embodiments, $X^{32.1}$ is independently —F. In embodiments, $X^{32.1}$ is independently —Cl. In embodiments, $X^{32.1}$ is independently —Br. In embodiments, $X^{32.1}$ is independently —I. In embodiments, $R^{32.1}$ is independently —$NH_2$. In embodiments, $R^{32.1}$ is independently —$NH(CH_3)$. In embodiments, $R^{32.1}$ is independently —$N(CH_3)_2$. In embodiments, $R^{32.1}$ is independently —$NH(CH_2CH_3)$. In embodiments, $R^{32.1}$ is independently —$N(CH_3)(CH_2CH_3)$. In embodiments, $R^{32.1}$ is independently —$N(CH_2CH_3)_2$. In embodiments, $R^{32.1}$ is independently —NH(unsubstituted $C_1$-$C_4$ alkyl). In embodiments, $R^{32.1}$ is independently —$N(CH_3)$(unsubstituted $C_1$-$C_4$ alkyl). In embodiments, $R^{32.1}$ is independently —N(unsubstituted $C_1$-$C_4$ alkyl)$_2$. In embodiments, $R^{32.1}$ is independently —$CH_2NH_2$. In embodiments, $R^{32.1}$ is independently —$CH_2NH(CH_3)$. In embodiments, $R^{32.1}$ is independently —$CH_2N(CH_3)_2$. In embodiments, $R^{32.1}$ is independently —$CH_2NH(CH_2CH_3)$. In embodiments, $R^{32.1}$ is independently —$CH_2N(CH_3)(CH_2CH_3)$. In embodiments, $R^{32.1}$ is independently —$CH_2N(CH_2CH_3)_2$. In embodiments, $R^{32.1}$ is independently —$CH_2NH$(unsubstituted $C_1$-$C_4$ alkyl). In embodiments, $R^{32.1}$ is independently —$CH_2N(CH_3)$(unsubstituted $C_1$-$C_4$ alkyl). In embodiments, $R^{32.1}$ is independently —$CH_2N$(unsubstituted $C_1$-$C_4$ alkyl)$_2$. In embodiments, $R^{32.1}$ is independently —$CH_2CH_2NH_2$. In embodiments, $R^{32.1}$ is independently —$CH_2CH_2NH(CH_3)$. In embodiments, $R^{32.1}$ is independently —$CH_2CH_2N(CH_3)_2$. In embodiments, $R^{32.1}$ is independently —$CH_2CH_2NH(CH_2CH_3)$. In embodiments, $R^{32.1}$ is independently —$CH_2CH_2N(CH_3)(CH_2CH_3)$. In embodiments, $R^{32.1}$ is independently —$CH_2CH_2N(CH_2CH_3)_2$. In embodiments, $R^{32.1}$ is independently —$CH_2CH_2NH$(unsubstituted $C_1$-$C_4$ alkyl). In embodiments, $R^{32.1}$ is independently —$CH_2CH_2N(CH_3)$(unsubstituted $C_1$-$C_4$ alkyl). In embodiments, $R^{32.1}$ is independently —$CH_2CH_2N$(unsubstituted $C_1$-$C_4$ alkyl)$_2$. In embodiments, $R^{32.1}$ is independently —NH(unsubstituted $C_1$-$C_8$ alkyl). In embodiments, $R^{32.1}$ is independently —$N(CH_3)$(unsubstituted $C_1$-$C_8$ alkyl). In embodiments, $R^{32.1}$ is independently —N(unsubstituted $C_1$-$C_8$ alkyl)$_2$. In embodiments, $R^{32.1}$ is independently —$CH_2NH$(unsubstituted $C_1$-$C_8$ alkyl). In embodiments, $R^{32.1}$ is independently —$CH_2N(CH_3)$(unsubstituted $C_1$-$C_8$ alkyl). In embodiments, $R^{32.1}$ is independently —$CH_2N$(unsubstituted $C_1$-$C_8$ alkyl)$_2$. In embodiments, $R^{32.1}$ is independently —$CH_2CH_2NH$(unsubstituted $C_1$-$C_8$ alkyl). In embodiments, $R^{32.1}$ is independently —$CH_2CH_2N(CH_3)$(unsubstituted $C_1$-$C_8$ alkyl). In embodiments, $R^{32.1}$ is independently —$CH_2CH_2N$(unsubstituted $C_1$-$C_8$ alkyl)$_2$. In embodiments, $R^{32.1}$ is independently —NH(unsubstituted $C_4$-$C_8$ alkyl). In embodiments, $R^{32.1}$ is independently —$N(CH_3)$(unsubstituted $C_4$-$C_8$ alkyl). In embodiments, $R^{32.1}$ is independently —N(unsubstituted $C_4$-$C_8$ alkyl)$_2$. In embodiments, $R^{32.1}$ is independently —$CH_2NH$(unsubstituted $C_4$-$C_8$ alkyl). In embodiments, $R^{32.1}$ is independently —$CH_2N(CH_3)$(unsubstituted $C_4$-$C_8$ alkyl). In embodiments, $R^{32.1}$ is independently —$CH_2N$(unsubstituted $C_4$-$C_8$ alkyl)$_2$. In embodiments, $R^{32.1}$ is independently —$CH_2CH_2NH$(unsubstituted $C_4$-$C_8$ alkyl). In embodiments, $R^{32.1}$ is independently —$CH_2CH_2N(CH_3)$(unsubstituted $C_4$-$C_8$ alkyl). In embodiments, $R^{32.1}$ is independently —$CH_2CH_2N$(unsubstituted $C_4$-$C_8$ alkyl)$_2$. In embodiments, $R^{32.1}$ is independently —NH (unsubstituted $C_1$-$C_8$ alkyl). In embodiments, $R^{32.1}$ is independently —$N(CH_3)$(unsubstituted $C_1$-$C_6$ alkyl). In embodiments, $R^{32.1}$ is independently —N(unsubstituted $C_1$-$C_6$ alkyl)$_2$. In embodiments, $R^{32.1}$ is independently —$CH_2NH$ (unsubstituted $C_1$-$C_6$ alkyl). In embodiments, $R^{32.1}$ is independently —$CH_2N(CH_3)$(unsubstituted $C_1$-$C_6$ alkyl). In embodiments, $R^{32.1}$ is independently —$CH_2N$(unsubstituted $C_1$-$C_6$ alkyl)$_2$. In embodiments, $R^{32.1}$ is independently —$CH_2CH_2NH$(unsubstituted $C_1$-$C_6$ alkyl). In embodiments, $R^{32.1}$ is independently —$CH_2CH_2N(CH_3)$(unsubstituted $C_1$-$C_6$ alkyl). In embodiments, $R^{32.1}$ is independently —$CH_2CH_2N$(unsubstituted $C_1$-$C_6$ alkyl)$_2$.

$R^{32.2}$ may be any value (e.g., be equal to) of $R^{32}$, including an aspect or an embodiment. In embodiments, $R^{32.2}$ is substituted or unsubstituted $C_1$-$C_6$ alkyl. In embodiments, $R^{32.2}$ is substituted or unsubstituted 2 to 6 membered heteroalkyl. In embodiments, $R^{32.2}$ is substituted or unsubstituted $C_3$-$C_8$ cycloalkyl. In embodiments, $R^{32.2}$ is substituted or unsubstituted 3 to 8 membered heterocycloalkyl. In embodiments, $R^{32.2}$ is substituted or unsubstituted phenyl. In embodiments, $R^{32.2}$ is substituted or unsubstituted 5 to 6 membered heteroaryl. In embodiments, $R^{32.2}$ is independently halogen. In embodiments, $R^{32.2}$ is independently —$CX^{32.2}_3$. In embodiments, $R^{32.2}$ is independently —$CHX^{32.2}_2$. In embodiments, $R^{32.2}$ is independently —$CH_2X^{32.2}$. In embodiments, $R^{32.2}$ is independently —$CH_3$. In embodiments, $R^{32.2}$ is independently —$CH_2CH_3$. In embodiments, $R^{32.2}$ is independently unsubstituted methyl, unsubstituted ethyl, unsubstituted isopropyl, or unsubstituted tert-butyl. In embodiments, $R^{32.2}$ is independently unsubstituted methyl. In embodiments, $R^{32.2}$ is independently unsubstituted ethyl. In embodiments, $R^{32.2}$ is independently unsubstituted propyl. In embodiments, $R^{32.2}$ is independently unsubstituted n-propyl. In embodiments, $R^{32.2}$ is independently unsubstituted isopropyl. In embodiments, $R^{32.2}$ is independently unsubstituted butyl. In embodiments, $R^{32.2}$ is independently unsubstituted n-butyl. In embodiments, $R^{32.2}$ is independently unsubstituted isobutyl. In embodiments, $R^{32.2}$ is independently unsubstituted sec-butyl. In embodiments, $R^{32.2}$ is independently unsubstituted tert-butyl. In embodiments, $R^{32.2}$ is independently unsubstituted pentyl. In embodiments, $R^{32.2}$ is independently unsubstituted hexyl. In embodiments, $R^{32.2}$ is independently unsubstituted heptyl. In embodiments, $R^{32.2}$ is independently unsubstituted octyl. In embodiments, $R^{32.2}$ is independently —$CF_3$. In embodiments, $R^{32.2}$ is independently —$CCl_3$. In embodiments, $R^{32.2}$ is independently —$CBr_3$. In embodiments, $R^{32.2}$ is independently —$CI_3$. In embodiments, $X^{32.2}$ is independently —F. In embodiments, $X^{32.2}$ is independently —Cl. In embodiments, $X^{32.2}$ is independently —Br. In embodiments, $X^{32.2}$ is independently —I. In embodiments, $R^{32.2}$ is independently —$NH_2$. In embodiments, $R^{32.2}$ is independently —$NH(CH_3)$. In embodiments, $R^{32.2}$ is independently —$N(CH_3)_2$. In embodiments, $R^{32.2}$ is independently —$NH(CH_2CH_3)$. In embodiments, $R^{32.2}$ is independently —$N(CH_3)(CH_2CH_3)$. In embodiments, $R^{32.2}$ is independently —$N(CH_2CH_3)_2$. In embodiments, $R^{32.2}$ is independently —NH(unsubstituted $C_1$-$C_4$ alkyl). In embodiments, $R^{32.2}$ is independently —$N(CH_3)$(unsubstituted $C_1$-$C_4$ alkyl). In embodiments, $R^{32.2}$ is independently —N(unsubstituted $C_1$-$C_4$ alkyl)$_2$. In embodiments, $R^{32.2}$ is independently —$CH_2NH_2$. In embodiments, $R^{32.2}$ is independently —$CH_2NH(CH_3)$. In embodiments, $R^{32.2}$ is independently —$CH_2N(CH_3)_2$. In embodiments, $R^{32.2}$ is independently —$CH_2NH(CH_2CH_3)$. In embodiments, $R^{32.2}$ is independently —$CH_2N(CH_3)(CH_2CH_3)$. In embodiments, $R^{32.2}$ is independently —$CH_2N(CH_2CH_3)_2$. In embodiments, $R^{32.2}$ is independently —$CH_2NH$(unsubstituted $C_1$-$C_4$ alkyl). In embodiments, $R^{32.2}$ is independently —$CH_2N(CH_3)$(unsubstituted $C_1$-$C_4$ alkyl). In embodiments, $R^{32.2}$ is independently —$CH_2N$(unsubstituted $C_1$-$C_4$ alkyl)$_2$. In embodiments, $R^{32.2}$ is independently —$CH_2CH_2NH_2$. In embodiments, $R^{32.2}$ is independently —$CH_2CH_2NH(CH_3)$. In embodiments, $R^{32.2}$ is independently —$CH_2CH_2N(CH_3)_2$. In embodiments, $R^{32.2}$ is independently —$CH_2CH_2NH(CH_2CH_3)$. In embodiments, $R^{32.2}$ is independently —$CH_2CH_2N(CH_3)(CH_2CH_3)$. In embodiments, $R^{32.2}$ is independently —$CH_2CH_2N(CH_2CH_3)_2$. In embodiments, $R^{32.2}$ is independently —$CH_2CH_2NH$(unsubstituted $C_1$-$C_4$ alkyl). In embodiments, $R^{32.2}$ is independently —$CH_2CH_2N(CH_3)$(unsubstituted $C_1$-$C_4$ alkyl). In embodiments, $R^{32.2}$ is independently —$CH_2CH_2N$(unsubstituted $C_1$-$C_4$ alkyl)$_2$. In embodiments, $R^{32.2}$ is independently —NH (unsubstituted $C_1$-$C_8$ alkyl). In embodiments, $R^{32.2}$ is independently —$N(CH_3)$(unsubstituted $C_1$-$C_8$ alkyl). In embodiments, $R^{32.2}$ is independently —N(unsubstituted $C_1$-$C_8$ alkyl)$_2$. In embodiments, $R^{32.2}$ is independently —$CH_2NH$ (unsubstituted $C_1$-$C_8$ alkyl). In embodiments, $R^{32.2}$ is independently —$CH_2N(CH_3)$(unsubstituted $C_1$-$C_8$ alkyl). In embodiments, $R^{32.2}$ is independently —$CH_2N$(unsubstituted $C_1$-$C_8$ alkyl)$_2$. In embodiments, $R^{32.2}$ is independently —$CH_2CH_2NH$(unsubstituted $C_1$-$C_8$ alkyl). In embodiments, $R^{32.2}$ is independently —$CH_2CH_2N(CH_3)$(unsubstituted $C_1$-$C_8$ alkyl). In embodiments, $R^{32.2}$ is independently —$CH_2CH_2N$(unsubstituted $C_1$-$C_8$ alkyl)$_2$. In embodiments, $R^{32.2}$ is independently —NH(unsubstituted $C_4$-$C_8$ alkyl). In embodiments, $R^{32.2}$ is independently —$N(CH_3)$(unsubstituted $C_4$-$C_8$ alkyl). In embodiments, $R^{32.2}$ is independently —N(unsubstituted $C_4$-$C_8$ alkyl)$_2$. In embodiments, $R^{32.2}$ is independently —$CH_2NH$(unsubstituted $C_4$-$C_8$ alkyl). In embodiments, $R^{32.2}$ is independently —$CH_2N(CH_3)$(unsubstituted $C_4$-$C_8$ alkyl). In embodiments, $R^{32.2}$ is independently —$CH_2N$(unsubstituted $C_4$-$C_8$ alkyl)$_2$. In embodiments, $R^{32.2}$ is independently —$CH_2CH_2NH$(unsubstituted $C_4$-$C_8$ alkyl). In embodiments, $R^{32.2}$ is independently —$CH_2CH_2N(CH_3)$(unsubstituted $C_4$-$C_8$ alkyl). In embodiments, $R^{32.2}$ is independently —$CH_2CH_2N$(unsubstituted $C_4$-$C_8$ alkyl)$_2$. In embodiments, $R^{32.2}$ is independently —NH (unsubstituted $C_1$-$C_8$ alkyl). In embodiments, $R^{32.2}$ is independently —$N(CH_3)$(unsubstituted $C_1$-$C_6$ alkyl). In embodiments, $R^{32.2}$ is independently —N(unsubstituted $C_1$-$C_6$ alkyl)$_2$. In embodiments, $R^{32.2}$ is independently —$CH_2NH$ (unsubstituted $C_1$-$C_6$ alkyl). In embodiments, $R^{32.2}$ is independently —$CH_2N(CH_3)$(unsubstituted $C_1$-$C_6$ alkyl). In embodiments, $R^{32.2}$ is independently —$CH_2N$(unsubstituted $C_1$-$C_6$ alkyl)$_2$. In embodiments, $R^{32.2}$ is independently —$CH_2CH_2NH$(unsubstituted $C_1$-$C_6$ alkyl). In embodiments, $R^{32.2}$ is independently —$CH_2CH_2N(CH_3)$(unsubstituted $C_1$-$C_6$ alkyl). In embodiments, $R^{32.2}$ is independently —$CH_2CH_2N$(unsubstituted $C_1$-$C_6$ alkyl$)_2$. In embodiments, $R^{32.2}$ is independently —F. In embodiments, $R^{32.2}$ is independently —Cl. In embodiments, $R^{32.2}$ is independently —Br. In embodiments, $R^{32.2}$ is independently —I.

In embodiments, $R^1$ is substituted or unsubstituted $C_1$-$C_6$ alkyl. In embodiments, $R^1$ is substituted or unsubstituted 2 to 6 membered heteroalkyl. In embodiments, $R^1$ is substituted or unsubstituted $C_3$-$C_8$ cycloalkyl. In embodiments, $R^1$ is substituted or unsubstituted 3 to 8 membered heterocycloalkyl. In embodiments, $R^1$ is substituted or unsubstituted phenyl. In embodiments, $R^1$ is substituted or unsubstituted 5 to 6 membered heteroaryl. In embodiments, $R^1$ is independently halogen. In embodiments, $R^1$ is independently —$CX^1_3$. In embodiments, $R^1$ is independently —$CHX^1_2$. In embodiments, $R^1$ is independently —$CH_2X^1$. In embodiments, $R^1$ is independently —$CH_3$. In embodiments, $R^1$ is independently —$CH_2CH_3$. In embodiments, $R^1$ is independently unsubstituted methyl, unsubstituted ethyl, unsubstituted isopropyl, or unsubstituted tert-butyl. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted sec-butyl. In embodiments, $R^1$ is independently unsubstituted tert-butyl. In embodiments, $R^1$ is independently unsubstituted pentyl. In embodiments, $R^1$ is independently unsubstituted hexyl. In embodiments, $R^1$ is independently unsubstituted heptyl. In embodiments, $R^1$ is independently unsubstituted octyl. In embodiments, $R^1$ is independently —$CF_3$. In embodiments, $R^1$ is independently —$CCl_3$. In embodiments, $R^1$ is independently —$CBr_3$. In embodiments, $R^1$ is independently —$CI_3$. In embodiments, $X^1$ is independently —F. In embodiments, $X^1$ is independently —Cl. In embodiments, $X^1$ is independently —Br. In embodiments, $X^1$ is independently —I. In embodiments, $R^1$ is independently —OH. In embodiments, $R^1$ is independently —SH. In embodiments, $R^1$ is independently —$OCX^1_3$. In embodiments, $R^1$ is independently —$OCHX^1_2$. In embodiments, $R^1$ is independently —$OCH_2X^1_3$. In embodiments, $R^1$ is independently —$OCH_3$. In embodiments, $R^1$ is independently —$OCH_2CH_3$. In embodiments, $R^1$ is independently —$SCH_3$. In embodiments, $R^1$ is independently —$SCH_2CH_3$. In embodiments, $R^1$ is independently —$OR^{1D}$. In embodiments, $R^1$ is independently —$SR^{1D}$.

In embodiments, $R^{1D}$ is substituted or unsubstituted $C_1$-$C_6$ alkyl. In embodiments, $R^{1D}$ is substituted or unsubstituted 2 to 6 membered heteroalkyl. In embodiments, $R^{1D}$ is substituted or unsubstituted $C_3$-$C_8$ cycloalkyl. In embodiments, $R^{1D}$ is substituted or unsubstituted 3 to 8 membered heterocycloalkyl. In embodiments, $R^{1D}$ is substituted or unsubstituted phenyl. In embodiments, $R^{1D}$ is substituted or unsubstituted 5 to 6 membered heteroaryl. In embodiments, $R^{1D}$ is independently halogen. In embodiments, $R^{1D}$ is independently —$CX^{1D}_3$. In embodiments, $R^{1D}$ is independently —$CHX^{1D}_2$. In embodiments, $R^{1D}$ is independently —$CH_2X^{1D}$. In embodiments, $R^{1D}$ is independently —$CH_3$. In embodiments, $R^{1D}$ is independently —$CH_2CH_3$. In embodiments, $R^{1D}$ is independently unsubstituted methyl, unsubstituted ethyl, unsubstituted isopropyl, or unsubstituted tert-butyl. In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted n-propyl. In embodiments, $R^{1D}$ is independently unsubstituted isopropyl. In embodiments, $R^{1D}$ is independently unsubstituted butyl. In embodiments, $R^{1D}$ is independently unsubstituted n-butyl. In embodiments, $R^{1D}$ is independently unsubstituted isobutyl. In embodiments, $R^{1D}$ is independently unsubstituted sec-butyl. In embodiments, $R^{1D}$ is independently unsubstituted tert-butyl. In embodiments, $R^{1D}$ is independently unsubstituted pentyl. In embodiments, $R^{1D}$ is independently unsubstituted hexyl. In embodiments, $R^{1D}$ is independently unsubstituted heptyl. In embodiments, $R^{1D}$ is independently unsubstituted octyl. In embodiments, $R^{1D}$ is independently —$CF_3$. In embodiments, $R^{1D}$ is independently —$CCl_3$. In embodiments, $R^{1D}$ is independently —$CBr_3$. In embodiments, $R^{1D}$ is independently —$CI_3$. In embodiments, $X^{1D}$ is independently —F. In embodiments, $X^{1D}$ is independently —Cl. In embodiments, $X^{1D}$ is independently —Br. In embodiments, $X^{1D}$ is independently —I.

In embodiments, $R^3$ is substituted or unsubstituted $C_1$-$C_6$ alkyl. In embodiments, $R^3$ is substituted or unsubstituted 2 to 6 membered heteroalkyl. In embodiments, $R^3$ is substituted or unsubstituted $C_3$-$C_8$ cycloalkyl. In embodiments, $R^3$ is substituted or unsubstituted 3 to 8 membered heterocycloalkyl. In embodiments, $R^3$ is substituted or unsubstituted phenyl. In embodiments, $R^3$ is substituted or unsubstituted 5 to 6 membered heteroaryl. In embodiments, $R^3$ is independently halogen. In embodiments, $R^3$ is independently —$CX^{33}$. In embodiments, $R^3$ is independently —$CHX^{32}$. In embodiments, $R^3$ is independently —$CH_2X^3$. In embodiments, $R^3$ is independently —$CH_3$. In embodiments, $R^3$ is independently —$CH_2CH_3$. In embodiments, $R^3$ is independently unsubstituted methyl, unsubstituted ethyl, unsubstituted isopropyl, or unsubstituted tert-butyl. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted n-propyl. In embodiments, $R^3$ is independently unsubstituted isopropyl. In embodiments, $R^3$ is independently unsubstituted butyl. In embodiments, $R^3$ is independently unsubstituted n-butyl. In embodiments, $R^3$ is independently unsubstituted isobutyl. In embodiments, $R^3$ is independently unsubstituted sec-butyl. In embodiments, $R^3$ is independently unsubstituted tert-butyl. In embodiments, $R^3$ is independently unsubstituted pentyl. In embodiments, $R^3$ is independently unsubstituted hexyl. In embodiments, $R^3$ is independently unsubstituted heptyl. In embodiments, $R^3$ is independently unsubstituted octyl. In embodiments, $R^3$ is independently —$CF_3$. In embodiments, $R^3$ is independently —$CCl_3$. In embodiments, $R^3$ is independently —$CBr_3$. In embodiments, $R^3$ is independently —$CI_3$. In embodiments, $X^3$ is independently —F. In embodiments, $X^3$ is independently —Cl. In embodiments, $X^3$ is independently —Br. In embodiments, $X^3$ is independently —I.

In some embodiments, a compound as described herein may include multiple instances of $R^{20}$, $R^{23}$, $R^{32}$, $R^{47}$, and/or other variables. In such embodiments, each variable may optional be different and be appropriately labeled to distinguish each group for greater clarity. For example, where each $R^{20}$, $R^{23}$, $R^{32}$, and/or $R^{47}$, is different, they may be referred to, for example, as $R^{20.1}$, $R^{20.2}$, $R^{20.3}$, $R^{20.4}$, $R^{20.5}$, $R^{23.1}$, $R^{23.2}$, $R^{23.3}$, $R^{23.4}$, $R^{32.1}$, $R^{32.2}$, $R^{32.3}$, $R^{32.4}$, $R^{32.5}$, $R^{47.1}$, $R^{47.2}$, $R^{47.3}$, $R^{47.4}$, $R^{47.5}$, $R^{47.6}$, $R^{47.7}$, $R^{47.8}$, $R^{47.9}$, or $R^{47.10}$, respectively, wherein the definition of $R^{20}$ is assumed by $R^{20.1}$, $R^{20.2}$, $R^{20.3}$, $R^{20.4}$, $R^{20.5}$; $R^{23}$ is assumed by $R^{23.1}$, $R^{23.2}$, $R^{23.3}$, $R^{23.4}$; $R^{32}$ is assumed by $R^{32.1}$, $R^{32.2}$, $R^{32.3}$, $R^{32.4}$, $R^{32.5}$; and/or $R^{47}$ is assumed by $R^{47.1}$, $R^{47.2}$, $R^{47.3}$, $R^{47.4}$, $R^{47.5}$, $R^{47.6}$, $R^{47.7}$, $R^{47.8}$, $R^{47.9}$, $R^{47.10}$. The variables used within a definition of $R^{20}$, $R^{23}$, $R^{32}$, $R^{47}$, and/or other variables that appear at multiple instances and are different may similarly be appropriately labeled to distinguish each group for greater clarity.

In embodiments, the compound is compound 1. In embodiments, the compound is compound 2. In embodiments, the compound is compound 3. In embodiments, the compound is compound 4. In embodiments, the compound is compound 5. In embodiments, the compound is compound 6. In embodiments, the compound is compound 7. In embodiments, the compound is compound 8. In embodiments, the compound is compound 9. In embodiments, the compound is compound 10. In embodiments, the compound is compound 11. In embodiments, the compound is compound 12. In embodiments, the compound is compound 13. In embodiments, the compound is compound 14. In embodiments, the compound is compound 15. In embodiments, the compound is compound 16. In embodiments, the compound is compound 17. In embodiments, the compound is compound 18. In embodiments, the compound is compound 19. In embodiments, the compound is compound 20. In embodiments, the compound is compound 21. In embodiments, the compound is compound 22. In embodiments, the compound is compound 23. In embodiments, the compound is compound 24. In embodiments, the compound is compound 25. In embodiments, the compound is compound 26. In embodiments, the compound is compound 27. In embodiments, the compound is compound 28. In embodiments, the compound is compound 29. In embodiments, the compound is compound 30. In embodiments, the compound is compound 31. In embodiments, the compound is compound 32. In embodiments, the compound is compound 33. In embodiments, the compound is compound 34. In embodiments, the compound is compound 35. In embodiments, the compound is compound 36. In embodiments, the compound is compound 37. In embodiments, the compound is compound 38. In embodiments, the compound is compound 39. In embodiments, the compound is compound 40. In embodiments, the compound is compound 41. In embodiments, the compound is compound 42. In embodiments, the compound is compound 43. In embodiments, the compound is compound 44. In embodiments, the compound is compound 45. In embodiments, the compound is compound 46. In embodiments, the compound is compound 47. In embodiments, the compound is compound 48. In embodiments, the compound is compound 49. In embodiments, the compound is compound 50. In embodiments, the compound is compound 51. In embodiments, the compound is compound 52. In embodiments, the compound is compound 53. In embodiments, the compound is compound 54. In embodiments, the compound is compound 55. In embodiments, the compound is compound 56. In embodiments, the compound is compound 57. In embodiments, the compound is compound 58. In embodiments, the compound is compound 59. In embodiments, the compound is compound 60. In embodiments, the compound is compound 61. In embodiments, the compound is compound 62. In embodiments, the compound is compound 63. In embodiments, the compound is compound 64. In embodiments, the compound is compound 65. In embodiments, the compound is compound 66. In embodiments, the compound is compound 67. In embodiments, the compound is compound 68. In embodiments, the compound is compound 69. In embodiments, the compound is compound 70. In embodiments, the compound is compound 71. In embodiments, the compound is compound 72. In embodiments, the compound is compound 73. In embodiments, the compound is compound 74. In embodiments, the compound is compound 75. In embodiments, the compound is compound 76. In embodiments, the compound is compound 77. In embodiments, the compound is compound 78. In embodiments, the compound is compound 79. In embodiments, the compound is compound 80. In embodiments, the compound is compound 81. In embodiments, the compound is compound 82. In embodiments, the compound is compound 83. In embodiments, the compound is compound 84. In embodiments, the compound is compound 85. In embodiments, the compound is compound 86. In embodiments, the compound is compound 87. In embodiments, the compound is compound 88. In embodiments, the compound is compound 89. In embodiments, the compound is compound 90. In embodiments, the compound is compound 91. In embodiments, the compound is compound 92. In embodiments, the compound is compound 93. In embodiments, the compound is compound 94. In embodiments, the compound is compound 95. In embodiments, the compound is compound 96. In embodiments, the compound is compound 97. In embodiments, the compound is compound 98. In embodiments, the compound is compound 99. In embodiments, the compound is compound 100. In embodiments, the compound is compound 101. In embodiments, the compound is compound 102. In embodiments, the compound is compound 103. In embodiments, the compound is compound 104. In embodiments, the compound is compound 105. In embodiments, the compound is compound 106. In embodiments, the compound is compound 107. In embodiments, the compound is compound 108. In embodiments, the compound is compound 109. In embodiments, the compound is compound 110. In embodiments, the compound is compound 111. In embodiments, the compound is compound 112. In embodiments, the compound is compound 113. In embodiments, the compound is compound 114. In embodiments, the compound is compound 115. In embodiments, the compound is compound 116. In embodiments, the compound is compound 117. In embodiments, the compound is compound 118. In embodiments, the compound is compound 119. In embodiments, the compound is compound 120. In embodiments, the compound is compound 121. In embodiments, the compound is compound 122. In embodiments, the compound is compound 123. In embodiments, the compound is compound 124. In embodiments, the compound is compound 125. In embodiments, the compound is compound 126. In embodiments, the compound is compound 127. In embodiments, the compound is compound 128. In embodiments, the compound is compound 129. In embodiments, the compound is compound 130. In embodiments, the compound is compound 131. In embodiments, the compound is compound 132. In embodiments, the compound is compound 133. In embodiments, the compound is compound 134. In embodiments, the compound is compound 135. In embodiments, the compound is compound 136. In embodiments, the compound is compound 137. In embodiments, the compound is compound 138. In embodiments, the compound is compound 139. In embodiments, the compound is compound 140. In embodiments, the compound is compound 141. In embodiments, the compound is compound 142. In embodiments, the compound is compound 143. In embodiments, the compound is compound 144. In embodiments, the compound is compound 145. In embodiments, the compound is compound 146. In embodiments, the compound is compound 147. In embodiments, the compound is compound 148. In embodiments, the compound is compound 149. In embodiments, the compound is compound 150. In embodiments, the compound is compound 151. In embodiments, the compound is compound 152. In embodiments, the compound is compound 153. In embodiments, the compound is compound 154. In embodiments, the compound is compound 155. In embodiments, the compound is compound 156. In embodiments, the compound is compound 157. In embodiments, the compound is compound 158. In embodiments, the compound is compound 159. In embodiments, the compound is compound 160. In embodiments, the compound is compound 161.

In embodiments, the compound (e.g., described herein) inhibits ITK more potently (e.g., preferentially or with greater affinity or with comparable level of inhibition at a lower concentration) than a different TEC kinase. In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits ITK at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits a different TEC kinase.

In embodiments, the compound (e.g., described herein) inhibits ITK more potently (e.g., preferentially or with greater affinity or with comparable level of inhibition at a lower concentration) than BTK. In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits ITK at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits BTK.

In embodiments, the compound (e.g., described herein) inhibits ITK more potently (e.g., preferentially or with greater affinity or with comparable level of inhibition at a lower concentration) than BMX. In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits ITK at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits BMX.

In embodiments, the compound (e.g., described herein) inhibits ITK more potently (e.g., preferentially or with greater affinity or with comparable level of inhibition at a lower concentration) than TXK. In embodiments, the potency of inhibition is measured by IC50 (e.g., in an in vivo assay, in a cell assay, in an in vitro assay). In embodiments, the potency of inhibition is measured by binding affinity (e.g., in an in vivo assay, in a cell assay, in an in vitro assay). In embodiments, the compound inhibits ITK at least 1.1, 1.2, 1.3, 1.4, 1.5, 2, 3, 4, 5, 6, 7, 8, 9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 20, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 20000, 30000, 40000, 50000, 60000, 70000, 80000, 90000, or 100000 times more potently than the compound inhibits TXK.

In embodiments, the compound (e.g., described herein) is capable of entering the central nervous system of a patient following administration outside of the central nervous system (e.g., systemic administration, i.v., or intraarterial).

In some embodiments, the compound is a compound described herein (e.g., in an aspect, embodiment, example, claim, table (e.g., Table 1 or Table 2), scheme, drawing, or FIGURE). In embodiments, the compound is one of Compound 1 to 161 described herein.

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, FIGURE, table, scheme, or claim). In embodiments, the compound is a compound described in Table 2.

Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic. In embodiments, the second agent is an anti-inflammatory agent. In embodiments, the second agent is an anti-autoimmune disease agent. In embodiments, the second agent is an anti-infectious disease agent.

Methods of Treatment

In an aspect is provided a method of treating cancer including administering to a subject in need thereof an effective amount of a compound described herein.

In embodiments, the cancer is a hematological cancer. In embodiments, the cancer is a blood cancer. In embodiments, the cancer is a metastatic cancer. In embodiments, the cancer is a leukemia (e.g., acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia). In embodiments, the cancer is a lymphoma (e.g., T-cell lymphoma, Precursor T-lymphoblastic lymphoma, Peripheral T-cell lymphoma, Cutaneous T-cell lymphoma, Adult T-cell leukemia/lymphoma, Angioimmunoblastic T-cell lymphoma, Extranodal natural killer/T-cell lymphoma, nasal type, Enteropathy-associated intestinal T-cell lymphoma, Anaplastic large cell lymphoma, or Peripheral T-cell lymphoma, unspecified).

In an aspect is provided a method of treating an inflammatory disease including administering to a subject in need thereof an effective amount of a compound described herein.

In embodiments, the inflammatory disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, or atopic dermatitis.

In an aspect is provided a method of treating an autoimmune disease including administering to a subject in need thereof an effective amount of a compound described herein.

In embodiments, the autoimmune disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis.

In an aspect is provided a method of treating an infectious disease including administering to a subject in need thereof an effective amount of a compound described herein.

In an aspect is provided a method of treating a disease associated with Interleukin-2-inducible T-cell kinase activity including administering to a subject in need thereof an effective amount of a compound described herein. In embodiments, the disease is associated with aberrant Interleukin-2-inducible T-cell kinase activity.

In embodiments, the method includes administering a second agent (e.g. therapeutic agent). In embodiments, the method includes administering a second agent (e.g. therapeutic agent) in a therapeutically effective amount. In embodiments, the second agent is an agent for treating cancer. In embodiments, the second agent is an anti-cancer agent. In embodiments, the second agent is a chemotherapeutic. In embodiments, the second agent is an anti-inflammatory agent.

Methods of Inhibition

In an aspect is provided a method of inhibiting Interleukin-2-inducible T-cell kinase activity including contacting the Interleukin-2-inducible T-cell kinase with a compound described herein. In embodiments, the Interleukin-2-inducible T-cell kinase is a human Interleukin-2-inducible T-cell kinase.

In an aspect is provided a method of inhibiting the activity of a TEC kinase family protein (e.g., TEC, BTK, ITK/EMT/TSK, BMX, and TXK/RLK), the method including contacting the TEC kinase family protein (e.g., TEC, BTK, ITK/EMT/TSK, BMX, and TXK/RLK) with a compound described herein.

In embodiments, the inhibition is competitive inhibition. In embodiments, the inhibition is irreversible. In embodiments, the inhibition is reversible. In embodiments, the compound covalently binds to the Interleukin-2-inducible T-cell kinase.

Where the compound covalently binds to the Interleukin-2-inducible T-cell kinase a Interleukin-2-inducible T-cell kinase protein (e.g., human Interleukin-2-inducible T-cell kinase) covalently bonded to a Interleukin-2-inducible T-cell kinase inhibitor is formed (also referred to herein as a "ITK-compound adduct"), as described below. In embodiments, the resulting covalent bond is reversible. Where the resulting covalent bond is reversible, the bonding reverses upon denaturation of the protein. Thus, in embodiments, the reversibility of a covalent bond between the compound and the Interleukin-2-inducible T-cell kinase upon denaturation of the Interleukin-2-inducible T-cell kinase avoids or decreases autoimmune response in a subject subsequent to administration of the compound (relative to irreversibility). Moreover, in embodiments, the reversibility of a covalent bond between the compound and the Interleukin-2-inducible T-cell kinase upon denaturation of the Interleukin-2-inducible T-cell kinase avoids or decreases the toxicity (e.g. liver toxicity) of the compound in a subject (relative to irreversibility).

Interleukin-2-Inducible T-Cell Kinase Protein

In an aspect is provided a Interleukin-2-inducible T-cell kinase protein covalently bonded to a compound described herein (e.g., Interleukin-2-inducible T-cell kinase inhibitor, Interleukin-2-inducible T-cell kinase antagonist, compound described herein, or a portion (e.g., the product of an electrophilic reaction with Cys442 of human ITK or cysteine corresponding to Cys442 of human ITK) of a compound described herein).

In embodiments, the compound is bonded to a cysteine residue (e.g., Cys442 of human ITK or cysteine corresponding to Cys442 of human ITK) of the Interleukin-2-inducible T-cell kinase protein. In embodiments, the compound is covalently bonded to a cysteine (e.g., Cys442 of human ITK or cysteine corresponding to Cys442 of human ITK) residue of the Interleukin-2-inducible T-cell kinase protein. In embodiments, the compound is reversibly covalently bonded to a cysteine residue (e.g., Cys442 of human ITK or cysteine corresponding to Cys442 of human ITK) of the Interleukin-2-inducible T-cell kinase protein. In embodiments, the compound is irreversibly covalently bonded to a cysteine residue (e.g., Cys442 of human ITK or cysteine corresponding to Cys442 of human ITK) of the Interleukin-2-inducible T-cell kinase protein. In embodiments, the compound is bonded (e.g., covalently, irreversibly covalently, or reversibly covalently) to an aspartate residue of the Interleukin-2-inducible T-cell kinase protein. In embodiments, the compound is bonded (e.g., covalently, irreversibly covalently, or reversibly covalently) to a glutamate residue of the Interleukin-2-inducible T-cell kinase protein. In embodiments, the compound is bonded (e.g., covalently, irreversibly covalently, or reversibly covalently) to an arginine residue of the Interleukin-2-inducible T-cell kinase protein. In embodiments, the compound is bonded (e.g., covalently, irreversibly covalently, or reversibly covalently) to a lysine residue of the Interleukin-2-inducible T-cell kinase protein. In embodiments, the compound is bonded (e.g., covalently, irreversibly covalently, or reversibly covalently) to a tyrosine residue of the Interleukin-2-inducible T-cell kinase protein.

In an embodiment, the Interleukin-2-inducible T-cell kinase protein is covalently bonded (e.g., reversibly or irreversibly) to a portion of a compound described herein (e.g., portion of a Interleukin-2-inducible T-cell kinase inhibitor, portion of a Interleukin-2-inducible T-cell kinase antagonist, or portion of a compound described herein).

In an aspect is provided a Interleukin-2-inducible T-cell kinase protein (e.g., human ITK) covalently bonded to a Interleukin-2-inducible T-cell kinase inhibitor (e.g., Interleukin-2-inducible T-cell kinase antagonist, compound described herein, or a portion of a compound described herein).

In embodiments, the Interleukin-2-inducible T-cell kinase protein (e.g., human Interleukin-2-inducible T-cell kinase) is covalently bonded to a Interleukin-2-inducible T-cell kinase inhibitor (e.g., Interleukin-2-inducible T-cell kinase antagonist, compound described herein, or a portion of a compound described herein). In embodiments, the Interleukin-2-inducible T-cell kinase protein (e.g., human Interleukin-2-inducible T-cell kinase) is irreversibly covalently bonded to a Interleukin-2-inducible T-cell kinase inhibitor (e.g., Interleukin-2-inducible T-cell kinase antagonist, compound described herein, or a portion of a compound described herein). In embodiments, the Interleukin-2-inducible T-cell kinase protein (e.g., human Interleukin-2-inducible T-cell kinase) is reversibly covalently bonded to a Interleukin-2-inducible T-cell kinase inhibitor (e.g., Interleukin-2-inducible T-cell kinase antagonist, compound described herein, or a portion of a compound described herein). In embodiments, the Interleukin-2-inducible T-cell kinase protein (e.g., human Interleukin-2-inducible T-cell kinase) is covalently bonded to a portion of a Interleukin-2-inducible T-cell kinase inhibitor (e.g., Interleukin-2-inducible T-cell kinase antagonist or compound described herein). In embodiments, the Interleukin-2-inducible T-cell kinase protein (e.g., human Interleukin-2-inducible T-cell kinase) is irreversibly covalently bonded to a portion of a Interleukin-2-inducible T-cell kinase inhibitor (e.g., Interleukin-2-inducible T-cell kinase antagonist or compound described herein). In embodiments, the Interleukin-2-inducible T-cell kinase protein (e.g., human Interleukin-2-inducible T-cell kinase) is reversibly covalently bonded to a portion of a Interleukin-2-inducible T-cell kinase inhibitor (e.g., Interleukin-2-inducible T-cell kinase antagonist or compound described herein). In embodiments, the Interleukin-2-inducible T-cell kinase inhibitor (e.g., Interleukin-2-inducible T-cell kinase antagonist or compound described herein) is bonded to a cysteine residue (e.g., Cys442 of human ITK or cysteine corresponding to Cys442 of human ITK) of the Interleukin-2-inducible T-cell kinase protein (e.g., human Interleukin-2-inducible T-cell kinase). In embodiments, the portion of a Interleukin-2-inducible T-cell kinase inhibitor (e.g., Interleukin-2-inducible T-cell kinase antagonist or compound described herein) is bonded to a cysteine residue (e.g., Cys442 of human ITK or cysteine corresponding to Cys442 of human ITK) of the Interleukin-2-inducible T-cell kinase protein (e.g., human Interleukin-2-inducible T-cell kinase).

In embodiments, the Interleukin-2-inducible T-cell kinase inhibitor (e.g., Interleukin-2-inducible T-cell kinase antagonist or compound described herein) is bonded to cysteine 442 of the Interleukin-2-inducible T-cell kinase protein (e.g., human Interleukin-2-inducible T-cell kinase). In embodiments, the Interleukin-2-inducible T-cell kinase inhibitor (e.g., Interleukin-2-inducible T-cell kinase antagonist or compound described herein) is bonded to cysteine 442 of the Interleukin-2-inducible T-cell kinase protein (e.g., human Interleukin-2-inducible T-cell kinase) corresponding to RefSeq (protein) NP_005537. In embodiments, the Interleukin-2-inducible T-cell kinase inhibitor (e.g., Interleukin-2-inducible T-cell kinase antagonist or compound described herein) interacts (e.g., contacts) with hydrophobic groups (e.g., in the active site) of the Interleukin-2-inducible T-cell kinase protein (e.g., human Interleukin-2-inducible T-cell kinase) corresponding to RefSeq (protein) NP_005537. In embodiments, the Interleukin-2-inducible T-cell kinase inhibitor (e.g., Interleukin-2-inducible T-cell kinase antagonist or compound described herein) interacts (e.g., contacts) with the active site of the Interleukin-2-inducible T-cell kinase protein (e.g., human Interleukin-2-inducible T-cell kinase). In embodiments, the Interleukin-2-inducible T-cell kinase inhibitor (e.g., Interleukin-2-inducible T-cell kinase antagonist or compound described herein) interacts (e.g., contacts) with the active site of the Interleukin-2-inducible T-cell kinase protein (e.g., human Interleukin-2-inducible T-cell kinase) corresponding to RefSeq (protein) NP_005537.

In embodiments, the Interleukin-2-inducible T-cell kinase inhibitor (e.g., Interleukin-2-inducible T-cell kinase antagonist or compound described herein) is bonded to the amino acid corresponding to cysteine 442 of the Interleukin-2-inducible T-cell kinase protein (e.g., human Interleukin-2-inducible T-cell kinase). In embodiments, the Interleukin-2-inducible T-cell kinase inhibitor (e.g., Interleukin-2-inducible T-cell kinase antagonist or compound described herein) is bonded to the amino acid corresponding to cysteine 442 of the Interleukin-2-inducible T-cell kinase protein (e.g., human Interleukin-2-inducible T-cell kinase) corresponding to RefSeq (protein) NP_005537. In embodiments, the Interleukin-2-inducible T-cell kinase inhibitor (e.g., Interleukin-2-inducible T-cell kinase antagonist or compound described herein) interacts (e.g., contacts) with the amino acids corresponding to the active site of the Interleukin-2-inducible T-cell kinase protein (e.g., human Interleukin-2-inducible T-cell kinase). In embodiments, the Interleukin-2-inducible T-cell kinase inhibitor (e.g., Interleukin-2-inducible T-cell kinase antagonist or compound described herein) interacts (e.g., contacts) with the amino acids corresponding to the active site of the Interleukin-2-inducible T-cell kinase protein (e.g., human Interleukin-2-inducible T-cell kinase) corresponding to RefSeq (protein) NP_005537.

In embodiments, a portion of the Interleukin-2-inducible T-cell kinase inhibitor (e.g., Interleukin-2-inducible T-cell kinase antagonist or compound described herein) is bonded to cysteine 442 of the Interleukin-2-inducible T-cell kinase protein (e.g., human Interleukin-2-inducible T-cell kinase). In embodiments, a portion of the Interleukin-2-inducible T-cell kinase inhibitor (e.g., Interleukin-2-inducible T-cell kinase antagonist or compound described herein) is bonded to cysteine 442 of the Interleukin-2-inducible T-cell kinase protein (e.g., human Interleukin-2-inducible T-cell kinase) corresponding to RefSeq (protein) NP_005537.

In embodiments, a portion of the Interleukin-2-inducible T-cell kinase inhibitor (e.g., Interleukin-2-inducible T-cell kinase antagonist or compound described herein) is bonded to the amino acid corresponding to cysteine 442 of the Interleukin-2-inducible T-cell kinase protein (e.g., human Interleukin-2-inducible T-cell kinase). In embodiments, a portion of the Interleukin-2-inducible T-cell kinase inhibitor (e.g., Interleukin-2-inducible T-cell kinase antagonist or compound described herein) is bonded to the amino acid corresponding to cysteine 442 of the Interleukin-2-inducible T-cell kinase protein (e.g., human Interleukin-2-inducible T-cell kinase) corresponding to RefSeq (protein) NP_005537. In embodiments, a portion of the Interleukin-2-inducible T-cell kinase inhibitor (e.g., Interleukin-2-inducible T-cell kinase antagonist or compound described herein) interacts (e.g., contacts) with the amino acids corresponding to the active site of the Interleukin-2-inducible T-cell kinase protein (e.g., human Interleukin-2-inducible T-cell kinase). In embodiments, a portion of the Interleukin-2-inducible T-cell kinase inhibitor (e.g., Interleukin-2-inducible T-cell kinase antagonist or compound described herein) interacts (e.g., contacts) with the amino acids corresponding to the active site of the Interleukin-2-inducible T-cell kinase protein (e.g., human Interleukin-2-inducible T-cell kinase) corresponding to RefSeq (protein) NP_005537.

In an aspect is provided a Interleukin-2-inducible T-cell kinase protein (e.g., human Interleukin-2-inducible T-cell kinase) covalently bonded to a compound described herein, or a portion of a compound described herein.

In embodiments, the Interleukin-2-inducible T-cell kinase protein (e.g., human Interleukin-2-inducible T-cell kinase) is covalently bonded to a compound described herein. In embodiments, the Interleukin-2-inducible T-cell kinase protein (e.g., human Interleukin-2-inducible T-cell kinase) is irreversibly covalently bonded to a compound described herein. In embodiments, the Interleukin-2-inducible T-cell kinase protein (e.g., human Interleukin-2-inducible T-cell kinase) is reversibly covalently bonded to a compound described herein. In embodiments, the Interleukin-2-inducible T-cell kinase protein (e.g., human Interleukin-2-inducible T-cell kinase) is covalently bonded to a portion of a compound described herein. In embodiments, the Interleukin-2-inducible T-cell kinase protein (e.g., human Interleukin-2-inducible T-cell kinase) is irreversibly covalently bonded to a portion of a compound described herein. In embodiments, the Interleukin-2-inducible T-cell kinase protein (e.g., human Interleukin-2-inducible T-cell kinase) is reversibly covalently bonded to a portion of a compound described herein. In embodiments, the compound is bonded to a cysteine residue of the Interleukin-2-inducible T-cell kinase protein (e.g., human Interleukin-2-inducible T-cell kinase). In embodiments, the portion of a compound is bonded to a cysteine residue of the Interleukin-2-inducible T-cell kinase protein (e.g., human Interleukin-2-inducible T-cell kinase).

In embodiments, the Interleukin-2-inducible T-cell kinase protein covalently bonded to a compound described herein is the product of a reaction between the Interleukin-2-inducible T-cell kinase protein and a compound described herein. It will be understood that the covalently bonded Interleukin-2-inducible T-cell kinase protein and the compound described herein are the remnants of the reactant Interleukin-2-inducible T-cell kinase protein and compound, wherein each reactant now participates in the covalent bond between the Interleukin-2-inducible T-cell kinase protein and compound. In embodiments of the covalently bonded Interleukin-2-inducible T-cell kinase protein and compound described herein, the remnant of the E substitutent is a linker including a covalent bond between the Interleukin-2-inducible T-cell kinase protein and the remainder of the compound described herein. It will be understood by a person of ordinary skill in the art that when a Interleukin-2-inducible T-cell kinase protein is covalently bonded to a compound described herein, the compound described forms a remnant of the pre-reacted compound described herein wherein a bond connects the remnant of the compound described herein to the remnant of the Interleukin-2-inducible T-cell kinase protein (e.g., cysteine sulfur, sulfur of amino acid corresponding to C442 of human Interleukin-2-inducible T-cell kinase, sulfur of C442 of human Interleukin-2-inducible T-cell kinase). In embodiments, the remnant of the E substituent is a linker selected from a bond, —$S(O)_2$—, —NH—, —O—, —S—, —C(O)—, —C(O)NH—, —NHC(O)—, —NHC(O)NH—, —NHC(O)NH—, —C(O)O—, —OC(O)—, —$CH_2$NH—, substituted (e.g., substituted with a substituent group, a size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{10}$ or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered). As a non-limiting example, the Interleukin-2-inducible T-cell kinase protein covalently bonded to a compound described herein may have the formula:

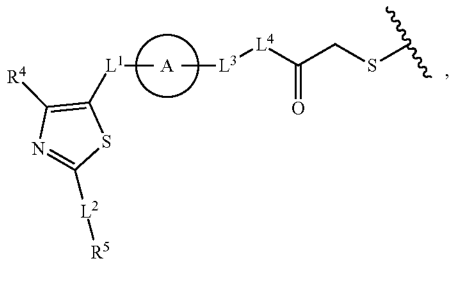

wherein S is the sulfur of a Interleukin-2-inducible T-cell kinase protein cysteine (e.g., corresponding to $C_{442}$ of human Interleukin-2-inducible T-cell kinase), which is bonded to the remainder of the Interleukin-2-inducible T-cell kinase protein and wherein $R^1$, $R^2$, $L^1$, $L^2$, z1, and z2 are as described herein.

PROVISIONAL EMBODIMENTS

Embodiment P1. A compound having the formula:

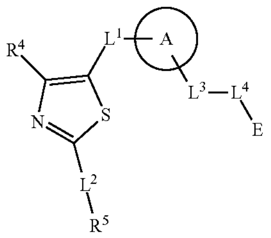

wherein, Ring A is

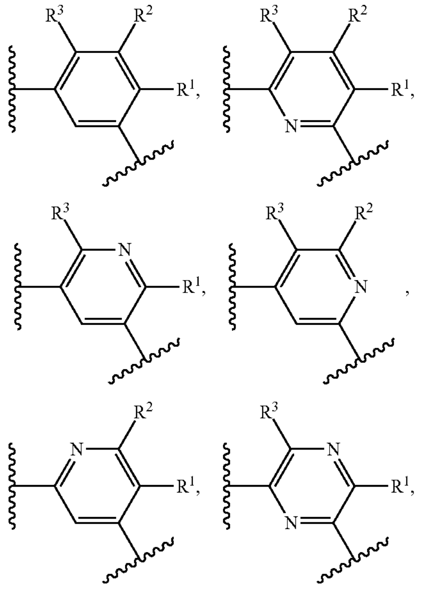

,

-continued

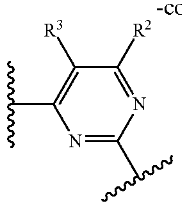,
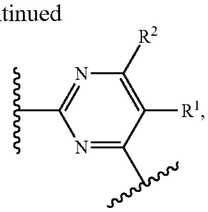,
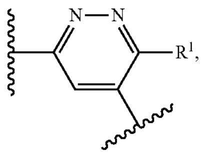,
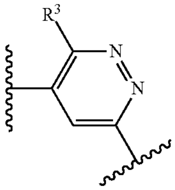,
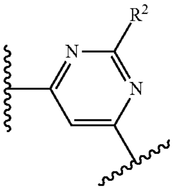 or
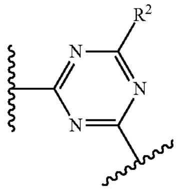;

$R^1$ is independently hydrogen, halogen, $-CX^1_3$, $-CHX^1_2$, $-CH_2X^1$, $-OCX^1_3$, $-OCH_2X^1$, $-OCHX^1_2$, —CN, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)\ R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $-CX^2_3$, $-CHX^2_2$, $-CH_2X^2$, $-OCX^2_3$, $-OCH_2X^2$, $-OCHX^2_2$, —CN, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)\ R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, $-CX^3_3$, $-CHX^3_2$, $-CH_2X^3$, $-OCX^3_3$, $-OCH_2X^3$, $-OCHX^3_2$, —CN, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)\ R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently hydrogen, halogen, $-CX^4_3$, $-CHX^{42}$, $-CH_2X^4$, $-OCX^4_3$, $-OCH_2X^4$, $-OCHX^4_2$, —CN, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)\ R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is —O—, —S—, or substituted or unsubstituted $C_1$-$C_2$ alkylene, or substituted or unsubstituted 2 membered heteroalkylene; $L^2$ is a bond, —NH—, —NHC(O)—; $L^3$ is a bond, $-S(O)_2-$, $-N(R^6)-$, —O—, —S—, —C(O)—, $-C(O)N(R^6)-$, $-N(R^6)C(O)-$, $-N(R^6)C(O)NH-$, $-NHC(O)N(R^6)-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^6$ is independently hydrogen, $-CX^6_3$, $-CHX^6_2$, $-CH_2X^6$, —CN, $-C(O)R^{6C}$, $-C(O)OR^{6C}$, $-C(O)NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^4$ is a bond, $-S(O)_2-$, $-N(R^7)-$, —O—, —S—, —C(O)—, $-C(O)N(R^7)-$, $-N(R^7)C(O)-$, $-N(R^7)C(O)NH-$, $-NHC(O)N(R^7)-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, $-CX^7_3$, $-CHX^7_2$, $-CH_2X^7$, —CN, $-C(O)R^{7C}$, $-C(O)OR^{7C}$, $-C(O)NR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; E is an electrophilic moiety; Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$, $R^{7A}$, $R^{7B}$, and $R^{7C}$ is independently hydrogen, $-CX_3$, —CN, —COOH, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; each X, $X^1$, $X^2$, $X^3$, $X^4$, $X^6$, and $X^7$ is independently —F, —Cl, —Br, or —I; n1, n2, n3, and n4 are independently an integer from 0 to 4; and m1, m2, m3, m4, v1, v2, v3, and v4 are independently 1 to 2.

Embodiment P2. The compound of Embodiment P1 having the formula:

(I)

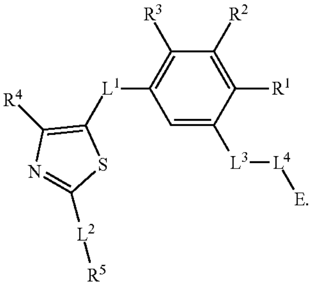

Embodiment P3. The compound of one of embodiments P1 to P2, wherein $L^1$ is —O—, —S—, or substituted or unsubstituted methylene.

Embodiment P4. The compound of one of embodiments P1 to P2, wherein $L^1$ is $—SCH_2—$.

Embodiment P5. The compound of one of embodiments P1 to P4, wherein $L^2$ is a bond.

Embodiment P6. The compound of one of embodiments P1 to P4, wherein $L^2$ is —NH—.

Embodiment P7. The compound of one of embodiments P1 to P4, wherein $L^2$ is —NHC(O)—.

Embodiment P8. The compound of one of embodiments P1 to P7, wherein $R^4$ is hydrogen.

Embodiment P9. The compound of one of embodiments P1 to P8, wherein $R^2$ is unsubstituted $C_1$-$C_2$ alkyl.

Embodiment P10. The compound of one of embodiments P1 to P8, wherein $R^2$ is unsubstituted methyl.

Embodiment P11. The compound of one of embodiments P1 to P8, wherein $R^2$ is hydrogen.

Embodiment P12. The compound of one of embodiments P1 to P3 having the formula:

(II)

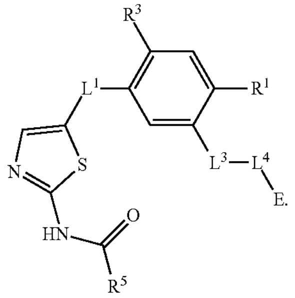

Embodiment P13. The compound of one of embodiments P1 to P3 having the formula:

(IIA)

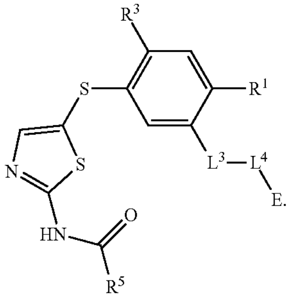

Embodiment P14. The compound of one of embodiments P1 to P3 having the formula:

(IIB)

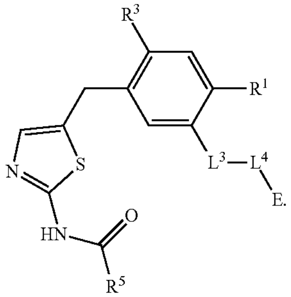

Embodiment P15. The compound of one of embodiments P1 to P3 having the formula:

(IIC)

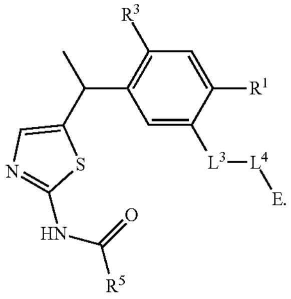

Embodiment P16. The compound of Embodiment P1 having the formula:

(III)

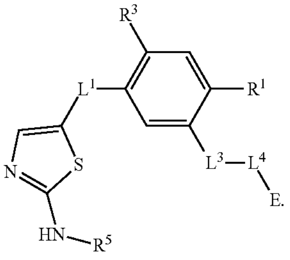

Embodiment P17. The compound of one of embodiments P1 or P16 having the formula:

(IIIA)

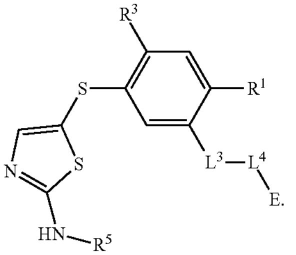

Embodiment P18. The compound of one of embodiments P1 to P16 having the formula:

(IIIB)

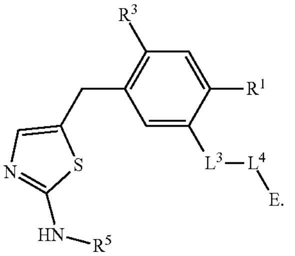

Embodiment P19. The compound of one of embodiments P1 to P16 having the formula:

(IIIC)

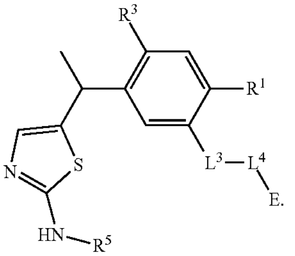

Embodiment P20. The compound of one of embodiments P1 to P19, wherein $R^1$ is independently hydrogen, halogen, $—CX^{13}$, $—CHX^{12}$, $—CH_2X^1$, $—OCX^{13}$, $—OCH_2X^1$, $—OCHX^{12}$, substituted or unsubstituted alkyl, or substituted or unsubstituted heteroalkyl.

Embodiment P21. The compound of one of embodiments P1 to 19, wherein $R^1$ is independently hydrogen, halogen, $—CX^{13}$, $—CHX^{12}$, $—CH_2X^1$, $—OCX^{13}$, $—OCH_2X^1$, $—OCHX^{12}$, substituted or unsubstituted ($C_1$-$C_4$) alkyl, or substituted or unsubstituted 2 to 4 membered heteroalkyl.

Embodiment P22. The compound of one of embodiments P1 to P19, wherein $R^1$ is hydrogen, halogen, $—CH_3$, $—CH_2CH_3$, $—CX^{13}$, $—CHX^{12}$, $—CH_2X^1$, $—OCH_3$, $—OCX^{13}$, $—OCH_2X^1$, $—OCHX^{12}$, $—SCH_3$, $—SCX^{13}$, $—SCH_2X^1$, or $—SCHX^1{}_2$.

Embodiment P23. The compound of one of embodiments P1 to P19, wherein $R^1$ is hydrogen, halogen, $—CH_3$, $—CH_2CH_3$, $—CF_3$, or $—OCH_3$.

Embodiment P24. The compound of one of embodiments P1 to P19, wherein $R^1$ is $—CH_3$, $—CH_2CH_3$, or $—OCH_3$.

Embodiment P25. The compound of one of embodiments P1 to P19, wherein $R^1$ is $—OCH_3$.

Embodiment P26. The compound of one of embodiments P1 to P25, wherein $R^3$ is independently hydrogen, halogen, $—CX^3{}_3$, $—CHX^3{}_2$, $—CH_2X^3$, $—OCX^3{}_3$, $—OCH_2X^3$, $—OCHX^3{}_2$, —CN, substituted or unsubstituted alkyl, or substituted or unsubstituted heteroalkyl.

Embodiment P27. The compound of one of embodiments P1 to P25, wherein $R^3$ is independently hydrogen, halogen, $—CX^3{}_3$, $—CHX^3{}_2$, $—CH_2X^3$, $—OCX^{33}$, $—OCH_2X^3$, $—OCHX^3{}_2$, —CN, substituted or unsubstituted ($C_1$-$C_4$) alkyl, or substituted or unsubstituted 2 to 4 membered heteroalkyl.

Embodiment P28. The compound of one of embodiments P1 to P25, wherein $R^3$ is hydrogen, halogen, $—CH_3$, $—CH_2CH_3$, $—CX^3{}_3$, $—CHX^3{}_2$, $—CH_2X^3$, $—OCH_3$, $—OCX^3{}_3$, $—OCH_2X^3$, $—OCHX^3{}_2$, —CN, $—SCH_3$, $—SCX^3{}_3$, $—SCH_2X^3$, or $—SCHX^3{}_2$.

Embodiment P29. The compound of one of embodiments P1 to P25, wherein $R^3$ is hydrogen, halogen, —CN, $—CH_3$, $—CF_3$, or $—OCH_3$.

Embodiment P30. The compound of one of embodiments P1 to P25, wherein $R^3$ is halogen or $—CH_3$.

Embodiment P31. The compound of one of embodiments P1 to P25, wherein $R^3$ is —Cl or $—CH_3$.

Embodiment P32. The compound of one of embodiments P1 to P25, wherein $R^3$ is $—CH_3$.

Embodiment P33. The compound of one of embodiments P1 to P32, wherein $R^5$ is independently substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl.

Embodiment P34. The compound of one of embodiments P1 to P32, wherein $R^5$ is independently substituted or unsubstituted ($C_1$-$C_4$) alkyl.

Embodiment P35. The compound of one of embodiments P1 to P32, wherein $R^5$ is independently unsubstituted ($C_1$-$C_4$) alkyl.

Embodiment P36. The compound of one of embodiments P1 to P32, wherein $R^5$ is independently unsubstituted methyl, unsubstituted ethyl, unsubstituted isopropyl, or unsubstituted tert-butyl.

Embodiment P37. The compound of one of embodiments P1 to P32, wherein $R^5$ is independently unsubstituted methyl or unsubstituted ethyl.

Embodiment P38. The compound of one of embodiments P1 to P32, wherein $R^5$ is independently substituted or unsubstituted 2 to 8 membered heteroalkyl.

Embodiment P39. The compound of one of embodiments P1 to P32, wherein $R^5$ is independently substituted or unsubstituted 2 to 4 membered heteroalkyl.

Embodiment P40. The compound of one of embodiments P1 to P32, wherein $R^5$ is independently unsubstituted 2 to 4 membered heteroalkyl.

Embodiment P41. The compound of one of embodiments P1 to P32, wherein $R^5$ is independently $—CH_2N(CH_3)_2$.

Embodiment P42. The compound of one of embodiments P1 to P32, wherein $R^5$ is independently substituted or unsubstituted ($C_3$-$C_6$) cycloalkyl.

Embodiment P43. The compound of one of embodiments P1 to P32, wherein $R^5$ is independently unsubstituted ($C_3$-$C_6$) cycloalkyl.

Embodiment P44. The compound of one of embodiments P1 to P32, wherein $R^5$ is independently unsubstituted cyclopropyl, unsubstituted cyclobutyl, or unsubstituted cyclopentyl.

Embodiment P45. The compound of one of embodiments P1 to P32, wherein $R^5$ is independently unsubstituted cyclopropyl or unsubstituted cyclobutyl.

Embodiment P46. The compound of one of embodiments P1 to P32, wherein $R^5$ is independently unsubstituted cyclopropyl.

Embodiment P47. The compound of one of embodiments P1 to P32, wherein $R^5$ is independently substituted or unsubstituted 3 to 6 membered heterocycloalkyl.

Embodiment P48. The compound of one of embodiments P1 to P32, wherein $R^5$ is independently substituted or unsubstituted 5 to 6 membered heterocycloalkyl.

Embodiment P49. The compound of one of embodiments P1 to P32, wherein $R^5$ is independently substituted or unsubstituted 6 membered heterocycloalkyl.

Embodiment P50. The compound of one of embodiments P1 to P32, wherein $R^5$ is independently substituted or unsubstituted piperidinyl.

Embodiment P51. The compound of one of embodiments P1 to P32, wherein $R^5$ is independently

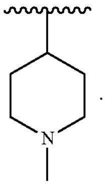

Embodiment P52. The compound of one of embodiments P1 to P32, wherein $R^5$ is independently substituted or unsubstituted phenyl.

Embodiment P53. The compound of one of embodiments P1 to P32, wherein $R^5$ is independently unsubstituted phenyl.

Embodiment P54. The compound of one of embodiments P1 to P32, wherein $R^5$ is independently 2-substituted phenyl.

Embodiment P55. The compound of one of embodiments P1 to P32, wherein $R^5$ is independently 3-substituted phenyl.

Embodiment P56. The compound of one of embodiments P1 to P32, wherein $R^5$ is independently 4-substituted phenyl.

Embodiment P57. The compound of one of embodiments P1 to P32, wherein $R^5$ is independently phenyl substituted with halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P58. The compound of one of embodiments P1 to P32, wherein $R^5$ is independently phenyl substituted with halogen, substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl.

Embodiment P59. The compound of one of embodiments P1 to P32, wherein $R^5$ is independently phenyl substituted with —F,

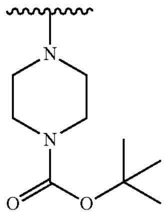
,
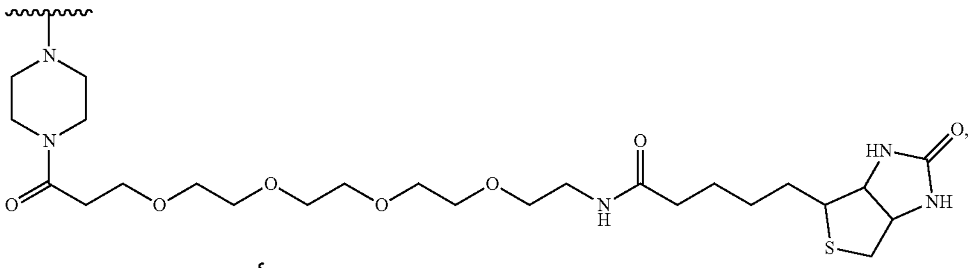

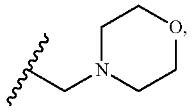
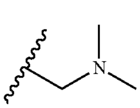
, or
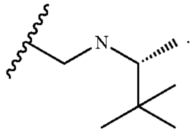

Embodiment P60. The compound of one of embodiments P1 to P32, wherein $R^5$ is independently

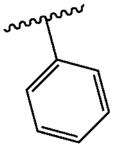
,
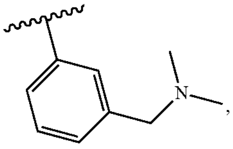
,
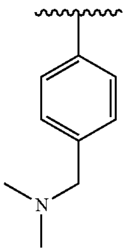
,
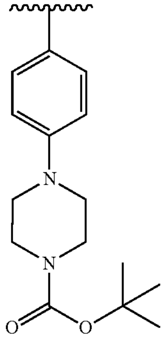
,

-continued

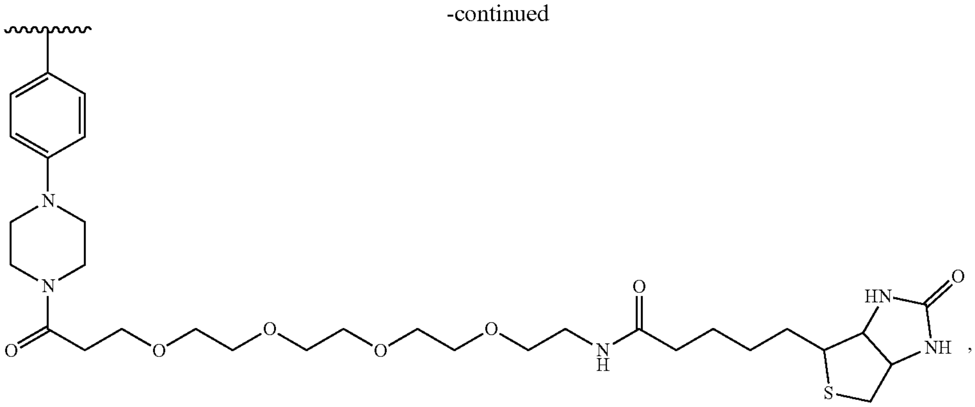
,

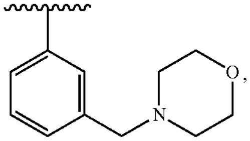
,
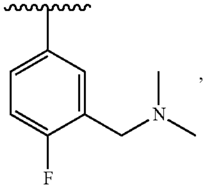
, or
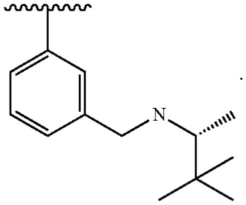
.

Embodiment P61. The compound of one of embodiments P1 to P32, wherein $R^5$ is independently

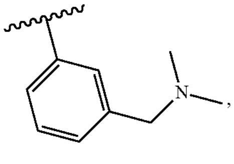
,
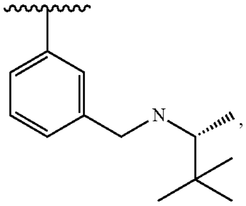
, or
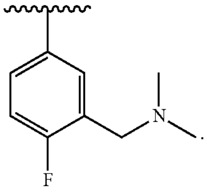
.

Embodiment P62. The compound of one of embodiments P1 to P32, wherein $R^5$ is independently substituted or unsubstituted heteroaryl.

Embodiment P63. The compound of one of embodiments P1 to P32, wherein $R^5$ is independently substituted or unsubstituted 5 to 6 membered heteroaryl.

Embodiment P64. The compound of one of embodiments P1 to P32, wherein $R^5$ is independently substituted or unsubstituted pyridyl, substituted or unsubstituted thienyl, substituted or unsubstituted furanyl, substituted or unsubstituted pyrrolyl, substituted or unsubstituted imidazolyl, substituted or unsubstituted pyrazolyl, substituted or unsubstituted thiazolyl, substituted or unsubstituted isothiazolyl, substituted or unsubstituted oxazolyl, or substituted or unsubstituted isoxazolyl.

Embodiment P65. The compound of one of embodiments P1 to P32, wherein $R^5$ is independently

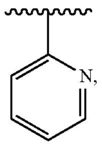
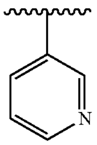
,
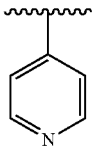
,
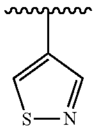
,
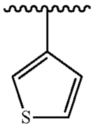
,
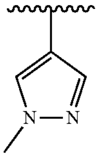
,
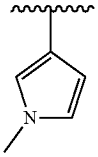
,
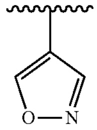
,
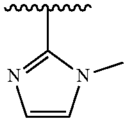
,
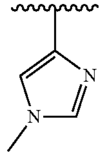
,
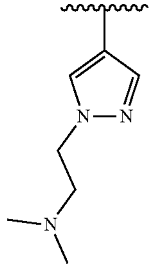
.

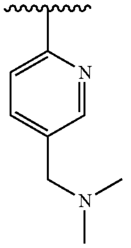
,
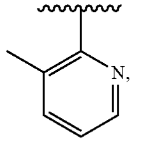
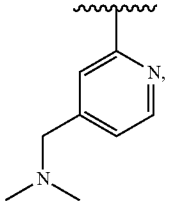

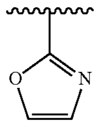
,
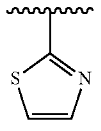
,
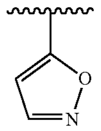
, or
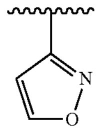
.

Embodiment P66. The compound of one of embodiments P1 to P32, wherein $R^5$ is independently

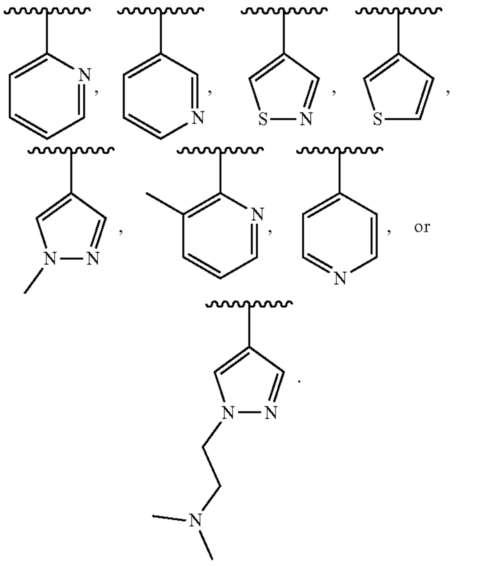

, , , , , , , or .

Embodiment P67. The compound of one of embodiments P1 to P66, wherein $L^3$ is a bond, —$N(R^6)$—, —C(O)—, or —C(O)$N(R^6)$—; and $R^6$ is independently hydrogen, —$CX^6_3$, —$CHX^6_2$, —$CH_2X^6$, or unsubstituted ($C_1$-$C_4$) alkyl.

Embodiment P68. The compound of one of embodiments P1 to P66, wherein $L^3$ is a bond, —$N(R^6)$—, —C(O)—, or —C(O)$N(R^6)$—; and $R^6$ is independently hydrogen or unsubstituted methyl.

Embodiment P69. The compound of one of embodiments P1 to P66, wherein $L^3$ is a bond, —C(O)—, —C(O)N($CH_3$)—, —N($CH_3$)—, or —NH—.

Embodiment P70. The compound of one of embodiments P1 to P66, wherein $L^3$ is a bond.

Embodiment P71. The compound of one of embodiments P1 to P66, wherein $L^3$ is —C(O)—.

Embodiment P72. The compound of one of embodiments P1 to P71, wherein $L^4$ is a bond, —$N(R^7)$—, —C(O)—, —C(O)$N(R^7)$—, substituted or unsubstituted heterocycloalkylene, substituted or unsubstituted fused ring heterocycloalkylene, substituted or unsubstituted spirocyclic heterocycloalkylene, or substituted or unsubstituted bridged ring heterocycloalkylene; and $R^7$ is independently hydrogen, —$CX^7_3$, —$CHX^7_2$, —$CH_2X^7$, or unsubstituted ($C_1$-$C_4$) alkyl.

Embodiment P73. The compound of one of embodiments P1 to P71, wherein $L^4$ is a bond, —$N(R^7)$—, substituted or unsubstituted heterocycloalkylene, substituted or unsubstituted fused ring heterocycloalkylene, substituted or unsubstituted spirocyclic heterocycloalkylene, or substituted or unsubstituted bridged ring heterocycloalkylene; and $R^7$ is independently hydrogen, —$CX^7_3$, —$CHX^7_2$, —$CH_2X^7$, or unsubstituted ($C_1$-$C_4$) alkyl.

Embodiment P74. The compound of one of embodiments P1 to P71, wherein $L^4$ is a bond, substituted or unsubstituted monocyclic heterocycloalkylene, substituted or unsubstituted fused ring heterocycloalkylene, or substituted or unsubstituted spirocyclic heterocycloalkylene, or substituted or unsubstituted bridged ring heterocycloalkylene.

Embodiment P75. The compound of one of embodiments P1 to P71, wherein $L^4$ is a substituted or unsubstituted 4 to 10 membered monocyclic heterocycloalkylene, substituted or unsubstituted 5 to 10 membered fused ring heterocycloalkylene, substituted or unsubstituted 6 to 10 membered spirocyclic heterocycloalkylene, or substituted or unsubstituted 5 to 10 membered bridged ring heterocycloalkylene.

Embodiment P76. The compound of one of embodiments P1 to P71, wherein $L^4$ is a substituted or unsubstituted 5 to 10 membered monocyclic heterocycloalkylene, substituted or unsubstituted 6 to 10 membered fused ring heterocycloalkylene, substituted or unsubstituted 7 to 10 membered spirocyclic heterocycloalkylene, or substituted or unsubstituted 5 to 10 membered bridged ring heterocycloalkylene.

Embodiment P77. The compound of one of embodiments P1 to P71, wherein $L^4$ is a substituted or unsubstituted 5 to 8 membered monocyclic heterocycloalkylene, substituted or unsubstituted 7 to 8 membered fused ring heterocycloalkylene, substituted or unsubstituted 7 to 8 membered spirocyclic heterocycloalkylene, or substituted or unsubstituted 7 to 8 membered bridged ring heterocycloalkylene.

Embodiment P78. The compound of one of embodiments P1 to P71, wherein $L^4$ is an unsubstituted 7 to 8 membered bridged ring heterocycloalkylene.

Embodiment P79. The compound of one of embodiments P1 to P71, wherein $L^4$ is an unsubstituted 7 to 8 membered fused ring heterocycloalkylene.

Embodiment P80. The compound of one of embodiments P1 to P71, wherein $L^4$ is an unsubstituted 7 to 8 membered spirocyclic heterocycloalkylene.

Embodiment P81. The compound of one of embodiments P1 to P71, wherein $L^4$ is a methyl-substituted, ethyl-substituted, cyano-substituted, halo-substituted, or unsubstituted 5 to 8 membered monocyclic heterocycloalkylene.

Embodiment P82. The compound of one of embodiments P1 to P71, wherein $L^4$ is an unsubstituted 5 to 8 membered monocyclic heterocycloalkylene.

Embodiment P83. The compound of one of embodiments P1 to P71, wherein $L^4$ is a methyl-substituted 5 to 8 membered monocyclic heterocycloalkylene, an ethyl-substituted 5 to 8 membered monocyclic heterocycloalkylene, an isopropyl-substituted 5 to 8 membered monocyclic heterocycloalkylene, or a tert-butyl-substituted 5 to 8 membered monocyclic heterocycloalkylene.

Embodiment P84. The compound of one of embodiments P1 to P71, wherein $L^4$ is a bond, —NH—,

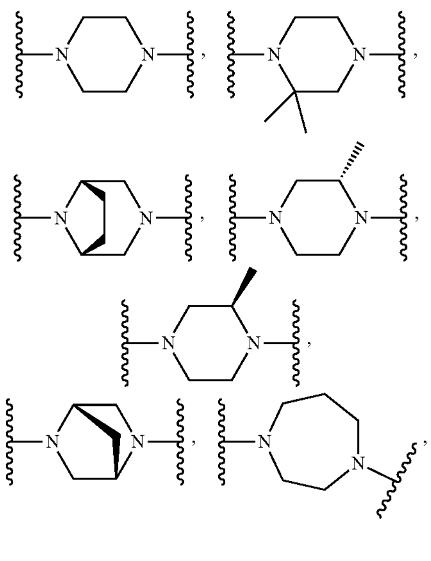

, , , , , ,

-continued
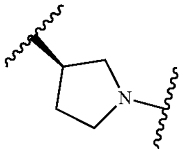, 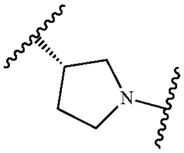,
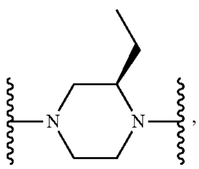, 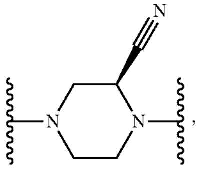,
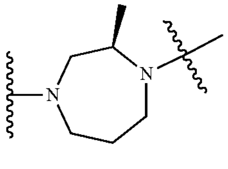, 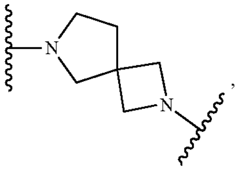,
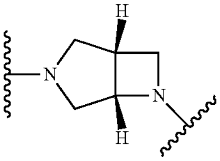,
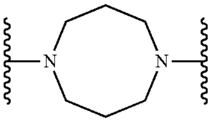, 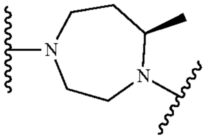,
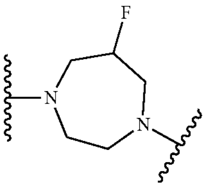, or 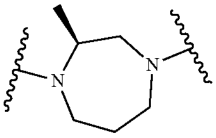,
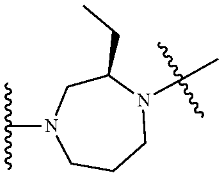,
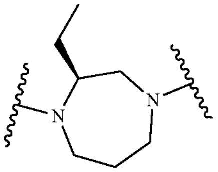, 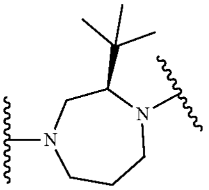,
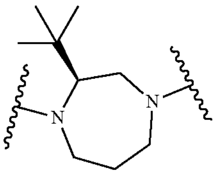, 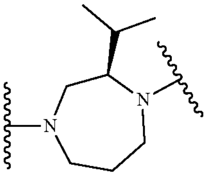,
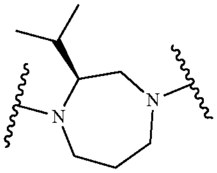, 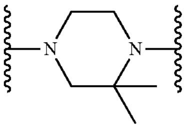,
-continued
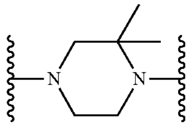, 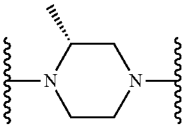,
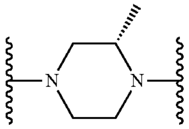, 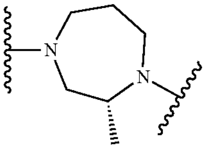, or
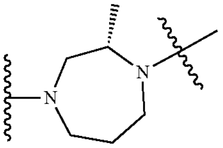.
Embodiment P85. The compound of one of embodiments P1 to P71, wherein $L^4$ is a bond, —NH—,
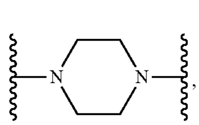, 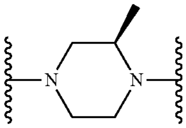,
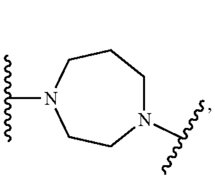, 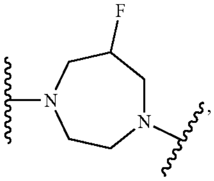,
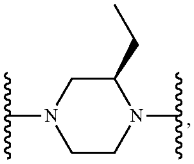, 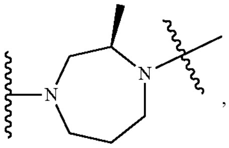,
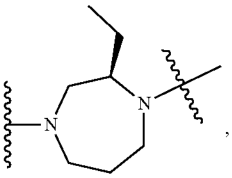, 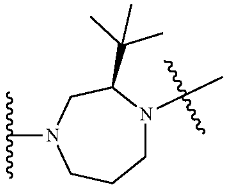, or
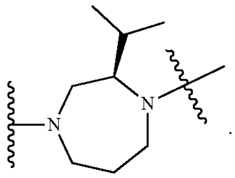.
Embodiment P86. The compound of one of embodiments P1 to P85, wherein E is a covalent cysteine modifier moiety.
Embodiment P87. The compound of one of embodiments P1 to P85, wherein E is

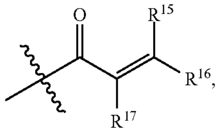 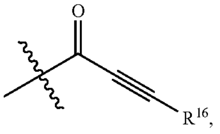

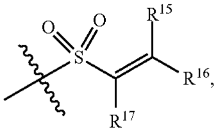 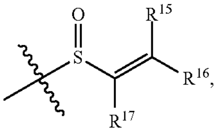

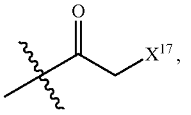 or 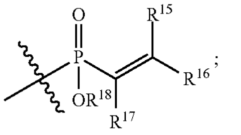

$R^{15}$ is independently hydrogen, halogen, $—CX^{15}_3$, $—CHX^{15}_2$, $—CH_2X^{15}$, —CN, $—SO_{n15}R^{15D}$, $—SO_{v15}NR^{15A}R^{15B}$, $—NHNR^{15A}R^{15B}$, $—ONR^{15A}R^{15B}$, $—NHC{=}(O)NHNR^{15A}R^{15B}$, $—NHC(O)NR^{15A}R^{15B}$, $—N(O)_{m15}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—OCX^{15}_3$, $—OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16}$ is independently hydrogen, halogen, $—CX^{16}_3$, $—CHX^{16}_2$, $—CH_2X^{16}$, —CN, $—SO_{n16}R^{16D}$, $—SO_{v16}NR^{16A}R^{16B}$, $—NHNR^{16A}R^{16B}$, $—ONR^{16A}R^{16B}$, $—NHC{=}(O)NHNR^{16A}R^{16B}$, $—NHC(O)NR^{16A}R^{16B}$, $—N(O)_{m16}$, $—NR^{16A}R^{16B}$, $—C(O)R^{16C}$, $—C(O)—OR^{16C}$, $—C(O)NR^{16A}R^{16B}$, $—OR^{16D}$, $—NR^{16A}SO_2R^{16D}$, $—NR^{16A}C(O)R^{16C}$, $—NR^{16A}C(O)OR^{16C}$, $—NR^{16A}OR^{16C}$, $—OCX^{16}_3$, $—OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $—CX^{17}_3$, $—CHX^{17}_2$, $—CH_2X^{17}$, —CN, $—SO_{n17}R^{17D}$, $—SO_{v17}NR^{17A}R^{17B}$, $—NHNR^{17A}R^{17B}$, $—ONR^{17A}R^{17B}$, $—NHC{=}(O)NHNR^{17A}R^{17B}$, $—NHC(O)NR^{17A}R^{17B}$, $—N(O)_{m17}$, $—NR^{17A}R^{17B}$, $—C(O)R^{17C}$, $—C(O)—OR^{17C}$, $—C(O)NR^{17A}R^{17B}$, $—OR^{17D}$, $—NR^{17A}SO_2R^{17D}$, $—NR^{17A}C(O)R^{17C}$, $—NR^{17A}C(O)OR^{17C}$, $—NR^{17A}OR^{17C}$, $—OCX^{17}_3$, $—OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, $—CX^{18}_3$, $—CHX^{18}_2$, $—CH_2X^{18}$, $—C(O)R^{18C}$, $—C(O)OR^{18C}$, $—C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{15A}$, $R^{15B}$, $R^{15C}$, $R^{15D}$, $R^{16A}$, $R^{16B}$, $R^{6C}$, $R^{16D}$, $R^{17A}$, $R^{17B}$, $R^{17C}$, $R^{17D}$, $R^{18A}$, $R^{18B}$, $R^{18C}$, $R^{18D}$, are independently hydrogen, $—CX_3$, —CN, —COOH, $—CONH_2$, $—CHX_2$, $—CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; each X, $X^{15}$, $X^{16}$, $X^{17}$ and $X^{18}$ is independently —F, —Cl, —Br, or —I; n15, n16, n17, v15, v16, and v17, are independently an integer from 0 to 4; and m15, m16, and m17 are independently 1 or 2.

Embodiment P88. The compound of Embodiment P87, wherein $R^{15}$ is independently hydrogen, halogen, $CX^{15}_3$, $—CHX^{15}_2$, $—CH_2X^{15}$, —CN, $—SR^{15D}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}C(O)R^{15C}$, $—NR^{15A}C(O)OR^{15C}$, $—OCX^{15}_3$, $—OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16}$ is independently hydrogen, halogen, $CX^{16}_3$, $—CHX^{16}_2$, $—CH_2X^{16}$, —CN, $—SR^{16D}$, $—NR^{16A}R^{16B}$, $—C(O)R^{16C}$, $—C(O)—OR^{16C}$, $—C(O)NR^{16A}R^{16B}$, $—OR^{16D}$, $—NR^{16A}C(O)R^{16C}$, $—NR^{16A}C(O)OR^{16C}$, $—OCX^{16}_3$, $—OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and $R^{17}$ is independently hydrogen, halogen, $—CX^{17}_3$, $—CHX^{17}_2$, $—CH_2X^{17}$, —CN, $—SR^{17D}$, $—NR^{17A}R^{17B}$, $—C(O)R^{17C}$, $—C(O)—OR^{17C}$, $—C(O)NR^{17A}R^{17B}$, $—OR^{17D}$, $—NR^{17A}C(O)R^{17C}$, $—NR^{17A}C(O)OR^{17C}$, $—OCX^{17}_3$, $—OCHX^{17}_2$, substituted or unsubstituted alkyl, or substituted or unsubstituted heteroalkyl.

Embodiment P89. The compound of one of embodiments P87 to P88, wherein $R^{15}$, $R^{16}$, $R^{17}$, and $R^{18}$ are hydrogen.

Embodiment P90. The compound of one of embodiments P87 to P89, wherein E is:

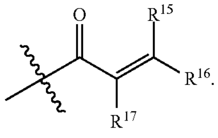

Embodiment P91. The compound of Embodiment P90, wherein $R^{15}$ is hydrogen; $R^{16}$ is hydrogen; and $R^{17}$ is hydrogen.

Embodiment P92. The compound of Embodiment P90, wherein $R^{15}$ is hydrogen; $R^{16}$ is hydrogen, $—CH_3$, $—CH_2NR^{16A}R^{16B}$, or

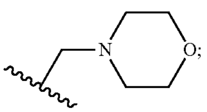 [SMILES: *CN1CCOCC1]

$R^{17}$ is hydrogen; and $R^{16A}$ and $R^{16B}$ are independently hydrogen or unsubstituted alkyl.

Embodiment P93. The compound of Embodiment P92, wherein $R^{16A}$ and $R^{16B}$ are independently unsubstituted methyl.

Embodiment P94. The compound of Embodiment P90, wherein $R^{15}$ is hydrogen; $R^{16}$ is hydrogen; $R^{17}$ is hydrogen, —$CH_3$, —$CH_2NR^{17A}R^{17B}$, or

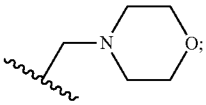 [SMILES: *CN1CCOCC1];

and $R^{17A}$ and $R^{17B}$ are independently hydrogen or unsubstituted alkyl.

Embodiment P95. The compound of Embodiment P94, wherein $R^{17A}$ and $R^{17B}$ are independently unsubstituted methyl.

Embodiment P96. The compound of Embodiment P90, wherein $R^{15}$ is hydrogen, —$CH_3$, —$CH_2NR^{15A}R^{15B}$, or

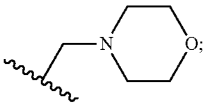 [SMILES: *CN1CCOCC1];

$R^{16}$ is hydrogen; $R^{17}$ is hydrogen; and $R^{15A}$ and $R^{15B}$ are independently hydrogen or unsubstituted alkyl.

Embodiment P97. The compound of Embodiment P96, wherein $R^{15A}$ and $R^{15B}$ are independently unsubstituted methyl.

Embodiment P98. The compound of one of embodiments P1 to P85, wherein E is —$C(O)CH{=}CH_2$, —$C(O)CH{=}CHCH_2N(CH_3)_2$, —$C(O)C({=}CH_2)CH_2N(CH_3)_2$, —$C(O)C{\equiv}CCH_3$, —$C(O)C({=}CH_2)CH_3$.

Embodiment P99. The compound of Embodiment P1 having the formula:

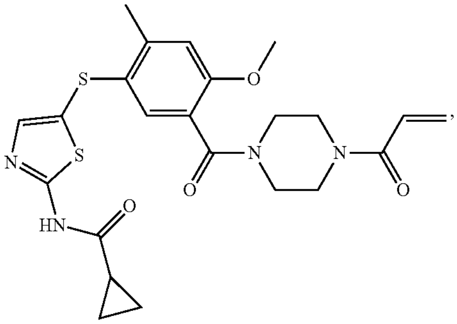,

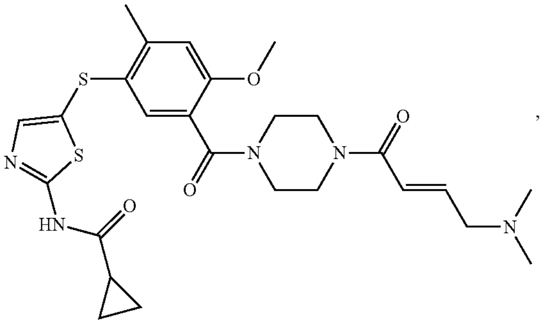,

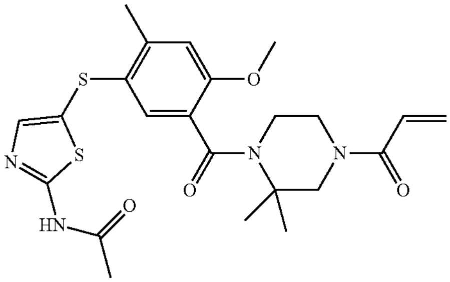,

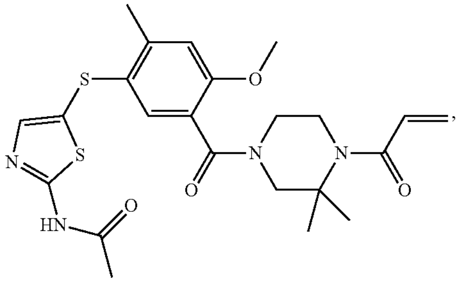,

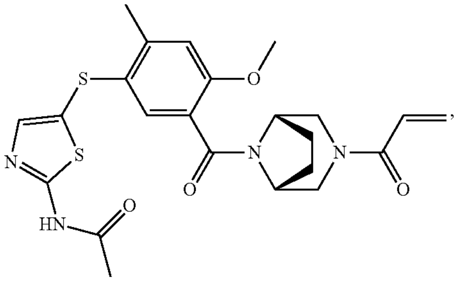,

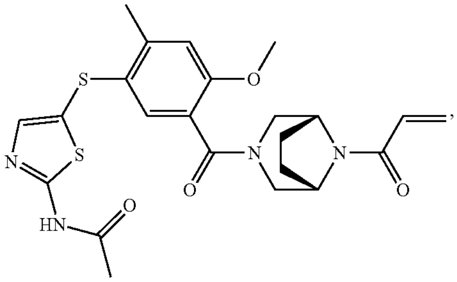,

-continued
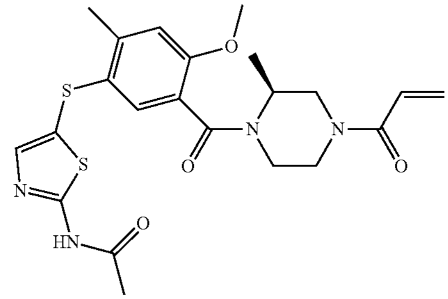,
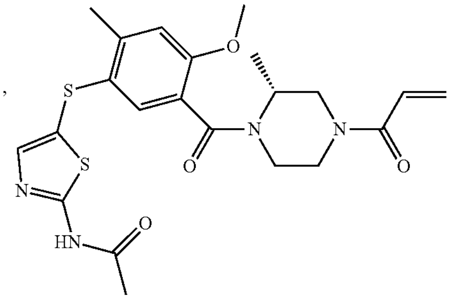,
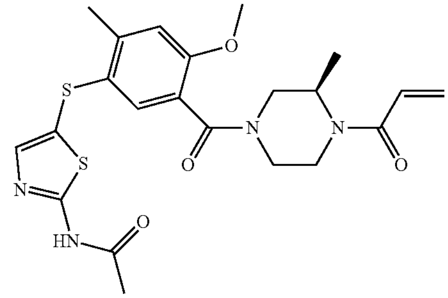,
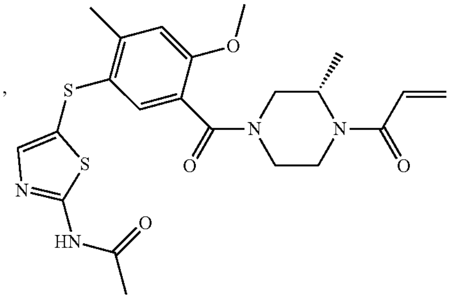,
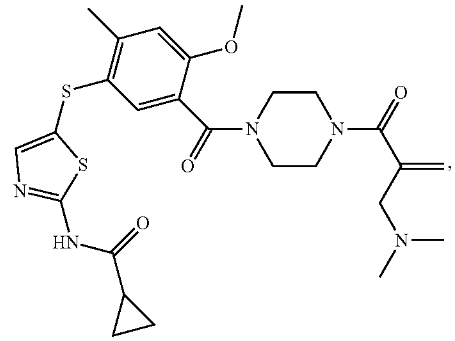,
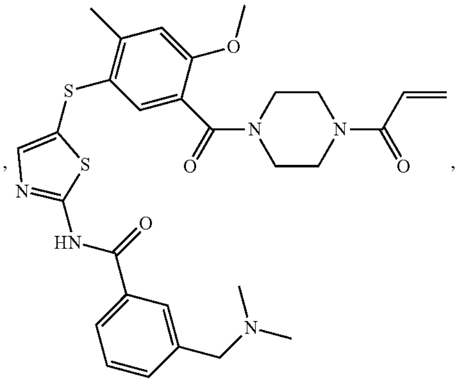,
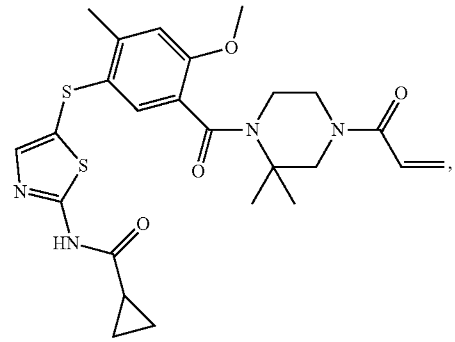,
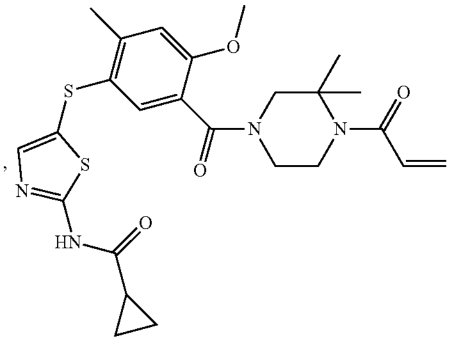,
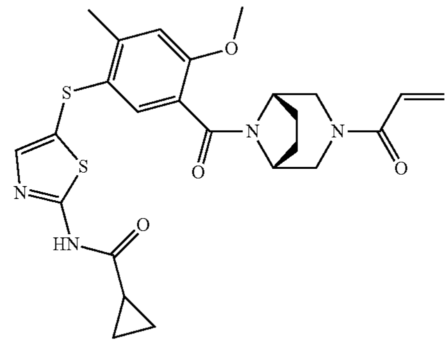,
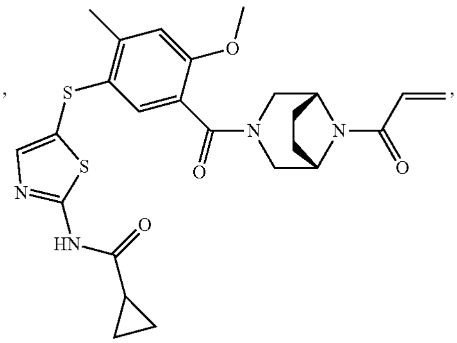, -continued
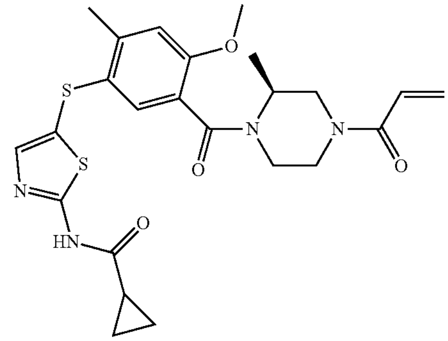,
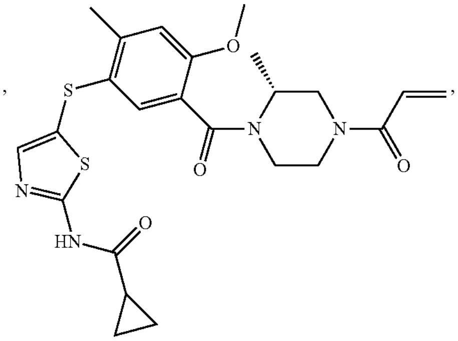,
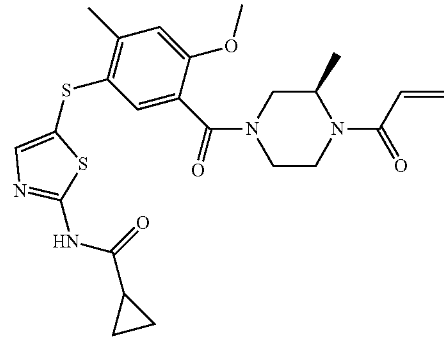,
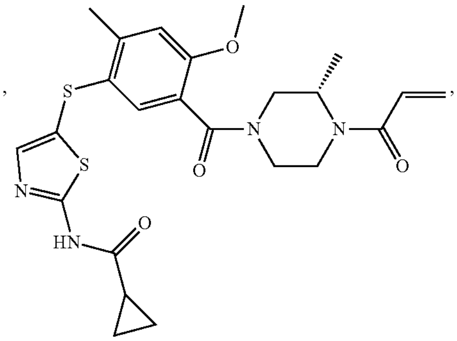,
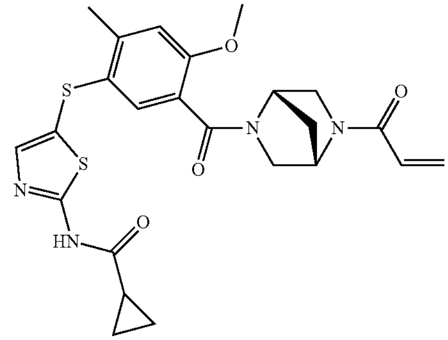,
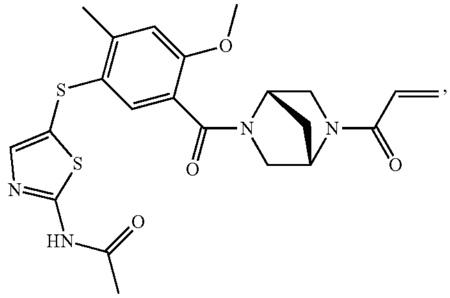,
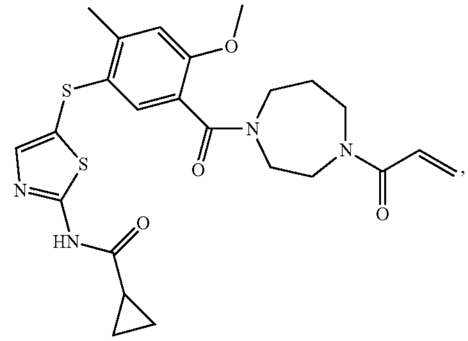,
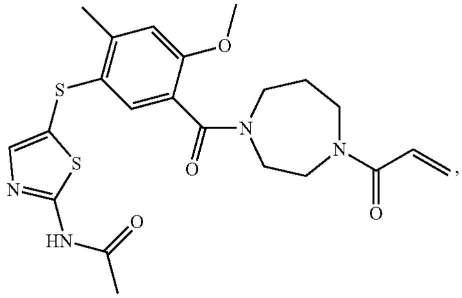,
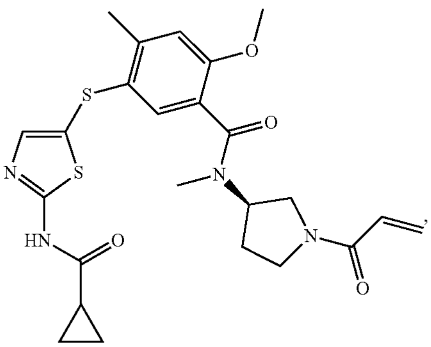,
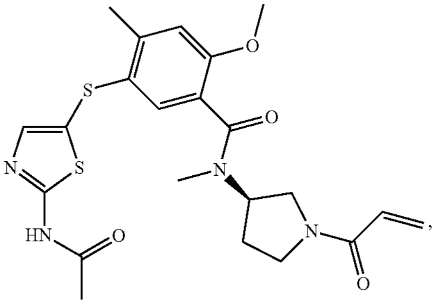, -continued
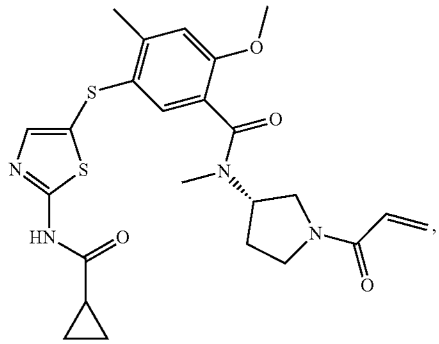
,
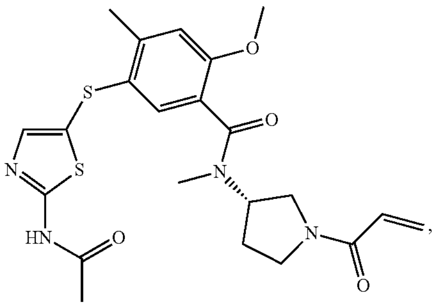
,
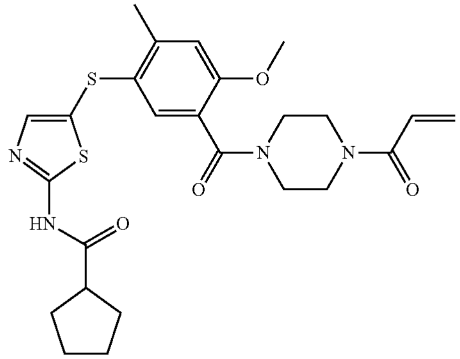
,
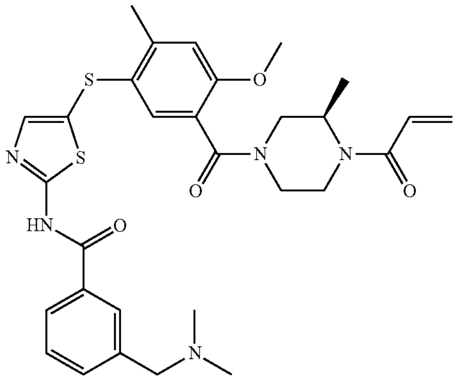
,
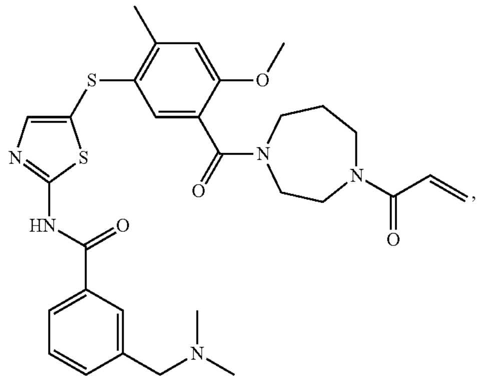
,
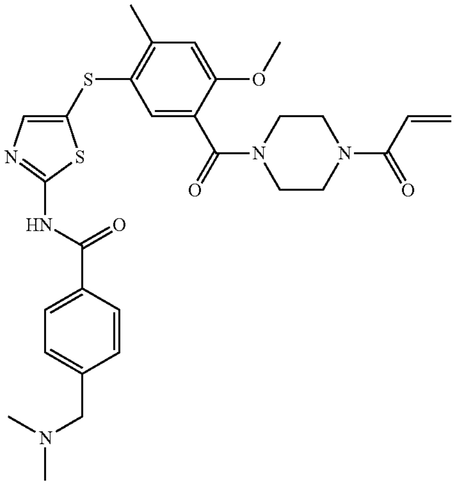
,
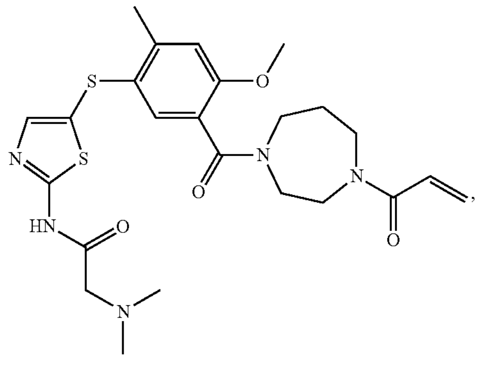
,
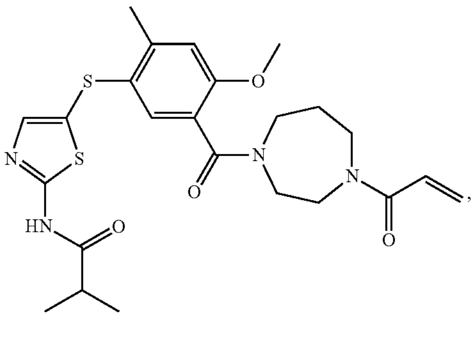
, -continued
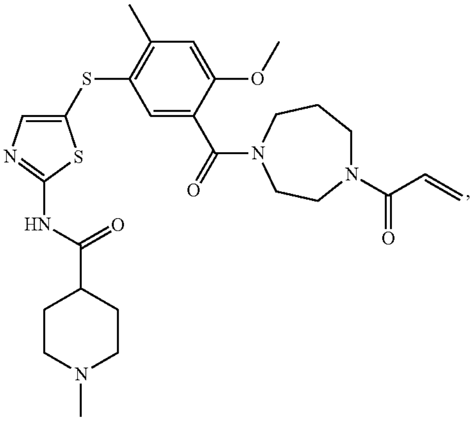,
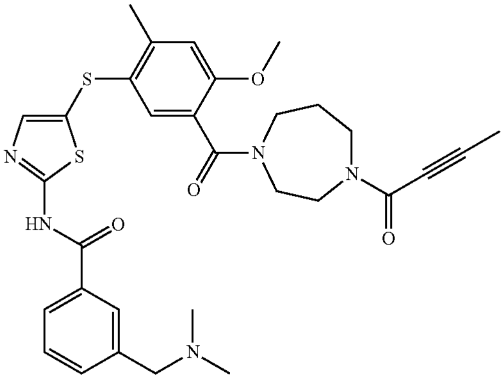,
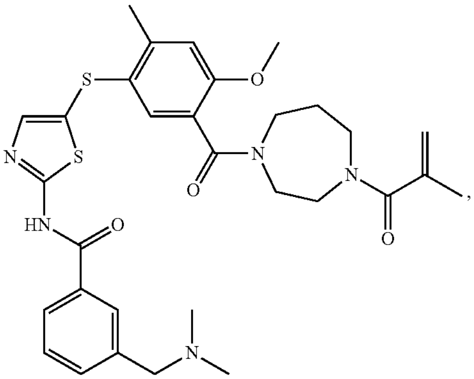,
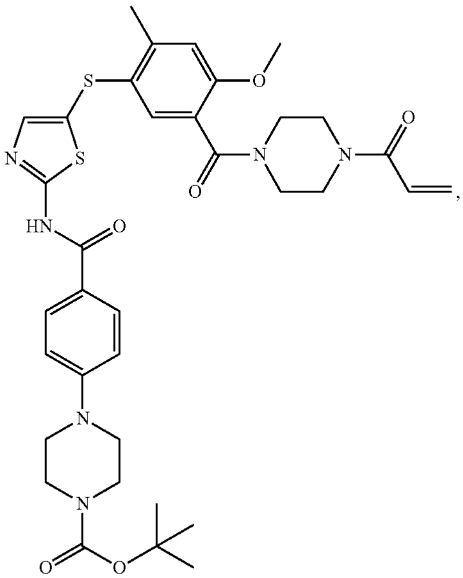,
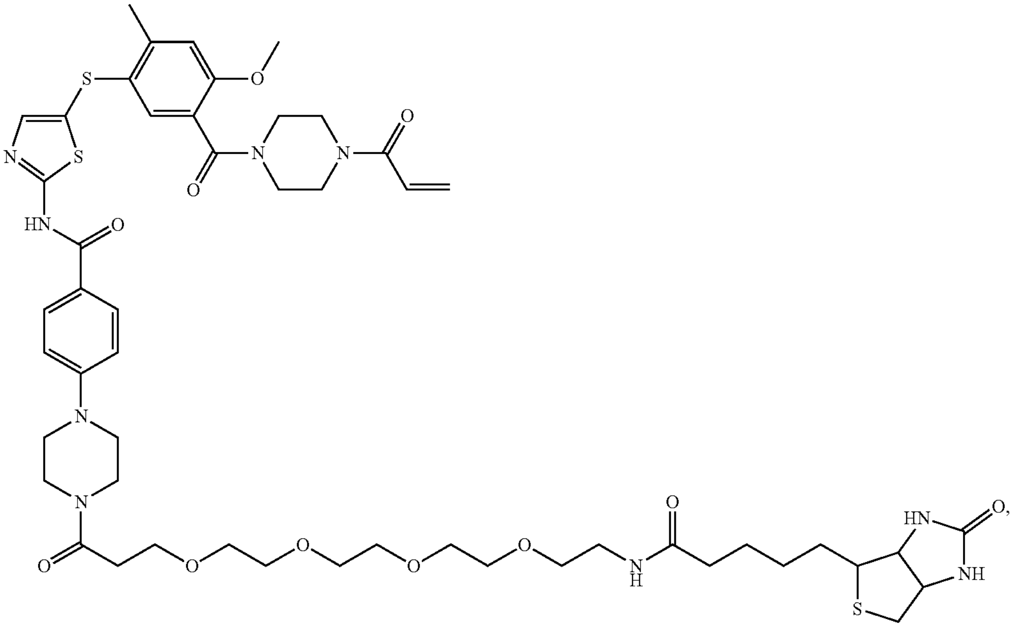, -continued
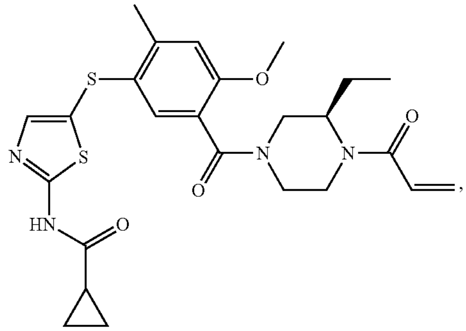
,
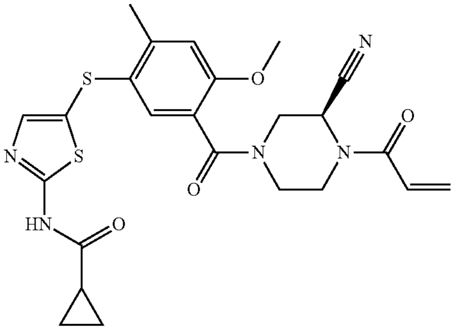
,
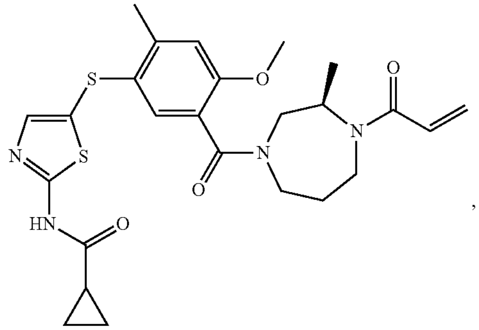
,
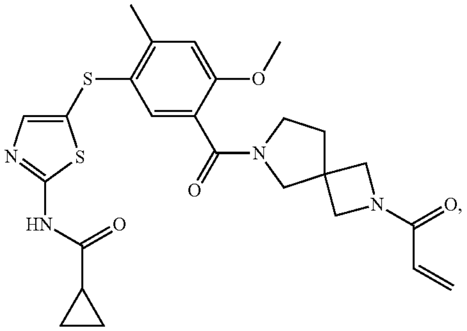
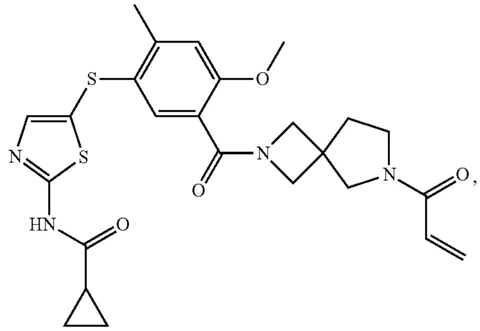
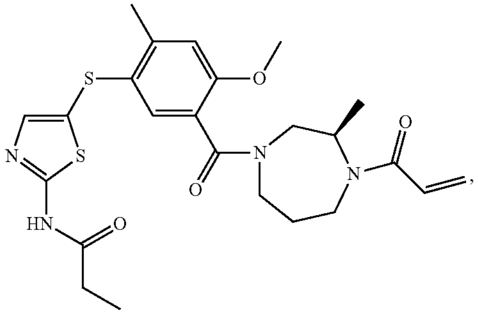
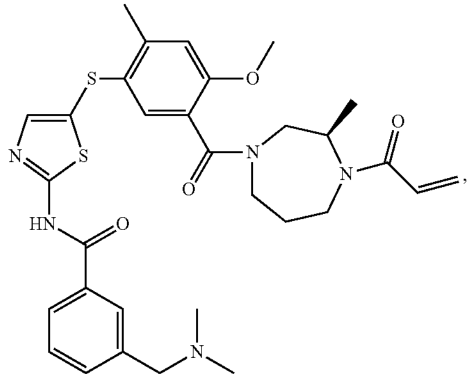
,
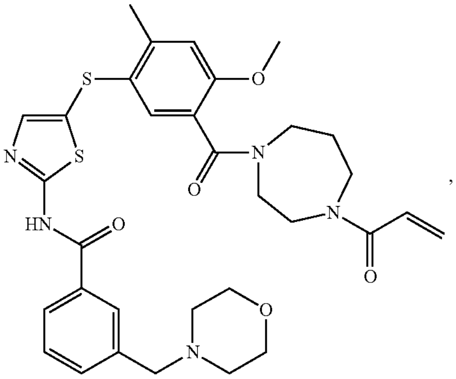
, -continued
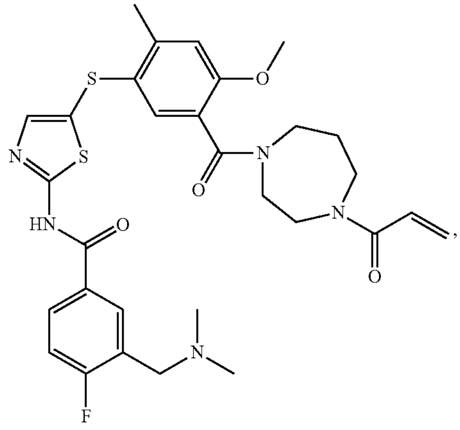
,
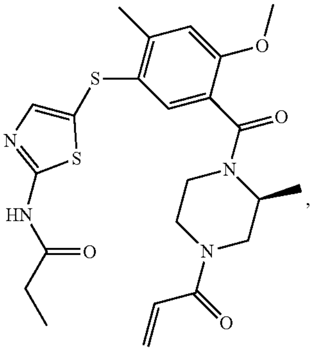
,
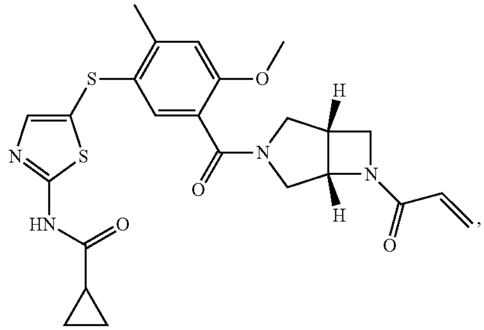
,
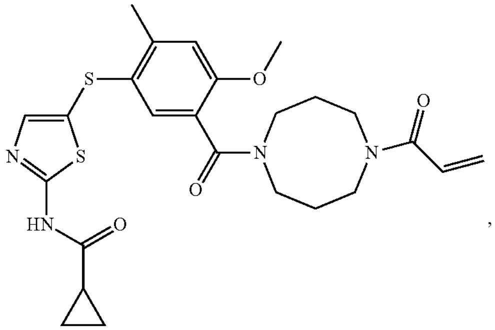
,
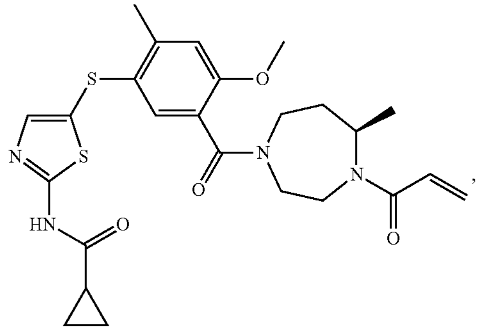
,
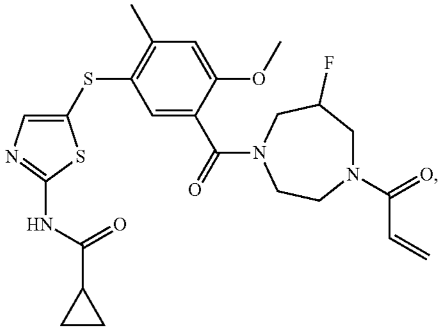
,
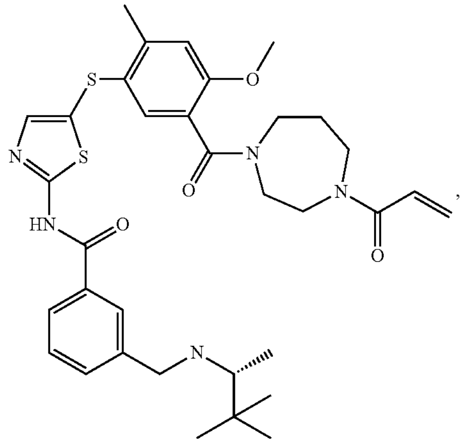
,
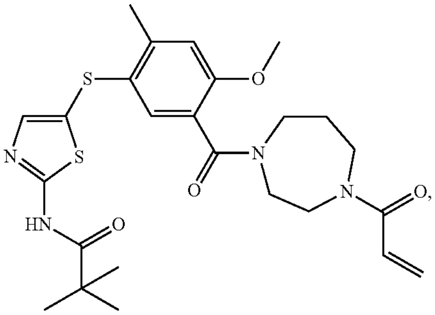
, -continued
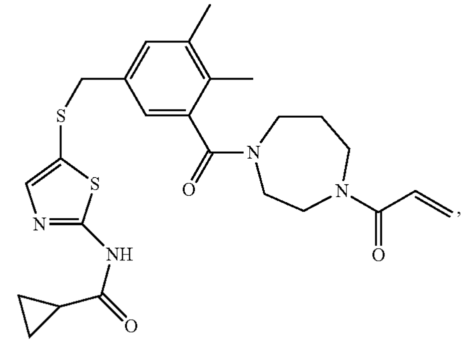,
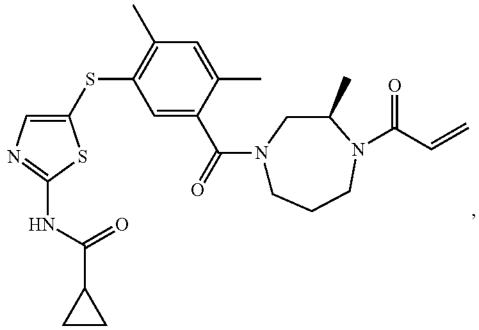,
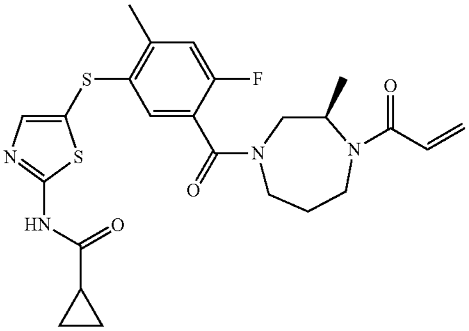,
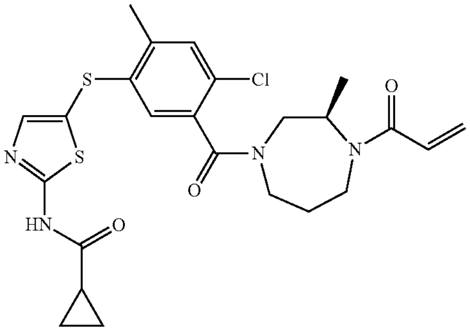,
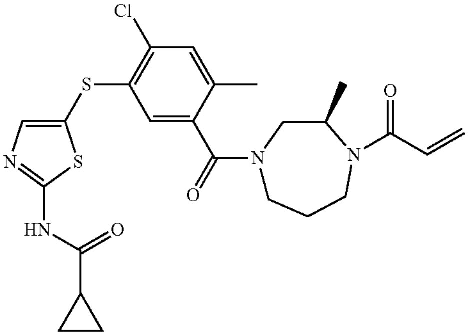,
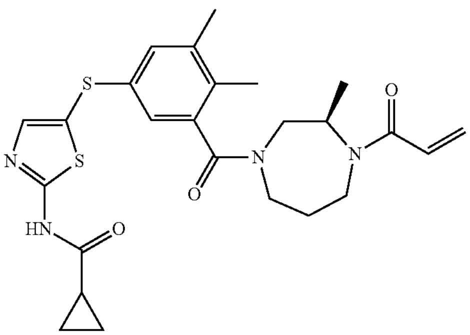,
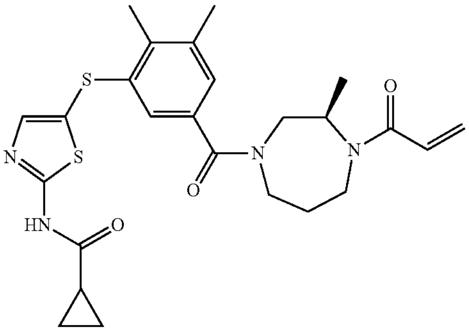,
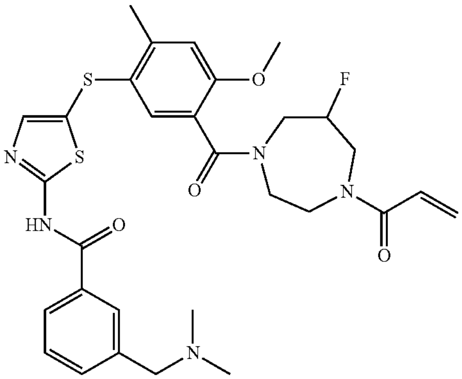,
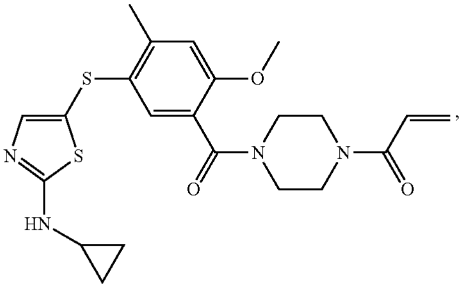,
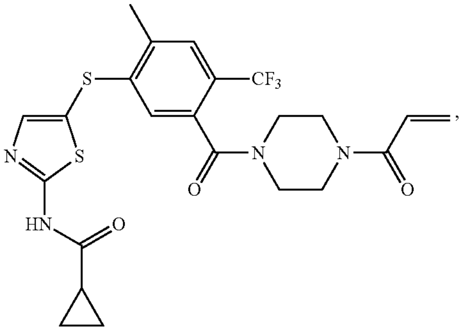, -continued
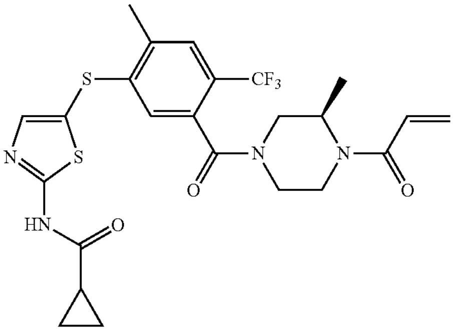,
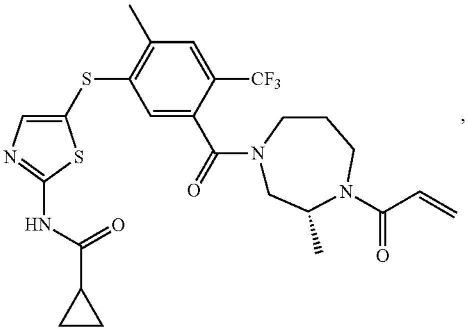,
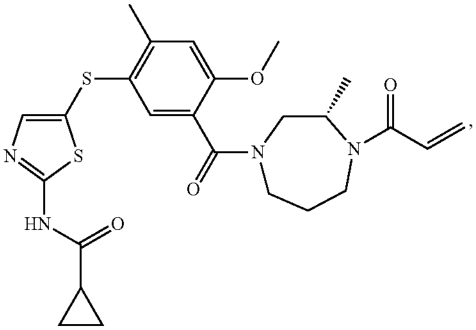,
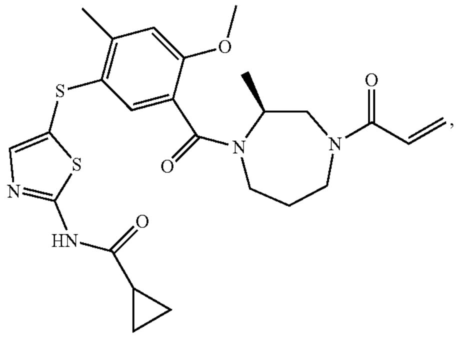,
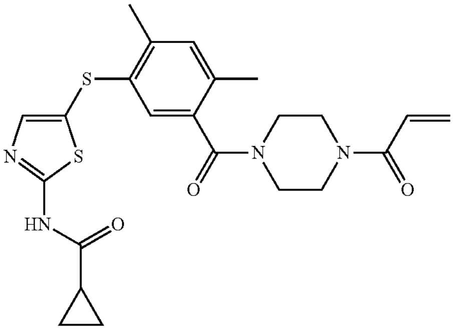,
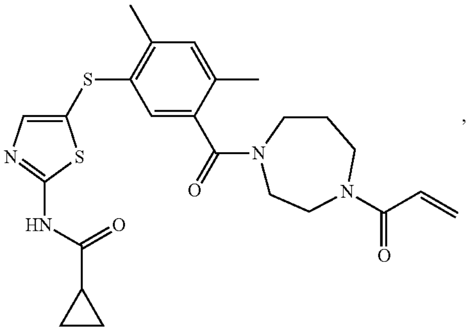,
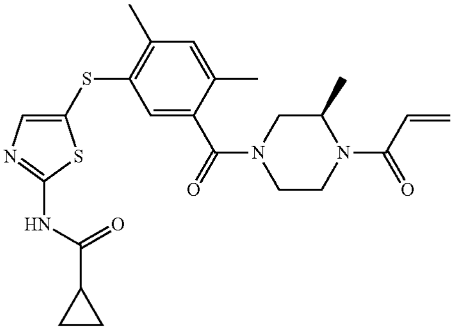,
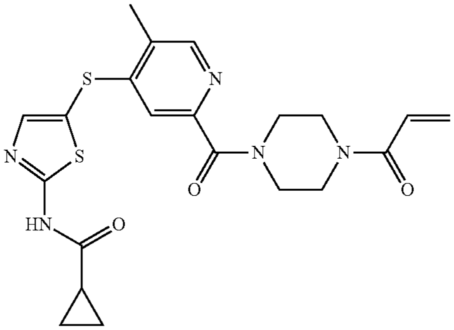,
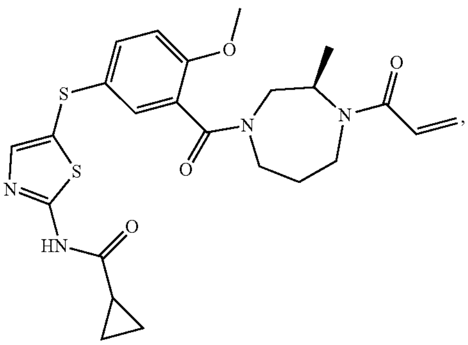,
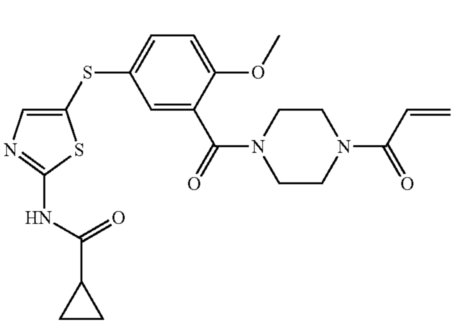, -continued
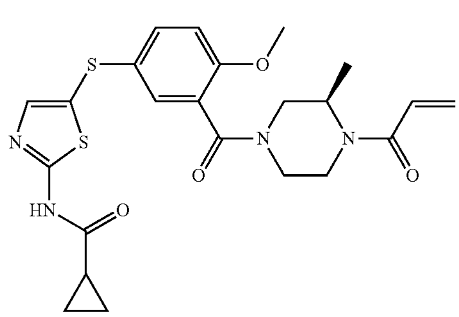
,
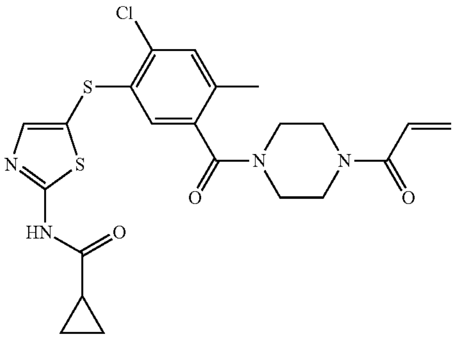
,
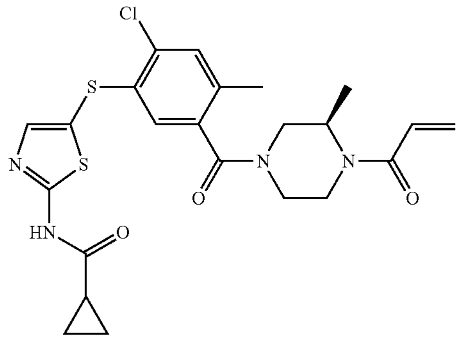
,
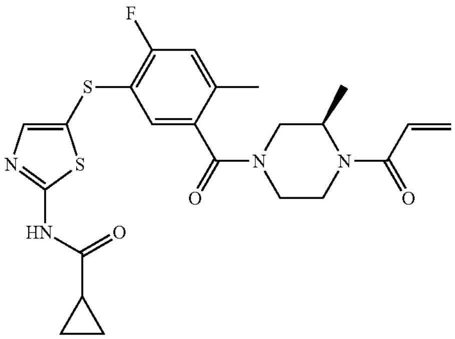
,
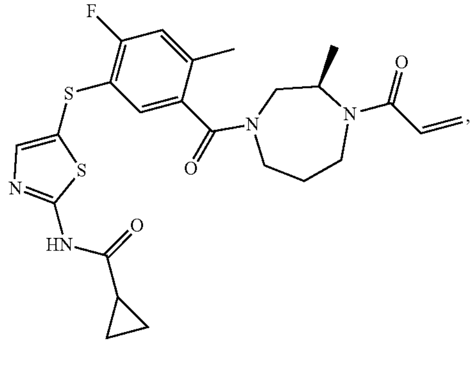
,
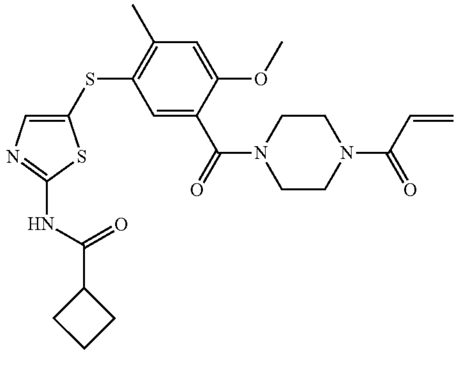
,
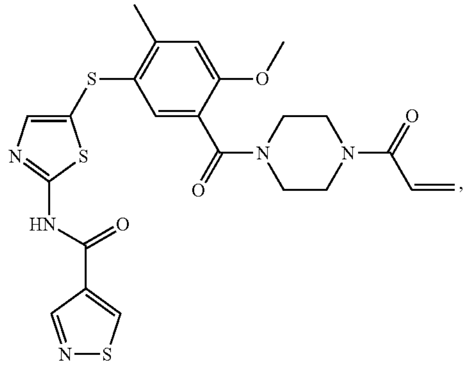
,
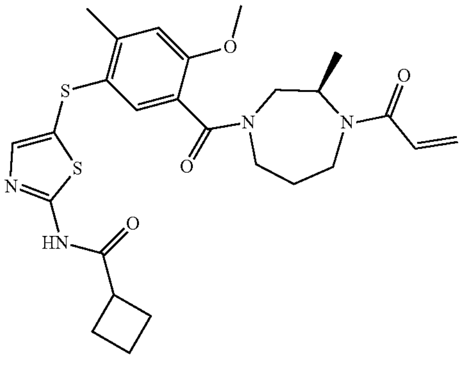
, -continued
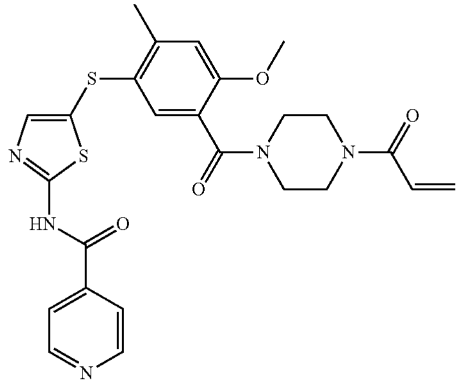,
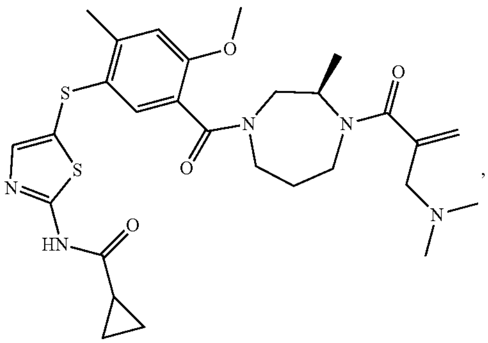,
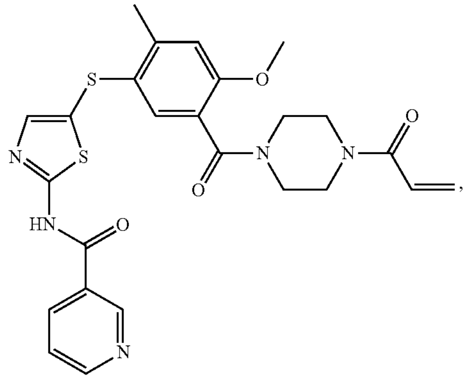,
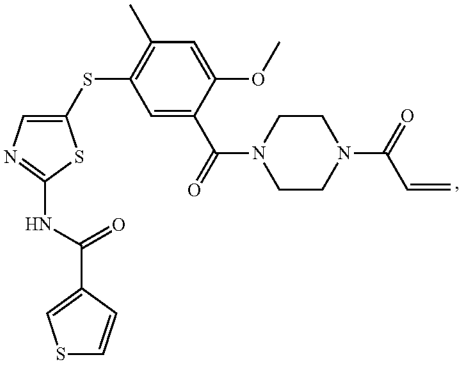,
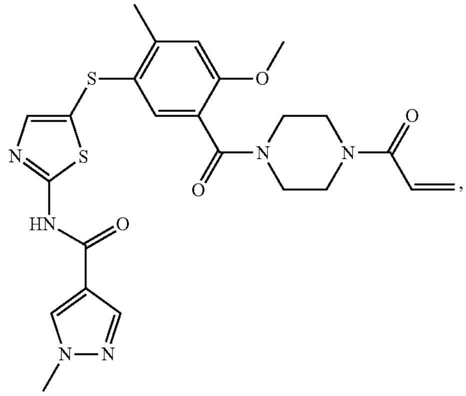,
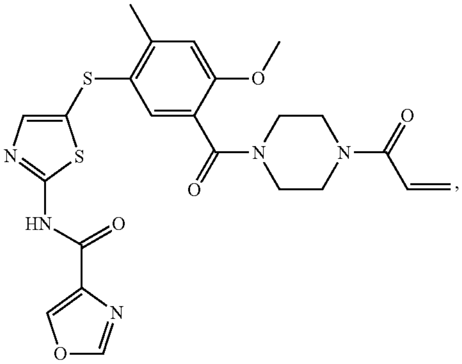,
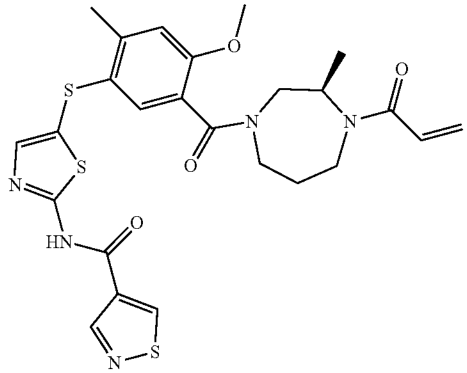,
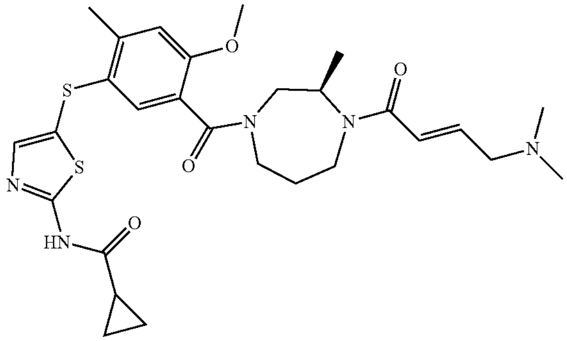, -continued
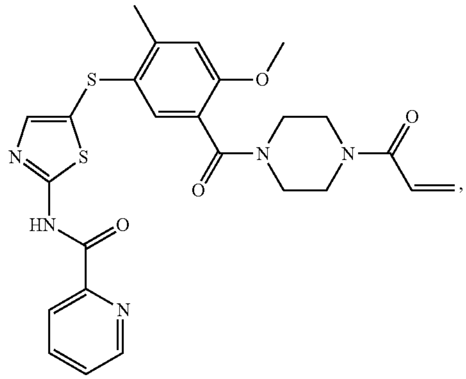
,
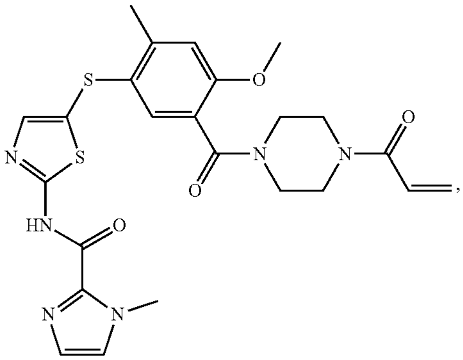
,
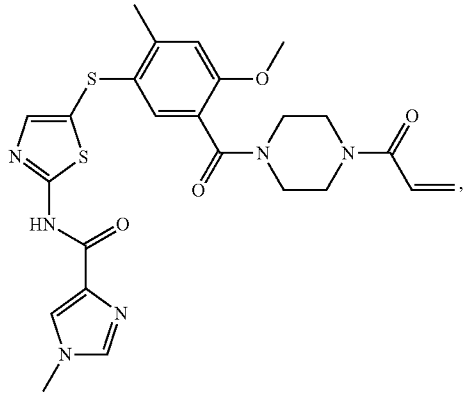
,
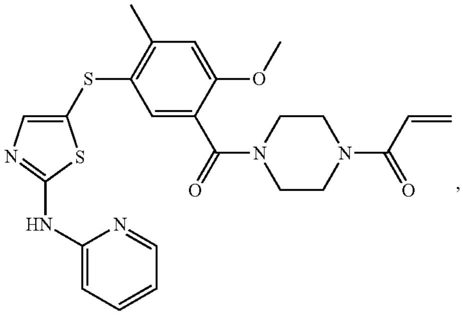
,
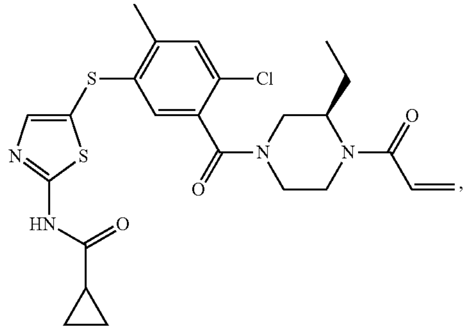
,
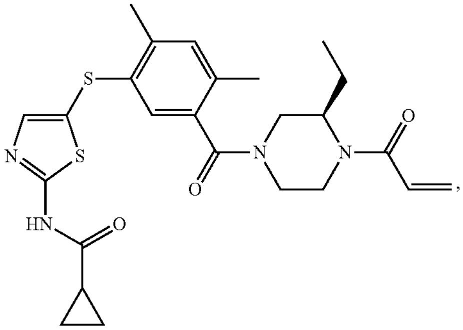
,
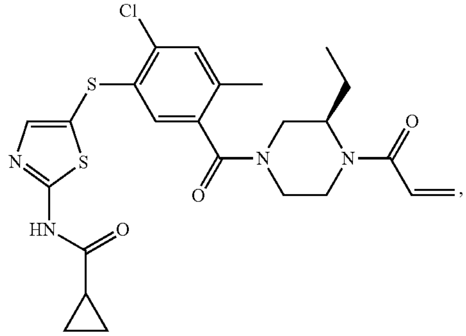
,
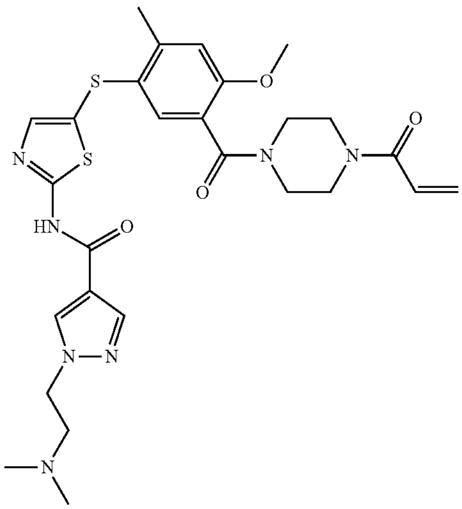
, -continued
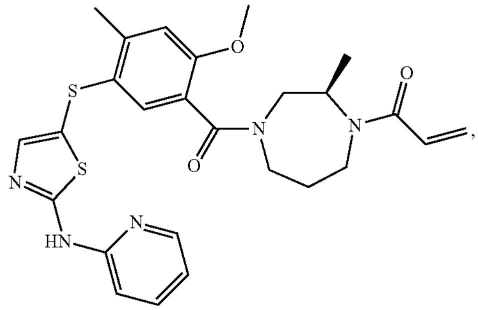,
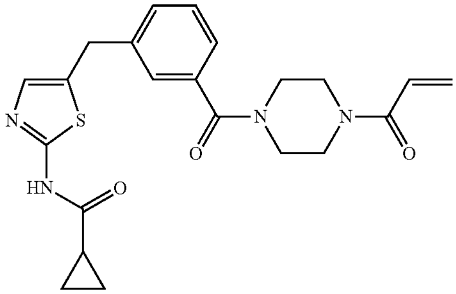,
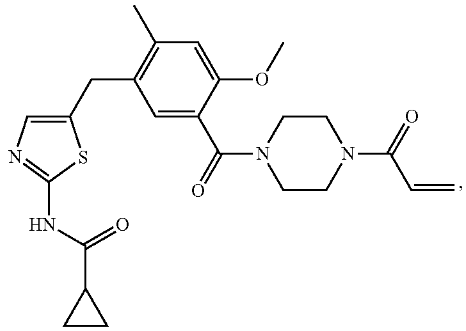, or
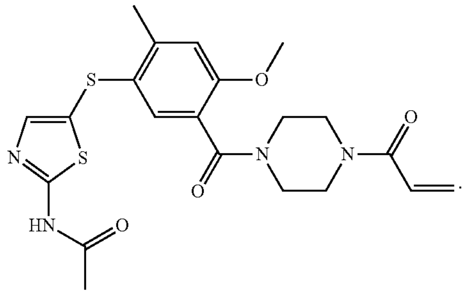.
Embodiment P100. The compound of Embodiment P1 having the formula:
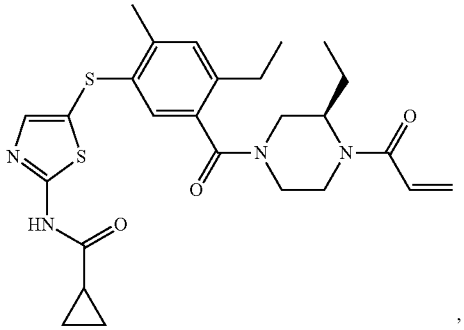,
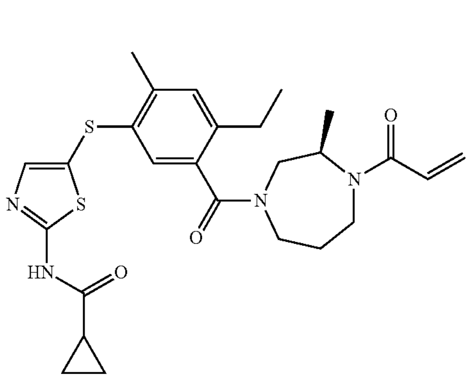,
-continued
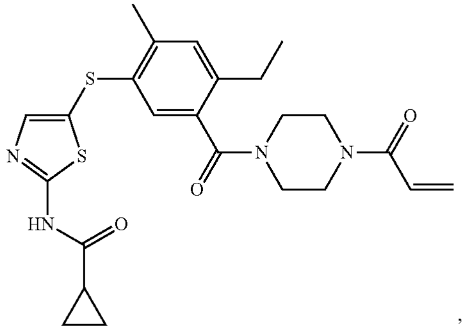,
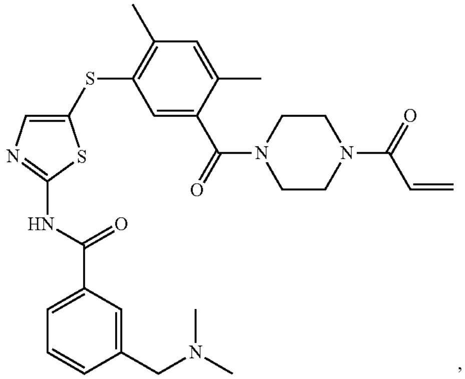, -continued
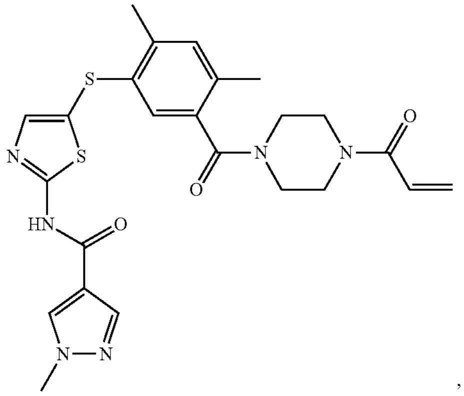
,
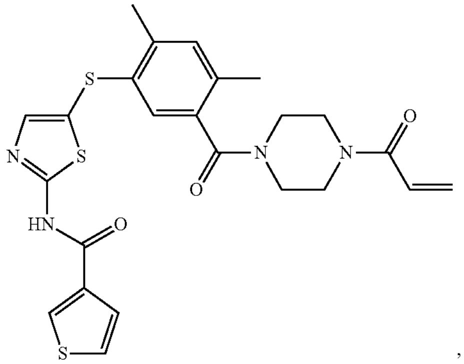
,
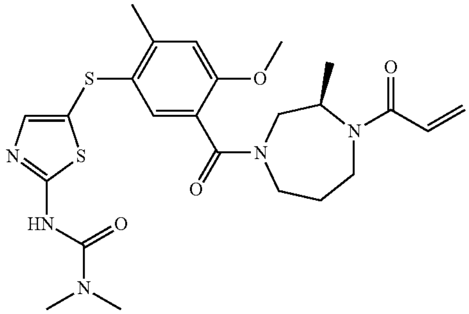
,
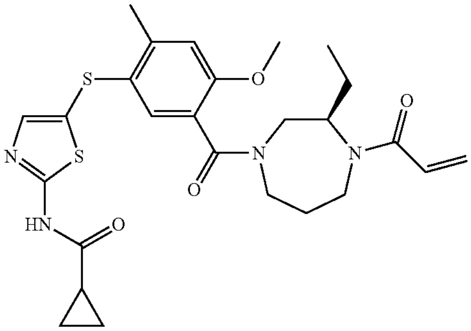
,
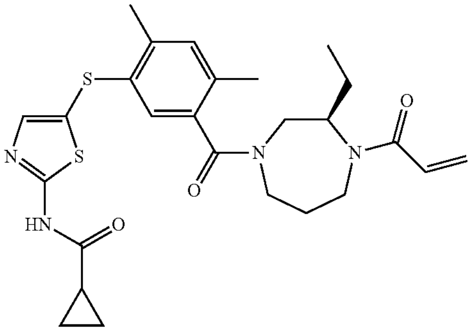
,
-continued
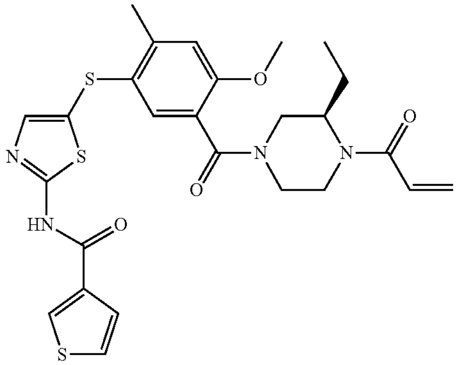
,
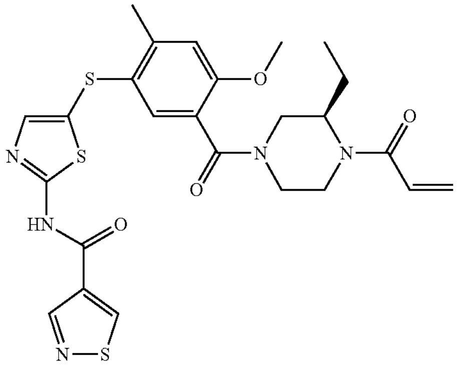
,
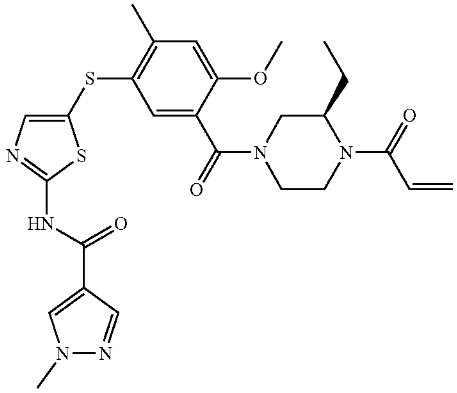
,
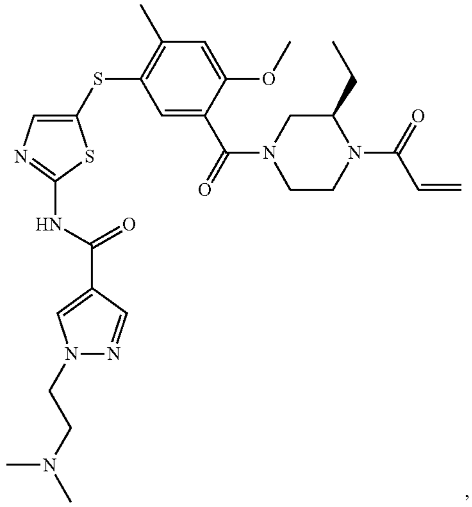
, -continued
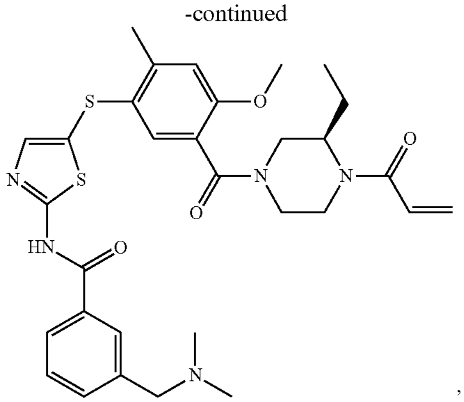
,
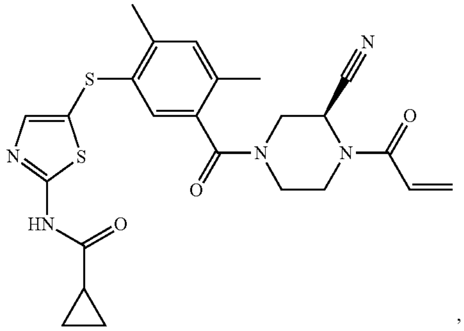
,
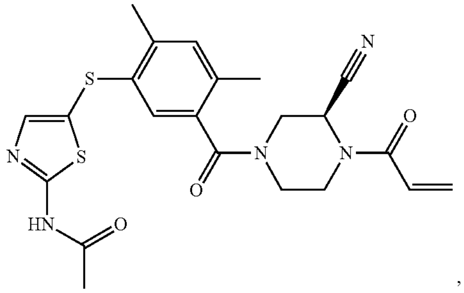
,
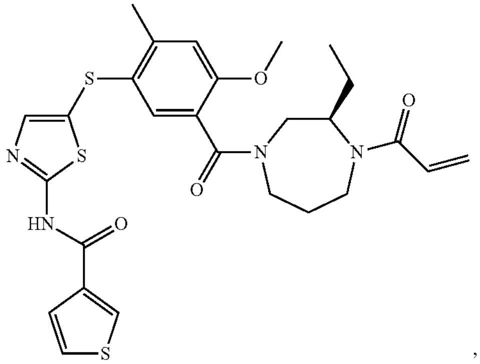
,
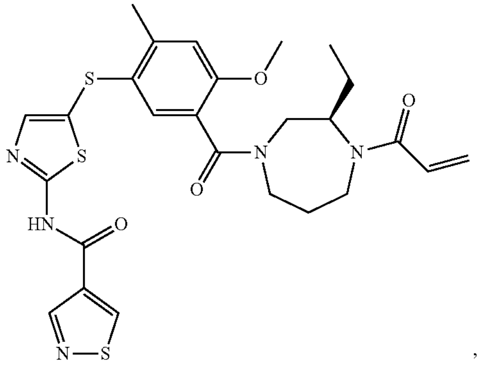
,
-continued
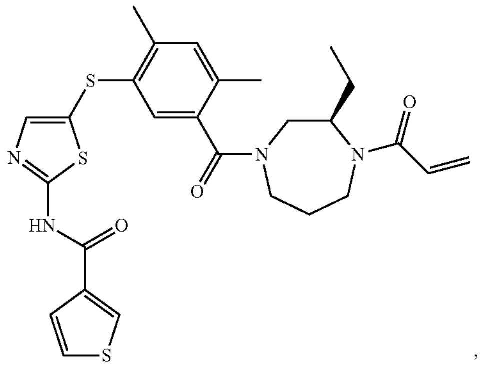
,
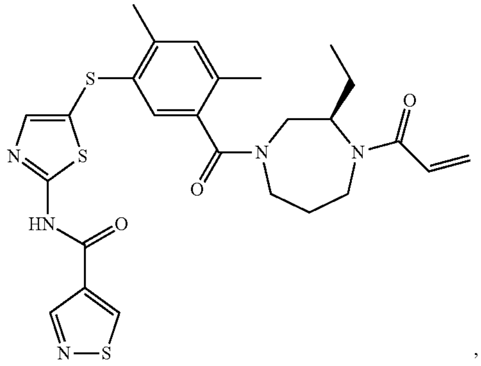
,
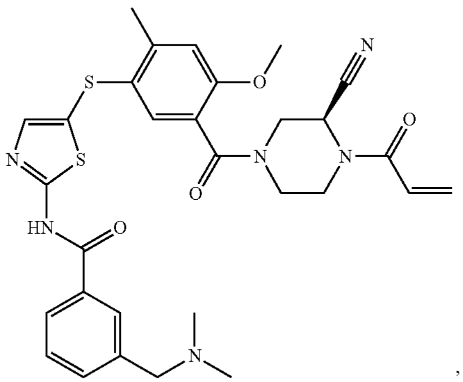
,
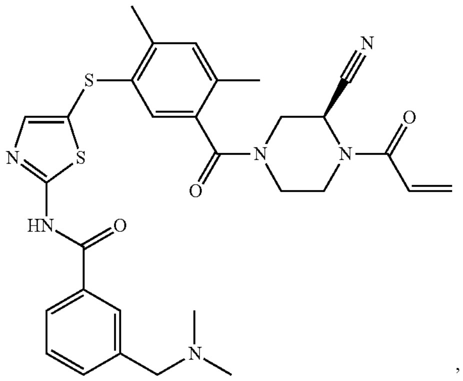
, -continued
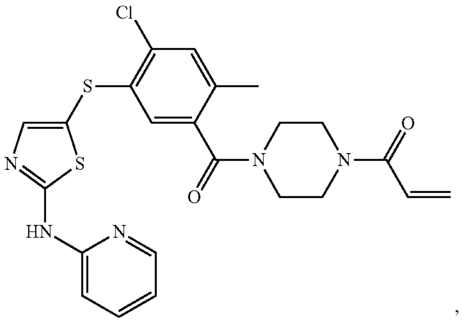
,
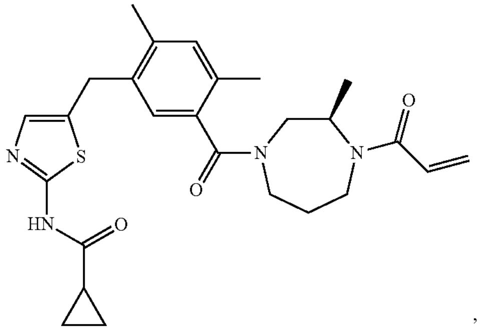
,
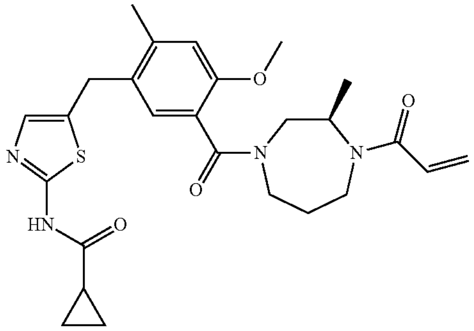
,
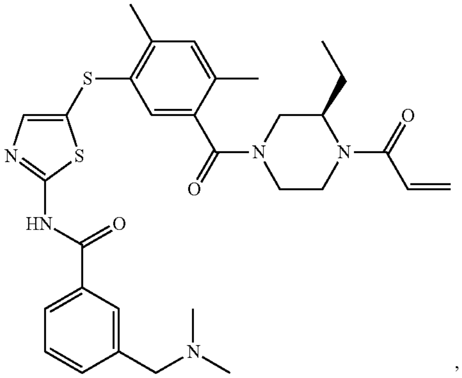
,
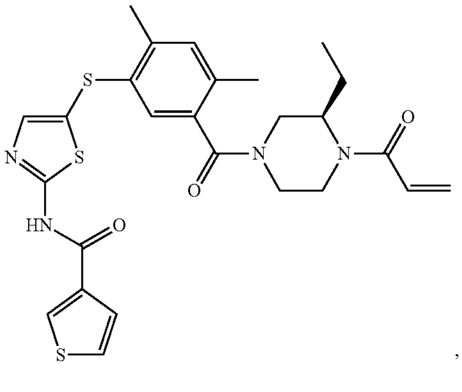
,
-continued
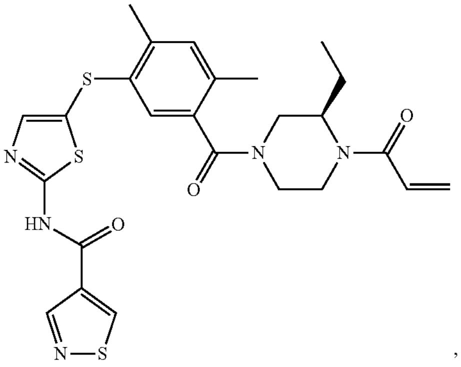
,
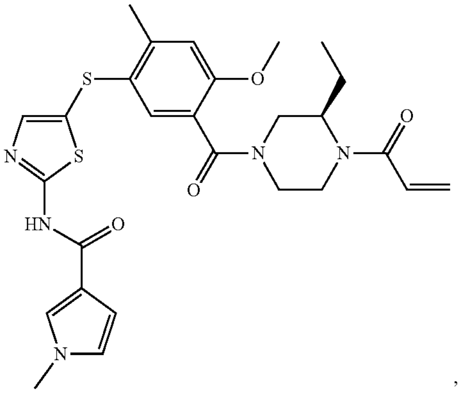
,
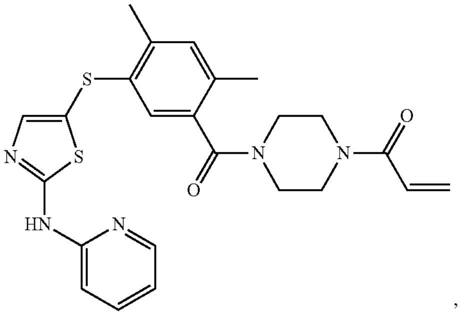
,
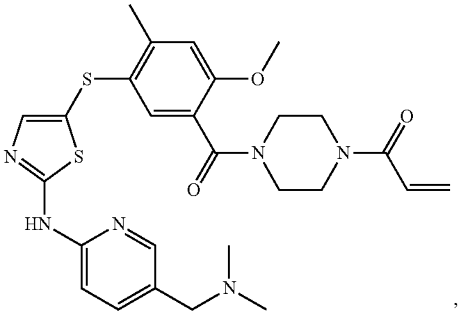
,
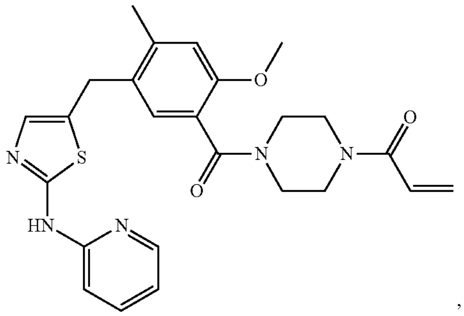
, or -continued

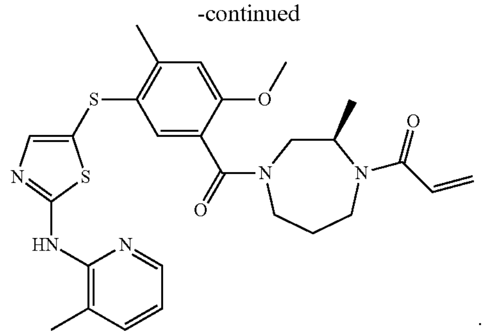

Embodiment P101. A pharmaceutical composition comprising the compound of any one of embodiments P1 to P100 and a pharmaceutically acceptable excipient.

Embodiment P102. A method of inhibiting a TEC kinase activity, said method comprising: contacting the TEC kinase with a compound of one of embodiments P1 to P100.

Embodiment P103. A method of inhibiting Interleukin-2-inducible T-cell kinase activity, said method comprising: contacting the Interleukin-2-inducible T-cell kinase with a compound of one of embodiments P1 to P100.

Embodiment P104. A method of treating cancer, said method comprising administering to a subject in need thereof an effective amount of a compound of one of embodiments P1 to P100.

Embodiment P105. An Interleukin-2-inducible T-cell kinase protein covalently bonded to a compound of one of embodiments P1 to P100.

Embodiment P106. The Interleukin-2-inducible T-cell kinase protein of Embodiment P105, wherein the compound is bonded to a cysteine residue of the protein.

Embodiment P107. An Interleukin-2-inducible T-cell kinase protein covalently bonded to a portion of a compound of one of embodiments P1 to P100.

Embodiment P108. An Interleukin-2-inducible T-cell kinase protein irreversibly covalently bonded to a portion of a compound of one of embodiments P1 to P100.

EMBODIMENTS

1. A compound having the formula:

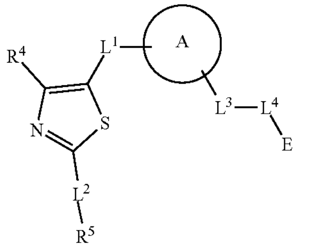

wherein,

Ring A is,

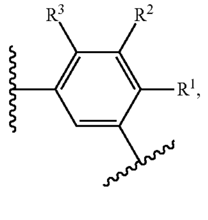,
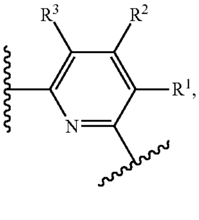,

-continued

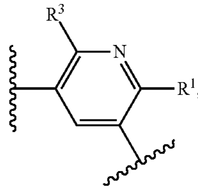,
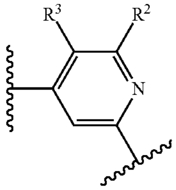,
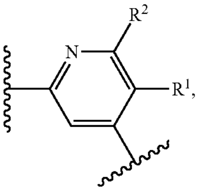,
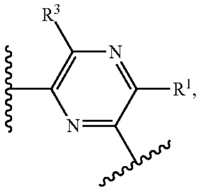,
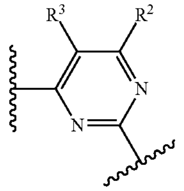,
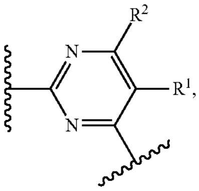,
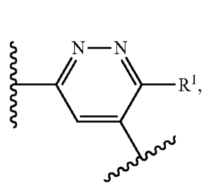,
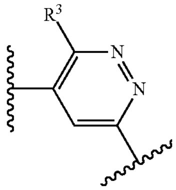,
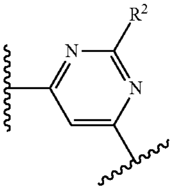
or
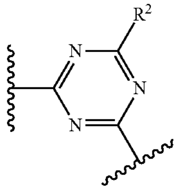;

$R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{1D}$, $—SO_{v1}NR^{1A}R^{1B}$, $—NHC(O)NR^{1A}R^{1B}$, $—N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{2D}$, $—SO_{v2}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{3D}$, $—SO_{v3}NR^{3A}R^{3B}$, $—NHC(O)NR^{3A}R^{3B}$, $—N(O)_{m3}$, $—NR^{3A}R^{3B}$, $—C(O)R^{3C}$, $—C(O)—OR^{3C}$, $—C(O)NR^{3A}R^{3B}$, $—OR^{3D}$, $—NR^{3A}SO_2R^{3D}$, $—NR^{3A}C(O)R^{3C}$, $—NR^{3A}C(O)OR^{3C}$, $—NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —C(O) $R^{4C}$, —C(O)—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ is —O—, —S—, or substituted or unsubstituted $C_1$-$C_2$ alkylene, or substituted or unsubstituted 2 membered heteroalkylene; $L^2$ is a bond, —NH—, —NHC(O)—; $L^3$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^6$ is independently hydrogen, —$CX^6_3$, —$CHX^6_2$, —$CH_2X^6$, —CN, —$C(O)R^{6C}$, —$C(O)OR^{6C}$, —$C(O)NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^4$ is a bond, —$S(O)_2$—, —$N(R^7)$—, —O—, —S—, —C(O)—, —$C(O)N(R^7)$—, —$N(R^7)C(O)$—, —$N(R^7)C(O)NH$—, —$NHC(O)N(R^7)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, —$CX^7_3$, —$CHX^7_2$, —$CH_2X^7$, —CN, —$C(O)R^{7C}$, —$C(O)OR^{7C}$, —$C(O)NR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; E is an electrophilic moiety; Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$, $R^{7A}$, $R^{7B}$, and $R^{7C}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; each X, $X^1$, $X^2$, $X^3$, $X^4$, $X^6$, and $X^7$ is independently —F, —Cl, —Br, or —I; n1, n2, n3, and n4 are independently an integer from 0 to 4; and m1, m2, m3, m4, v1, v2, v3, and v4 are independently 1 to 2.

Embodiment 2. The compound of embodiment 1 having the formula:

(I)

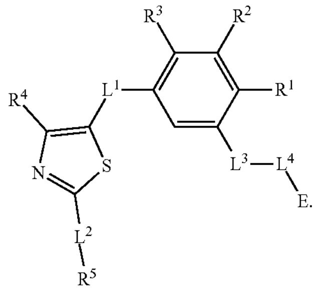

Embodiment 3. The compound of one of embodiments 1 to 2, wherein $L^1$ is —O—, —S—, or substituted or unsubstituted methylene.

Embodiment 4. The compound of one of embodiments 1 to 2, wherein $L^1$ is —$SCH_2$—.

Embodiment 5. The compound of one of embodiments 1 to 2, wherein $L^1$ is —$CH(CH_3)$—.

Embodiment 6. The compound of one of embodiments 1 to 5, wherein $L^2$ is a bond.

Embodiment 7. The compound of one of embodiments 1 to 5, wherein $L^2$ is —NH—.

Embodiment 8. The compound of one of embodiments 1 to 5, wherein $L^2$ is —NHC(O)—.

Embodiment 9. The compound of one of embodiments 1 to 8, wherein $R^4$ is hydrogen.

Embodiment 10. The compound of one of embodiments 1 to 9, wherein $R^2$ is unsubstituted $C_1$-$C_2$ alkyl.

Embodiment 11. The compound of one of embodiments 1 to 9, wherein $R^2$ is unsubstituted methyl.

Embodiment 12. The compound of one of embodiments 1 to 9, wherein $R^2$ is hydrogen.

Embodiment 13. The compound of one of embodiments 1 to 5 having the formula:

(II)

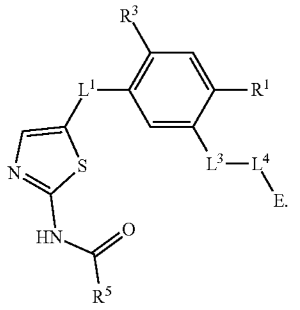

Embodiment 14. The compound of one of embodiments 1 to 3 having the formula:

(IIA)

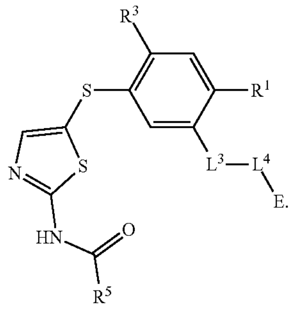

Embodiment 15. The compound of one of embodiments 1 to 3 having the formula:

(IIB)

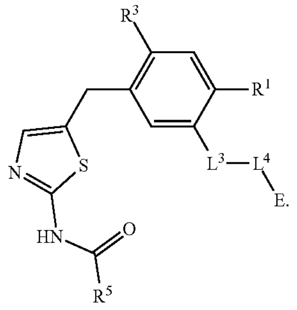

Embodiment 16. The compound of one of embodiments 1 to 3 having the formula:

(IIC)

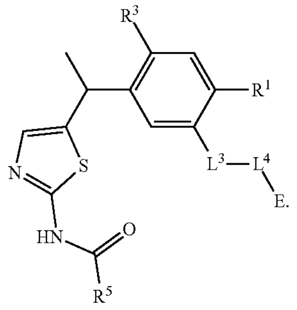

Embodiment 17. The compound of embodiment 1 to 5 having the formula:

(III)

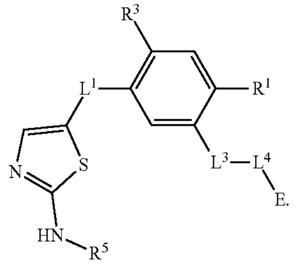

Embodiment 18. The compound of one of embodiments 1 to 3 having the formula:

(IIIA)

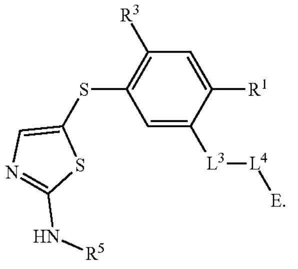

Embodiment 19. The compound of one of embodiments 1 to 3 having the formula:

(IIIB)

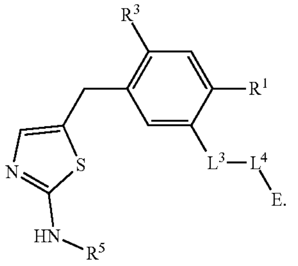

Embodiment 20. The compound of one of embodiments 1 to 3 having the formula:

(IIIC)

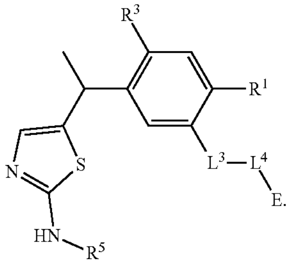

Embodiment 21. The compound of one of embodiments 1 to 20, wherein $R^1$ is independently hydrogen, halogen, —$CX^1_3$, —$CHX^1_2$, —$CH_2X^1$, —$OCX^1_3$, —$OCH_2X^1$, —$OCHX^1_2$, substituted or unsubstituted alkyl, or substituted or unsubstituted heteroalkyl.

Embodiment 22. The compound of one of embodiments 1 to 20, wherein $R^1$ is independently hydrogen, halogen, —$CX^1_3$, —$CHX^1_2$, —$CH_2X^1$, —$OCX^1_3$, —$OCH_2X^1$, —$OCHX^1_2$, substituted or unsubstituted ($C_1$-$C_4$) alkyl, or substituted or unsubstituted 2 to 4 membered heteroalkyl.

Embodiment 23. The compound of one of embodiments 1 to 20, wherein $R^1$ is hydrogen, halogen, —$CH_3$, —$CH_2CH_3$, —$CX^1_3$, —$CHX^1_2$, —$CH_2X^1$, —$OCH_3$, —$OCX^1_3$, —$OCH_2X^1$, —$OCHX^1_2$, —$SCH_3$, —$SCX^1_3$, —$SCH_2X^1$, or —$SCHX^1_2$.

Embodiment 24. The compound of one of embodiments 1 to 20, wherein $R^1$ is hydrogen, halogen, —$CH_3$, —$CH_2CH_3$, —$CF_3$, or —$OCH_3$.

Embodiment 25. The compound of one of embodiments 1 to 20, wherein $R^1$ is —$CH_3$, —$CH_2CH_3$, or —$OCH_3$.

Embodiment 26. The compound of one of embodiments 1 to 20, wherein $R^1$ is —$OCH_3$.

Embodiment 27. The compound of one of embodiments 1 to 26, wherein $R^3$ is independently hydrogen, halogen, —$CX^3_3$, —$CHX^3_2$, —$CH_2X^3$, —$OCX^3_3$, —$OCH_2X^3$, —$OCHX^3_2$, —CN, substituted or unsubstituted alkyl, or substituted or unsubstituted heteroalkyl.

Embodiment 28. The compound of one of embodiments 1 to 26, wherein $R^3$ is independently hydrogen, halogen, —$CX^3_3$, —$CHX^3_2$, —$CH_2X^3$, —$OCX^3_3$, —$OCH_2X^3$, —$OCHX^3_2$, —CN, substituted or unsubstituted ($C_1$-$C_4$) alkyl, or substituted or unsubstituted 2 to 4 membered heteroalkyl.

Embodiment 29. The compound of one of embodiments 1 to 26, wherein $R^3$ is hydrogen, halogen, —$CH_3$, —$CH_2CH_3$, —$CX^3_3$, —$CHX^3_2$, —$CH_2X^3$, —$OCH_3$, —$OCX^3_3$, —$OCH_2X^3$, —$OCHX^3_2$, —CN, —$SCH_3$, —$SCX^3_3$, —$SCH_2X^3$, or —$SCHX^3_2$.

Embodiment 30. The compound of one of embodiments 1 to 26, wherein $R^3$ is hydrogen, halogen, —CN, —$CH_3$, —$CF_3$, or —$OCH_3$.

Embodiment 31. The compound of one of embodiments 1 to 26, wherein $R^3$ is halogen or —$CH_3$.

Embodiment 32. The compound of one of embodiments 1 to 26, wherein $R^3$ is —Cl or —$CH_3$.

Embodiment 33. The compound of one of embodiments 1 to 26, wherein $R^3$ is —$CH_3$.

Embodiment 34. The compound of one of embodiments 1 to 33, wherein $R^5$ is independently substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl.

Embodiment 35. The compound of one of embodiments 1 to 33, wherein $R^5$ is independently substituted or unsubstituted ($C_1$-$C_4$) alkyl.

Embodiment 36. The compound of one of embodiments 1 to 33, wherein $R^5$ is independently unsubstituted ($C_1$-$C_4$) alkyl.

Embodiment 37. The compound of one of embodiments 1 to 33, wherein $R^5$ is independently unsubstituted methyl, unsubstituted ethyl, unsubstituted isopropyl, or unsubstituted tert-butyl.

Embodiment 38. The compound of one of embodiments 1 to 33, wherein $R^5$ is independently unsubstituted methyl or unsubstituted ethyl.

Embodiment 39. The compound of one of embodiments 1 to 33, wherein $R^5$ is independently substituted or unsubstituted 2 to 8 membered heteroalkyl.

Embodiment 40. The compound of one of embodiments 1 to 33, wherein $R^5$ is independently substituted or unsubstituted 2 to 4 membered heteroalkyl.

Embodiment 41. The compound of one of embodiments 1 to 33, wherein $R^5$ is independently unsubstituted 2 to 4 membered heteroalkyl.

Embodiment 42. The compound of one of embodiments 1 to 33, wherein $R^5$ is independently —$CH_2N(CH_3)_2$.

Embodiment 43. The compound of one of embodiments 1 to 33, wherein $R^5$ is independently substituted or unsubstituted ($C_3$-$C_6$) cycloalkyl.

Embodiment 44. The compound of one of embodiments 1 to 33, wherein $R^5$ is independently unsubstituted ($C_3$-$C_6$) cycloalkyl.

Embodiment 45. The compound of one of embodiments 1 to 33, wherein $R^5$ is independently unsubstituted cyclopropyl, unsubstituted cyclobutyl, or unsubstituted cyclopentyl.

Embodiment 46. The compound of one of embodiments 1 to 33, wherein $R^5$ is independently unsubstituted cyclopropyl or unsubstituted cyclobutyl.

Embodiment 47. The compound of one of embodiments 1 to 33, wherein $R^5$ is independently unsubstituted cyclopropyl.

Embodiment 48. The compound of one of embodiments 1 to 33, wherein $R^5$ is independently substituted or unsubstituted 3 to 6 membered heterocycloalkyl.

Embodiment 49. The compound of one of embodiments 1 to 33, wherein $R^5$ is independently substituted or unsubstituted 5 to 6 membered heterocycloalkyl.

Embodiment 50. The compound of one of embodiments 1 to 33, wherein $R^5$ is independently substituted or unsubstituted 6 membered heterocycloalkyl.

Embodiment 51. The compound of one of embodiments 1 to 33, wherein $R^5$ is independently substituted or unsubstituted piperidinyl.

Embodiment 52. The compound of one of embodiments 1 to 33, wherein $R^5$ is independently

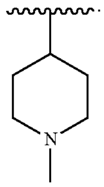 [SMILES: *C1CCN(C)CC1]

Embodiment 53. The compound of one of embodiments 1 to 33, wherein $R^5$ is independently substituted or unsubstituted phenyl.

Embodiment 54. The compound of one of embodiments 1 to 33, wherein $R^5$ is independently unsubstituted phenyl.

Embodiment 55. The compound of one of embodiments 1 to 33, wherein $R^5$ is independently 2-substituted phenyl.

Embodiment 56. The compound of one of embodiments 1 to 33, wherein $R^5$ is independently 3-substituted phenyl.

Embodiment 57. The compound of one of embodiments 1 to 33, wherein $R^5$ is independently 4-substituted phenyl.

Embodiment 58. The compound of one of embodiments 1 to 33, wherein $R^5$ is independently phenyl substituted with halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 59. The compound of one of embodiments 1 to 33, wherein $R^5$ is independently phenyl substituted with halogen, substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl.

Embodiment 60. The compound of one of embodiments 1 to 33, wherein $R^5$ is independently phenyl substituted with —F,

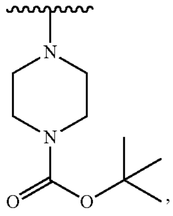,
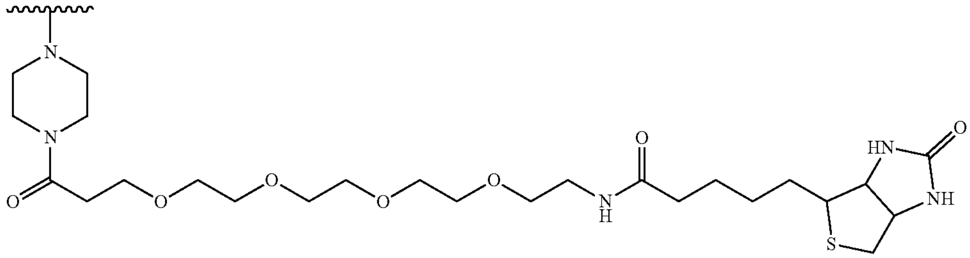,
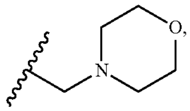
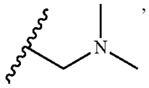, or
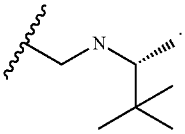.

Embodiment 61. The compound of one of embodiments 1 to 33, wherein $R^5$ is independently

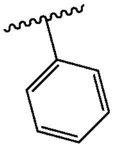,
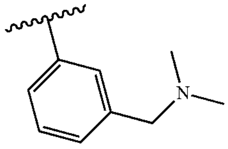,
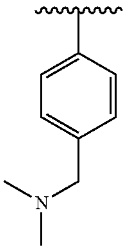,
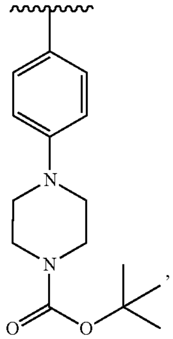,
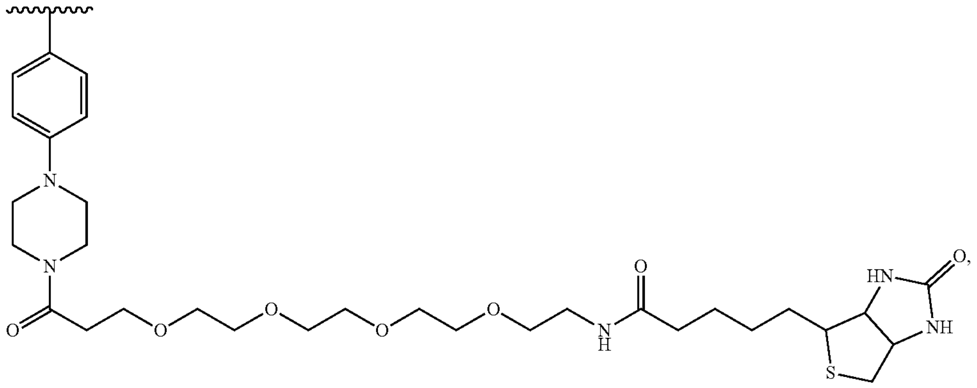
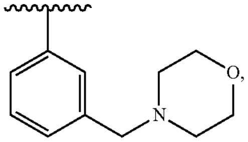
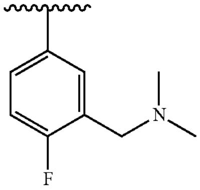, or
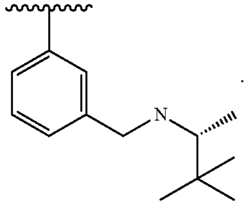.

Embodiment 62. The compound of one of embodiments 1 to 33, wherein $R^5$ is independently

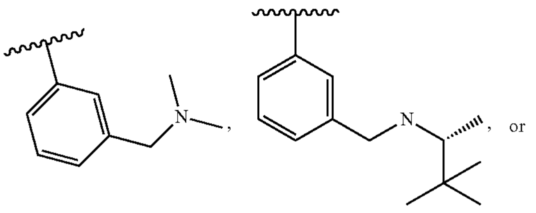

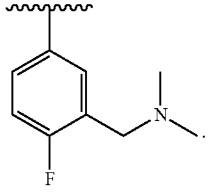

Embodiment 63. The compound of one of embodiments 1 to 33, wherein $R^5$ is independently substituted or unsubstituted heteroaryl.

Embodiment 64. The compound of one of embodiments 1 to 33, wherein $R^5$ is independently substituted or unsubstituted 5 to 6 membered heteroaryl.

Embodiment 65. The compound of one of embodiments 1 to 33, wherein $R^5$ is independently substituted or unsubstituted pyridyl, substituted or unsubstituted thienyl, substituted or unsubstituted furanyl, substituted or unsubstituted pyrrolyl, substituted or unsubstituted imidazolyl, substituted or unsubstituted pyrazolyl, substituted or unsubstituted thiazolyl, substituted or unsubstituted isothiazolyl, substituted or unsubstituted oxazolyl, or substituted or unsubstituted isoxazolyl.

Embodiment 66. The compound of one of embodiments 1 to 33, wherein $R^5$ is independently

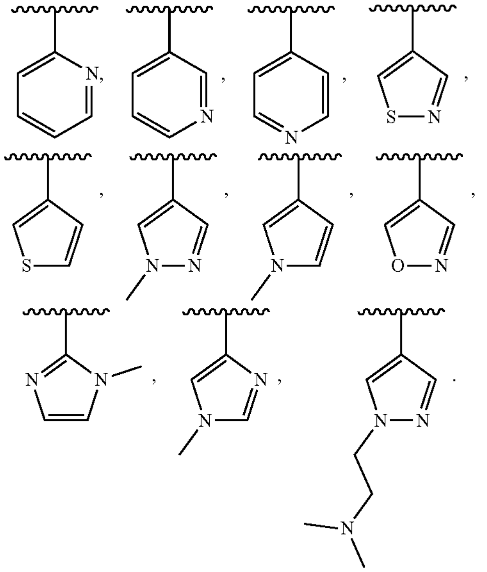

-continued

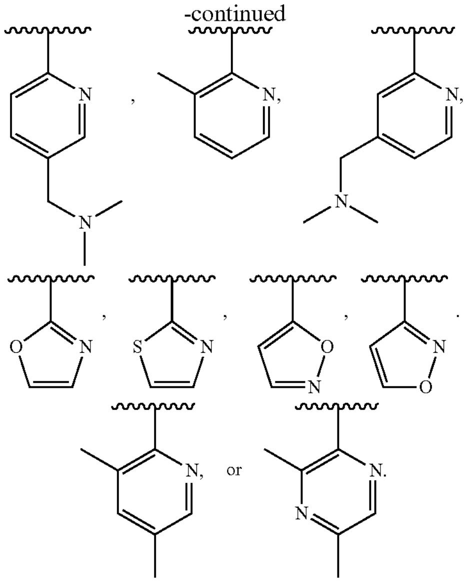

Embodiment 67. The compound of one of embodiments 1 to 33, wherein $R^5$ is independently

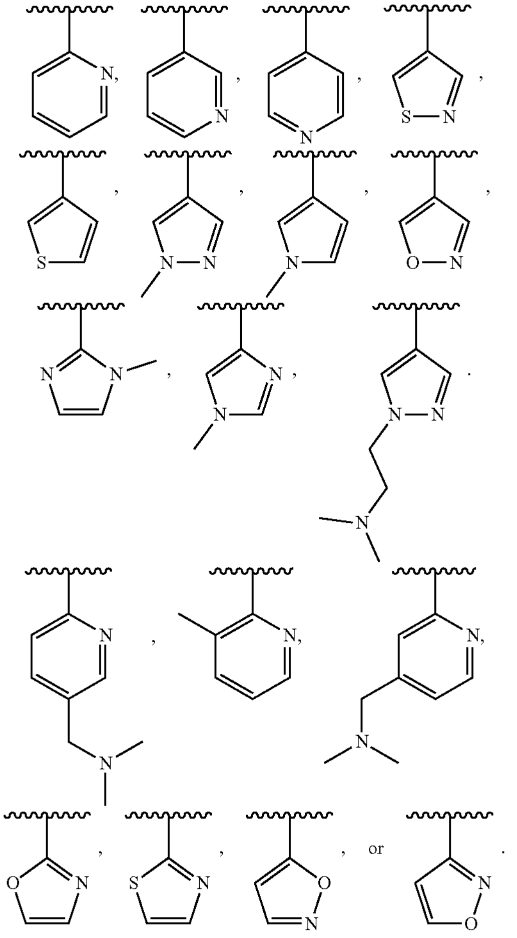

Embodiment 68. The compound of one of embodiments 1 to 33, wherein $R^5$ is independently

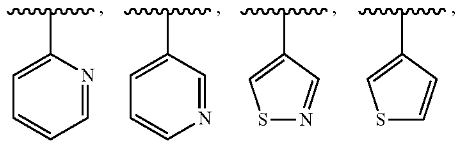

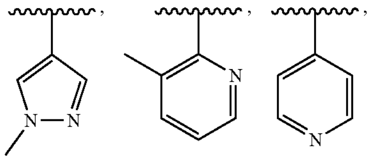

or

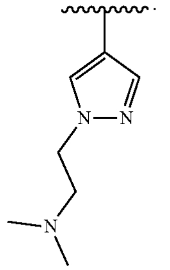

Embodiment 69. The compound of one of embodiments 1 to 68, wherein $L^3$ is a bond, —$N(R^6)$—, —C(O)—, or —C(O)$N(R^6)$—; and $R^6$ is independently hydrogen, —$CX^6_3$, —$CHX^6_2$, —$CH_2X^6$, or unsubstituted ($C_1$-$C_4$) alkyl.

Embodiment 70. The compound of one of embodiments 1 to 68, wherein $L^3$ is a bond, —$N(R^6)$—, —C(O)—, or —C(O)$N(R^6)$—; and $R^6$ is independently hydrogen or unsubstituted methyl.

Embodiment 71. The compound of one of embodiments 1 to 68, wherein $L^3$ is a bond, —C(O)—, —C(O)$N(CH_3)$—, —$N(CH_3)$—, or —NH—.

Embodiment 72. The compound of one of embodiments 1 to 68, wherein $L^3$ is a bond.

Embodiment 73. The compound of one of embodiments 1 to 68, wherein $L^3$ is —C(O)—.

Embodiment 74. The compound of one of embodiments 1 to 68, wherein $L^3$ is —C(O)$N(CH_3)$—.

Embodiment 75. The compound of one of embodiments 1 to 74, wherein $L^4$ is a bond, —$N(R^7)$—, —C(O)—, —C(O) $N(R^7)$—, substituted or unsubstituted heterocycloalkylene, substituted or unsubstituted fused ring heterocycloalkylene, substituted or unsubstituted spirocyclic heterocycloalkylene, or substituted or unsubstituted bridged ring heterocycloalkylene; and $R^7$ is independently hydrogen, —$CX^7_3$, —$CHX^7_2$, —$CH_2X^7$, or unsubstituted ($C_1$-$C_4$) alkyl.

Embodiment 76. The compound of one of embodiments 1 to 74, wherein $L^4$ is a bond, —$N(R^7)$—, substituted or unsubstituted heterocycloalkylene, substituted or unsubstituted fused ring heterocycloalkylene, substituted or unsubstituted spirocyclic heterocycloalkylene, or substituted or unsubstituted bridged ring heterocycloalkylene; and $R^7$ is independently hydrogen, —$CX^7_3$, —$CHX^7_2$, —$CH_2X^7$, or unsubstituted ($C_1$-$C_4$) alkyl.

Embodiment 77. The compound of one of embodiments 1 to 74, wherein $L^4$ is a bond, substituted or unsubstituted monocyclic heterocycloalkylene, substituted or unsubstituted fused ring heterocycloalkylene, or substituted or unsubstituted spirocyclic heterocycloalkylene, or substituted or unsubstituted bridged ring heterocycloalkylene.

Embodiment 78. The compound of one of embodiments 1 to 74, wherein $L^4$ is a substituted or unsubstituted 4 to 10 membered monocyclic heterocycloalkylene, substituted or unsubstituted 5 to 10 membered fused ring heterocycloalkylene, substituted or unsubstituted 6 to 10 membered spirocyclic heterocycloalkylene, or substituted or unsubstituted 5 to 10 membered bridged ring heterocycloalkylene.

Embodiment 79. The compound of one of embodiments 1 to 74, wherein $L^4$ is a substituted or unsubstituted 5 to 10 membered monocyclic heterocycloalkylene, substituted or unsubstituted 6 to 10 membered fused ring heterocycloalkylene, substituted or unsubstituted 7 to 10 membered spirocyclic heterocycloalkylene, or substituted or unsubstituted 5 to 10 membered bridged ring heterocycloalkylene.

Embodiment 80. The compound of one of embodiments 1 to 74, wherein $L^4$ is a substituted or unsubstituted 5 to 8 membered monocyclic heterocycloalkylene, substituted or unsubstituted 7 to 8 membered fused ring heterocycloalkylene, substituted or unsubstituted 7 to 8 membered spirocyclic heterocycloalkylene, or substituted or unsubstituted 7 to 8 membered bridged ring heterocycloalkylene.

Embodiment 81. The compound of one of embodiments 1 to 74, wherein $L^4$ is an unsubstituted 7 to 8 membered bridged ring heterocycloalkylene.

Embodiment 82. The compound of one of embodiments 1 to 74, wherein $L^4$ is an unsubstituted 7 to 8 membered fused ring heterocycloalkylene.

Embodiment 83. The compound of one of embodiments 1 to 74, wherein $L^4$ is an unsubstituted 7 to 8 membered spirocyclic heterocycloalkylene.

Embodiment 84. The compound of one of embodiments 1 to 74, wherein $L^4$ is a methyl-substituted, ethyl-substituted, cyano-substituted, halo-substituted, or unsubstituted 5 to 8 membered monocyclic heterocycloalkylene.

Embodiment 85. The compound of one of embodiments 1 to 74, wherein $L^4$ is an unsubstituted 5 to 8 membered monocyclic heterocycloalkylene.

Embodiment 86. The compound of one of embodiments 1 to 74, wherein $L^4$ is a methyl-substituted 5 to 8 membered monocyclic heterocycloalkylene, an ethyl-substituted 5 to 8 membered monocyclic heterocycloalkylene, an isopropyl-substituted 5 to 8 membered monocyclic heterocycloalkylene, or a tert-butyl-substituted 5 to 8 membered monocyclic heterocycloalkylene.

Embodiment 87. The compound of one of embodiments 1 to 74, wherein $L^4$ is a bond, —NH—,

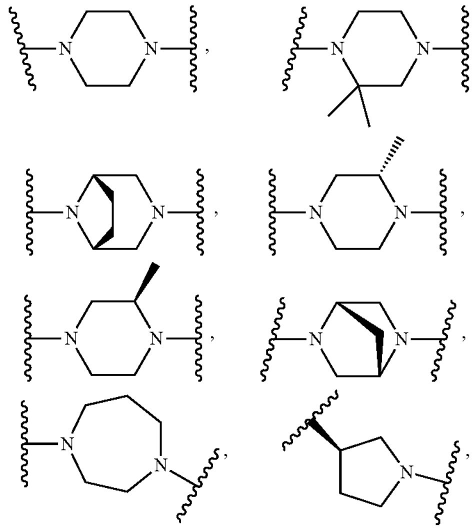

-continued
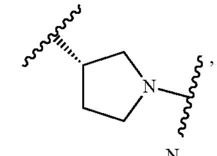,
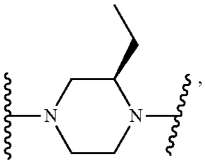,
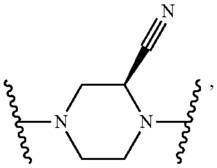,
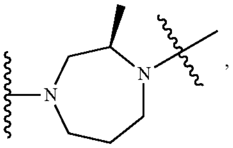,
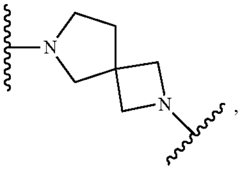,
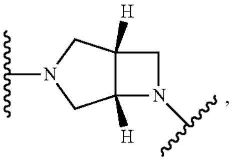,
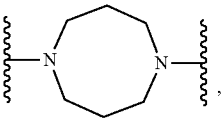,
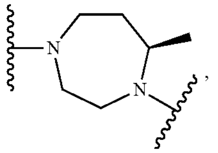,
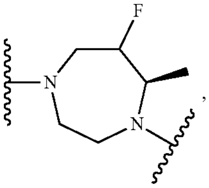, or
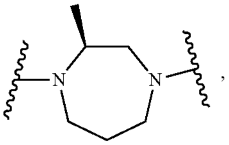,
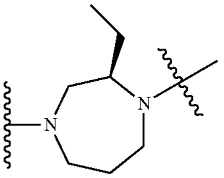,
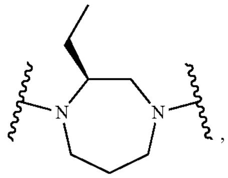,
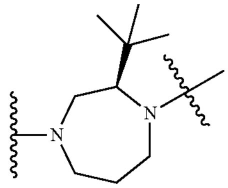,
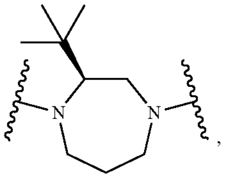,
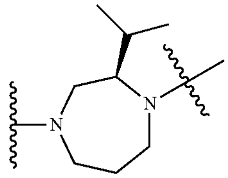,
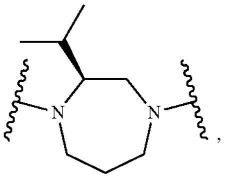,
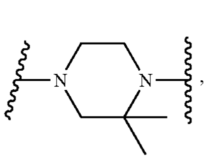,
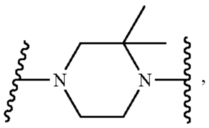,
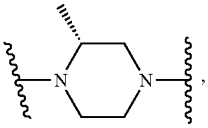,
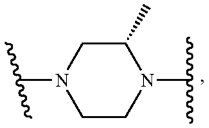,
-continued
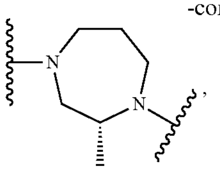,
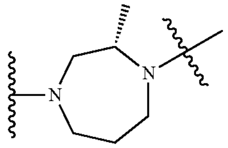,
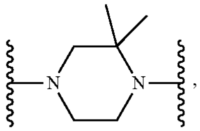,
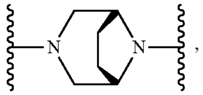,
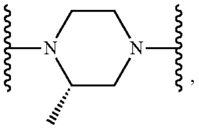, or
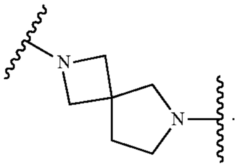.
Embodiment 88. The compound of one of embodiments 1 to 74, wherein $L^4$ is a bond, —NH—,
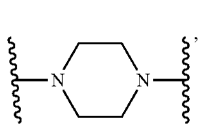,
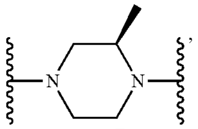,
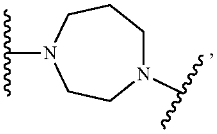,
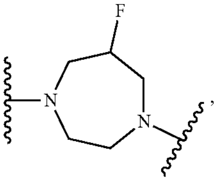,
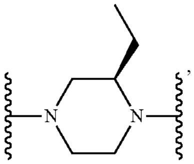,
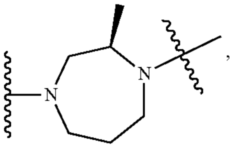,
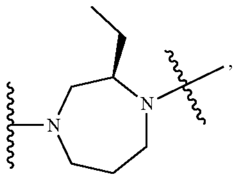,
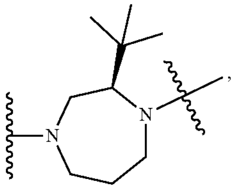, or
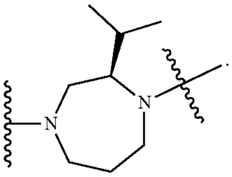.
Embodiment 89. The compound of one of embodiments 1 to 74, wherein $L^4$ is
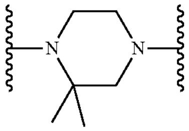,
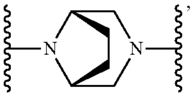

-continued

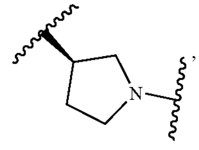,
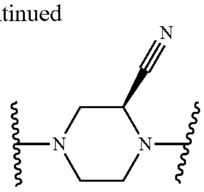,
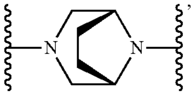,
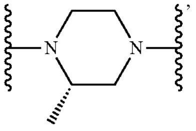, or
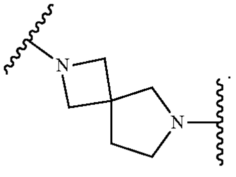.

Embodiment 90. The compound of one of embodiments 1 to 89, wherein E is a covalent cysteine modifier moiety.

Embodiment 91. The compound of one of embodiments 1 to 89, wherein E is

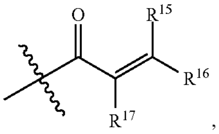,
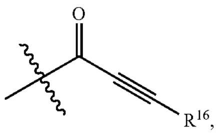
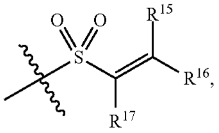
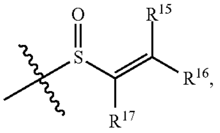
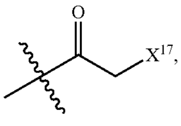 or
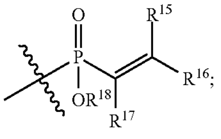

$R^{15}$ is independently hydrogen, halogen, $—CX^{15}_3$, $—CHX^{15}_2$, $—CH_2X^{15}$, —CN, $—SO_{n15}R^{15D}$, $—SO_{v15}NR^{15A}R^{15B}$, $—NHNR^{15A}R^{15B}$, $—NHNR^{15A}R^{15B}$, $—NHC{=}(O)NHNR^{15A}R^{15B}$, $—NHC(O)NR^{15A}R^{15B}$, $—N(O)_{m15}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—OCX^{15}_3$, $—OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16}$ is independently hydrogen, halogen, $—CX^{16}_3$, $—CHX^{16}_2$, $—CH_2X^{16}$, —CN, $—SO_{n16}R^{16D}$, $—SO_{v16}NR^{16A}R^{16B}$, $—NHNR^{16A}R^{16B}$, $—ONR^{16A}R^{16B}$, $—NHC{=}(O)NHNR^{16A}R^{16B}$, $—NHC(O)NR^{16A}R^{16B}$, $—N(O)_{m16}$, $—NR^{16A}R^{16B}$, $—C(O)R^{16C}$, $—C(O)—OR^{16C}$, $—C(O)NR^{16A}R^{16B}$, $—OR^{16D}$, $—NR^{16A}SO_2R^{16D}$, $—NR^{16A}C(O)R^{16C}$, $—NR^{16A}C(O)OR^{16C}$, $—NR^{16A}OR^{16C}$, $—OCX^{16}_3$, $—OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $—CX^{17}_3$, $—CHX^{17}_2$, $—CH_2X^{17}$, —CN, $—SO_{n17}R^{17D}$, $—SO_{v17}NR^{17A}R^{17B}$, $—NHNR^{17A}R^{17B}$, $—ONR^{17A}R^{17B}$, $—NHC{=}(O)NHNR^{17A}R^{17B}$, $—NHC(O)NR^{17A}R^{17B}$, $N(O)_{m17}$, $—NR^{17A}R^{17B}$, $—C(O)R^{17C}$, $—C(O)—OR^{17C}$, $—C(O)NR^{17A}R^{17B}$, $—OR^{17D}$, $—NR^{17A}SO_2R^{17D}$, $—NR^{17A}C(O)R^{17C}$, $—NR^{17A}C(O)OR^{17C}$, $—NR^{17A}OR^{17C}$, $—OCX^{17}_3$, $—OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, $—CX^{18}_3$, $—CHX^{18}_2$, $—CH_2X^{18}$, $—C(O)R^{18C}$, $—C(O)OR^{18C}$, $—C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{15A}R^{15B}$, $R^{15C}$, $R^{15D}$, $R^{16A}$, $R^{16B}$, $R^{6C}$, $R^{16D}$, $R^{17A}$, $R^{17B}$, $R^{17C}$, $R^{17D}$, $R^{18A}$, $R^{18B}$, $R^{18C}$, $R^{18D}$ are independently hydrogen, $—CX_3$, —CN, —COOH, $—CONH_2$, $—CHX_2$, $—CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; each X, $X^{15}$, $X^{16}$, $X^{17}$ and $X^{18}$ is independently —F, —Cl, —Br, or —I; n15, n16, n17, v15, v16, and v17, are independently an integer from 0 to 4; and m15, m16, and m17 are independently 1 or 2.

Embodiment 92. The compound of embodiment 91, wherein $R^{15}$ is independently hydrogen, halogen, $CX^{15}_3$, $—CHX^{15}_2$, $—CH_2X^{15}$, —CN, $—SR^{15D}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}C(O)R^{15C}$, $—NR^{15A}C(O)OR^{15C}$, $—OCX^{15}_3$, $—OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16}$ is independently hydrogen, halogen, $CX^{16}_3$, $—CHX^{16}_2$, $—CH_2X^{16}$, —CN, $—SR^{16D}$, $—NR^{16A}R^{16B}$, $—C(O)R^{16C}$, $—C(O)—OR^{16C}$, $—C(O)NR^{16A}R^{16B}$, $—OR^{16D}$, $—NR^{16A}C(O)R^{16C}$, $—NR^{16A}C(O)OR^{16C}$, $—OCX^{16}_3$, $—OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and $R^{17}$ is independently hydrogen, halogen, $—CX^{17}_3$, $—CHX^{17}_2$, $—CH_2X^{17}$, —CN, $—SR^{17D}$, $—NR^{17A}R^{17B}$, $—C(O)R^{17C}$, $—C(O)—OR^{17C}$, $—C(O)NR^{17A}R^{17B}$, $—OR^{17D}$, $—NR^{17A}C(O)R^{17C}$, $—NR^{17A}C(O)OR^{17C}$, $—OCX^{17}_3$, $—OCHX^{17}_2$, substituted or unsubstituted alkyl, or substituted or unsubstituted heteroalkyl.

Embodiment 93. The compound of one of embodiments 91 to 92, wherein $R^{15}$, $R^{16}$, $R^{17}$, and $R^{18}$ are hydrogen.

Embodiment 94. The compound of one of embodiments 91 to 93, wherein E is:

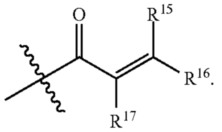

Embodiment 95. The compound of embodiment 94, wherein $R^{15}$ is hydrogen; $R^{16}$ is hydrogen; and $R^{17}$ is hydrogen.

Embodiment 96. The compound of embodiment 94, wherein $R^{15}$ is hydrogen; $R^{16}$ is hydrogen, $—CH_3$, $—CH_2NR^{16A}R^{16B}$, or

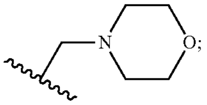 [SMILES: *CN1CCOCC1]

$R^{17}$ is hydrogen; and $R^{16A}$ and $R^{16B}$ are independently hydrogen or unsubstituted alkyl.

Embodiment 97. The compound of embodiment 96, wherein $R^{16A}$ and $R^{16B}$ are independently unsubstituted methyl.

Embodiment 98. The compound of embodiment 94, wherein $R^{15}$ is hydrogen; $R^{16}$ is hydrogen; $R^{17}$ is hydrogen, $—CH_3$, $—CH_2NR^{17A}R^{17B}$, or

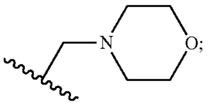 [SMILES: *CN1CCOCC1]

and $R^{17A}$ and $R^{17B}$ are independently hydrogen or unsubstituted alkyl.

Embodiment 99. The compound of embodiment 98, wherein $R^{17A}$ and $R^{17B}$ are independently unsubstituted methyl.

Embodiment 100. The compound of embodiment 94, wherein $R^{15}$ is hydrogen, $—CH_3$, $—CH_2NR^{15A}R^{15B}$, or

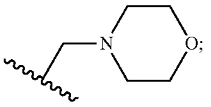 [SMILES: *CN1CCOCC1]

$R^{16}$ is hydrogen; R" is hydrogen; and $R^{15A}$ and $R^{15B}$ are independently hydrogen or unsubstituted alkyl.

Embodiment 101. The compound of embodiment 100, wherein $R^{15A}$ and $R^{15B}$ are independently unsubstituted methyl.

Embodiment 102. The compound of one of embodiments 1 to 89, wherein E is $—C(O)CH{=}CH_2$, $—C(O)CH{=}CHCH_2N(CH_3)_2$, $—C(O)C({=}CH_2)CH_2N(CH_3)_2$, $—C(O)C{\equiv}CCH_3$, $—C(O)C({=}CH_2)CH_3$.

Embodiment 103. The compound of embodiment 1 having the formula:

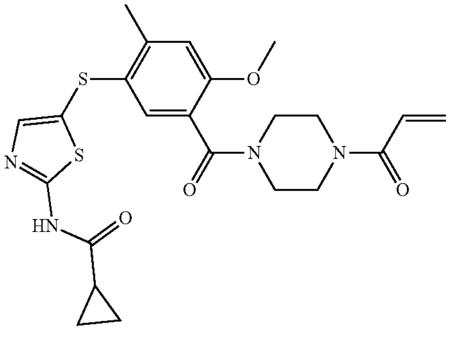

,

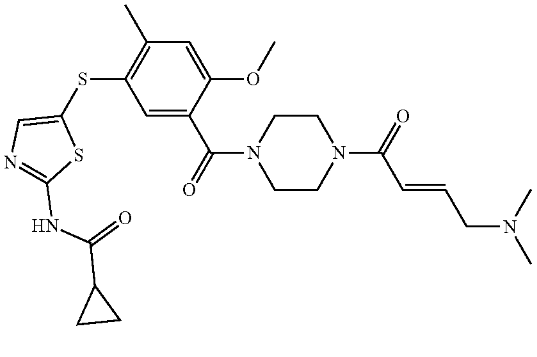

,

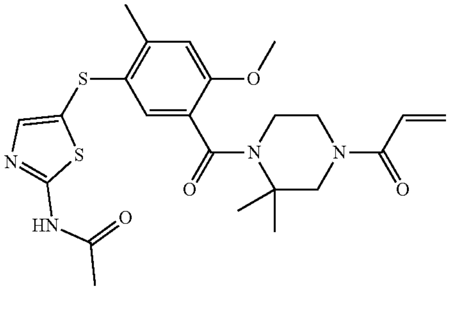

,

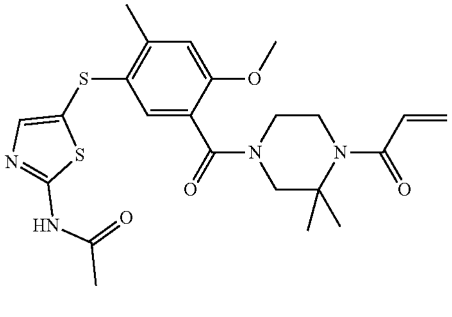

,

-continued
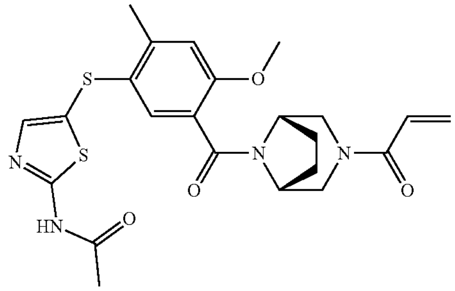
,
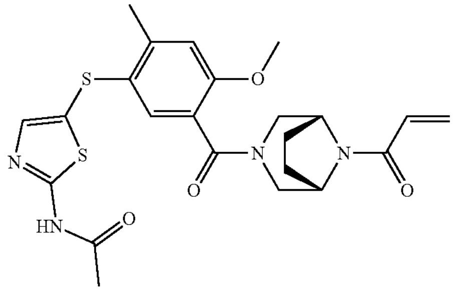
,
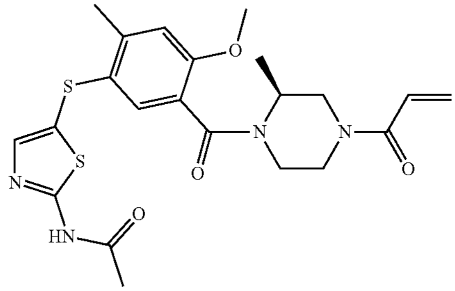
,
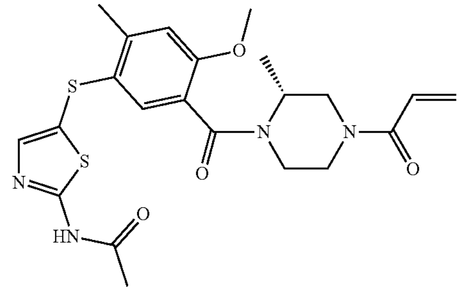
,
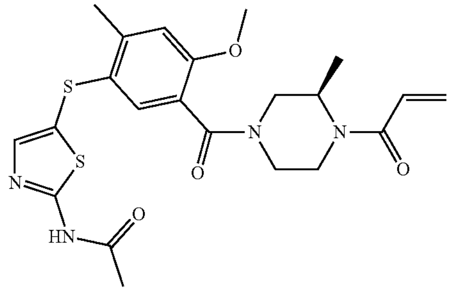
,
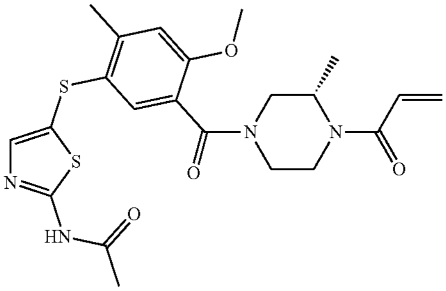
,
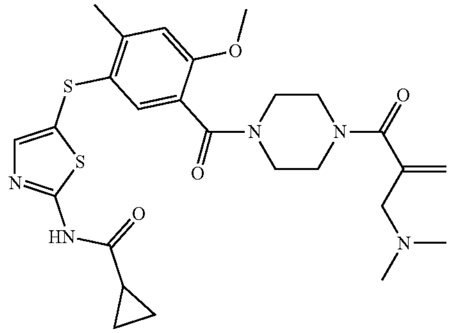
,
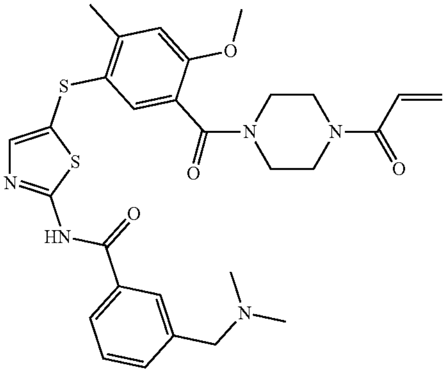
,
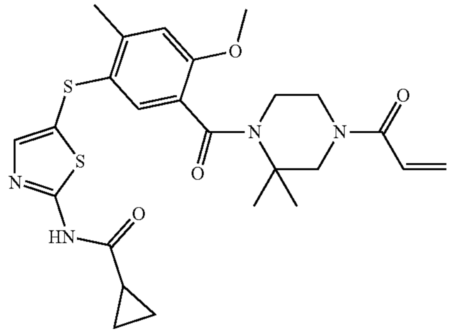
,
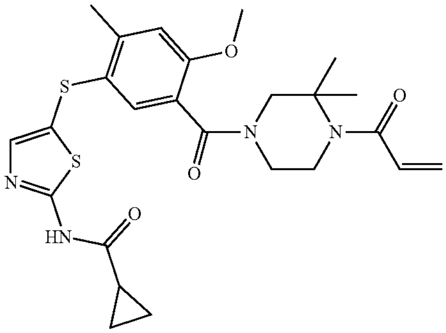
, -continued
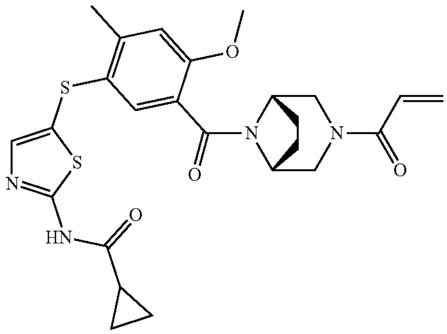
,
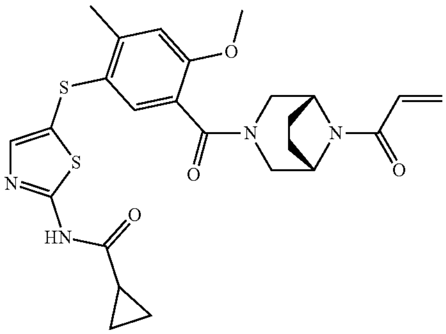
,
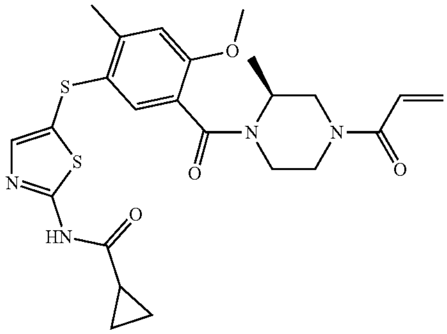
,
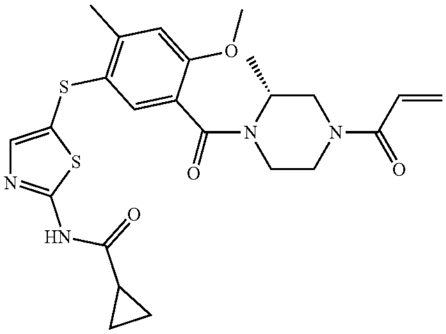
,
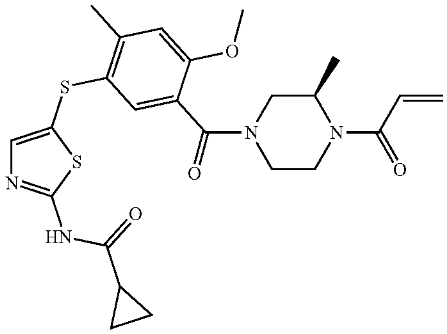
,
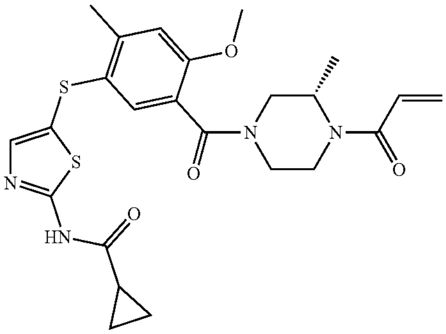
,
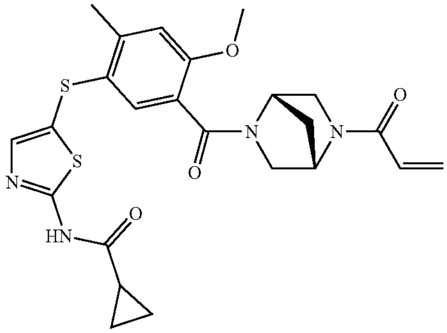
,
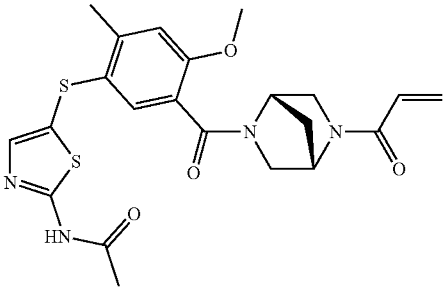
,
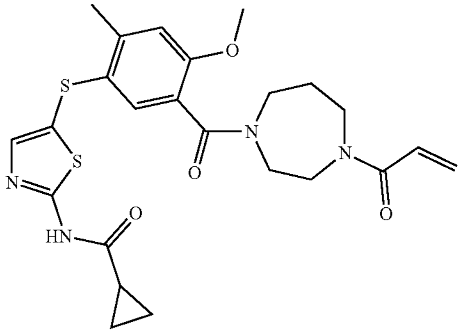
,
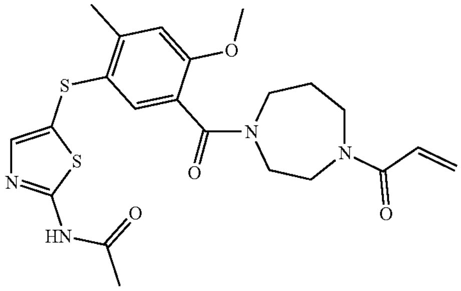
, -continued
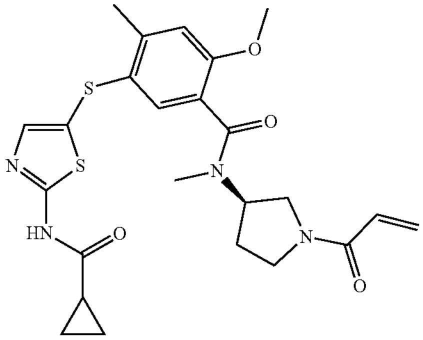
,
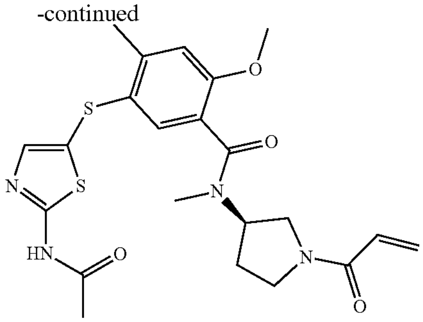
,
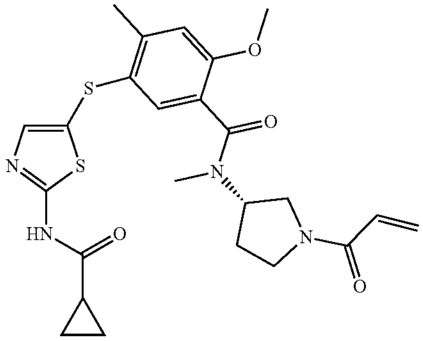
,
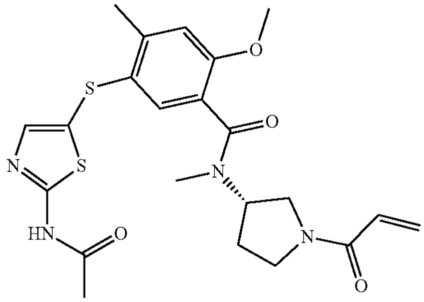
,
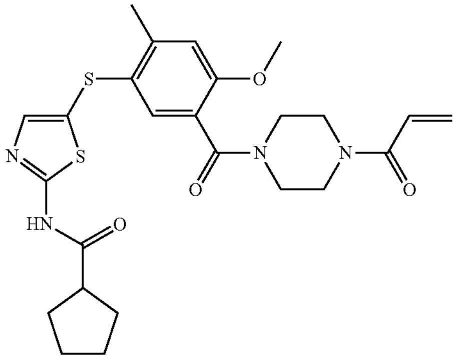
,
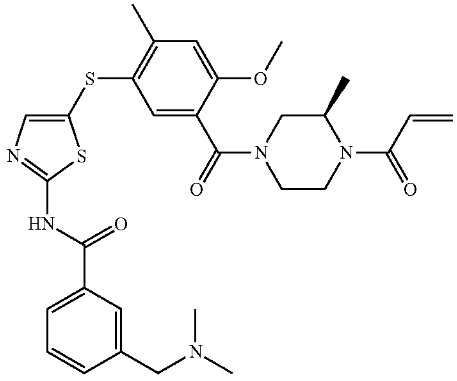
,
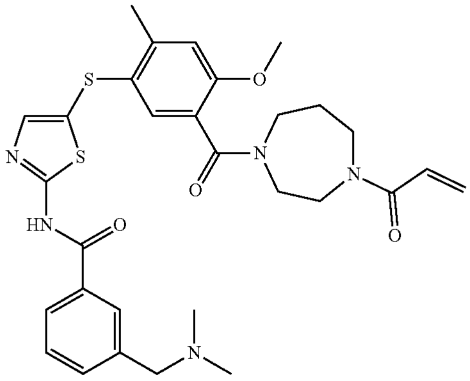
,
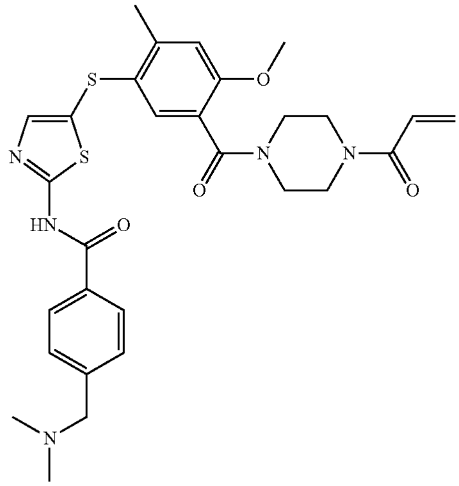
, -continued
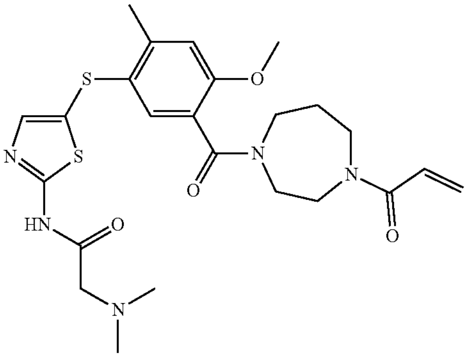
,
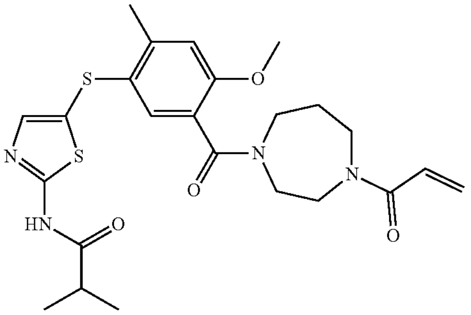
,
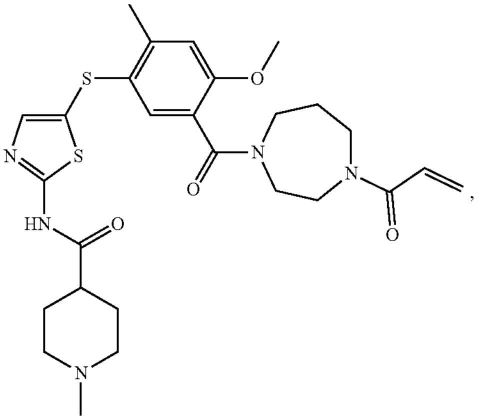
,
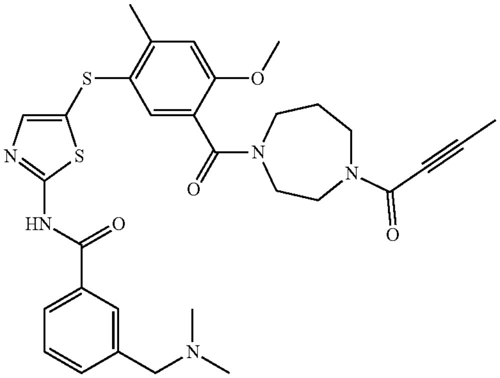
,
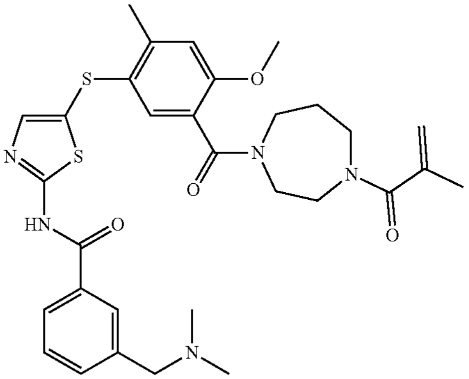
,
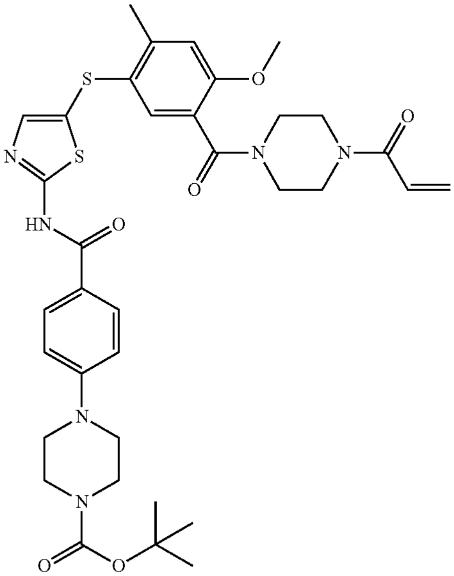
, -continued
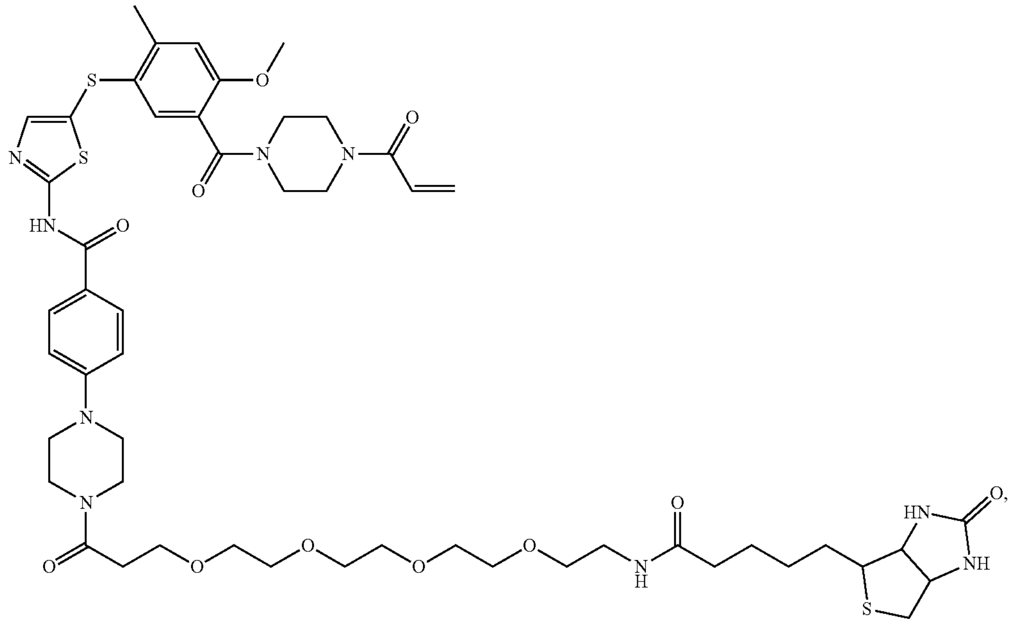,
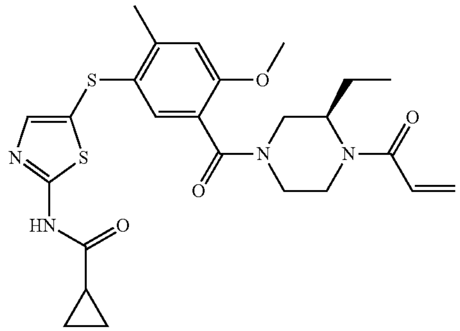,
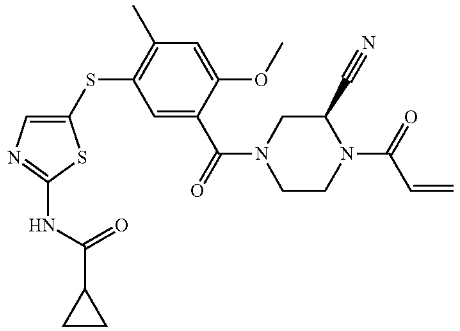,
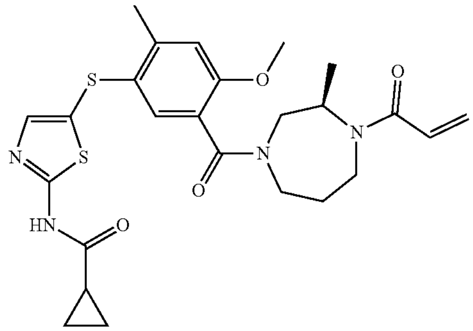,
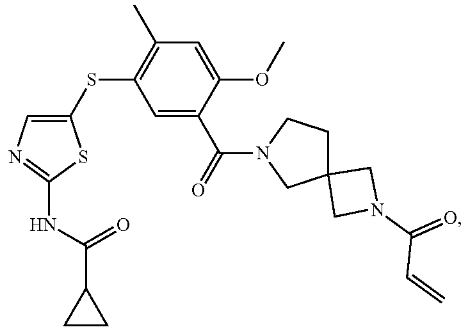,
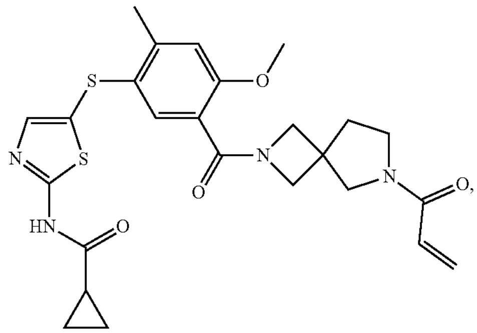,
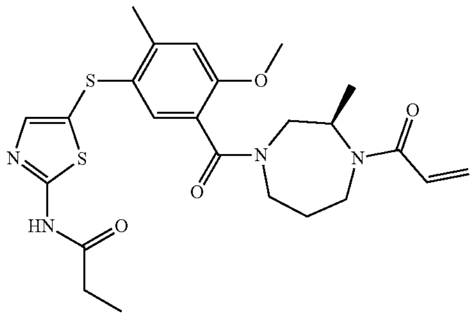, -continued
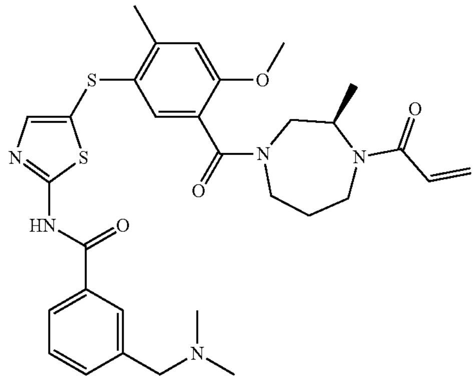,
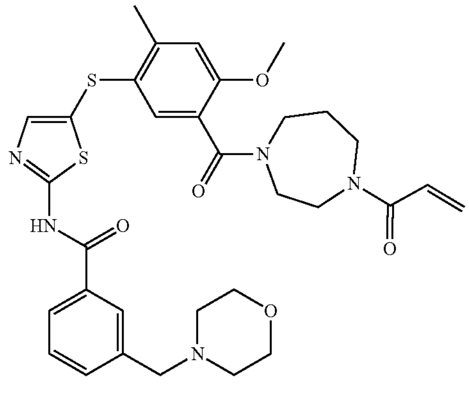,
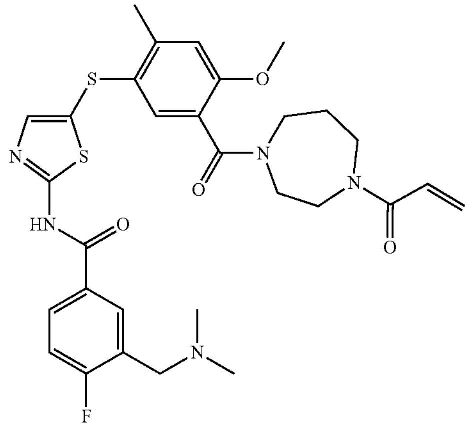,
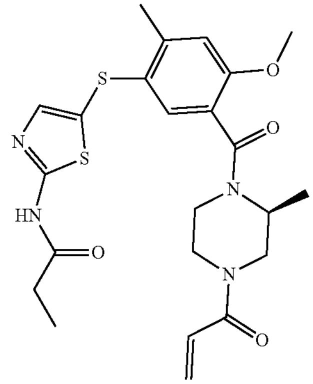,
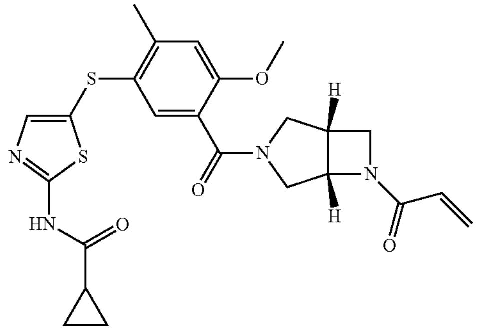,
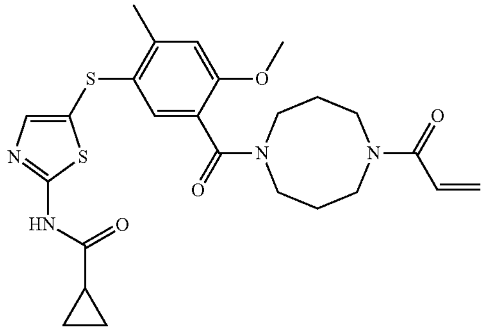,
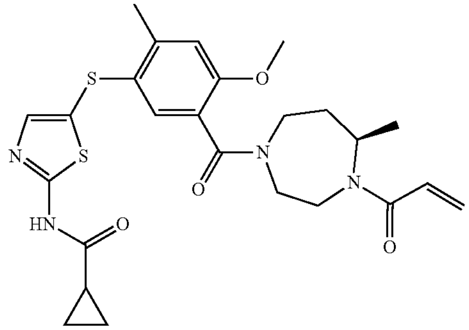,
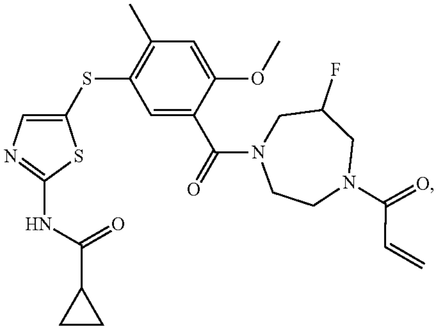

-continued
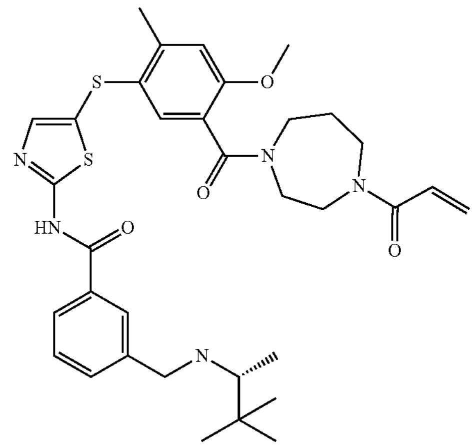
,
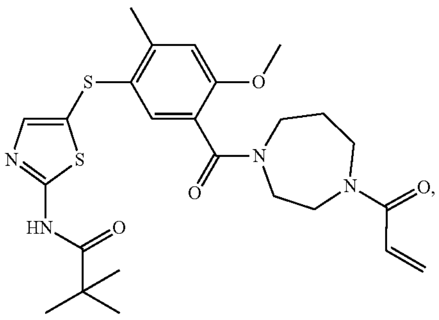
,
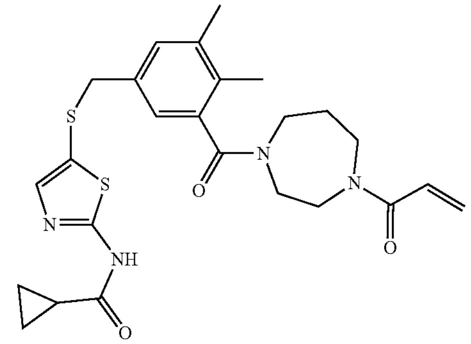
,
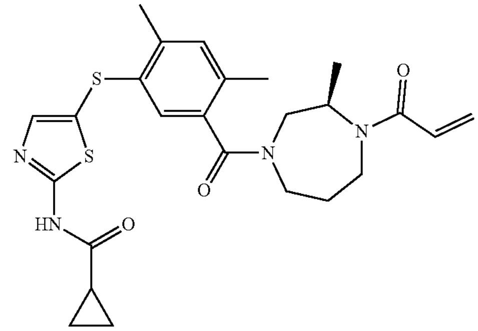
,
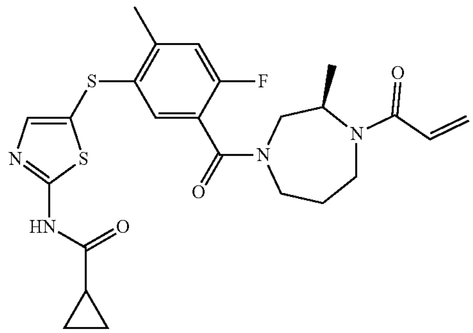
,
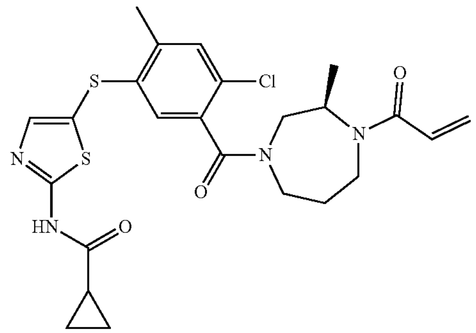
,
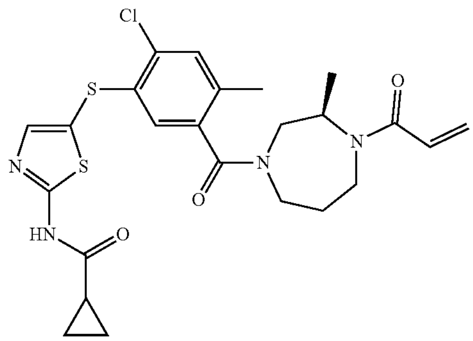
,
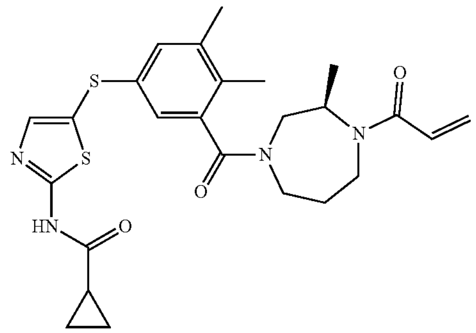
, -continued
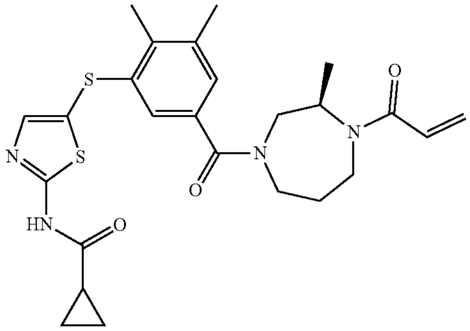,
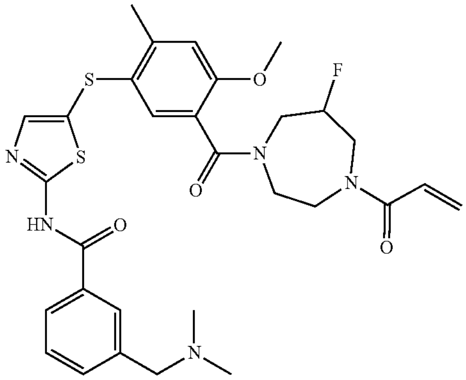,
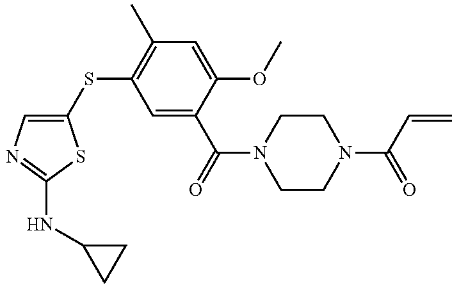,
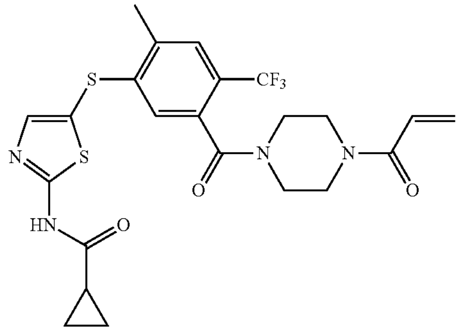,
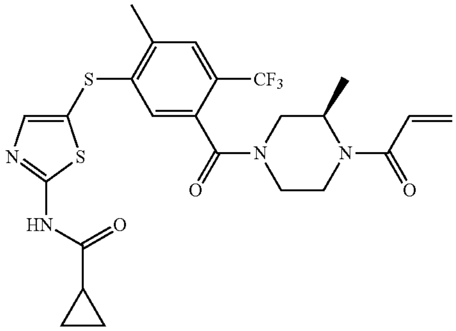,
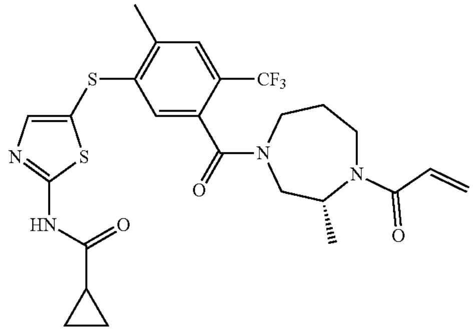,
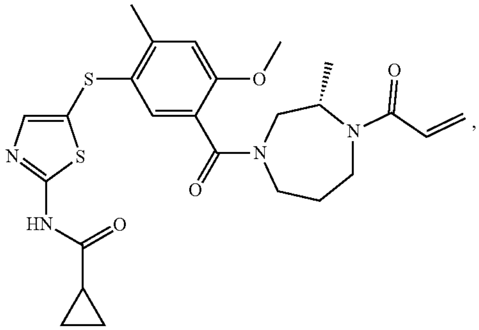,
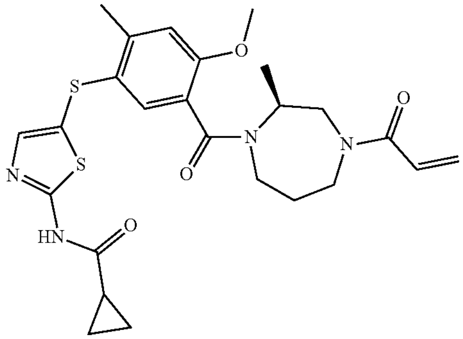,
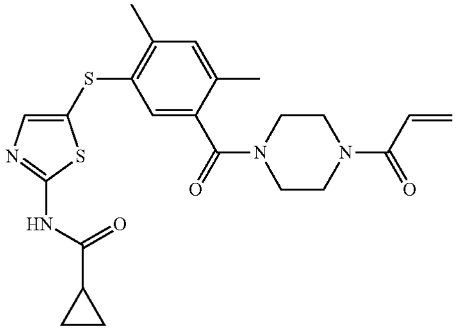,
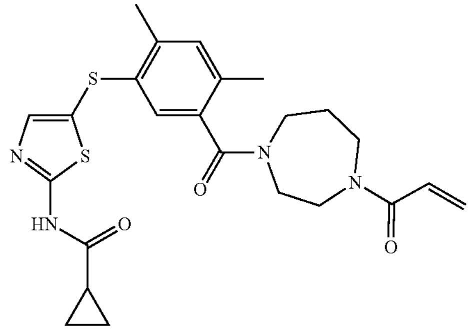, -continued
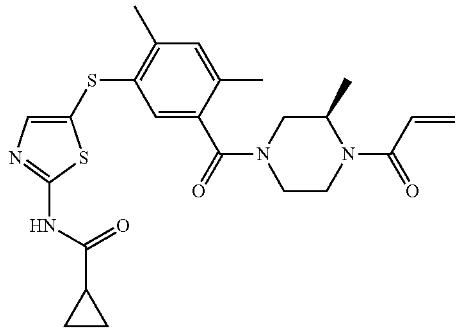
,
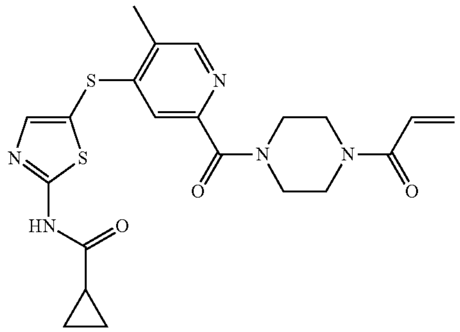
,
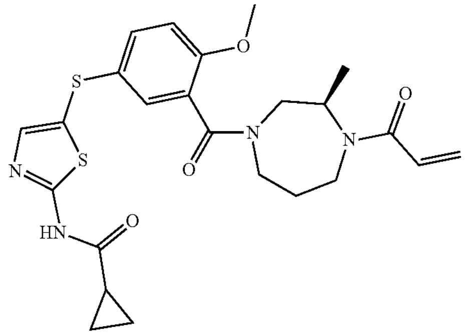
,
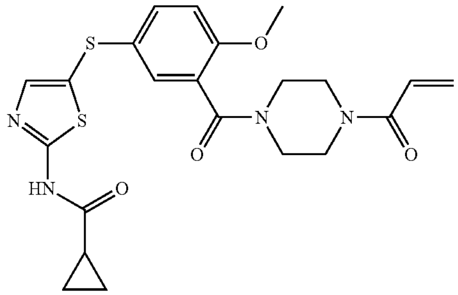
,
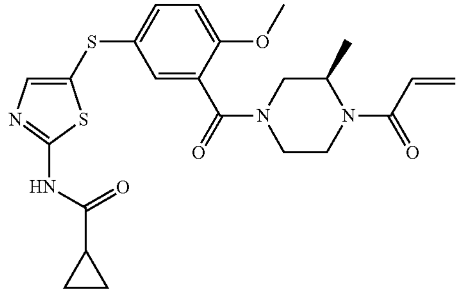
,
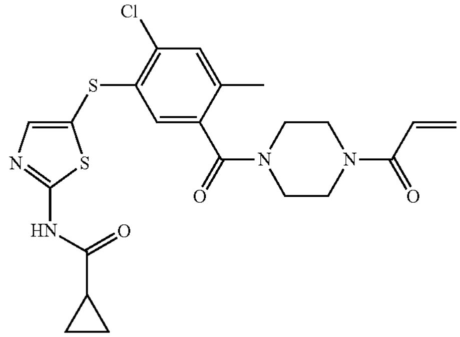
,
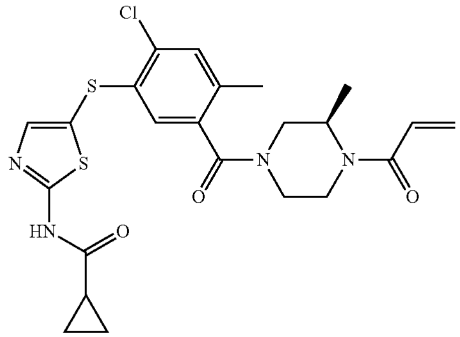
,
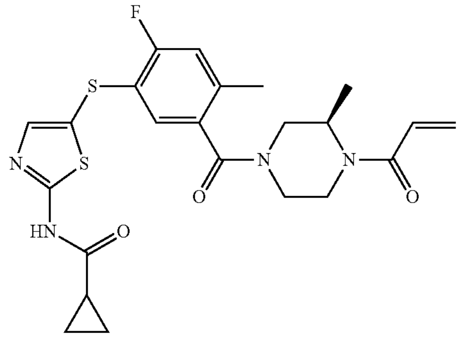
,
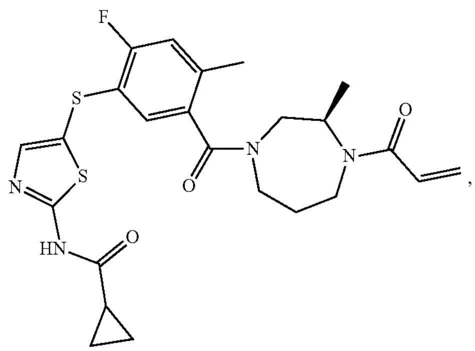
,
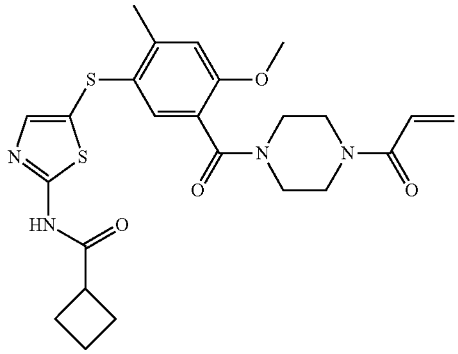
, -continued
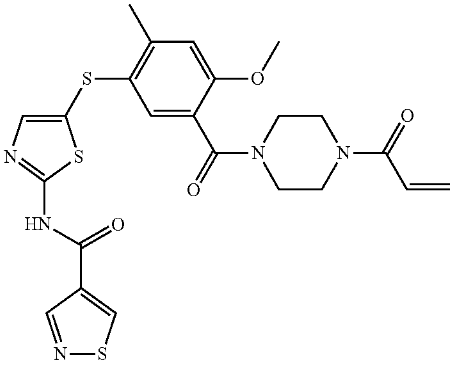,
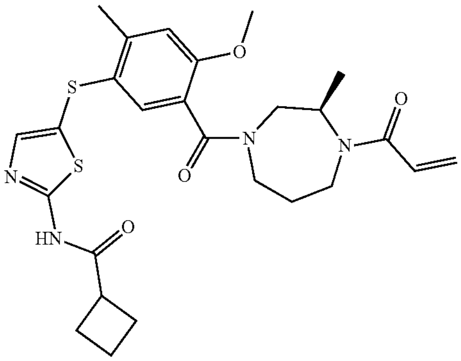,
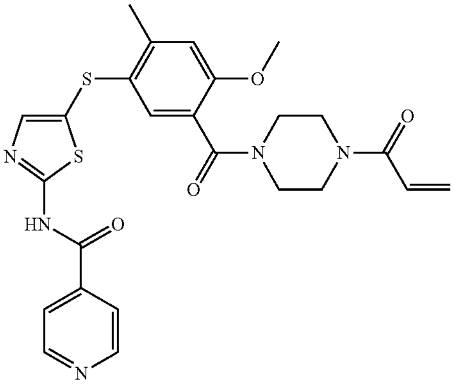,
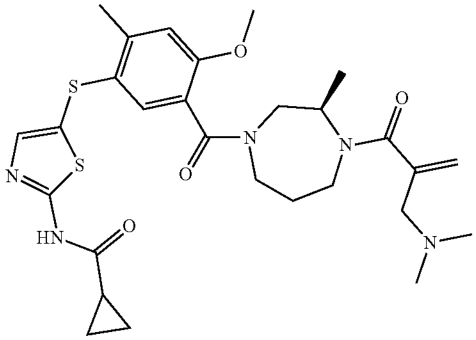,
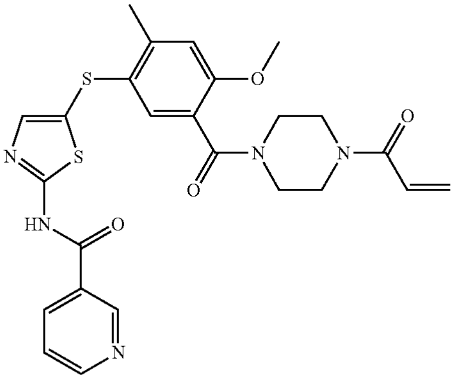,
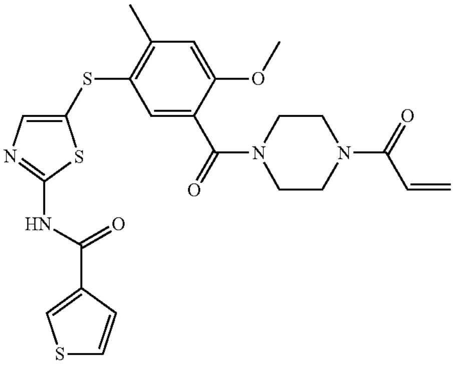,
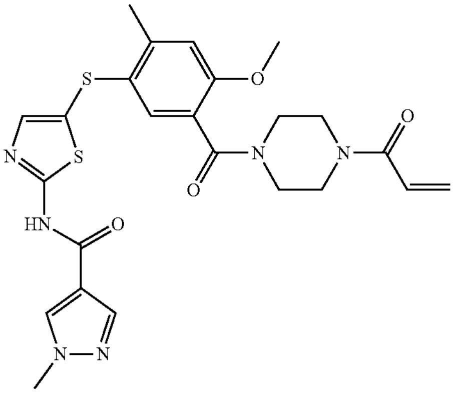,
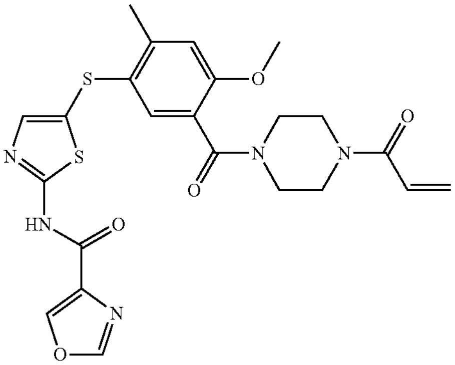, -continued
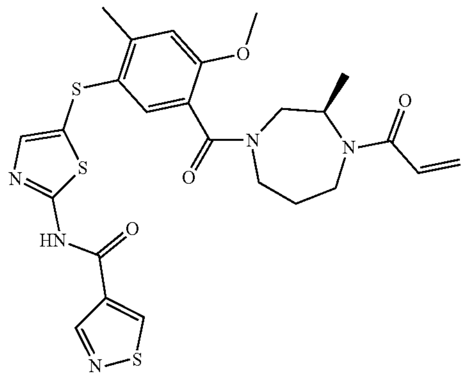
,
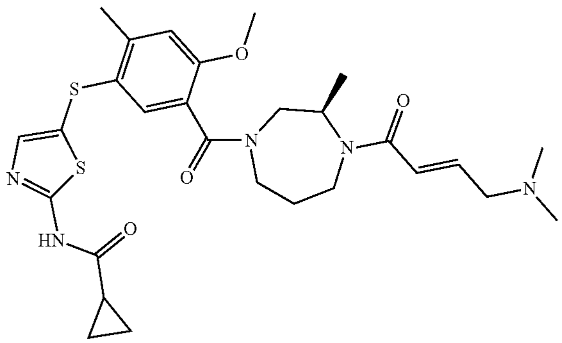
,
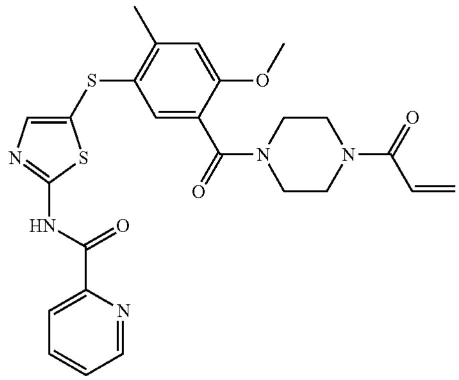
,
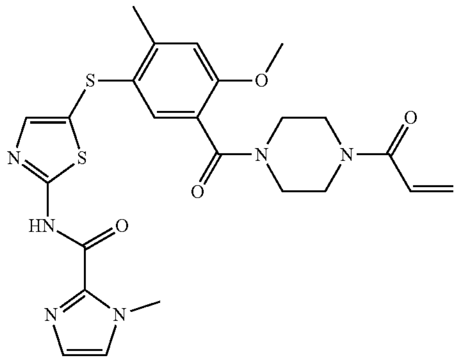
,
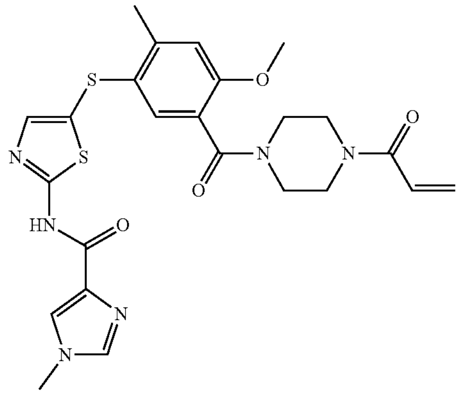
,
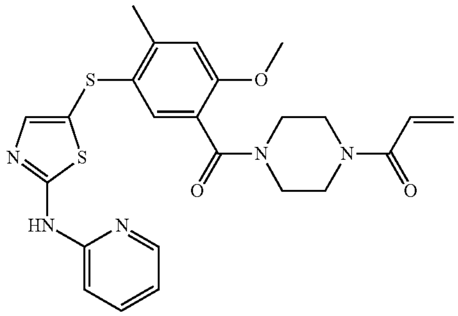
,
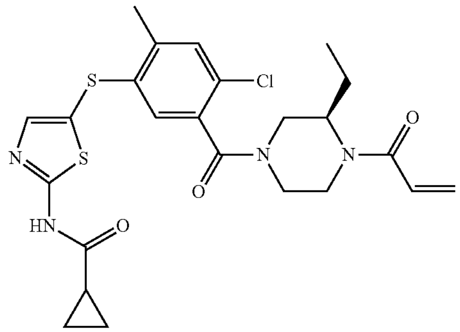
,
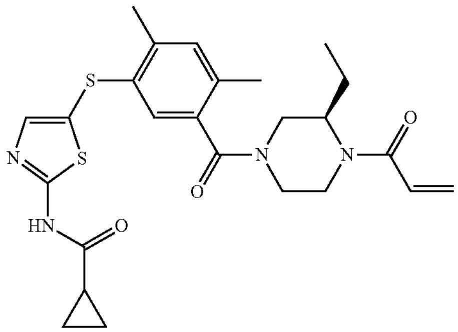
, -continued
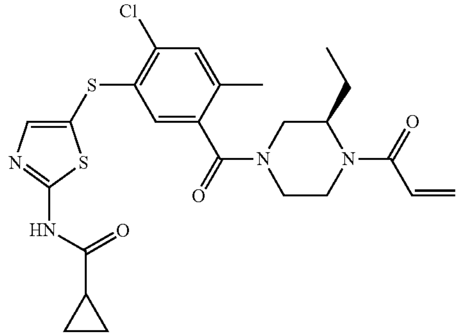
,
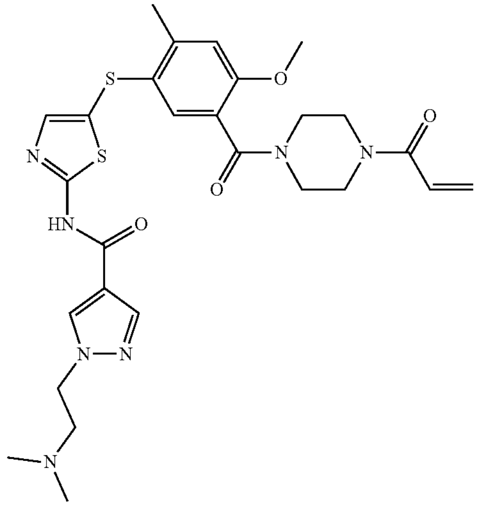
,
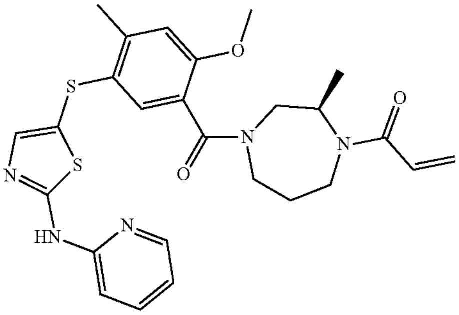
,
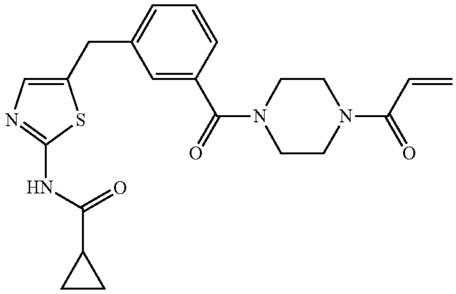
,
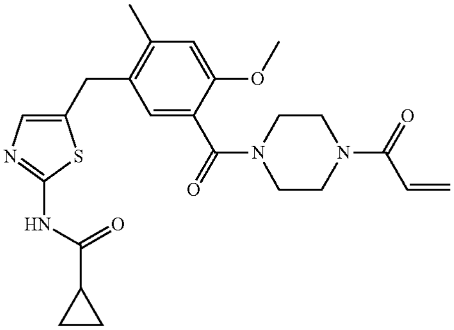
,
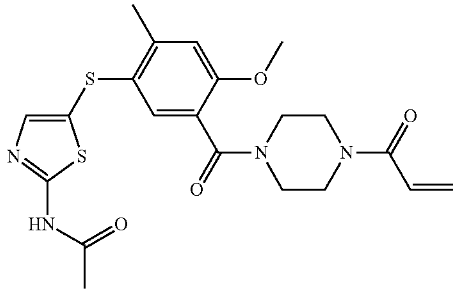
,
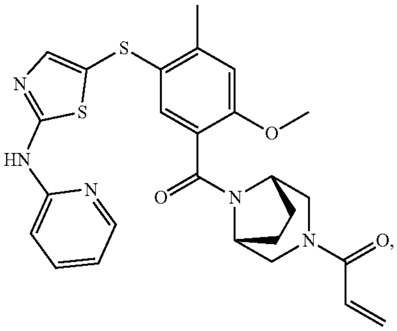
,
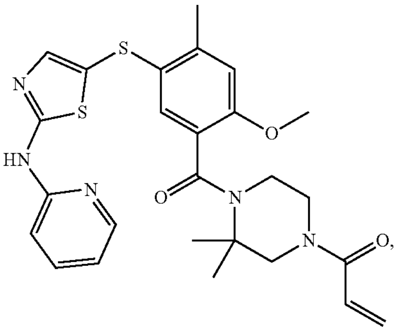
, -continued
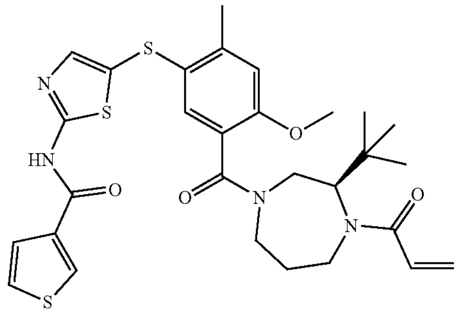
,
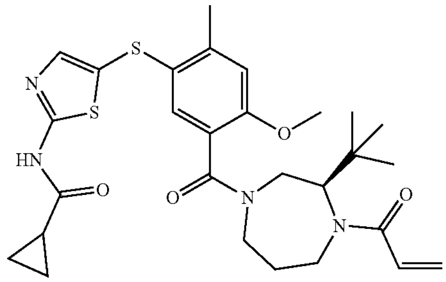
,
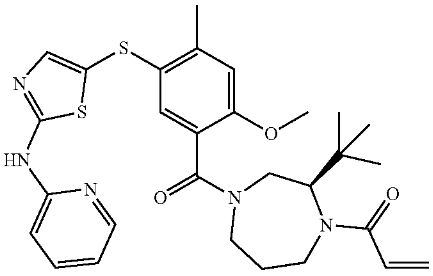
,
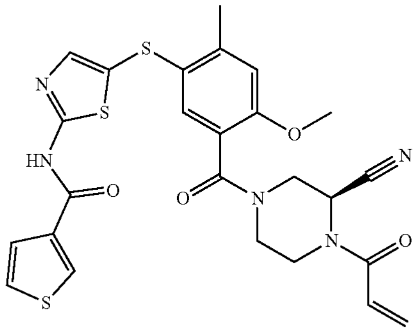
,
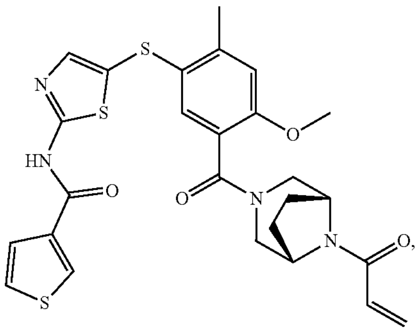
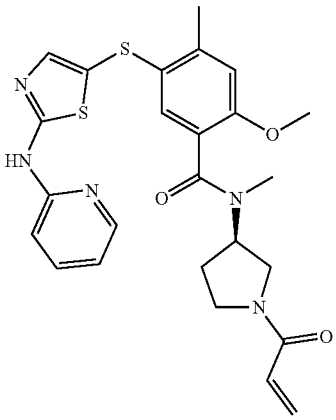
,
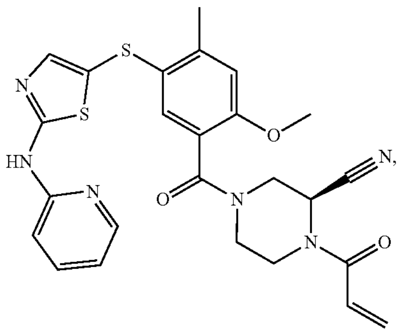
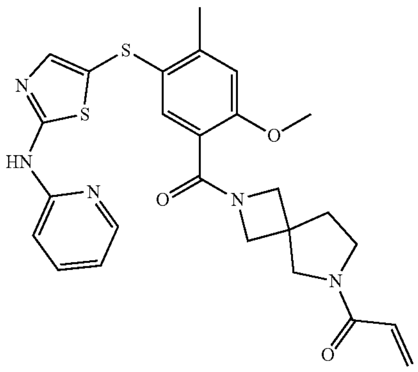
, -continued
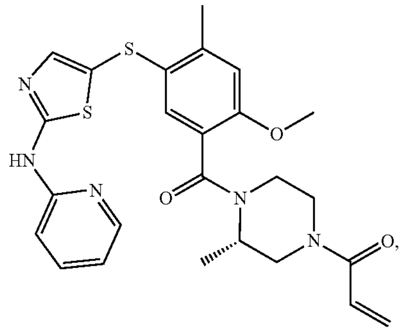
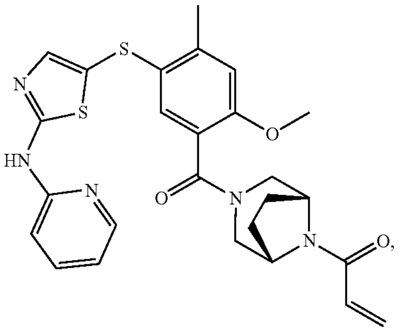
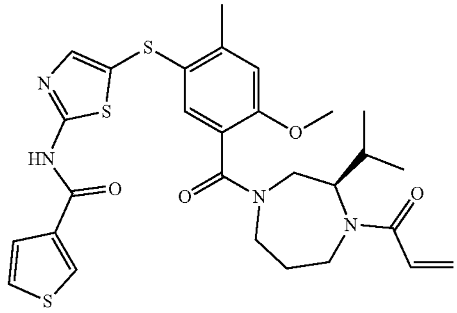
,
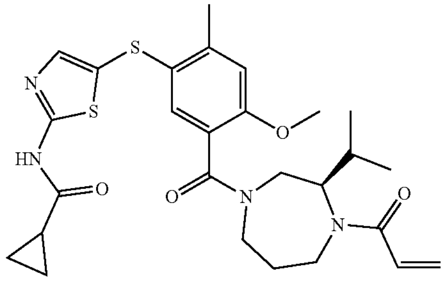
,
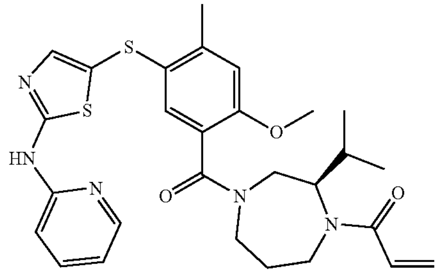
,
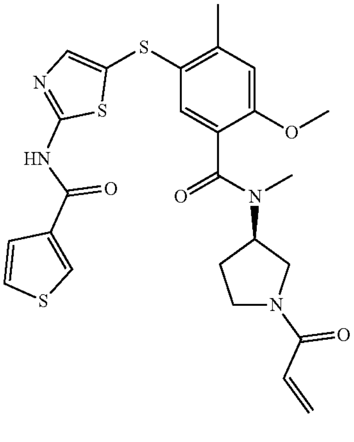
,
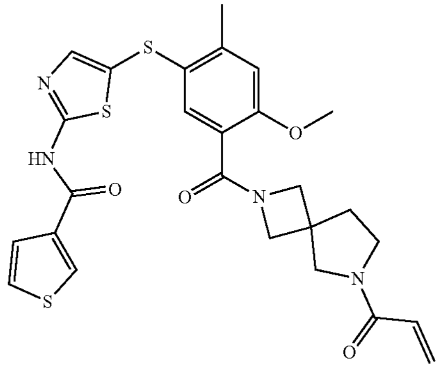
,
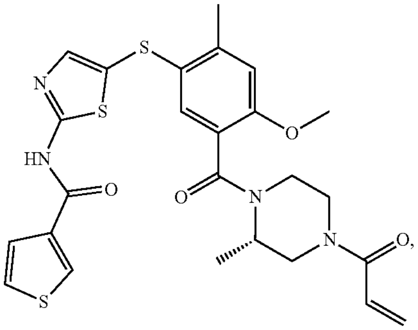

-continued
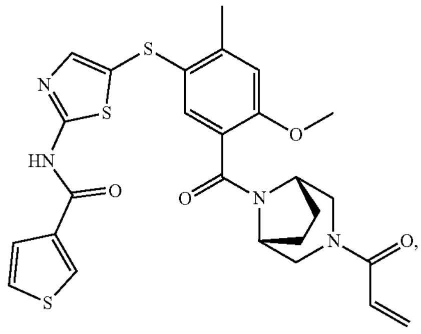,
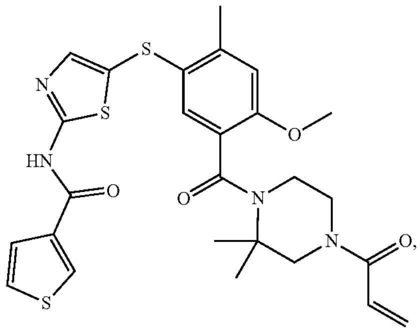,
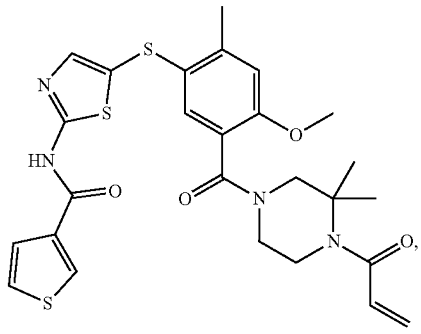,
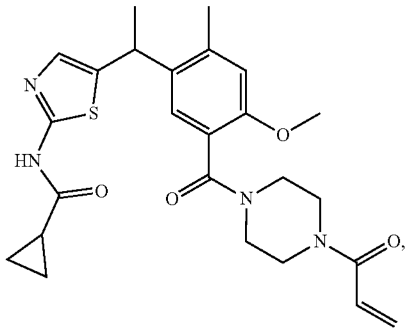,
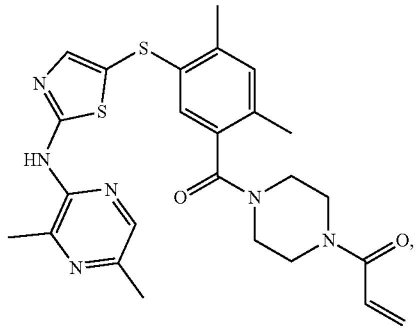,
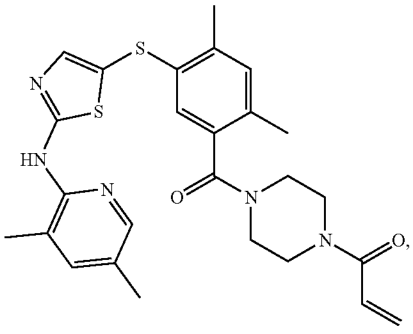, or
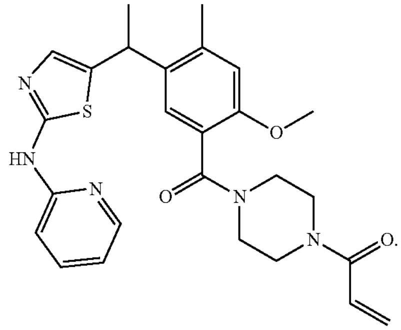.

Embodiment 104. The compound of embodiment 1 having the formula:
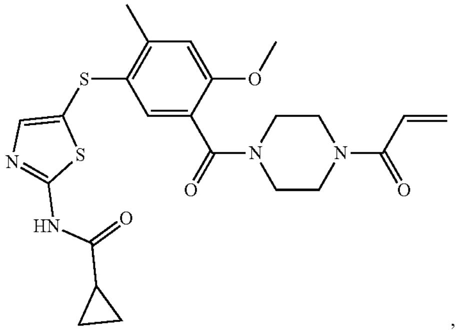
,
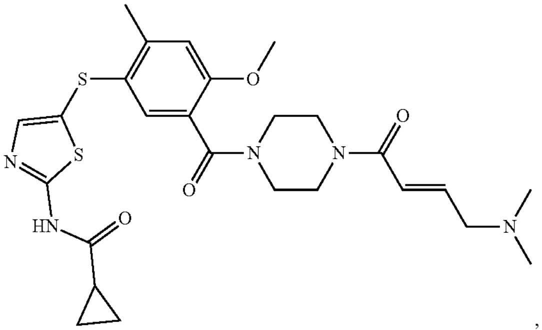
,
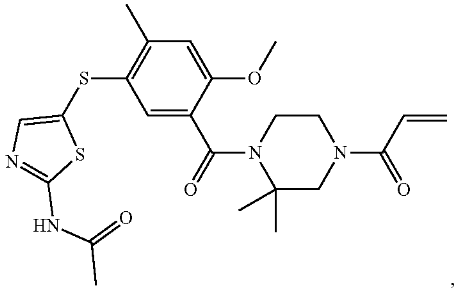
,
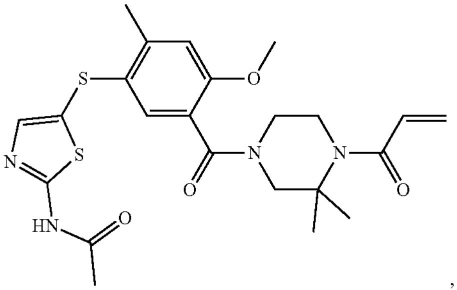
,
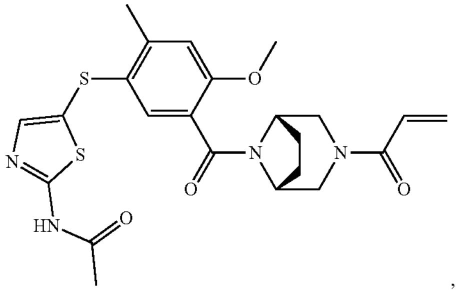
,
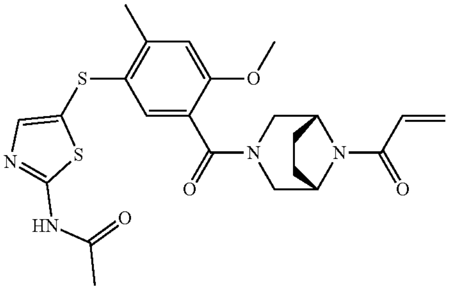
,
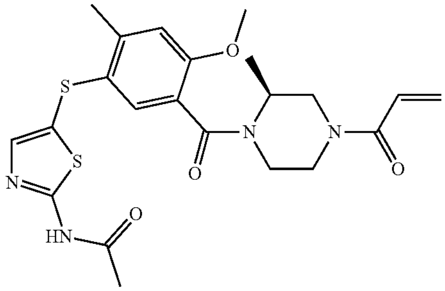
,
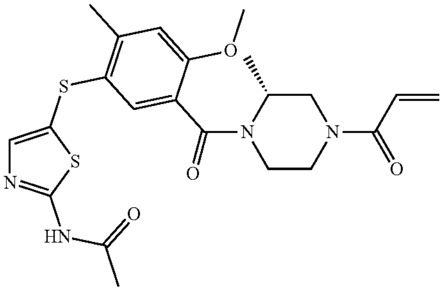
,
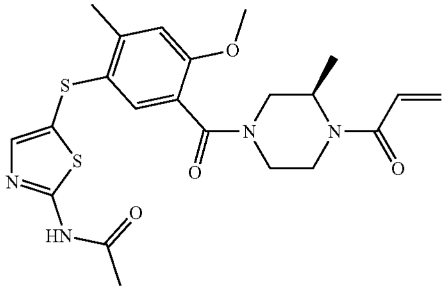
,
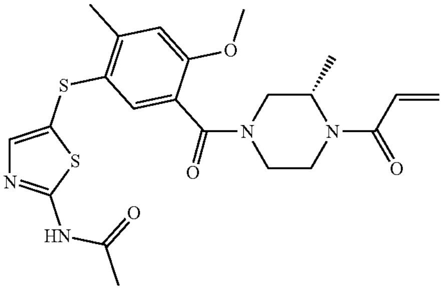
, -continued
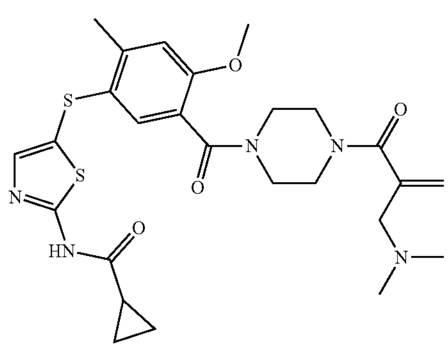
,
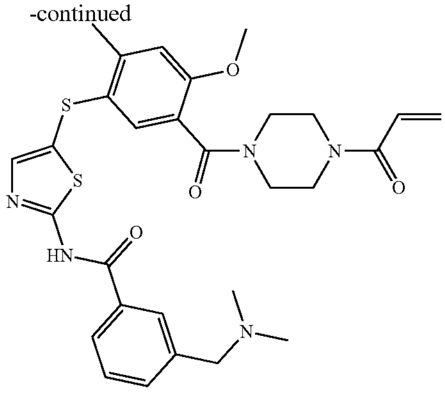
,
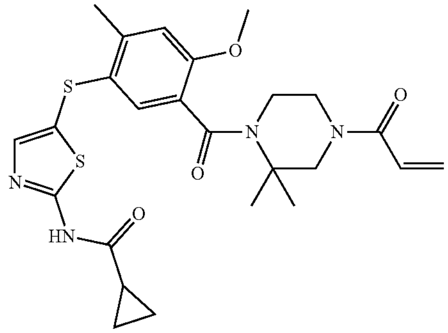
,
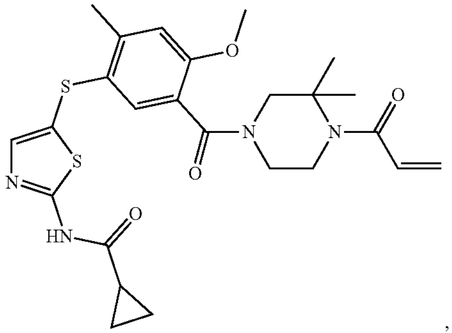
,
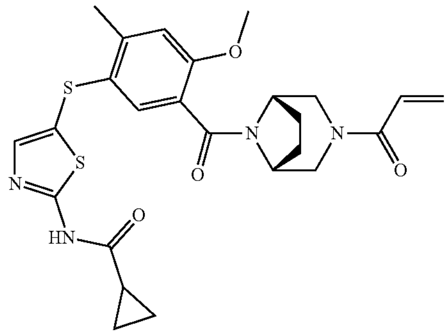
,
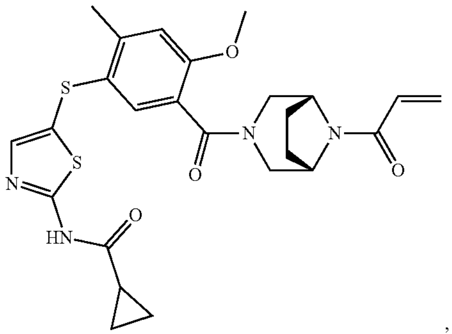
,
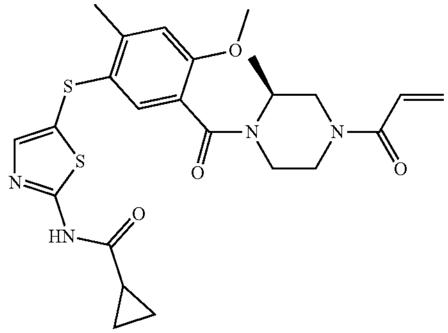
,
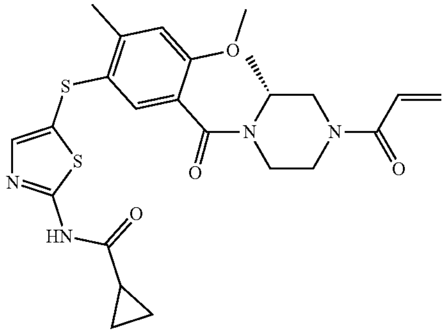
,
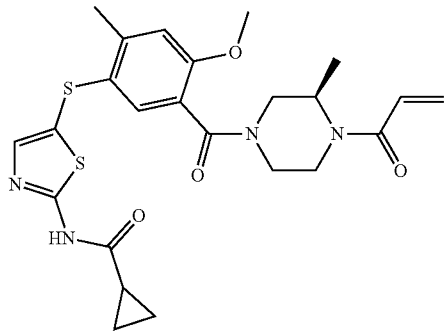
,
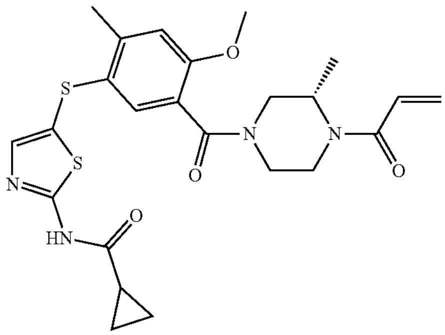
, -continued
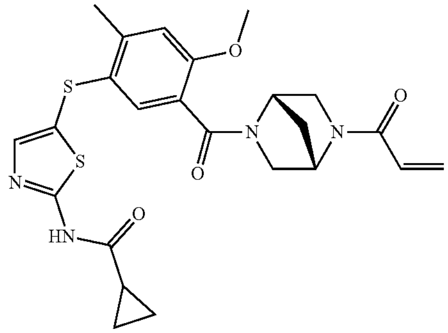
,
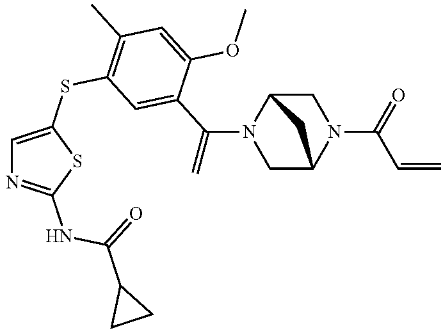
,
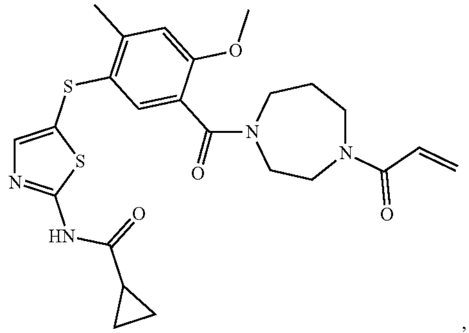
,
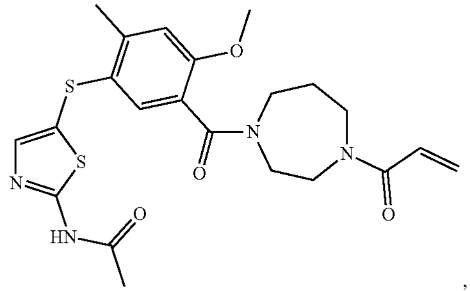
,
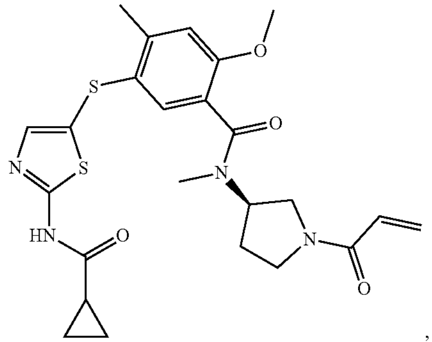
,
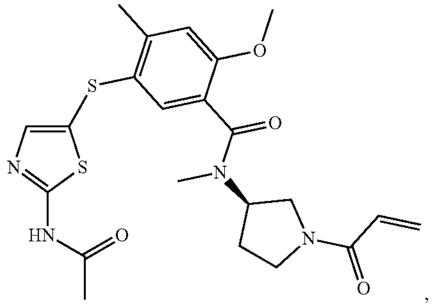
,
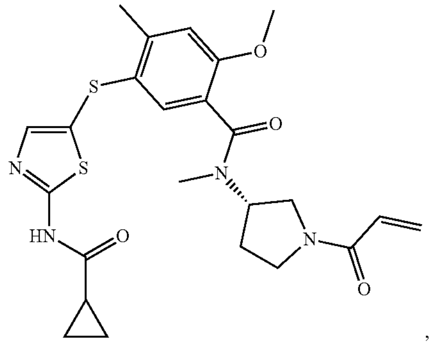
,
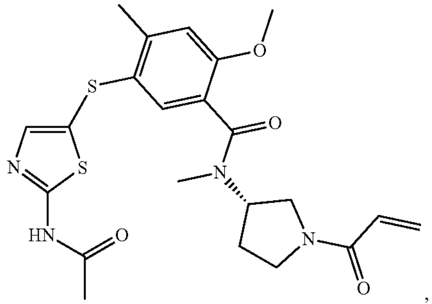
, -continued
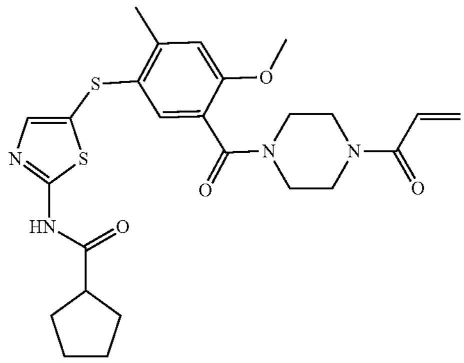
,
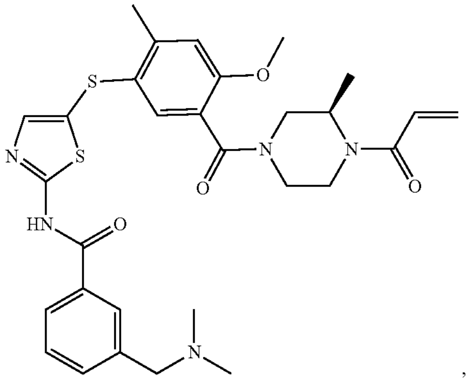
,
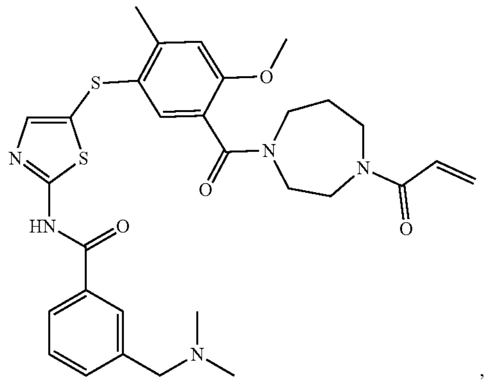
,
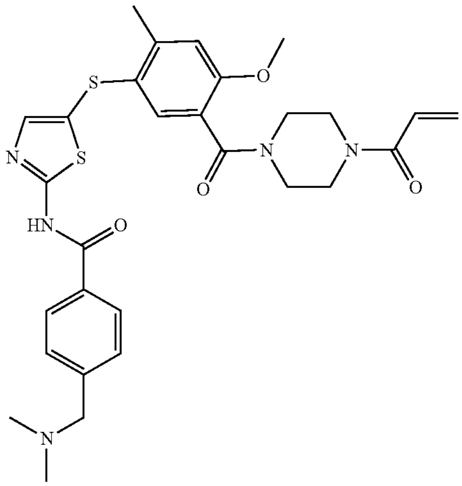
,
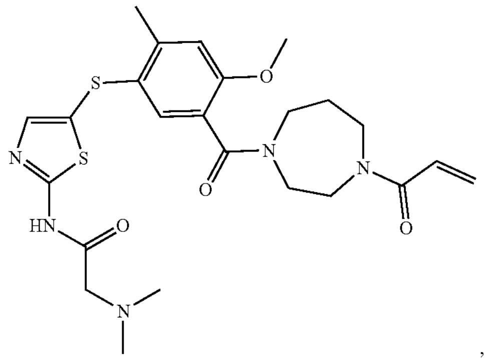
,
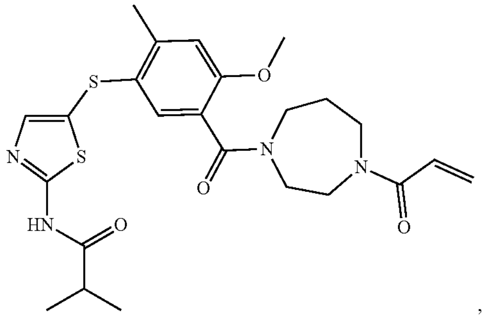
,
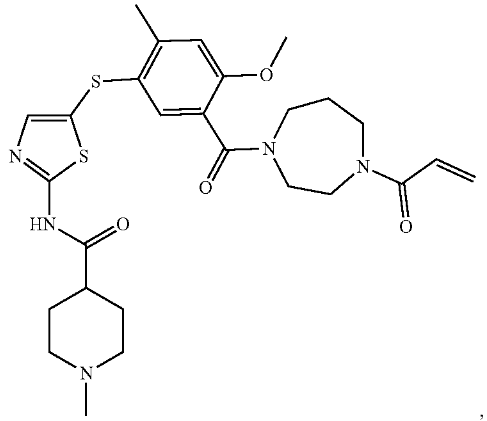
,
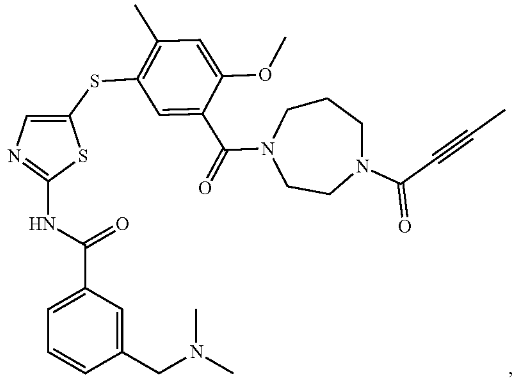
, -continued
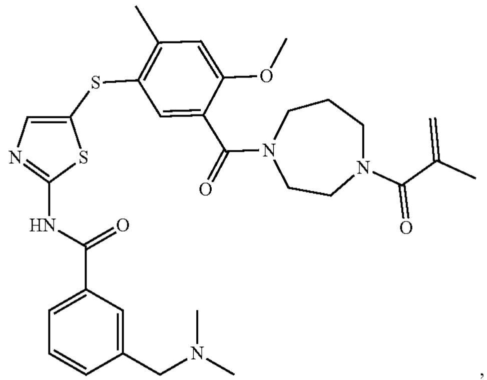
,
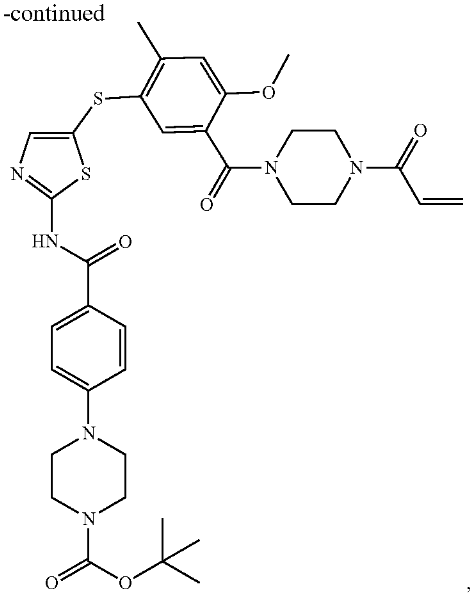
,
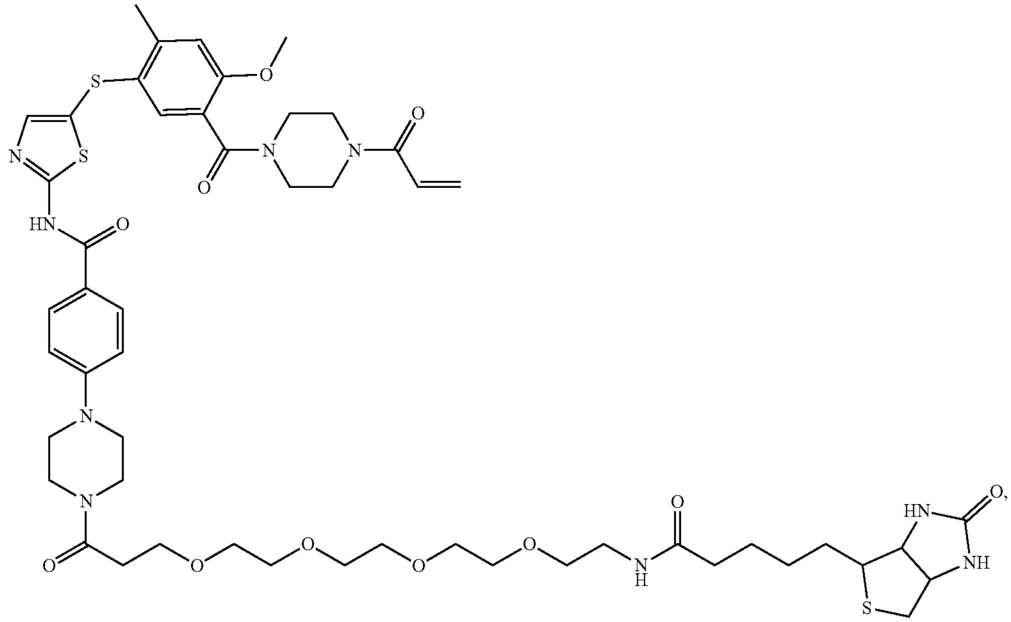
,
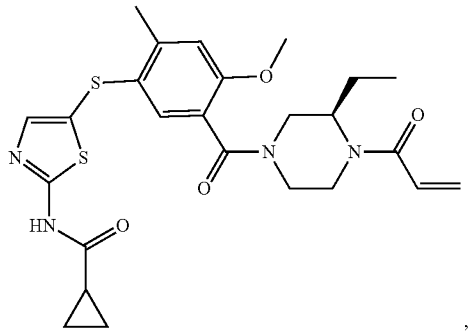
,
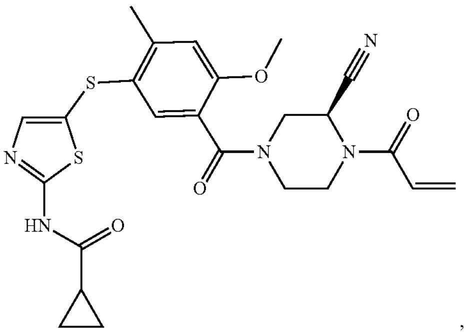
, -continued
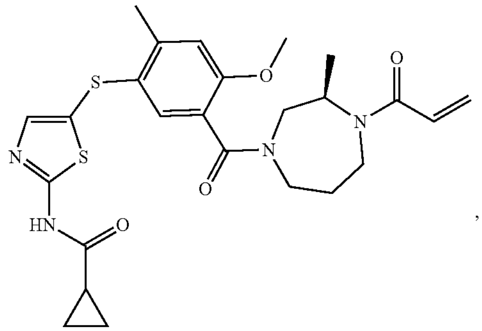
,
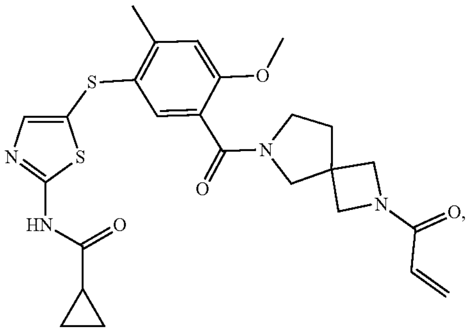
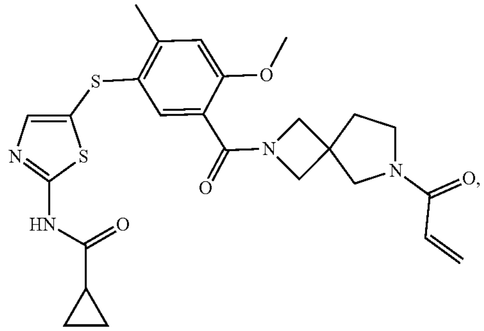
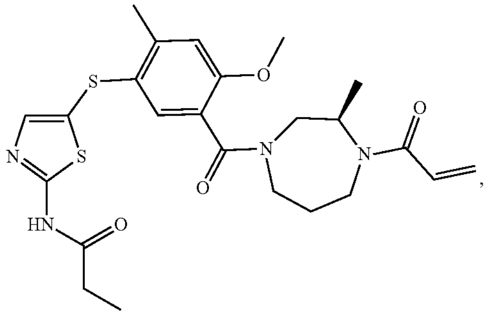
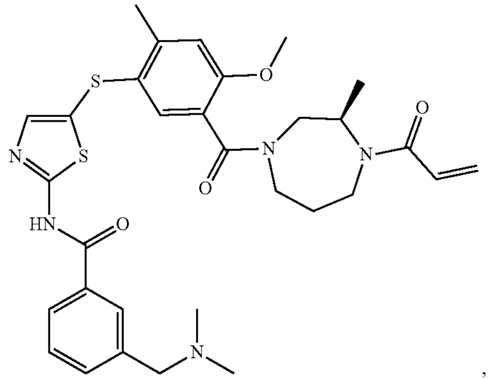
,
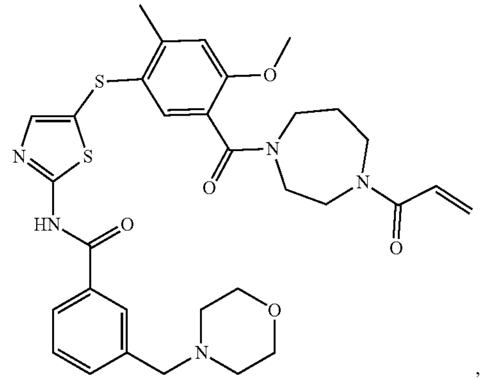
,
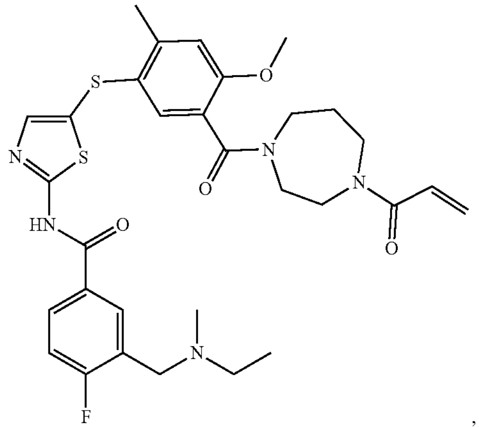
,
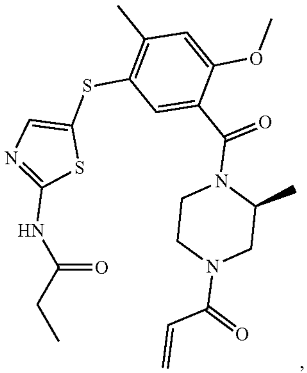
, -continued
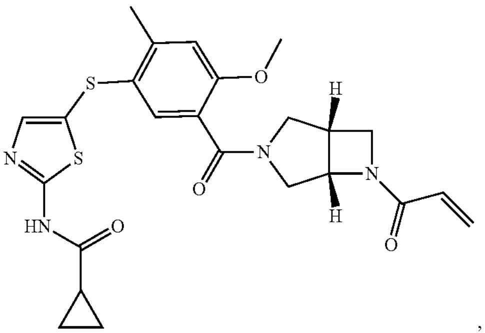
,
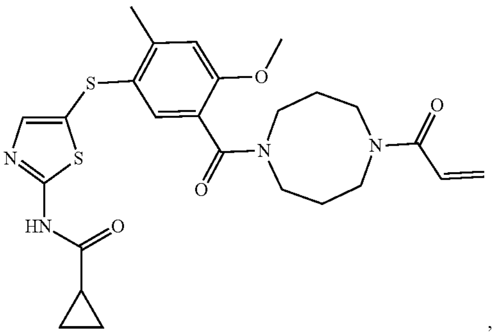
,
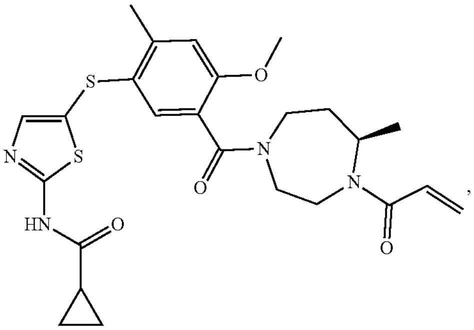
,
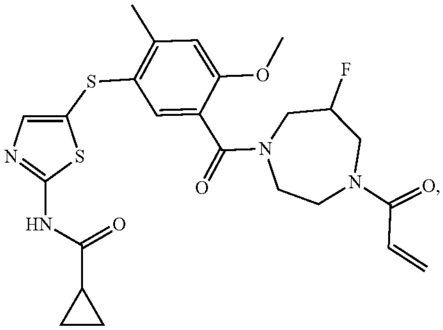
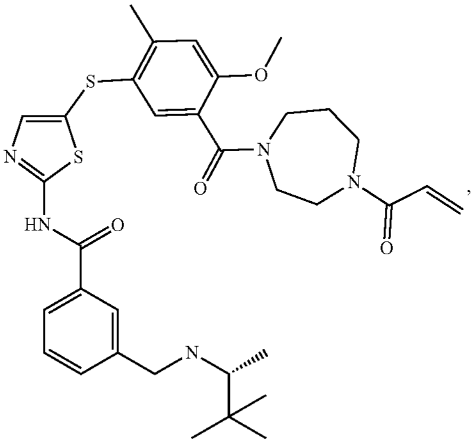
,
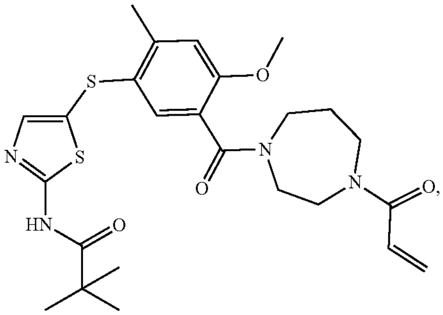
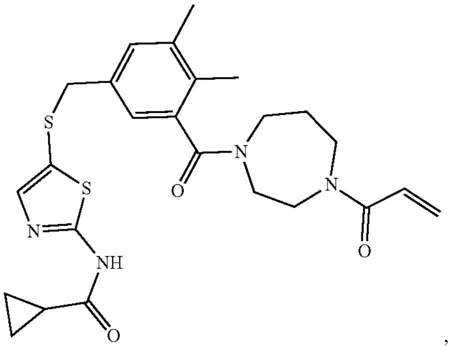
,
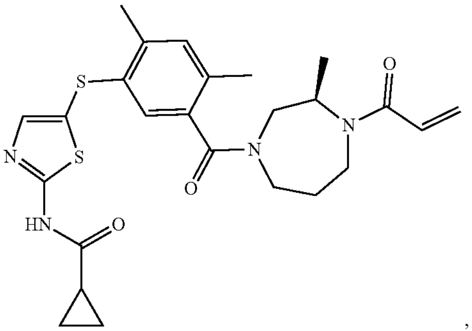
, -continued
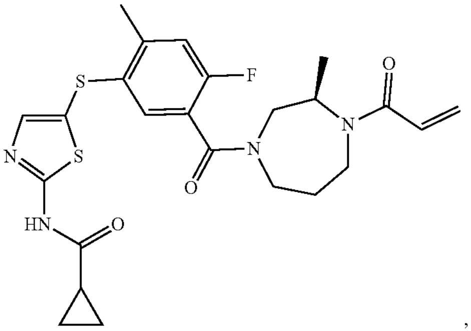
,
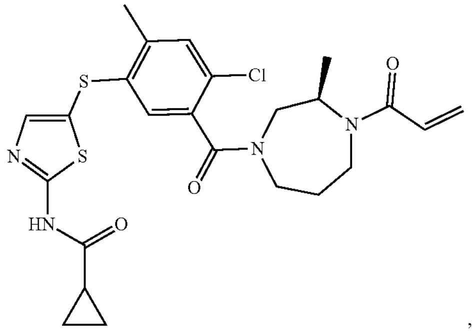
,
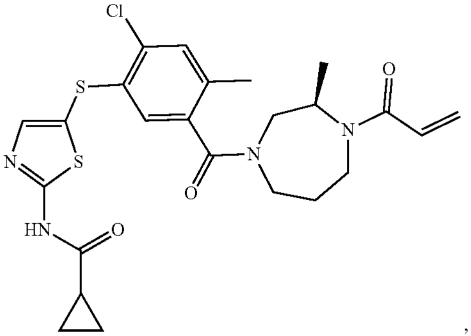
,
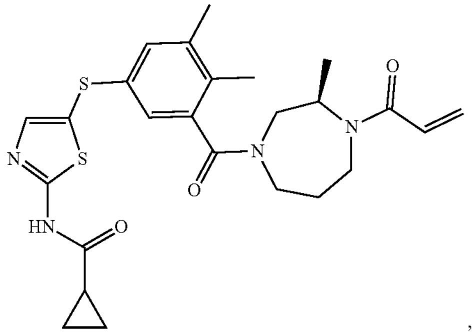
,
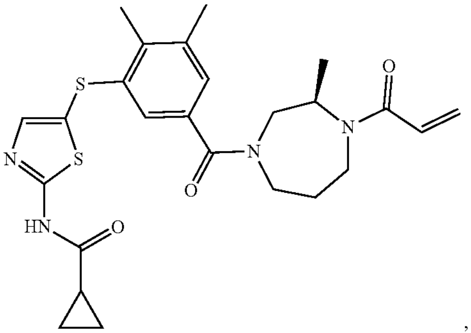
,
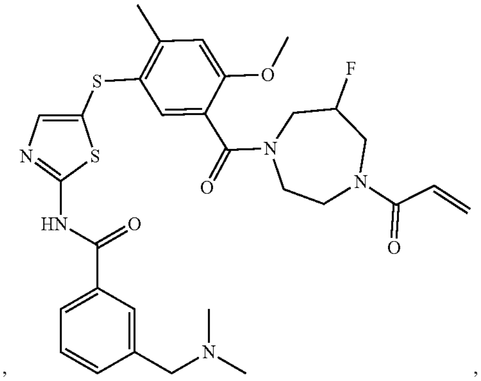
,
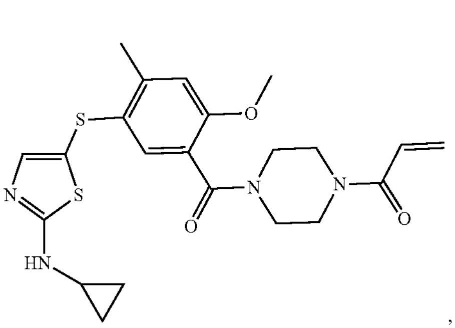
,
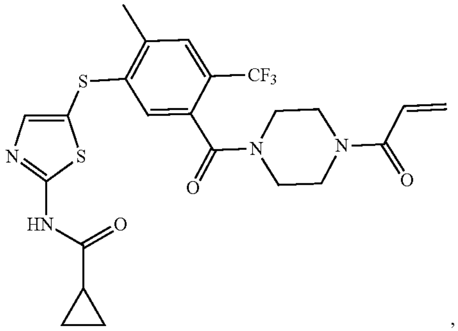
,
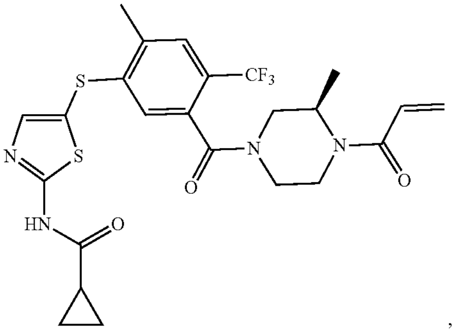
,
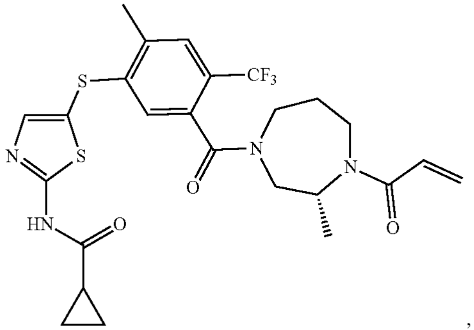
, -continued
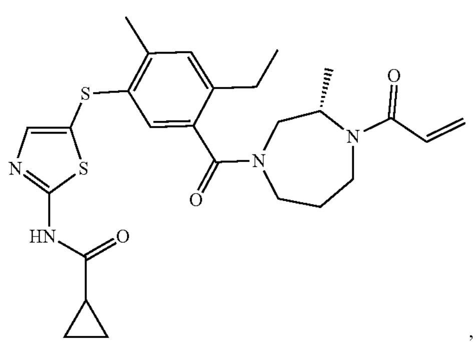
,
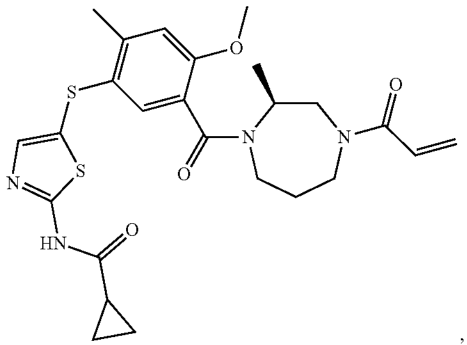
,
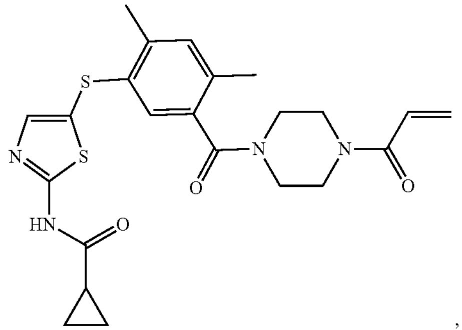
,
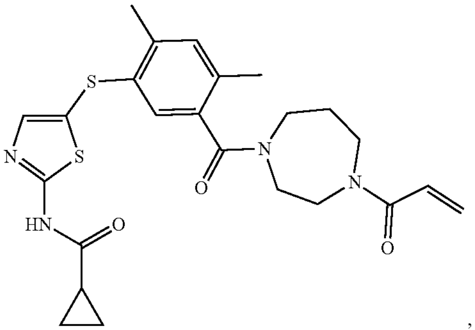
,
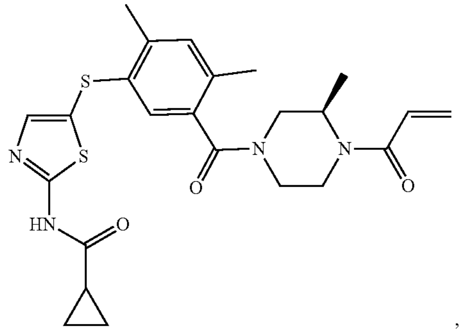
,
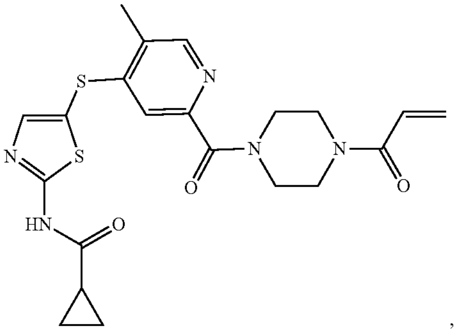
,
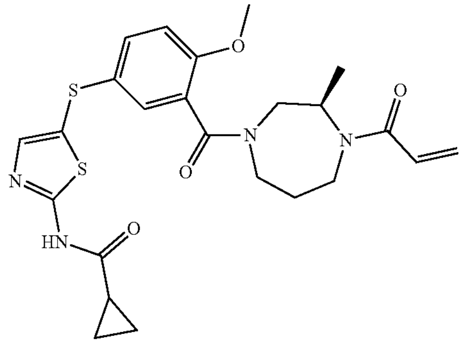
,
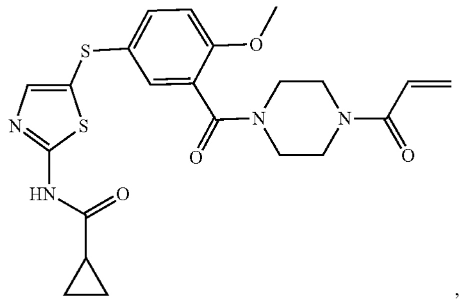
,
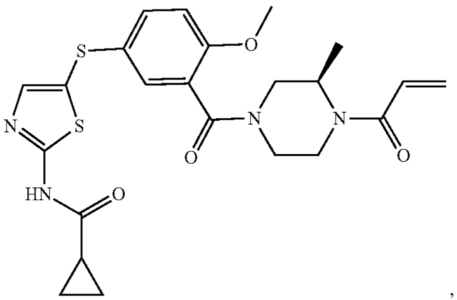
, -continued
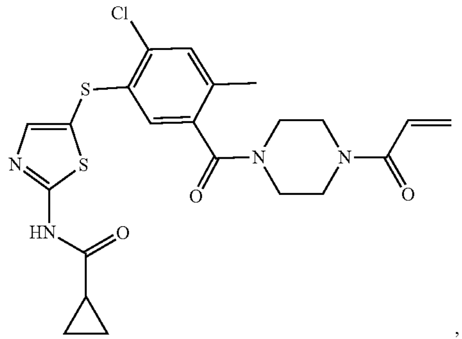
,
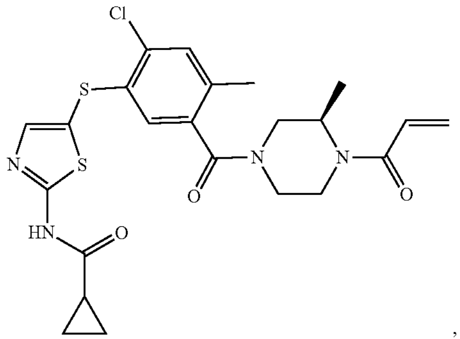
,
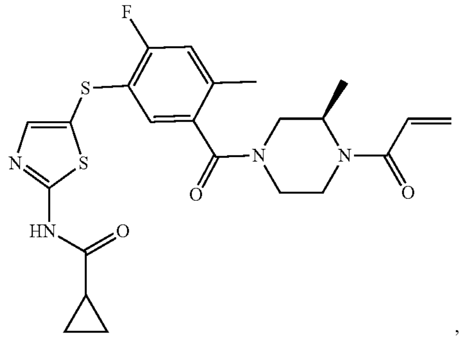
,
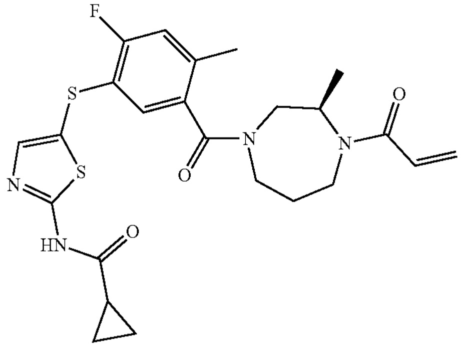
,
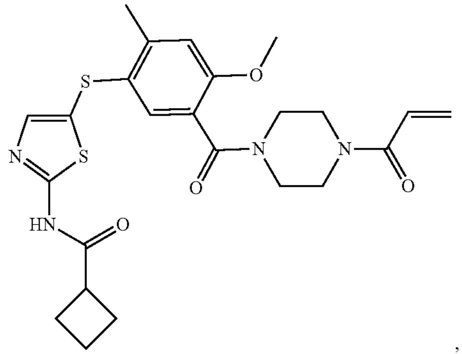
,
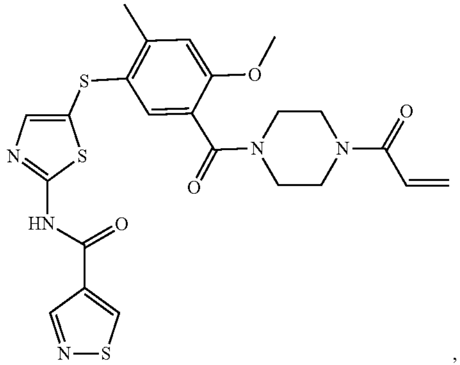
,
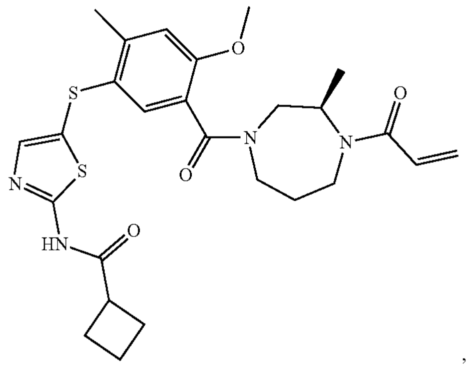
,
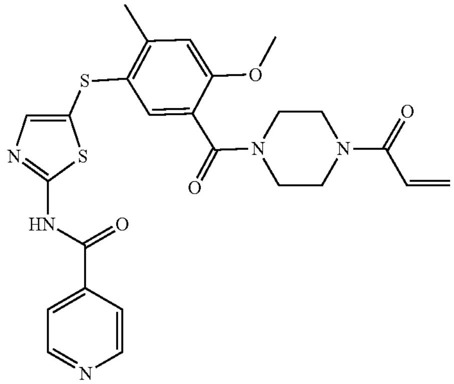
, -continued
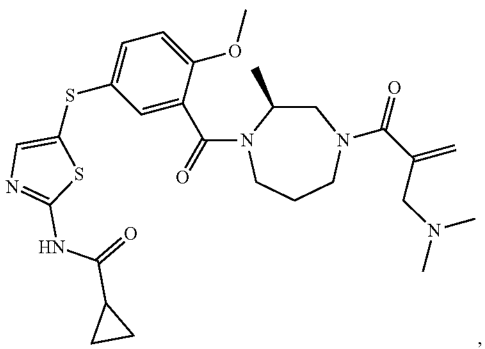
,
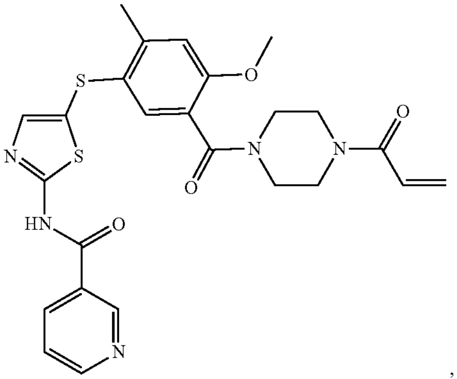
,
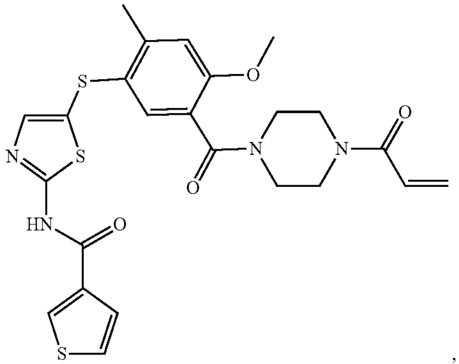
,
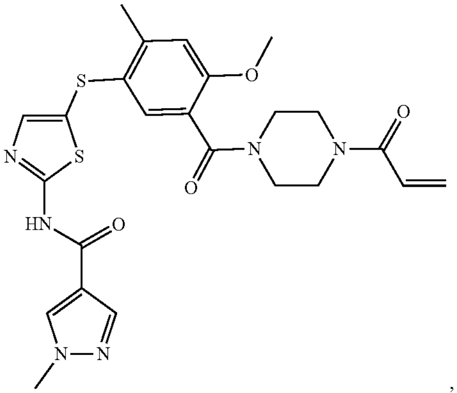
,
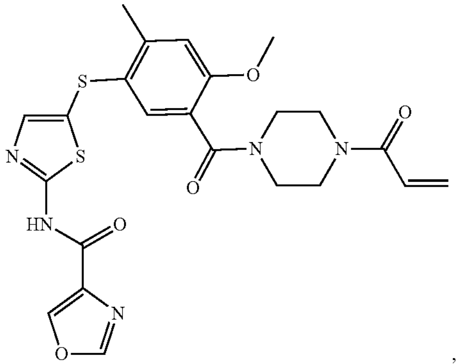
,
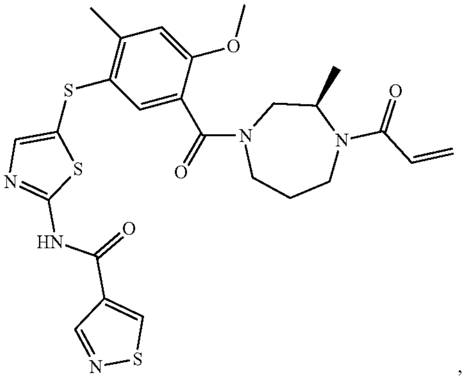
,
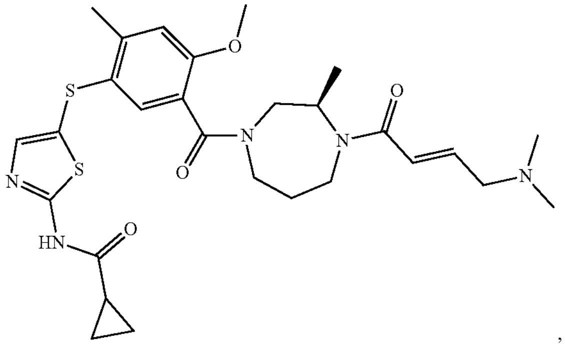
,
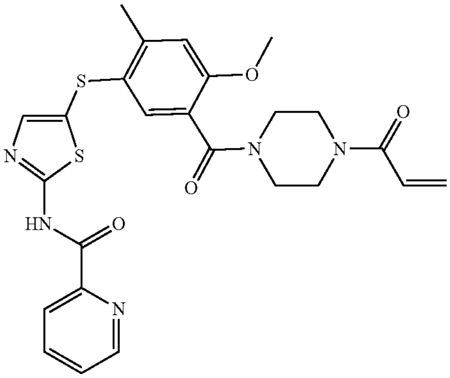
, -continued
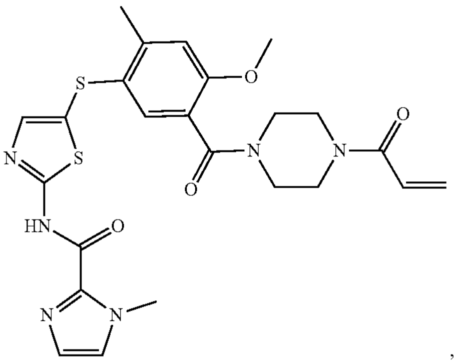
,
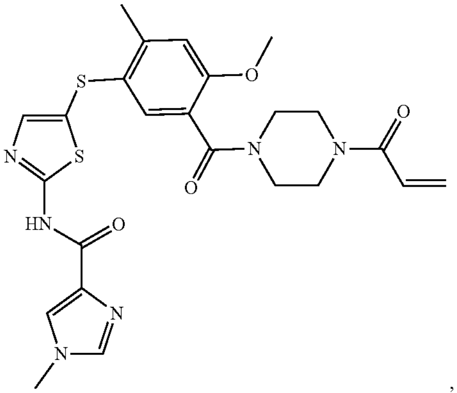
,
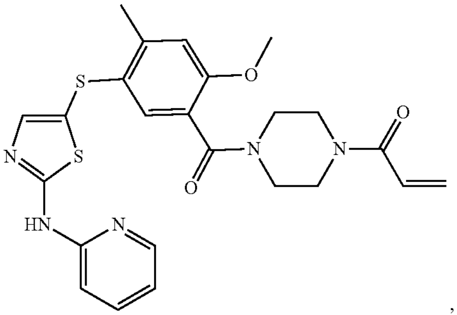
,
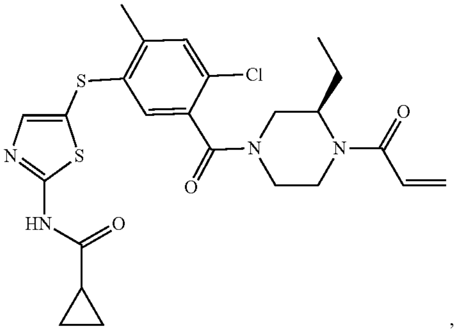
,
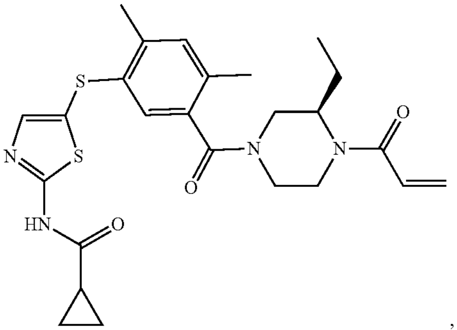
,
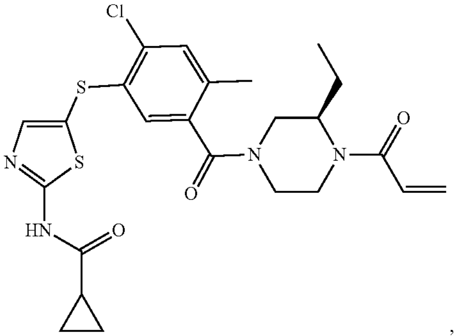
,
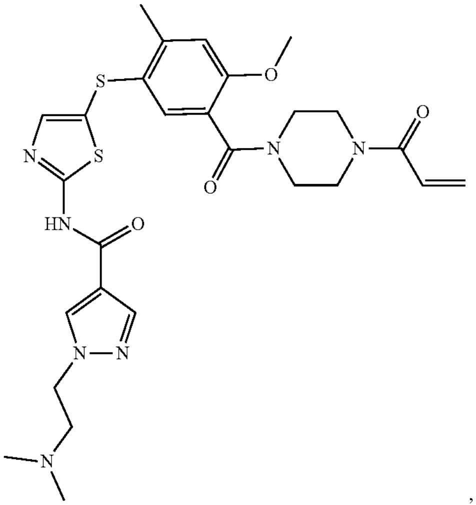
,
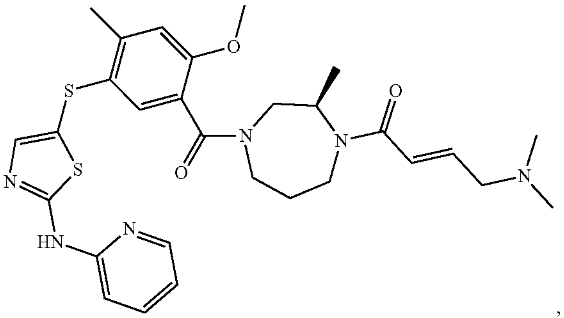
, -continued
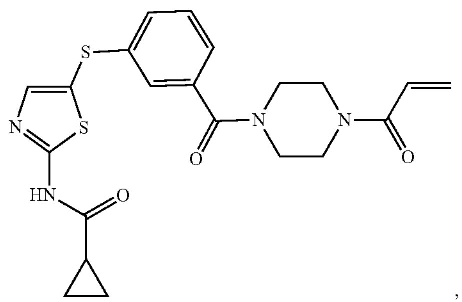
,
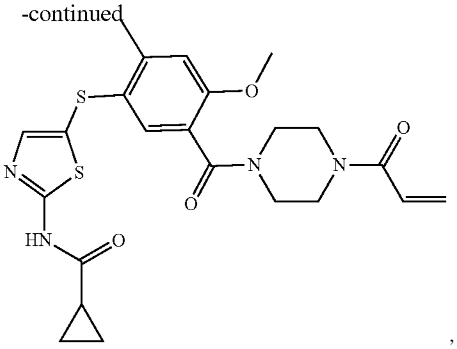
, or
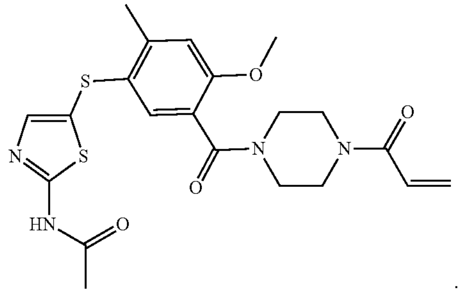
.
Embodiment 105. The compound of embodiment 1 having the formula:
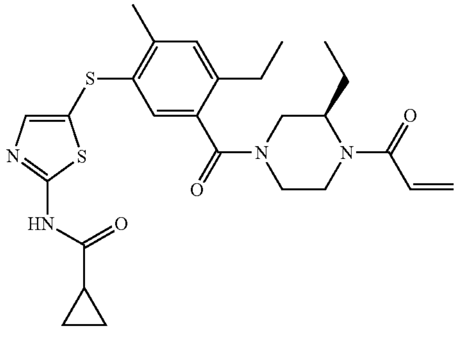
,
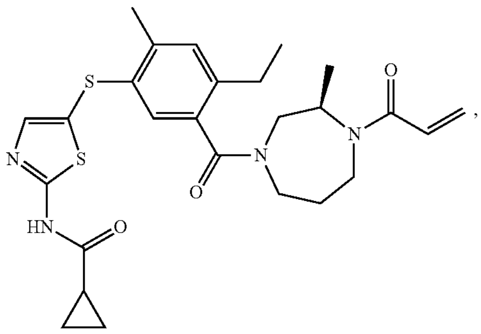
,
-continued
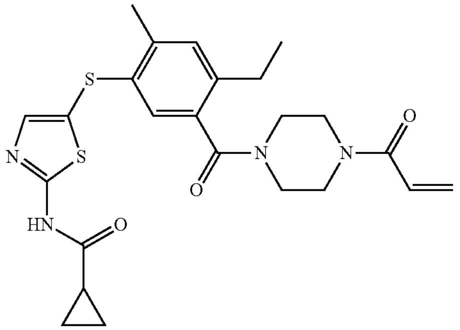
,
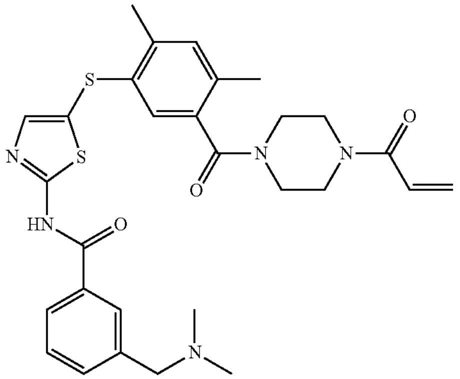
, -continued
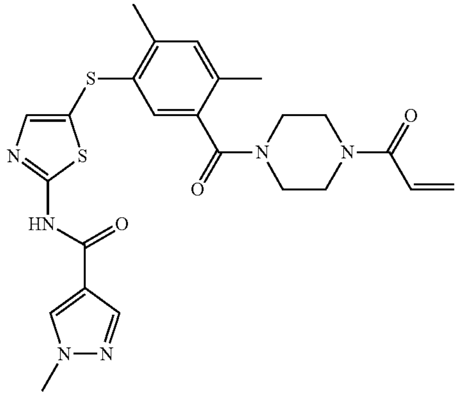
,
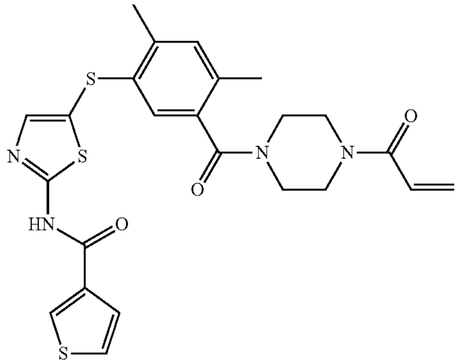
,
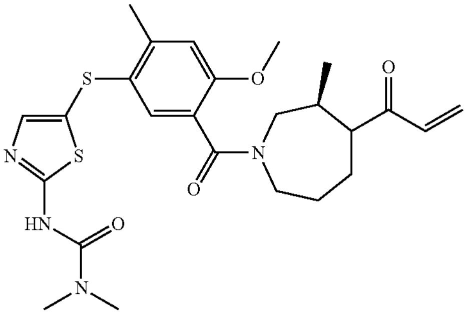
,
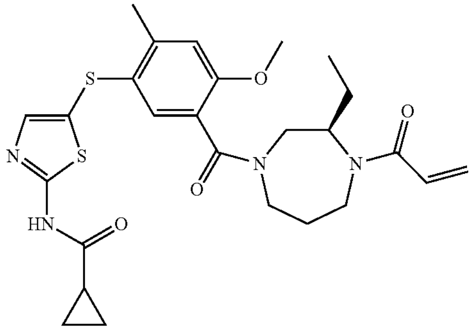
,
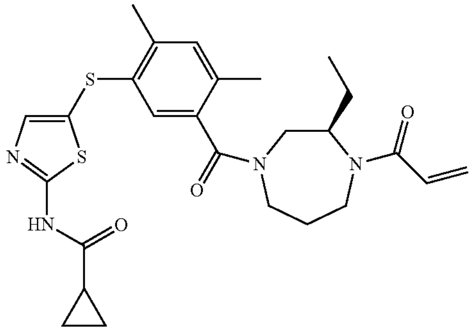
,
-continued
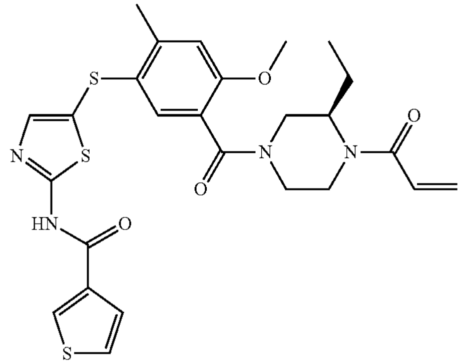
,
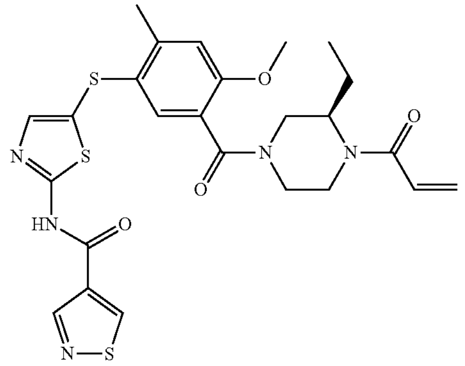
,
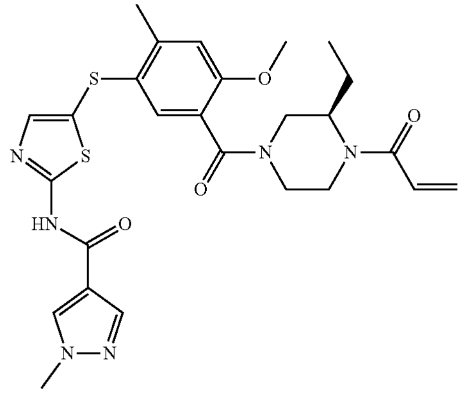
,
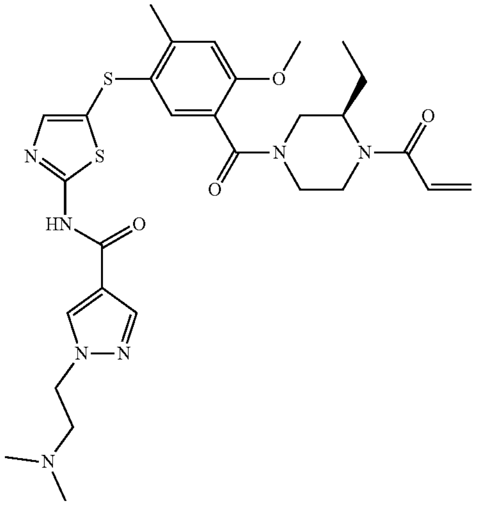
, -continued
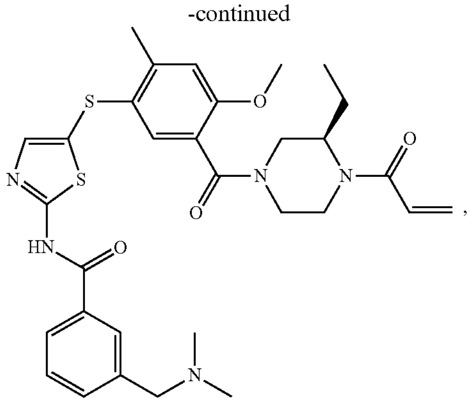
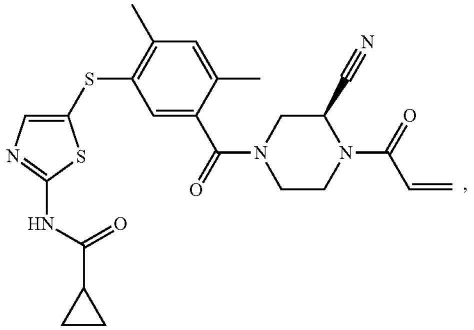
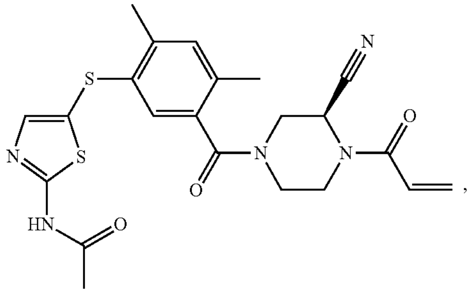
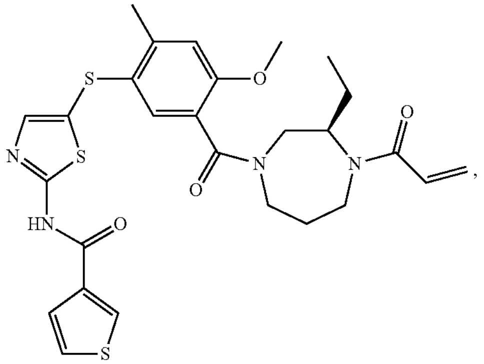
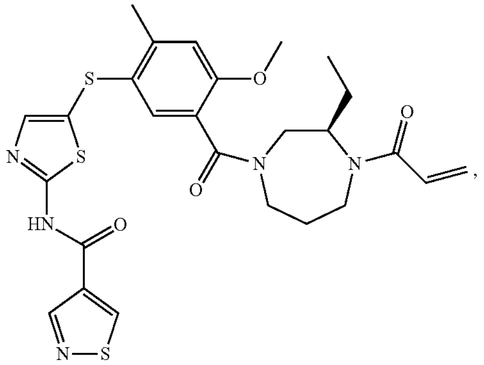
-continued
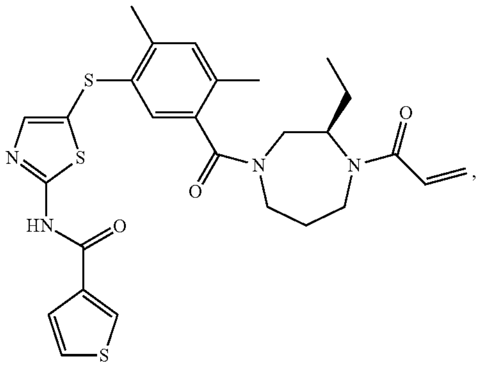
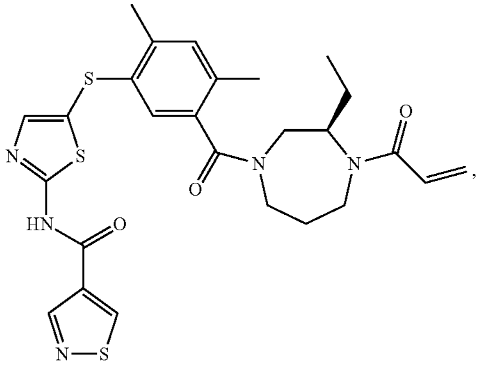
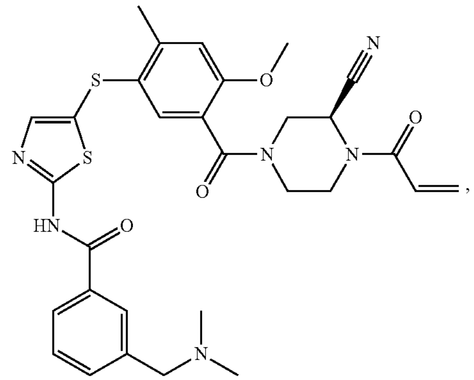
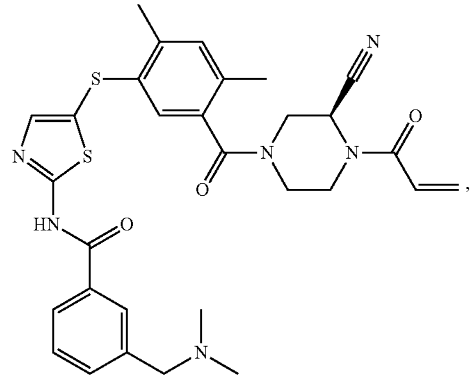

-continued
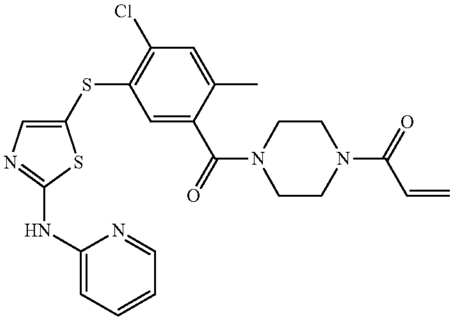
,
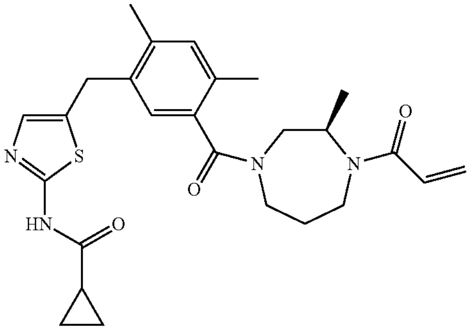
,
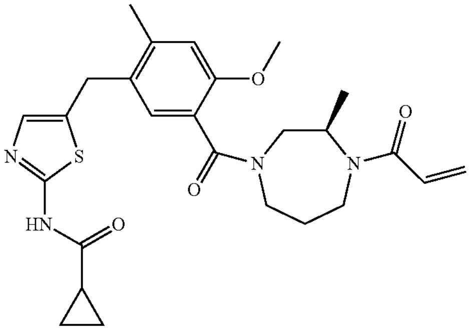
,
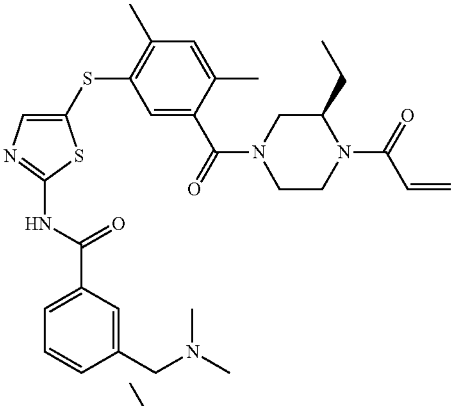
,
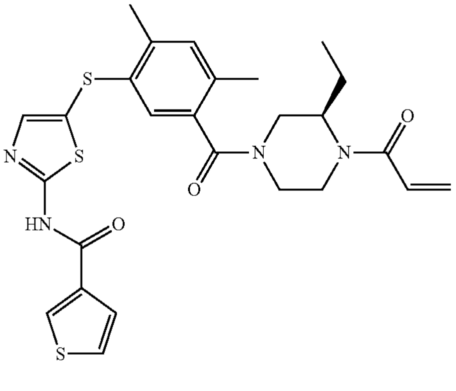
,
-continued
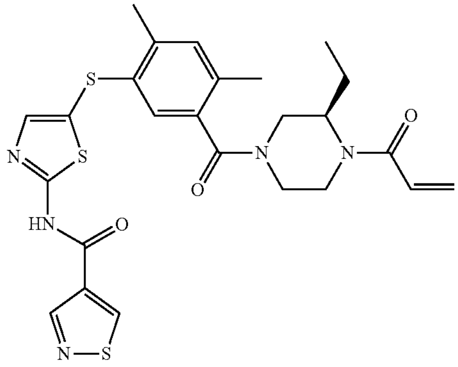
,
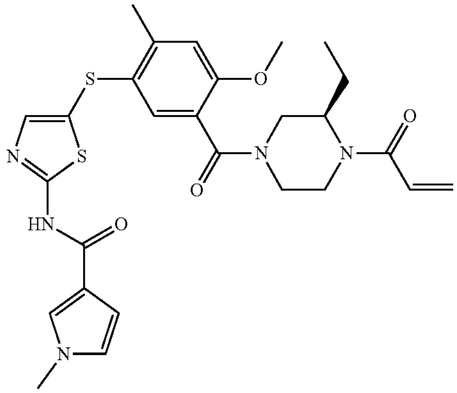
,
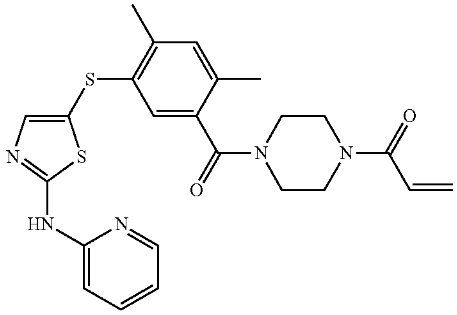
,
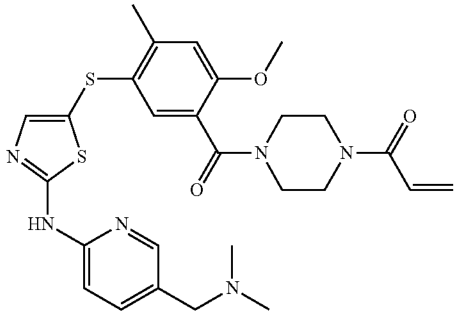
,
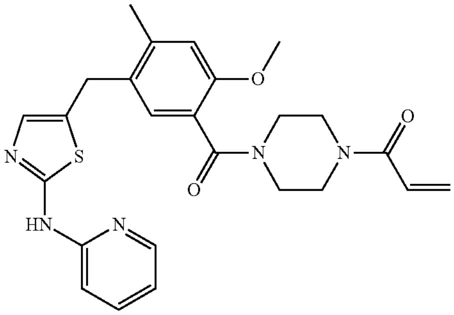
, or -continued
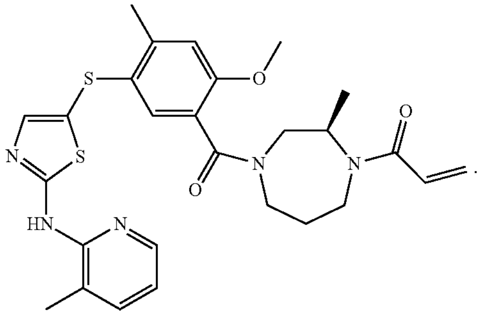
Embodiment 106. The compound of embodiment 1 having the formula:
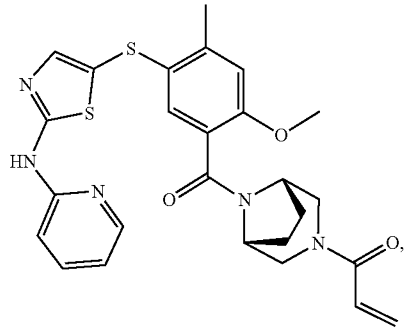
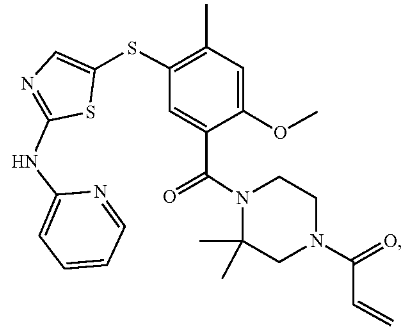
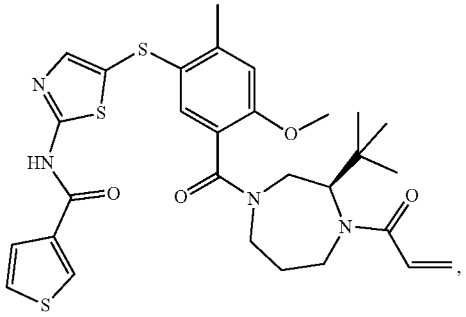
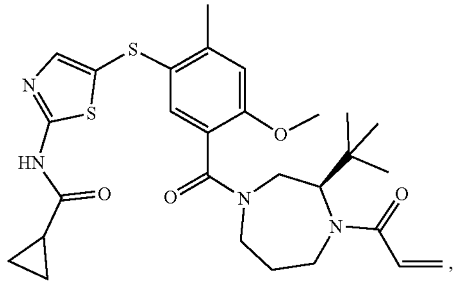
-continued
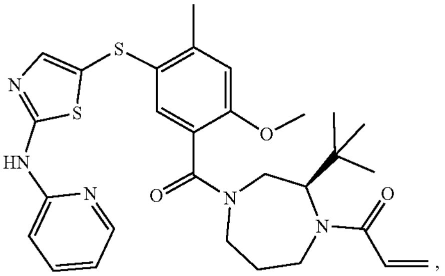
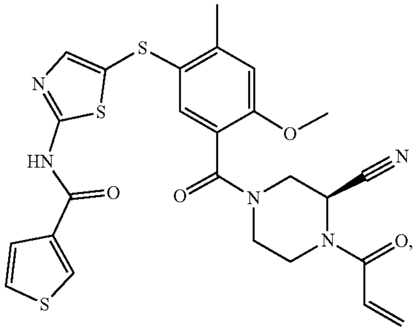
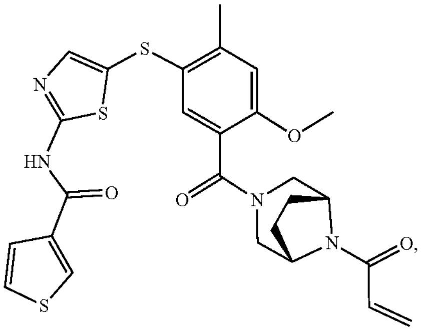
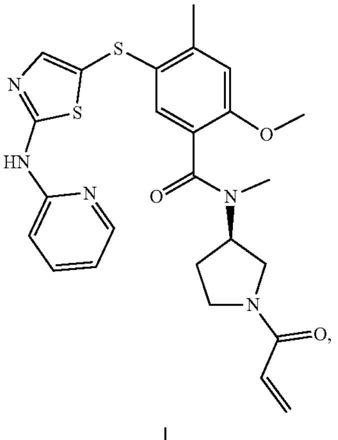
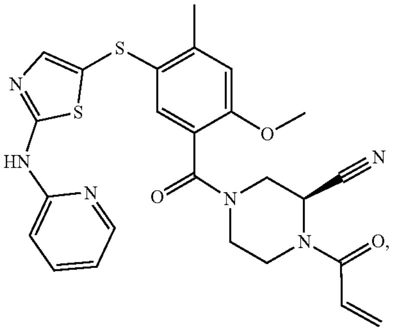

-continued
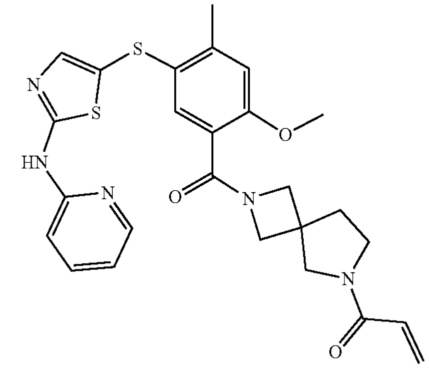
,
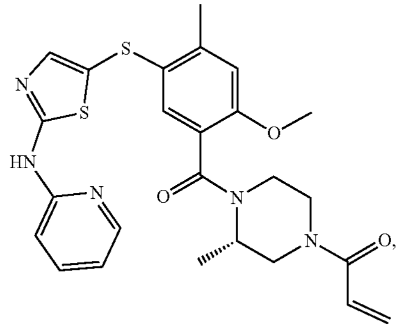
,
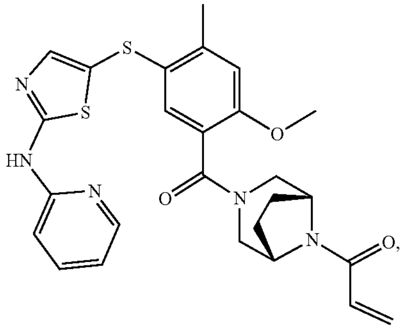
,
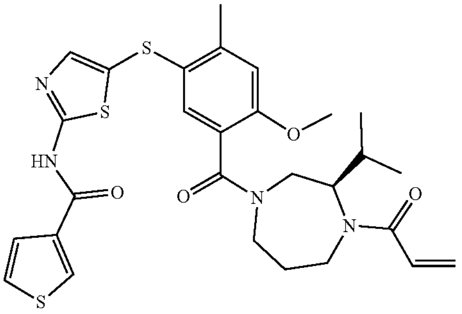
,
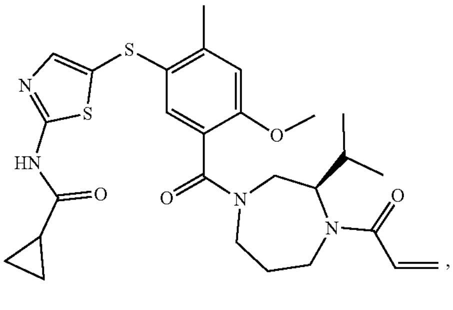
,
-continued
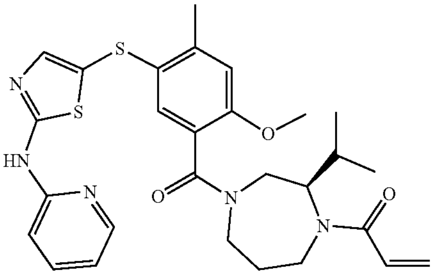
,
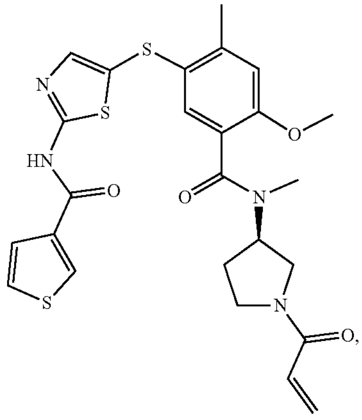
,
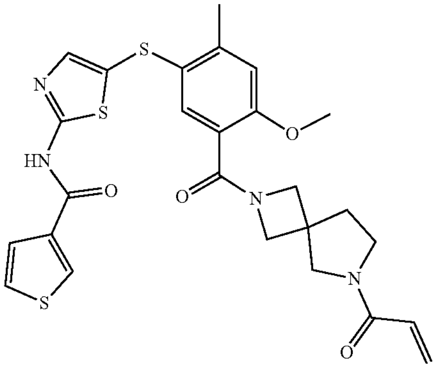
,
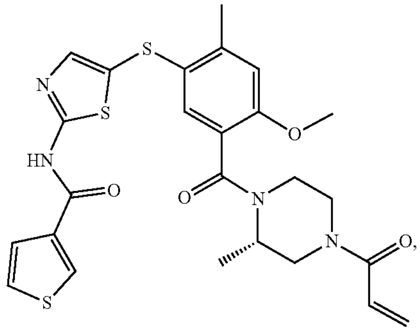
,
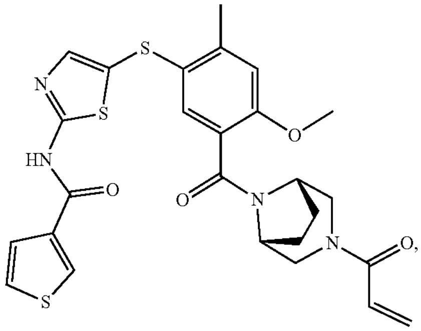
, -continued
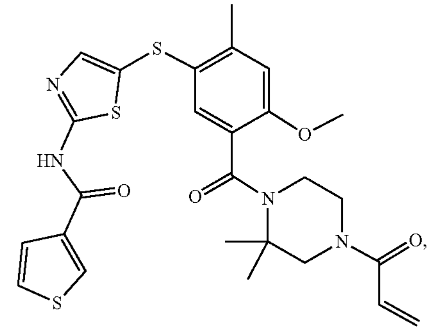
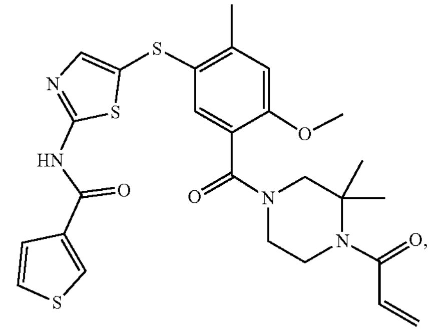
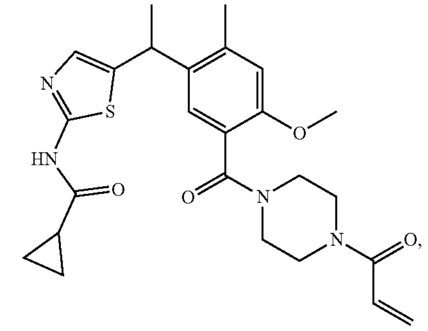
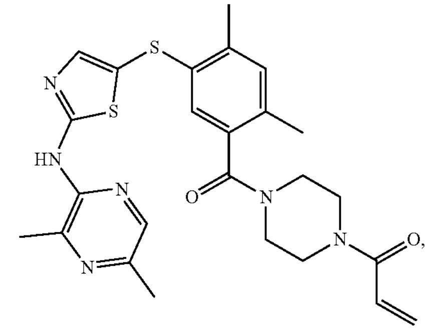
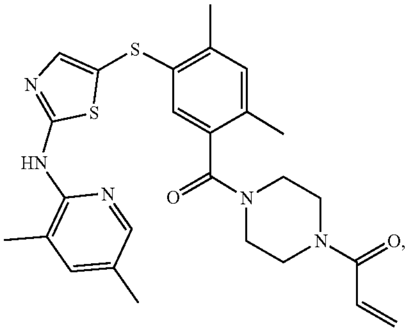
or
-continued
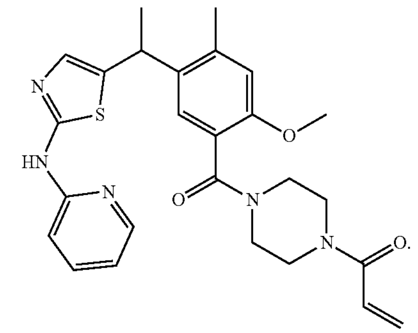
Embodiment 107. The compound of embodiment 1 having the formula:
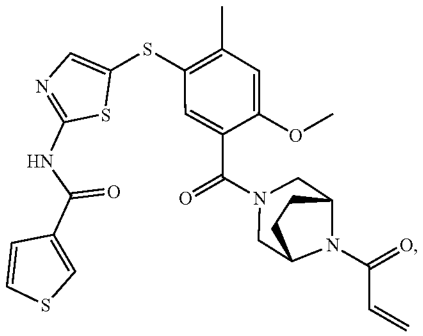
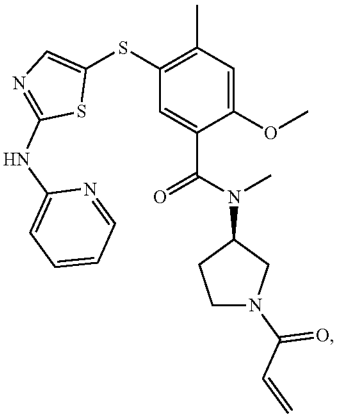
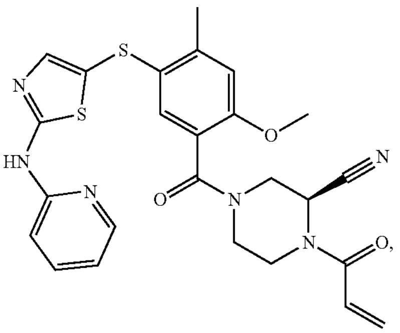

-continued

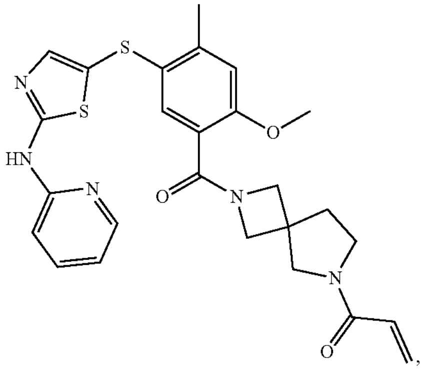

,

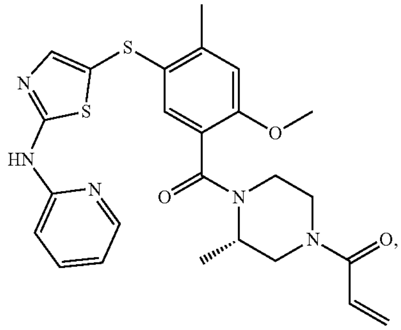

,

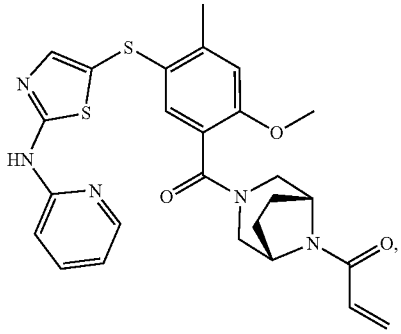

,

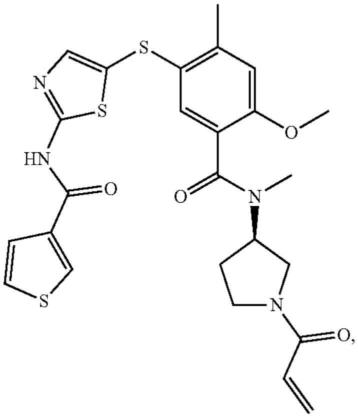

,

-continued

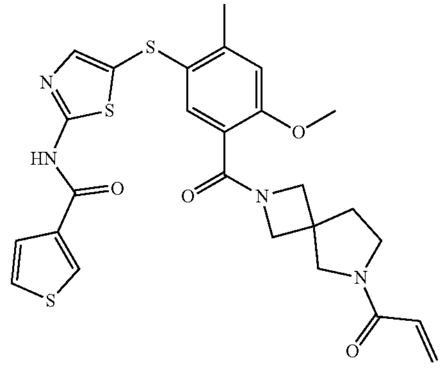

,

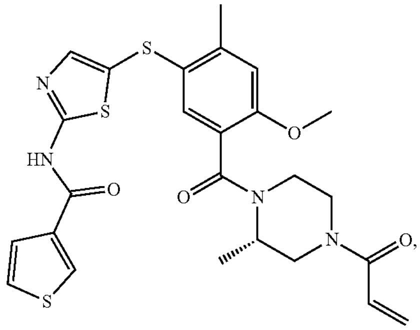

,

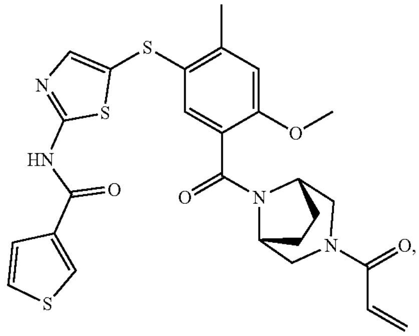

, or

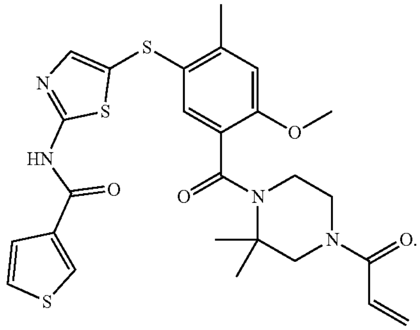

.

Embodiment 108. A pharmaceutical composition comprising the compound of any one of embodiments 1 to 107 and a pharmaceutically acceptable excipient.

Embodiment 109. A method of inhibiting a TEC kinase activity, said method comprising: contacting the TEC kinase with a compound of one of embodiments 1 to 107.

Embodiment 110. A method of inhibiting Interleukin-2-inducible T-cell kinase activity, said method comprising: contacting the Interleukin-2-inducible T-cell kinase with a compound of one of embodiments 1 to 107.

Embodiment 111. A method of treating cancer, said method comprising administering to a subject in need thereof an effective amount of a compound of one of embodiments 1 to 107.

Embodiment 112. An Interleukin-2-inducible T-cell kinase protein covalently bonded to a compound of one of embodiments 1 to 107.

Embodiment 113. The Interleukin-2-inducible T-cell kinase protein of embodiment 112, wherein the compound is bonded to a cysteine residue of the protein.

Embodiment 114. An Interleukin-2-inducible T-cell kinase protein covalently bonded to a portion of a compound of one of embodiments 1 to 107.

Embodiment 115. An Interleukin-2-inducible T-cell kinase protein irreversibly covalently bonded to a portion of a compound of one of embodiments 1 to 107.

EXAMPLES

General Synthetic Procedures

Scheme 1: Method A

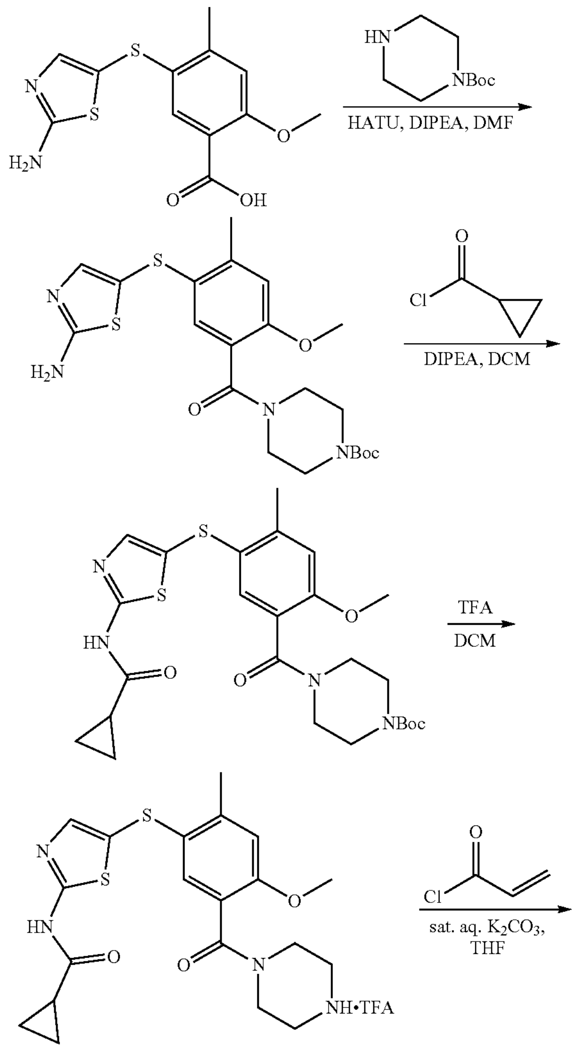

-continued

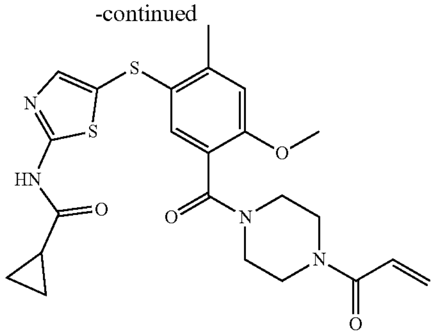

Example 1: N-[5-[4-methoxy-2-methyl-5-(4-prop-2-enoylpiperazine-1-carbonyl)phenyl]sulfanylthiazol-2-yl]cyclopropanecarboxamide Step 1: tert-butyl 4-[5-(2-aminothiazol-5-yl)sulfanyl-2-methoxy-4-methyl-benzoyl]piperazine-1-carboxylate

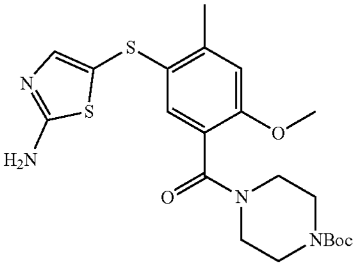 [SMILES: COc1cc(C)c(Sc2cnc(N)s2)cc1C(=O)N1CCN(C(=O)OC(C)(C)C)CC1]

To a stirred mixture of 5-(2-aminothiazol-5-yl)sulfanyl-2-methoxy-4-methyl-benzoic acid (1.5 g, 5.06 mmol), tert-butyl piperazine-1-carboxylate (989.79 mg, 5.31 mmol) and DIPEA (4.44 mL, 10.12 mmol) in DMF (10 mL) was added HATU (2.1 g, 5.31 mmol). The resulting mixture was stirred at room temperature for 1 h and was then extracted with EtOAc (3×200 mL), and washed with 0.2 M aq. HCl (200 mL) and brine (100 mL). The combined organic extracts were dried over anhydrous $MgSO_4$, filtered and concentrated. Silica gel chromatography (DCM, MeOH) afforded the title compound (1.66 g). MS (ES) m/z 465.2 (M+H).

Step 2: tert-butyl 4-[5-[2-(cyclopropanecarbonylamino)thiazol-5-yl]sulfanyl-2-methoxy-4-methyl-benzoyl]piperazine-1-carboxylate

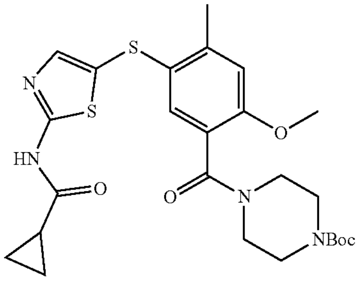 [SMILES: COc1cc(C)c(Sc2cnc(NC(=O)C3CC3)s2)cc1C(=O)N1CCN(C(=O)OC(C)(C)C)CC1]

To a stirred solution of tert-butyl 4-[5-(2-aminothiazol-5-yl)sulfanyl-2-methoxy-4-methyl-benzoyl]piperazine-1-carboxylate (1.66 g, 3.57 mmol) and cyclopropanecarbonyl chloride (356.62 uL, 3.93 mmol) in DCM (20 mL) was added DIPEA (3.14 mL, 7.15 mmol). The resulting solution was stirred at room temperature for 1 h and was then extracted with EtOAc (3×100 mL), and washed with 0.2 M aq. HCl (2×60 mL) and brine (50 mL). The combined organic extracts were dried over anhydrous MgSO4, filtered and concentrated. Silica gel chromatography (hexane, EtOAc) afforded the title compound (1.34 g). MS (ES) m/z 533.2 (M+H).

Step 3: N-[5-[4-methoxy-2-methyl-5-(piperazine-1-carbonyl)phenyl]sulfanylthiazol-2-yl]cyclopropanecarboxamide; 2,2,2-trifluoroacetic Acid

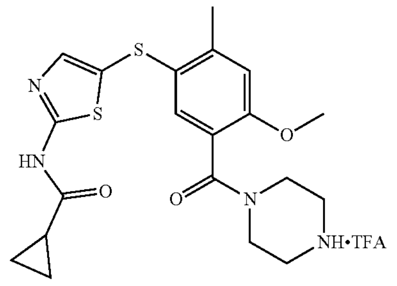

To a stirred solution of tert-butyl 4-[5-[2-(cyclopropanecarbonylamino)thiazol-5-yl]sulfanyl-2-methoxy-4-methyl-benzoyl]piperazine-1-carboxylate (1.34 g, 2.52 mmol) in DCM (10 mL) was added TFA (4.81 mL, 62.89 mmol). The resulting solution was stirred at room temperature for 1 h and was concentrated to afford the crude title compound (1.37 g). MS (ES) m/z 433.1 (M+H).

Step 4: N-[5-[4-methoxy-2-methyl-5-(4-prop-2-enoylpiperazine-1-carbonyl)phenyl]sulfanylthiazol-2-yl]cyclopropanecarboxamide

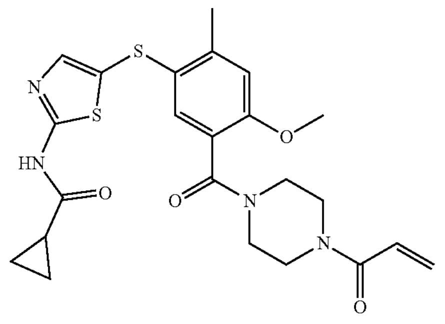 [SMILES: C=CC(=O)N1CCN(C(=O)c2cc(Sc3cnc(NC(=O)C4CC4)s3)c(C)cc2OC)CC1]

To a stirred solution of N-[5-[4-methoxy-2-methyl-5-(piperazine-1-carbonyl)phenyl]sulfanylthiazol-2-yl]cyclopropanecarboxamide; 2,2,2-trifluoroacetic acid (1.37 g, 2.51 mmol), sat. aq. K2CO3 (8 mL) and THE (15 mL) was added acryloyl chloride (244.38 uL, 3.01 mmol). The resulting mixture was stirred at room temperature for 1 h and was then extracted with EtOAc (2×50 mL), and washed with water (15 mL). The combined organic extracts were dried over anhydrous MgSO4, filtered and concentrated. Silica gel chromatography (DCM, MeOH) afforded the title compound (969 mg). MS (ES) m/z 487.1 (M+H).

Scheme 2: Method B

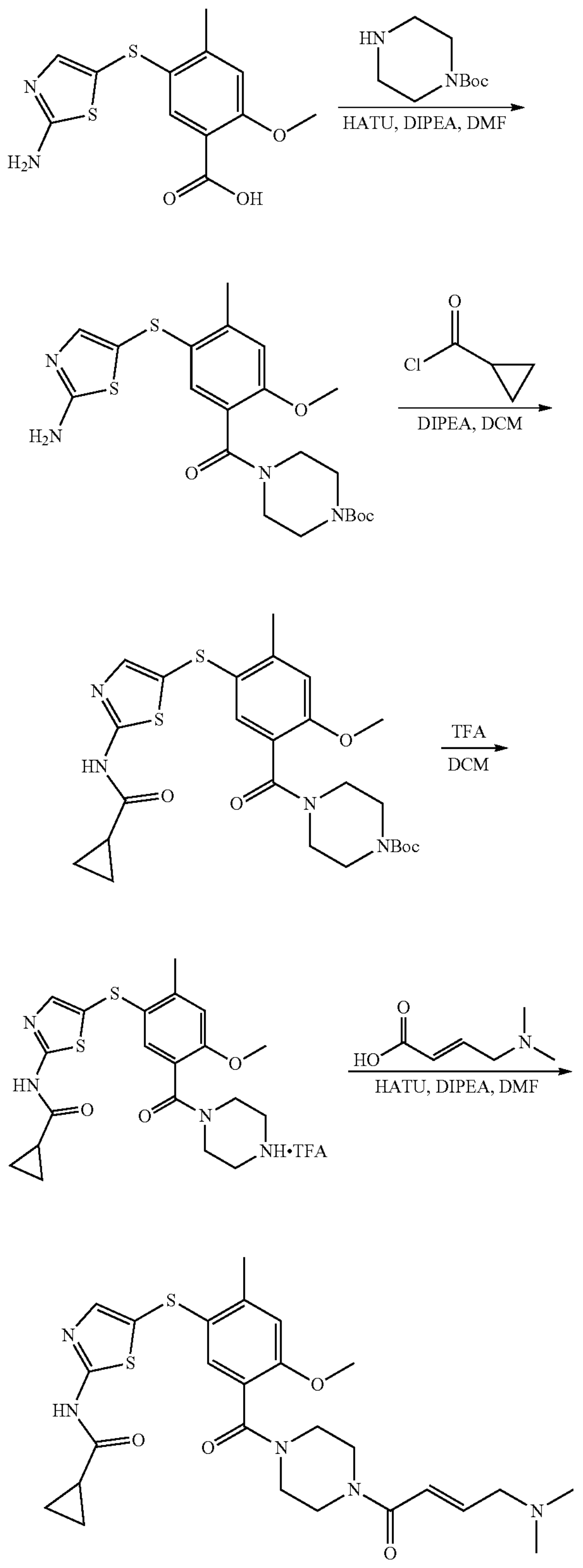

Example 2: N-[5-[5-[4-[(E)-4-(dimethylamino)but-2-enoyl]piperazine-1-carbonyl]-4-methoxy-2-methyl-phenyl]sulfanylthiazol-2-yl]cyclopropanecarboxamide Steps 1-3: Same as Method A Step 4: N-[5-[5-[4-[(E)-4-(dimethylamino)but-2-enoyl]piperazine-1-carbonyl]-4-methoxy-2-methyl-phenyl]sulfanylthiazol-2-yl]cyclopropanecarboxamide

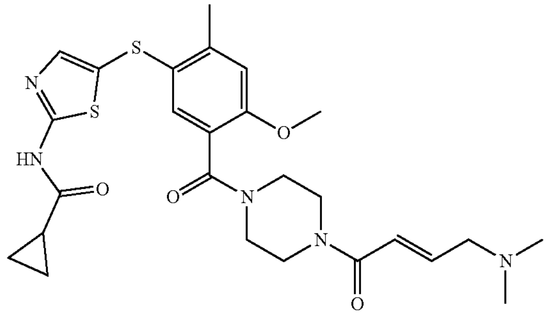 [SMILES: COc1cc(C)c(Sc2cnc(NC(=O)C3CC3)s2)cc1C(=O)N1CCN(C(=O)/C=C/CN(C)C)CC1]

To a stirred solution of N-[5-[4-methoxy-2-methyl-5-(piperazine-1-carbonyl)phenyl]sulfanylthiazol-2-yl]cyclopropanecarboxamide; 2,2,2-trifluoroacetic acid (148 mg, 0.27 mmol), (E)-4-(dimethylamino)but-2-enoic acid hydrochloride (49.33 mg, 0.3 mmol) and DIPEA (0.48 mL, 1.08 mmol) in DMF (1.5 mL) was added HATU (102.96 mg, 0.27 mmol). The resulting mixture was stirred at room temperature for 4 h and was then concentrated. Silica gel chromatography (DCM:MeOH:aq. 28% NH4OH; 100:10:1) afforded the title compound (11 mg). MS (ES) m/z 544.3 (M+H).

Scheme 3: Method C

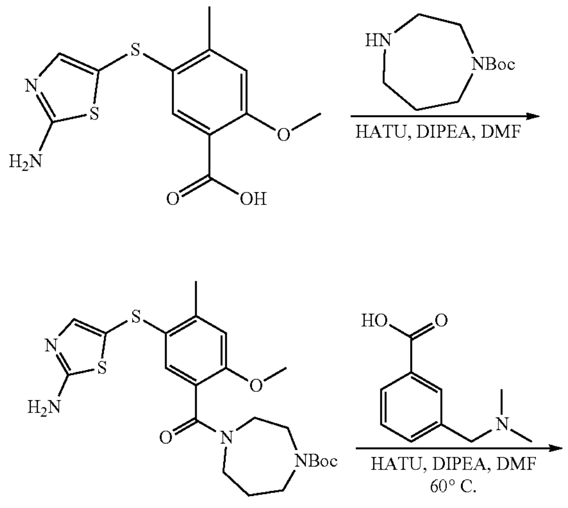

-continued

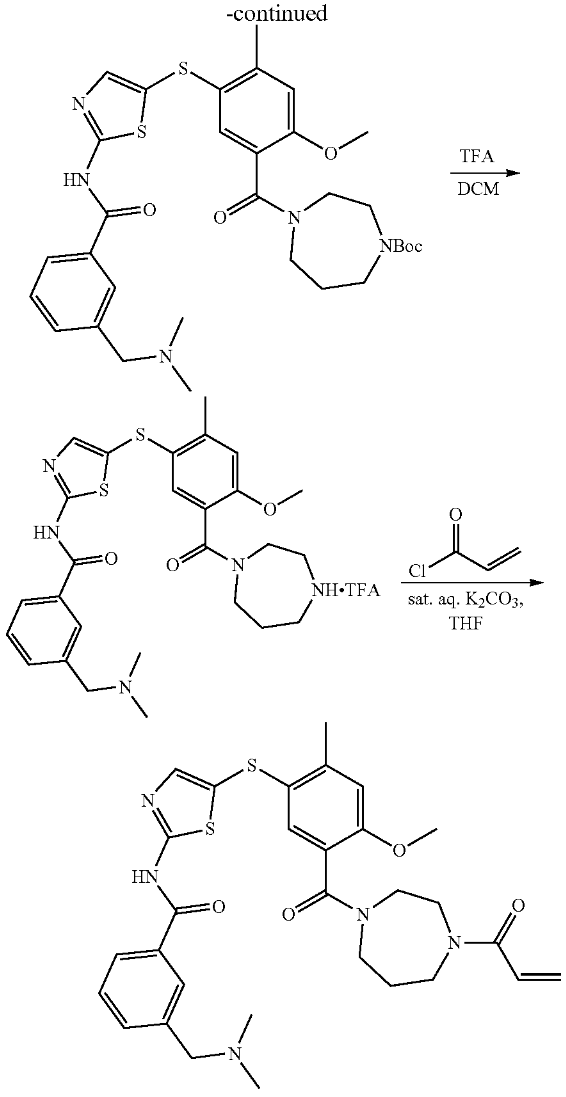

Example 3: 3-[(dimethylamino)methyl]-N-[5-[4-methoxy-2-methyl-5-(4-prop-2-enoyl-1,4-diazepane-1-carbonyl)phenyl]sulfanylthiazol-2-yl]benzamide Step 1: tert-butyl 4-[5-(2-aminothiazol-5-yl)sulfanyl-2-methoxy-4-methyl-benzoyl]-1,4-diazepane-1-carboxylate

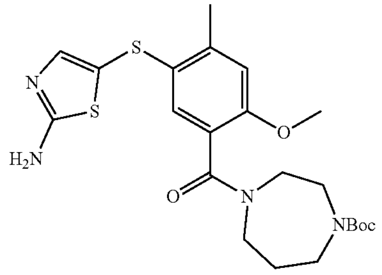 [SMILES: COc1cc(C)c(Sc2cnc(N)s2)cc1C(=O)N1CCCN(C(=O)OC(C)(C)C)CC1]

To a stirred solution of 5-(2-aminothiazol-5-yl)sulfanyl-2-methoxy-4-methyl-benzoic acid (1 g, 3.37 mmol), 1-bochomopiperazine (743.35 mg, 3.71 mmol) and DIPEA (3.04 mL, 6.92 mmol) in DMF (10 mL) was added HATU (1.41 g, 3.71 mmol). The resulting mixture was stirred at room temperature for 1 h and was then extracted with EtOAc (3×200 mL), and washed with 0.2 M aq. HCl (250 mL) and brine (100 mL). The combined organic extracts were dried over anhydrous MgSO4, filtered and concentrated. Silica gel chromatography (DCM, MeOH) afforded the title compound (975 mg). MS (ES) m/z 423.0 (M+H).

Step 2: tert-butyl 4-[5-[2-[[3-[(dimethylamino) methyl]benzoyl]amino]thiazol-5-yl]sulfanyl-2-methoxy-4-methyl-benzoyl]-1,4-diazepane-1-carboxylate

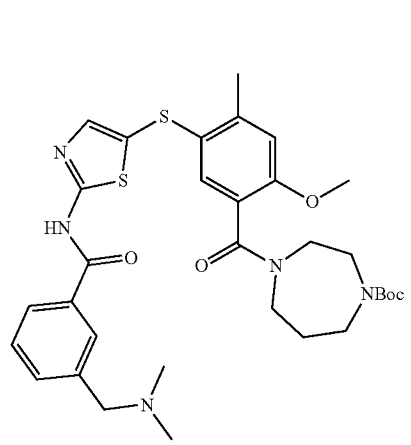 [SMILES: COc1cc(C)c(Sc2cnc(NC(=O)c3cccc(CN(C)C)c3)s2)cc1C(=O)N1CCCN(C(=O)OC(C)(C)C)CC1]

To a stirred solution of tert-butyl 4-[5-(2-aminothiazol-5-yl)sulfanyl-2-methoxy-4-methyl-benzoyl]-1,4-diazepane-1-carboxylate (1.64 g, 3.43 mmol), 3-[(dimethylamino) methyl]benzoic acid (1.54 g, 8.57 mmol) and DIPEA (4.51 mL, 10.3 mmol) in DMF (10 mL) was added HATU (3.26 g, 8.57 mmol). The resulting mixture was stirred at 60° C. for 16 h and was then extracted with EtOAc (3×150 mL), and washed with 0.2 M aq. HCl (100 mL) and brine (100 mL). The combined organic extracts were dried over anhydrous MgSO4, filtered and concentrated. Silica gel chromatography (DCM, MeOH) afforded the title compound (1.9 g). MS (ES) m/z 640.3 (M+H).

Step 3: N-[5-[5-(1,4-diazepane-1-carbonyl)-4-methoxy-2-methyl-phenyl]sulfanylthiazol-2-yl]-3-[(dimethylamino)methyl]benzamide; 2,2,2-trifluoroacetic Acid

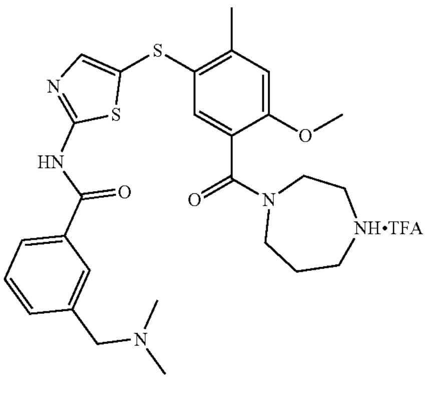

To a stirred solution of tert-butyl 4-[5-[2-[[3-[(dimethylamino)methyl]benzoyl]amino]thiazol-5-yl]sulfanyl-2-methoxy-4-methyl-benzoyl]-1,4-diazepane-1-carboxylate (1.9 g, 2.97 mmol) in DCM (15 mL) was added TFA (6.82 mL, 89.1 mmol). The resulting solution was stirred at room temperature for 1 h and was concentrated to afford the crude title compound (1.94 g). MS (ES) m/z 540.2 (M+H).

Step 4: 3-[(dimethylamino)methyl]-N-[5-[4-methoxy-2-methyl-5-(4-prop-2-enoyl-1,4-diazepane-1-carbonyl)phenyl]sulfanylthiazol-2-yl]benzamide

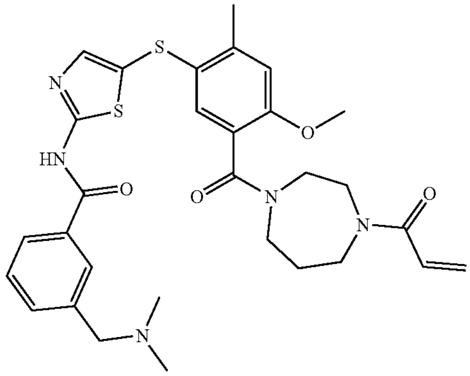 [SMILES: C=CC(=O)N1CCCN(C(=O)c2cc(Sc3cnc(NC(=O)c4cccc(CN(C)C)c4)s3)c(C)cc2OC)CC1]

To a stirred solution of N-[5-[5-(1,4-diazepane-1-carbonyl)-4-methoxy-2-methyl-phenyl]sulfanylthiazol-2-yl]-3-[(dimethylamino)methyl]benzamide; 2,2,2-trifluoroacetic acid (1.94 g, 2.97 mmol) in THF (15 mL) and sat. aq. K2CO3 (8 mL) was added acryloyl chloride (482.2 uL, 5.94 mmol). The resulting mixture was stirred at room temperature for 1 h and was then extracted with EtOAc (2×50 mL), and washed with water (20 mL) and brine (20 mL). The combined organic extracts were dried over anhydrous MgSO4, filtered and concentrated. Silica gel chromatography (DCM, MeOH) afforded the title compound (170 mg). MS (ES) m/z 594.2 (M+H).

Scheme 4: Method D

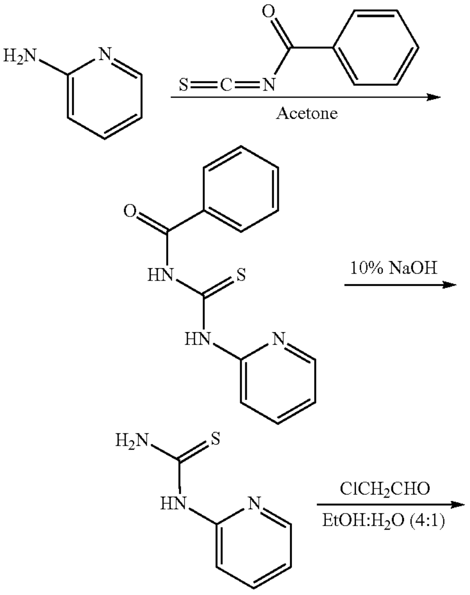

-continued

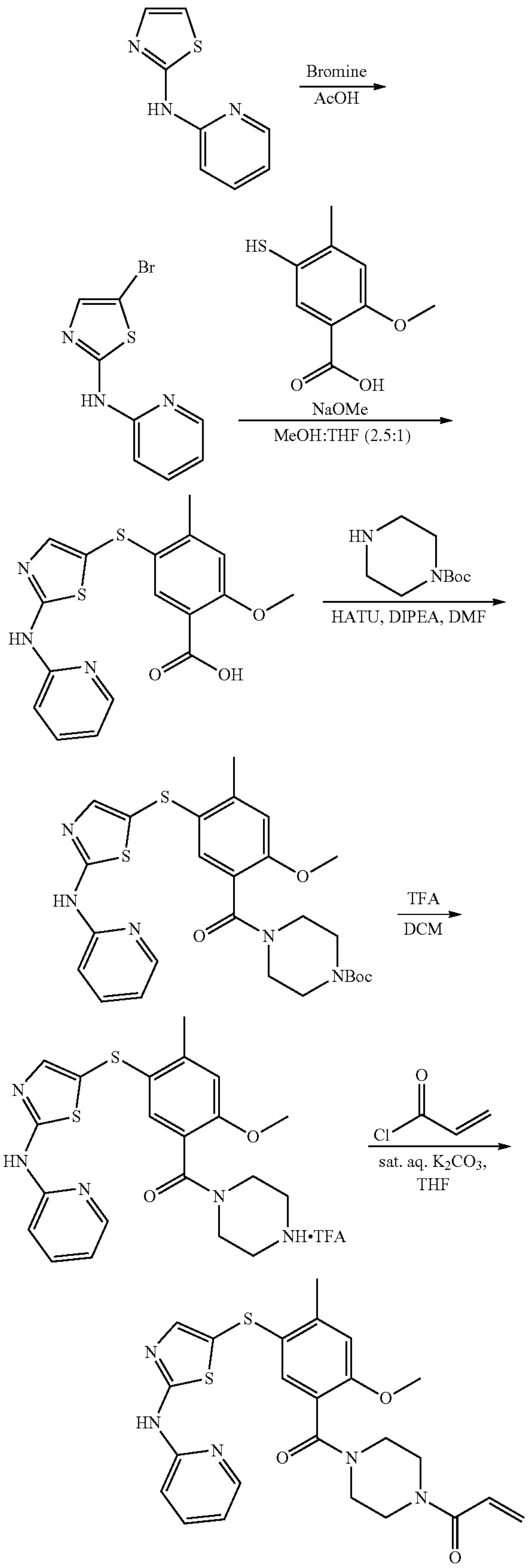

Example 4: 1-[4-[2-methoxy-4-methyl-5-[2-(2-pyridylamino)thiazol-5-yl]sulfanyl-benzoyl]piperazin-1-yl]prop-2-en-1-one Step 1: N-(pyridin-2-ylcarbamothioyl)benzamide

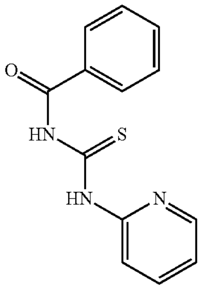 [SMILES: O=C(NC(=S)Nc1ccccn1)c1ccccc1]

To a stirred solution of pyridine-2-amine (940 mg, 10 mmol) in acetone (20 mL) was added benzoyl isothiocyanate (1.63 g, 10 mmol). After 35 min, the suspension was cooled to 0° C. and diluted in water (100 mL). The precipitate was filtered, washed with water and dried in vacuo. The solid was triturated with Et2O to afford the title compound (2.3 g). MS (ES) m/z (M+H).

Step 2: 1-(pyridin-2-yl)thiourea

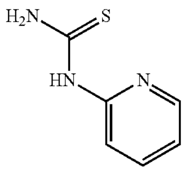

A suspension of N-(pyridin-2-ylcarbamothioyl)benzamide (2.3 g, 8.95 mmol) in 10% aq. NaOH solution (10.4 mL, 26 mmol) was stirred at room temperature for 10 min, and was then heated to reflux for an additional 10 min. The mixture was cooled to 0° C., diluted in water (100 mL) and extracted with EtOAc (3×150 mL). The combined organic extracts were dried over anhydrous MgSO4, filtered and concentrated to afford the crude title compound (1.2 g). MS (ES) m/z (M+H).

Step 3: N-(pyridin-2-yl)thiazol-2-amine

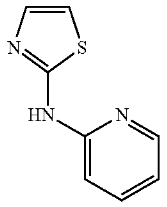 [SMILES: c1ccc(Nc2nccs2)nc1]

To a stirred suspension of 1-(pyridin-2-yl)thiourea (1.2 g, 7.8 mmol) in EtOH (20 mL) and water (4 mL) was added chloroacetaldehyde (4.21 mL, 31.2 mmol). The resulting mixture was heated to reflux for 4 h. The solution was then cooled to room temperature and concentrated in vacuo. Silica gel chromatography afforded the title compound (1.2 g). MS (ES) m/z (M+H).

Step 4: 5-bromo-N-(pyridin-2-yl)thiazol-2-amine

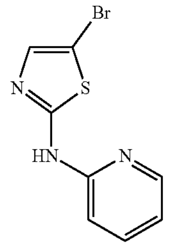 [SMILES: Brc1cnc(Nc2ccccn2)s1]

To a stirred solution of Br2 (0.6 mL, 11 mmol) in AcOH (15 mL) was added a solution of N-(pyridin-2-yl)thiazol-2-amine (1.4 g, 5.5 mmol) in AcOH (10 mL) dropwise. The resulting mixture was stirred at 40° C. for 3 h, then cooled to 0° C. and quenched with aqueous sodium bisulfite solution (60 mL). The precipitated solid was filtered, washed with water and dried in vacuo to afford the title compound (1.4 g). MS (ES) m/z (M+H).

Step 5: 2-methoxy-4-methyl-5-((2-(pyridin-2-ylamino)thiazol-5-yl)thio)benzoic Acid

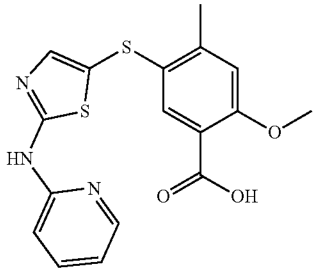 [SMILES: COc1cc(C)c(Sc2cnc(Nc3ccccn3)s2)cc1C(=O)O]

To a suspension of 5-mercapto-2-methoxy-4-methylbenzoic acid (1.2 g, 6 mmol) in methanol (20 mL) was added NaBH4 (450 mg, 12 mmol) at 0° C. After 10 min, 5-bromo-N-(pyridin-2-yl)thiazol-2-amine (1.2 g, 5.5 mmol) was added followed by sodium methoxide (891 mg, 16.5 mmol) at 0° C. After 3 h at 0° C., the reaction mixture was concentrated. The concentrate was acidified with 1 N aq. HCl to pH 7. The precipitate was filtered, washed with water and Et2O, and dried in vacuo. Preparative HPLC afforded the title compound (107 mg). MS (ES) m/z (M+H).

Step 6: tert-butyl 4-[2-methoxy-4-methyl-5-[2-(2-pyridylamino)thiazol-5-yl]sulfanyl-benzoyl]piperazine-1-carboxylate

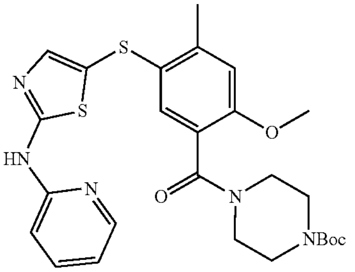 [SMILES: COc1cc(C)c(Sc2cnc(Nc3ccccn3)s2)cc1C(=O)N1CCN(C(=O)OC(C)(C)C)CC1]

To a stirred solution of 2-methoxy-4-methyl-5-[2-(2-pyridylamino)thiazol-5-yl]sulfanyl-benzoic acid (50 mg, 0.13 mmol), tert-butyl piperazine-1-carboxylate (27.43 mg, 0.15 mmol) and DIPEA (0.12 mL, 0.27 mmol) in DMF (2 mL) was added HATU (56 mg, 0.15 mmol). After 1 h, the reaction mixture was extracted with EtOAc (3×20 mL), and washed with 0.2 M aq. HCl (20 mL) and brine (20 mL). The combined organic extracts were dried over anhydrous MgSO4, filtered and concentrated. Silica gel chromatography (DCM, MeOH) afforded the title compound (46 mg). MS (ES) m/z 542.2 (M+H).

Step 7: [2-methoxy-4-methyl-5-[2-(2-pyridylamino)thiazol-5-yl]sulfanyl-phenyl]-piperazin-1-yl-methanone; 2,2,2-trifluoroacetic Acid

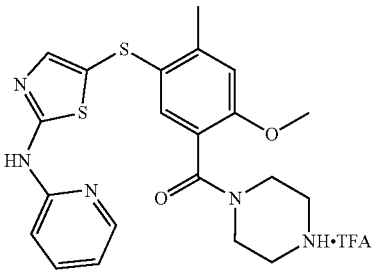

To a stirred solution of tert-butyl 4-[2-methoxy-4-methyl-5-[2-(2-pyridylamino)thiazol-5-yl]sulfanyl-benzoyl]piperazine-1-carboxylate (46 mg, 0.08 mmol) in DCM (2 mL) was added TFA (0.19 mL, 2.55 mmol). After 1 h, the reaction mixture concentrated to afford the crude title compound (47 mg). MS (ES) m/z 442.1 (M+H).

Step 8: 1-[4-[2-methoxy-4-methyl-5-[2-(2-pyridylamino)thiazol-5-yl]sulfanyl-benzoyl]piperazin-1-yl]prop-2-en-1-one

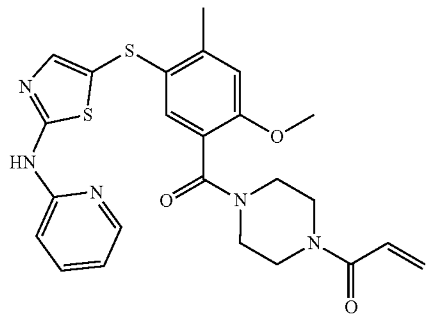 [SMILES: C=CC(=O)N1CCN(C(=O)c2cc(Sc3cnc(Nc4ccccn4)s3)c(C)cc2OC)CC1]

To a stirred solution of [2-methoxy-4-methyl-5-[2-(2-pyridylamino)thiazol-5-yl]sulfanyl-phenyl]-piperazin-1-yl-methanone; 2,2,2-trifluoroacetic acid (47 mg, 0.08 mmol) in THE (6 mL) and sat. aq. K2CO3 (4 mL) was added acryloyl chloride (7.56 uL, 0.09 mmol). The resulting mixture was stirred at room temperature for 1 h and was then extracted with EtOAc (2×15 mL), and washed with water (10 mL) and brine (10 mL). The combined organic extracts were dried over anhydrous MgSO4, filtered and concentrated. Silica gel chromatography (DCM, MeOH) afforded the title compound (30 mg). MS (ES) m/z 496.1 (M+H).

Scheme 5: Method E

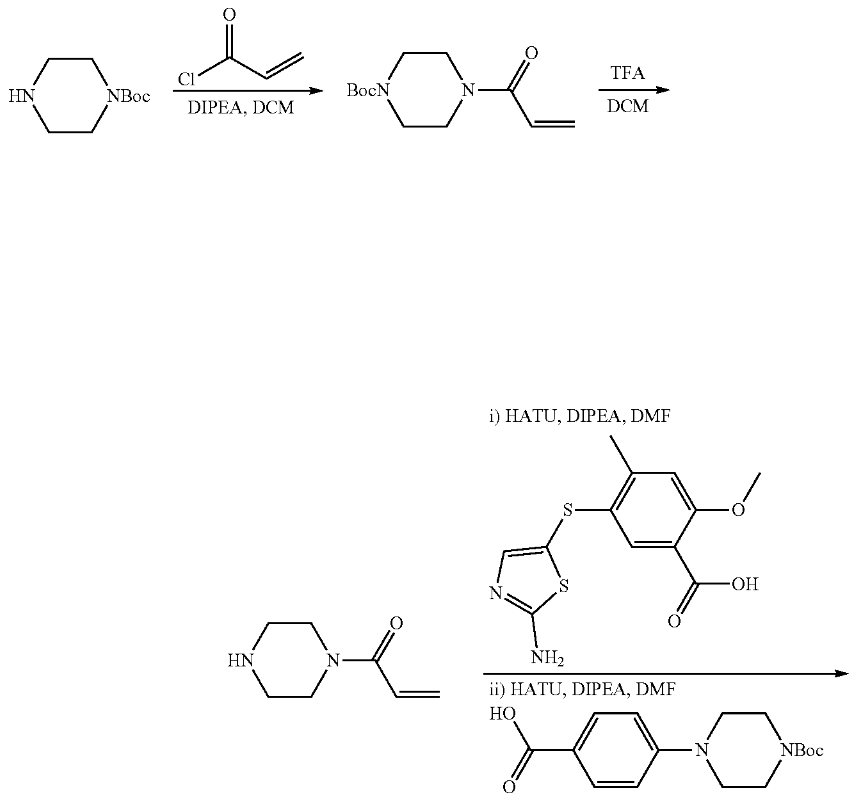

-continued
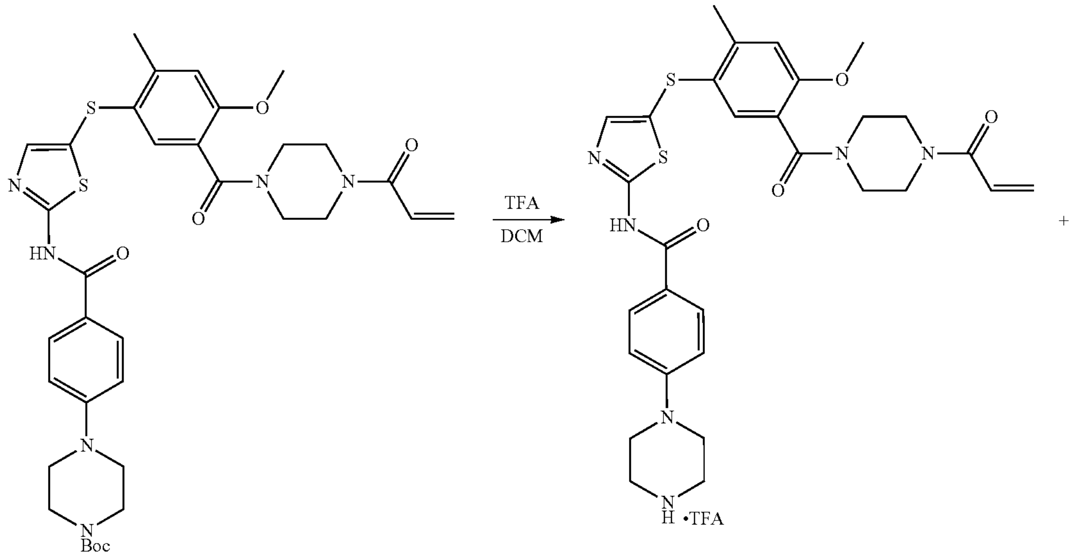
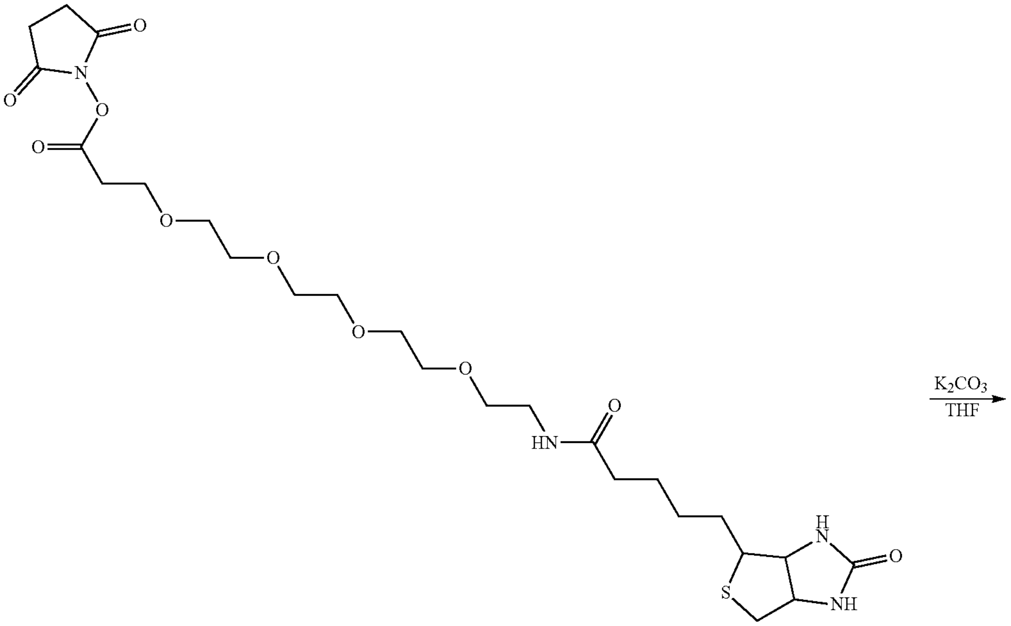

-continued

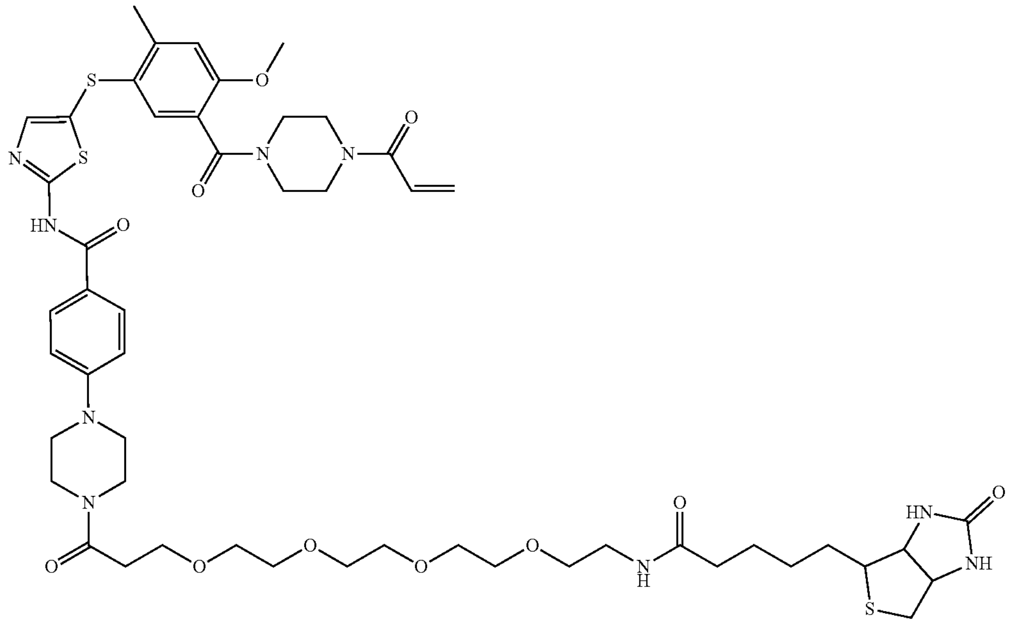

Example 5: N-[5-[4-methoxy-2-methyl-5-(4-prop-2-enoylpiperazine-1-carbonyl)phenyl]sulfanylthiazol-2-yl]-4-[4-[3-[2-[2-[2-[2-[5-(2-oxo-1,3,3a,4,6,6a-hexahydrothieno[3,4-d]imidazol-4-yl) pentanoylamino]ethoxy]ethoxy]ethoxy]ethoxy] propanoyl]piperazin-1-yl]benzamide Step 1: tert-butyl 4-prop-2-enoylpiperazine-1-carboxylate

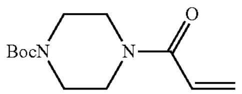

To a stirred solution of tert-butyl piperazine-1-carboxylate (500 mg, 2.68 mmol) and DIPEA (2.36 mL, 5.37 mmol) in DCM (6 mL) was added acryloyl chloride (0.22 mL, 2.68 mmol). The resulting mixture was stirred at room temperature for 30 min and was then extracted with DCM (2×25 mL), and washed with 2 M aq. citric acid (2×50 mL) and brine (50 mL). The combined organic extracts were dried over Na2SO4, filtered and concentrated to afford the crude title compound (633 mg). MS (ES) m/z 263.1 (M+23).

Step 2: 1-piperazin-1-ylprop-2-en-1-one; 2,2,2-trifluoroacetic Acid

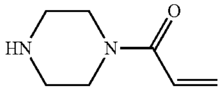

To a stirred solution of tert-butyl 4-prop-2-enoylpiperazine-1-carboxylate (431 mg, 1.79 mmol) in DCM (2 mL) was added TFA (2 mL, 25.96 mmol). The resulting solution was stirred at room temperature for 1 h and was then concentrated to afford the crude title compound (455 mg). MS (ES) m/z 163.1 (M+23).

Step 3: tert-butyl 4-[4-[[5-[4-methoxy-2-methyl-5-(4-prop-2-enoylpiperazine-1-carbonyl)phenyl]sulfanylthiazol-2-yl]carbamoyl]phenyl]piperazine-1-carboxylate

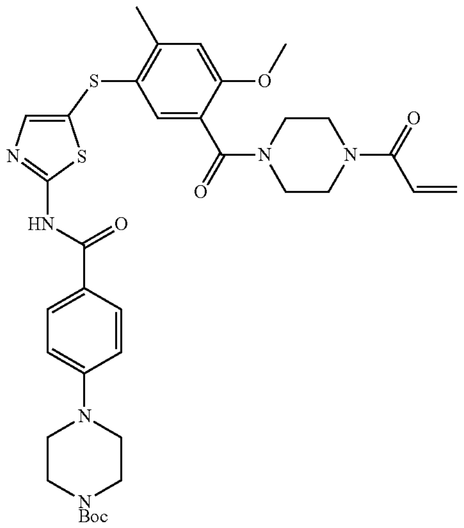 [SMILES: C=CC(=O)N1CCN(C(=O)c2cc(Sc3cnc(NC(=O)c4ccc(N5CCN(C(=O)OC(C)(C)C)CC5)cc4)s3)c(C)cc2OC)CC1]

To a stirred solution of 5-(2-aminothiazol-5-yl)sulfanyl-2-methoxy-4-methyl-benzoic acid (530.46 mg, 1.79 mmol), 1-piperazin-1-ylprop-2-en-1-one; 2,2,2-trifluoroacetic acid (455 mg, 1.79 mmol) and DIPEA (3.93 mL, 8.95 mmol) in DMF (5 mL) was added HATU (680.56 mg, 1.79 mmol). After 2 h, 4-(4-tert-butoxycarbonylpiperazin-1-yl)benzoic acid (1.37 g, 4.47 mmol), HATU (1.70 g, 4.47 mmol) and DIPEA (3.93 mL, 8.95 mmol) in DMF (5 mL) was added. The resulting mixture was heated to 80° C. After 4 h, the reaction mixture was extracted with EtOAc (2×100 mL), 2 M aq. citric acid (2×200 mL) and brine (100 mL). The combined organic extracts were dried over Na2SO4, filtered and concentrated. Silica gel chromatography (DCM, MeOH) afforded the title compound (471 mg). MS (ES) m/z 707.3 (M+H).

Step 4: N-[5-[4-methoxy-2-methyl-5-(4-prop-2-enoylpiperazine-1-carbonyl)phenyl]sulfanylthiazol-2-yl]-4-piperazin-1-yl-benzamide; 2,2,2-trifluoroacetic Acid

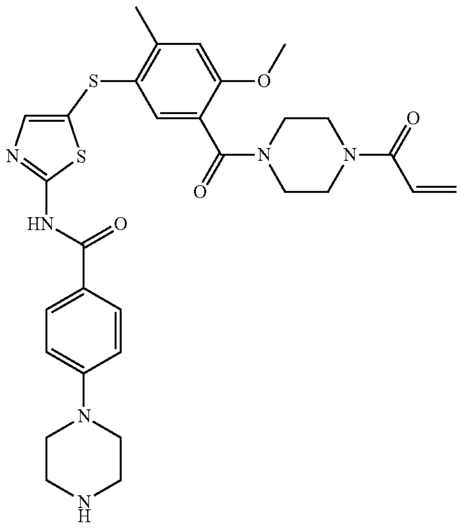 [SMILES: C=CC(=O)N1CCN(C(=O)c2cc(Sc3cnc(NC(=O)c4ccc(N5CCNCC5)cc4)s3)c(C)cc2OC)CC1]

To a stirred solution of tert-butyl 4-[4-[[5-[4-methoxy-2-methyl-5-(4-prop-2-enoylpiperazine-1-carbonyl)phenyl]sulfanylthiazol-2-yl]carbamoyl]phenyl]piperazine-1-carboxylate (18.6 mg, 0.03 mmol) in DCM (0.2 mL) was added TFA (0.2 mL, 2.6 mmol). The resulting solution was stirred at room temperature for 30 min and was then concentrated to afford the crude title compound (19 mg). MS (ES) m/z 607.1 (M+H).

Step 5: N-[5-[4-methoxy-2-methyl-5-(4-prop-2-enoylpiperazine-1-carbonyl)phenyl]sulfanylthiazol-2-yl]-4-[4-[3-[2-[2-[2-[2-[5-(2-oxo-1,3,3a,4,6,6a-hexahydrothieno[3,4-d]imidazol-4-yl)pentanoylamino]ethoxy]ethoxy]ethoxy]ethoxy]propanoyl]piperazin-1-yl]benzamide

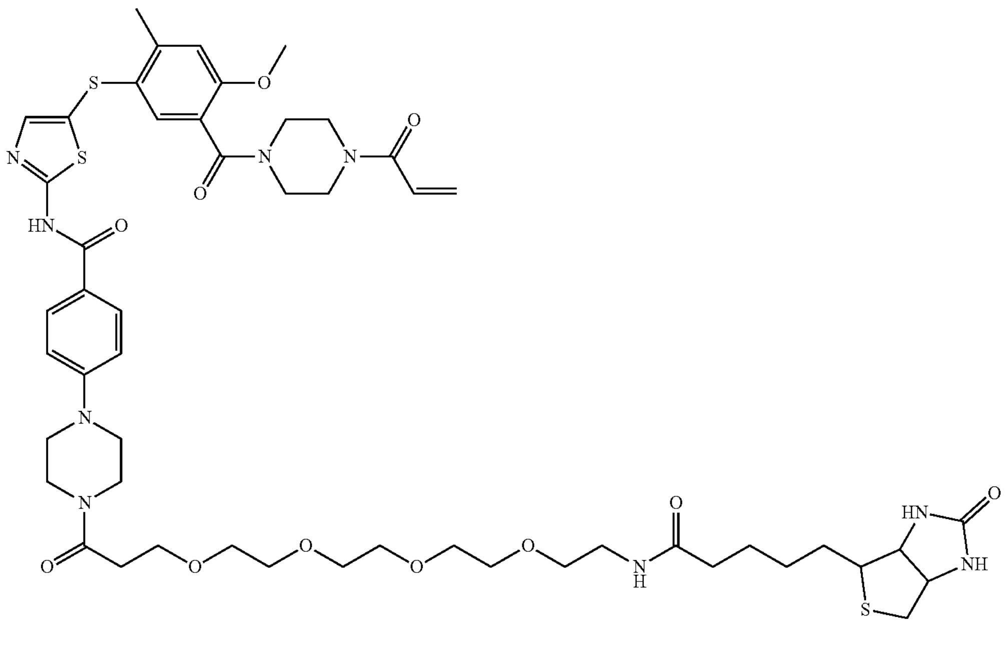 [SMILES: C=CC(=O)N1CCN(C(=O)c2cc(Sc3cnc(NC(=O)c4ccc(N5CCN(C(=O)CCOCCOCCOCCOCCNC(=O)CCCCC6SCC7NC(=O)NC76)CC5)cc4)s3)c(C)cc2OC)CC1]

To a stirred solution of N-[5-[4-methoxy-2-methyl-5-(4-prop-2-enoylpiperazine-1-carbonyl)phenyl]sulfanylthiazol-2-yl]-4-piperazin-1-yl-benzamide; 2,2,2-trifluoroacetic acid (109 mg, 0.15 mmol) and K2CO3 (125.4 mg, 0.91 mmol) in THE (0.2 mL) was added (2,5-dioxopyrrolidin-1-yl) 3-[2-[2-[2-[2-[5-(2-oxo-1,3,3a,4,6,6a-hexahydrothieno[3,4-d]imidazol-4-yl)pentanoylamino]ethoxy]ethoxy]ethoxy]ethoxy]propanoate (97.92 mg, 0.17 mmol). The resulting mixture was heated to 45° C. for 3 h and was then concentrated. The obtained residue was dissolved in DCM and MeOH, filtered and concentrated. Silica gel chromatography (DCM, MeOH) afforded the title compound (115 mg). MS (ES) m/z 1081.4 (M+H).

General Synthetic Procedures of Intermediates

Scheme 6: Method F

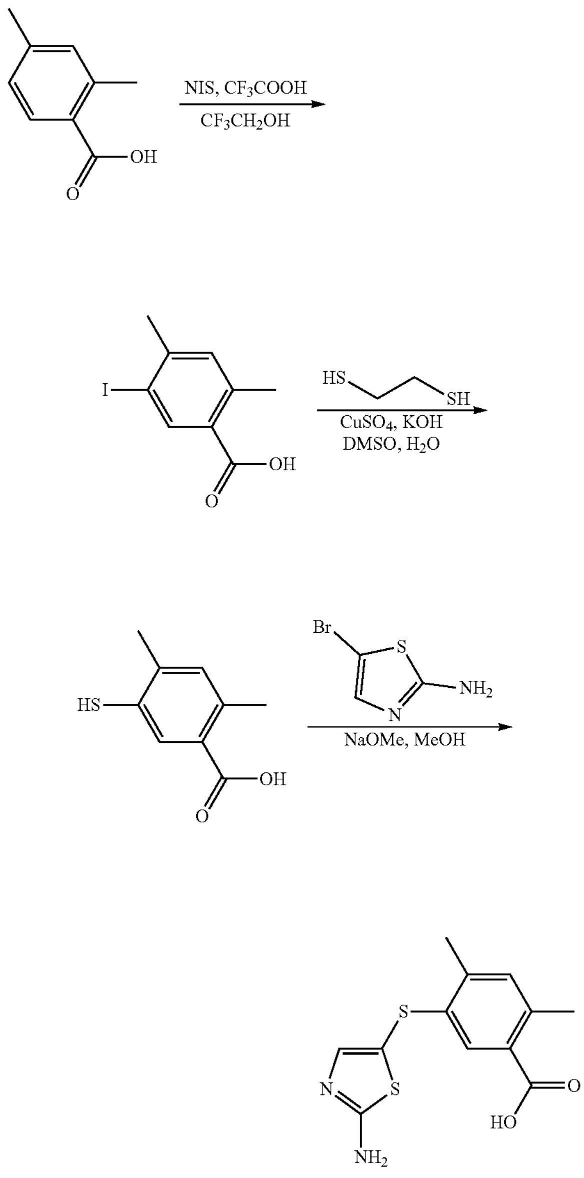

Example 6: 5-(2-aminothiazol-5-ylthio)-2,4-dimethylbenzoic Acid

Step 1: 5-iodo-2,4-dimethylbenzoic Acid

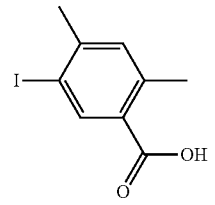

To a stirred solution of 2,4-dimethylbenzoic acid (1.5 g, 10 mmol) in CF3CH2OH (10 mL) was added NIS (3.375 g, 15 mmol) and CF3COOH (1.71 g, 15 mmol) and was heated at 70° C. After 12 h, the precipitate was collected by filtration and washed with EtOAc (20 mL) to afford the title compound (2.35 g). MS (ES) m/z 275 (M).

Step 2: 5-mercapto-2,4-dimethylbenzoic Acid

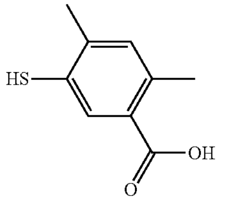

To a degassed stirred solution of 5-iodo-2,4-dimethylbenzoic acid (2.35 g, 8.5 mmol) in DMSO (20 mL) was added CuSO4·5H2O (106 mg, 0.43 mmol.), KOH (2.38 g, 42.5 mmol) and a solution of 1,2-ethanedithiol (1.6 g, 17 mmol) in water (2 mL) under nitrogen. The resulting solution was heated at 90° C. After stirring overnight, the reaction mixture was cooled to 25° C., quenched with aq. 5% HCl solution (50 mL) and extracted with EtOAc (2×50 mL). The combined organic extracts were washed with water (20 mL) and brine (20 mL), dried over anhydrous Na2SO4, filtered and concentrated to afford the crude title compound (1.5 g). MS (ES) m/z 183 (M+H).

Step 3: 5-(2-aminothiazol-5-ylthio)-2,4-dimethylbenzoic Acid

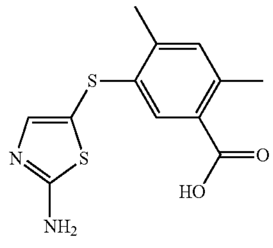 [SMILES: Cc1cc(C)c(C(=O)O)cc1Sc1cnc(N)s1]

To a stirred suspension of 5-mercapto-2,4-dimethylbenzoic acid (728 mg, 4 mmol) and 5-bromothiazol-2-amine (926 mg, 5.2 mmol) in MeOH (30 mL) was added a solution of MeONa (1.08 g, 20 mmol) in MeOH dropwise at 0-5° C. under argon. After 1 h at room temperature, the mixture was cooled to 0° C. and acidified with a 4 M solution of HCl in dioxane to pH 2. The reaction mixture was filtered, washed with MeOH and concentrated. Preparative HPLC afforded the title compound (98 mg). MS (ES) m/z 281 (M+H).

Scheme 7: Method G

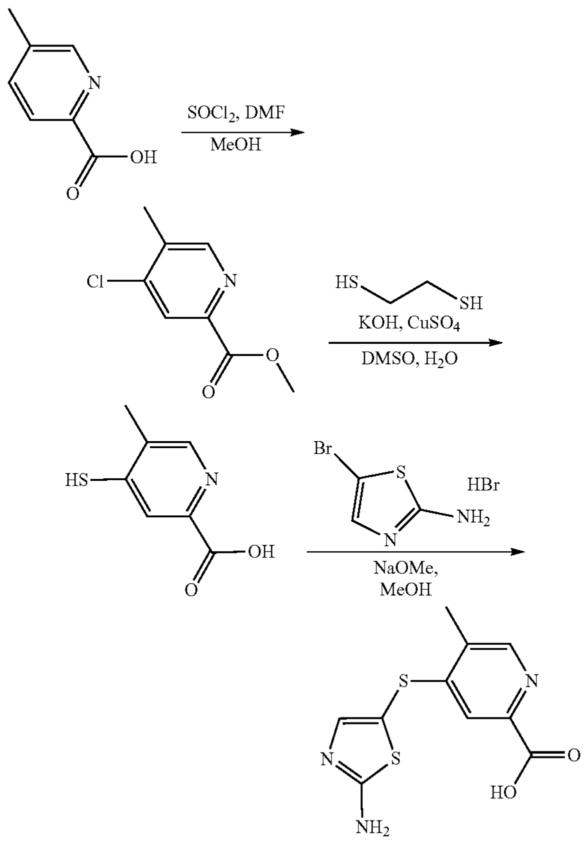

Example 7: 4-(2-aminothiazol-5-ylthio)-5-methylpicolinic Acid

Step 1: methyl 4-chloro-5-methylpicolinate

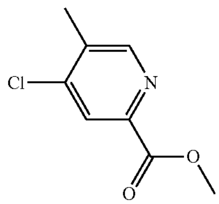

To a stirred solution of 5-methylpicolinic acid (2.5 g, 18 mmol) in SOCl2 (10 mL) was slowly added DMF (21.3 mg, 3 mmol). The resulting solution was heated to 72° C. for 12 h. After cooling to room temperature, the mixture was diluted with toluene and concentrated to near dryness in vacuo. MeOH was added to the obtained oily residue. The contents were stirred for 2 h at 30° C. After filtration, aq. 15% Na2CO3 was added to the filter cake to adjust its pH to 7, and then washed with cold MeOH to afford the title compound (220 mg). MS (ES) m/z 186 (M+H).

Step 2: 4-mercapto-5-methylpicolinic Acid

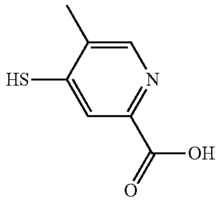

To a stirred solution of methyl 4-chloro-5-methylpicolinate (220 mg, 1.2 mmol) in DMSO (10 mL) purged and maintained under an inert atmosphere of N2, was added CuSO4·5H2O (15 mg, 0.06 mmol.), KOH (336 mg, 6 mmol) and a solution of 1,2-ethanedithiol (226 mg, 2.4 mmol) in water (1 mL). The resulting solution was heated to 90° C. overnight, cooled to 25° C. and concentrated to afford the crude title compound. MS (ES) m/z 170 (M+H).

Step 3: 4-(2-aminothiazol-5-ylthio)-5-methylpicolinic Acid

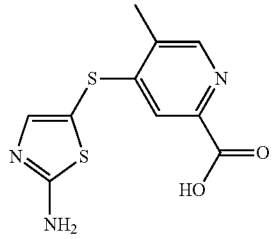 [SMILES: Cc1cnc(C(=O)O)cc1Sc1cnc(N)s1]

To a stirred suspension of 4-mercapto-5-methylpicolinic acid and 5-bromothiazol-2-amine hydrobromide (387 mg, 1.5 mmol) in MeOH (20 mL) maintained under an inert atmosphere of argon was added a solution of MeONa (1.08 g, 20 mmol) in MeOH dropwise at 0-5° C. The cooling bath was removed and the solution was stirred at room temperature for 1 h. The mixture was cooled to 0° C. and acidified with a 4 M solution of HCl in dioxane to adjust the pH to 2. Precipitated salts were filtered and washed with MeOH. The filtrate was concentrated under reduced pressure. Preparative HPLC afforded the title compound (85 mg). MS (ES) m/z 268 (M+H).

Scheme 8: Method H

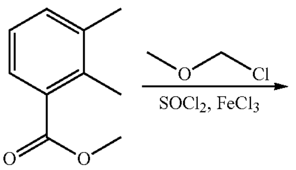

-continued

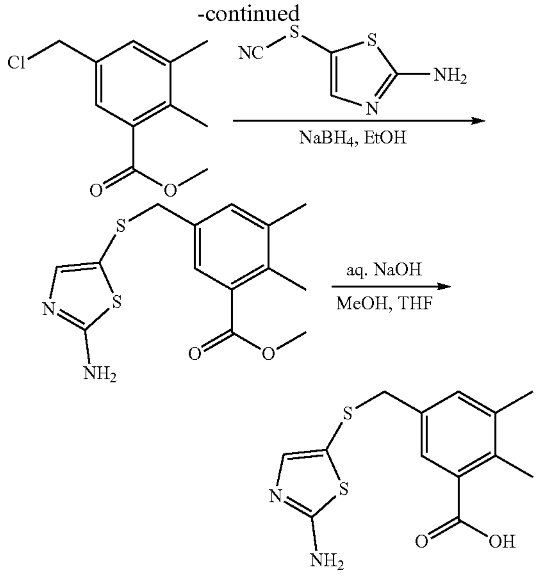

Example 8: 5-((2-aminothiazol-5-yl)methyl)-2,3-dimethylbenzoic Acid

Step 1: methyl 5-(chloromethyl)-2,3-dimethylbenzoate

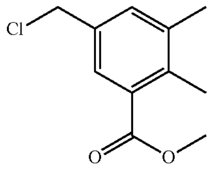

To a stirred solution of methyl 2,3-dimethylbenzoate (2.0 g, 12.2 mmol) in 1,2-dichloroethane (10 mL) were added chloromethyl methyl ether (5 mL, 36.0 mmol), thionyl chloride (0.36 mL, 5.0 mmol) and ferric chloride (0.4 g, 2.4 mmol) at 0° C. The resulting mixture was heated to 55° C. for 2 h. After cooling to room temperature, the mixture was extracted with EtOAc (3×100 mL) and washed with water (20 mL) and brine (20 mL). The combined organic extracts were dried over anhydrous MgSO4, filtered and concentrated. Silica gel chromatography (hexane:EtOAc) afforded the title compound (1.1 g). MS (ES) m/z 213 (M+H).

Step 2: methyl 5-((2-aminothiazol-5-yl)methyl)-2,3-dimethylbenzoate

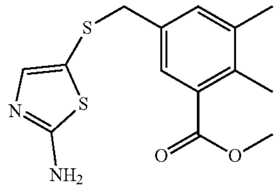

To a stirred solution of 5-thiocyanatothiazol-2-amine (497 mg, 3.8 mmol) in EtOH (18 mL) was added NaBH4 (238 mg, 6.3 mmol) by small portions at 0° C. The resulting mixture was stirred for 2 h at 0-5° C. before addition of acetone (2.8 mL). The stirring was continued for another 10 min. A solution of methyl 5-(chloromethyl)-2,3-dimethylbenzoate (800 mg, 3.7 mmol) in EtOH (10 mL) was then added. The resulting mixture was stirred at room temperature for 16 h. The solvent was evaporated under vacuum. The obtained residue was diluted in EtOAc (100 mL) and washed with brine (20 mL). The organic extract was dried over anhydrous MgSO4, filtered and concentrated. Silica gel chromatography afforded the title compound (1.1 g). MS (ES) m/z 309 (M+H).

Step 3: 5-((2-aminothiazol-5-yl)methyl)-2,3-dimethylbenzoic Acid

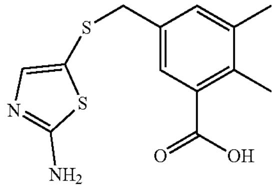 [SMILES: Cc1cc(CSc2cnc(N)s2)cc(C(=O)O)c1C]

To a stirred solution of methyl 5-((2-aminothiazol-5-yl)methyl)-2,3-dimethylbenzoate (500 mg, 1.6 mmol) in MeOH (5 mL) and THE (5 mL) was added 2 N aq. NaOH (5 mL). After stirring overnight, water (25 mL) was added and the solution was adjusted to pH 6 with 2 N aq. HCl. The reaction mixture was extracted with EtOAc (3×25 mL). The combined organic extracts were dried over anhydrous MgSO4, filtered and concentrated to afford the title compound (300 mg). MS (ES) m/z 295 (M+H).

Scheme 9: Method I

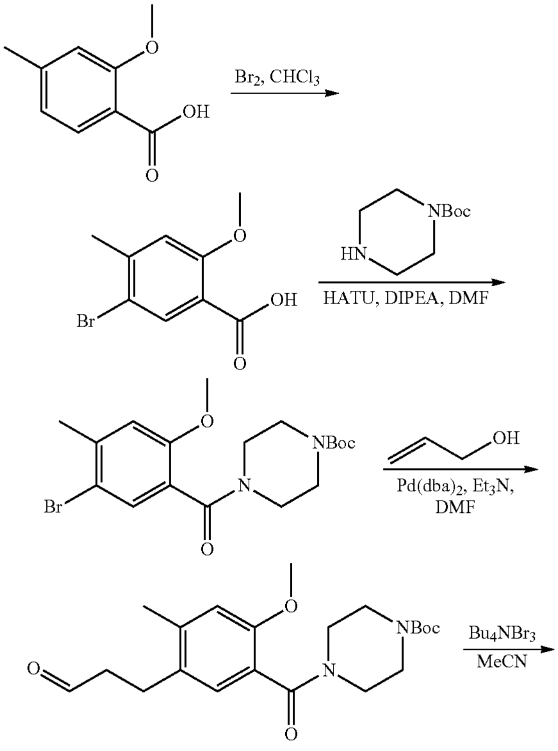

-continued

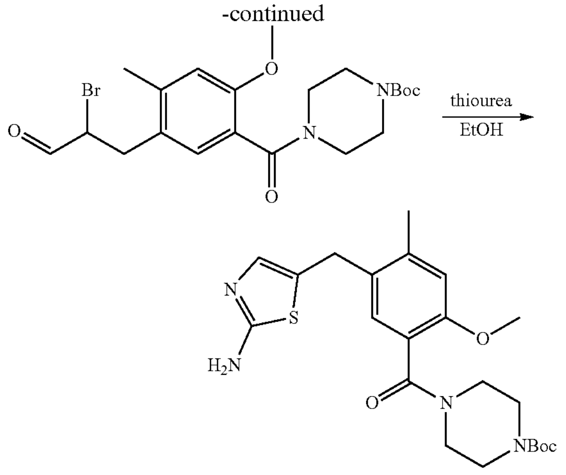

Example 9: tert-butyl 4-(5-((2-aminothiazol-5-yl) methyl)-2-methoxy-4-methylbenzoyl)piperazine-1-carboxylate Step 1: 5-bromo-2-methoxy-4-methylbenzoic Acid

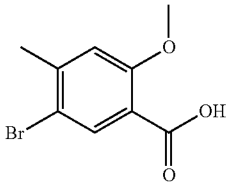

To a stirred solution of 2-methoxy-4-methylbenzoic acid (1 g, 5.49 mmol) in CHCl3 (30 mL) was added Br2 (0.283 mL, 5.49 mmol) dropwise at 0° C. The resulting mixture was stirred at room temperature for 16 h. The solvent was removed under reduced pressure and was washed with Et2O to afford the crude title compound (1.44 g). MS (ES) m/z 243 (M).

Step 2: tert-butyl 4-(5-bromo-2-methoxy-4-methylbenzoyl)piperazine-1-carboxylate

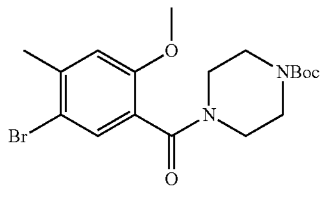 [SMILES: COc1cc(C)c(Br)cc1C(=O)N1CCN(C(=O)OC(C)(C)C)CC1]

To a stirred mixture of 5-bromo-2-methoxy-4-methylbenzoic acid (1.44 g, 5.89 mmol), tert-butyl piperazine-1-carboxylate (1.35 g, 7.25 mmol) and DIPEA (1.52 g, 11.78 mmol) in DMF (15 mL) was added HATU (2.7 mg, 7.25 mmol) at 0° C. The resulting mixture was stirred at room temperature for 4 h and was then extracted with EtOAc (3×200 mL), and washed with brine (2×250 mL). The combined organic extracts were dried over anhydrous Na2SO4, filtered and concentrated in vacuo. Silica gel chromatography (DCM, MeOH) afforded the title compound (2.09 g). MS (ES) m/z 413 (M+H).

Step 3: tert-butyl 4-(2-methoxy-4-methyl-5-(3-oxopropyl)benzoyl)piperazine-1-carboxylate

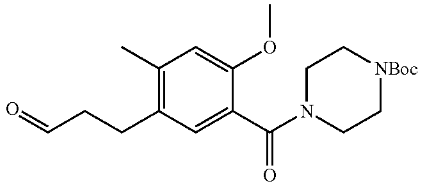 [SMILES: COc1cc(C)c(CCC=O)cc1C(=O)N1CCN(C(=O)OC(C)(C)C)CC1]

To a stirred mixture of tert-butyl 4-(5-bromo-2-methoxy-4-methylbenzoyl)piperazine-1-carboxylate (1 g, 2.42 mmol), prop-2-en-1-ol (155 mg, 2.66 mmol), Pd(dba)2 (28 mg, 0.048 mmol), 2-[bis(1,1-dimethylethyl)phosphino]-1-phenyl-1H-indole (49 mg, 0.15 mmol) in DMF (10 mL) was added Et3N (0.52 g, 2.66 mmol). After stirring at 100° C. for 1 h, the solvent was removed under reduced pressure. Silica gel chromatography (DCM, MeOH) afforded the title compound (279 mg). MS (ES) m/z 391 (M+H).

Step 4: tert-butyl 4-(5-(2-bromo-3-oxopropyl)-2-methoxy-4-methylbenzoyl)piperazine-1-carboxylate

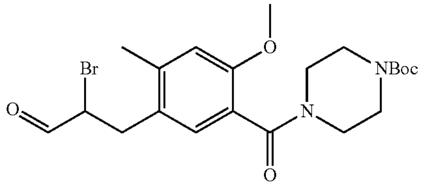 [SMILES: COc1cc(C)c(CC(Br)C=O)cc1C(=O)N1CCN(C(=O)OC(C)(C)C)CC1]

To a stirred solution of tert-butyl 4-(2-methoxy-4-methyl-5-(3-oxopropyl)benzoyl)piperazine-1-carboxylate (270 mg, 0.69 mmol) in MeCN (5 mL) was added tetrabutylammonium tribromide (334 mg, 0.69 mmol). The resulting mixture was stirred at room temperature for 30 min. The solvent was evaporated and the mixture was extracted with EtOAc (3×55 mL). The combined organic extracts were washed with water (30 mL) and brine (30 mL), dried over anhydrous Na2SO4, filtered and concentrated in vacuo to afford the crude title compound (310 mg). MS (ES) m/z 469 (M+H).

Step 5: tert-butyl 4-(5-((2-aminothiazol-5-yl) methyl)-2-methoxy-4-methylbenzoyl)piperazine-1-carboxylate

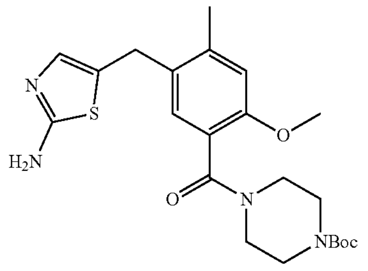 [SMILES: COc1cc(C)c(Cc2cnc(N)s2)cc1C(=O)N1CCN(C(=O)OC(C)(C)C)CC1]

To a stirred mixture of tert-butyl 4-(5-(2-bromo-3-oxo-propyl)-2-methoxy-4-methylbenzoyl)piperazine-1-carboxylate (310 mg, 0.66 mmol) in EtOH (6 mL) was added thiourea (201 mg, 2.64 mmol). The resulting mixture was heated to reflux for 15 h. The solvent was removed under reduced pressure and the mixture was extracted with EtOAc (3x50 mL). The combined organic extracts were dried over anhydrous Na2SO4, filtered and concentrated. Silica gel chromatography afforded the title compound (102 mg). MS (ES) m/z 447 (M+H).

Scheme 10: Method J

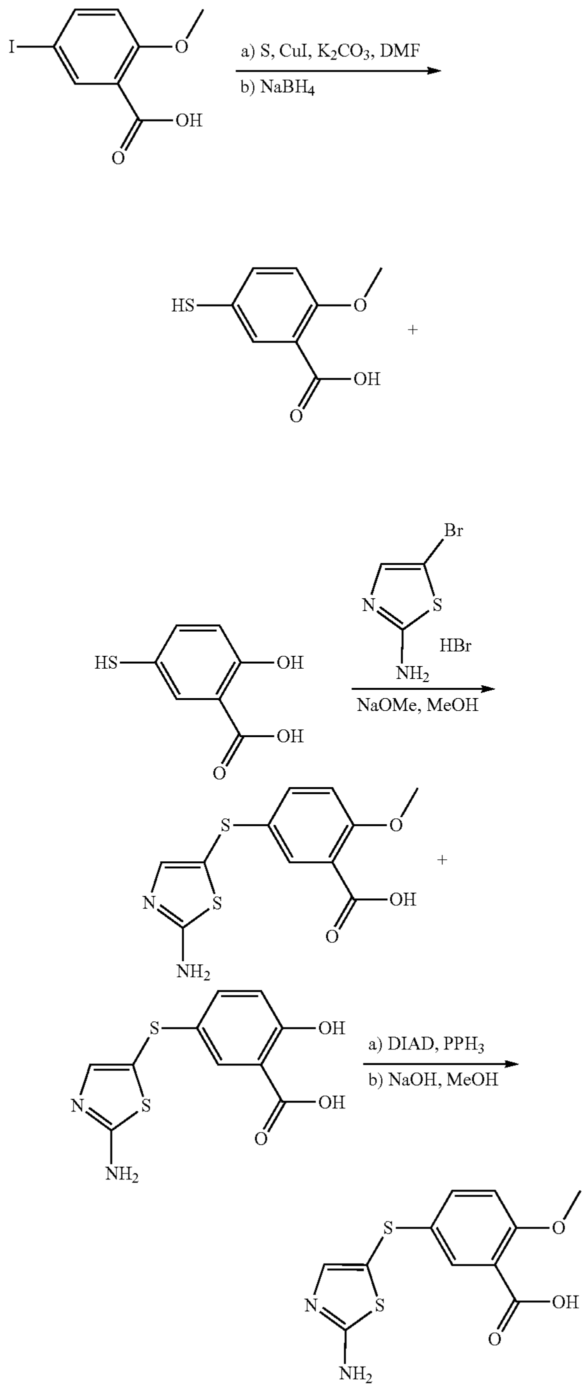

Example 10: 5-(2-aminothiazol-5-ylthio)-2-methoxybenzoic Acid

Step 1: 5-mercapto-2-methoxybenzoic Acid

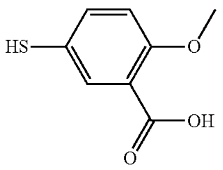

To a stirred a solution of 5-iodo-2-methoxybenzoic acid (940 mg, 3.4 mmol) in DMF (10 mL) purged and maintained under an inert atmosphere of N2 was added CuI (65 mg, 0.34 mmol.), K2CO3 (925 mg, 6.7 mmol), and S (320 mg, 10 mmol). The mixture was heated to 90° C. overnight, cooled to 0° C., and quenched with NaBH4 (380 mg, 10 mmol). The resulting mixture was then stirred at 40° C. for 5 h, cooled to 25° C., quenched with aq. 5% HCl solution (50 mL), and extracted with EtOAc (2x50 mL). The combined organic extracts were washed with water (20 mL) and brine (20 mL), dried over anhydrous Na2SO4, filtered and concentrated to afford a crude mixture of the title compound and 2-hydroxy-5-mercaptobenzoic acid (1.1 g). MS (ES) m/z 183 (M−H).

Step 2: 5-(2-aminothiazol-5-ylthio)-2-methoxybenzoic Acid

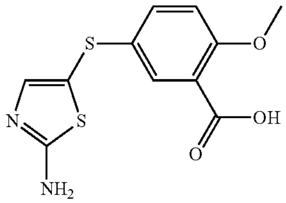 [SMILES: COc1ccc(Sc2cnc(N)s2)cc1C(=O)O]

To a stirred suspension of 5-mercapto-2-methoxybenzoic acid (1.1 g, 3 mmol) and 5-bromothiazol-2-amine hydrobromide (774 mg, 3 mmol) in MeOH (50 mL) maintained under an inert atmosphere of argon, was added a solution of MeONa (1.62 g, 10 mmol) in MeOH dropwise at 0-5° C. The cooling bath was removed and the resulting solution was stirred at room temperature for 1 h. The mixture was cooled to 0° C. and acidified with a 4 M solution of HCl in dioxane to adjust the pH to 2. Precipitated salts were filtered and washed with MeOH. The filtrate was concentrated under reduced pressure. Prep-HPLC afforded a mixture of the title compound and 5-((2-aminothiazol-5-yl)thio)-2-hydroxybenzoic acid (800 mg). MS (ES) m/z 283 (M+H).

Step 3: 5-(2-aminothiazol-5-ylthio)-2-methoxybenzoic Acid

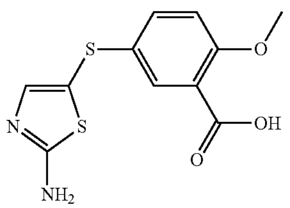 [SMILES: COc1ccc(Sc2cnc(N)s2)cc1C(=O)O]

To a stirred solution of TPP (1.57 g, 6 mmol) in MeOH (10 mL) and THE (10 mL) was added DIAD (1.21 g, 6 mmol). After 5 min, 5-(2-aminothiazol-5-ylthio)-2-methoxybenzoic acid (800 mg, 3 mmol) was then added. The resulting mixture was stirred at room temperature for an additional 4 h and was concentrated in vacuo. Silica gel chromatography afforded the corresponding ester which was treated with a solution of NaOH (1.5 eq) in MeOH at room temperature for 2 h to afford the title compound (694 mg). MS (ES) m/z 283 (M+H).

Scheme 11: Method K

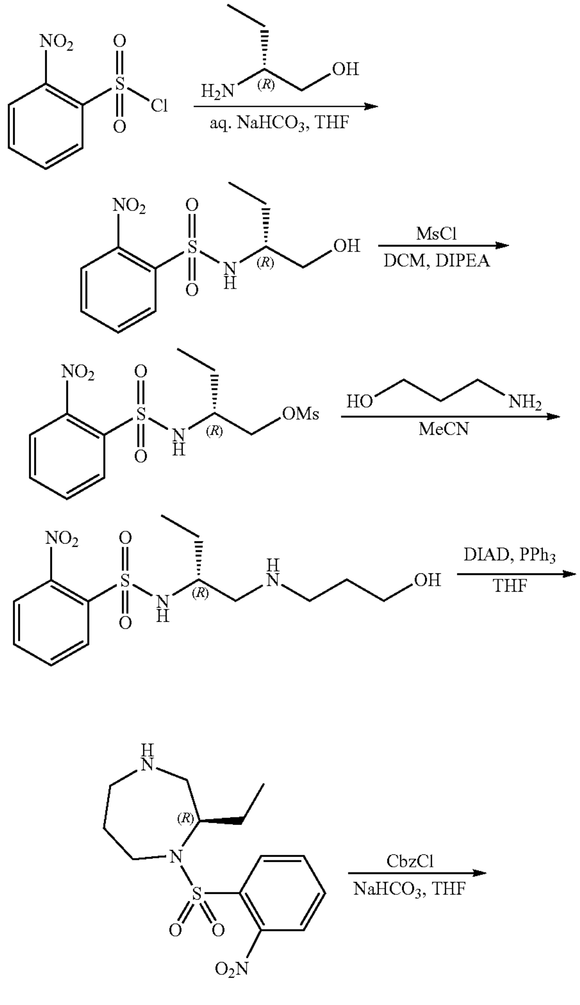

-continued

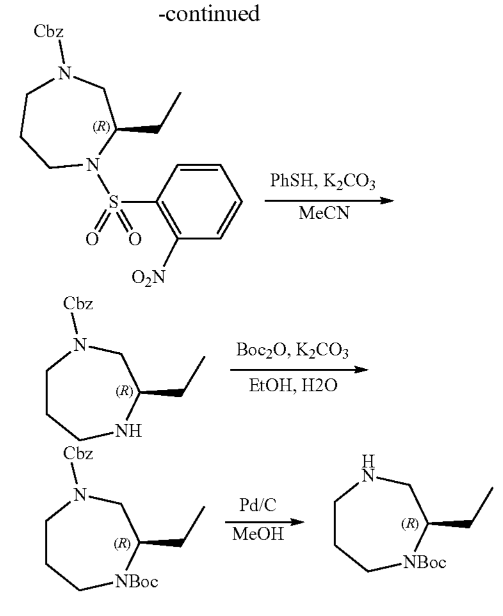

Example 11: (R)-tert-butyl 2-ethyl-1,4-diazepane-1-carboxylate

Step 1: (R)—N-(1-hydroxybutan-2-yl)-2-nitrobenzenesulfonamide

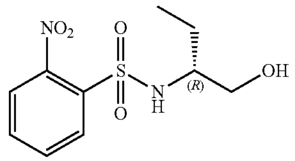

To a stirred solution of (R)-2-aminobutan-1-ol (5.437 g, 61 mmol) and NaHCO3 (6.56 g, 72.1 mmol) in water (17 mL) was gradually added a solution of 2-nitrobenzenesulfonyl chloride (10 g, 44.64 mmol) in THF (17 mL) at 0° C. The resulting mixture was stirred at room temperature for 15 h. The mixture was poured into water and extracted with EtOAc. The combined organic extracts were washed with brine, dried over anhydrous Na2SO4, filtered and concentrated in vacuo to afford the crude title compound (12.87 g). MS (ES) m/z 275 (M+H).

Step 2: (R)-2-(2-nitrophenylsulfonamido)butyl Methanesulfonate

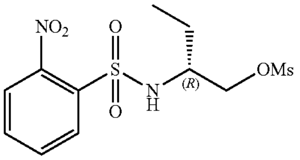

To a stirred solution of (R)—N-(1-hydroxybutan-2-yl)-2-nitrobenzenesulfonamide (12.87 g, 46.924 mmol) and Et3N (7.108 g, 70.4 mmol) in DCM (63 mL) was gradually added a solution of MsCl (5.38 g, 46.924 mmol) in DCM (4 mL) at 0° C. The resulting mixture was stirred at room temperature for 20 h and was then extracted with DCM. The combined organic extracts were washed with brine, dried over anhydrous Na2SO4, filtered and concentrated in vacuo to afford the crude title compound (13.42 g). MS (ES) m/z 353 (M+H).

Step 3: (R)—N-(1-(3-hydroxypropylamino)butan-2-yl)-2-nitrobenzenesulfonamide

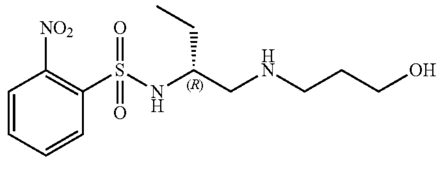

To a stirred solution of 3-aminopropan-1-ol (9.14 g, 121.8 mmol) in MeCN (64 mL) was gradually added a solution of (R)-2-(2-nitrophenylsulfonamido)butyl methanesulfonate (13.42 g, 32.1 mmol) in MeCN (64 mL). The resulting mixture was stirred at room temperature for 16 h and was then concentrated in vacuo. Water was added, the solution was acidified with 6 N HCl to pH 4 and was extracted with EtOAc. The aqueous phase was made alkaline by adding K2CO3 to pH 9, and was extracted again with EtOAc. The combined organic extracts were washed with brine, dried over anhydrous Na2SO4, filtered and concentrated in vacuo to afford the crude title compound (12.15 g). MS (ES) m/z 332 (M+H).

Step 4: (R)-2-ethyl-1-(2-nitrophenylsulfonyl)-1,4-diazepane

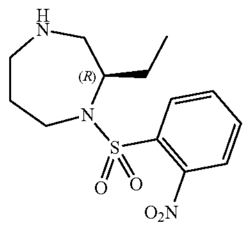

To a stirred solution of (R)—N-(1-(3-hydroxypropylamino)butan-2-yl)-2-nitrobenzenesulfonamide (12.15 g, 36.67 mmol) and Ph3P (12.5 g, 47.67 mmol) in THF (80 mL) was gradually added a solution of DIAD (9.936 g, 49.14 mmol) at 0° C. The resulting mixture was stirred at room temperature for 18 h and was then concentrated in vacuo. Water was added, the solution was acidified with 6 N HCl to adjust its pH to 4 and was extracted with EtOAc. The aqueous phase was made alkaline by adding K2CO3 to pH 9, and was extracted again with EtOAc. The combined organic extracts were washed with brine, dried over anhydrous Na2SO4, filtered and concentrated in vacuo to afford the crude title compound (7.89 g). MS (ES) m/z 314 (M+H).

Step 5: (R)-benzyl 3-ethyl-4-(2-nitrophenylsulfonyl)-1,4-diazepane-1-carboxylate

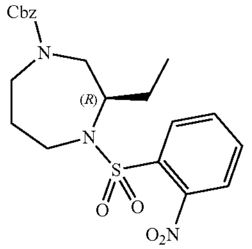

To a stirred solution of (R)-2-ethyl-1-(2-nitrophenylsulfonyl)-1,4-diazepane (7.89 g, 25.18 mmol) and $NaHCO_3$ (3.172 g, 37.77 mmol) in THE (30 mL) and water (25 mL) was gradually added a solution of CbzCl (6.013 g, 35.25 mmol) in THE (20 mL) at 0° C. The resulting mixture was stirred at room temperature for 15 h, then poured into water and extracted with EtOAc. The combined organic extracts were washed with brine, dried over anhydrous Na2SO4, filtered and concentrated in vacuo. Silica gel chromatography (DCM, MeOH) afforded the title compound (6.35 g). MS (ES) m/z 448 (M+H).

Step 6: (R)-benzyl 3-ethyl-1,4-diazepane-1-carboxylate

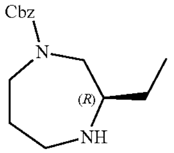

To a stirred solution of (R)-benzyl 3-ethyl-4-(2-nitrophenylsulfonyl)-1,4-diazepane-1-carboxylate (6.35 g, 14.19 mmol) and K2CO3 (3.91 g, 28.38 mmol) in MeCN (60 mL) was added PhSH (2.91 mL, 28.38 mmol). The resulting mixture was heated to 50° C. for 6.5 h and was then extracted with EtOAc. The aqueous layer was made alkaline by adding K2CO3 to pH 12, and was extracted again with EtOAc. The combined organic extracts were dried over anhydrous Na2SO4, filtered and concentrated in vacuo. Silica gel chromatography (DCM, MeOH) afforded the title compound (2.85 g). MS (ES) m/z 263 (M+H).

Step 7: (R)-4-benzyl 1-tert-butyl 2-ethyl-1,4-diazepane-1,4-dicarboxylate

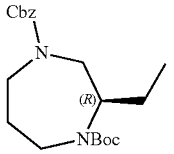

To a stirred solution of (R)-benzyl 3-ethyl-1,4-diazepane-1-carboxylate (2.851 g, 10.87 mmol) and K2CO3 (2.25 g, 16.3 mmol) in EtOH (30 mL) and water (8 mL) was gradually added Boc20 (3.558 g, 16.3 mmol) at 0° C. The resulting mixture was stirred at room temperature for 1.5 h and was then extracted with EtOAc. The combined organic extracts were washed with brine, dried over anhydrous Na2SO4, filtered and concentrated in vacuo. Silica gel chromatography (hexane, EtOAc) afforded the title compound (3 g). MS (ES) m/z 385 (M+Na).

Step 8: (R)-tert-butyl 2-ethyl-1,4-diazepane-1-carboxylate

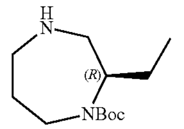

To a solution of (R)-4-benzyl 1-tert-butyl 2-ethyl-1,4-diazepane-1,4-dicarboxylate (2.851 g, 10.87 mmol) in MeOH (15 mL) was added 10% Pd/C (173 mg). The resulting mixture was stirred at room temperature for 15 h under a hydrogen atmosphere. The catalyst was removed by filtration through a pad of Celite and the filtrate was concentrated in vacuo to afford the crude title compound (0.98 g). MS (ES) m/z 229 (M+H).

Scheme 12: Method L

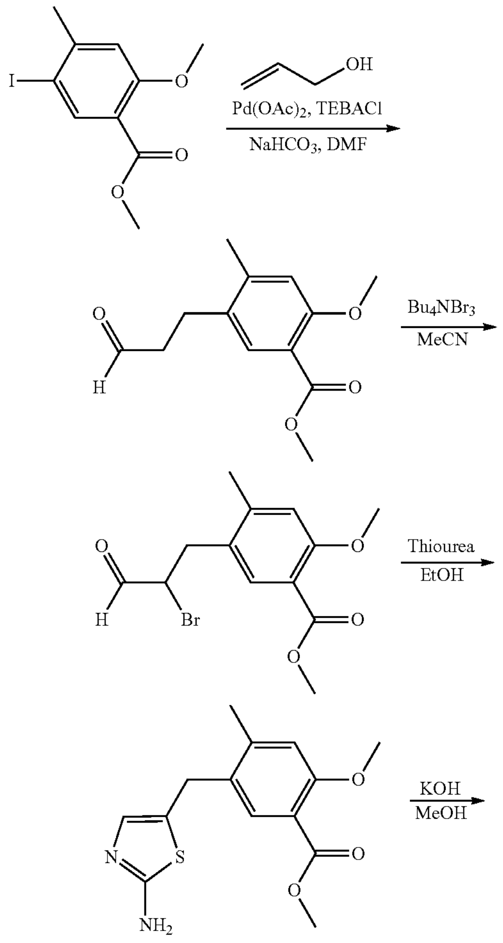

-continued

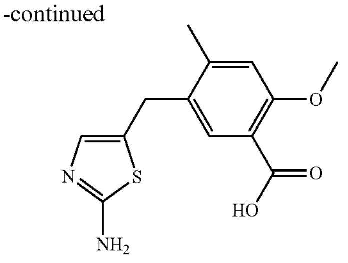

Example 12: 5-((2-aminothiazol-5-yl)methyl)-2-methoxybenzoic Acid

Step 1: methyl 2-methoxy-4-methyl-5-(3-oxopropyl)benzoate

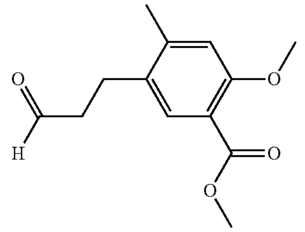 [SMILES: COC(=O)c1cc(CCC=O)c(C)cc1OC]

To a stirred solution of methyl 5-iodo-2-methoxy-4-methylbenzoate (6 g, 19.6 mmol) and prop-2-en-1-ol (2.28 g, 39.2 mmol) in DMF (60 mL) was added Pd(OAc)2 (220 mg, 0.98 mmol), benzyl trimethylammonium chloride (4.464 g, 19.6 mmol) and NaHCO3 (3.296 g, 39.2 mmol). The resulting mixture was heated to 60° C. for 2 h, and the mixture was then extracted with EtOAc. The combined organic extracts were washed with water and brine, dried over anhydrous Na2SO4, filtered and concentrated in vacuo. Silica gel chromatography (PE, EtOAc) afforded the title compound (2.5 g). MS (ES) m/z 237 (M+H).

Step 2: methyl 5-(2-bromo-3-oxopropyl)-2-methoxy-4-methylbenzoate

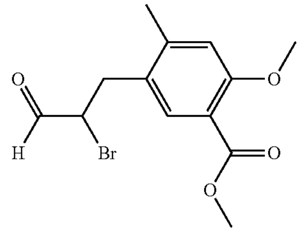 [SMILES: COC(=O)c1cc(CC(Br)C=O)c(C)cc1OC]

To a stirred solution of methyl 2-methoxy-4-methyl-5-(3-oxopropyl)benzoate (2.5 g, 10.6 mmol) in MeCN (65 mL) was added tetrabutylammonium tribromide (4.60 g, 9.54 mmol). The resulting mixture was stirred at room temperature for 30 min. The solvent was evaporated and the mixture was extracted with EtOAc (3×155 mL). The combined organic extracts were washed with water (30 mL) and brine (30 mL), dried over anhydrous Na2SO4, filtered and concentrated in vacuo to afford the crude title compound (3 g). MS (ES) m/z 315 (M+H).

Step 3: methyl 5-((2-aminothiazol-5-yl)methyl)-2-methoxy-4-methylbenzoate

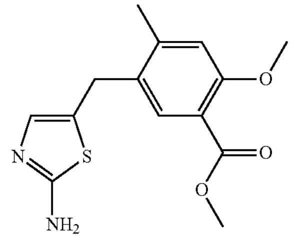 [SMILES: COC(=O)c1cc(Cc2cnc(N)s2)c(C)cc1OC]

To a stirred solution of methyl 5-(2-bromo-3-oxopropyl)-2-methoxy-4-methylbenzoate (3 g, 9.52 mmol) in EtOH (42 mL) was added thiourea (2.9 g, 38.1 mmol). The resulting mixture was heated to reflux for 15 h. The solvent was removed under reduced pressure and the mixture was extracted with EtOAc. The combined organic extracts were dried over anhydrous Na2SO4, filtered and concentrated in vacuo. Silica gel chromatography afforded the title compound (710 mg). MS (ES) m/z 293 (M+H).

Step 4: 5-((2-aminothiazol-5-yl)methyl)-2-methoxybenzoic Acid

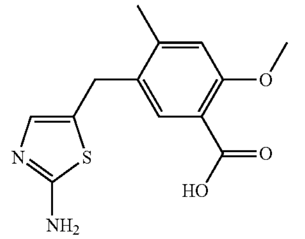 [SMILES: COc1cc(C)c(Cc2cnc(N)s2)cc1C(=O)O]

To a stirred solution of methyl 5-((2-aminothiazol-5-yl) methyl)-2-methoxy-4-methylbenzoate (710 mg, 2.43 mmol) in MeOH (20 mL) and water (2 mL) was added KOH (435 mg, 7.77 mmol). The resulting mixture was heated to 50° C. for 15 h. The solvent was removed under reduced pressure and the mixture was extracted with EtOAc. The pH of the aqueous layer was adjusted to 5-6. The formed precipitate was collected by filtration and dried in vacuo to afford the title compound (309 mg). MS (ES) m/z 279 (M+H).

Scheme 14: Method N

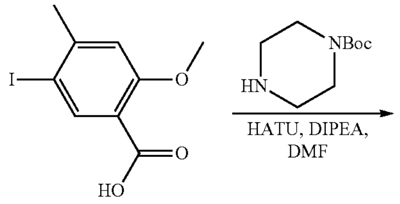

-continued

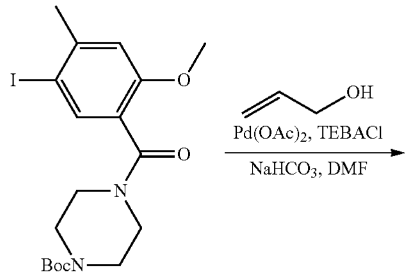

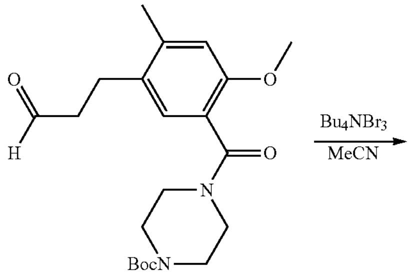

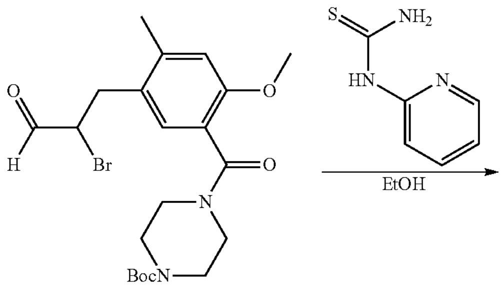

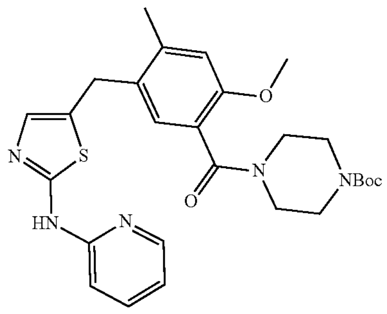

Example 14: tert-butyl 4-(2-methoxy-4-methyl-5-((2-(pyridin-2-ylamino)thiazol-5-yl)methyl)benzoyl) piperazine-1-carboxylate Step 1: tert-butyl 4-(5-iodo-2-methoxy-4-methyl-benzoyl)piperazine-1-carboxylate

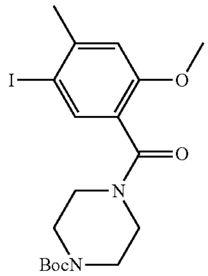 [SMILES: COc1cc(C)c(I)cc1C(=O)N1CCN(C(=O)OC(C)(C)C)CC1]

To a stirred mixture of 5-iodo-2-methoxy-4-methylbenzoic acid (2.23 g, 7.64 mmol), tert-butyl piperazine-1-carboxylate (1.7 g, 9.16 mmol) and DIPEA (1.971 g, 15.28 mmol) in DMF (15 mL) was added and HATU (3.48 g, 9.16 mmol) at 0° C. The resulting mixture was stirred at room temperature for 4 h and was then extracted with EtOAc. The combined organic extracts were washed with brine (2×250 mL), dried over Na2SO4 and concentrated in vacuo. Silica gel chromatography (DCM, MeOH) afforded the title compound (3.26 g). MS (ES) m/z 461 (M+H).

Step 2: tert-butyl 4-(2-methoxy-4-methyl-5-(3-oxo-propyl)benzoyl)piperazine-1-carboxylate

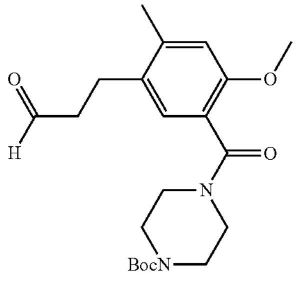 [SMILES: COc1cc(C)c(CCC=O)cc1C(=O)N1CCN(C(=O)OC(C)(C)C)CC1]

To a stirred mixture of tert-butyl 4-(5-iodo-2-methoxy-4-methylbenzoyl)piperazine-1-carboxylate (2.05 g, 4.44 mmol) and prop-2-en-1-ol (0.45 g, 8.89 mmol) in DMF (13 mL) was added Pd(OAc)2 (50 mg, 0.22 mmol), benzyl trimethylammonium chloride (0.97 g, 4.44 mmol) and NaHCO3 (0.75 g, 8.89 mmol). The resulting mixture was heated to 60° C. for 2 h and was then extracted with EtOAc. The combined organic extracts were washed with brine, dried over anhydrous Na2SO4, filtered and concentrated in vacuo. Silica gel chromatography (PE, EtOAc) afforded the title compound (1.4 g). MS (ES) m/z 391 (M+H).

Step 3: tert-butyl 4-(5-(2-bromo-3-oxopropyl)-2-methoxy-4-methylbenzoyl)piperazine-1-carboxylate

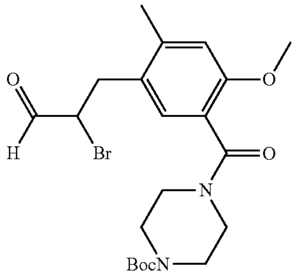 [SMILES: COc1cc(C)c(CC(Br)C=O)cc1C(=O)N1CCN(C(=O)OC(C)(C)C)CC1]

To a stirred solution of tert-butyl 4-(2-methoxy-4-methyl-5-(3-oxopropyl)benzoyl)piperazine-1-carboxylate (1 g, 2.56 mmol) in MeCN (30 mL) was added tetrabutylammonium tribromide (1.44 g, 2.98 mmol). The resulting mixture was stirred at room temperature for 30 min. The solvent was evaporated, and the mixture was extracted with EtOAc (3×155 mL). The combined organic extracts were washed with water (30 mL) and brine (30 mL), dried over anhydrous Na2SO4, filtered and concentrated in vacuo to afford the crude title compound (0.79 g). MS (ES) m/z 471 (M−H).

Step 4: tert-butyl 4-(2-methoxy-4-methyl-5-((2-(pyridin-2-ylamino)thiazol-5-yl)methyl)benzoyl) piperazine-1-carboxylate

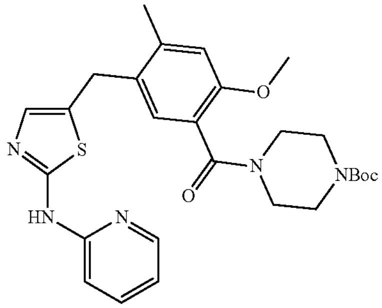 [SMILES: COc1cc(C)c(Cc2cnc(Nc3ccccn3)s2)cc1C(=O)N1CCN(C(=O)OC(C)(C)C)CC1]

To a stirred solution of tert-butyl 4-(5-(2-bromo-3-oxopropyl)-2-methoxy-4-methylbenzoyl)piperazine-1-carboxylate (790 mg, 1.9 mmol) in EtOH (15 mL) was added 1-(pyridin-2-yl)thiourea (310 mg, 1.96 mmol). The resulting mixture was heated to reflux for 4 h and the solvent was then removed under reduced pressure. Sat. aq. NaHCO3 was added and the mixture was extracted with EtOAc. The combined organic extracts were dried over anhydrous Na2SO4, filtered and concentrated in vacuo. Silica gel chromatography afforded the title compound (261 mg). MS (ES) m/z 524 (M+H).

TABLE 1

| Final compounds (structures, names, masses and methods used for their synthesis) | | |
|---|---|---|
| Compound | MS (ES) m/z | Method Used |
| 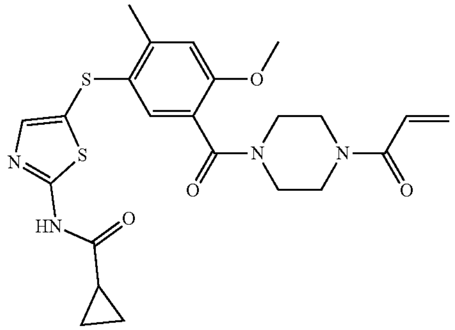 [SMILES: C=CC(=O)N1CCN(C(=O)c2cc(Sc3cnc(NC(=O)C4CC4)s3)c(C)cc2OC)CC1] N-[5-[4-methoxy-2-methyl-5-(4-prop-2-enoylpiperazine-1-carbonyl)phenyl]sulfanylthiazol-2-yl]cyclopropanecarboxamide | Compound 1 487.1 (M + H) | A |
| 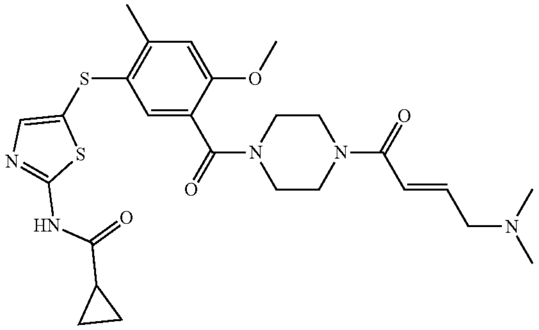 [SMILES: COc1cc(C)c(Sc2cnc(NC(=O)C3CC3)s2)cc1C(=O)N1CCN(C(=O)/C=C/CN(C)C)CC1] N-[5-[5-[4-[(E)-4-(dimethylamino)but-2-enoyl]piperazine-1-carbonyl]-4-methoxy-2-methyl-phenyl]sulfanylthiazol-2-yl ]cyclopropanecarboxamide | Compound 3 544.3 (M + H) | B |
| 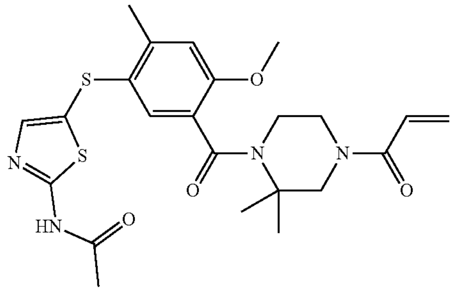 [SMILES: C=CC(=O)N1CCN(C(=O)c2cc(Sc3cnc(NC(C)=O)s3)c(C)cc2OC)C(C)(C)C1] N-[5-[5-(2,2-dimethyl-4-prop-2-enoyl-piperazine-1-carbonyl)-4-methoxy-2-methyl-phenyl]sulfanylthiazol-2-yl]acetamide | Compound 5 489.2 (M + H) | A |

TABLE 1-continued

Final compounds (structures, names, masses and methods used for their synthesis)

| Compound | MS (ES) m/z | Method Used |
| --- | --- | --- |
| 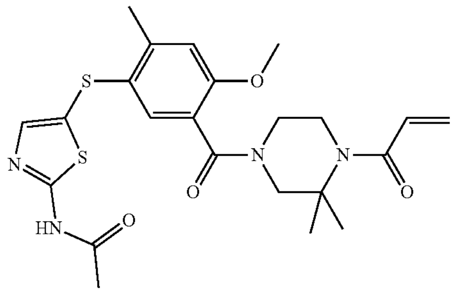 [SMILES: C=CC(=O)N1CCN(C(=O)c2cc(Sc3cnc(NC(C)=O)s3)c(C)cc2OC)CC1(C)C]<br>N-[5-15-(3,3-dimethyl-4-prop-2-enoyl-piperazine-1-carbonyl)-4-methoxy-2-methyl-phenyl]sulfanylthiazol-2-yl]acetamide | Compound 6<br>489.2 (M + H) | A |
| 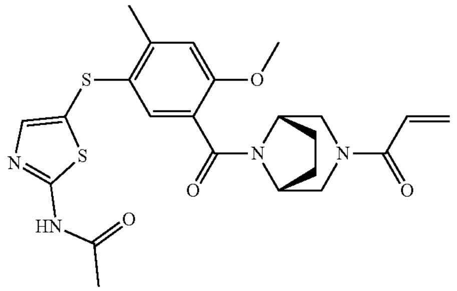 [SMILES: C=CC(=O)N1C[C@H]2CC[C@@H](C1)N2C(=O)c1cc(Sc2cnc(NC(C)=O)s2)c(C)cc1OC]<br>N-[5-[4-methoxy-2-methyl-5-(3-prop-2-enoyl-3,8-diazabicyclo[3.2.1]octane-8-carbonyl)phenyl]sulfanylthiazol-2-yl]acetamide | Compound 7<br>487.1 (M + H) | A |
| 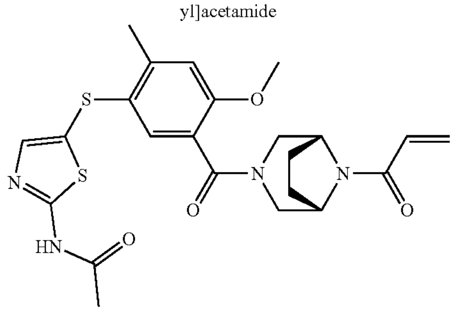<br>N-[5-[4-methoxy-2-methyl-5-(8-prop-2-enoyl-3,8-diazabicyclo[3.2.1]octane-3-carbonyl)phenyl]sulfanylthiazol-2-yl]acetamide | Compound 8<br>487.1 (M + H) | A |
| 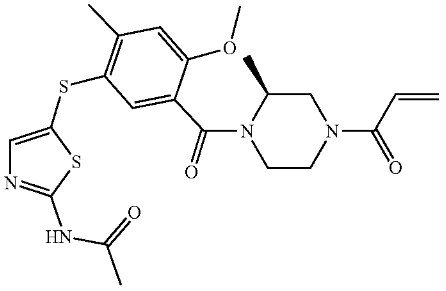 [SMILES: C=CC(=O)N1CCN(C(=O)c2cc(Sc3cnc(NC(C)=O)s3)c(C)cc2OC)[C@@H](C)C1]<br>N-[5-[4-methoxy-2-methyl-5-[(2S)-2-methyl-4-prop-2-enoyl-piperazine-1-carbonyl]phenyl]sulfanylthiazol-2-yl]acetamide | Compound 9<br>475.3 (M + H) | A |

TABLE 1-continued

| Final compounds (structures, names, masses and methods used for their synthesis) | | |
|---|---|---|
| Compound | MS (ES) m/z | Method Used |
| 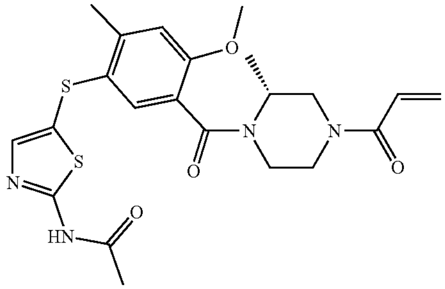 [SMILES: C=CC(=O)N1CCN(C(=O)c2cc(Sc3cnc(NC(C)=O)s3)c(C)cc2OC)[C@H](C)C1] N-[5-[4-methoxy-2-methyl-5-[(2R)-2-methyl-4-prop-2-enoyl-piperazine-1-carbonyl]phenyl]sulfanylthiazol-2-yl]acetamide | Compound 10 475.1 (M + H) | A |
| 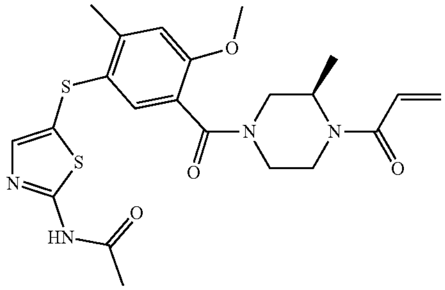 [SMILES: C=CC(=O)N1CCN(C(=O)c2cc(Sc3cnc(NC(C)=O)s3)c(C)cc2OC)C[C@H]1C] N-[5-[4-methoxy-2-methyl-5-[(3R)-3-methyl-4-prop-2-enoyl-piperazine-1-carbonyl]phenyl]sulfanylthiazol-2-yl]acetamide | Compound 11 475.1 (M + H) | A |
| 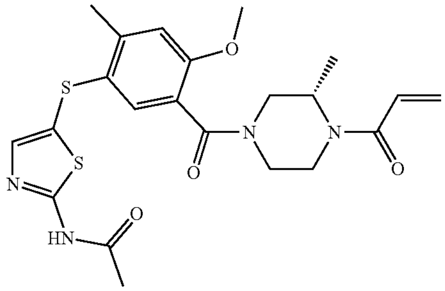 [SMILES: C=CC(=O)N1CCN(C(=O)c2cc(Sc3cnc(NC(C)=O)s3)c(C)cc2OC)C[C@@H]1C] N-[5-[4-methoxy-2-methyl-5-[(3S)-3-methyl-4-prop-2-enoyl-piperazine-1-carbonyl]phenyl]sulfanylthiazol-2-yl]acetamide | Compound 12 475.1 (M + H) | A |

TABLE 1-continued

| Final compounds (structures, names, masses and methods used for their synthesis) | | |
|---|---|---|
| Compound | MS (ES) m/z | Method Used |
| 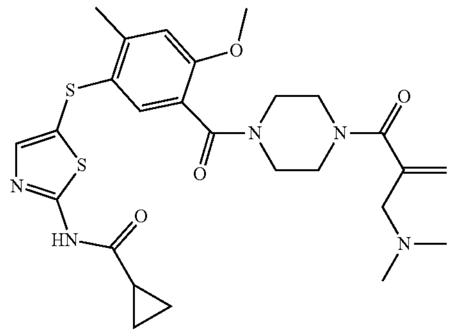 [SMILES: C=C(CN(C)C)C(=O)N1CCN(C(=O)c2cc(Sc3cnc(NC(=O)C4CC4)s3)c(C)cc2OC)CC1] N-[5-[5-[4-[2-[(dimethylamino)methyl]prop-2-enoyl]piperazine-1-carbonyl]-4-methoxy-2-methyl-phenyl]sulfanylthiazol-2-yl]cyclopropanecarboxamide | Compound 13 544.3 (M + H) | B |
| 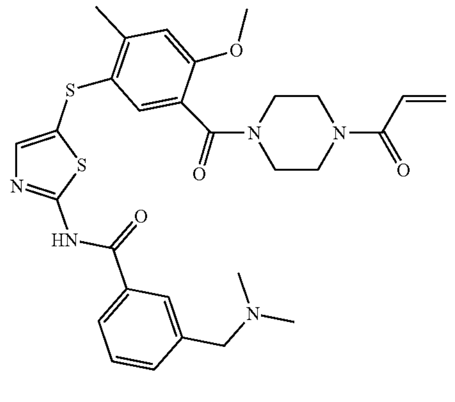 [SMILES: C=CC(=O)N1CCN(C(=O)c2cc(Sc3cnc(NC(=O)c4cccc(CN(C)C)c4)s3)c(C)cc2OC)CC1] 3-[(dimethylamino)methyl]-N-[5-[4-methoxy-2-methyl-5-(4-prop-2-enoylpiperazine-1-carbonyl)phenyl]sulfanylthiazol-2-yl]benzamide | Compound 14 580.3 (M + H) | C |
| 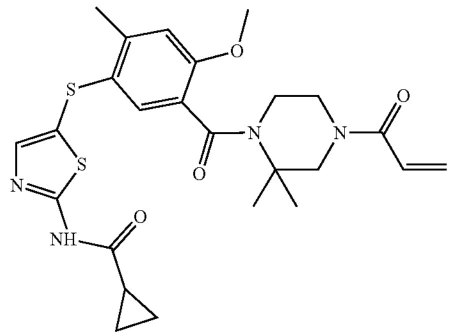 [SMILES: C=CC(=O)N1CCN(C(=O)c2cc(Sc3cnc(NC(=O)C4CC4)s3)c(C)cc2OC)C(C)(C)C1] N-[5-[5-(2,2-dimethyl-4-prop-2-enoyl-piperazine-1-carbonyl)-4-methoxy-2-methyl-phenyl]sulfanylthiazol-2-yl]cyclopropanecarboxamide | Compound 15 515.2 (M + H) | A |

TABLE 1-continued

| Final compounds (structures, names, masses and methods used for their synthesis) | | |
|---|---|---|
| Compound | MS (ES) m/z | Method Used |
| 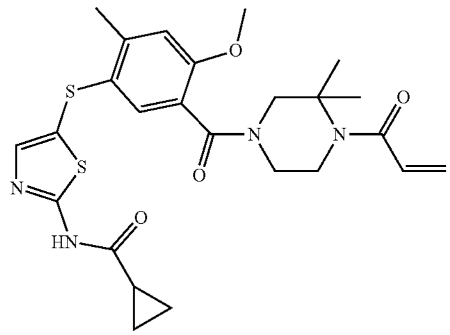 [SMILES: C=CC(=O)N1CCN(C(=O)c2cc(Sc3cnc(NC(=O)C4CC4)s3)c(C)cc2OC)CC1(C)C] N-[5-[5-(3,3-dimethyl-4-prop-2-enoyl-piperazine-1-carbonyl)-4-methoxy-2-methyl-phenyl]sulfanylthiazol-2-yl]cyclopropanecarboxamide | Compound 16 515.2 (M + H) | A |
| 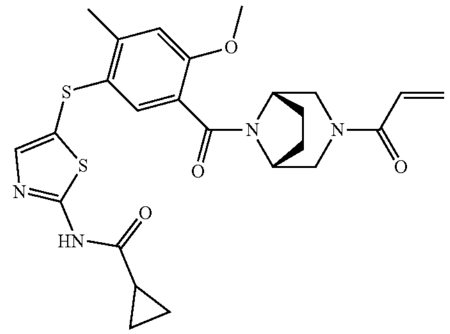 [SMILES: C=CC(=O)N1C[C@H]2CC[C@@H](C1)N2C(=O)c1cc(Sc2cnc(NC(=O)C3CC3)s2)c(C)cc1OC] N-[5-[4-methoxy-2-methyl-5-[(1S,5R)-3-prop- fihenoyl-3,8-diazabicyclo[3.2.1]octane-8-carbonyl]phenyl]sulfanylthiazol-2-yl]cyclopropanecarboxamide | Compound 17 513.2 (M + H) | A |
| 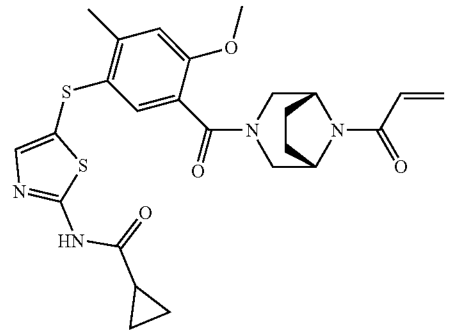 [SMILES: C=CC(=O)N1[C@@H]2CC[C@H]1CN(C(=O)c1cc(Sc3cnc(NC(=O)C4CC4)s3)c(C)cc1OC)C2] N-[5-[4-methoxy-2-methyl-5-[(1R,5S)-8-prop-2-enoyl-3,8-diazabicyclo[3.2.1]octane-3-carbonyl]phenyl]sulfanylthiazol-2-yl]cyclopropanecarboxamide | Compound 18 513.2 (M + H) | A |

TABLE 1-continued

| Final compounds (structures, names, masses and methods used for their synthesis) | | |
|---|---|---|
| Compound | MS (ES) m/z | Method Used |
| 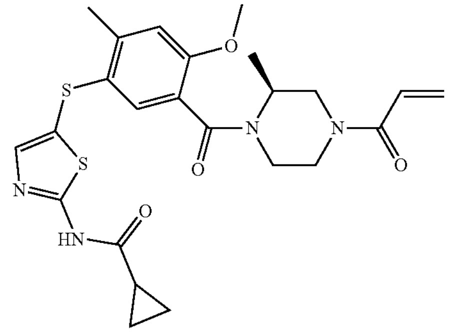 [SMILES: C=CC(=O)N1CCN(C(=O)c2cc(Sc3cnc(NC(=O)C4CC4)s3)c(C)cc2OC)[C@@H](C)C1] N-[5-[4-methoxy-2-methyl-5-[(2S)-2-methyl-4-prop-2-enoyl-piperazine-1-carbonyl]phenyl]sulfanylthiazol-2-yl]cyclopropanecarboxamide | Compound 19 501.0 (M + H) | A |
| 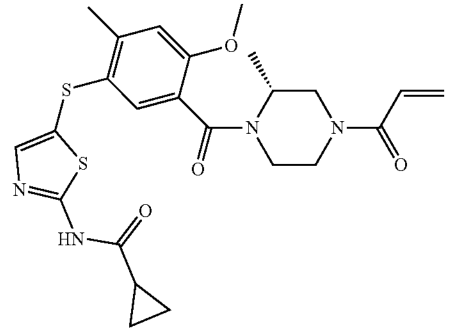 [SMILES: C=CC(=O)N1CCN(C(=O)c2cc(Sc3cnc(NC(=O)C4CC4)s3)c(C)cc2OC)[C@H](C)C1] N-[5-[4-methoxy-2-methyl-5-[(2R)-2-methyl-4-prop-2-enoyl-piperazine-1-carbonyl]phenyl]sulfanylthiazol-2-yl]cyclopropanecarboxamide | Compound 20 501.2 (M + H) | A |
| 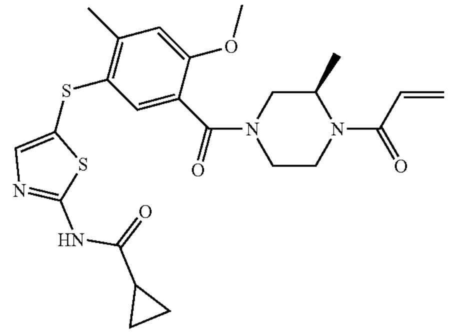 [SMILES: C=CC(=O)N1CCN(C(=O)c2cc(Sc3cnc(NC(=O)C4CC4)s3)c(C)cc2OC)C[C@H]1C] N-[5-[4-methoxy-2-methyl-5-[(3R)-3-methyl-4-prop-2-enoyl-piperazine-1-carbonyl]phenyl]sulfanylthiazol-2-yl]cyclopropanecarboxamide | Compound 21 501.2 (M + H) | A |

TABLE 1-continued

| Final compounds (structures, names, masses and methods used for their synthesis) | | |
|---|---|---|
| Compound | MS (ES) m/z | Method Used |
| 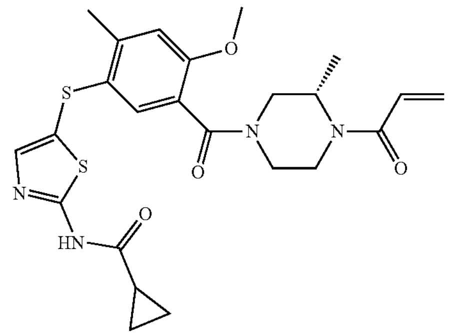 [SMILES: C=CC(=O)N1CCN(C(=O)c2cc(Sc3cnc(NC(=O)C4CC4)s3)c(C)cc2OC)C[C@@H]1C]<br>N-[5-[4-methoxy-2-methyl-5-[(3S)-3-methyl-4-prop-2-enoyl-piperazine-1-carbonyl]phenyl]sulfanylthiazol-2-yl]cyclopropanecarboxamide | Compound 22<br>501.0 (M + H) | A |
| 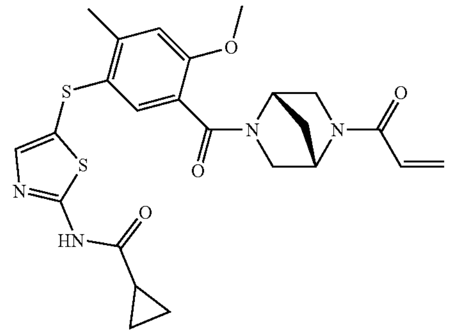 [SMILES: C=CC(=O)N1C[C@@H]2C[C@H]1CN2C(=O)c1cc(Sc2cnc(NC(=O)C3CC3)s2)c(C)cc1OC]<br>N-[5-[4-methoxy-2-methyl-5-[(1S,4S)-5-prop-2-enoyl-2,5-diazabicyclo[2.2.1]heptane-2-carbonyl]phenyl]sulfanylthiazol-2-yl]cyclopropanecarboxamide | Compound 23<br>499.1 (M + H) | A |
| 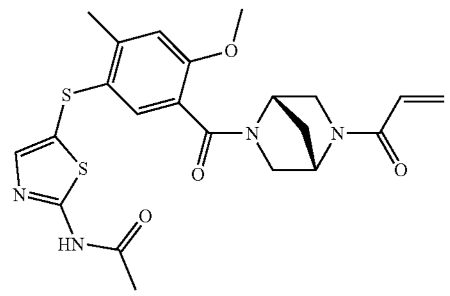 [SMILES: C=CC(=O)N1C[C@@H]2C[C@H]1CN2C(=O)c1cc(Sc2cnc(NC(C)=O)s2)c(C)cc1OC]<br>N-[5-[4-methoxy-2-methyl-5-[(1S,4S)-5-prop-2-enoyl-2,5-diazabicyclo[2.2.1]heptane-2-carbonyl]phenyl]sulfanylthiazol-2-yl]acetamide | Compound 24<br>473.1 (M + H) | A |

TABLE 1-continued

| Final compounds (structures, names, masses and methods used for their synthesis) | | |
|---|---|---|
| Compound | MS (ES) m/z | Method Used |
| 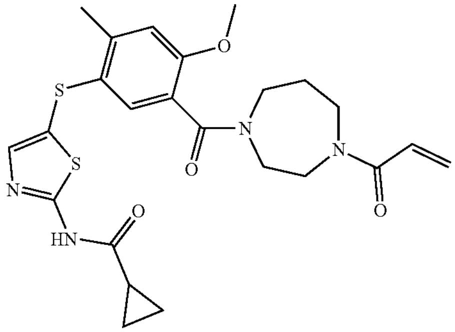 [SMILES: C=CC(=O)N1CCCN(C(=O)c2cc(Sc3cnc(NC(=O)C4CC4)s3)c(C)cc2OC)CC1] N-[5-[4-methoxy-2-methyl-5-(4-prop-2-enoyl-1,4-diazepane-1-carbonyl)phenyl]sulfanylthiazol-2-yl]cyclopropanecarboxamide | Compound 25 501.2 (M + H) | A |
| 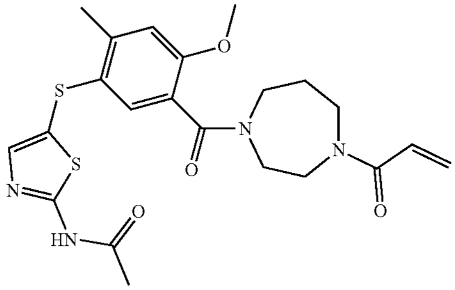 [SMILES: C=CC(=O)N1CCCN(C(=O)c2cc(Sc3cnc(NC(C)=O)s3)c(C)cc2OC)CC1] N-[5-[4-methoxy-2-methyl-5-(4-prop-2-enoyl-1,4-diazepane-1-carbonyl)phenyl]sulfanylthiazol-2-yl]acetamide | Compound 26 475.1 (M + H) | A |
| 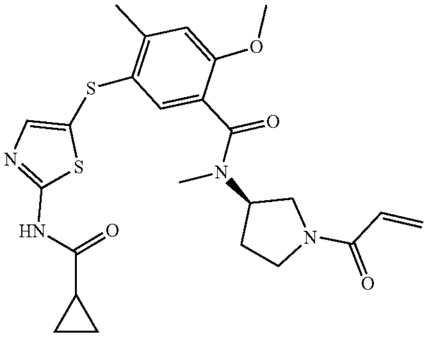 [SMILES: C=CC(=O)N1CC[C@@H](N(C)C(=O)c2cc(Sc3cnc(NC(=O)C4CC4)s3)c(C)cc2OC)C1] 5-[2-(cyclopropanecarbonylamino)thiazol-5-yl]sulfanyl-2-methoxy-N,4-dimethyl-N-[(3R)-1-prop-2-enoylpyrrolidin-3-yl]benzamide | Compound 27 501.2 (M + H) | A |

TABLE 1-continued

| Final compounds (structures, names, masses and methods used for their synthesis) | | |
|---|---|---|
| Compound | MS (ES) m/z | Method Used |
| 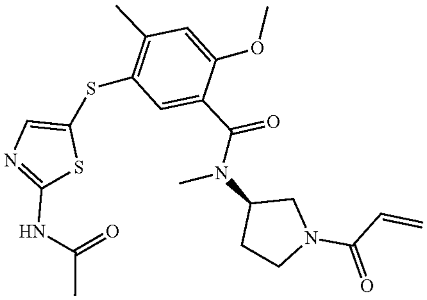 [SMILES: C=CC(=O)N1CC[C@@H](N(C)C(=O)c2cc(Sc3cnc(NC(C)=O)s3)c(C)cc2OC)C1] 5-(2-acetamidothiazol-5-yl)sulfanyl-2-methoxy-N,4-dimethyl-N-[(3R)-1-prop-2-enoylpyrrolidin-3-yl]benzamide | Compound 28 475.1 (M + H) | A |
| 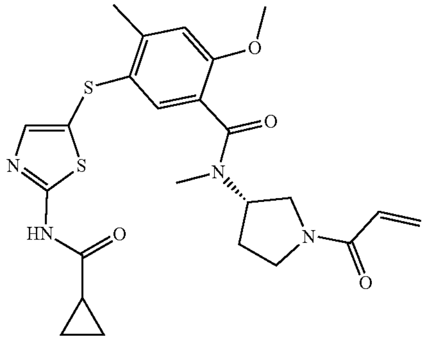 [SMILES: C=CC(=O)N1CC[C@H](N(C)C(=O)c2cc(Sc3cnc(NC(=O)C4CC4)s3)c(C)cc2OC)C1] 5-[2-(cyclopropanecarbonylamino)thiazol-5-yl]sulfanyl-2-methoxy-N,4-dimethyl-N-[(3S)-1-prop-2-enoylpyrrolidin-3-yl]benzamide | Compound 29 501.2 (M + H) | A |
| 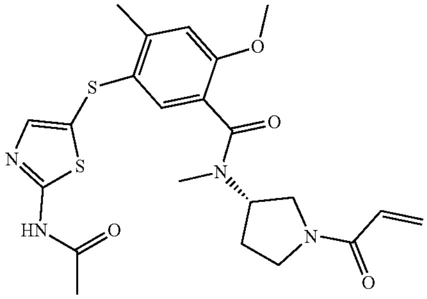 [SMILES: C=CC(=O)N1CC[C@H](N(C)C(=O)c2cc(Sc3cnc(NC(C)=O)s3)c(C)cc2OC)C1] 5-(2-acetamidothiazol-5-yl)sulfanyl-2-methoxy-N,4-dimethyl-N-[(3S)-1-prop-2-enoylpyrrolidin-3-yl]benzamide | Compound 30 475.1 (M + H) | A |

TABLE 1-continued

| Final compounds (structures, names, masses and methods used for their synthesis) | | |
|---|---|---|
| Compound | MS (ES) m/z | Method Used |
| 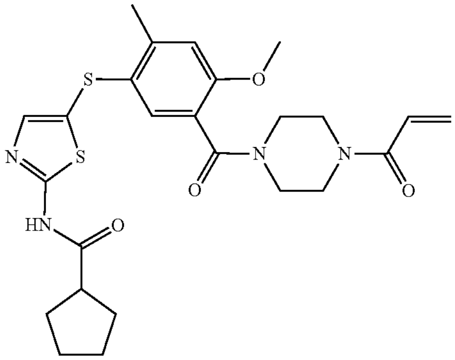 [SMILES: C=CC(=O)N1CCN(C(=O)c2cc(Sc3cnc(NC(=O)C4CCCC4)s3)c(C)cc2OC)CC1] N-[5-[4-methoxy-2-methyl-5-(4-prop-2-enoylpiperazine-1-carbonyl)phenyl]sulfanylthiazol-2-yl]cyclopentanecarboxamide | Compound 31 515.2 (M + H) | A |
| 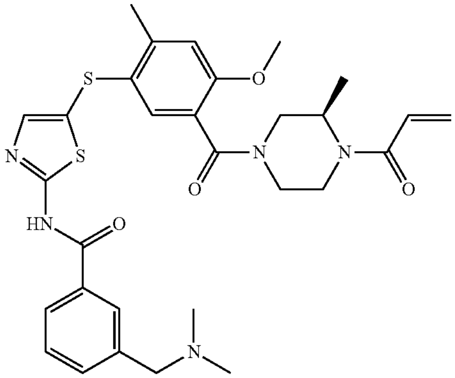 [SMILES: C=CC(=O)N1CCN(C(=O)c2cc(Sc3cnc(NC(=O)c4cccc(CN(C)C)c4)s3)c(C)cc2OC)C[C@H]1C] 3-[(dimethylamino)methyl]-N-[5-[4-methoxy-2-methyl-5-[(3R)-3-methyl-4-prop-2-enoyl-piperazine-1-carbonyl]phenyl]sulfanylthiazol-2-yl]benzamide | Compound 32 594.2 (M + H) | C |
| 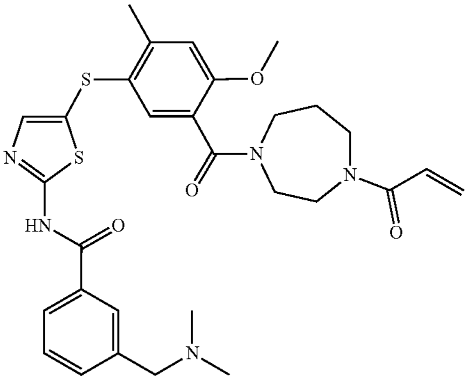 [SMILES: C=CC(=O)N1CCCN(C(=O)c2cc(Sc3cnc(NC(=O)c4cccc(CN(C)C)c4)s3)c(C)cc2OC)CC1] 3-[(dimethylamino)methyl]-N-[5-[4-methoxy-2-methyl-5-(4-prop-2-enoyl-1,4-diazepane-1-carbonyl)phenyl]sulfanylthiazol-2-yl]benzamide | Compound 33 594.2 (M + H) | C |

TABLE 1-continued

Final compounds (structures, names, masses and methods used for their synthesis)

| Compound | MS (ES) m/z | Method Used |
|---|---|---|
| 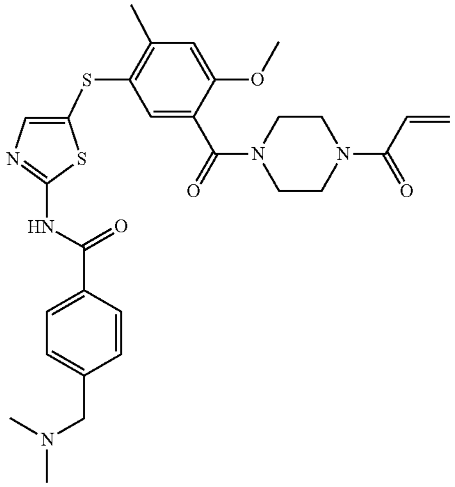 [SMILES: C=CC(=O)N1CCN(C(=O)c2cc(Sc3cnc(NC(=O)c4ccc(CN(C)C)cc4)s3)c(C)cc2OC)CC1]<br>4-[(dimethylamino)methyl]-N-[5-[4-methoxy-2-methyl-5-(4-prop-2-enoylpiperazine-1-carbonyl)phenyl]sulfanylthiazol-2-yl]benzamide | Compound 34<br>580.3 (M + H) | C |
| 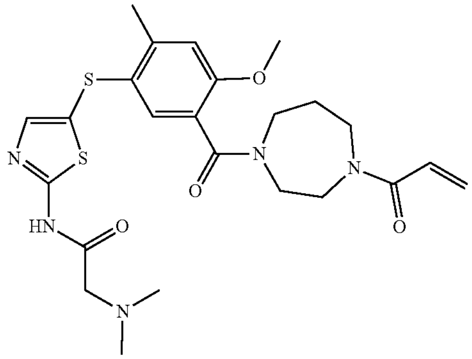 [SMILES: C=CC(=O)N1CCCN(C(=O)c2cc(Sc3cnc(NC(=O)CN(C)C)s3)c(C)cc2OC)CC1]<br>2-(dimethylamino)-N-[5-[4-methoxy-2-methyl-5-(4-prop-2-enoyl-1,4-diazepane-1-carbonyl)phenyl]sulfanylthiazol-2-yl]acetamide | Compound 35<br>518.2 (M + H) | C |
| 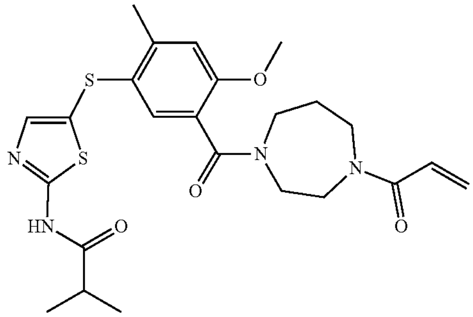 [SMILES: C=CC(=O)N1CCCN(C(=O)c2cc(Sc3cnc(NC(=O)C(C)C)s3)c(C)cc2OC)CC1]<br>N-[5-[4-methoxy-2-methyl-5-(4-prop-2-enoyl-1,4-diazepane-1-carbonyl)phenyl]sulfanylthiazol-2-yl]-2-methyl-propanamide | Compound 36<br>503.1 (M + H) | A |

TABLE 1-continued

| Final compounds (structures, names, masses and methods used for their synthesis) | | |
|---|---|---|
| Compound | MS (ES) m/z | Method Used |
| 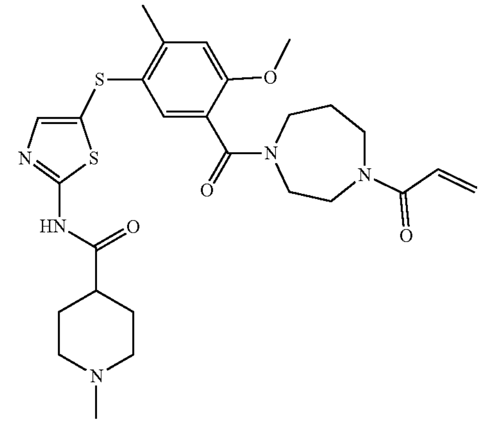 [SMILES: C=CC(=O)N1CCCN(C(=O)c2cc(Sc3cnc(NC(=O)C4CCN(C)CC4)s3)c(C)cc2OC)CC1]<br>N-[5-[4-methoxy-2-methyl-5-(4-prop-2-enoyl-1,4-diazepane-1-carbonyl)phenyl]sulfanylthiazol-2-yl]-1-methyl-piperidine-4-carboxamide | Compound 37<br>558.2 (M + H) | C |
| 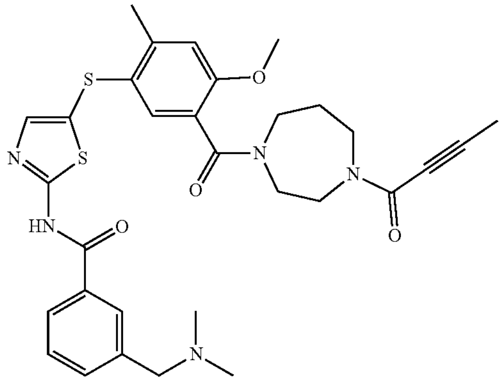 [SMILES: CC#CC(=O)N1CCCN(C(=O)c2cc(Sc3cnc(NC(=O)c4cccc(CN(C)C)c4)s3)c(C)cc2OC)CC1]<br>N-[5-[5-(4-but-2-ynoyl-1,4-diazepane-1-carbonyl)-4-methoxy-2-methyl-phenyl]sulfanylthiazol-2-yl]-3-[(dimethylamino)methyl]benzamide | Compound 38<br>606.2 (M + H) | B/C |
| 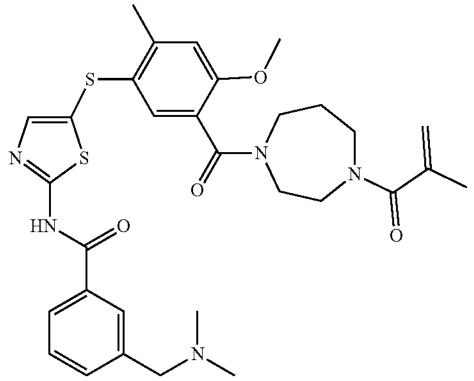 [SMILES: C=C(C)C(=O)N1CCCN(C(=O)c2cc(Sc3cnc(NC(=O)c4cccc(CN(C)C)c4)s3)c(C)cc2OC)CC1]<br>3-[(dimethylamino)methyl]-N-[5-[4-methoxy-2-methyl-5-[4-(2-methylprop-2-enoyl)-1,4-diazepane-1-carbonyl]phenyl]sulfanylthiazol-2-yl]benzamide | Compound 39<br>608.3 (M + H) | C |

TABLE 1-continued

| Final compounds (structures, names, masses and methods used for their synthesis) | | |
|---|---|---|
| Compound | MS (ES) m/z | Method Used |
| 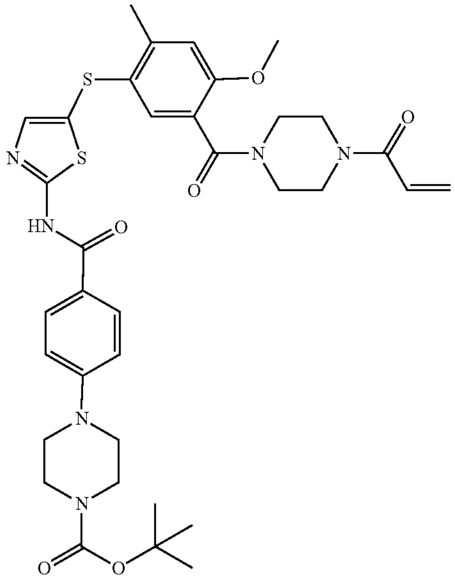 [SMILES: C=CC(=O)N1CCN(C(=O)c2cc(Sc3cnc(NC(=O)c4ccc(N5CCN(C(=O)OC(C)(C)C)CC5)cc4)s3)c(C)cc2OC)CC1] tert-butyl 4-[4-[[5-[4-methoxy-2-methyl-5-(4-prop-2-enoylpiperazine-1-carbonyl)phenyl]sulfanylthiazol-2-yl]carbamoyl]phenyl]piperazine-1-carboxylate | Compound 40 707.3 (M + H) | E |
| 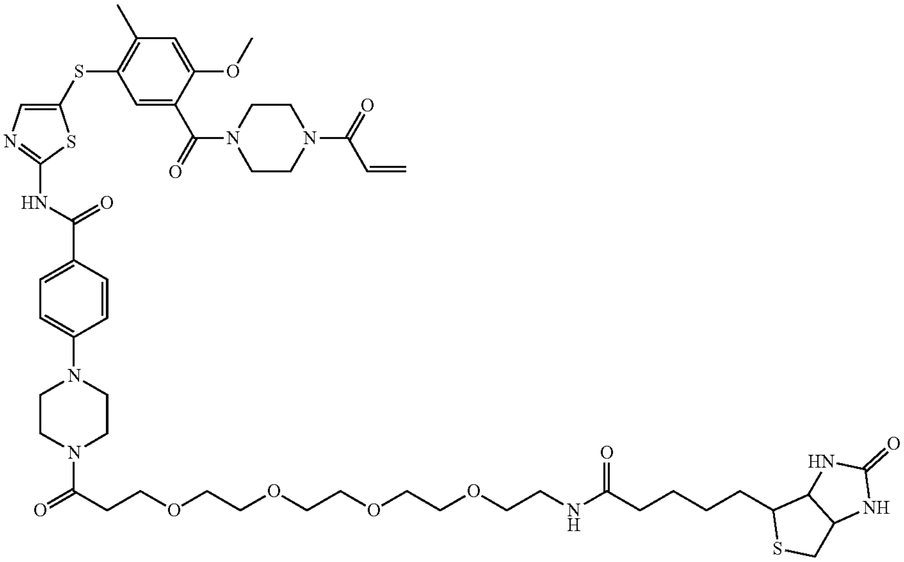 N-[5-[4-methoxy-2-methyl-5-(4-prop-2-enoylpiperazine-1-carbonyl)phenyl]sulfanylthiazol-2-yl]-4-[4-[3-[2-[2-[2-[5-(2-oxo-1,3,3a,4,6,6a-hexahydrothieno[3,4-d]imidazol-4-yl)pentanoylamino]ethoxy]erhoxy]ethoxy]propanoyl]piperazin-1-yl]benzamide | Compound 41 1081.4 (M + H) | E |

TABLE 1-continued

| Final compounds (structures, names, masses and methods used for their synthesis) | | |
|---|---|---|
| Compound | MS (ES) m/z | Method Used |
| 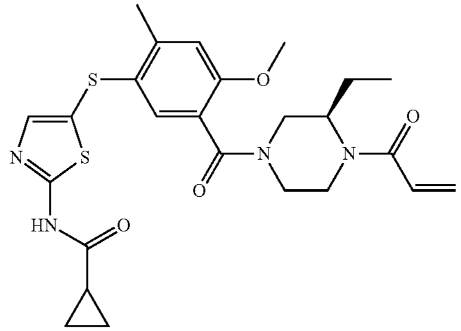 [SMILES: C=CC(=O)N1CCN(C(=O)c2cc(Sc3cnc(NC(=O)C4CC4)s3)c(C)cc2OC)C[C@H]1CC]<br>N-[5-[5-[(3R)-3-ethyl-4-prop-2-enoyl-piperazine-1-carbonyl]-4-methoxy-2-methyl-phenyl]sulfanylthiazol-2-yl]cyclopropanecarboxamide | Compound 42<br>515.2 (M + H) | A |
| 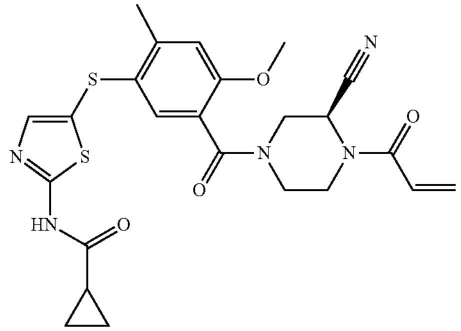 [SMILES: C=CC(=O)N1CCN(C(=O)c2cc(Sc3cnc(NC(=O)C4CC4)s3)c(C)cc2OC)C[C@H]1C#N]<br>N-[5-[5-[(3S)-3-cyano-4-prop-2-enoyl-piperazine-1-carbonyl]-4-methoxy-2-methyl-phenyl]sulfanylthiazol-2-yl]cyclopropanecarboxamide | Compound 43<br>512.2 (M + H) | A |
| 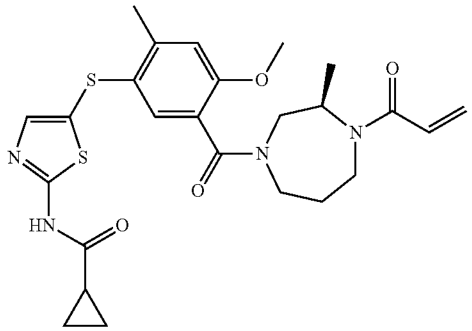 [SMILES: C=CC(=O)N1CCCN(C(=O)c2cc(Sc3cnc(NC(=O)C4CC4)s3)c(C)cc2OC)C[C@H]1C]<br>N-[5-[4-methoxy-2-methyl-5-[(3R)-3-methyl-4-prop-2-enoyl-1,4-diazepane-1-carbonyl]phenyl]sulfanylthiazol-2-yl]cyclopropanecarboxamide | Compound 44<br>515.2 (M + H) | A |

TABLE 1-continued

| Final compounds (structures, names, masses and methods used for their synthesis) | | |
|---|---|---|
| Compound | MS (ES) m/z | Method Used |
| 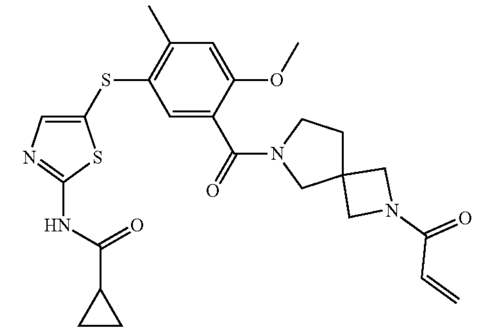 [SMILES: C=CC(=O)N1CC2(CCN(C(=O)c3cc(Sc4cnc(NC(=O)C5CC5)s4)c(C)cc3OC)C2)C1] N-[5-[4-methoxy-2-methyl-5-(2-prop-2-enoyl-2,7-diazaspiro[3.4]octane-7-carbonyl)phenyl]sulfanylthiazol-2-yl]cyclopropanecarboxamide | Compound 45 513.2 (M + H) | A |
| 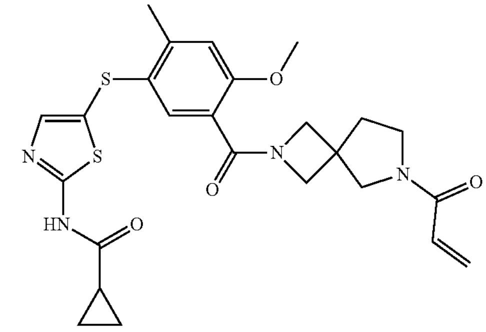 [SMILES: C=CC(=O)N1CCC2(C1)CN(C(=O)c1cc(Sc3cnc(NC(=O)C4CC4)s3)c(C)cc1OC)C2] N-[5-[4-methoxy-2-methyl-5-(7-prop-2-enoyl-2,7-diazaspiro[3.4]octane-2-carbonyl)phenyl]sulfanylthiazol-2-yl]cyclopropanecarboxamide | Compound 46 513.0 (M + H) | A |
| 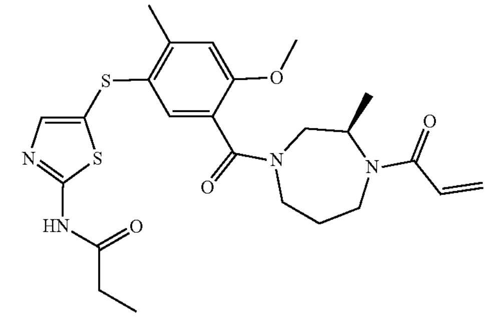 [SMILES: C=CC(=O)N1CCCN(C(=O)c2cc(Sc3cnc(NC(=O)CC)s3)c(C)cc2OC)C[C@H]1C] N-[5-[4-methoxy-2-methyl-5-[(3R)-3-methyl-4-prop-2-enoyl-1,4-diazepane-1-carbonyl]phenyl]sulfanylthiazol-2-yl]propanamide | Compound 47 503.1 (M + H) | A |

TABLE 1-continued

| Final compounds (structures, names, masses and methods used for their synthesis) | | |
|---|---|---|
| Compound | MS (ES) m/z | Method Used |
| 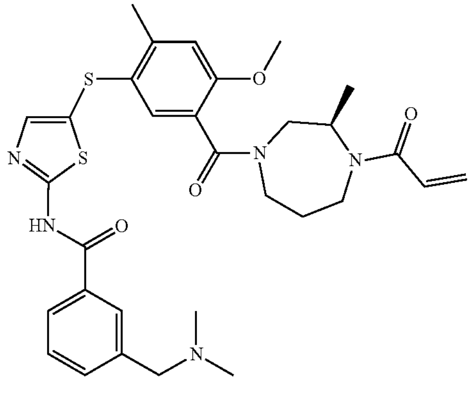 [SMILES: C=CC(=O)N1CCCN(C(=O)c2cc(Sc3cnc(NC(=O)c4cccc(CN(C)C)c4)s3)c(C)cc2OC)C[C@H]1C] 3-[(dimethylamino)methyl]-N-[5-[4-methoxy-2-methyl-5-[(3R)-3-methyl-4-prop-2-enoyl-1,4-diazepane-1-carbonyl]phenyl]sulfanylthiazol-2-yl]benzamide | Compound 48 608.3 (M + H) | C |
| 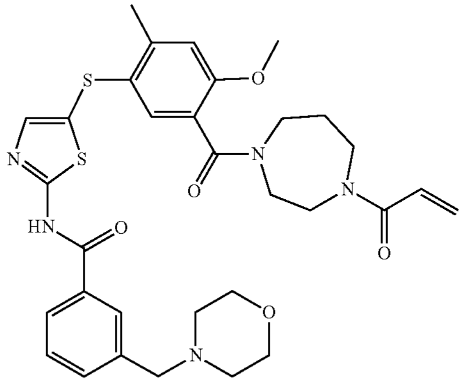 [SMILES: C=CC(=O)N1CCCN(C(=O)c2cc(Sc3cnc(NC(=O)c4cccc(CN5CCOCC5)c4)s3)c(C)cc2OC)CC1] N-[5-[4-methoxy-2-methyl-5-(4-prop-2-enoyl-1,4-diazepane-1-carbonyl)phenyl]sulfanylthiazol-2-yl]-3-(morpholinomethyl)benzamide | Compound 49 636.2 (M + H) | C |
| 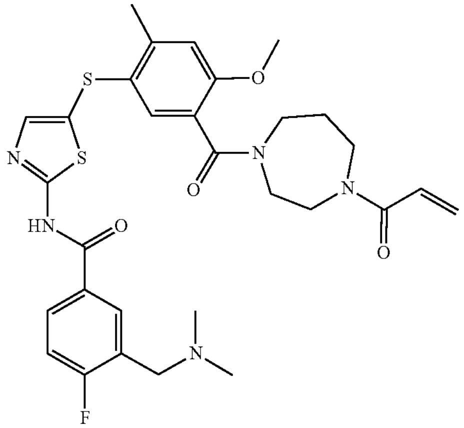 [SMILES: C=CC(=O)N1CCCN(C(=O)c2cc(Sc3cnc(NC(=O)c4ccc(F)c(CN(C)C)c4)s3)c(C)cc2OC)CC1] 3-[(dimethylamino)methyl]-4-fluoro-N-[5-[4-methoxy-2-methyl-5-(4-prop-2-enoyl-1,4-diazepane-1-carbonyl)phenyl]sulfanylthiazol-2-yl]benzamide | Compound 50 612.2 (M + H) | C |

TABLE 1-continued

| Final compounds (structures, names, masses and methods used for their synthesis) | | |
|---|---|---|
| Compound | MS (ES) m/z | Method Used |
| 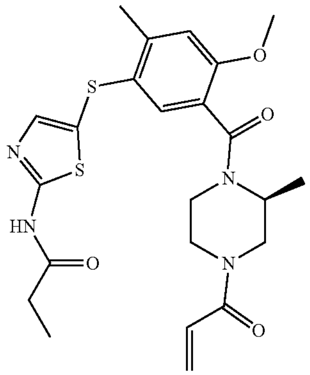 [SMILES: C=CC(=O)N1CCN(C(=O)c2cc(Sc3cnc(NC(=O)CC)s3)c(C)cc2OC)[C@@H](C)C1] N-[5-[4-methoxy-2-methyl-5-[(2S)-2-methyl-4-prop-2-enoyl-piperazine-1-carbonyl]phenyl]sulfanylthiazol-2-yl]propanamide | Compound 51 489.2 (M + H) | A |
| 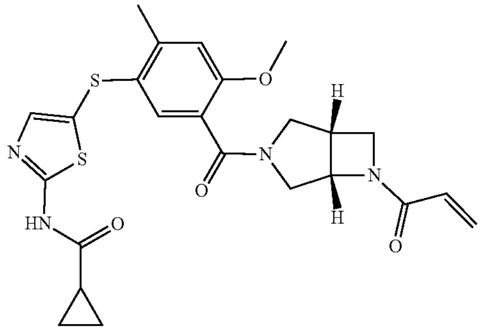 [SMILES: C=CC(=O)N1C[C@H]2CN(C(=O)c3cc(Sc4cnc(NC(=O)C5CC5)s4)c(C)cc3OC)C[C@H]21] N-[5-[4-methoxy-2-methyl-5-[(IR,5S)-6-prop-2-enoyl-3,6-diazabicyclo[3.2.0]heptane-3-carbonyl]phenyl]sulfanylthiazol-2-yl]cyclopropanecarboxamide | Compound 52 498.3 (M + H) | A |
| 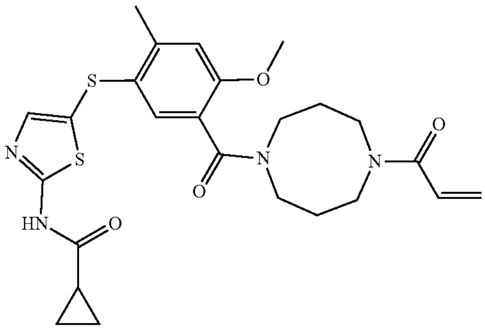 [SMILES: C=CC(=O)N1CCCN(C(=O)c2cc(Sc3cnc(NC(=O)C4CC4)s3)c(C)cc2OC)CCC1] N-[5-[4-methoxy-2-methyl-5-(5-prop-2-enoyl-1,5-diazocane-1-carbonyl)phenyl]sulfanylthiazol-2-yl]cyclopropanecarboxamide | Compound 53 515.2 (M + H) | A |

TABLE 1-continued

| Final compounds (structures, names, masses and methods used for their synthesis) | | |
|---|---|---|
| Compound | MS (ES) m/z | Method Used |
| 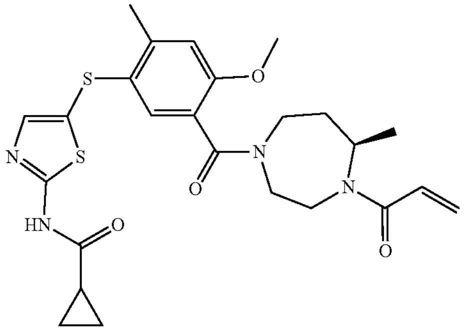 [SMILES: C=CC(=O)N1CCN(C(=O)c2cc(Sc3cnc(NC(=O)C4CC4)s3)c(C)cc2OC)CC[C@H]1C]<br>N-[5-[4-methoxy-2-methyl-5-[(5R)-5-methyl-4-prop-2-enoyl-1,4-diazepane-1-carbonyl]phenyl]sulfanylthiazol-2-yl]cyclopropanecarboxamide | Compound 54<br>515.2 (M + H) | A |
| 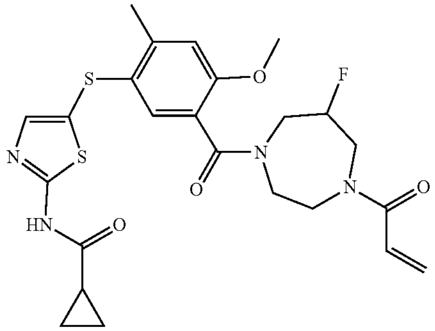 [SMILES: C=CC(=O)N1CCN(C(=O)c2cc(Sc3cnc(NC(=O)C4CC4)s3)c(C)cc2OC)CC(F)C1]<br>N-[5-[5-(6-fluoro-4-prop-2-enoyl-1,4-diazepane-1-carbonyl)-4-methoxy-2-methyl-phenyl]sulfanylthiazol-2-yl]cyclopropanecarboxamide | Compound 55<br>519.2 (M + H) | A |
| 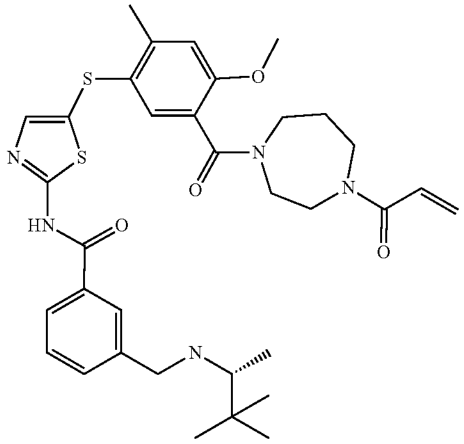<br>N-[5-[4-methoxy-2-methyl-5-(4-prop-2-enoyl-1,4-diazepane-1-carbonyl)phenyl]sulfanylthiazol-2-yl]-3-[[[(1R)-1,2,2-trimethylpropyl]amino]methyl]benzamide | Compound 56<br>650.3 (M + H) | C |

TABLE 1-continued

| Final compounds (structures, names, masses and methods used for their synthesis) | | |
|---|---|---|
| Compound | MS (ES) m/z | Method Used |
| 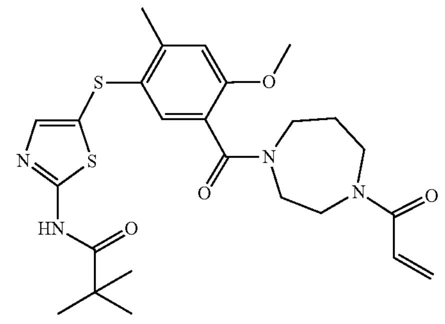 [SMILES: C=CC(=O)N1CCCN(C(=O)c2cc(Sc3cnc(NC(=O)C(C)(C)C)s3)c(C)cc2OC)CC1]<br>N-[5-[4-methoxy-2-methyl-5-(4-prop-2-enoyl-1,4-diazepane-1-carbonyl)phenyl]sulfanylthiazol-2-yl]-2.2-dimethyl-propanamide | Compound 57<br>517.3 (M + H) | A |
| 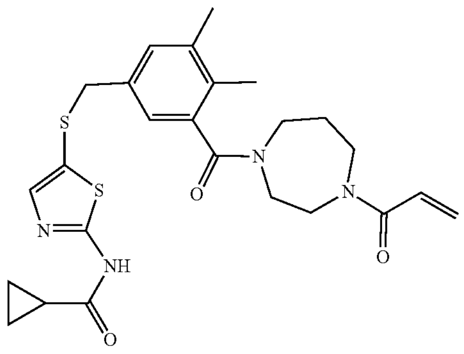 [SMILES: C=CC(=O)N1CCCN(C(=O)c2cc(CSc3cnc(NC(=O)C4CC4)s3)cc(C)c2C)CC1]<br>N-[5-[[3,4-dimethyl-5-(4-prop-2-enoyl-1,4-diazepane-1-carbonyl)phenyl]methylsulfanyl]thiazol-2-yl]cyclopropanecarboxamide | Compound 58<br>499.1 (M + H) | A/H |
| 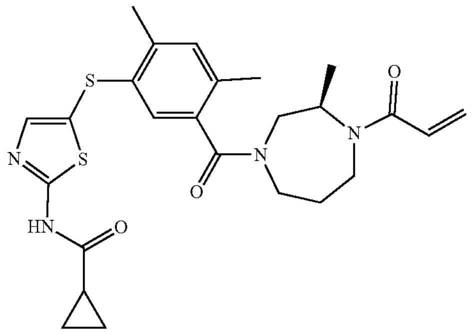 [SMILES: C=CC(=O)N1CCCN(C(=O)c2cc(Sc3cnc(NC(=O)C4CC4)s3)c(C)cc2C)C[C@H]1C]<br>N-[5-[2,4-dimethyl-5-[(3R)-3-methyl-4-prop-2-enoyl-1,4-diazepane-1-carbonyl]phenyl]sulfanylthiazol-2-yl]cyclopropanecarboxamide | Compound 59<br>499.3 (M + H) | A/F |

TABLE 1-continued

| Final compounds (structures, names, masses and methods used for their synthesis) | | |
|---|---|---|
| Compound | MS (ES) m/z | Method Used |
| 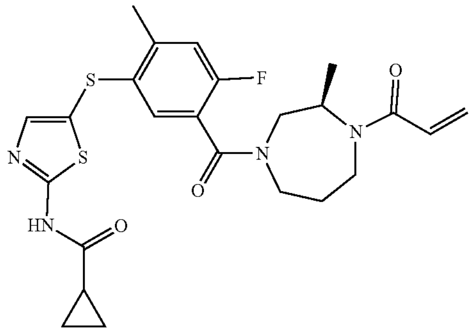 [SMILES: C=CC(=O)N1CCCN(C(=O)c2cc(Sc3cnc(NC(=O)C4CC4)s3)c(C)cc2F)C[C@H]1C] N-[5-[4-fluoro-2-methyl-5-[(3R)-3-methyl-4-prop-2-enoyl-1,4-diazepane-1-carbonyl]phenyl]sulfanylthiazol-2-yl]cyclopropanecarboxamide | Compound 60 503.1 (M + H) | A/F |
| 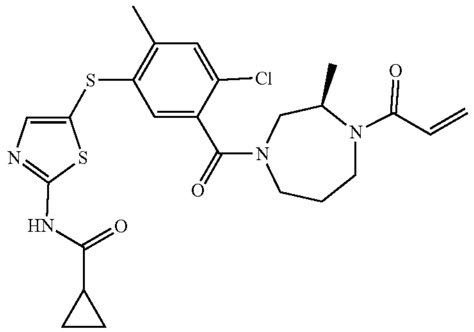 N-[5-[4-chloro-2-methyl-5-[(3R)-3-methyl-4-prop-2-enoyl-1,4-diazepane-1-carbonyl]phenyl]sulfanylthiazol-2-yl]cyclopropanecarboxamide | Compound 61 519.0 (M) | A/F |
| 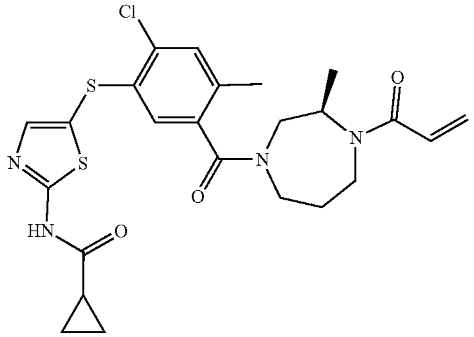 [SMILES: C=CC(=O)N1CCCN(C(=O)c2cc(Sc3cnc(NC(=O)C4CC4)s3)c(Cl)cc2C)C[C@H]1C] N-[5-[2-chloro-4-methyl-5-[(3R)-3-methyl-4-prop-2-enoyl-1,4-diazepane-1-carbonyl]phenyl]sulfanylthiazol-2-yl]cyclopropanecarboxamide | Compound 62 519.0 (M) | A/F |

TABLE 1-continued

| Final compounds (structures, names, masses and methods used for their synthesis) | | |
|---|---|---|
| Compound | MS (ES) m/z | Method Used |
| 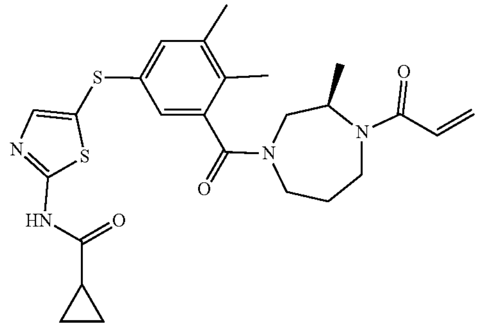 [SMILES: C=CC(=O)N1CCCN(C(=O)c2cc(Sc3cnc(NC(=O)C4CC4)s3)cc(C)c2C)C[C@H]1C] N-[5-[3,4-dimethyl-5-[(3R)-3-methyl-4-prop-2-enoyl-1,4-diazepane-1-carbonyl]phenyl]sulfanylthiazol-2-yl]cyclopropanecarboxamide | Compound 63 499.1 (M + H) | A/F |
| 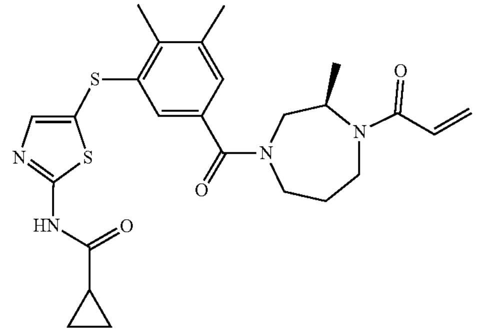 [SMILES: C=CC(=O)N1CCCN(C(=O)c2cc(C)c(C)c(Sc3cnc(NC(=O)C4CC4)s3)c2)C[C@H]1C] N-[5-[2,3-dimethyl-5-[(3R)-3-methyl-4-prop-2-enoyl-1,4-diazepane-1-carbonyl]phenyl]sulfanylthiazol-2-yl]cyclopropanecarboxamide | Compound 64 499.1 (M + H) | A/F |
| 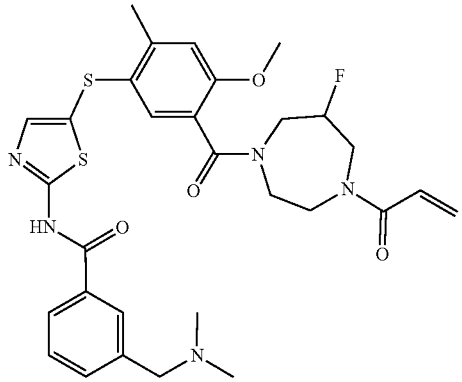 [SMILES: C=CC(=O)N1CCN(C(=O)c2cc(Sc3cnc(NC(=O)c4cccc(CN(C)C)c4)s3)c(C)cc2OC)CC(F)C1] 3-[(dimethylamino)methyl]-N-[5-[5-(6-fluoro-4-prop-2-enoyl-1,4-diazepane-1-carbonyl)-4-methoxy-2-methyl-phenyl]sulfanylthiazol-2-yl]benzamide | Compound 66 612.2 (M + H) | C |

TABLE 1-continued

| Final compounds (structures, names, masses and methods used for their synthesis) | | |
|---|---|---|
| Compound | MS (ES) m/z | Method Used |
| 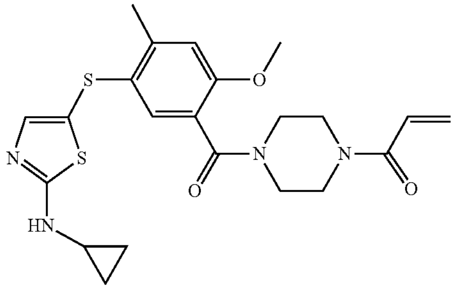 [SMILES: C=CC(=O)N1CCN(C(=O)c2cc(Sc3cnc(NC4CC4)s3)c(C)cc2OC)CC1]<br>1-[4-[5-[2-(cyclopropylamino)thiazol-5-yl]sulfanyl-2-mthoxy-4-methyl-benzoyl]piperazin-1-yl]prop-2-en-1-one | Compound 67<br>459.2 (M + H) | A |
| 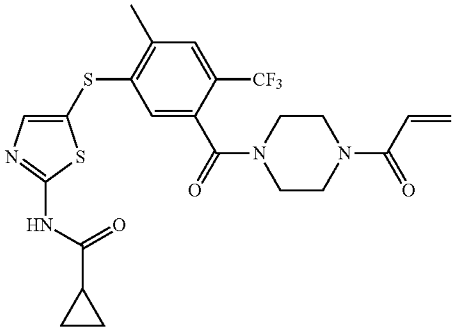<br>N-[5-[2-methyl-5-(4-prop-2-enoylpiperazine-1-carbonyl)-4-(trifluoromethyl)phenyl]sulfanylthiazol-2-yl]cyclopropanecarboxamide | Compound 68<br>525.0 (M + H) | A/F |
| 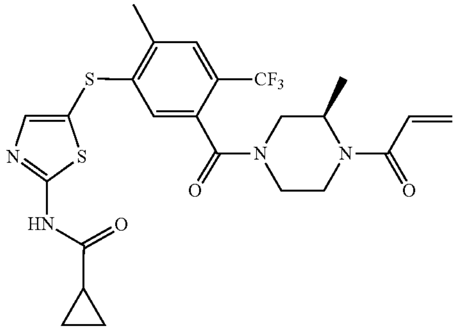<br>N-[5-[2-methyl-5-[(3R)-3-methyl-4-prop-2-enoyl-piperazine-1-carbonyl]-4-(trifluoromethyl)phenyl]sulfanylthiazol-2-yl]cyclopropanecarboxamide | Compound 69<br>539.2 (M + H) | A/F |

TABLE 1-continued

| Final compounds (structures, names, masses and methods used for their synthesis) | | |
|---|---|---|
| Compound | MS (ES) m/z | Method Used |
| 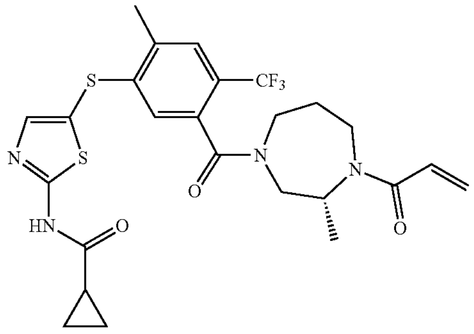 [SMILES: C=CC(=O)N1CCCN(C(=O)c2cc(Sc3cnc(NC(=O)C4CC4)s3)c(C)cc2C(F)(F)F)C[C@H]1C] N-[5-[2-methyl-5-[(3R)-3-methyl-4-prop-2-enoyl-1,4-diazepane-1-carbonyl]-4-(trifluoromethyl)phenyl]sulfanylthiazol-2-yl]cyclopropanecarboxamide | Compound 70 553.1 (M + H) | A/F |
| 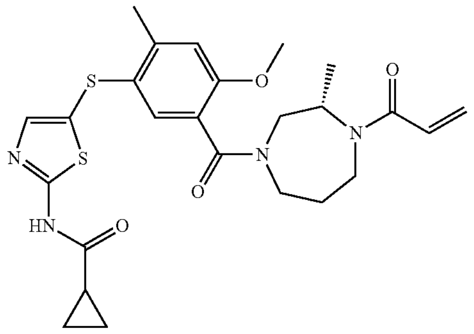 [SMILES: C=CC(=O)N1CCCN(C(=O)c2cc(Sc3cnc(NC(=O)C4CC4)s3)c(C)cc2OC)C[C@@H]1C] N-[5-[4-methoxy-2-methyl-5-[(3S)-3-methyl-4-prop-2-enoyl-1,4-diazepane-1-carbonyl]phenyl]sulfanylthiazol-2-yl]cyclopropanecarboxamide | Compound 71 515.2 (M + H) | A |
| 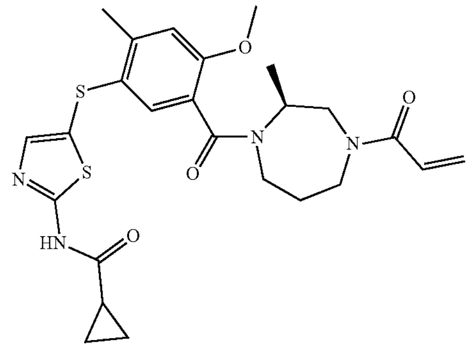 [SMILES: C=CC(=O)N1CCCN(C(=O)c2cc(Sc3cnc(NC(=O)C4CC4)s3)c(C)cc2OC)[C@@H](C)C1] N-[5-[4-methoxy-2-methyl-5-[(2S)-2-methyl-4-prop-2-enoyl-1,4-diazepane-1-carbonyl]phenyl]sulfanylthiazol-2-yl]cyclopropanecarboxamide | Compound 72 515.2 (M + H) | A |

TABLE 1-continued

| Final compounds (structures, names, masses and methods used for their synthesis) | | |
|---|---|---|
| Compound | MS (ES) m/z | Method Used |
| 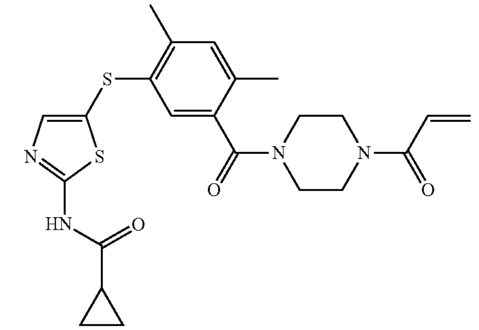 [SMILES: C=CC(=O)N1CCN(C(=O)c2cc(Sc3cnc(NC(=O)C4CC4)s3)c(C)cc2C)CC1] N-[5-[2,4-dimethyl-5-(4-prop-2-enoylpiperazine-1-carbonyl)phenyl]sulfanylthiazol-2-yl]cyclopropanecarboxamide | Compound 73 471.0 (M + H) | A/F |
| 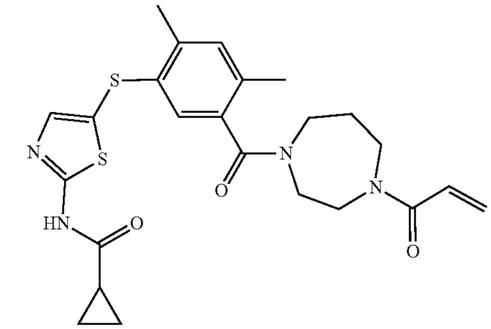 [SMILES: C=CC(=O)N1CCCN(C(=O)c2cc(Sc3cnc(NC(=O)C4CC4)s3)c(C)cc2C)CC1] N-[5-[2,4-dimethyl-5-(4-prop-2-enoyl-1,4-diazepane-1-carbonyl)phenyl]sulfanylthiazol-2-yl]cyclopropanecarboxamide | Compound 74 485.1 (M + H) | A/F |
| 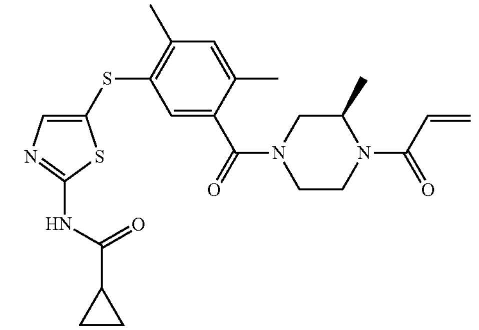 [SMILES: C=CC(=O)N1CCN(C(=O)c2cc(Sc3cnc(NC(=O)C4CC4)s3)c(C)cc2C)C[C@H]1C] N-[5-[2,4-dimethyl-5-[(3R)-3-methyl-4-prop-2-enoyl-piperazine-1-carbonyl]phenyl]sulfanylthiazol-2-yl]cyclopropanecarboxamide | Compound 75 485.1 (M + H) | A/F |

TABLE 1-continued

| Final compounds (structures, names, masses and methods used for their synthesis) | | |
|---|---|---|
| Compound | MS (ES) m/z | Method Used |
| 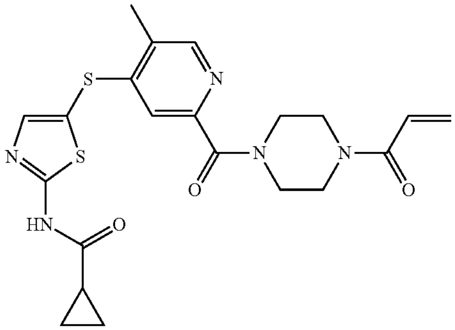 [SMILES: C=CC(=O)N1CCN(C(=O)c2cc(Sc3cnc(NC(=O)C4CC4)s3)c(C)cn2)CC1] N-[5-[5-methyl-2-(4-prop-2-enoylpiperazine-1-carbonyl)-4-pyridyl]sulfanyl]thiazol-2-yl]cyclopropanecarboxamide | Compound 76 458.1 (M + H) | A/G |
| 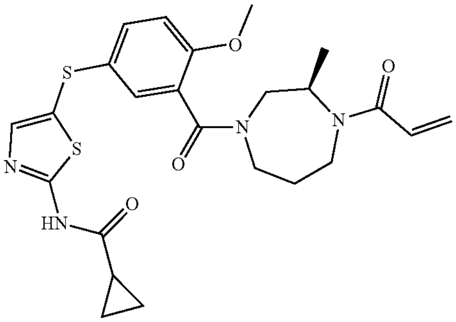 [SMILES: C=CC(=O)N1CCCN(C(=O)c2cc(Sc3cnc(NC(=O)C4CC4)s3)ccc2OC)C[C@H]1C] N-[5-[4-methoxy-3-[(3R)-3-methyl-4-prop-2-enoyl-1,4-diazepane-1-carbonyl]phenyl]sulfanylthiazol-2-yl]cyclopropanecarboxamide | Compound 77 501.2 (M + H) | A/J |
| 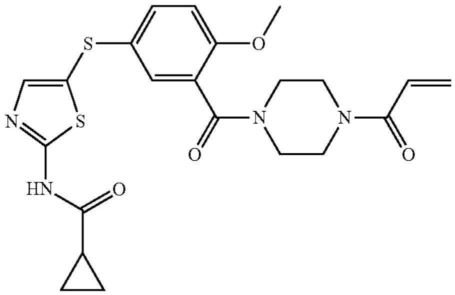 [SMILES: C=CC(=O)N1CCN(C(=O)c2cc(Sc3cnc(NC(=O)C4CC4)s3)ccc2OC)CC1] N-[5-[4-methoxy-3-(4-prop-2-enoylpiperazine-1-carbonyl)phenyl]sulfanylthiazol-2-yl]cyclopropanecarboxamide | Compound 78 473.1 (M + H) | A/J |

TABLE 1-continued

| Compound | MS (ES) m/z | Method Used |
|---|---|---|
| Final compounds (structures, names, masses and methods used for their synthesis) | | |
| 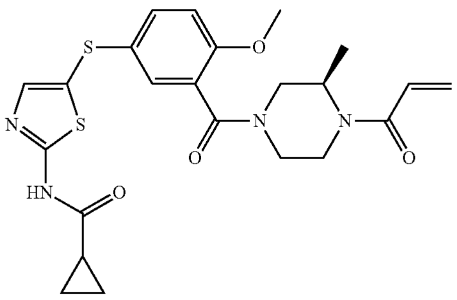 [SMILES: C=CC(=O)N1CCN(C(=O)c2cc(Sc3cnc(NC(=O)C4CC4)s3)ccc2OC)C[C@H]1C] N-[5-[4-methoxy-3-[(3R)-3-methyl-4-prop-2-enoyl-piperazine-1-carbonyl]phenyl]sulfanylthiazol-2-yl]cyclopropanecarboxamide | Compound 79 487.1 (M + H) | A/J |
| 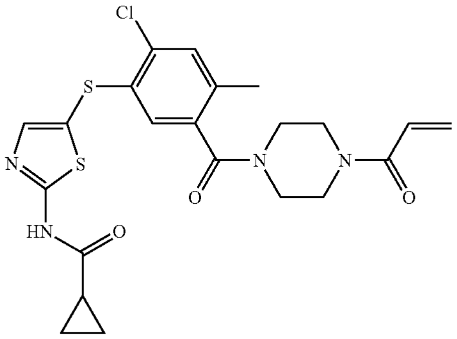 [SMILES: C=CC(=O)N1CCN(C(=O)c2cc(Sc3cnc(NC(=O)C4CC4)s3)c(Cl)cc2C)CC1] N-[5-[2-chloro-4-methyl-5-(4-prop-2-enoylpiperazine-1-carbonyl)phenyl]sulfanylthiazol-2-yl]cyclopropanecarboxamide | Compound 80 491.1 (M + H) | A/F |
| 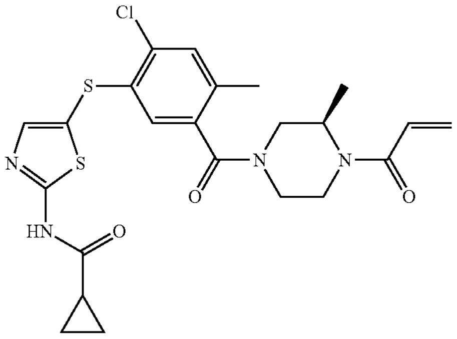 N-[5-[2-chloro-4-methyl-5-[(3R)-3-methyl-4-prop-2-enoyl-piperazine-1-carbonyl]phenyl]sulfanylthiazol-2-yl]cyclopropanecarboxamide | Compound 81 505.1 (M + H) | A/F |

TABLE 1-continued

| Final compounds (structures, names, masses and methods used for their synthesis) | | |
|---|---|---|
| Compound | MS (ES) m/z | Method Used |
| 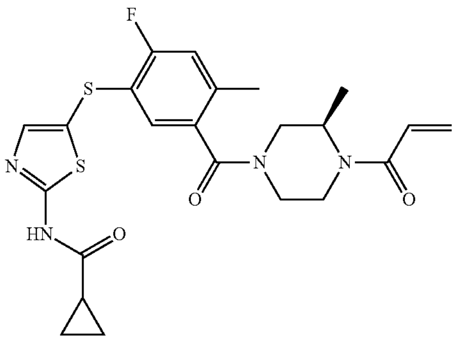 N-[5-[2-fluoro-4-methyl-5-[(3R)-3-methyl-4-prop-2-enoyl-piperazine-1-carbonyl]phenyl]sulfanylthiazol-2-yl]cyclopropanecarboxamide | Compound 82 489.2 (M + H) | A/F |
| 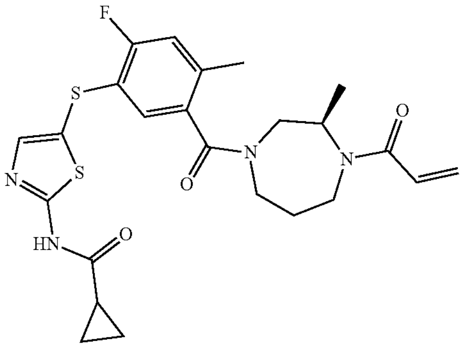 [SMILES: C=CC(=O)N1CCCN(C(=O)c2cc(Sc3cnc(NC(=O)C4CC4)s3)c(F)cc2C)C[C@H]1C] N-[5-[2-fluoro-4-methyl-5-[(3R)-3-methyl-4-prop-2-enoyl-1,4-diazepane-1-carbonyl]phenyl]sulfanylthiazol-2-yl]cyclopropanecarboxamide | Compound 83 503.1 (M + H) | A/F |
| 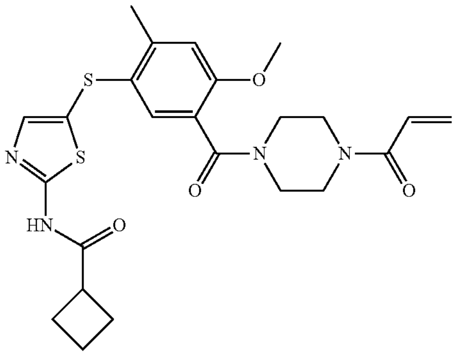 [SMILES: C=CC(=O)N1CCN(C(=O)c2cc(Sc3cnc(NC(=O)C4CCC4)s3)c(C)cc2OC)CC1] N-[5-[4-methoxy-2-methyl-5-(4-prop-2-enoylpiperazine-1-carbonyl)phenyl]sulfanylthiazol-2-yl]cyclobutanecarboxamide | Compound 84 501.2 (M + H) | A |

TABLE 1-continued

| Final compounds (structures, names, masses and methods used for their synthesis) | | |
|---|---|---|
| Compound | MS (ES) m/z | Method Used |
| 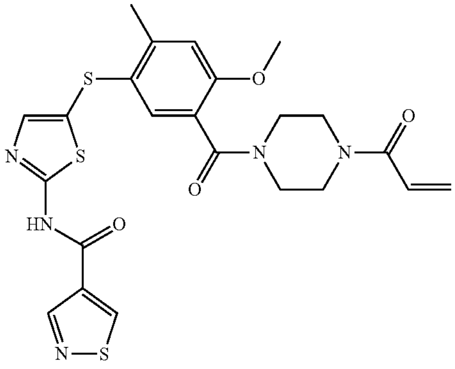 [SMILES: C=CC(=O)N1CCN(C(=O)c2cc(Sc3cnc(NC(=O)c4cnsc4)s3)c(C)cc2OC)CC1] N-[5-[4-methoxy-2-methyl-5-(4-prop-2-enoylpiperazine-1-callhonyl)phenyl]sulfanylthiazol-2-yl]isothiazole-4-carboxamide | Compound 85 530.0 (M + H) | C |
| 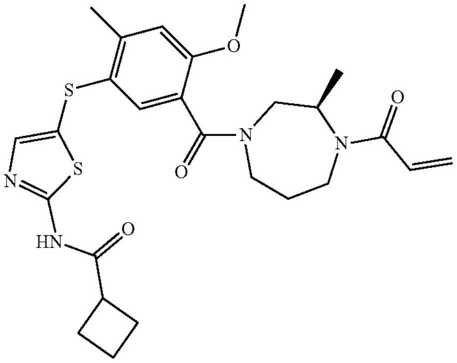 [SMILES: C=CC(=O)N1CCCN(C(=O)c2cc(Sc3cnc(NC(=O)C4CCC4)s3)c(C)cc2OC)C[C@H]1C] N-[5-[4-methoxy-2-methyl-5-[(3R)-3-methyl-4-prop-2-enoyl-1,4-diazepane-1-carbonyl]phenyl]sulfanylthiazol-2-yl]cyclobutanecarboxamide | Compound 86 529.3 (M + H) | A |
| 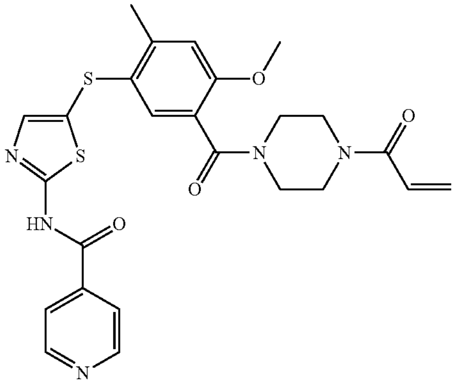 [SMILES: C=CC(=O)N1CCN(C(=O)c2cc(Sc3cnc(NC(=O)c4ccncc4)s3)c(C)cc2OC)CC1] N-[5-[4-methoxy-2-methyl-5-(4-prop-2-enoylpiperazine-1-carbonyl)phenyl]sulfanylthiazol-2-yl]pyridine-4-carboxamide | Compound 87 524.2 (M + H) | C |

TABLE 1-continued

| Final compounds (structures, names, masses and methods used for their synthesis) | | |
|---|---|---|
| Compound | MS (ES) m/z | Method Used |
| 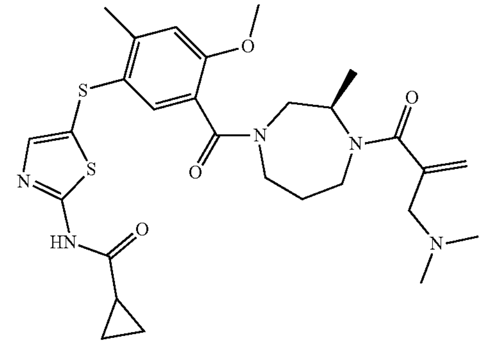 [SMILES: C=C(CN(C)C)C(=O)N1CCCN(C(=O)c2cc(Sc3cnc(NC(=O)C4CC4)s3)c(C)cc2OC)C[C@H]1C] N-[5-[5-[(3R)-4-[2-[(dimethylamino)methyl]prop-2-enoyl]-3-methyl-1,4-diazepane-1-carbonyl]-4-methoxy-2-methyl-phenyl]sulfanylthiazol-2-yl]cyclopropanecarboxamide | Compound 88 572.2 (M + H) | B |
| 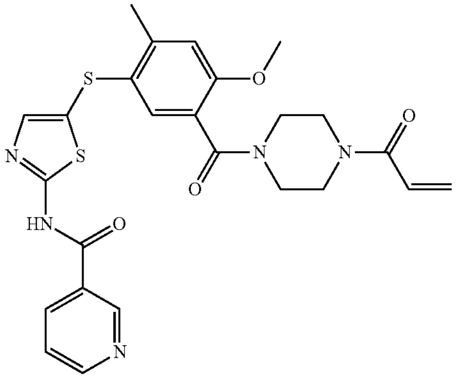 [SMILES: C=CC(=O)N1CCN(C(=O)c2cc(Sc3cnc(NC(=O)c4cccnc4)s3)c(C)cc2OC)CC1] N-[5-[4-methoxy-2-methyl-5-(4-prop-2-enoylpiperazine-1-carbonyl)phenyl]sulfanylthiazol-2-yl]pyridine-3-carboxamide | Compound 89 524.2 (M + H) | C |
| 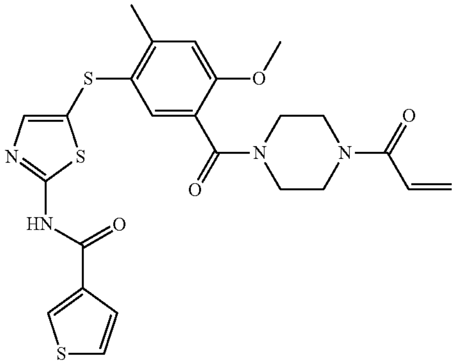 [SMILES: C=CC(=O)N1CCN(C(=O)c2cc(Sc3cnc(NC(=O)c4ccsc4)s3)c(C)cc2OC)CC1] N-[5-[4-methoxy-2-methyl-5-(4-prop-2-enoylpiperazine-1-carbonyl)phenyl]sulfanylthiazol-2-yl]thiophene-3-carboxamide | Compound 90 529.1 (M + H) | C |

TABLE 1-continued

| Final compounds (structures, names, masses and methods used for their synthesis) | | |
|---|---|---|
| Compound | MS (ES) m/z | Method Used |
| 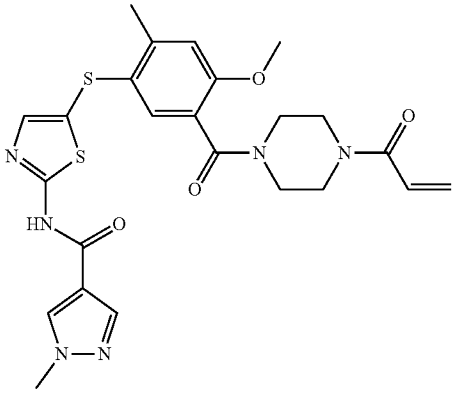 [SMILES: C=CC(=O)N1CCN(C(=O)c2cc(Sc3cnc(NC(=O)c4cnn(C)c4)s3)c(C)cc2OC)CC1] N-[5-[4-methoxy-2-methyl-5-(4-prop-2-enoylpiperazine-1-carbonyl)phenyl]sulfanylthiazol-2-yl]-1-methyl-pyrazole-4-carboxamide | Compound 91 527.2 (M + H) | C |
| 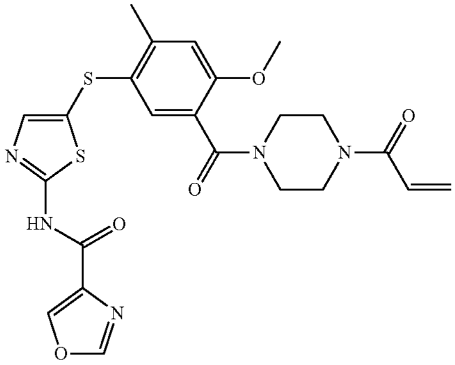 N-[5-[4-methoxy-2-methyl-5-(4-prop-2-enoylpiperazine-1-carbonyl)phenyl]sulfanylthiazol-2-yl]oxazole-4-carboxamide | Compound 92 514.1 (M + H) | C |
| 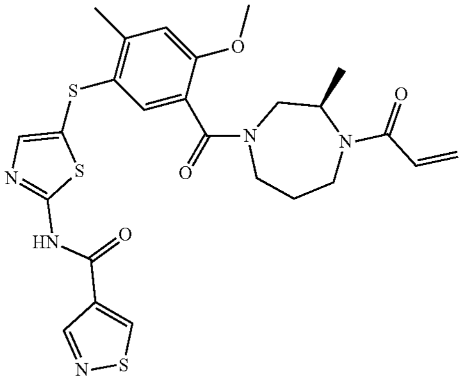 [SMILES: C=CC(=O)N1CCCN(C(=O)c2cc(Sc3cnc(NC(=O)c4cnsc4)s3)c(C)cc2OC)C[C@H]1C] N-[5-[4-methoxy-2-methyl-5-[(3R)-3-methyl-4-prop-2-enoyl-1,4-diazepane-1-carbonyl]phenyl]sulfanylthiazol-2-yl]isothiazole-4-carboxamide | Compound 93 558.0 (M + H) | C |

TABLE 1-continued

| Final compounds (structures, names, masses and methods used for their synthesis) | | |
|---|---|---|
| Compound | MS (ES) m/z | Method Used |
| 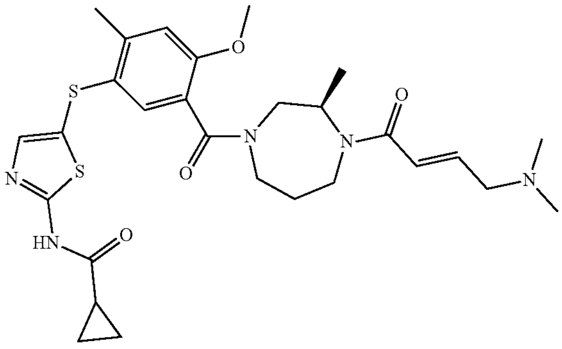 [SMILES: COc1cc(C)c(Sc2cnc(NC(=O)C3CC3)s2)cc1C(=O)N1CCCN(C(=O)/C=C/CN(C)C)[C@H](C)C1] N-[5-[5-[(3R)-4-[(E)-4-(dimethylamino)but-2-enoyl]-3-methyl-1,4-diazepane-1-carbonyl]-4-methoxy-2-methyl-phenyl]sulfanylthiazol-2-yl]cyclopropanecarboxamide | Compound 94 572.2 (M + H) | B |
| 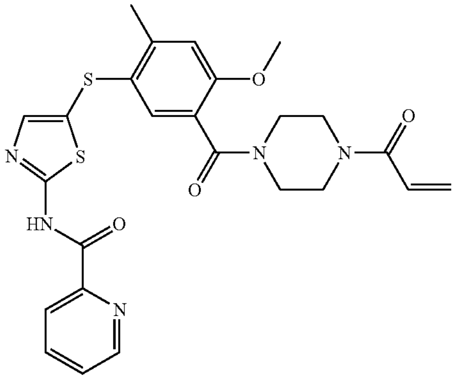 [SMILES: C=CC(=O)N1CCN(C(=O)c2cc(Sc3cnc(NC(=O)c4ccccn4)s3)c(C)cc2OC)CC1] N-[5-[4-methoxy-2-methyl-5-(4-prop-2-enoylpiperazine-1-carbonyl)phenyl]sulfanylthiazol-2-yl]pyridine-2-carboxamide | Compound 95 524.2 (M + H) | C |
| 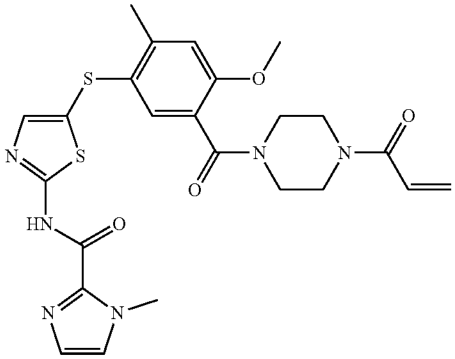 [SMILES: C=CC(=O)N1CCN(C(=O)c2cc(Sc3cnc(NC(=O)c4nccn4C)s3)c(C)cc2OC)CC1] N-[5-[4-methoxy-2-methyl-5-(4-prop-2-enoylpiperazine-1-carbonyl)phenyl]sulfanylthiazol-2-yl]-1-methyl-imidazole-2-carboxamide | Compound 96 527.2 (M + H) | C |

TABLE 1-continued

| Final compounds (structures, names, masses and methods used for their synthesis) | | |
|---|---|---|
| Compound | MS (ES) m/z | Method Used |
| 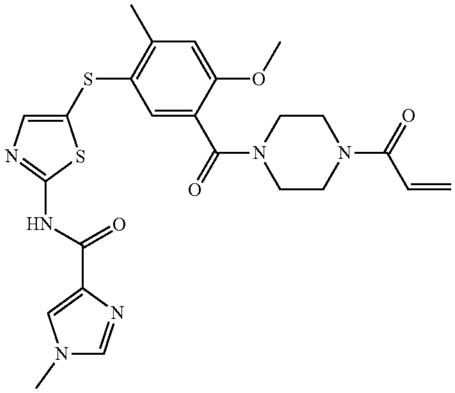 [SMILES: C=CC(=O)N1CCN(C(=O)c2cc(Sc3cnc(NC(=O)c4cn(C)cn4)s3)c(C)cc2OC)CC1]<br>N-[5-[4-methoxy-2-methyl-5-(4-prop-2-enoylpiperazine-1-carbonyl)phenyl]sulfanylthiazol-2-yl]-1-methyl-imidazole-4-carboxamide | Compound 97<br>527.2 (M + H) | C |
| 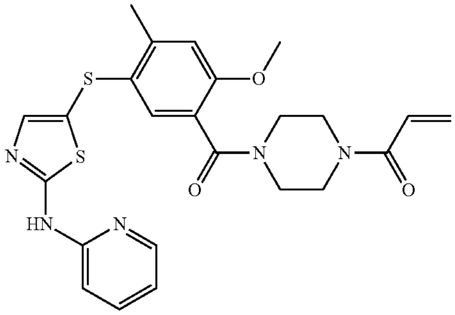 [SMILES: C=CC(=O)N1CCN(C(=O)c2cc(Sc3cnc(Nc4ccccn4)s3)c(C)cc2OC)CC1]<br>1-[4-[2-methoxy-4-methyl-5-[2-(2-pyridylamino)thiazol-5-yl]sulfanyl-benzoyl]piperazin-1-yl]prop-2-en-1-one | Compound 98<br>496.1 (M + H) | D |
| 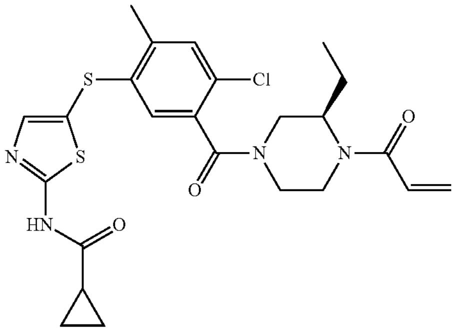 [SMILES: C=CC(=O)N1CCN(C(=O)c2cc(Sc3cnc(NC(=O)C4CC4)s3)c(C)cc2Cl)C[C@H]1CC]<br>N-[5-[4-chloro-5-[(3R)-3-ethyl-4-prop-2-enoyl-piperazine-1-carbonyl]-2-methyl-phenyl]sulfanylthiazol-2-yl]cyclopropanecarboxamide | Compound 99<br>519.2 (M + H) | A/F |

TABLE 1-continued

| Final compounds (structures, names, masses and methods used for their synthesis) | | |
|---|---|---|
| Compound | MS (ES) m/z | Method Used |
| 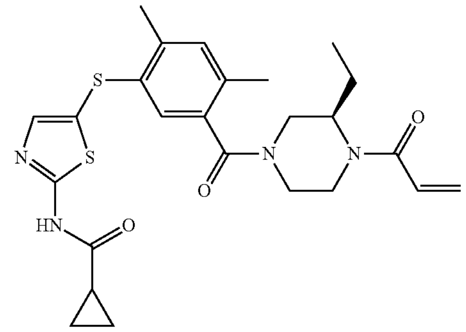 [SMILES: C=CC(=O)N1CCN(C(=O)c2cc(Sc3cnc(NC(=O)C4CC4)s3)c(C)cc2C)C[C@H]1CC]<br>N-[5-[5-[(3R)-3-ethyl-4-prop-2-enoyl-piperazine-1-carbonyl]-2,4-dimethyl-phenyl]sulfanylthiazol-2-yl]cyclopropanecarboxamide | Compound 100<br>499.1 (M + H) | A/F |
| 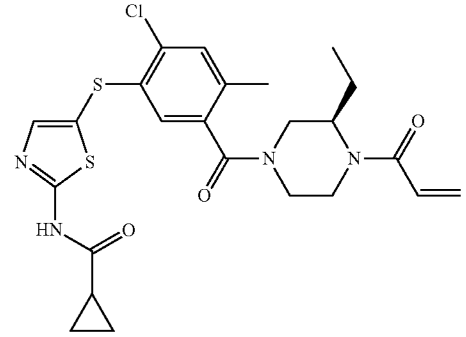 [SMILES: C=CC(=O)N1CCN(C(=O)c2cc(Sc3cnc(NC(=O)C4CC4)s3)c(Cl)cc2C)C[C@H]1CC]<br>N-[5-[2-chloro-5-[(3R)-3-ethyl-4-prop-2-enoyl-piperazine-1-carbonyl]-4-methyl-phenyl]sulfanylthiazol-2-yl]cyclopropanecarboxamide | Compound 101<br>519.0 (M + H) | A/F |
| 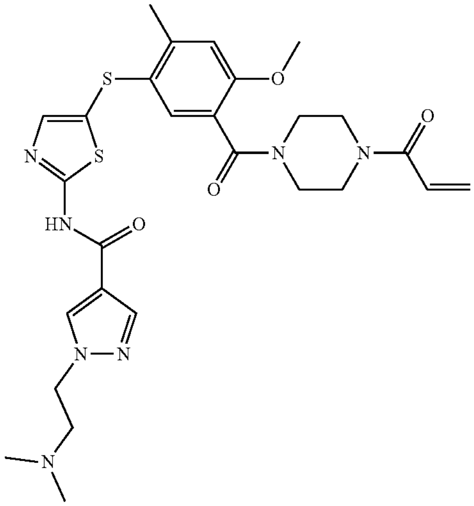 [SMILES: C=CC(=O)N1CCN(C(=O)c2cc(Sc3cnc(NC(=O)c4cnn(CCN(C)C)c4)s3)c(C)cc2OC)CC1]<br>1-[2-(dimethylamino)ethyl]-N-[5-[4-methoxy-2-methyl-5-(4-prop-2-enoylpiperazine-1-carbonyl)phenyl]sulfanylthiazol-2-yl]pyrazole-4-carboxamide | Compound 102<br>584.2 (M + H) | C |

TABLE 1-continued

| Final compounds (structures, names, masses and methods used for their synthesis) | | |
|---|---|---|
| Compound | MS (ES) m/z | Method Used |
| 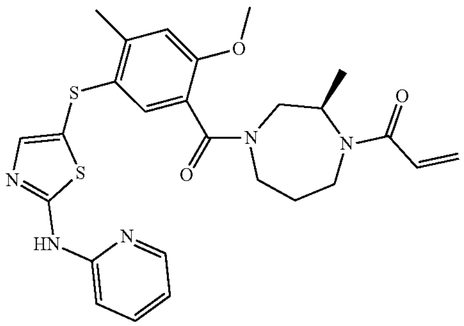 [SMILES: C=CC(=O)N1CCCN(C(=O)c2cc(Sc3cnc(Nc4ccccn4)s3)c(C)cc2OC)C[C@H]1C] 1-[(2R)-4-[2-methoxy-4-methyl-5-[2-(2-pyridylamino)thiazol-5-yl]sulfanyl-benzoyl]-2-methyl-1,4-diazepan-1-yl]prop-2-en-1-one | Compound 103 524.2 (M + H) | D |
| 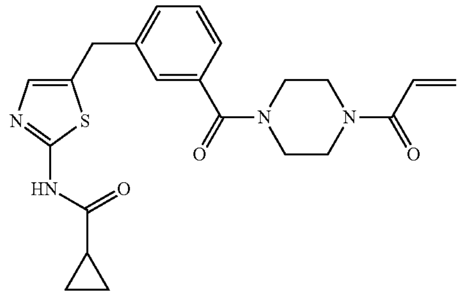 [SMILES: C=CC(=O)N1CCN(C(=O)c2cccc(Cc3cnc(NC(=O)C4CC4)s3)c2)CC1] N-[5-[[3-(4-prop-2-enoylpiperazine-1-carbonyl)phenyl]methyl]thiazol-2-yl]cyclopropanecarboxamide | Compound 4 425.1 (M + H) | I |
| 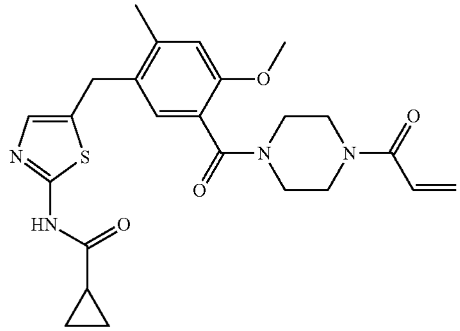 [SMILES: C=CC(=O)N1CCN(C(=O)c2cc(Cc3cnc(NC(=O)C4CC4)s3)c(C)cc2OC)CC1] N-[5-[[4-methoxy-2-methyl-5-(4-prop-2-enoylpiperazine-1-chponyl)phenyl]methyl]thiazol-2-yl]cyclopropanecarboxamide | Compound 65 469.3 (M + H) | I |

TABLE 1-continued

| Compound | MS (ES) m/z | Method Used |
|---|---|---|
| 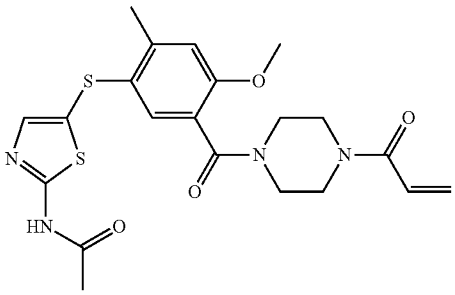 [SMILES: C=CC(=O)N1CCN(C(=O)c2cc(Sc3cnc(NC(C)=O)s3)c(C)cc2OC)CC1]<br>N-[5-[4-methoxy-2-methyl-5-(4-prop-2-enoylpiperazine-1-carbonyl)phenyl]sulfanylthiazol-2-yl]acetamide | Compound 2<br>461.1 (M + H) | A |
| 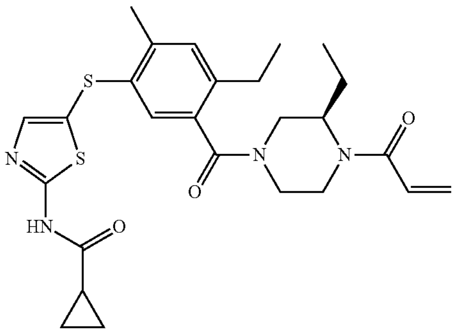 [SMILES: C=CC(=O)N1CCN(C(=O)c2cc(Sc3cnc(NC(=O)C4CC4)s3)c(C)cc2CC)C[C@H]1CC]<br>N-[5-[4-ethyl-5-[(3R)-3-ethyl-4-prop-2-enoyl-piperazine-1-carbonyl]-2-methyl-phenyl]sulfanylthiazol-2-yl]cyclopropanecarboxamide | Compound 104<br>513.2 (M + H) | A/F |
| 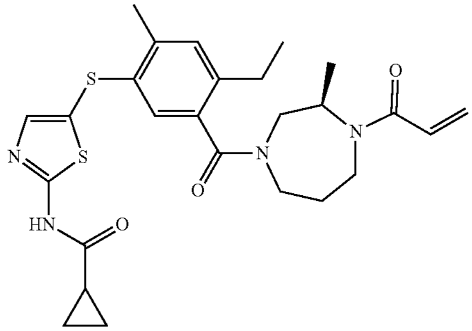 [SMILES: C=CC(=O)N1CCCN(C(=O)c2cc(Sc3cnc(NC(=O)C4CC4)s3)c(C)cc2CC)C[C@H]1C]<br>N-[5-[4-ethyl-2-methyl-5-[(3R)-3-methyl-4-prop-2-enoyl-1,4-diazepane-1-carbonyl]phenyl]sulfanylthiazol-2-yl]cyclopropanecarboxamide | Compound 105<br>513.2 (M + H) | A/F |

Final compounds (structures, names, masses and methods used for their synthesis)

TABLE 1-continued

| Final compounds (structures, names, masses and methods used for their synthesis) | | |
|---|---|---|
| Compound | MS (ES) m/z | Method Used |
| 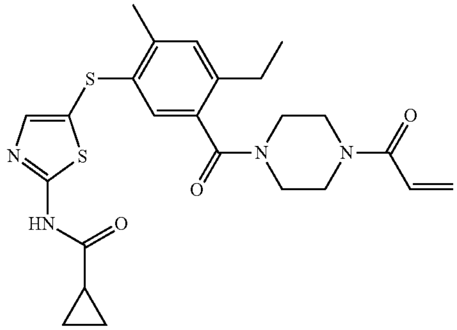<br>N-[5-[4-ethyl-2-methyl-5-(4-prop-2-enoylpiperazine-1-carbonyl)phenyl]sulfanylthiazol-2-yl]cyclopropanecarboxamide | Compound 106<br>485.1 (M + H) | A/F |
| 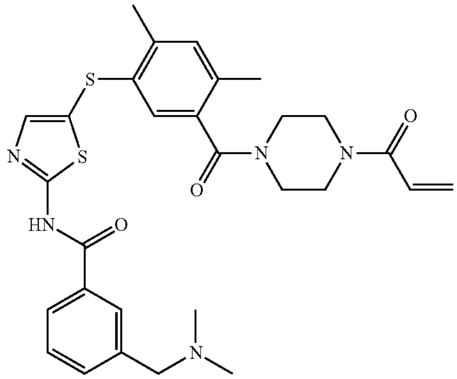 [SMILES: C=CC(=O)N1CCN(C(=O)c2cc(Sc3cnc(NC(=O)c4cccc(CN(C)C)c4)s3)c(C)cc2C)CC1]<br>3-[(dimethylamino)methyl]-N-[5-[2,4-dimethyl-5-(4-prop-2-enoylpiperazine-1-carbonyl)phenyl]sulfanylthiazol-2-yl]benzamide | Compound 107<br>564.2 (M + H) | C/F |
| 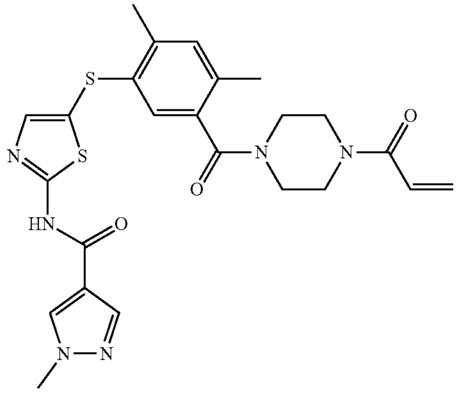 [SMILES: C=CC(=O)N1CCN(C(=O)c2cc(Sc3cnc(NC(=O)c4cnn(C)c4)s3)c(C)cc2C)CC1]<br>N-[5-[2,4-dimethyl-5-(4-prop-2-enoylpiperazine-1-carbonyl)phenyl]sulfanylthiazol-2-yl]-1-methyl-pyrazole-4-carboxamide | Compound 108<br>511.1 (M + H) | C/F |

TABLE 1-continued

| Final compounds (structures, names, masses and methods used for their synthesis) | | |
|---|---|---|
| Compound | MS (ES) m/z | Method Used |
| 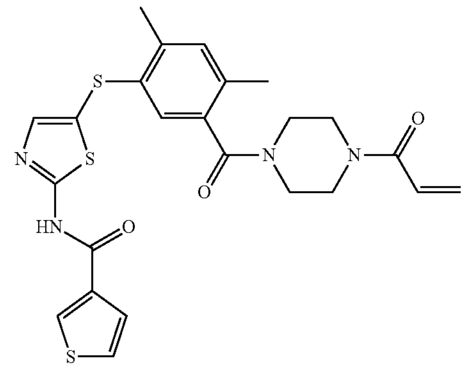 N-[5-[2,4-dimethyl-5-(4-prop-2-enoylpiperazine-1-carbonyl)phenyl]sulfanylthiazol-2-yl]thiophene-3-carboxamide | Compound 109 513.0 (M + H) | C/F |
| 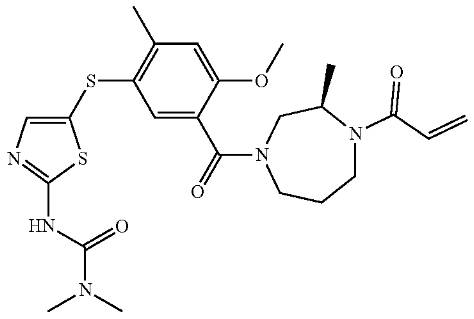 [SMILES: C=CC(=O)N1CCCN(C(=O)c2cc(Sc3cnc(NC(=O)N(C)C)s3)c(C)cc2OC)C[C@H]1C] 3-[5-[4-methoxy-2-methyl-5-[(3R)-3-methyl-4-prop-2-enoyl-1,4-diazepane-1-carbonyl]phenyl]sulfanylthiazol-2-yl]-1,1-dimethyl-urea | Compound 110 518.2 (M + H) | A |
| 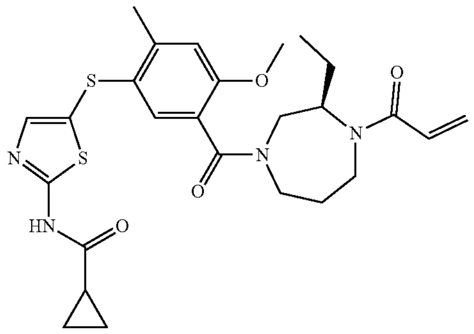 N-[5-[5-[(3R)-3-ethyl-4-prop-2-enoyl-1,4-diazepane-1-carbonyl]-4-methoxy-2-methyl-phenyl]sulfanylthiazol-2-yl]cyclopropanecarboxamide | Compound 111 529.2 (M + H) | A/K |

TABLE 1-continued

| Final compounds (structures, names, masses and methods used for their synthesis) | | |
|---|---|---|
| Compound | MS (ES) m/z | Method Used |
| 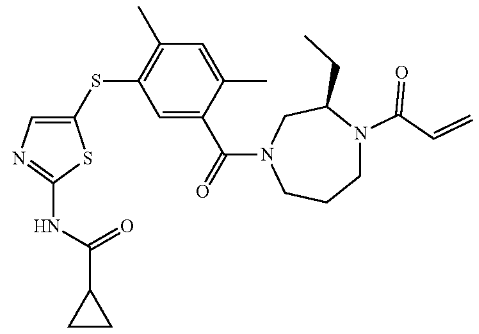 [SMILES: C=CC(=O)N1CCCN(C(=O)c2cc(Sc3cnc(NC(=O)C4CC4)s3)c(C)cc2C)C[C@H]1CC] N-[5-[5-[(3R)-3-ethyl-4-prop-2-enoyl-1,4-diazepane-1-carbonyl]-2,4-dimethyl-phenyl]sulfanylthiazol-2-yl]cyclopropanecarboxamide | Compound 112 513.2 (M + H) | A/F/K |
| 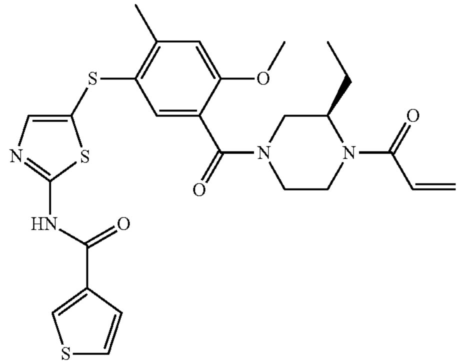 [SMILES: C=CC(=O)N1CCN(C(=O)c2cc(Sc3cnc(NC(=O)c4ccsc4)s3)c(C)cc2OC)C[C@H]1CC] N-[5-[5-[(3R)-3-ethyl-4-prop-2-enoyl-piperazine-1-carbonyl]-4-methoxy-2-methyl-phenyl]sulfanylthiazol-2-yl]thiophene-3-carboxamide | Compound 113 557.2 (M + H) | C |
| 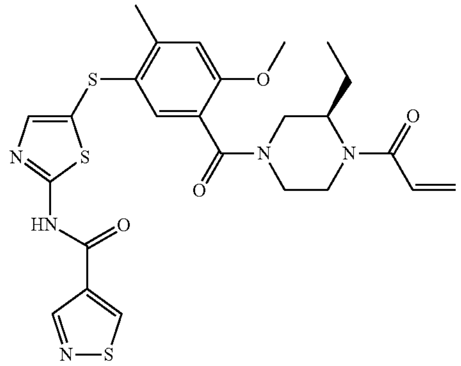 [SMILES: C=CC(=O)N1CCN(C(=O)c2cc(Sc3cnc(NC(=O)c4cnsc4)s3)c(C)cc2OC)C[C@H]1CC] N-[5-[5-[(3R)-3-ethyl-4-prop-2-enoyl-piperazine-1-carbonyl]-4-methoxy-2-methyl-phenyl]sulfanylthiazol-2-yl]isothiazole-4-carboxamide | Compound 114 558.0 (M + H) | C |

TABLE 1-continued

Final compounds (structures, names, masses and methods used for their synthesis)

| Compound | MS (ES) m/z | Method Used |
| --- | --- | --- |
| 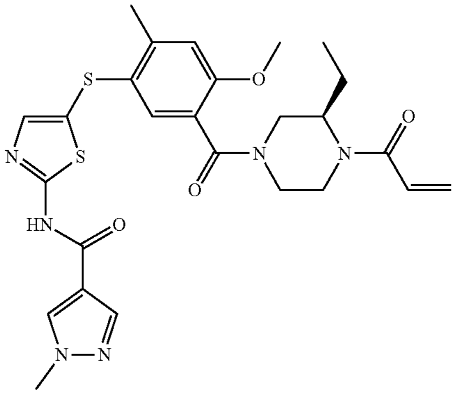 [SMILES: C=CC(=O)N1CCN(C(=O)c2cc(Sc3cnc(NC(=O)c4cnn(C)c4)s3)c(C)cc2OC)C[C@H]1CC] N-[5-[5-[(3R)-3-ethyl-4-prop-2-enoyl-piperazine-1-carbonyl]-4-methoxy-2-methyl-phenyl]sulfanylthiazol-2-yl]-1-methyl-pyrazole-4-carboxamide | Compound 115 555.2 (M + H) | C |
| 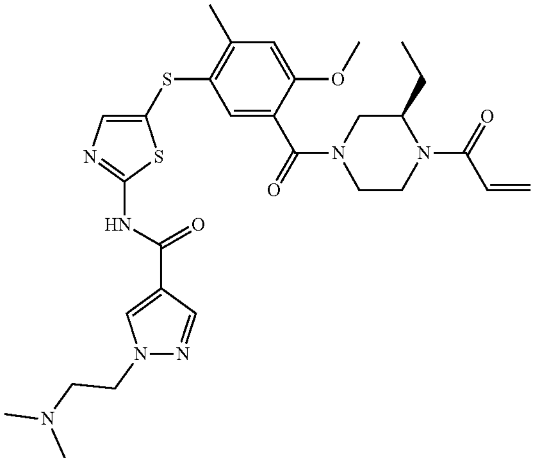 [SMILES: C=CC(=O)N1CCN(C(=O)c2cc(Sc3cnc(NC(=O)c4cnn(CCN(C)C)c4)s3)c(C)cc2OC)C[C@H]1CC] 1-[2-(dimethylamino)ethyl]-N-[5-[5-[(3R)-3-ethyl-4-prop-2-enoyl-piperazine-1-carbonyl]-4-methoxy-2-methyl-phenyl]sulfanylthiazol-2-yl]pyrazole-4-carboxamide | Compound 116 612.2 (M + H) | C |
| 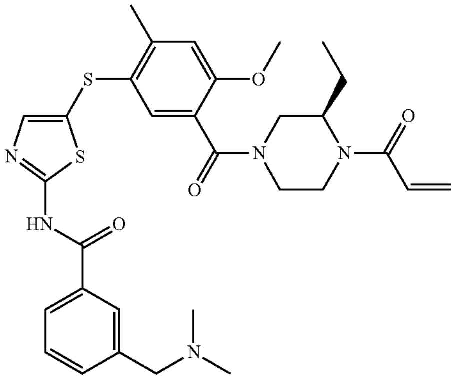 [SMILES: C=CC(=O)N1CCN(C(=O)c2cc(Sc3cnc(NC(=O)c4cccc(CN(C)C)c4)s3)c(C)cc2OC)C[C@H]1CC] 3-[(dimethylamino)methyl]-N-[5-[5-[(3R)-3-ethyl-4-prop-2-enoyl-piperazine-1-carbonyl]-4-methoxy-2-methyl-phenyl]sulfanylthiazol-2-yl]benzamide | Compound 117 608.3 (M + H) | C |

TABLE 1-continued

<table>
<tr><th colspan="3">Final compounds (structures, names, masses and methods used for their synthesis)</th></tr>
<tr><th>Compound</th><th>MS (ES) m/z</th><th>Method Used</th></tr>
<tr><td>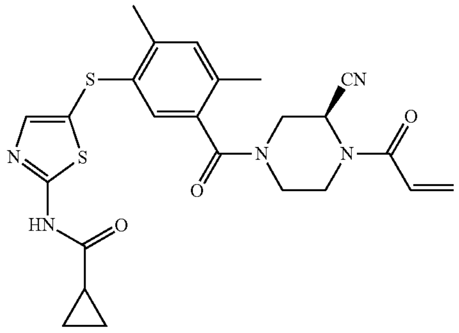 [SMILES: C=CC(=O)N1CCN(C(=O)c2cc(Sc3cnc(NC(=O)C4CC4)s3)c(C)cc2C)C[C@H]1C#N]<br>N-[5-[5-[(3S)-3-cyano-4-prop-2-enoyl-piperazine-1-carbonyl]-2,4-dimethyl-phenyl]sulfanylthiazol-2-yl]cyclopropanecarboxamide</td><td>Compound 118<br>496.1 (M + H)</td><td>A/F</td></tr>
<tr><td>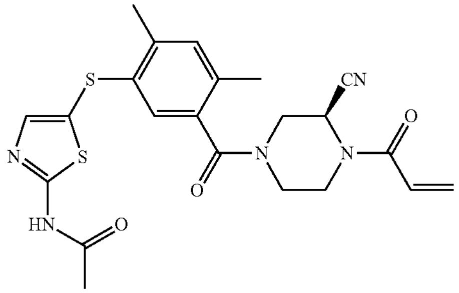 [SMILES: C=CC(=O)N1CCN(C(=O)c2cc(Sc3cnc(NC(C)=O)s3)c(C)cc2C)C[C@H]1C#N]<br>N-[5-[5-[(3S)-3-cyano-4-prop-2-enoyl-piperazine-1-carbonyl]-2,4-dimethyl-phenyl]sulfanylthiazol-2-yl]acetamide</td><td>Compound 119<br>470.1 (M + H)</td><td>A/F</td></tr>
<tr><td>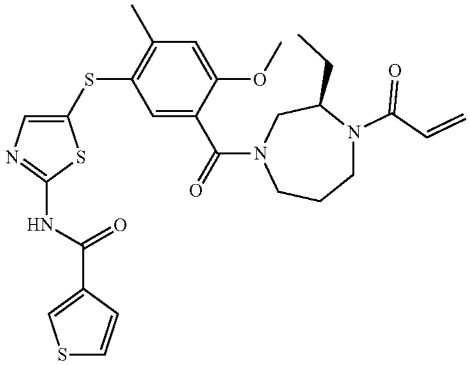 [SMILES: C=CC(=O)N1CCCN(C(=O)c2cc(Sc3cnc(NC(=O)c4ccsc4)s3)c(C)cc2OC)C[C@H]1CC]<br>N-[5-[5-[(3R)-3-ethyl-4-prop-2-enoyl-1,4-diazepane-1-carbonyl]-4-methoxy-2-methyl-phenyl]sulfanylthiazol-2-yl ]thiophene-3-carboxamide</td><td>Compound 120<br>571.1 (M + H)</td><td>C/K</td></tr>
</table>

TABLE 1-continued

| Final compounds (structures, names, masses and methods used for their synthesis) | | |
|---|---|---|
| Compound | MS (ES) m/z | Method Used |
| 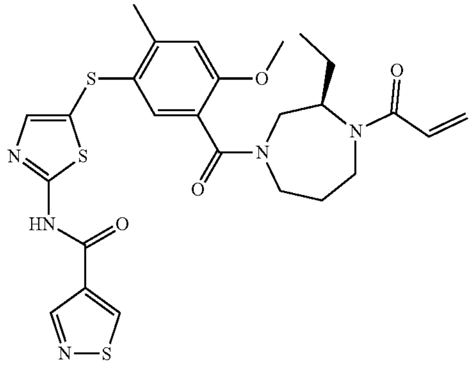 [SMILES: C=CC(=O)N1CCCN(C(=O)c2cc(Sc3cnc(NC(=O)c4cnsc4)s3)c(C)cc2OC)C[C@H]1CC] N-[5-[5-[(3R)-3-ethyl-4-prop-2-enoyl-1,4-diazepane-1-carbonyl]-4-methoxy-2-methyl-phenyl]sulfanylthiazol-2-yl]isothiazole-4-carboxamide | Compound 121 572.2 (M + H) | C/K |
| 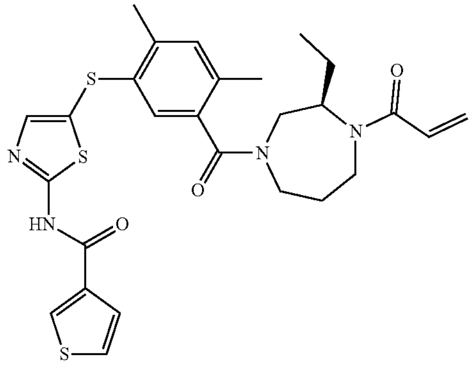 [SMILES: C=CC(=O)N1CCCN(C(=O)c2cc(Sc3cnc(NC(=O)c4ccsc4)s3)c(C)cc2C)C[C@H]1CC] N-[5-[5-[(3R)-3-ethyl-4-prop-2-enoyl-1,4-diazepane-1-carbonyl]-2,4-dimethyl-phenyl]sulfanylthiazol-2-yl]thiophene-3-carboxamide | Compound 122 555.2 (M + H) | C/F/K |
| 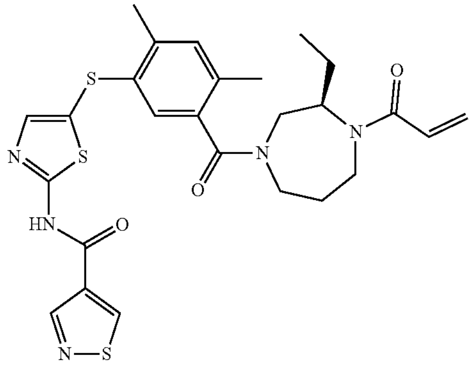 [SMILES: C=CC(=O)N1CCCN(C(=O)c2cc(Sc3cnc(NC(=O)c4cnsc4)s3)c(C)cc2C)C[C@H]1CC] N-[5-[5-[(3R)-3-ethyl-4-prop-2-enoyl-1,4-diazepane-1-carbonyl]-2,4-dimethyl-phenyl]sulfanylthiazol-2-yl]isothiazole-4-carboxamide | Compound 123 556.1 (M + H) | C/F/K |

TABLE 1-continued

| Final compounds (structures, names, masses and methods used for their synthesis) | | |
|---|---|---|
| Compound | MS (ES) m/z | Method Used |
| 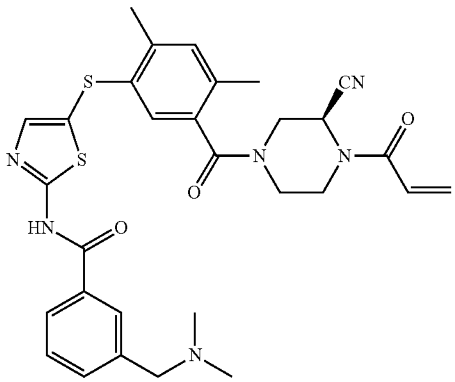 N-[5-[5-[(3S)-3-cyano-4-prop-2-enoyl-piperazine-1-carbonyl]-4-methoxy-2-methyl-phenyl]sulfanylthiazol-2-yl]-3-[(dimethylamino)methyl]benzamide | Compound 124 605.2 (M + H) | C/F |
| 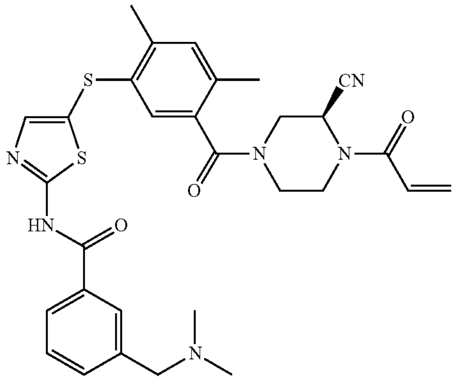 [SMILES: C=CC(=O)N1CCN(C(=O)c2cc(Sc3cnc(NC(=O)c4cccc(CN(C)C)c4)s3)c(C)cc2C)C[C@H]1C#N] N-[5-[5-[(3S)-3-cyano-4-prop-2-enoyl-piperazine-1-carbonyl]-2,4-dimethyl-phenyl]sulfanylthiazol-2-yl]-3-(dimethwamino)methyllbenzamide | Compound 125 589.3 (M + H) | C/F |
| 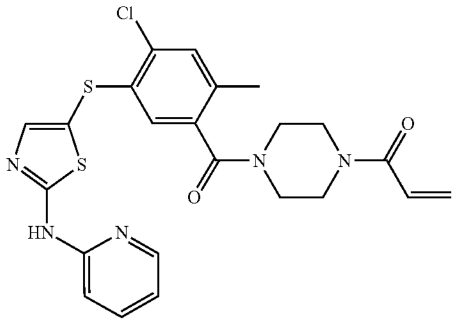 [SMILES: C=CC(=O)N1CCN(C(=O)c2cc(Sc3cnc(Nc4ccccn4)s3)c(Cl)cc2C)CC1] 1-[4-[4-chloro-2-methyl-5-[2-(2-pyridylamino)thiazol-5-yl]sulfanyl-benzoyl]piperazin-1-ylprop-2-en-1-one | Compound 126 500.1 (M + H) | D/F |

TABLE 1-continued

| Final compounds (structures, names, masses and methods used for their synthesis) | | |
|---|---|---|
| Compound | MS (ES) m/z | Method Used |
| 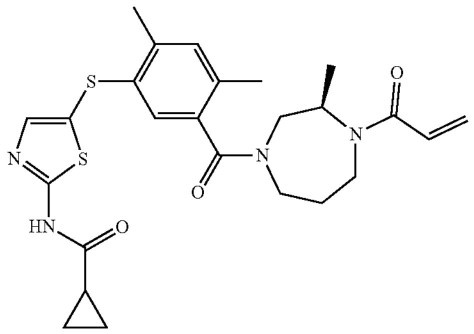 [SMILES: C=CC(=O)N1CCCN(C(=O)c2cc(Sc3cnc(NC(=O)C4CC4)s3)c(C)cc2C)C[C@H]1C] N-[5-[[2,4-dimethyl-5-[(3R)-3-methyl-4-prop-2-enoyl-1,4-diazepane-1-carbonyl]phenyl]methyl]thiazol-2-yl]cyclopropanecarboxamide | Compound 127 481.3 (M + H) | L |
| 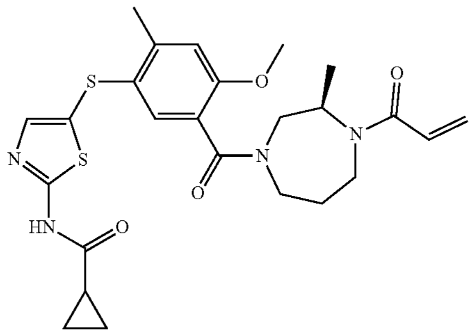 [SMILES: C=CC(=O)N1CCCN(C(=O)c2cc(Sc3cnc(NC(=O)C4CC4)s3)c(C)cc2OC)C[C@H]1C] N-[5-[[4-methoxy-2-methyl-5-[(3R)-3-methyl-4-prop-2-enoyl-1,4-diazepane-1-carbonyl]phenyl]methyl]thiazol-2-yl]cyclopropanecarboxamide | Compound 128 497.3 (M + H) | L |
| 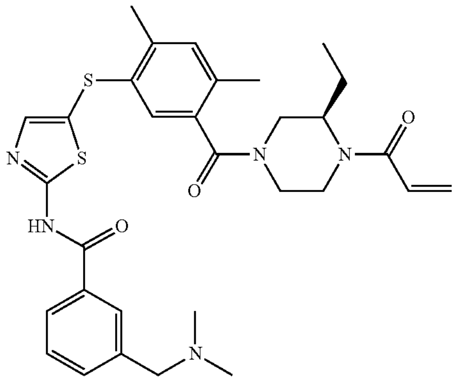 [SMILES: C=CC(=O)N1CCN(C(=O)c2cc(Sc3cnc(NC(=O)c4cccc(CN(C)C)c4)s3)c(C)cc2C)C[C@H]1CC] 3-[(dimethylamino)methyl]-N-[5-[5-[(3R)-3-ethyl-4-prop-2-enoyl-piperazine-1-carbonyl]-2,4-dimethyl-phenyl]sulfanylthiazol-2-yl]benzamide | Compound 129 592.3 (M + H) | C/F |

TABLE 1-continued

| Final compounds (structures, names, masses and methods used for their synthesis) | | |
|---|---|---|
| Compound | MS (ES) m/z | Method Used |
| 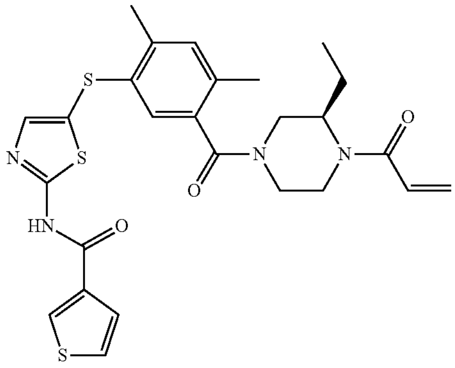 [SMILES: C=CC(=O)N1CCN(C(=O)c2cc(Sc3cnc(NC(=O)c4ccsc4)s3)c(C)cc2C)C[C@H]1CC] N-[5-[5-[(3R)-3-ethyl-4-prop-2-enoyl-piperazine-1-carbonyl]-2,4-dimethyl-phenyl]sulfanylthiazol-2-yl]thiophene-3-carboxamide | Compound 130 541.1 (M + H) | C/F |
| 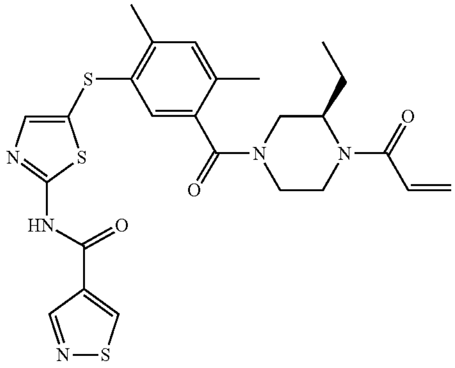 [SMILES: C=CC(=O)N1CCN(C(=O)c2cc(Sc3cnc(NC(=O)c4cnsc4)s3)c(C)cc2C)C[C@H]1CC] N-[5-[5-[(3R)-3-ethyl-4-prop-2-enoyl-piperazine-1-carbonyl]-2,4-dimethyl-phenyl]sulfanylthiazol-2-yl]isothiazole-4-carboxamide | Compound 131 542.2 (M + H) | C/F |
| 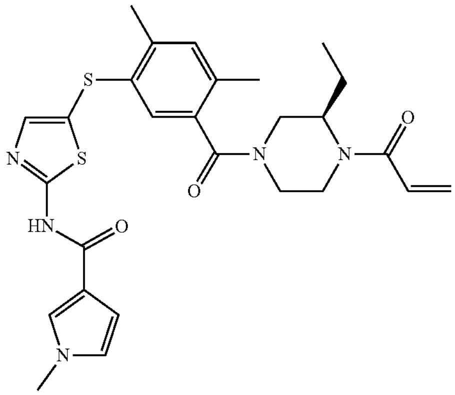 N-[5-[5-[(3R)-3-ethyl-4-prop-2-enoyl-piperazine-1-carbonyl]-4-methoxy-2-methyl-phenyl]sulfanylthiazol-2-yl]-1-methyl-pyrrole-3-carboxamide | Compound 132 554.2 (M + H) | C/F |

TABLE 1-continued

| Final compounds (structures, names, masses and methods used for their synthesis) | | |
|---|---|---|
| Compound | MS (ES) m/z | Method Used |
| 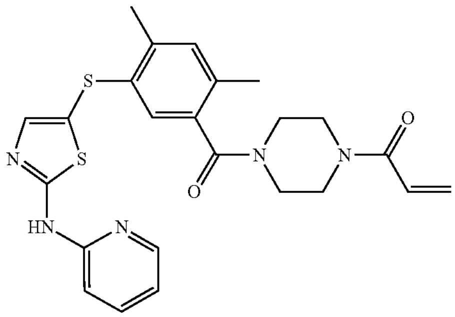 [SMILES: C=CC(=O)N1CCN(C(=O)c2cc(Sc3cnc(Nc4ccccn4)s3)c(C)cc2C)CC1] 1-[4-[2,4-dimethyl-5-[2-(2-pyridylamino)thiazol-5-yl]sulfanyl-benzoyl]piperazin-1-yl]prop-2-en-1-one | Compound 133 480.2 (M + H) | L |
| 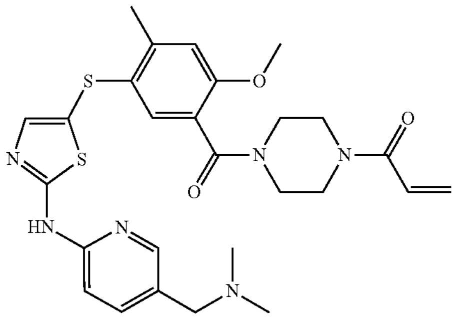 [SMILES: C=CC(=O)N1CCN(C(=O)c2cc(Sc3cnc(Nc4ccc(CN(C)C)cn4)s3)c(C)cc2OC)CC1] 1-[4-[5-[2-[[5-[(dimethylamino)methyl]-2-pyridyl]amino]thiazol-5-yl]sulfanyl-2-methoxy-4-methyl-benzoyl]piperazin-1-yl]prop-2-en-1-one | Compound 134 553.3 (M + H) | D |
| 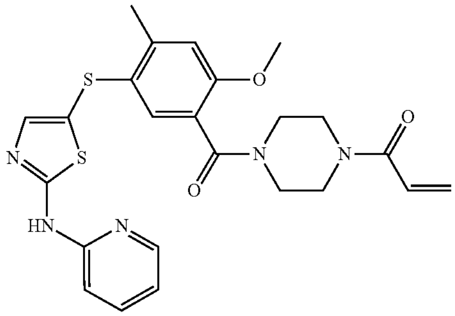 [SMILES: C=CC(=O)N1CCN(C(=O)c2cc(Sc3cnc(Nc4ccccn4)s3)c(C)cc2OC)CC1] 1-[4-[2-methoxy-4-methyl-5-[[2-(2-pyridylamino)thiazol-5-yl]methyl]benzoyl]piperazin-1-yl]prop-2-en-1-one | Compound 135 478.1 (M + H) | N |

TABLE 1-continued

| Final compounds (structures, names, masses and methods used for their synthesis) | | |
|---|---|---|
| Compound | MS (ES) m/z | Method Used |
| 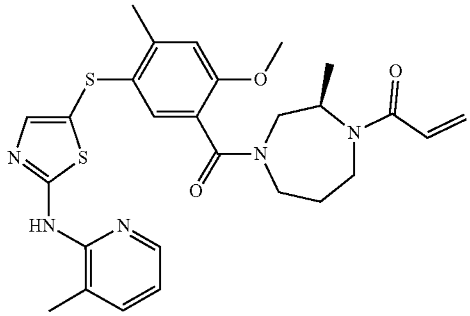 [SMILES: C=CC(=O)N1CCCN(C(=O)c2cc(Sc3cnc(Nc4ncccc4C)s3)c(C)cc2OC)C[C@H]1C] 1-[(2R)-4-[2-methoxy-4-methyl-5-[2-[(3-methyl-2-pyridyl)amino]thiazol-5-yl]sulfanyl-benzoyl]-2-methyl-1,4-diazepan-1-yl]prop-2-en-1-one | Compound 136 538.1 (M + H) | D |
| 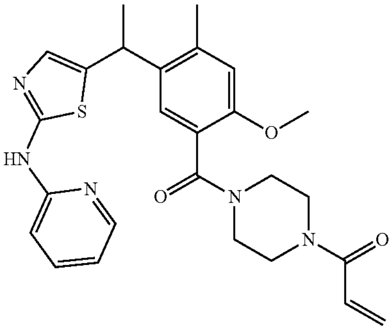 [SMILES: C=CC(=O)N1CCN(C(=O)c2cc(C(C)c3cnc(Nc4ccccn4)s3)c(C)cc2OC)CC1] 1-(4-(2-methoxy-4-methyl-5-(1-(2-(pyridin-2-ylamino)thiazol-5-yl)ethyl)benzoyl)piperazin-1-yl)prop-2-en-1-one | Compound 137 MS (M + H) 492.2 | N |
| 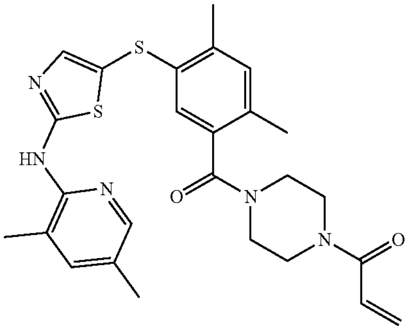 1-(4-(5-((2-((3,5-dimethylpyridin-2-yl)amino)thiazol-5-yl)thio)-2,4-dimethylbenzoyl)piperazin-1-yl)prop-2-en-1-one | Compound 138 MS (M + H) 508.3 | D |

TABLE 1-continued

| Final compounds (structures, names, masses and methods used for their synthesis) | | |
|---|---|---|
| Compound | MS (ES) m/z | Method Used |
| 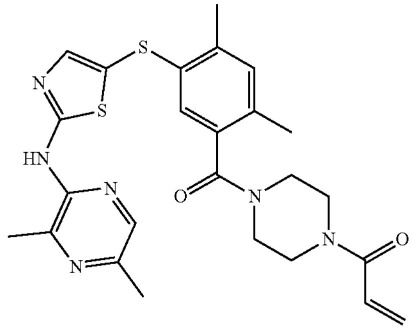 [SMILES: C=CC(=O)N1CCN(C(=O)c2cc(Sc3cnc(Nc4ncc(C)nc4C)s3)c(C)cc2C)CC1] 1-(4-(5-((2-((3,5-dimethylpyrazin-2-yl)amino)thiazol-5-yl)thio)-2,4-dimethylbenzoyl)piperazin-1-yl)prop-2-en-1-one | Compound 139 MS (M + H) 509.1 | D |
| 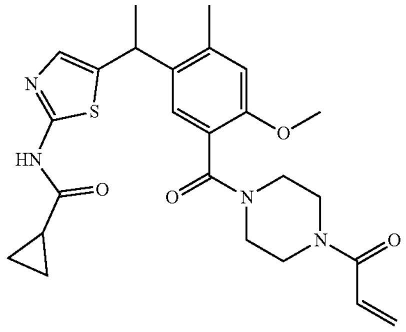 [SMILES: C=CC(=O)N1CCN(C(=O)c2cc(C(C)c3cnc(NC(=O)C4CC4)s3)c(C)cc2OC)CC1] N-(5-(1-(5-(4-acryloylpiperazine-1-carbonyl)-4-methoxy-2-methylphenyl)ethyl)thiazol-2-yl)cyclopropanecarboxamide | Compound 140 MS (M + H) 483.2 | I |
| 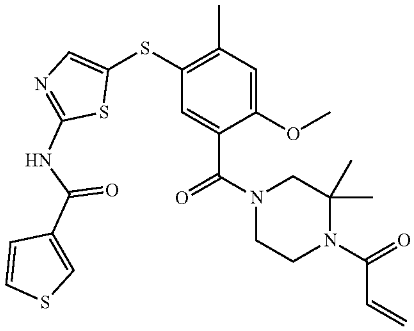 [SMILES: C=CC(=O)N1CCN(C(=O)c2cc(Sc3cnc(NC(=O)c4ccsc4)s3)c(C)cc2OC)CC1(C)C] N-(5-((5-(4-acryloyl-3,3-dimethylpiperazine-1-carbonyl)-4-methoxy-2-methylphenyl)thio)thiazol-2-yl)thiophene-3-carboxamide | Compound 141 MS (M + H) 556.8 | C |

TABLE 1-continued

| Final compounds (structures, names, masses and methods used for their synthesis) | | |
|---|---|---|
| Compound | MS (ES) m/z | Method Used |
| 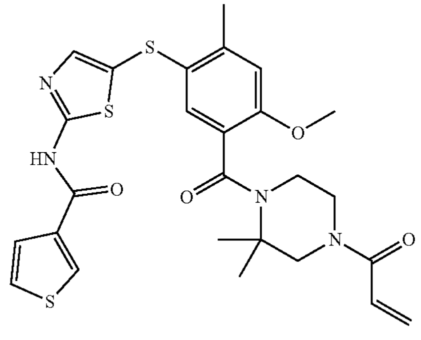 [SMILES: C=CC(=O)N1CCN(C(=O)c2cc(Sc3cnc(NC(=O)c4ccsc4)s3)c(C)cc2OC)C(C)(C)C1] N-(5-((5-(4-acryloyl-2,2-dimethylpiperazine-1-carbonyl)-4-methoxy-2-methylphenyl)thio)thiazol-2-yl)thiophene-3-carboxamide | Compound 142 MS (M + H) 557.2 | C |
| 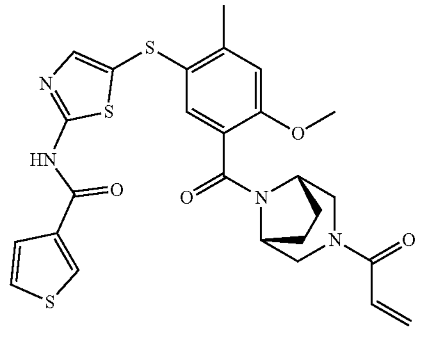 [SMILES: C=CC(=O)N1C[C@H]2CC[C@@H](C1)N2C(=O)c1cc(Sc2cnc(NC(=O)c3ccsc3)s2)c(C)cc1OC] N-(5-((5-((1R,5S)-3-acryloyl-3,8-diazabicyclo[3.2.1]octane-8-carbonyl)-4-methoxy-2-methylphenyl)thio)thiazol-2-yl)thiophene-3-carboxamide | Compound 143 MS (M + H) 554.8 | C |
| 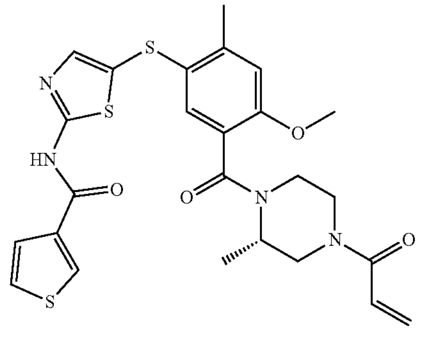 [SMILES: C=CC(=O)N1CCN(C(=O)c2cc(Sc3cnc(NC(=O)c4ccsc4)s3)c(C)cc2OC)[C@@H](C)C1] (S)-N-(5-((5-(4-acryloyl-2-methylpiperazine-1-carbonyl)-4-methoxy-2-methylphenyl)thio)thiazol-2-yl)thiophene-3-carboxamide | Compound 144 MS (M + H) 543.2 | C |

TABLE 1-continued

| Final compounds (structures, names, masses and methods used for their synthesis) | | |
|---|---|---|
| Compound | MS (ES) m/z | Method Used |
| 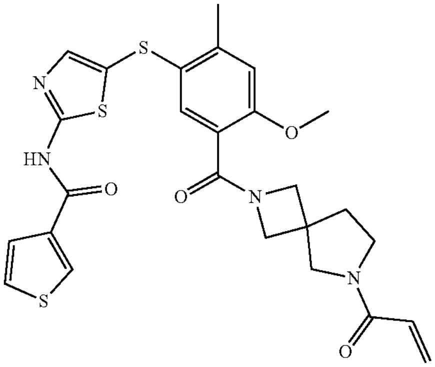 [SMILES: C=CC(=O)N1CCC2(C1)CN(C(=O)c1cc(Sc3cnc(NC(=O)c4ccsc4)s3)c(C)cc1OC)C2] N-(5-((5-(6-acryloyl-2,6-diazaspiro[3.4]octane-2-carbonyl)-4-methoxy-2-methylphenyl)thio)thiazol-2-yl)thiophene-3-carboxamide | Compound 145 MS (M + H) 555.2 | C |
| 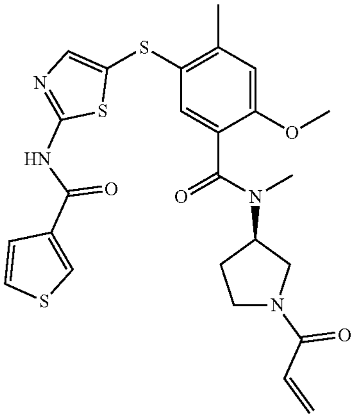 [SMILES: C=CC(=O)N1CC[C@@H](N(C)C(=O)c2cc(Sc3cnc(NC(=O)c4ccsc4)s3)c(C)cc2OC)C1] (R)-N-(5-((5-((1-acryloylpyrrolidin-3-yl)(methyl)carbamoyl)-4-methoxy-2-methylphenyl)thio)thiazol-2-yl)thiophene-3-carboxamide | Compound 146 MS (M + H) 542.8 | C |
| 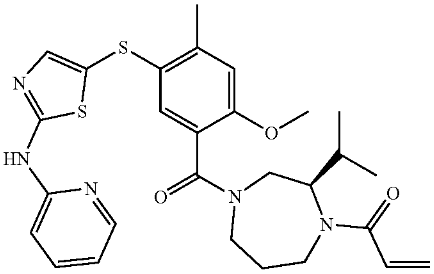 [SMILES: C=CC(=O)N1CCCN(C(=O)c2cc(Sc3cnc(Nc4ccccn4)s3)c(C)cc2OC)C[C@H]1C(C)C] (R)-1-(2-isopropyl-4-(2-methoxy-4-methyl-5-((2-(pyridin-2-ylamino)thiazol-5-yl)thio)benzoyl)-1,4-diazepan-1-yl)prop-2-en-1-one | Compound 147 MS (M + H) 551.8 | D |

TABLE 1-continued

| Final compounds (structures, names, masses and methods used for their synthesis) | | |
|---|---|---|
| Compound | MS (ES) m/z | Method Used |
| 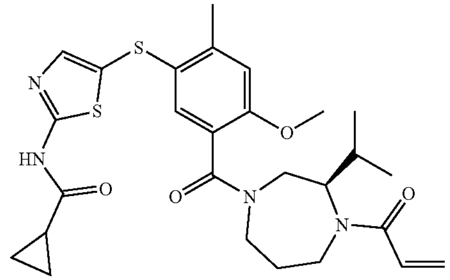 [SMILES: C=CC(=O)N1CCCN(C(=O)c2cc(Sc3cnc(NC(=O)C4CC4)s3)c(C)cc2OC)C[C@H]1C(C)C] (R)-N-(5-((5-(4-acryloyl-3-isopropyl-1,4-diazepane-1-carbonyl)-4-methoxy-2-methylphenyl)thio)thiazol-2-yl)cyclopropanecarboxamide | Compound 148 MS (M + H) 542.8 | A |
| 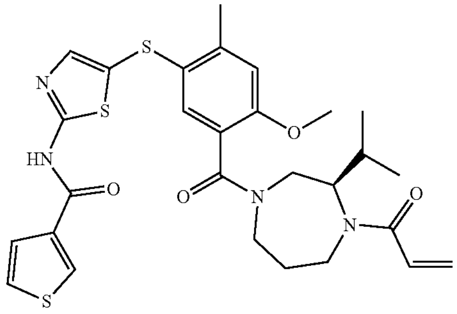 [SMILES: C=CC(=O)N1CCCN(C(=O)c2cc(Sc3cnc(NC(=O)c4ccsc4)s3)c(C)cc2OC)C[C@H]1C(C)C] (R)-N-(5-((5-(4-acryloyl-3-isopropyl-1,4-diazepane-1-carbonyl)-4-methoxy-2-methylphenyl)thio)thiazol-2-yl)thiophene-3-carboxamide | Compound 149 MS (M + H) 584.7 | C |
| 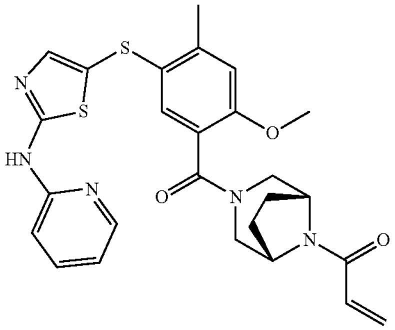 [SMILES: C=CC(=O)N1[C@@H]2CC[C@H]1CN(C(=O)c1cc(Sc3cnc(Nc4ccccn4)s3)c(C)cc1OC)C2] 1-((1R,5S)-3-(2-methoxy-4-methyl-5-((2-(pyridin-2-ylamino)thiazol-5-yl)thio)benzoyl)-3,8-diazabicyclo[3.2.1]octan-8-yl)prop-2-en-1-one | Compound 150 MS (M + H) 522.2 | D |

TABLE 1-continued

| Final compounds (structures, names, masses and methods used for their synthesis) | | |
|---|---|---|
| Compound | MS (ES) m/z | Method Used |
| 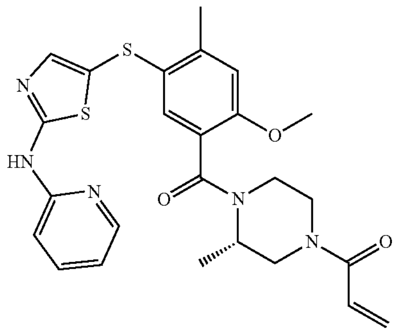 [SMILES: C=CC(=O)N1CCN(C(=O)c2cc(Sc3cnc(Nc4ccccn4)s3)c(C)cc2OC)[C@@H](C)C1] (S)-1-(4-(2-methoxy-4-methyl-5-((2-(pyridin-2-ylamino)thiazol-5-yl)thio)benzoyl)-3-methylpiperazin-1-yl)prop-2-en-1-one | Compound 151 MS (M + H) 510.2 | D |
| 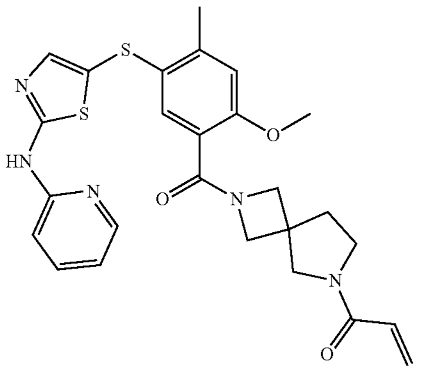 [SMILES: C=CC(=O)N1CCC2(C1)CN(C(=O)c1cc(Sc3cnc(Nc4ccccn4)s3)c(C)cc1OC)C2] 1-(2-(2-methoxy-4-methyl-5-((2-(pyridin-2-ylamino)thiazol-5-yl)thio)benzoyl)-2,6-diazaspiro[3.4]octan-6-yl)prop-2-en-1-one | Compound 152 MS (M + H) 521.6 | D |
| 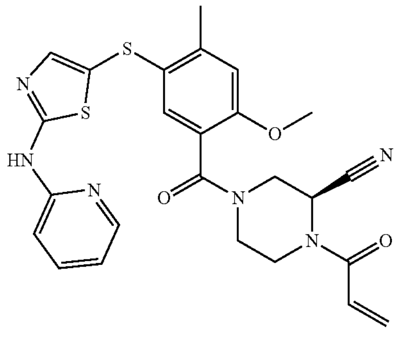 [SMILES: C=CC(=O)N1CCN(C(=O)c2cc(Sc3cnc(Nc4ccccn4)s3)c(C)cc2OC)C[C@H]1C#N] (S)-1-acryloyl-4-(2-methoxy-4-methyl-5-((2-(pyridin-2-ylamino)thiazol-5-yl)thio)benzoyl)piperazine-2-carbonitrile | Compound 153 MS (M + H) 520.6 | D |

TABLE 1-continued

| Final compounds (structures, names, masses and methods used for their synthesis) | | |
|---|---|---|
| Compound | MS (ES) m/z | Method Used |
| 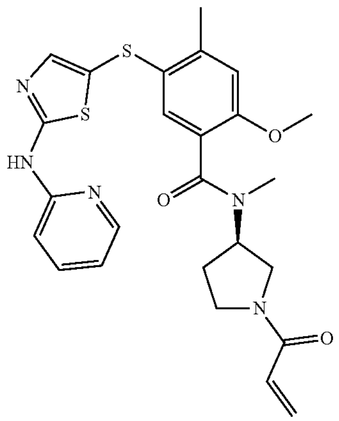 [SMILES: C=CC(=O)N1CC[C@@H](N(C)C(=O)c2cc(Sc3cnc(Nc4ccccn4)s3)c(C)cc2OC)C1] (R)-N-(1-acryloylpyrrolidin-3-yl)-2-methoxy-N,4-dimethyl-5-((2-(pyridin-2-ylamino)thiazol-5-yl)thio)benzamide | Compound 154 MS (M + H) 509.6 | D |
| 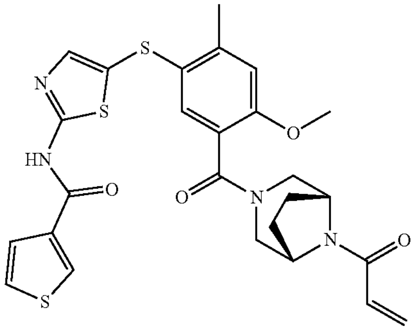 [SMILES: C=CC(=O)N1[C@@H]2CC[C@H]1CN(C(=O)c1cc(Sc3cnc(NC(=O)c4ccsc4)s3)c(C)cc1OC)C2] N-(5-((5-((IR,5S)-8-acryloyl-3,8-diazabicyclo[3.2.1]octane-3-carbonyl)-4-methoxy-2-methylphenyl)thio)thiazol-aryl)thiophene-3-carboxamide | Compound 155 MS (M + H) 555.2 | C |
| 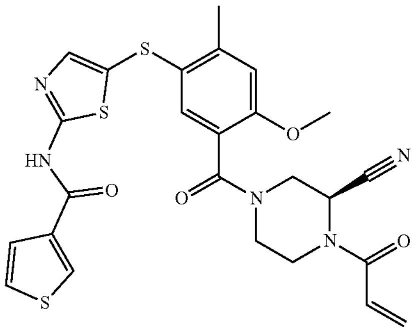 [SMILES: C=CC(=O)N1CCN(C(=O)c2cc(Sc3cnc(NC(=O)c4ccsc4)s3)c(C)cc2OC)C[C@H]1C#N] (S)-N-(5-((5-(4-acryloyl-3-cyanopiperazine-1-carbonyl)-4-methoxy-2-methylphenyl)thio)thiazol-2-yl)thiophene-3-carboxamide | Compound 156 MS (M + H) 553.5 | C |

TABLE 1-continued

| Final compounds (structures, names, masses and methods used for their synthesis) | | |
|---|---|---|
| Compound | MS (ES) m/z | Method Used |
| 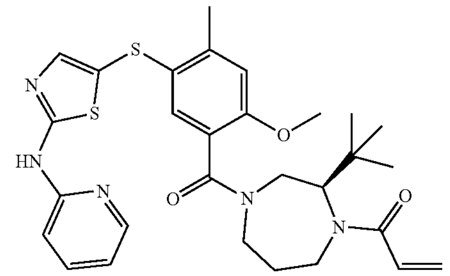 [SMILES: C=CC(=O)N1CCCN(C(=O)c2cc(Sc3cnc(Nc4ccccn4)s3)c(C)cc2OC)C[C@H]1C(C)(C)C] (R)-1-(2-(tert-butyl)-4-(2-methoxy-4-methyl-5-((2-(pyridin-2-ylamino)thiazol-5-yl)thio)benzoyl)-1,4-diazepan-1-yl)prop-2-en-1-one | Compound 157 MS (M + H) 566.3 | D |
| 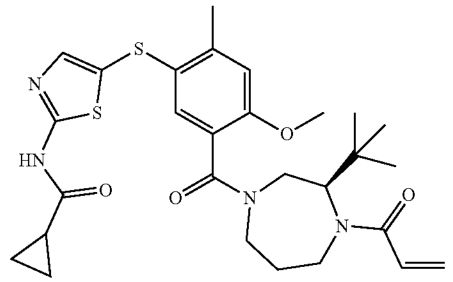 [SMILES: C=CC(=O)N1CCCN(C(=O)c2cc(Sc3cnc(NC(=O)C4CC4)s3)c(C)cc2OC)C[C@H]1C(C)(C)C] (R)-N-(5-((5-(4-acryloyl-3-(tert-butyl)-1,4-diazepane-1-carbonyl)-4-methoxy-2-methylphenyl)thio)thiazol-2-yl)cyclopropanecarboxamide | Compound 158 MS (M + H) 557.2 | A |
| 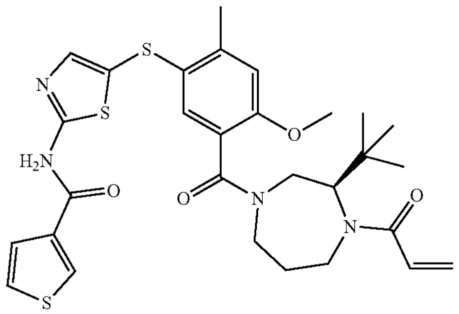 [SMILES: C=CC(=O)N1CCCN(C(=O)c2cc(Sc3cnc(NC(=O)c4ccsc4)s3)c(C)cc2OC)C[C@H]1C(C)(C)C] (R)-N-(5-((5-(4-acryloyl-3-(tert-butyl)-1,4-diazepane-1-carbonyl)-4-methoxy-2-methylphenyl)thio)thiazol-2-yl)thiophene-3-carboxamide | Compound 159 MS (M + H) 599.2 | C |

TABLE 1-continued

Final compounds (structures, names, masses and methods used for their synthesis)

| Compound | MS (ES) m/z | Method Used |
| --- | --- | --- |
| 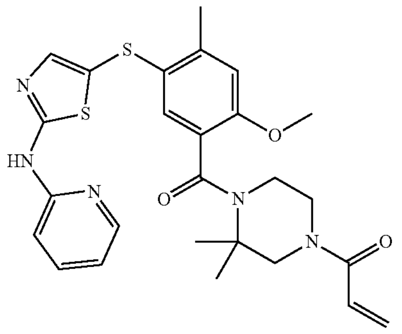 [SMILES: C=CC(=O)N1CCN(C(=O)c2cc(Sc3cnc(Nc4ccccn4)s3)c(C)cc2OC)C(C)(C)C1] 1-(4-(2-methoxy-4-methyl-5-((2-(pyridin-2-ylamino)thiazol-5-yl)thio)benzoyl)-3,3-dimethylpiperazin-1-yl)prop-2-en-1-one | Compound 160 MS (M + H) 523.6 | D |
| 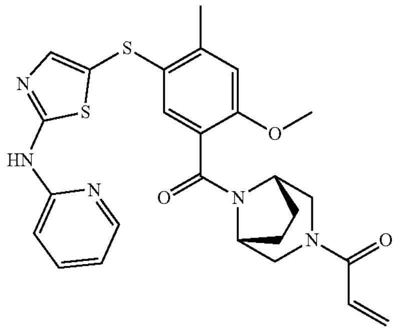 [SMILES: C=CC(=O)N1C[C@H]2CC[C@@H](C1)N2C(=O)c1cc(Sc2cnc(Nc3ccccn3)s2)c(C)cc1OC] 1-((1R,5S)-8-(2-methoxy-4-methyl-5-((2-(pyridin-2-ylamino)thiazol-5-yl)thio)benzoyl)-3,8-diazabicyclo[3.2.1]octan-3-yl)prop-2-en-1-one | Compound 161 MS (M + H) 521.6 | D |
| 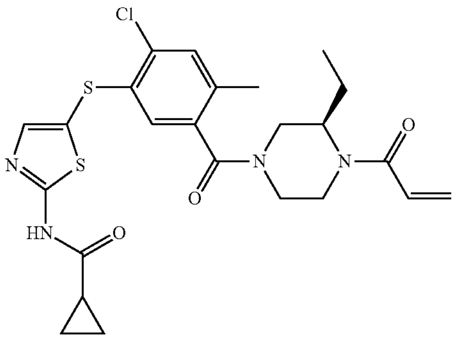 [SMILES: C=CC(=O)N1CCN(C(=O)c2cc(Sc3cnc(NC(=O)C4CC4)s3)c(Cl)cc2C)C[C@H]1CC] N-[5-[2-chloro-5-[(3R)-3-ethyl-4-prop-2-enoyl-piperazine-1-carbonyl]-4-methyl-phenyl]sulfanylthiazol-2-yl]cyclopropanecarboxamide | Compound 101 MS 519.0 (M + H) | A/F |

TABLE 1-continued

| Final compounds (structures, names, masses and methods used for their synthesis) | | |
|---|---|---|
| Compound | MS (ES) m/z | Method Used |
| 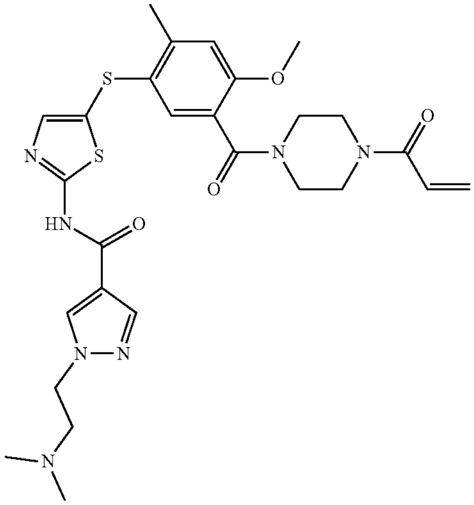 [SMILES: C=CC(=O)N1CCN(C(=O)c2cc(Sc3cnc(NC(=O)c4cnn(CCN(C)C)c4)s3)c(C)cc2OC)CC1] 1-[2-(dimethylamino)ethyl ]-N-[5-14-methoxy-2-methyl-5-(4-prop-2-enoylpiperazine-1-carbonyl)phenyl]sulfanylthiazol-2-yl]pyrazole-4-carboxamide | Compound 102 MS 584.2 (M + H) | C |
| 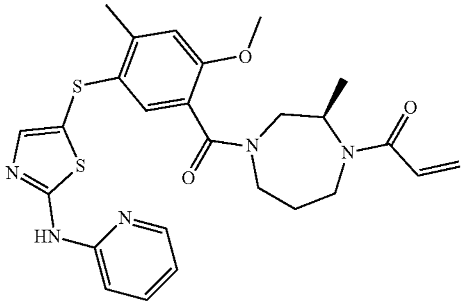 [SMILES: C=CC(=O)N1CCCN(C(=O)c2cc(Sc3cnc(Nc4ccccn4)s3)c(C)cc2OC)C[C@H]1C] 1-[(2R)-4-[2-methoxy-4-methyl-5-[2-(2-pyridylamino)thiazol-5-yl]sulfanyl-benzoyl]-2-methyl-1,4-diazepan-1-yl]prop-2-en-1-one | Compound 103 MS 524.2 (M + H) | D |

TABLE 2

| Compound | Compound name and IC50s |
|---|---|
| Compounds and IC50 values against select targets. IC50 ranges: A < 10 nM, 10 nM <= B < 100 nM, 100 nM <= C < 1000 nM, 1000 nM <= D < 10000, 10000 <= E. | |
| 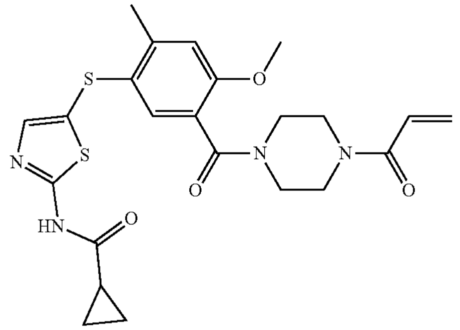 [SMILES: C=CC(=O)N1CCN(C(=O)c2cc(Sc3cnc(NC(=O)C4CC4)s3)c(C)cc2OC)CC1] | Compound 1<br>ITK (nM) A<br>TXK (nM) A<br>TXK/ITK 7.378<br>JAK3 (nM) C<br>BTK (nM) C |
| 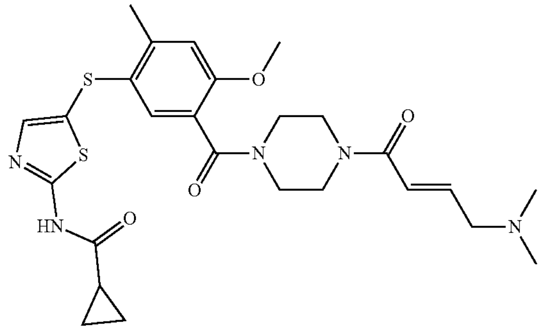 [SMILES: COc1cc(C)c(Sc2cnc(NC(=O)C3CC3)s2)cc1C(=O)N1CCN(C(=O)/C=C/CN(C)C)CC1] | Compound 3<br>ITK (nM) B<br>TXK (nM) C<br>TXK/ITK 5.162<br>JAK3 (nM) E<br>BTK (nM) D |
| 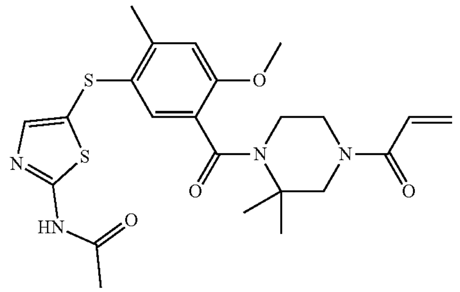 [SMILES: C=CC(=O)N1CCN(C(=O)c2cc(Sc3cnc(NC(C)=O)s3)c(C)cc2OC)C(C)(C)C1] | Compound 5<br>ITK (nM) A<br>TXK (nM) A<br>TXK/ITK 1.9721<br>JAK3 (nM) C<br>BTK (nM) B |
| 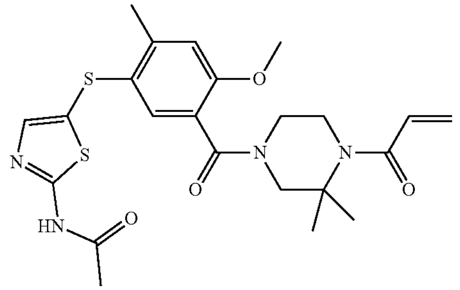 [SMILES: C=CC(=O)N1CCN(C(=O)c2cc(Sc3cnc(NC(C)=O)s3)c(C)cc2OC)CC1(C)C] | Compound 6<br>ITK (nM) B<br>TXK (nM) C<br>TXK/ITK 5.9566<br>JAK3 (nM) D<br>BTK (nM) D |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 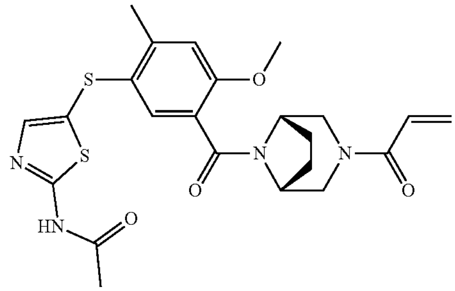 [SMILES: C=CC(=O)N1C[C@H]2CC[C@@H](C1)N2C(=O)c1cc(Sc2cnc(NC(C)=O)s2)c(C)cc1OC] | Compound 7<br>ITK (nM) A<br>TXK (nM) B<br>TXK/ITK 11.993<br>JAK3 (nM) B<br>BTK (nM) B |
| 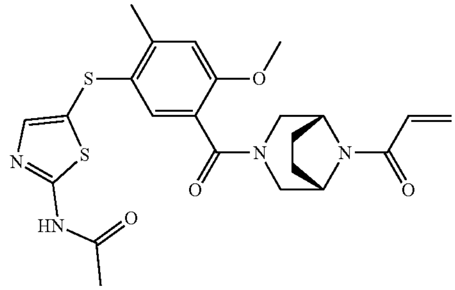 [SMILES: C=CC(=O)N1[C@@H]2CC[C@H]1CN(C(=O)c1cc(Sc3cnc(NC(C)=O)s3)c(C)cc1OC)C2] | Compound 8<br>ITK (nM) A<br>TXK (nM) B<br>TXK/ITK 11.265<br>JAK3 (nM) C<br>BTK (nM) B |
| 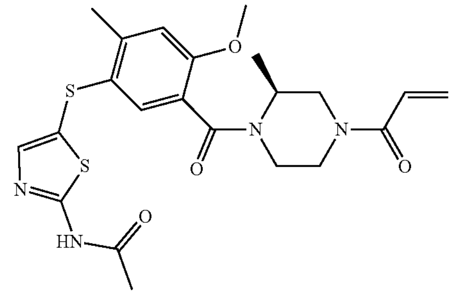 [SMILES: C=CC(=O)N1CCN(C(=O)c2cc(Sc3cnc(NC(C)=O)s3)c(C)cc2OC)[C@@H](C)C1] | Compound 9<br>ITK (nM) A<br>TXK (nM) B<br>TXK/ITK 14.236<br>JAK3 (nM) C<br>BTK (nM) C |
| 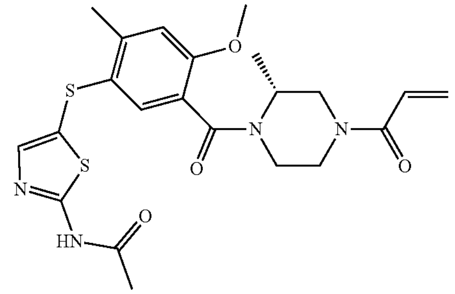 [SMILES: C=CC(=O)N1CCN(C(=O)c2cc(Sc3cnc(NC(C)=O)s3)c(C)cc2OC)[C@H](C)C1] | Compound 10<br>ITK (nM) B<br>TXK (nM) C<br>TXK/ITK 8.0758<br>JAK3 (nM) D<br>BTK (nM) C |
| 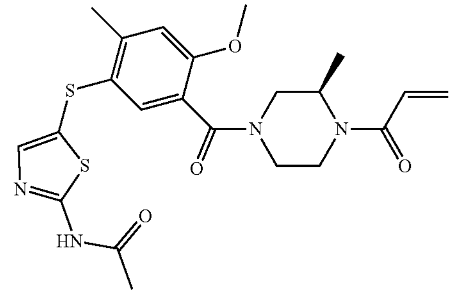 [SMILES: C=CC(=O)N1CCN(C(=O)c2cc(Sc3cnc(NC(C)=O)s3)c(C)cc2OC)C[C@H]1C] | Compound 11<br>ITK (nM) A<br>TXK (nM) C<br>TXK/ITK 25.051<br>JAK3 (nM) D<br>BTK (nM) D |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 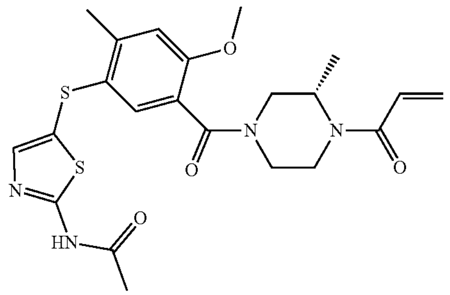 [SMILES: C=CC(=O)N1CCN(C(=O)c2cc(Sc3cnc(NC(C)=O)s3)c(C)cc2OC)C[C@@H]1C] | Compound 12<br>ITK (nM) B<br>TXK (nM) C<br>TXK/ITK 14.784<br>JAK3 (nM) C<br>BTK (nM) C |
| 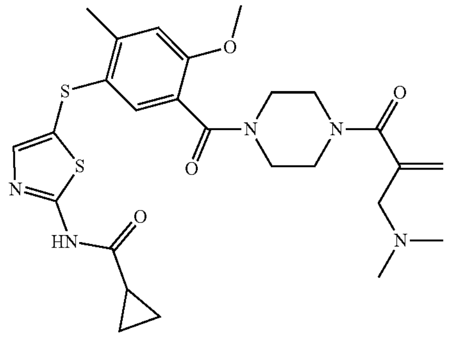 [SMILES: C=C(CN(C)C)C(=O)N1CCN(C(=O)c2cc(Sc3cnc(NC(=O)C4CC4)s3)c(C)cc2OC)CC1] | Compound 13<br>ITK (nM) B<br>TXK (nM) C<br>TXK/ITK 22.987<br>JAK3 (nM) D<br>BTK (nM) D |
| 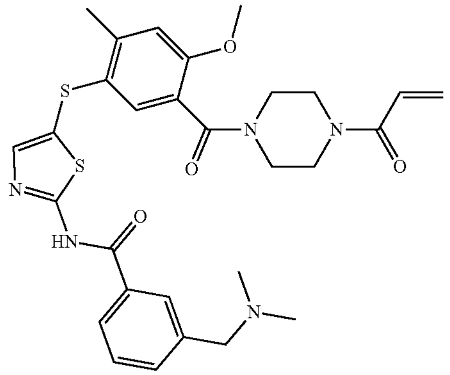 [SMILES: C=CC(=O)N1CCN(C(=O)c2cc(Sc3cnc(NC(=O)c4cccc(CN(C)C)c4)s3)c(C)cc2OC)CC1] | Compound 14<br>ITK (nM) A<br>TXK (nM) C<br>TXK/ITK 79.163<br>JAK3 (nM) D<br>BTK (nM) C |
| 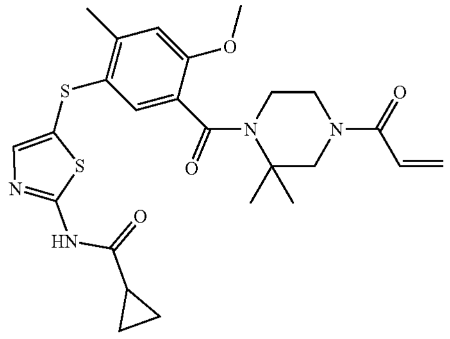 [SMILES: C=CC(=O)N1CCN(C(=O)c2cc(Sc3cnc(NC(=O)C4CC4)s3)c(C)cc2OC)C(C)(C)C1] | Compound 15<br>ITK (nM) A<br>TXK (nM) A<br>TXK/ITK 1.1111<br>JAK3 (nM) B<br>BTK (nM) A |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 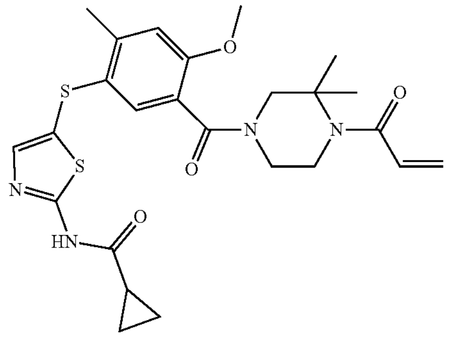 [SMILES: C=CC(=O)N1CCN(C(=O)c2cc(Sc3cnc(NC(=O)C4CC4)s3)c(C)cc2OC)CC1(C)C] | Compound 16<br>ITK (nM) B<br>TXK (nM) B<br>TXK/ITK 4.9287<br>JAK3 (nM) C<br>BTK (nM) C |
| 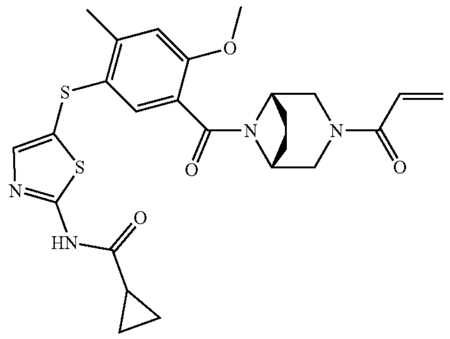 [SMILES: C=CC(=O)N1C[C@H]2CC[C@@H](C1)N2C(=O)c1cc(Sc2cnc(NC(=O)C3CC3)s2)c(C)cc1OC] | Compound 17<br>ITK (nM) A<br>TXK (nM) A<br>TXK/ITK 5.4235<br>JAK3 (nM) B<br>BTK (nM) A |
| 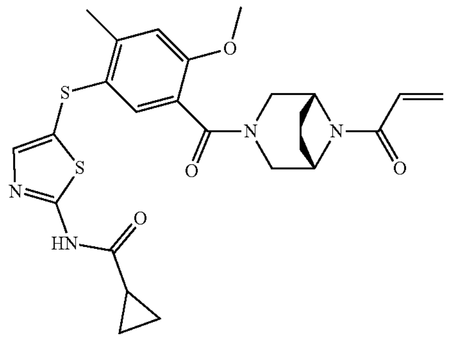 [SMILES: C=CC(=O)N1[C@@H]2CC[C@H]1CN(C(=O)c1cc(Sc3cnc(NC(=O)C4CC4)s3)c(C)cc1OC)C2] | Compound 18<br>ITK (nM) A<br>TXK (nM) A<br>TXK/ITK 2.8993<br>JAK3 (nM) B<br>BTK (nM) B |
| 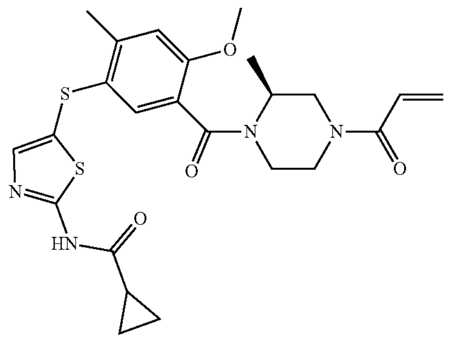 [SMILES: C=CC(=O)N1CCN(C(=O)c2cc(Sc3cnc(NC(=O)C4CC4)s3)c(C)cc2OC)[C@@H](C)C1] | Compound 19<br>ITK (nM) A<br>TXK (nM) A<br>TXK/ITK 6.5873<br>JAK3 (nM) C<br>BTK (nM) B |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 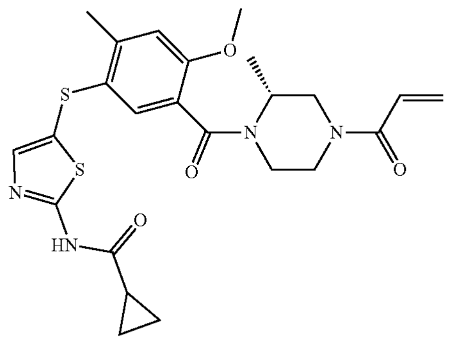 [SMILES: C=CC(=O)N1CCN(C(=O)c2cc(Sc3cnc(NC(=O)C4CC4)s3)c(C)cc2OC)[C@H](C)C1] | Compound 20<br>ITK (nM) A<br>TXK (nM) B<br>TXK/ITK 2.2433<br>JAK3 (nM) C<br>BTK (nM) C |
| 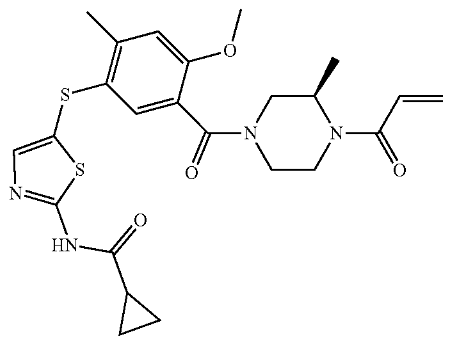 [SMILES: C=CC(=O)N1CCN(C(=O)c2cc(Sc3cnc(NC(=O)C4CC4)s3)c(C)cc2OC)C[C@H]1C] | Compound 21<br>ITK (nM) A<br>TXK (nM) B<br>TXK/ITK 22.223<br>JAK3 (nM) C<br>BTK (nM) C |
| 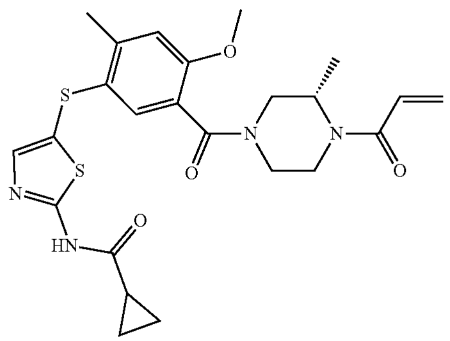 [SMILES: C=CC(=O)N1CCN(C(=O)c2cc(Sc3cnc(NC(=O)C4CC4)s3)c(C)cc2OC)C[C@@H]1C] | Compound 22<br>ITK (nM) A<br>TXK (nM) B<br>TXK/ITK 6.7674<br>JAK3 (nM) C<br>BTK (nM) C |
| 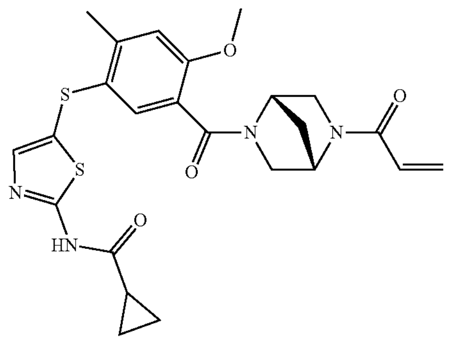 [SMILES: C=CC(=O)N1C[C@@H]2C[C@H]1CN2C(=O)c1cc(Sc2cnc(NC(=O)C3CC3)s2)c(C)cc1OC] | Compound 23<br>ITK (nM) A<br>TXK (nM) A<br>TXK/ITK 1.4139<br>JAK3 (nM) B<br>BTK (nM) A |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 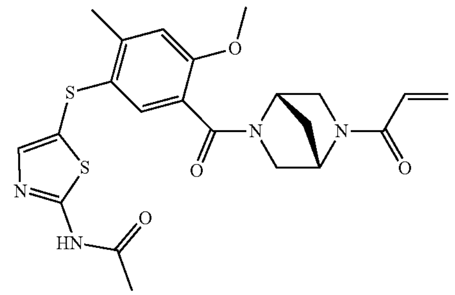 [SMILES: C=CC(=O)N1C[C@@H]2C[C@H]1CN2C(=O)c1cc(Sc2cnc(NC(C)=O)s2)c(C)cc1OC] | Compound 24<br>ITK (nM) A<br>TXK (nM) B<br>TXK/ITK 6.6876<br>JAK3 (nM) C<br>BTK (nM) B |
| 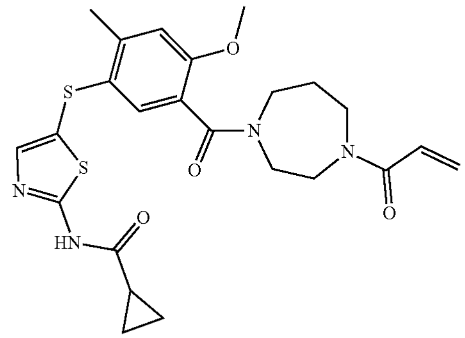 [SMILES: C=CC(=O)N1CCCN(C(=O)c2cc(Sc3cnc(NC(=O)C4CC4)s3)c(C)cc2OC)CC1] | Compound 25<br>ITK (nM) A<br>TXK (nM) B<br>TXK/ITK 20.879<br>JAK3 (nM) C<br>BTK (nM) C |
| 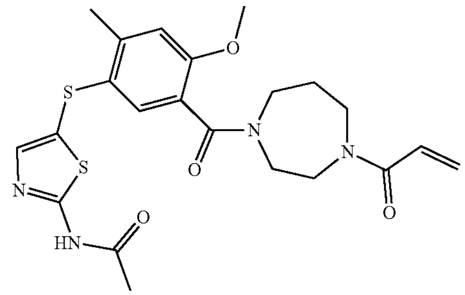 [SMILES: C=CC(=O)N1CCCN(C(=O)c2cc(Sc3cnc(NC(C)=O)s3)c(C)cc2OC)CC1] | Compound 26<br>ITK (nM) B<br>TXK (nM) C<br>TXK/ITK 26.486<br>JAK3 (nM) D<br>BTK (nM) D |
| 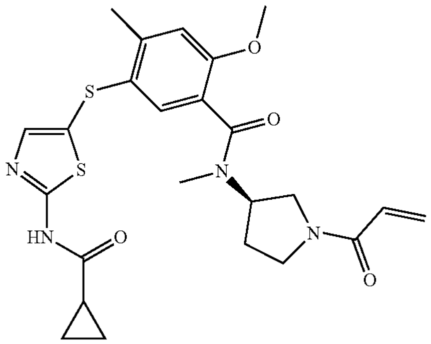 [SMILES: C=CC(=O)N1CC[C@@H](N(C)C(=O)c2cc(Sc3cnc(NC(=O)C4CC4)s3)c(C)cc2OC)C1] | Compound 27<br>ITK (nM) A<br>TXK (nM) A<br>TXK/ITK 2.0165<br>JAK3 (nM) A<br>BTK (nM) A |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 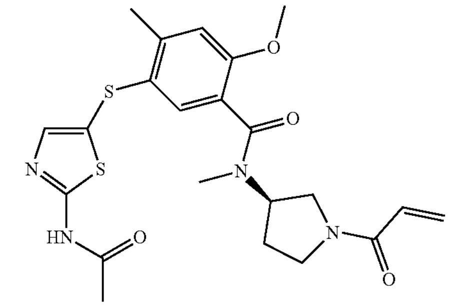 [SMILES: C=CC(=O)N1CC[C@@H](N(C)C(=O)c2cc(Sc3cnc(NC(C)=O)s3)c(C)cc2OC)C1] | Compound 28<br>ITK (nM) A<br>TXK (nM) B<br>TXK/ITK 5.5925<br>JAK3 (nM) B<br>BTK (nM) A |
| 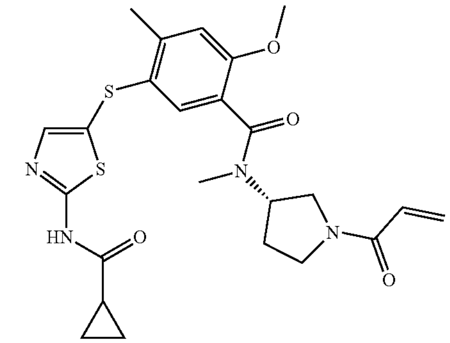 [SMILES: C=CC(=O)N1CC[C@H](N(C)C(=O)c2cc(Sc3cnc(NC(=O)C4CC4)s3)c(C)cc2OC)C1] | Compound 29<br>ITK (nM) A<br>TXK (nM) A<br>TXK/ITK 2.1804<br>JAK3 (nM) C<br>BTK (nM) C |
| 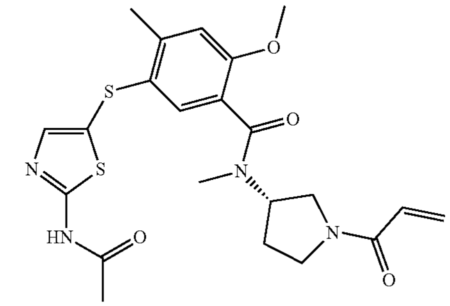 [SMILES: C=CC(=O)N1CC[C@H](N(C)C(=O)c2cc(Sc3cnc(NC(C)=O)s3)c(C)cc2OC)C1] | Compound 30<br>ITK (nM) B<br>TXK (nM) B<br>TXK/ITK 3.101<br>JAK3 (nM) D<br>BTK (nM) C |
| 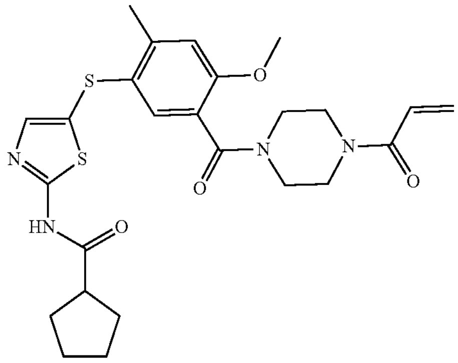 [SMILES: C=CC(=O)N1CCN(C(=O)c2cc(Sc3cnc(NC(=O)C4CCCC4)s3)c(C)cc2OC)CC1] | Compound 31<br>ITK (nM) B<br>TXK (nM) C<br>TXK/ITK 19.291<br>JAK3 (nM) D<br>BTK (nM) D |

TABLE 2-continued
Compounds and IC50 values against select targets. IC50 ranges: A < 10 nM, 10 nM <= B < 100 nM, 100 nM <= C < 1000 nM, 1000 nM <= D < 10000, 10000 <= E.
| Compound | Compound name and IC50s |
|---|---|
| 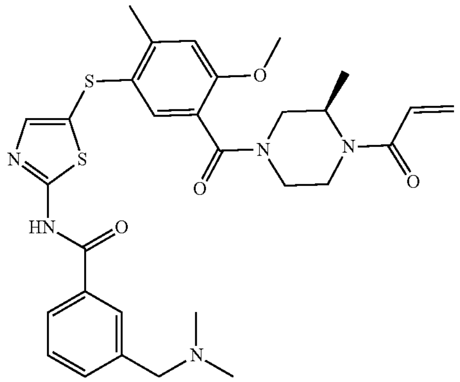 [SMILES: C=CC(=O)N1CCN(C(=O)c2cc(Sc3cnc(NC(=O)c4cccc(CN(C)C)c4)s3)c(C)cc2OC)C[C@H]1C] | Compound 32<br>ITK (nM) A<br>TXK (nM) C<br>TXK/ITK 81.114<br>JAK3 (nM) D<br>BTK (nM) C |
| 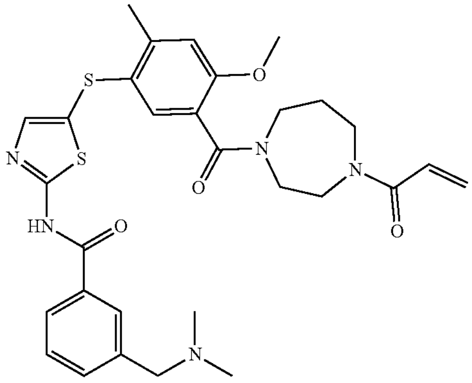 [SMILES: C=CC(=O)N1CCCN(C(=O)c2cc(Sc3cnc(NC(=O)c4cccc(CN(C)C)c4)s3)c(C)cc2OC)CC1] | Compound 33<br>ITK (nM) A<br>TXK (nM) D<br>TXK/ITK 239.91<br>JAK3 (nM) D<br>BTK (nM) C |
| 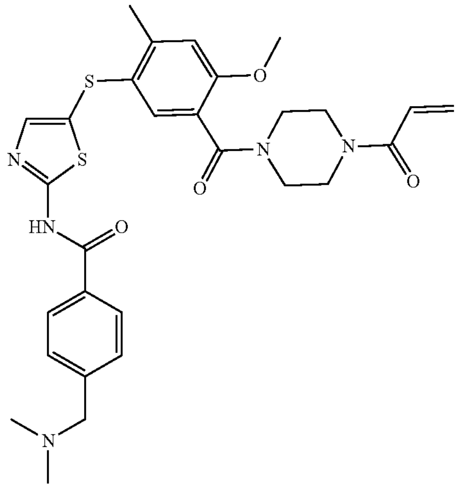 [SMILES: C=CC(=O)N1CCN(C(=O)c2cc(Sc3cnc(NC(=O)c4ccc(CN(C)C)cc4)s3)c(C)cc2OC)CC1] | Compound 34<br>ITK (nM) A<br>TXK (nM) B<br>TXK/ITK 33.121<br>JAK3 (nM) C<br>BTK (nM) B |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 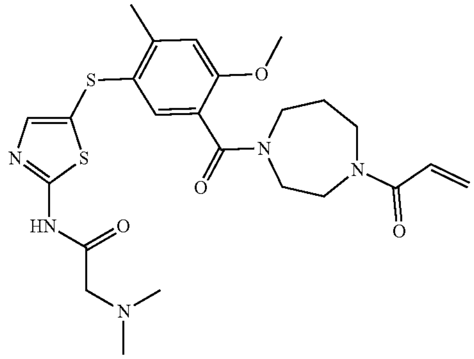 [SMILES: C=CC(=O)N1CCCN(C(=O)c2cc(Sc3cnc(NC(=O)CN(C)C)s3)c(C)cc2OC)CC1] | Compound 35<br>ITK (nM) C<br>TXK (nM) E<br>TXK/ITK 48.433<br>JAK3 (nM) E<br>BTK (nM) E |
| 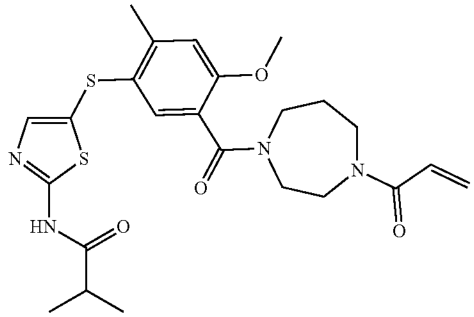 [SMILES: C=CC(=O)N1CCCN(C(=O)c2cc(Sc3cnc(NC(=O)C(C)C)s3)c(C)cc2OC)CC1] | Compound 36<br>ITK (nM) B<br>TXK (nM) D<br>TXK/ITK 72.34<br>JAK3 (nM) E<br>BTK (nM) D |
| 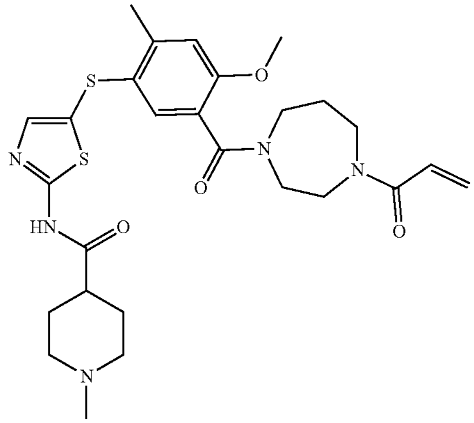 [SMILES: C=CC(=O)N1CCCN(C(=O)c2cc(Sc3cnc(NC(=O)C4CCN(C)CC4)s3)c(C)cc2OC)CC1] | Compound 37<br>ITK (nM) C<br>TXK (nM) E<br>TXK/ITK 46.119<br>JAK3 (nM) E<br>BTK (nM) E |
| 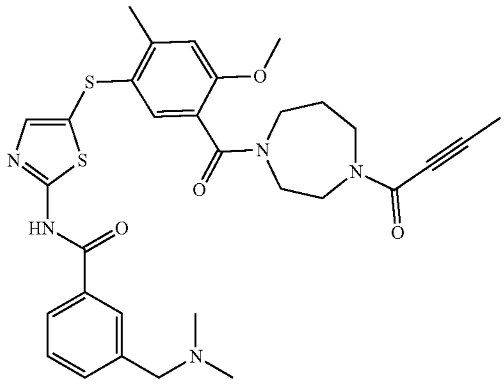 [SMILES: CC#CC(=O)N1CCCN(C(=O)c2cc(Sc3cnc(NC(=O)c4cccc(CN(C)C)c4)s3)c(C)cc2OC)CC1] | Compound 38<br>ITK (nM) B<br>TXK (nM) D<br>TXK/ITK 28.189<br>JAK3 (nM) E<br>BTK (nM) D |

TABLE 2-continued
Compounds and IC50 values against select targets. IC50 ranges: A < 10 nM, 10 nM <= B < 100 nM, 100 nM <= C < 1000 nM, 1000 nM <= D < 10000, 10000 <= E.
| Compound | Compound name and IC50s |
|---|---|
| 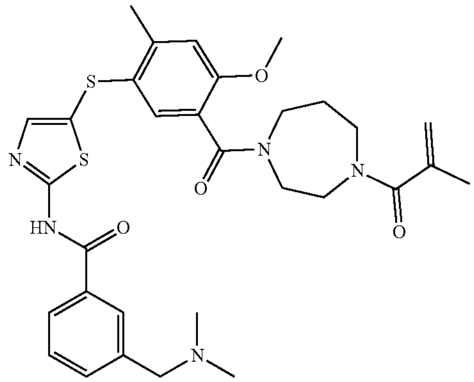 [SMILES: C=C(C)C(=O)N1CCCN(C(=O)c2cc(Sc3cnc(NC(=O)c4cccc(CN(C)C)c4)s3)c(C)cc2OC)CC1] | Compound 39<br>ITK (nM) C<br>TXK (nM) D<br>TXK/ITK 1.5<br>JAK3 (nM) E<br>BTK (nM) E |
| 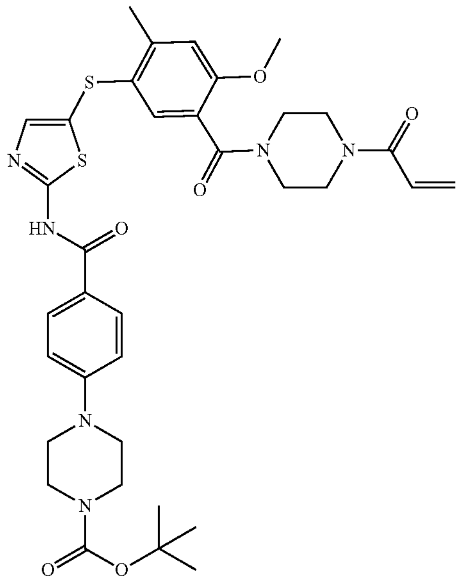 [SMILES: C=CC(=O)N1CCN(C(=O)c2cc(Sc3cnc(NC(=O)c4ccc(N5CCN(C(=O)OC(C)(C)C)CC5)cc4)s3)c(C)cc2OC)CC1] | Compound 40<br>ITK (nM) A<br>TXK (nM) B<br>TXK/ITK 14.491<br>JAK3 (nM) C<br>BTK (nM) C |

TABLE 2-continued
| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 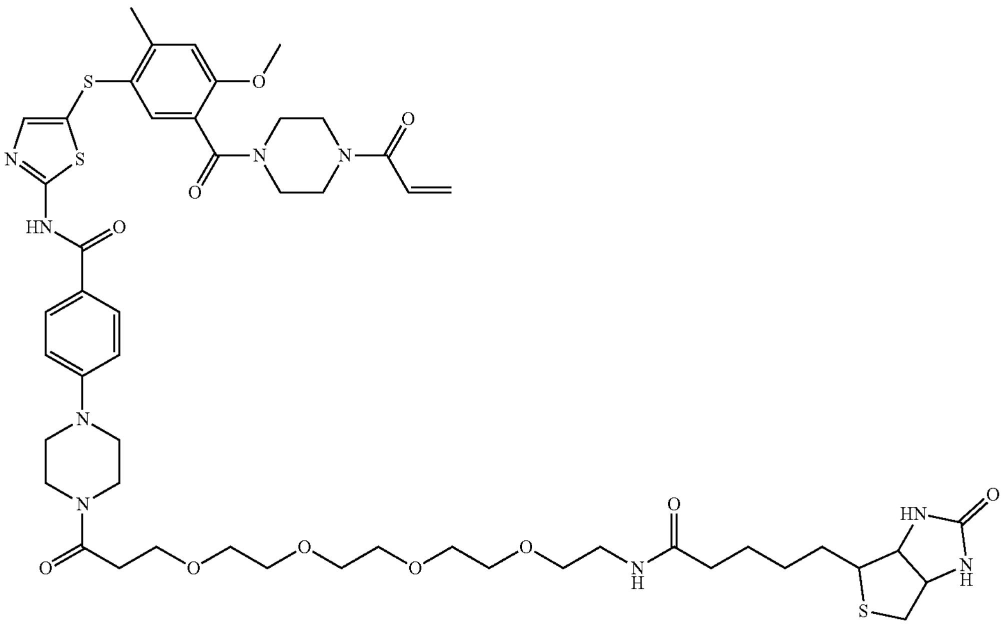 [SMILES: C=CC(=O)N1CCN(C(=O)c2cc(Sc3cnc(NC(=O)c4ccc(N5CCN(C(=O)CCOCCOCCOCCOCCNC(=O)CCCCC6SCC7NC(=O)NC76)CC5)cc4)s3)c(C)cc2OC)CC1] | Compound 41 ITK (nM) A TXK (nM) B TXK/ITK 21.91 JAK3 (nM) B BTK (nM) B |
| 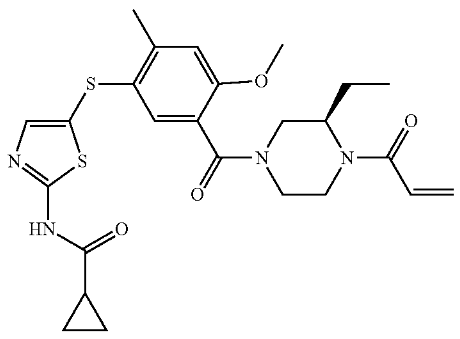 [SMILES: C=CC(=O)N1CCN(C(=O)c2cc(Sc3cnc(NC(=O)C4CC4)s3)c(C)cc2OC)C[C@H]1CC] | Compound 42 ITK (nM) A TXK (nM) B TXK/ITK 10.152 JAK3 (nM) D BTK (nM) D |
| 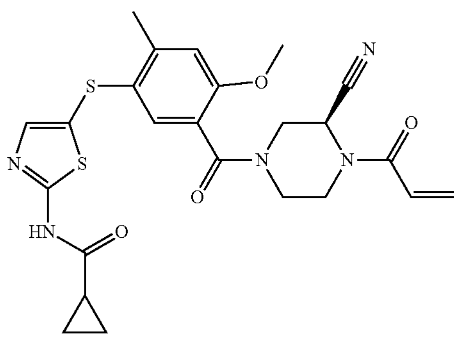 [SMILES: C=CC(=O)N1CCN(C(=O)c2cc(Sc3cnc(NC(=O)C4CC4)s3)c(C)cc2OC)C[C@H]1C#N] | Compound 43 ITK (nM) A TXK (nM) A TXK/ITK 3.4821 JAK3 (nM) B BTK (nM) B |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 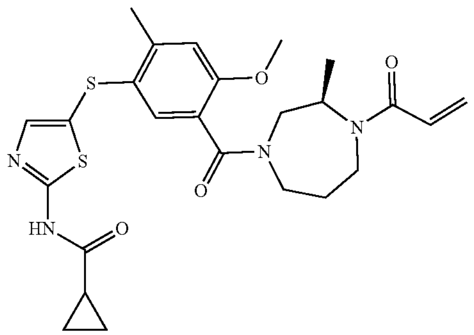 [SMILES: C=CC(=O)N1CCCN(C(=O)c2cc(Sc3cnc(NC(=O)C4CC4)s3)c(C)cc2OC)C[C@H]1C] | Compound 44<br>ITK (nM) A<br>TXK (nM) C<br>TXK/ITK 116.56<br>JAK3 (nM) D<br>BTK (nM) C |
| 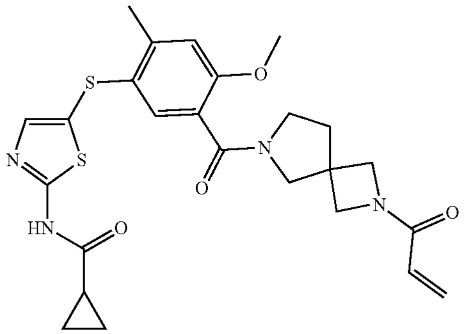 [SMILES: C=CC(=O)N1CC2(CCN(C(=O)c3cc(Sc4cnc(NC(=O)C5CC5)s4)c(C)cc3OC)C2)C1] | Compound 45<br>ITK (nM) A<br>TXK (nM) A<br>TXK/ITK 4.1551<br>JAK3 (nM) B<br>BTK (nM) B |
| 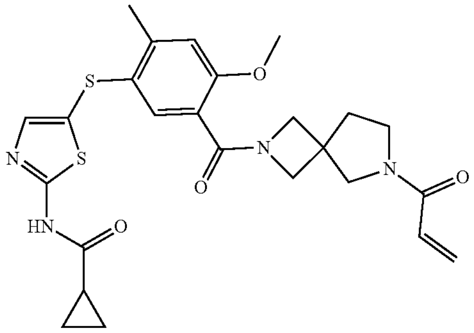 [SMILES: C=CC(=O)N1CCC2(C1)CN(C(=O)c1cc(Sc3cnc(NC(=O)C4CC4)s3)c(C)cc1OC)C2] | Compound 46<br>ITK (nM) A<br>TXK (nM) A<br>TXK/ITK 3.4072<br>JAK3 (nM) C<br>BTK (nM) B |
| 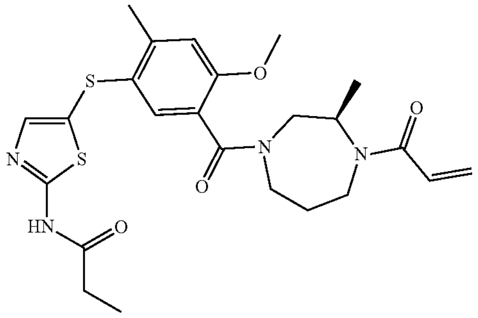 [SMILES: C=CC(=O)N1CCCN(C(=O)c2cc(Sc3cnc(NC(=O)CC)s3)c(C)cc2OC)C[C@H]1C] | Compound 47<br>ITK (nM) B<br>TXK (nM) E<br>TXK/ITK 181.42<br>JAK3 (nM) E<br>BTK (nM) E |

TABLE 2-continued
| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 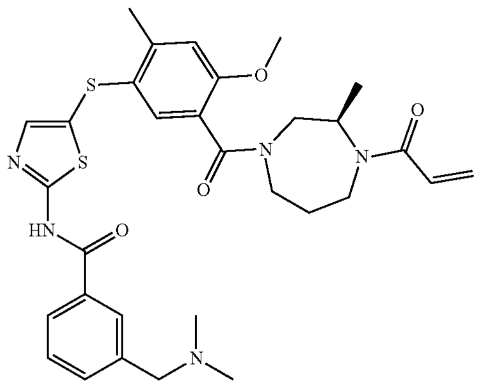 [SMILES: C=CC(=O)N1CCCN(C(=O)c2cc(Sc3cnc(NC(=O)c4cccc(CN(C)C)c4)s3)c(C)cc2OC)C[C@H]1C] | Compound 48<br>ITK (nM) B<br>TXK (nM) E<br>TXK/ITK 519.55<br>JAK3 (nM) E<br>BTK (nM) D |
| 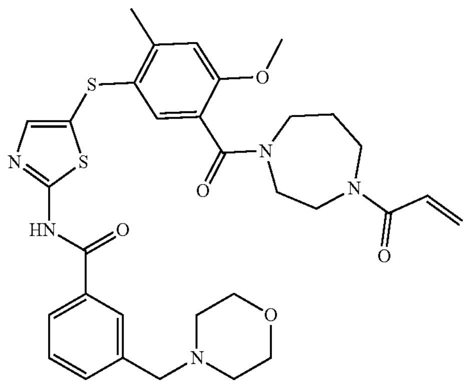 [SMILES: C=CC(=O)N1CCCN(C(=O)c2cc(Sc3cnc(NC(=O)c4cccc(CN5CCOCC5)c4)s3)c(C)cc2OC)CC1] | Compound 49<br>ITK (nM) B<br>TXK (nM) D<br>TXK/ITK 37.652<br>JAK3 (nM) D<br>BTK (nM) D |
| 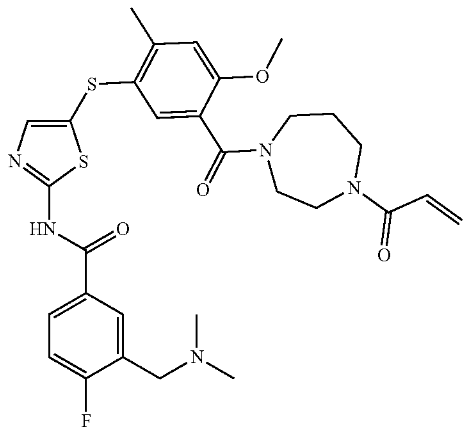 [SMILES: C=CC(=O)N1CCCN(C(=O)c2cc(Sc3cnc(NC(=O)c4ccc(F)c(CN(C)C)c4)s3)c(C)cc2OC)CC1] | Compound 50<br>ITK (nM) A<br>TXK (nM) D<br>TXK/ITK 230.63<br>JAK3 (nM) D<br>BTK (nM) C |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 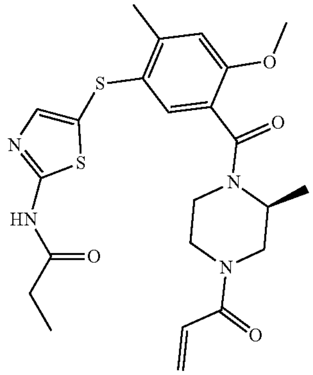 [SMILES: C=CC(=O)N1CCN(C(=O)c2cc(Sc3cnc(NC(=O)CC)s3)c(C)cc2OC)[C@@H](C)C1] | Compound 51<br>ITK (nM) A<br>TXK (nM) B<br>TXK/ITK 14.645<br>JAK3 (nM) D<br>BTK (nM) C |
| 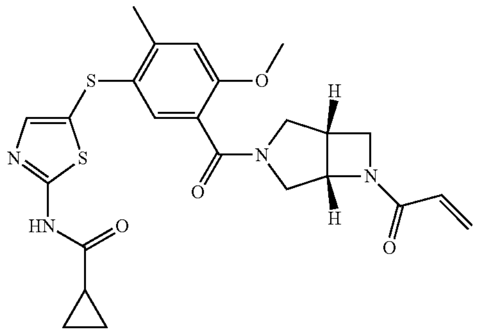 [SMILES: C=CC(=O)N1C[C@H]2CN(C(=O)c3cc(Sc4cnc(NC(=O)C5CC5)s4)c(C)cc3OC)C[C@H]21] | Compound 52<br>ITK (nM) A<br>TXK (nM) B<br>TXK/ITK 30.127<br>JAK3 (nM) D<br>BTK (nM) C |
| 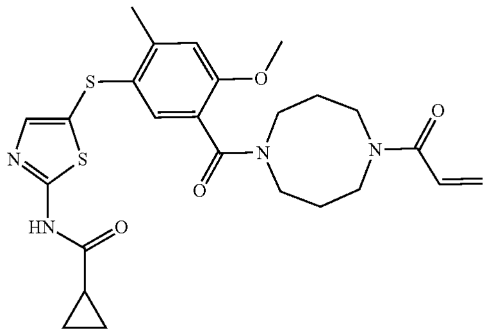 [SMILES: C=CC(=O)N1CCCN(C(=O)c2cc(Sc3cnc(NC(=O)C4CC4)s3)c(C)cc2OC)CCC1] | Compound 53<br>ITK (nM) A<br>TXK (nM) C<br>TXK/ITK 22.871<br>JAK3 (nM) D<br>BTK (nM) C |
| 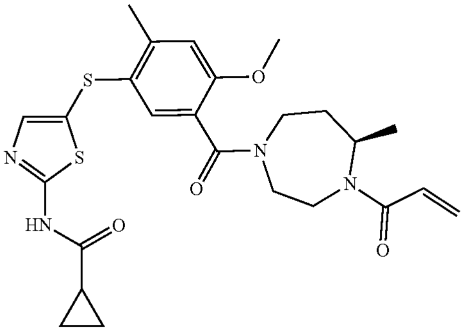 [SMILES: C=CC(=O)N1CCN(C(=O)c2cc(Sc3cnc(NC(=O)C4CC4)s3)c(C)cc2OC)CC[C@H]1C] | Compound 54<br>ITK (nM) B<br>TXK (nM) B<br>TXK/ITK 0.804<br>JAK3 (nM) D<br>BTK (nM) D |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 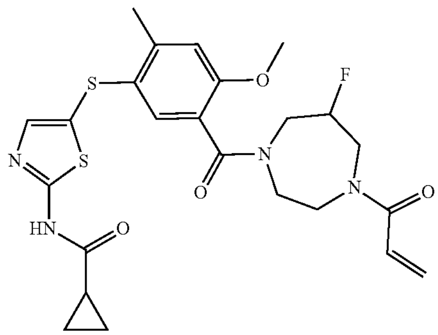 [SMILES: C=CC(=O)N1CCN(C(=O)c2cc(Sc3cnc(NC(=O)C4CC4)s3)c(C)cc2OC)CC(F)C1] | Compound 55<br>ITK (nM) A<br>TXK (nM) A<br>TXK/ITK 6.2416<br>JAK3 (nM) B<br>BTK (nM) B |
| 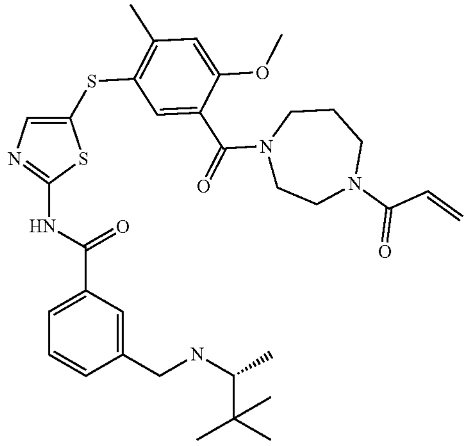 [SMILES: C=CC(=O)N1CCCN(C(=O)c2cc(Sc3cnc(NC(=O)c4cccc(CN[C@H](C)C(C)(C)C)c4)s3)c(C)cc2OC)CC1] | Compound 56<br>ITK (nM) A<br>TXK (nM) D<br>TXK/ITK 168.17<br>JAK3 (nM) D<br>BTK (nM) C |
| 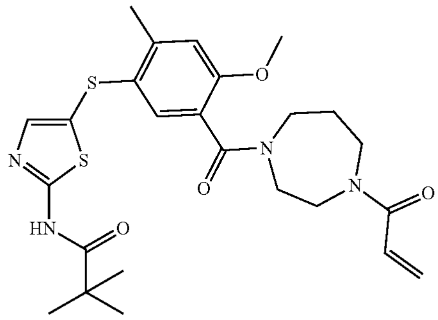 [SMILES: C=CC(=O)N1CCCN(C(=O)c2cc(Sc3cnc(NC(=O)C(C)(C)C)s3)c(C)cc2OC)CC1] | Compound 57<br>ITK (nM) C<br>TXK (nM) E<br>TXK/ITK 15.564<br>JAK3 (nM) E<br>BTK (nM) E |
| 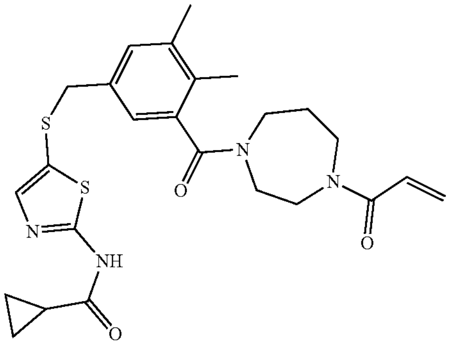 [SMILES: C=CC(=O)N1CCCN(C(=O)c2cc(CSc3cnc(NC(=O)C4CC4)s3)cc(C)c2C)CC1] | Compound 58<br>ITK (nM) D<br>TXK (nM) D<br>TXK/ITK 2.9749<br>JAK3 (nM) D<br>BTK (nM) E |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 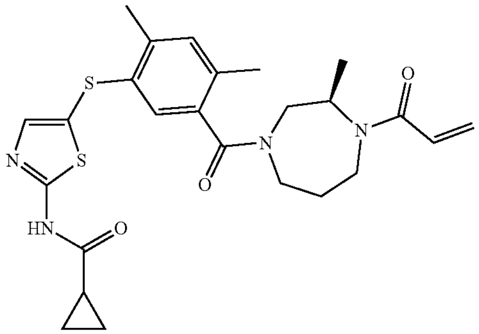 [SMILES: C=CC(=O)N1CCCN(C(=O)c2cc(Sc3cnc(NC(=O)C4CC4)s3)c(C)cc2C)C[C@H]1C] | Compound 59<br>ITK (nM) A<br>TXK (nM) C<br>TXK/ITK 166.05<br>JAK3 (nM) D<br>BTK (nM) D |
| 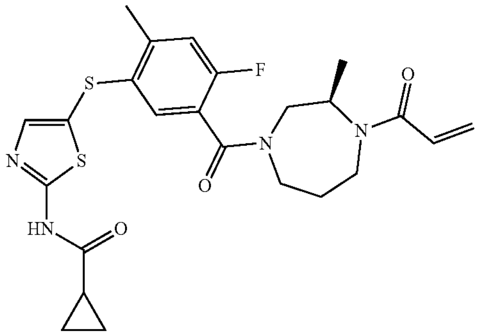 [SMILES: C=CC(=O)N1CCCN(C(=O)c2cc(Sc3cnc(NC(=O)C4CC4)s3)c(C)cc2F)C[C@H]1C] | Compound 60<br>ITK (nM) B<br>TXK (nM) D<br>TXK/ITK 21.785<br>JAK3 (nM) E<br>BTK (nM) E |
| 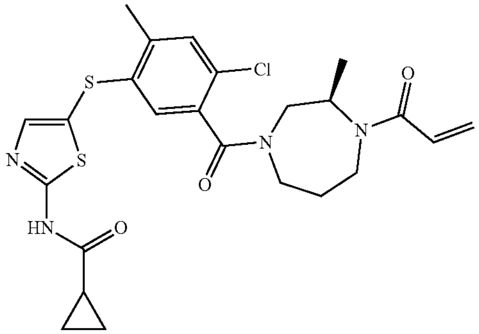 [SMILES: C=CC(=O)N1CCCN(C(=O)c2cc(Sc3cnc(NC(=O)C4CC4)s3)c(C)cc2Cl)C[C@H]1C] | Compound 61<br>ITK (nM) B<br>TXK (nM) C<br>TXK/ITK 50.716<br>JAK3 (nM) D<br>BTK (nM) E |
| 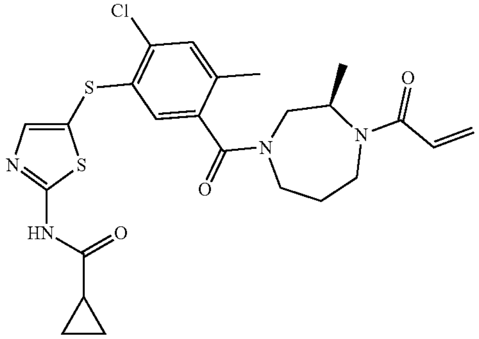 [SMILES: C=CC(=O)N1CCCN(C(=O)c2cc(Sc3cnc(NC(=O)C4CC4)s3)c(Cl)cc2C)C[C@H]1C] | Compound 62<br>ITK (nM) A<br>TXK (nM) D<br>TXK/ITK 320.16<br>JAK3 (nM) D<br>BTK (nM) D |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 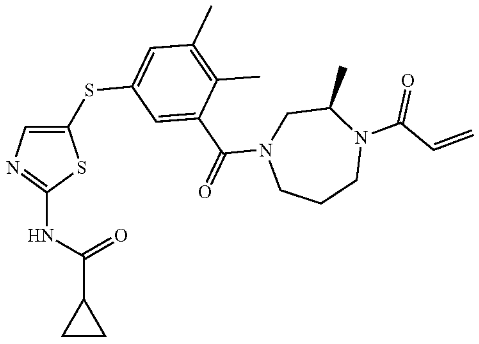 [SMILES: C=CC(=O)N1CCCN(C(=O)c2cc(Sc3cnc(NC(=O)C4CC4)s3)cc(C)c2C)C[C@H]1C] | Compound 63<br>ITK (nM) C<br>TXK (nM) D<br>TXK/ITK 61.086<br>JAK3 (nM) E<br>BTK (nM) E |
| 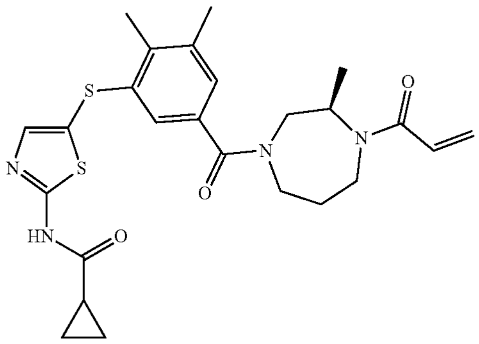 [SMILES: C=CC(=O)N1CCCN(C(=O)c2cc(C)c(C)c(Sc3cnc(NC(=O)C4CC4)s3)c2)C[C@H]1C] | Compound 64<br>ITK (nM) C<br>TXK (nM) D<br>TXK/ITK 11.944<br>JAK3 (nM) E<br>BTK (nM) E |
| 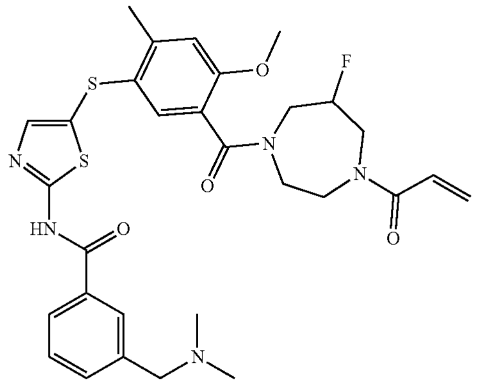 [SMILES: C=CC(=O)N1CCN(C(=O)c2cc(Sc3cnc(NC(=O)c4cccc(CN(C)C)c4)s3)c(C)cc2OC)CC(F)C1] | Compound 66<br>ITK (nM) A<br>TXK (nM) C<br>TXK/ITK 70.047<br>JAK3 (nM) C<br>BTK (nM) C |
| 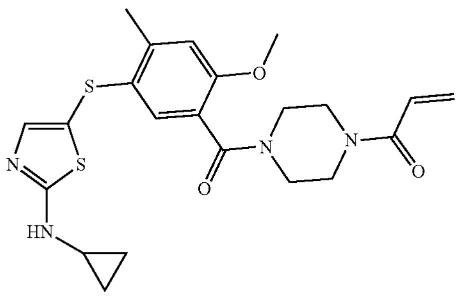 [SMILES: C=CC(=O)N1CCN(C(=O)c2cc(Sc3cnc(NC4CC4)s3)c(C)cc2OC)CC1] | Compound 67<br>ITK (nM) E<br>TXK (nM) D<br>TXK/ITK 0.634<br>JAK3 (nM) D<br>BTK (nM) E |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 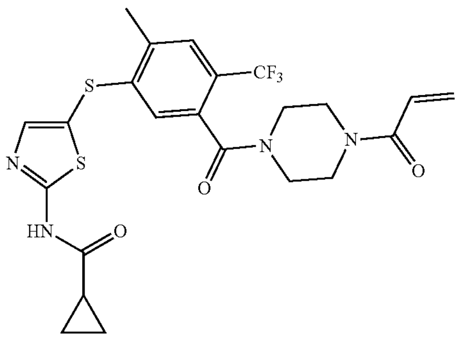 [SMILES: C=CC(=O)N1CCN(C(=O)c2cc(Sc3cnc(NC(=O)C4CC4)s3)c(C)cc2C(F)(F)F)CC1] | Compound 68<br>ITK (nM) B<br>TXK (nM) C<br>TXK/ITK 3.6548<br>JAK3 (nM) D<br>BTK (nM) E |
| 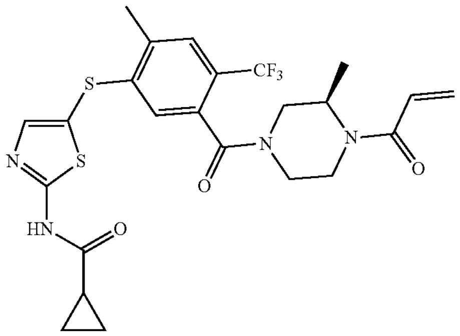 [SMILES: C=CC(=O)N1CCN(C(=O)c2cc(Sc3cnc(NC(=O)C4CC4)s3)c(C)cc2C(F)(F)F)C[C@H]1C] | Compound 69<br>ITK (nM) C<br>TXK (nM) C<br>TXK/ITK 4.9369<br>JAK3 (nM) D<br>BTK (nM) E |
| 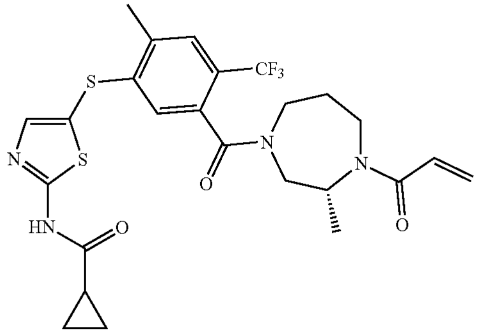 [SMILES: C=CC(=O)N1CCCN(C(=O)c2cc(Sc3cnc(NC(=O)C4CC4)s3)c(C)cc2C(F)(F)F)C[C@H]1C] | Compound 70<br>ITK (nM) B<br>TXK (nM) D<br>TXK/ITK 35.68<br>JAK3 (nM) E<br>BTK (nM) E |
| 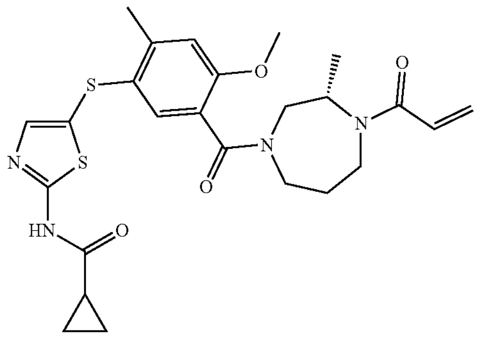 [SMILES: C=CC(=O)N1CCCN(C(=O)c2cc(Sc3cnc(NC(=O)C4CC4)s3)c(C)cc2OC)C[C@@H]1C] | Compound 71<br>ITK (nM) B<br>TXK (nM) C<br>TXK/ITK 16.128<br>JAK3 (nM) D<br>BTK (nM) D |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
| --- | --- |
| 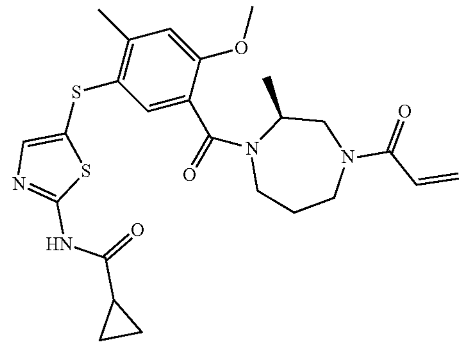 [SMILES: C=CC(=O)N1CCCN(C(=O)c2cc(Sc3cnc(NC(=O)C4CC4)s3)c(C)cc2OC)[C@@H](C)C1] | Compound 72<br>ITK (nM) C<br>TXK (nM) D<br>TXK/ITK 1.1846<br>JAK3 (nM) E<br>BTK (nM) E |
| 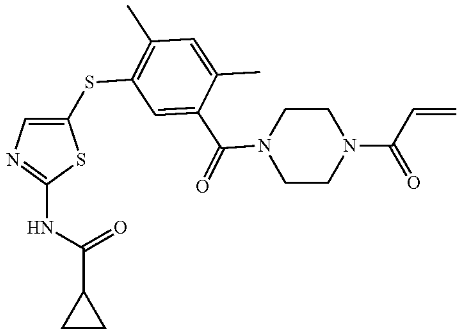 [SMILES: C=CC(=O)N1CCN(C(=O)c2cc(Sc3cnc(NC(=O)C4CC4)s3)c(C)cc2C)CC1] | Compound 73<br>ITK (nM) A<br>TXK (nM) B<br>TXK/ITK 3.2627<br>JAK3 (nM) C<br>BTK (nM) C |
| 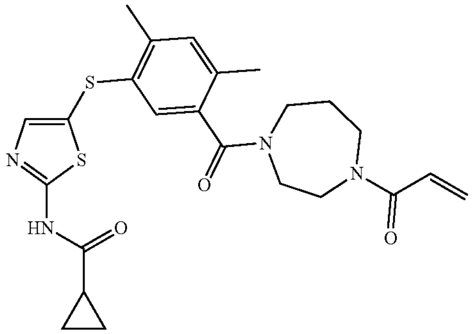 [SMILES: C=CC(=O)N1CCCN(C(=O)c2cc(Sc3cnc(NC(=O)C4CC4)s3)c(C)cc2C)CC1] | Compound 74<br>ITK (nM) A<br>TXK (nM) C<br>TXK/ITK 16.033<br>JAK3 (nM) C<br>BTK (nM) C |
| 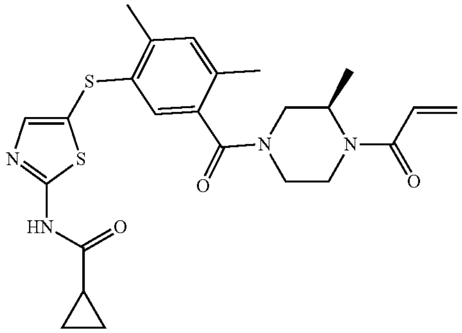 [SMILES: C=CC(=O)N1CCN(C(=O)c2cc(Sc3cnc(NC(=O)C4CC4)s3)c(C)cc2C)C[C@H]1C] | Compound 75<br>ITK (nM) A<br>TXK (nM) B<br>TXK/ITK 8.0145<br>JAK3 (nM) C<br>BTK (nM) D |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 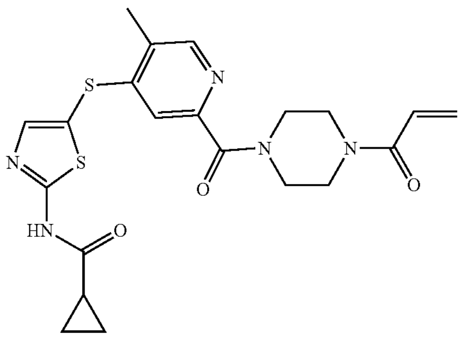 [SMILES: C=CC(=O)N1CCN(C(=O)c2cc(Sc3cnc(NC(=O)C4CC4)s3)c(C)cn2)CC1] | Compound 76<br>ITK (nM) E<br>TXK (nM) E<br>TXK/ITK 1<br>JAK3 (nM) E<br>BTK (nM) E |
| 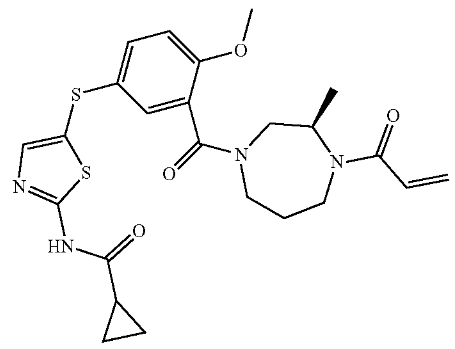 [SMILES: C=CC(=O)N1CCCN(C(=O)c2cc(Sc3cnc(NC(=O)C4CC4)s3)ccc2OC)C[C@H]1C] | Compound 77<br>ITK (nM) B<br>TXK (nM) D<br>TXK/ITK 95.398<br>JAK3 (nM) D<br>BTK (nM) E |
| 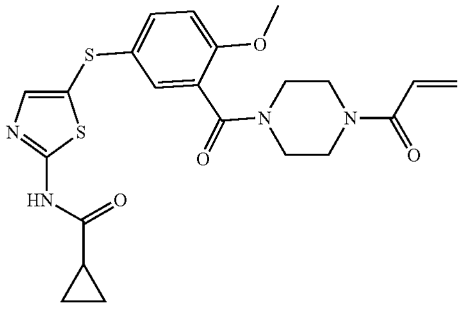 [SMILES: C=CC(=O)N1CCN(C(=O)c2cc(Sc3cnc(NC(=O)C4CC4)s3)ccc2OC)CC1] | Compound 78<br>ITK (nM) A<br>TXK (nM) B<br>TXK/ITK 10.586<br>JAK3 (nM) C<br>BTK (nM) C |
| 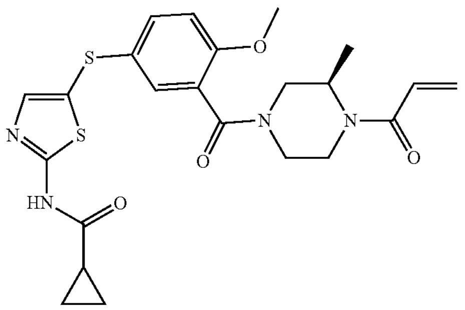 [SMILES: C=CC(=O)N1CCN(C(=O)c2cc(Sc3cnc(NC(=O)C4CC4)s3)ccc2OC)C[C@H]1C] | Compound 79<br>ITK (nM) B<br>TXK (nM) C<br>TXK/ITK 21.331<br>JAK3 (nM) C<br>BTK (nM) E |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 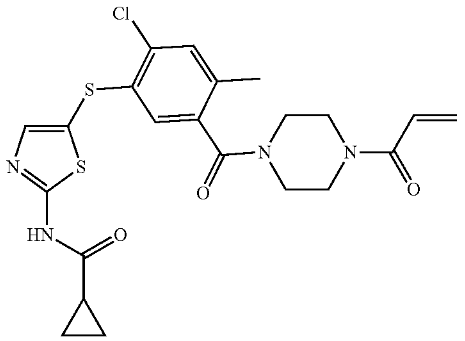 [SMILES: C=CC(=O)N1CCN(C(=O)c2cc(Sc3cnc(NC(=O)C4CC4)s3)c(Cl)cc2C)CC1] | Compound 80<br>ITK (nM) A<br>TXK (nM) B<br>TXK/ITK 8.1619<br>JAK3 (nM) B<br>BTK (nM) C |
| 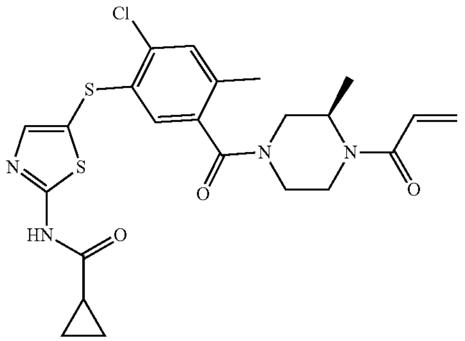 [SMILES: C=CC(=O)N1CCN(C(=O)c2cc(Sc3cnc(NC(=O)C4CC4)s3)c(Cl)cc2C)C[C@H]1C] | Compound 81<br>ITK (nM) A<br>TXK (nM) C<br>TXK/ITK 19.042<br>JAK3 (nM) C<br>BTK (nM) D |
| 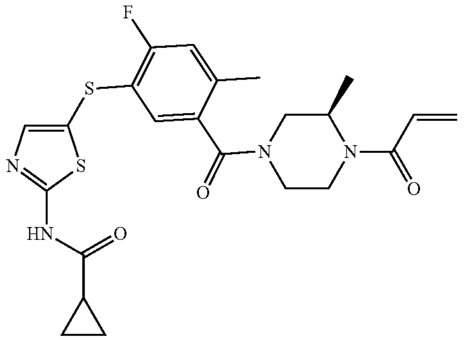 [SMILES: C=CC(=O)N1CCN(C(=O)c2cc(Sc3cnc(NC(=O)C4CC4)s3)c(F)cc2C)C[C@H]1C] | Compound 82<br>ITK (nM) B<br>TXK (nM) C<br>TXK/ITK 9.2468<br>JAK3 (nM) C<br>BTK (nM) E |
| 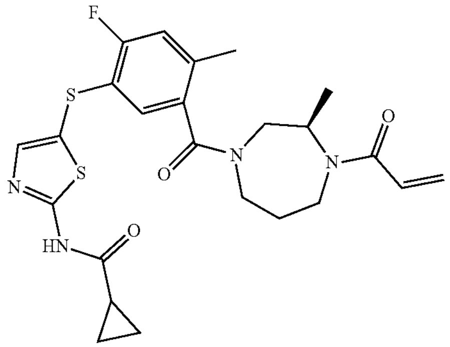 [SMILES: C=CC(=O)N1CCCN(C(=O)c2cc(Sc3cnc(NC(=O)C4CC4)s3)c(F)cc2C)C[C@H]1C] | Compound 83<br>ITK (nM) B<br>TXK (nM) D<br>TXK/ITK 45.317<br>JAK3 (nM) D<br>BTK (nM) E |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 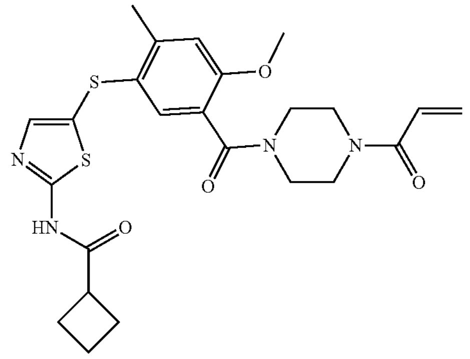 [SMILES: C=CC(=O)N1CCN(C(=O)c2cc(Sc3cnc(NC(=O)C4CCC4)s3)c(C)cc2OC)CC1] | Compound 84<br>ITK (nM) A<br>TXK (nM) B<br>TXK/ITK 21.948<br>JAK3 (nM) D<br>BTK (nM) D |
| 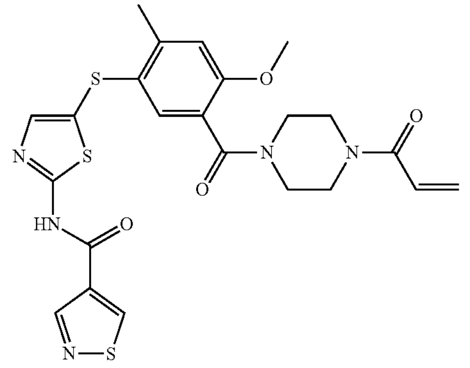 [SMILES: C=CC(=O)N1CCN(C(=O)c2cc(Sc3cnc(NC(=O)c4cnsc4)s3)c(C)cc2OC)CC1] | Compound 85<br>ITK (nM) A<br>TXK (nM) B<br>TXK/ITK 33.582<br>JAK3 (nM) C<br>BTK (nM) C |
| 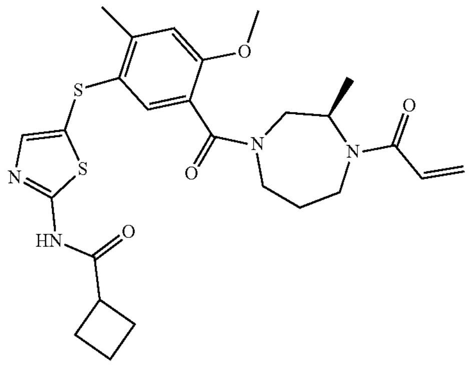 [SMILES: C=CC(=O)N1CCCN(C(=O)c2cc(Sc3cnc(NC(=O)C4CCC4)s3)c(C)cc2OC)C[C@H]1C] | Compound 86<br>ITK (nM) B<br>TXK (nM) D<br>TXK/ITK 227.64<br>JAK3 (nM) E<br>BTK (nM) E |
| 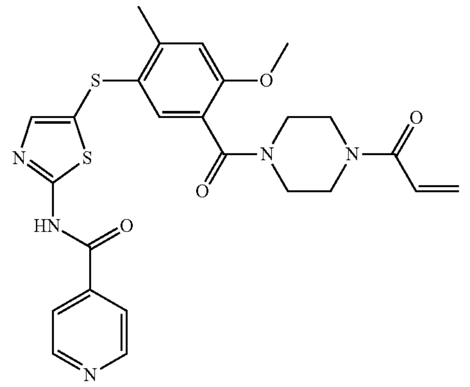 [SMILES: C=CC(=O)N1CCN(C(=O)c2cc(Sc3cnc(NC(=O)c4ccncc4)s3)c(C)cc2OC)CC1] | Compound 87<br>ITK (nM) A<br>TXK (nM) C<br>TXK/ITK 74.161<br>JAK3 (nM) D<br>BTK (nM) C |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 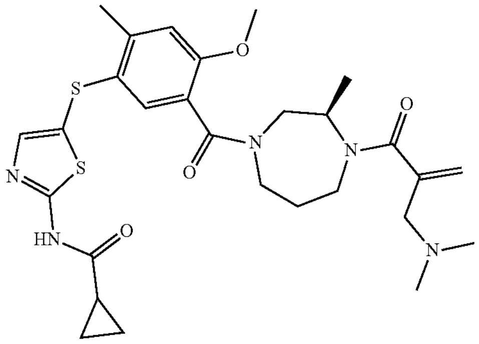 [SMILES: C=C(CN(C)C)C(=O)N1CCCN(C(=O)c2cc(Sc3cnc(NC(=O)C4CC4)s3)c(C)cc2OC)C[C@H]1C] | Compound 88<br>ITK (nM) C<br>TXK (nM) E<br>TXK/ITK 30.436<br>JAK3 (nM) E<br>BTK (nM) E |
| 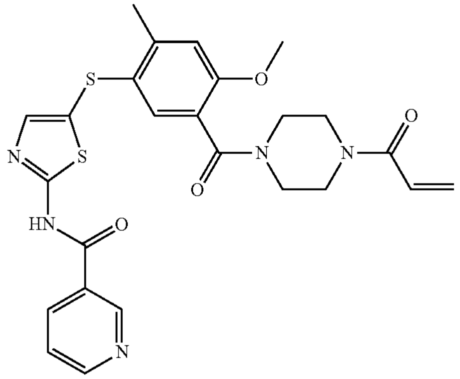 [SMILES: C=CC(=O)N1CCN(C(=O)c2cc(Sc3cnc(NC(=O)c4cccnc4)s3)c(C)cc2OC)CC1] | Compound 89<br>ITK (nM) A<br>TXK (nM) C<br>TXK/ITK 45.743<br>JAK3 (nM) D<br>BTK (nM) C |
| 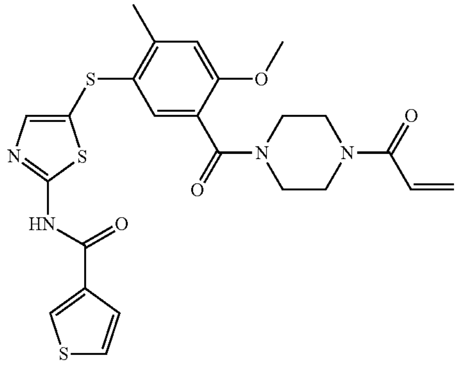 [SMILES: C=CC(=O)N1CCN(C(=O)c2cc(Sc3cnc(NC(=O)c4ccsc4)s3)c(C)cc2OC)CC1] | Compound 90<br>ITK (nM) A<br>TXK (nM) A<br>TXK/ITK 8.3141<br>JAK3 (nM) B<br>BTK (nM) B |
| 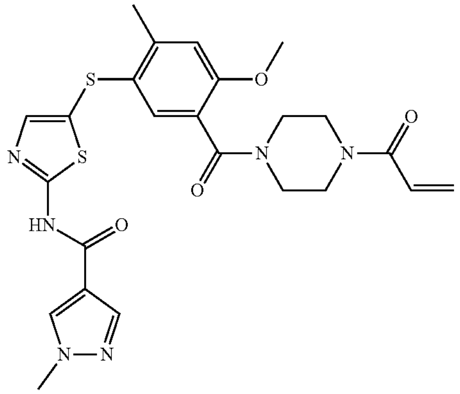 [SMILES: C=CC(=O)N1CCN(C(=O)c2cc(Sc3cnc(NC(=O)c4cnn(C)c4)s3)c(C)cc2OC)CC1] | Compound 91<br>ITK (nM) A<br>TXK (nM) B<br>TXK/ITK 20.093<br>JAK3 (nM) C<br>BTK (nM) B |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 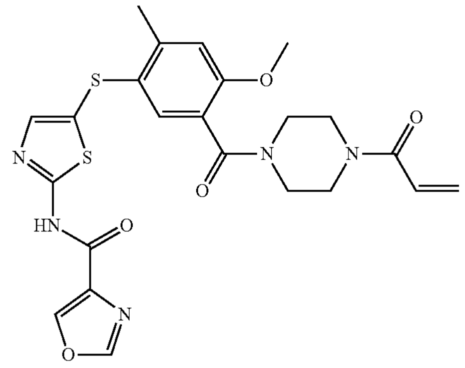 | Compound 92<br>ITK (nM) A<br>TXK (nM) C<br>TXK/ITK 19.123<br>JAK3 (nM) C<br>BTK (nM) C |
| 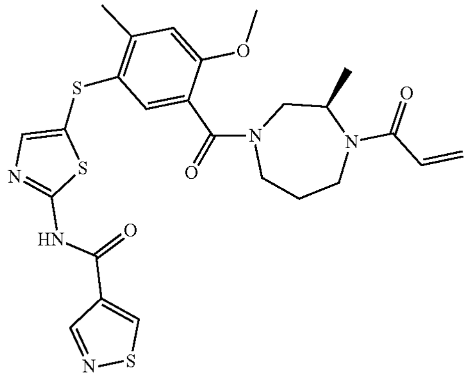 [SMILES: C=CC(=O)N1CCCN(C(=O)c2cc(Sc3cnc(NC(=O)c4cnsc4)s3)c(C)cc2OC)C[C@H]1C] | Compound 93<br>ITK (nM) A<br>TXK (nM) C<br>TXK/ITK 252.91<br>JAK3 (nM) E<br>BTK (nM) D |
| 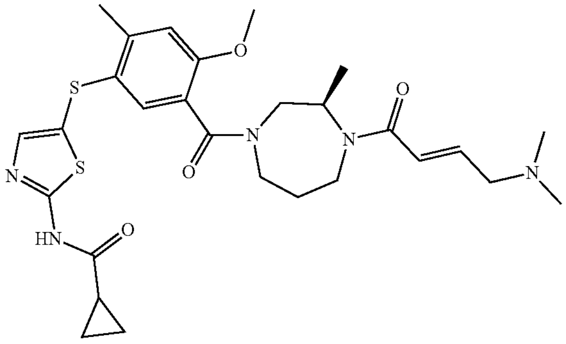 [SMILES: COc1cc(C)c(Sc2cnc(NC(=O)C3CC3)s2)cc1C(=O)N1CCCN(C(=O)/C=C/CN(C)C)[C@H](C)C1] | Compound 94<br>ITK (nM) C<br>TXK (nM) E<br>TXK/ITK 61.81<br>JAK3 (nM) E<br>BTK (nM) E |
| 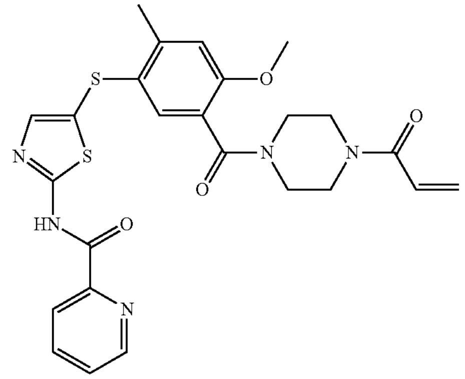 [SMILES: C=CC(=O)N1CCN(C(=O)c2cc(Sc3cnc(NC(=O)c4ccccn4)s3)c(C)cc2OC)CC1] | Compound 95<br>ITK (nM) B<br>TXK (nM) C<br>TXK/ITK 14.201<br>JAK3 (nM) D<br>BTK (nM) C |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 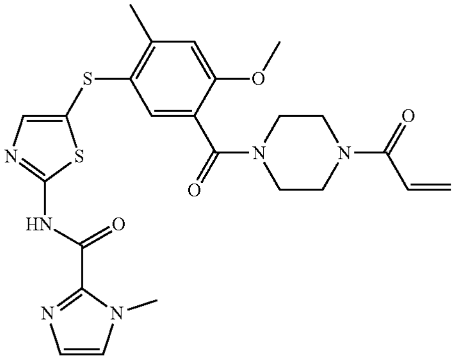 [SMILES: C=CC(=O)N1CCN(C(=O)c2cc(Sc3cnc(NC(=O)c4nccn4C)s3)c(C)cc2OC)CC1] | Compound 96<br>ITK (nM) A<br>TXK (nM) B<br>TXK/ITK 11.966<br>JAK3 (nM) C<br>BTK (nM) C |
| 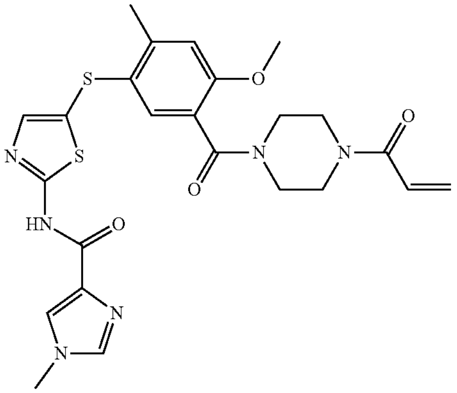 [SMILES: C=CC(=O)N1CCN(C(=O)c2cc(Sc3cnc(NC(=O)c4cn(C)cn4)s3)c(C)cc2OC)CC1] | Compound 97<br>ITK (nM) A<br>TXK (nM) C<br>TXK/ITK 12.995<br>JAK3 (nM) D<br>BTK (nM) C |
| 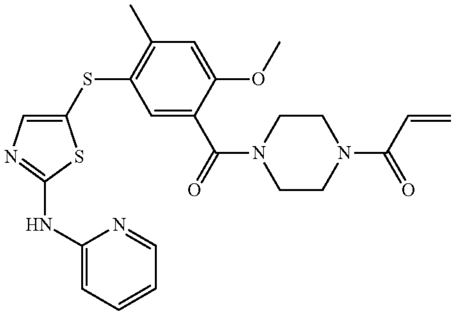 [SMILES: C=CC(=O)N1CCN(C(=O)c2cc(Sc3cnc(Nc4ccccn4)s3)c(C)cc2OC)CC1] | Compound 98<br>ITK (nM) A<br>TXK (nM) A<br>TXK/ITK 8.2157<br>JAK3 (nM) B<br>BTK (nM) A |
| 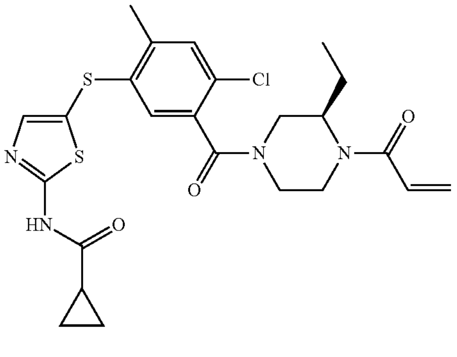 | Compound 99<br>ITK (nM) B<br>TXK (nM) B<br>TXK/ITK 4.279<br>JAK3 (nM) C<br>BTK (nM) D |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 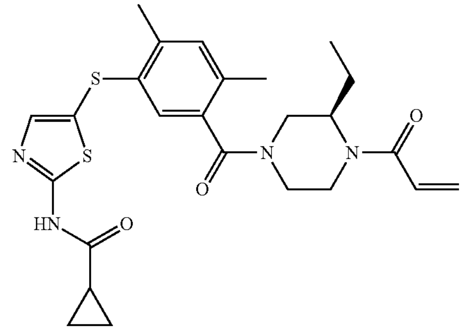 | Compound 100<br>ITK (nM) A<br>TXK (nM) B<br>TXK/ITK 8.8107<br>JAK3 (nM) C<br>BTK (nM) D |
| 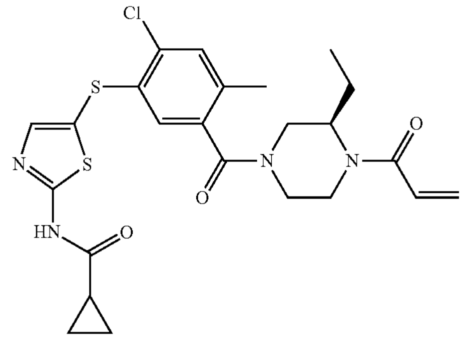 [SMILES: C=CC(=O)N1CCN(C(=O)c2cc(Sc3cnc(NC(=O)C4CC4)s3)c(Cl)cc2C)C[C@H]1CC] | Compound 101<br>ITK (nM) B<br>TXK (nM) C<br>TXK/ITK 14.4<br>JAK3 (nM) C<br>BTK (nM) E |
| 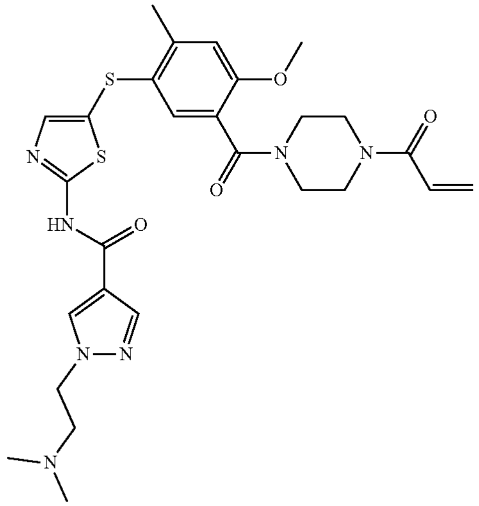 [SMILES: C=CC(=O)N1CCN(C(=O)c2cc(Sc3cnc(NC(=O)c4cnn(CCN(C)C)c4)s3)c(C)cc2OC)CC1] | Compound 102<br>ITK (nM) A<br>TXK (nM) B<br>TXK/ITK 32.9<br>JAK3 (nM) C<br>BTK (nM) B |
| 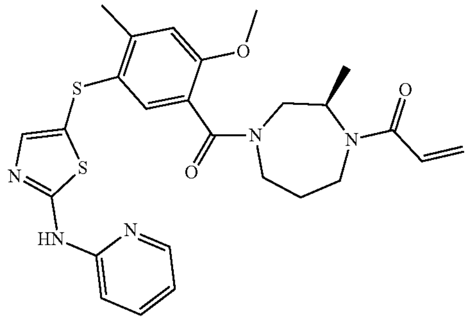 [SMILES: C=CC(=O)N1CCCN(C(=O)c2cc(Sc3cnc(Nc4ccccn4)s3)c(C)cc2OC)C[C@H]1C] | Compound 103<br>ITK (nM) A<br>TXK (nM) B<br>TXK/ITK 47.6<br>JAK3 (nM) C<br>BTK (nM) C |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 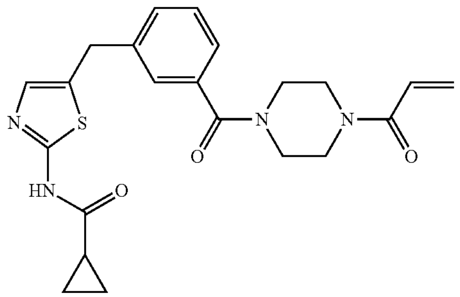 [SMILES: C=CC(=O)N1CCN(C(=O)c2cccc(Cc3cnc(NC(=O)C4CC4)s3)c2)CC1] | Compound 4<br>ITK (nM) B<br>TXK (nM) B<br>TXK/ITK 0.3296<br>JAK3 (nM) C<br>BTK (nM) C |
| 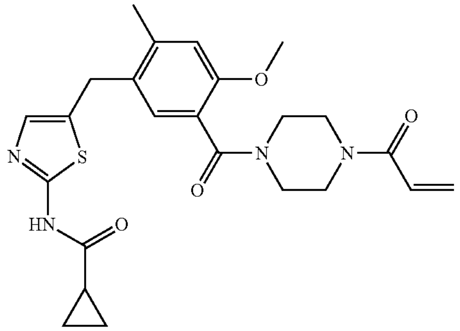 [SMILES: C=CC(=O)N1CCN(C(=O)c2cc(Cc3cnc(NC(=O)C4CC4)s3)c(C)cc2OC)CC1] | Compound 65<br>ITK (nM) A<br>TXK (nM) A<br>TXK/ITK 0.392<br>JAK3 (nM) C<br>BTK (nM) B |
| 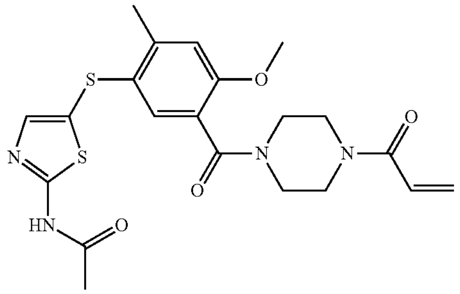 [SMILES: C=CC(=O)N1CCN(C(=O)c2cc(Sc3cnc(NC(C)=O)s3)c(C)cc2OC)CC1] | Compound 2<br>ITK (nM) A<br>TXK (nM) C<br>TXK/ITK 19.869<br>JAK3 (nM) C<br>BTK (nM) C |
| 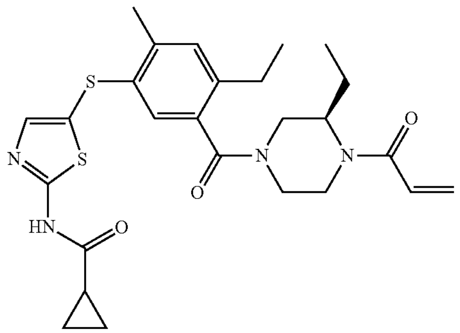 [SMILES: C=CC(=O)N1CCN(C(=O)c2cc(Sc3cnc(NC(=O)C4CC4)s3)c(C)cc2CC)C[C@H]1CC] | Compound 104<br>ITK (nM) A<br>TXK (nM) B<br>TXK/ITK 3.6<br>JAK3 (nM) C<br>BTK (nM) C |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 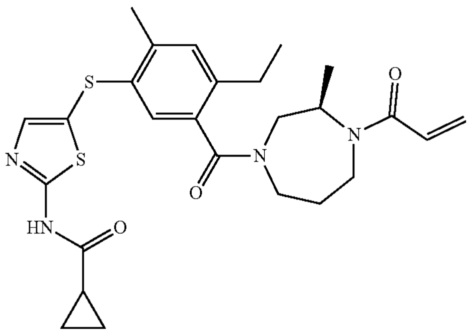 [SMILES: C=CC(=O)N1CCCN(C(=O)c2cc(Sc3cnc(NC(=O)C4CC4)s3)c(C)cc2CC)C[C@H]1C] | Compound 105<br>ITK (nM) A<br>TXK (nM) C<br>TXK/ITK 12.3<br>JAK3 (nM) D<br>BTK (nM) C |
| 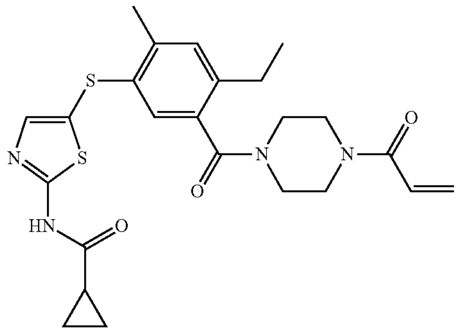 | Compound 106<br>ITK (nM) A<br>TXK (nM) A<br>TXK/ITK 2.9<br>JAK3 (nM) B<br>BTK (nM) B |
| 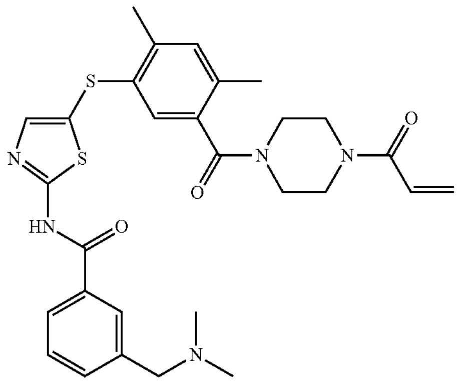 [SMILES: C=CC(=O)N1CCN(C(=O)c2cc(Sc3cnc(NC(=O)c4cccc(CN(C)C)c4)s3)c(C)cc2C)CC1] | Compound 107<br>ITK (nM) A<br>TXK (nM) B<br>TXK/ITK 61.8<br>JAK3 (nM) C<br>BTK (nM) C |
| 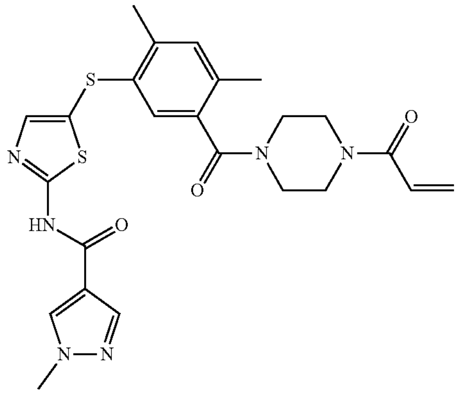 [SMILES: C=CC(=O)N1CCN(C(=O)c2cc(Sc3cnc(NC(=O)c4cnn(C)c4)s3)c(C)cc2C)CC1] | Compound 108<br>ITK (nM) A<br>TXK (nM) B<br>TXK/ITK 12.1<br>JAK3 (nM) C<br>BTK (nM) C |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 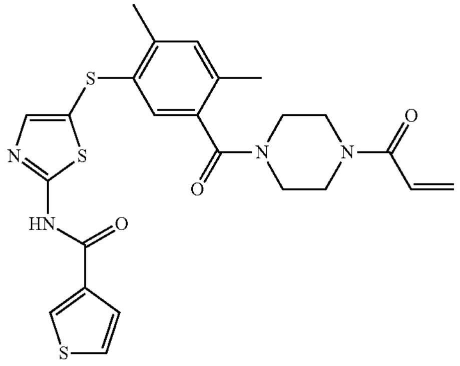 | Compound 109<br>ITK (nM) A<br>TXK (nM) B<br>TXK/ITK 13.5<br>JAK3 (nM) B<br>BTK (nM) B |
| 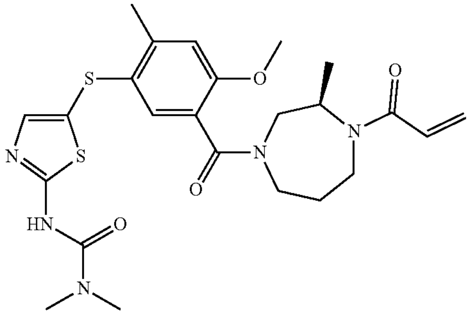 [SMILES: C=CC(=O)N1CCCN(C(=O)c2cc(Sc3cnc(NC(=O)N(C)C)s3)c(C)cc2OC)C[C@H]1C] | Compound 110<br>ITK (nM) C<br>TXK (nM) E<br>TXK/ITK 46.6<br>JAK3 (nM) D<br>BTK (nM) E |
| 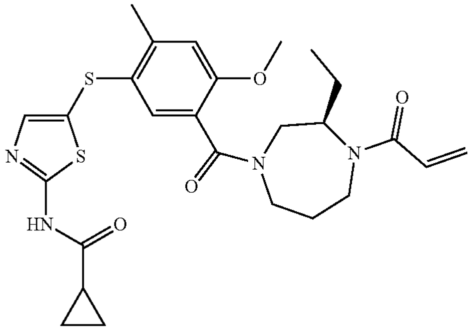 [SMILES: C=CC(=O)N1CCCN(C(=O)c2cc(Sc3cnc(NC(=O)C4CC4)s3)c(C)cc2OC)C[C@H]1CC] | Compound 111<br>ITK (nM) A<br>TXK (nM) C<br>TXK/ITK 81.1<br>JAK3 (nM) D<br>BTK (nM) C |
| 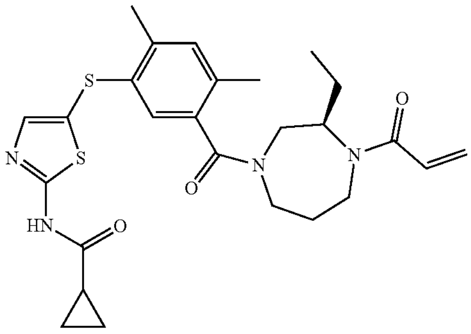 [SMILES: C=CC(=O)N1CCCN(C(=O)c2cc(Sc3cnc(NC(=O)C4CC4)s3)c(C)cc2C)C[C@H]1CC] | Compound 112<br>ITK (nM) A<br>TXK (nM) C<br>TXK/ITK 118.0<br>JAK3 (nM) D<br>BTK (nM) C |

TABLE 2-continued
Compounds and IC50 values against select targets. IC50 ranges: A < 10 nM, 10 nM <= B < 100 nM, 100 nM <= C < 1000 nM, 1000 nM <= D < 10000, 10000 <= E.
| Compound | Compound name and IC50s |
|---|---|
| 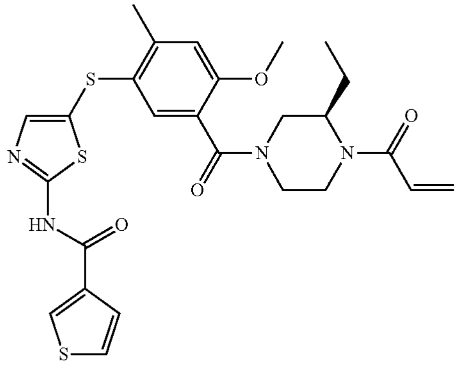 [SMILES: C=CC(=O)N1CCN(C(=O)c2cc(Sc3cnc(NC(=O)c4ccsc4)s3)c(C)cc2OC)C[C@H]1CC] | Compound 113<br>ITK (nM) A<br>TXK (nM) B<br>TXK/ITK 12.1<br>JAK3 (nM) C<br>BTK (nM) B |
| 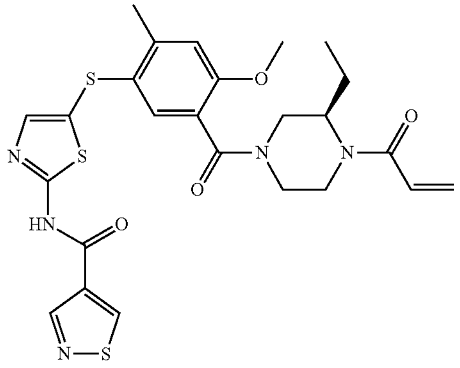 | Compound 114<br>ITK (nM) A<br>TXK (nM) B<br>TXK/ITK 30.1<br>JAK3 (nM) D<br>BTK (nM) C |
| 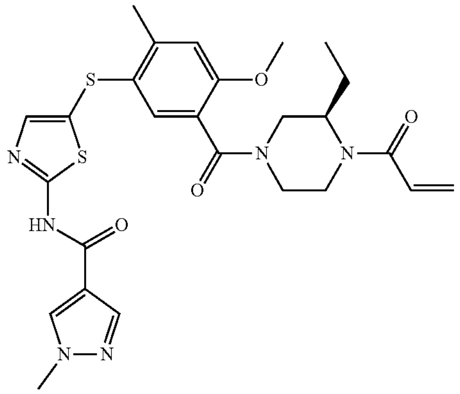 [SMILES: C=CC(=O)N1CCN(C(=O)c2cc(Sc3cnc(NC(=O)c4cnn(C)c4)s3)c(C)cc2OC)C[C@H]1CC] | Compound 115<br>ITK (nM) A<br>TXK (nM) B<br>TXK/ITK 9.8<br>JAK3 (nM) D<br>BTK (nM) C |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 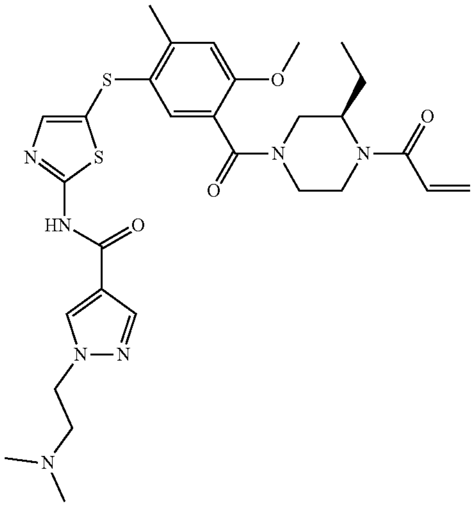 [SMILES: C=CC(=O)N1CCN(C(=O)c2cc(Sc3cnc(NC(=O)c4cnn(CCN(C)C)c4)s3)c(C)cc2OC)C[C@H]1CC] | Compound 116<br>ITK (nM) A<br>TXK (nM) B<br>TXK/ITK 23.3<br>JAK3 (nM) D<br>BTK (nM) C |
| 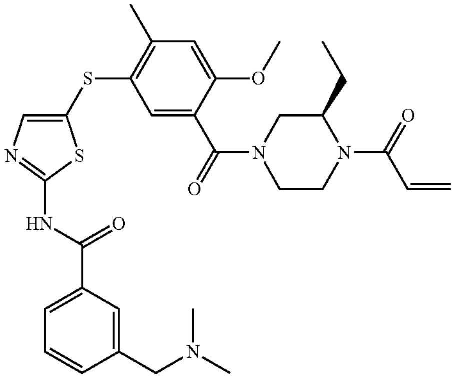 [SMILES: C=CC(=O)N1CCN(C(=O)c2cc(Sc3cnc(NC(=O)c4cccc(CN(C)C)c4)s3)c(C)cc2OC)C[C@H]1CC] | Compound 117<br>ITK (nM) A<br>TXK (nM) B<br>TXK/ITK 65.5<br>JAK3 (nM) D<br>BTK (nM) C |
| 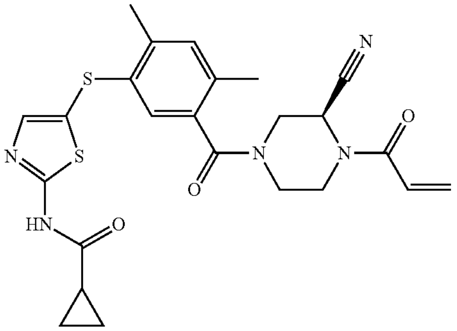 [SMILES: C=CC(=O)N1CCN(C(=O)c2cc(Sc3cnc(NC(=O)C4CC4)s3)c(C)cc2C)C[C@H]1C#N] | Compound 118<br>ITK (nM) E<br>TXK (nM) A<br>TXK/ITK<br>JAK3 (nM) A<br>BTK (nM) A |
| 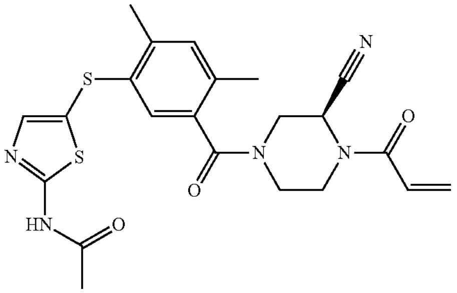 [SMILES: C=CC(=O)N1CCN(C(=O)c2cc(Sc3cnc(NC(C)=O)s3)c(C)cc2C)C[C@H]1C#N] | Compound 119<br>ITK (nM) A<br>TXK (nM) A<br>TXK/ITK 3.2<br>JAK3 (nM) A<br>BTK (nM) B |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 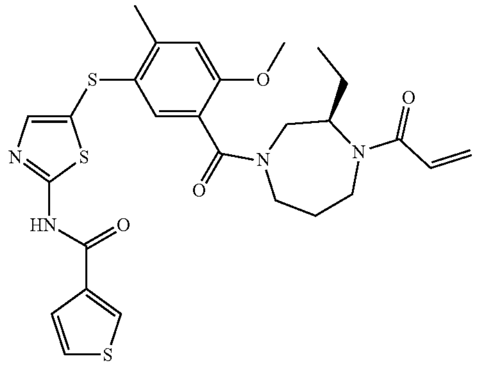 [SMILES: C=CC(=O)N1CCCN(C(=O)c2cc(Sc3cnc(NC(=O)c4ccsc4)s3)c(C)cc2OC)C[C@H]1CC] | Compound 120<br>ITK (nM) A<br>TXK (nM) C<br>TXK/ITK 66.4<br>JAK3 (nM) D<br>BTK (nM) C |
| 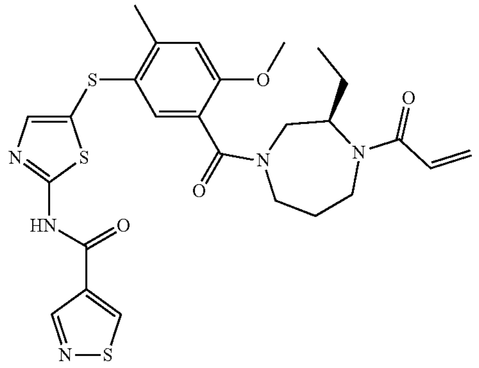 [SMILES: C=CC(=O)N1CCCN(C(=O)c2cc(Sc3cnc(NC(=O)c4cnsc4)s3)c(C)cc2OC)C[C@H]1CC] | Compound 121<br>ITK (nM) A<br>TXK (nM) C<br>TXK/ITK 146.1<br>JAK3 (nM) D<br>BTK (nM) C |
| 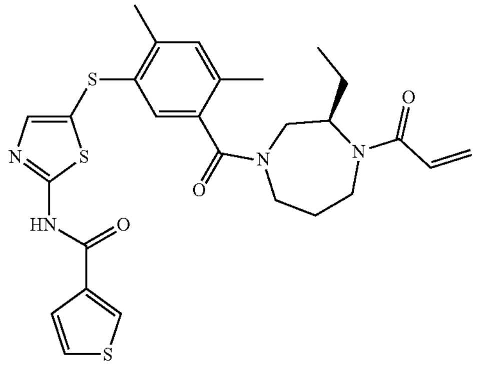 | Compound 122<br>ITK (nM) A<br>TXK (nM) C<br>TXK/ITK 118.5<br>JAK3 (nM) C<br>BTK (nM) C |
| 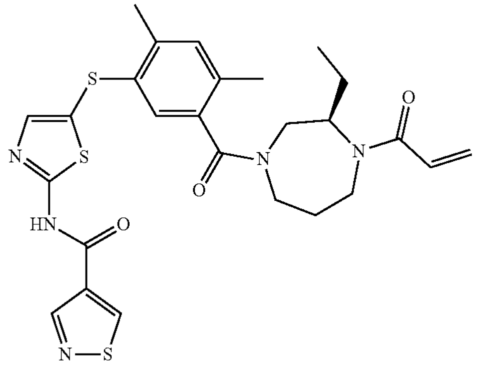 [SMILES: C=CC(=O)N1CCCN(C(=O)c2cc(Sc3cnc(NC(=O)c4cnsc4)s3)c(C)cc2C)C[C@H]1CC] | Compound 123<br>ITK (nM) A<br>TXK (nM) C<br>TXK/ITK 144.0<br>JAK3 (nM) D<br>BTK (nM) C |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 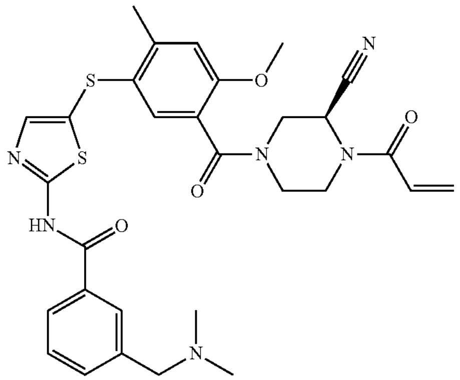 [SMILES: C=CC(=O)N1CCN(C(=O)c2cc(Sc3cnc(NC(=O)c4cccc(CN(C)C)c4)s3)c(C)cc2OC)C[C@H]1C#N] | Compound 124<br>ITK (nM) A<br>TXK (nM) A<br>TXK/ITK 5.9<br>JAK3 (nM) A<br>BTK (nM) A |
| 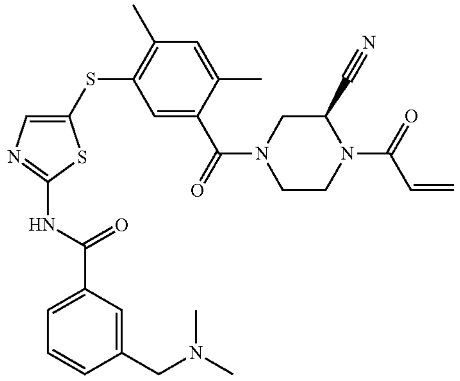 [SMILES: C=CC(=O)N1CCN(C(=O)c2cc(Sc3cnc(NC(=O)c4cccc(CN(C)C)c4)s3)c(C)cc2C)C[C@H]1C#N] | Compound 125<br>ITK (nM) A<br>TXK (nM) A<br>TXK/ITK 2.3<br>JAK3 (nM) A<br>BTK (nM) B |
| 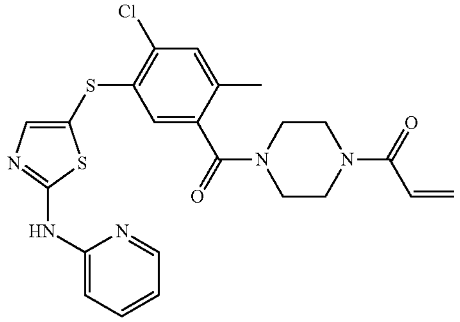 [SMILES: C=CC(=O)N1CCN(C(=O)c2cc(Sc3cnc(Nc4ccccn4)s3)c(Cl)cc2C)CC1] | Compound 126<br>ITK (nM) A<br>TXK (nM) B<br>TXK/ITK 13.5<br>JAK3 (nM) B<br>BTK (nM) B |
| 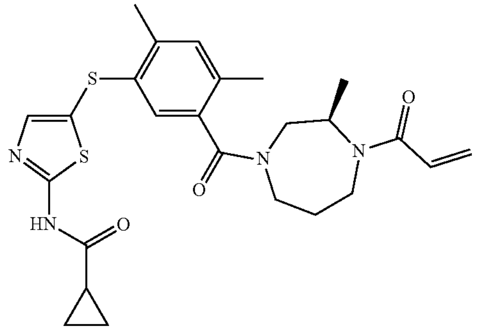 [SMILES: C=CC(=O)N1CCCN(C(=O)c2cc(Sc3cnc(NC(=O)C4CC4)s3)c(C)cc2C)C[C@H]1C] | Compound 127<br>ITK (nM) B<br>TXK (nM) C<br>TXK/ITK 7.6<br>JAK3 (nM) E<br>BTK (nM) C |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 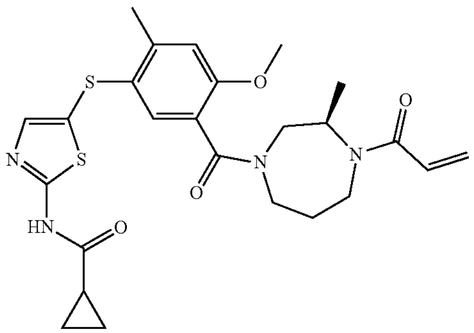 [SMILES: C=CC(=O)N1CCCN(C(=O)c2cc(Sc3cnc(NC(=O)C4CC4)s3)c(C)cc2OC)C[C@H]1C] | Compound 128<br>ITK (nM) B<br>TXK (nM) C<br>TXK/ITK 12.8<br>JAK3 (nM) E<br>BTK (nM) C |
| 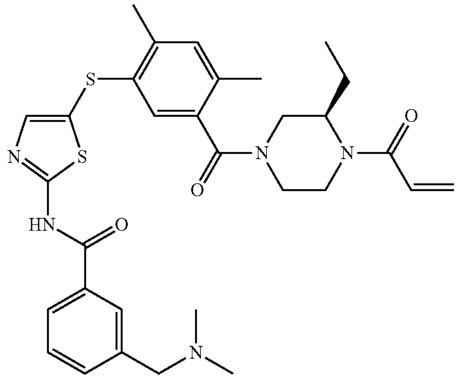 [SMILES: C=CC(=O)N1CCN(C(=O)c2cc(Sc3cnc(NC(=O)c4cccc(CN(C)C)c4)s3)c(C)cc2C)C[C@H]1CC] | Compound 129<br>ITK (nM) A<br>TXK (nM) B<br>TXK/ITK 46.0<br>JAK3 (nM) C<br>BTK (nM) B |
| 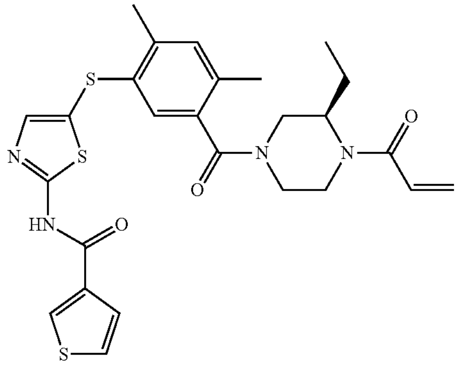 [SMILES: C=CC(=O)N1CCN(C(=O)c2cc(Sc3cnc(NC(=O)c4ccsc4)s3)c(C)cc2C)C[C@H]1CC] | Compound 130<br>ITK (nM) A<br>TXK (nM) B<br>TXK/ITK 7.0<br>JAK3 (nM) C<br>BTK (nM) C |
| 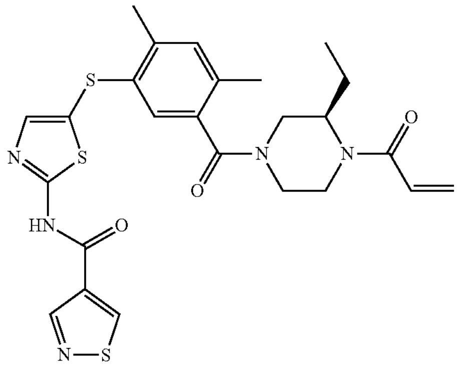 [SMILES: C=CC(=O)N1CCN(C(=O)c2cc(Sc3cnc(NC(=O)c4cnsc4)s3)c(C)cc2C)C[C@H]1CC] | Compound 131<br>ITK (nM) A<br>TXK (nM) B<br>TXK/ITK 11.0<br>JAK3 (nM) C<br>BTK (nM) C |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 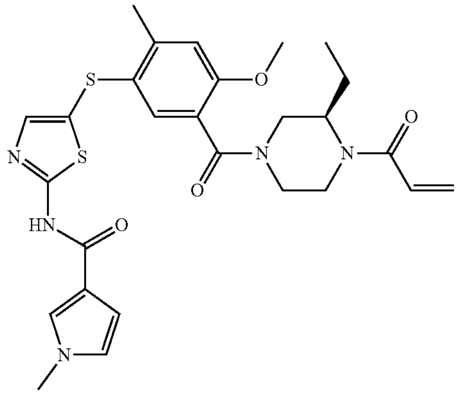 [SMILES: C=CC(=O)N1CCN(C(=O)c2cc(Sc3cnc(NC(=O)c4ccn(C)c4)s3)c(C)cc2OC)C[C@H]1CC] | Compound 132<br>ITK (nM) A<br>TXK (nM) B<br>TXK/ITK 2.9<br>JAK3 (nM) C<br>BTK (nM) C |
| 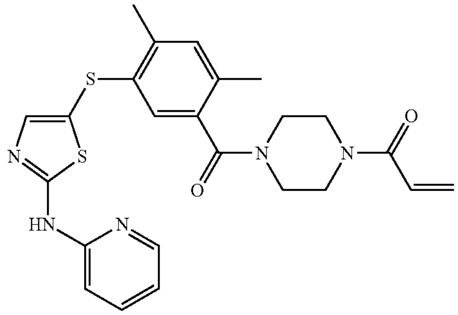 [SMILES: C=CC(=O)N1CCN(C(=O)c2cc(Sc3cnc(Nc4ccccn4)s3)c(C)cc2C)CC1] | Compound 133<br>ITK (nM) A<br>TXK (nM) A<br>TXK/ITK 4.6<br>JAK3 (nM) B<br>BTK (nM) B |
| 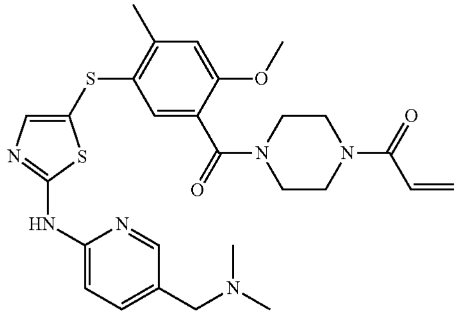 [SMILES: C=CC(=O)N1CCN(C(=O)c2cc(Sc3cnc(Nc4ccc(CN(C)C)cn4)s3)c(C)cc2OC)CC1] | Compound 134<br>ITK (nM) A<br>TXK (nM) A<br>TXK/ITK<br>JAK3 (nM) B<br>BTK (nM) A |
| 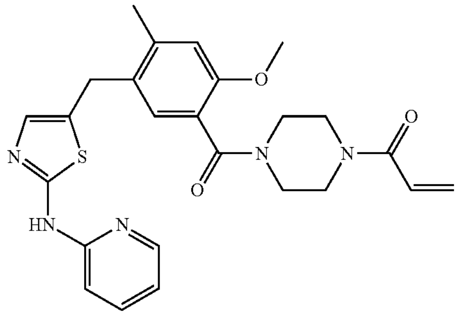 [SMILES: C=CC(=O)N1CCN(C(=O)c2cc(Cc3cnc(Nc4ccccn4)s3)c(C)cc2OC)CC1] | Compound 135<br>ITK (nM) A<br>TXK (nM) A<br>TXK/ITK 0.38<br>JAK3 (nM) C<br>BTK (nM) A |

TABLE 2-continued

| Compound | Compound name and IC50s |
|---|---|
| Compounds and IC50 values against select targets. IC50 ranges: A < 10 nM, 10 nM <= B < 100 nM, 100 nM <= C < 1000 nM, 1000 nM <= D < 10000, 10000 <= E. | |
| 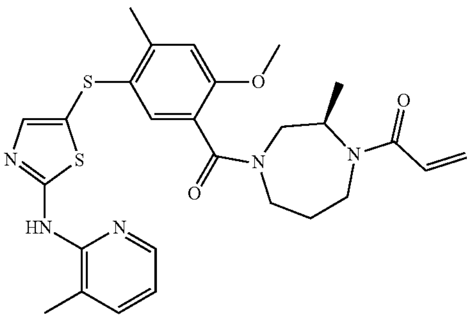 [SMILES: C=CC(=O)N1CCCN(C(=O)c2cc(Sc3cnc(Nc4ncccc4C)s3)c(C)cc2OC)C[C@H]1C] | Compound 136<br>ITK (nM) A<br>TXK (nM) B<br>TXK/ITK 42<br>JAK3 (nM) C<br>BTK (nM) B |
| 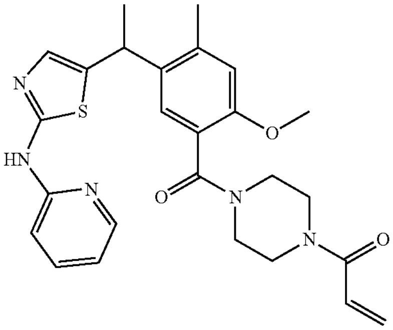 [SMILES: C=CC(=O)N1CCN(C(=O)c2cc(C(C)c3cnc(Nc4ccccn4)s3)c(C)cc2OC)CC1] | Compound 137<br>ITK (nM) A<br>TXK (nM) A<br>TXK/ITK 0.93<br>JAK3 (nM) C<br>BTK (nM) A |
| 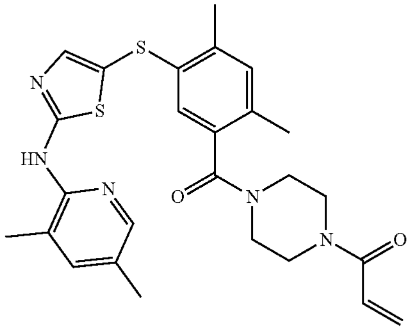 [SMILES: C=CC(=O)N1CCN(C(=O)c2cc(Sc3cnc(Nc4ncc(C)cc4C)s3)c(C)cc2C)CC1] | Compound 138<br>ITK (nM) B<br>TXK (nM) B<br>TXK/ITK 3.29<br>JAK3 (nM)C<br>BTK (nM) C |
| 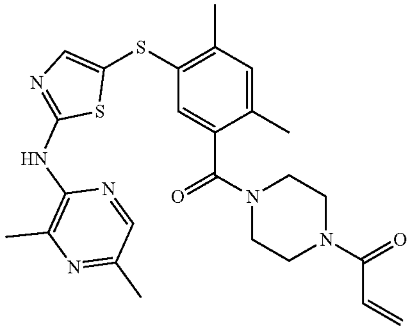 | Compound 139<br>ITK (nM) B<br>TXK (nM) B<br>TXK/ITK 4.65<br>JAK3 (nM)C<br>BTK (nM) C |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 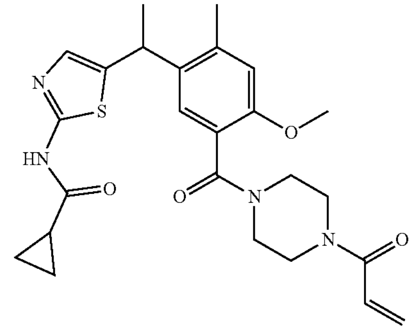 [SMILES: C=CC(=O)N1CCN(C(=O)c2cc(C(C)c3cnc(NC(=O)C4CC4)s3)c(C)cc2OC)CC1] | Compound 140<br>ITK (nM) A<br>TXK (nM) B<br>TXK/ITK 2.66<br>JAK3 (nM) D<br>BTK (nM) B |
| 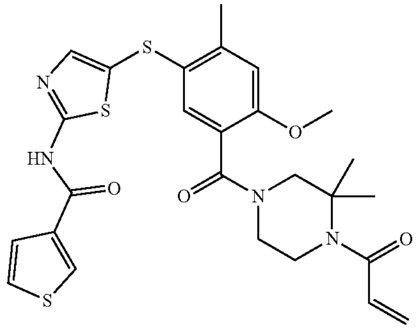 [SMILES: C=CC(=O)N1CCN(C(=O)c2cc(Sc3cnc(NC(=O)c4ccsc4)s3)c(C)cc2OC)CC1(C)C] | Compound 141<br>ITK (nM) A<br>TXK (nM) B<br>TXK/ITK 14.70<br>JAK3 (nM) C<br>BTK (nM) B |
| 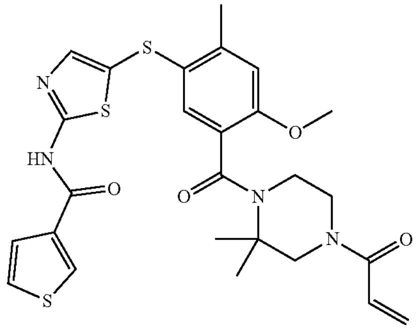 [SMILES: C=CC(=O)N1CCN(C(=O)c2cc(Sc3cnc(NC(=O)c4ccsc4)s3)c(C)cc2OC)C(C)(C)C1] | Compound 142<br>ITK (nM) A<br>TXK (nM) A<br>TXK/ITK 1.00<br>JAK3 (nM) A<br>BTK (nM) A |
| 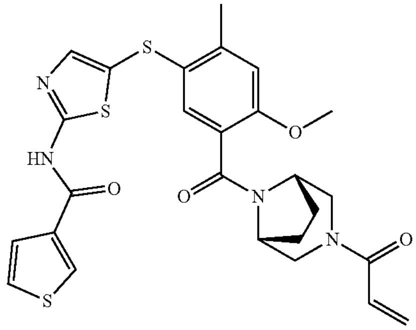 [SMILES: C=CC(=O)N1C[C@H]2CC[C@@H](C1)N2C(=O)c1cc(Sc2cnc(NC(=O)c3ccsc3)s2)c(C)cc1OC] | Compound 143<br>ITK (nM) A<br>TXK (nM) A<br>TXK/ITK 3.51<br>JAK3 (nM)B<br>BTK (nM) A |

TABLE 2-continued

Compounds and IC50 values against select targets. IC50 ranges: A < 10 nM, 10 nM <= B < 100 nM, 100 nM <= C < 1000 nM, 1000 nM <= D < 10000, 10000 <= E.

| Compound | Compound name and IC50s |
|---|---|
| 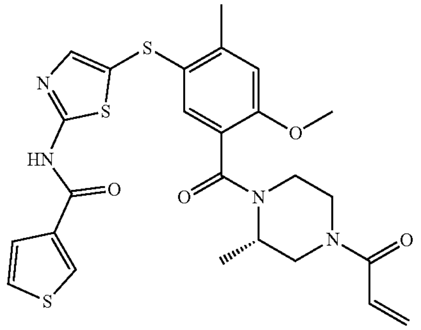 [SMILES: C=CC(=O)N1CCN(C(=O)c2cc(Sc3cnc(NC(=O)c4ccsc4)s3)c(C)cc2OC)[C@@H](C)C1] | Compound 144<br>ITK (nM) A<br>TXK (nM) B<br>TXK/ITK 18.84<br>JAK3 (nM) C<br>BTK (nM) B |
| 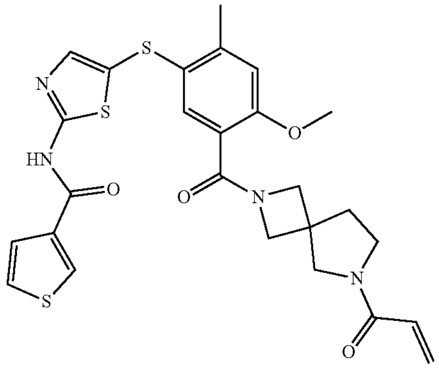 [SMILES: C=CC(=O)N1CCC2(C1)CN(C(=O)c1cc(Sc3cnc(NC(=O)c4ccsc4)s3)c(C)cc1OC)C2] | Compound 145<br>ITK (nM) A<br>TXK (nM) A<br>TXK/ITK 3.86<br>JAK3 (nM) B<br>BTK (nM) A |
| 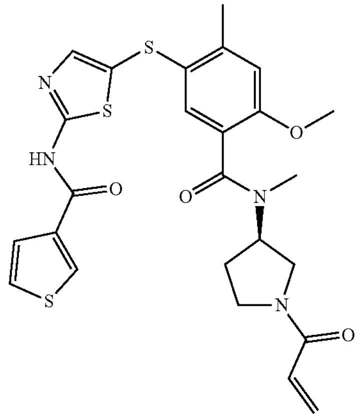 [SMILES: C=CC(=O)N1CC[C@@H](N(C)C(=O)c2cc(Sc3cnc(NC(=O)c4ccsc4)s3)c(C)cc2OC)C1] | Compound 146<br>ITK (nM) A<br>TXK (nM) A<br>TXK/ITK 3.19<br>JAK3 (nM) A<br>BTK (nM) A |
| 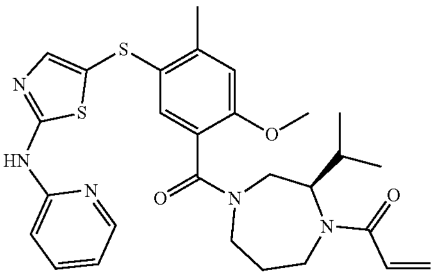 [SMILES: C=CC(=O)N1CCCN(C(=O)c2cc(Sc3cnc(Nc4ccccn4)s3)c(C)cc2OC)C[C@H]1C(C)C] | Compound 147<br>ITK (nM) A<br>TXK (nM) C<br>TXK/ITK 29.58<br>JAK3 (nM) D<br>BTK (nM) B |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 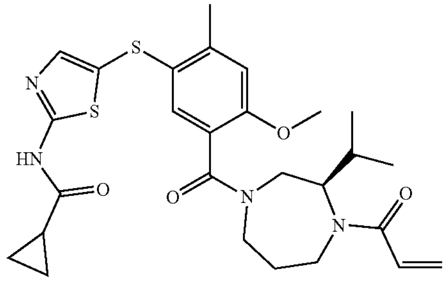 [SMILES: C=CC(=O)N1CCCN(C(=O)c2cc(Sc3cnc(NC(=O)C4CC4)s3)c(C)cc2OC)C[C@H]1C(C)C] | Compound 148<br>ITK (nM) A<br>TXK (nM) C<br>TXK/ITK 82.31<br>JAK3 (nM) E<br>BTK (nM) C |
| 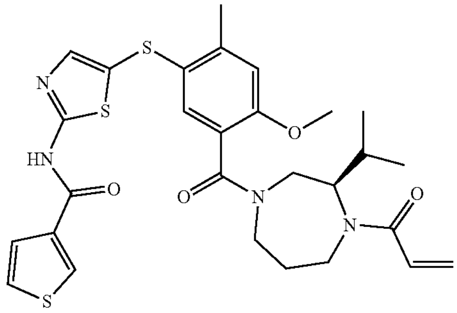 [SMILES: C=CC(=O)N1CCCN(C(=O)c2cc(Sc3cnc(NC(=O)c4ccsc4)s3)c(C)cc2OC)C[C@H]1C(C)C] | Compound 149<br>ITK (nM) A<br>TXK (nM) C<br>TXK/ITK 171.45<br>JAK3 (nM) E<br>BTK (nM) B |
| 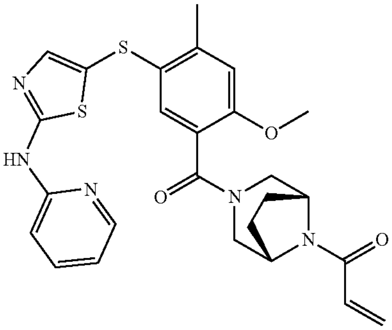 [SMILES: C=CC(=O)N1[C@@H]2CC[C@H]1CN(C(=O)c1cc(Sc3cnc(Nc4ccccn4)s3)c(C)cc1OC)C2] | Compound 150<br>ITK (nM) A<br>TXK (nM) A<br>TXK/ITK 1.76<br>JAK3 (nM) B<br>BTK (nM) A |
| 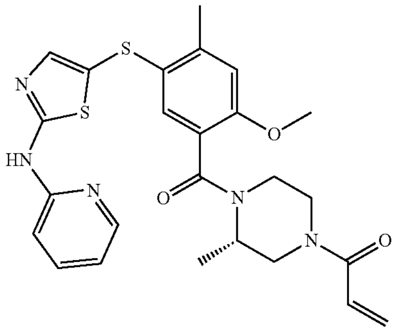 [SMILES: C=CC(=O)N1CCN(C(=O)c2cc(Sc3cnc(Nc4ccccn4)s3)c(C)cc2OC)[C@@H](C)C1] | Compound 151<br>ITK (nM)A<br>TXK (nM) A<br>TXK/ITK 6.43<br>JAK3 (nM) B<br>BTK (nM) B |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 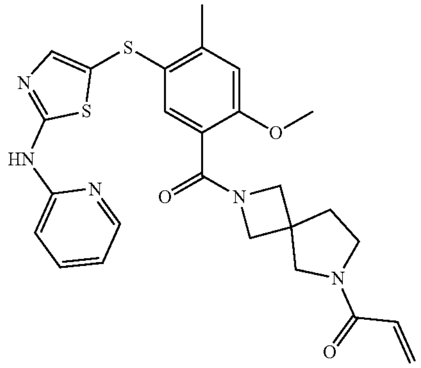 [SMILES: C=CC(=O)N1CCC2(C1)CN(C(=O)c1cc(Sc3cnc(Nc4ccccn4)s3)c(C)cc1OC)C2] | Compound 152<br>ITK (nM) A<br>TXK (nM) A<br>TXK/ITK 2.06<br>JAK3 (nM)C<br>BTK (nM) B |
| 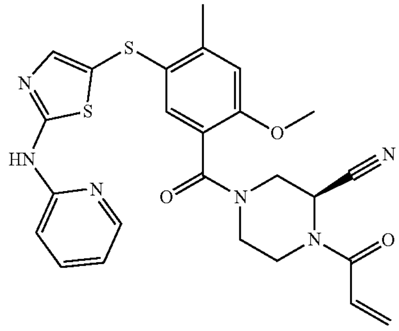 [SMILES: C=CC(=O)N1CCN(C(=O)c2cc(Sc3cnc(Nc4ccccn4)s3)c(C)cc2OC)C[C@H]1C#N] | Compound 153<br>ITK (nM) A<br>TXK (nM)<br>TXK/ITK 0.61<br>JAK3 (nM) A<br>BTK (nM) A |
| 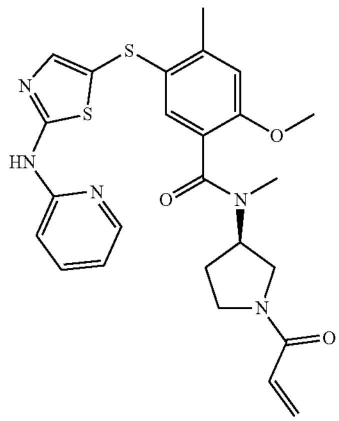 [SMILES: C=CC(=O)N1CC[C@@H](N(C)C(=O)c2cc(Sc3cnc(Nc4ccccn4)s3)c(C)cc2OC)C1] | Compound 154<br>ITK (nM) A<br>TXK (nM) A<br>TXK/ITK 1.01<br>JAK3 (nM) A<br>BTK (nM) A |
| 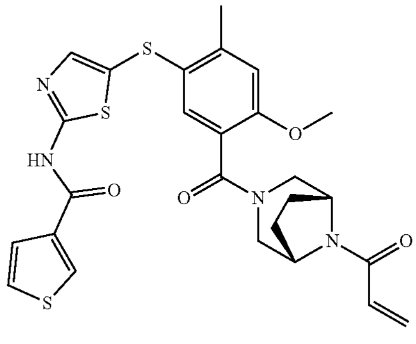 [SMILES: C=CC(=O)N1[C@@H]2CC[C@H]1CN(C(=O)c1cc(Sc3cnc(NC(=O)c4ccsc4)s3)c(C)cc1OC)C2] | Compound 155<br>ITK (nM) A<br>TXK (nM) A<br>TXK/ITK 2.73<br>JAK3 (nM) B<br>BTK (nM) A |

TABLE 2-continued

| Compounds and IC50 values against select targets. IC50 ranges: A < 10 nM, 10 nM <= B < 100 nM, 100 nM <= C < 1000 nM, 1000 nM <= D < 10000, 10000 <= E. | |
|---|---|
| Compound | Compound name and IC50s |
| 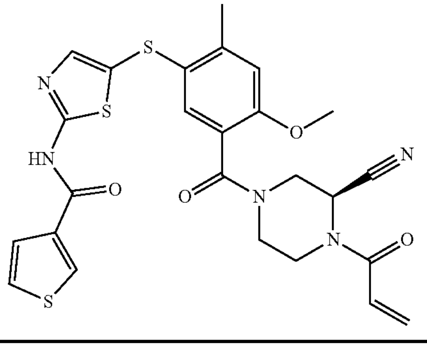 | Compound 156<br>ITK (nM) A<br>TXK (nM) A<br>TXK/ITK 3.09<br>JAK3 (nM) A<br>BTK (nM) A |

TABLE 3

| Rat PO PK | | | | |
|---|---|---|---|---|
| compound | Jurkat IL2 $IC_{50}$ nM | PO 6 mpk $C_{max}$ (ng/mL) | $AUC_{last}$ h*ng/mL | F % |
| Compound 33 | 100 | 15.7 | 0.4 | 0.4 |
| Compound 50 | 36 | 25.2 | 3.4 | 3.4 |
| Compound 1 | 10 | 97 | 10.9 | 10.9 |
| Compound 21 | 53 | 148 | 18.1 | 18.1 |
| Compound 44 | 31 | 75 | 12.5 | 12.5 |

TABLE 4

| Mouse PO PK | | | | |
|---|---|---|---|---|
| compound | Jurkat IL2 $IC_{50}$ nM | PO 10 mpk $C_{max}$ (ng/mL) | $AUC_{last}$ h*ng/mL | F % |
| Compound 1 | 10 | 613 | 335 | 20.1 |
| Compound 21 | 53 | 292 | 215 | 10.5 |

TABLE 4-continued

| Mouse PO PK | | | | |
|---|---|---|---|---|
| compound | Jurkat IL2 $IC_{50}$ nM | PO 10 mpk $C_{max}$ (ng/mL) | $AUC_{last}$ h*ng/mL | F % |
| Compound 44 | 31 | 368 | 226 | 9.8 |
| Compound 90 | 33 | 527 | 419 | 20 |

TABLE 5

| Mouse IP PK | | | | |
|---|---|---|---|---|
| compound | Jurkat IL2 $IC_{50}$ nM | PO 8 mpk $C_{max}$ (ng/mL) | $AUC_{last}$ h*ng/mL | F % |
| Compound 33 | 100 | 819 | 1250 | 75 |

TABLE 6

| NMR data | | |
|---|---|---|
| 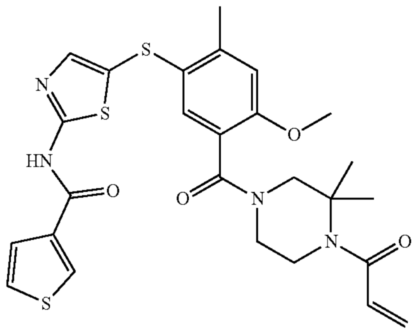 [SMILES: C=CC(=O)N1CCN(C(=O)c2cc(Sc3cnc(NC(=O)c4ccsc4)s3)c(C)cc2OC)CC1(C)C]<br>N-(5-((5-(4-acryloyl-3,3-dimethylpiperazine-1-carbonyl)-4-methoxy-2-methylphenyl)thio)thiazol-2-yl)thiophene-3-carboxamide | Compound 141 | $^{1}H$ NMR (400 MHz, DMSO, ppm): δ 12.74 (br s, 1H), 8.59 (s, 1H), 7.77-7.69 (m, 3H), 7.07 (s, 1H), 6.98 (s, 1H), 6.60 (m, 1H), 5.95 (m, 1H), 5.53 (m, 1H), 3.78 (s, 3H), 3.55-3.48 (m, 3H), 3.17-2.73 (m, 3H), 2.51 (s, 3H), 1.42-1.13 (m, 6H). |

TABLE 6-continued

| NMR data | | |
|---|---|---|
| 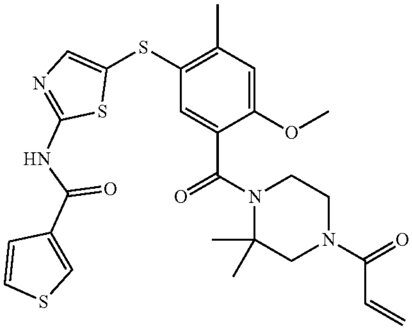 [SMILES: C=CC(=O)N1CCN(C(=O)c2cc(Sc3cnc(NC(=O)c4ccsc4)s3)c(C)cc2OC)C(C)(C)C1]<br>N-(5-((5-(4-acryloyl-2,2-dimethylpiperazine-1-carbonyl)-4-methoxy-2-methylphenyl)thio)thiazol-2-yl)thiophene-3-carboxamide | Compound 142 | $^1$H NMR (400 MHz, DMSO, ppm): δ 12.75 (br s, 1H), 8.61 (s, 1H), 7.76-7.67 (m, 3H), 7.06 (s, 1H), 6.98 (s, 1H), 6.60 (m, 1H), 6.12 (m, 1H), 5.65 (m, 1H), 3.79 (s, 3H), 3.65-3.36 (m, 6H), 2.51 (s, 3H), 1.43 (s, 6H). |
| 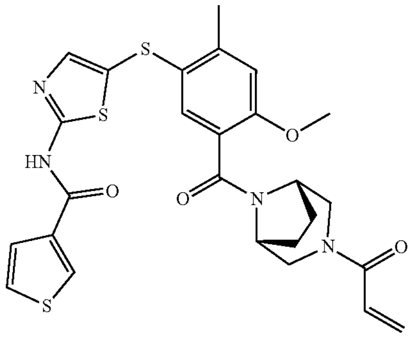 [SMILES: C=CC(=O)N1C[C@H]2CC[C@@H](C1)N2C(=O)c1cc(Sc2cnc(NC(=O)c3ccsc3)s2)c(C)cc1OC]<br>N-(5-((5-((1R,5S)-3-acryloyl-3,8-diazabicyclo[3.2.1]octane-8-carbonyl)-4-methoxy-2-methylphenyl)thio)thiazol-2-yl)thiophene-3-carboxamide | Compound 143 | $^1$H NMR (400 MHz, DMSO, ppm): δ 12.75 (br s, 1H), 8.61 (s, 1H), 7.77-7.71 (m, 3H), 7.18 (m, 1H), 7.09 (s, 1H), 6.73-6.60 (m, 1H), 6.07 (m, 1H), 5.71-5.56 (m, 1H), 4.62-3.92 (m, 2H), 3.76 (s, 3H), 3.61-2.68 (m, 4H), 2.51 (s, 3H), 1.78-1.24 (s, 4H). |
| 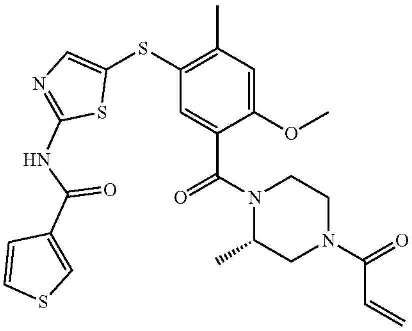 [SMILES: C=CC(=O)N1CCN(C(=O)c2cc(Sc3cnc(NC(=O)c4ccsc4)s3)c(C)cc2OC)[C@@H](C)C1]<br>(S)-N-(5-((5-(4-acryloyl-2,methylpiperazine-1-carbonyl)-4-methoxy-2-methylphenyl)thio)thiazol-2-yl)thiophene-3-carboxamide | Compound 144 | $^1$H NMR (400 MHz, DMSO, ppm): δ 12.76 (br s, 1H), 8.61 (s, 1H), 7.77-7.71 (m, 3H), 7.06-6.98 (m, 2H), 6.70 (br s, 1H), 6.07 (m, 1H), 5.66 (m, 1H), 4.26 (m, 3H), 3.77 (s, 3H), 2.92 (m, 4H), 2.50 (s, 3H), 1.00 (m, 3H). |

TABLE 6-continued

| NMR data | | |
|---|---|---|
| 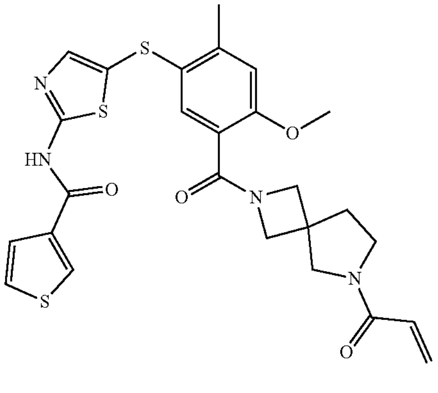 [SMILES: C=CC(=O)N1CCC2(C1)CN(C(=O)c1cc(Sc3cnc(NC(=O)c4ccsc4)s3)c(C)cc1OC)C2] N-(5-((5-(6-acryloyl-2,6-diazapiro[3.4]octane-2-carbonyl)-4-methoxy-2-methylphenyl)thio)thiazol-2-yl)thiophene-3-carboxamide | Compound 145 | $^1$H NMR (400 MHz, DMSO, ppm): δ 12.7 (br s, 1H), 8.72 (s, 1H), 7.78-7.68 (m, 3H), 7.06 (m, 2H), 6.47 (br s, 1H), 6.07 (m, 1H), 5.63 (m, 1H), 3.91-3.32 (m, 7H), 3.73 (s, 3H), 2.50 (s, 3H), 2.00 (m, 3H). |
| 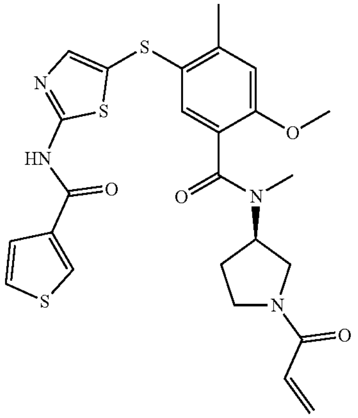 [SMILES: C=CC(=O)N1CC[C@@H](N(C)C(=O)c2cc(Sc3cnc(NC(=O)c4ccsc4)s3)c(C)cc2OC)C1] (R)-N-(5-((5-((1-acryloylpyrrolidin-3-yl)(methyl)carbamoyl)-4-methoxy-2-methylphenyl)thio)thiazol-2-yl)thiophene-3-carboxamide | Compound 146 | $^1$H NMR (400 MHz, DMSO, ppm): δ 12.7 (br s, 1H), 8.61 (s, 1H), 7.77-7.71 (m, 3H), 7.06 (m, 2H), 6.59 (m, 1H), 6.03 (m, 1H), 5.53 (m, 1H), 4.07 (m, 1H), 3.89 (s, 3H), 3.59 (m, 2H), 2.85 (s, 3H), 2.47 (s, 3H), 2.02 (m, 2H), 1.20 (m, 2H). |
| 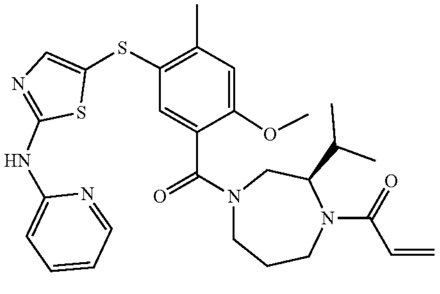 [SMILES: C=CC(=O)N1CCCN(C(=O)c2cc(Sc3cnc(Nc4ccccn4)s3)c(C)cc2OC)C[C@H]1C(C)C] (R)-1-(2-isopropy-4-(2-methoxy-methyl-5-((2-(pyridin-2-ylamino)thiazol-5-yl)thio)benzoyl)1,4-diazepan-1-yl)prop-2-en-1-one | Compound 147 | $^1$H NMR (400 MHz, DMSO, ppm): δ 11.56 (br s, 1H), 8.28 (s, 1H), 7.75-7.50 (m, 2H), 7.08-6.95 (m, 3H), 6.78 (s, 1H), 6.60 (m, 1H), 6.13 (m, 1H), 5.70-5.32 (m, 1H), 4.63-2.89 (m, 10H), 2.46 (m, 3H), 1.76-0.49 (m, 9H). |

TABLE 6-continued

| NMR data | | |
|---|---|---|
| 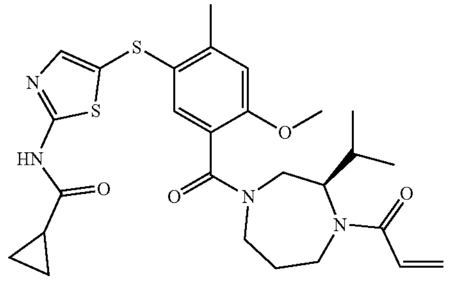 [SMILES: C=CC(=O)N1CCCN(C(=O)c2cc(Sc3cnc(NC(=O)C4CC4)s3)c(C)cc2OC)C[C@H]1C(C)C]<br>(R)-N-(5-((5-(4-acryloyl-3-isopropyl-1,4-diazepane-1-carbonyl)-4-methoxy-2-methylphenyl)thio)thiazol-2-yl)cyclopropanecarboxamide | Compound 148 | $^1$H NMR (400 MHz, DMSO, ppm): δ 12.60 (br s, 1H), 7.60 (m, 1H), 7.01-6.61 (m, 3H), 6.03 (m, 1H), 5.75-5.57 (m, 1H), 4.64-3.00 (m, 11H), 2.45 (s, 3H), 1.92-0.62 (m, 13H). |
| 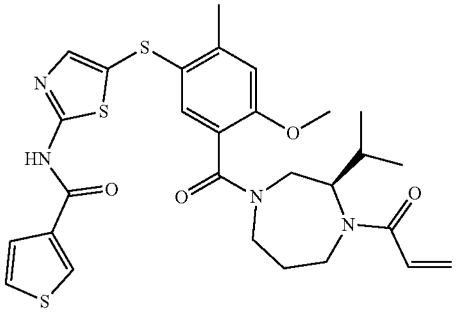 [SMILES: C=CC(=O)N1CCCN(C(=O)c2cc(Sc3cnc(NC(=O)c4ccsc4)s3)c(C)cc2OC)C[C@H]1C(C)C]<br>(R)-N-(5-((5-(4-acryloyl-3-isopropyl-1,4-diazepane-1-carbonyl)-4-methoxy-2-methylphenyl)thio)thiazol-2-yl)thiophene-3-carboxamide | Compound 149 | $^1$H NMR (400 MHz, DMSO, ppm): δ 12.73 (br s, 1H), 8.61 (s, 1H), 7.72 (m, 3H), 7.00-6.55 (m, 3H), 6.23 (m, 1H), 5.59 (m, 1H), 4.60-2.90 (m, 10H), 2.33 (s, 3H), 1.69-0.51 (m, 9H). |
| 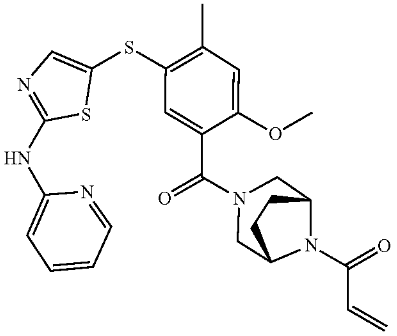 [SMILES: C=CC(=O)N1[C@@H]2CC[C@H]1CN(C(=O)c1cc(Sc3cnc(Nc4ccccn4)s3)c(C)cc1OC)C2]<br>1-((1R,5S)-3-(2-methoxy-4-methyl-5-((2-(pyridin-2-ylamino)thiazol-5-yl)thio)benzoyl-3,8-diazabicyclo[3.2.1]octan-8-yl)prop-2-en-1-one | Compound 150 | $^1$H NMR (400 MHz, DMSO, ppm): δ 11.62 (br s, 1H), 8.27 (s, 1H), 7.72 (m, 2H), 7.08-6.95 (m, 3H), 6.60 (m, 1H), 6.15 (m, 1H), 5.70 (m, 1H), 4.58 (m, 1H), 4.24 (m, 1H), 3.75 (m, 3H), 3.06 (m, 2H), 2.33 (s, 3H), 1.51 (m, 6H). |

TABLE 6-continued

| NMR data | | |
|---|---|---|
| 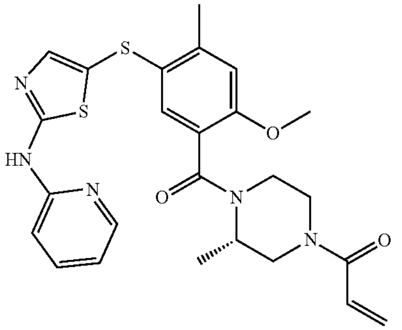 [SMILES: C=CC(=O)N1CCN(C(=O)c2cc(Sc3cnc(Nc4ccccn4)s3)c(C)cc2OC)[C@@H](C)C1]<br>(S)-1-(4-(2-methoxy-4-methyl-5-((2-(pyridin-2-ylamino)thiazol-5-yl)thio)benzoyl)-3-methylpiperazin-1-yl)prop-2-en-1-one | Compound 151 | $^1$H NMR (400 MHz, DMSO, ppm): δ 8.25 (m, 1H), 7.70 (m, 3H), 7.04-6.7 (m, 4H), 6.10 (m, 1H), 5.67 (m, 1H), 4.24 (m, 2H), 3.76 (s, 3H), 3.17-2.92 (m, 6H), 2.46 (s, 3H), 1.22 (m, 1H), 1.00 (m, 2H). |
| 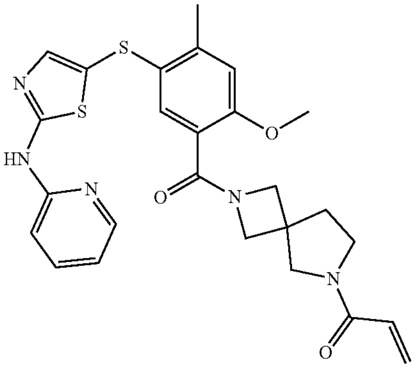 [SMILES: C=CC(=O)N1CCC2(C1)CN(C(=O)c1cc(Sc3cnc(Nc4ccccn4)s3)c(C)cc1OC)C2]<br>1-(2-methoxy-4-methyl-5-((2-(pyridin-2-ylamino)thiazol-5-yl)thio)benzoyl-2,6-diazaspiro[34]octan-6-yl)prop-2-en-1-one | Compound 152 | $^1$H NMR (400 MHz, DMSO, ppm): δ 8.28 (d, J = 4.0 Hz, 1H), 7.73 (m, 2H), 7.66 (s, 1H), 7.07-6.95 (m, 3H), 6.45 (m, 1H), 6.08 (m, 1H), 5.65 (m, 1H), 3.81-3.27 (m, 8H), 3.69 (s, 3H), 2.40 (s, 3H), 1.95 (m, 2H). |
| 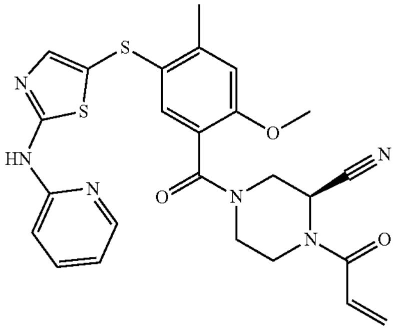 [SMILES: C=CC(=O)N1CCN(C(=O)c2cc(Sc3cnc(Nc4ccccn4)s3)c(C)cc2OC)C[C@H]1C#N]<br>(S)-1-acryloyl-4-(2-methoxy-4-methyl-5-((2-(pyridin-2-ylamino)thiazol-5-yl)thio)benzoyl)piperazine-2-carbonitrile | Compound 153 | $^1$H NMR (400 MHz, DMSO, ppm): δ 12.75, (br s, 1H), 8.61 (s, 1H), 7.70 (m, 4H), 7.11 (m, 2H), 6.23 (m, 1H), 6.45 (m, 1H), 5.85 (m, 1H), 5.71 (m, 1H), 5.51 (m, 1H), 3.78 (s, 3H), 3.50-2.90 (m, 4H), 2.54 (s, 3H), 1.26 (m, 1H). |

TABLE 6-continued

| NMR data | | |
|---|---|---|
| 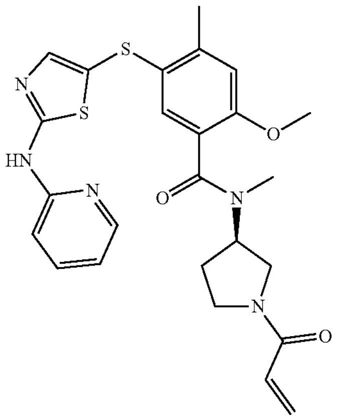 [SMILES: C=CC(=O)N1CC[C@@H](N(C)C(=O)c2cc(Sc3cnc(Nc4ccccn4)s3)c(C)cc2OC)C1] (R)-N-(1-acryloylpyrrolidin-3-yl)-2-methoxy-N,4-dimethyl-5-((2-pyridin-2-ylamino)thiazol-5-yl)thio)benzamide | Compound 154 | $^1$H NMR (400 MHz, DMSO, ppm): δ 8.27 (s, 1H), 7.75-7.64 (m, 2H), 7.04-6.85 (m, 3H), 6.52 (m, 1H), 6.31 (m, 1H), 6.16 (m, 1H), 5.65 (m, 1H), 4.06 (m, 1H), 3.77 (s, 3H), 3.54-3.24 (m, 3H), 2.82 (s, 2H), 2.63 (m, 1H), 2.45 (s, 3H), 2.08 (m, 4H). |
| 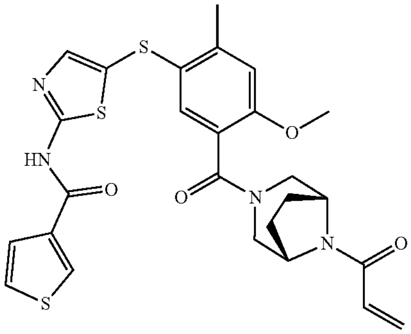 [SMILES: C=CC(=O)N1[C@@H]2CC[C@H]1CN(C(=O)c1cc(Sc3cnc(NC(=O)c4ccsc4)s3)c(C)cc1OC)C2] N-(5-((5-((1R,5S)-8-acryloyl-3,8-diazabicyclo[3.2.1]octane-3-carbonyl)-4-methoxy-2-methylphenyl)thio)thiazol-2-yl)thiophene-3-carboxamide | Compound 155 | $^1$H NMR (400 MHz, DMSO, ppm): δ 12.77 (br s, 1H), 8.60 (s, 1H), 7.70 (m, 3H), 7.00 (m, 2H), 6.58 (m, 1H), 6.14 (m, 1H), 5.70 (m, 1H), 4.58 (m, 1H), 4.36 (m, 1H), 3.76 (s, 3H), 3.08 (m, 2H), 2.75 (s, 2H), 2.50 (s, 3H), 1.52 (m, 4H). |
| 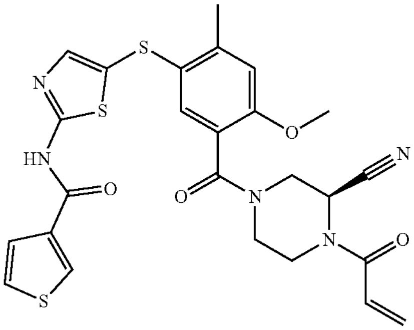 [SMILES: C=CC(=O)N1CCN(C(=O)c2cc(Sc3cnc(NC(=O)c4ccsc4)s3)c(C)cc2OC)C[C@H]1C#N] (S)-N-(5-((5-(4-acryloyl-3-cyanopiperazine-1-carbonyl)-4-methoxy-2-methylphenyl)thio)thiazol-2-yl)thiophene-3-carboxamide | Compound 156 | $^1$H NMR (400 MHz, DMSO, ppm): δ 11.60 (br s, 1H), 8.28 (s, 1H), 7.64 (m, 3H), 7.07-6.91 (m, 3H), 6.23 (m, 1H), 5.83 (m, 1H), 5.47 (m, 1H), 4.67 (m, 2H), 3.77 (s, 3H), 3.32 (m, 2H), 2.99 (m, 2H), 2.46 (s, 3H). |

TABLE 6-continued

| NMR data | | |
|---|---|---|
| 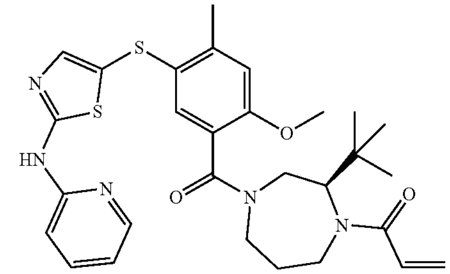<br>(R)-1-(2-tert-butyl)-4-(2-methoxy-4-methyl-5-((2-(pyridin-2-ylamino)thiazol-5-yl)thio)benzoyl)1,4-diazepan-1-yl)prop-2-en-1-one | Compound 157 | $^1$H NMR (400 MHz, DMSO, ppm): δ 11.60 (br s, 1H), 8.50 (s, 1H), 7.75-6.63 (m, 5H), 6.20 (m, 1H), 5.70 (m, 1H), 4.84-3.13 (m, 8H), 3.78 (s, 3H), 2.30 (m, 3H), 1.47 (m, 2H), 0.90 (s, 9H), 0.54 (m, 1H). |
| 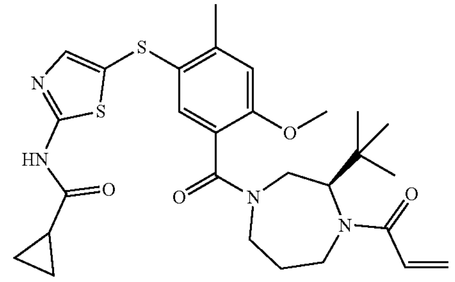 [SMILES: C=CC(=O)N1CCCN(C(=O)c2cc(Sc3cnc(NC(=O)C4CC4)s3)c(C)cc2OC)C[C@H]1C(C)(C)C]<br>(R)-N-(5-((5-(4-acryloyl-3-(tert-butyl)-1,4-diazepane-1-carbonyl)-4-methoxy-2-methylphenyl)thio)thiazol-2-yl)cyclopropanecarboxamide | Compound 158 | $^1$H NMR (400 MHz, DMSO, ppm): δ 12.60 (br s, 1H), 7.58 (m, 1H), 7.19-6.57 (m, 3H), 6.22 (m, 1H), 5.70 (m, 1H), 4.83-3.04 (m, 11H), 3.78 (s, 3H), 2.33 (m, 3H), 1.94 (m, 1H), 0.89 (s, 9H), 0.60 (m, 1H). |
| 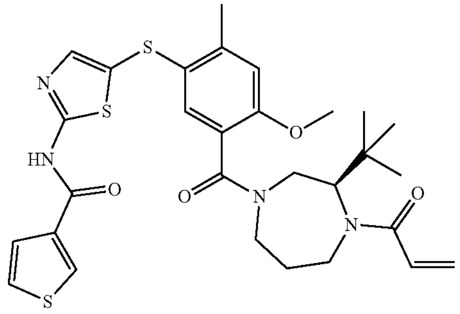 [SMILES: C=CC(=O)N1CCCN(C(=O)c2cc(Sc3cnc(NC(=O)c4ccsc4)s3)c(C)cc2OC)C[C@H]1C(C)(C)C]<br>(R)-N-(5-((5-(4-acryloyl-3-(tert-butyl)-1,4-diazepane-1-carbonyl)-4-methoxy-2-methylphenyl)thio)thiazol-2-yl)thiophene-3-carboxamide | Compound 159 | $^1$H NMR (400 MHz, DMSO, ppm): δ 12.74 (br s, 1H), 8.60 (m, 1H), 7.70 (m, 3H), 7.10-6.64 (m, 3H), 6.15 (m, 1H), 5.65 (m, 1H), 4.71-3.85 (m, 3H), 3.74 (s, 3H), 3.51 (m, 1H), 3.12 (m, 2H), 2.34 (s, 3H), 1.24 (m, 3H), 0.91 (s, 9H). |
| 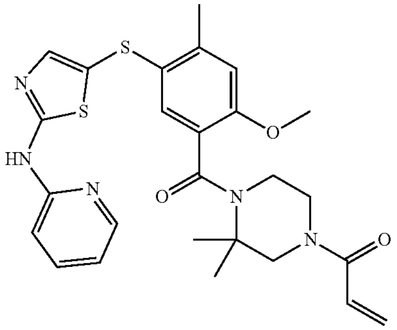 [SMILES: C=CC(=O)N1CCN(C(=O)c2cc(Sc3cnc(Nc4ccccn4)s3)c(C)cc2OC)C(C)(C)C1]<br>1-4-(2-methoxy-4-methyl-5-((2-(pyridin-2-ylamino)thiazol-5-yl)thio)benzoyl)-3,3-dimethylpiperazin-1-yl)prop-2-en-1-one | Compound 160 | $^1$H NMR (400 MHz, DMSO, ppm): δ 11.60 (br s, 1H), 8.29 (s, 1H), 7.73 (m, 1H), 7.64 (s, 1H), 7.02-6.91 (m, 3H), 6.80-6.45 (m, 1H), 6.13 (m, 1H), 5.70 (m, 1H), 3.78 (s, 3H), 3.60-3.35 (m, 6H), 2.46 (s, 3H), 1.41 (s, 6H). |

TABLE 6-continued

| NMR data | |
|---|---|
| 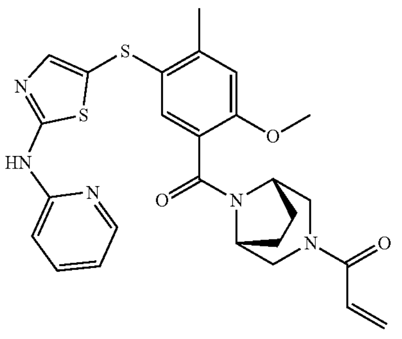 [SMILES: C=CC(=O)N1C[C@H]2CC[C@@H](C1)N2C(=O)c1cc(Sc2cnc(Nc3ccccn3)s2)c(C)cc1OC]<br>1-((1R,5S)-3-(2-methoxy-4-methyl-5-((2-(pyridin-2-ylamino)thiazol-5-yl)thio)benzoyl-3,8-diazabicyclo[3.2.1]octan-3-yl)prop-2-en-1-one | Compound 161 $^1$H NMR (400 MHz, DMSO, ppm): δ 11.60 (br s, 1H), 8.27 (s, 1H), 7.74 (m, 1H), 7.64 (s, 1H), 7.06-6.95 (m, 4H), 6.80-6.45 (m, 1H), 6.09 (m, 1H), 5.65 (m, 1H), 4.64 (s, 1H), 4.28-3.94 (m, 2H), 3.78 (s, 3H), 3.60-3.35 (m, 2H), 2.46 (s, 3H), 1.44 (s, 4H). |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

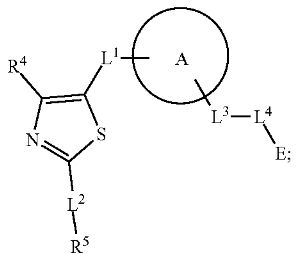

wherein:

Ring A is

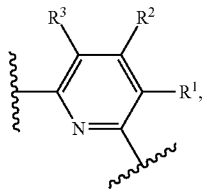

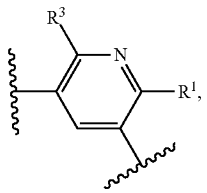

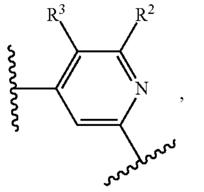

, or

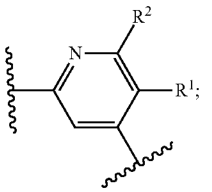

$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —$N(O)_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$N(O)_{m3}$, —$NR^{3A}R^{3B}$, —C(O)$R^{3C}$, —C(O)—$OR^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —$N(O)_{m4}$, —$NR^{4A}R^{4B}$, —C(O)$R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ is —O—, —S—, or substituted or unsubstituted $C_1$-$C_2$ alkylene, or substituted or unsubstituted 2 membered heteroalkylene;

$L^2$ is a bond, —NH—, or —NHC(O)—;

$L^3$ is a bond, $—S(O)_2—$, $—N(R^6)—$, —O—, —S—, —C(O)—, $—C(O)N(R^6)—$, $—N(R^6)C(O)—$, $—N(R^6)C(O)NH—$, $—NHC(O)N(R^6)—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^6$ is hydrogen, $—CX^6{}_3$, $—CHX^6{}_2$, $—CH_2X^6$, —CN, $—C(O)R^{6C}$, $—C(O)OR^{6C}$, $—C(O)NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, $—S(O)_2—$, $—N(R^7)—$, —O—, —S—, —C(O)—, $—C(O)N(R^7)—$, $—N(R^7)C(O)—$, $—N(R^7)C(O)NH—$, $—NHC(O)N(R^7)—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^7$ is hydrogen, $—CX^7{}_3$, $—CHX^7{}_2$, $—CH_2X^7$, —CN, $—C(O)R^{7C}$, $—C(O)OR^{7C}$, $—C(O)NR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is

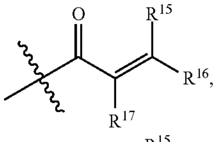 ,

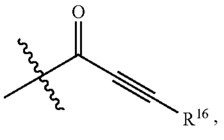 ,

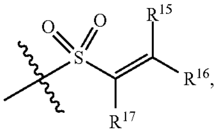 ,

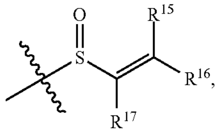 ,

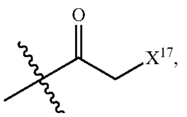 , or

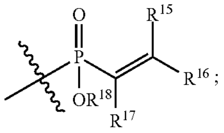 ;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{6A}$, $R^{6B}$, $R^{6C}$, $R^{7A}$, $R^{7B}$, and $R^{7C}$ are each independently hydrogen, $—CX_3$, —CN, —COOH, $—CONH_2$, $—CHX_2$, $—CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom are optionally joined to form a substituted or unsubstituted heterocycloalkyl or substituted or unsubstituted heteroaryl; $R^{2A}$ and $R^{2B}$ substituents bonded to the same nitrogen atom are optionally joined to form a substituted or unsubstituted heterocycloalkyl or substituted or unsubstituted heteroaryl; $R^{3A}$ and $R^{3B}$ substituents bonded to the same nitrogen atom are optionally joined to form a substituted or unsubstituted heterocycloalkyl or substituted or unsubstituted heteroaryl; $R^{4A}$ and $R^{4B}$ substituents bonded to the same nitrogen atom are optionally joined to form a substituted or unsubstituted heterocycloalkyl or substituted or unsubstituted heteroaryl; $R^{6A}$ and $R^{6B}$ substituents bonded to the same nitrogen atom are optionally joined to form a substituted or unsubstituted heterocycloalkyl or substituted or unsubstituted heteroaryl; $R^{7A}$ and $R^{7B}$ substituents bonded to the same nitrogen atom are optionally joined to form a substituted or unsubstituted heterocycloalkyl or substituted or unsubstituted heteroaryl;

X, $X^1$, $X^2$, $X^3$, $X^4$, $X^6$, and $X^7$ are each independently —F, —Cl, —Br, or —I;

n1, n2, n3, and n4 are independently an integer from 0 to 2;

m1, m2, m3, m4, v1, v2, v3, and v4 are independently 1 to 2;

$R^{15}$ is hydrogen, halogen, $—CX^{15}{}_3$, $—CHX^{15}{}_2$, $—CH_2X^{15}$, —CN, $—SO_{n15}R^{15D}$, $—SO_{v15}NR^{15A}R^{15B}$, $—NHNR^{15A}R^{15B}$, $—ONR^{15A}R^{15B}$, $—NHC{=}(O)NHNR^{15A}R^{15B}$, $—NHC(O)NR^{15A}R^{15B}$, $—N(O)_{m15}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—OCX^{15}{}_3$, $—OCHX^{15}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is hydrogen, halogen, $—CX^{16}{}_3$, $—CHX^{16}{}_2$, $—CH_2X^{16}$, —CN, $—SO_{n16}R^{16D}$, $—SO_{v16}NR^{16A}R^{16B}$, $—NHNR^{16A}R^{16B}$, $—ONR^{16A}R^{16B}$, $—NHC{=}(O)NHNR^{16A}R^{16B}$, $—NHC(O)NR^{16A}R^{16B}$, $—N(O)_{m16}$, $—NR^{16A}R^{16B}$, $C(O)R^{16C}$, $—C(O)—OR^{16C}$, $C(O)NR^{16A}R^{16B}$, $—OR^{16D}$, $—NR^{16A}SO_2R^{16D}$, $—NR^{16A}C(O)R^{16C}$, $—NR^{16A}C(O)OR^{16C}$, $—NR^{16A}OR^{16C}$, $—OCX^{16}{}_3$, $—OCHX^{16}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is hydrogen, halogen, $—CX^{17}_3$, $—CHX^{17}_2$, $—CH_2X^{17}$, —CN, $—SO_{n17}R^{17D}$, $—SO_{v17}NR^{17A}R^{17B}$, $—NHNR^{17A}R^{17B}$, $—ONR^{17A}R^{17B}$, $—NHC{=}(O)NHNR^{17A}R^{17B}$, $—NHC(O)NR^{17A}R^{17B}$, $—N(O)_{m17}$, $—NR^{17A}R^{17B}$, $—C(O)R^{17C}$, $—C(O)—OR^{17C}$, $—C(O)NR^{17A}R^{17B}$, $—OR^{17D}$, $—NR^{17A}SO_2R^{17D}$, $—NR^{17A}C(O)R^{17C}$, $—NR^{17A}C(O)OR^{17C}$, $—NR^{17A}OR^{17C}$, $—OCX^{17}_3$, $—OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is hydrogen, $—CX^{18}_3$, $—CHX^{18}_2$, $—CH_2X^{18}$, $—C(O)R^{18C}$, $—C(O)OR^{18C}$, $—C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, and $R^{18C}$ are independently hydrogen, $—CX_3$, —CN, —COOH, $—CONH_2$, $—CHX_2$, $—CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom are optionally joined to form a substituted or unsubstituted heterocycloalkyl or substituted or unsubstituted heteroaryl; $R^{16A}$ and $R^{16B}$ substituents bonded to the same nitrogen atom are optionally joined to form a substituted or unsubstituted heterocycloalkyl or substituted or unsubstituted heteroaryl; $R^{17A}$ and $R^{17B}$ substituents bonded to the same nitrogen atom are optionally joined to form a substituted or unsubstituted heterocycloalkyl or substituted or unsubstituted heteroaryl; $R^{18A}$ and $R^{18B}$ substituents bonded to the same nitrogen atom are optionally joined to form a substituted or unsubstituted heterocycloalkyl or substituted or unsubstituted heteroaryl;

X, $X^{15}$, $X^{16}$, $X^{17}$ and $X^{18}$ are independently —F, —Cl, —Br, or —I;

n15, n16, n17, v15, v16, and v17, are independently an integer from 0 to 2; and m15, m16, and m17 are independently 1 or 2.

2. The compound of claim 1, wherein Ring A is

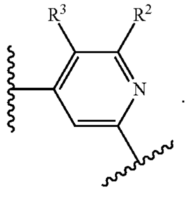

.

3. The compound of claim 1, having the formula:

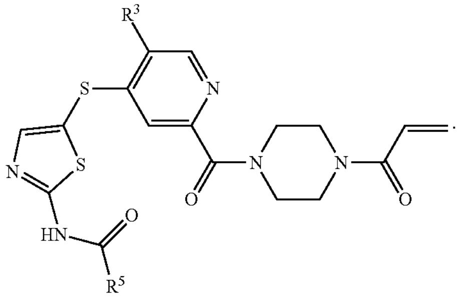

.

4. The compound of claim 1, having the formula:

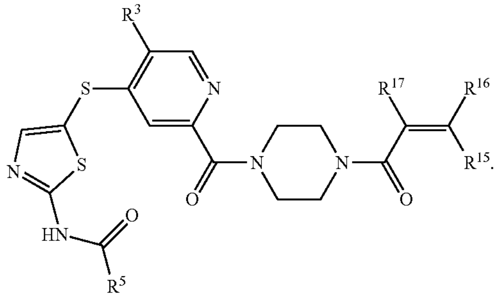

.

wherein $R^{15}$ is hydrogen, halogen, $—CX^{15}_3$, $—CHX^{15}_2$, $—CH_2X^{15}$, —CN, $—SO_{n15}R^{15D}$, $—SO_{v15}NR^{15A}R^{15B}$, $—NHNR^{15A}R^{15B}$, $—ONR^{15A}R^{15B}$, $—NHC{=}(O)NHNR^{15A}R^{15B}$, $—NHC(O)NR^{15A}R^{15B}$, $—N(O)_{m15}$, $—NR^{15A}R^{15B}$, $—C(O)R^{15C}$, $—C(O)—OR^{15C}$, $—C(O)NR^{15A}R^{15B}$, $—OR^{15D}$, $—NR^{15A}SO_2R^{15D}$, $—NR^{15A}C(O)R^{15C}$, $—NR^{15A}C(O)OR^{15C}$, $—NR^{15A}OR^{15C}$, $—OCX^{15}_3$, $—OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is hydrogen, halogen, $—CX^{16}_3$, $—CHX^{16}_2$, $—CH_2X^{16}$, —CN, $—SO_{n16}R^{16D}$, $—SO_{v16}NR^{16A}R^{16B}$, $—NHNR^{16A}R^{16B}$, $—ONR^{16A}R^{16B}$, $—NHC{=}(O)\ NHNR^{16A}R^{16B}$, $—NHC(O)NR^{16A}R^{16B}$, $—N(O)_{m16}$, $—NR^{16A}R^{16B}$, $—C(O)R^{16C}$, $—C(O)—OR^{16C}$, $—C(O)NR^{16A}R^{16B}$, $—OR^{16D}$, $—NR^{16A}SO_2R^{16D}$, $—NR^{16A}C(O)R^{16C}$, $—NR^{16A}C(O)OR^{16C}$, $—NR^{16A}OR^{16C}$, $—OCX^{16}_3$, $—OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is hydrogen, halogen, $—CX^{17}_3$, $—CHX^{17}_2$, $—CH_2X^{17}$, —CN, $—SO_{n17}R^{17D}$, $—SO_{v17}NR^{17A}R^{17B}$, $—NHNR^{17A}R^{17B}$, $—ONR^{17A}R^{17B}$, $—NHC{=}(O)\ NHNR^{17A}R^{17B}$, $—NHC(O)NR^{17A}R^{17B}$, $—N(O)_{m17}$, $—NR^{17A}R^{17B}$, $—C(O)\ R^{17C}$, $—C(O)—OR^{17C}$, $—C(O)NR^{17A}R^{17B}$, $—OR^{17D}$, $—NR^{17A}SO_2R^{17D}$, $—NR^{17A}C(O)R^{17C}$, $—NR^{17A}C(O)OR^{17C}$, $—NR^{17A}OR^{17C}$, $—OCX^{17}_3$, $—OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom is optionally joined to form a substituted or unsubstituted heterocycloalkyl or substituted or unsubstituted heteroaryl; $R^{16A}$ and $R^{16B}$ substituents bonded to the same nitrogen atom is optionally joined to form a substituted or unsubstituted heterocycloalkyl or substituted or unsubstituted heteroaryl; $R^{17A}$ and $R^{17B}$ substituents bonded to the same nitrogen atom is optionally joined to form a substituted or unsubstituted heterocycloalkyl or substituted or unsubstituted heteroaryl; $R^{18A}$ and $R^{18B}$ substituents bonded to the same nitrogen atom is optionally joined to form a substituted or unsubstituted heterocycloalkyl or substituted or unsubstituted heteroaryl;

$X^{15}$, $X^{16}$, and $X^{17}$ are independently —F, —Cl, —Br, or —I;

n15, n16, n17, v15, v16, and v17, are independently an integer from 0 to 2; and m15, m16, and m17 are independently 1 or 2.

5. The compound of claim 4, wherein $R^3$ is hydrogen and $R^4$ is hydrogen.

6. The compound of claim 1, having the formula:

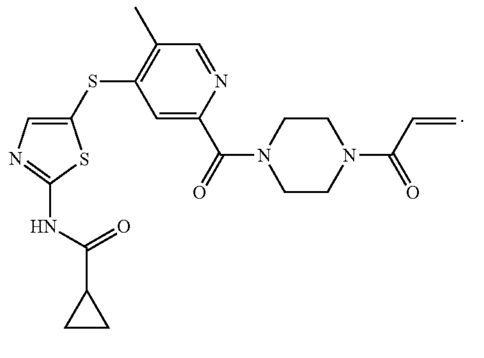 [SMILES: C=CC(=O)N1CCN(C(=O)c2cc(Sc3cnc(NC(=O)C4CC4)s3)c(C)cn2)CC1]

7. The compound of claim 1, wherein $L^1$ is —O—, —S—, or substituted or unsubstituted methylene.

8. The compound of claim 1, wherein $R^1$ is hydrogen, halogen, —$CX^1_3$, —$CHX^1_2$, —$CH_2X^1$, —$OCX^1_3$, —$OCH_2X^1$, —$OCHX^1_2$, substituted or unsubstituted alkyl, or substituted or unsubstituted heteroalkyl.

9. The compound of claim 1, wherein $R^1$ is hydrogen, halogen, —$CH_3$, —$CH_2CH_3$, —$CX^1_3$, —$CHX^1_2$, —$CH_2X^1$, —$OCH_3$, —$OCX^1_3$, —$OCH_2X^1$, —$OCHX^1_2$, —$SCH_3$, —$SCX^1_3$, —$SCH_2X^1$, or —$SCHX^1_2$.

10. The compound of claim 1, wherein $R^3$ is hydrogen, halogen, —$CX^3_3$, —$CHX^3_2$, —$CH_2X^3$, —$OCX^3_3$, —$OCH_2X^3$, —$OCHX^3_2$, —CN, substituted or unsubstituted alkyl, or substituted or unsubstituted heteroalkyl.

11. The compound of claim 1, wherein $R^3$ is hydrogen, halogen, —$CH_3$, —$CH_2CH_3$, —$CX^3_3$, —$CHX^3_2$, —$CH_2X^3$, —$OCH_3$, —$OCX^3_3$, —$OCH_2X^3$, —$OCHX^3_2$, —CN, —$SCH_3$, —$SCX^3_3$, —$SCH_2X^3$, or —$SCHX^3_2$.

12. The compound of claim 1, wherein $R^5$ is substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl.

13. The compound of claim 1, wherein $R^5$ is unsubstituted cyclopropyl, unsubstituted cyclobutyl, or unsubstituted cyclopentyl.

14. The compound of claim 1, wherein $R^5$ is substituted or unsubstituted ($C_1$-$C_8$) alkyl, substituted or unsubstituted 2 to 8 membered heteroalkyl, substituted or unsubstituted ($C_3$-$C_6$) cycloalkyl, substituted or unsubstituted 3 to 6 membered heterocycloalkyl, substituted or unsubstituted phenyl, or substituted or unsubstituted 5 to 6 membered heteroaryl.

15. The compound of claim 1, wherein $L^4$ is a bond, —$N(R^7)$—, —C(O)—, —$C(O)N(R^7)$—, substituted or unsubstituted heterocycloalkylene, substituted or unsubstituted fused ring heterocycloalkylene, substituted or unsubstituted spirocyclic heterocycloalkylene, or substituted or unsubstituted bridged ring heterocycloalkylene; and $R^7$ is independently hydrogen, —$CX^7_3$, —$CHX^7_2$, —$CH_2X^7$, or unsubstituted ($C_1$-$C_4$) alkyl.

16. The compound of claim 1, wherein $L^4$ is

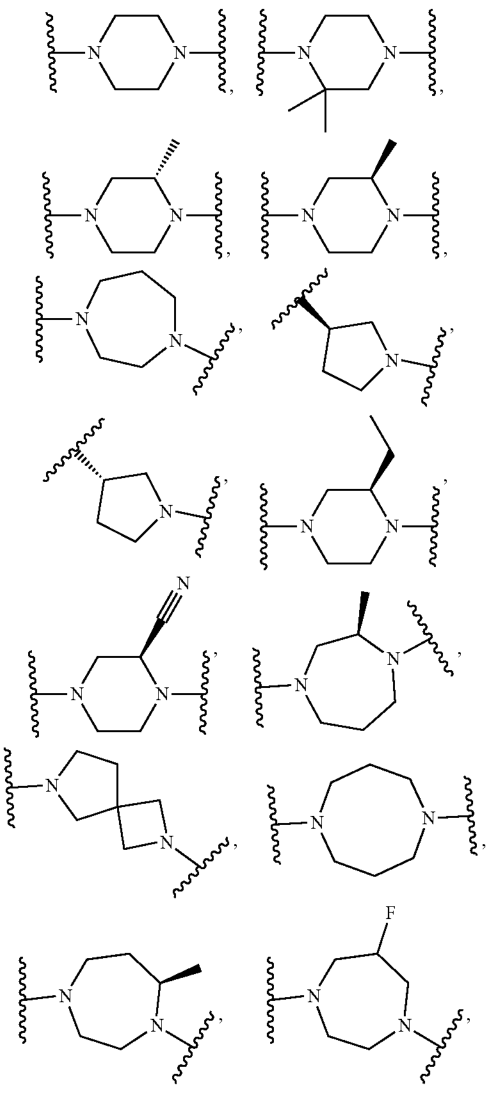

-continued

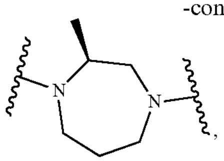,
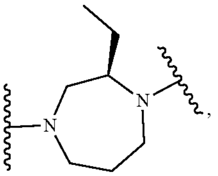,
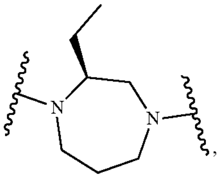,
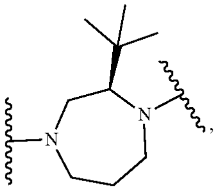,
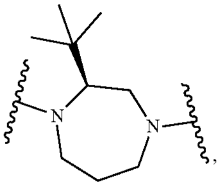,
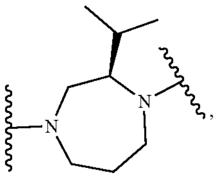,
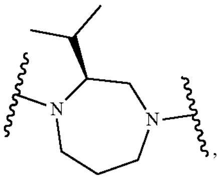,
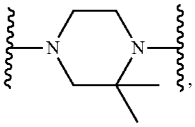,
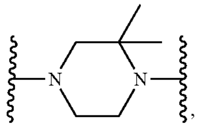,
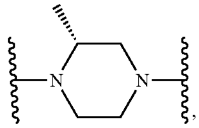,
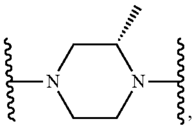,
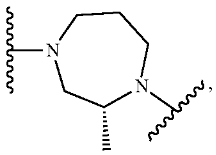, -continued

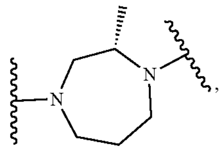,
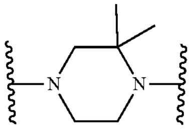, or
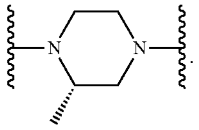.

17. The compound of claim 1, wherein:

E is

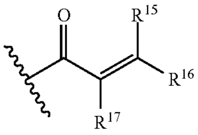 or 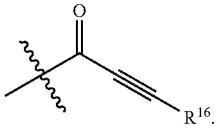.

18. The compound of claim 1, wherein E is —C(O)CH═$CH_2$, —C(O)CH═$CHCH_2N(CH_3)_2$, —C(O)C(═$CH_2$)$CH_2N(CH_3)_2$, —C(O)C≡$CCH_3$, or —C(O)C(═$CH_2$)$CH_3$.

19. A pharmaceutical composition comprising the compound of claim 1 and a pharmaceutically acceptable excipient.

20. A method of treating cancer in a subject in need thereof, the method comprising administering to the subject an effective amount of the compound of claim 1, wherein the cancer is chronic lymphocytic leukemia, lymphoblastic T cell leukemia, or T cell lymphoma.

* * * * *